US012558161B2

(12) United States Patent
Gullotti et al.

(10) Patent No.: US 12,558,161 B2
(45) Date of Patent: Feb. 24, 2026

(54) INTRAOPERATIVE ALIGNMENT ASSESSMENT SYSTEM AND METHOD

(71) Applicant: GLOBUS MEDICAL, INC., Audubon, PA (US)

(72) Inventors: David Michael Gullotti, Towson, MD (US); Amir Hossein Soltanianzadeh, Baltimore, MD (US); Nicholas Theodore, Ruxton, MD (US); Edward Frederick Ruppel, III, Saratoga, CA (US); Saki Fujita, Baltimore, MD (US); Nicholas Griesmer Franconi, Pittsburgh, PA (US); Miguel Antonio Inserni, Alamo, CA (US); Jennifer Lin, Oceanside, NY (US); Robert Li, Cypress, CA (US); Ali Uneri, Baltimore, MD (US); Sritam Parashar Rout, Methuen, MA (US); Marc Chelala, Montreal (CA); Kyle Robert Cowdrick, Lilburn, GA (US); Maria Fernanda Torres, Caracas (VE)

(73) Assignee: Globus Medical, Inc., Audubon, PA (US)

( * ) Notice: Subject to any disclaimer, the term of this patent is extended or adjusted under 35 U.S.C. 154(b) by 1054 days.

(21) Appl. No.: 16/926,390

(22) Filed: Jul. 10, 2020

(65) Prior Publication Data

US 2020/0405395 A1 Dec. 31, 2020

Related U.S. Application Data

(63) Continuation-in-part of application No. 16/237,443, filed on Dec. 31, 2018, now Pat. No. 11,540,767,
(Continued)

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/25* (2016.02); *A61B 90/39* (2016.02); *G16H 10/60* (2018.01);
(Continued)

(58) Field of Classification Search
CPC .................... G16H 50/30; G16H 10/60; A61B 2090/3966; A61B 90/39; A61B 34/10;
(Continued)

(56) References Cited

U.S. PATENT DOCUMENTS 6,956,202 B2 10/2005 Sabczynski et al.
2003/0069591 A1* 4/2003 Carson .................. A61B 90/36
606/130
(Continued)

FOREIGN PATENT DOCUMENTS

DE 102015102776 A1 9/2016
KR 1020130094295 A 8/2013
(Continued)

OTHER PUBLICATIONS

International Search Report and Written Opinion for International Application No. PCT/US2018/068212, mailed Jun. 26, 2019, 19 pages.
(Continued)

*Primary Examiner* — Sameh R Boles

(57) ABSTRACT

Some embodiments provide systems, assemblies, and methods of analyzing patient anatomy, including providing an analysis of a patient's spine, and also analyzing the biomechanical effects of implants. In some embodiments, the systems, assemblies, and/or methods can include obtaining
(Continued)

initial patient data, acquiring spinal alignment and contour information, acquiring flexibility and/or biomechanical information, registering patient anatomical landmarks of interest relative to fiducial markers, analyzing databases of measurements and patient data to predict postoperative patient outcomes. Further, in some embodiments, the systems, assemblies, and/or methods can assess localized anatomical features of the patient, and obtain anatomical region data. In some embodiments, the systems, assemblies, and/or methods can also analyze the localized anatomy and therapeutic device location and contouring. Further, the systems, assemblies, and/or methods can output localized anatomical analyses and therapeutic device contouring data and/or imagery on a display according to some embodiments.

13 Claims, 447 Drawing Sheets

Related U.S. Application Data which is a continuation-in-part of application No. 16/026,754, filed on Jul. 3, 2018, now abandoned.

(60) Provisional application No. 62/884,032, filed on Aug. 7, 2019, provisional application No. 62/528,390, filed on Jul. 3, 2017.

(51) Int. Cl.
| | |
|---|---|
| *A61B 90/00* | (2016.01) |
| *G16H 10/60* | (2018.01) |
| *G16H 50/30* | (2018.01) |

(52) U.S. Cl.
CPC ........ *G16H 50/30* (2018.01); *A61B 2034/102* (2016.02); *A61B 2034/105* (2016.02); *A61B 2090/3966* (2016.02)

(58) Field of Classification Search
CPC .............. A61B 34/25; A61B 2034/102; A61B 2034/105
See application file for complete search history.

(56) References Cited

U.S. PATENT DOCUMENTS

| | | | |
|---|---|---|---|
| 2005/0004451 A1 | 1/2005 | Vilsmeier | |
| 2005/0165292 A1 | 7/2005 | Simon et al. | |
| 2006/0009780 A1 | 1/2006 | Foley et al. | |
| 2006/0173269 A1* | 8/2006 | Glossop ................... | A61B 5/06 |
| | | | 600/407 |
| 2007/0167787 A1 | 7/2007 | Glossop et al. | |
| 2008/0167547 A1 | 7/2008 | Bova | |
| 2008/0294258 A1* | 11/2008 | Revie ................... | A61B 5/6878 |
| | | | 623/18.11 |
| 2010/0160771 A1 | 6/2010 | Gielen | |
| 2014/0316420 A1 | 10/2014 | Ballard et al. | |
| 2015/0051489 A1 | 2/2015 | Caluser et al. | |
| 2015/0088093 A1 | 3/2015 | Goetz | |
| 2016/0242857 A1 | 8/2016 | Scholl | |
| 2017/0258526 A1* | 9/2017 | Lang ................. | A61B 17/1742 |
| 2019/0000372 A1 | 1/2019 | Gullotti et al. | |
| 2019/0209080 A1 | 7/2019 | Gullotti et al. | |

FOREIGN PATENT DOCUMENTS

| | | |
|---|---|---|
| WO | 2013044157 A1 | 3/2013 |
| WO | 2017077356 A1 | 5/2017 |

OTHER PUBLICATIONS

International Search Report and Written Opinion for International Application No. PCT/US2018/040754, mailed Oct. 26, 2018, 9 pages.

* cited by examiner

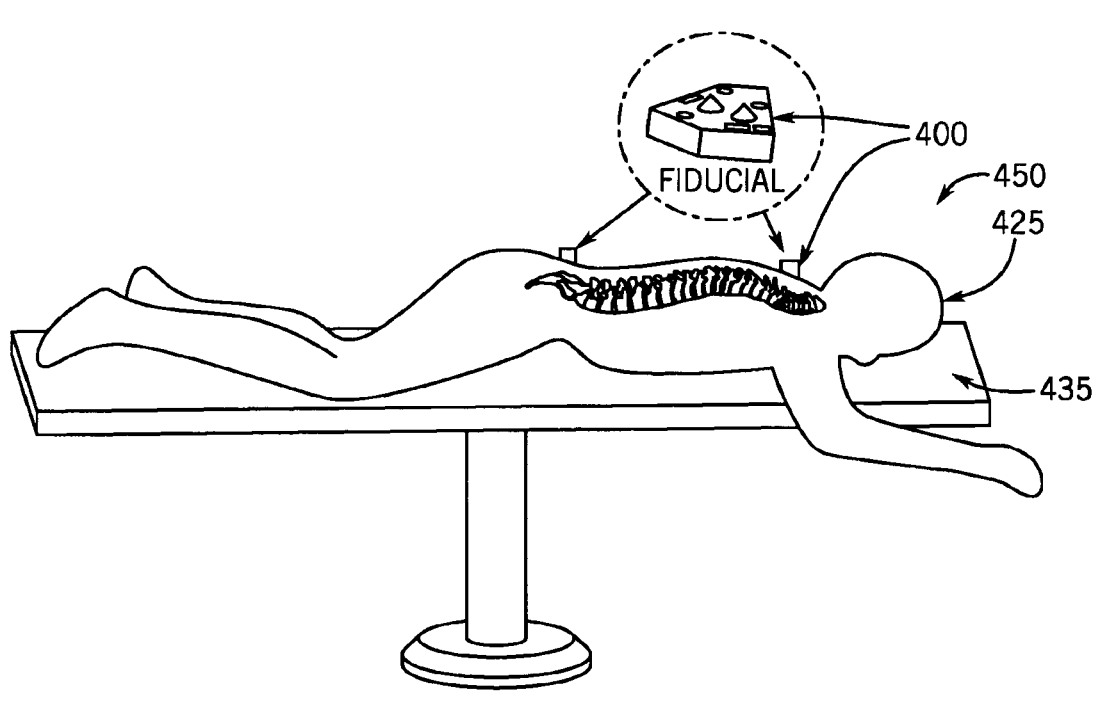
FIG. 4A
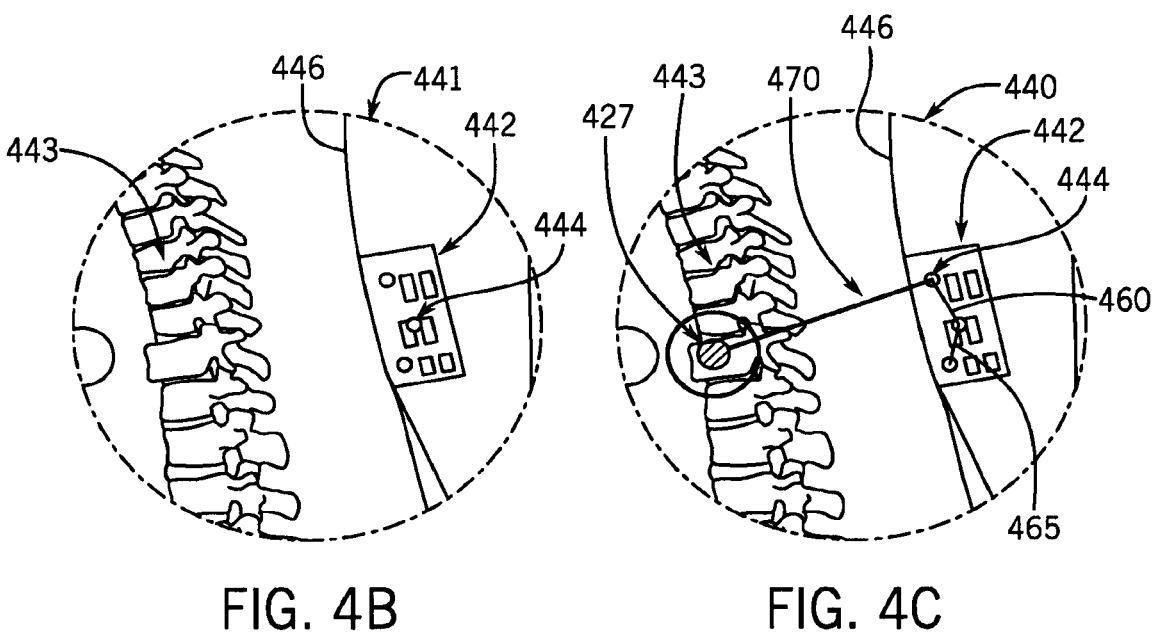
FIG. 4B                    FIG. 4C

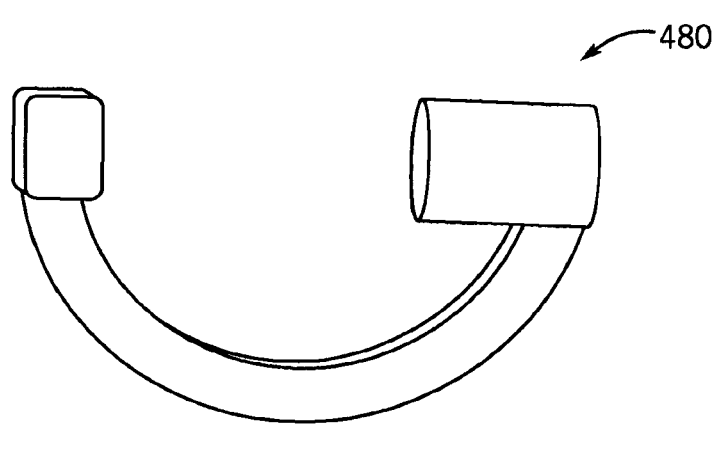
FIG. 4D
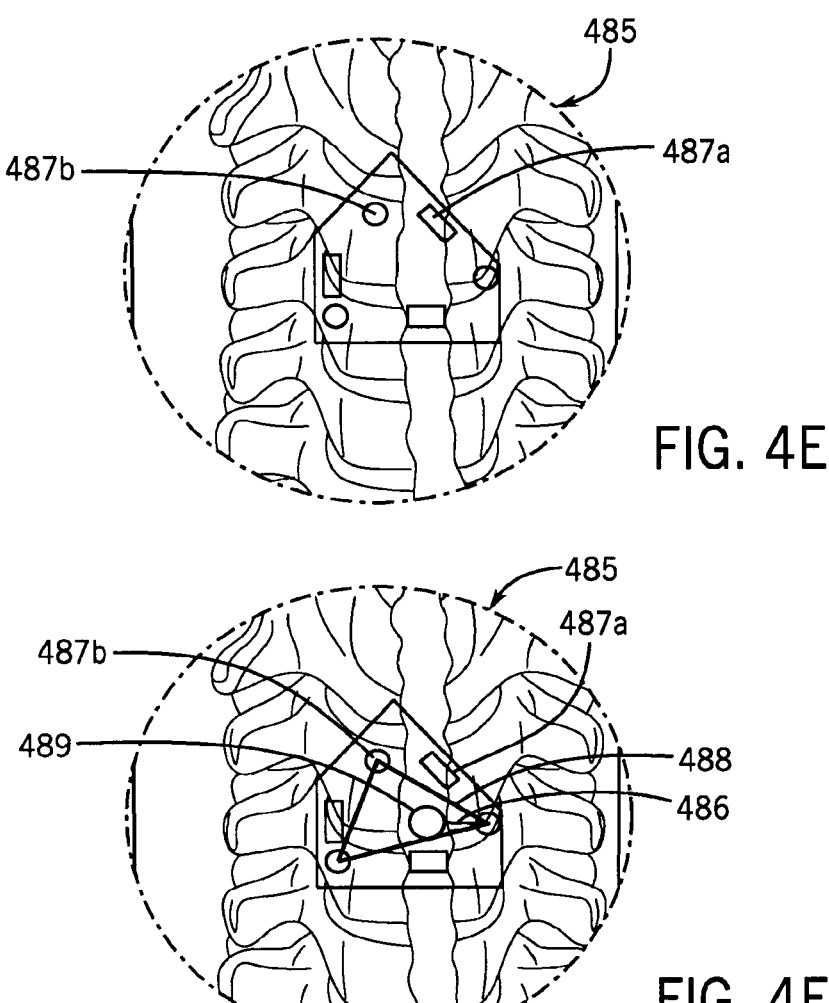
FIG. 4E
FIG. 4F

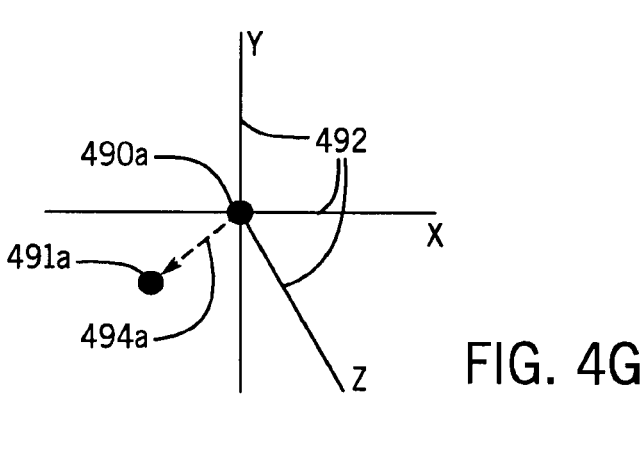
FIG. 4G
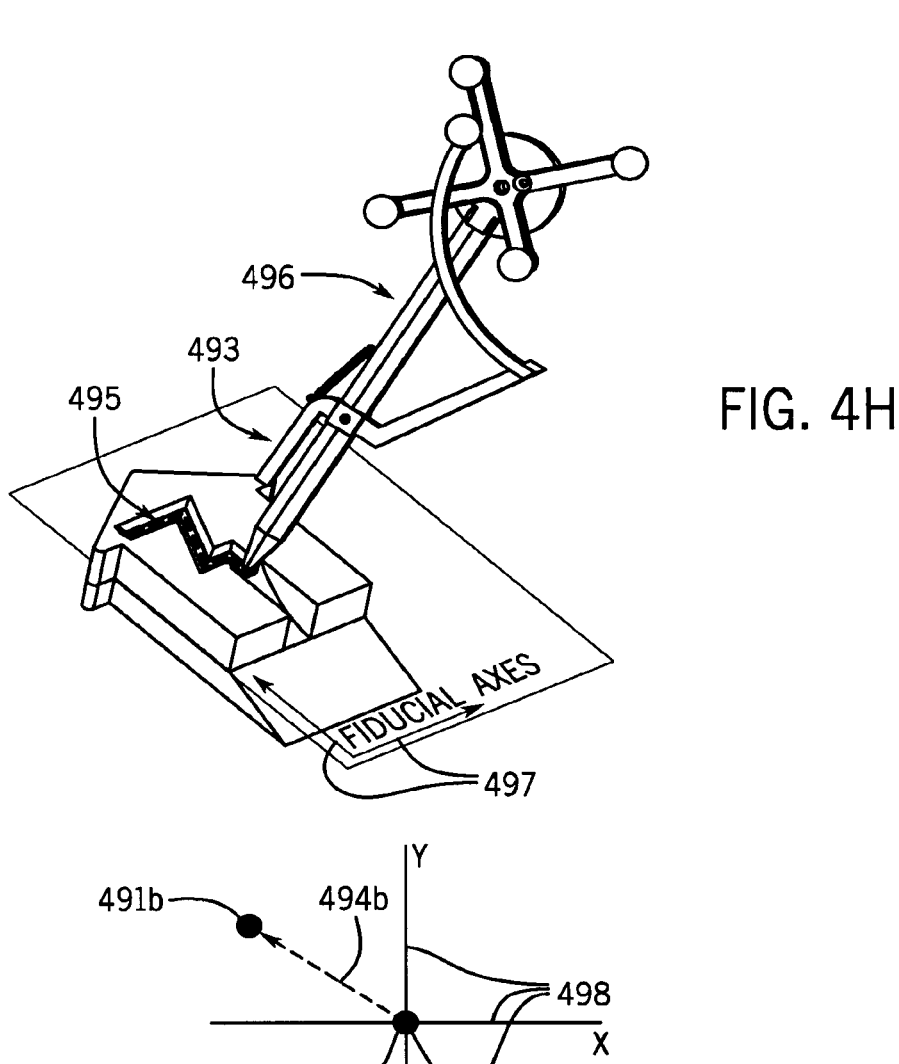
FIG. 4H
FIG. 4I

2000

2005

2010

2001

2010

2025

2024

2005

2044

2010

2001

2025

2024

2044

2044

2001

2010

2010

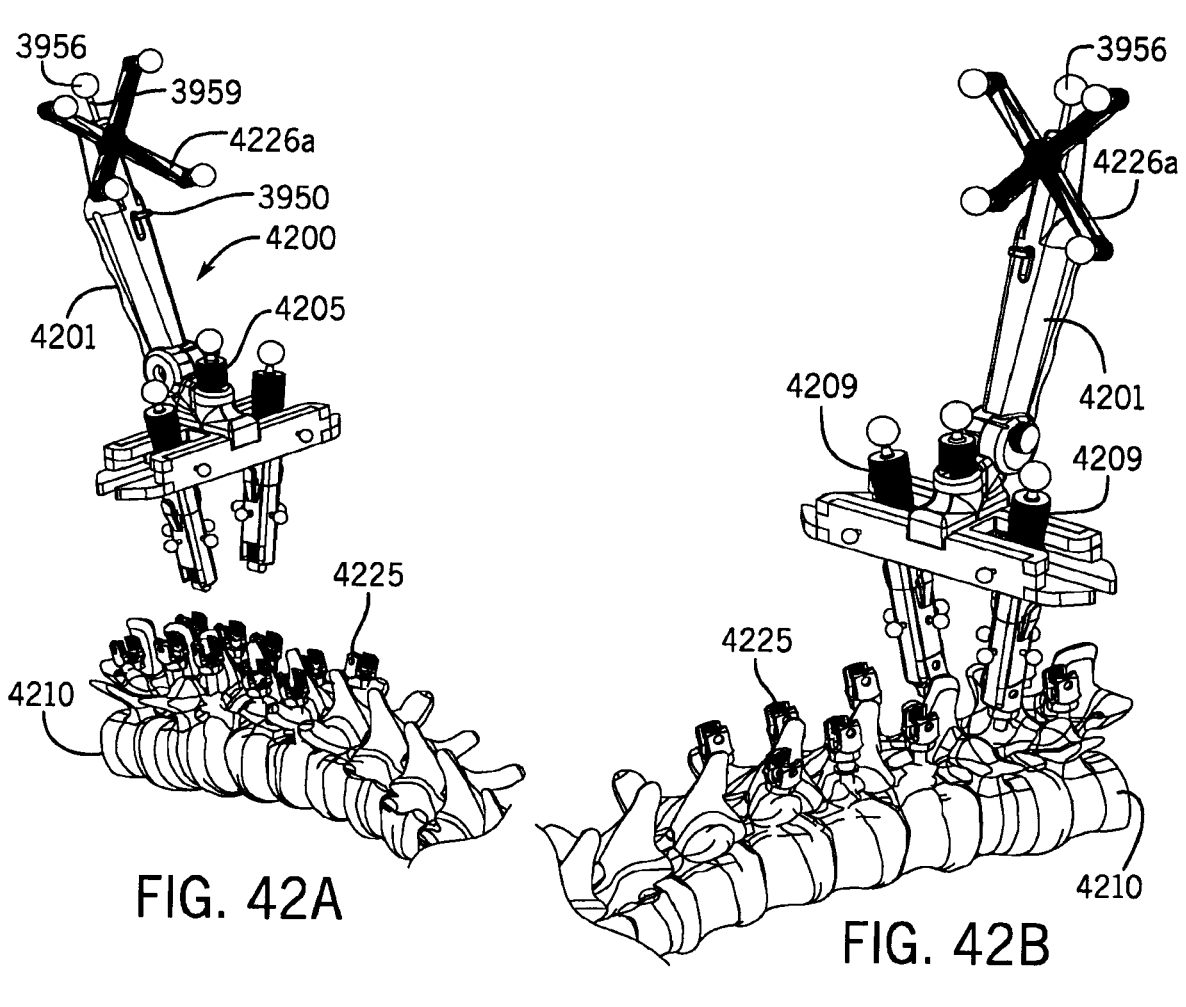
FIG. 42A
FIG. 42B
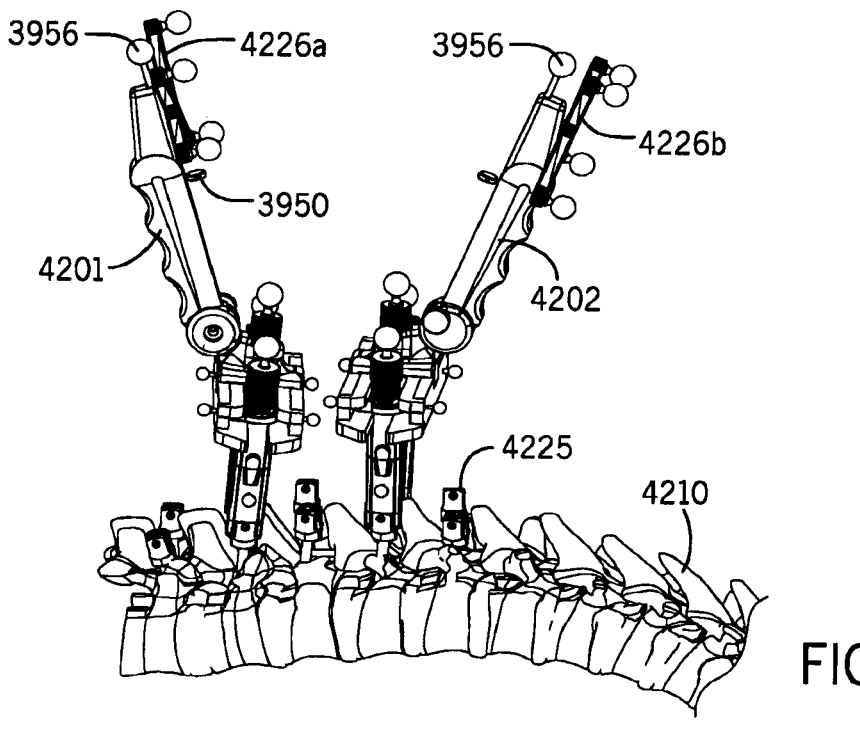
FIG. 42C

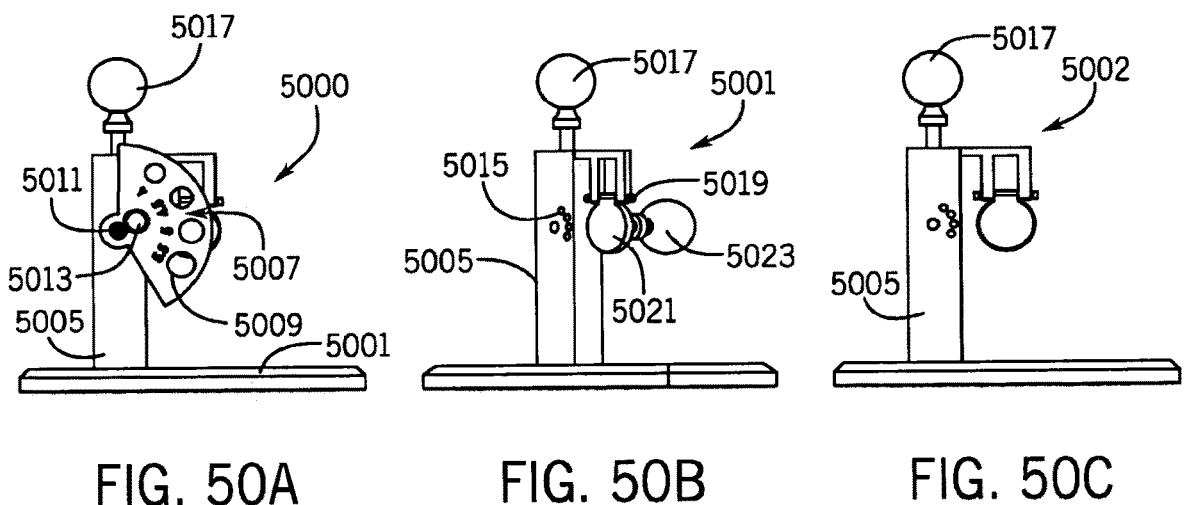
FIG. 50A          FIG. 50B          FIG. 50C
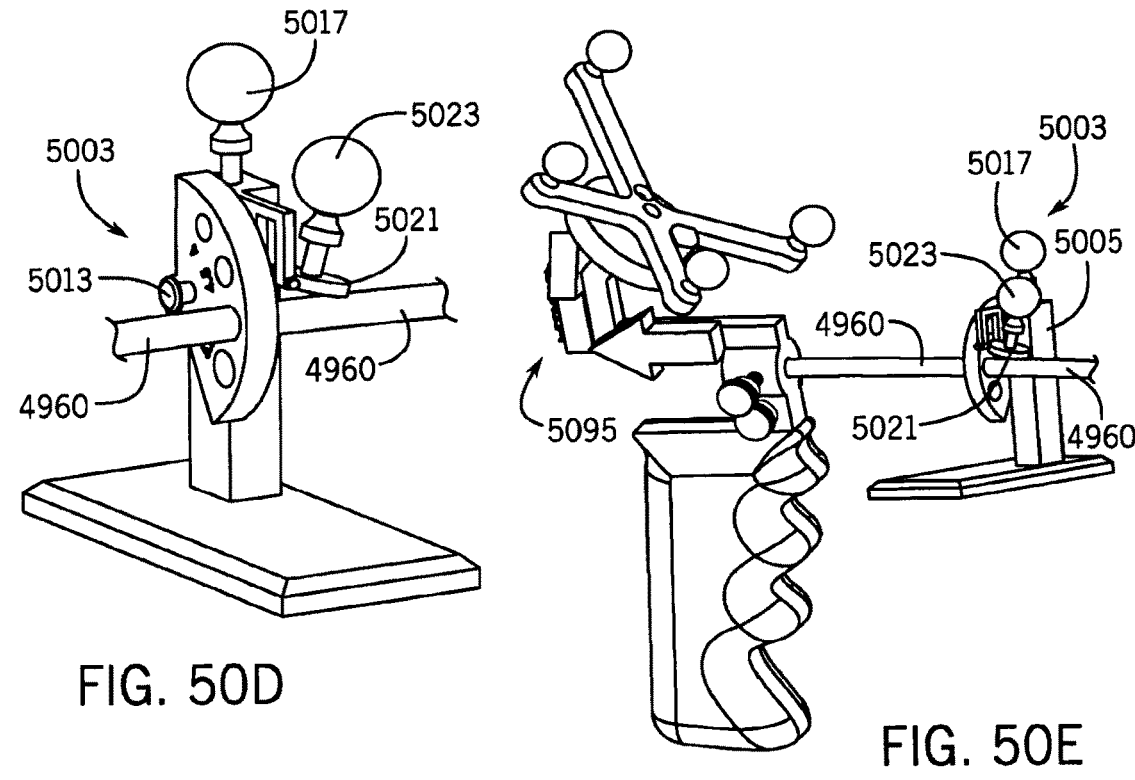
FIG. 50D
FIG. 50E

PERSPECTIVE TRACINGS WITH DEPTH TRANSLATION

○ CERVICAL FIDUCIAL
* CERVICOTHORACIC SKIN TRACING
* * LUMBOSACRAL SKIN TRACING
○ PELVIC FIDUCIAL
* SURGICAL SITE: LAMINA TRACING

FIG. 63

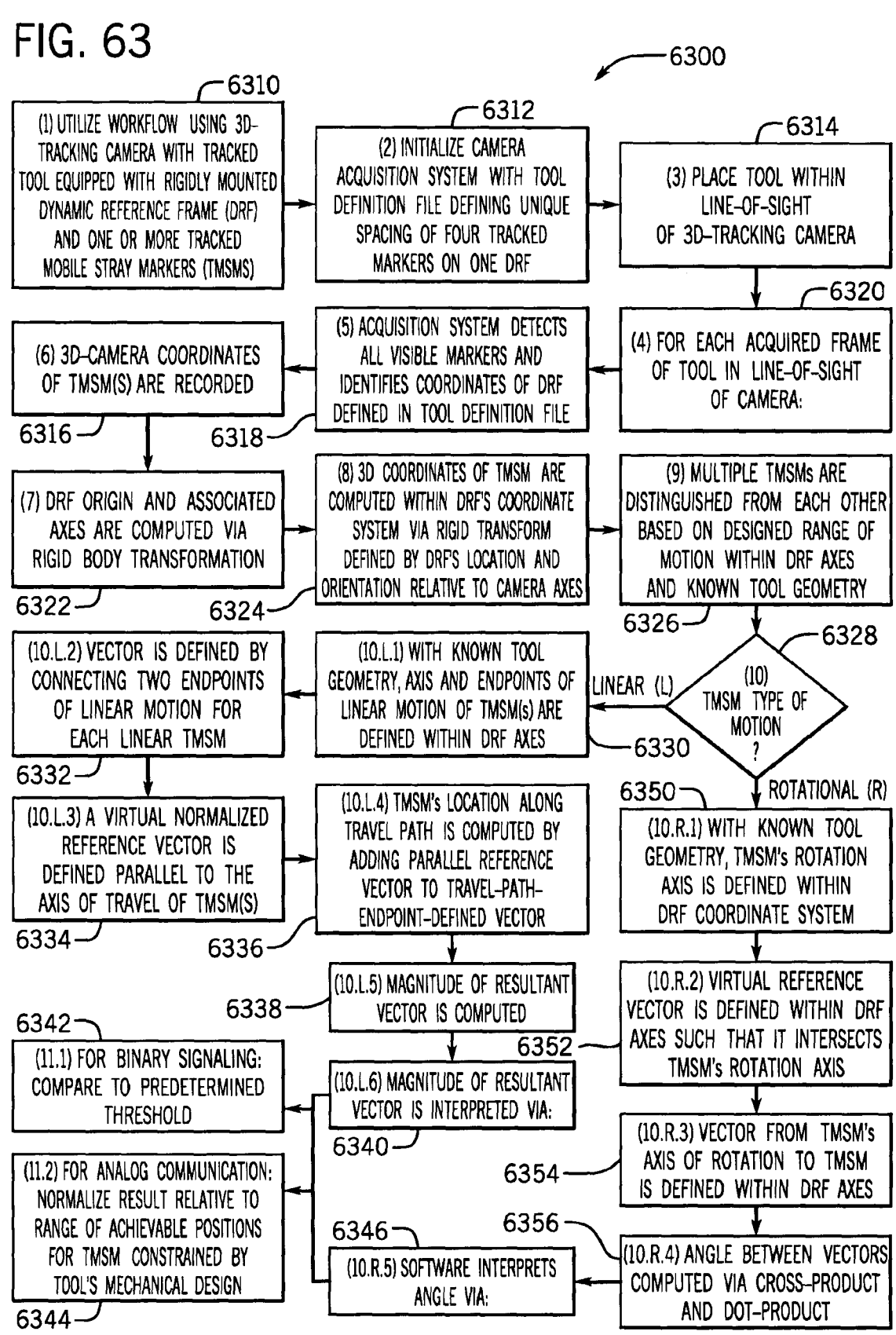

6310
(1) UTILIZE WORKFLOW USING 3D-TRACKING CAMERA WITH TRACKED TOOL EQUIPPED WITH RIGIDLY MOUNTED DYNAMIC REFERENCE FRAME (DRF) AND ONE OR MORE TRACKED MOBILE STRAY MARKERS (TMSMS)

6312
(2) INITIALIZE CAMERA ACQUISITION SYSTEM WITH TOOL DEFINITION FILE DEFINING UNIQUE SPACING OF FOUR TRACKED MARKERS ON ONE DRF 6314
(3) PLACE TOOL WITHIN LINE-OF-SIGHT OF 3D-TRACKING CAMERA 6320
(4) FOR EACH ACQUIRED FRAME OF TOOL IN LINE-OF-SIGHT OF CAMERA:

6318
(5) ACQUISITION SYSTEM DETECTS ALL VISIBLE MARKERS AND IDENTIFIES COORDINATES OF DRF DEFINED IN TOOL DEFINITION FILE 6316
(6) 3D-CAMERA COORDINATES OF TMSM(S) ARE RECORDED 6322
(7) DRF ORIGIN AND ASSOCIATED AXES ARE COMPUTED VIA RIGID BODY TRANSFORMATION 6324
(8) 3D COORDINATES OF TMSM ARE COMPUTED WITHIN DRF'S COORDINATE SYSTEM VIA RIGID TRANSFORM DEFINED BY DRF'S LOCATION AND ORIENTATION RELATIVE TO CAMERA AXES 6326
(9) MULTIPLE TMSMs ARE DISTINGUISHED FROM EACH OTHER BASED ON DESIGNED RANGE OF MOTION WITHIN DRF AXES AND KNOWN TOOL GEOMETRY 6328
(10) TMSM TYPE OF MOTION ?

6330
LINEAR (L)

6350
ROTATIONAL (R)

6330
(10.L.1) WITH KNOWN TOOL GEOMETRY, AXIS AND ENDPOINTS OF LINEAR MOTION OF TMSM(s) ARE DEFINED WITHIN DRF AXES 6332
(10.L.2) VECTOR IS DEFINED BY CONNECTING TWO ENDPOINTS OF LINEAR MOTION FOR EACH LINEAR TMSM 6334
(10.L.3) A VIRTUAL NORMALIZED REFERENCE VECTOR IS DEFINED PARALLEL TO THE AXIS OF TRAVEL OF TMSM(S)

6336
(10.L.4) TMSM's LOCATION ALONG TRAVEL PATH IS COMPUTED BY ADDING PARALLEL REFERENCE VECTOR TO TRAVEL-PATH-ENDPOINT-DEFINED VECTOR 6338
(10.L.5) MAGNITUDE OF RESULTANT VECTOR IS COMPUTED 6340
(10.L.6) MAGNITUDE OF RESULTANT VECTOR IS INTERPRETED VIA:

6342
(11.1) FOR BINARY SIGNALING: COMPARE TO PREDETERMINED THRESHOLD 6344
(11.2) FOR ANALOG COMMUNICATION: NORMALIZE RESULT RELATIVE TO RANGE OF ACHIEVABLE POSITIONS FOR TMSM CONSTRAINED BY TOOL'S MECHANICAL DESIGN 6350
(10.R.1) WITH KNOWN TOOL GEOMETRY, TMSM's ROTATION AXIS IS DEFINED WITHIN DRF COORDINATE SYSTEM 6352
(10.R.2) VIRTUAL REFERENCE VECTOR IS DEFINED WITHIN DRF AXES SUCH THAT IT INTERSECTS TMSM's ROTATION AXIS 6354
(10.R.3) VECTOR FROM TMSM's AXIS OF ROTATION TO TMSM IS DEFINED WITHIN DRF AXES 6356
(10.R.4) ANGLE BETWEEN VECTORS COMPUTED VIA CROSS-PRODUCT AND DOT-PRODUCT 6346
(10.R.5) SOFTWARE INTERPRETS ANGLE VIA:

6300

6405

6425

6430

6410

6415

6456

6450

θ

6444

6410

6415

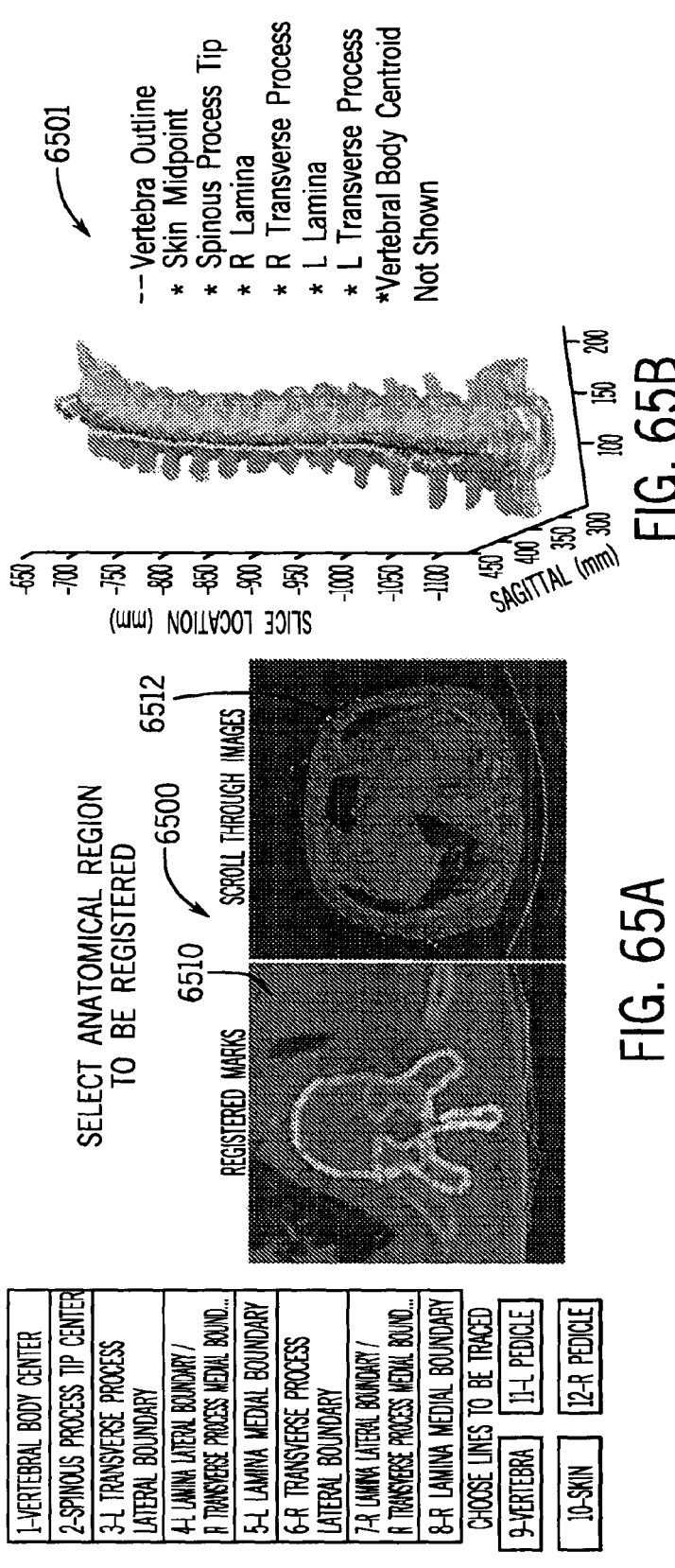

-- Vertebra Outline
* Skin Midpoint
* Spinous Process Tip
* R Lamina
* R Transverse Process
* L Lamina
* L Transverse Process
*Vertebral Body Centroid
Not Shown

SELECT ANATOMICAL REGION
TO BE REGISTERED

6500

6510     6512

REGISTERED MARKS     SCROLL THROUGH IMAGES

1-VERTEBRAL BODY CENTER
2-SPINOUS PROCESS TIP CENTER
3-L TRANSVERSE PROCESS LATERAL BOUNDARY
4-L LAMINA LATERAL BOUNDARY / R TRANSVERSE PROCESS MEDIAL BOUND...
5-L LAMINA MEDIAL BOUNDARY
6-R TRANSVERSE PROCESS LATERAL BOUNDARY
7-R LAMINA LATERAL BOUNDARY / R TRANSVERSE PROCESS MEDIAL BOUND...
8-R LAMINA MEDIAL BOUNDARY

CHOOSE LINES TO BE TRACED

9-VERTEBRA    11-L PEDICLE

10-SKIN    12-R PEDICLE

6601

LEFT LAMINA TRACING

POSTERIOR

6603

6605

ANTERIOR

COMPUTED VERTEBRAL
BODY CENTROID TRACING

RIGHT

SUPERIOR

LEFT

INFERIOR

TRACED COORDINATE OF
LEFT LAMINA

TRACED COORDINATE OF
RIGHT LAMINA 6607    6609

6601

CROSS-SECTIONAL VIEW
OF SPINE WITH
BILATERALLY-TRACED
LAMINA

ORTHOGONAL LINE
GENERATED FROM
MIDPOINT OF TRACED
LAMINAE

6611

6613

6615

COMPUTED COORDINATE
OF VERTEBRAL CENTROID

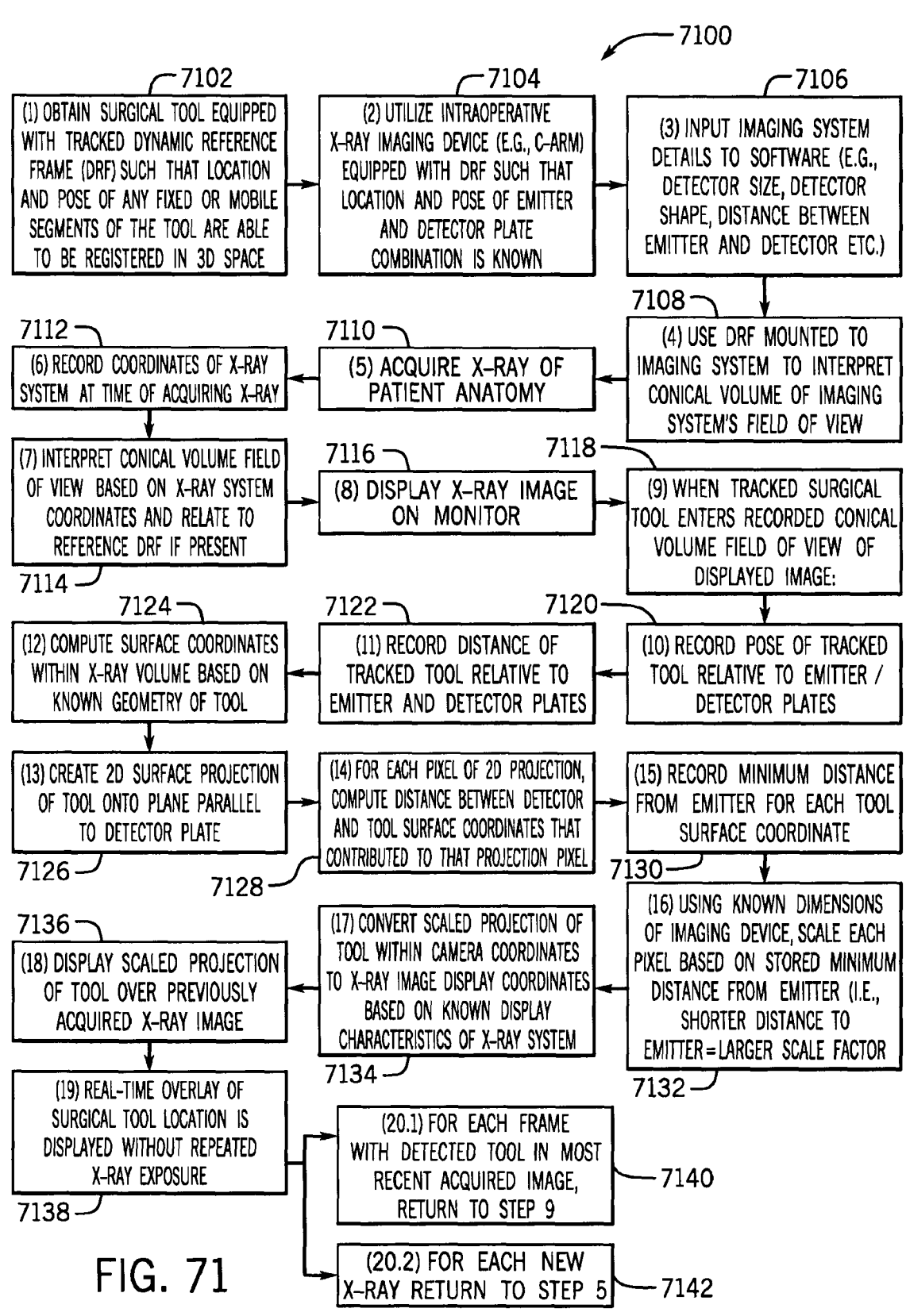

7100

7102
(1) OBTAIN SURGICAL TOOL EQUIPPED WITH TRACKED DYNAMIC REFERENCE FRAME (DRF) SUCH THAT LOCATION AND POSE OF ANY FIXED OR MOBILE SEGMENTS OF THE TOOL ARE ABLE TO BE REGISTERED IN 3D SPACE 7104
(2) UTILIZE INTRAOPERATIVE X-RAY IMAGING DEVICE (E.G., C-ARM) EQUIPPED WITH DRF SUCH THAT LOCATION AND POSE OF EMITTER AND DETECTOR PLATE COMBINATION IS KNOWN 7106
(3) INPUT IMAGING SYSTEM DETAILS TO SOFTWARE (E.G., DETECTOR SIZE, DETECTOR SHAPE, DISTANCE BETWEEN EMITTER AND DETECTOR ETC.)

7108
(4) USE DRF MOUNTED TO IMAGING SYSTEM TO INTERPRET CONICAL VOLUME OF IMAGING SYSTEM'S FIELD OF VIEW 7112
(6) RECORD COORDINATES OF X-RAY SYSTEM AT TIME OF ACQUIRING X-RAY 7110
(5) ACQUIRE X-RAY OF PATIENT ANATOMY 7114
(7) INTERPRET CONICAL VOLUME FIELD OF VIEW BASED ON X-RAY SYSTEM COORDINATES AND RELATE TO REFERENCE DRF IF PRESENT 7116
(8) DISPLAY X-RAY IMAGE ON MONITOR 7118
(9) WHEN TRACKED SURGICAL TOOL ENTERS RECORDED CONICAL VOLUME FIELD OF VIEW OF DISPLAYED IMAGE:

7124
(12) COMPUTE SURFACE COORDINATES WITHIN X-RAY VOLUME BASED ON KNOWN GEOMETRY OF TOOL 7122
(11) RECORD DISTANCE OF TRACKED TOOL RELATIVE TO EMITTER AND DETECTOR PLATES 7120
(10) RECORD POSE OF TRACKED TOOL RELATIVE TO EMITTER / DETECTOR PLATES 7126
(13) CREATE 2D SURFACE PROJECTION OF TOOL ONTO PLANE PARALLEL TO DETECTOR PLATE 7128
(14) FOR EACH PIXEL OF 2D PROJECTION, COMPUTE DISTANCE BETWEEN DETECTOR AND TOOL SURFACE COORDINATES THAT CONTRIBUTED TO THAT PROJECTION PIXEL 7130
(15) RECORD MINIMUM DISTANCE FROM EMITTER FOR EACH TOOL SURFACE COORDINATE 7136
(18) DISPLAY SCALED PROJECTION OF TOOL OVER PREVIOUSLY ACQUIRED X-RAY IMAGE 7134
(17) CONVERT SCALED PROJECTION OF TOOL WITHIN CAMERA COORDINATES TO X-RAY IMAGE DISPLAY COORDINATES BASED ON KNOWN DISPLAY CHARACTERISTICS OF X-RAY SYSTEM 7132
(16) USING KNOWN DIMENSIONS OF IMAGING DEVICE, SCALE EACH PIXEL BASED ON STORED MINIMUM DISTANCE FROM EMITTER (I.E., SHORTER DISTANCE TO EMITTER=LARGER SCALE FACTOR)

7138
(19) REAL-TIME OVERLAY OF SURGICAL TOOL LOCATION IS DISPLAYED WITHOUT REPEATED X-RAY EXPOSURE 7140
(20.1) FOR EACH FRAME WITH DETECTED TOOL IN MOST RECENT ACQUIRED IMAGE, RETURN TO STEP 9

7142
(20.2) FOR EACH NEW X-RAY RETURN TO STEP 5

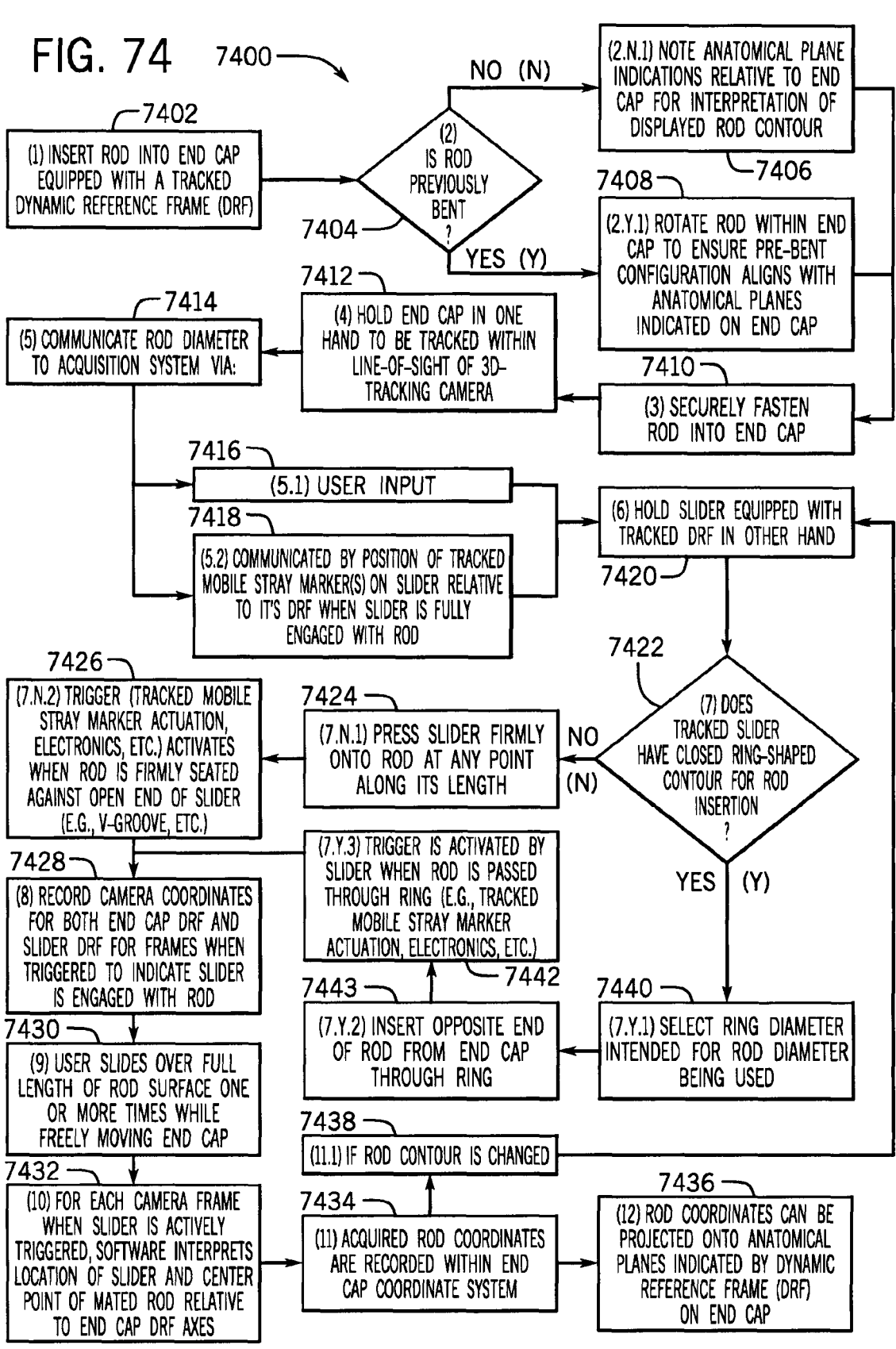

7400

7402
(1) INSERT ROD INTO END CAP EQUIPPED WITH A TRACKED DYNAMIC REFERENCE FRAME (DRF)

7404
(2) IS ROD PREVIOUSLY BENT ?

NO (N)

(2.N.1) NOTE ANATOMICAL PLANE INDICATIONS RELATIVE TO END CAP FOR INTERPRETATION OF DISPLAYED ROD CONTOUR
7406

7408
(2.Y.1) ROTATE ROD WITHIN END CAP TO ENSURE PRE-BENT CONFIGURATION ALIGNS WITH ANATOMICAL PLANES INDICATED ON END CAP

YES (Y)

7410
(3) SECURELY FASTEN ROD INTO END CAP 7412
(4) HOLD END CAP IN ONE HAND TO BE TRACKED WITHIN LINE-OF-SIGHT OF 3D-TRACKING CAMERA 7414
(5) COMMUNICATE ROD DIAMETER TO ACQUISITION SYSTEM VIA:

7416
(5.1) USER INPUT 7418
(5.2) COMMUNICATED BY POSITION OF TRACKED MOBILE STRAY MARKER(S) ON SLIDER RELATIVE TO IT'S DRF WHEN SLIDER IS FULLY ENGAGED WITH ROD (6) HOLD SLIDER EQUIPPED WITH TRACKED DRF IN OTHER HAND
7420

7422
(7) DOES TRACKED SLIDER HAVE CLOSED RING-SHAPED CONTOUR FOR ROD INSERTION ?

7426
(7.N.2) TRIGGER (TRACKED MOBILE STRAY MARKER ACTUATION, ELECTRONICS, ETC.) ACTIVATES WHEN ROD IS FIRMLY SEATED AGAINST OPEN END OF SLIDER (E.G., V-GROOVE, ETC.)

7424
(7.N.1) PRESS SLIDER FIRMLY ONTO ROD AT ANY POINT ALONG ITS LENGTH

NO (N)

YES (Y)

7440
(7.Y.1) SELECT RING DIAMETER INTENDED FOR ROD DIAMETER BEING USED (7.Y.3) TRIGGER IS ACTIVATED BY SLIDER WHEN ROD IS PASSED THROUGH RING (E.G., TRACKED MOBILE STRAY MARKER ACTUATION, ELECTRONICS, ETC.)
7442

7443
(7.Y.2) INSERT OPPOSITE END OF ROD FROM END CAP THROUGH RING 7428
(8) RECORD CAMERA COORDINATES FOR BOTH END CAP DRF AND SLIDER DRF FOR FRAMES WHEN TRIGGERED TO INDICATE SLIDER IS ENGAGED WITH ROD 7430
(9) USER SLIDES OVER FULL LENGTH OF ROD SURFACE ONE OR MORE TIMES WHILE FREELY MOVING END CAP 7432
(10) FOR EACH CAMERA FRAME WHEN SLIDER IS ACTIVELY TRIGGERED, SOFTWARE INTERPRETS LOCATION OF SLIDER AND CENTER POINT OF MATED ROD RELATIVE TO END CAP DRF AXES 7434
(11) ACQUIRED ROD COORDINATES ARE RECORDED WITHIN END CAP COORDINATE SYSTEM 7438
(11.1) IF ROD CONTOUR IS CHANGED 7436
(12) ROD COORDINATES CAN BE PROJECTED ONTO ANATOMICAL PLANES INDICATED BY DYNAMIC REFERENCE FRAME (DRF) ON END CAP

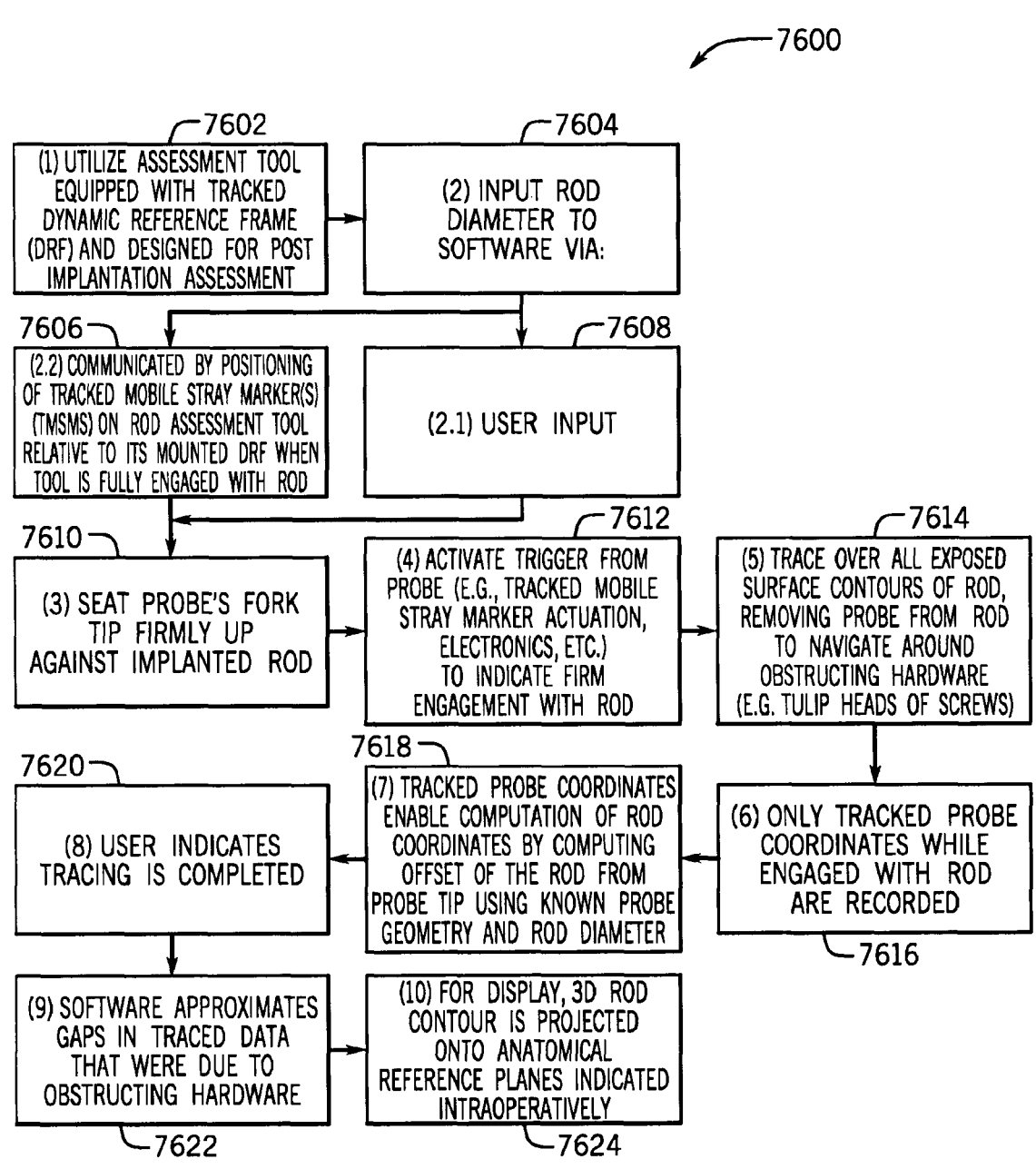

—7600

7602
(1) UTILIZE ASSESSMENT TOOL EQUIPPED WITH TRACKED DYNAMIC REFERENCE FRAME (DRF) AND DESIGNED FOR POST IMPLANTATION ASSESSMENT 7604
(2) INPUT ROD DIAMETER TO SOFTWARE VIA:

7606
(2.2) COMMUNICATED BY POSITIONING OF TRACKED MOBILE STRAY MARKER(S) (TMSMS) ON ROD ASSESSMENT TOOL RELATIVE TO ITS MOUNTED DRF WHEN TOOL IS FULLY ENGAGED WITH ROD 7608
(2.1) USER INPUT 7610
(3) SEAT PROBE'S FORK TIP FIRMLY UP AGAINST IMPLANTED ROD 7612
(4) ACTIVATE TRIGGER FROM PROBE (E.G., TRACKED MOBILE STRAY MARKER ACTUATION, ELECTRONICS, ETC.) TO INDICATE FIRM ENGAGEMENT WITH ROD 7614
(5) TRACE OVER ALL EXPOSED SURFACE CONTOURS OF ROD, REMOVING PROBE FROM ROD TO NAVIGATE AROUND OBSTRUCTING HARDWARE (E.G. TULIP HEADS OF SCREWS)

7620
(8) USER INDICATES TRACING IS COMPLETED 7618
(7) TRACKED PROBE COORDINATES ENABLE COMPUTATION OF ROD COORDINATES BY COMPUTING OFFSET OF THE ROD FROM PROBE TIP USING KNOWN PROBE GEOMETRY AND ROD DIAMETER (6) ONLY TRACKED PROBE COORDINATES WHILE ENGAGED WITH ROD ARE RECORDED
7616

(9) SOFTWARE APPROXIMATES GAPS IN TRACED DATA THAT WERE DUE TO OBSTRUCTING HARDWARE
7622

(10) FOR DISPLAY, 3D ROD CONTOUR IS PROJECTED ONTO ANATOMICAL REFERENCE PLANES INDICATED INTRAOPERATIVELY
7624

FIG. 76

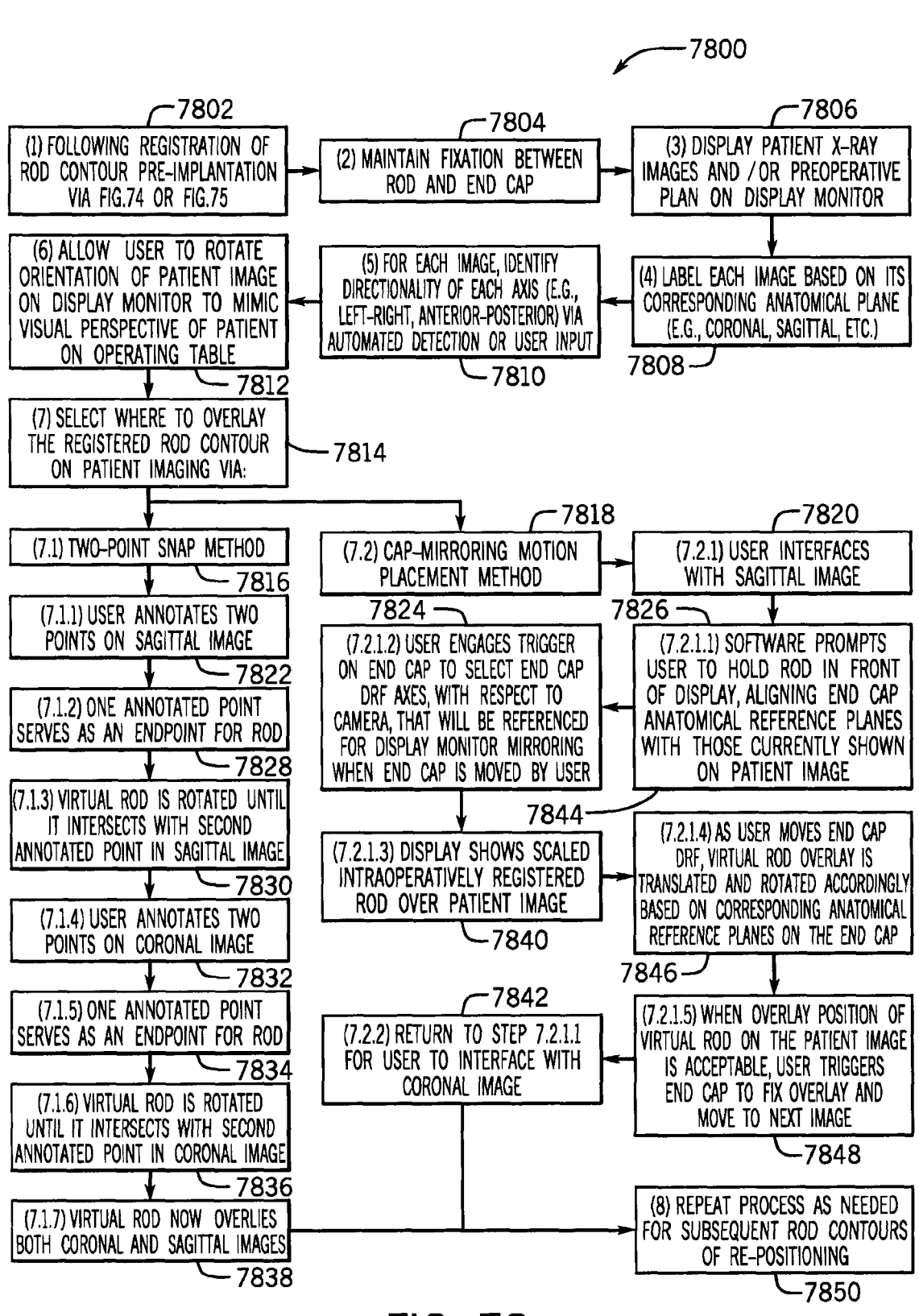

7800

7802
(1) FOLLOWING REGISTRATION OF ROD CONTOUR PRE-IMPLANTATION VIA FIG.74 OR FIG.75

7804
(2) MAINTAIN FIXATION BETWEEN ROD AND END CAP 7806
(3) DISPLAY PATIENT X-RAY IMAGES AND /OR PREOPERATIVE PLAN ON DISPLAY MONITOR 7808
(4) LABEL EACH IMAGE BASED ON ITS CORRESPONDING ANATOMICAL PLANE (E.G., CORONAL, SAGITTAL, ETC.)

7810
(5) FOR EACH IMAGE, IDENTIFY DIRECTIONALITY OF EACH AXIS (E.G., LEFT-RIGHT, ANTERIOR-POSTERIOR) VIA AUTOMATED DETECTION OR USER INPUT 7812
(6) ALLOW USER TO ROTATE ORIENTATION OF PATIENT IMAGE ON DISPLAY MONITOR TO MIMIC VISUAL PERSPECTIVE OF PATIENT ON OPERATING TABLE 7814
(7) SELECT WHERE TO OVERLAY THE REGISTERED ROD CONTOUR ON PATIENT IMAGING VIA:

7816
(7.1) TWO-POINT SNAP METHOD 7822
(7.1.1) USER ANNOTATES TWO POINTS ON SAGITTAL IMAGE 7828
(7.1.2) ONE ANNOTATED POINT SERVES AS AN ENDPOINT FOR ROD 7830
(7.1.3) VIRTUAL ROD IS ROTATED UNTIL IT INTERSECTS WITH SECOND ANNOTATED POINT IN SAGITTAL IMAGE 7832
(7.1.4) USER ANNOTATES TWO POINTS ON CORONAL IMAGE 7834
(7.1.5) ONE ANNOTATED POINT SERVES AS AN ENDPOINT FOR ROD 7836
(7.1.6) VIRTUAL ROD IS ROTATED UNTIL IT INTERSECTS WITH SECOND ANNOTATED POINT IN CORONAL IMAGE 7838
(7.1.7) VIRTUAL ROD NOW OVERLIES BOTH CORONAL AND SAGITTAL IMAGES 7818
(7.2) CAP-MIRRORING MOTION PLACEMENT METHOD 7824
(7.2.1.2) USER ENGAGES TRIGGER ON END CAP TO SELECT END CAP DRF AXES, WITH RESPECT TO CAMERA, THAT WILL BE REFERENCED FOR DISPLAY MONITOR MIRRORING WHEN END CAP IS MOVED BY USER 7840
(7.2.1.3) DISPLAY SHOWS SCALED INTRAOPERATIVELY REGISTERED ROD OVER PATIENT IMAGE 7842
(7.2.2) RETURN TO STEP 7.2.1.1 FOR USER TO INTERFACE WITH CORONAL IMAGE 7820
(7.2.1) USER INTERFACES WITH SAGITTAL IMAGE 7826
(7.2.1.1) SOFTWARE PROMPTS USER TO HOLD ROD IN FRONT OF DISPLAY, ALIGNING END CAP ANATOMICAL REFERENCE PLANES WITH THOSE CURRENTLY SHOWN ON PATIENT IMAGE 7844
7846
(7.2.1.4) AS USER MOVES END CAP DRF, VIRTUAL ROD OVERLAY IS TRANSLATED AND ROTATED ACCORDINGLY BASED ON CORRESPONDING ANATOMICAL REFERENCE PLANES ON THE END CAP 7848
(7.2.1.5) WHEN OVERLAY POSITION OF VIRTUAL ROD ON THE PATIENT IMAGE IS ACCEPTABLE, USER TRIGGERS END CAP TO FIX OVERLAY AND MOVE TO NEXT IMAGE 7850
(8) REPEAT PROCESS AS NEEDED FOR SUBSEQUENT ROD CONTOURS OF RE-POSITIONING

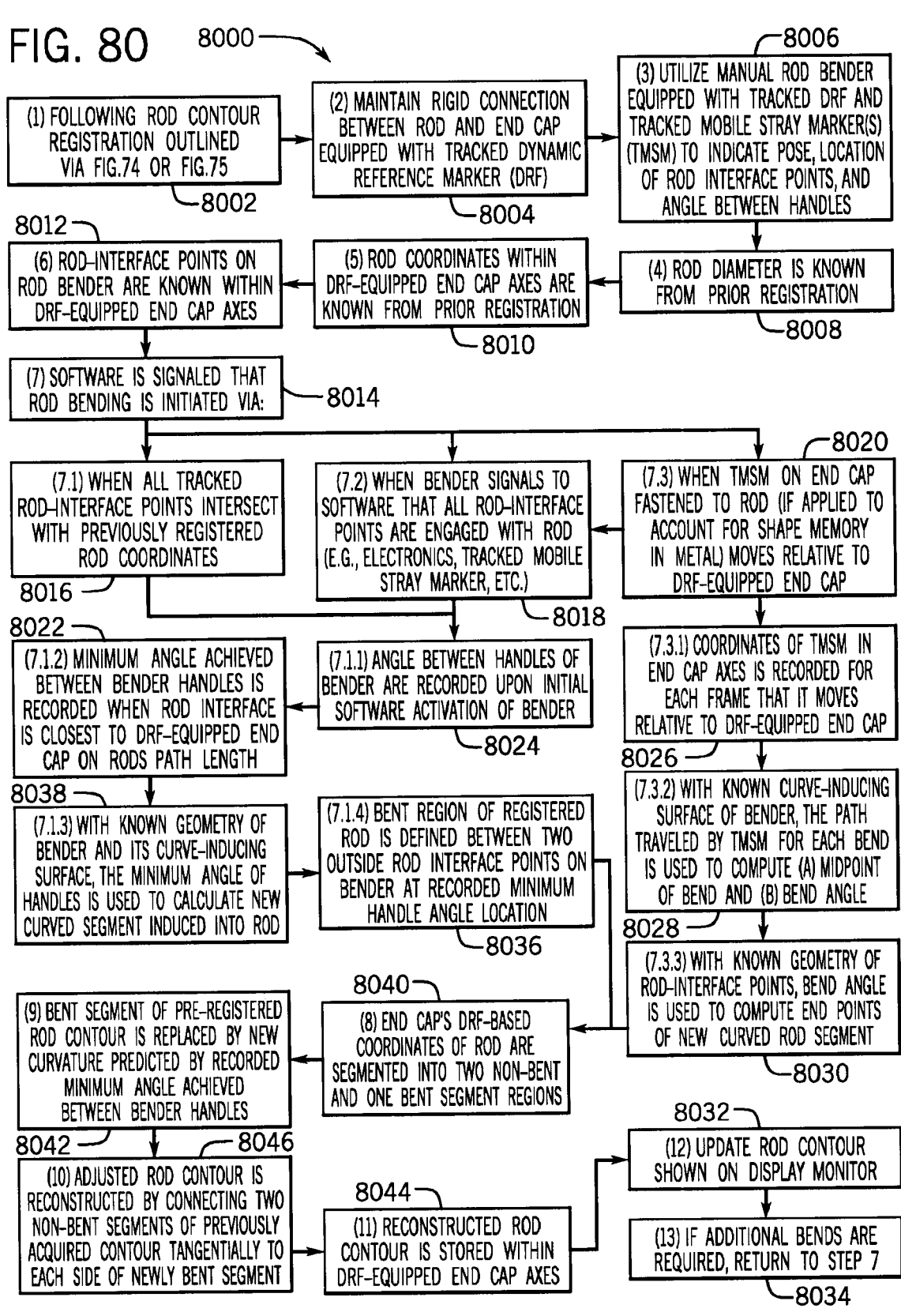

(1) FOLLOWING ROD CONTOUR REGISTRATION OUTLINED VIA FIG.74 OR FIG.75 — 8002

(2) MAINTAIN RIGID CONNECTION BETWEEN ROD AND END CAP EQUIPPED WITH TRACKED DYNAMIC REFERENCE MARKER (DRF) — 8004

(3) UTILIZE MANUAL ROD BENDER EQUIPPED WITH TRACKED DRF AND TRACKED MOBILE STRAY MARKER(S) (TMSM) TO INDICATE POSE, LOCATION OF ROD INTERFACE POINTS, AND ANGLE BETWEEN HANDLES — 8006

8012 — (6) ROD-INTERFACE POINTS ON ROD BENDER ARE KNOWN WITHIN DRF-EQUIPPED END CAP AXES (5) ROD COORDINATES WITHIN DRF-EQUIPPED END CAP AXES ARE KNOWN FROM PRIOR REGISTRATION — 8010

(4) ROD DIAMETER IS KNOWN FROM PRIOR REGISTRATION — 8008

(7) SOFTWARE IS SIGNALED THAT ROD BENDING IS INITIATED VIA: — 8014

(7.1) WHEN ALL TRACKED ROD-INTERFACE POINTS INTERSECT WITH PREVIOUSLY REGISTERED ROD COORDINATES
8016

(7.2) WHEN BENDER SIGNALS TO SOFTWARE THAT ALL ROD-INTERFACE POINTS ARE ENGAGED WITH ROD (E.G., ELECTRONICS, TRACKED MOBILE STRAY MARKER, ETC.) — 8018

(7.3) WHEN TMSM ON END CAP FASTENED TO ROD (IF APPLIED TO ACCOUNT FOR SHAPE MEMORY IN METAL) MOVES RELATIVE TO DRF-EQUIPPED END CAP — 8020

8022 — (7.1.2) MINIMUM ANGLE ACHIEVED BETWEEN BENDER HANDLES IS RECORDED WHEN ROD INTERFACE IS CLOSEST TO DRF-EQUIPPED END CAP ON RODS PATH LENGTH (7.1.1) ANGLE BETWEEN HANDLES OF BENDER ARE RECORDED UPON INITIAL SOFTWARE ACTIVATION OF BENDER — 8024

(7.3.1) COORDINATES OF TMSM IN END CAP AXES IS RECORDED FOR EACH FRAME THAT IT MOVES RELATIVE TO DRF-EQUIPPED END CAP
8026

8038 — (7.1.3) WITH KNOWN GEOMETRY OF BENDER AND ITS CURVE-INDUCING SURFACE, THE MINIMUM ANGLE OF HANDLES IS USED TO CALCULATE NEW CURVED SEGMENT INDUCED INTO ROD (7.1.4) BENT REGION OF REGISTERED ROD IS DEFINED BETWEEN TWO OUTSIDE ROD INTERFACE POINTS ON BENDER AT RECORDED MINIMUM HANDLE ANGLE LOCATION — 8036

(7.3.2) WITH KNOWN CURVE-INDUCING SURFACE OF BENDER, THE PATH TRAVELED BY TMSM FOR EACH BEND IS USED TO COMPUTE (A) MIDPOINT OF BEND AND (B) BEND ANGLE
8028

(7.3.3) WITH KNOWN GEOMETRY OF ROD-INTERFACE POINTS, BEND ANGLE IS USED TO COMPUTE END POINTS OF NEW CURVED ROD SEGMENT — 8030

(9) BENT SEGMENT OF PRE-REGISTERED ROD CONTOUR IS REPLACED BY NEW CURVATURE PREDICTED BY RECORDED MINIMUM ANGLE ACHIEVED BETWEEN BENDER HANDLES
8042

8040 — (8) END CAP'S DRF-BASED COORDINATES OF ROD ARE SEGMENTED INTO TWO NON-BENT AND ONE BENT SEGMENT REGIONS

8046 — (10) ADJUSTED ROD CONTOUR IS RECONSTRUCTED BY CONNECTING TWO NON-BENT SEGMENTS OF PREVIOUSLY ACQUIRED CONTOUR TANGENTIALLY TO EACH SIDE OF NEWLY BENT SEGMENT

8044 — (11) RECONSTRUCTED ROD CONTOUR IS STORED WITHIN DRF-EQUIPPED END CAP AXES

8032 — (12) UPDATE ROD CONTOUR SHOWN ON DISPLAY MONITOR

(13) IF ADDITIONAL BENDS ARE REQUIRED, RETURN TO STEP 7 — 8034

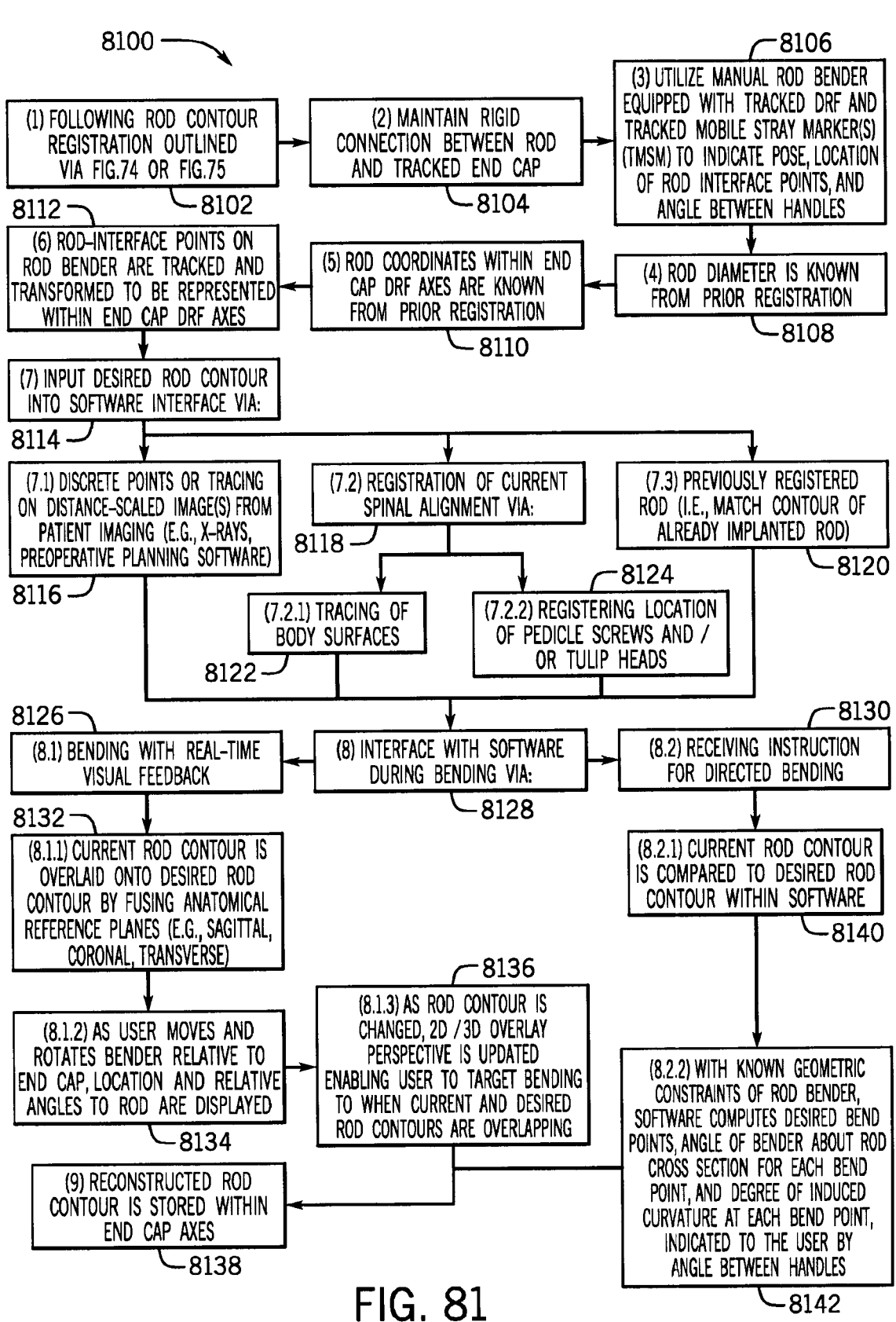

8100

(1) FOLLOWING ROD CONTOUR REGISTRATION OUTLINED VIA FIG.74 OR FIG.75
8102

(2) MAINTAIN RIGID CONNECTION BETWEEN ROD AND TRACKED END CAP
8104

(3) UTILIZE MANUAL ROD BENDER EQUIPPED WITH TRACKED DRF AND TRACKED MOBILE STRAY MARKER(S) (TMSM) TO INDICATE POSE, LOCATION OF ROD INTERFACE POINTS, AND ANGLE BETWEEN HANDLES
8106

8112

(6) ROD-INTERFACE POINTS ON ROD BENDER ARE TRACKED AND TRANSFORMED TO BE REPRESENTED WITHIN END CAP DRF AXES (5) ROD COORDINATES WITHIN END CAP DRF AXES ARE KNOWN FROM PRIOR REGISTRATION
8110

(4) ROD DIAMETER IS KNOWN FROM PRIOR REGISTRATION
8108

(7) INPUT DESIRED ROD CONTOUR INTO SOFTWARE INTERFACE VIA:
8114

(7.1) DISCRETE POINTS OR TRACING ON DISTANCE-SCALED IMAGE(S) FROM PATIENT IMAGING (E.G., X-RAYS, PREOPERATIVE PLANNING SOFTWARE)
8116

(7.2) REGISTRATION OF CURRENT SPINAL ALIGNMENT VIA:
8118

(7.3) PREVIOUSLY REGISTERED ROD (I.E., MATCH CONTOUR OF ALREADY IMPLANTED ROD)
8120

(7.2.1) TRACING OF BODY SURFACES
8122

(7.2.2) REGISTERING LOCATION OF PEDICLE SCREWS AND / OR TULIP HEADS
8124

8126

(8.1) BENDING WITH REAL-TIME VISUAL FEEDBACK (8) INTERFACE WITH SOFTWARE DURING BENDING VIA:
8128

(8.2) RECEIVING INSTRUCTION FOR DIRECTED BENDING
8130

8132

(8.1.1) CURRENT ROD CONTOUR IS OVERLAID ONTO DESIRED ROD CONTOUR BY FUSING ANATOMICAL REFERENCE PLANES (E.G., SAGITTAL, CORONAL, TRANSVERSE)

(8.2.1) CURRENT ROD CONTOUR IS COMPARED TO DESIRED ROD CONTOUR WITHIN SOFTWARE
8140

(8.1.3) AS ROD CONTOUR IS CHANGED, 2D /3D OVERLAY PERSPECTIVE IS UPDATED ENABLING USER TO TARGET BENDING TO WHEN CURRENT AND DESIRED ROD CONTOURS ARE OVERLAPPING
8136

(8.1.2) AS USER MOVES AND ROTATES BENDER RELATIVE TO END CAP, LOCATION AND RELATIVE ANGLES TO ROD ARE DISPLAYED
8134

(9) RECONSTRUCTED ROD CONTOUR IS STORED WITHIN END CAP AXES
8138

(8.2.2) WITH KNOWN GEOMETRIC CONSTRAINTS OF ROD BENDER, SOFTWARE COMPUTES DESIRED BEND POINTS, ANGLE OF BENDER ABOUT ROD CROSS SECTION FOR EACH BEND POINT, AND DEGREE OF INDUCED CURVATURE AT EACH BEND POINT, INDICATED TO THE USER BY ANGLE BETWEEN HANDLES
8142

FIG. 81

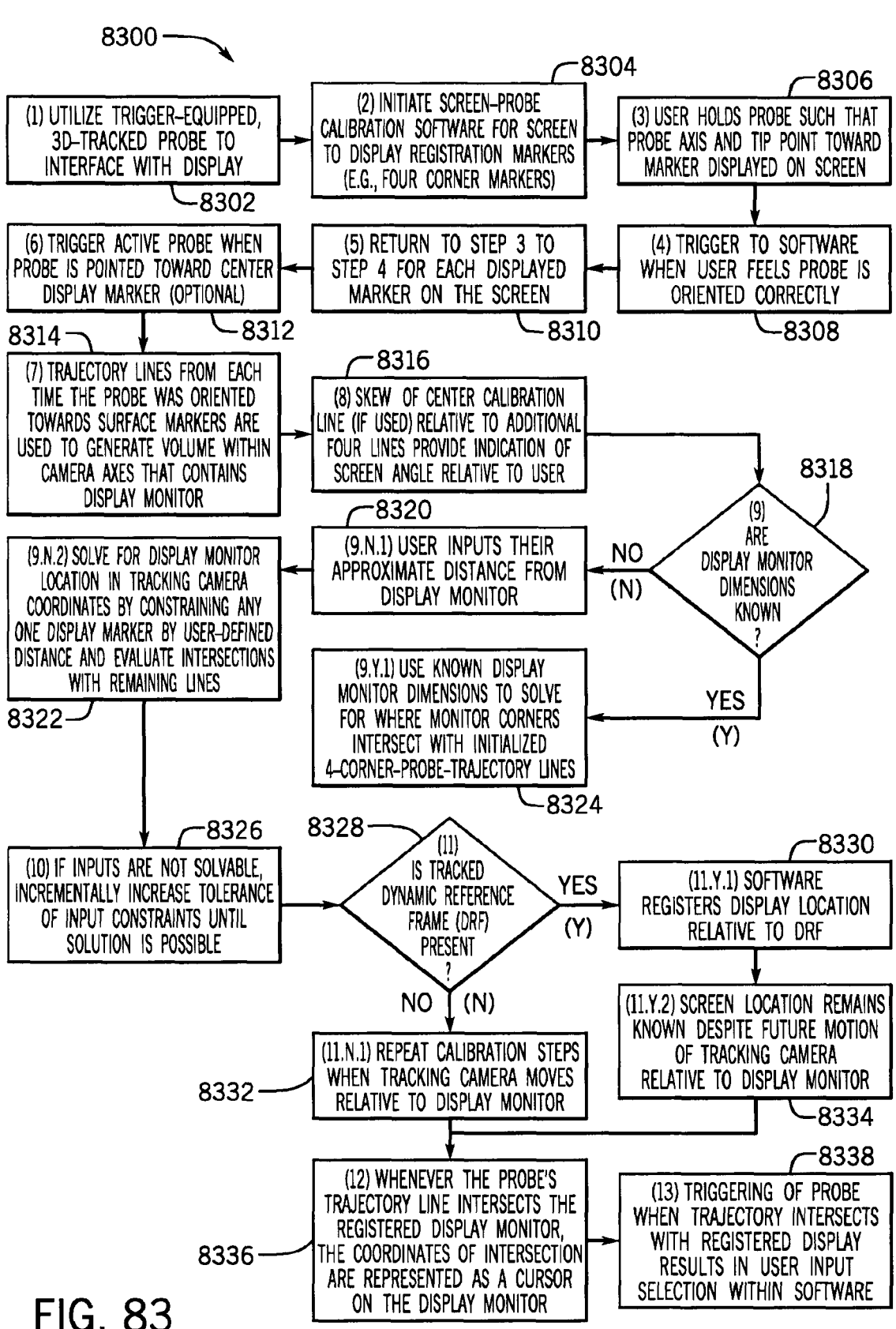

8300

(1) UTILIZE TRIGGER-EQUIPPED, 3D-TRACKED PROBE TO INTERFACE WITH DISPLAY
8302

(2) INITIATE SCREEN-PROBE CALIBRATION SOFTWARE FOR SCREEN TO DISPLAY REGISTRATION MARKERS (E.G., FOUR CORNER MARKERS)
8304

(3) USER HOLDS PROBE SUCH THAT PROBE AXIS AND TIP POINT TOWARD MARKER DISPLAYED ON SCREEN
8306

(6) TRIGGER ACTIVE PROBE WHEN PROBE IS POINTED TOWARD CENTER DISPLAY MARKER (OPTIONAL)
8312

(5) RETURN TO STEP 3 TO STEP 4 FOR EACH DISPLAYED MARKER ON THE SCREEN
8310

(4) TRIGGER TO SOFTWARE WHEN USER FEELS PROBE IS ORIENTED CORRECTLY
8308

8314
(7) TRAJECTORY LINES FROM EACH TIME THE PROBE WAS ORIENTED TOWARDS SURFACE MARKERS ARE USED TO GENERATE VOLUME WITHIN CAMERA AXES THAT CONTAINS DISPLAY MONITOR 8316
(8) SKEW OF CENTER CALIBRATION LINE (IF USED) RELATIVE TO ADDITIONAL FOUR LINES PROVIDE INDICATION OF SCREEN ANGLE RELATIVE TO USER 8318
(9) ARE DISPLAY MONITOR DIMENSIONS KNOWN ?

(9.N.2) SOLVE FOR DISPLAY MONITOR LOCATION IN TRACKING CAMERA COORDINATES BY CONSTRAINING ANY ONE DISPLAY MARKER BY USER-DEFINED DISTANCE AND EVALUATE INTERSECTIONS WITH REMAINING LINES
8322

8320
(9.N.1) USER INPUTS THEIR APPROXIMATE DISTANCE FROM DISPLAY MONITOR

NO (N)

(9.Y.1) USE KNOWN DISPLAY MONITOR DIMENSIONS TO SOLVE FOR WHERE MONITOR CORNERS INTERSECT WITH INITIALIZED 4-CORNER-PROBE-TRAJECTORY LINES
8324

YES (Y)

8326
(10) IF INPUTS ARE NOT SOLVABLE, INCREMENTALLY INCREASE TOLERANCE OF INPUT CONSTRAINTS UNTIL SOLUTION IS POSSIBLE 8328
(11) IS TRACKED DYNAMIC REFERENCE FRAME (DRF) PRESENT ?

YES (Y)

8330
(11.Y.1) SOFTWARE REGISTERS DISPLAY LOCATION RELATIVE TO DRF

NO (N)

(11.N.1) REPEAT CALIBRATION STEPS WHEN TRACKING CAMERA MOVES RELATIVE TO DISPLAY MONITOR
8332

(11.Y.2) SCREEN LOCATION REMAINS KNOWN DESPITE FUTURE MOTION OF TRACKING CAMERA RELATIVE TO DISPLAY MONITOR
8334

(12) WHENEVER THE PROBE'S TRAJECTORY LINE INTERSECTS THE REGISTERED DISPLAY MONITOR, THE COORDINATES OF INTERSECTION ARE REPRESENTED AS A CURSOR ON THE DISPLAY MONITOR
8336

8338
(13) TRIGGERING OF PROBE WHEN TRAJECTORY INTERSECTS WITH REGISTERED DISPLAY RESULTS IN USER INPUT SELECTION WITHIN SOFTWARE

FIG. 83

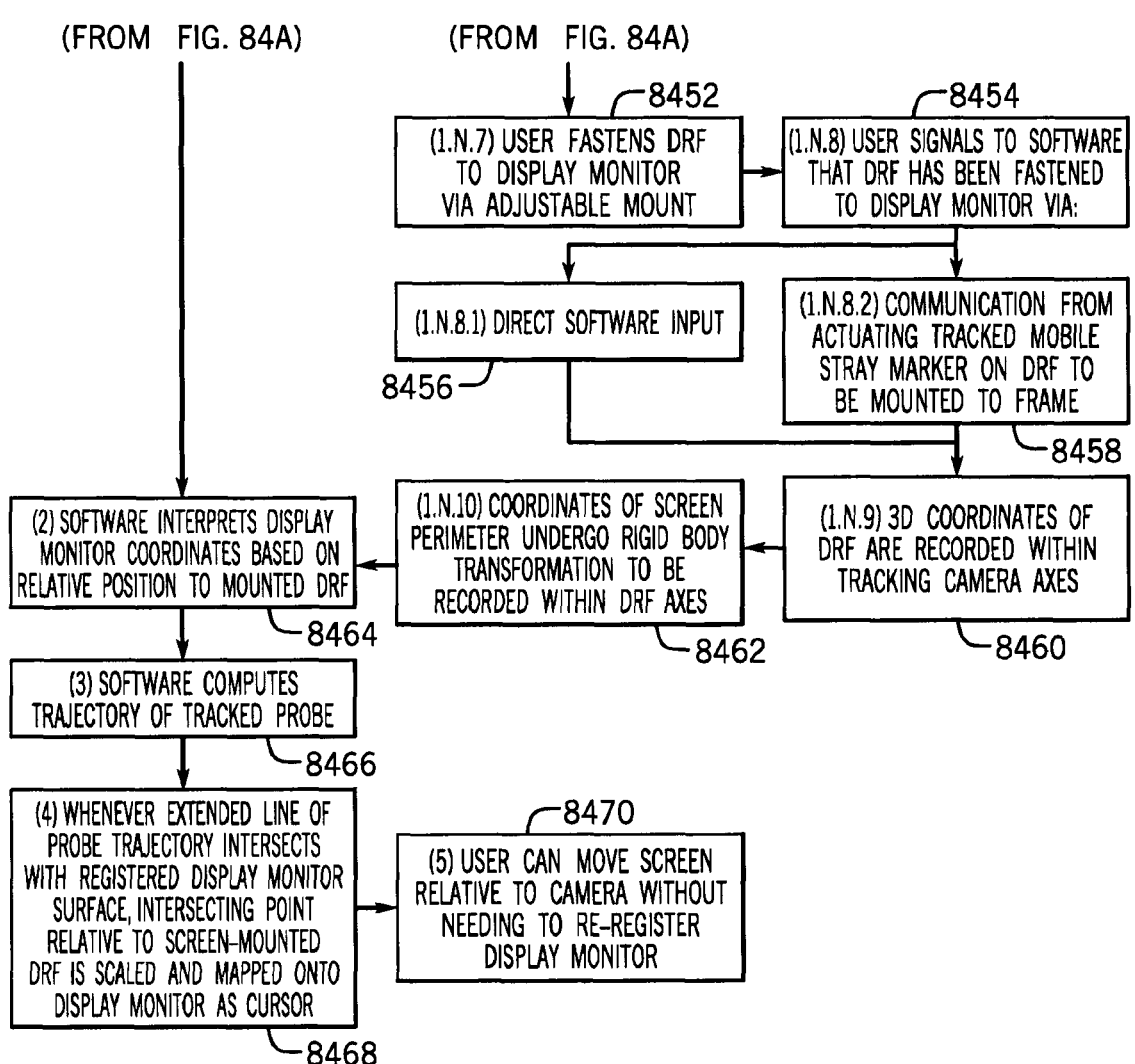

(FROM FIG. 84A)          (FROM FIG. 84A)

8452

(1.N.7) USER FASTENS DRF TO DISPLAY MONITOR VIA ADJUSTABLE MOUNT

8454

(1.N.8) USER SIGNALS TO SOFTWARE THAT DRF HAS BEEN FASTENED TO DISPLAY MONITOR VIA:

(1.N.8.1) DIRECT SOFTWARE INPUT

8456

(1.N.8.2) COMMUNICATION FROM ACTUATING TRACKED MOBILE STRAY MARKER ON DRF TO BE MOUNTED TO FRAME

8458

(2) SOFTWARE INTERPRETS DISPLAY MONITOR COORDINATES BASED ON RELATIVE POSITION TO MOUNTED DRF

8464

(1.N.10) COORDINATES OF SCREEN PERIMETER UNDERGO RIGID BODY TRANSFORMATION TO BE RECORDED WITHIN DRF AXES

8462

(1.N.9) 3D COORDINATES OF DRF ARE RECORDED WITHIN TRACKING CAMERA AXES

8460

(3) SOFTWARE COMPUTES TRAJECTORY OF TRACKED PROBE

8466

(4) WHENEVER EXTENDED LINE OF PROBE TRAJECTORY INTERSECTS WITH REGISTERED DISPLAY MONITOR SURFACE, INTERSECTING POINT RELATIVE TO SCREEN-MOUNTED DRF IS SCALED AND MAPPED ONTO DISPLAY MONITOR AS CURSOR

8468

8470

(5) USER CAN MOVE SCREEN RELATIVE TO CAMERA WITHOUT NEEDING TO RE-REGISTER DISPLAY MONITOR

FIG. 84B

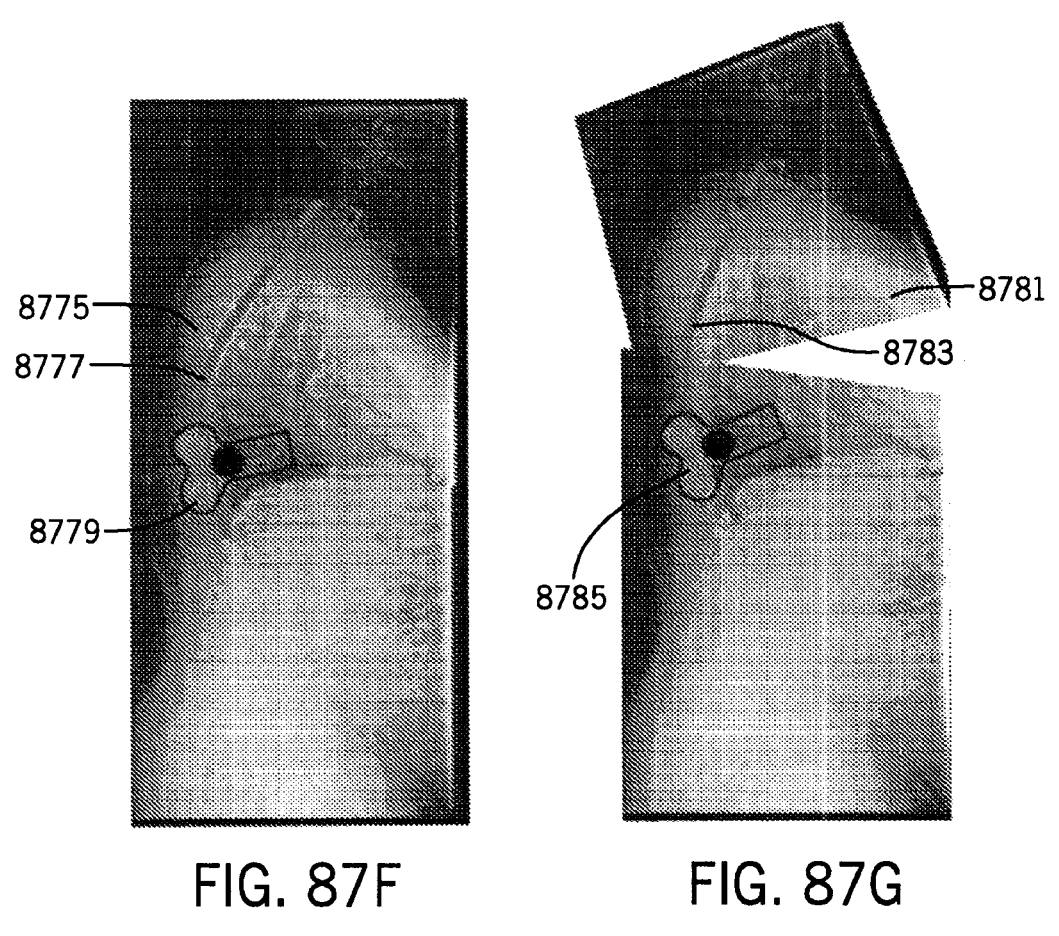
FIG. 87F           FIG. 87G
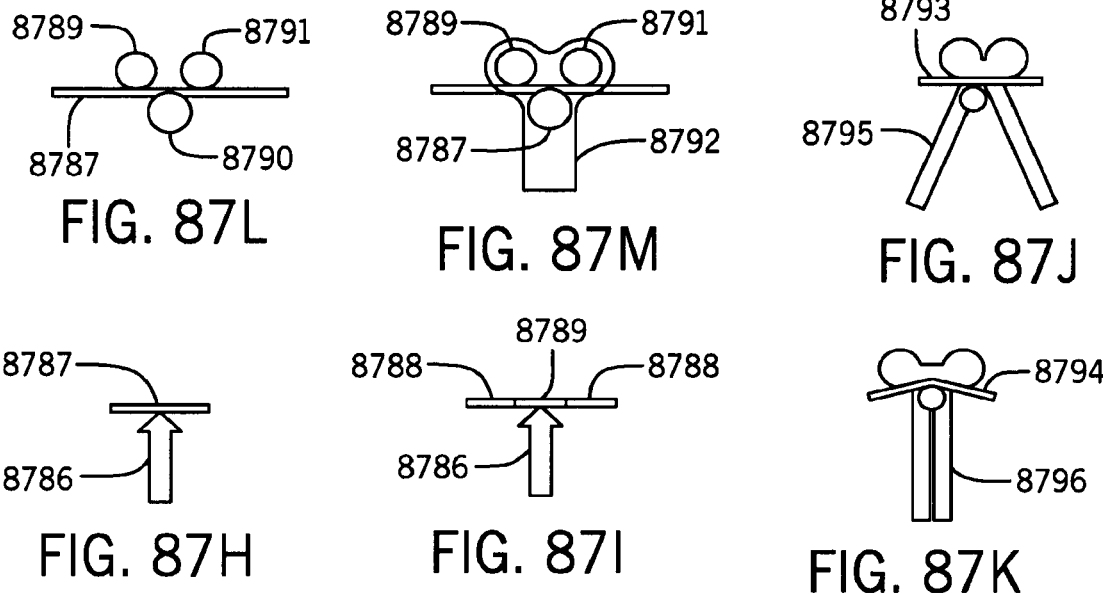
FIG. 87L      FIG. 87M      FIG. 87J
FIG. 87H      FIG. 87I      FIG. 87K

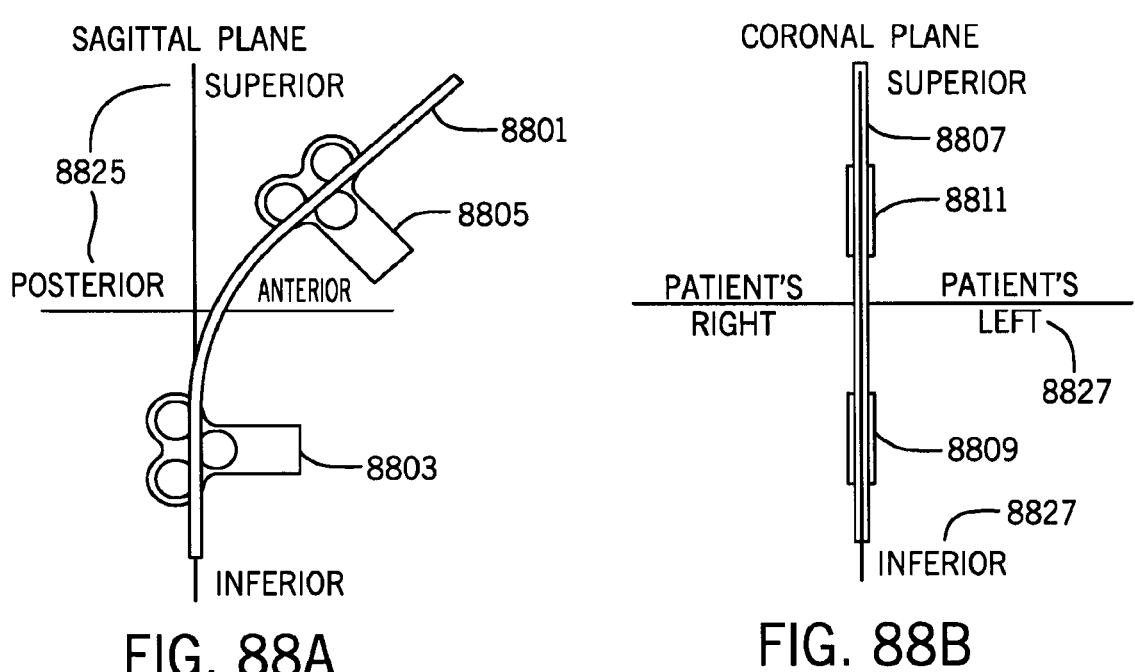
FIG. 88A
FIG. 88B
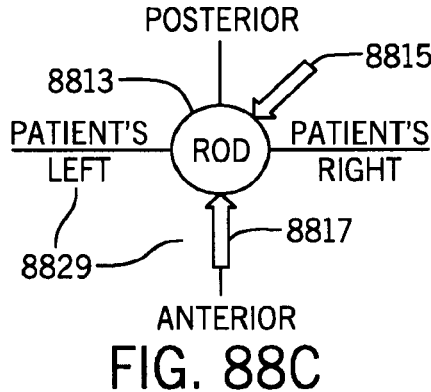
FIG. 88C
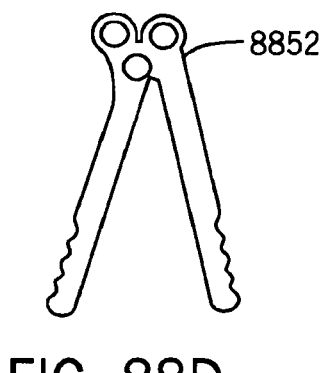
FIG. 88D
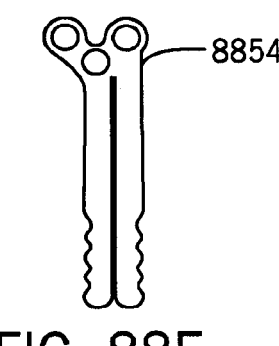
FIG. 88E
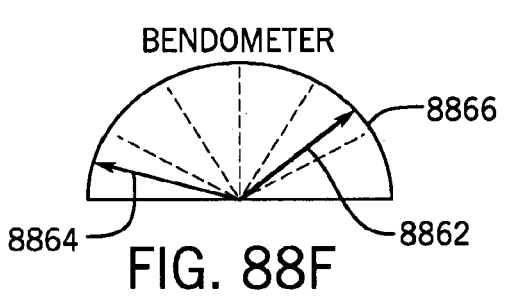
FIG. 88F

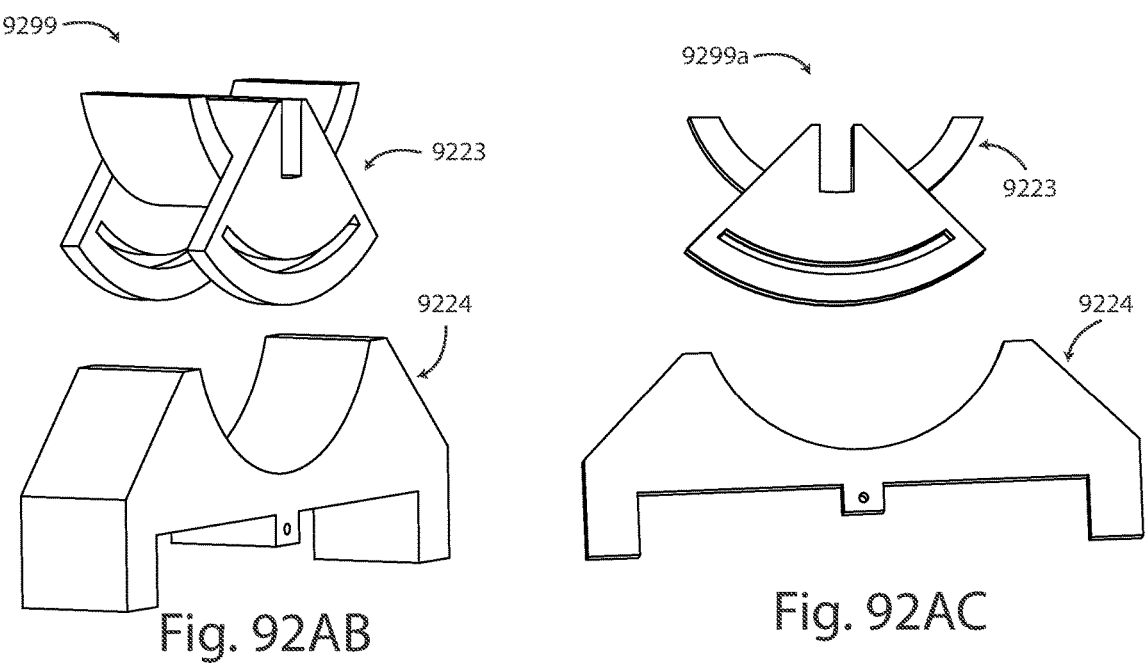
Fig. 92AB
Fig. 92AC
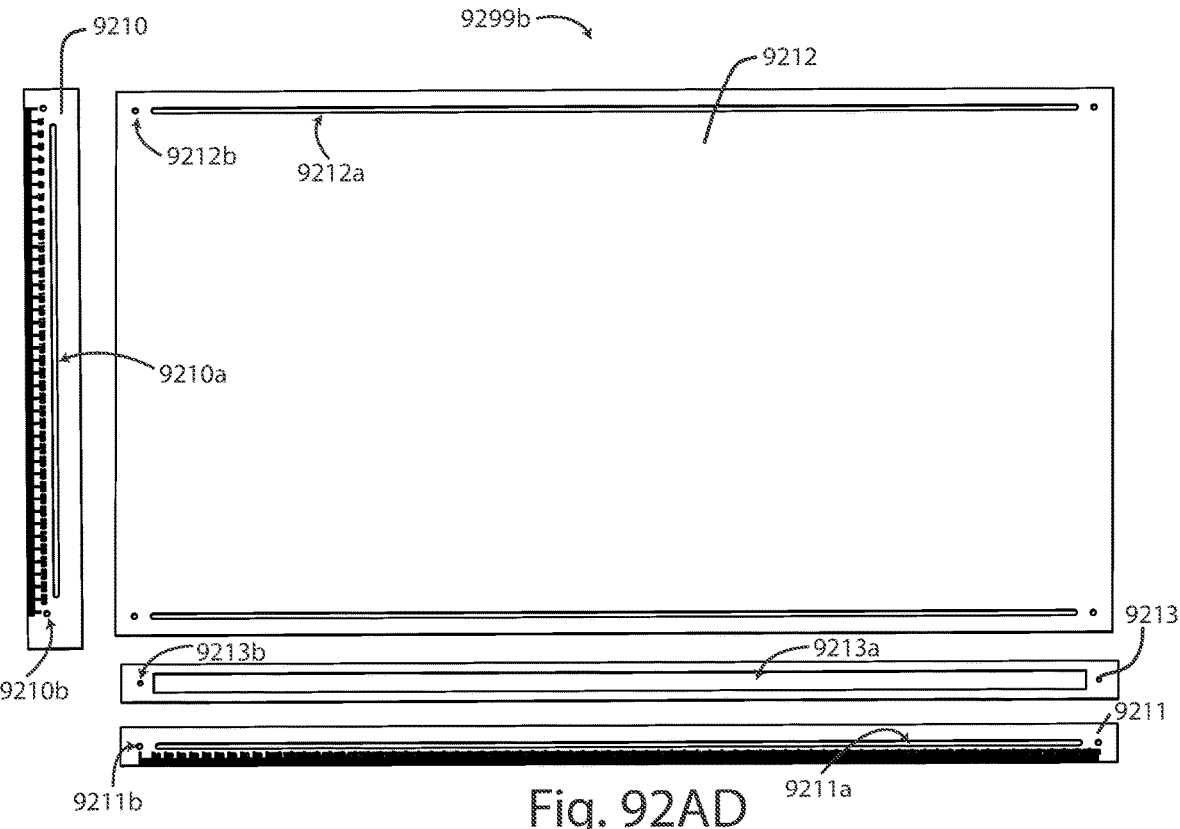
Fig. 92AD

9604

9602

9601

9400

9400

9670

9602

9400

9755 ⟍
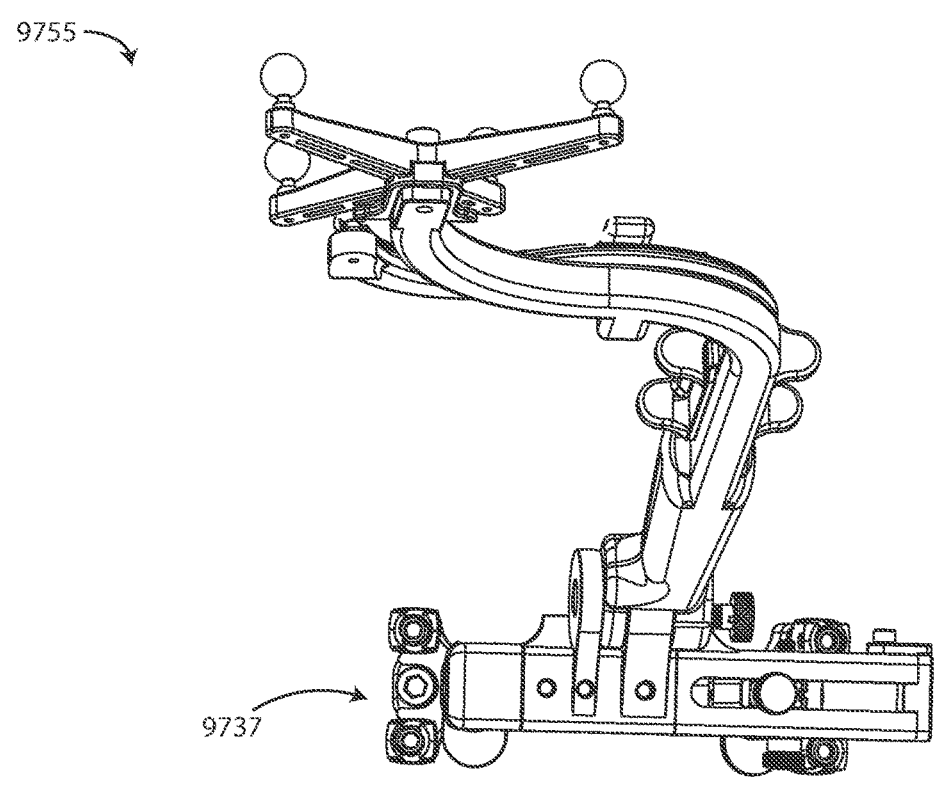
9737
9736
FIG. 97K
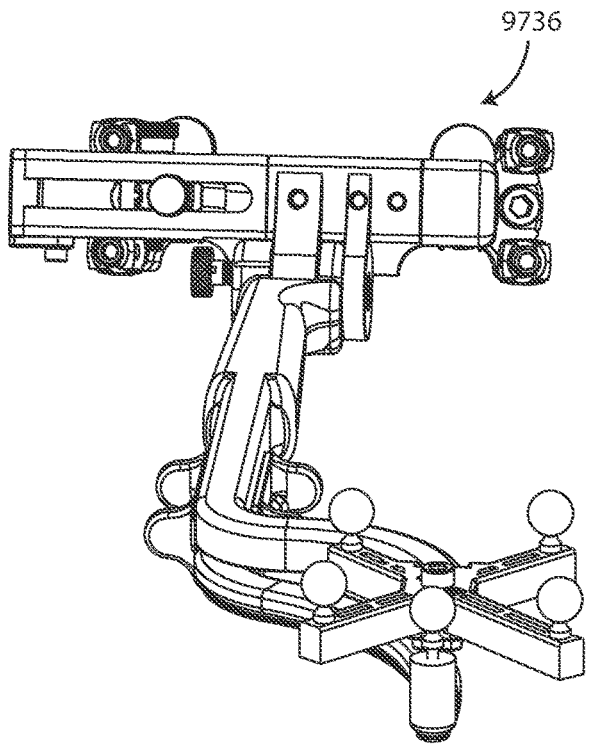

9960

9953

9961

9962

9963

9964

9970

9953

9961

9964

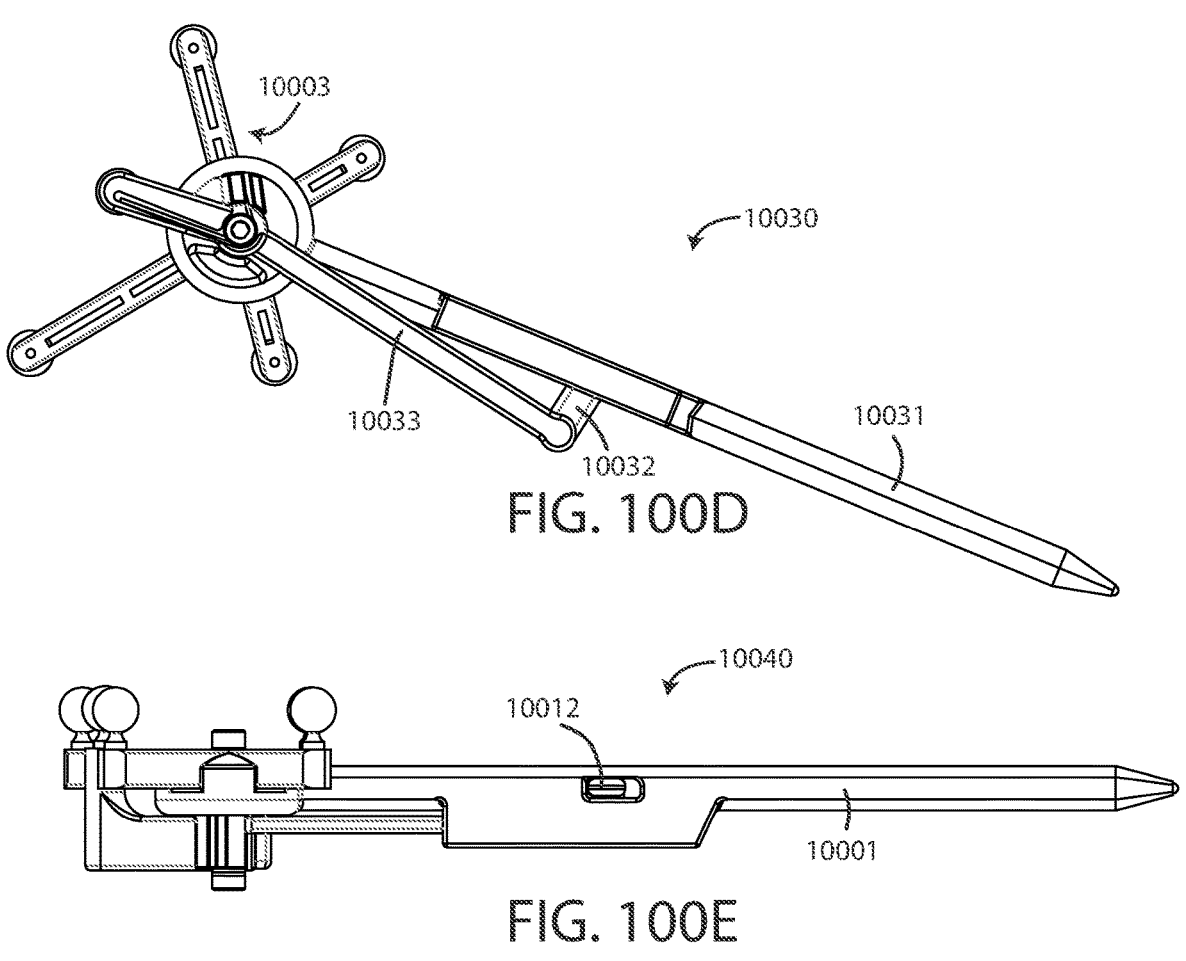
FIG. 100D
FIG. 100E
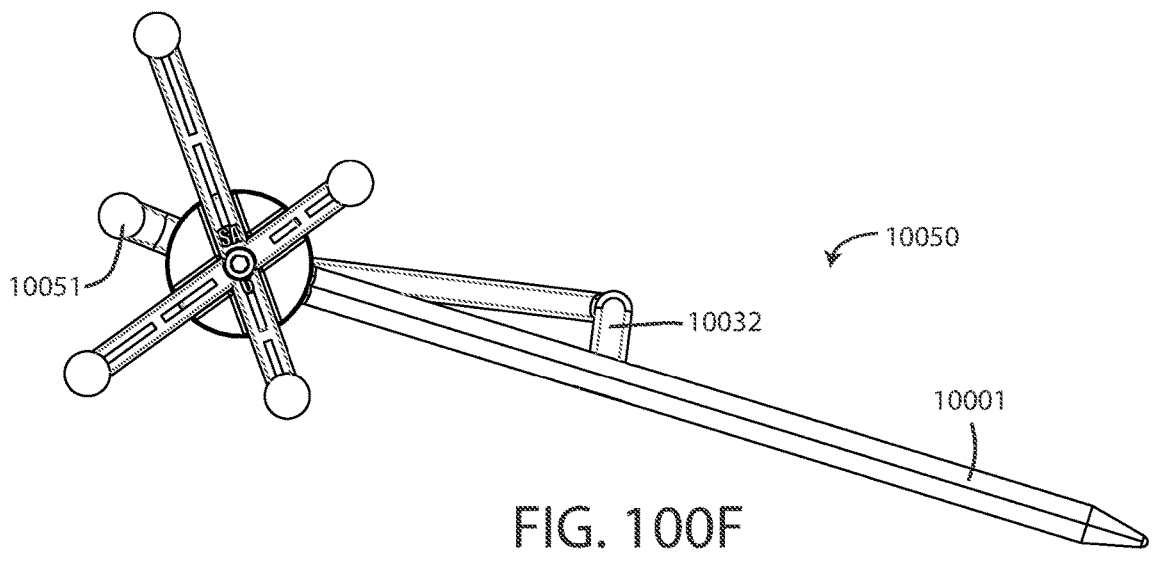
FIG. 100F

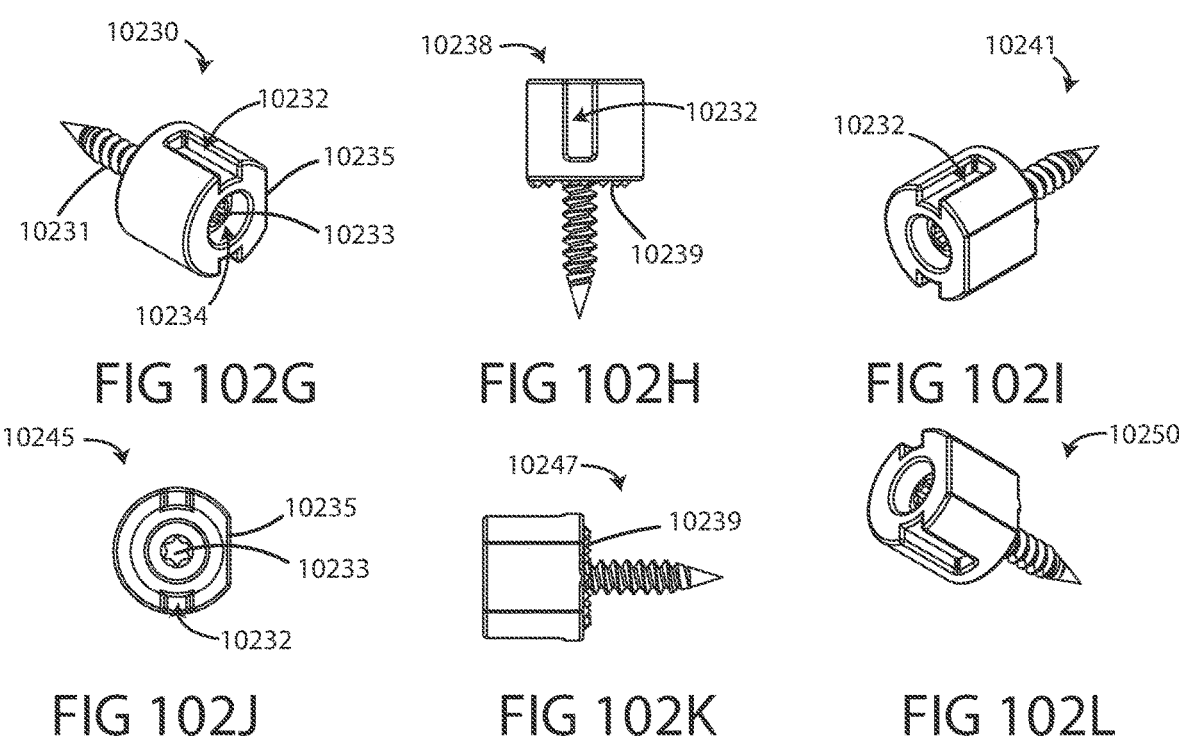
FIG 102G      FIG 102H      FIG 102I
FIG 102J      FIG 102K      FIG 102L
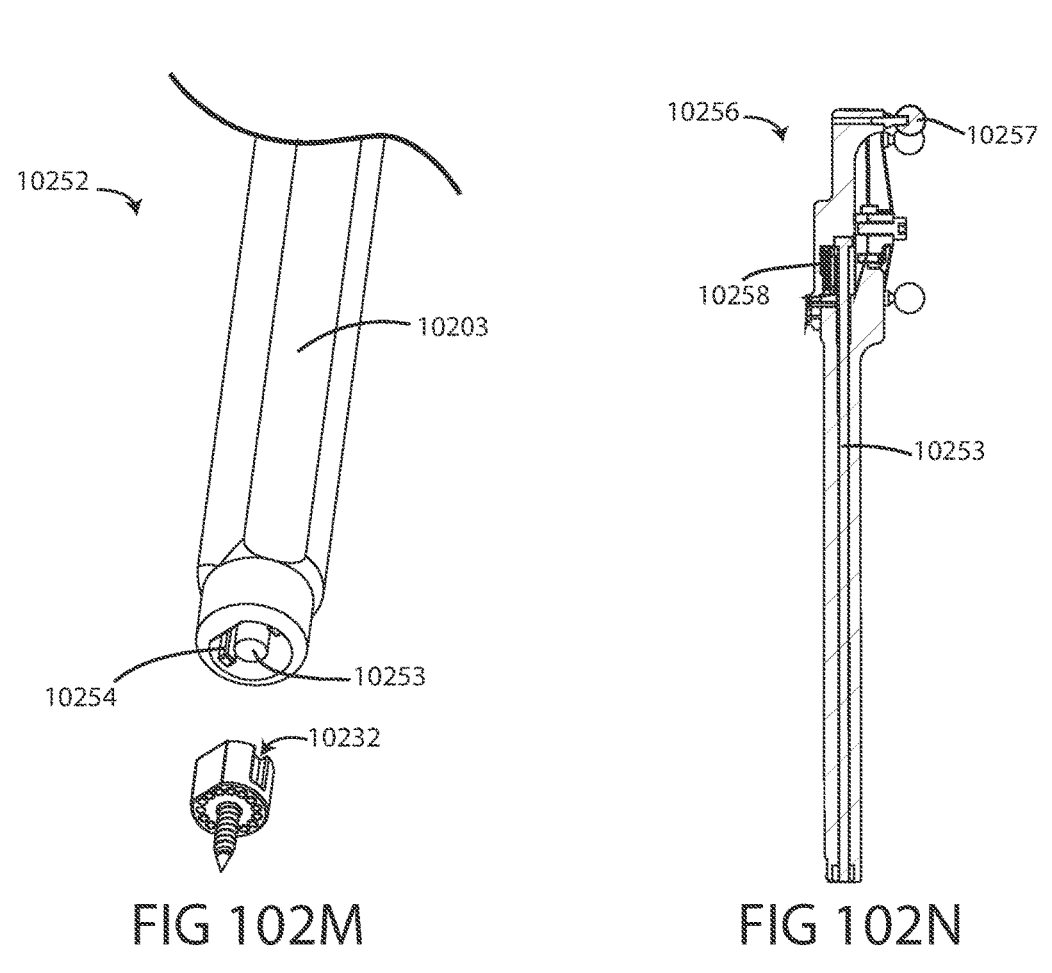
FIG 102M      FIG 102N

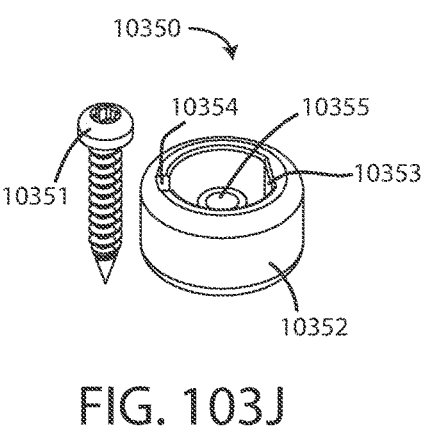
FIG. 103J
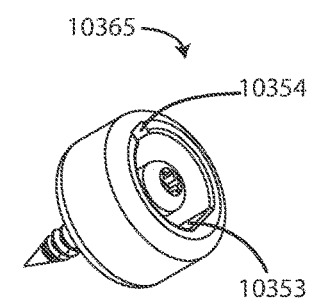
FIG. 103K
FIG. 103L
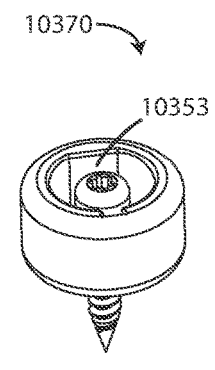
FIG. 103M
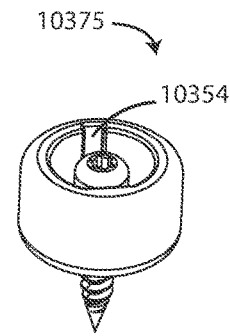
FIG. 103N
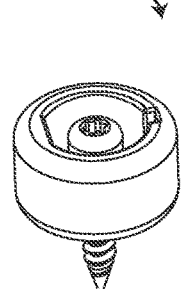
FIG. 103O
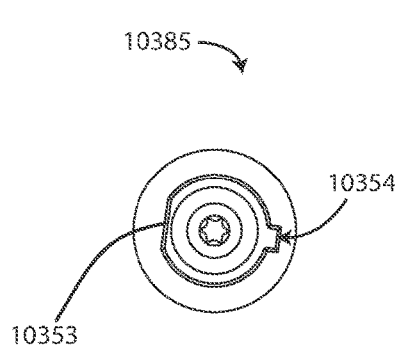
FIG. 103P
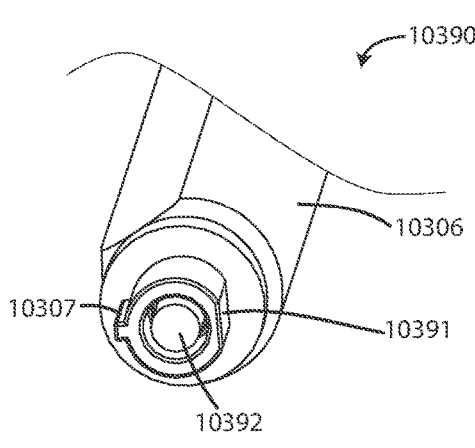
FIG. 103Q

10550

10560

10518

10519

10513

10502

10501b

10502

10501a

10562

10505

10561

10650

10654

10659

10660

10656

10658

10635

10651

10655

10652

10619

10661

10631

10653

10611

10657

10860 —→

10865 —→

10878

10890

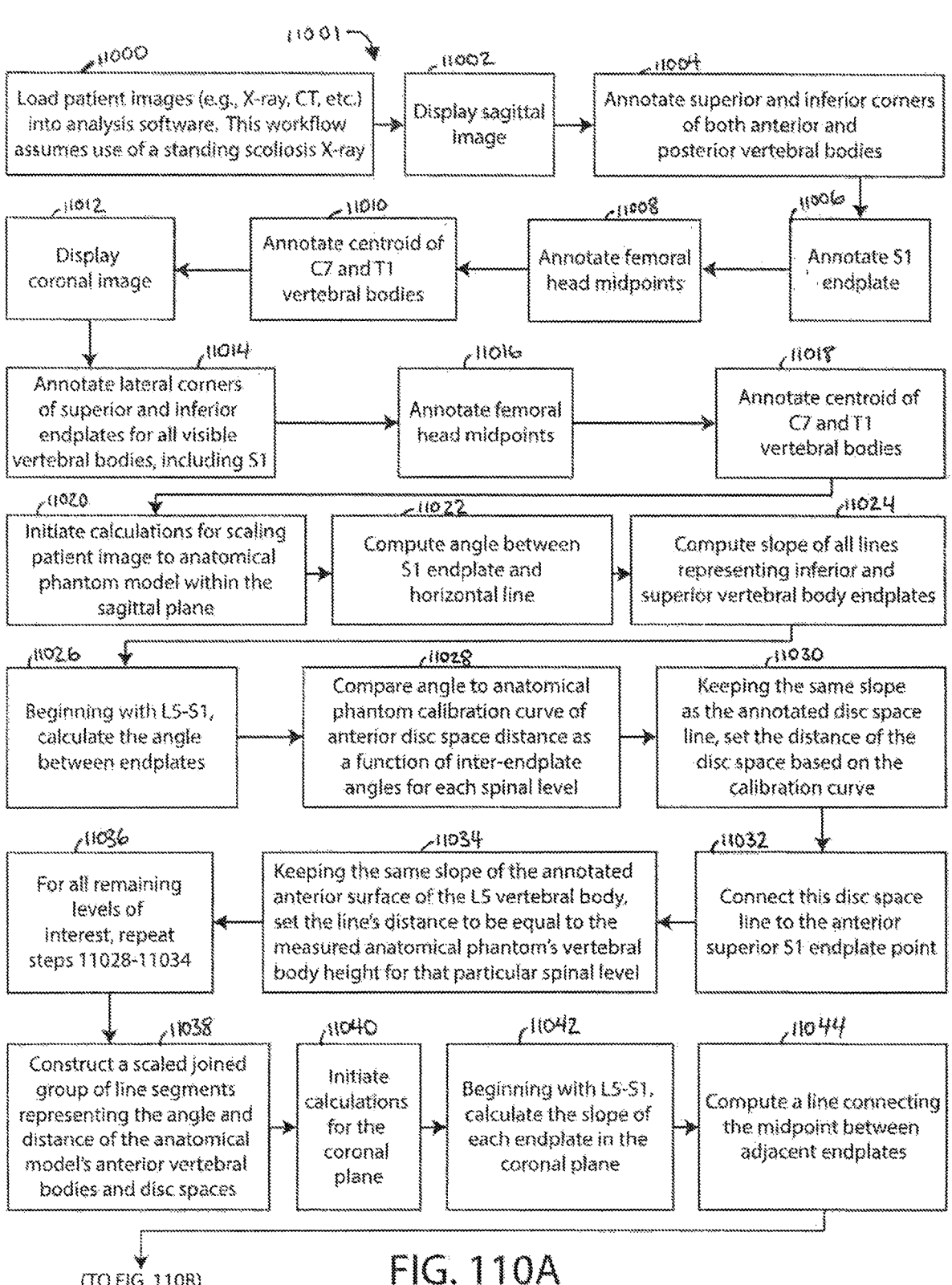

11000
Load patient images (e.g., X-ray, CT, etc.) into analysis software. This workflow assumes use of a standing scoliosis X-ray 11002
Display sagittal Image 11004
Annotate superior and inferior corners of both anterior and posterior vertebral bodies 11012
Display coronal image 11010
Annotate centroid of C7 and T1 vertebral bodies 11008
Annotate femoral head midpoints 11006
Annotate S1 endplate 11014
Annotate lateral corners of superior and inferior endplates for all visible vertebral bodies, including S1

11016
Annotate femoral head midpoints

11018
Annotate centroid of C7 and T1 vertebral bodies

11020
Initiate calculations for scaling patient image to anatomical phantom model within the sagittal plane 11022
Compute angle between S1 endplate and horizontal line 11024
Compute slope of all lines representing inferior and superior vertebral body endplates 11026
Beginning with L5-S1, calculate the angle between endplates 11028
Compare angle to anatomical phantom calibration curve of anterior disc space distance as a function of inter-endplate angles for each spinal level 11030
Keeping the same slope as the annotated disc space line, set the distance of the disc space based on the calibration curve 11036
For all remaining levels of interest, repeat steps 11028-11034

11034
Keeping the same slope of the annotated anterior surface of the L5 vertebral body, set the line's distance to be equal to the measured anatomical phantom's vertebral body height for that particular spinal level 11032
Connect this disc space line to the anterior superior S1 endplate point 11038
Construct a scaled joined group of line segments representing the angle and distance of the anatomical model's anterior vertebral bodies and disc spaces 11040
Initiate calculations for the coronal plane 11042
Beginning with L5-S1, calculate the slope of each endplate in the coronal plane 11044
Compute a line connecting the midpoint between adjacent endplates (TO FIG. 110B)

FIG. 110A

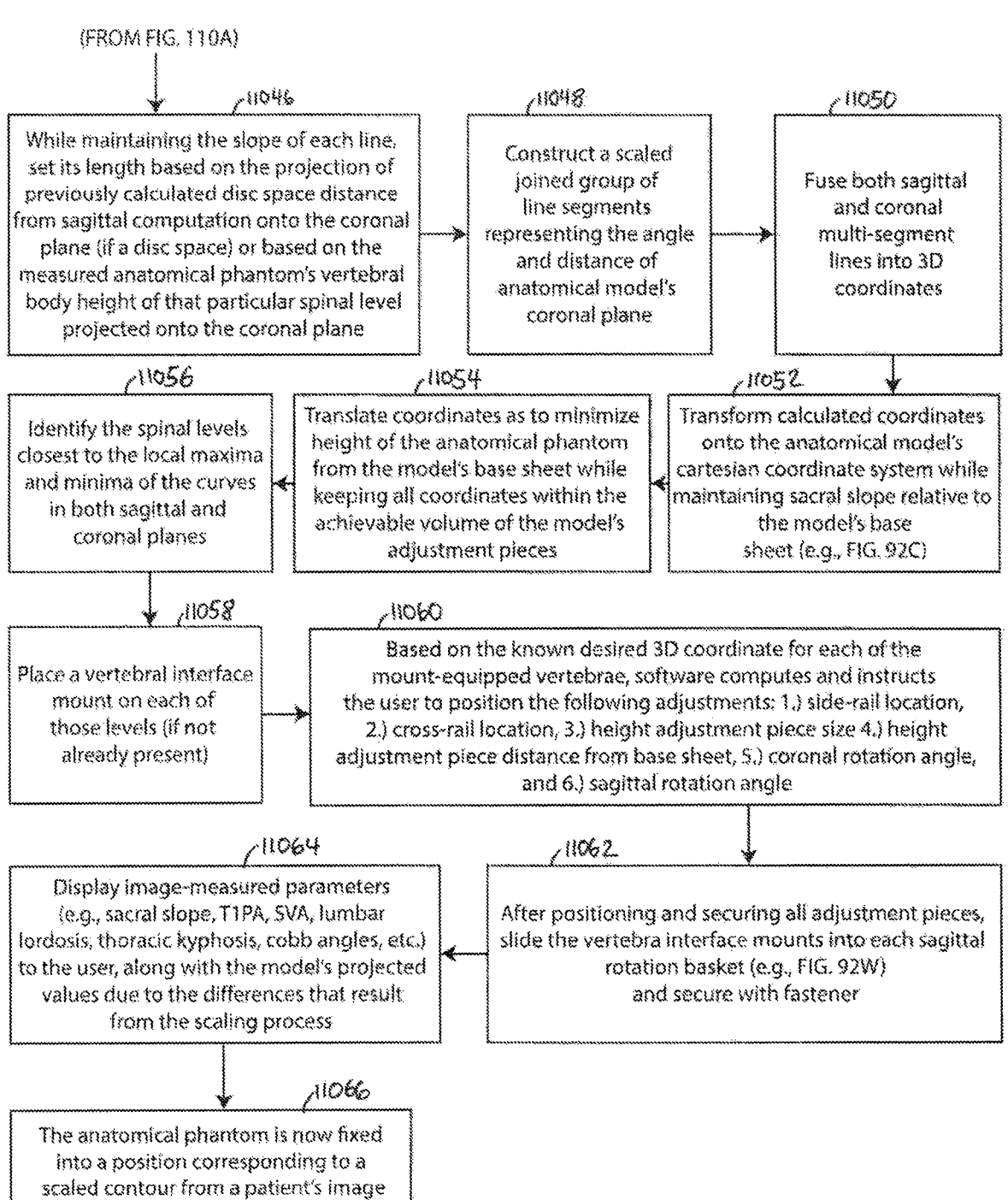

(FROM FIG. 110A)

11046
While maintaining the slope of each line, set its length based on the projection of previously calculated disc space distance from sagittal computation onto the coronal plane (if a disc space) or based on the measured anatomical phantom's vertebral body height of that particular spinal level projected onto the coronal plane

11048
Construct a scaled joined group of line segments representing the angle and distance of anatomical model's coronal plane

11050
Fuse both sagittal and coronal multi-segment lines into 3D coordinates

11056
Identify the spinal levels closest to the local maxima and minima of the curves in both sagittal and coronal planes

11054
Translate coordinates as to minimize height of the anatomical phantom from the model's base sheet while keeping all coordinates within the achievable volume of the model's adjustment pieces

11052
Transform calculated coordinates onto the anatomical model's cartesian coordinate system while maintaining sacral slope relative to the model's base sheet (e.g., FIG. 92C)

11058
Place a vertebral interface mount on each of those levels (if not already present)

11060
Based on the known desired 3D coordinate for each of the mount-equipped vertebrae, software computes and instructs the user to position the following adjustments: 1.) side-rail location, 2.) cross-rail location, 3.) height adjustment piece size 4.) height adjustment piece distance from base sheet, 5.) coronal rotation angle, and 6.) sagittal rotation angle

11064
Display image-measured parameters (e.g., sacral slope, T1PA, SVA, lumbar lordosis, thoracic kyphosis, cobb angles, etc.) to the user, along with the model's projected values due to the differences that result from the scaling process

11062
After positioning and securing all adjustment pieces, slide the vertebra interface mounts into each sagittal rotation basket (e.g., FIG. 92W) and secure with fastener

11066
The anatomical phantom is now fixed into a position corresponding to a scaled contour from a patient's image

FIG. 110B

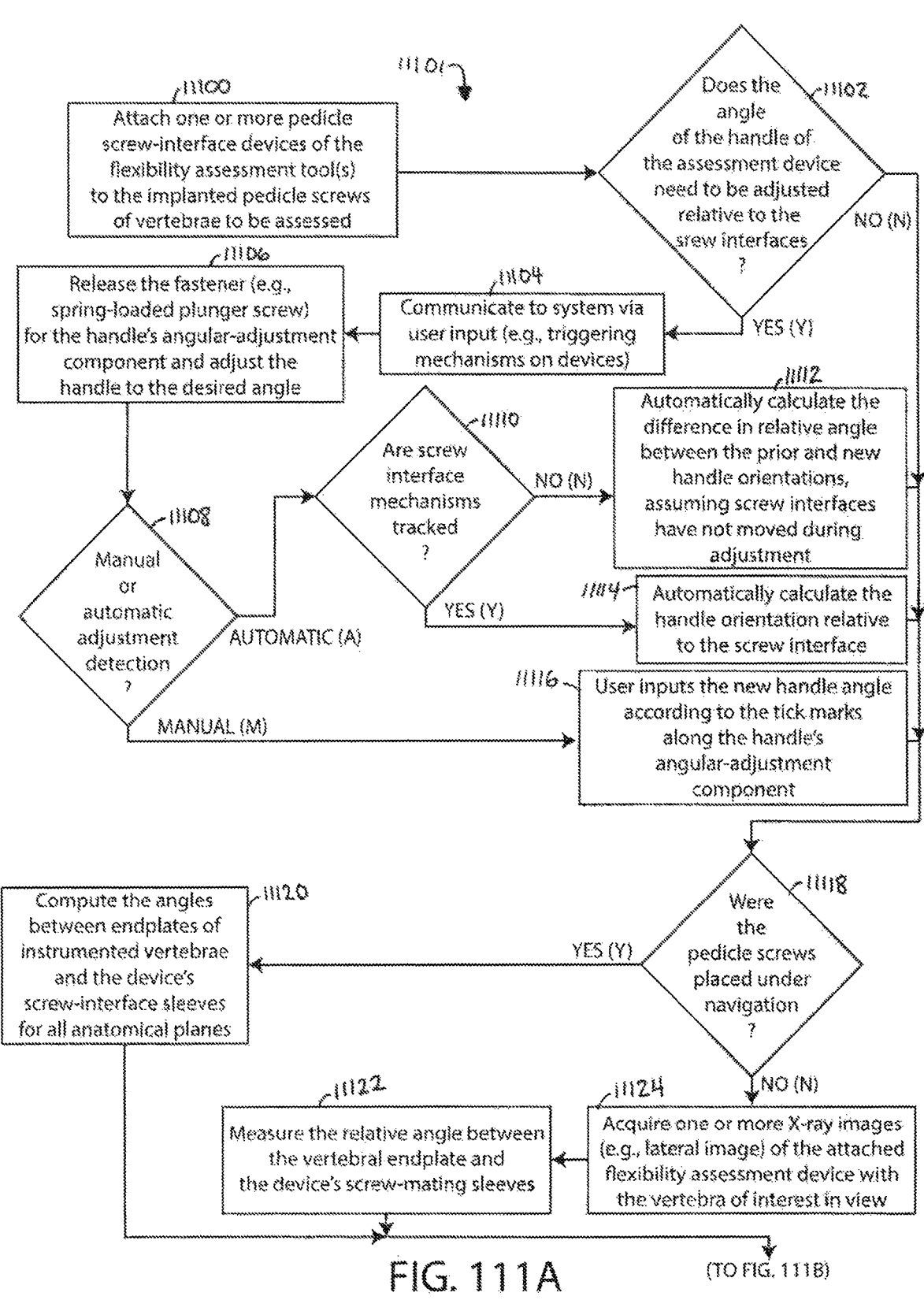
FIG. 111A    (TO FIG. 111B)

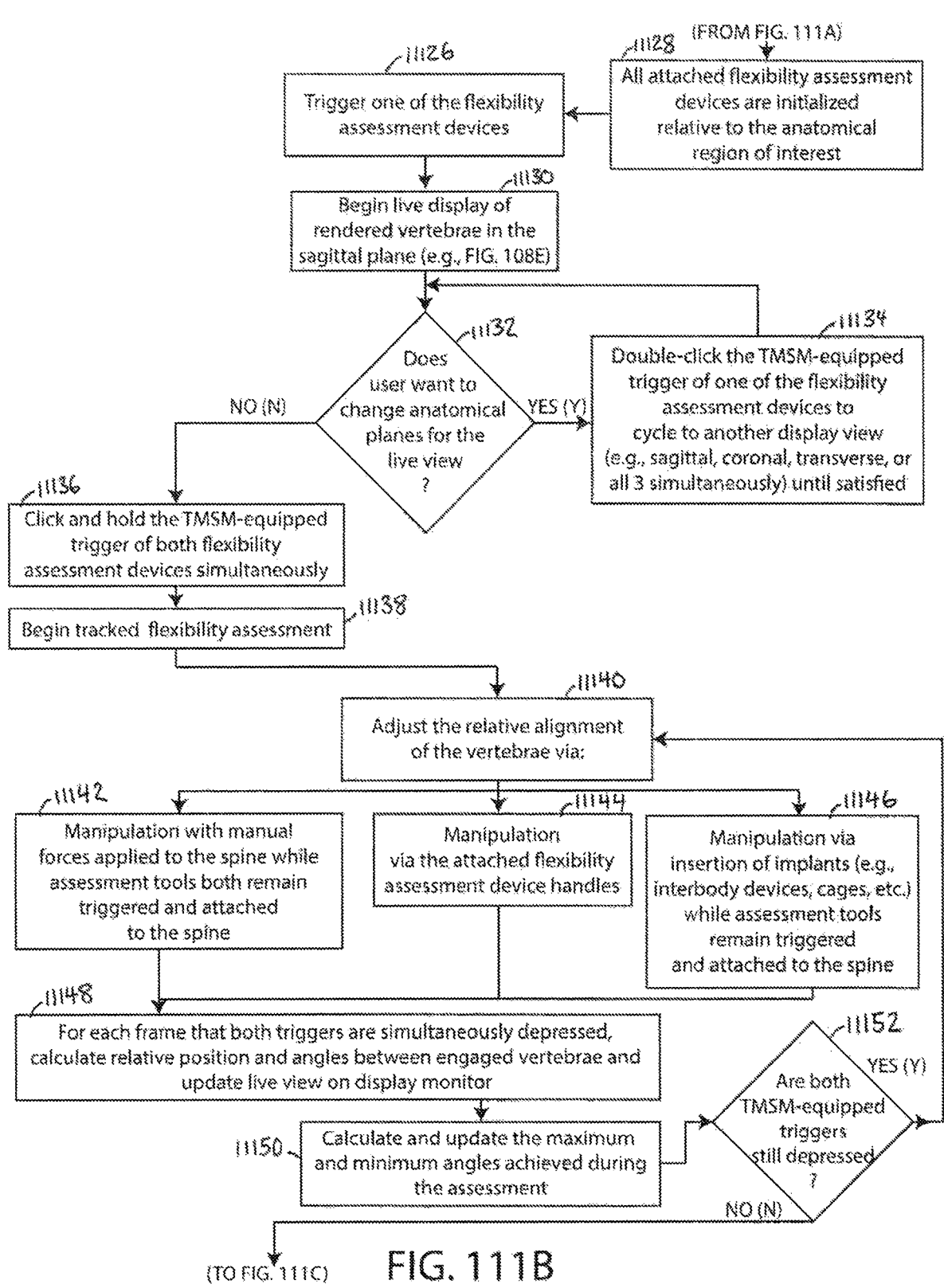

FIG. 111B (FROM FIG. 111A)

1126 — Trigger one of the flexibility assessment devices

1128 — All attached flexibility assessment devices are initialized relative to the anatomical region of interest 1130 — Begin live display of rendered vertebrae in the sagittal plane (e.g., FIG. 108E)

1132 — Does user want to change anatomical planes for the live view ?

YES (Y)

1134 — Double-click the TMSM-equipped trigger of one of the flexibility assessment devices to cycle to another display view (e.g., sagittal, coronal, transverse, or all 3 simultaneously) until satisfied

NO (N)

1136 — Click and hold the TMSM-equipped trigger of both flexibility assessment devices simultaneously 1138 — Begin tracked flexibility assessment 1140 — Adjust the relative alignment of the vertebrae via:

1142 — Manipulation with manual forces applied to the spine while assessment tools both remain triggered and attached to the spine 1144 — Manipulation via the attached flexibility assessment device handles 1146 — Manipulation via insertion of implants (e.g., interbody devices, cages, etc.) while assessment tools remain triggered and attached to the spine 1148 — For each frame that both triggers are simultaneously depressed, calculate relative position and angles between engaged vertebrae and update live view on display monitor 1150 — Calculate and update the maximum and minimum angles achieved during the assessment 1152 — Are both TMSM-equipped triggers still depressed ?

YES (Y)

(FROM FIG. 111B)

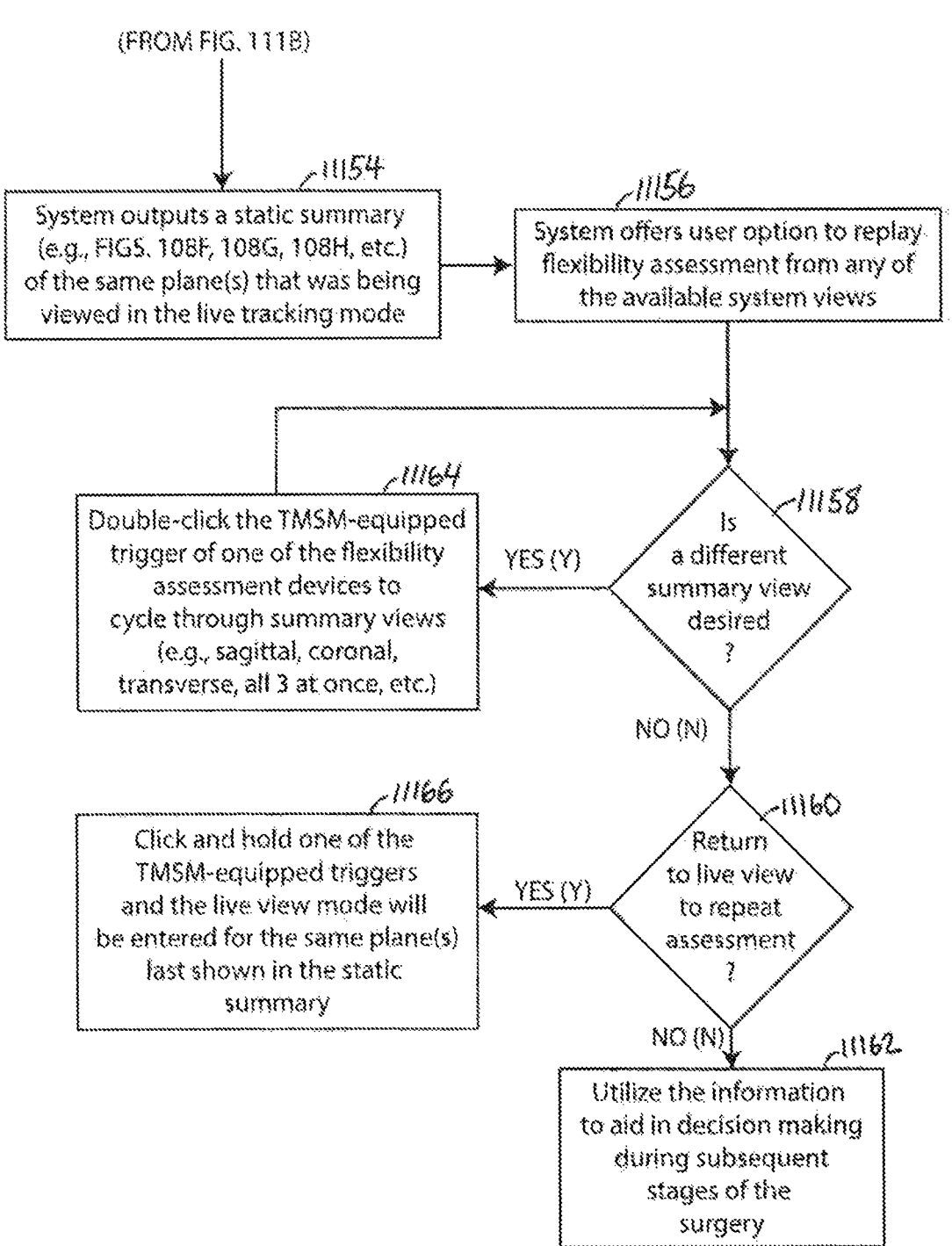

System outputs a static summary
(e.g., FIGS. 108F, 108G, 108H, etc.)
of the same plane(s) that was being
viewed in the live tracking mode

11154

System offers user option to replay
flexibility assessment from any of
the available system views

11156

Double-click the TMSM-equipped
trigger of one of the flexibility
assessment devices to
cycle through summary views
(e.g., sagittal, coronal,
transverse, all 3 at once, etc.)

11164

Is
a different
summary view
desired
?

11158

YES (Y)

NO (N)

Click and hold one of the
TMSM-equipped triggers
and the live view mode will
be entered for the same plane(s)
last shown in the static
summary

11166

Return
to live view
to repeat
assessment
?

11160

YES (Y)

NO (N)

Utilize the information
to aid in decision making
during subsequent
stages of the
surgery

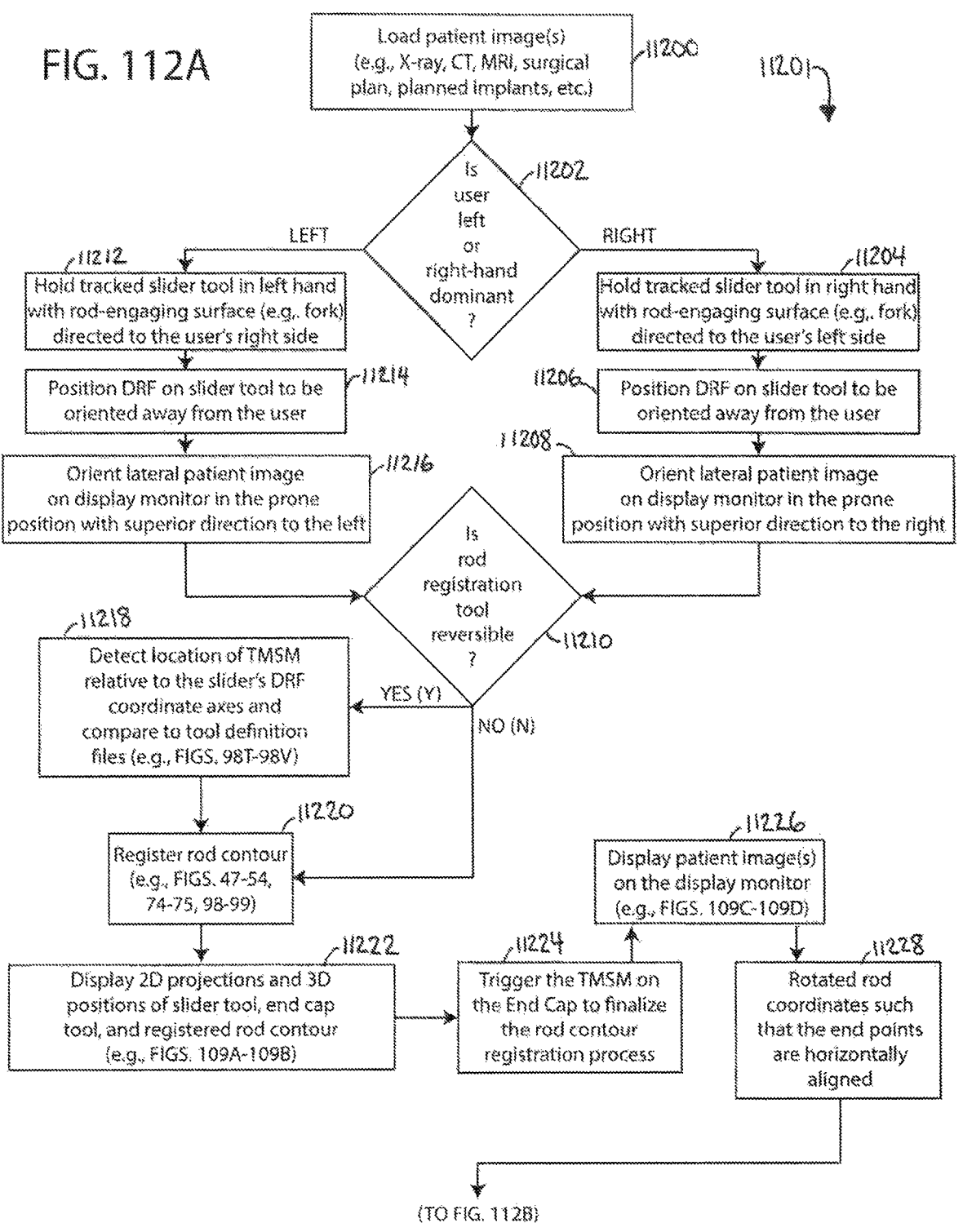

Load patient image(s) (e.g., X-ray, CT, MRI, surgical plan, planned implants, etc.) —11200

11201

Is user left or right-hand dominant ? —11202

LEFT

RIGHT

11212— Hold tracked slider tool in left hand with rod-engaging surface (e.g., fork) directed to the user's right side 11204— Hold tracked slider tool in right hand with rod-engaging surface (e.g., fork) directed to the user's left side Position DRF on slider tool to be oriented away from the user —11214

11206— Position DRF on slider tool to be oriented away from the user

Orient lateral patient image on display monitor in the prone position with superior direction to the left —11216

11208— Orient lateral patient image on display monitor in the prone position with superior direction to the right Is rod registration tool reversible ? —11210

11218— Detect location of TMSM relative to the slider's DRF coordinate axes and compare to tool definition files (e.g., FIGS. 98T-98V)

YES (Y)

NO (N)

Register rod contour (e.g., FIGS. 47-54, 74-75, 98-99) —11220

11226— Display patient image(s) on the display monitor (e.g., FIGS. 109C-109D)

Display 2D projections and 3D positions of slider tool, end cap tool, and registered rod contour (e.g., FIGS. 109A-109B) —11222

Trigger the TMSM on the End Cap to finalize the rod contour registration process —11224

Rotated rod coordinates such that the end points are horizontally aligned —11228

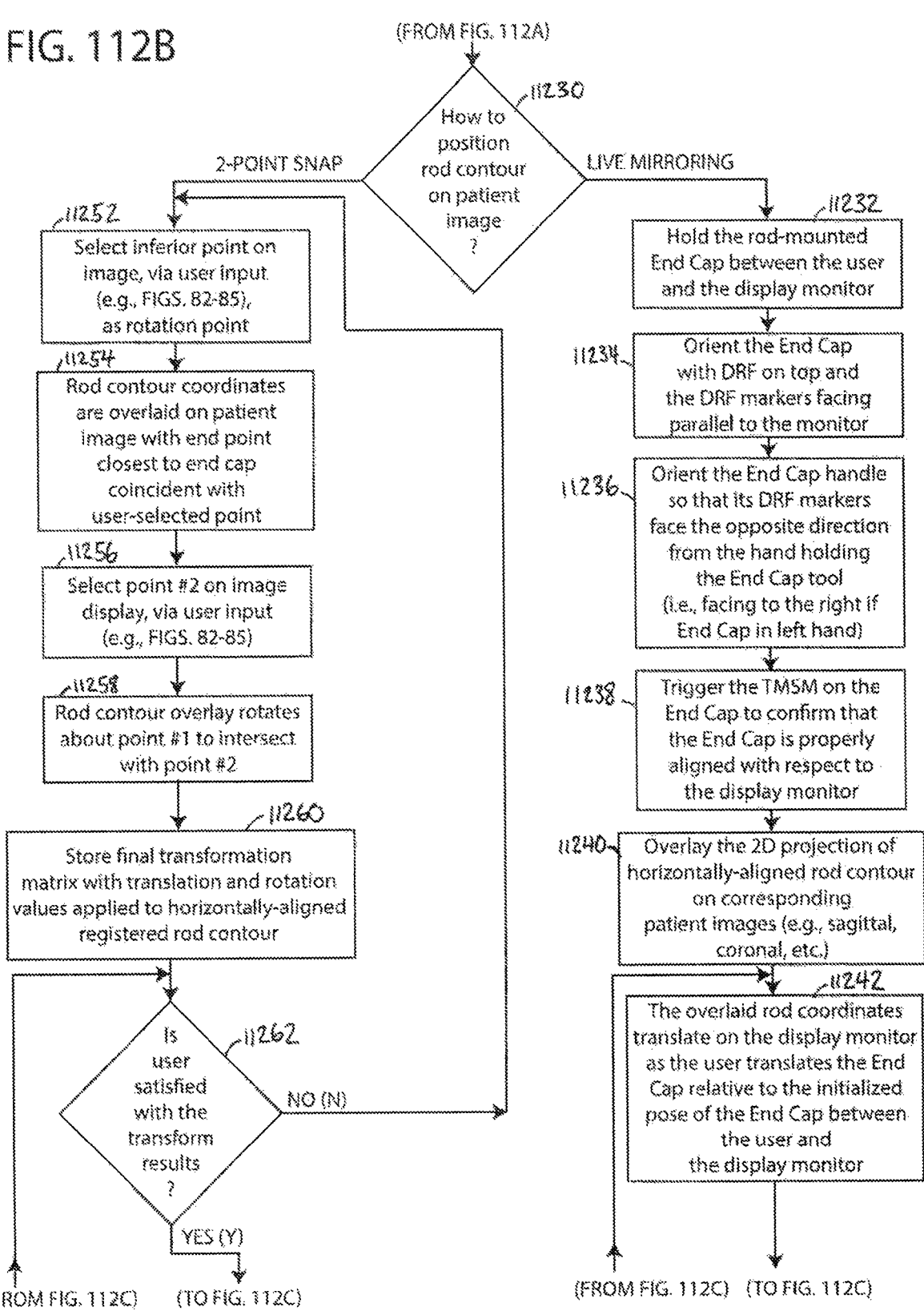

(FROM FIG. 112A)

11230

How to position rod contour on patient image ?

2-POINT SNAP

LIVE MIRRORING

11252

Select inferior point on image, via user input (e.g., FIGS. 82-85), as rotation point

11254

Rod contour coordinates are overlaid on patient image with end point closest to end cap coincident with user-selected point

11256

Select point #2 on image display, via user input (e.g., FIGS. 82-85)

11258

Rod contour overlay rotates about point #1 to intersect with point #2

11260

Store final transformation matrix with translation and rotation values applied to horizontally-aligned registered rod contour

11262

Is user satisfied with the transform results ?

NO (N)

YES (Y)

(FROM FIG. 112C)     (TO FIG. 112C)

11232

Hold the rod-mounted End Cap between the user and the display monitor

11234

Orient the End Cap with DRF on top and the DRF markers facing parallel to the monitor

11236

Orient the End Cap handle so that its DRF markers face the opposite direction from the hand holding the End Cap tool (i.e., facing to the right if End Cap in left hand)

11238

Trigger the TMSM on the End Cap to confirm that the End Cap is properly aligned with respect to the display monitor

11240

Overlay the 2D projection of horizontally-aligned rod contour on corresponding patient images (e.g., sagittal, coronal, etc.)

11242

The overlaid rod coordinates translate on the display monitor as the user translates the End Cap relative to the initialized pose of the End Cap between the user and the display monitor (FROM FIG. 112C)    (TO FIG. 112C)

FIG. 112C (TO FIG. 112B)    (FROM FIG. 112B)

(TO FIG. 112B)    (FROM FIG. 112B)

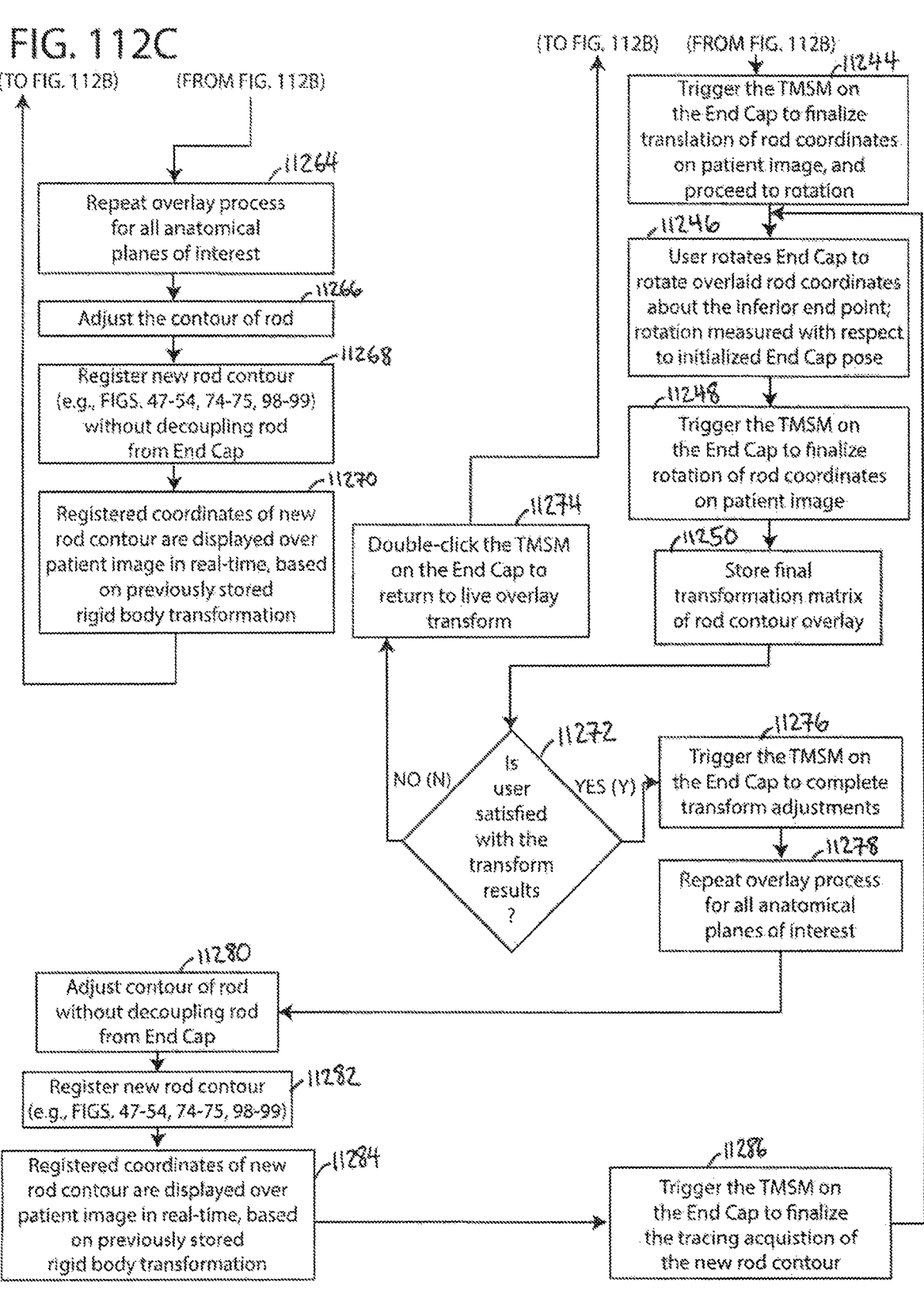

11264
Repeat overlay process for all anatomical planes of interest

11266
Adjust the contour of rod

11268
Register new rod contour (e.g., FIGS. 47-54, 74-75, 98-99) without decoupling rod from End Cap 11270
Registered coordinates of new rod contour are displayed over patient image in real-time, based on previously stored rigid body transformation 11244
Trigger the TMSM on the End Cap to finalize translation of rod coordinates on patient image, and proceed to rotation 11246
User rotates End Cap to rotate overlaid rod coordinates about the inferior end point; rotation measured with respect to initialized End Cap pose 11248
Trigger the TMSM on the End Cap to finalize rotation of rod coordinates on patient image 11250
Store final transformation matrix of rod contour overlay 11274
Double-click the TMSM on the End Cap to return to live overlay transform 11272
Is user satisfied with the transform results?    NO (N)    YES (Y)

11276
Trigger the TMSM on the End Cap to complete transform adjustments

11278
Repeat overlay process for all anatomical planes of interest

11280
Adjust contour of rod without decoupling rod from End Cap

11282
Register new rod contour (e.g., FIGS. 47-54, 74-75, 98-99)

11284
Registered coordinates of new rod contour are displayed over patient image in real-time, based on previously stored rigid body transformation 11286
Trigger the TMSM on the End Cap to finalize the tracing acquistion of the new rod contour

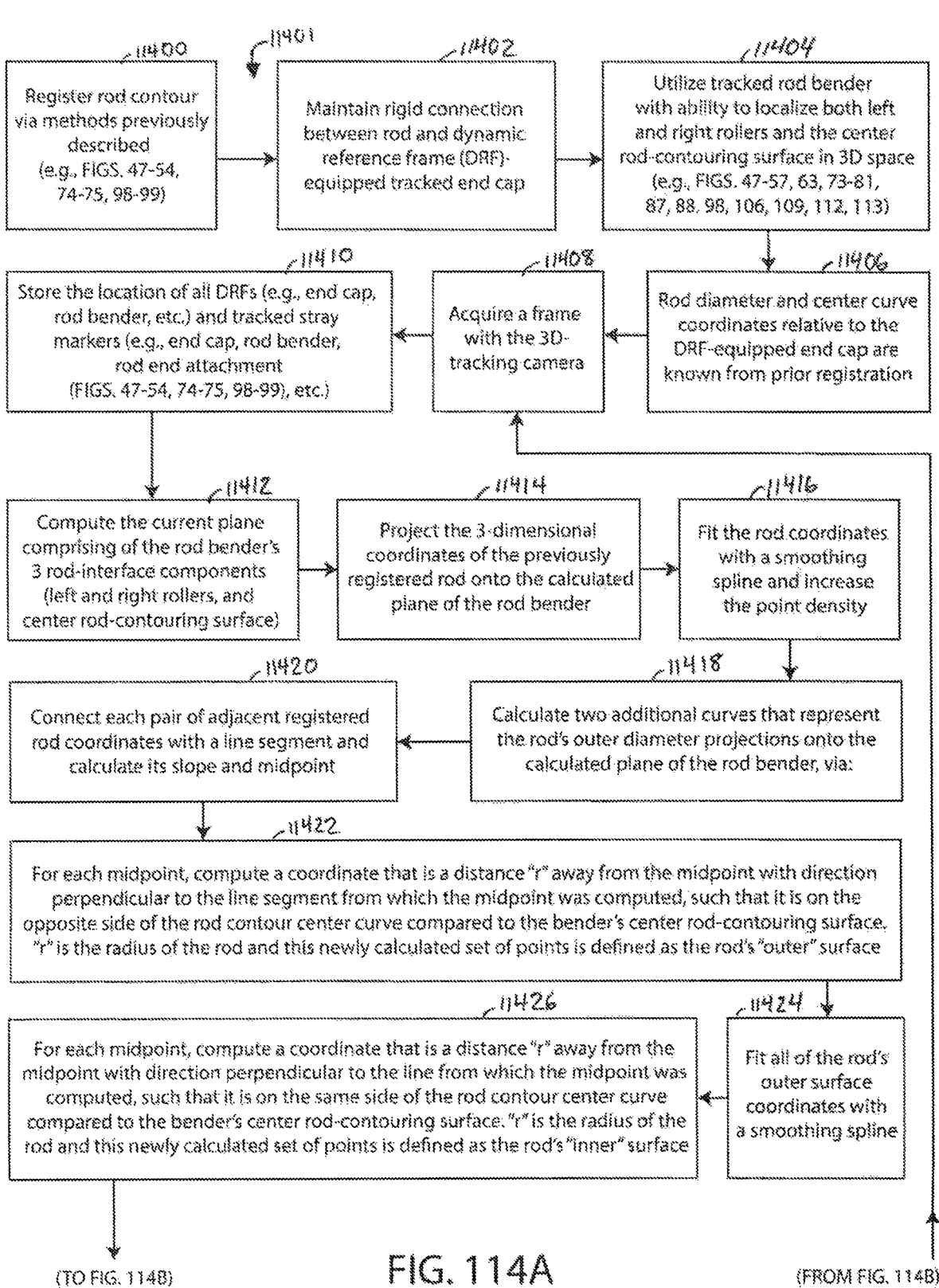

*1400*
Register rod contour via methods previously described (e.g., FIGS. 47-54, 74-75, 98-99)

*1401*

*1402*
Maintain rigid connection between rod and dynamic reference frame (DRF)-equipped tracked end cap

*1404*
Utilize tracked rod bender with ability to localize both left and right rollers and the center rod-contouring surface in 3D space (e.g., FIGS. 47-57, 63, 73-81, 87, 88, 98, 106, 109, 112, 113)

*1410*
Store the location of all DRFs (e.g., end cap, rod bender, etc.) and tracked stray markers (e.g., end cap, rod bender, rod end attachment (FIGS. 47-54, 74-75, 98-99), etc.)

*1408*
Acquire a frame with the 3D-tracking camera

*1406*
Rod diameter and center curve coordinates relative to the DRF-equipped end cap are known from prior registration

*1412*
Compute the current plane comprising of the rod bender's 3 rod-interface components (left and right rollers, and center rod-contouring surface)

*1414*
Project the 3-dimensional coordinates of the previously registered rod onto the calculated plane of the rod bender

*1416*
Fit the rod coordinates with a smoothing spline and increase the point density

*1420*
Connect each pair of adjacent registered rod coordinates with a line segment and calculate its slope and midpoint

*1418*
Calculate two additional curves that represent the rod's outer diameter projections onto the calculated plane of the rod bender, via:

*1422*
For each midpoint, compute a coordinate that is a distance "r" away from the midpoint with direction perpendicular to the line segment from which the midpoint was computed, such that it is on the opposite side of the rod contour center curve compared to the bender's center rod-contouring surface. "r" is the radius of the rod and this newly calculated set of points is defined as the rod's "outer" surface

*1426*
For each midpoint, compute a coordinate that is a distance "r" away from the midpoint with direction perpendicular to the line from which the midpoint was computed, such that it is on the same side of the rod contour center curve compared to the bender's center rod-contouring surface. "r" is the radius of the rod and this newly calculated set of points is defined as the rod's "inner" surface

*1424*
Fit all of the rod's outer surface coordinates with a smoothing spline (TO FIG. 114B)

FIG. 114A (FROM FIG. 114B)

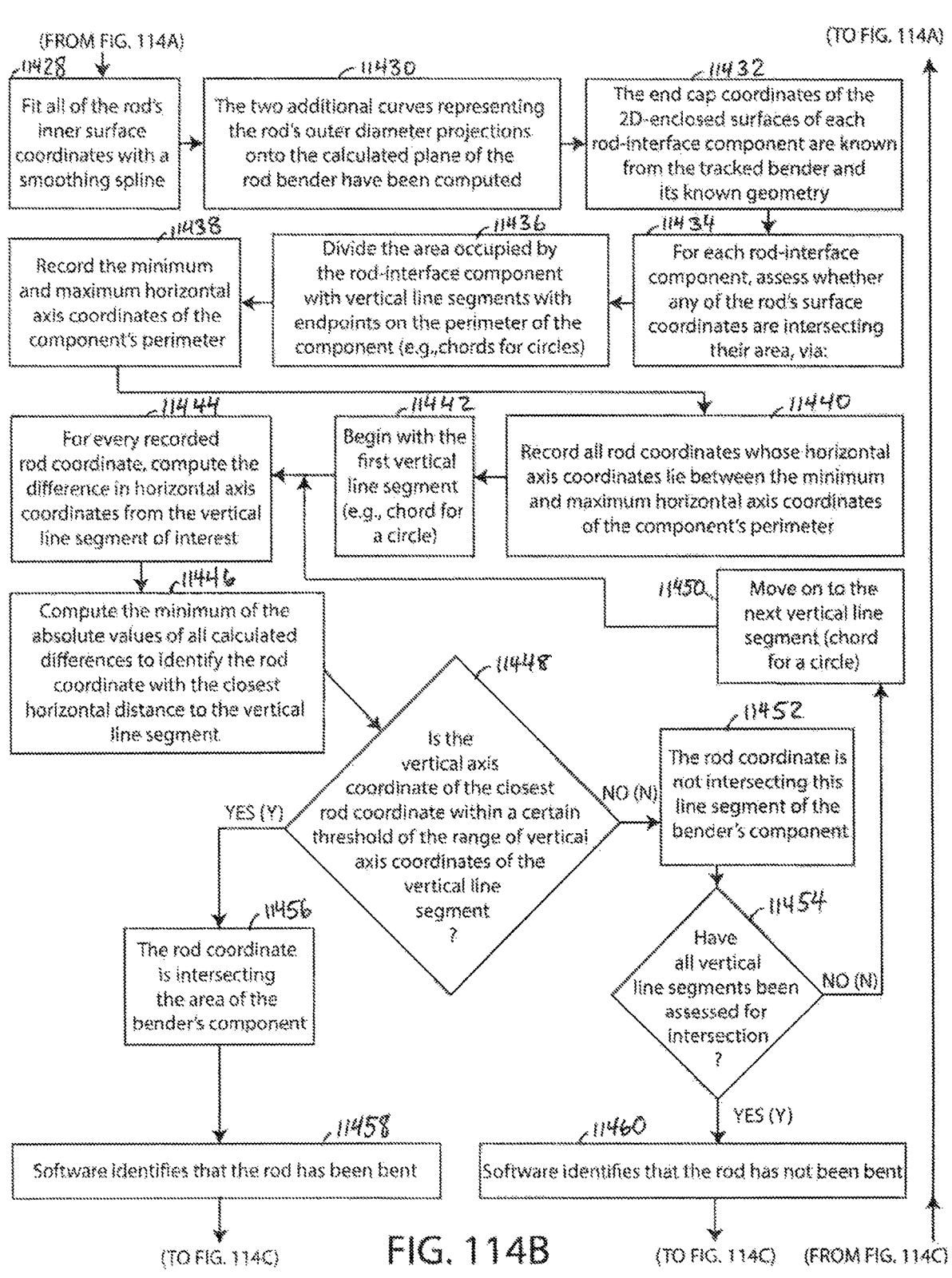

(FROM FIG. 114A)

(TO FIG. 114A)

11428
Fit all of the rod's inner surface coordinates with a smoothing spline

11430
The two additional curves representing the rod's outer diameter projections onto the calculated plane of the rod bender have been computed 11432
The end cap coordinates of the 2D-enclosed surfaces of each rod-interface component are known from the tracked bender and its known geometry 11438
Record the minimum and maximum horizontal axis coordinates of the component's perimeter 11436
Divide the area occupied by the rod-interface component with vertical line segments with endpoints on the perimeter of the component (e.g.,chords for circles)

11434
For each rod-interface component, assess whether any of the rod's surface coordinates are intersecting their area, via:

11444
For every recorded rod coordinate, compute the difference in horizontal axis coordinates from the vertical line segment of interest 11442
Begin with the first vertical line segment (e.g., chord for a circle)

11440
Record all rod coordinates whose horizontal axis coordinates lie between the minimum and maximum horizontal axis coordinates of the component's perimeter 11446
Compute the minimum of the absolute values of all calculated differences to identify the rod coordinate with the closest horizontal distance to the vertical line segment 11450
Move on to the next vertical line segment (chord for a circle)

11448
Is the vertical axis coordinate of the closest rod coordinate within a certain threshold of the range of vertical axis coordinates of the vertical line segment ?

NO (N)

11452
The rod coordinate is not intersecting this line segment of the bender's component

YES (Y)

11456
The rod coordinate is intersecting the area of the bender's component

11454
Have all vertical line segments been assessed for intersection ?

NO (N)

YES (Y)

11458
Software identifies that the rod has been bent

11460
Software identifies that the rod has not been bent (TO FIG. 114C)

FIG. 114B (TO FIG. 114C)    (FROM FIG. 114C)

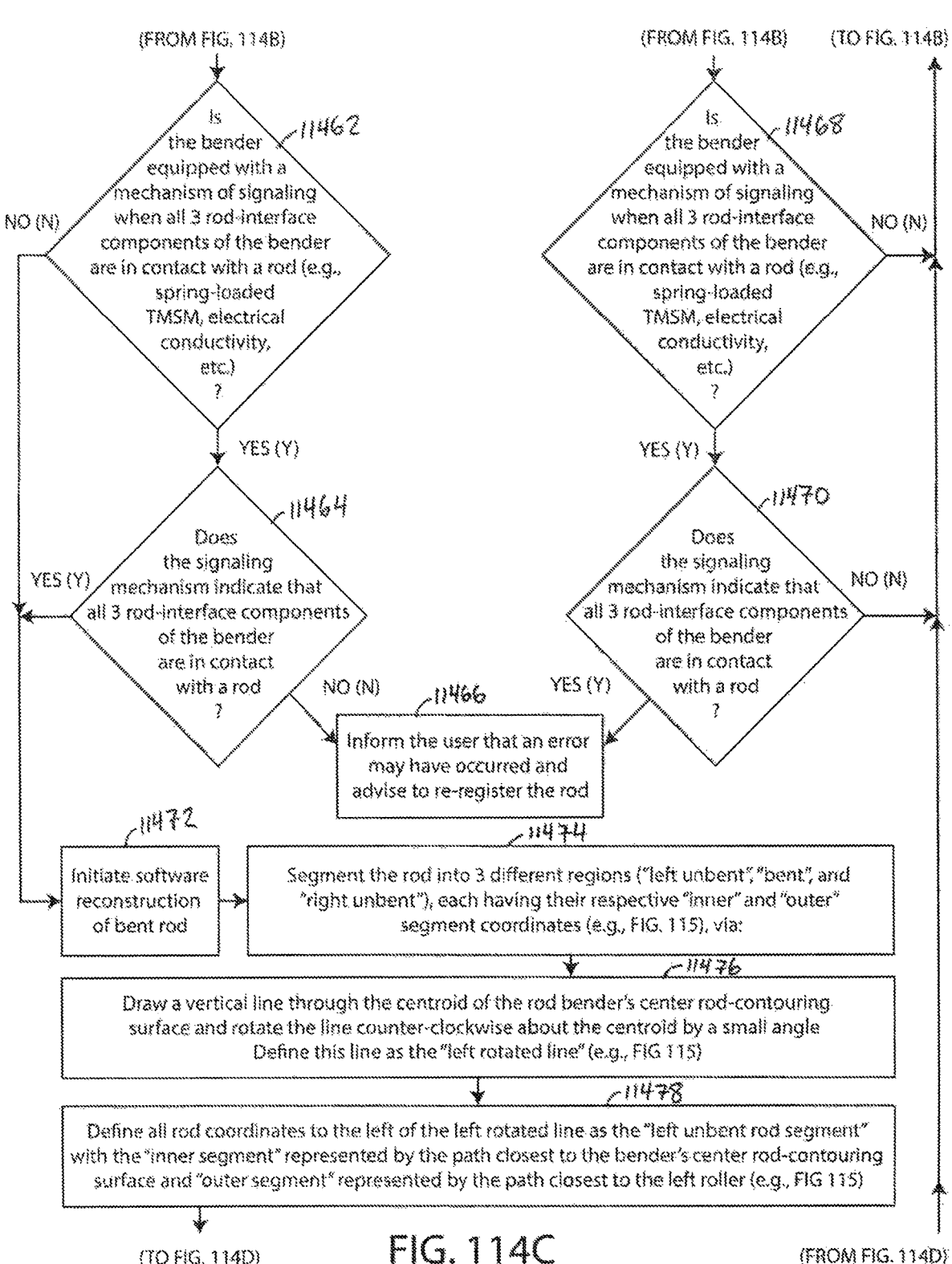

(FROM FIG. 114B)          (FROM FIG. 114B)     (TO FIG. 114B)

11462

Is the bender equipped with a mechanism of signaling when all 3 rod-interface components of the bender are in contact with a rod (e.g., spring-loaded TMSM, electrical conductivity, etc.)?

NO (N)

YES (Y)

11464

Does the signaling mechanism indicate that all 3 rod-interface components of the bender are in contact with a rod?

YES (Y)          NO (N)

11468

Is the bender equipped with a mechanism of signaling when all 3 rod-interface components of the bender are in contact with a rod (e.g., spring-loaded TMSM, electrical conductivity, etc.)?

NO (N)

YES (Y)

11470

Does the signaling mechanism indicate that all 3 rod-interface components of the bender are in contact with a rod?

NO (N)

YES (Y)

11466

Inform the user that an error may have occurred and advise to re-register the rod

11472

Initiate software reconstruction of bent rod

11474

Segment the rod into 3 different regions ("left unbent", "bent", and "right unbent"), each having their respective "inner" and "outer" segment coordinates (e.g., FIG. 115), via:

11476

Draw a vertical line through the centroid of the rod bender's center rod-contouring surface and rotate the line counter-clockwise about the centroid by a small angle Define this line as the "left rotated line" (e.g., FIG 115)

11478

Define all rod coordinates to the left of the left rotated line as the "left unbent rod segment" with the "inner segment" represented by the path closest to the bender's center rod-contouring surface and "outer segment" represented by the path closest to the left roller (e.g., FIG 115)

(TO FIG. 114D)          FIG. 114C          (FROM FIG. 114D)

(FROM FIG. 114C)                                        (TO FIG. 114C)

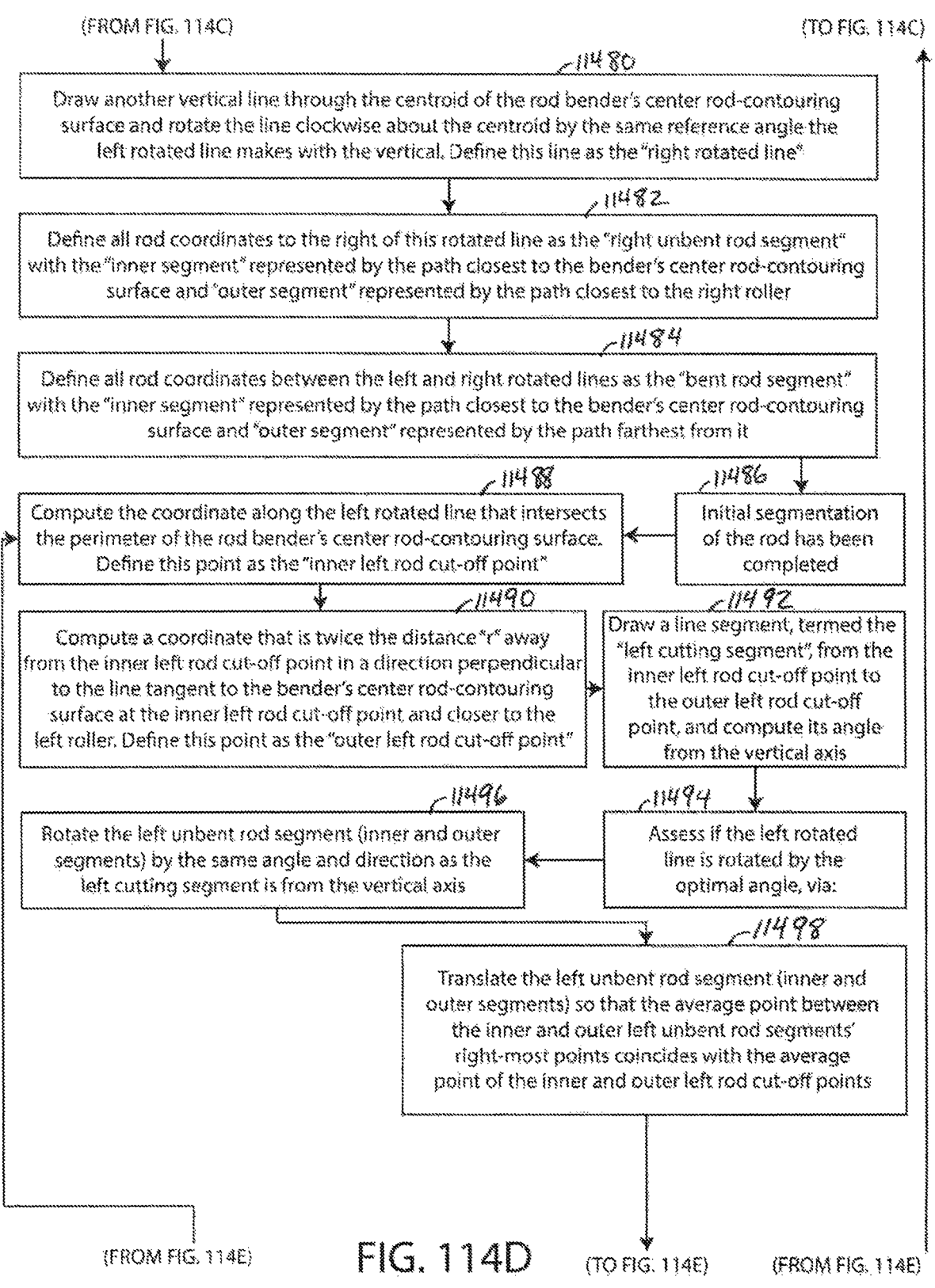

*11480*

Draw another vertical line through the centroid of the rod bender's center rod-contouring surface and rotate the line clockwise about the centroid by the same reference angle the left rotated line makes with the vertical. Define this line as the "right rotated line"

*11482*

Define all rod coordinates to the right of this rotated line as the "right unbent rod segment" with the "inner segment" represented by the path closest to the bender's center rod-contouring surface and "outer segment" represented by the path closest to the right roller

*11484*

Define all rod coordinates between the left and right rotated lines as the "bent rod segment" with the "inner segment" represented by the path closest to the bender's center rod-contouring surface and "outer segment" represented by the path farthest from it

*11488*

Compute the coordinate along the left rotated line that intersects the perimeter of the rod bender's center rod-contouring surface. Define this point as the "inner left rod cut-off point"

*11486*

Initial segmentation of the rod has been completed

*11490*

Compute a coordinate that is twice the distance "r" away from the inner left rod cut-off point in a direction perpendicular to the line tangent to the bender's center rod-contouring surface at the inner left rod cut-off point and closer to the left roller. Define this point as the "outer left rod cut-off point"

*11492*

Draw a line segment, termed the "left cutting segment", from the inner left rod cut-off point to the outer left rod cut-off point, and compute its angle from the vertical axis

*11496*

Rotate the left unbent rod segment (inner and outer segments) by the same angle and direction as the left cutting segment is from the vertical axis

*11494*

Assess if the left rotated line is rotated by the optimal angle, via:

*11498*

Translate the left unbent rod segment (inner and outer segments) so that the average point between the inner and outer left unbent rod segments' right-most points coincides with the average point of the inner and outer left rod cut-off points (FROM FIG. 114E)                FIG. 114D        (TO FIG. 114E)        (FROM FIG. 114E)

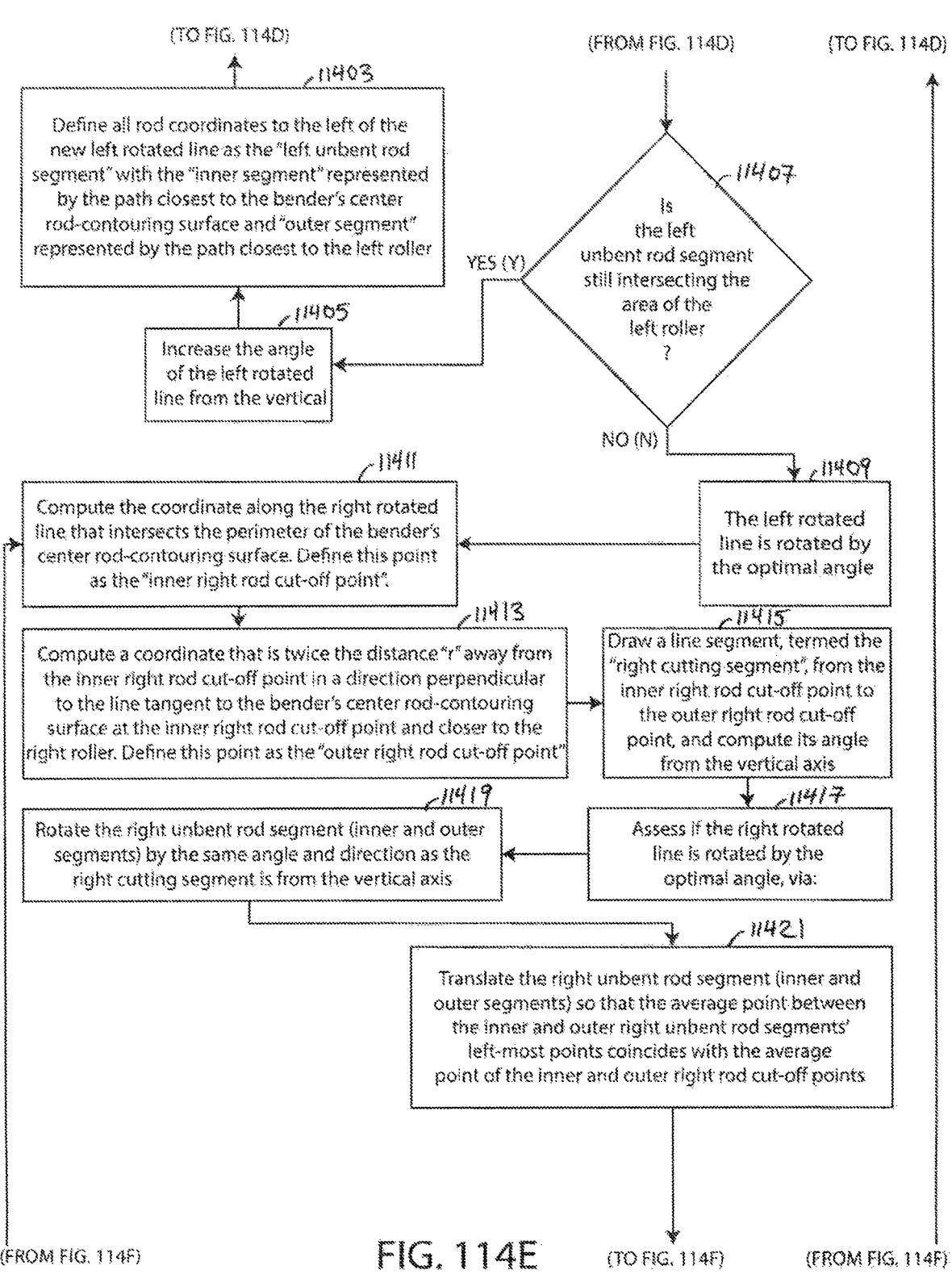

(TO FIG. 114D)     (FROM FIG. 114D)     (TO FIG. 114D)

11403

Define all rod coordinates to the left of the new left rotated line as the "left unbent rod segment" with the "inner segment" represented by the path closest to the bender's center rod-contouring surface and "outer segment" represented by the path closest to the left roller

11407

Is the left unbent rod segment still intersecting the area of the left roller ?

YES (Y)

11405

Increase the angle of the left rotated line from the vertical

NO (N)

11409

The left rotated line is rotated by the optimal angle

11411

Compute the coordinate along the right rotated line that intersects the perimeter of the bender's center rod-contouring surface. Define this point as the "inner right rod cut-off point".

11413

Compute a coordinate that is twice the distance "r" away from the inner right rod cut-off point in a direction perpendicular to the line tangent to the bender's center rod-contouring surface at the inner right rod cut-off point and closer to the right roller. Define this point as the "outer right rod cut-off point"

11415

Draw a line segment, termed the "right cutting segment", from the inner right rod cut-off point to the outer right rod cut-off point, and compute its angle from the vertical axis

11419

Rotate the right unbent rod segment (inner and outer segments) by the same angle and direction as the right cutting segment is from the vertical axis

11417

Assess if the right rotated line is rotated by the optimal angle, via:

11421

Translate the right unbent rod segment (inner and outer segments) so that the average point between the inner and outer right unbent rod segments' left-most points coincides with the average point of the inner and outer right rod cut-off points (FROM FIG. 114F)     FIG. 114E     (TO FIG. 114F)     (FROM FIG. 114F)

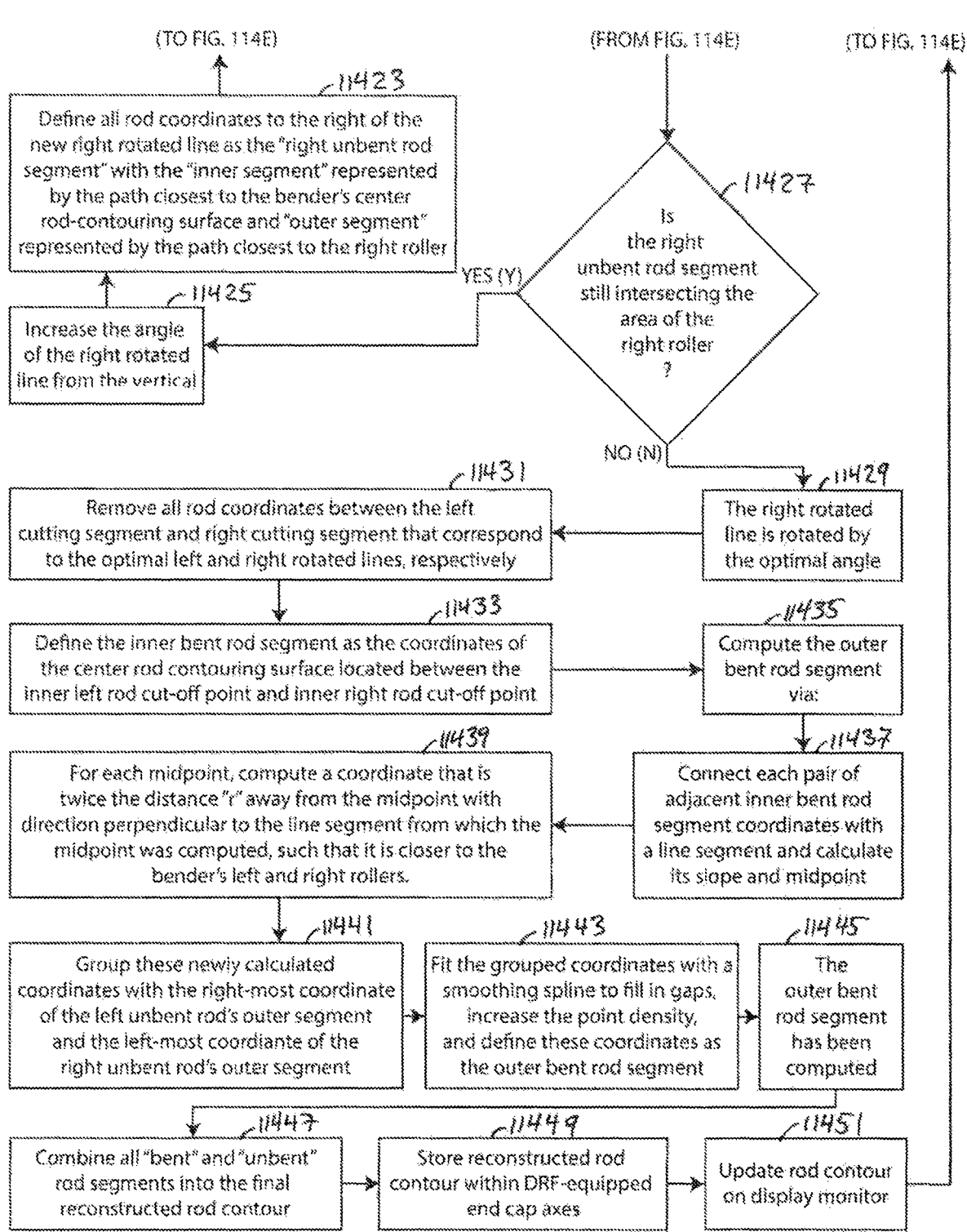

(TO FIG. 114E)                    (FROM FIG. 114E)                    (TO FIG. 114E)

11423
Define all rod coordinates to the right of the new right rotated line as the "right unbent rod segment" with the "inner segment" represented by the path closest to the bender's center rod-contouring surface and "outer segment" represented by the path closest to the right roller 11427
Is the right unbent rod segment still intersecting the area of the right roller?

YES (Y)

11425
Increase the angle of the right rotated line from the vertical

NO (N)

11429
The right rotated line is rotated by the optimal angle

11431
Remove all rod coordinates between the left cutting segment and right cutting segment that correspond to the optimal left and right rotated lines, respectively 11433
Define the inner bent rod segment as the coordinates of the center rod contouring surface located between the inner left rod cut-off point and inner right rod cut-off point 11435
Compute the outer bent rod segment via:

11439
For each midpoint, compute a coordinate that is twice the distance "r" away from the midpoint with direction perpendicular to the line segment from which the midpoint was computed, such that it is closer to the bender's left and right rollers.

11437
Connect each pair of adjacent inner bent rod segment coordinates with a line segment and calculate its slope and midpoint 11441
Group these newly calculated coordinates with the right-most coordinate of the left unbent rod's outer segment and the left-most coordiante of the right unbent rod's outer segment 11443
Fit the grouped coordinates with a smoothing spline to fill in gaps, increase the point density, and define these coordinates as the outer bent rod segment 11445
The outer bent rod segment has been computed 11447
Combine all "bent" and "unbent" rod segments into the final reconstructed rod contour 11449
Store reconstructed rod contour within DRF-equipped end cap axes 11451
Update rod contour on display monitor

FIG. 114F

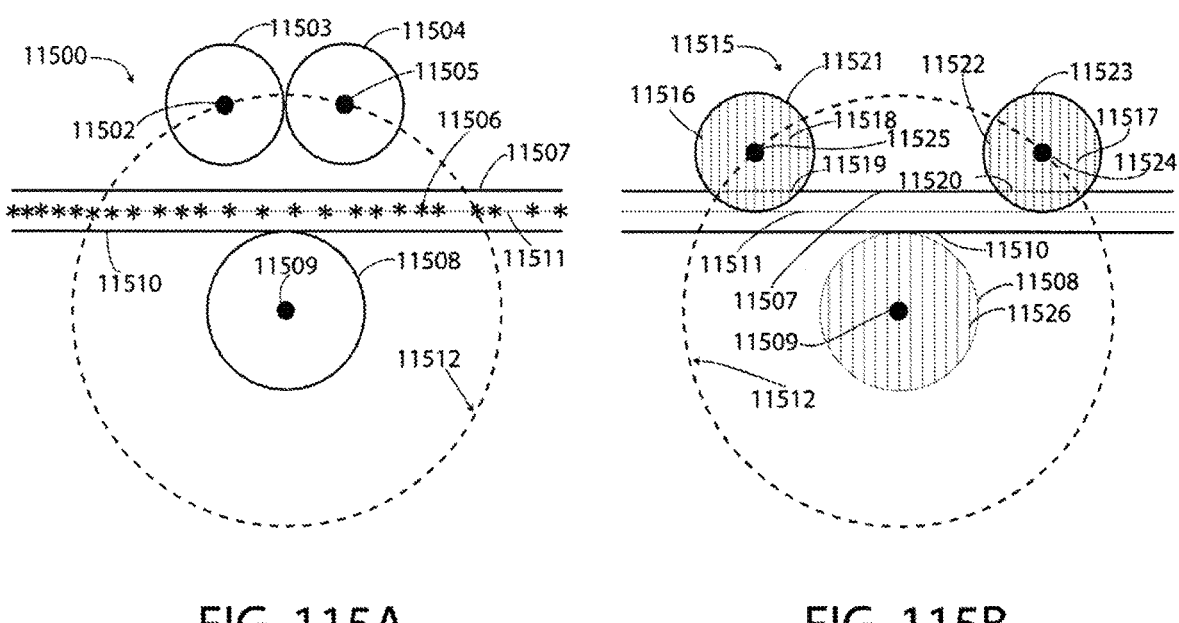
FIG. 115A                    FIG. 115B
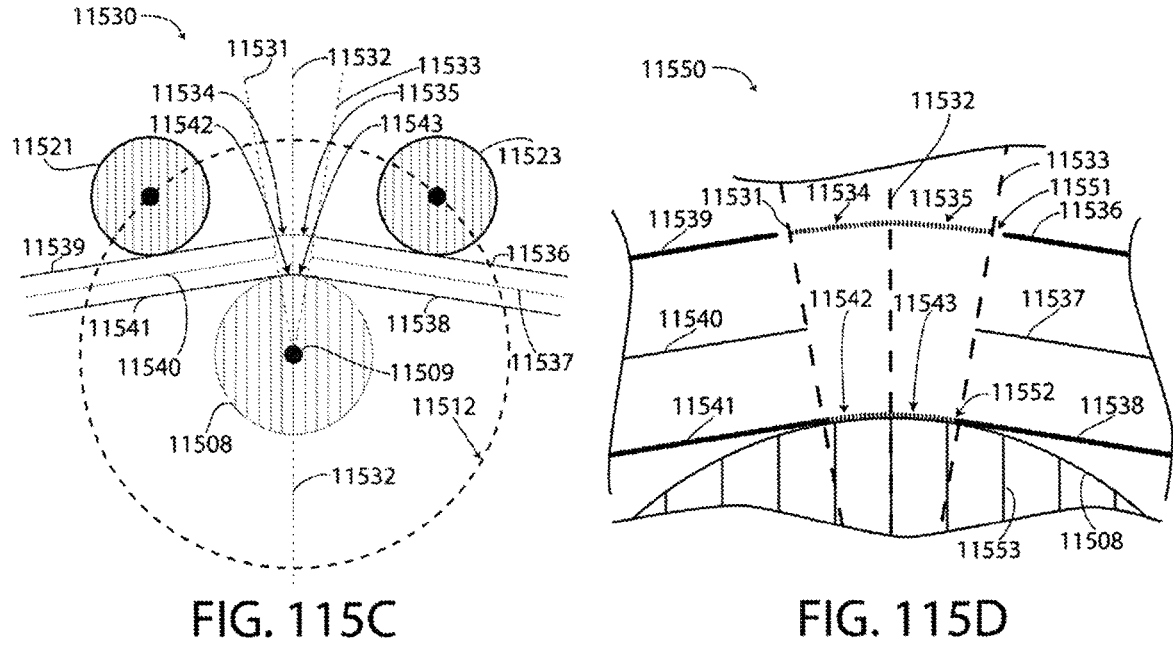
FIG. 115C                    FIG. 115D

FIG. 118A
FIG. 118B
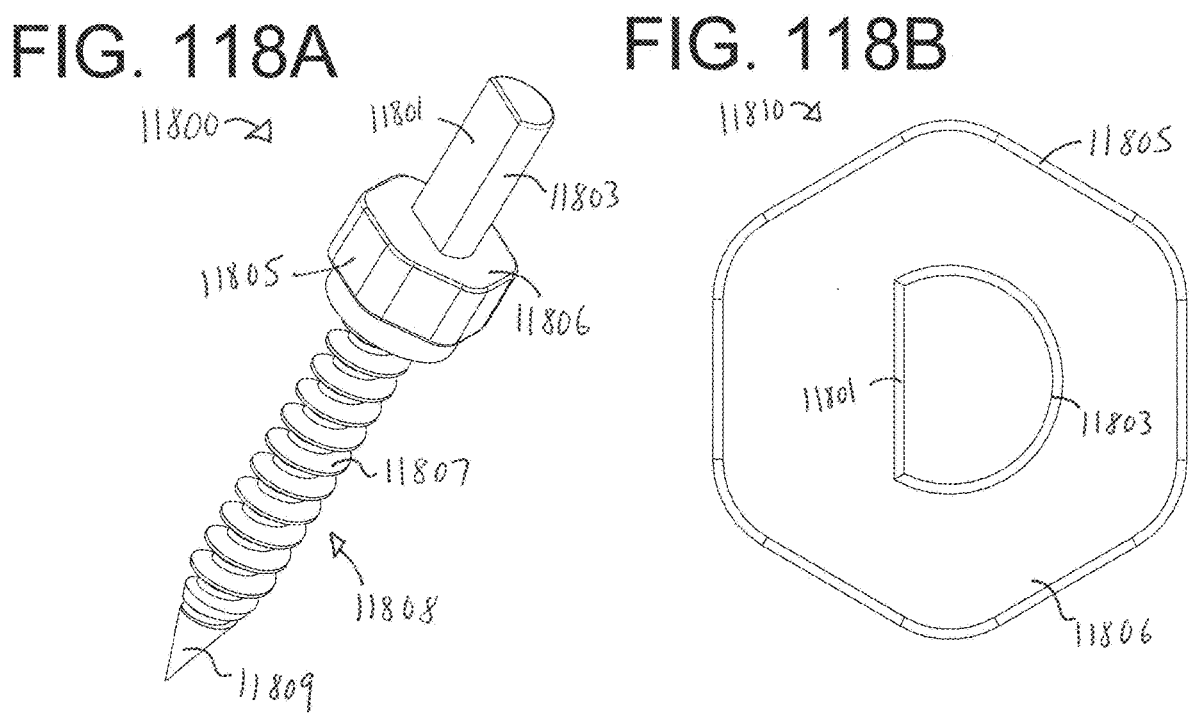
FIG. 118C
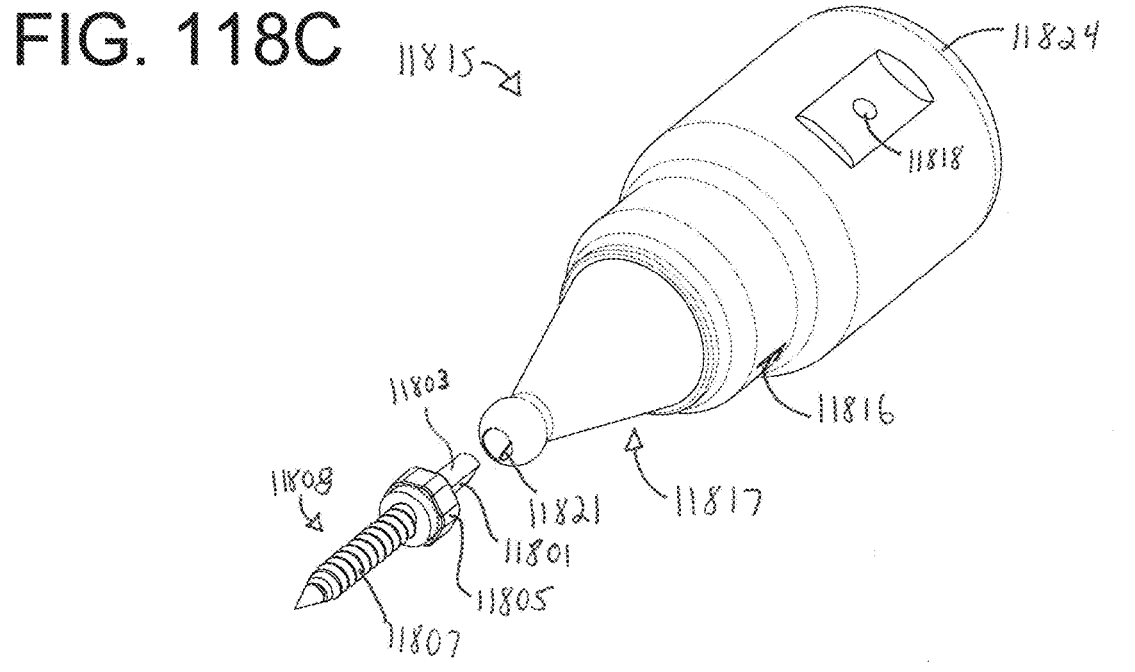

11930

11938

11937

11936

11935

11933

11932

11931

11901

11903

11908

11907

12100

12103

12105

12103

12103

12105

12103

12101

12109

12107

12106

12135

12131

12103

12123

12125

FIG. 122A
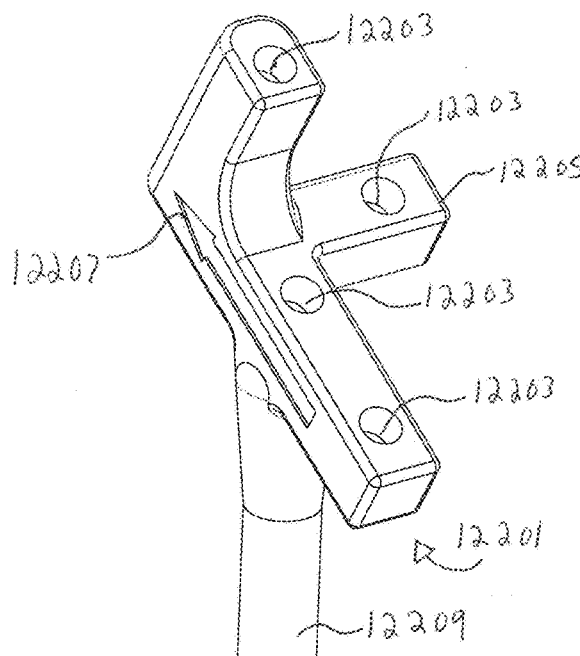
FIG. 122B
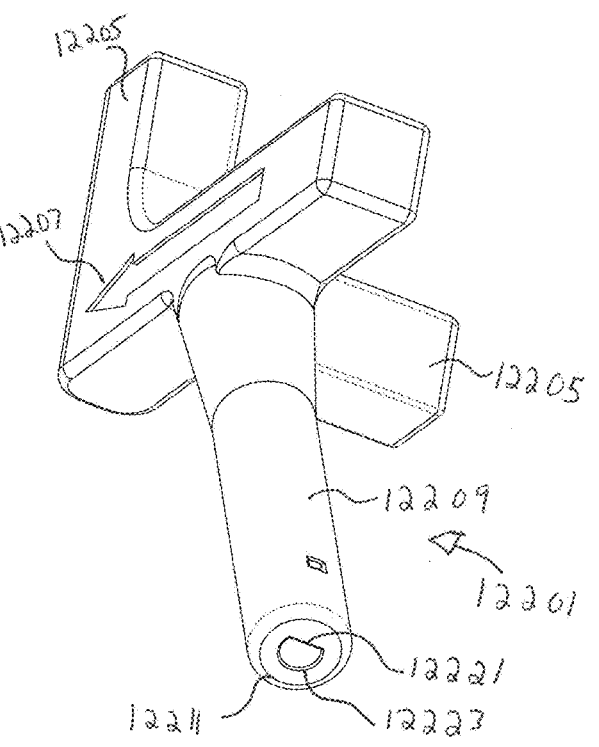
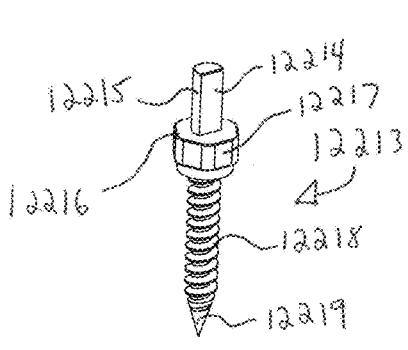
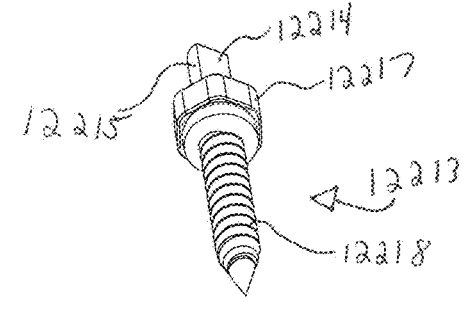

12320

12305

12307

12301

12309

12308

12311

12315

12307

12301

12309

12308

12313

12325

12303

12303

12303

12307

12301

12309

12308

12313

12311

FIG. 125C
FIG. 125D
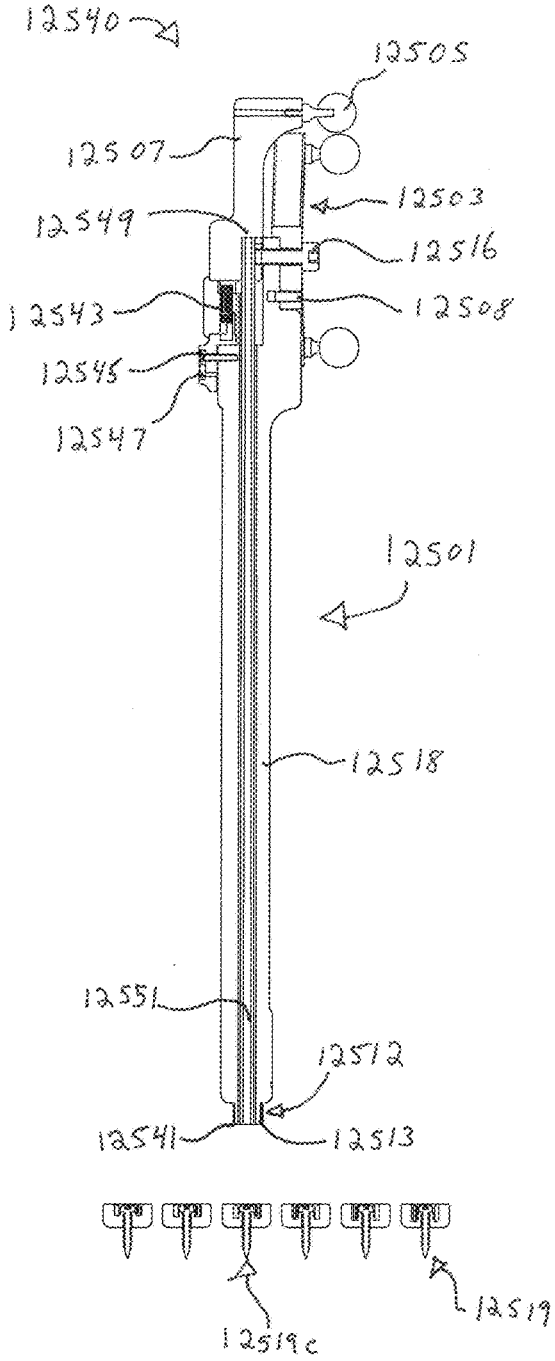
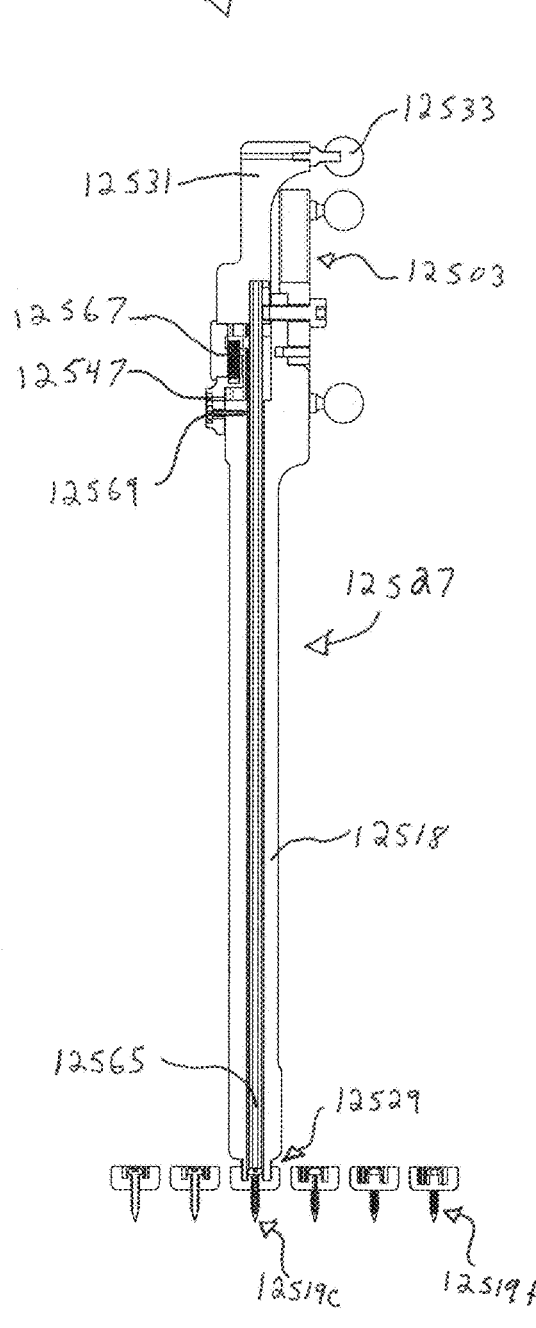

12600

12607

12607

12622

12617

12615

12616

12628

12630

12609

12603

12624

12614

12619

12621

12625

12623

12627

12601

12607

12607

12613

12611

12613

FIG. 128A
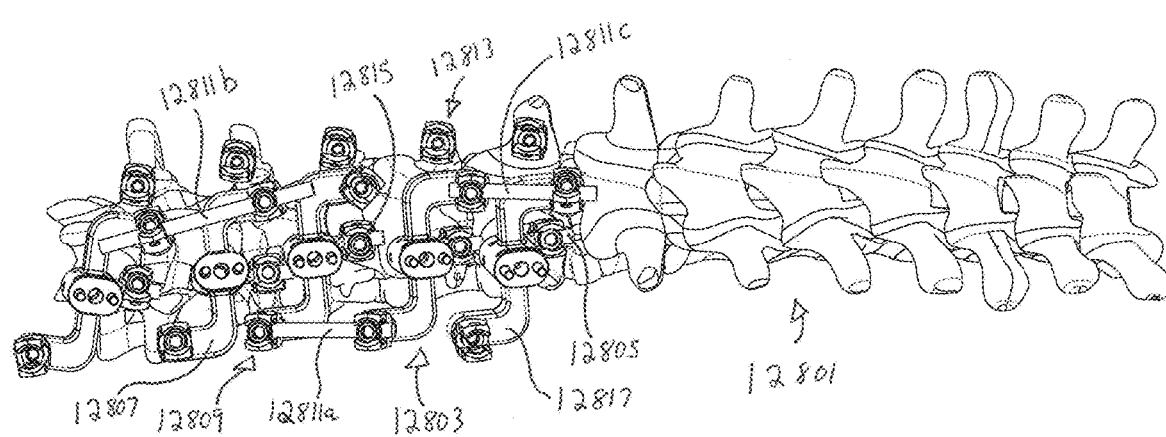
FIG. 128B
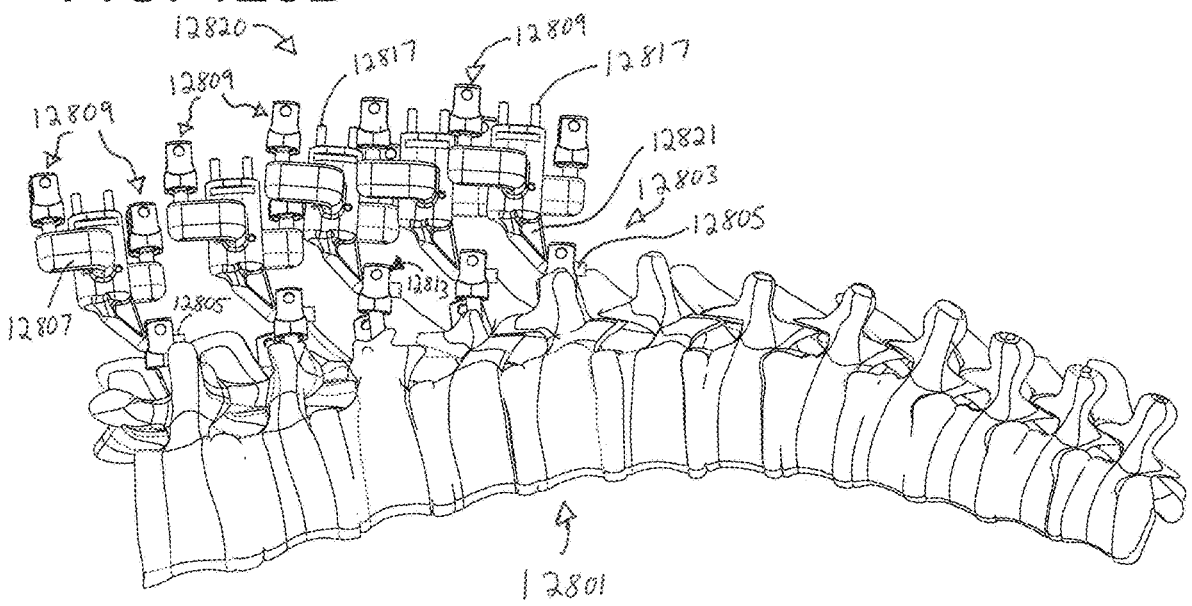

Figure 133G:
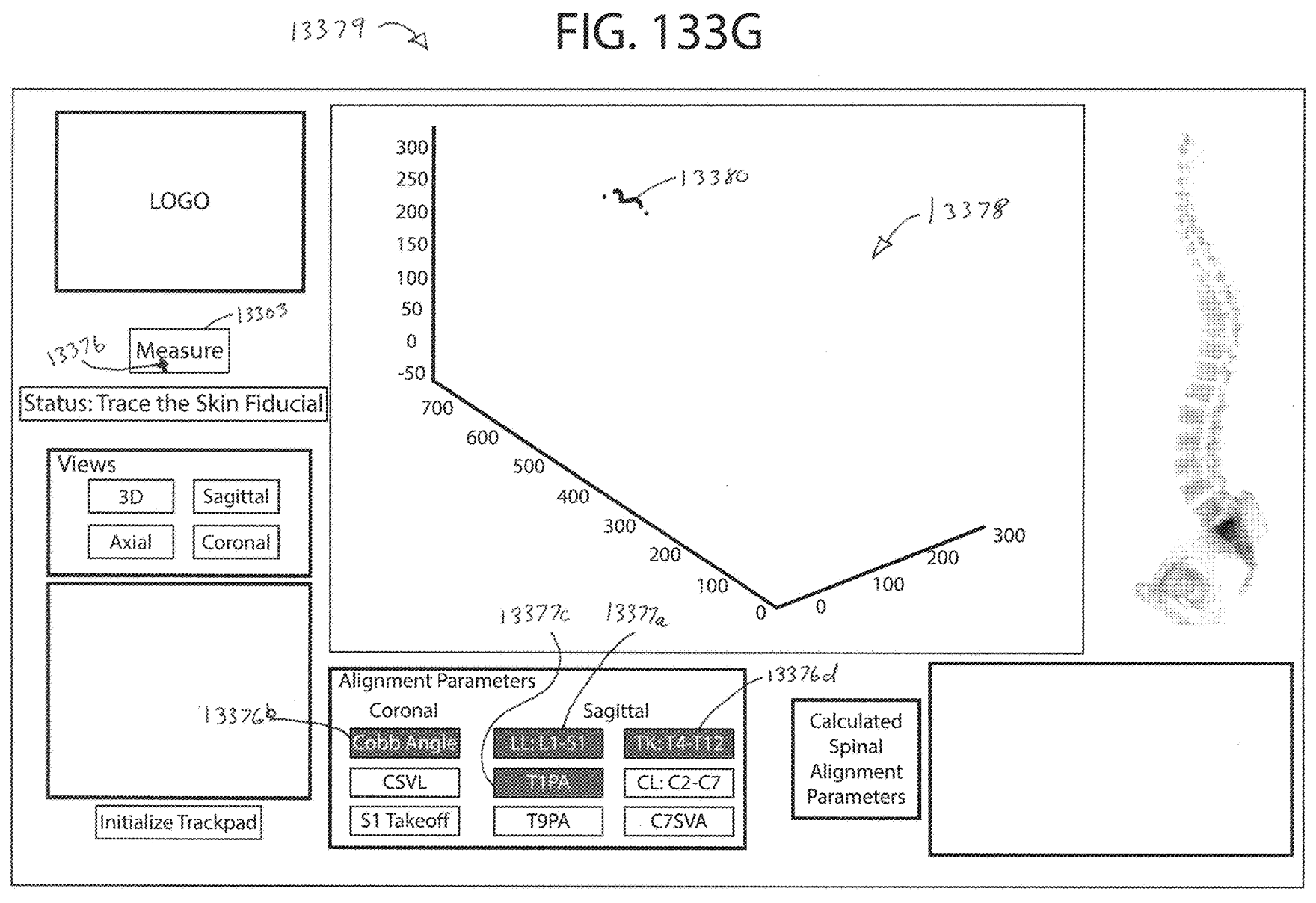

LOGO

Measure

Status: Trace the Skin Fiducial

Views

3D | Sagittal
Axial | Coronal

Alignment Parameters

Coronal
COBB ANGLE
CSVL
S1 Takeoff

Sagittal
PI-LL-S1 | LS-PI/LL-T12
TPA | CL: C2-C7
T9PA | C7SVA

Calculated Spinal Alignment Parameters

Initialize Trackpad

Figure 133N:
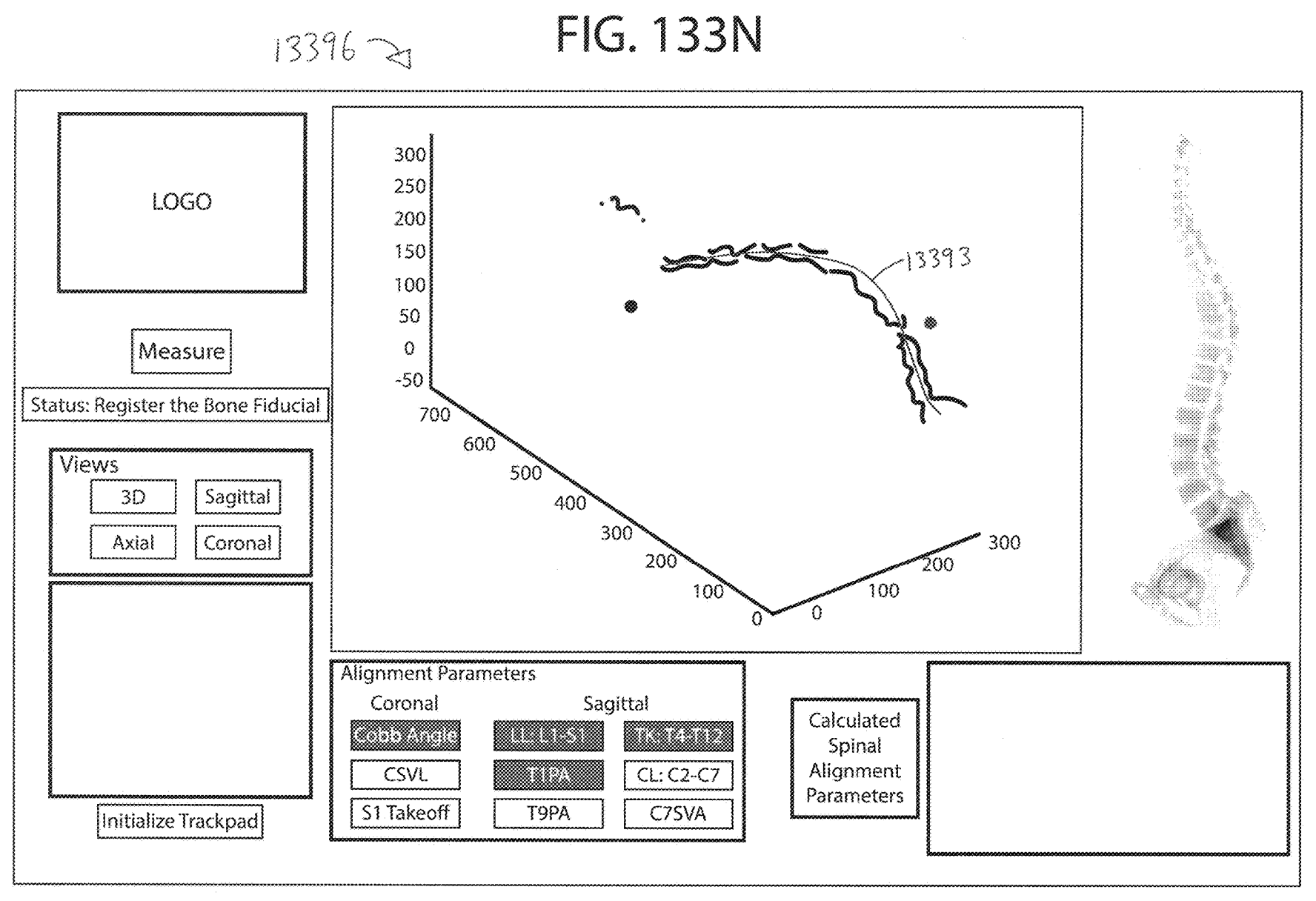

LOGO

Measure

Status: Register the Bone Fiducial

Views

3D    Sagittal

Axial    Coronal

Initialize Trackpad

Alignment Parameters

Coronal    Sagittal

Cobb Angle    PI LL S    PI: PI-LL

CSVL    TPA    CL: C2-C7

S1 Takeoff    T9PA    C7SVA

Calculated Spinal Alignment Parameters

FIG. 1330
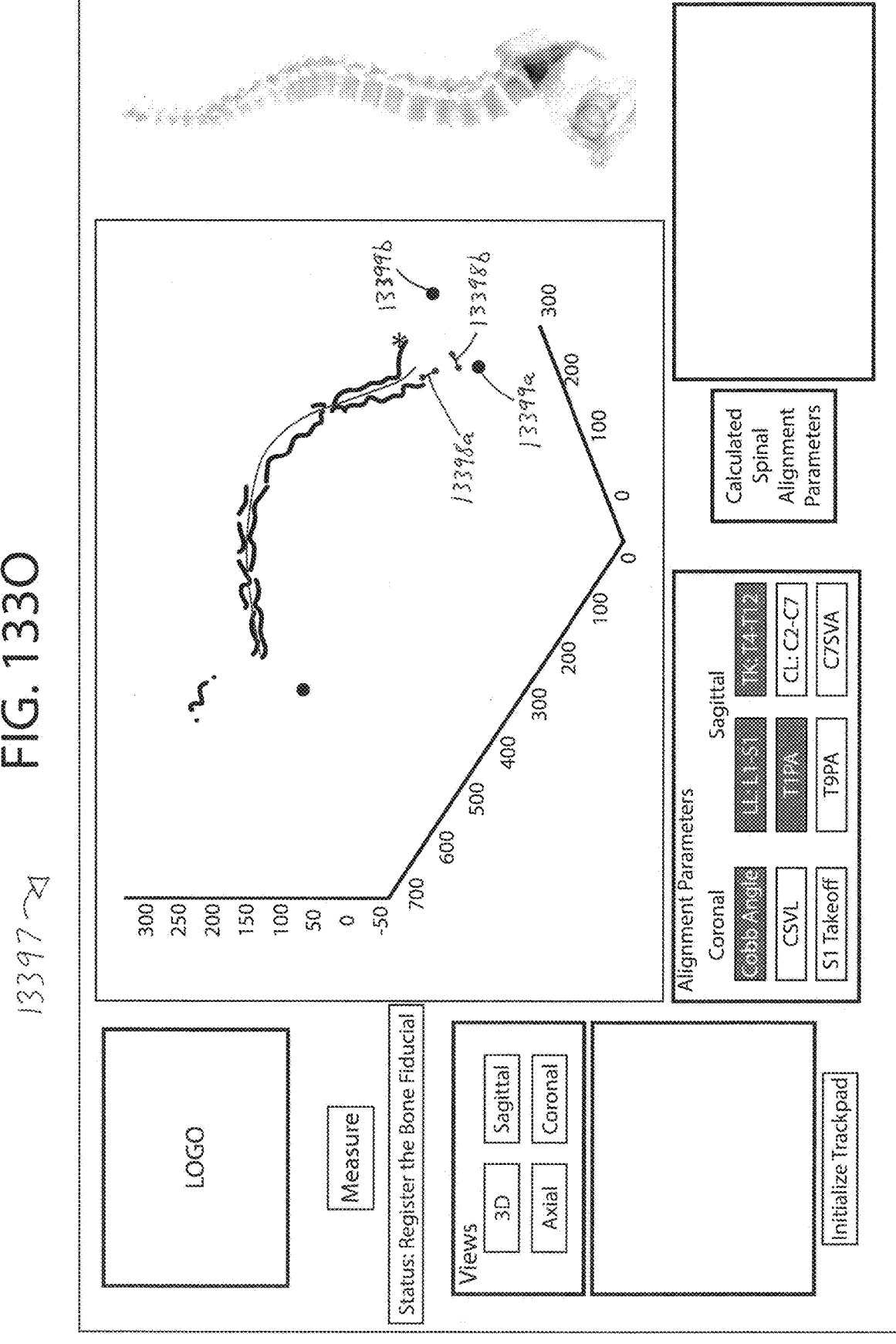

Logo

Status:
Register
the
L4 Vertebra

13656

Axial Plane Summary: Max CCW Twist (HF) Angle = -6.5 Degrees

13658

13651

13662

13660

Logo

Posterior

Anterior

Right (Head First)

Left (Head First)

Status: 3D Assessment Replay

13664

13602

13666

13670

13668

Logo

Posterior

Anterior

Right

Left

Superior

Inferior

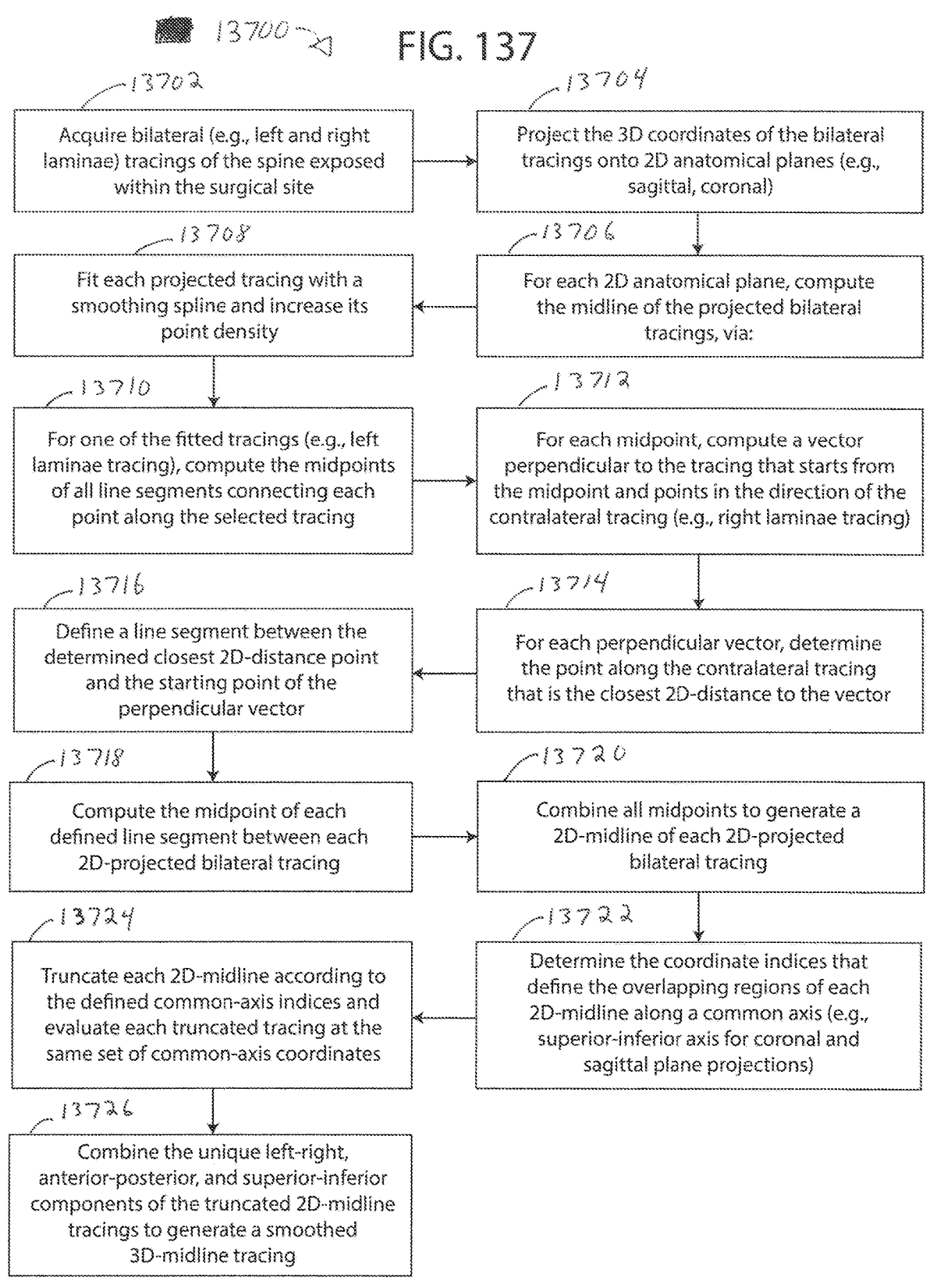

13702
Acquire bilateral (e.g., left and right laminae) tracings of the spine exposed within the surgical site 13704
Project the 3D coordinates of the bilateral tracings onto 2D anatomical planes (e.g., sagittal, coronal)

13708
Fit each projected tracing with a smoothing spline and increase its point density 13706
For each 2D anatomical plane, compute the midline of the projected bilateral tracings, via:

13710
For one of the fitted tracings (e.g., left laminae tracing), compute the midpoints of all line segments connecting each point along the selected tracing 13712
For each midpoint, compute a vector perpendicular to the tracing that starts from the midpoint and points in the direction of the contralateral tracing (e.g., right laminae tracing)

13716
Define a line segment between the determined closest 2D-distance point and the starting point of the perpendicular vector 13714
For each perpendicular vector, determine the point along the contralateral tracing that is the closest 2D-distance to the vector 13718
Compute the midpoint of each defined line segment between each 2D-projected bilateral tracing 13720
Combine all midpoints to generate a 2D-midline of each 2D-projected bilateral tracing 13724
Truncate each 2D-midline according to the defined common-axis indices and evaluate each truncated tracing at the same set of common-axis coordinates 13722
Determine the coordinate indices that define the overlapping regions of each 2D-midline along a common axis (e.g., superior-inferior axis for coronal and sagittal plane projections)

13726
Combine the unique left-right, anterior-posterior, and superior-inferior components of the truncated 2D-midline tracings to generate a smoothed 3D-midline tracing

FIG. 138A

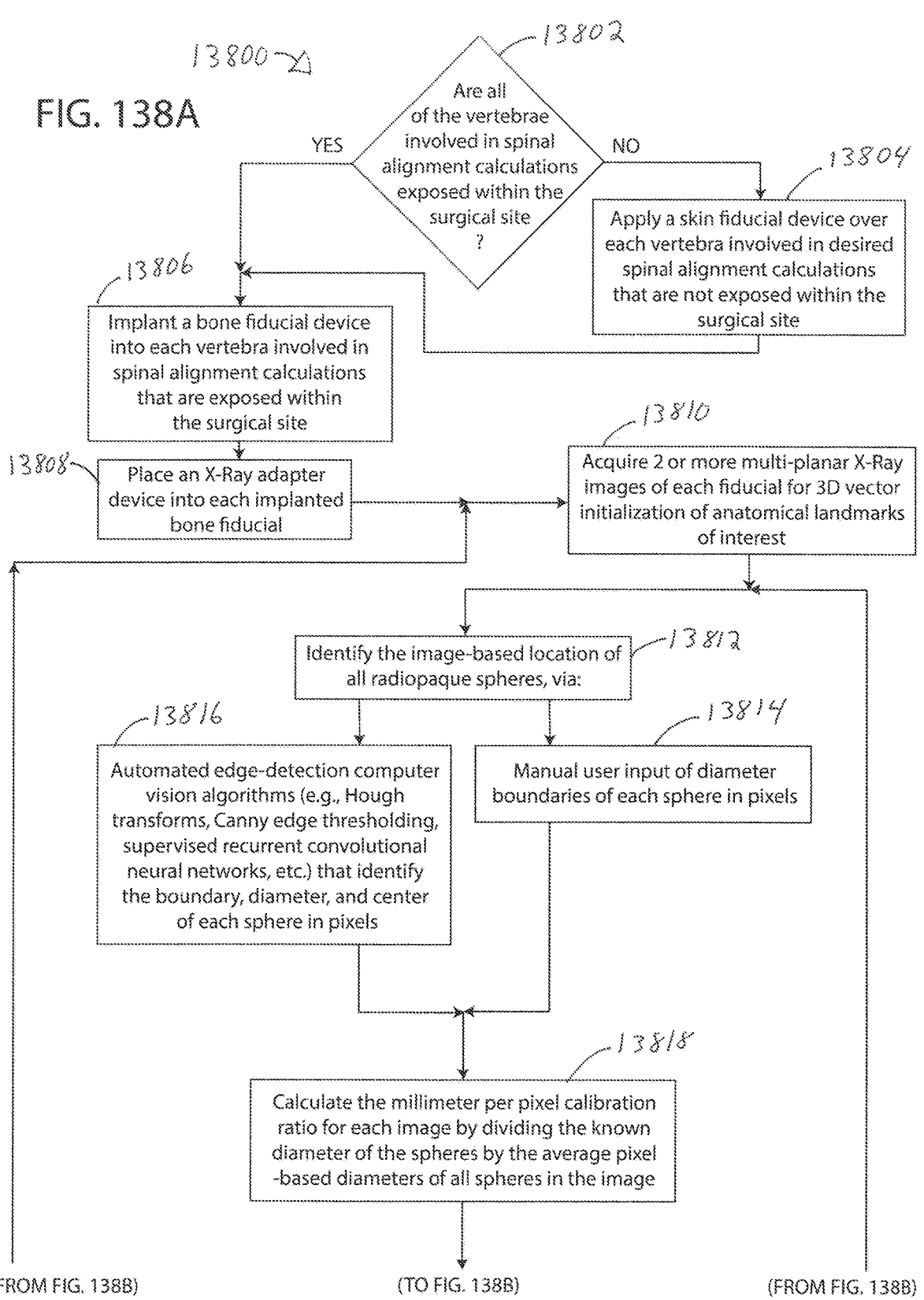

13800

13802

Are all of the vertebrae involved in spinal alignment calculations exposed within the surgical site ?

YES

NO

13804

Apply a skin fiducial device over each vertebra involved in desired spinal alignment calculations that are not exposed within the surgical site

13806

Implant a bone fiducial device into each vertebra involved in spinal alignment calculations that are exposed within the surgical site

13808

Place an X-Ray adapter device into each implanted bone fiducial

13810

Acquire 2 or more multi-planar X-Ray images of each fiducial for 3D vector initialization of anatomical landmarks of interest

13812

Identify the image-based location of all radiopaque spheres, via:

13816

Automated edge-detection computer vision algorithms (e.g., Hough transforms, Canny edge thresholding, supervised recurrent convolutional neural networks, etc.) that identify the boundary, diameter, and center of each sphere in pixels

13814

Manual user input of diameter boundaries of each sphere in pixels

13818

Calculate the millimeter per pixel calibration ratio for each image by dividing the known diameter of the spheres by the average pixel-based diameters of all spheres in the image (FROM FIG. 138B)          (TO FIG. 138B)          (FROM FIG. 138B)

FIG. 138B
(FROM FIG. 138A)

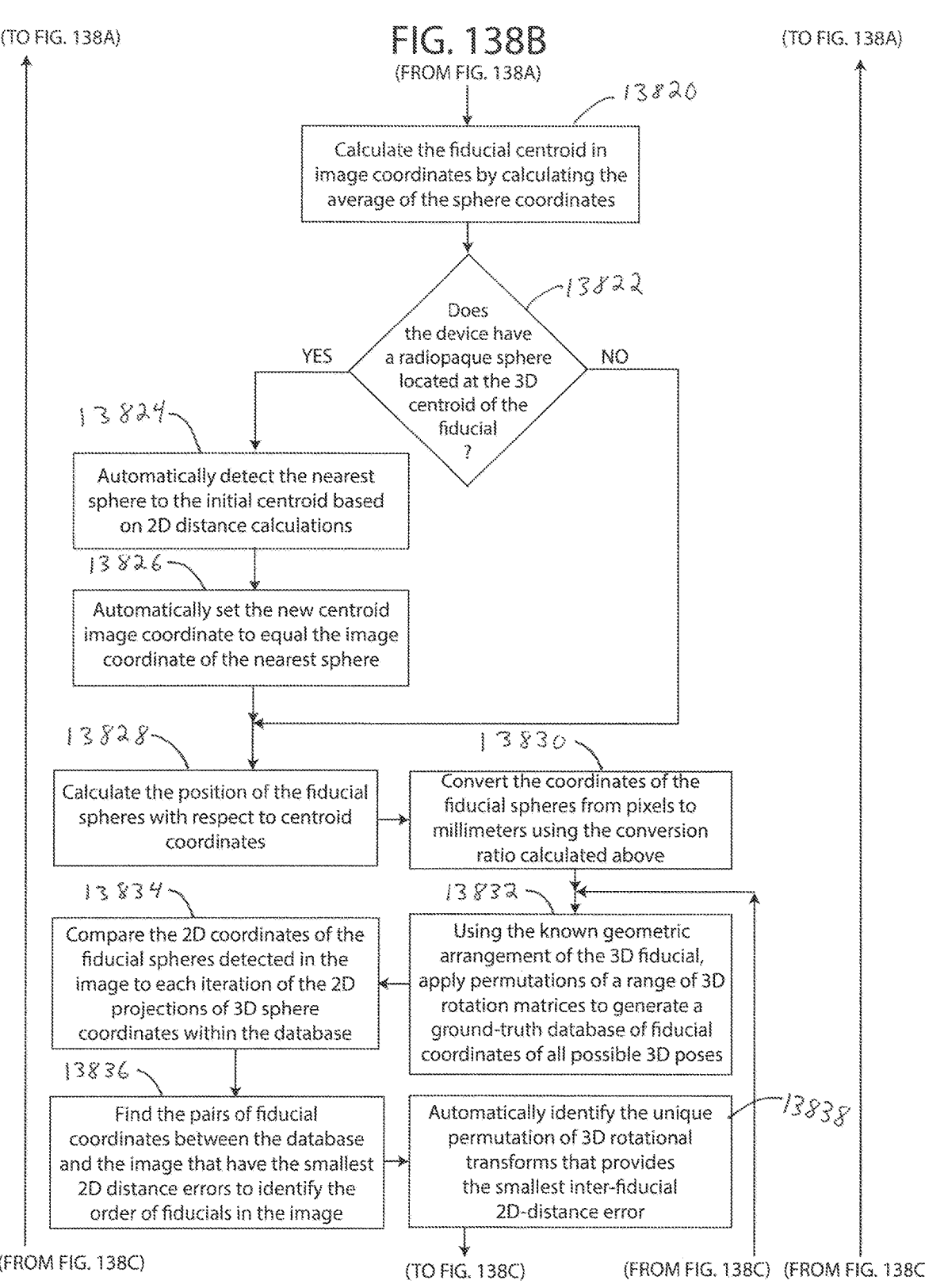

Calculate the fiducial centroid in image coordinates by calculating the average of the sphere coordinates

13822

Does the device have a radiopaque sphere located at the 3D centroid of the fiducial ?

YES

NO

13824

Automatically detect the nearest sphere to the initial centroid based on 2D distance calculations

13826

Automatically set the new centroid image coordinate to equal the image coordinate of the nearest sphere

13828

Calculate the position of the fiducial spheres with respect to centroid coordinates

13830

Convert the coordinates of the fiducial spheres from pixels to millimeters using the conversion ratio calculated above

13834

Compare the 2D coordinates of the fiducial spheres detected in the image to each iteration of the 2D projections of 3D sphere coordinates within the database

13832

Using the known geometric arrangement of the 3D fiducial, apply permutations of a range of 3D rotation matrices to generate a ground-truth database of fiducial coordinates of all possible 3D poses

13836

Find the pairs of fiducial coordinates between the database and the image that have the smallest 2D distance errors to identify the order of fiducials in the image

13838

Automatically identify the unique permutation of 3D rotational transforms that provides the smallest inter-fiducial 2D-distance error (TO FIG. 138A)

(FROM FIG. 138C)

(TO FIG. 138C)

(FROM FIG. 138C)    (FROM FIG. 138C)

(FROM FIG. 138B)

FIG. 138D

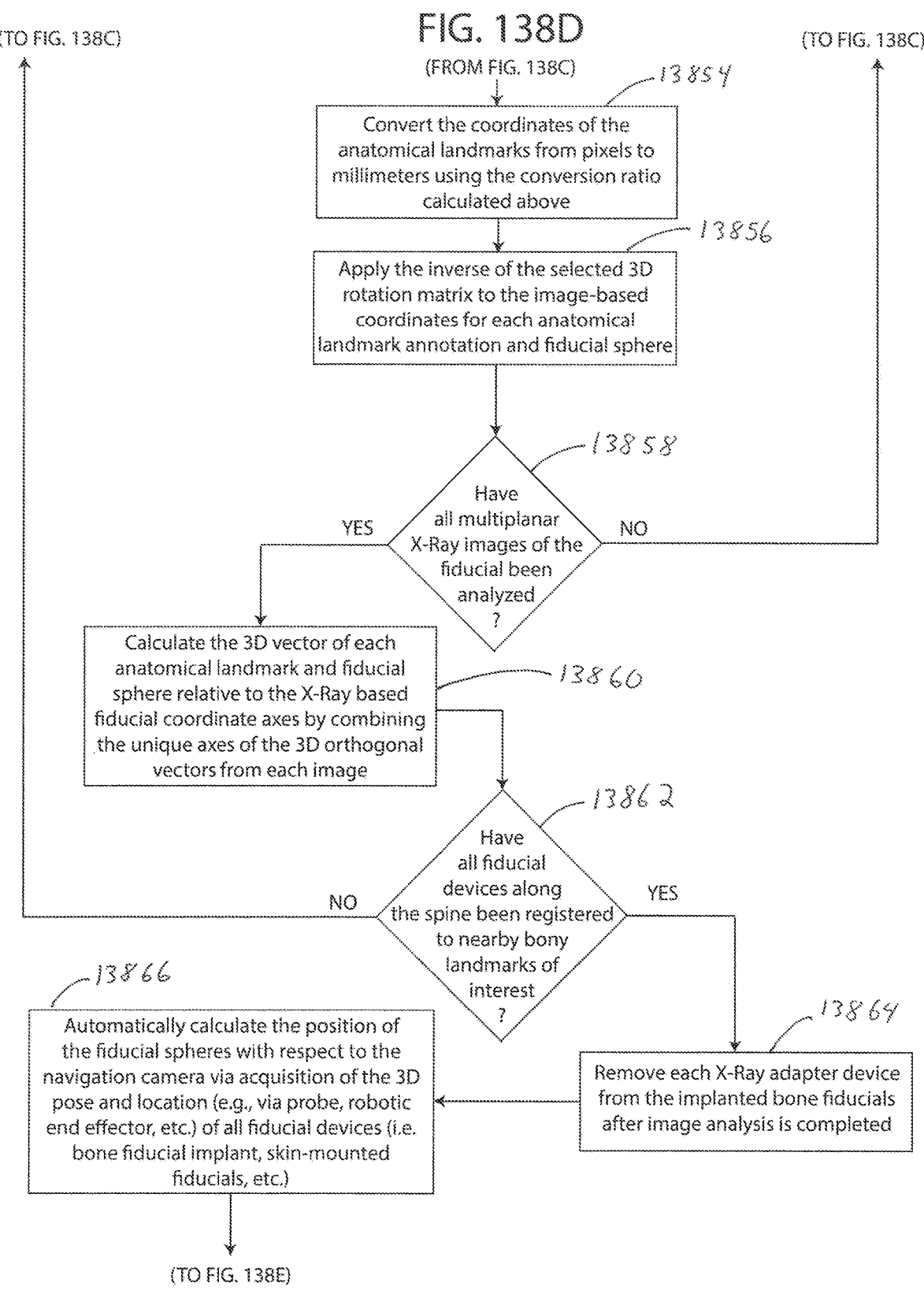

(TO FIG. 138C)

(FROM FIG. 138C)

13854

Convert the coordinates of the anatomical landmarks from pixels to millimeters using the conversion ratio calculated above

13856

Apply the inverse of the selected 3D rotation matrix to the image-based coordinates for each anatomical landmark annotation and fiducial sphere

13858

Have all multiplanar X-Ray images of the fiducial been analyzed?

YES     NO (TO FIG. 138C)

13860

Calculate the 3D vector of each anatomical landmark and fiducial sphere relative to the X-Ray based fiducial coordinate axes by combining the unique axes of the 3D orthogonal vectors from each image

13862

Have all fiducial devices along the spine been registered to nearby bony landmarks of interest?

NO     YES

13866

Automatically calculate the position of the fiducial spheres with respect to the navigation camera via acquisition of the 3D pose and location (e.g., via probe, robotic end effector, etc.) of all fiducial devices (i.e. bone fiducial implant, skin-mounted fiducials, etc.)

13864

Remove each X-Ray adapter device from the implanted bone fiducials after image analysis is completed (TO FIG. 138E)

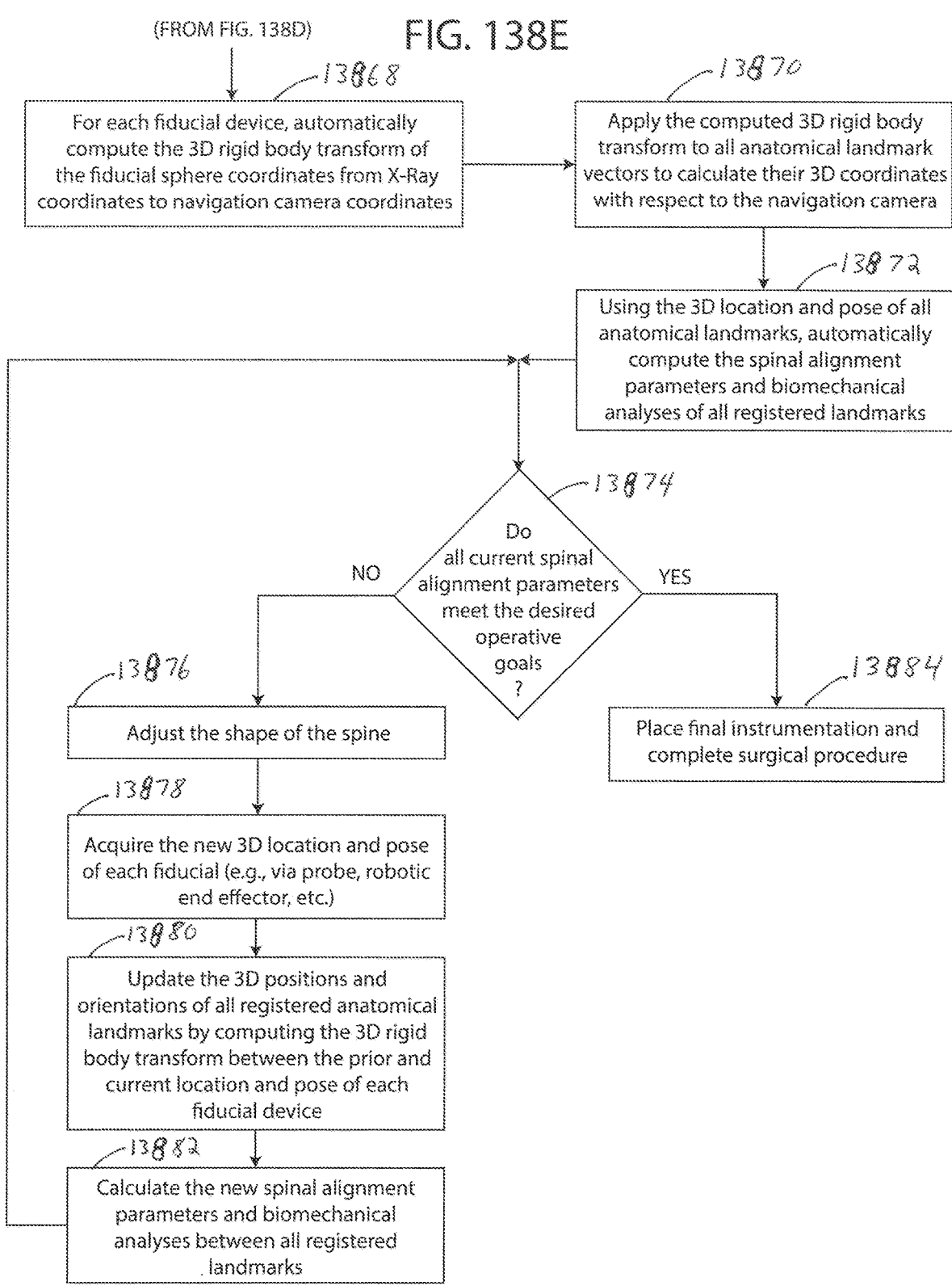

(FROM FIG. 138D)

For each fiducial device, automatically compute the 3D rigid body transform of the fiducial sphere coordinates from X-Ray coordinates to navigation camera coordinates

13870

Apply the computed 3D rigid body transform to all anatomical landmark vectors to calculate their 3D coordinates with respect to the navigation camera

13872

Using the 3D location and pose of all anatomical landmarks, automatically compute the spinal alignment parameters and biomechanical analyses of all registered landmarks

13874

Do all current spinal alignment parameters meet the desired operative goals ?

NO

YES

13876

Adjust the shape of the spine

13884

Place final instrumentation and complete surgical procedure

13878

Acquire the new 3D location and pose of each fiducial (e.g., via probe, robotic end effector, etc.)

13880

Update the 3D positions and orientations of all registered anatomical landmarks by computing the 3D rigid body transform between the prior and current location and pose of each fiducial device

13882

Calculate the new spinal alignment parameters and biomechanical analyses between all registered landmarks

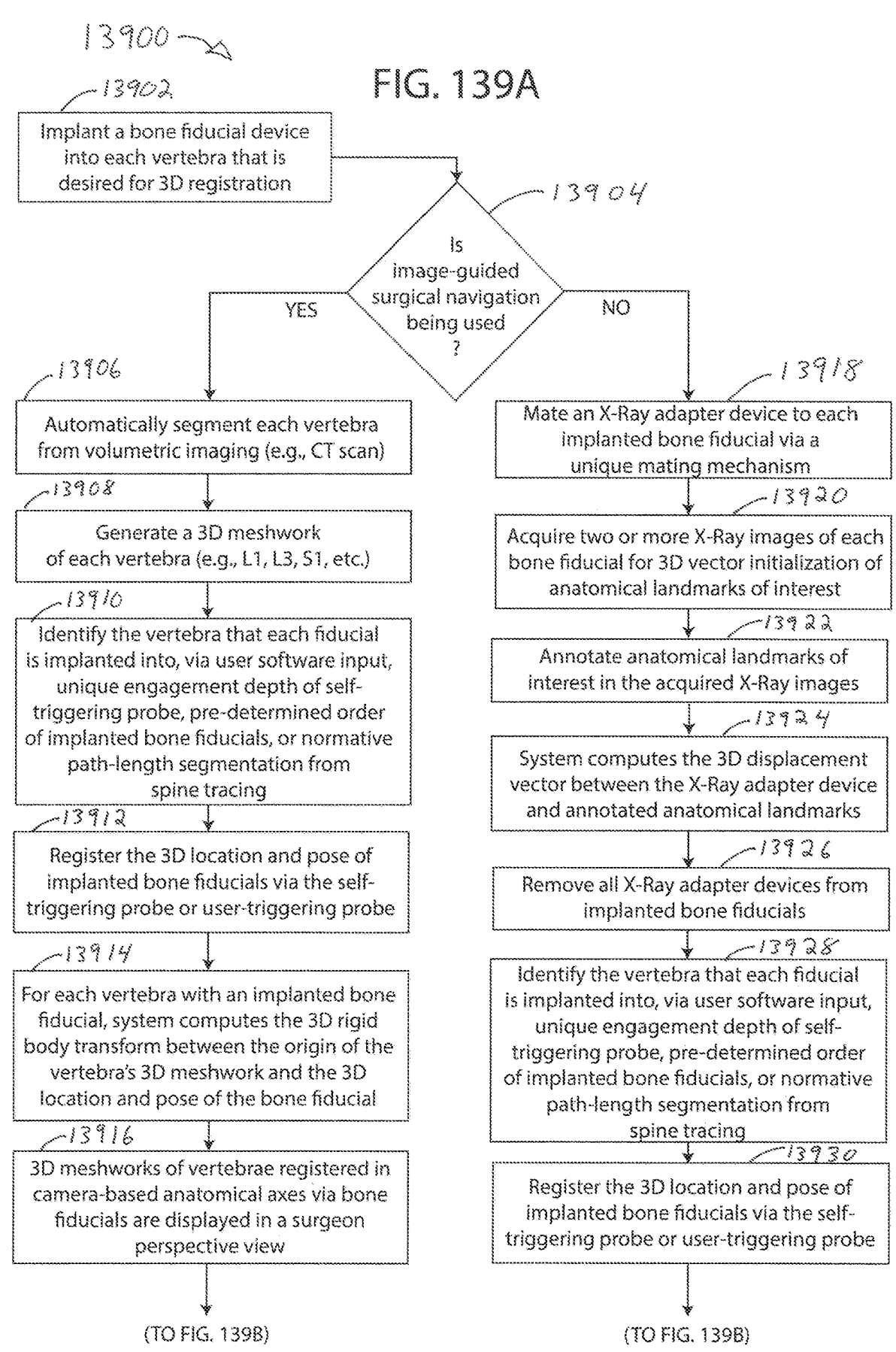

13902

Implant a bone fiducial device into each vertebra that is desired for 3D registration

13904

Is image-guided surgical navigation being used ?

YES     NO

13906

Automatically segment each vertebra from volumetric imaging (e.g., CT scan)

13908

Generate a 3D meshwork of each vertebra (e.g., L1, L3, S1, etc.)

13910

Identify the vertebra that each fiducial is implanted into, via user software input, unique engagement depth of self-triggering probe, pre-determined order of implanted bone fiducials, or normative path-length segmentation from spine tracing

13912

Register the 3D location and pose of implanted bone fiducials via the self-triggering probe or user-triggering probe

13914

For each vertebra with an implanted bone fiducial, system computes the 3D rigid body transform between the origin of the vertebra's 3D meshwork and the 3D location and pose of the bone fiducial

13916

3D meshworks of vertebrae registered in camera-based anatomical axes via bone fiducials are displayed in a surgeon perspective view (TO FIG. 139B)

13918

Mate an X-Ray adapter device to each implanted bone fiducial via a unique mating mechanism

13920

Acquire two or more X-Ray images of each bone fiducial for 3D vector initialization of anatomical landmarks of interest

13922

Annotate anatomical landmarks of interest in the acquired X-Ray images

13924

System computes the 3D displacement vector between the X-Ray adapter device and annotated anatomical landmarks

13926

Remove all X-Ray adapter devices from implanted bone fiducials

13928

Identify the vertebra that each fiducial is implanted into, via user software input, unique engagement depth of self-triggering probe, pre-determined order of implanted bone fiducials, or normative path-length segmentation from spine tracing

13930

Register the 3D location and pose of implanted bone fiducials via the self-triggering probe or user-triggering probe (TO FIG. 139B)

FIG. 139B

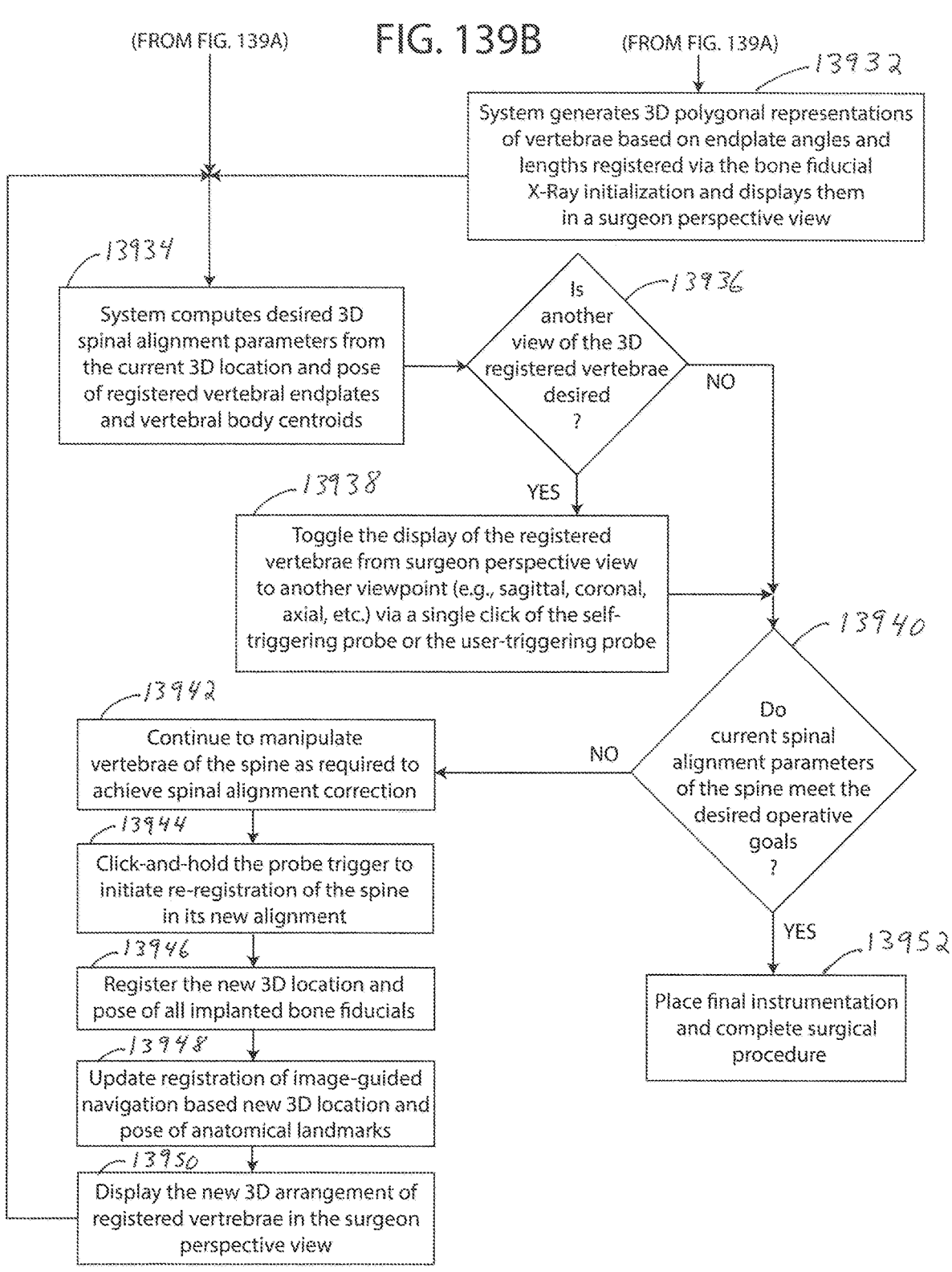

(FROM FIG. 139A)     (FROM FIG. 139A)     13932

System generates 3D polygonal representations of vertebrae based on endplate angles and lengths registered via the bone fiducial X-Ray initialization and displays them in a surgeon perspective view

13934

System computes desired 3D spinal alignment parameters from the current 3D location and pose of registered vertebral endplates and vertebral body centroids

13936

Is another view of the 3D registered vertebrae desired ?   NO

YES

13938

Toggle the display of the registered vertebrae from surgeon perspective view to another viewpoint (e.g., sagittal, coronal, axial, etc.) via a single click of the self-triggering probe or the user-triggering probe

13940

Do current spinal alignment parameters of the spine meet the desired operative goals ?

13942

Continue to manipulate vertebrae of the spine as required to achieve spinal alignment correction   NO

13944

Click-and-hold the probe trigger to initiate re-registration of the spine in its new alignment

13946

Register the new 3D location and pose of all implanted bone fiducials

13948

Update registration of image-guided navigation based new 3D location and pose of anatomical landmarks

13950

Display the new 3D arrangement of registered vertebrae in the surgeon perspective view

YES   13952

Place final instrumentation and complete surgical procedure

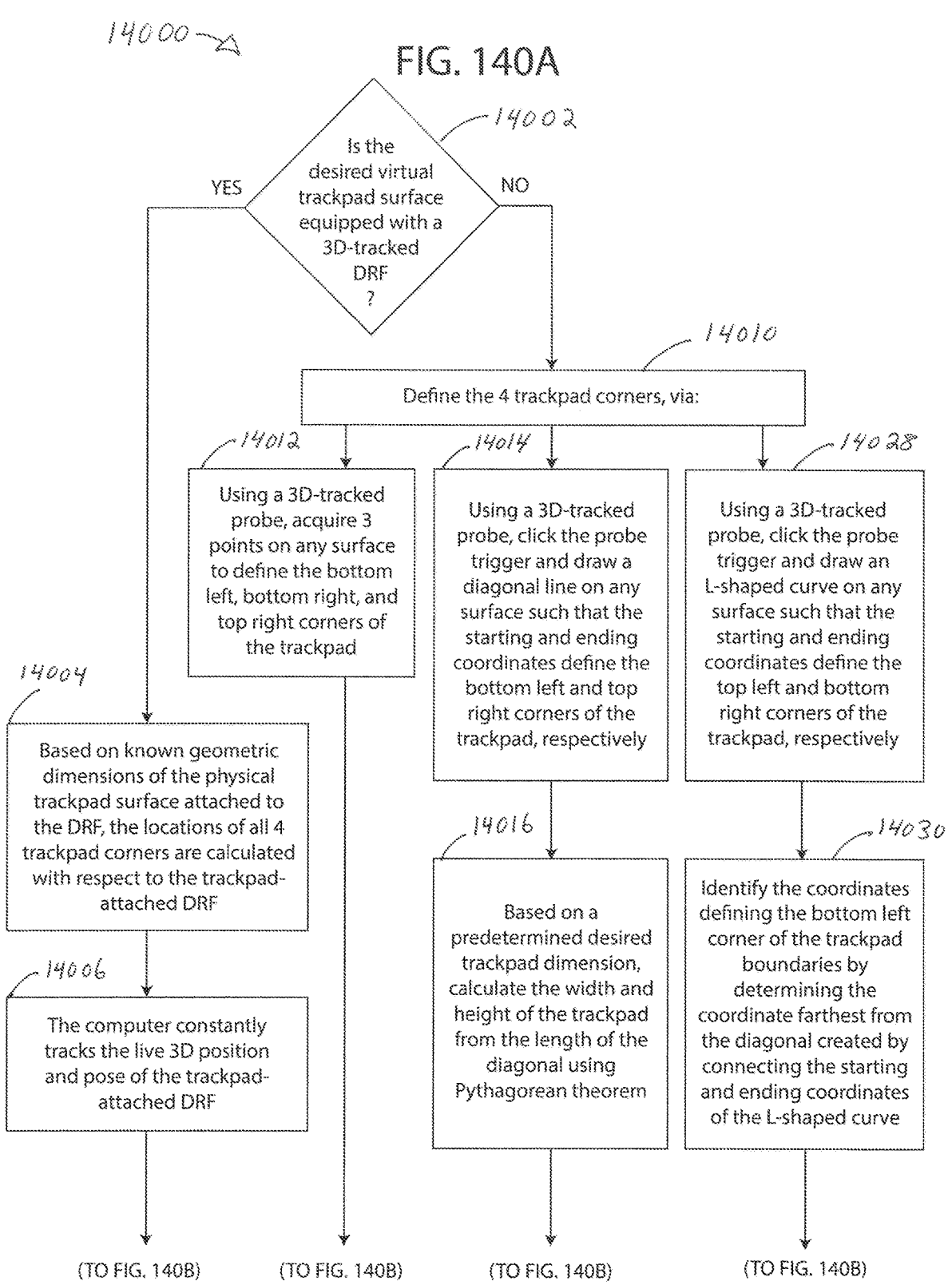

14002

Is the desired virtual trackpad surface equipped with a 3D-tracked DRF ?

YES          NO

14010

Define the 4 trackpad corners, via:

14012

Using a 3D-tracked probe, acquire 3 points on any surface to define the bottom left, bottom right, and top right corners of the trackpad

14014

Using a 3D-tracked probe, click the probe trigger and draw a diagonal line on any surface such that the starting and ending coordinates define the bottom left and top right corners of the trackpad, respectively

14028

Using a 3D-tracked probe, click the probe trigger and draw an L-shaped curve on any surface such that the starting and ending coordinates define the top left and bottom right corners of the trackpad, respectively

14004

Based on known geometric dimensions of the physical trackpad surface attached to the DRF, the locations of all 4 trackpad corners are calculated with respect to the trackpad-attached DRF

14016

Based on a predetermined desired trackpad dimension, calculate the width and height of the trackpad from the length of the diagonal using Pythagorean theorem

14030

Identify the coordinates defining the bottom left corner of the trackpad boundaries by determining the coordinate farthest from the diagonal created by connecting the starting and ending coordinates of the L-shaped curve

14006

The computer constantly tracks the live 3D position and pose of the trackpad-attached DRF (TO FIG. 140B)          (TO FIG. 140B)          (TO FIG. 140B)          (TO FIG. 140B)

FIG. 140B

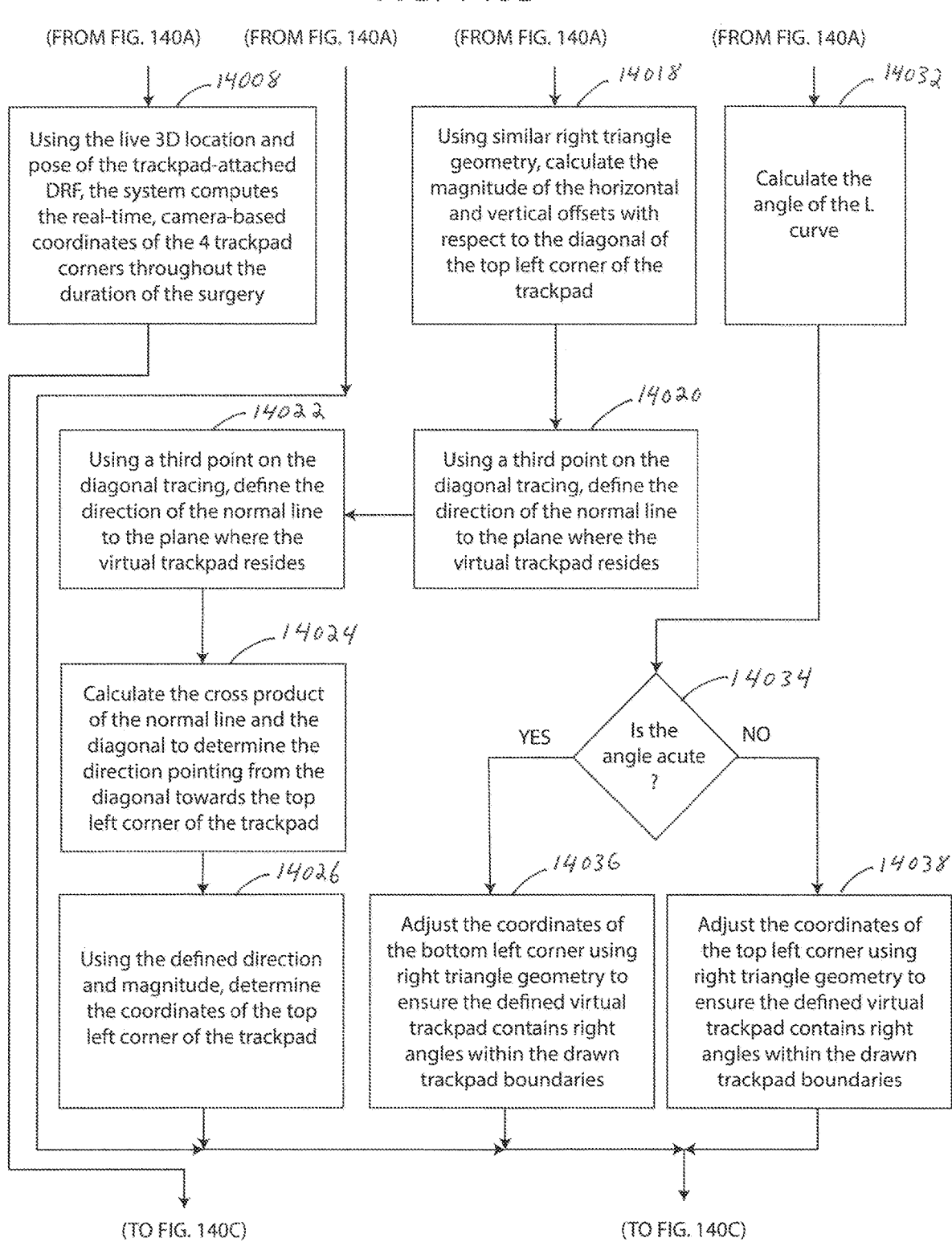

(FROM FIG. 140A)   (FROM FIG. 140A)   (FROM FIG. 140A)   (FROM FIG. 140A)

14008

Using the live 3D location and pose of the trackpad-attached DRF, the system computes the real-time, camera-based coordinates of the 4 trackpad corners throughout the duration of the surgery

14018

Using similar right triangle geometry, calculate the magnitude of the horizontal and vertical offsets with respect to the diagonal of the top left corner of the trackpad

14032

Calculate the angle of the L curve

14022

Using a third point on the diagonal tracing, define the direction of the normal line to the plane where the virtual trackpad resides

14020

Using a third point on the diagonal tracing, define the direction of the normal line to the plane where the virtual trackpad resides

14024

Calculate the cross product of the normal line and the diagonal to determine the direction pointing from the diagonal towards the top left corner of the trackpad

14034

Is the angle acute ?

YES    NO

14026

Using the defined direction and magnitude, determine the coordinates of the top left corner of the trackpad

14036

Adjust the coordinates of the bottom left corner using right triangle geometry to ensure the defined virtual trackpad contains right angles within the drawn trackpad boundaries

14038

Adjust the coordinates of the top left corner using right triangle geometry to ensure the defined virtual trackpad contains right angles within the drawn trackpad boundaries (TO FIG. 140C)          (TO FIG. 140C)

FIG. 140C

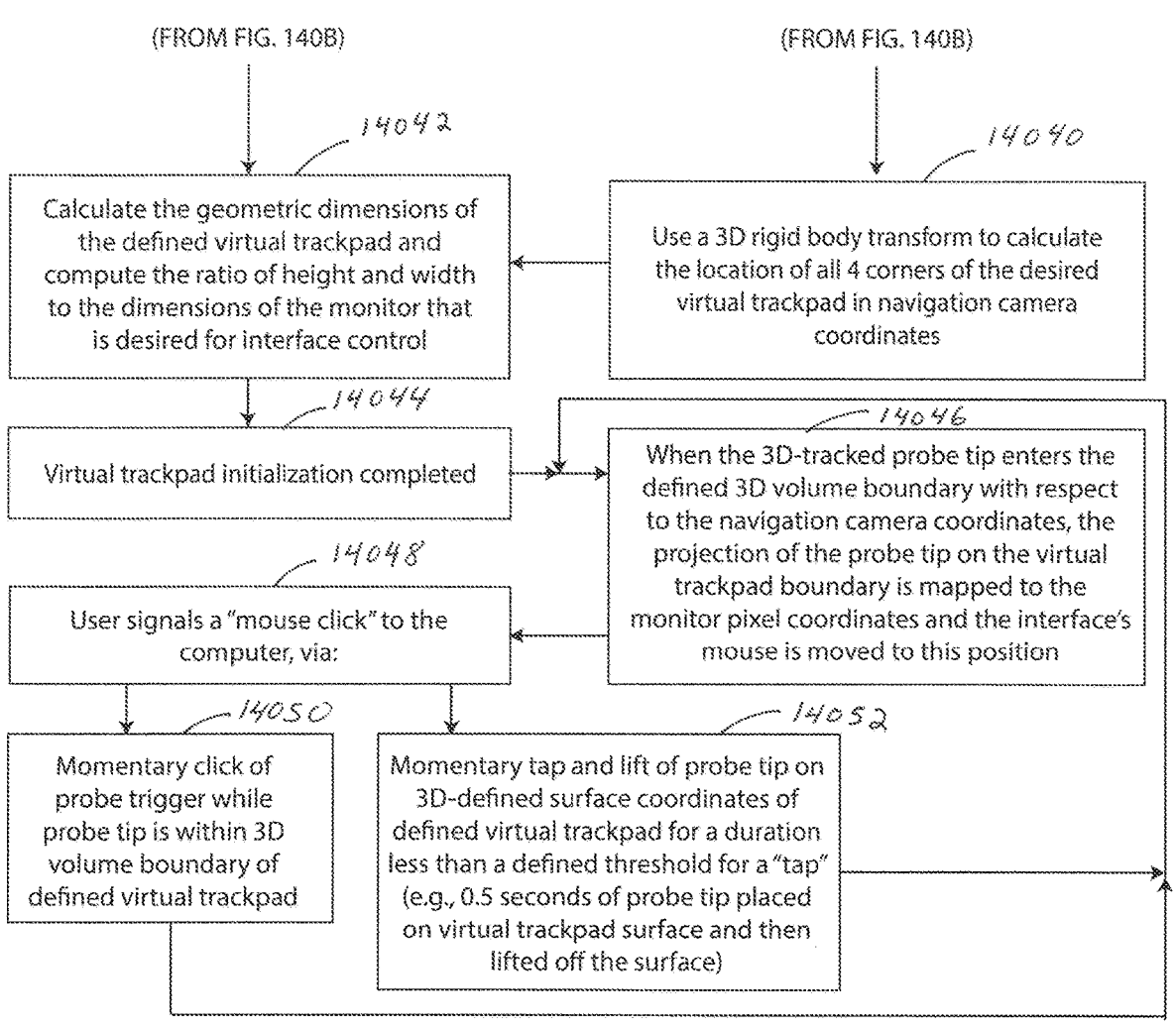

(FROM FIG. 140B)

(FROM FIG. 140B)

14042

Calculate the geometric dimensions of the defined virtual trackpad and compute the ratio of height and width to the dimensions of the monitor that is desired for interface control

14040

Use a 3D rigid body transform to calculate the location of all 4 corners of the desired virtual trackpad in navigation camera coordinates

14044

Virtual trackpad initialization completed

14046

When the 3D-tracked probe tip enters the defined 3D volume boundary with respect to the navigation camera coordinates, the projection of the probe tip on the virtual trackpad boundary is mapped to the monitor pixel coordinates and the interface's mouse is moved to this position

14048

User signals a "mouse click" to the computer, via:

14050

Momentary click of probe trigger while probe tip is within 3D volume boundary of defined virtual trackpad

14052

Momentary tap and lift of probe tip on 3D-defined surface coordinates of defined virtual trackpad for a duration less than a defined threshold for a "tap" (e.g., 0.5 seconds of probe tip placed on virtual trackpad surface and then lifted off the surface)

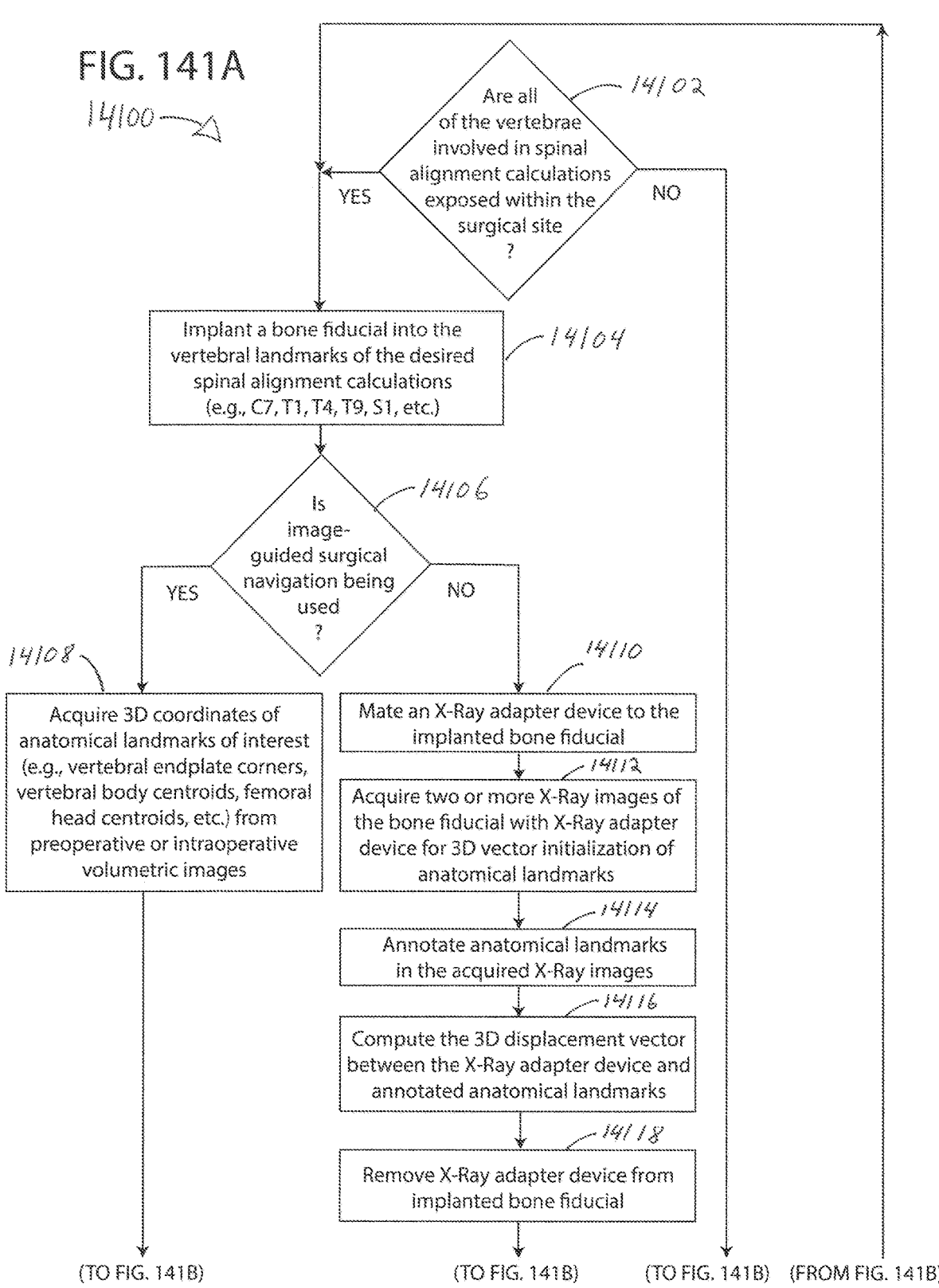

Are all of the vertebrae involved in spinal alignment calculations exposed within the surgical site ? — 14102

YES          NO

Implant a bone fiducial into the vertebral landmarks of the desired spinal alignment calculations (e.g., C7, T1, T4, T9, S1, etc.) — 14104

Is image-guided surgical navigation being used ? — 14106

YES          NO

14108 —
Acquire 3D coordinates of anatomical landmarks of interest (e.g., vertebral endplate corners, vertebral body centroids, femoral head centroids, etc.) from preoperative or intraoperative volumetric images 14110 —
Mate an X-Ray adapter device to the implanted bone fiducial 14112 —
Acquire two or more X-Ray images of the bone fiducial with X-Ray adapter device for 3D vector initialization of anatomical landmarks 14114 —
Annotate anatomical landmarks in the acquired X-Ray images 14116 —
Compute the 3D displacement vector between the X-Ray adapter device and annotated anatomical landmarks 14118 —
Remove X-Ray adapter device from implanted bone fiducial (TO FIG. 141B)          (TO FIG. 141B)          (TO FIG. 141B)     (FROM FIG. 141B)

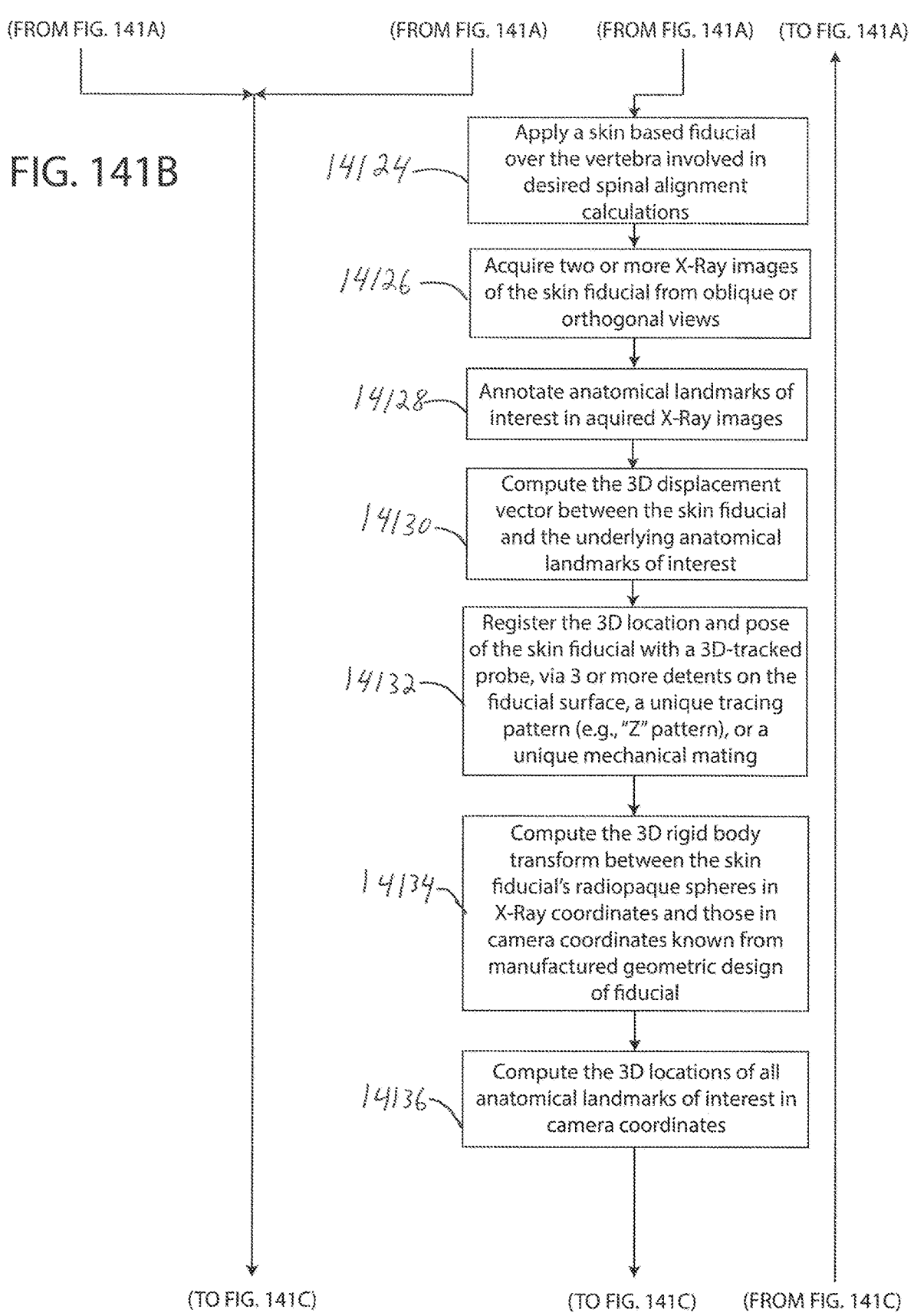

FIG. 141B (FROM FIG. 141A)     (FROM FIG. 141A)     (FROM FIG. 141A)     (TO FIG. 141A)

14124 — Apply a skin based fiducial over the vertebra involved in desired spinal alignment calculations 14126 — Acquire two or more X-Ray images of the skin fiducial from oblique or orthogonal views 14128 — Annotate anatomical landmarks of interest in aquired X-Ray images 14130 — Compute the 3D displacement vector between the skin fiducial and the underlying anatomical landmarks of interest 14132 — Register the 3D location and pose of the skin fiducial with a 3D-tracked probe, via 3 or more detents on the fiducial surface, a unique tracing pattern (e.g., "Z" pattern), or a unique mechanical mating 14134 — Compute the 3D rigid body transform between the skin fiducial's radiopaque spheres in X-Ray coordinates and those in camera coordinates known from manufactured geometric design of fiducial 14136 — Compute the 3D locations of all anatomical landmarks of interest in camera coordinates (TO FIG. 141C)     (TO FIG. 141C)     (FROM FIG. 141C)

(FROM FIG. 141B)    FIG. 141C    (FROM FIG. 141B)    (TO FIG. 141B)

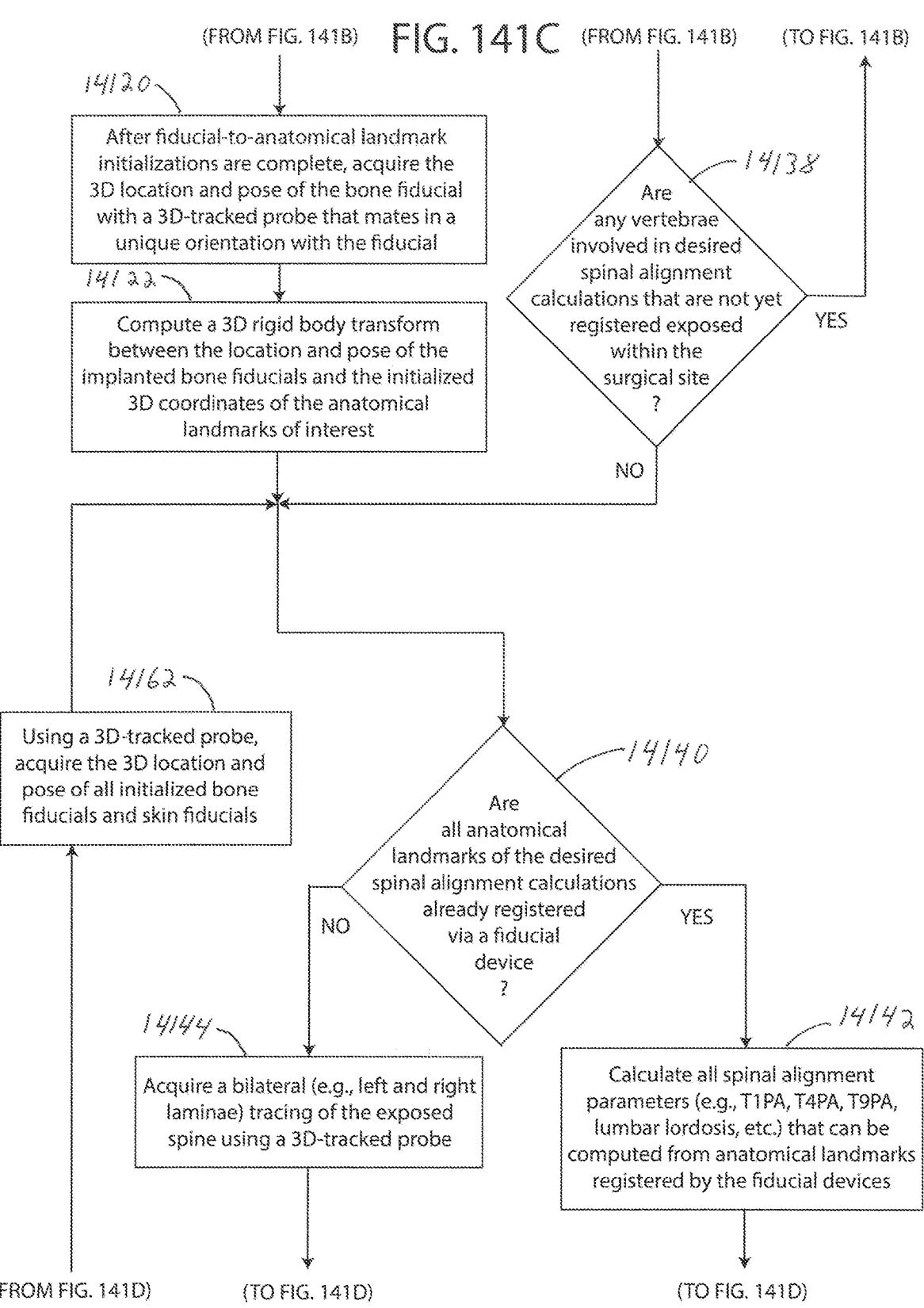

*14120*

After fiducial-to-anatomical landmark initializations are complete, acquire the 3D location and pose of the bone fiducial with a 3D-tracked probe that mates in a unique orientation with the fiducial

*14122*

Compute a 3D rigid body transform between the location and pose of the implanted bone fiducials and the initialized 3D coordinates of the anatomical landmarks of interest

*14138*

Are any vertebrae involved in desired spinal alignment calculations that are not yet registered exposed within the surgical site ?

YES

NO

*14162*

Using a 3D-tracked probe, acquire the 3D location and pose of all initialized bone fiducials and skin fiducials

*14140*

Are all anatomical landmarks of the desired spinal alignment calculations already registered via a fiducial device ?

NO

YES

*14144*

Acquire a bilateral (e.g., left and right laminae) tracing of the exposed spine using a 3D-tracked probe

*14142*

Calculate all spinal alignment parameters (e.g., T1PA, T4PA, T9PA, lumbar lordosis, etc.) that can be computed from anatomical landmarks registered by the fiducial devices (FROM FIG. 141D)    (TO FIG. 141D)    (TO FIG. 141D)

(TO FIG. 141C)    (FROM FIG. 141C)    FIG. 141D    (FROM FIG. 141C)

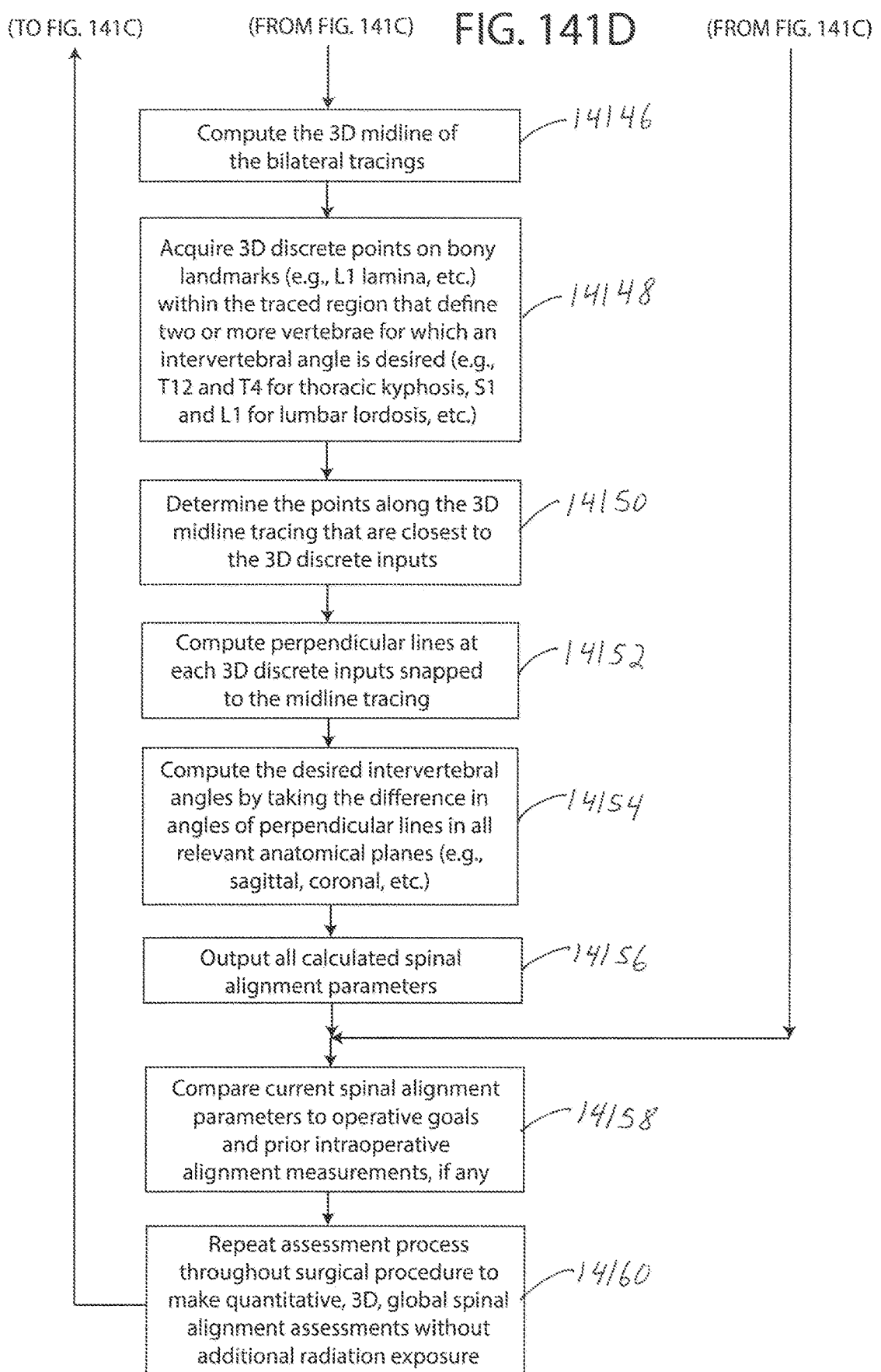

Compute the 3D midline of
the bilateral tracings                    — 14146

Acquire 3D discrete points on bony
landmarks (e.g., L1 lamina, etc.)
within the traced region that define
two or more vertebrae for which an      — 14148
intervertebral angle is desired (e.g.,
T12 and T4 for thoracic kyphosis, S1
and L1 for lumbar lordosis, etc.)

Determine the points along the 3D
midline tracing that are closest to      — 14150
the 3D discrete inputs Compute perpendicular lines at
each 3D discrete inputs snapped          — 14152
to the midline tracing Compute the desired intervertebral
angles by taking the difference in
angles of perpendicular lines in all     — 14154
relevant anatomical planes (e.g.,
sagittal, coronal, etc.)

Output all calculated spinal
alignment parameters                     — 14156

Compare current spinal alignment
parameters to operative goals
and prior intraoperative                 — 14158
alignment measurements, if any Repeat assessment process
throughout surgical procedure to
make quantitative, 3D, global spinal     — 14160
alignment assessments without
additional radiation exposure

FIG. 144A
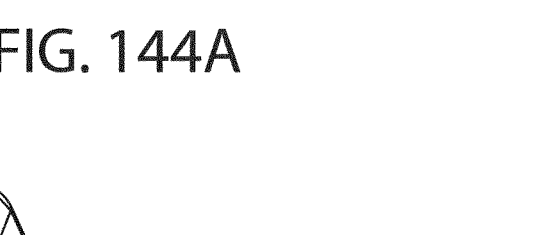
14400
14414
14416a
14401
14406a
14402a
14408a
14418      14417
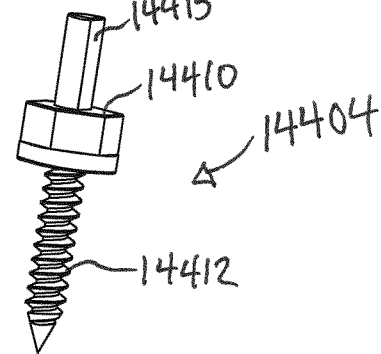
14415
14410
14404
14412

FIG. 147F 14750
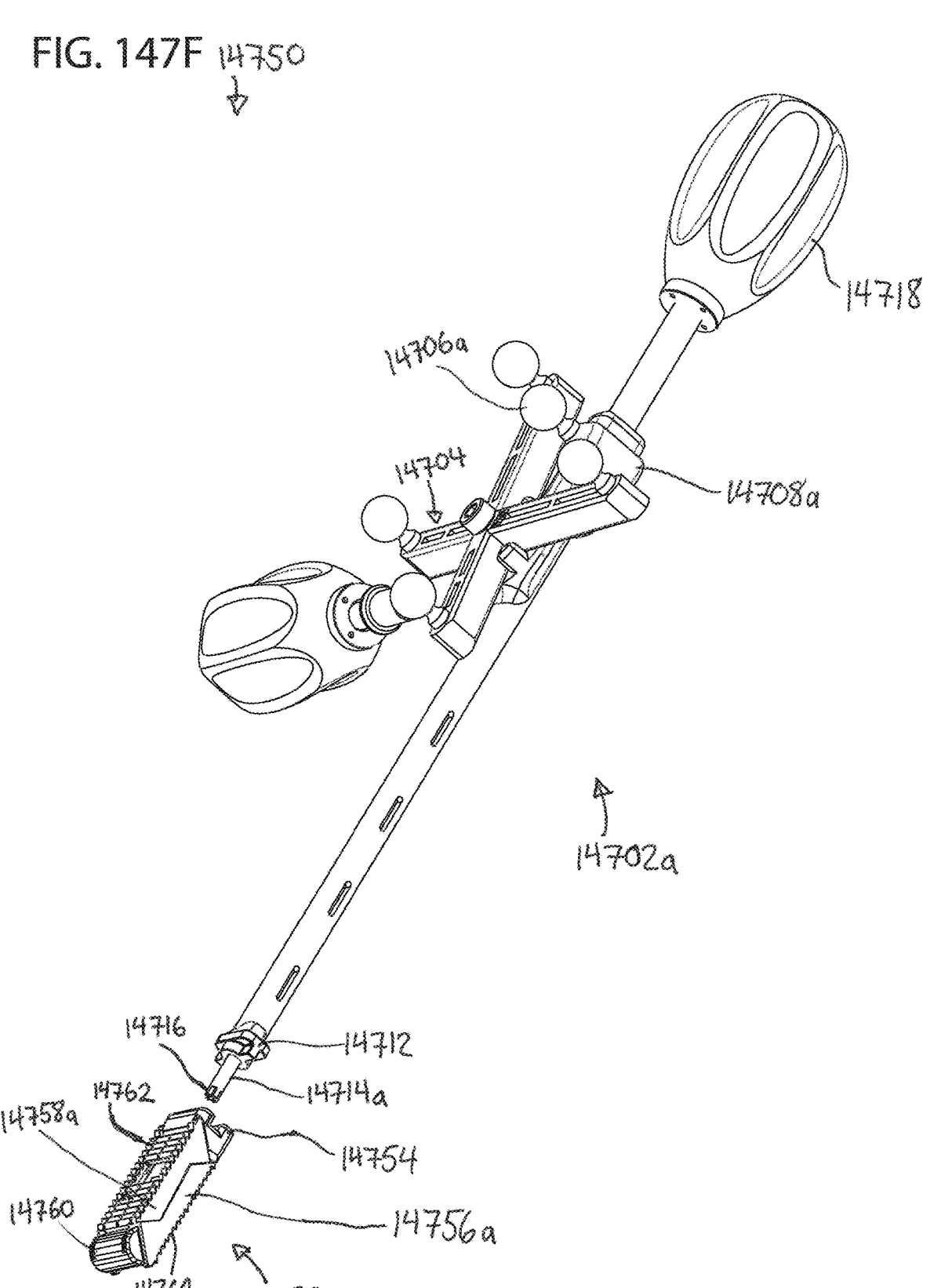
14718
14706a
14704
14708a
14702a
14716
14712
14762
14714a
14758a
14754
14760
14756a
14762
14752a

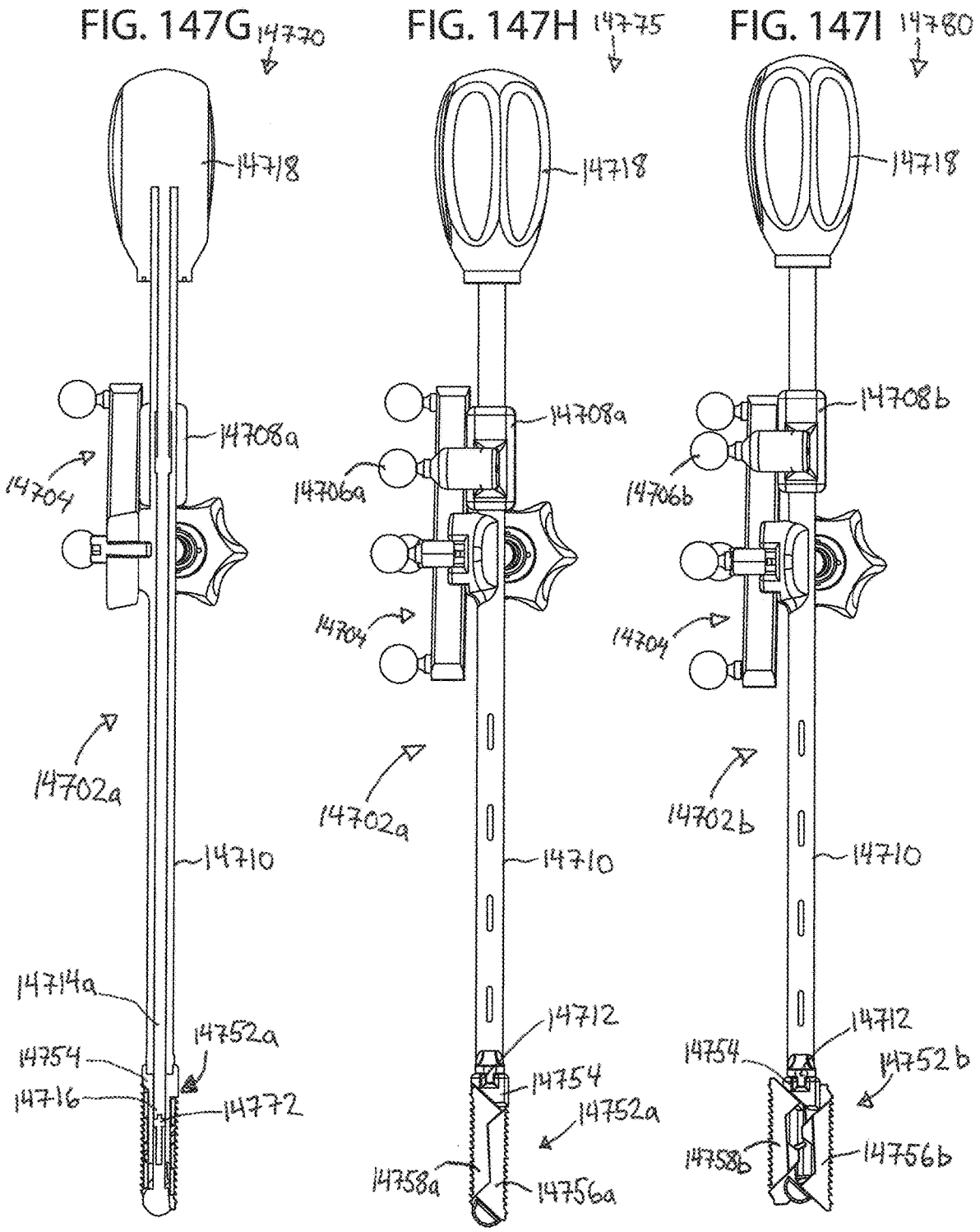
FIG. 147G 14770
FIG. 147H 14775
FIG. 147I 14780
14718
14708a
14704
14702a
14710
14714a
14754
14716
14752a
14772
14706a
14702a
14712
14754
14752a
14758a
14756a
14708b
14706b
14704
14702b
14710
14754
14712
14758b
14752b
14756b

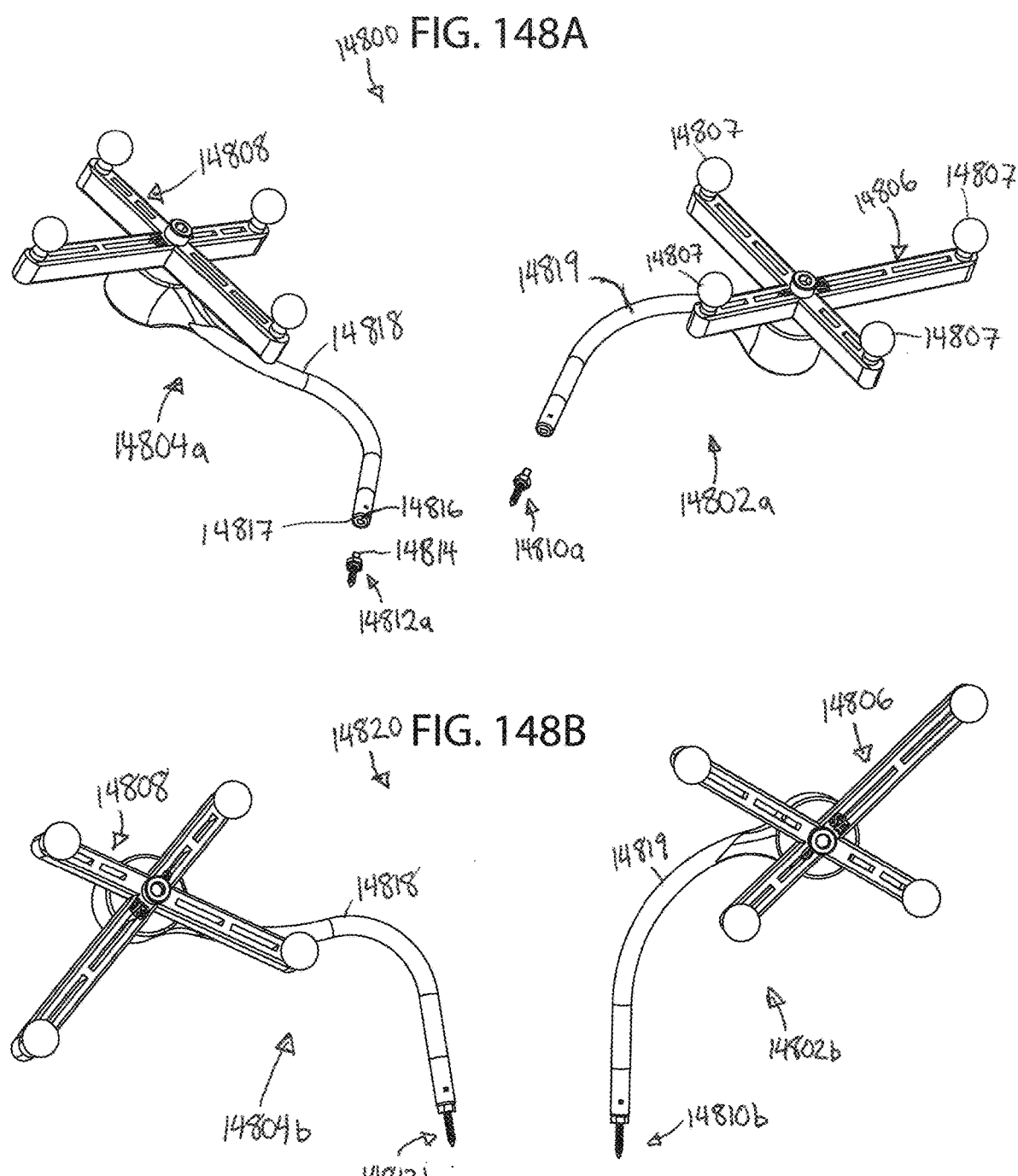
14800 FIG. 148A
14808
14807
14806 14807
14819
14807
14807
14818
14804a
14816
14817
14814
14810a
14812a
14802a
14820 FIG. 148B
14806
14808
14818
14819
14804b
14802b
14812b
14810b FIG. 148E
14840
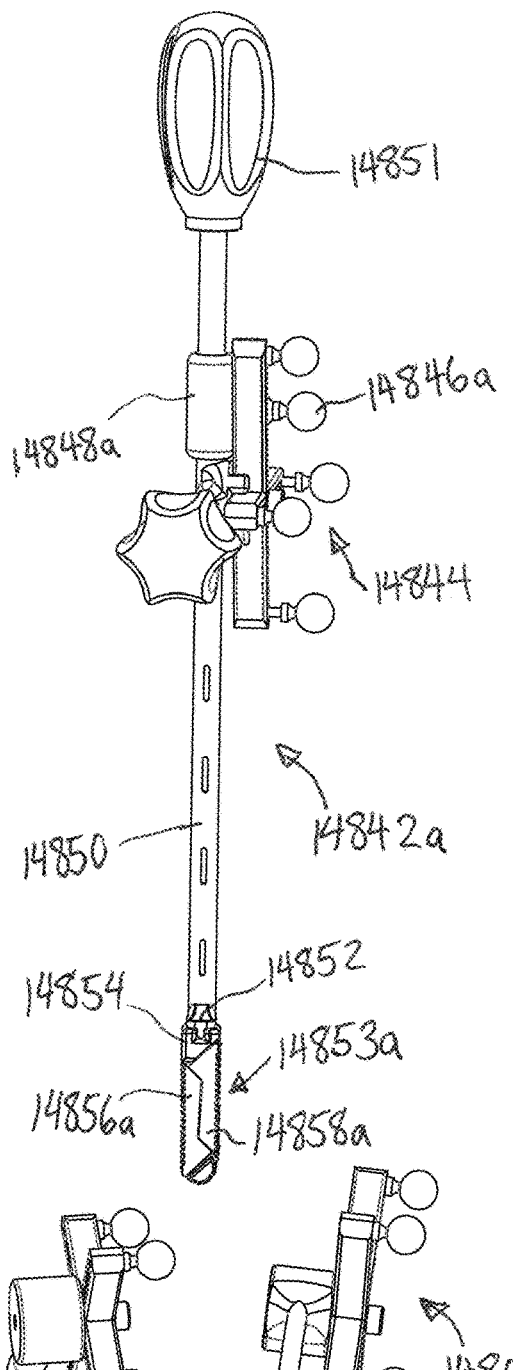
14851
14846a
14848a
14844
14842a
14850
14854
14852
14853a
14856a
14858a
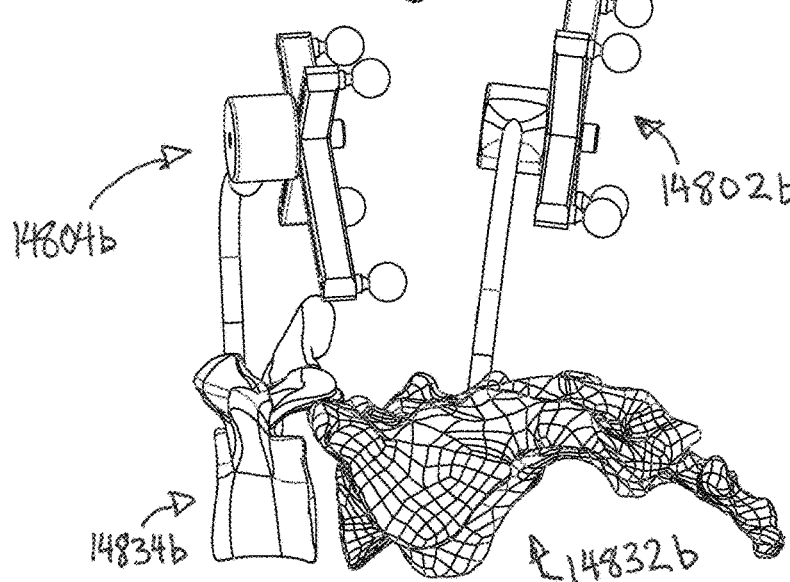
14804b
14802b
14834b
14832b

14851

14865

14842c

14848b

14846b

14844

14804c

14802c

14867

14834c

14832c

14856c

14853c

14858c

14875

14851

14850

14848b

14846b

14842c

14844

14804c

14802c

14834c

14832c

14880

14848b

14846b

14842d

14844

14804c

14884

14882

14802c

14886

14834c

14853d

14832c

14900

14910

14908a

14906a

14902a

14904

14911

14914a

14913a

14912a

14970

14935b

14933

14937b

14931c

14902b

14939c

14914b

14912c

15027

15015

15021a

15017a

15023a

15025

15004

15019

15028

15002a

15029a

15008a

15033a

15031a

15040

15027

15023b

15021b

15017b

15025

15002b

15029b

15008b

15033b

15031b

15130 FIG. 151C
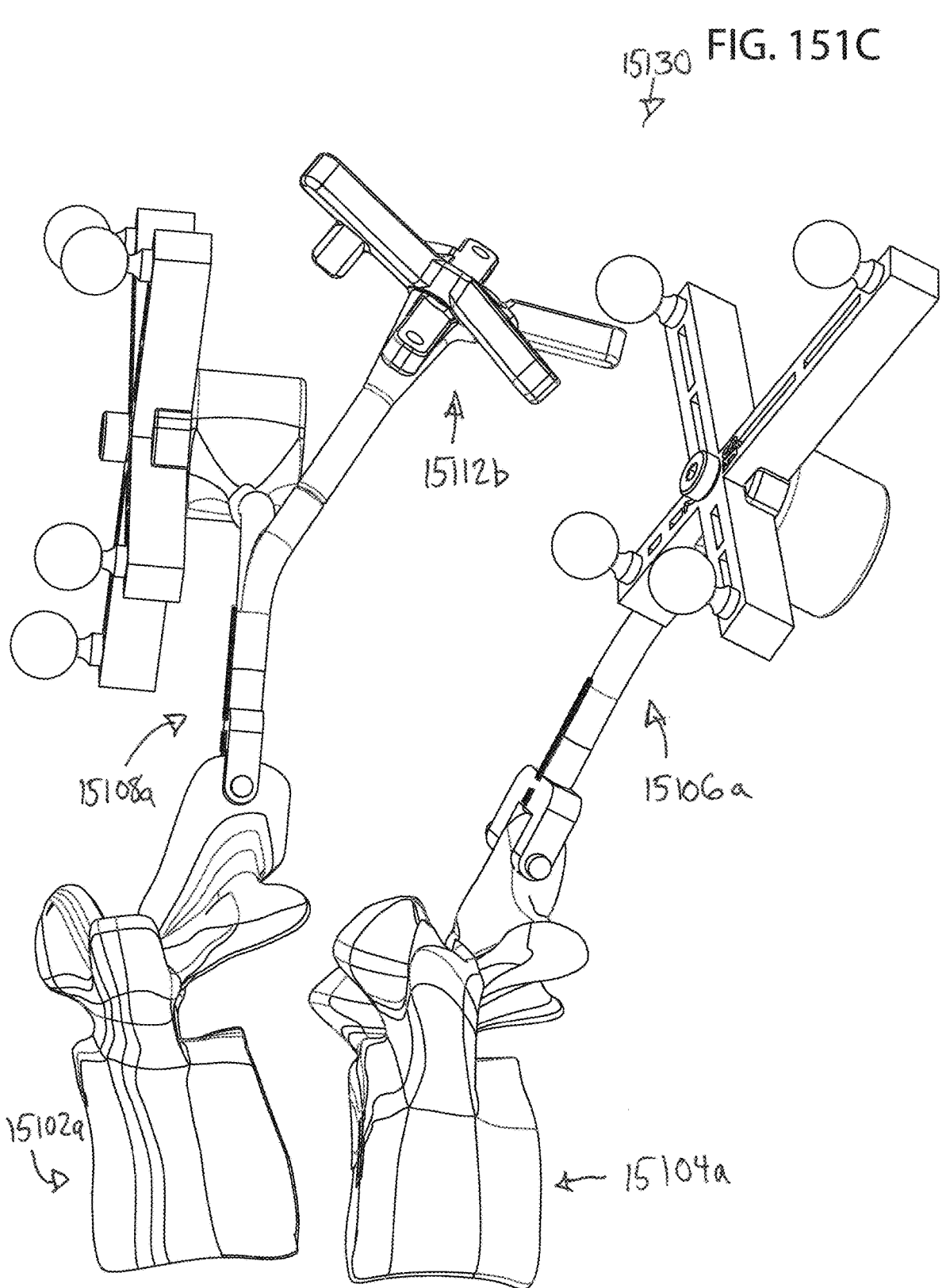

15148

15140

15146

15144

15142

15150

15114

15108b

15106b

15102b

15104b

15152

FIG. 152D
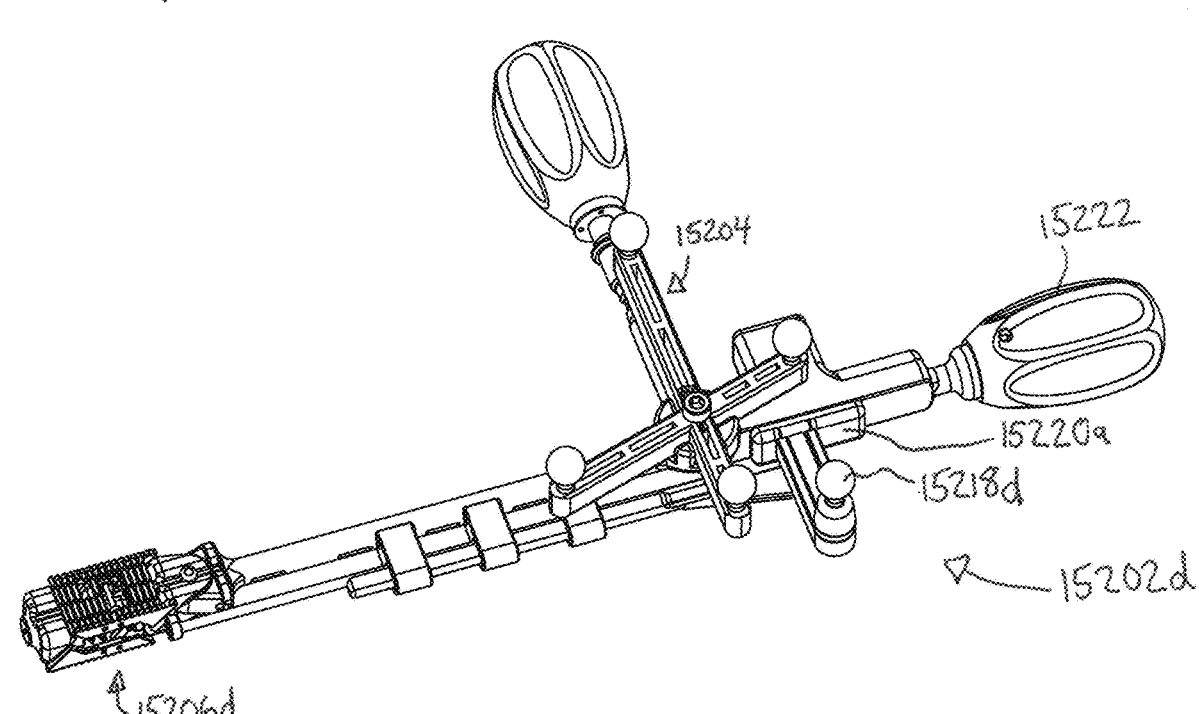
FIG. 152E
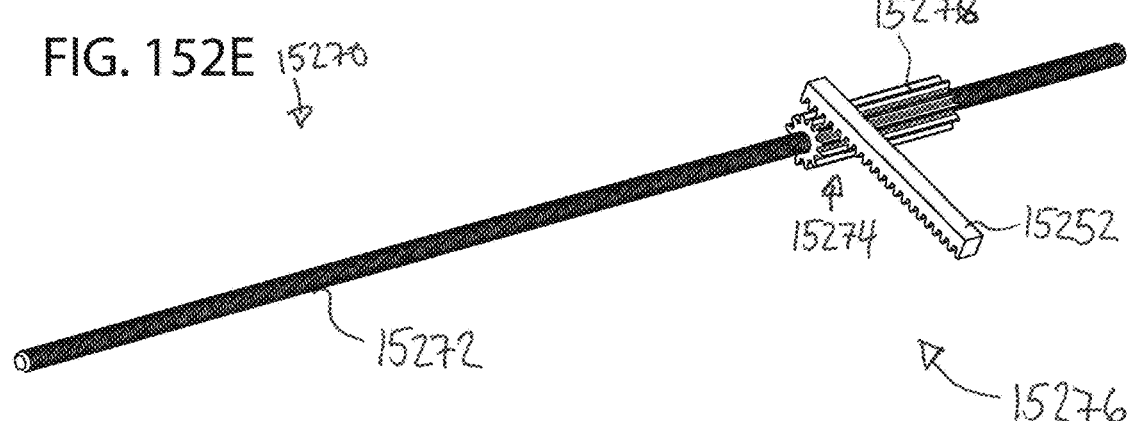

FIG. 153F 15360
FIG. 153G 15361
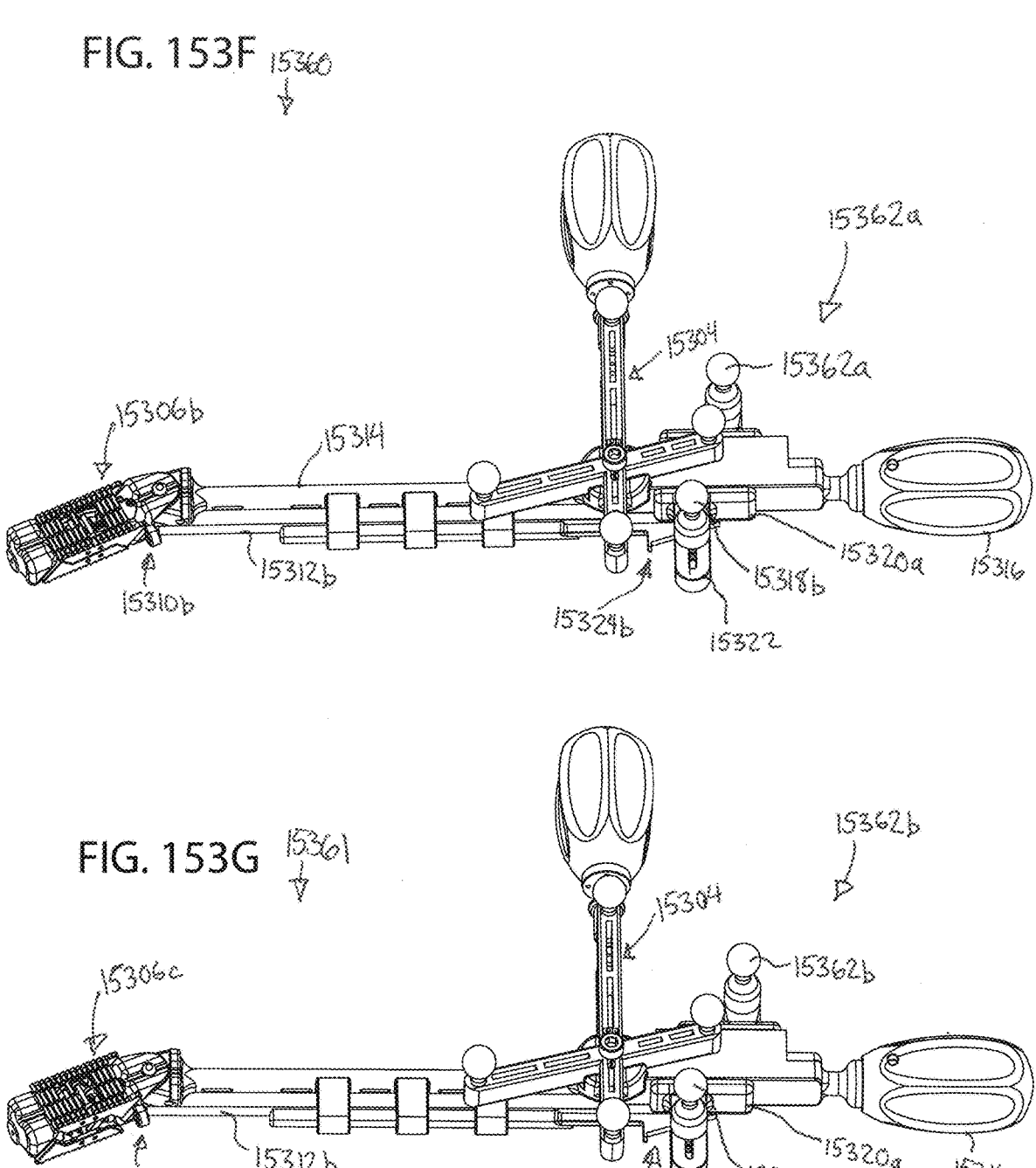

15500

15512

15510

15506a

15508a

15504

15502a

15510

15514a

15516

15522

15518

15520a

15540

15512

15506a

15508a

15502b

15522

15514b

15520b

15550

15512

15506b

15508b

15502c

15522

15520c

15552

15620

15604

15610

15602b

15614b

15612b

15630

15604

15602b

15610

15639a

15614b

15637a

15634a

15632a

15636a

15638a

15635

15604

15602c

15610

15634b

15632b

15636b

15638b

15614c

15640

15602d

15612c

15632b

15634b

15636b

15614d

15638b

Status:
Live 3D
Cage & Vertebrae

L4-L5 (sagittal): 3.8°
L4-L5 (Coronal): 4.8°
L4-L5 (Axial): 13.1°

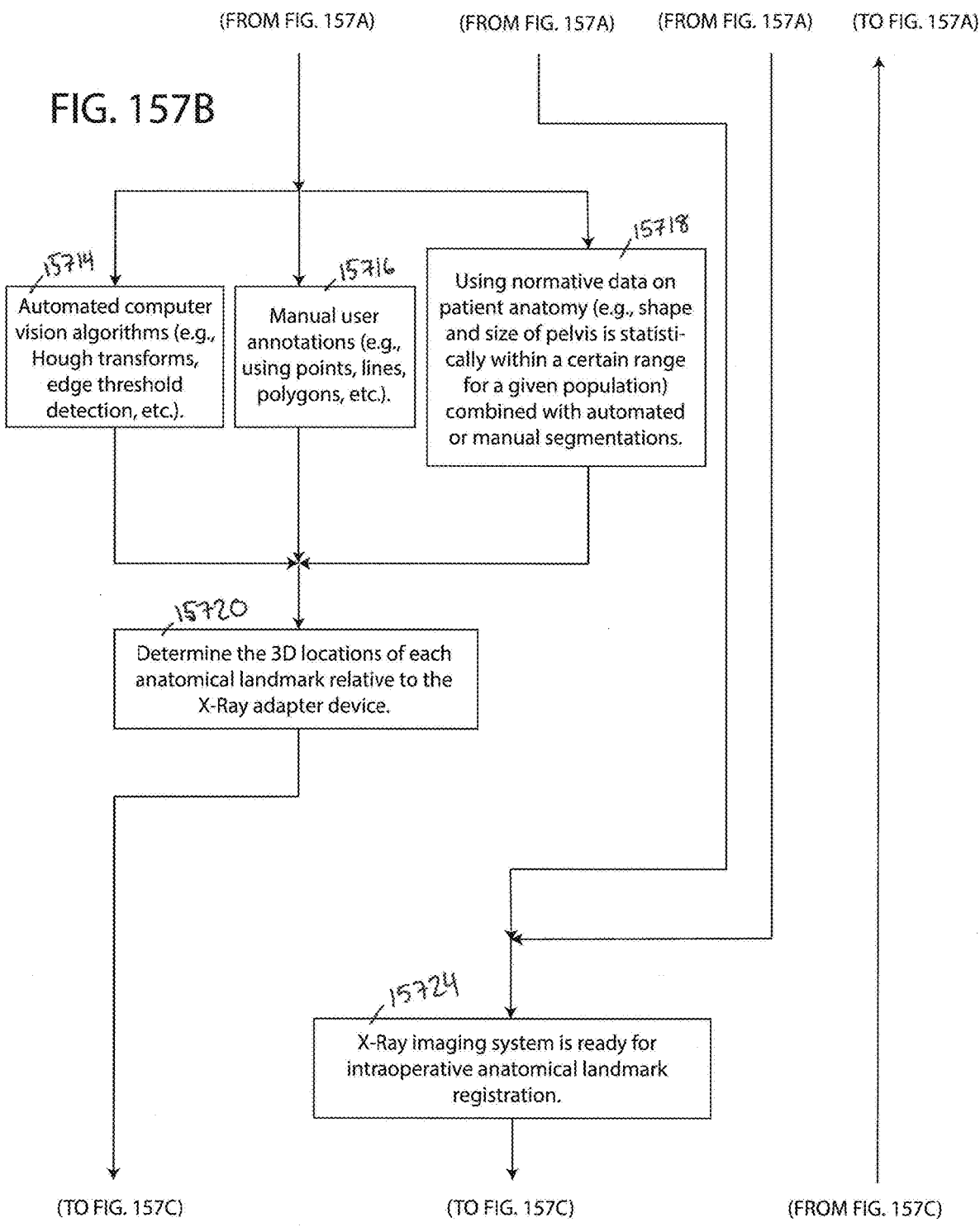

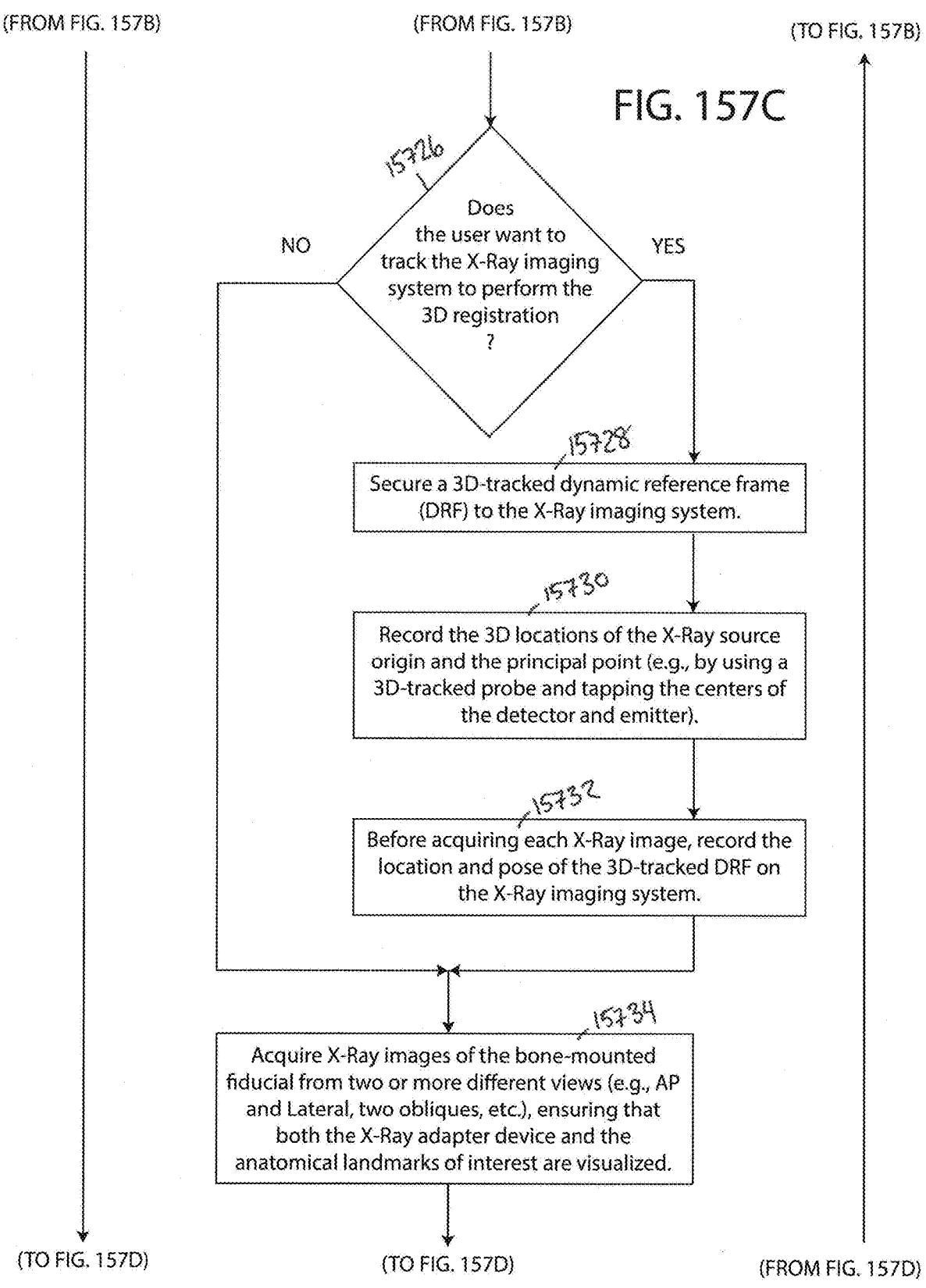

(FROM FIG. 157B)        (FROM FIG. 157B)        (TO FIG. 157B)

Does the user want to track the X-Ray imaging system to perform the 3D registration ?

NO        YES

15728

Secure a 3D-tracked dynamic reference frame (DRF) to the X-Ray imaging system.

15730

Record the 3D locations of the X-Ray source origin and the principal point (e.g., by using a 3D-tracked probe and tapping the centers of the detector and emitter).

15732

Before acquiring each X-Ray image, record the location and pose of the 3D-tracked DRF on the X-Ray imaging system.

15734

Acquire X-Ray images of the bone-mounted fiducial from two or more different views (e.g., AP and Lateral, two obliques, etc.), ensuring that both the X-Ray adapter device and the anatomical landmarks of interest are visualized.

(TO FIG. 157D)        (TO FIG. 157D)        (FROM FIG. 157D)

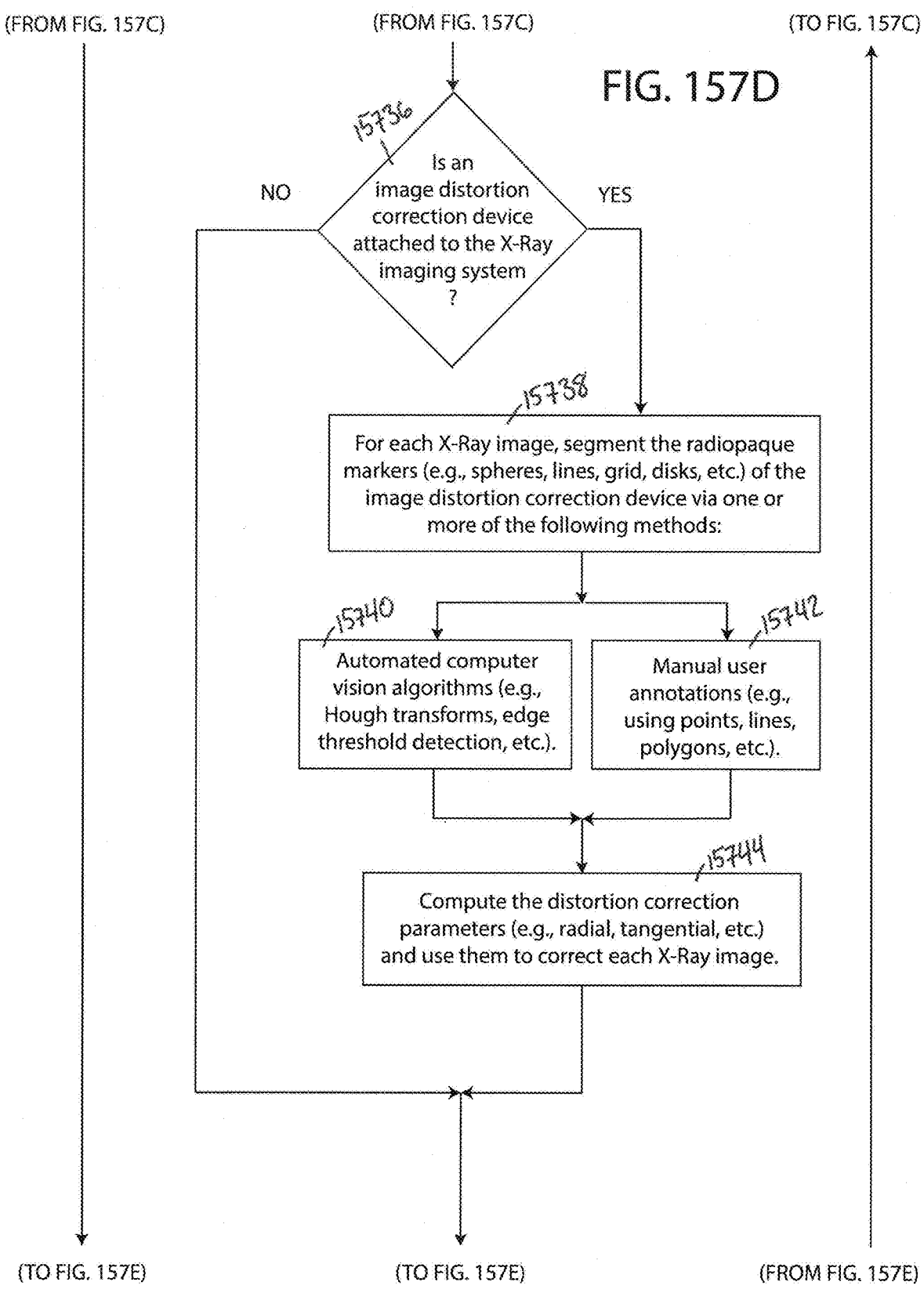

(FROM FIG. 157C)      (FROM FIG. 157C)      (TO FIG. 157C)

Is an image distortion correction device attached to the X-Ray imaging system ?

NO     YES

15738

For each X-Ray image, segment the radiopaque markers (e.g., spheres, lines, grid, disks, etc.) of the image distortion correction device via one or more of the following methods:

15740

Automated computer vision algorithms (e.g., Hough transforms, edge threshold detection, etc.).

15742

Manual user annotations (e.g., using points, lines, polygons, etc.).

15744

Compute the distortion correction parameters (e.g., radial, tangential, etc.) and use them to correct each X-Ray image.

(TO FIG. 157E)      (TO FIG. 157E)      (FROM FIG. 157E)

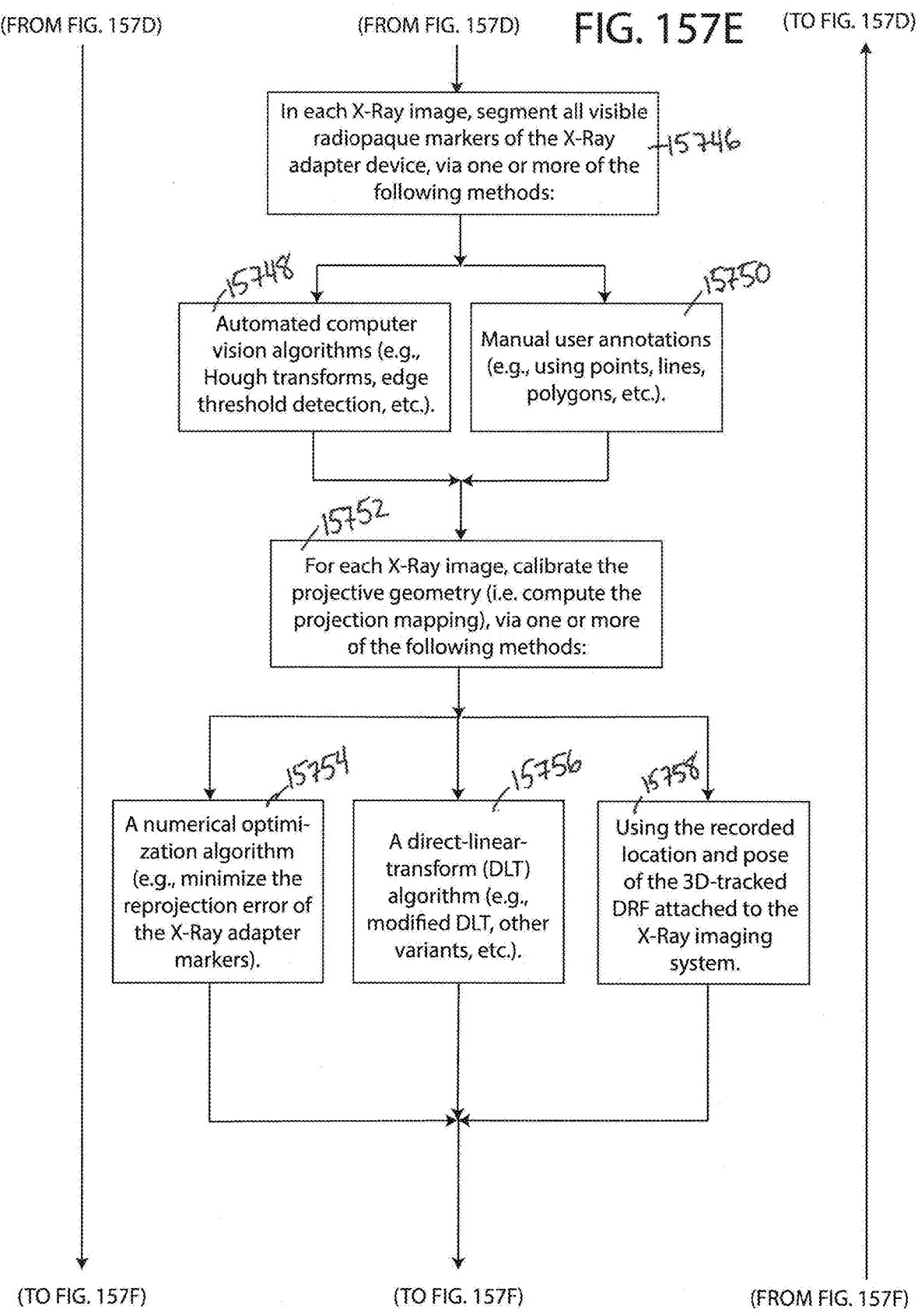

(FROM FIG. 157D)      (FROM FIG. 157D)     FIG. 157E     (TO FIG. 157D)

In each X-Ray image, segment all visible radiopaque markers of the X-Ray adapter device, via one or more of the following methods: — 15746

Automated computer vision algorithms (e.g., Hough transforms, edge threshold detection, etc.). — 15748

Manual user annotations (e.g., using points, lines, polygons, etc.). — 15750

For each X-Ray image, calibrate the projective geometry (i.e. compute the projection mapping), via one or more of the following methods: — 15752

A numerical optimization algorithm (e.g., minimize the reprojection error of the X-Ray adapter markers). — 15754

A direct-linear-transform (DLT) algorithm (e.g., modified DLT, other variants, etc.). — 15756

Using the recorded location and pose of the 3D-tracked DRF attached to the X-Ray imaging system. — 15758

(TO FIG. 157F)      (TO FIG. 157F)     (FROM FIG. 157F)

(FROM FIG. 157E)     (FROM FIG. 157E)     (TO FIG. 157E)

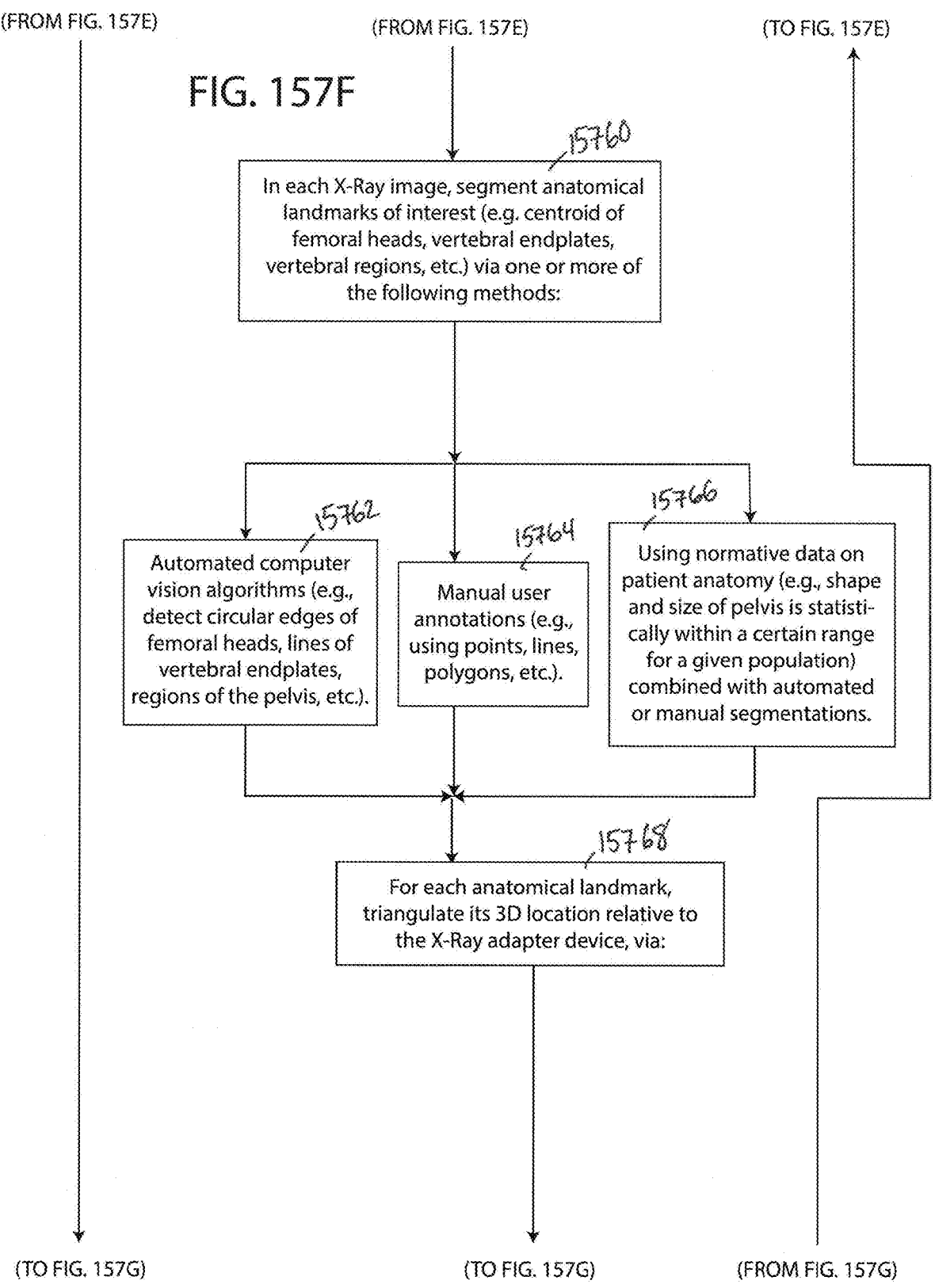

In each X-Ray image, segment anatomical landmarks of interest (e.g. centroid of femoral heads, vertebral endplates, vertebral regions, etc.) via one or more of the following methods:

15762

Automated computer vision algorithms (e.g., detect circular edges of femoral heads, lines of vertebral endplates, regions of the pelvis, etc.).

15764

Manual user annotations (e.g., using points, lines, polygons, etc.).

15766

Using normative data on patient anatomy (e.g., shape and size of pelvis is statistically within a certain range for a given population) combined with automated or manual segmentations.

15768

For each anatomical landmark, triangulate its 3D location relative to the X-Ray adapter device, via:

(TO FIG. 157G)     (TO FIG. 157G)     (FROM FIG. 157G)

(FROM FIG. 157G)          (FROM FIG. 157G)          (TO FIG. 157G)

FIG. 157H

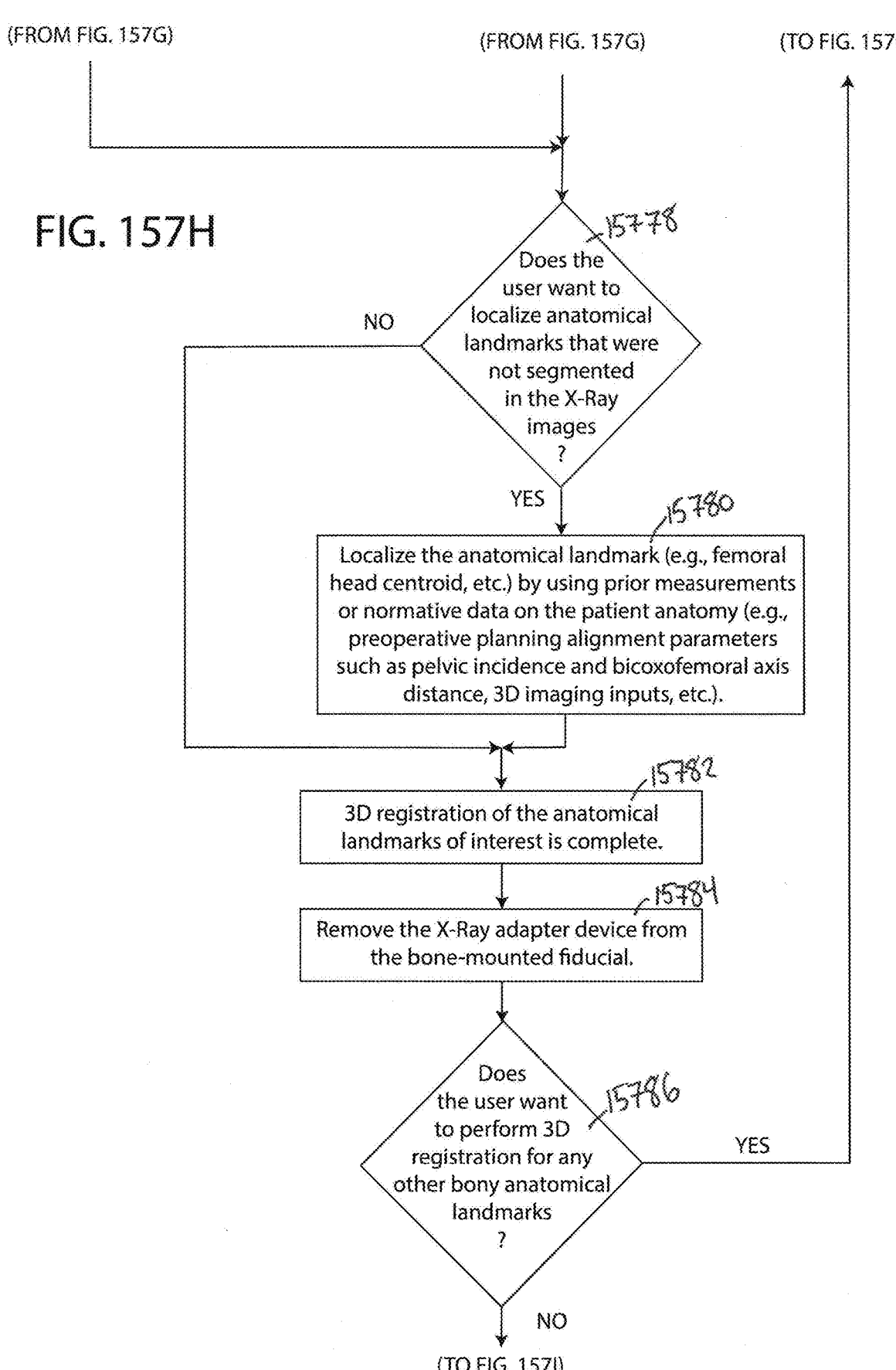

Does the user want to localize anatomical landmarks that were not segmented in the X-Ray images? 15778

NO

YES

Localize the anatomical landmark (e.g., femoral head centroid, etc.) by using prior measurements or normative data on the patient anatomy (e.g., preoperative planning alignment parameters such as pelvic incidence and bicoxofemoral axis distance, 3D imaging inputs, etc.). 15780

3D registration of the anatomical landmarks of interest is complete. 15782

Remove the X-Ray adapter device from the bone-mounted fiducial. 15784

Does the user want to perform 3D registration for any other bony anatomical landmarks? 15786

YES

NO (TO FIG. 157I)

(FROM FIG. 157H)

FIG. 157I

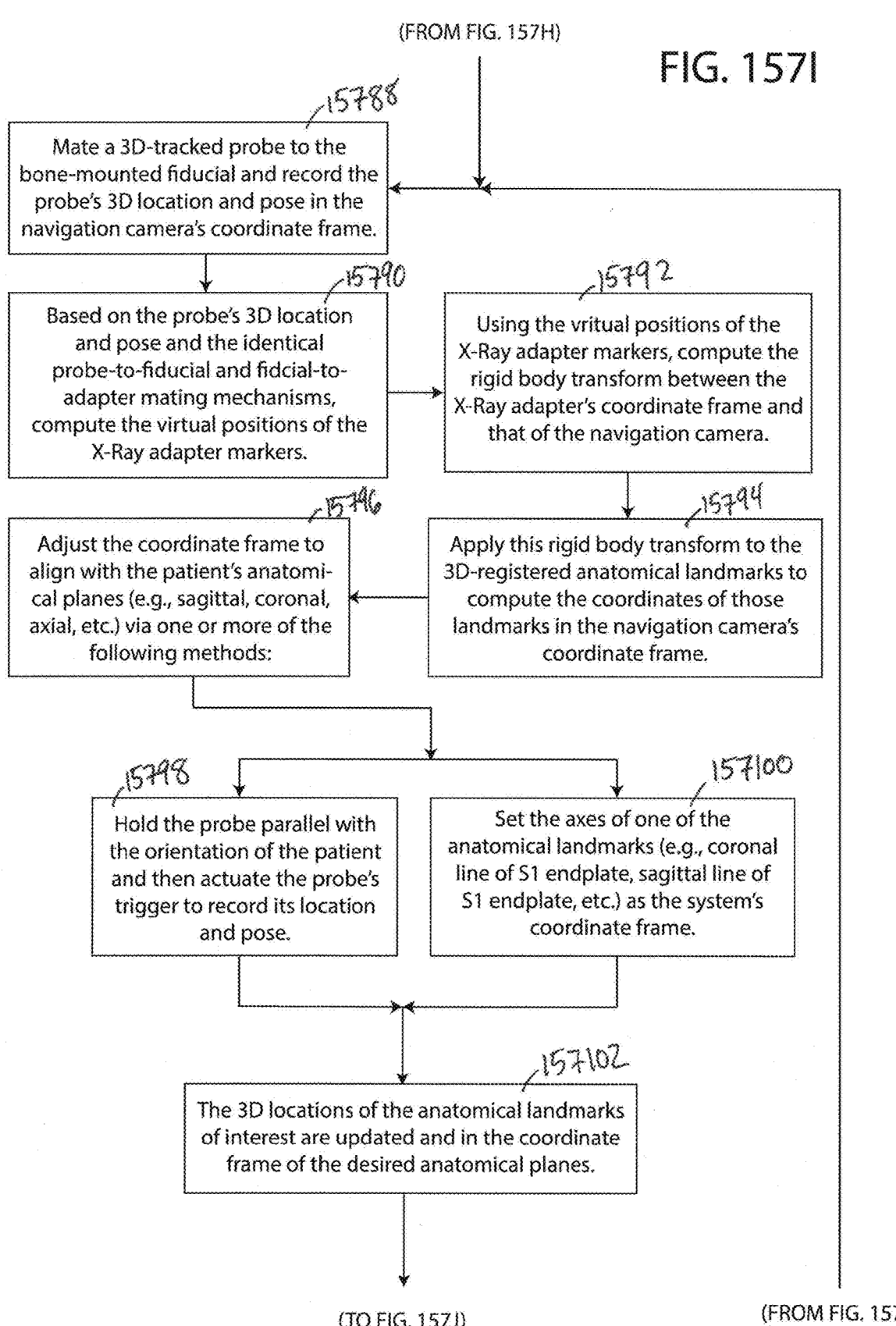

15788

Mate a 3D-tracked probe to the bone-mounted fiducial and record the probe's 3D location and pose in the navigation camera's coordinate frame.

15790

Based on the probe's 3D location and pose and the identical probe-to-fiducial and fidcial-to-adapter mating mechanisms, compute the virtual positions of the X-Ray adapter markers.

15792

Using the vritual positions of the X-Ray adapter markers, compute the rigid body transform between the X-Ray adapter's coordinate frame and that of the navigation camera.

15796

Adjust the coordinate frame to align with the patient's anatomical planes (e.g., sagittal, coronal, axial, etc.) via one or more of the following methods:

15794

Apply this rigid body transform to the 3D-registered anatomical landmarks to compute the coordinates of those landmarks in the navigation camera's coordinate frame.

15798

Hold the probe parallel with the orientation of the patient and then actuate the probe's trigger to record its location and pose.

157100

Set the axes of one of the anatomical landmarks (e.g., coronal line of S1 endplate, sagittal line of S1 endplate, etc.) as the system's coordinate frame.

157102

The 3D locations of the anatomical landmarks of interest are updated and in the coordinate frame of the desired anatomical planes.

(TO FIG. 157J)              (FROM FIG. 157J)

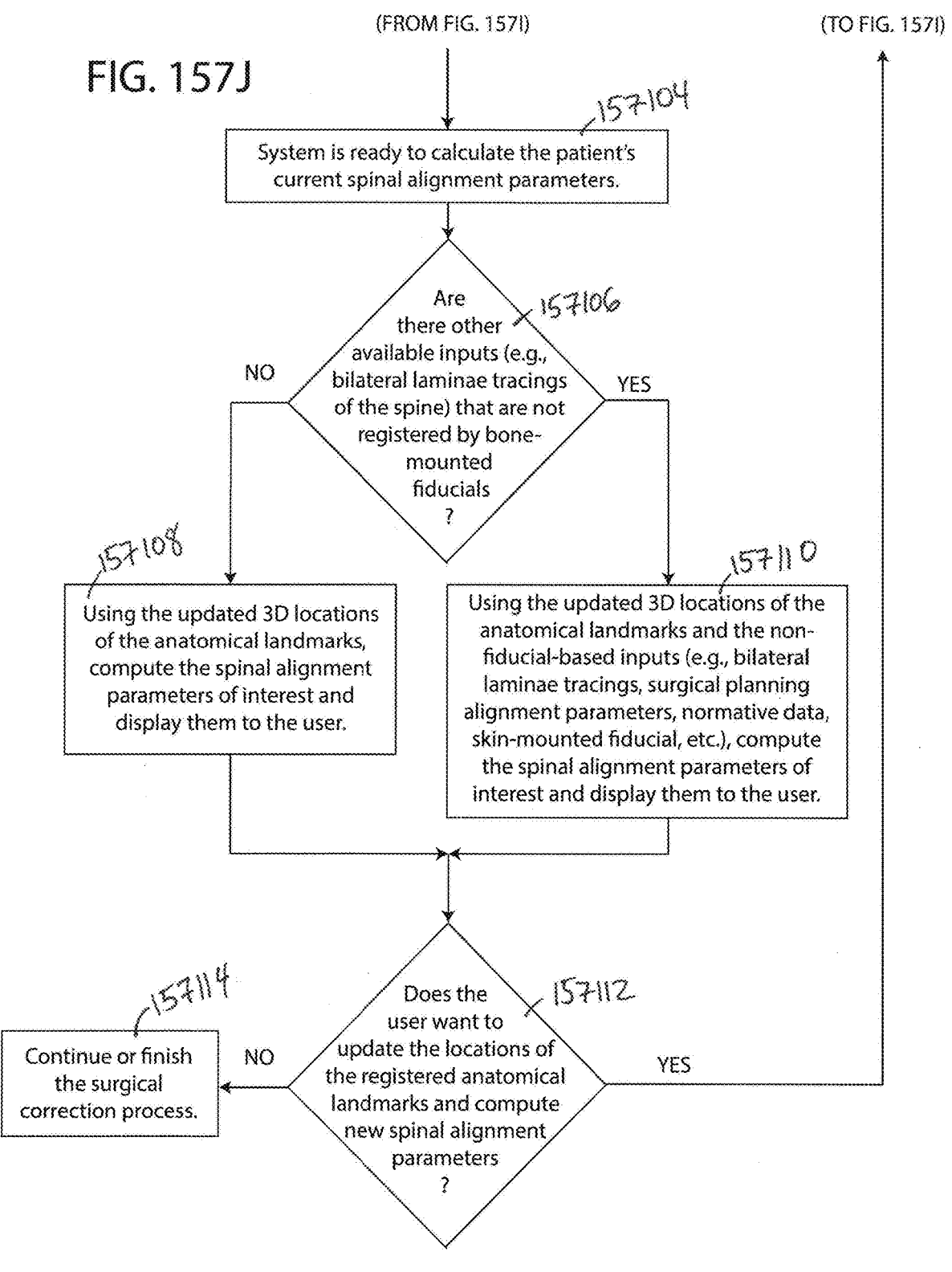

FIG. 157J (FROM FIG. 157I)

(TO FIG. 157I)

157104
System is ready to calculate the patient's current spinal alignment parameters.

157106
Are there other available inputs (e.g., bilateral laminae tracings of the spine) that are not registered by bone-mounted fiducials?

NO          YES

157108
Using the updated 3D locations of the anatomical landmarks, compute the spinal alignment parameters of interest and display them to the user.

157110
Using the updated 3D locations of the anatomical landmarks and the non-fiducial-based inputs (e.g., bilateral laminae tracings, surgical planning alignment parameters, normative data, skin-mounted fiducial, etc.), compute the spinal alignment parameters of interest and display them to the user.

157112
Does the user want to update the locations of the registered anatomical landmarks and compute new spinal alignment parameters?

NO          YES

157114
Continue or finish the surgical correction process.

FIG. 158A

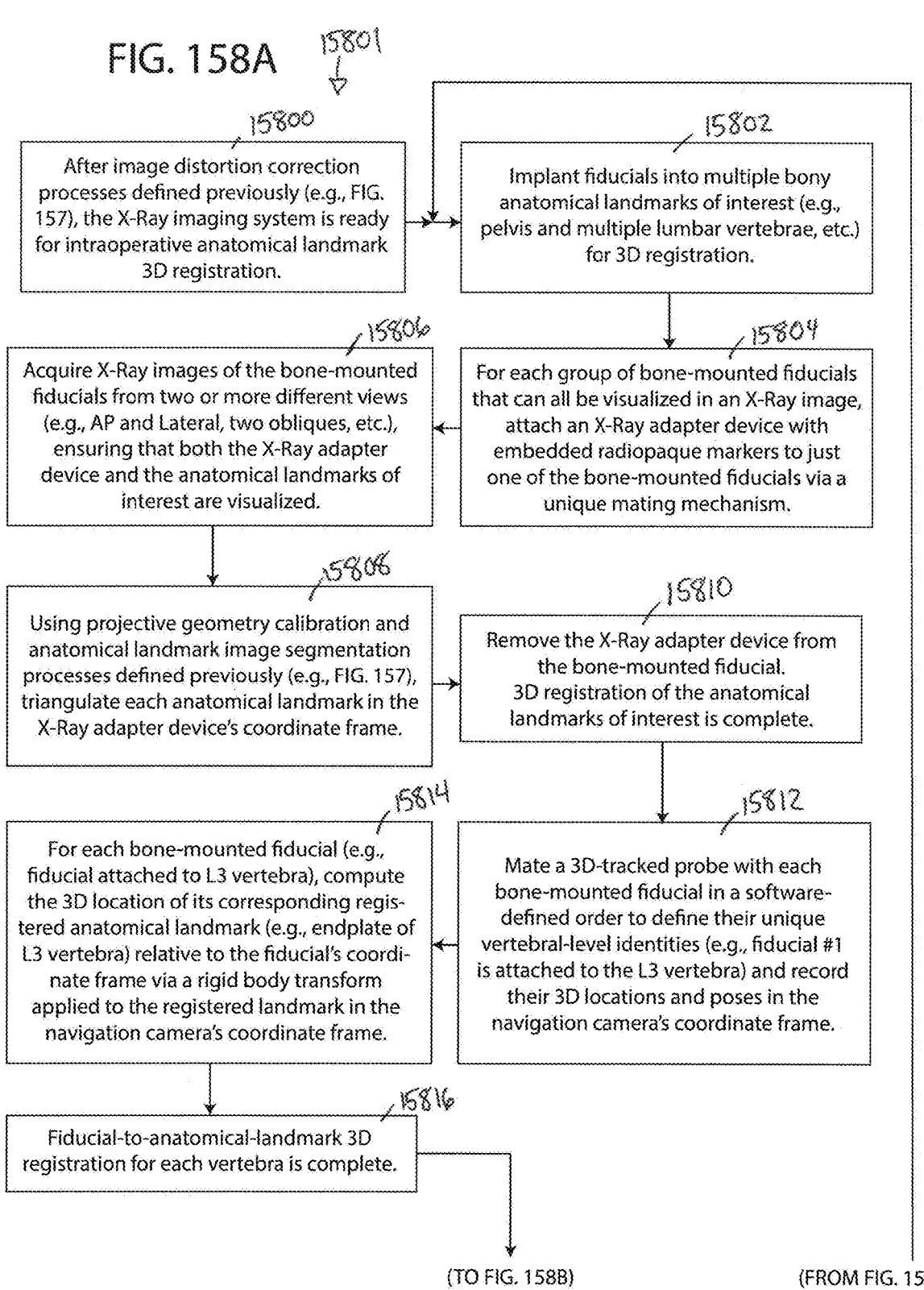

15801

15800
After image distortion correction processes defined previously (e.g., FIG. 157), the X-Ray imaging system is ready for intraoperative anatomical landmark 3D registration.

15802
Implant fiducials into multiple bony anatomical landmarks of interest (e.g., pelvis and multiple lumbar vertebrae, etc.) for 3D registration.

15806
Acquire X-Ray images of the bone-mounted fiducials from two or more different views (e.g., AP and Lateral, two obliques, etc.), ensuring that both the X-Ray adapter device and the anatomical landmarks of interest are visualized.

15804
For each group of bone-mounted fiducials that can all be visualized in an X-Ray image, attach an X-Ray adapter device with embedded radiopaque markers to just one of the bone-mounted fiducials via a unique mating mechanism.

15808
Using projective geometry calibration and anatomical landmark image segmentation processes defined previously (e.g., FIG. 157), triangulate each anatomical landmark in the X-Ray adapter device's coordinate frame.

15810
Remove the X-Ray adapter device from the bone-mounted fiducial.
3D registration of the anatomical landmarks of interest is complete.

15814
For each bone-mounted fiducial (e.g., fiducial attached to L3 vertebra), compute the 3D location of its corresponding registered anatomical landmark (e.g., endplate of L3 vertebra) relative to the fiducial's coordinate frame via a rigid body transform applied to the registered landmark in the navigation camera's coordinate frame.

15812
Mate a 3D-tracked probe with each bone-mounted fiducial in a software-defined order to define their unique vertebral-level identities (e.g., fiducial #1 is attached to the L3 vertebra) and record their 3D locations and poses in the navigation camera's coordinate frame.

15816
Fiducial-to-anatomical-landmark 3D registration for each vertebra is complete.

(TO FIG. 158B)        (FROM FIG. 158B)

FIG. 158B (FROM FIG. 158A)          (TO FIG. 158A)

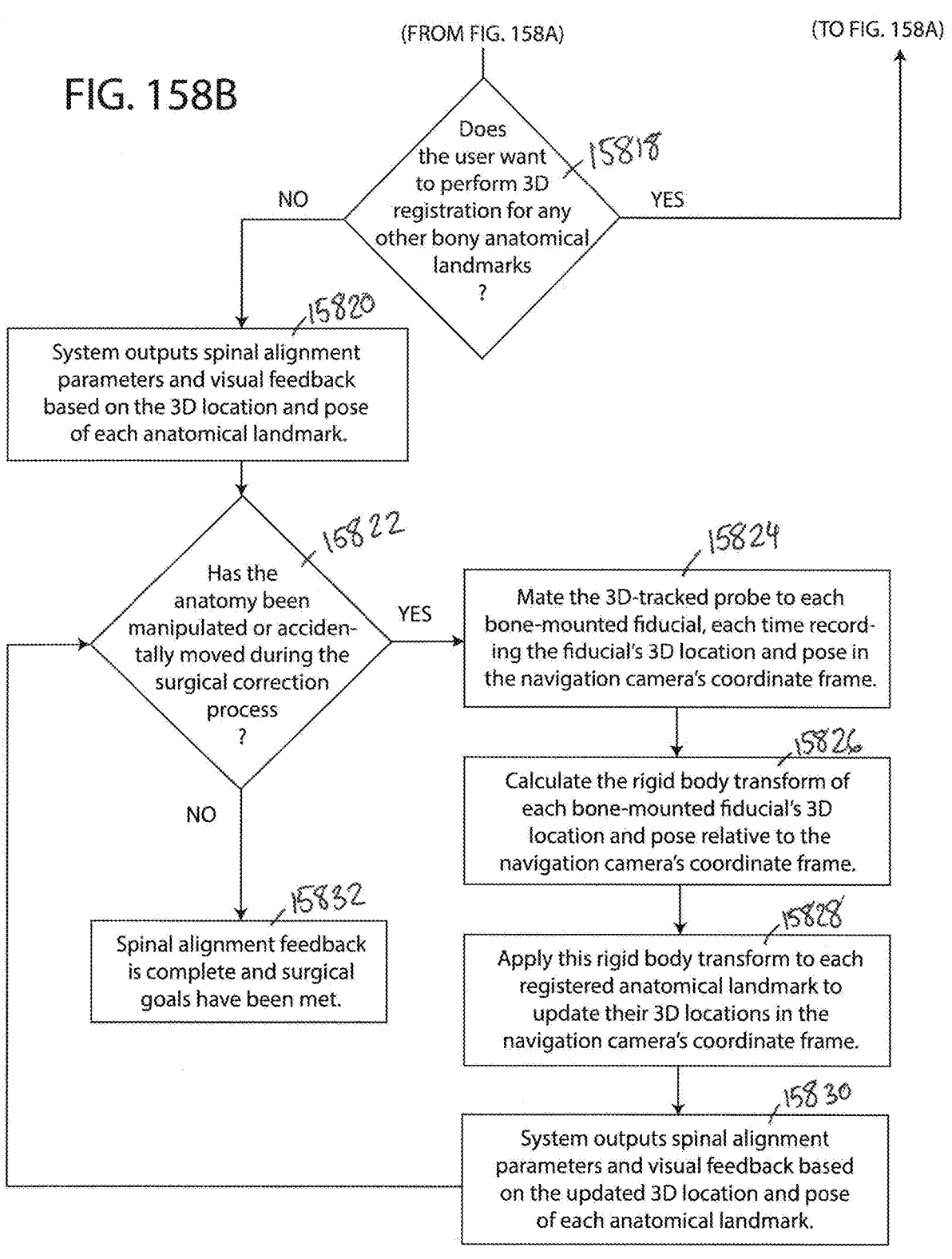

Does the user want to perform 3D registration for any other bony anatomical landmarks ? 15818

NO          YES

15820
System outputs spinal alignment parameters and visual feedback based on the 3D location and pose of each anatomical landmark.

15822
Has the anatomy been manipulated or accidentally moved during the surgical correction process ?

YES

15824
Mate the 3D-tracked probe to each bone-mounted fiducial, each time recording the fiducial's 3D location and pose in the navigation camera's coordinate frame.

15826
Calculate the rigid body transform of each bone-mounted fiducial's 3D location and pose relative to the navigation camera's coordinate frame.

15828
Apply this rigid body transform to each registered anatomical landmark to update their 3D locations in the navigation camera's coordinate frame.

NO

15832
Spinal alignment feedback is complete and surgical goals have been met.

15830
System outputs spinal alignment parameters and visual feedback based on the updated 3D location and pose of each anatomical landmark.

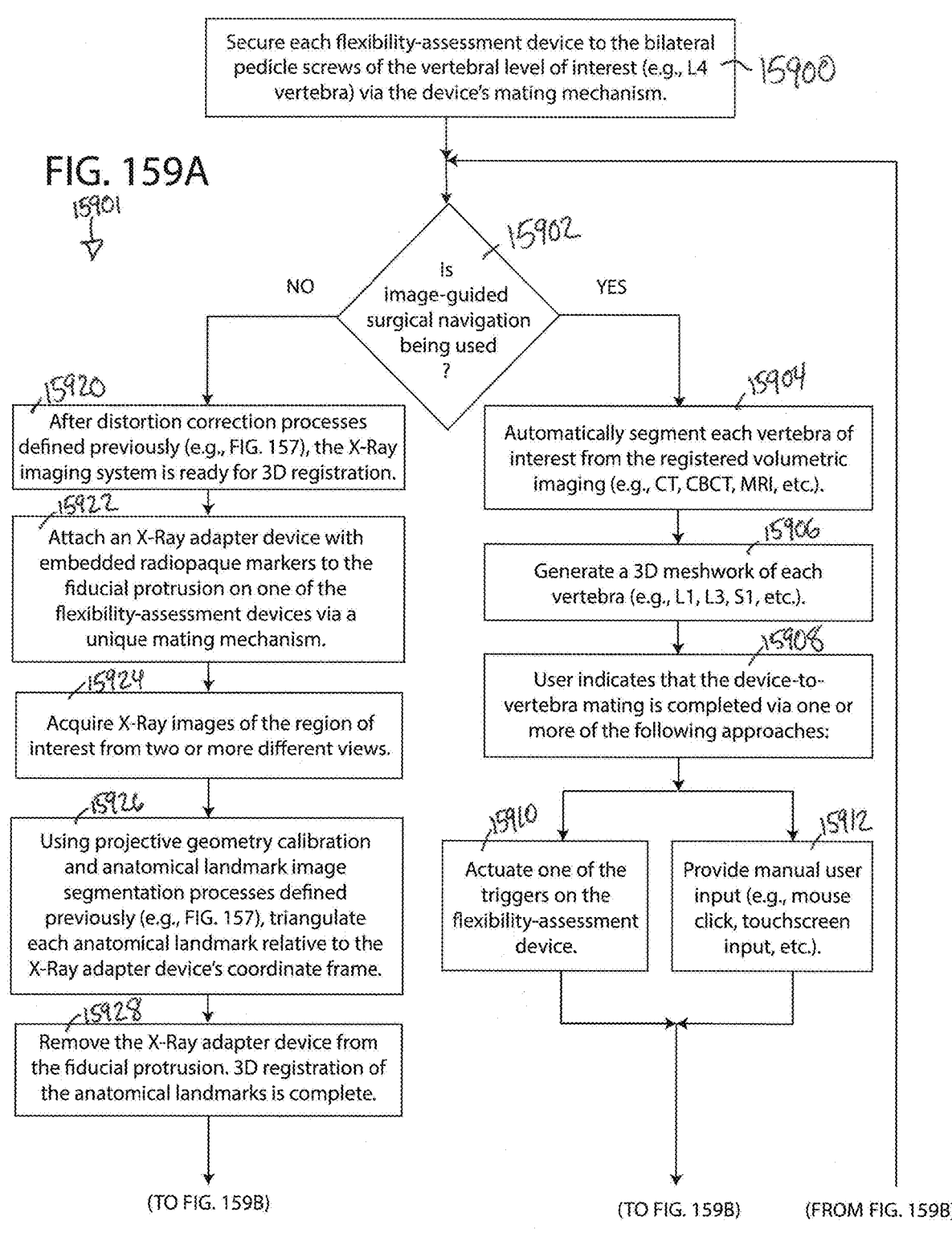

FIG. 159A

Secure each flexibility-assessment device to the bilateral pedicle screws of the vertebral level of interest (e.g., L4 vertebra) via the device's mating mechanism. 15900

15901

Is image-guided surgical navigation being used? 15902

NO

YES

After distortion correction processes defined previously (e.g., FIG. 157), the X-Ray imaging system is ready for 3D registration. 15920

Attach an X-Ray adapter device with embedded radiopaque markers to the fiducial protrusion on one of the flexibility-assessment devices via a unique mating mechanism. 15922

Acquire X-Ray images of the region of interest from two or more different views. 15924

Using projective geometry calibration and anatomical landmark image segmentation processes defined previously (e.g., FIG. 157), triangulate each anatomical landmark relative to the X-Ray adapter device's coordinate frame. 15926

Remove the X-Ray adapter device from the fiducial protrusion. 3D registration of the anatomical landmarks is complete. 15928

Automatically segment each vertebra of interest from the registered volumetric imaging (e.g., CT, CBCT, MRI, etc.). 15904

Generate a 3D meshwork of each vertebra (e.g., L1, L3, S1, etc.). 15906

User indicates that the device-to-vertebra mating is completed via one or more of the following approaches: 15908

Actuate one of the triggers on the flexibility-assessment device. 15910

Provide manual user input (e.g., mouse click, touchscreen input, etc.). 15912

(FROM FIG. 159B)

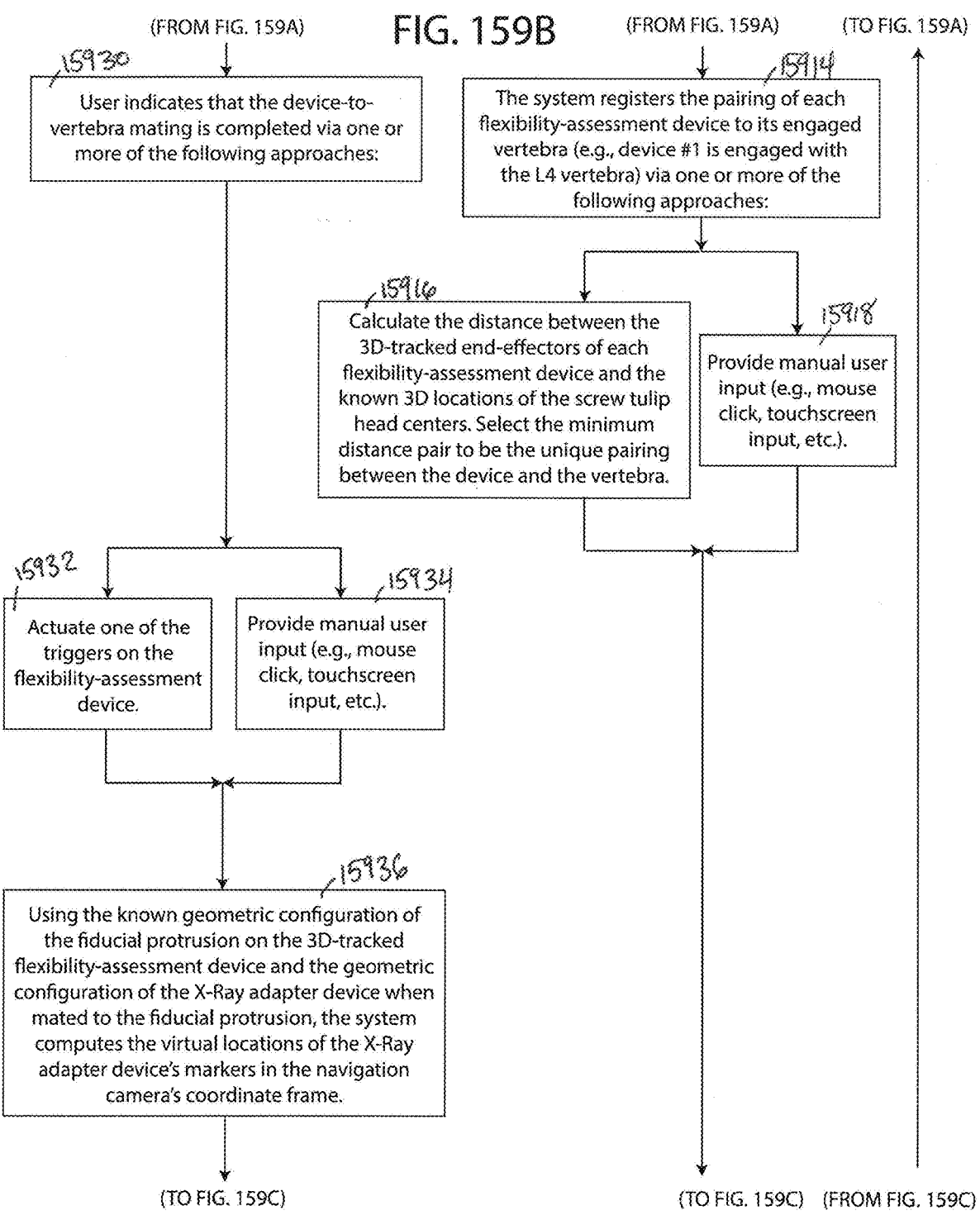

(FROM FIG. 159A)    FIG. 159B    (FROM FIG. 159A)    (TO FIG. 159A)

15930

User indicates that the device-to-vertebra mating is completed via one or more of the following approaches:

15914

The system registers the pairing of each flexibility-assessment device to its engaged vertebra (e.g., device #1 is engaged with the L4 vertebra) via one or more of the following approaches:

15916

Calculate the distance between the 3D-tracked end-effectors of each flexibility-assessment device and the known 3D locations of the screw tulip head centers. Select the minimum distance pair to be the unique pairing between the device and the vertebra.

15918

Provide manual user input (e.g., mouse click, touchscreen input, etc.).

15932

Actuate one of the triggers on the flexibility-assessment device.

15934

Provide manual user input (e.g., mouse click, touchscreen input, etc.).

15936

Using the known geometric configuration of the fiducial protrusion on the 3D-tracked flexibility-assessment device and the geometric configuration of the X-Ray adapter device when mated to the fiducial protrusion, the system computes the virtual locations of the X-Ray adapter device's markers in the navigation camera's coordinate frame.

(TO FIG. 159C)    (TO FIG. 159C)   (FROM FIG. 159C)

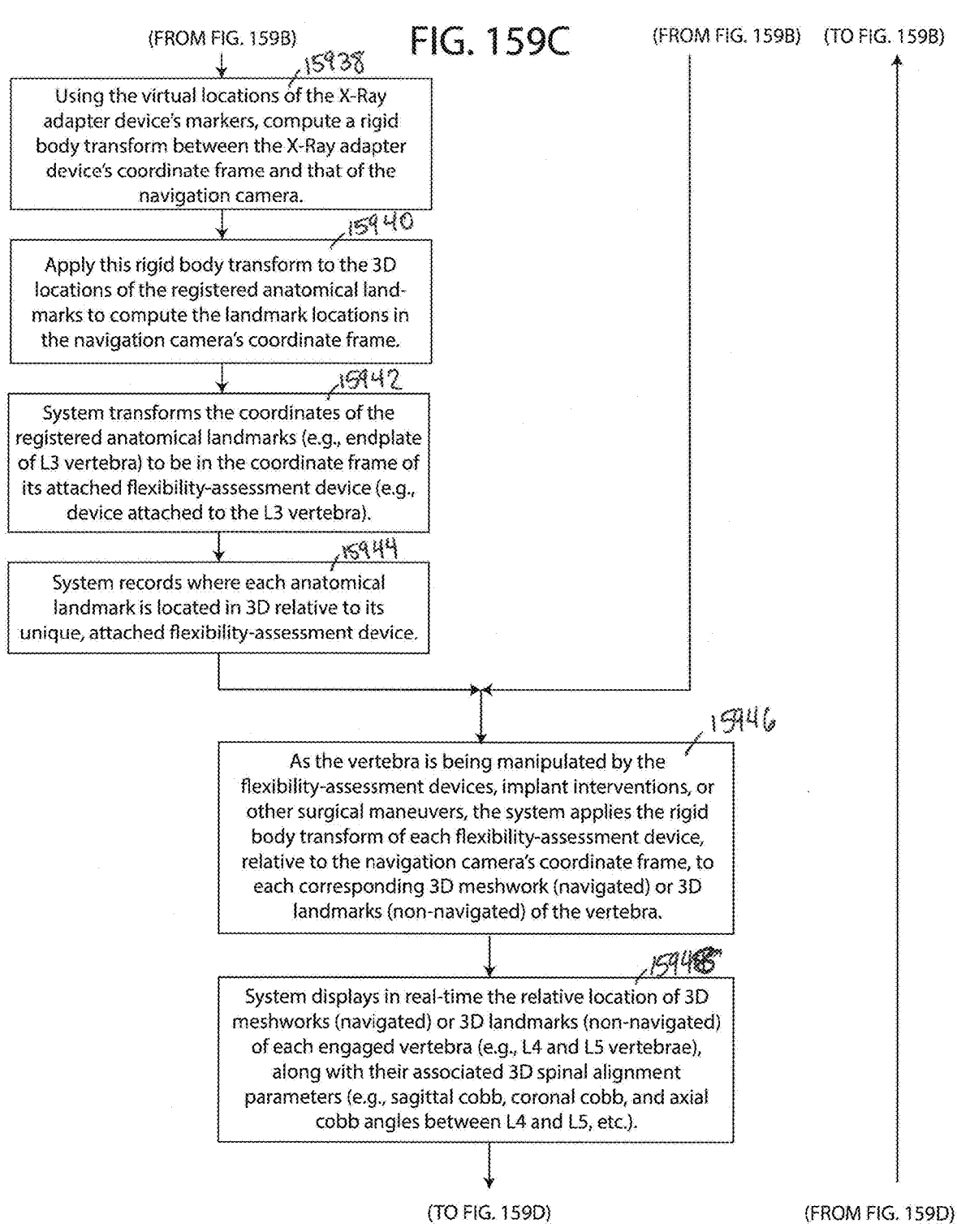

(FROM FIG. 159B)     FIG. 159C     (FROM FIG. 159B)    (TO FIG. 159B)

15938

Using the virtual locations of the X-Ray adapter device's markers, compute a rigid body transform between the X-Ray adapter device's coordinate frame and that of the navigation camera.

15940

Apply this rigid body transform to the 3D locations of the registered anatomical land-marks to compute the landmark locations in the navigation camera's coordinate frame.

15942

System transforms the coordinates of the registered anatomical landmarks (e.g., endplate of L3 vertebra) to be in the coordinate frame of its attached flexibility-assessment device (e.g., device attached to the L3 vertebra).

15944

System records where each anatomical landmark is located in 3D relative to its unique, attached flexibility-assessment device.

15946

As the vertebra is being manipulated by the flexibility-assessment devices, implant interventions, or other surgical maneuvers, the system applies the rigid body transform of each flexibility-assessment device, relative to the navigation camera's coordinate frame, to each corresponding 3D meshwork (navigated) or 3D landmarks (non-navigated) of the vertebra.

15948

System displays in real-time the relative location of 3D meshworks (navigated) or 3D landmarks (non-navigated) of each engaged vertebra (e.g., L4 and L5 vertebrae), along with their associated 3D spinal alignment parameters (e.g., sagittal cobb, coronal cobb, and axial cobb angles between L4 and L5, etc.).

(TO FIG. 159D)        (FROM FIG. 159D)

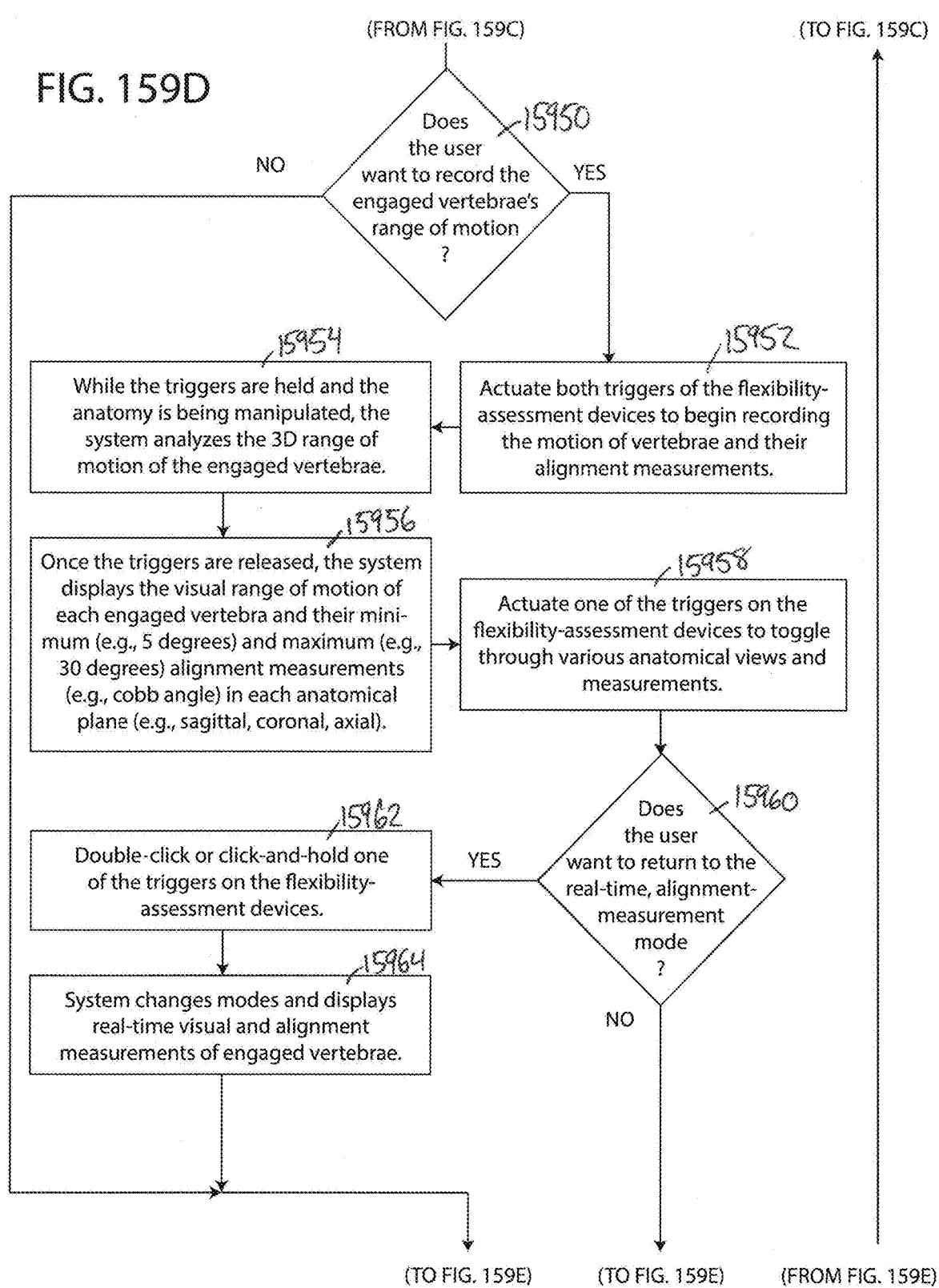

FIG. 159D (FROM FIG. 159C)

(TO FIG. 159C)

Does the user want to record the engaged vertebrae's range of motion? — 15950

NO

YES

While the triggers are held and the anatomy is being manipulated, the system analyzes the 3D range of motion of the engaged vertebrae. — 15954

Actuate both triggers of the flexibility-assessment devices to begin recording the motion of vertebrae and their alignment measurements. — 15952

Once the triggers are released, the system displays the visual range of motion of each engaged vertebra and their minimum (e.g., 5 degrees) and maximum (e.g., 30 degrees) alignment measurements (e.g., cobb angle) in each anatomical plane (e.g., sagittal, coronal, axial). — 15956

Actuate one of the triggers on the flexibility-assessment devices to toggle through various anatomical views and measurements. — 15958

Double-click or click-and-hold one of the triggers on the flexibility-assessment devices. — 15962

YES

Does the user want to return to the real-time, alignment-measurement mode? — 15960

NO

System changes modes and displays real-time visual and alignment measurements of engaged vertebrae. — 15964

(TO FIG. 159E)     (TO FIG. 159E)     (FROM FIG. 159E)

(FROM FIG. 159D)  (FROM FIG. 159D)  (TO FIG. 159D)

FIG. 159E

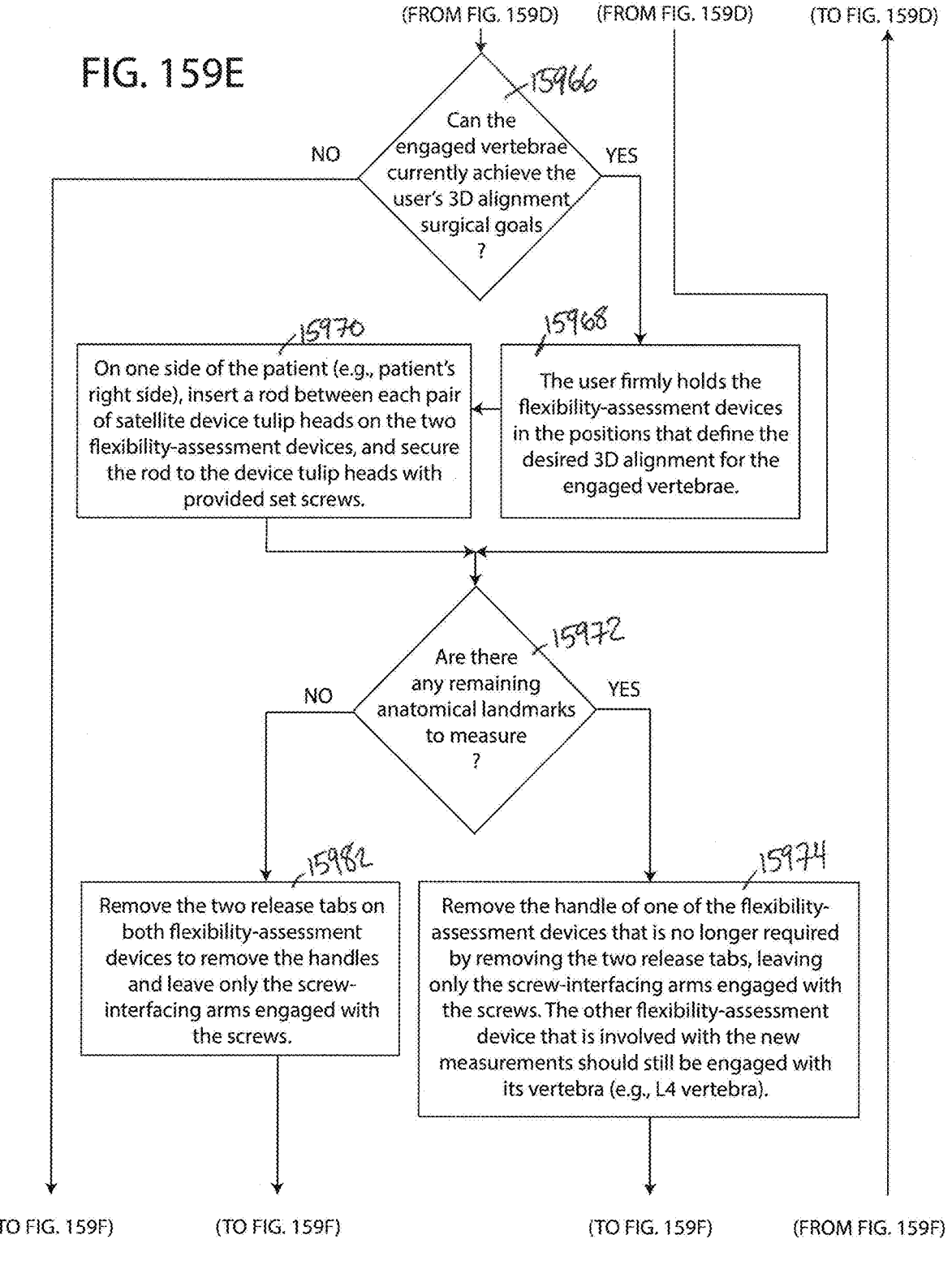

*15966*

Can the engaged vertebrae currently achieve the user's 3D alignment surgical goals ?

NO  YES

*15970*

On one side of the patient (e.g., patient's right side), insert a rod between each pair of satellite device tulip heads on the two flexibility-assessment devices, and secure the rod to the device tulip heads with provided set screws.

*15968*

The user firmly holds the flexibility-assessment devices in the positions that define the desired 3D alignment for the engaged vertebrae.

*15972*

Are there any remaining anatomical landmarks to measure ?

NO  YES

*15982*

Remove the two release tabs on both flexibility-assessment devices to remove the handles and leave only the screw-interfacing arms engaged with the screws.

*15974*

Remove the handle of one of the flexibility-assessment devices that is no longer required by removing the two release tabs, leaving only the screw-interfacing arms engaged with the screws. The other flexibility-assessment device that is involved with the new measurements should still be engaged with its vertebra (e.g., L4 vertebra).

(TO FIG. 159F)  (TO FIG. 159F)  (TO FIG. 159F)  (FROM FIG. 159F)

FIG. 159F

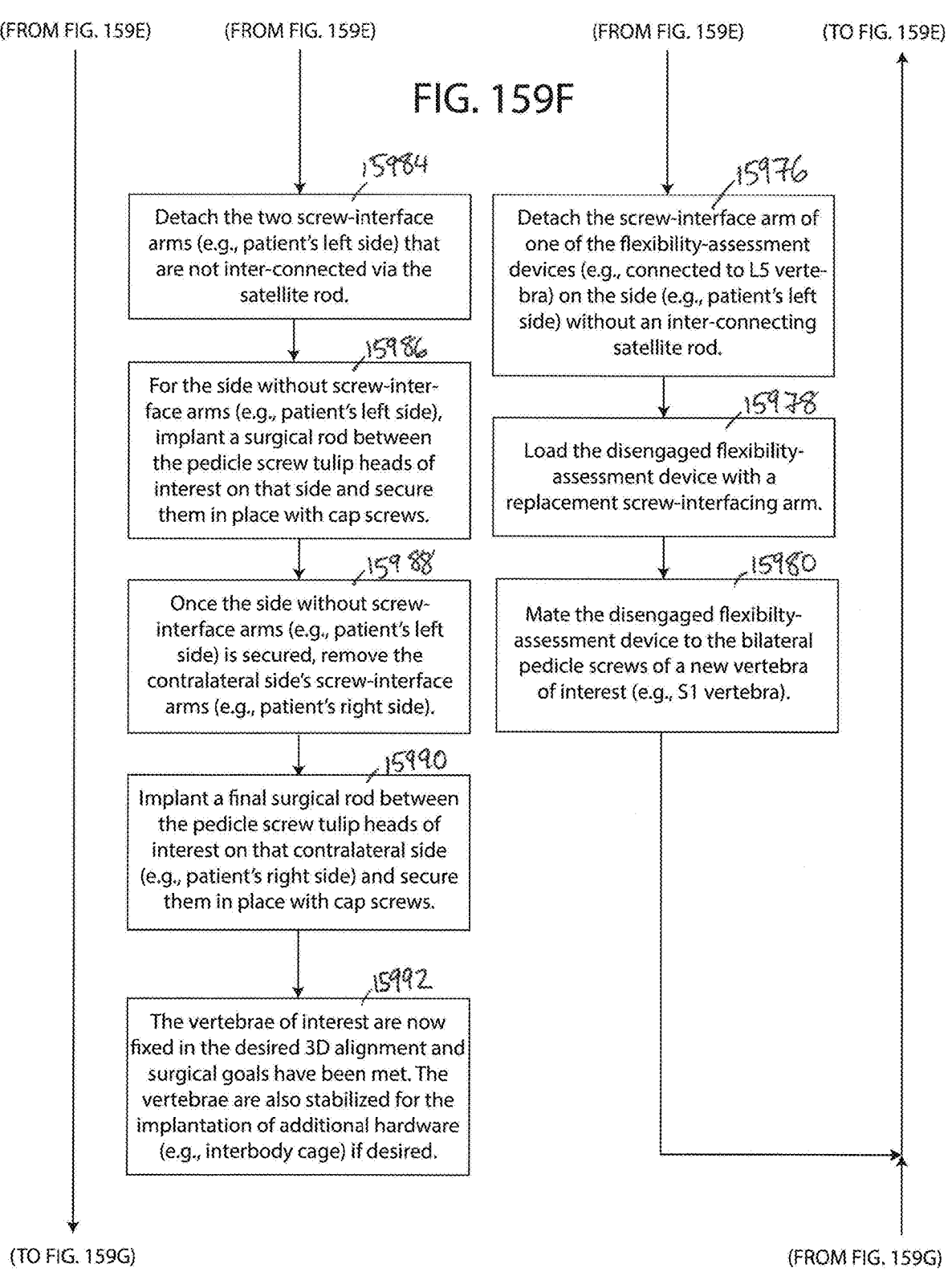

15984

Detach the two screw-interface arms (e.g., patient's left side) that are not inter-connected via the satellite rod.

15986

For the side without screw-interface arms (e.g., patient's left side), implant a surgical rod between the pedicle screw tulip heads of interest on that side and secure them in place with cap screws.

15988

Once the side without screw-interface arms (e.g., patient's left side) is secured, remove the contralateral side's screw-interface arms (e.g., patient's right side).

15990

Implant a final surgical rod between the pedicle screw tulip heads of interest on that contralateral side (e.g., patient's right side) and secure them in place with cap screws.

15992

The vertebrae of interest are now fixed in the desired 3D alignment and surgical goals have been met. The vertebrae are also stabilized for the implantation of additional hardware (e.g., interbody cage) if desired.

15976

Detach the screw-interface arm of one of the flexibility-assessment devices (e.g., connected to L5 vertebra) on the side (e.g., patient's left side) without an inter-connecting satellite rod.

15978

Load the disengaged flexibility-assessment device with a replacement screw-interfacing arm.

15980

Mate the disengaged flexibilty-assessment device to the bilateral pedicle screws of a new vertebra of interest (e.g., S1 vertebra).

(FROM FIG. 159F)

Remove both of the flexibility-assessment devices.

15996

Are there any remaining anatomical landmarks to measure ?

YES

NO

15998

Flexibility assessment is complete. Continue and finish surgical correction process.

FIG. 160A 16001

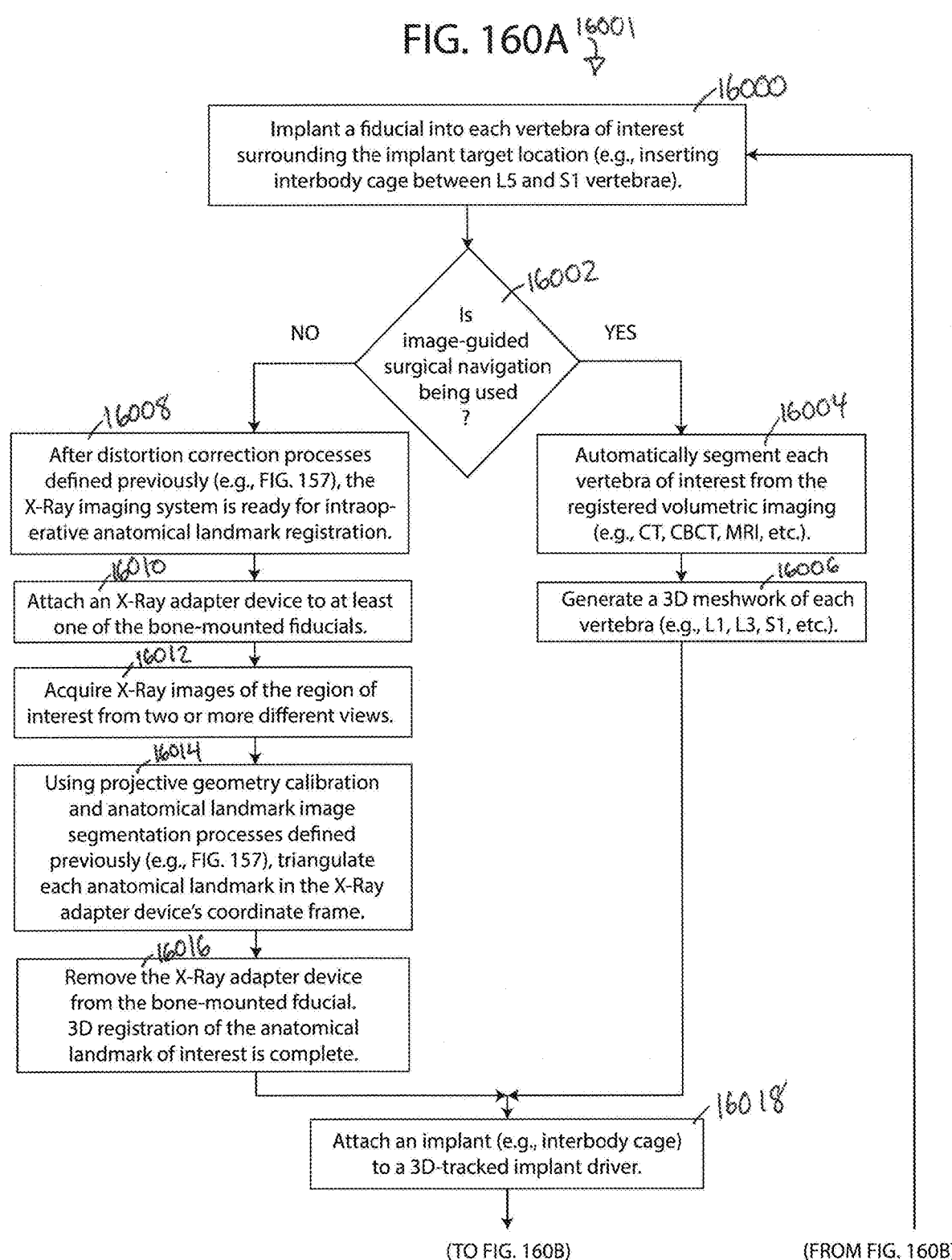

16000
Implant a fiducial into each vertebra of interest surrounding the implant target location (e.g., inserting interbody cage between L5 and S1 vertebrae).

16002
Is image-guided surgical navigation being used?

NO

YES

16008
After distortion correction processes defined previously (e.g., FIG. 157), the X-Ray imaging system is ready for intraoperative anatomical landmark registration.

16004
Automatically segment each vertebra of interest from the registered volumetric imaging (e.g., CT, CBCT, MRI, etc.).

16010
Attach an X-Ray adapter device to at least one of the bone-mounted fiducials.

16006
Generate a 3D meshwork of each vertebra (e.g., L1, L3, S1, etc.).

16012
Acquire X-Ray images of the region of interest from two or more different views.

16014
Using projective geometry calibration and anatomical landmark image segmentation processes defined previously (e.g., FIG. 157), triangulate each anatomical landmark in the X-Ray adapter device's coordinate frame.

16016
Remove the X-Ray adapter device from the bone-mounted fducial. 3D registration of the anatomical landmark of interest is complete.

16018
Attach an implant (e.g., interbody cage) to a 3D-tracked implant driver.

(TO FIG. 160B)                    (FROM FIG. 160B)

FIG. 160B

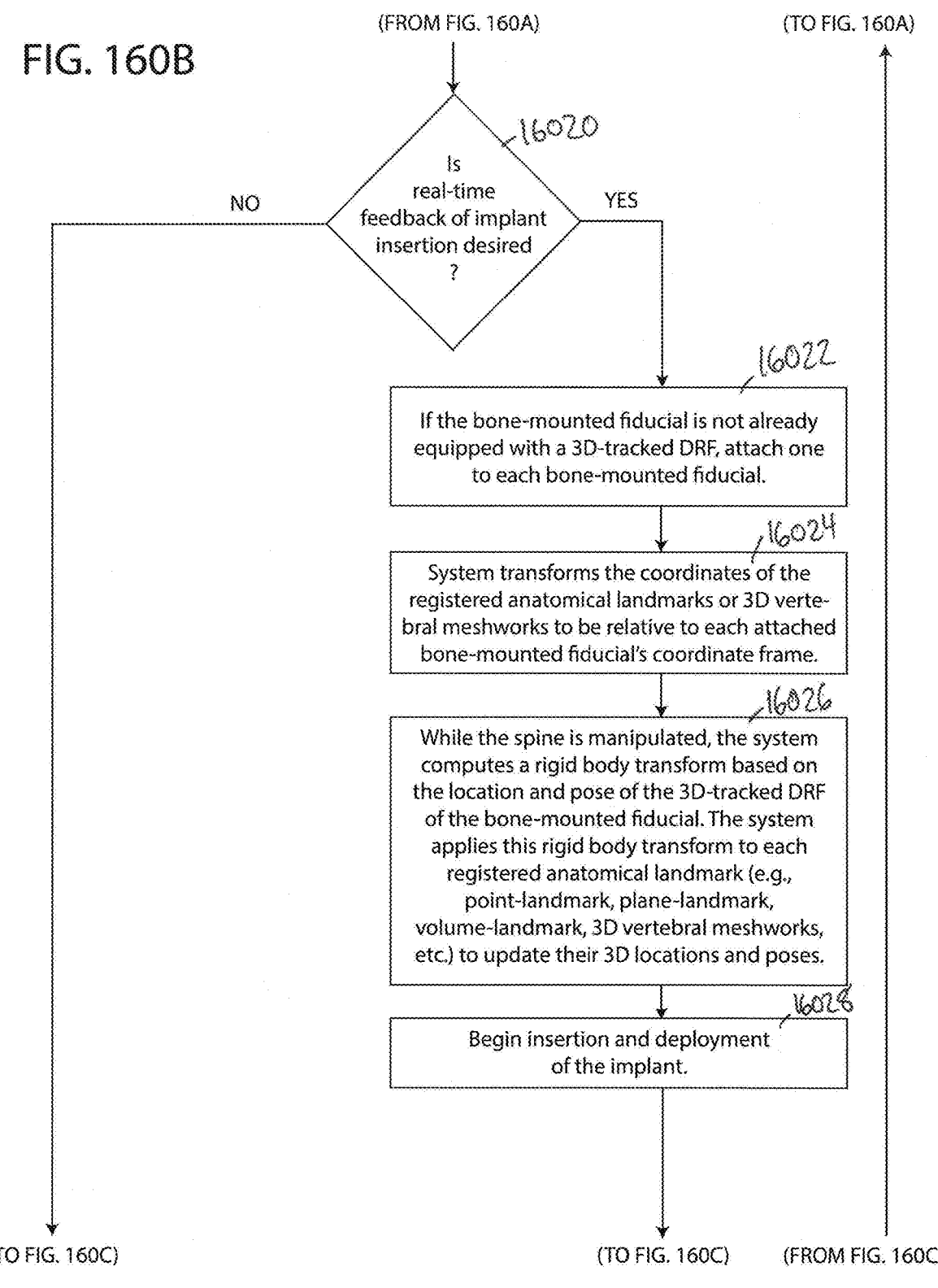

(FROM FIG. 160A)

Is real-time feedback of implant insertion desired ?

NO

YES

16022

If the bone-mounted fiducial is not already equipped with a 3D-tracked DRF, attach one to each bone-mounted fiducial.

16024

System transforms the coordinates of the registered anatomical landmarks or 3D vertebral meshworks to be relative to each attached bone-mounted fiducial's coordinate frame.

16026

While the spine is manipulated, the system computes a rigid body transform based on the location and pose of the 3D-tracked DRF of the bone-mounted fiducial. The system applies this rigid body transform to each registered anatomical landmark (e.g., point-landmark, plane-landmark, volume-landmark, 3D vertebral meshworks, etc.) to update their 3D locations and poses.

16028

Begin insertion and deployment of the implant.

(FROM FIG. 160C)

FIG. 160C (FROM FIG. 160B)          (FROM FIG. 160B)          (TO FIG. 160B)

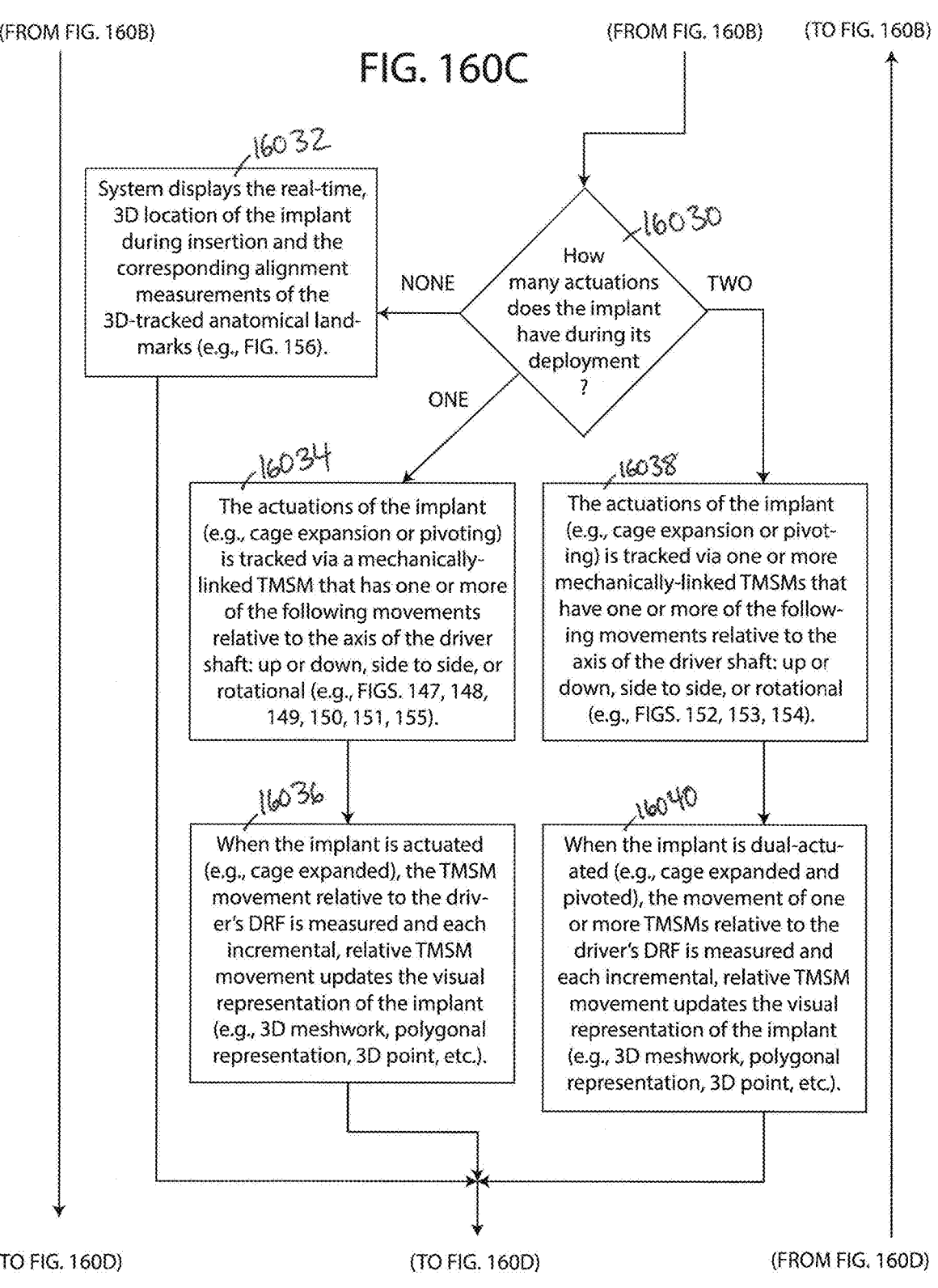

1632

System displays the real-time, 3D location of the implant during insertion and the corresponding alignment measurements of the 3D-tracked anatomical land-marks (e.g., FIG. 156).

16030

How many actuations does the implant have during its deployment?

NONE          TWO          ONE

16034

The actuations of the implant (e.g., cage expansion or pivoting) is tracked via a mechanically-linked TMSM that has one or more of the following movements relative to the axis of the driver shaft: up or down, side to side, or rotational (e.g., FIGS. 147, 148, 149, 150, 151, 155).

16038

The actuations of the implant (e.g., cage expansion or pivot-ing) is tracked via one or more mechanically-linked TMSMs that have one or more of the follow-ing movements relative to the axis of the driver shaft: up or down, side to side, or rotational (e.g., FIGS. 152, 153, 154).

16036

When the implant is actuated (e.g., cage expanded), the TMSM movement relative to the driv-er's DRF is measured and each incremental, relative TMSM movement updates the visual representation of the implant (e.g., 3D meshwork, polygonal representation, 3D point, etc.).

16040

When the implant is dual-actu-ated (e.g., cage expanded and pivoted), the movement of one or more TMSMs relative to the driver's DRF is measured and each incremental, relative TMSM movement updates the visual representation of the implant (e.g., 3D meshwork, polygonal representation, 3D point, etc.).

(TO FIG. 160D)          (TO FIG. 160D)          (FROM FIG. 160D)

FIG. 160D

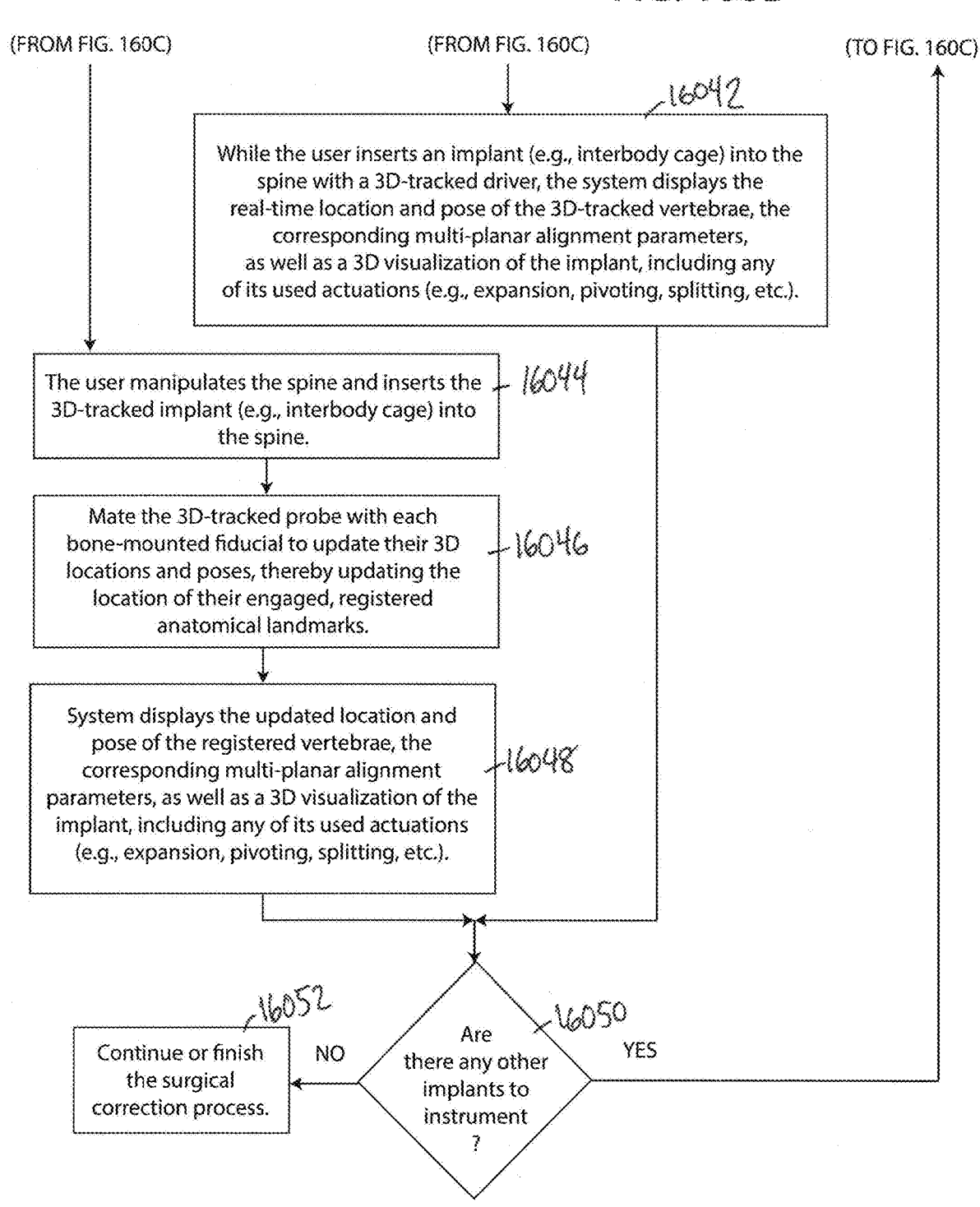

(FROM FIG. 160C)    (FROM FIG. 160C)    (TO FIG. 160C)

16042

While the user inserts an implant (e.g., interbody cage) into the spine with a 3D-tracked driver, the system displays the real-time location and pose of the 3D-tracked vertebrae, the corresponding multi-planar alignment parameters, as well as a 3D visualization of the implant, including any of its used actuations (e.g., expansion, pivoting, splitting, etc.).

16044

The user manipulates the spine and inserts the 3D-tracked implant (e.g., interbody cage) into the spine.

16046

Mate the 3D-tracked probe with each bone-mounted fiducial to update their 3D locations and poses, thereby updating the location of their engaged, registered anatomical landmarks.

16048

System displays the updated location and pose of the registered vertebrae, the corresponding multi-planar alignment parameters, as well as a 3D visualization of the implant, including any of its used actuations (e.g., expansion, pivoting, splitting, etc.).

16052

Continue or finish the surgical correction process.

NO

16050

Are there any other implants to instrument?

YES

Logo

View:
3D
Perspective

INTRAOPERATIVE ALIGNMENT ASSESSMENT SYSTEM AND METHOD

RELATED APPLICATIONS

This application is a continuation-in-part application of U.S. patent application Ser. No. 16/237,443, filed on Dec. 31, 2018, which is a continuation-in-part of U.S. patent application Ser. No. 16/026,754, filed Jul. 3, 2018, which claims priority to U.S. Provisional Patent Application No. 62/528,390, filed on Jul. 3, 2017, the entire contents of which are incorporated herein by reference. This application also claims priority to U.S. Provisional Patent Application No. 62/884,032, filed Aug. 7, 2019.

BACKGROUND

Current tools limit a surgeon's ability to quickly and accurately assess the intraoperative alignment of their patient's spine, especially after the spine has been manipulated during a correction. In addition, most of the state-of-the-art options introduce or rely on excessive radiation exposure, inadequate visualization of anatomical landmark(s) of interest, and lengthy disruptions to the surgical workflow.

Accordingly, new systems and methods are needed analyzing and providing a patient's spinal alignment information and therapeutic device data. The method ideally should include obtaining initial patient data, and acquiring spinal alignment contour information, assessing localized anatomical features of the patient, and obtaining anatomical region data. The system and method should include analyzing the localized anatomy and therapeutic device location and contouring resulting in an output including a localized anatomical analysis and a display of therapeutic device contouring data.

SUMMARY

Some embodiments include a system comprising at least one dynamic reference frame (DRF) configured so that any fixed or mobile portion of the DRF, or any assembly or component coupled to the DRF can be registered in 3D space using a plurality of trackable markers. In some embodiments, the plurality of trackable markers includes at least one moveable or triggerable marker. Some embodiments include at least one user-actuation trigger or actuator coupled to the at least one moveable or triggerable marker that can trigger or actuate the at least one moveable or triggerable marker. Some further embodiments include at least one 3D tracking camera or imaging system configured to track one or more of the plurality of trackable markers. In some embodiments, the system includes a processor and a memory coupled to the processor, wherein the memory stores instructions executable by the processor to track one or more 3D coordinates of one or more of the plurality of trackable markers.

Some further embodiments include a method of analyzing and providing spinal alignment anatomical information and therapeutic device data, comprising obtaining initial patient data, acquiring alignment contour information, assessing localized anatomical features, obtaining anatomical region data, analyzing localized anatomy, analyzing therapeutic device location and contouring, and/or outputting on a display the localized anatomical analyses and therapeutic device contouring data.

Some further embodiments include an anatomical marking or tracking system comprising a lower fiducial alignment assembly and a complementary upper fiducial alignment assembly. In some embodiments, the lower fiducial alignment assembly is configured to couple to an anatomy, and the upper fiducial alignment assembly is configured to align to at least a portion of the lower fiducial assembly using at least one characteristic of the lower fiducial alignment assembly and the upper fiducial alignment assembly.

Some embodiments include radiopaque markers configured to be visually observable using an X-ray source or imager, where the radiopaque markers are at least partially embedded in at least one of the lower fiducial alignment assembly and a complementary upper fiducial alignment assembly.

In some embodiments, the at least one characteristic comprises at least one magnet. In some embodiments, the at least one characteristic comprises at least one protrusion configured to at least partially insert or mate with at least one mating aperture. In some embodiments, the at least one protrusion comprises at least one protrusion extending from a mating surface of the lower fiducial alignment assembly. In some further embodiments, the at least one mating aperture is positioned through a mating surface of the upper fiducial alignment assembly.

In some embodiments of the invention, the lower fiducial alignment assembly and complementary upper fiducial alignment assembly are configured to be at least partially aligned and coupled at an interface through surgical drapes or towels, where the interface comprises at least a portion of the surgical drapes or towels positioned between at least a portion of the lower fiducial alignment assembly and complementary upper fiducial alignment assembly.

In some further embodiments, the upper fiducial alignment assembly comprises at least one groove positioned in an upper surface, where the at least one groove is configured to be tracked by a tracking probe to determine a unique identity of the system as well as interpret its location and pose in space.

In some embodiments, the at least one groove comprises a "z" geometry configured to accommodate and/or guide a tracking probe. In some further embodiments, the at least one groove comprises a sloped decline configured to facilitate a user tracing a probe from the upper surface of the upper surface of the upper fiducial alignment assembly down to a body surface onto which the system is placed.

In some embodiments, the lower fiducial alignment assembly is configured and arranged to adhere to a skin surface. In some further embodiments, the lower fiducial alignment assembly and/or upper fiducial alignment assembly can comprise a guide indicative of how a user should position the system. In some embodiments, the guide comprises an arrow shape indicative of a position or orientation. In some embodiments of the system, the radiopaque markers comprise three or more markers positioned with respect to each other to enable calculation of 3D pose information.

Some further embodiments comprise a tracking probe configured to couple to at least a portion of the upper fiducial alignment assembly. In some embodiments, the tracking probe is configured to couple to at least one groove of the upper fiducial alignment assembly to determine a unique identity of the system as well as interpret its location and pose in space.

Some embodiments include a tracking system comprising a lower fiducial alignment assembly and a complementary upper fiducial alignment assembly, where the lower fiducial alignment assembly is configured to couple to an anatomy, and the upper fiducial alignment assembly is configured to align to at least a portion of the lower fiducial assembly using at least one characteristic of the lower fiducial alignment assembly and the upper fiducial alignment assembly. In some further embodiments, the radiopaque markers are configured to be visually observable using an X-ray source or imager, and the radiopaque markers are at least partially embedded in at least one of the lower fiducial alignment assembly and a complementary upper fiducial alignment assembly. Some embodiments also include at least one tracking probe assembly configured to couple to at least a portion of the upper fiducial alignment assembly, and at least one groove positioned in the upper fiducial alignment assembly. In some embodiments, the at least one groove is configured to be tracked by the at least one tracking probe assembly to determine a unique identity of the system as well as interpret its location and pose in space.

In some embodiments of the tracking system, the at least one characteristic comprises at least one magnet. In some embodiments of the tracking system, the at least one characteristic comprises at least one protrusion configured to at least partially insert or mate with at least one mating aperture, where the at least one protrusion extends from the mating surface of the lower fiducial alignment assembly, and the at least one mating aperture is positioned through a mating surface of the upper fiducial alignment assembly.

Some embodiments of the tracking system include at least one groove that comprises a "z" geometry configured to accommodate and/or guide the tracking probe. In some embodiments, the at least one groove comprises a sloped decline configured to facilitate a user tracing a probe from the upper surface of the upper surface of the upper fiducial alignment assembly down to a body surface onto which at least the lower fiducial alignment assembly is placed.

Some embodiments include a tracking system comprising a tracking probe assembly comprising a probe shaft with a depressible sliding shaft tip, and a mount with a trackable mobile stray marker at one end of the probe shaft, and a plurality of depth-stops at the opposite end of the probe shaft. Further, some embodiments include a dynamic reference frame coupled to the probe shaft adjacent the mount.

Some embodiments further comprise at least one depth-stop fiducial. In some embodiments, the plurality of depth-stops comprises a series of concentrically-oriented, varying diameter protrusions. In some embodiments, the one or more of the plurality of depth-stops are configured to actuate the depressible sliding shaft tip. Further, in some embodiments, the one or more of the plurality of depth-stops are configured to actuate the depressible sliding shaft tip when forced against a depth-stop fiducial with specific inner diameters, the actuation configured to provide identifiable deflections of the trackable mobile stray marker.

In some embodiments, the probe shaft is spring-loaded. In some embodiments, the dynamic reference frame comprises at least one tracking marker. In some embodiments, the dynamic reference frame comprises four tracking markers, with two of the four tracking markers extending to one side of the probe shaft and two of the four tracking markers extending to an opposite side of the probe shaft. Some embodiments further comprise an asymmetric protruding extrusion configured to engage with a corresponding slot of a depth-stop fiducial.

In some embodiments of the invention, an engagement of the asymmetric protruding extrusion with a corresponding slot of a depth-stop fiducial can enable the system to register a unique orientation of the coordinate axes of the depth-stop fiducial, and/or detect how the depth-stop fiducial rotates and translates in 3D space between one or more registrations.

Some further embodiments comprise a fiduciary assembly comprising a lower fiducial alignment assembly and a complementary upper fiducial alignment assembly, where the lower fiducial alignment assembly is configured to couple to an anatomy, and the upper fiducial alignment assembly is configured to align to at least a portion of the lower fiducial assembly using at least one characteristic of the lower fiducial alignment assembly and the upper fiducial alignment assembly. In some embodiments, the at least one groove is positioned in the upper fiducial alignment assembly, and the at least one groove is configured to be tracked by tracking probe to determine a unique identity of the system as well as interpret its location and pose in space.

In some embodiments, the tracking system comprises radiopaque markers configured to be visually observable using an X-ray source or imager, where the radiopaque markers are at least partially embedded in at least one of the lower fiducial alignment assembly and a complementary upper fiducial alignment assembly. In some embodiments, the at least one characteristic comprises at least one magnet. In some embodiments, the at least one characteristic comprises at least one protrusion configured to at least partially insert into or mate with at least one mating aperture, and the at least one protrusion extends from the mating surface of the lower fiducial alignment assembly, and further, the at least one mating aperture is positioned through a mating surface of the upper fiducial alignment assembly.

Some embodiments include a tracking system comprising a tracking probe assembly comprising a probe shaft with a depressible sliding shaft tip, and a mount with a trackable mobile stray marker at one end of the probe shaft, and a plurality of depth-stops at the opposite end of the probe shaft. Further, some embodiments include a dynamic reference frame coupled to the probe shaft adjacent the mount, and a lower fiducial alignment assembly and a complementary upper fiducial alignment assembly. In some embodiments, the lower fiducial alignment assembly is configured to couple to an anatomy, and the upper fiducial alignment assembly is configured to align to at least a portion of the lower fiducial assembly using an embedded or coupled element of the lower fiducial alignment assembly and the upper fiducial alignment assembly. Further, some embodiments include at least one groove positioned in the upper fiducial alignment assembly, where the at least one groove is configured to be tracked by the tracking probe assembly. Further, some embodiments of the tracking system further comprise radiopaque markers configured to be visually observable using an X-ray source or imager, and where the radiopaque markers are at least partially embedded in at least one of the lower fiducial alignment assembly and a complementary upper fiducial alignment assembly. In some embodiments, the at least one embedded or coupled element comprises at least one magnet. In some embodiments, the at least one embedded or coupled element comprises at least one at least one protrusion configured to at least partially insert or mate with at least one mating aperture, where the at least one protrusion extends from the mating surface of the lower fiducial alignment assembly, and the at least one mating aperture is positioned through a mating surface of the upper fiducial alignment assembly.

Some embodiments include a marker system comprising a lower fiducial alignment assembly and a complementary upper fiducial alignment assembly, where the lower fiducial alignment assembly is configured to couple to an anatomy, and the upper fiducial alignment assembly is configured to align to at least a portion of the lower fiducial assembly, and the radiopaque markers are configured to be visually observable using an X-ray source or imager, and extend from the complementary upper fiducial alignment assembly.

In some embodiments, the radiopaque markers comprise three radiopaque markers. In some further embodiments, the radiopaque markers are positioned on corners of the upper fiducial alignment assembly. In some embodiments, the lower fiducial alignment assembly/or a complementary upper fiducial alignment assembly include slots. In some further embodiments, an upper surface of the upper fiducial alignment assembly comprises a depression or contour configured to be probed by a tracking probe shaft or tip.

In some embodiments, the lower fiducial alignment assembly and complementary upper fiducial alignment assembly are configured to be at least partially aligned and coupled at an interface through surgical drapes or towels, where the interface comprises at least a portion of the surgical drapes or towels positioned between at least a portion of the lower fiducial alignment assembly and complementary upper fiducial alignment assembly.

Some embodiments further comprise a tracking probe assembly comprising a probe shaft and at least one coupled dynamic reference frame including optically trackable markers.

Some embodiments include an anatomy analysis method comprising providing at least one trackable surgical tool including a tool dynamic reference frame and at least one trackable marker, where the at least one trackable surgical tool is configured so that any fixed or mobile portion of the at least one trackable surgical tool can be registered in 3D space. In some embodiments, the method includes providing at least one 3D tracking camera or imaging system configured to track the at least one trackable marker. In some embodiments, the method includes providing a topological optical surface registration system. In some embodiments, the method includes providing a malleable contour element coupled to at least a portion of a patient. In some embodiments, the method includes providing an electromechanical 3D-tracking system, where the electromechanical 3D-tracking provides a system including at least one physically coupled probe, where the at least one physically coupled probe is configured to be tracked in 3D space while coupled to the malleable contour element and/or at least a portion of a patient, and tracing at least a portion of an anatomy of a patient. In some embodiments, the method includes registering the location of one or more fiducial markers inside or outside a surgical site of the patient. In some further embodiments, the method includes registering a contour of at least a portion of the patient using the malleable contour element. In some embodiments, the method includes providing a processor and a memory coupled to the processor, where the memory stores anatomy contour measurement instructions executable by the processor to track 3D coordinates of one or more of the fiducial markers. In some embodiments, the instructions executable by the processor including outputting on a display an anatomical imaging analysis of at least a portion of the patient, and one or more anatomical landmarks registered by the electromechanical 3D-tracking system that are adjusted in position and orientation to the registered contour.

Some embodiments of the invention include a trackable probe assembly comprising a trackable dynamic reference frame coupled or integrated to a probe shaft, where the dynamic reference frame includes at least one marker. Some embodiments include a user actuable marker coupled to a user triggerable assembly including a trigger, and at least one probe tip extending from the probe shaft.

In some embodiments, the trigger comprises a depressible tab positioned at one end of a pivotable arm, where the user actuable marker is coupled to the opposite end of the pivotable arm, the pivotable arm configured and arranged to enable rotation of the user actuable marker. In some further embodiments, the trigger comprises a trigger tab mounted to an extension of a rotatable trigger arm, where the user actuable marker is coupled to the opposite end of the rotatable trigger arm, and is configured and arranged to be rotated in an arc pathway determined by angular displacement of the trigger arm following user actuation of the trigger tab.

In some embodiments, the user triggerable assembly includes a two-link arm link coupled to a slidable shaft, where the user actuable marker is coupled to the slidable shaft, and is configured and arranged to enable movement of the user actuable marker that is coaxial with the probe shaft when the two-link arm link is actuated by user actuation of the trigger.

Some embodiments include an implantable rod analysis system comprising a trackable slider assembly comprising a handle including a dynamic reference frame mounting arm extending from one end, and a rod engagement assembly at an opposite end, the rod engagement assembly configured to slide along a surface of the implantable rod. Some embodiments further comprise a dynamic reference frame (DRF) coupled to the dynamic reference frame mounting arm or configured to be coupled onto the dynamic reference frame mounting arm. Some embodiments include a trackable end cap assembly comprising a rod mounting assembly that can engage and secure one end of the implantable rod, and a dynamic reference frame including trackable markers.

In some embodiments, the system further comprises a 3D tracking camera or imaging system configured to track the at least one trackable marker, and a processor and a memory coupled to the processor, where the memory stores anatomy contour measurement instructions executable by the processor to track 3D coordinates of at least one fixed or mobile marker, and output on a display an anatomical imaging analysis of at least a portion of a patient, and one or more anatomical landmarks and registered contour of the implantable rod.

Some embodiments include an implantable rod adjustment and measurement system comprising a trackable rod bender assembly comprising a roller assembly including three rollers arranged on a pair rotatable handles and at least one trackable marker, where the roller assembly can grip a surface of an implantable rod, slide along a surface of the implantable rod, and/or bend the implantable rod. Some embodiments include a trackable end cap assembly comprising a rod mounting assembly that can engage and secure one end of the implantable rod, and a dynamic reference frame including trackable markers. In some embodiments, at least one of the handles includes a coupled dynamic reference frame including at least one trackable marker. Some further embodiments include a 3D tracking camera or imaging system configured to track the at least one trackable marker, a processor and a memory coupled to the processor, where the memory storing anatomy contour measurement instructions executable by the processor. In some embodiments, the instructions operate a method including tracking 3D coordinates of at least one fixed or mobile marker, and outputting on a display an anatomical imaging analyses of at least a portion of a patient, one or more anatomical landmarks and registered contour of the implantable rod and to display an illustration of a bending of the implantable rod.

Some embodiments include an assembly comprising an adjustable bracket including a fixed shoulder at one end and an adjustable channel at an opposite end, where the adjustable channel extends at least partially to the fixed shoulder. Further, some embodiments include a first side arm extending from the fixed shoulder, and a second side arm extending from the adjustable channel, where the first and second side arms each configured to couple with a pedicle screw. In some embodiments, the second side arm is configured and arranged to be moveable in the adjustable channel enabling the distance between the first and second side arms to be adjusted. Some further embodiments include a handle extending from the adjustable bracket, and at least one dynamic reference frame (DRF) coupled to the handle, where the DRF includes at least one trackable marker.

Some embodiments include a system comprising an assembly comprising an adjustable bracket including a fixed shoulder at one end and an adjustable channel at an opposite end, where the adjustable channel extends at least partially to the fixed shoulder. Some further embodiments include a first side arm extending from the fixed shoulder, and a second side arm extending from the adjustable channel, where the first and second side arms are each configured to couple to a pedicle screw. Some embodiments include a handle extending from the adjustable bracket, and at least one dynamic reference frame (DRF) coupled to the handle, where the DRF includes at least one trackable marker, and where the second side arm is configured and arranged to be moveable in the adjustable channel enabling the distance between the first and second side arms to be adjusted. Further, some embodiments include at least one 3D tracking camera or imaging system configured to track the at least one trackable marker, and a processor and a memory coupled to the processor. In some embodiments, the memory stores instructions executable by the processor to track 3D coordinates of one or more of trackable markers, and output on a display an anatomical imaging analysis of at least a portion of a patient, and one or more anatomical landmarks and representation of at least a portion of the assembly based on the 3D coordinates.

Some embodiments include a fiducial system comprising a probe assembly comprising, and a trackable dynamic reference frame coupled or integrated to a probe shaft. Some embodiments include a moveable post with trackable marker that is slidably positioned in the probe shaft. Some embodiments include at least one probe tip extrusion tab configured and arranged to engage a mating portion of an implantable mating screw. Some embodiments include a spring-loaded plunger movable positioned in the probe shaft, and configured to be actuated against a surface of the mating screw, elevating the moveable post with trackable marker to a triggered state defined by mating of the probe assembly with the mating screw.

Some embodiments of the invention include an an assembly comprising an adjustable bracket including a fixed shoulder at one end and an adjustable channel at an opposite end, where the adjustable channel extending at least partially to the fixed shoulder, and a first side arm extending from the fixed shoulder, and a second side arm extending from the adjustable channel, the first and second side arms each configured to couple with a pedicle screw. Some further embodiments include at least one adjustable screw interface extending from at least one of the first side arm and the second side arm, and including a tool mating tip configured to engage a screw mating attachment comprising a depth-stop, and where the second side arm is configured and arranged to be moveable in the adjustable channel enabling the distance between the first and second side arms to be adjusted.

Some embodiments further comprise a handle extending from the adjustable bracket, and at least one dynamic reference frame (DRF) coupled to the handle, where the DRF includes at least one trackable marker.

In some embodiments, the system comprises an assembly comprising an adjustable bracket including a fixed shoulder at one end and an adjustable channel at an opposite end, where the adjustable channel extends at least partially to the fixed shoulder, and a first side arm extending from the fixed shoulder, and further, a second side arm extending from the adjustable channel, the first and second side arms each configured to couple with a pedicle screw. Some embodiments include at least one adjustable screw interface extending from at least one of the first side arm and the second side arm, where the at least one adjustable screw interface includes a tool mating tip configured to engage a screw mating attachment comprising a depth-stop. Further, some embodiments include a handle extending from the adjustable bracket, and at least one dynamic reference frame (DRF) coupled to the handle, where the DRF includes at least one trackable marker. In some embodiments, the second side arm is configured and arranged to be moveable in the adjustable channel enabling the distance between the first and second side arms to be adjusted. Further, some embodiments include providing at least one 3D tracking camera or imaging system configured to track the at least one trackable marker, and a processor and a memory coupled to the processor. In some embodiments, the memory stores instructions executable by the processor to track 3D coordinates of one or more of trackable markers, and output on a display an anatomical imaging analysis of at least a portion of a patient, and one or more anatomical landmarks and representation of at least a portion of the assembly based on the 3D coordinates.

Some embodiments include a method comprising acquiring at least one X-ray image from a patient, where the patient is positioned with at least one dynamic reference frame and at least one trackable marker enabling any portion of the patient to be registered in 3D space and any portion of the acquired X-ray image to include at least one tracked 3D coordinate. Further, the method includes calculating the position and orientation of at least one portion of the patient from the at least one X-ray image and the at least one tracked 3D coordinate. Further, the method includes calculating and scaling 3D coordinates of the at least one X-ray image to a phantom model. Further, the method includes transforming 3D coordinates to cartesian coordinates of the phantom model. Further, the method includes providing a phantom model mounting assembly including at least one dynamic reference frame. Further, the method includes positioning at least one portion of the phantom model onto the phantom model mounting assembly based on one or more of the cartesian coordinates and a position of the at least one dynamic reference frame.

Some embodiments include a 3D trackable probe system comprising a probe assembly comprising a trackable dynamic reference frame coupled or integrated to a probe shaft, where the dynamic reference frame includes at least one marker. Some embodiments include a user actuable marker coupled to a user triggerable assembly including a trigger, and at least one probe tip extending from the probe shaft, and at least one 3D tracking camera or imaging system configured to track the at least one trackable marker. Some embodiments include a processor and a memory coupled to the processor, where the memory stores instructions executable by the processor to track 3D coordinates of one or more of trackable markers, and calculate a 3D position and pose of the probe assembly.

In some embodiments, the trigger comprises a depressible tab positioned at one end of a pivotable arm, where the user actuable marker is coupled to the opposite end of the pivotable arm, the pivotable arm configured and arranged to enable rotation of the user actuable marker.

In some embodiments, the trigger comprises a trigger tab mounted to an extension of a rotatable trigger arm, where the user actuable marker is coupled to the opposite end of the rotatable trigger arm, and is configured and arranged to be rotated in an arc pathway determined by angular displacement of the trigger arm following user actuation of the trigger tab.

In some embodiments, the user triggerable assembly includes a two-link arm link coupled to a slidable shaft, where the user actuable marker is coupled to the slidable shaft, and is configured and arranged to enable movement of the user actuable marker that is coaxial with the probe shaft when the two-link arm link is actuated by user actuation of the trigger.

Some embodiments include a probe assembly comprising a probe shaft including one or more coaxial depth-stops proximate one end of the probe shaft and a trackable dynamic reference frame integrated or coupled proximate an opposite end of the probe shaft, where the one or more of the coaxial depth-stops are configured to couple or mate with one or more depth-stop fiducials. Some further embodiments include a moveable shaft slidably positioned at least partially within the probe shaft, where the moveable shaft includes a probe tip at one end and a trackable marker at an opposite end.

In some embodiments, the probe assembly is configured and arranged so that during use, coupling of the probe-tip with a body surface with movement of the moveable shaft comprises movement of the trackable marker away from the body to a distance determined by the one or more depth-stop fiducials. In some further embodiments, one or more of the coaxial depth-stops comprise an alignment protrusion configured and arranged to mate, interlock, or couple with a complementary slot, cavity, or receptible of the one or more depth-stop fiducials.

Some embodiments include a system comprising a trackable surgical tool including a tool dynamic reference frame and at least one trackable marker, where the trackable surgical tool is configured so that any fixed or mobile portion of the trackable surgical tool can be registered in 3D space. Some embodiments include a processor and a memory coupled to the processor, where the memory stores instructions executed by the processor to acquire at least one X-ray image from a patient wherein the location and pose of the emitter and detector are known or determined, and using at least one X-ray imager mounted dynamic reference frame, determine a conical imaging volume of an X-ray imager coupled to the processor. Further, in some embodiments, the memory stores instructions executed by the processor to record pose of the trackable surgical tool, and visually display, on an external display or device, in response to a calculated position of the trackable surgical tool in the conical imaging volume, a scaled projection of the trackable surgical tool over at least a portion of the X-ray image displayed on the external display or device.

Some embodiments include a trackable probe comprising at least one trackable dynamic reference frame (DRF)

including at least one trackable marker, and at least one movable trackable marker coupled to the DRF. Some embodiments include a mating protrusion extending from the DRF including a mating slot or cavity. Some embodiments include at least one probe extension including a mating element, where the mating element is configured for insertion and/or sliding in the mating slot or cavity.

In some embodiments, the at least one movable trackable marker is positioned coupled to a slidable insert of the mating protrusion. In some embodiments, the at least one movable trackable marker is spring-loaded, where movement of the at least one movable trackable marker is governed by the spring-loading.

Some embodiments include a fiducial patch comprising a body-surface mountable article including a plurality of radiopaque markers arranged between a plurality of radiopaque grid lines. In some embodiments, the radiopaque markers comprise at least one of colors or shades of grey, letters, numbers, symbols, and icons. Some embodiments further comprise adhesive at least partially covering one side of the body-surface mountable article, the one side being a side intended for coupling to a body surface. some embodiments further comprise at least one radiopaque lining that at least partially matches one or more of the plurality of radiopaque markers.

Some embodiments include a probe assembly comprising a trackable probe including a trackable dynamic reference frame integrated or coupled to a first end of the probe, and rod-centering fork positioned at a second end of the probe, the rod-centering fork comprising a bifurcating structure configured to engage an implantable or implanted rod. Some embodiments include a depressible shaft positioned at least partially within the probe, where the depressible shaft includes a probe tip at one end and a trackable marker at an opposite end.

Some embodiments include an adjustable depth-stop positioned adjacent the first end of the probe, where the adjustable depth-stop is configured to control a maximum extension of the depressible shaft and probe tip. Some embodiments include at least one shaft guide configured to prevent rotation of the depressible shaft;

Some embodiments further comprise a spring assembly coupled to the first end of the probe, where the spring assembly is configured to spring-load the depressible shaft. In some embodiments, the trackable dynamic reference frame includes at least one coupled trackable marker.

Some embodiments include an electromechanical 3D tracking system comprising an extensible cord system including two or more extensible cords retractable or extendible from a spool, and two or more ball-in-socket assemblies, where each extensible cord extends from a ball-in-socket assembly. Further, some embodiments include at least one position or movement sensor configured for measuring a position or movement of each ball-in-socket assembly, and at least one sensor configured for determining an extended length of each extensible cord. Some embodiments include a data acquisition system configured to receive sensor data from the at least one position or movement sensor and the at least one sensor, and to calculate movement and/or at least one 3D coordinate of at least a portion of a probe coupled to the extensible cords.

Some embodiments include an implanted rod manipulator comprising a handle, and a dynamic tracking frame positioned extending from a first end of the handle, where the dynamic tracking frame includes at least on trackable marker. Some embodiments include a rod interface head positioned extending from a second end of the handle opposite the first end, where the rod interface head includes a concave surface configured to couple to a surface of an implantable or implanted rod. Further, some embodiments include a moveable sliding tip positioned extending through the rod interface head. In some embodiments, the moveable sliding tip is coupled to a spring-load the depressible shaft.

Some embodiments further comprise a moveable trackable marker coupled to the moveable sliding tip, where a position of the moveable trackable marker relative to the first end of the handle is dependent on at least one of a rod coupled to the rod interface head and the position of the moveable sliding tip in the rod interface head.

Some embodiments include a method comprising positioning a trackable probe in-line and/or parallel to an anatomical alignment of a patient, and triggering the trackable probe to communicate a reference plane initialization. Further, in some embodiments, the method comprises calculating a 3D pose of a dynamic reference frame as analogous for the patient's anatomical planes, and registering three or more points to establish anatomical planes on which to project acquired data.

In some embodiments of the method, the dynamic reference frame is attached to the patient. In some embodiments of the method, the dynamic reference frame is coupled to a surgical table or adjacent surface, where the dynamic reference frame is adjacent to the patient.

Some embodiments include a method of analyzing and providing a patient's spinal alignment information and therapeutic device data. In some embodiments, the method can comprise obtaining initial patient data, and acquiring spinal alignment contour information. In some embodiments, the method can comprise assessing localized anatomical features of the patient, and obtaining anatomical region data. In some embodiments, the method can include analyzing the localized anatomy and therapeutic device location and contouring. In some embodiments, the method can output localized anatomical analyses and therapeutic device contouring data on a display.

DESCRIPTION OF THE DRAWINGS

FIG. 4A illustrates an assembly or operation process for a skin-surface-mounted fiducial being applied to a patient's posterior skin as they are positioned prone on an operative table in accordance with some embodiments of the invention.

FIG. 4B illustrates a sample lateral radiograph of skin fiducials applied to an anatomical model in accordance with some embodiments of the invention.

FIG. 4C illustrates the sample lateral radiograph of FIG. 4B with annotated vectors in accordance with some embodiments of the invention.

FIG. 4D illustrates a C-arm based mount a type of an X-ray imaging system that can be utilized for image acquisition and subsequent initialization of fiducial markers in accordance with some embodiments of the invention.

FIG. 4E illustrates a sample X-ray image of a spine-fiducial pair from a different imaging angle from that of FIGS. 4A and 4B in accordance with some embodiments of the invention.

FIG. 4F illustrates the sample X-ray image of FIG. 4E including annotated vectors in accordance with some embodiments of the invention.

FIG. 4G illustrates 3D axes relative to the fiducial origin point onto which displacement vectors drawn over each of the 2D X-rays are able to be added based on input or calculated angle between each X-ray image plane in accordance with some embodiments of the invention.

FIG. 4H illustrates a system and method of localizing the fiducial in 3D tracking camera coordinates in accordance with some embodiments of the invention.

FIG. 4I displays the axes of a 3D-acquisition system with which the unique location and pose of the fiducial was registered as of FIG. 4H in accordance with some embodiments of the invention.

FIG. 42A illustrates the flexibly assessment device of FIGS. 39A-39F, and 40A-40C equipped with detachable screw interface components, previously described in FIG. 41 with adjustable cross-linking devices, described below in reference to FIG. 43A-43F in accordance with some embodiments of the invention.

FIG. 42B illustrates the flexibility assessment device described previously in relation to FIG. 42A substantially rigidly coupled to the pedicle screws by interfacing with the tulip heads in accordance with some embodiments of the invention.

FIG. 42C illustrates a second flexibility assessment device interfacing with a spinal level at a user-defined distance from the already mated device described previously in relation to FIGS. 39A-39F, 41A-41D, and 42A-42B in accordance with some embodiments of the invention.

FIG. 46D illustrates a virtual overlay of a tracked surgical tool positioned close to the X-ray detector on top of an X-ray image of the spine in accordance with some embodiments of the invention.

FIG. 46E illustrates an X-ray imaging and tracking system in accordance with some embodiments of the invention.

FIG. 46F illustrates a virtual overlay of a tracked surgical tool positioned close to the emitter as shown in FIG. 46E in accordance with some embodiments of the invention.

FIG. 46G illustrates a virtual overlay of a tracked surgical tool that has been turned 90 degrees from the tool position previously described in FIGS. 46D-46F in accordance with some embodiments of the invention.

FIG. 47A illustrates components of a tracked end cap in accordance with some embodiments of the invention.

FIG. 47B illustrates components of a tracked slider designed to interface with a rod fixed to a tracked end cap, described previously in relation to FIG. 47A in accordance with some embodiments of the invention.

FIG. 48A illustrates a close-up view of a portion of an end cap in accordance with some embodiments of the invention.

FIG. 48B illustrates a perspective view of an end cap assembled from components of FIG. 47A in accordance with some embodiments of the invention.

FIG. 48C illustrates a side view of the end cap of FIG. 48B in accordance with some embodiments of the invention.

FIGS. 49A-49C illustrates a single-ring rod assessment device assembly in accordance with some embodiments of the invention.

FIG. 49D illustrates the assembly of FIGS. 49A-49C coupled with a rod and tracked end cap previously described in relation to FIGS. 47A, and 48A-48B in accordance with some embodiments of the invention.

FIGS. 50A-50D illustrates a fixed-base, variable-ring, mobile rod assessment device in accordance with some embodiments of the invention.

FIG. 50E illustrates the fixed-base, variable-ring, mobile rod assessment device of FIGS. 50A-50D engaged with a rod coupled to an end cap in accordance with some embodiments of the invention.

FIGS. 51A-51G illustrates various views of a handheld, mobile rod contour assessment device in accordance with some embodiments of the invention.

Figures 51A, 51B, 51C, 51D, 51E, 51F, 51G, 51H, 51I:
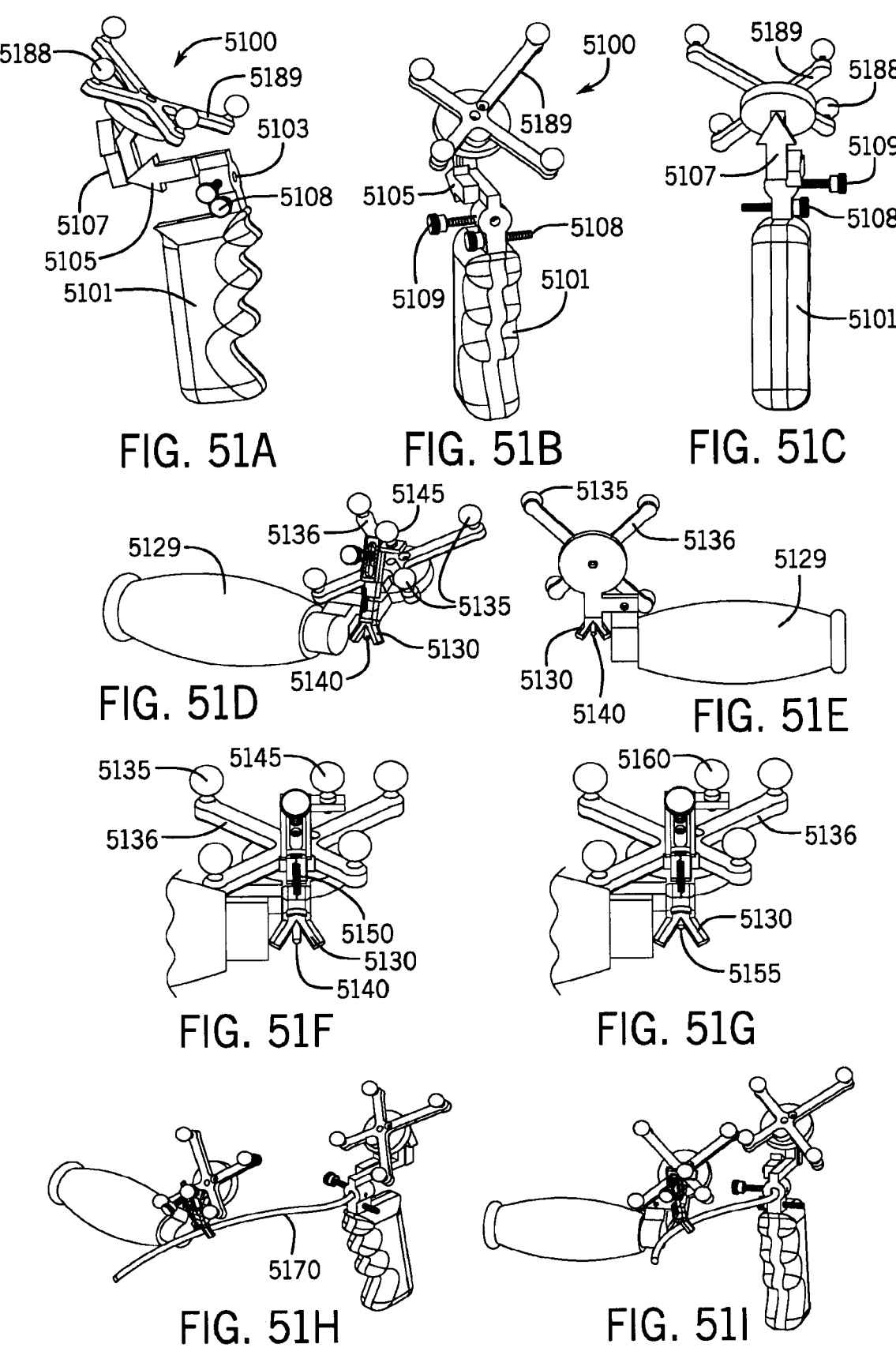

FIG. 51H-51I illustrates views of a process or method of registering the contour of a rod prior to implantation with the handheld, mobile rod contour assessment device of FIGS. 51A-51G in accordance with some embodiments of the invention.

Figures 52A, 52B, 52C, 52D:
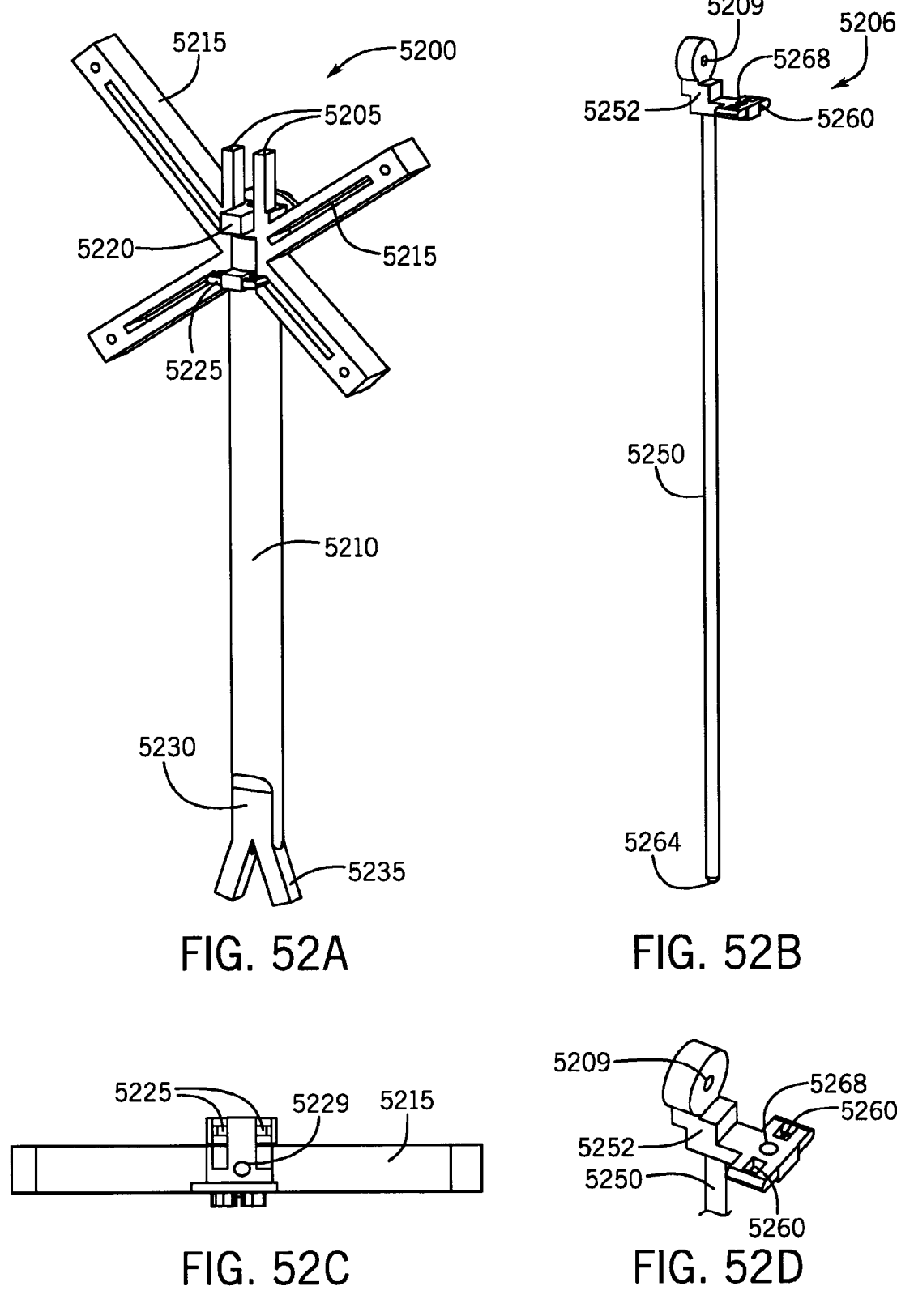

FIG. 52A illustrates a component of a TMSM-based, implanted rod contour assessment device in accordance with some embodiments of the invention.

FIG. 52B illustrates a depressible sliding shaft for coupling to the component of FIG. 52A in accordance with some embodiments of the invention.

FIG. 52C illustrates a top view of the component of FIG. 52A in accordance with some embodiments of the invention.

FIG. 52D illustrates a close-up perspective view of the depressible sliding shaft of FIG. 52B in accordance with some embodiments of the invention.

Figures 53A, 53B:
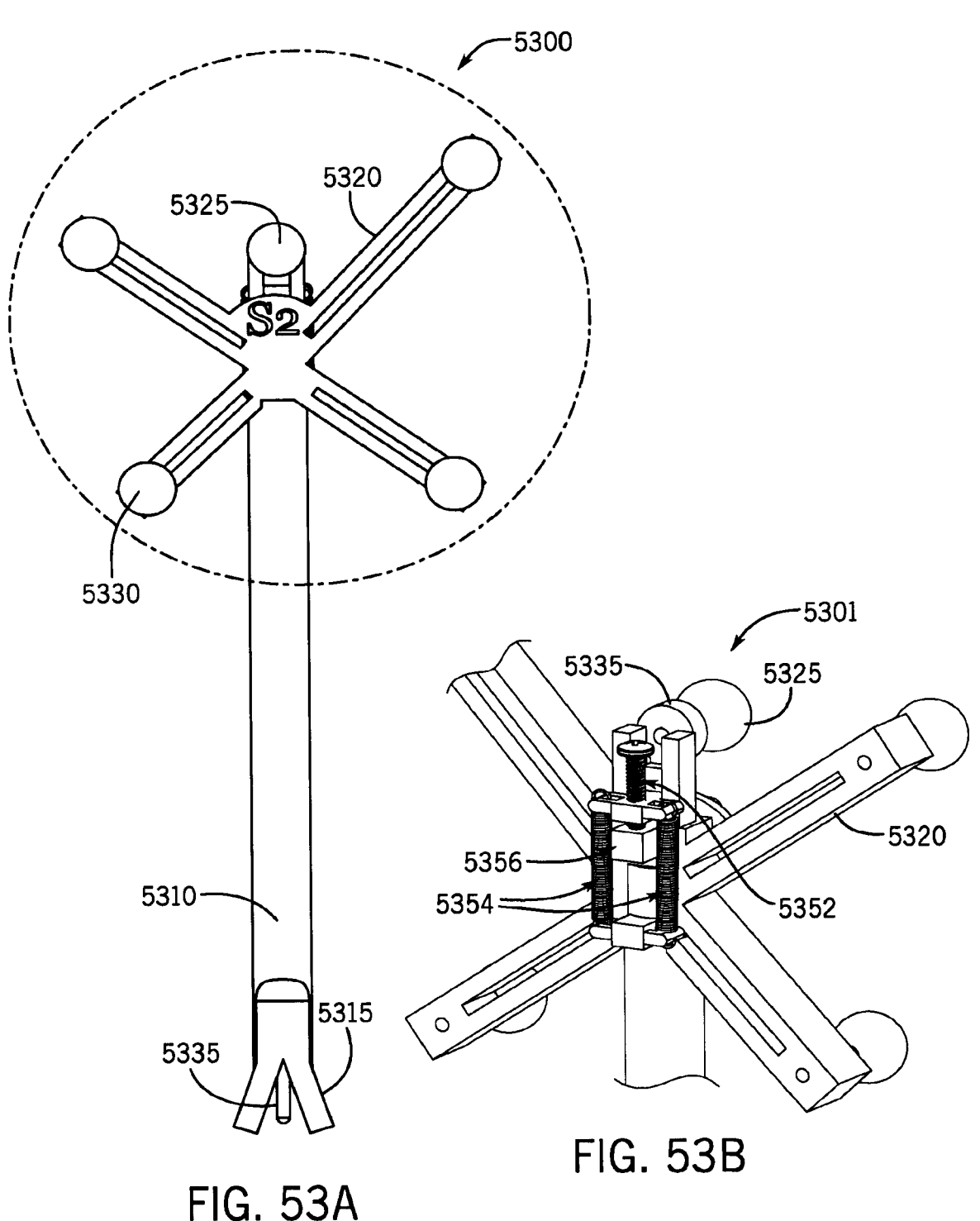

FIG. 53A illustrates an assembly of components of FIGS. 52A and 52B used to assess the contour of a rod after it has been implanted within the surgical site in accordance with some embodiments of the invention.

FIG. 53B illustrates a close-up rear view of a portion of the assembly of FIG. 53A in accordance with some embodiments of the invention.

Figures 53C, 53D:
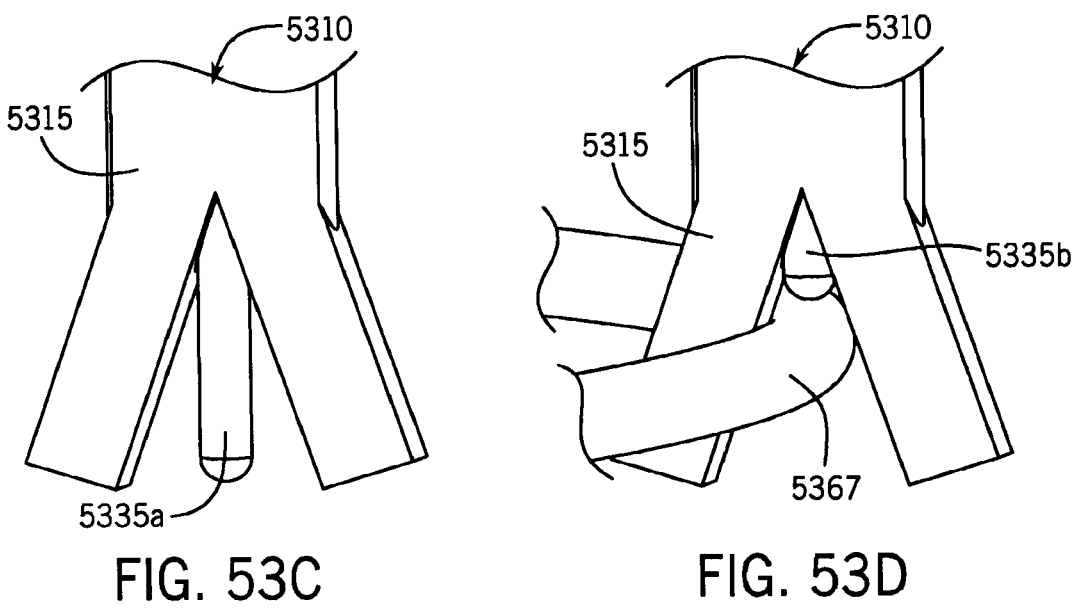

FIG. 53C illustrates a close-up view of the rod-interface region of the assembly of FIGS. 53A-53B in accordance with some embodiments of the invention.

FIG. 53D illustrates the assembly of FIGS. 53A-53C interfacing with a rod in accordance with some embodiments of the invention.

Figures 53E, 53F:
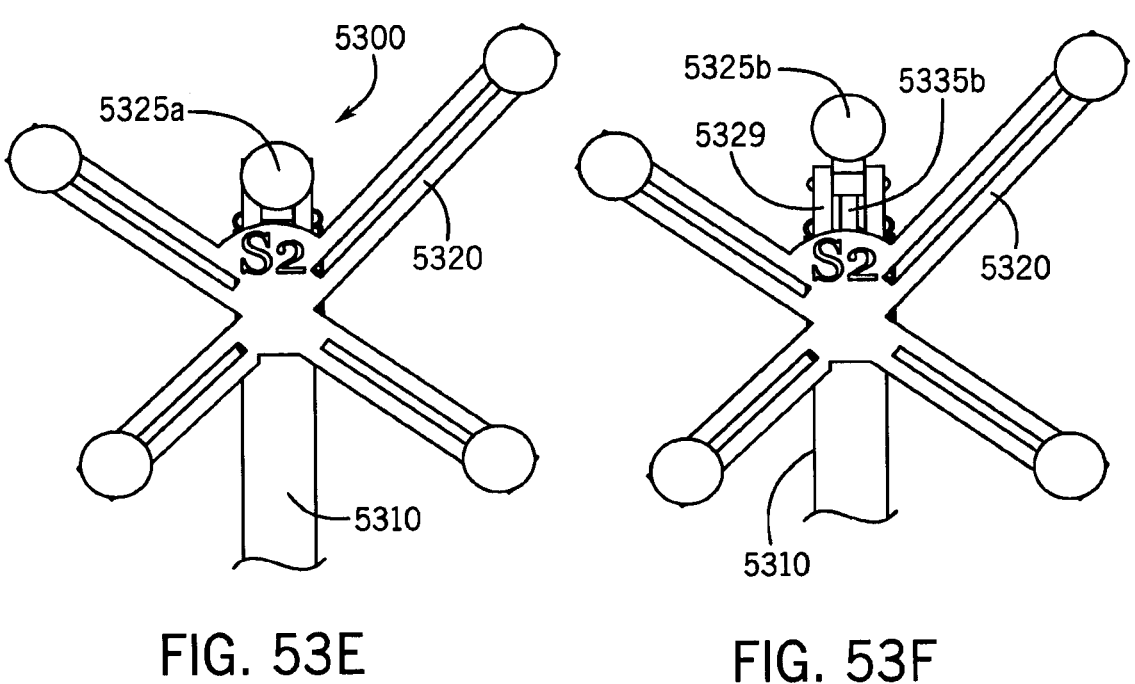

FIGS. 53E-53F illustrates close-up views of a trackable DRF portion of the assembly view of FIGS. 53A-53D in accordance with some embodiments of the invention.

Figures 54A, 54B, 54C, 54D:
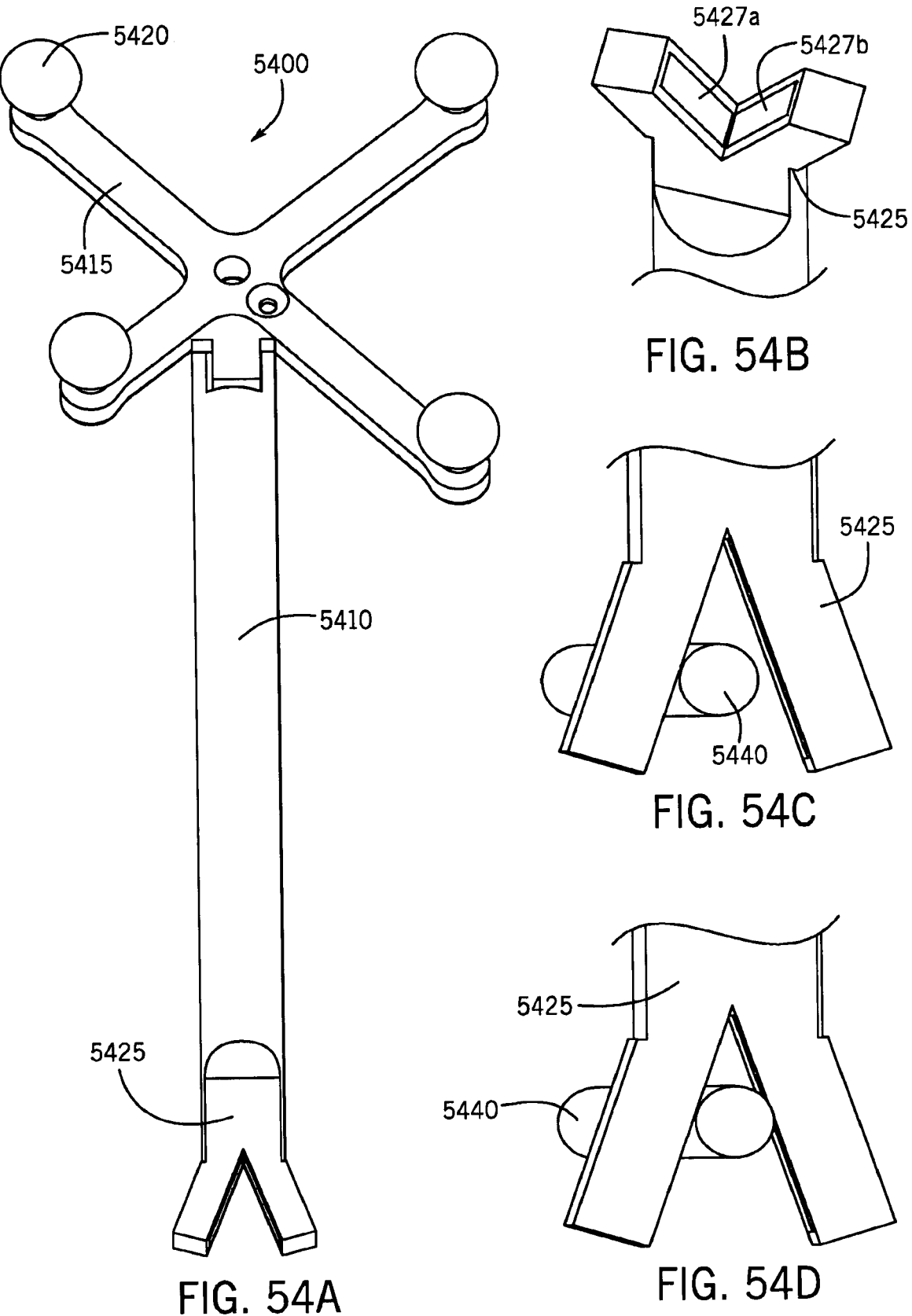

FIG. 54A illustrates a conductivity-based rod contour assessment device in accordance with some embodiments of the invention.

FIG. 54B illustrates a rod-centering fork and electrical contact pads of the device of FIG. 54A in accordance with some embodiments of the invention.

FIGS. 54C-54D illustrates the rod-centering fork of FIG. 54B interacting with a rod in accordance with some embodiments of the invention.

FIGS. 55A-55I illustrates various views of a 3D-tracked, manual mobile rod bender in accordance with some embodiments of the invention.

FIGS. 56A-56F illustrate various views of a tracked DRF-equipped end cap, pre-registered rod, and manual bender equipped with TMSMs accordance with some embodiments of the invention.

Figures 57A, 57B, 57C, 57D:
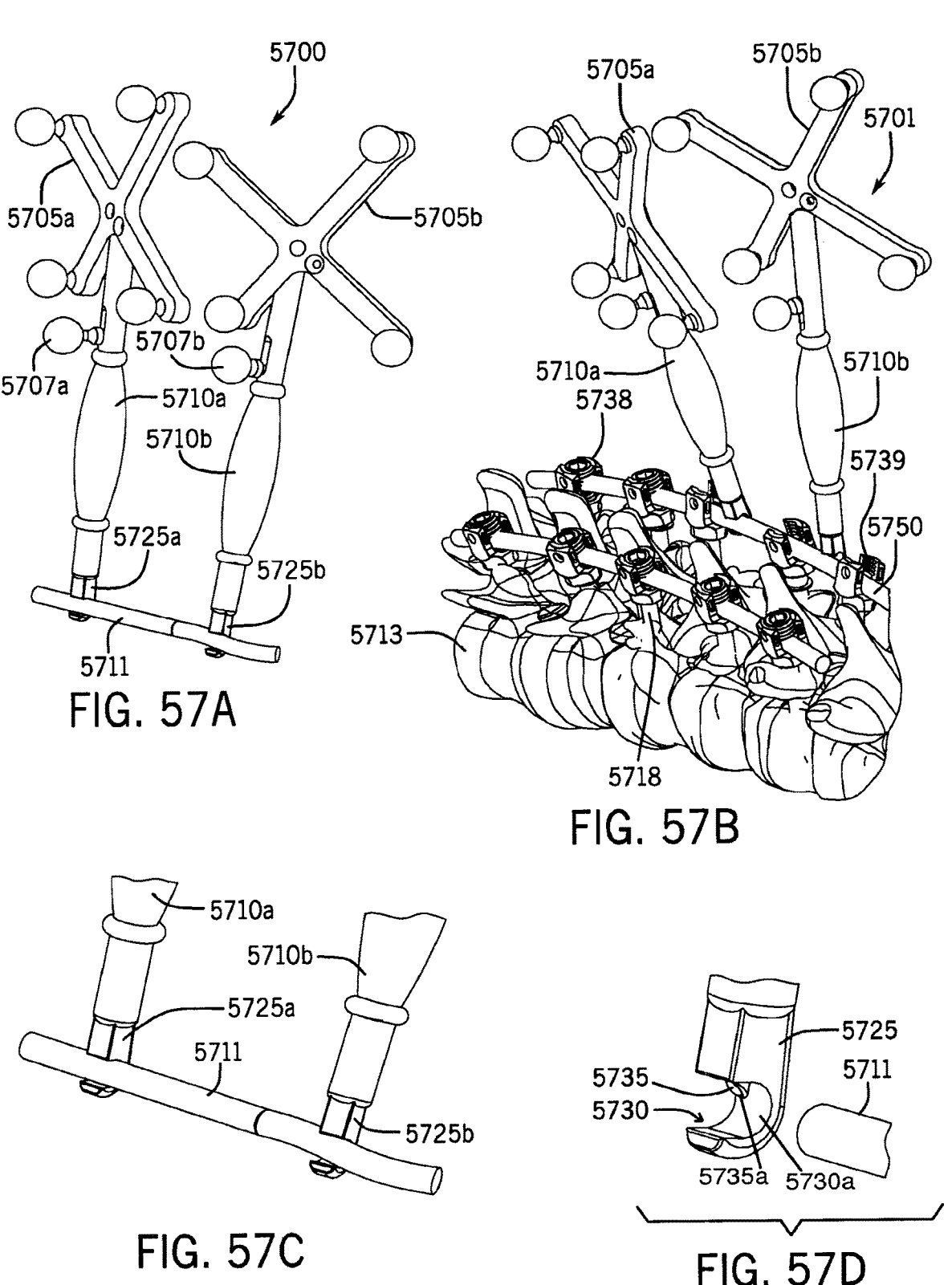

FIG. 57A illustrates a DRF-tracked and trigger-equipped in-situ benders coupled to a rod in accordance with some embodiments of the invention.

FIG. 57B illustrates a DRF-tracked and trigger-equipped in-situ benders coupled to a rod coupled to a spine in accordance with some embodiments of the invention.

FIG. 57C illustrates a close-up assembly view of the rod of FIG. 57A in accordance with some embodiments of the invention.

FIG. 57D illustrates a close-up view of a rod interface head of the bender shown in FIG. 57A including a view of a depressible sliding shaft tip in an extended position in accordance with some embodiments of the invention.

Figure 58:
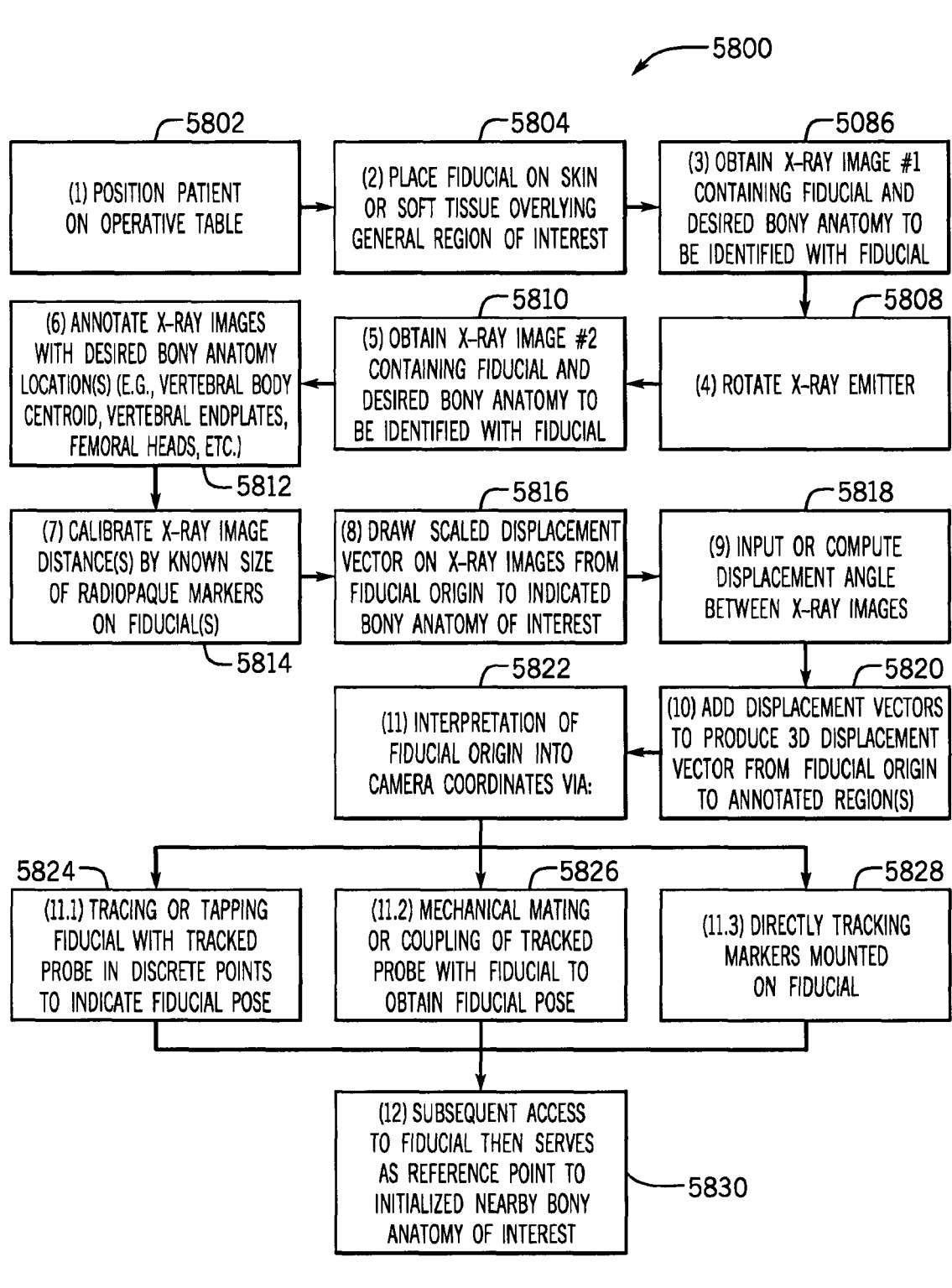

FIG. 58 illustrates a workflow to initialize skin-mounted, or percutaneous, fiducials with two or more X-ray images intraoperatively in accordance with some embodiments of the invention.

Figure 59:
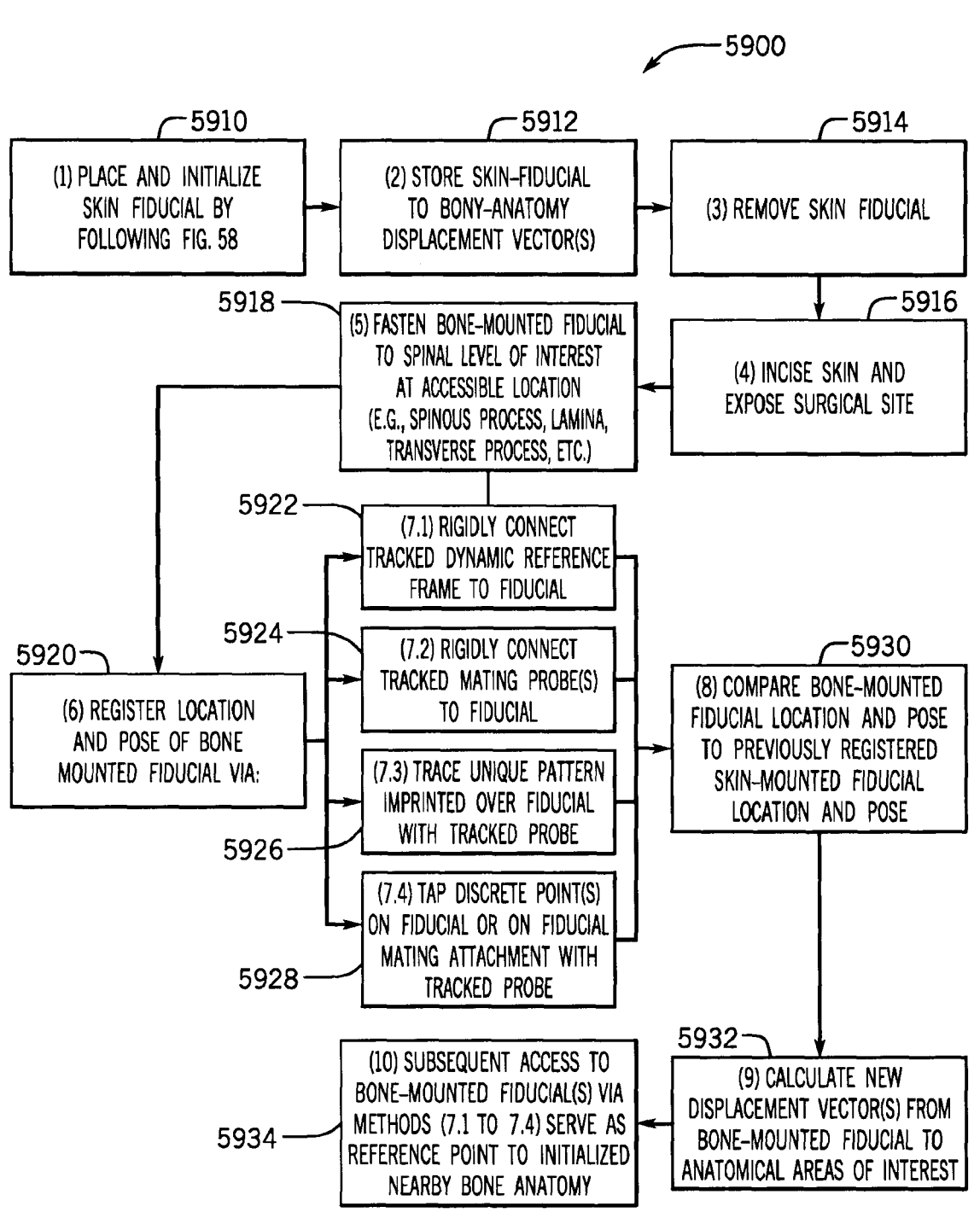

FIG. 59 illustrates a workflow to initialize one or more bone-mounted fiducials placed intraoperatively with 2 or more X-ray images taken before placement of the bone-mounted fiducials in accordance with some embodiments of the invention.

Figure 60:
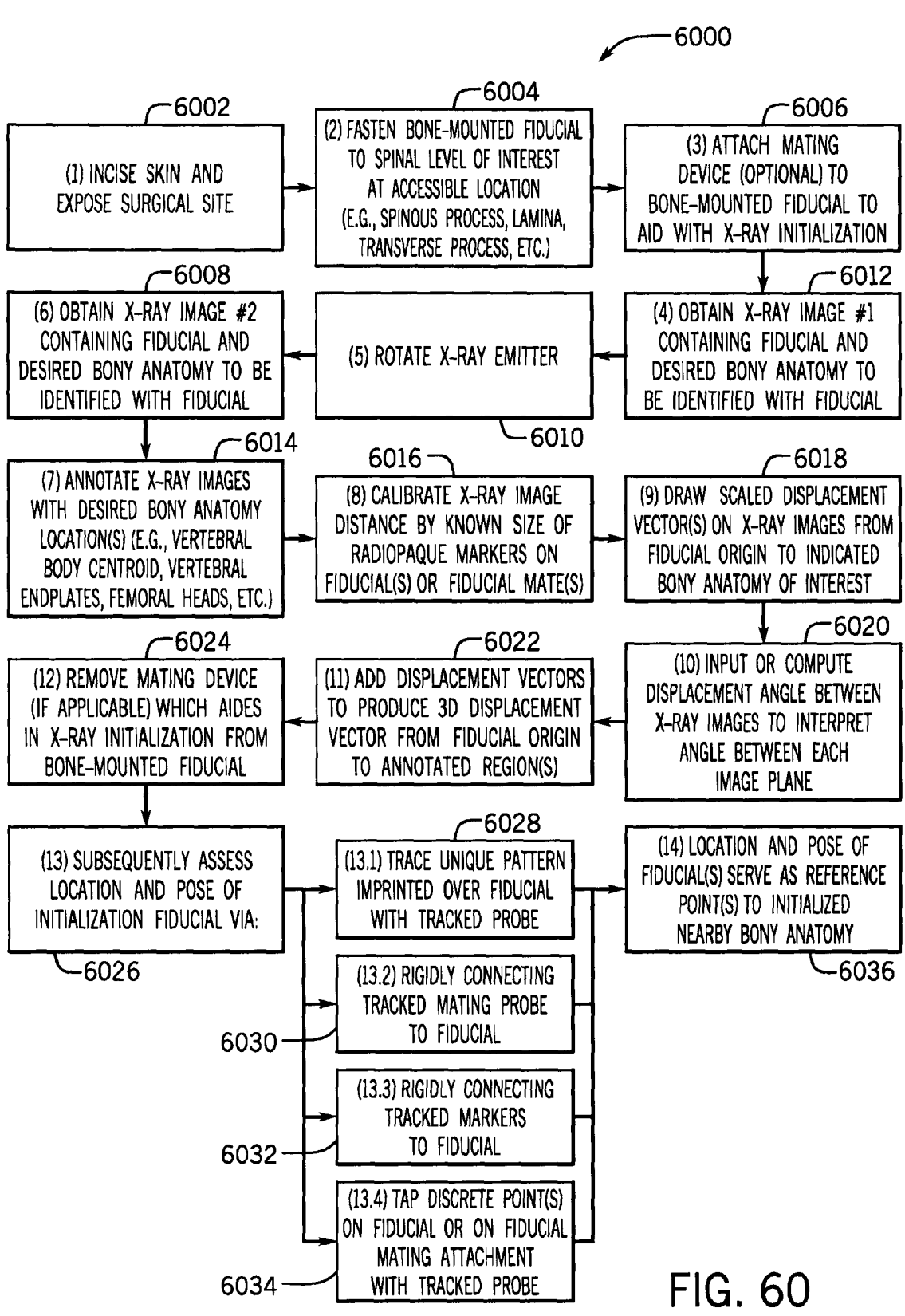

FIG. 60 shows a workflow to initialize one or more bone-mounted fiducials placed intraoperatively with 2 or more X-ray images taken after placement of the bone-mounted fiducials in accordance with some embodiments of the invention.

Figure 61:
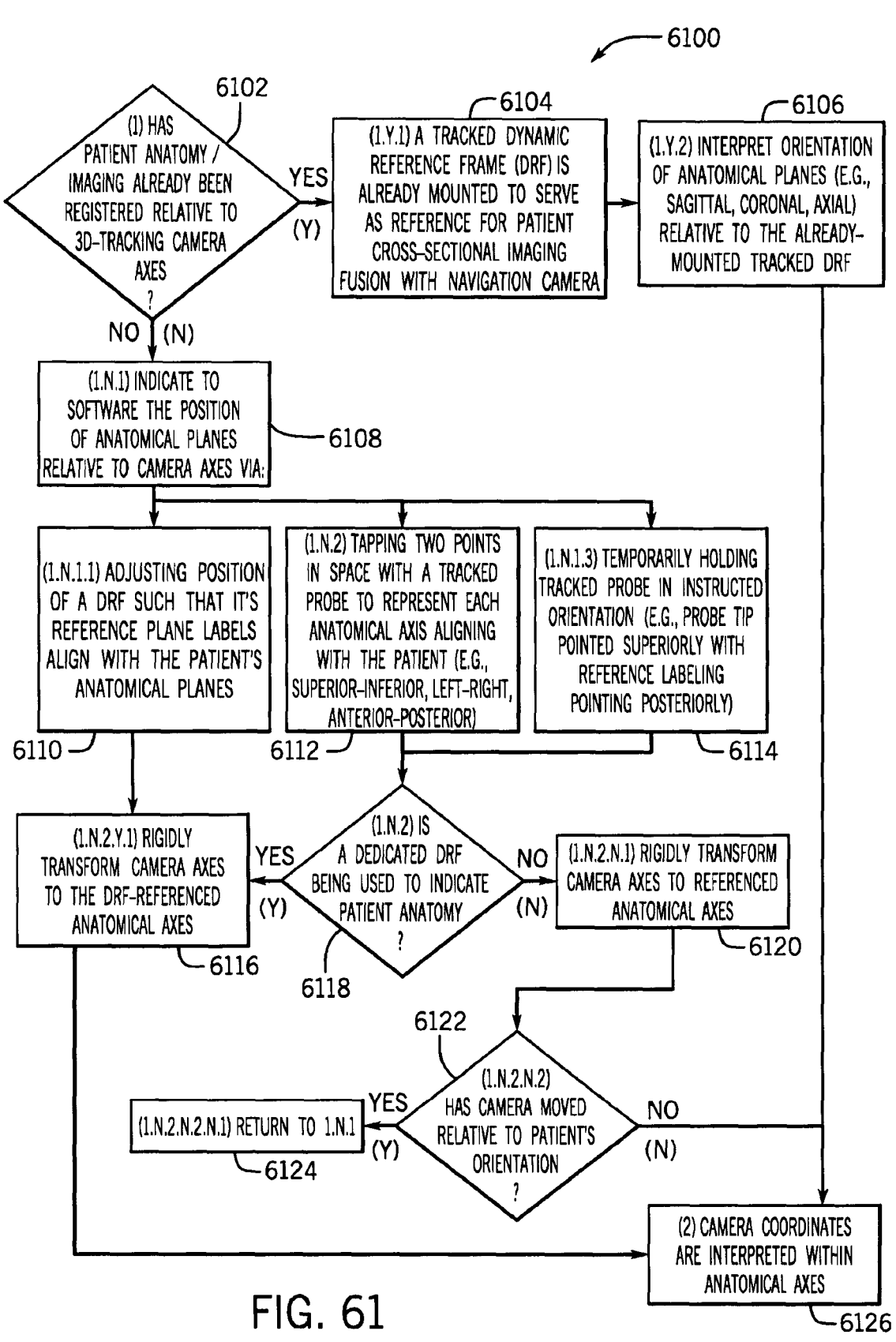

FIG. 61 illustrates methods of registering anatomical reference planes intraoperatively in accordance with some embodiments of the invention.

Figure 62A:
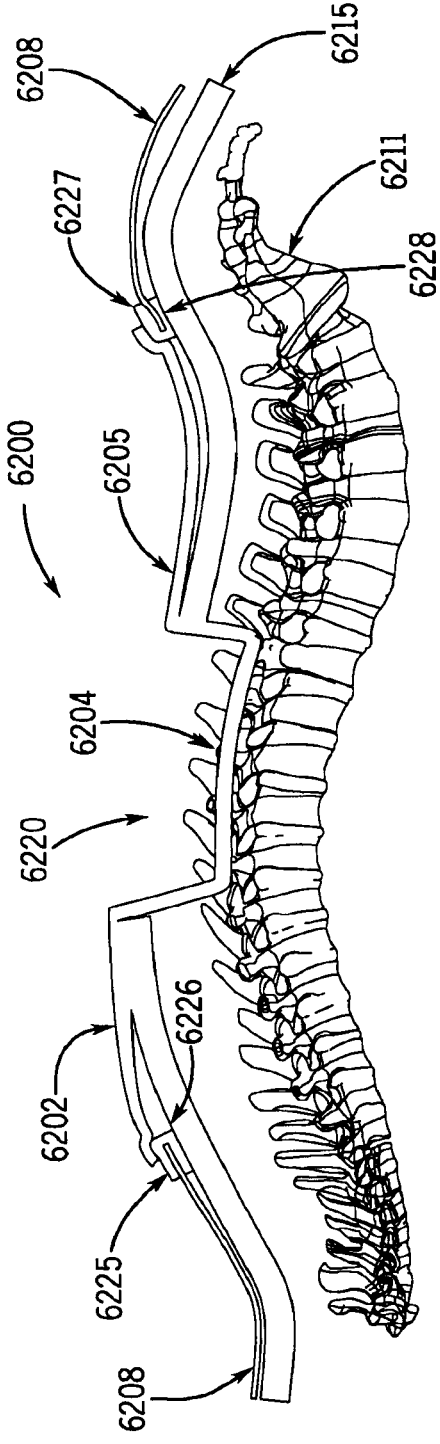

FIG. 62A illustrates an arrangement for acquiring information regarding the contour of the spine via tracing over body surfaces using a tracked probe in accordance with some embodiments of the invention.

Figures 62B, 62C:
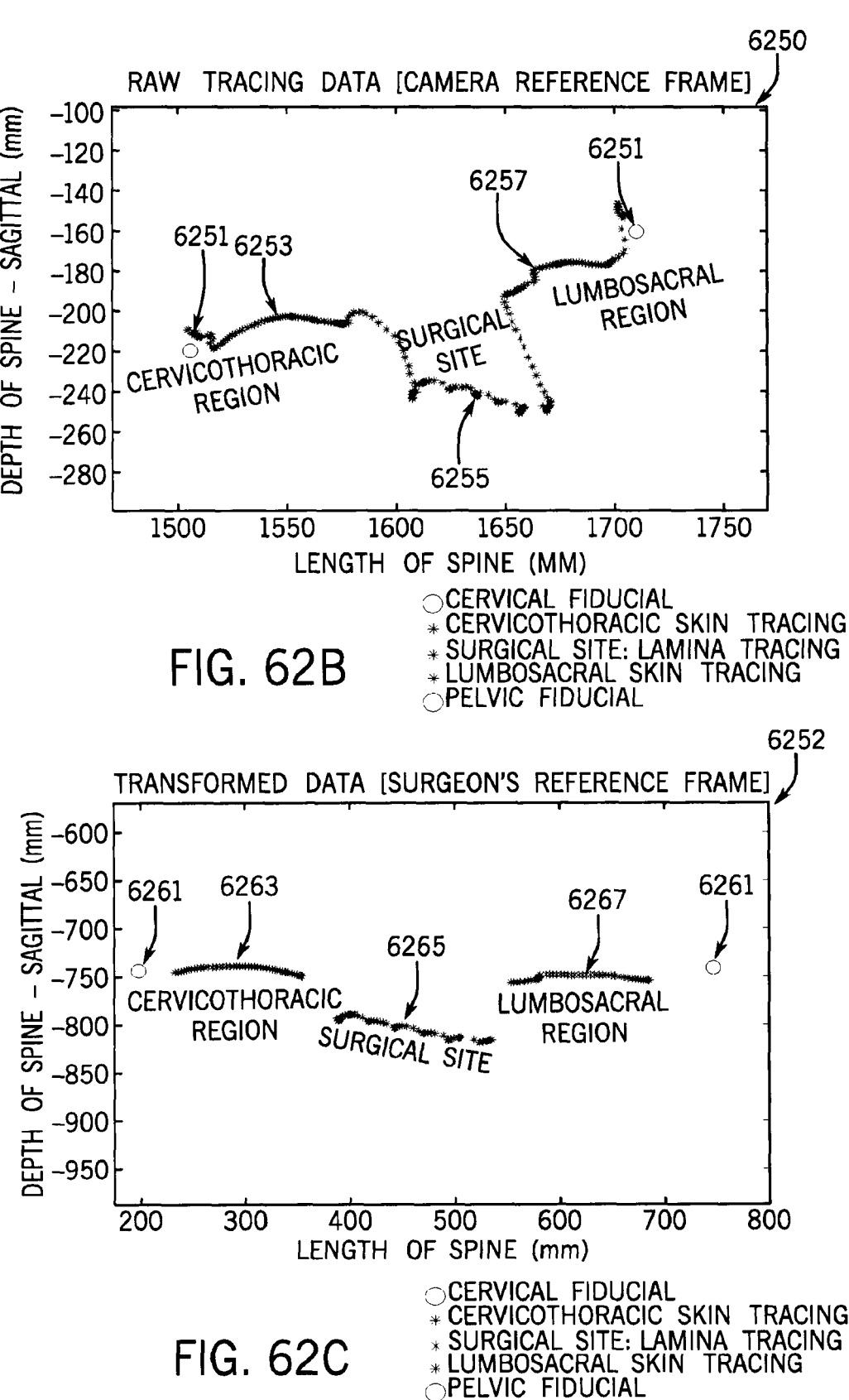

FIG. 62B illustrates a display of the acquired body surface contours via tracing with a 3D-tracked probe in accordance with some embodiments of the invention.

FIG. 62C illustrates a display of transformed tracing data in accordance with some embodiments of the invention.

Figure 62D:
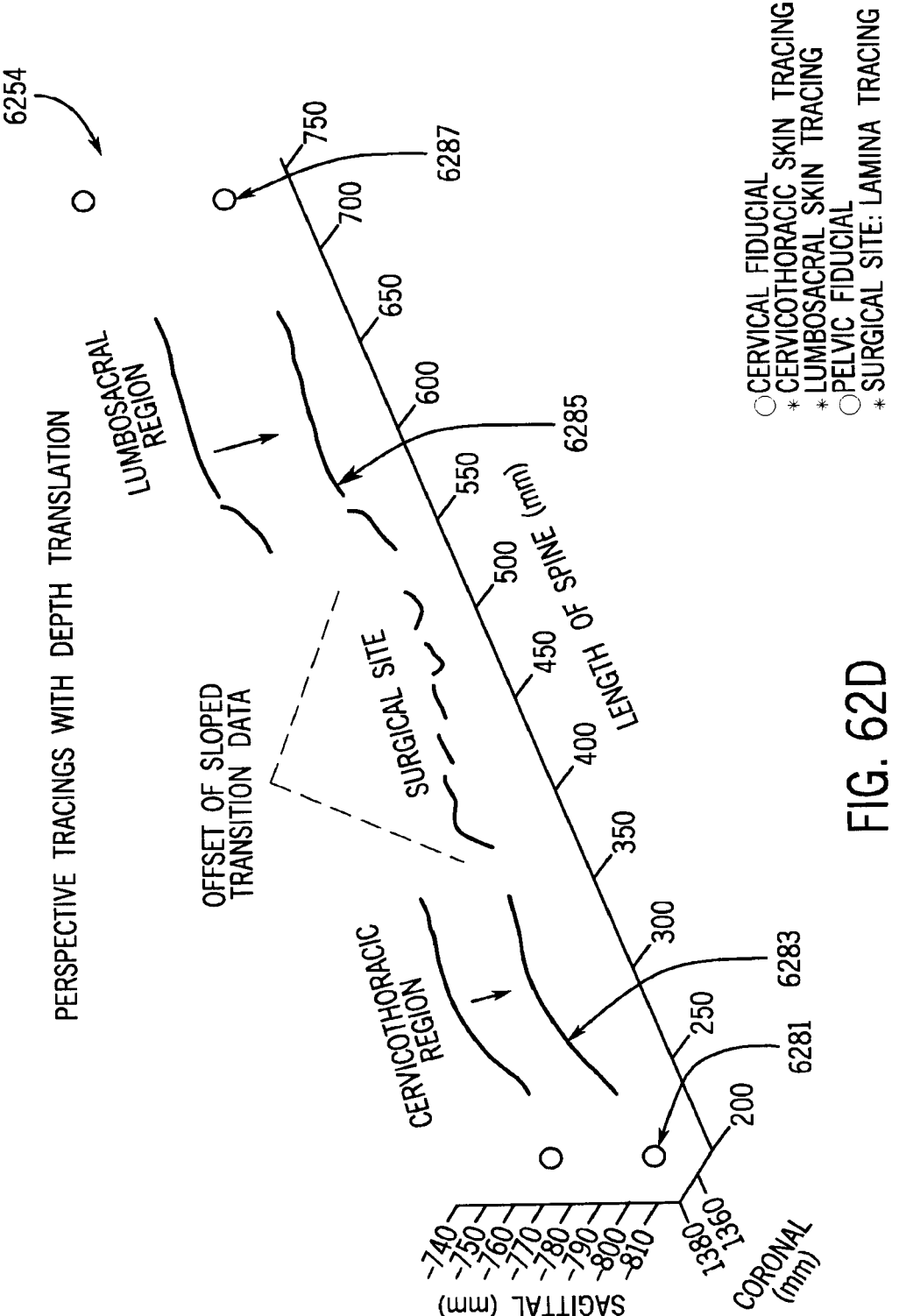

FIG. 62D illustrates a display of the data of FIGS. 62B-62C with depth translation in accordance with some embodiments of the invention.

FIG. 63 shows a workflow for analog triggering detection of one or more tracked mobile stray marker (TMSM) relative to a tracked tool with a dynamic reference frame (DRF) in accordance with some embodiments of the invention.

Figures 64A, 64B:
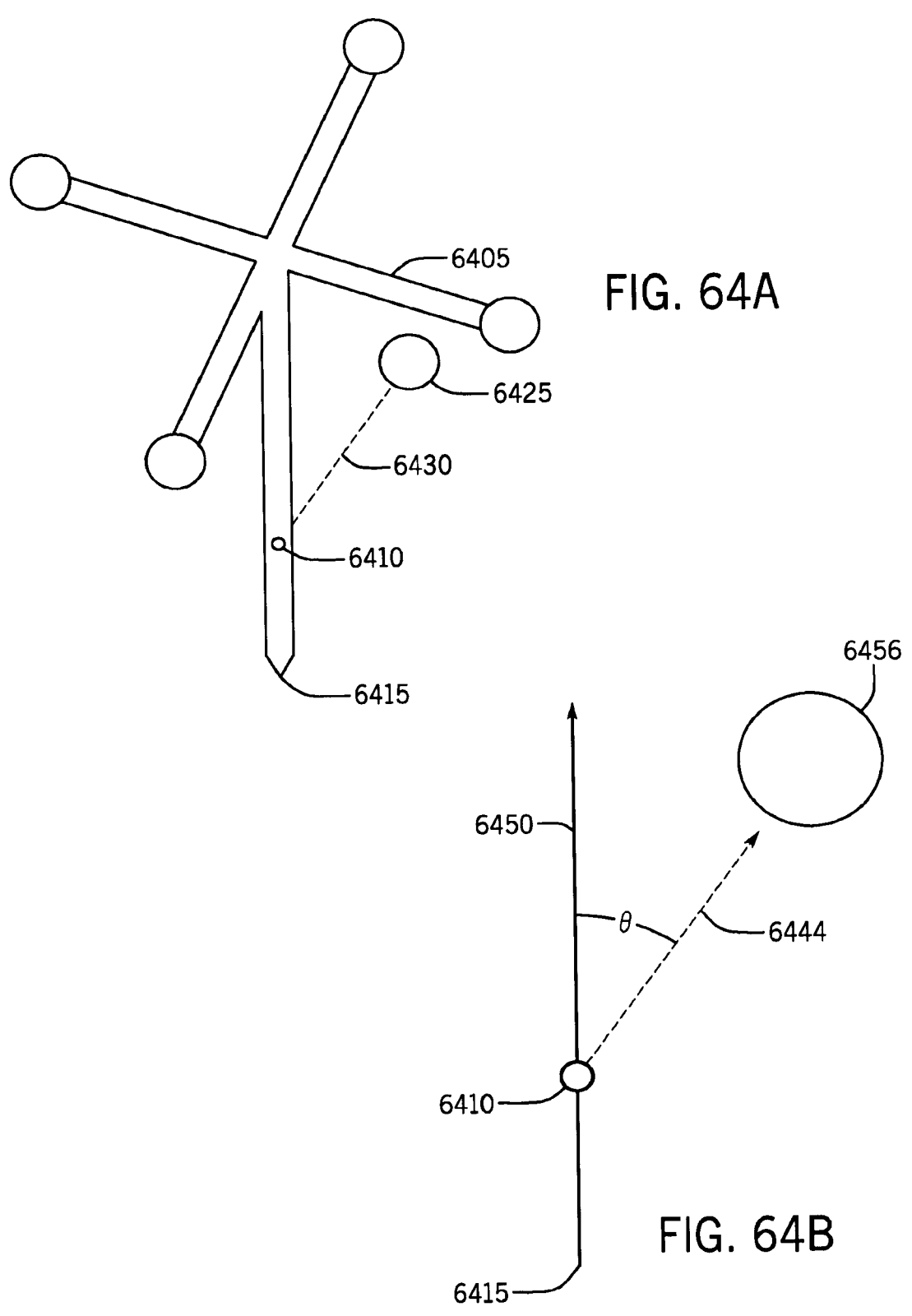

FIG. 64A illustrates a tracking probe assembly in accordance with some embodiments of the invention.

FIG. 64B illustrates an interpretation and calculation of the position of a rotating TMSM relative to the DRF on a probe as described previously in relation to FIG. 64A in accordance with some embodiments of the invention.

FIG. 65A illustrates displays of a discrete body surface or bony surface annotations on cross-sectional images used for initialization of patient-specific interpretation of body and bony surface tracings with a 3D-tracked probe in accordance with some embodiments of the invention.

FIG. 65B illustrates 3D perspective of cross-sectional annotations from the CT scan in accordance with some embodiments of the invention.

Figure 65C:
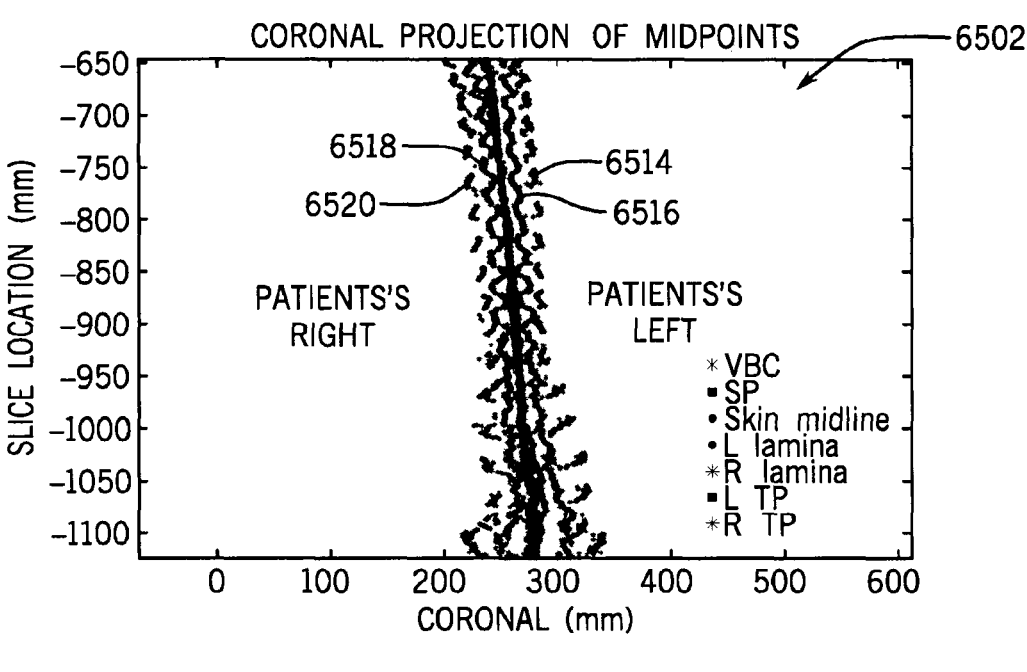

FIG. 65C illustrates a plot of coronal projected coordinates in accordance with some embodiments of the invention.

Figure 65D:
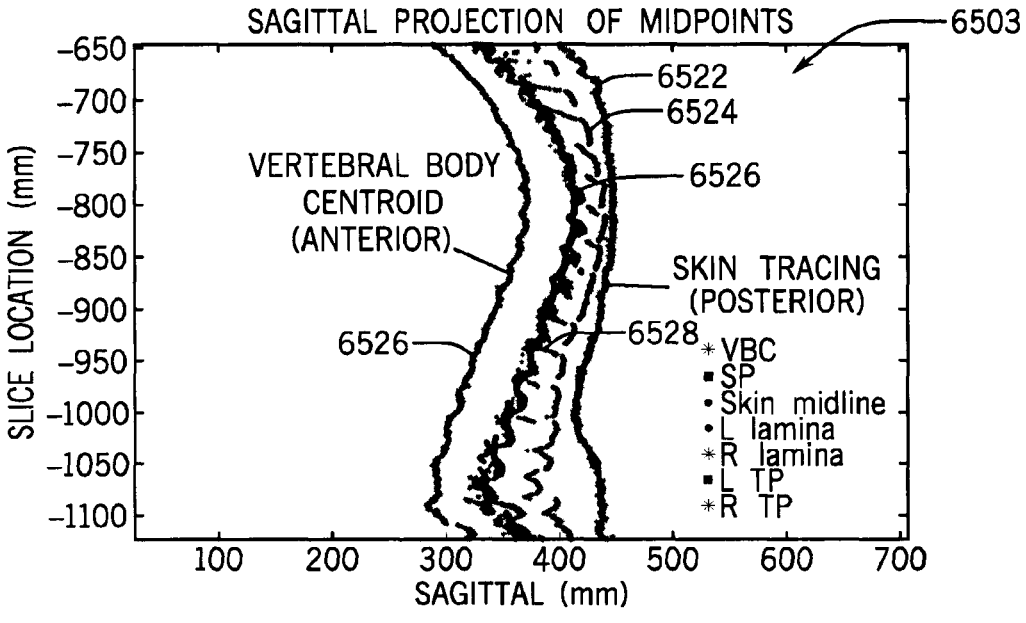

FIG. 65D illustrates a plot of sagittal projected coordinates in accordance with some embodiments of the invention.

Figure 65E:
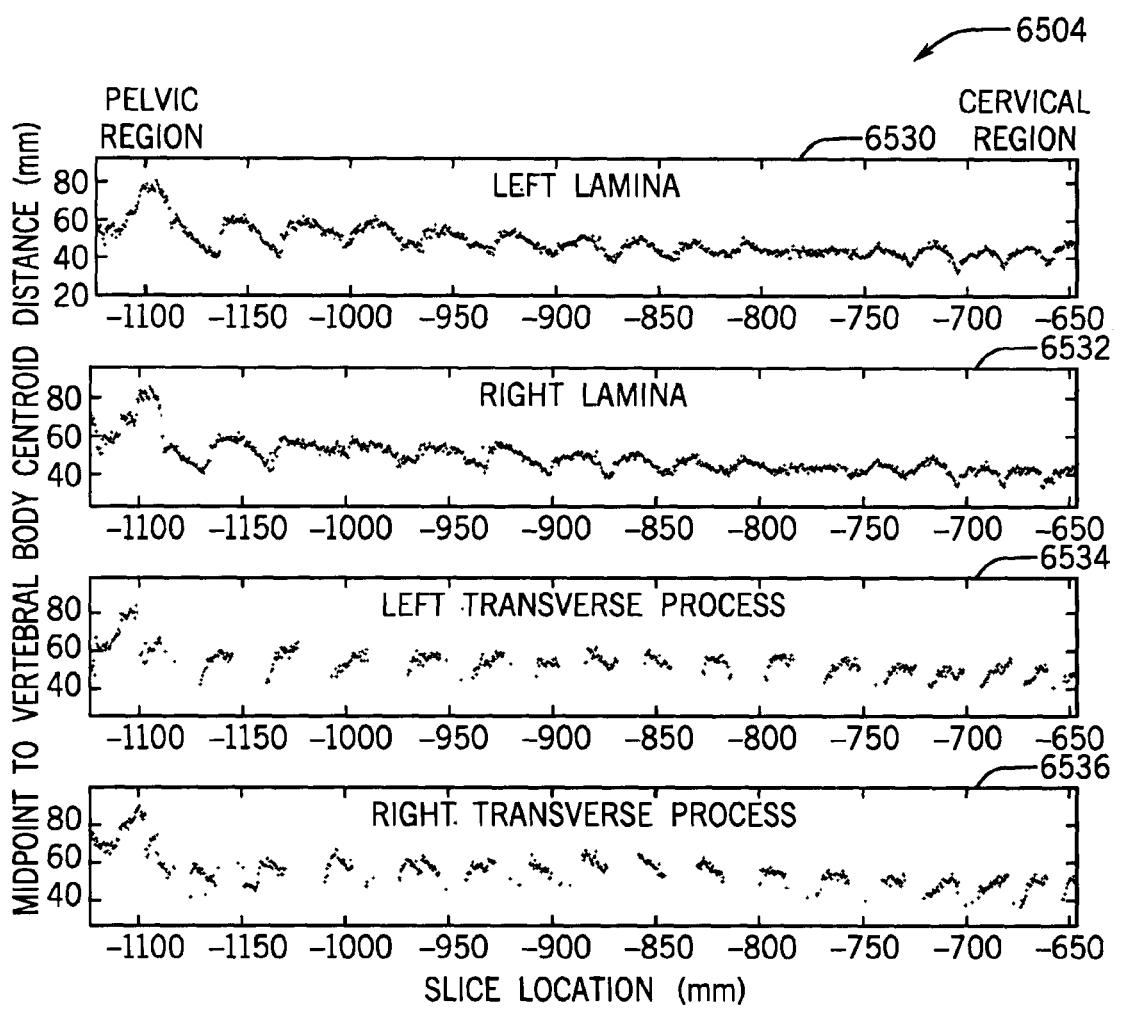

FIG. 65E illustrates computed cross-sectional distances between corresponding anatomical landmarks and vertebral body centroids in accordance with some embodiments of the invention.

Figure 66A:
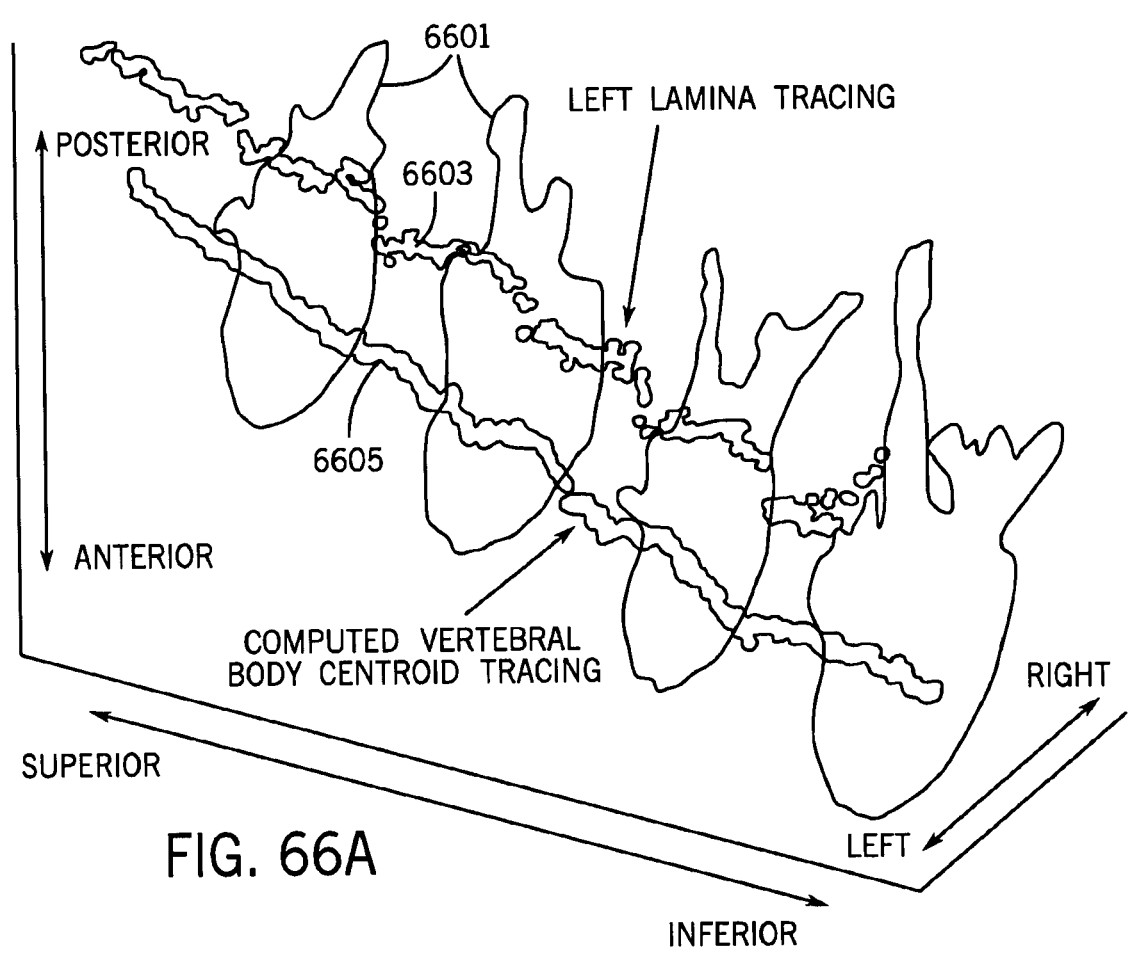

FIG. 66A illustrates a display of cross-sectional slices of vertebra (a) in their relative anatomical axes in accordance with some embodiments of the invention.

Figure 66B:
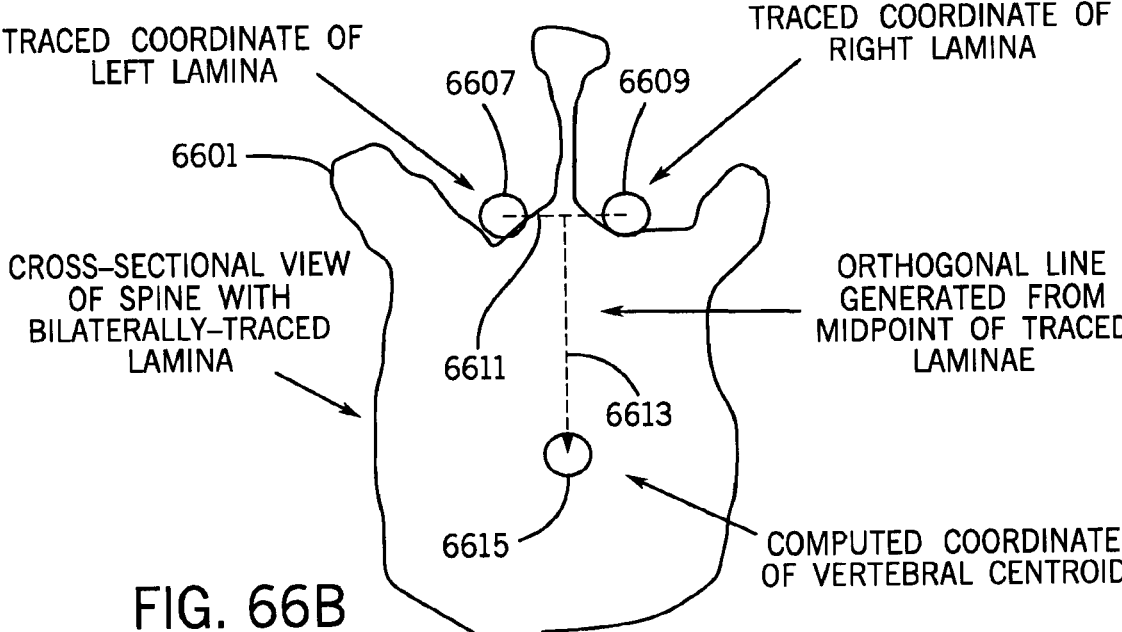

FIG. 66B illustrates a display of a vertebral body calculated via bilaterally traced coordinates and patient initialization data in accordance with some embodiments of the invention.

Figure 67:
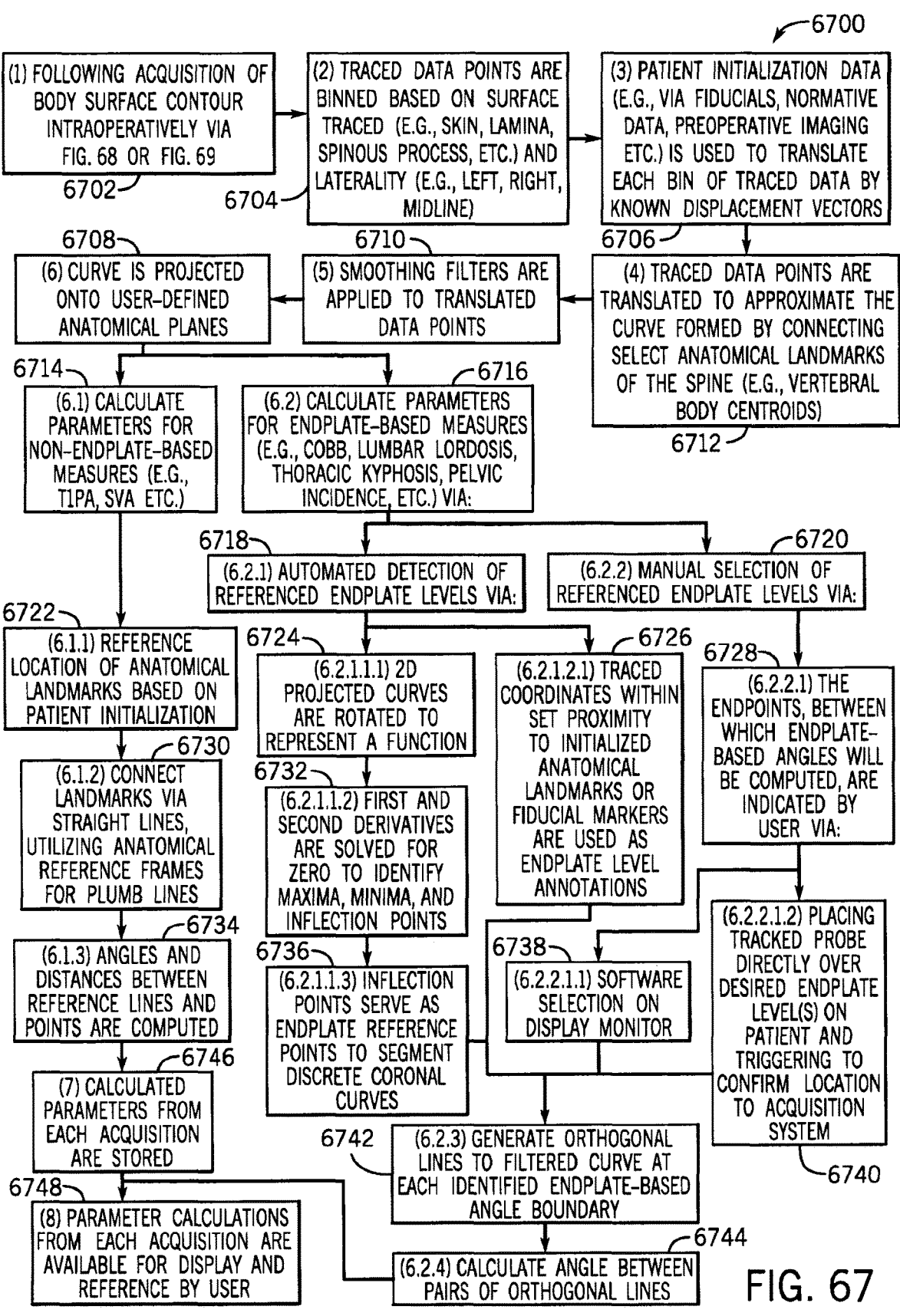

FIG. 67 illustrates a workflow to calculate spinal alignment parameters based on intraoperative tracing in accordance with some embodiments of the invention.

Figure 68:
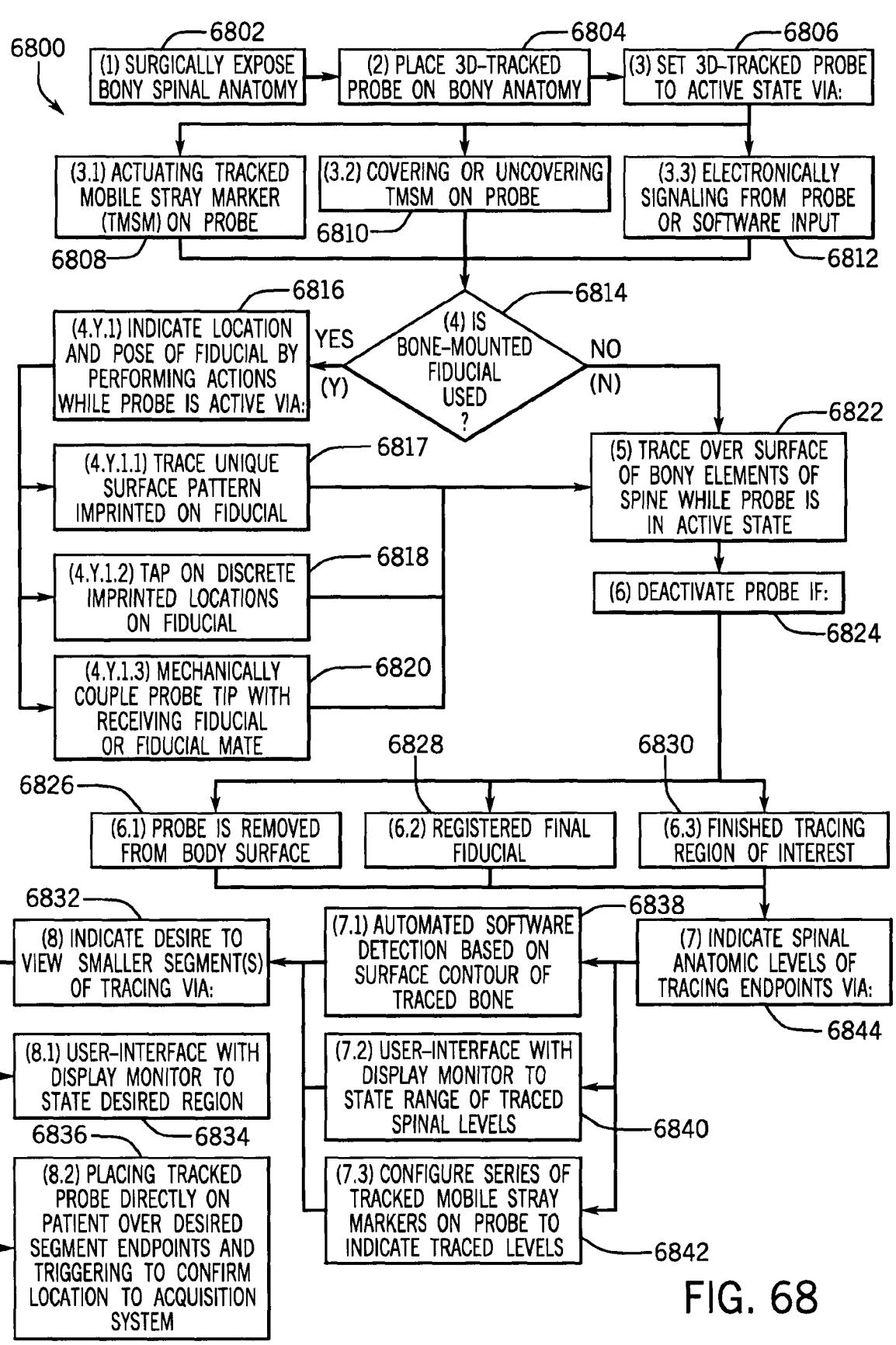

FIG. 68 illustrates a workflow to acquire a spinal alignment curve using probe-based tracing within only the surgical site in accordance with some embodiments of the invention.

Figure 69:
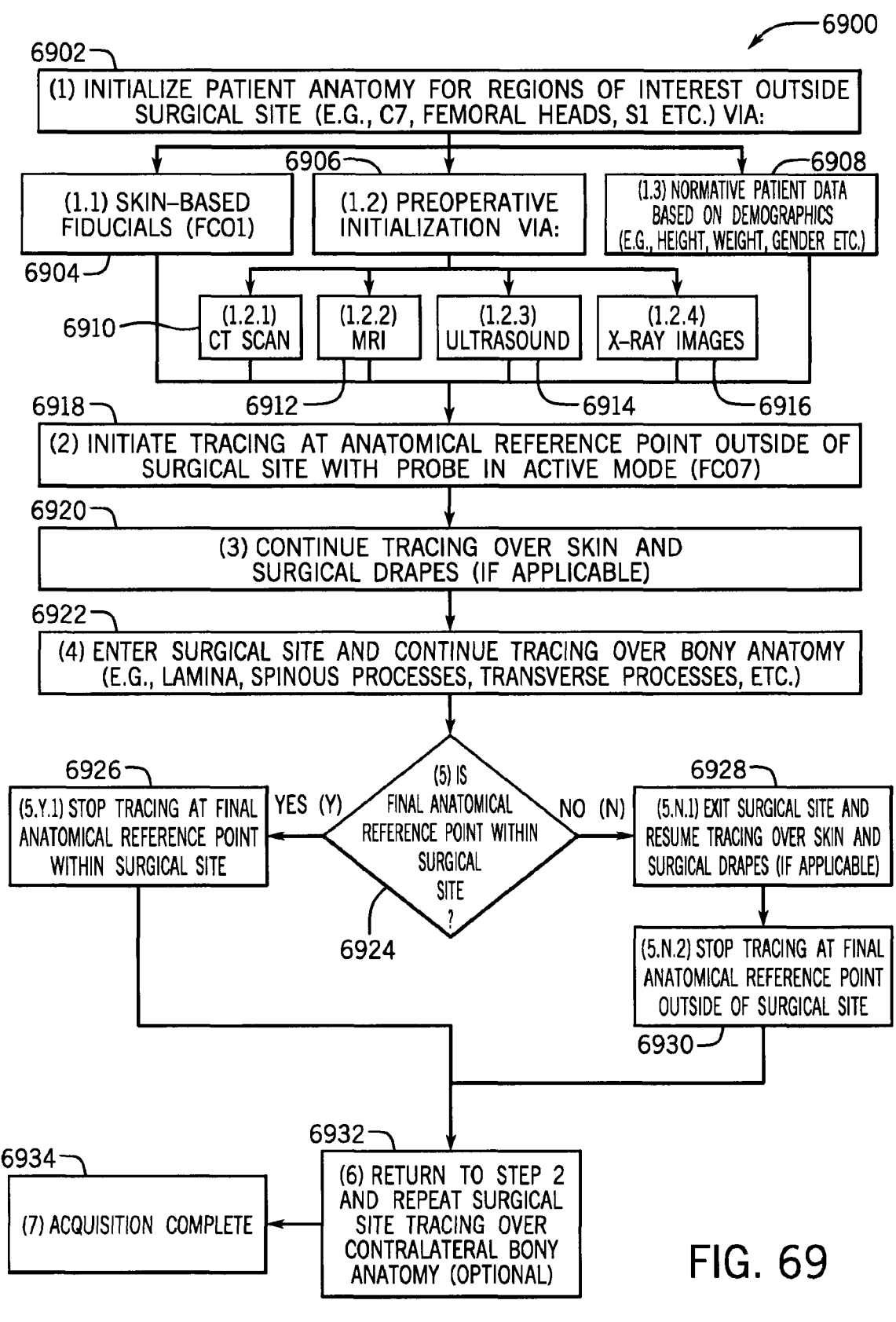

FIG. 69 illustrates a workflow to acquire a spinal alignment curve using probe-based tracing data spanning beyond the surgical site in accordance with some embodiments of the invention.

Figure 70:
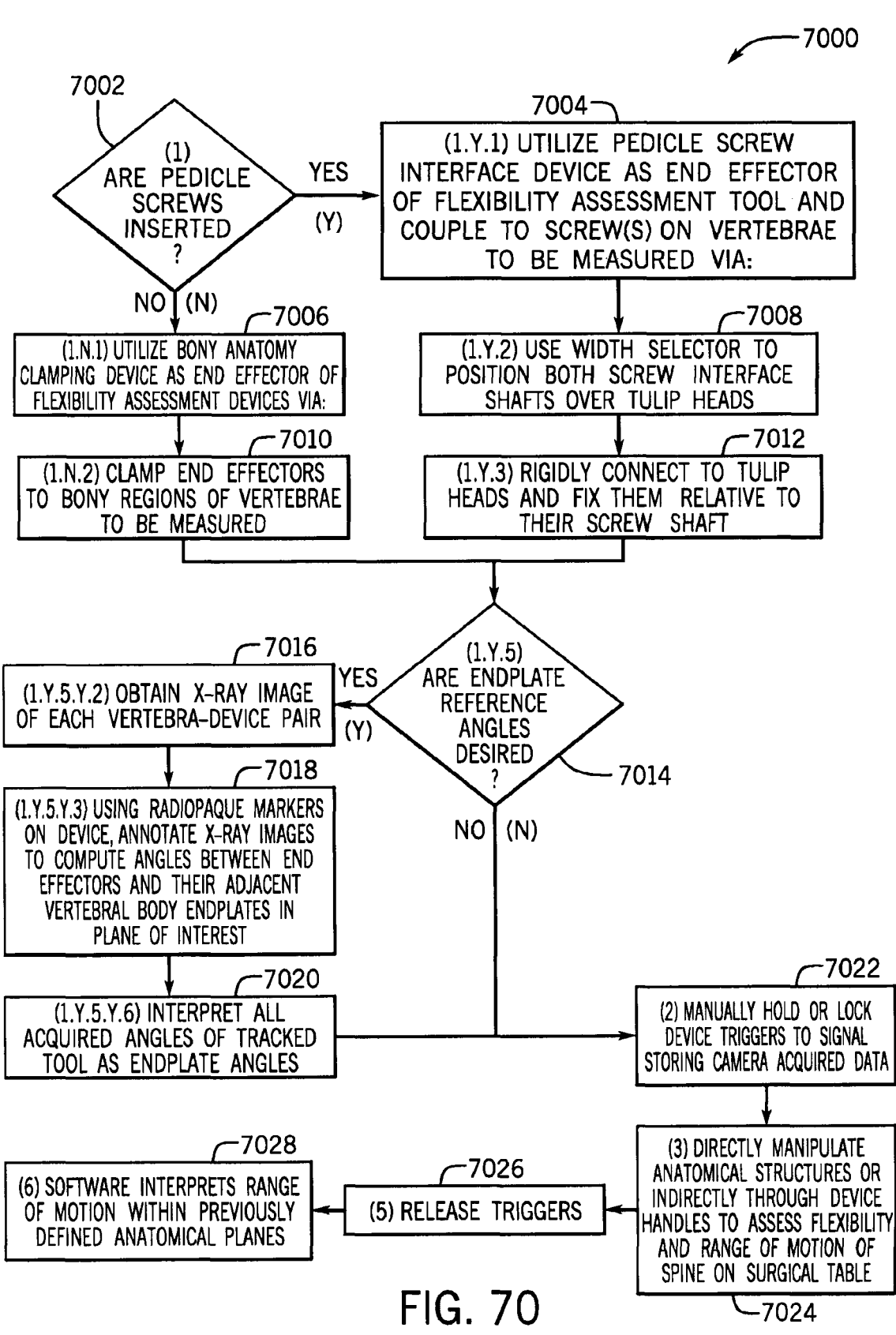

FIG. 70 illustrates a workflow to assess flexibility of the spine intraoperatively using flexibility assessment device in accordance with some embodiments of the invention.

FIG. 71 illustrates a workflow of producing real-time overlays of surgical instruments over intraoperative X-rays in accordance with some embodiments of the invention.

Figure 72:
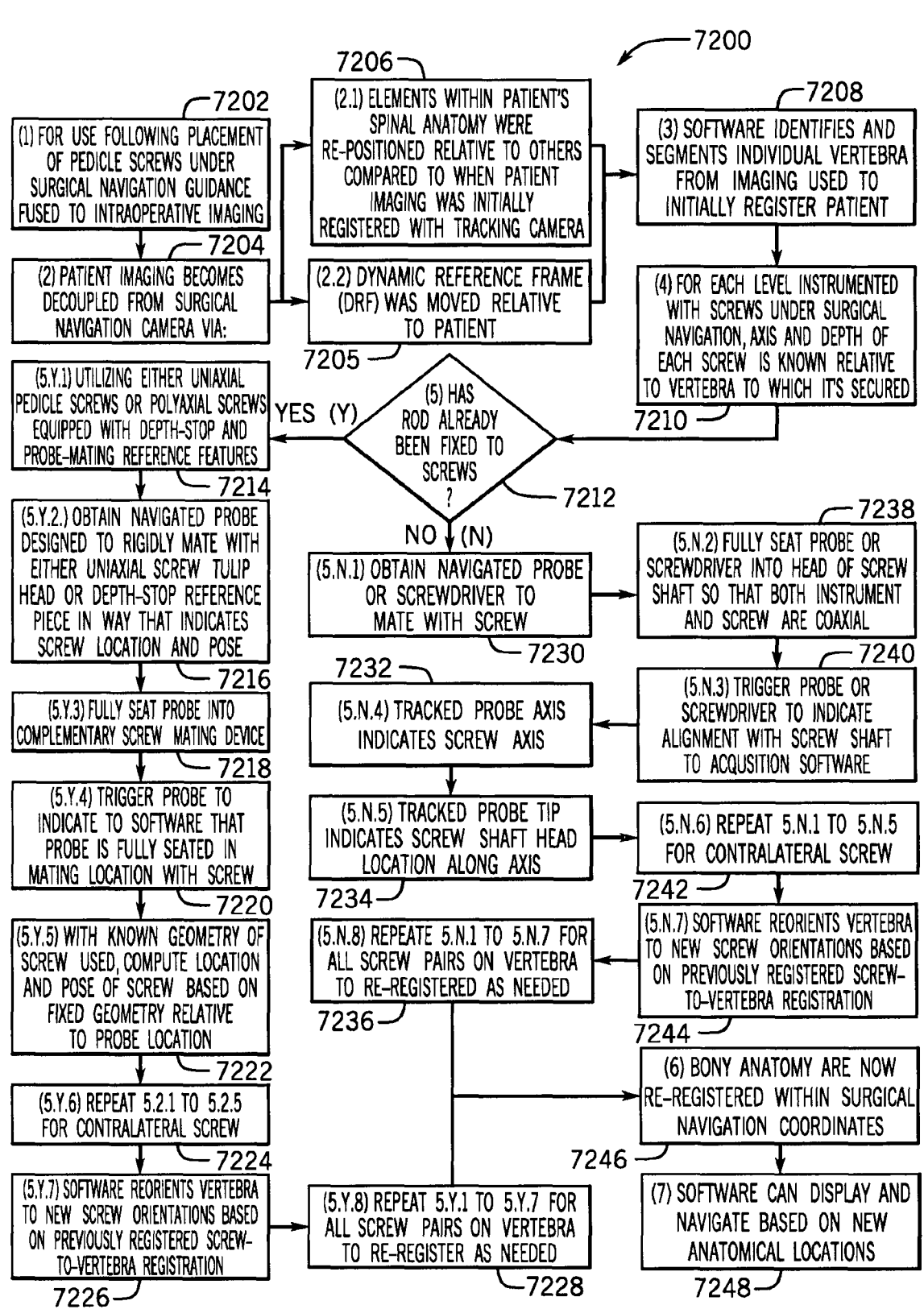

FIG. 72 shows a workflow to rapidly re-register a surgical navigation system after a navigated/registered screw insertion in accordance with some embodiments of the invention.

Figure 73A:
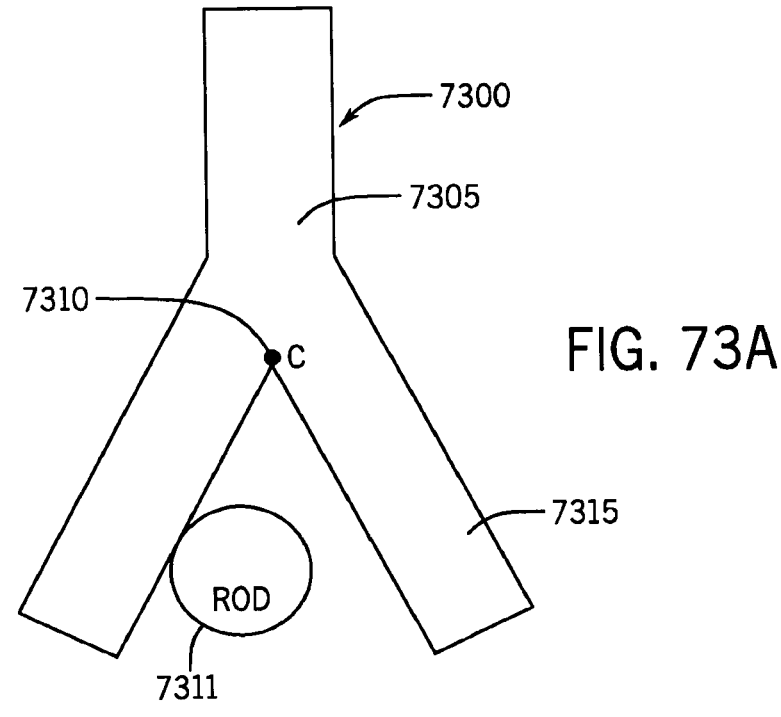

FIG. 73A illustrates a rod-centering fork on the end of a tool shaft in accordance with some embodiments of the invention.

Figure 73B:
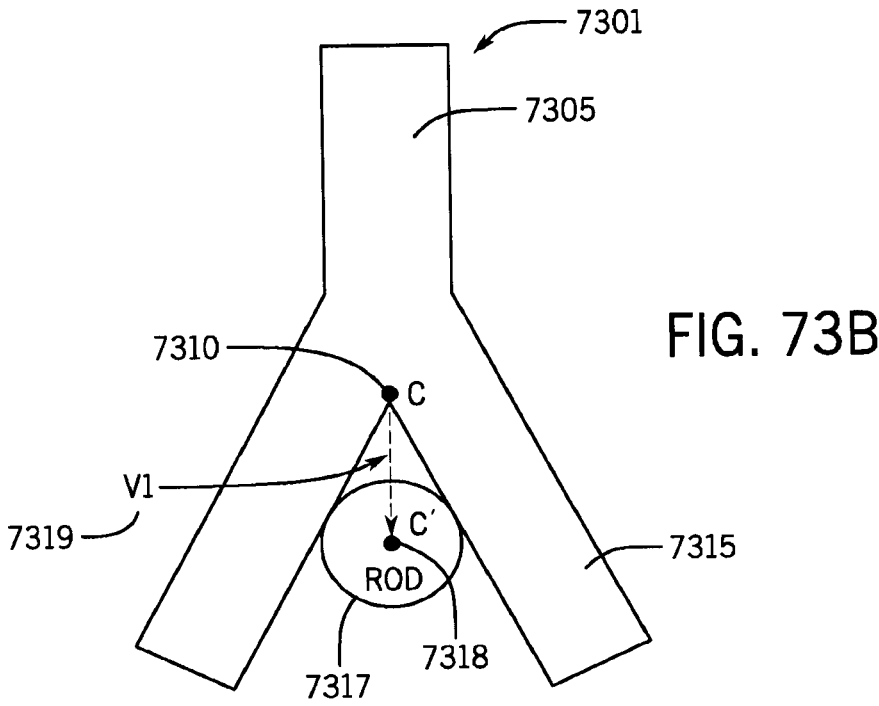

FIG. 73B illustrates the fork of FIG. 73A fully engaged with a rod in accordance with some embodiments of the invention.

FIG. 74 illustrates a workflow to assess the contour of a rod prior to implantation using two handheld tracked tools in accordance with some embodiments of the invention.

Figure 75:
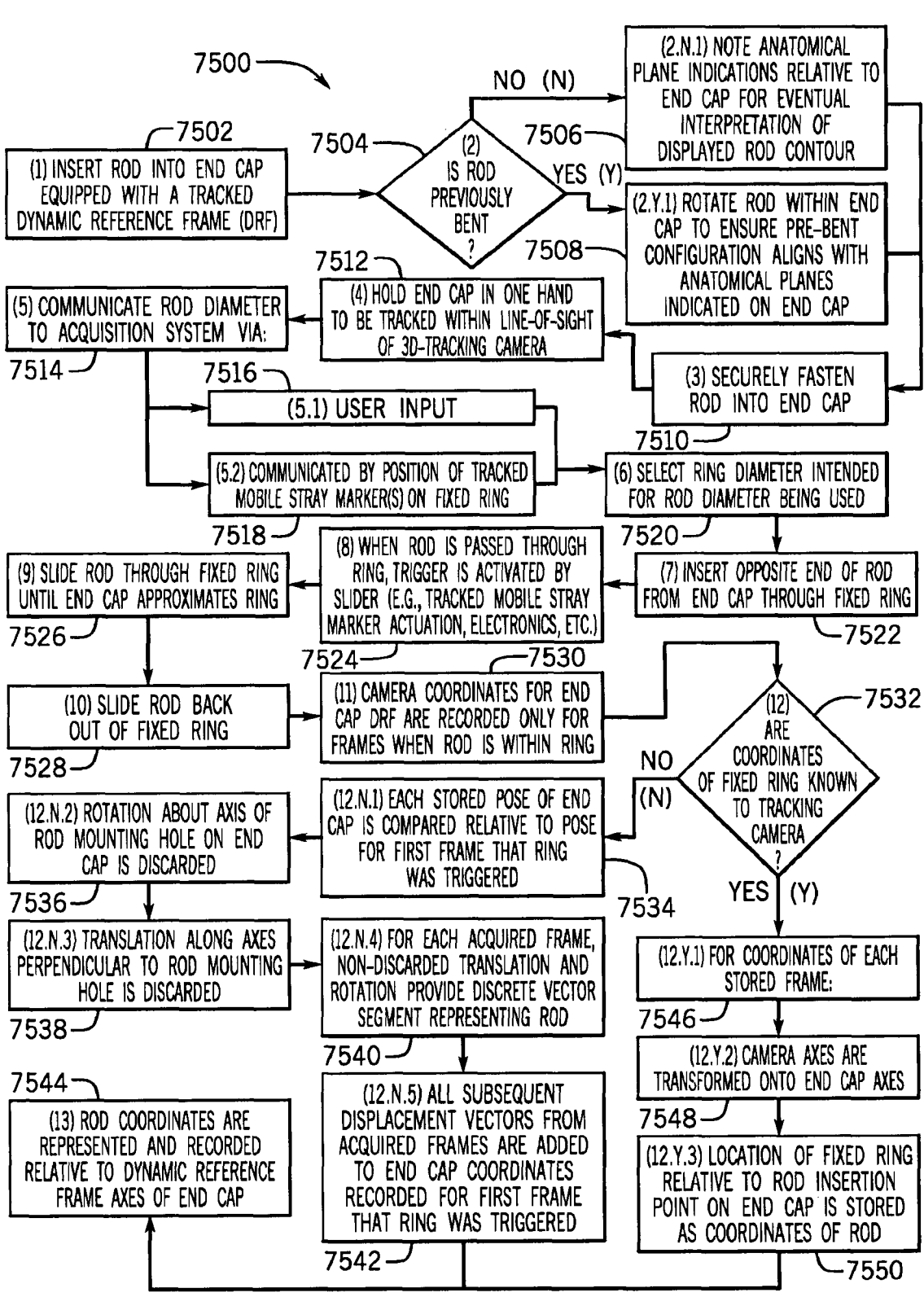

FIG. 75 illustrates a workflow to assess the contour of a rod prior to implantation using one handheld tracked tool and one substantially rigidly fixed ring in accordance with some embodiments of the invention.

FIG. 76 illustrates a workflow to assess the contour of a rod after implantation in accordance with some embodiments of the invention.

Figures 77A, 77B, 77C:
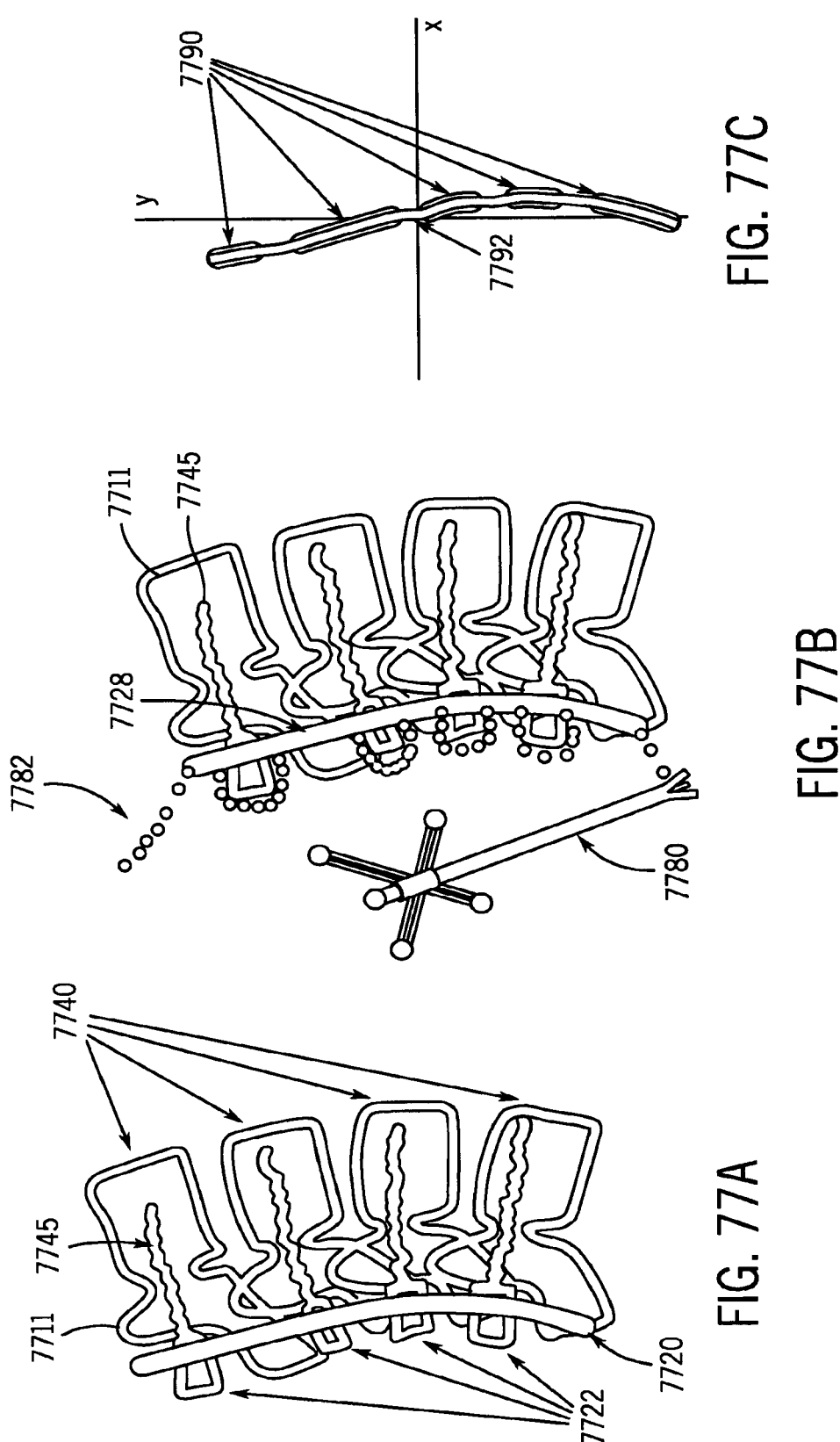

FIGS. 77A-77C illustrate various displays of interpretation of data generated by assessment of a rod contour after a rod has been implanted to tulip heads within a surgical site in accordance with some embodiments of the invention.

FIG. 78 illustrates a workflow for interactive user placement of a registered rod as an overlay on patient images on a display monitor in accordance with some embodiments of the invention.

FIGS. 79A-79G display processes of interpreting and calculating a tracked rod bending device in accordance with some embodiments of the invention.

FIG. 80 illustrates a workflow for manually bending a rod prior to its implantation with real-time feedback of its dynamic contour in accordance with some embodiments of the invention.

FIG. 81 shows a workflow for manually bending a rod prior to its implantation with directed software input to overlay a projection of the dynamic rod contour onto an intraoperative X-ray image in accordance with some embodiments of the invention.

Figures 82A, 82B:
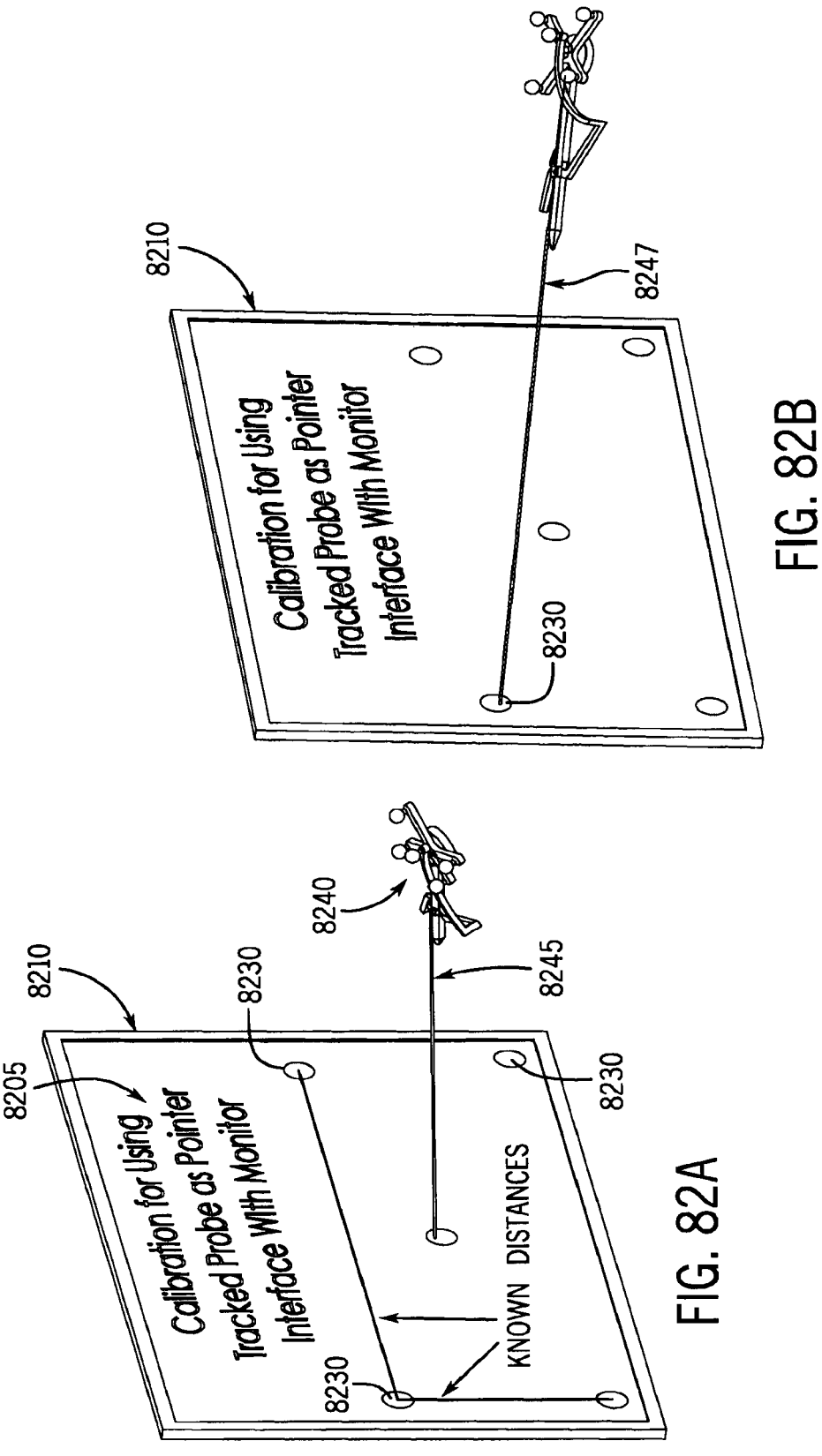

FIGS. 82A-82B illustrates processes or methods of a probe calibration in accordance with some embodiments of the invention.

FIG. 83 illustrates a workflow to utilize a trigger-equipped probe to serve as a laser pointer analog for a user-interface system with a non-tracked display in accordance with some embodiments of the invention.

Figure 84A:
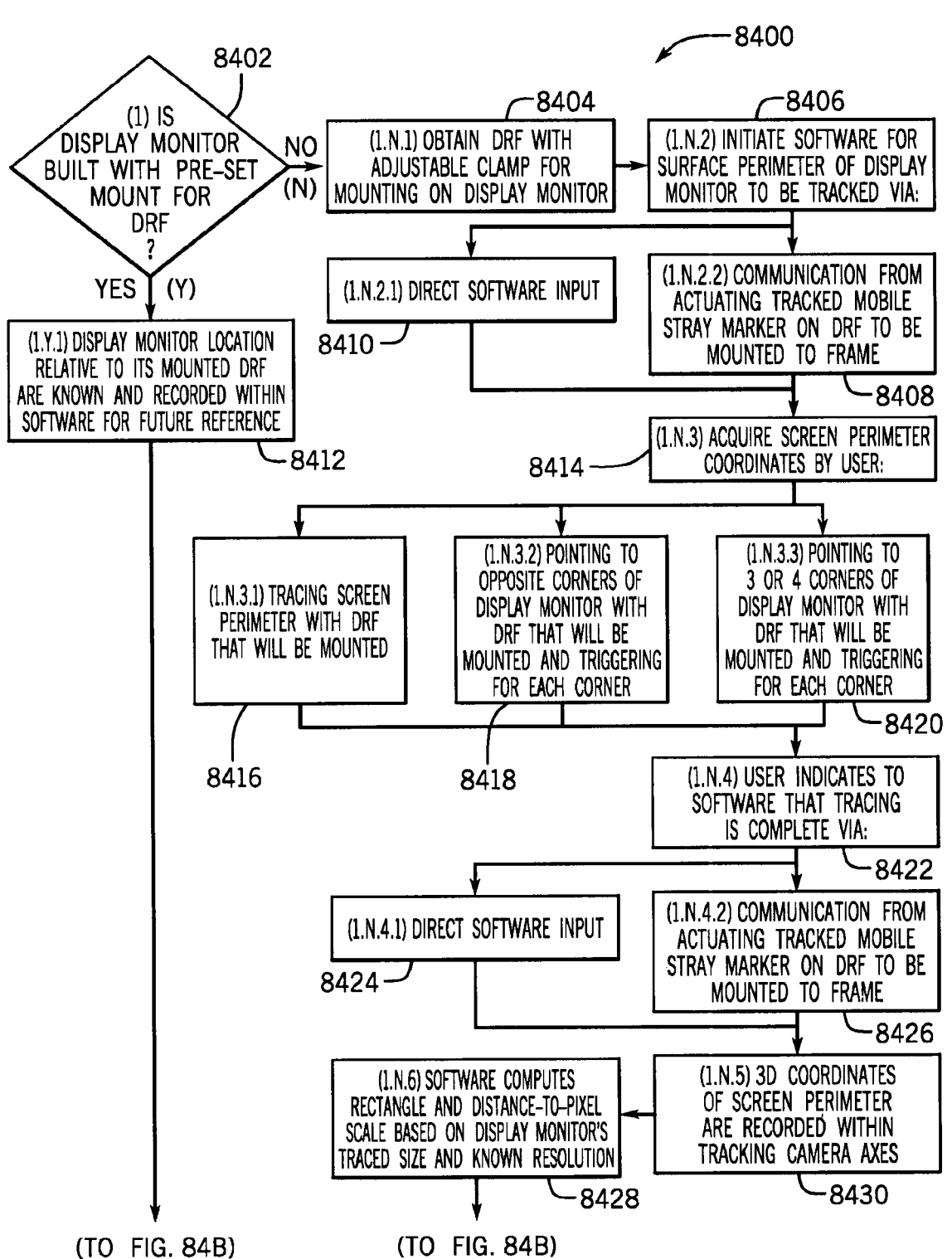

FIGS. 84A-84B illustrates a workflow to utilize a trigger-equipped probe to serve as a laser pointer analog for a user-interface with a 3D-tracked display monitor in accordance with some embodiments of the invention.

Figure 85:
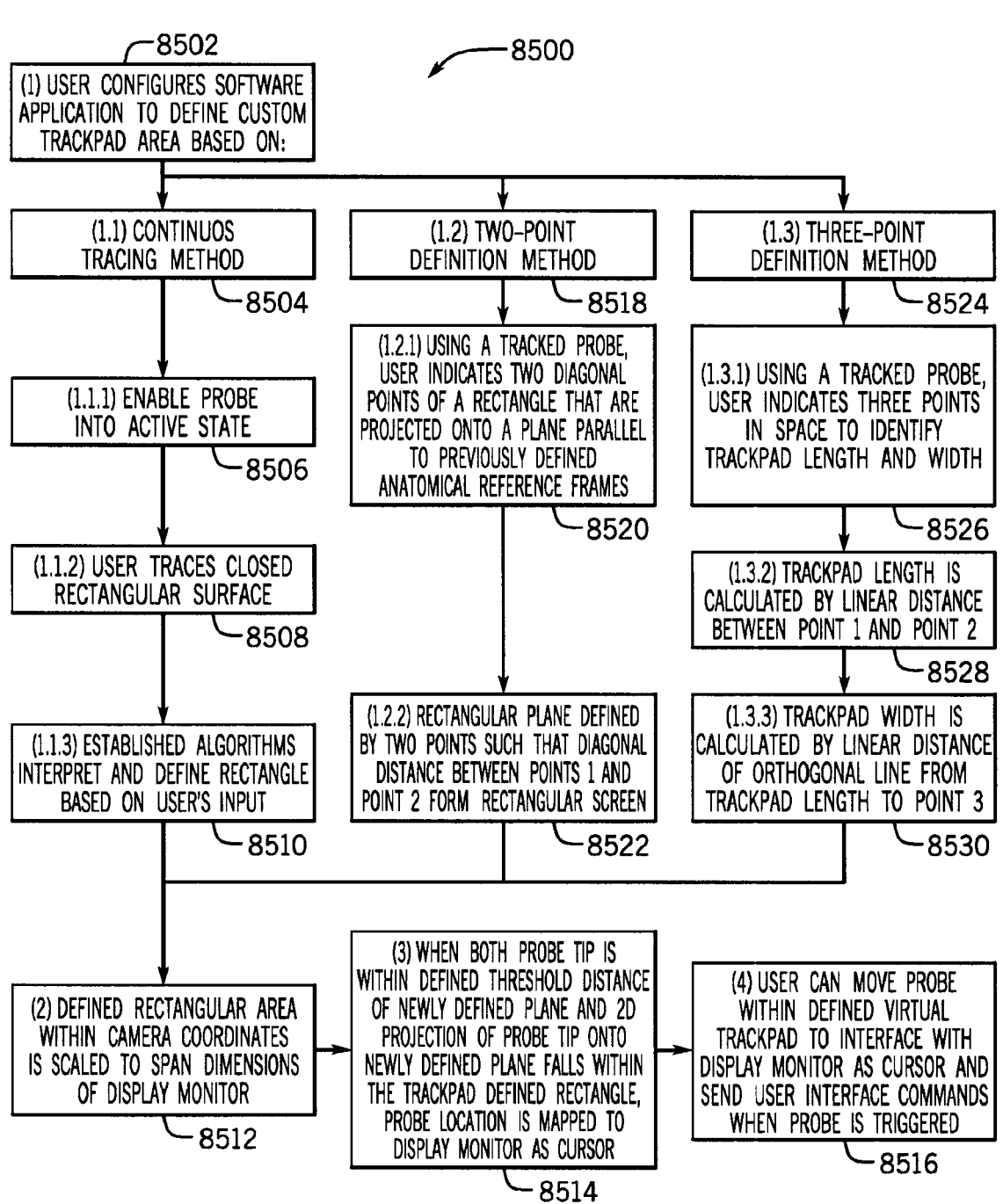

FIG. 85 illustrates a workflow to utilize a trigger-equipped probe to serve as an interface device for a non-tracked display via a user-defined trackpad analog in accordance with some embodiments of the invention.

FIGS. 86A-86D illustrates output displays of alignment assessments in accordance with some embodiments of the invention.

Figures 87A, 87B, 87C, 87D, 87E:
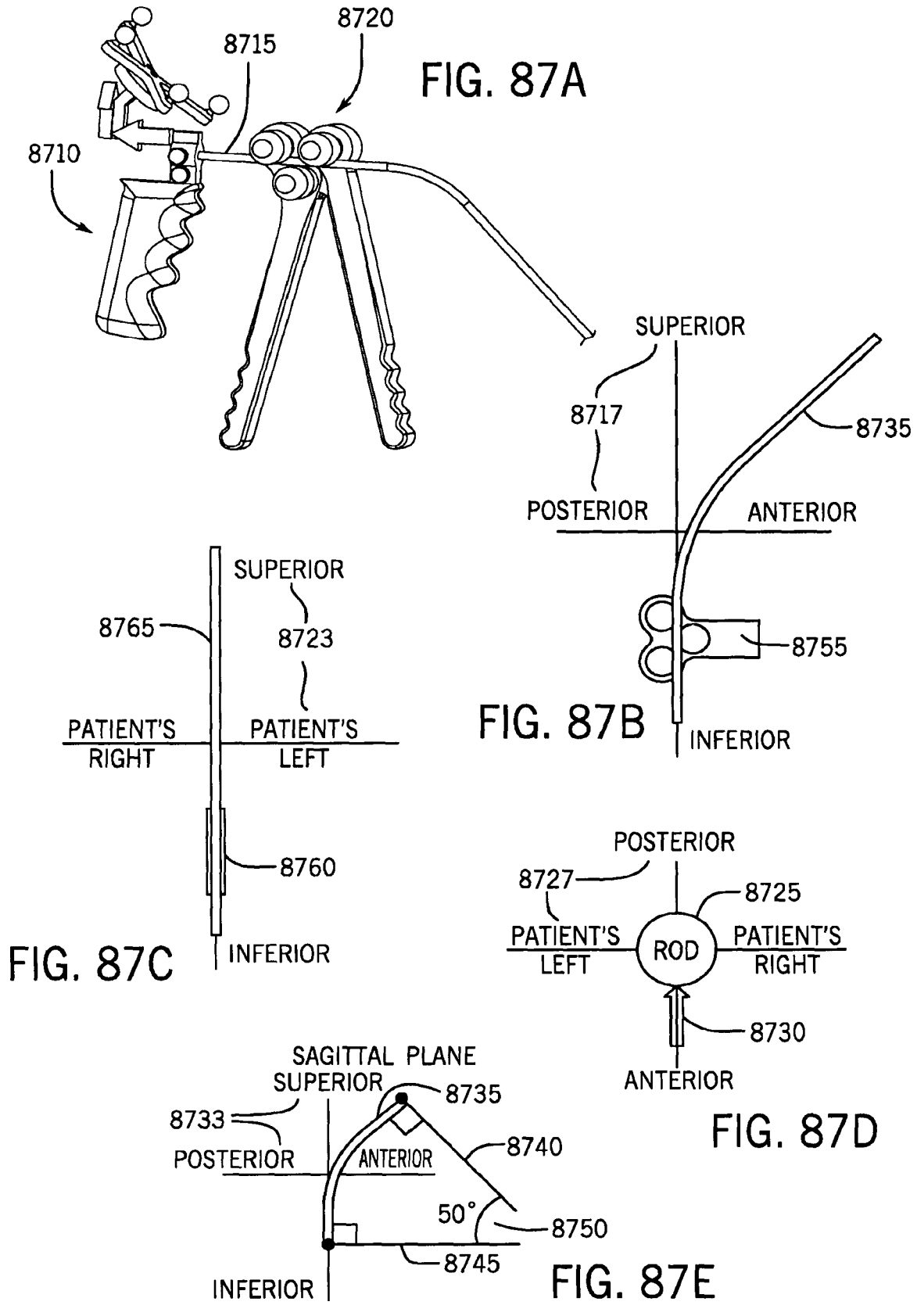

FIG. 87A illustrates a rod with previously registered contour fixed to a tracked DRF-equipped end cap and interacting with a tracked rod bender in accordance with some embodiments of the invention.

FIG. 87B illustrates a sagittal projection of the registered rod contour in accordance with some embodiments of the invention.

FIG. 87C illustrates a coronal projection of the registered rod contour in accordance with some embodiments of the invention.

FIG. 87D illustrates a display of the location of a rod bender's center rod contouring surface relative to a cross-sectional view of the rod in accordance with some embodiments of the invention.

FIG. 87E illustrates a display of a sagittal projection of the registered rod contour in accordance with some embodiments of the invention.

FIG. 87F illustrates a sagittal patient image with an overlay of a registered rod contour as well as an overlay display of the location of a tracked rod bender relative to the previously registered rod in accordance with some embodiments of the invention.

FIG. 87G illustrates a sagittal patient image adjusted for operative planning with an overlay of a registered rod contour as well as an overlay display of the location of a tracked rod bender relative to the previously registered rod in accordance with some embodiments of the invention.

FIGS. 87H-87I include displays of a rod and rod bender's location on display monitor in accordance with some embodiments of the invention.

FIGS. 87J-87M illustrates a display of a bender and rod in accordance with some embodiments of the invention.

FIG. 88A illustrates a sagittal projection of a registered rod contour, a display of the current location of the rod bender relative to the registered rod contour, a display of the software-instructed location where the user should place the rod-bender, and anatomical axes labels in accordance with some embodiments of the invention.

FIG. 88B illustrates a display of FIG. 88A as applied to the coronal plane in accordance with some embodiments of the invention.

FIG. 88C illustrates a cross-sectional display of the rod, the current location of the rod bender's center contouring surface, the software-instructed location of where the rod bender's center contouring surface should be placed, and anatomical axes labels in accordance with some embodiments of the invention.

FIG. 88D illustrates a display representation of the current relative position of the bender's handles, directly related to the degree of bending induced on a rod of known diameter in accordance with some embodiments of the invention.

FIG. 88E illustrates a display representation of the software-instructed relative position of the bender's handles (k), directly related to the degree of bending induced on a rod of known diameter in accordance with some embodiments of the invention.

FIG. 88F illustrates a bend angle display gauge in accordance with some embodiments of the invention.

Figure 89:
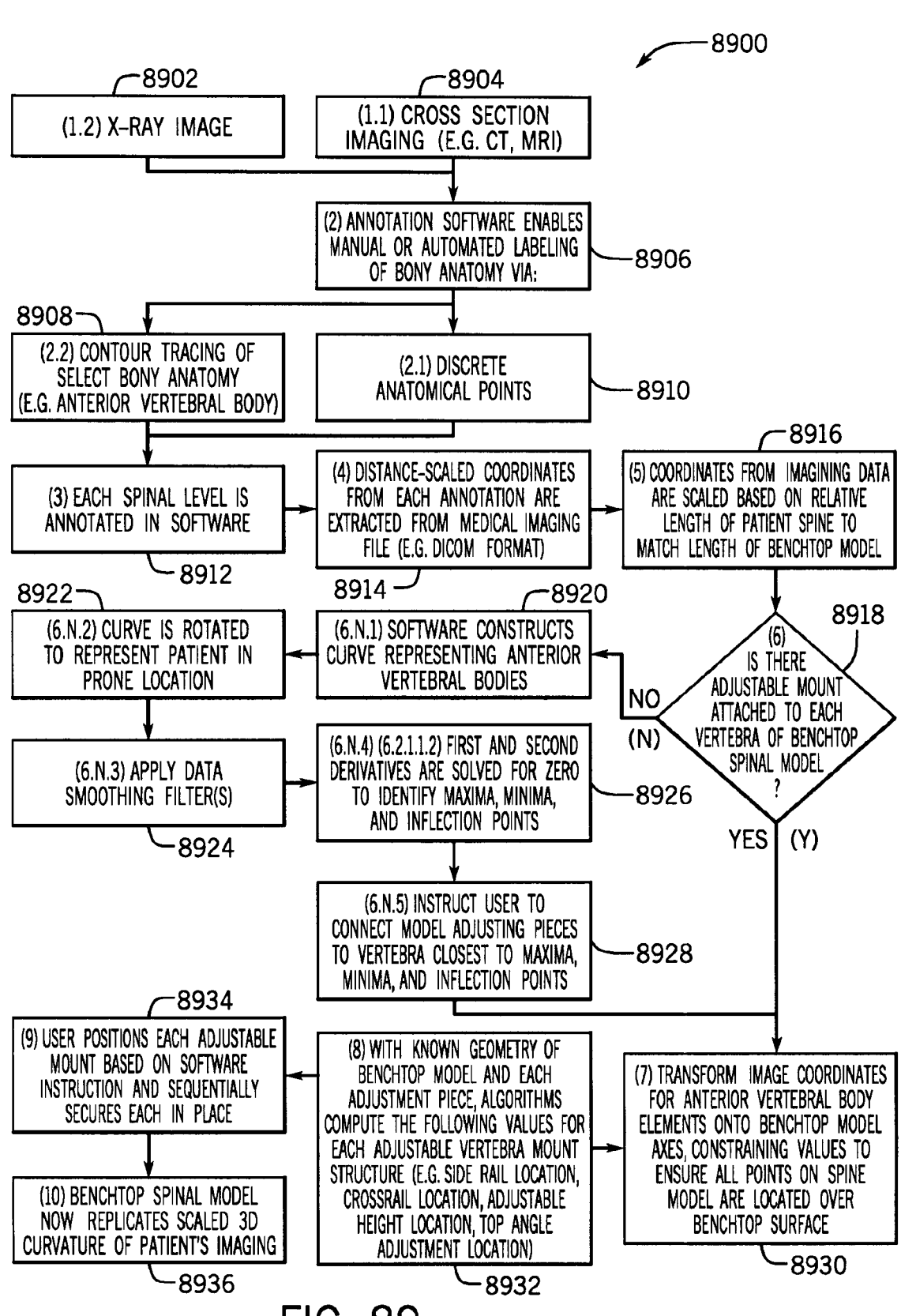

FIG. 89 shows a workflow to match the adjustable benchtop spinal model to mimic alignment parameters from patient-specific imaging in accordance with some embodiments of the invention.

Figures 90A, 90B, 90C, 90D:
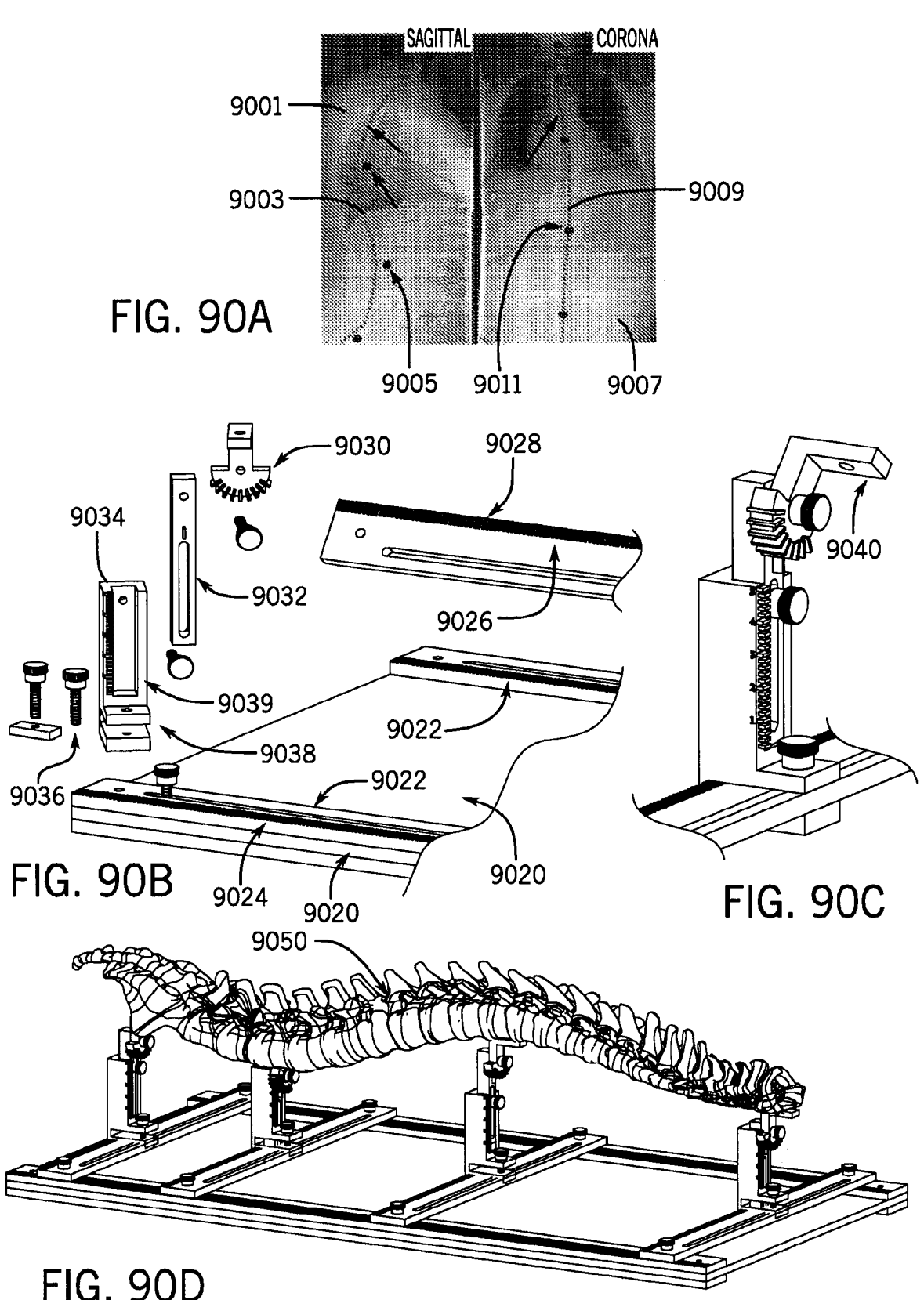

FIG. 90A illustrates sagittal and coronal patient images with overlaid sagittal and coronal contour tracings of the spine, discrete software-instructed placement of adjustable mounts onto the anatomical model, and instructions for the coordinates of each of those adjustable mounts to be positioned on the adjustable benchtop model in accordance with some embodiments of the invention.

FIG. 90B illustrates an anatomical model mounting exploded assembly in accordance with some embodiments of the invention.

FIG. 90C illustrates a fastening interface for anatomical model in accordance with some embodiments of the invention.

FIG. 90D illustrates a mounted spine anatomical model in accordance with some embodiments of the invention.

Figures 91A, 91B, 91C:
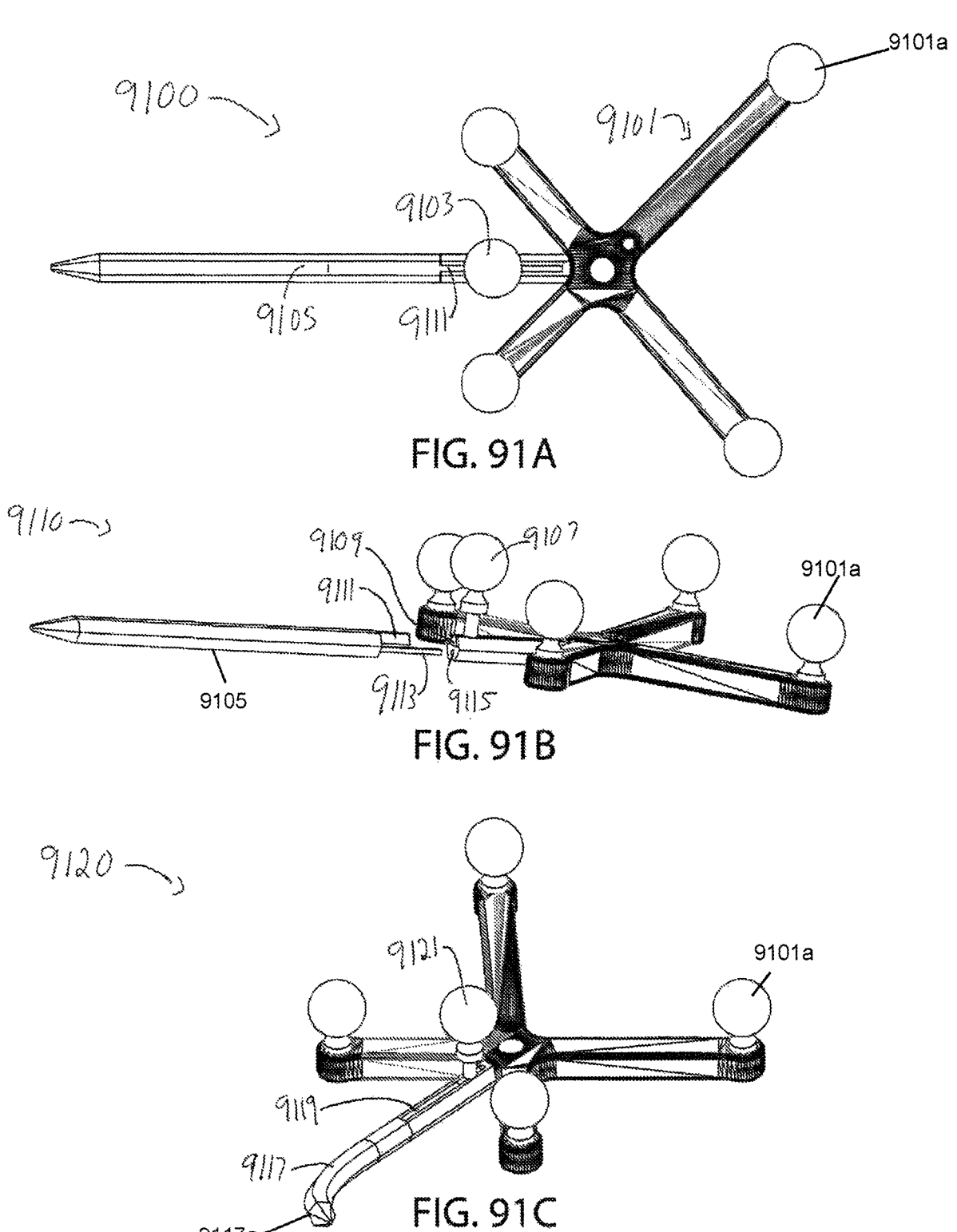

FIG. 91A illustrates a top view of a modular 3D-tracked tool with a straight extension that is fully engaged into the tool's base in accordance with some embodiments of the invention.

FIG. 91B illustrates a perspective view of a modular 3D-tracked tool with a straight extension that is disengaged with the tool's base as described previously in relation to FIG. 91A in accordance with some embodiments of the invention.

FIG. 91C illustrates a perspective view of a modular 3D-tracked tool with a curved extension that is fully engaged into the tool's base as described previously in relation to FIGS. 91A-91B in accordance with some embodiments of the invention.

Figure 92A:
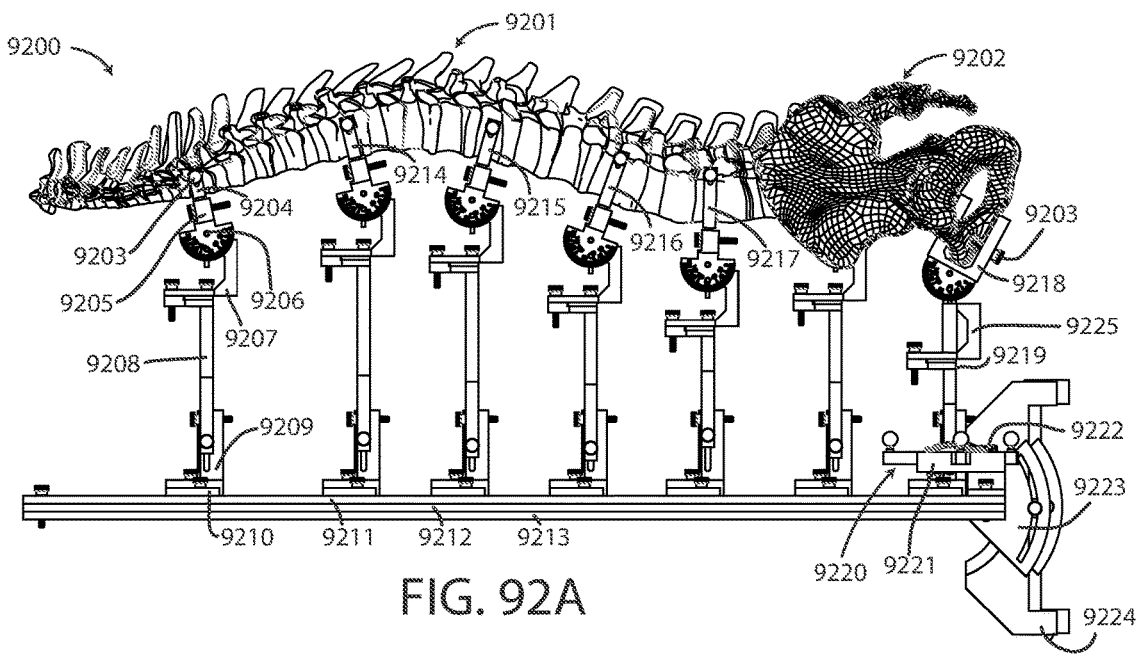
Figure 92B:
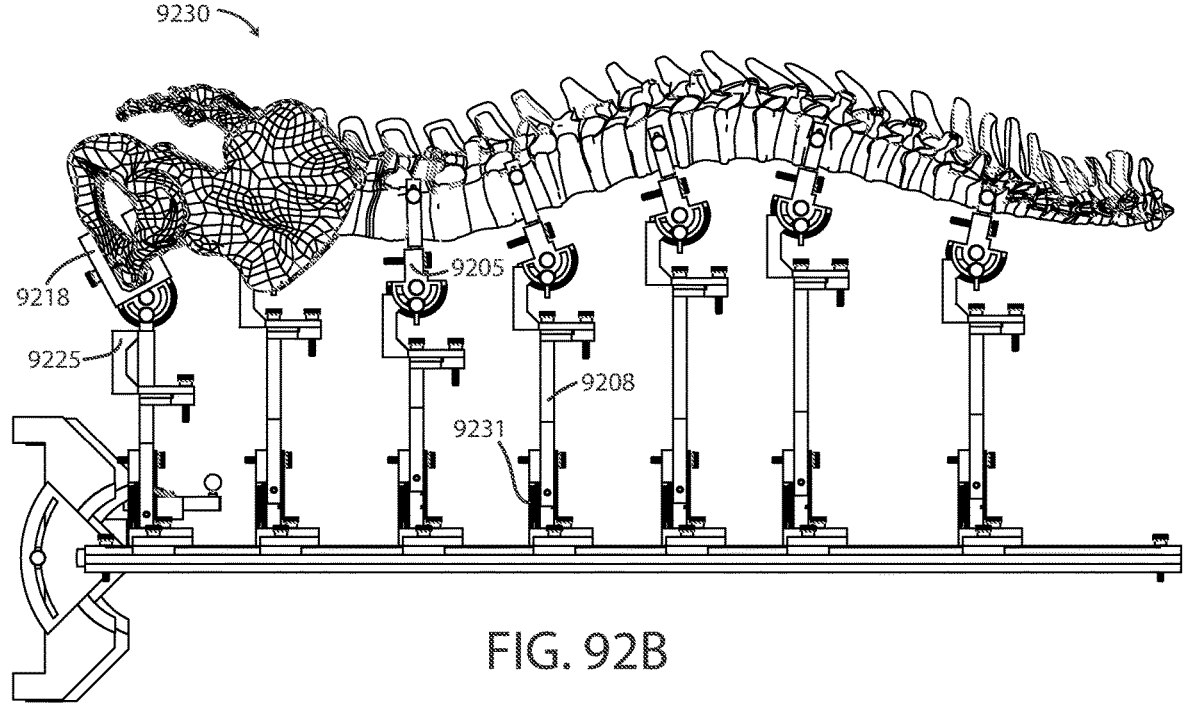

FIGS. 92A-92B illustrate side views of an adjustable phantom spine model holder with vertebral holders substantially rigidly engaged with select vertebrae and the pelvis of the model in accordance with some embodiments of the invention.

Figure 92C:
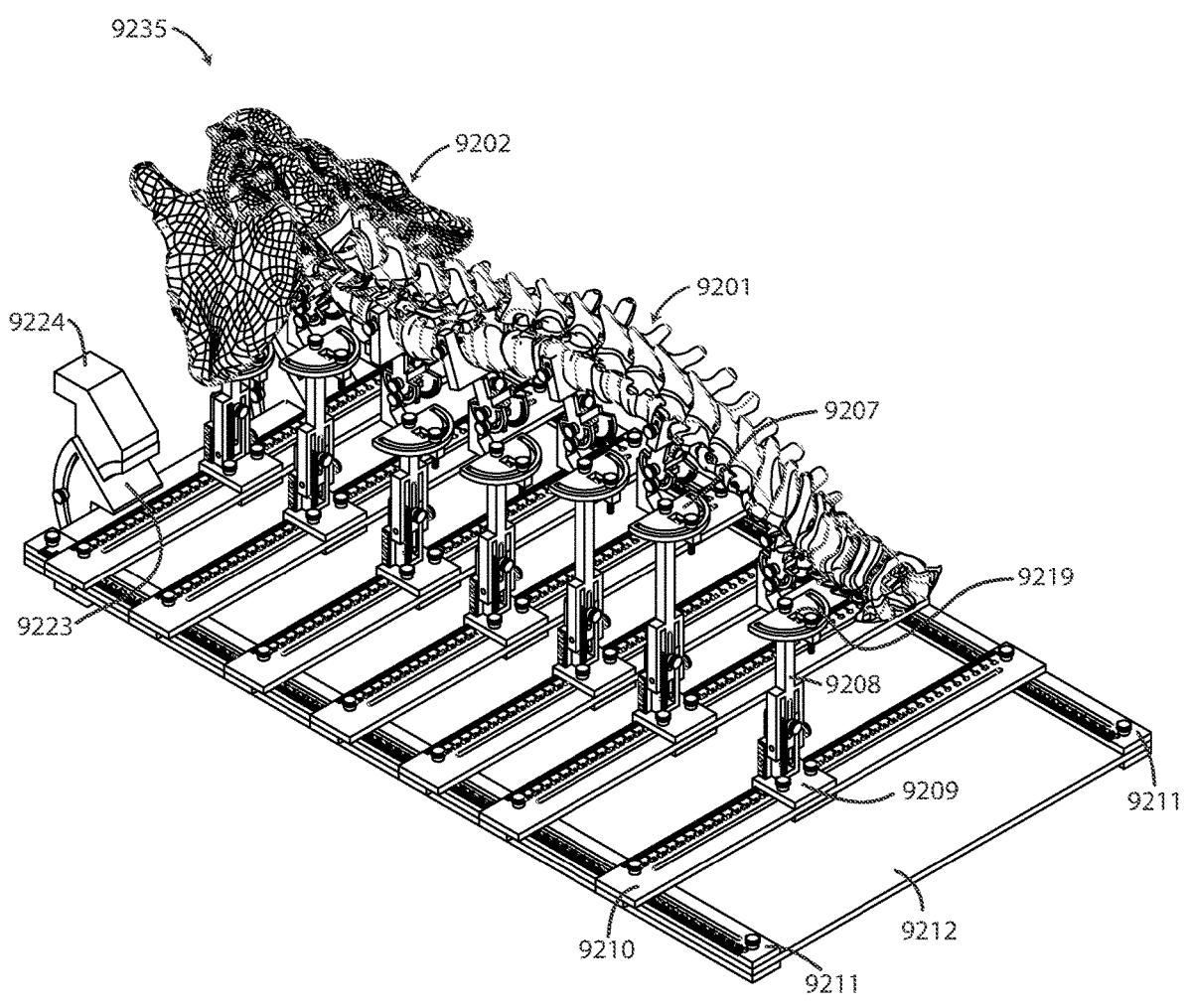

FIG. 92C illustrates a perspective view of an adjustable phantom spine model holder with vertebral holders substantially rigidly engaged with select vertebrae and the pelvis of the model as described previously in relation to FIGS. 92A-92B in accordance with some embodiments of the invention.

Figure 92D:
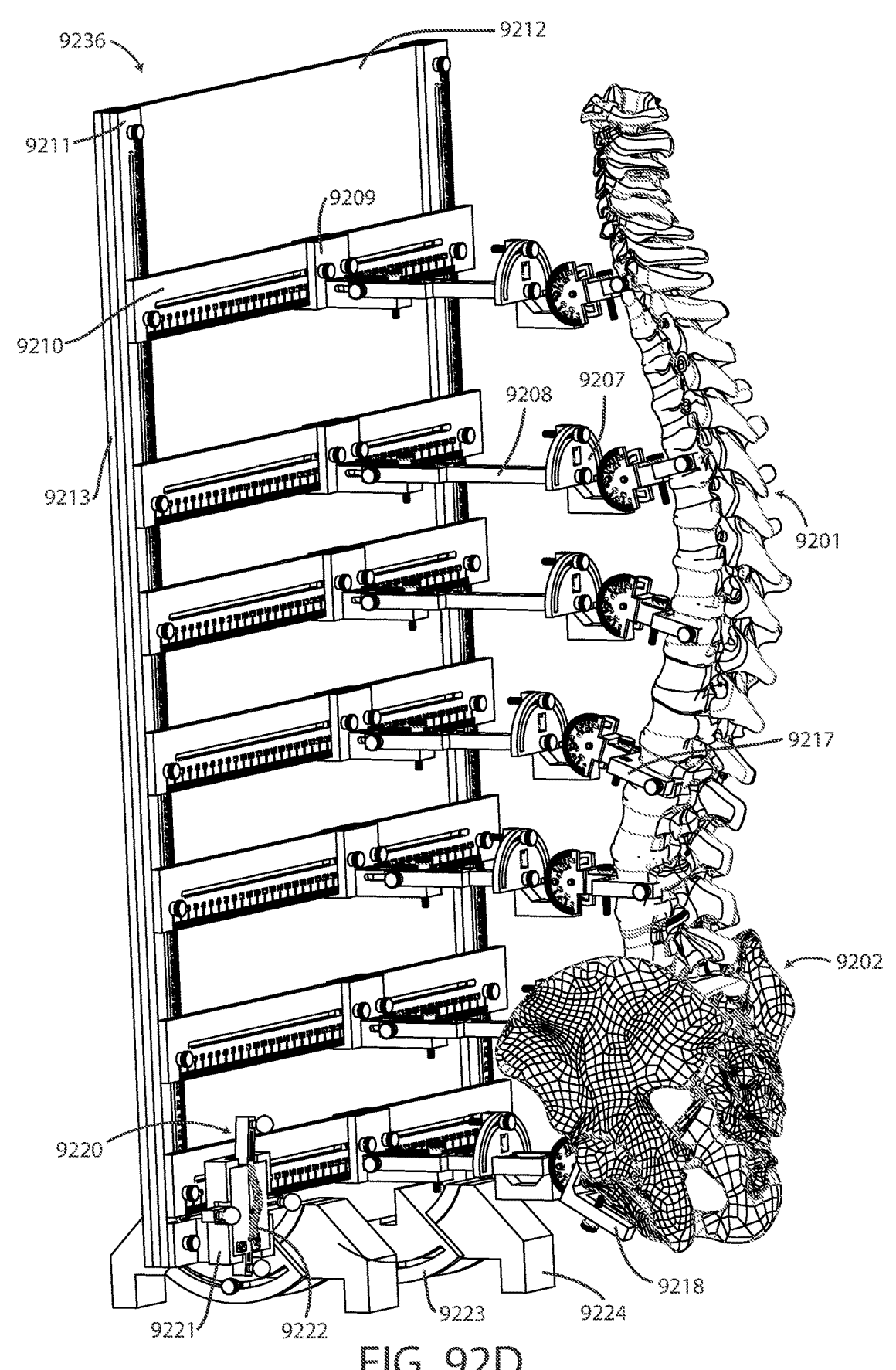

FIG. 92D illustrates a perspective view of an adjustable phantom spine model holder in an upright position via an adjustable base holder as described previously in relation to FIGS. 92A-92C in accordance with some embodiments of the invention.

Figure 92E:
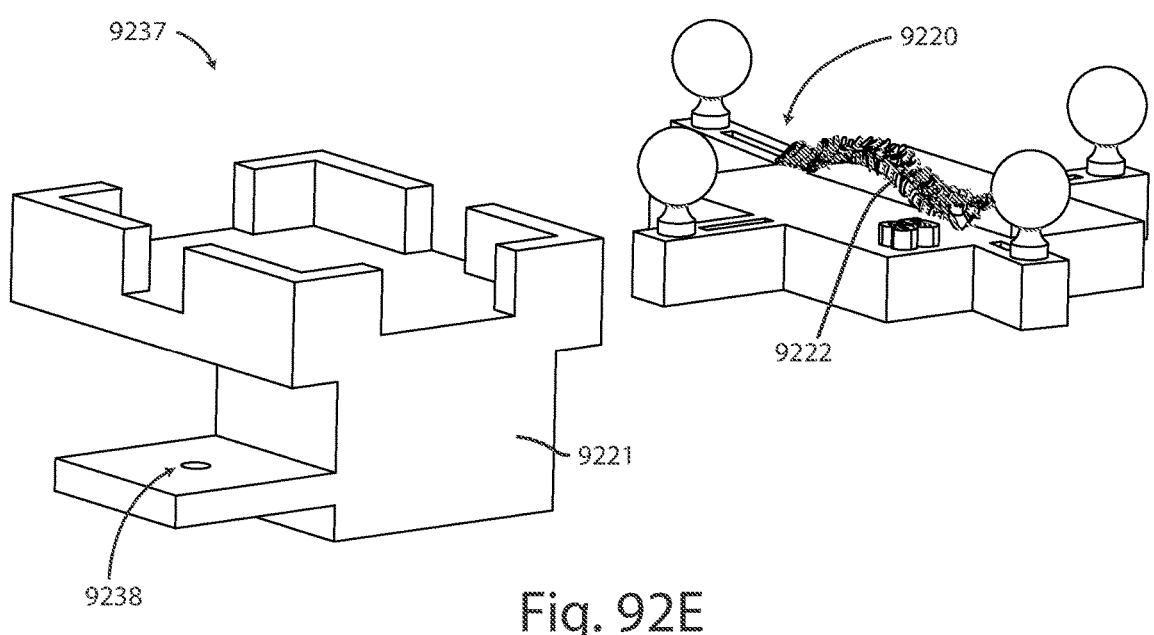
Figure 92F:
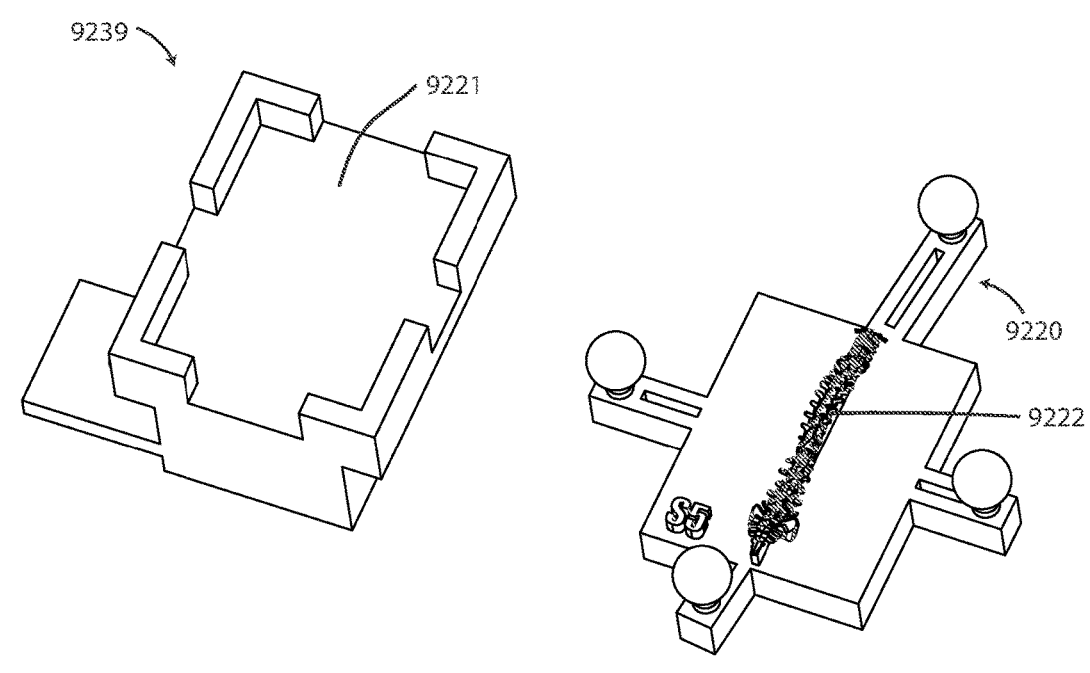

FIGS. 92E-92F illustrate perspective assembly views of a DRF and associated mount for attaching the DRF to an adjustable phantom spine model holder's base platform as described previously in relation to FIGS. 92A-92D in accordance with some embodiments of the invention.

Figures 92G, 92H, 92I, 92J, 92K, 92L, 92M, 92N, 92O:
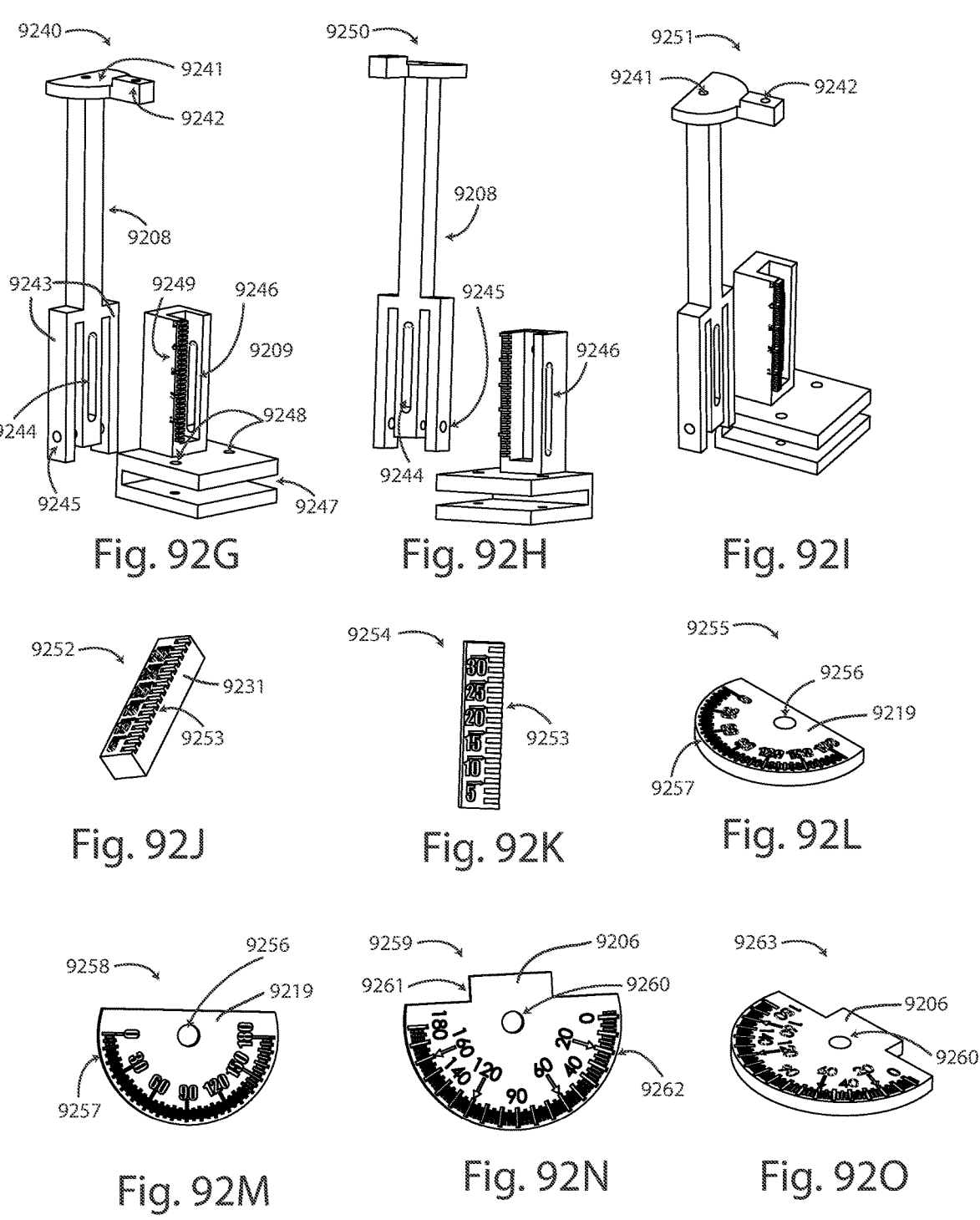

FIGS. 92G-92I illustrate perspective assembly views of a base mount and vertical height adjustment for attaching to an adjustable phantom spine model holder as described previously in relation to FIGS. 92A-92F in accordance with some embodiments of the invention.

FIG. 92J illustrates a perspective view of a vertical height indicator for a base mount of an adjustable phantom spine model holder as described previously in relation to FIGS. 92A-92I in accordance with some embodiments of the invention.

FIG. 92K illustrates a front view of a vertical height indicator for a base mount of an adjustable phantom spine model holder as described previously in relation to FIGS. 92A-92J in accordance with some embodiments of the invention.

FIG. 92L illustrates a perspective view of a sagittal angle indicator for a pelvis mount of an adjustable phantom spine model holder as described previously in relation to FIGS. 92A-92K in accordance with some embodiments of the invention.

FIG. 92M illustrates a front view of a sagittal angle indicator for a pelvis mount of an adjustable phantom spine model holder as described previously in relation to FIGS. 92A-92L in accordance with some embodiments of the invention.

FIG. 92N illustrates a front view of a sagittal angle indicator for a vertebral holder of an adjustable phantom spine model holder as described previously in relation to FIGS. 92A-92M in accordance with some embodiments of the invention.

FIG. 92O illustrates a perspective view of a sagittal angle indicator for a vertebral holder of an adjustable phantom spine model holder as described previously in relation to FIGS. 92A-92N in accordance with some embodiments of the invention.

Figures 92P, 92Q, 92R, 92S, 92T, 92U, 92V, 92W, 92X:
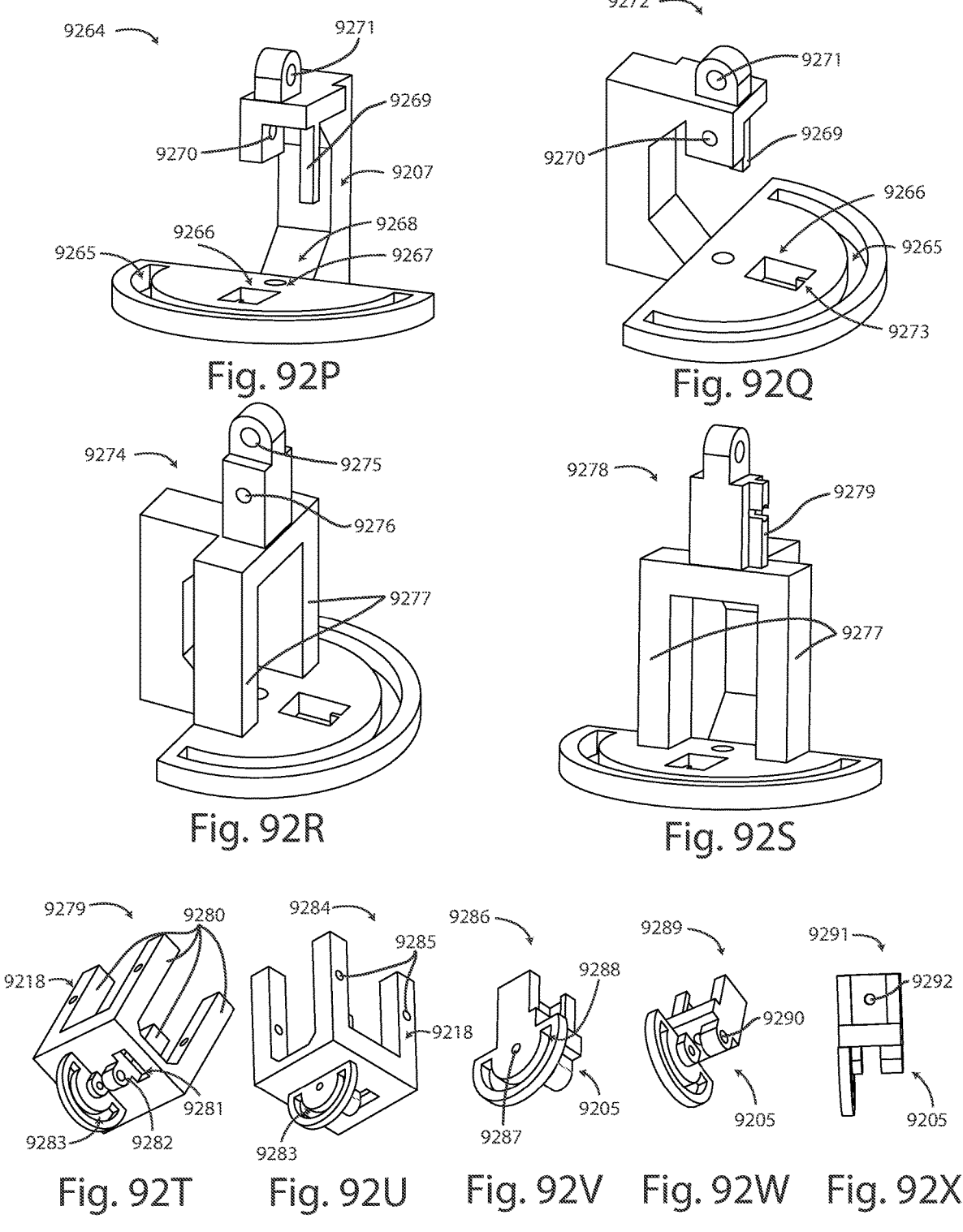

FIGS. 92P-92Q illustrate perspective views of a sagittal angle adjustment component for a vertebral holder of an adjustable phantom spine model holder as described previously in relation to FIGS. 92A-92O in accordance with some embodiments of the invention.

FIGS. 92R-92S illustrate perspective views of a sagittal angle adjustment component for a pelvis mount of an adjustable phantom spine model holder as described previously in relation to FIGS. 92A-92Q in accordance with some embodiments of the invention.

FIGS. 92T-92U illustrate perspective views of a pelvic angle adjustment component for a vertebral holder of an adjustable phantom spine model holder as described previously in relation to FIGS. 92A-92S in accordance with some embodiments of the invention.

FIGS. 92V-92X illustrate perspective views of a sagittal angle adjustment component for a vertebral holder of an adjustable phantom spine model holder as described previously in relation to FIGS. 92A-92U in accordance with some embodiments of the invention.

Figure 92Y:
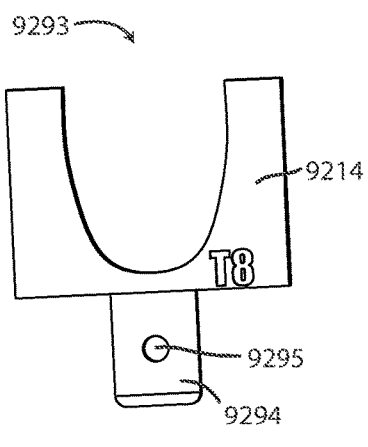

FIG. 92Y illustrates a front view of a vertebral interface component for a vertebral holder of an adjustable phantom spine model holder as described previously in relation to FIGS. 92A-92X in accordance with some embodiments of the invention.

Figure 92Z:
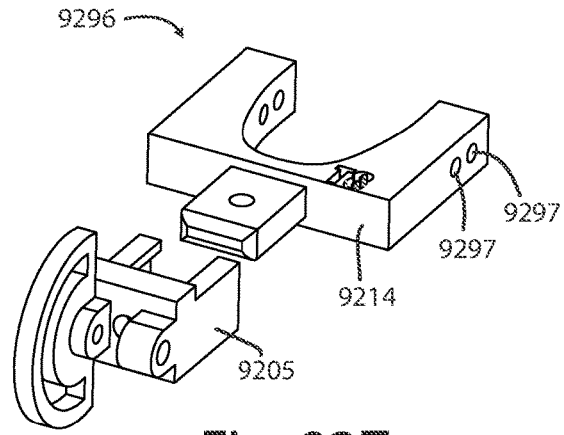
Figure 92A:
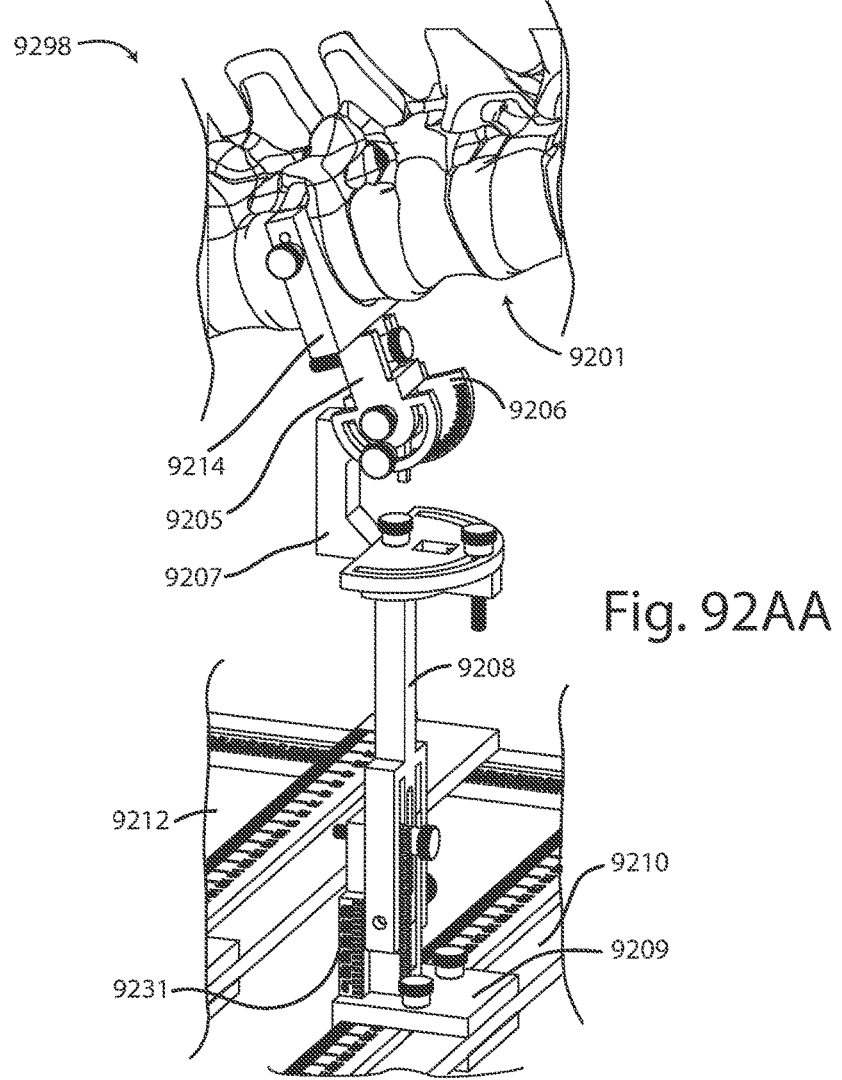

FIG. 92Z illustrates a perspective view of a vertebral interface component and sagittal angle adjustment component for a vertebral holder of an adjustable phantom spine model holder as described previously in relation to FIGS. 92A-92Y in accordance with some embodiments of the invention.

FIG. 92AA illustrates a perspective view of an adjustable vertebral holder substantially rigidly engaged with a phantom spine model holder as described previously in relation to FIGS. 92A-92Z in accordance with some embodiments of the invention.

FIG. 92AB illustrates a perspective assembly view of an adjustable vertical base holder of an adjustable phantom spine model holder as described previously in relation to FIGS. 92A-92AA in accordance with some embodiments of the invention.

FIG. 92AC illustrates a front assembly view of an adjustable vertical base holder of an adjustable phantom spine model holder as described previously in relation to FIGS. 92A-92AB in accordance with some embodiments of the invention.

FIG. 92AD illustrates a front assembly view of a base platform and cross-rails of an adjustable phantom spine model holder as described previously in relation to FIGS. 92A-92AC in accordance with some embodiments of the invention.

Figure 93A:
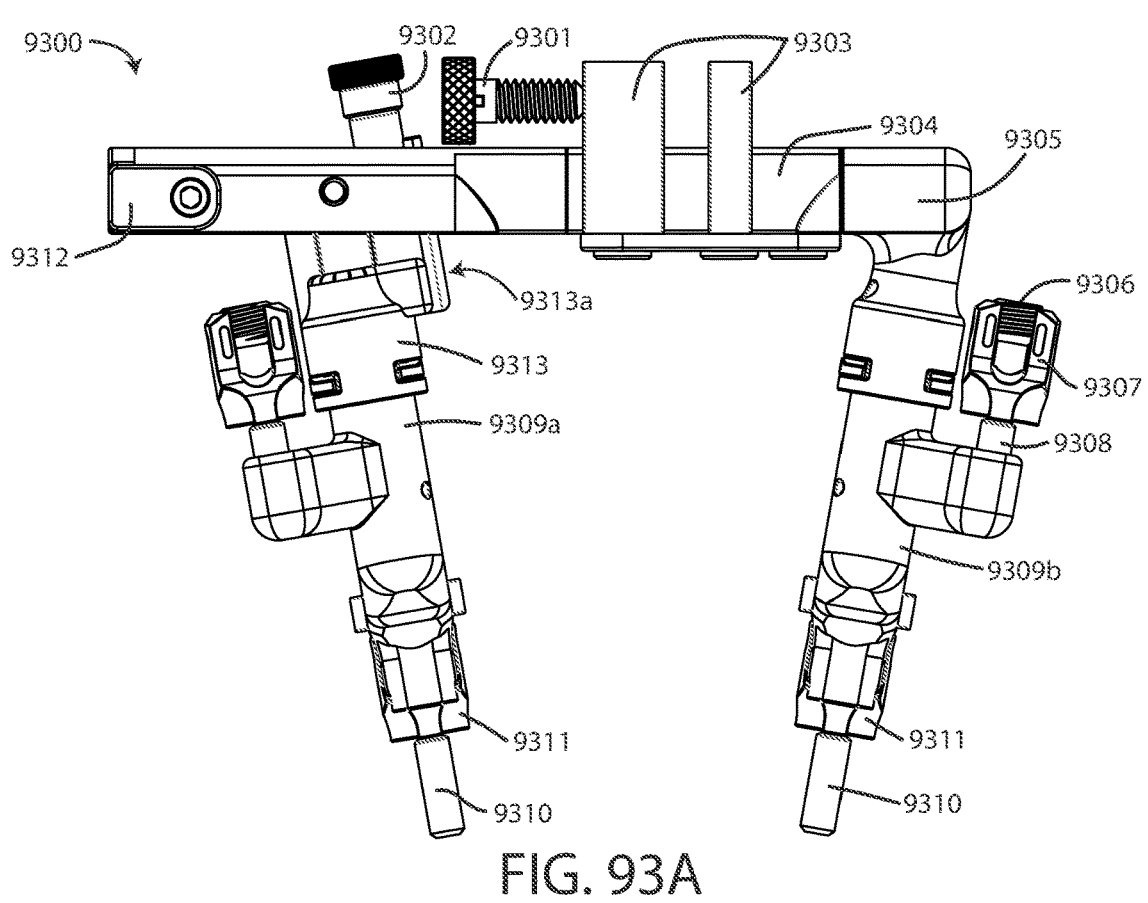

FIG. 93A illustrates a rear view of an adjustable pedicle screw interface base, with one fixed side arm and one side arm with height and angle adjustments, of a flexibility assessment device.

Figure 93B:
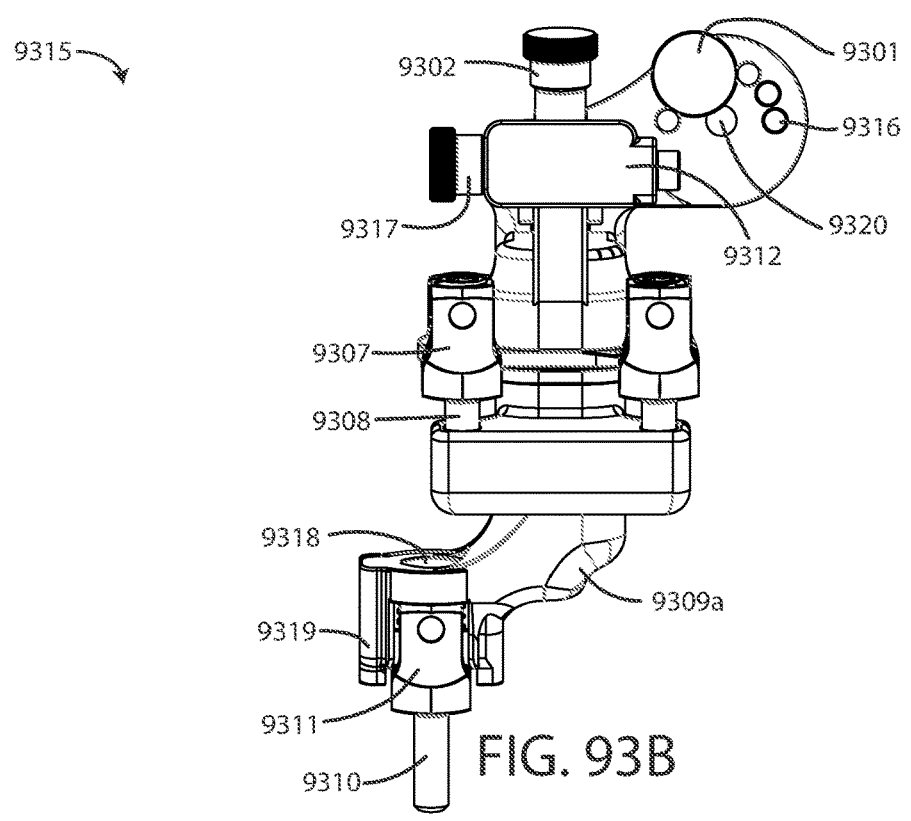

FIG. 93B illustrates a side view of an adjustable pedicle screw interface base, with one fixed side arm and one side arm with height and angle adjustments, of a flexibility assessment device as described previously in relation to FIG. 93A in accordance with some embodiments of the invention.

Figures 93C, 93D:
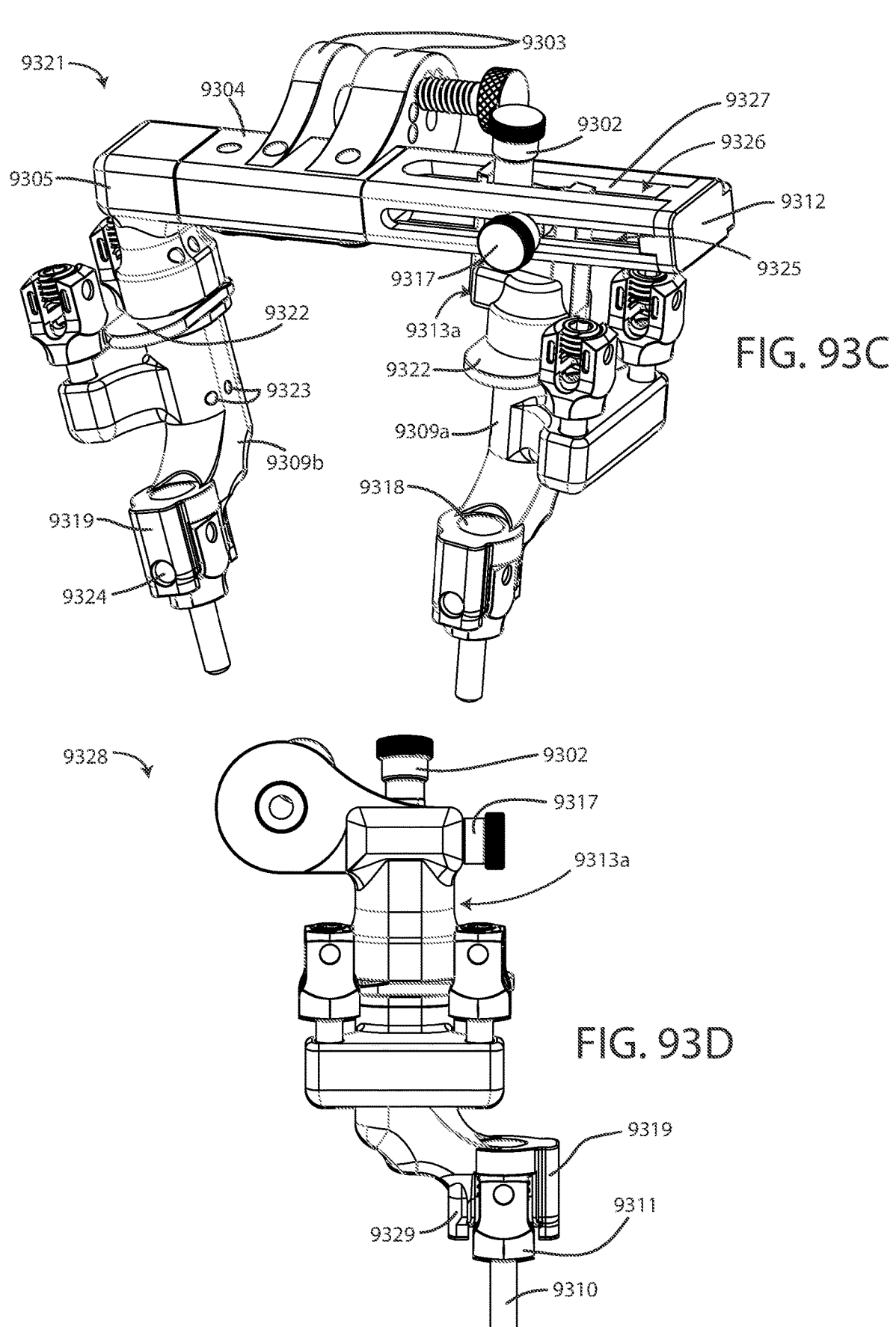

FIG. 93C illustrates a perspective view of an adjustable pedicle screw interface base, with one fixed side arm and one side arm with height and angle adjustments, of a flexibility assessment device as described previously in relation to FIGS. 93A-93B in accordance with some embodiments of the invention.

FIG. 93D illustrates a side view of an adjustable pedicle screw interface base, with one fixed side arm and one side arm with height and angle adjustments, of a flexibility assessment device as described previously in relation to FIGS. 93A-93C in accordance with some embodiments of the invention.

Figures 93E, 93F:
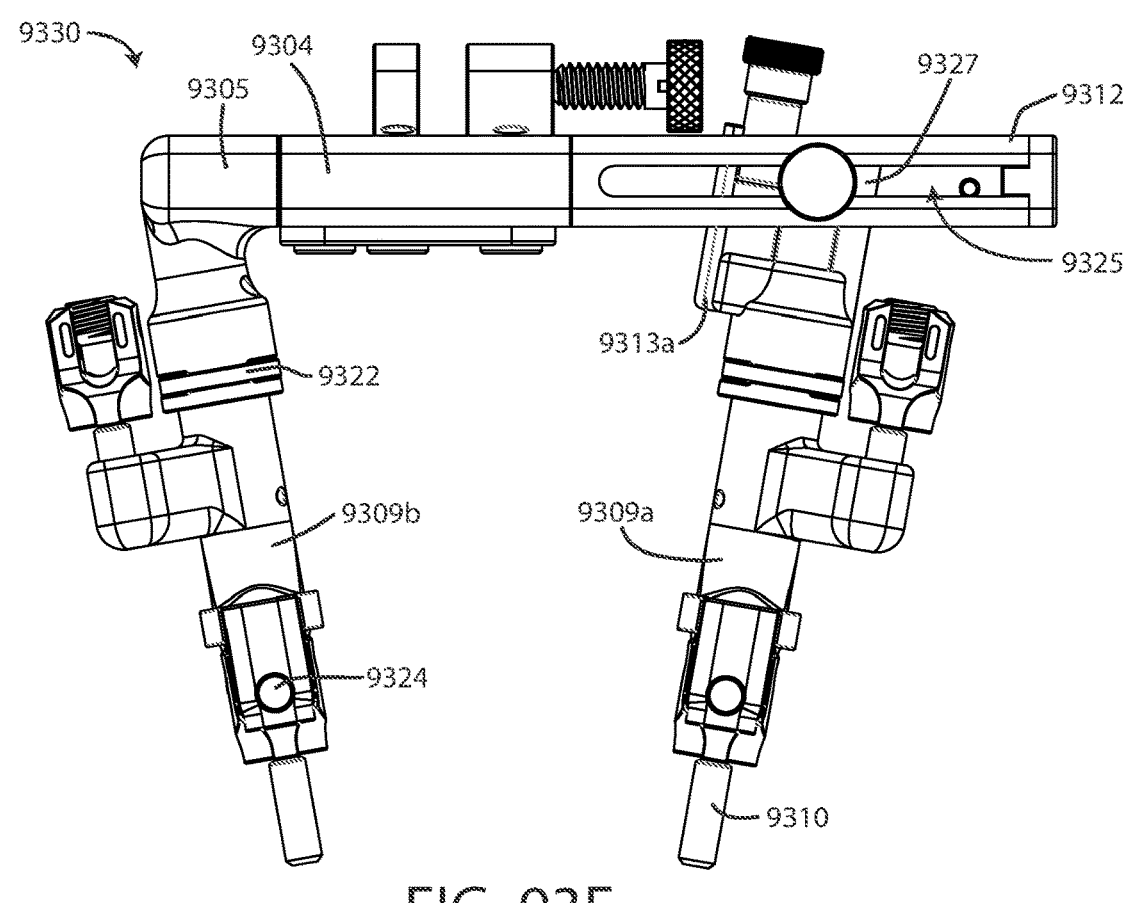

FIG. 93E illustrates a front view of an adjustable pedicle screw interface base, with one fixed side arm and one side arm with height and angle adjustments, of a flexibility assessment device as described previously in relation to FIGS. 93A-93D in accordance with some embodiments of the invention.

FIG. 93F illustrates a top view of an adjustable pedicle screw interface base, with one fixed side arm and one side arm with height and angle adjustments, of a flexibility assessment device as described previously in relation to FIGS. 93A-93E in accordance with some embodiments of the invention.

Figure 93G:
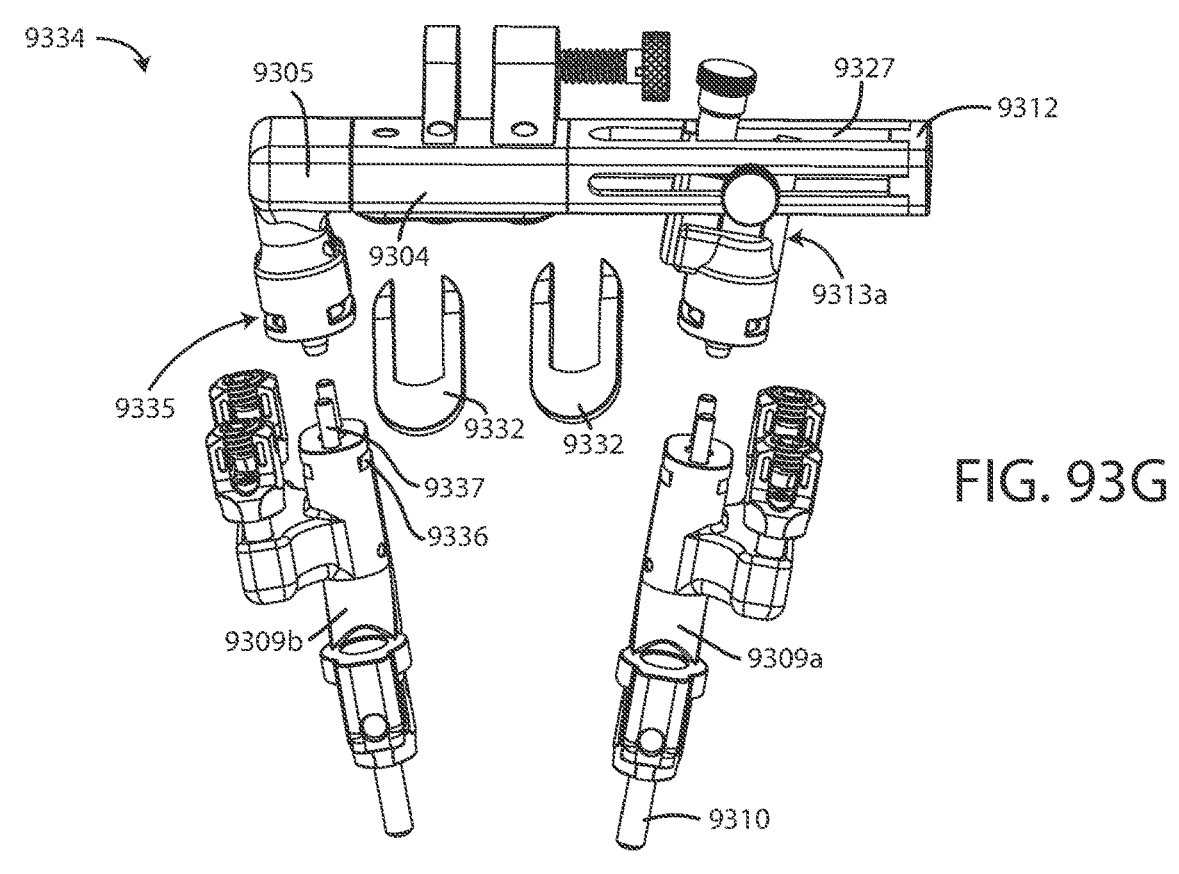

FIG. 93G illustrates an assembly view of an adjustable pedicle screw interface base, with one fixed side arm and one side arm with height and angle adjustments, of a flexibility assessment device as described previously in relation to FIGS. 93A-93F in accordance with some embodiments of the invention.

Figure 93H:
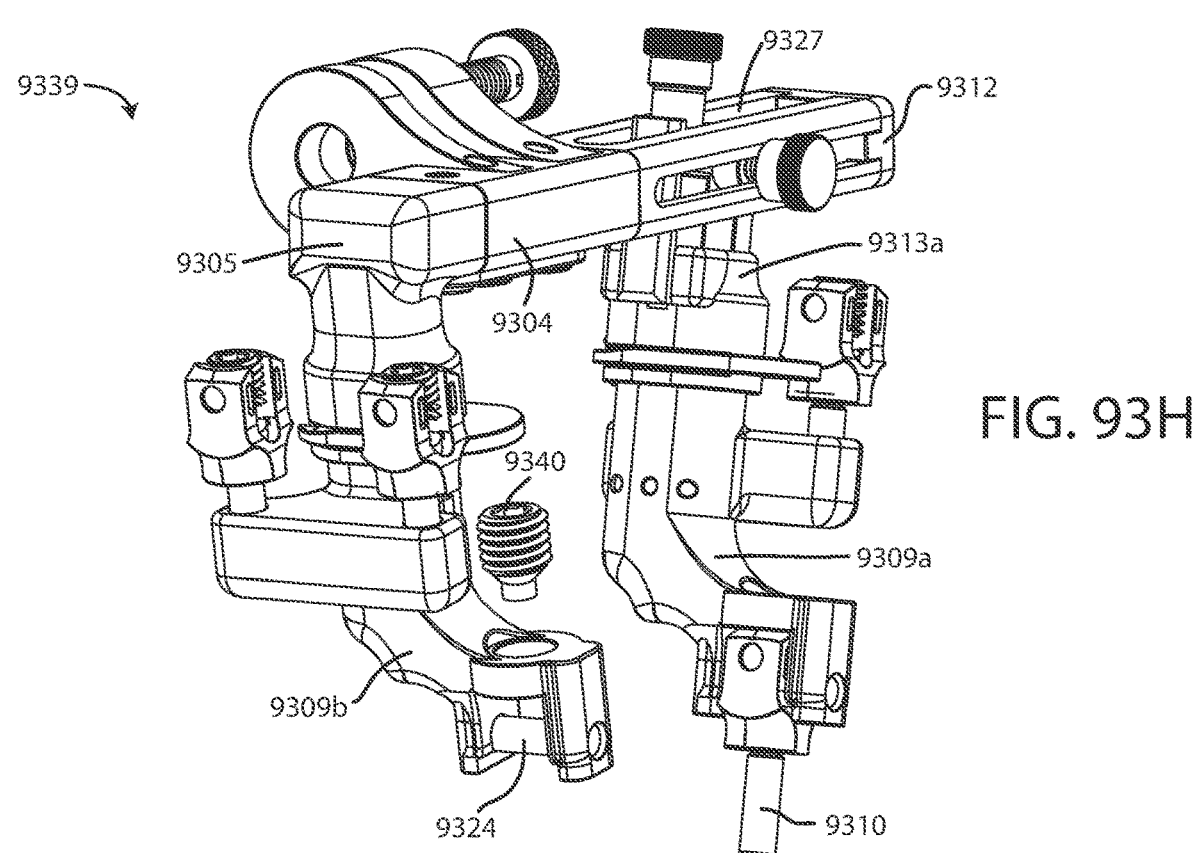

FIG. 93H illustrates a perspective view of an adjustable pedicle screw interface base, with one fixed side arm and one side arm with height and angle adjustments, of a flexibility assessment device as described previously in relation to FIGS. 93A-93G in accordance with some embodiments of the invention.

Figures 93I, 93J:
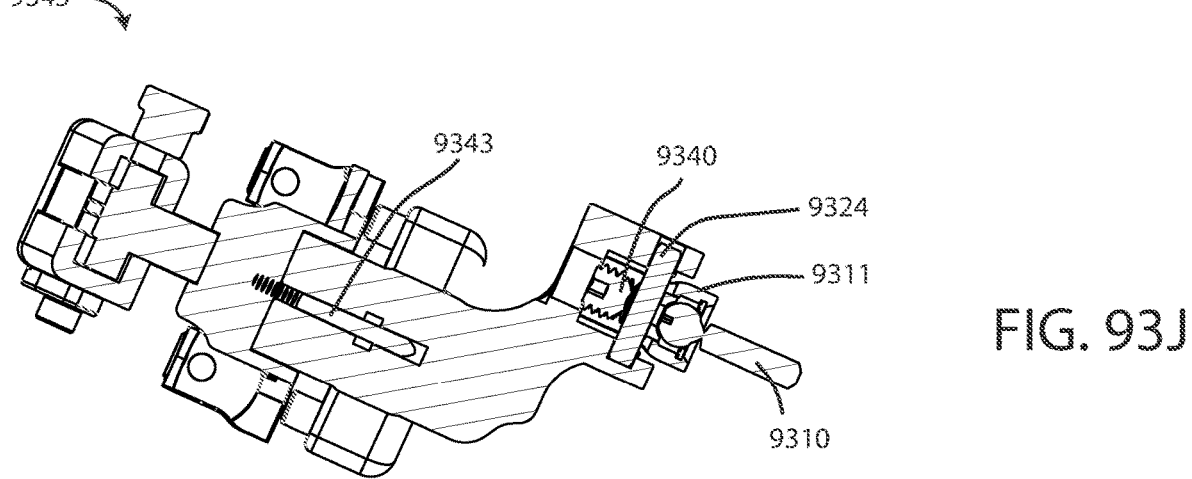

FIG. 93I illustrates a perspective assembly view of an adjustable pedicle screw interface base, with one fixed side arm and one side arm with height and angle adjustments, of a flexibility assessment device as described previously in relation to FIGS. 93A-93H in accordance with some embodiments of the invention.

FIG. 93J illustrates a cross-sectional view of the side arm of an adjustable pedicle screw interface base, with one fixed side arm and one side arm with height and angle adjustments, of a flexibility assessment device as described previously in relation to FIGS. 93A-93I in accordance with some embodiments of the invention.

Figure 94A:
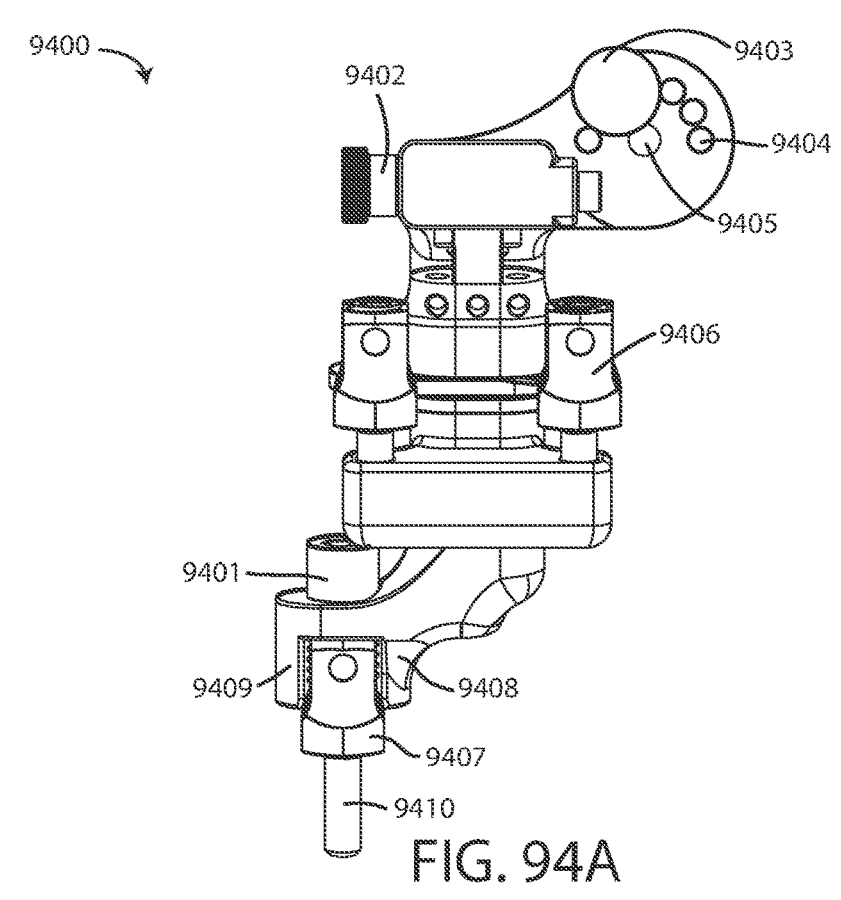

FIG. 94A illustrates a side view of an adjustable pedicle screw interface base, with one fixed side arm and one side arm with angle adjustment, of a flexibility assessment device in accordance with some embodiments of the invention.

Figure 94B:
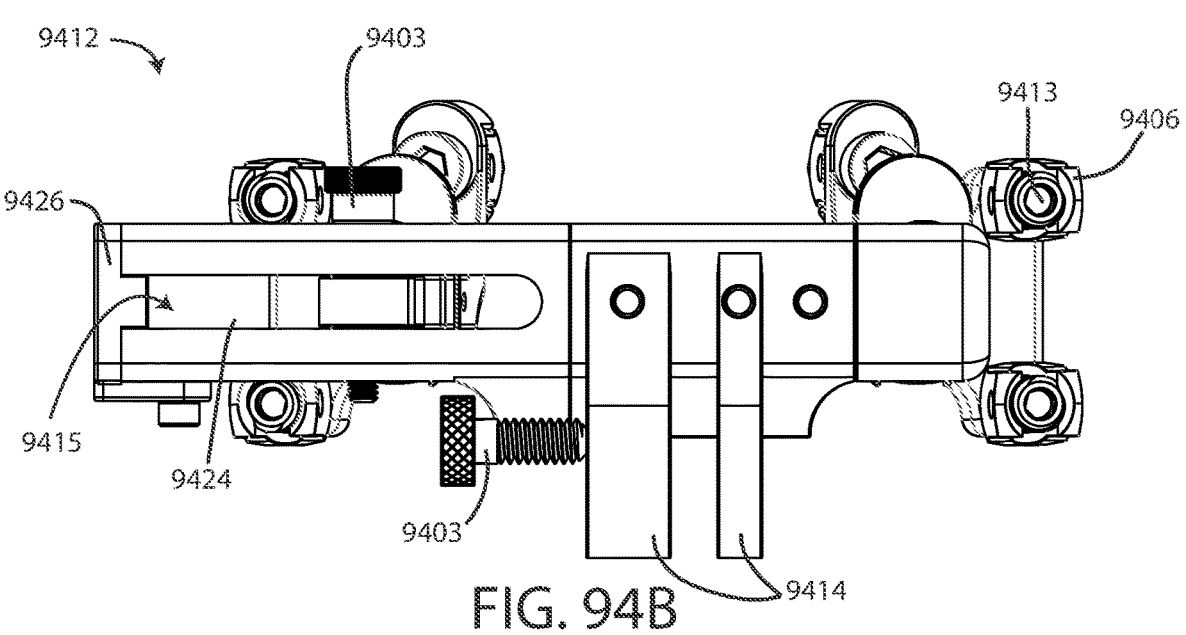

FIG. 94B illustrates a top view of an adjustable pedicle screw interface base, with one fixed side arm and one side arm with angle adjustment, of a flexibility assessment device as described previously in relation to FIG. 94A in accordance with some embodiments of the invention.

Figures 94C, 94D:
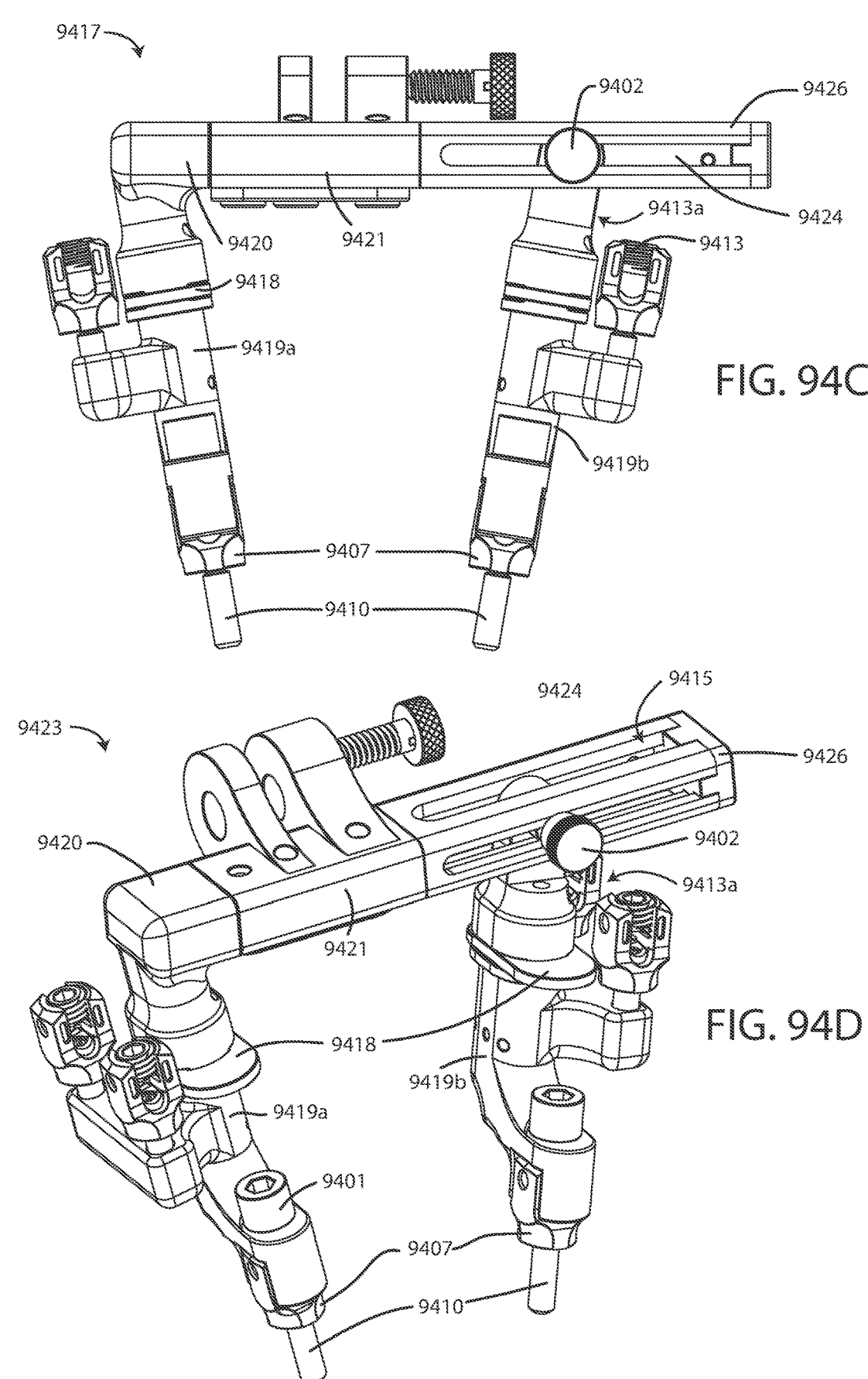

FIG. 94C illustrates a front view of an adjustable pedicle screw interface base, with one fixed side arm and one side arm with angle adjustment, of a flexibility assessment device as described previously in relation to FIGS. 94A-94B in accordance with some embodiments of the invention.

FIG. 94D illustrates a perspective view of an adjustable pedicle screw interface base, with one fixed side arm and one side arm with angle adjustment, of a flexibility assessment device as described previously in relation to FIGS. 94A-94C in accordance with some embodiments of the invention.

Figure 94E:
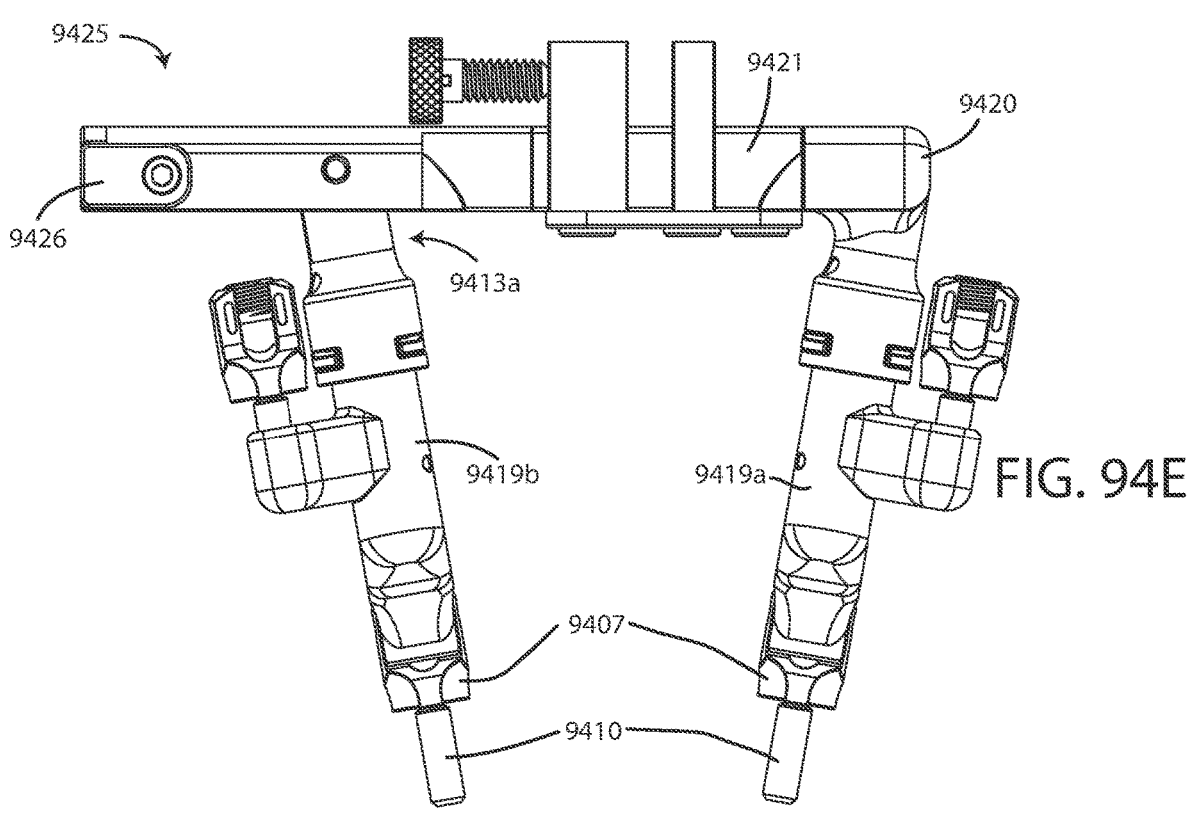

FIG. 94E illustrates a rear view of an adjustable pedicle screw interface base, with one fixed side arm and one side arm with angle adjustment, of a flexibility assessment device as described previously in relation to FIGS. 94A-94D in accordance with some embodiments of the invention.

Figure 94F:
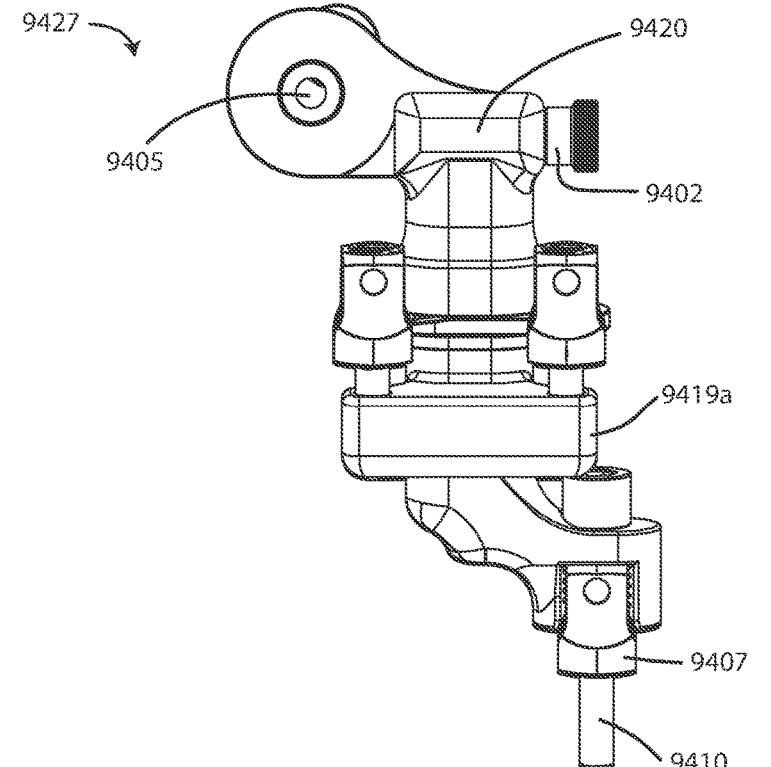

FIG. 94F illustrates a side view of an adjustable pedicle screw interface base, with one fixed side arm and one side arm with angle adjustment, of a flexibility assessment device as described previously in relation to FIGS. 94A-94E in accordance with some embodiments of the invention.

Figures 94G, 94H:
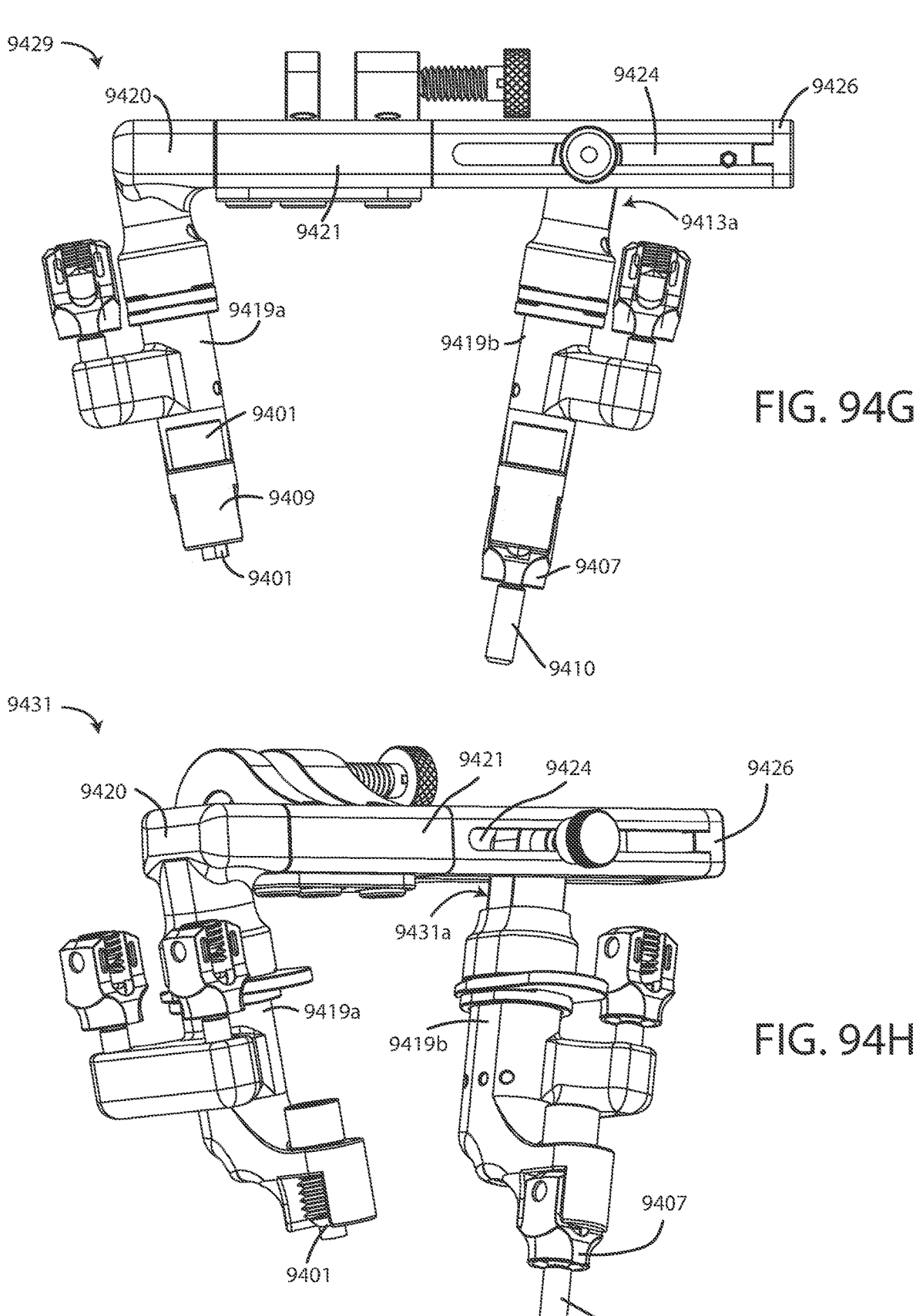

FIG. 94G illustrates a front view of an adjustable pedicle screw interface base, with one fixed side arm without an attached pedicle screw and one side arm with angle adjustment that is attached to a pedicle screw, of a flexibility assessment device as described previously in relation to FIGS. 94A-94F in accordance with some embodiments of the invention.

FIG. 94H illustrates a perspective view of an adjustable pedicle screw interface base, with one fixed side arm without an attached pedicle screw and one side arm with angle adjustment that is attached to a pedicle screw, of a flexibility assessment device as described previously in relation to FIGS. 94A-94G in accordance with some embodiments of the invention.

Figures 95A, 95B:
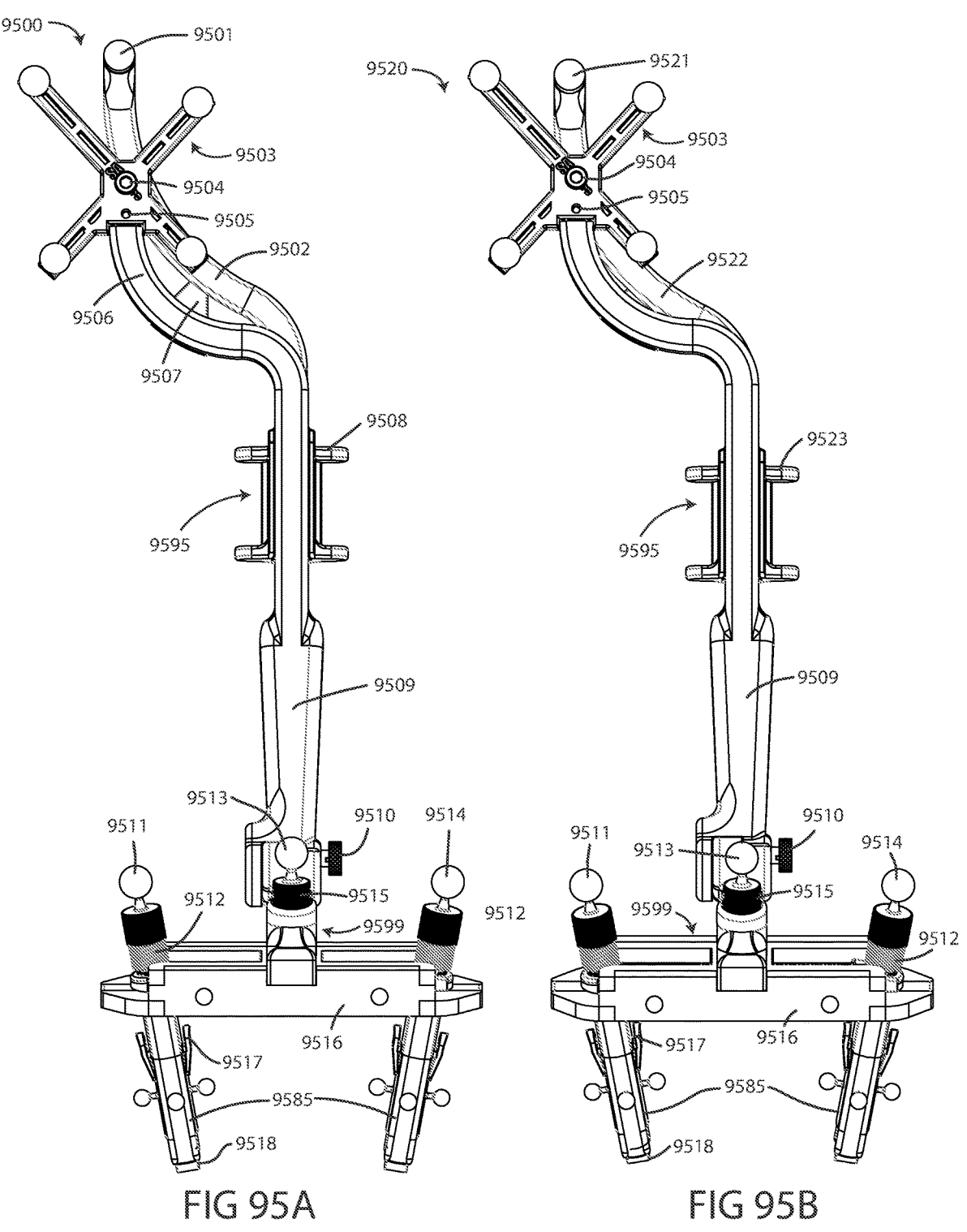

FIGS. 95A-95B illustrate front views of a front-facing flexibility assessment device in a triggered and untriggered state in accordance with some embodiments of the invention.

Figures 95C, 95D:
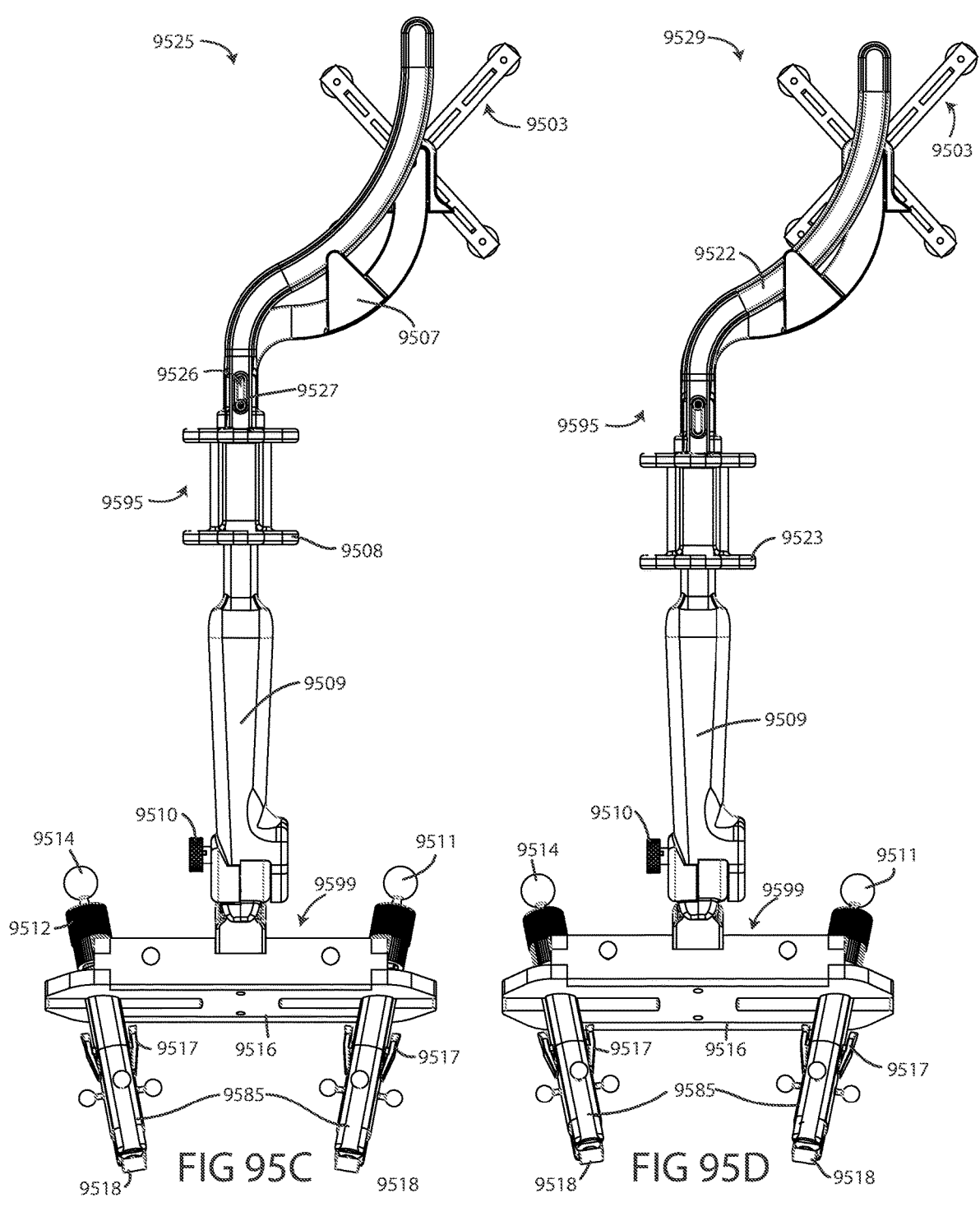

FIGS. 95C-95D illustrate rear views of a front-facing flexibility assessment device in a triggered and untriggered state as described previously in relation to FIGS. 95A-95B in accordance with some embodiments of the invention.

Figures 95E, 95F:
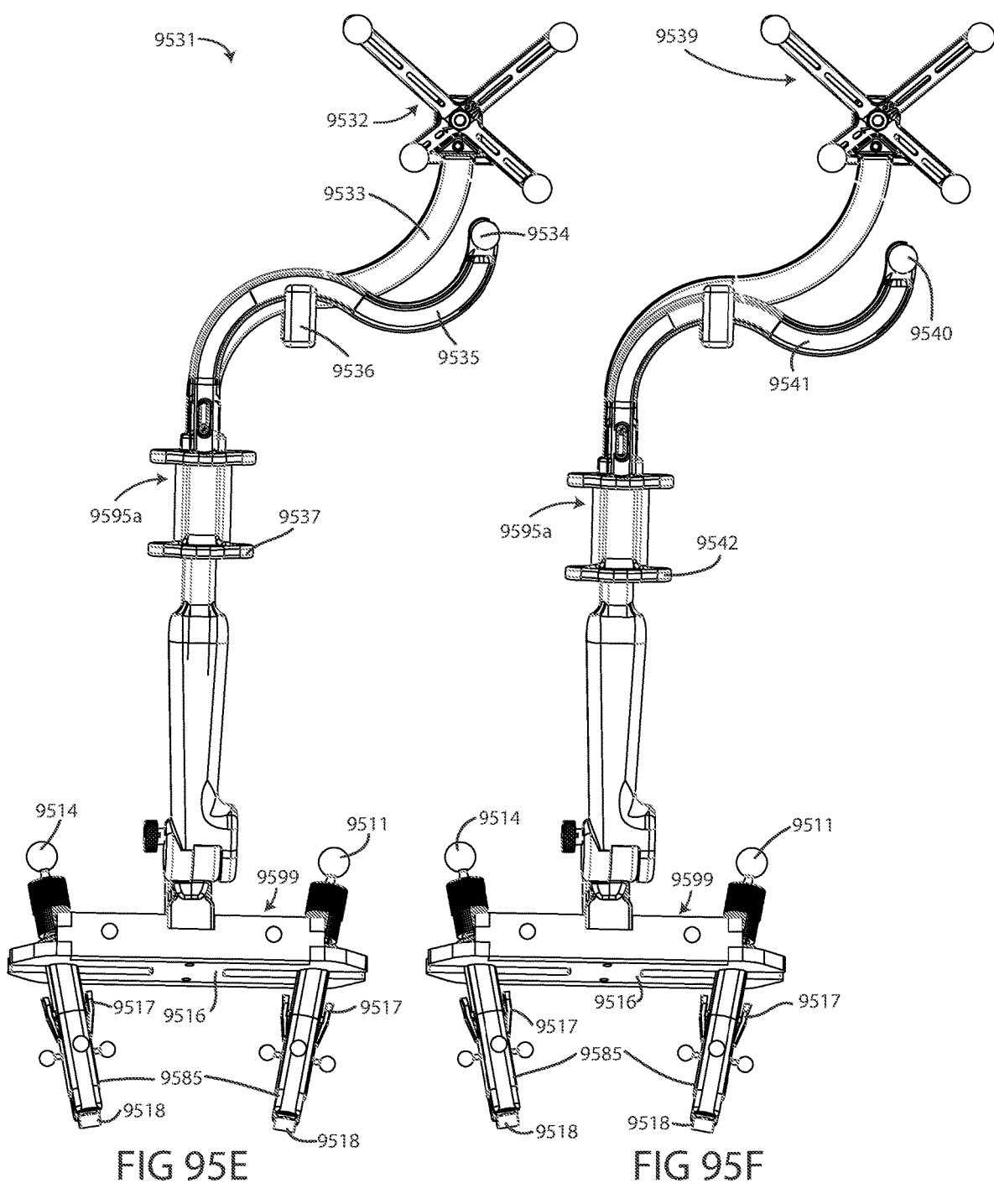

FIGS. 95E-95F illustrate front views of a back-facing flexibility assessment device in a triggered and untriggered state as described previously in relation to FIGS. 95A-95D in accordance with some embodiments of the invention.

Figure 95G:
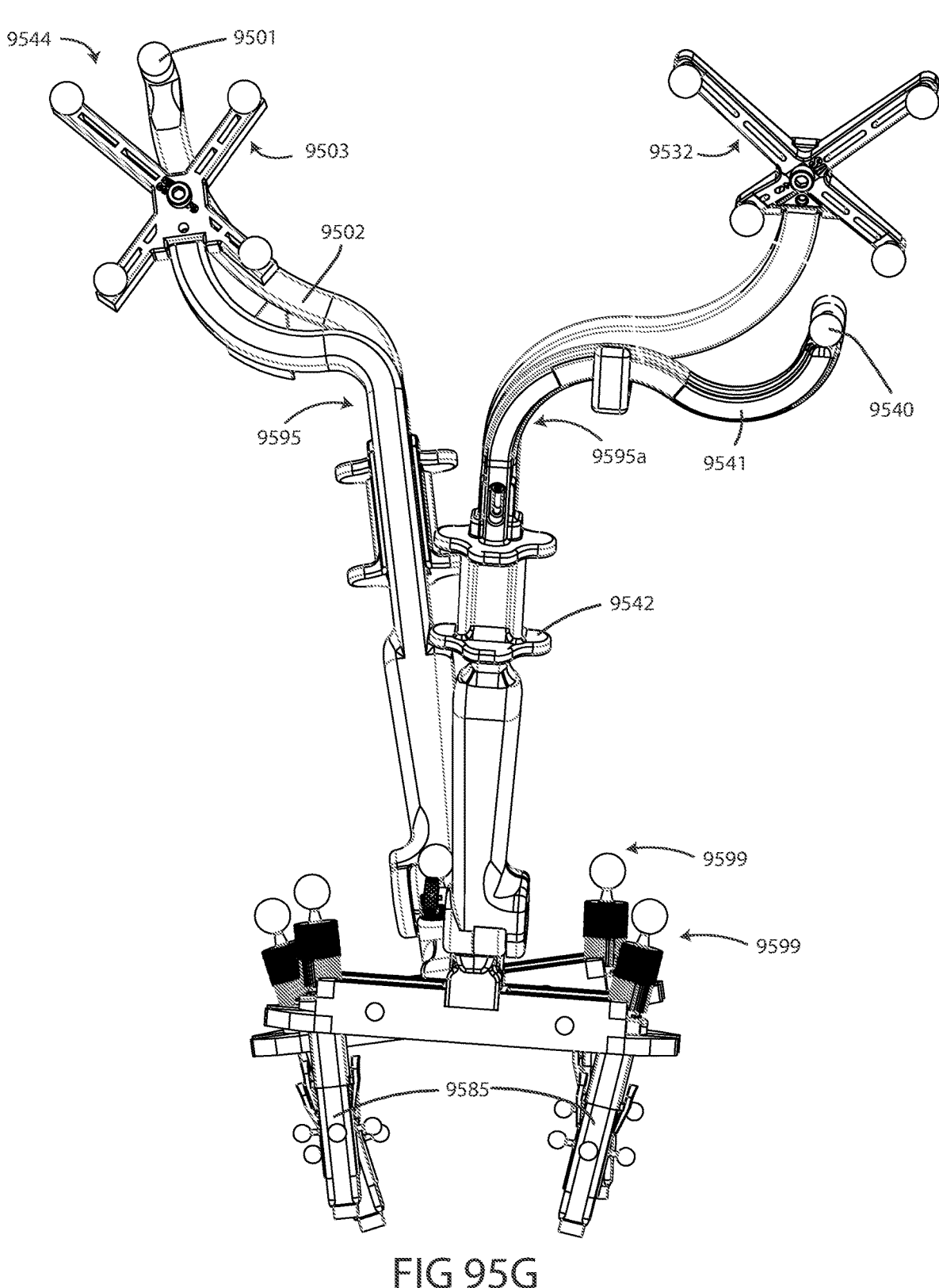

FIG. 95G illustrates a front view of both back-facing and front-facing flexibility assessment devices as described previously in relation to FIGS. 95A-95F in accordance with some embodiments of the invention.

Figure 95H:
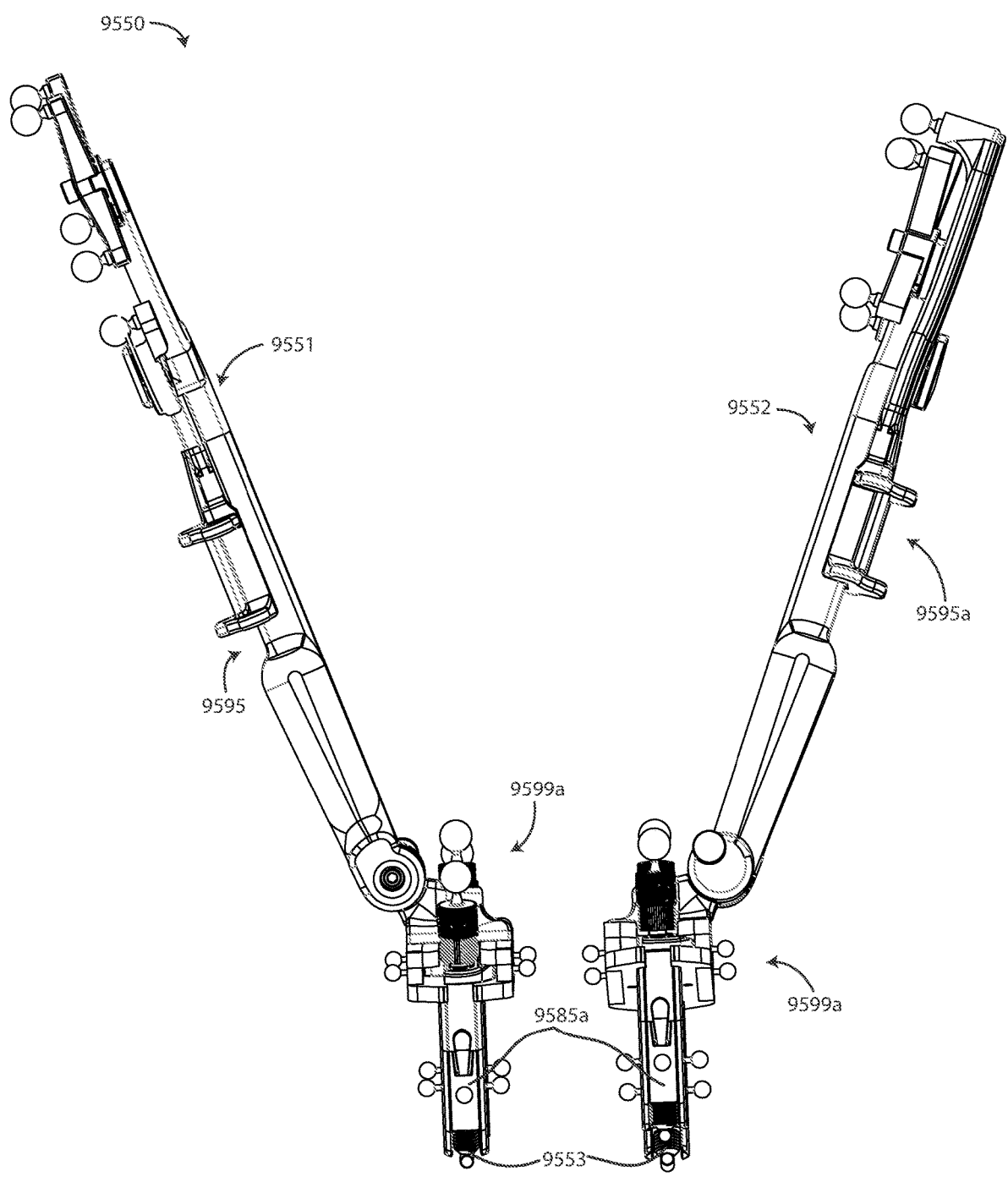

FIG. 95H illustrates a side view of both back-facing and front-facing flexibility assessment devices as described previously in relation to FIGS. 95A-95G in accordance with some embodiments of the invention.

Figure 95I:
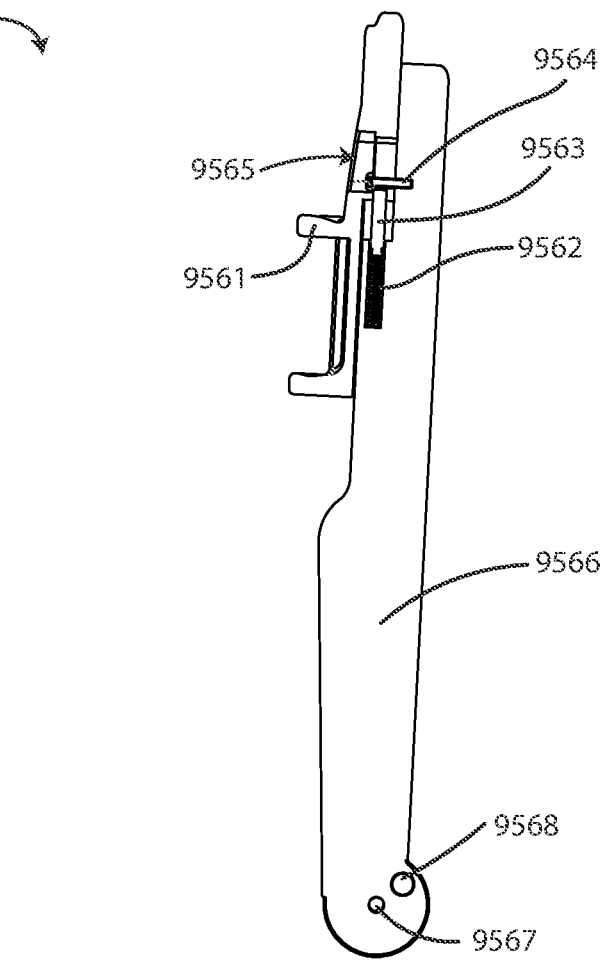

FIG. 95I illustrates a cross-sectional view of a triggering mechanism of a handle of a flexibility assessment device as described previously in relation to FIGS. 95A-95H in accordance with some embodiments of the invention.

Figure 96A:
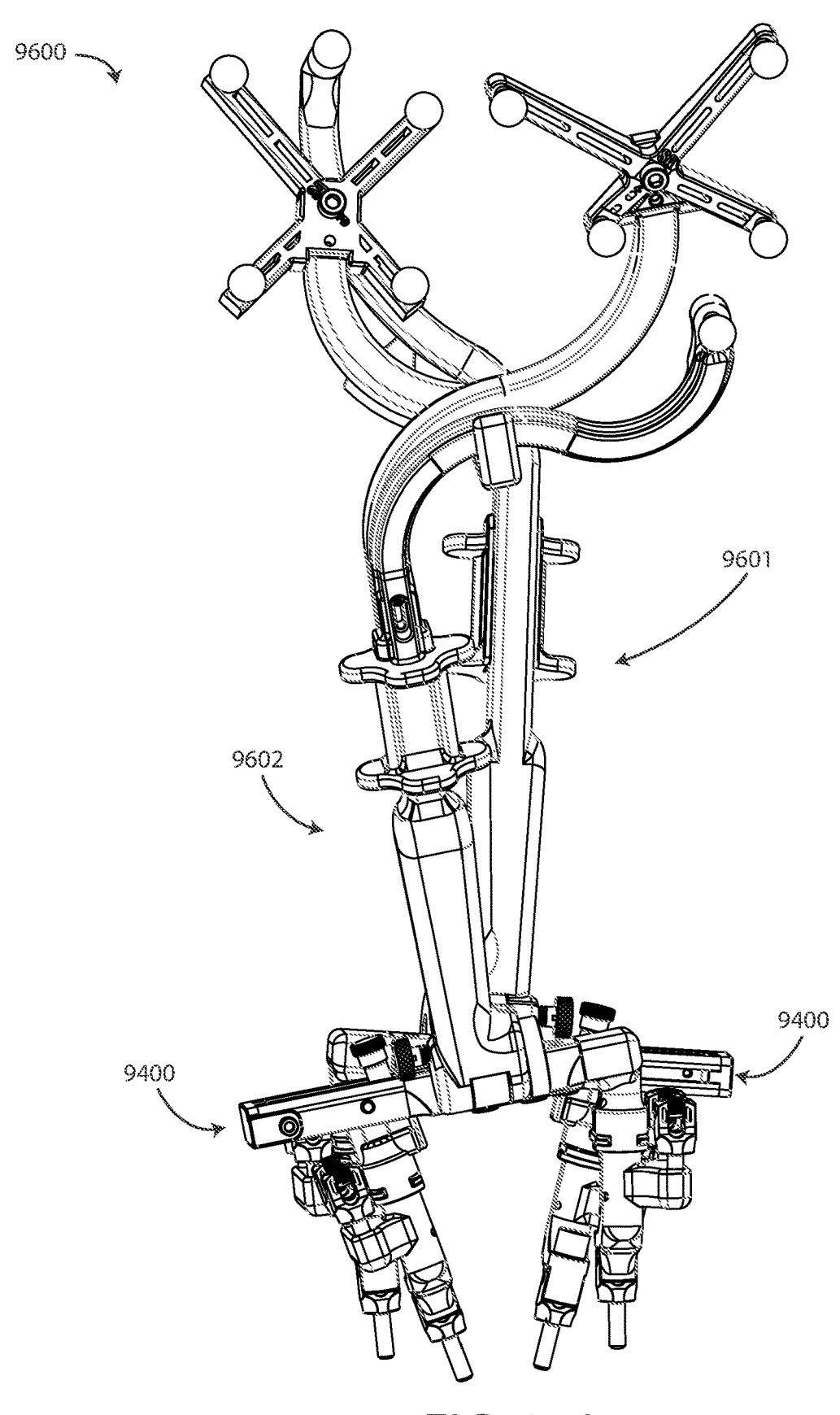

FIG. 96A illustrates a front view of both back-facing and front-facing flexibility assessment devices attached to an adjustable pedicle screw interface with accessory pedicle screw mounts in accordance with some embodiments of the invention.

Figure 96B:
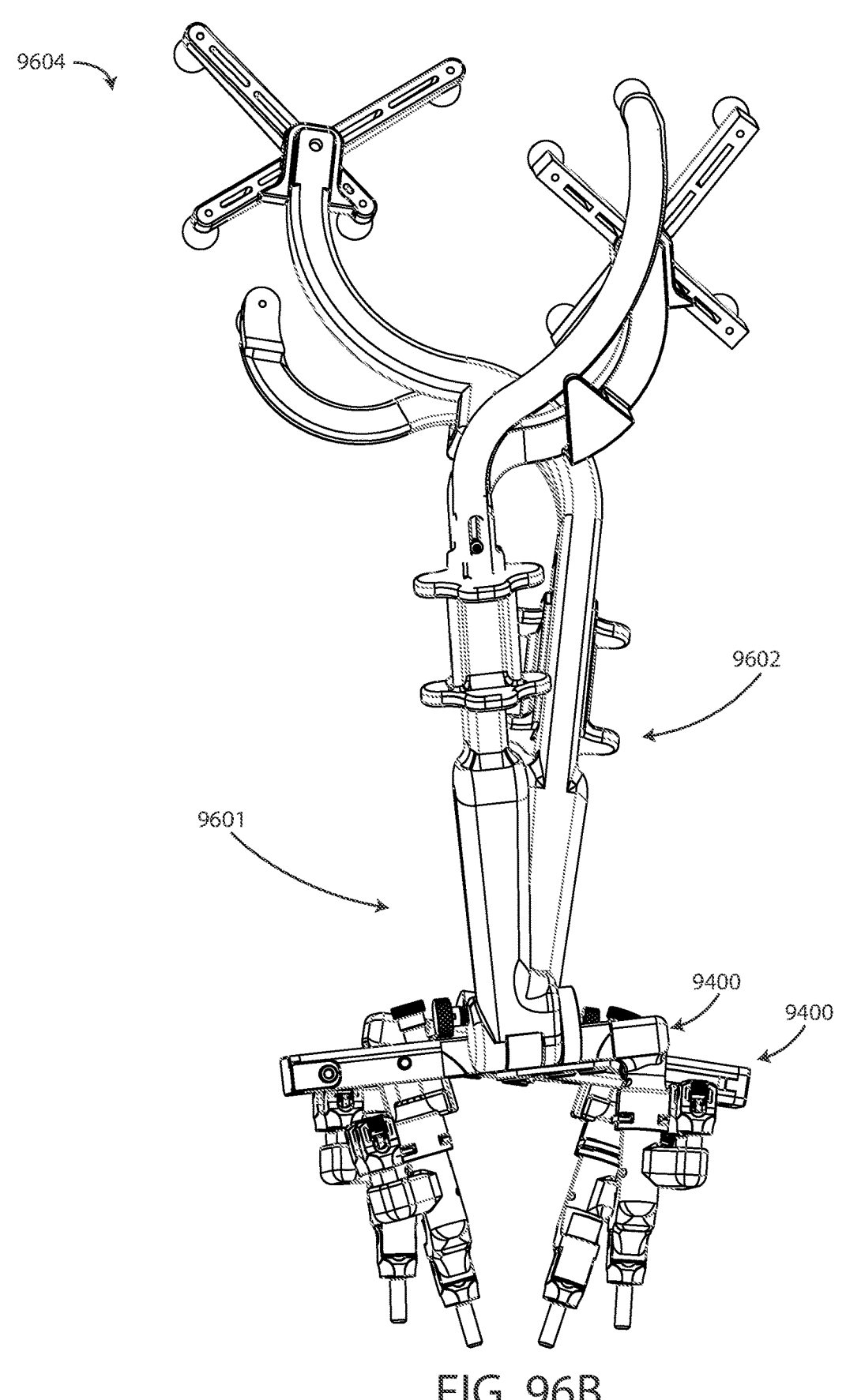

FIG. 96B illustrates a rear view of both back-facing and front-facing flexibility assessment devices attached to an adjustable pedicle screw interface with accessory pedicle screw mounts as described previously in relation to FIG. 96A in accordance with some embodiments of the invention.

Figure 96C:
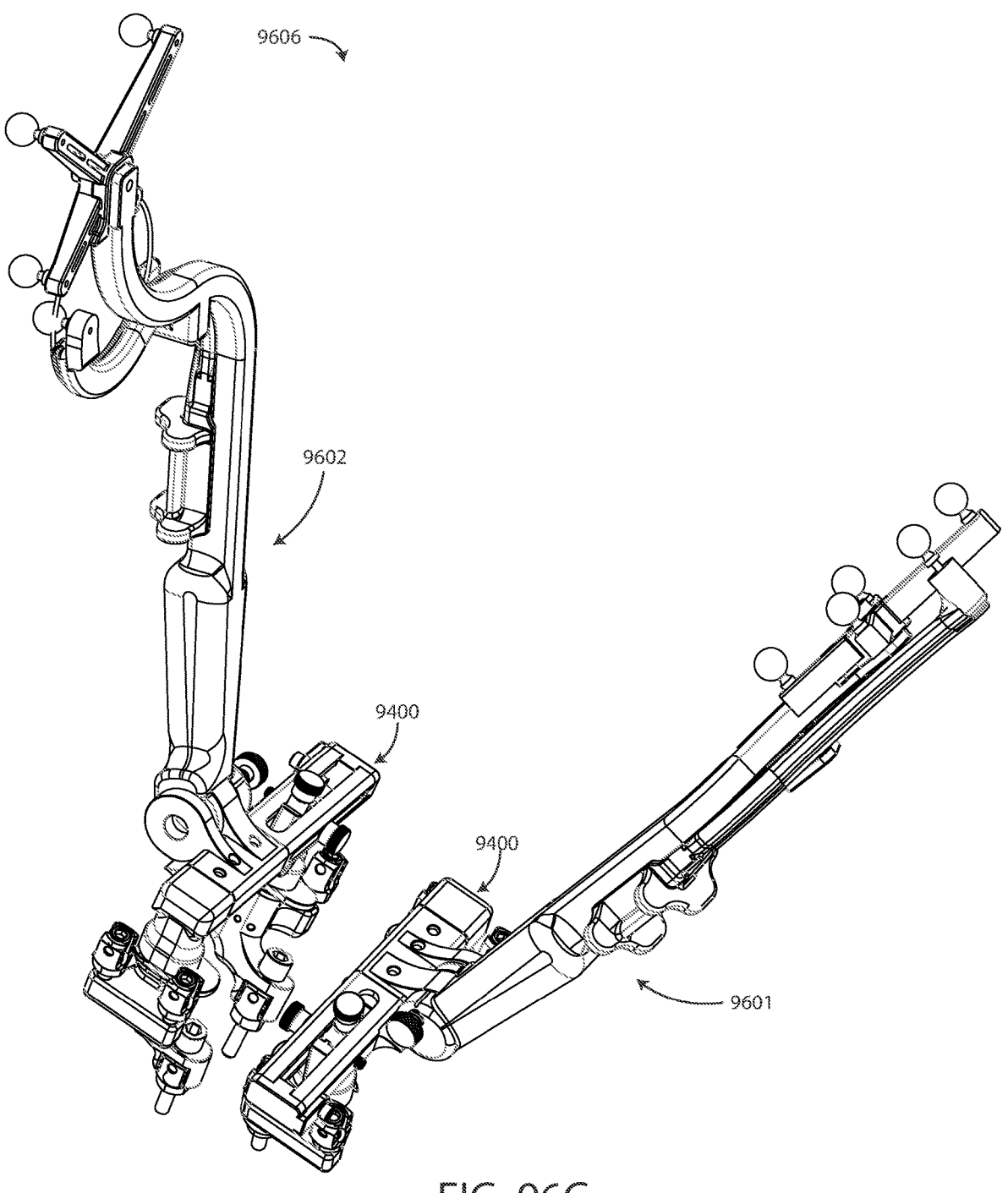

FIG. 96C illustrates a perspective view of both back-facing and front-facing flexibility assessment devices attached to an adjustable pedicle screw interface with accessory pedicle screw mounts as described previously in relation to FIGS. 96A-96B in accordance with some embodiments of the invention.

Figure 96D:
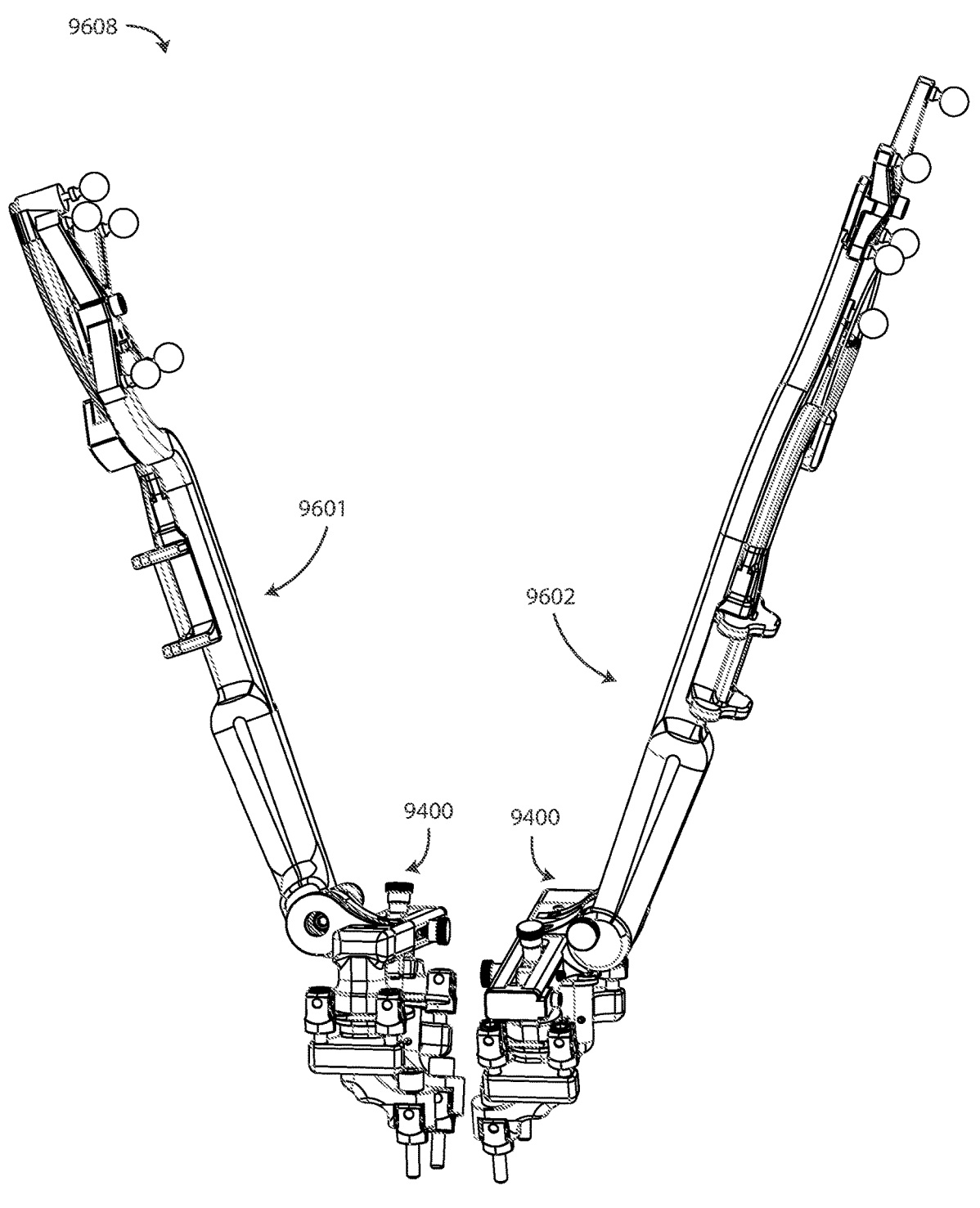

FIG. 96D illustrates a side view of both back-facing and front-facing flexibility assessment devices attached to an adjustable pedicle screw interface with accessory pedicle screw mounts as described previously in relation to FIGS. 96A-96C in accordance with some embodiments of the invention.

Figure 96E:
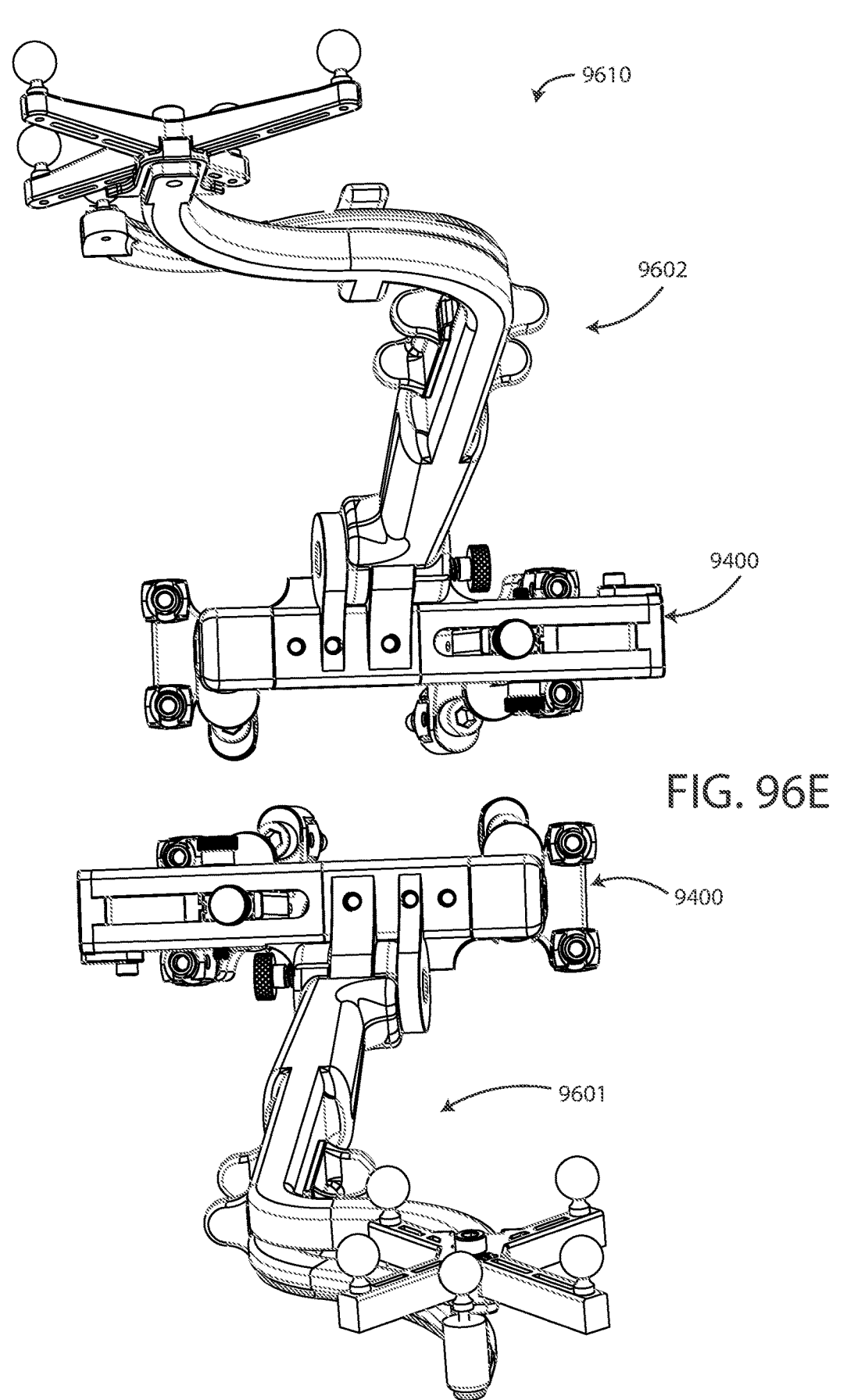

FIG. 96E illustrates a top view of both back-facing and front-facing flexibility assessment devices attached to an adjustable pedicle screw interface with accessory pedicle screw mounts as described previously in relation to FIGS. 96A-96D in accordance with some embodiments of the invention.

Figures 96F, 96G, 96H:
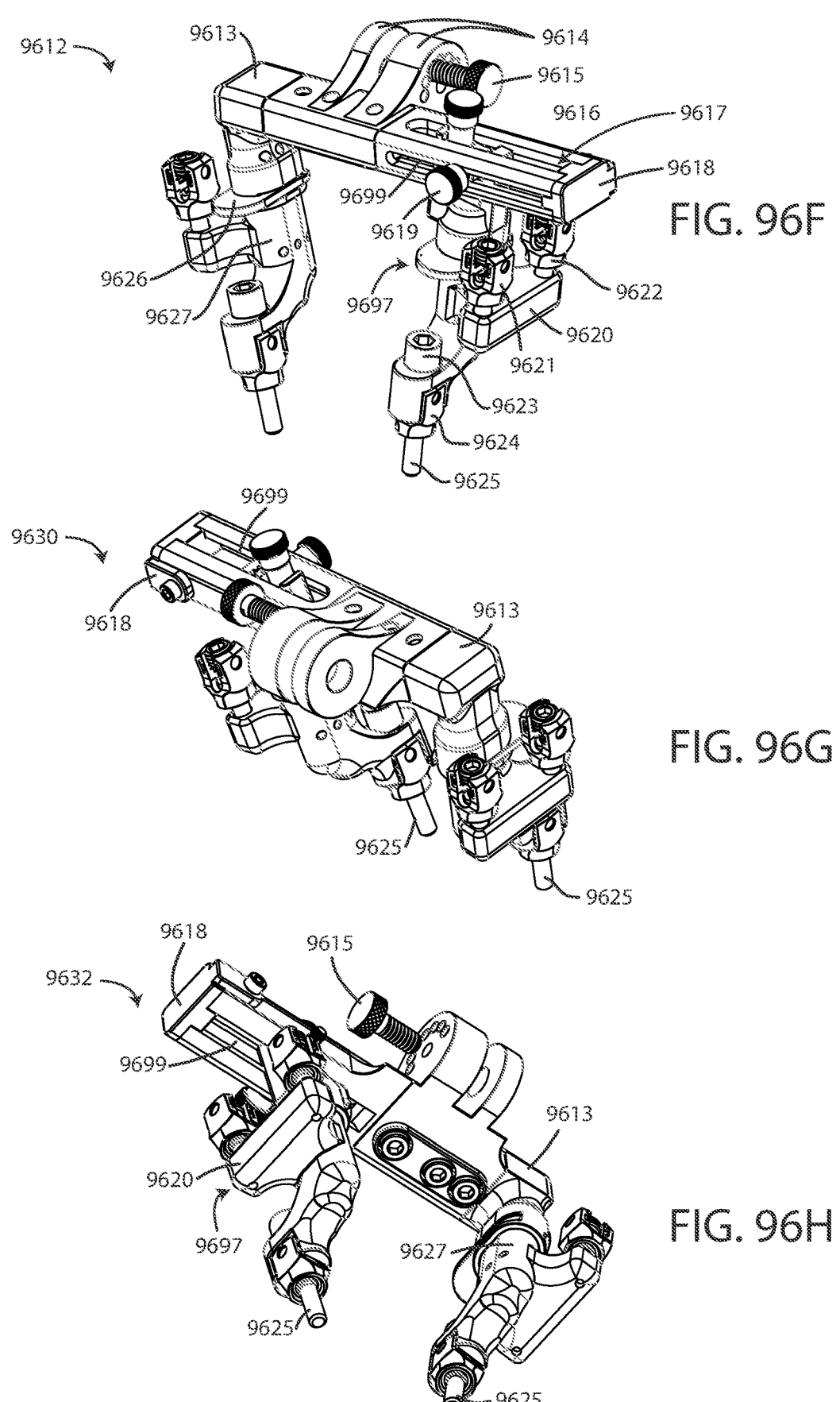

FIGS. 96F-96H illustrate perspective views of an adjustable pedicle screw interface with embedded screw-mating fasteners and accessory pedicle screw mounts as described previously in relation to FIGS. 96A-96E in accordance with some embodiments of the invention.

Figure 96I:
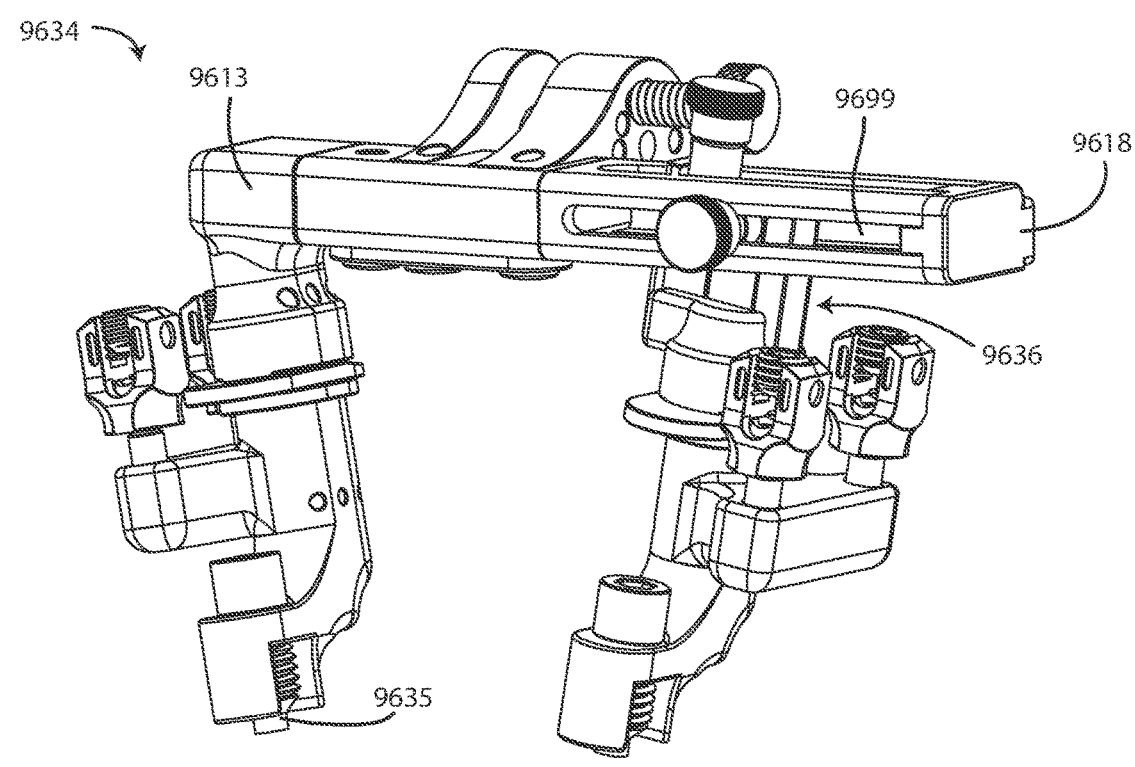
Figure 96J:
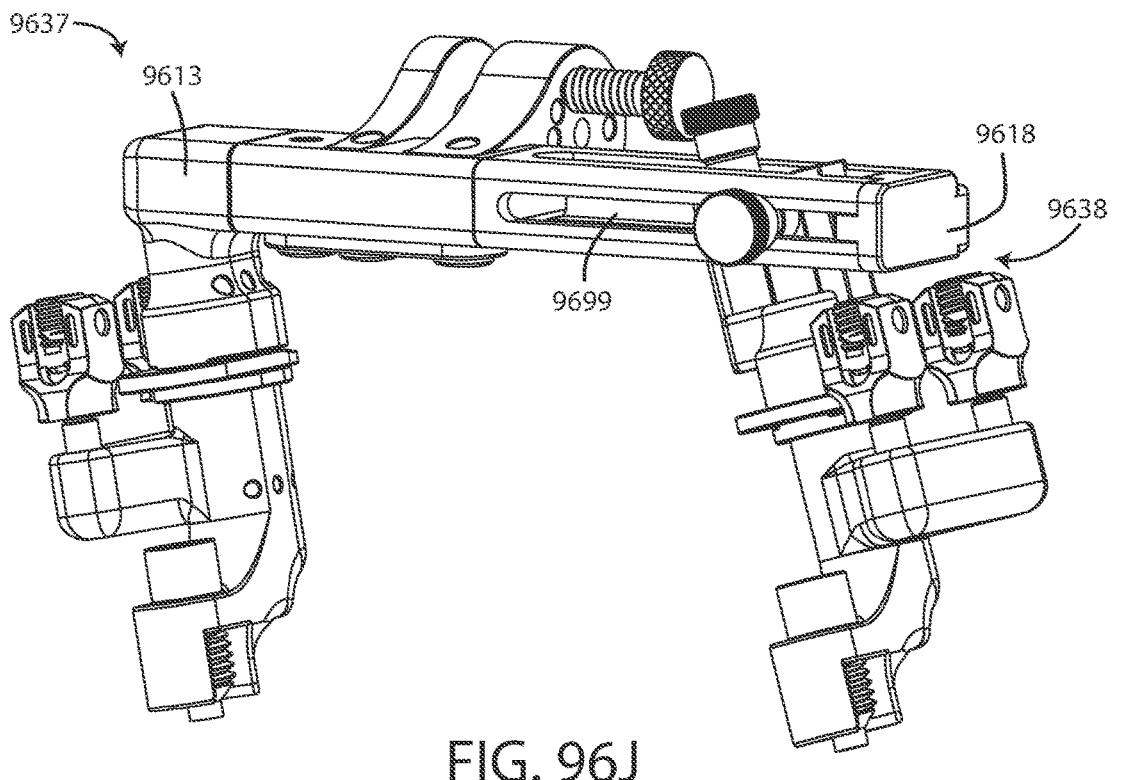

FIGS. 96I-96J illustrate perspective views of an adjustable pedicle screw interface with embedded screw-mating fasteners and accessory pedicle screw mounts, with the pedicle screw interfaces of the side arms not engaged with a pedicle screw, as described previously in relation to FIGS. 96A-96H in accordance with some embodiments of the invention.

Figure 96K:
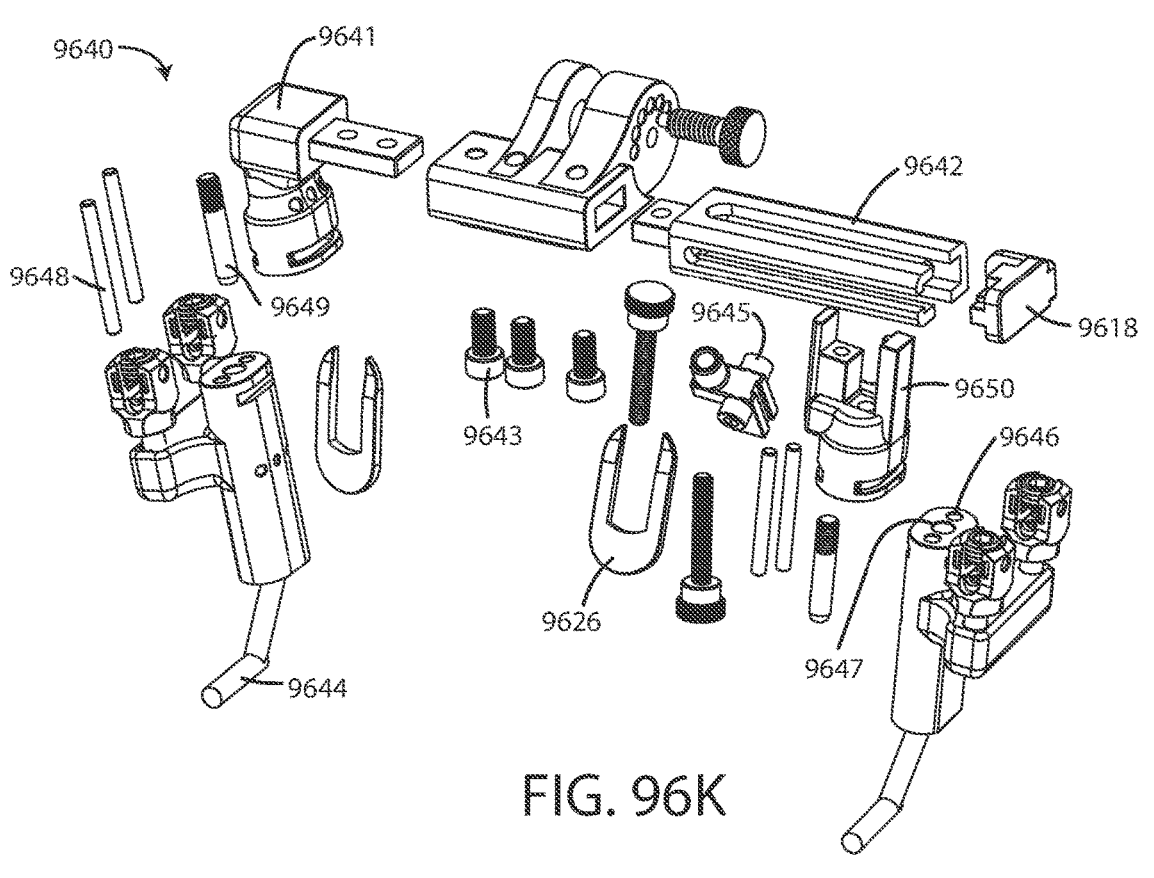
Figure 96L:
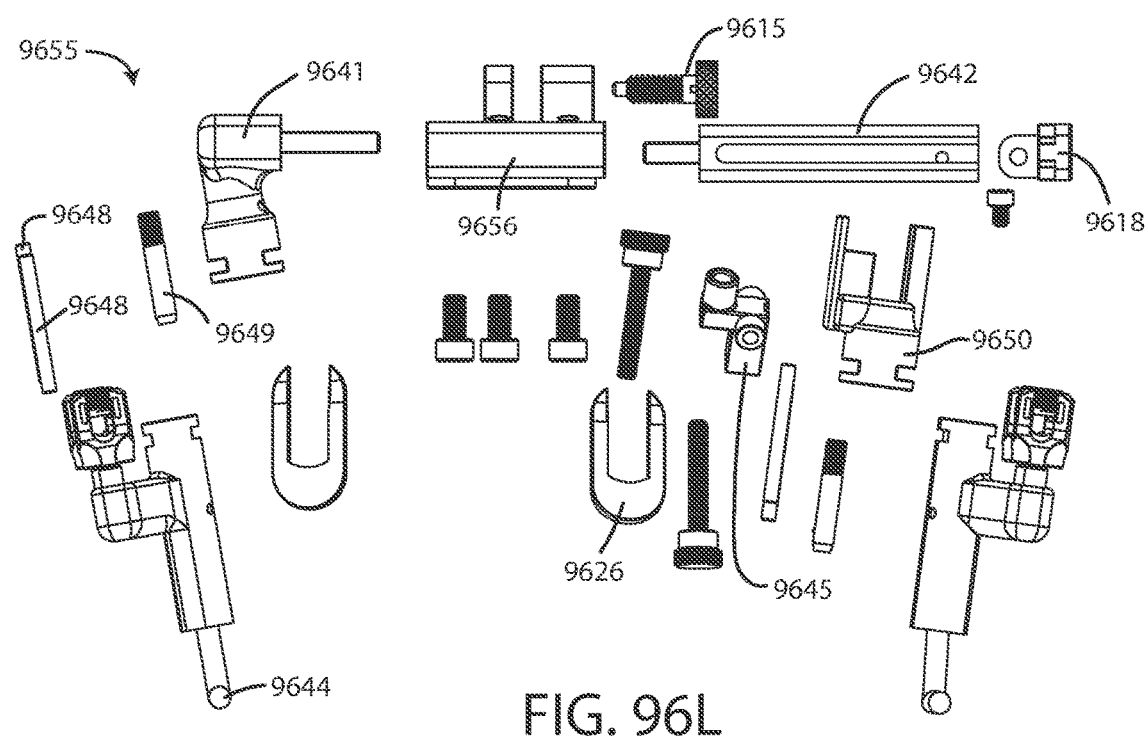

FIGS. 96K-96L illustrate exploded assembly views of an adjustable pedicle screw interface with embedded screw-mating fasteners and accessory pedicle screw mounts, with the pedicle screw interfaces of the distal end of the side arms containing a rod extension for mating with pedicle screw tulip heads, as described previously in relation to FIGS. 96A-96J in accordance with some embodiments of the invention.

Figure 96M:
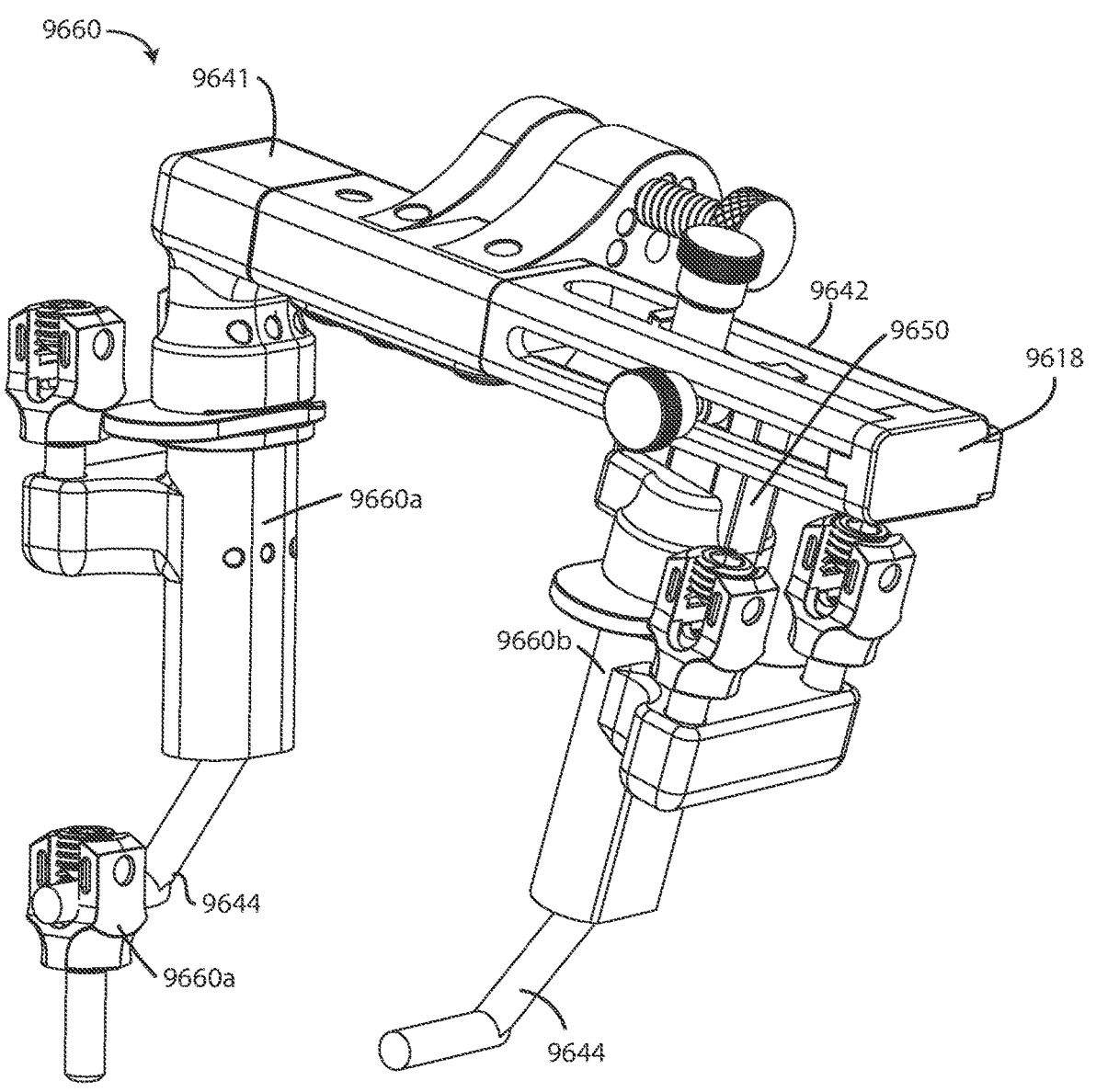

FIG. 96M illustrates a perspective view of an adjustable pedicle screw interface with embedded screw-mating fasteners and accessory pedicle screw mounts, with the pedicle screw interfaces of the distal end of the side arms containing a rod extension for mating with pedicle screw tulip heads, as described previously in relation to FIGS. 96A-96L in accordance with some embodiments of the invention.

Figure 96N:
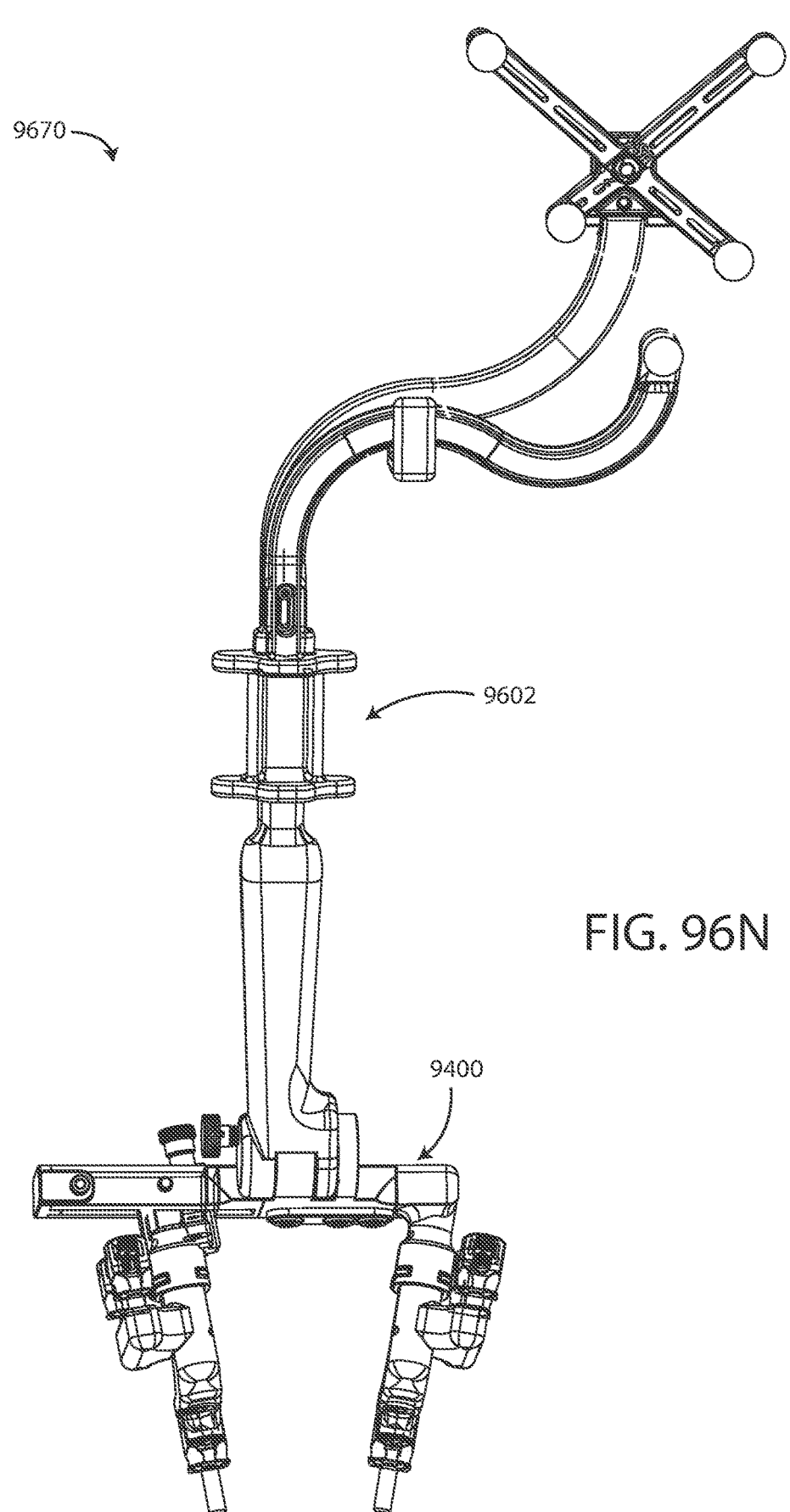

FIG. 96N illustrates a rear view of a back-facing flexibility assessment device in a triggered state with an adjustable pedicle screw interface as described previously in relation to FIGS. 96A-96M in accordance with some embodiments of the invention.

Figure 96O:
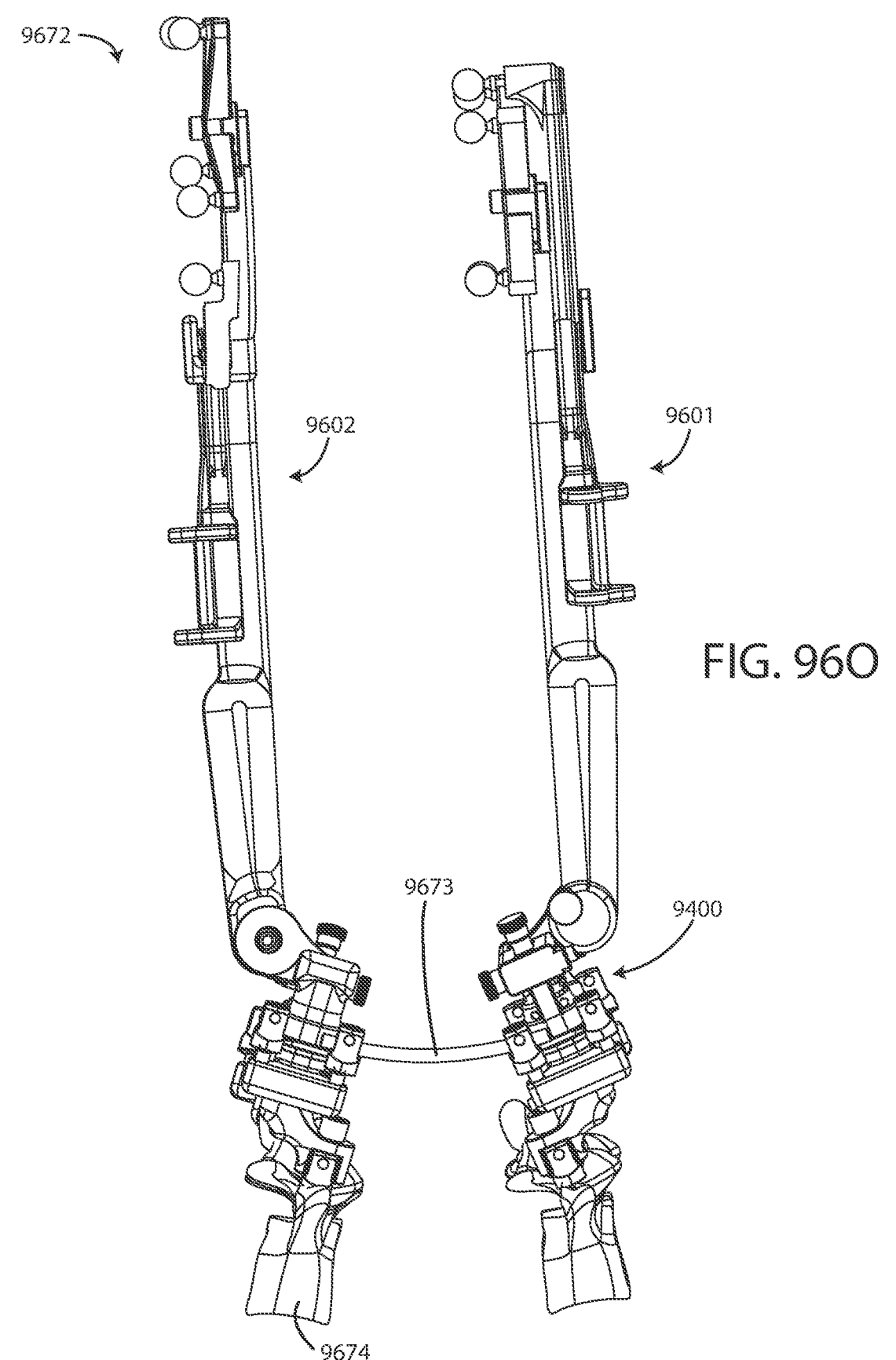

FIG. 96O illustrates a side view of both back-facing and front-facing flexibility assessment devices with adjustable pedicle screw interfaces that are substantially rigidly fixed in their relative orientations to one another while the devices are substantially rigidly engaged with vertebrae, as described previously in relation to FIGS. 96A-96N in accordance with some embodiments of the invention.

Figure 96P:
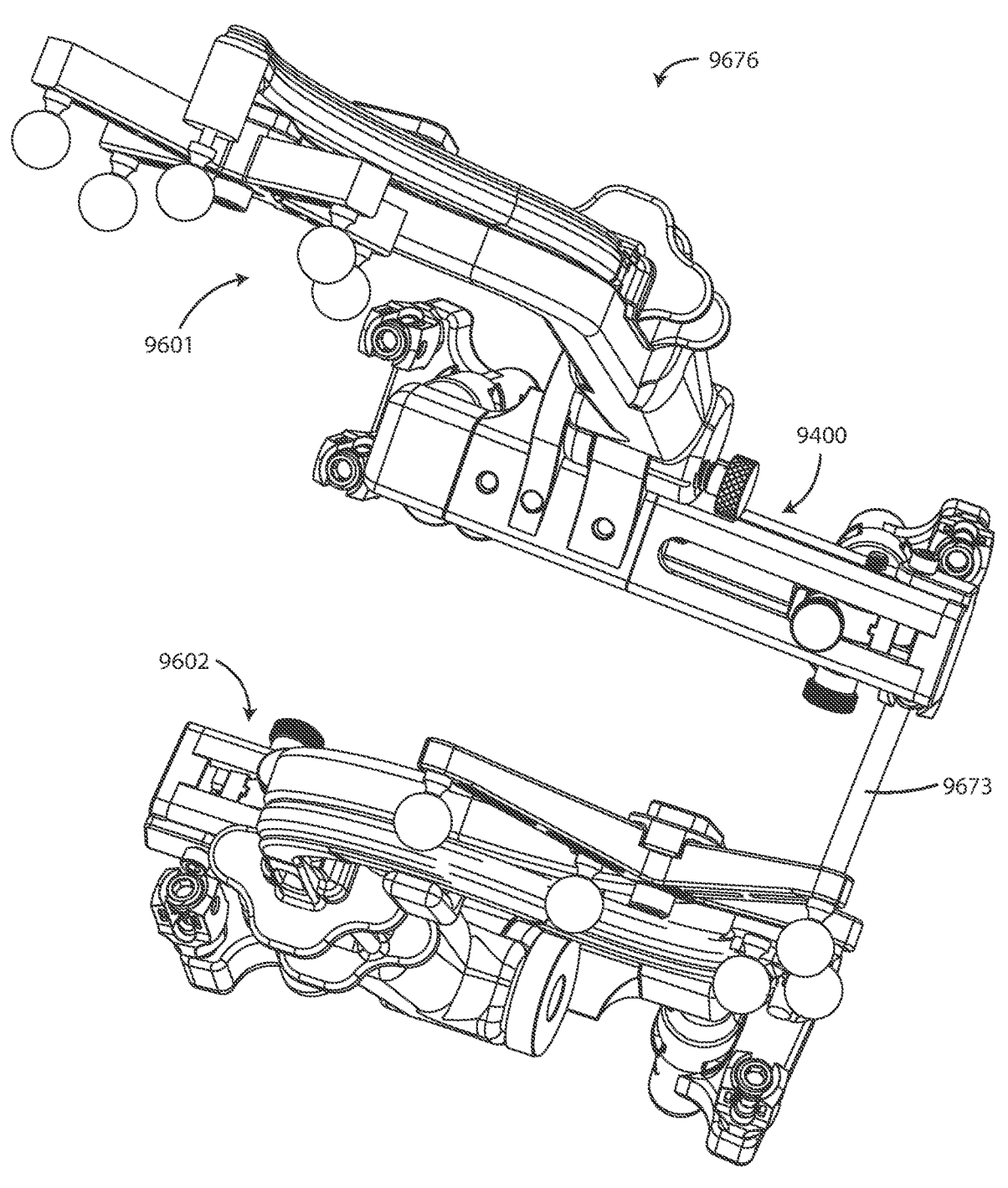

FIG. 96P illustrates a perspective view of both back-facing and front-facing flexibility assessment devices with adjustable pedicle screw interfaces that are substantially rigidly fixed in their relative orientations to one another, as described previously in relation to FIGS. 96A-96O in accordance with some embodiments of the invention.

Figure 96Q:
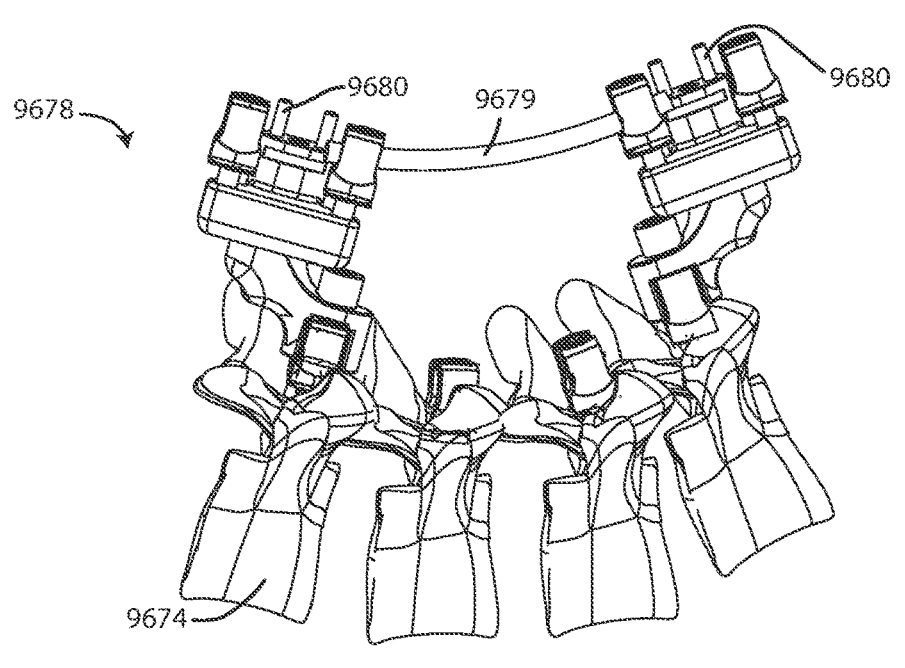

FIG. 96Q illustrates a side view of the bottom half side arm components of the flexibility assessment devices that are substantially rigidly linked to one another and engaged with the vertebrae, as described previously in relation to FIGS. 96A-96P in accordance with some embodiments of the invention.

Figure 96R:
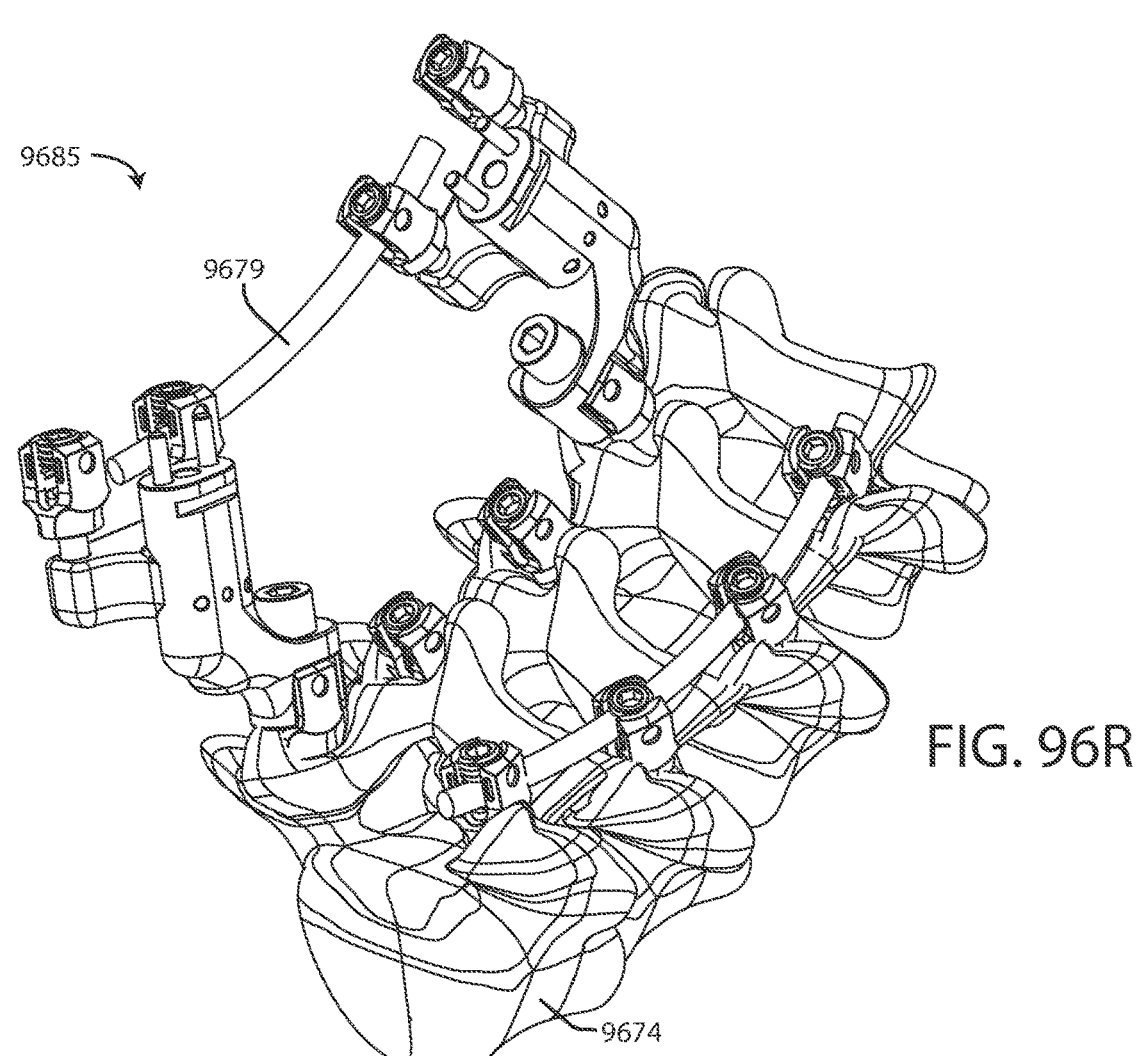

FIG. 96R illustrates a perspective view of the bottom half side arm components of the flexibility assessment devices that are substantially rigidly linked to one another and engaged with the vertebrae, as described previously in relation to FIGS. 96A-96Q in accordance with some embodiments of the invention.

Figure 96S:
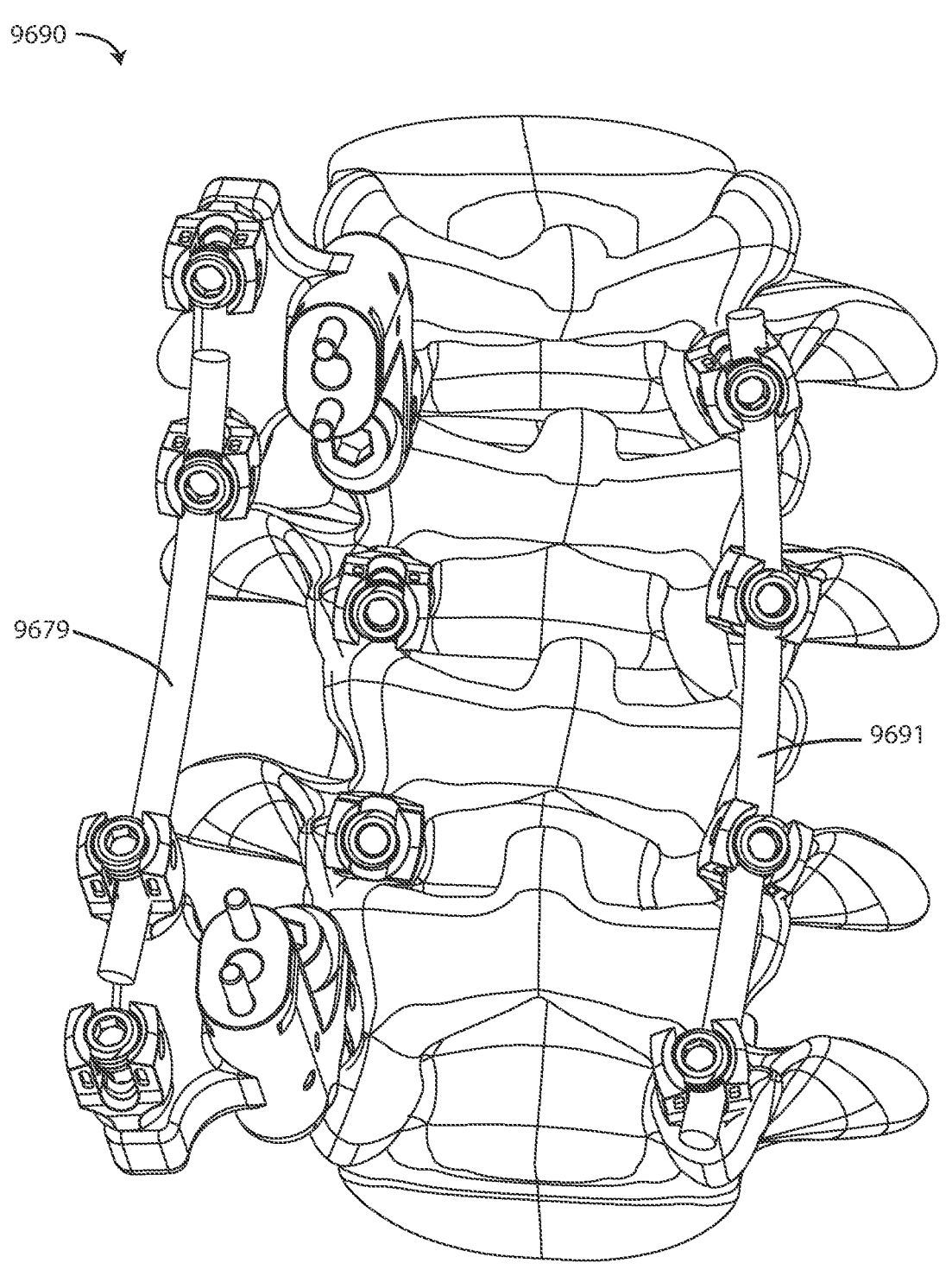

FIG. 96S illustrates a top view of the bottom half side arm components of the flexibility assessment devices that are substantially rigidly linked to one another and engaged with the vertebrae, as described previously in relation to FIGS. 96A-96R in accordance with some embodiments of the invention.

Figures 97A, 97B, 97C, 97D, 97E:
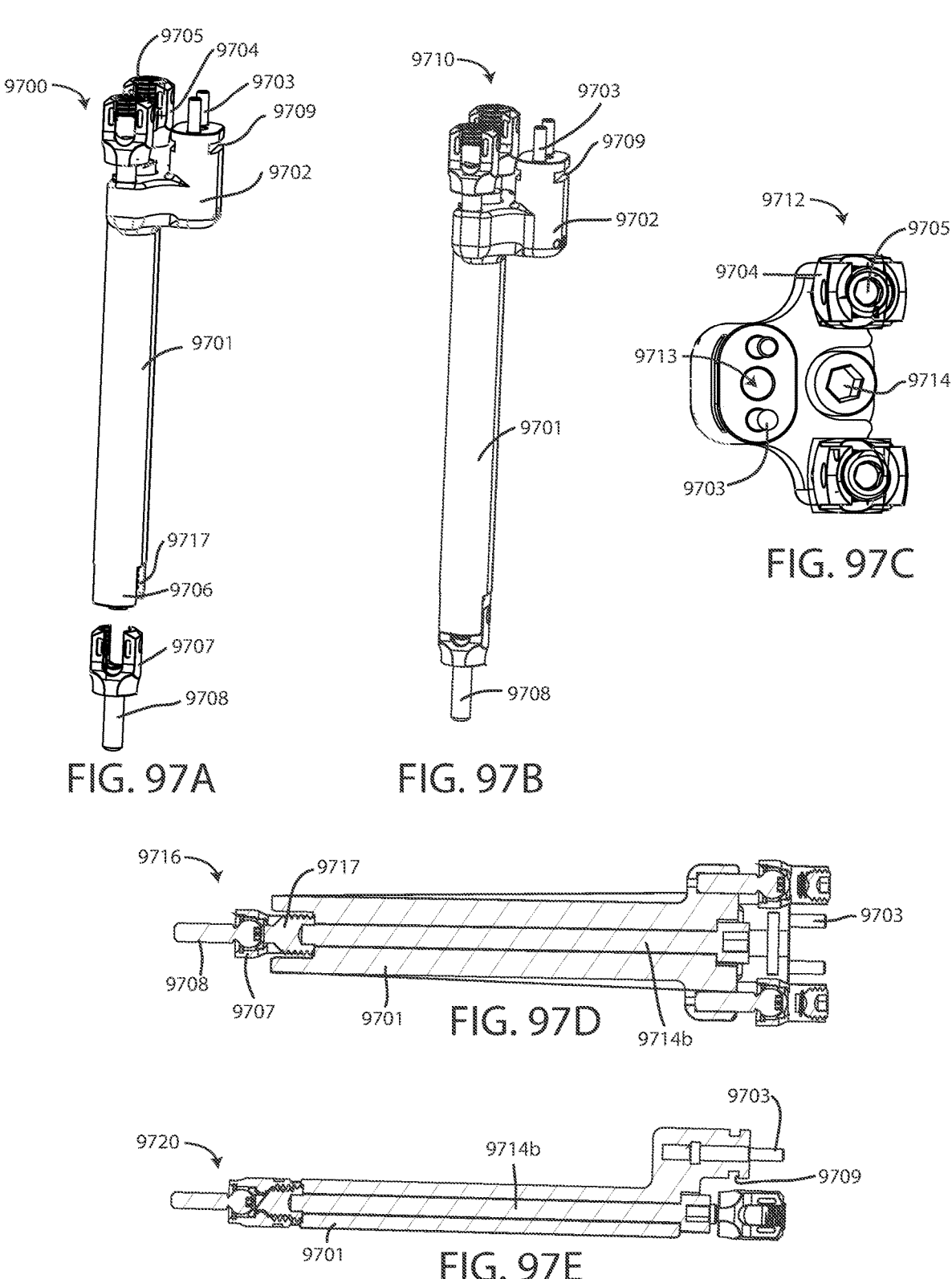

FIGS. 97A-97B illustrate side views of an extended side arm of a flexibility assessment device that is substantially rigidly attached and unattached to a pedicle screw in accordance with some embodiments of the invention.

FIG. 97C illustrates a top view of an extended side arm of a flexibility assessment device as described previously in relation to FIGS. 97A-97B in accordance with some embodiments of the invention.

FIGS. 97D-97E illustrate cross-sectional views of an extended side arm of a flexibility assessment device that is substantially rigidly attached to pedicle screw as described previously in relation to FIGS. 97A-97C in accordance with some embodiments of the invention.

Figure 97F:
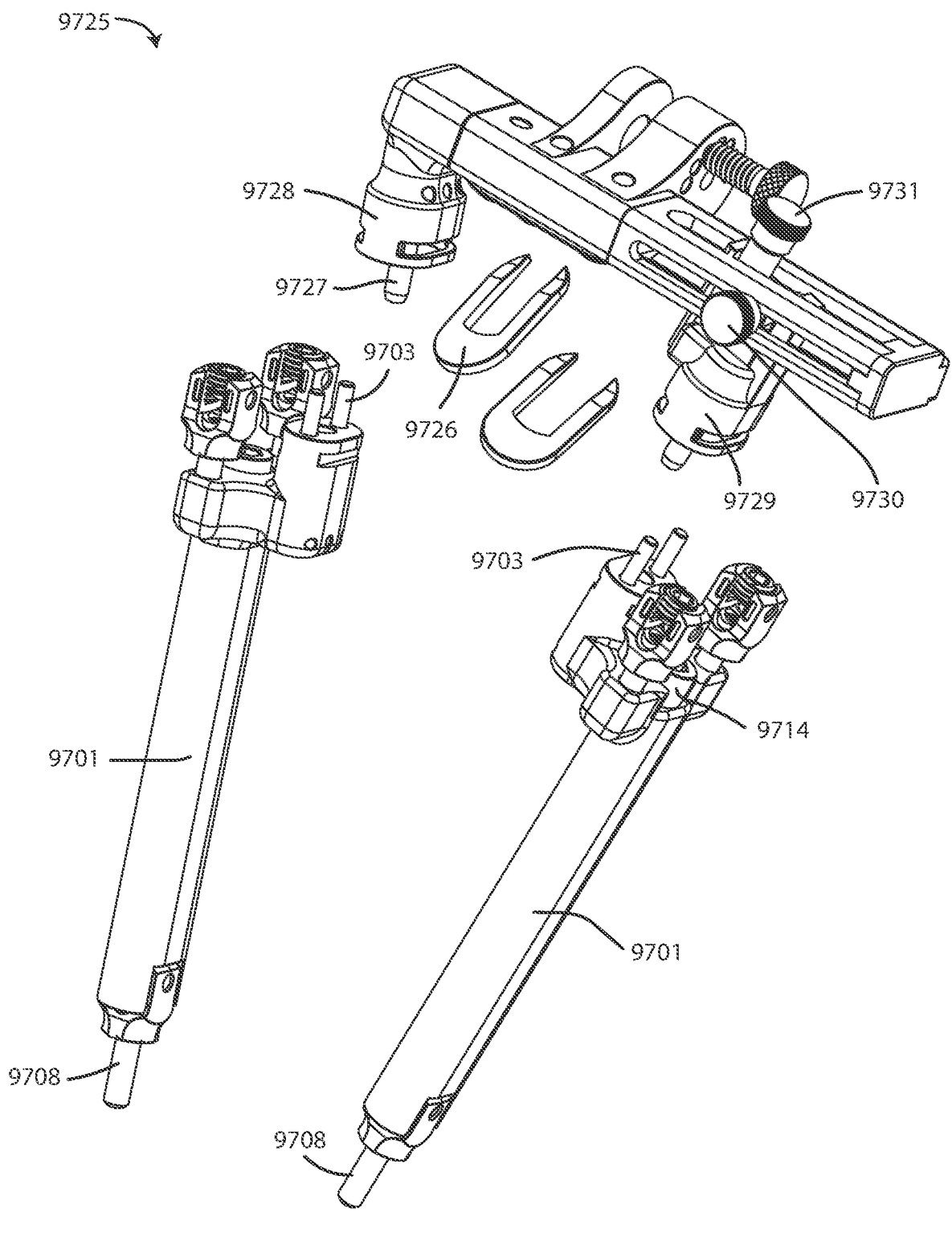

FIG. 97F illustrates an exploded assembly view of extended, adjustable screw interfaces of the flexibility assessment device that are substantially rigidly attached to pedicle screws as described previously in relation to FIGS. 97A-97E in accordance with some embodiments of the invention.

Figure 97G:
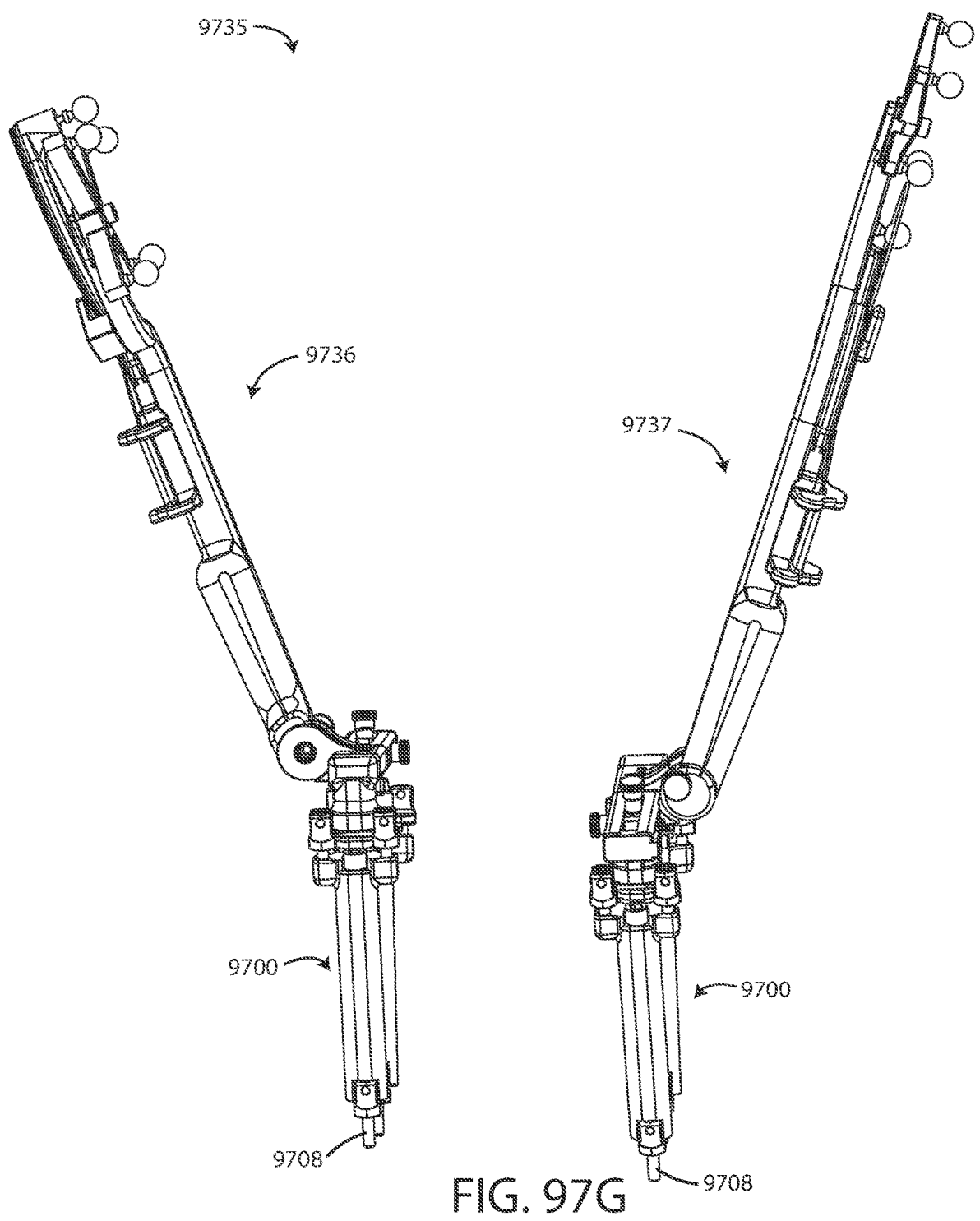

FIG. 97G illustrates a side view of extended, adjustable screw interfaces of the flexibility assessment devices that are substantially rigidly attached to pedicle screws as described previously in relation to FIGS. 97A-97F in accordance with some embodiments of the invention.

Figure 97H:
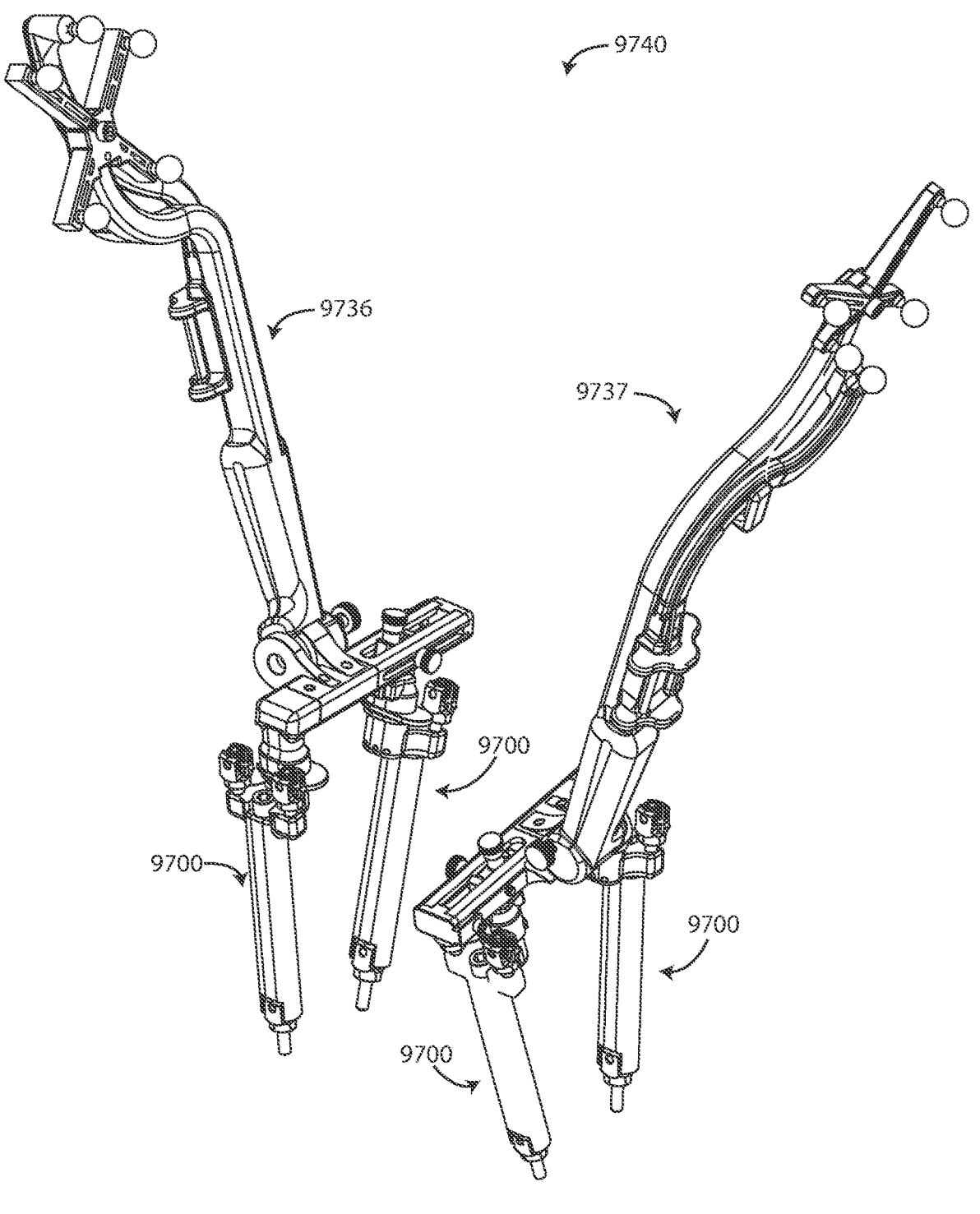

FIG. 97H illustrates a perspective view of extended, adjustable screw interfaces of the flexibility assessment devices that are substantially rigidly attached to pedicle screws as described previously in relation to FIGS. 97A-97G in accordance with some embodiments of the invention.

Figure 97I:
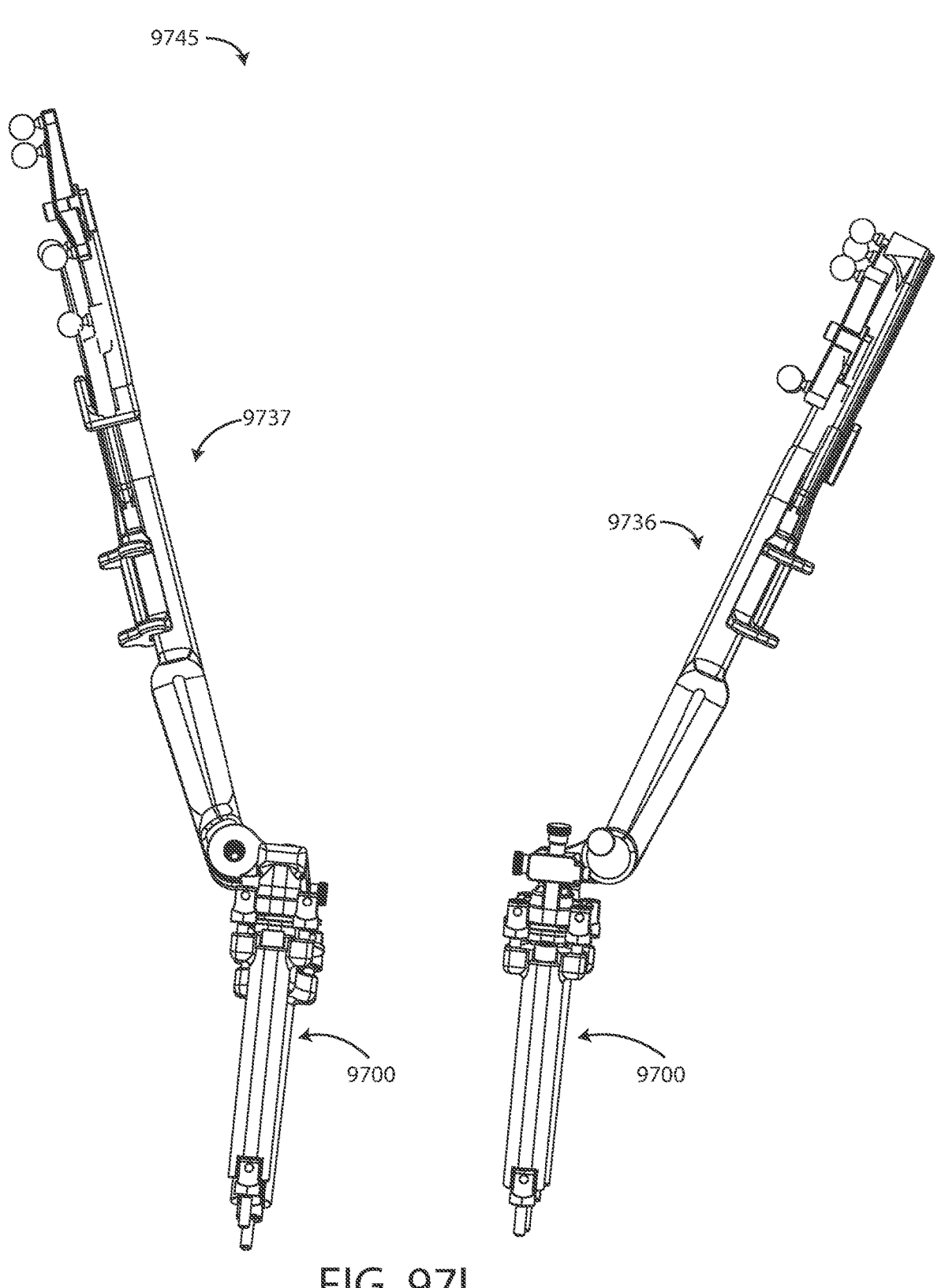

FIG. 97I illustrates a side view of extended, adjustable screw interfaces of the flexibility assessment devices that are substantially rigidly attached to pedicle screws as described previously in relation to FIGS. 97A-97H in accordance with some embodiments of the invention.

Figure 97J:
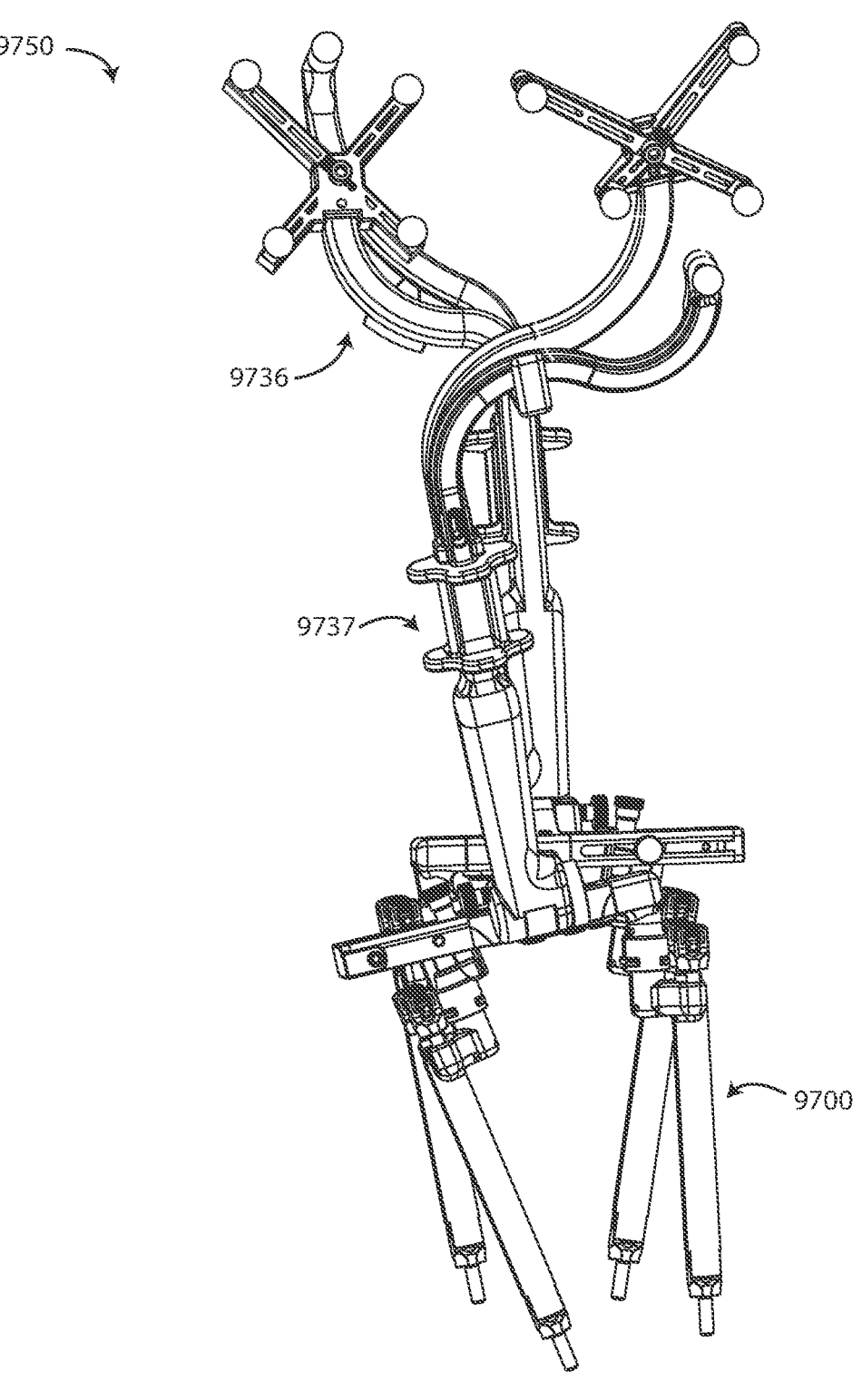

FIG. 97J illustrates a front view of extended, adjustable screw interfaces of the flexibility assessment devices that are substantially rigidly attached to pedicle screws as described previously in relation to FIGS. 97A-97I in accordance with some embodiments of the invention.

FIG. 97K illustrates a top view of extended, adjustable screw interfaces of the flexibility assessment devices that are substantially rigidly attached to pedicle screws as described previously in relation to FIGS. 97A-97J in accordance with some embodiments of the invention.

Figure 97L:
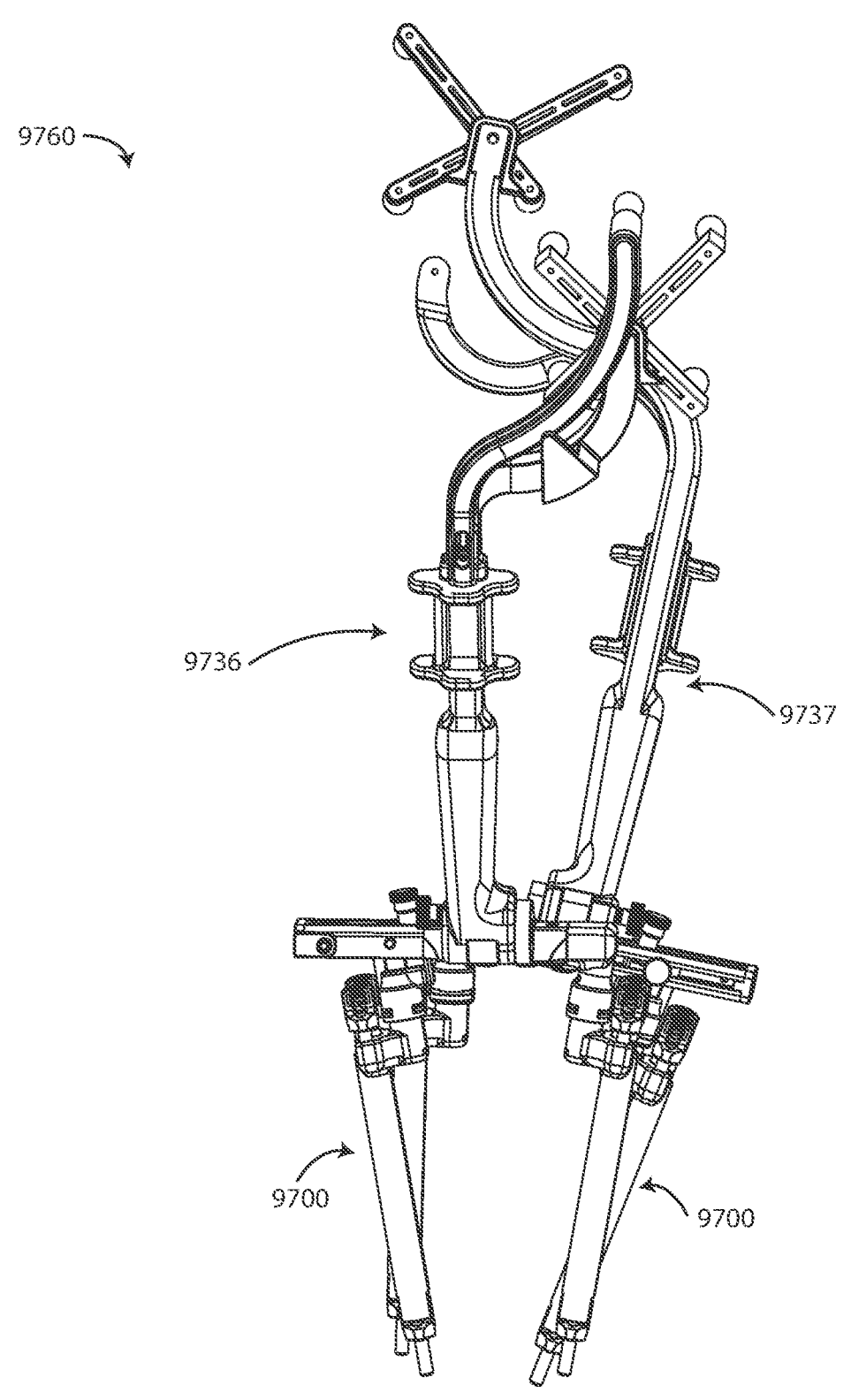

FIG. 97L illustrates a rear view of extended, adjustable screw interfaces of the flexibility assessment devices that are substantially rigidly attached to pedicle screws as described previously in relation to FIGS. 97A-97K in accordance with some embodiments of the invention.

Figures 98A, 98B, 98C:
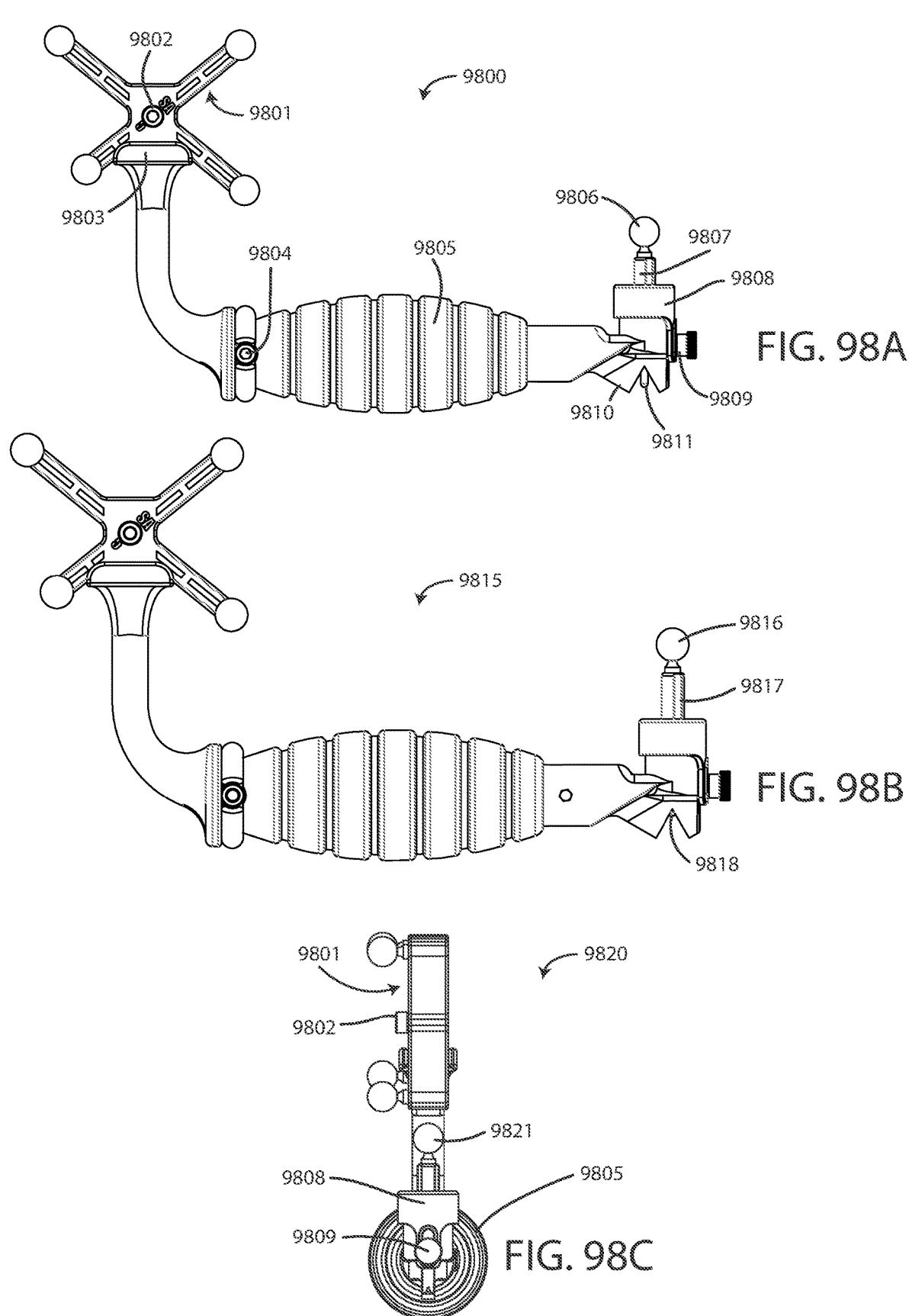

FIGS. 98A-98B illustrate front views of a rod contour registration tool in an active and inactive triggering state in accordance with some embodiments of the invention.

FIG. 98C illustrates a side view of a rod contour registration tool as described previously in relation to FIGS. 98A-98B in accordance with some embodiments of the invention.

Figures 98D, 98E, 98F, 98G:
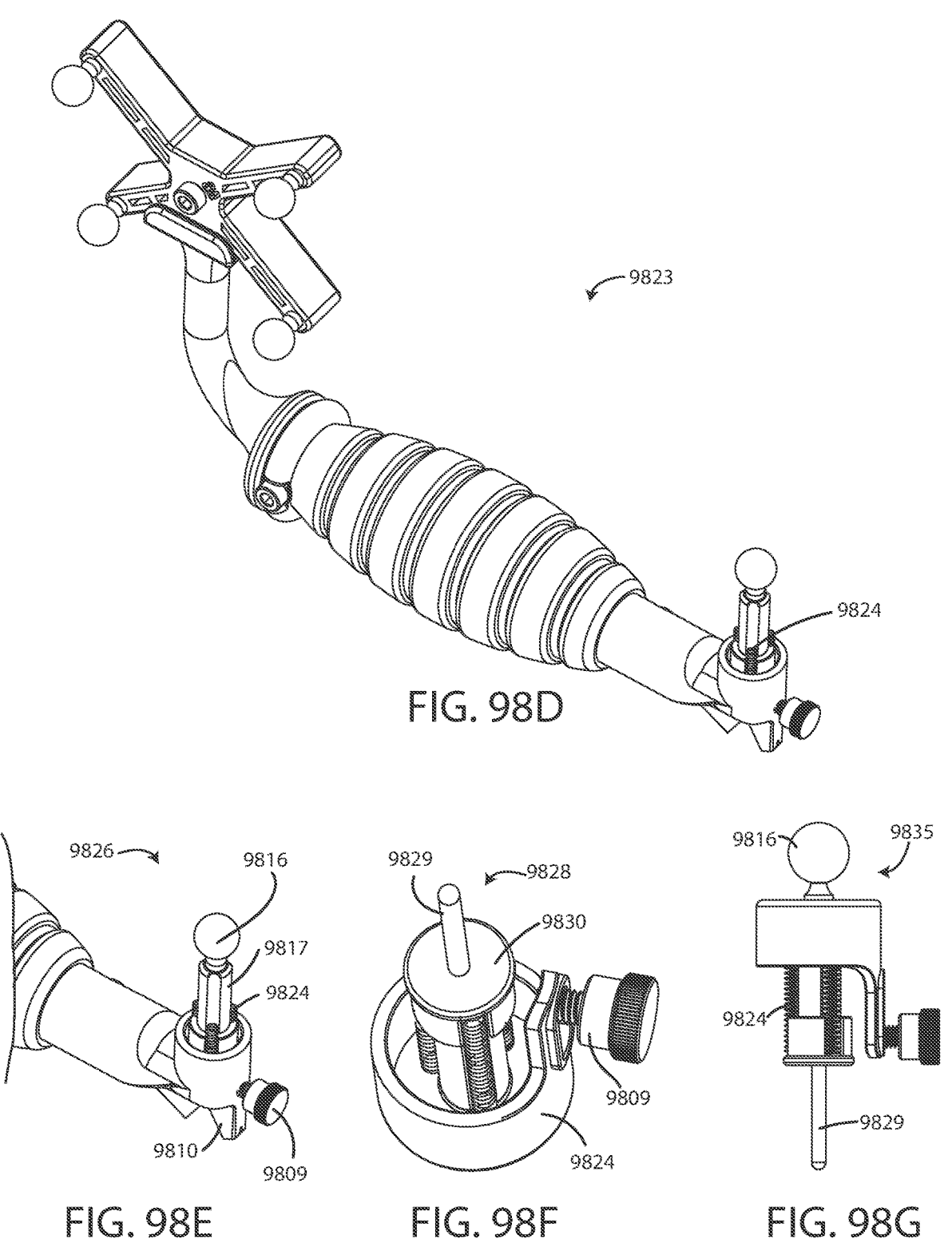

FIG. 98D illustrates a perspective view of a rod contour registration tool as described previously in relation to FIGS. 98A-98C in accordance with some embodiments of the invention.

FIGS. 98E-98F illustrate perspective views of a triggering mechanism of a rod contour registration tool as described previously in relation to FIGS. 98A-98D in accordance with some embodiments of the invention.

FIG. 98G illustrates a side view of a triggering mechanism of a rod contour registration tool as described previously in relation to FIGS. 98A-98F in accordance with some embodiments of the invention.

Figures 98H, 98I, 98J, 98K:
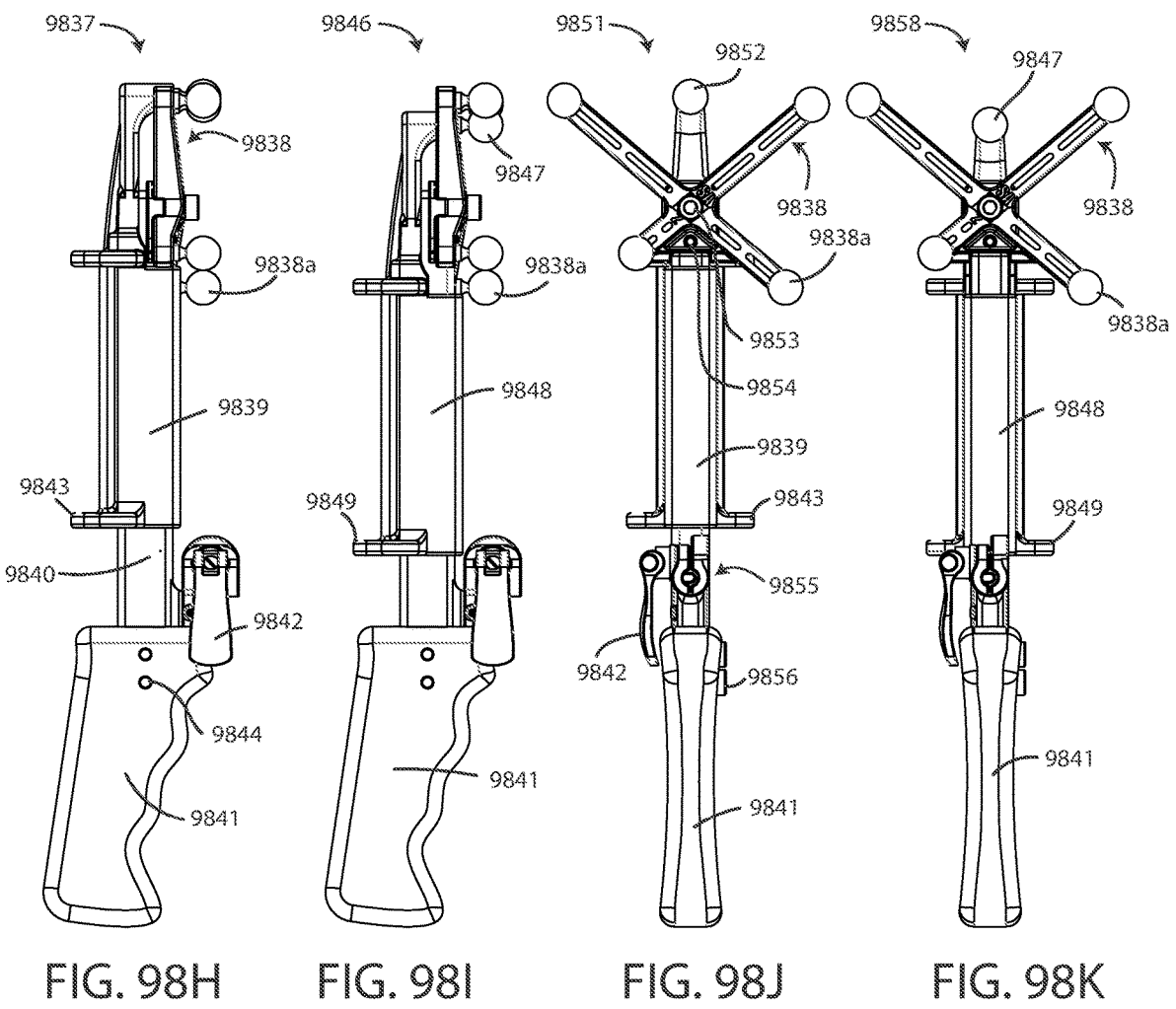

FIG. 98H illustrates a side view of a coordinate reference tool in an inactive triggered state as described previously in relation to FIGS. 98A-98G in accordance with some embodiments of the invention.

FIG. 98I illustrates a side view of a coordinate reference tool in an active triggered state as described previously in relation to FIGS. 98A-98H in accordance with some embodiments of the invention.

FIG. 98J illustrates a front view of a coordinate reference tool in an inactive triggered state as described previously in relation to FIGS. 98A-98I in accordance with some embodiments of the invention.

FIG. 98K illustrates a front view of a coordinate reference tool in an active triggered state as described previously in relation to FIGS. 98A-98J in accordance with some embodiments of the invention.

Figures 98L, 98M, 98N:
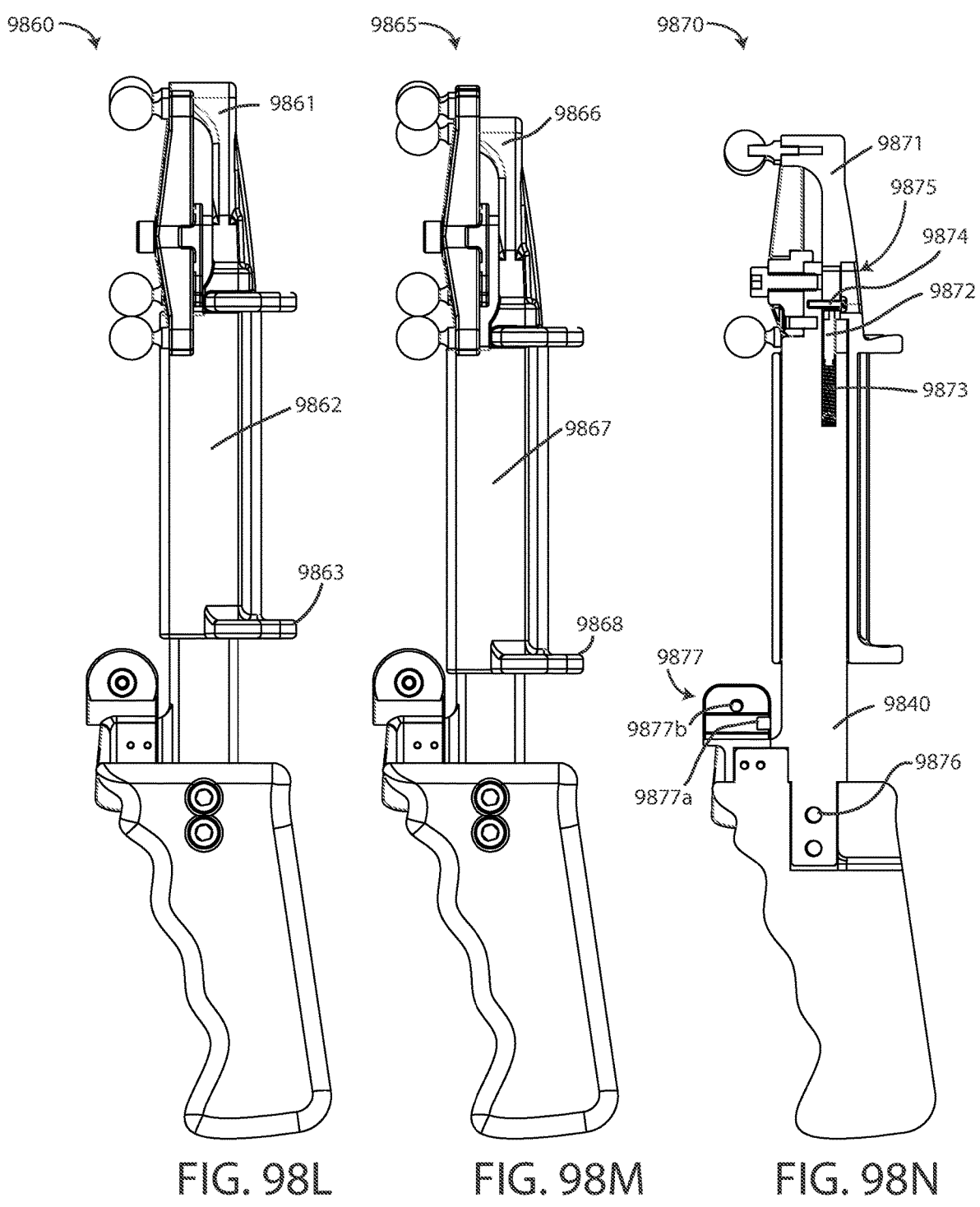

FIG. 98L illustrates a side view of a coordinate reference tool in an inactive triggered state as described previously in relation to FIGS. 98A-98K in accordance with some embodiments of the invention.

FIG. 98M illustrates a side view of a coordinate reference tool in an active triggered state as described previously in relation to FIGS. 98A-98L in accordance with some embodiments of the invention.

FIG. 98N illustrates a cross-sectional view of a coordinate reference tool in an inactive triggered state as described previously in relation to FIGS. 98A-98M in accordance with some embodiments of the invention.

FIGS. 98O-98S illustrate perspective views of a rod attached to a coordinate reference tool and a rod contour registration tool engaged with the rod as described previously in relation to FIGS. 98A-98N in accordance with some embodiments of the invention.

Figures 98O, 98P:
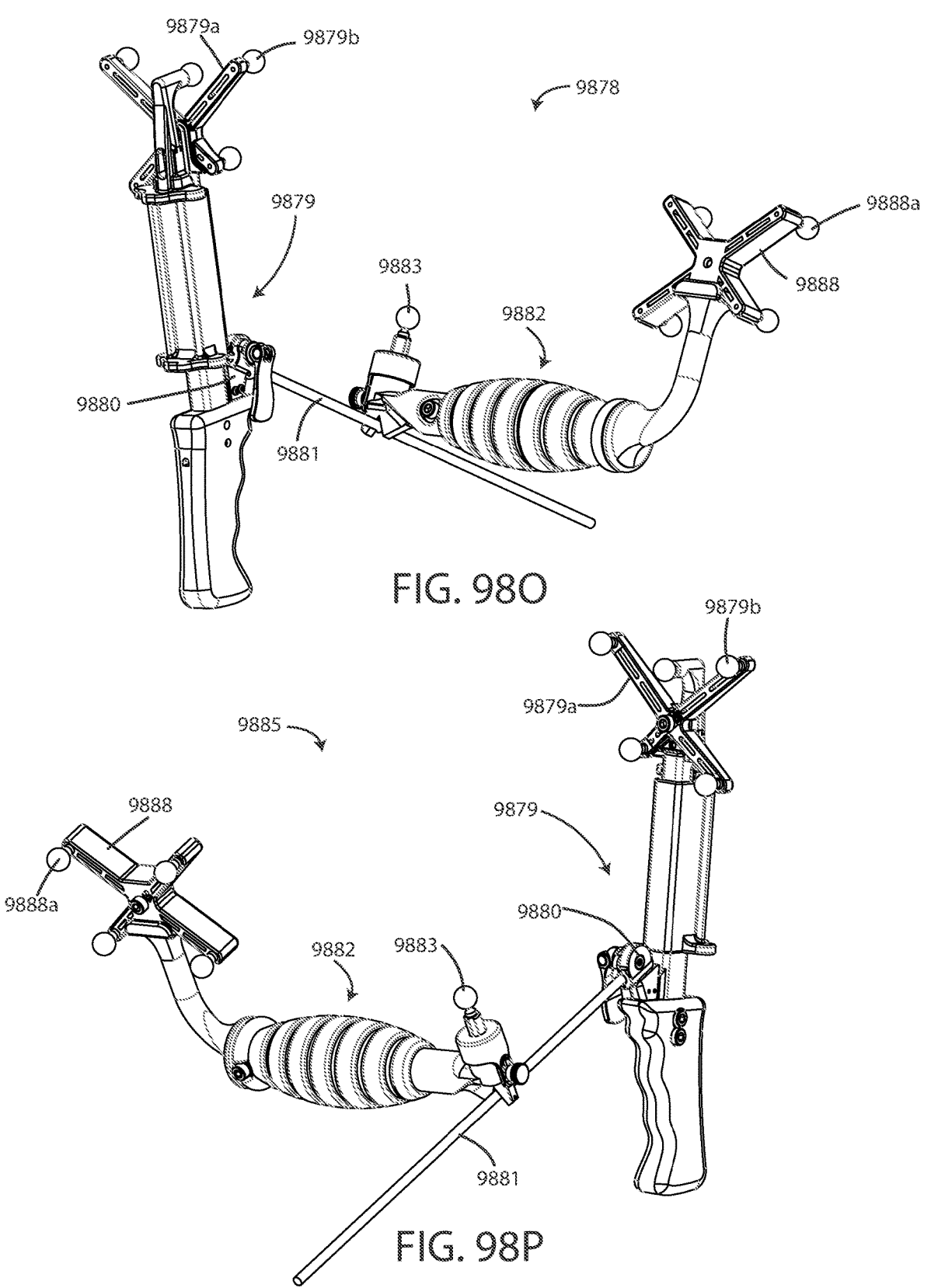
Figures 98Q, 98R:
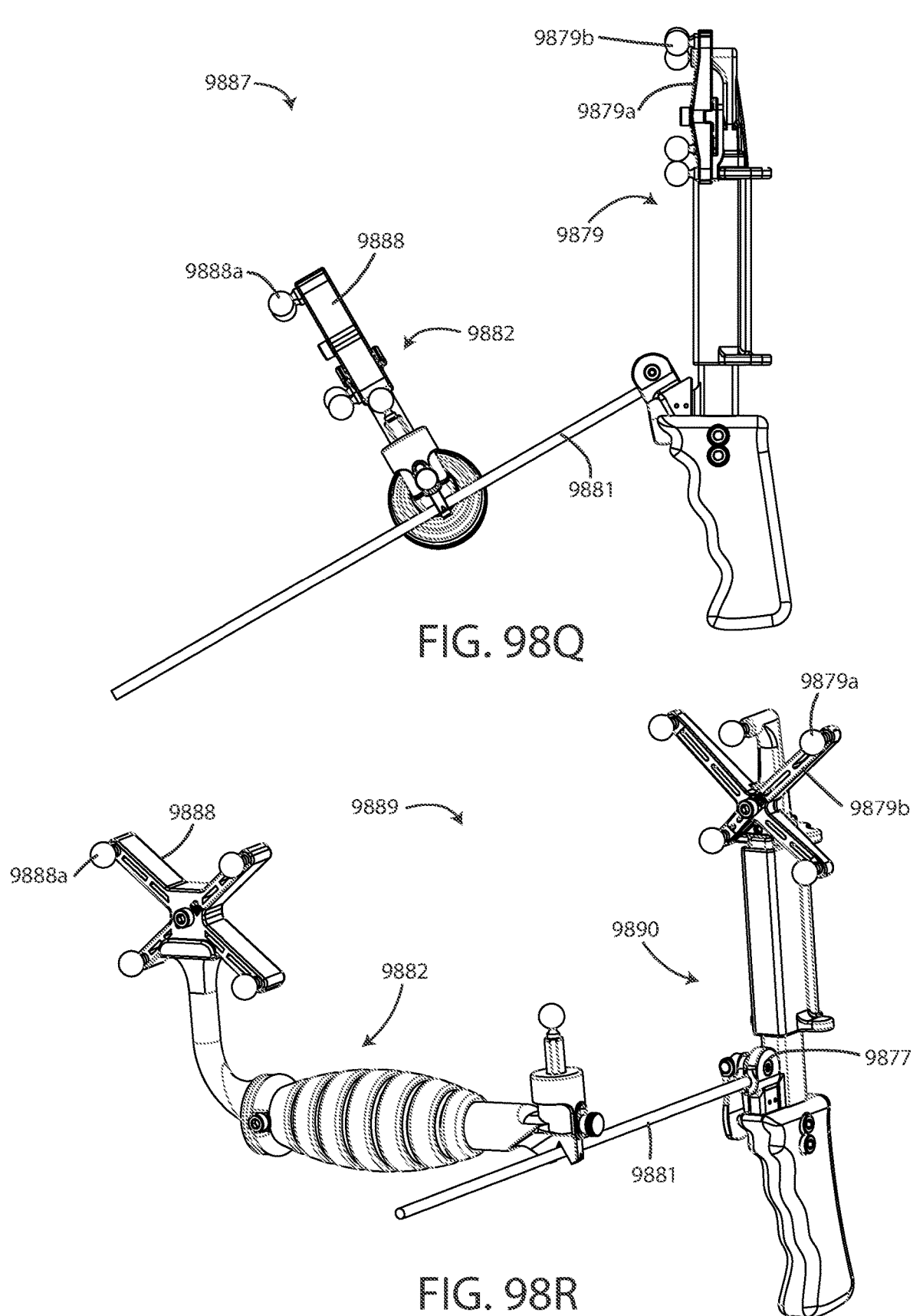
Figure 98S:
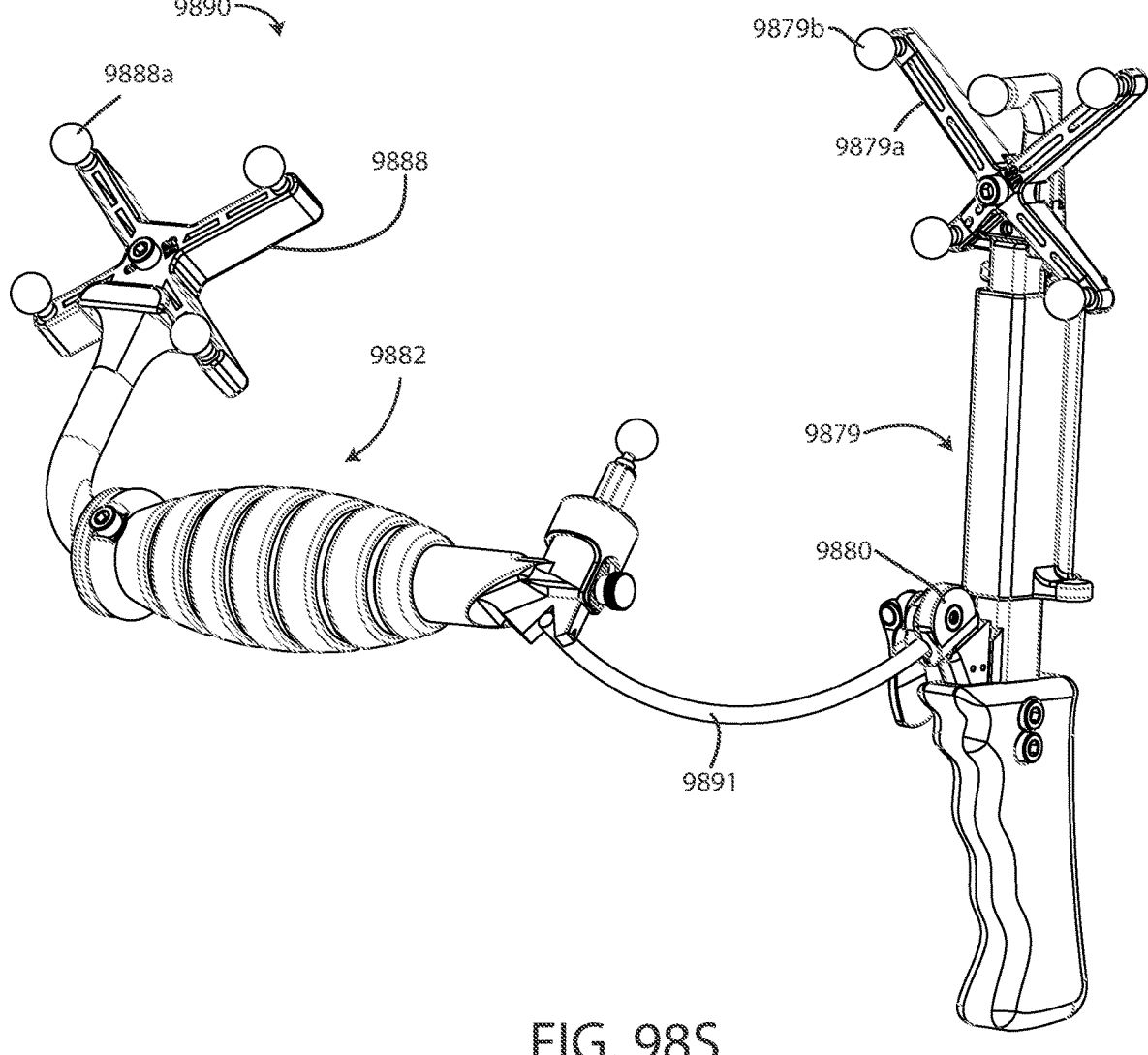
Figure 98T:
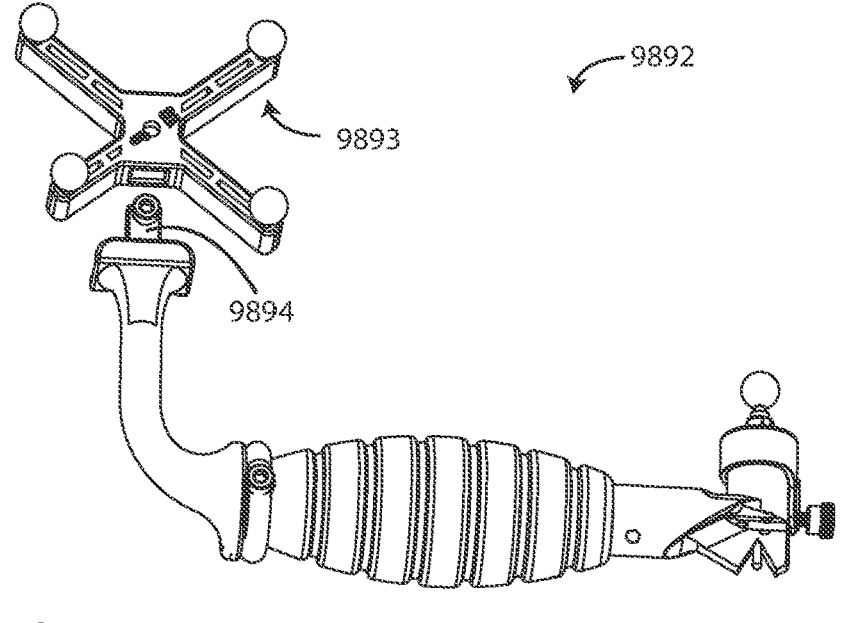
Figure 98U:
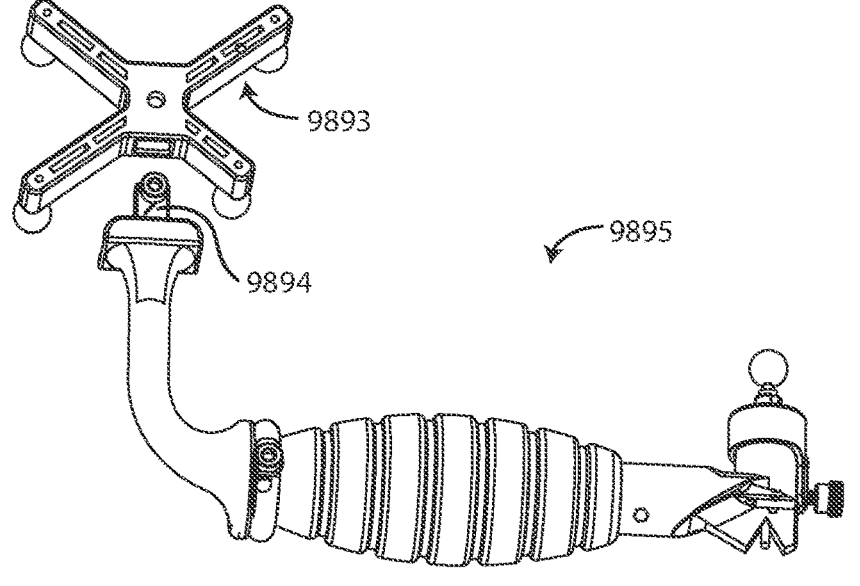
Figure 98V:
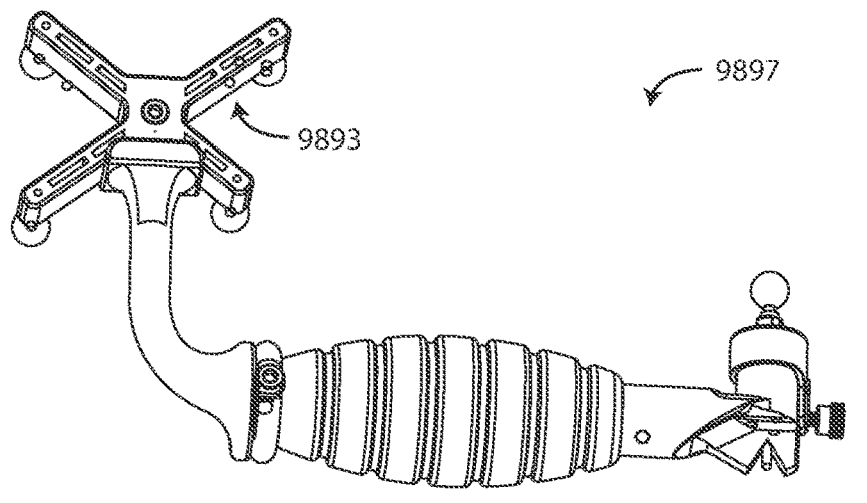

FIGS. 98T-98V illustrate perspective views of a rod contour registration tool with a reversible DRF-mounting mechanism as described previously in relation to FIGS. 98A-98S in accordance with some embodiments of the invention.

Figures 99A, 99B, 99C, 99D:
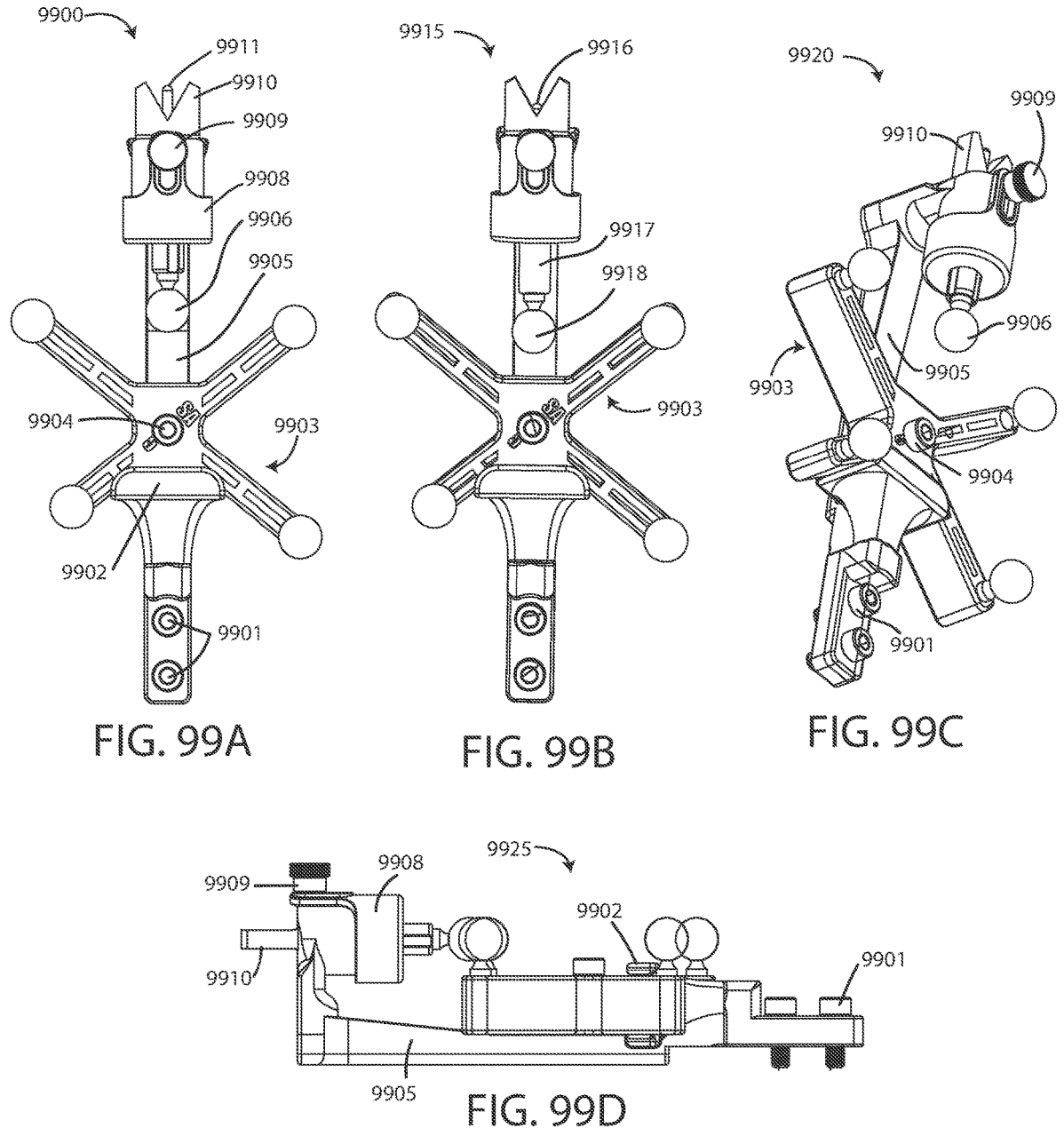

FIG. 99A illustrates a front view of a rod contour registration tool attachment in an inactive triggering state in accordance with some embodiments of the invention.

FIG. 99B illustrates a front view of a rod contour registration tool attachment in an active triggering state as described previously in relation to FIG. 99A in accordance with some embodiments of the invention.

FIG. 99C illustrates a perspective view of a rod contour registration tool attachment in an inactive triggering state as described previously in relation to FIGS. 99A-99B in accordance with some embodiments of the invention.

FIG. 99D illustrates a side view of a rod contour registration tool attachment as described previously in relation to FIGS. 99A-99C in accordance with some embodiments of the invention.

Figures 99E, 99F, 99G, 99H:
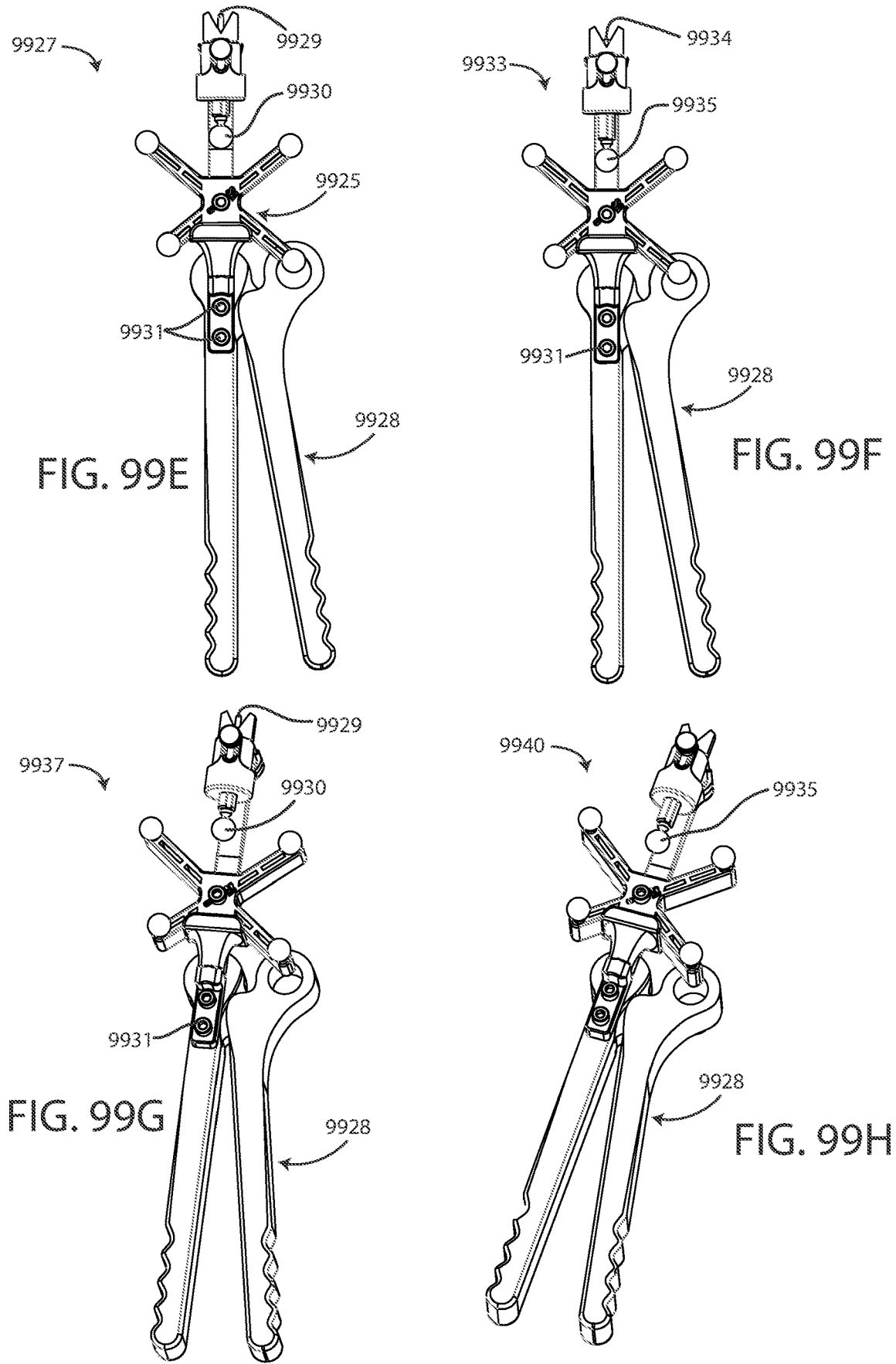

FIGS. 99E-99F illustrate rear views of a rod bender with a rod contour registration tool attachment mounted onto the rod bender as described previously in relation to FIGS. 99A-99D in accordance with some embodiments of the invention.

FIGS. 99G-99H illustrate back perspective views of a rod bender with a rod contour registration tool attachment mounted onto the rod bender as described previously in relation to FIGS. 99A-99F in accordance with some embodiments of the invention.

Figures 99I, 99J:
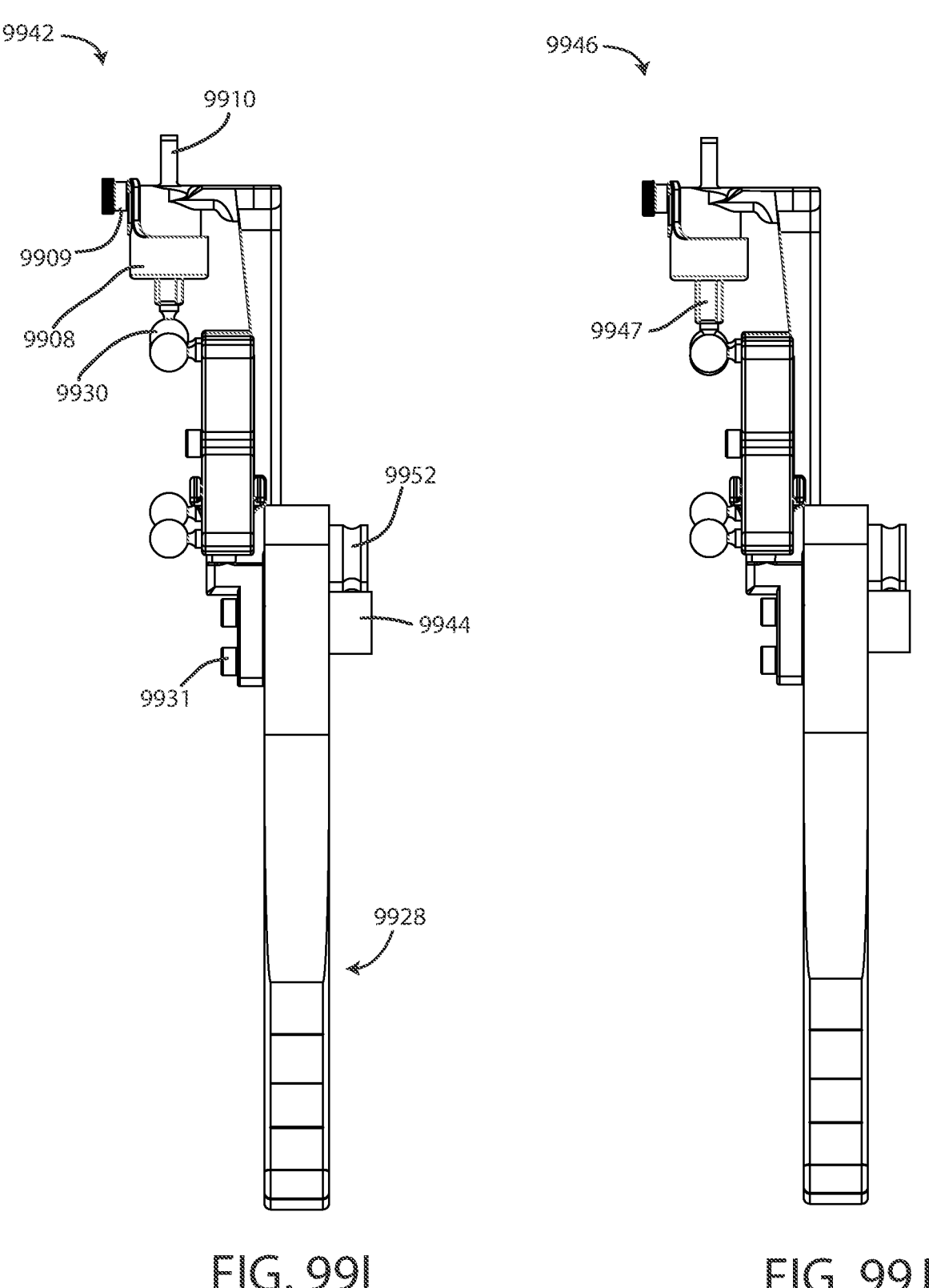

FIGS. 99I-99J illustrate side views of a rod bender with a rod contour registration tool attachment mounted onto the rod bender, with the trigger in an active and inactive state as described previously in relation to FIGS. 99A-99H in accordance with some embodiments of the invention.

Figure 99K:
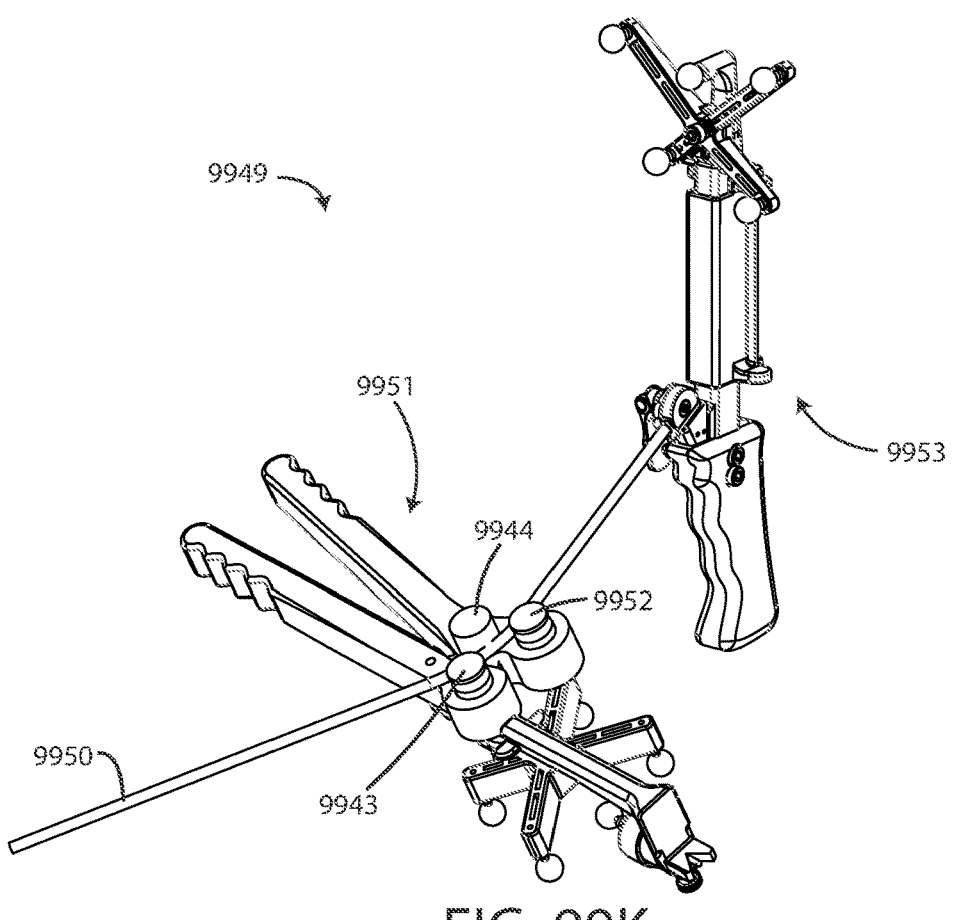
Figure 99L:
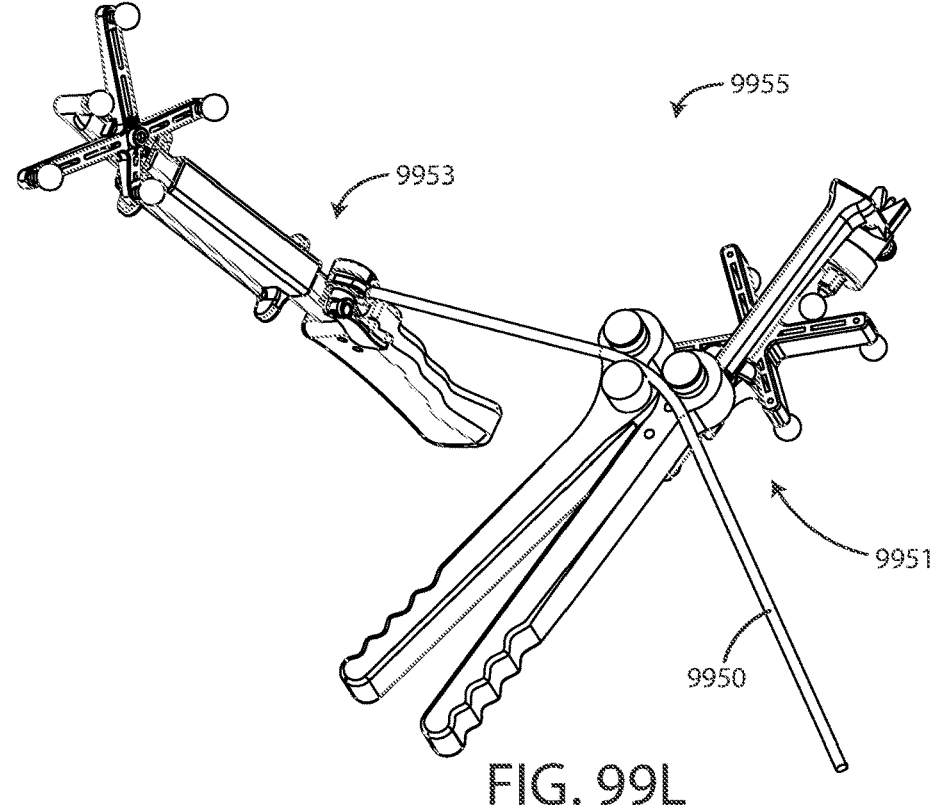

FIGS. 99K-99L illustrate perspective views of a rod bender with a rod contour registration tool attachment mounted onto the rod bender, with the rod bender actively contouring a rod mounted to a coordinate reference tool, as described previously in relation to FIGS. 99A-99J in accordance with some embodiments of the invention.

Figures 99M, 99N:
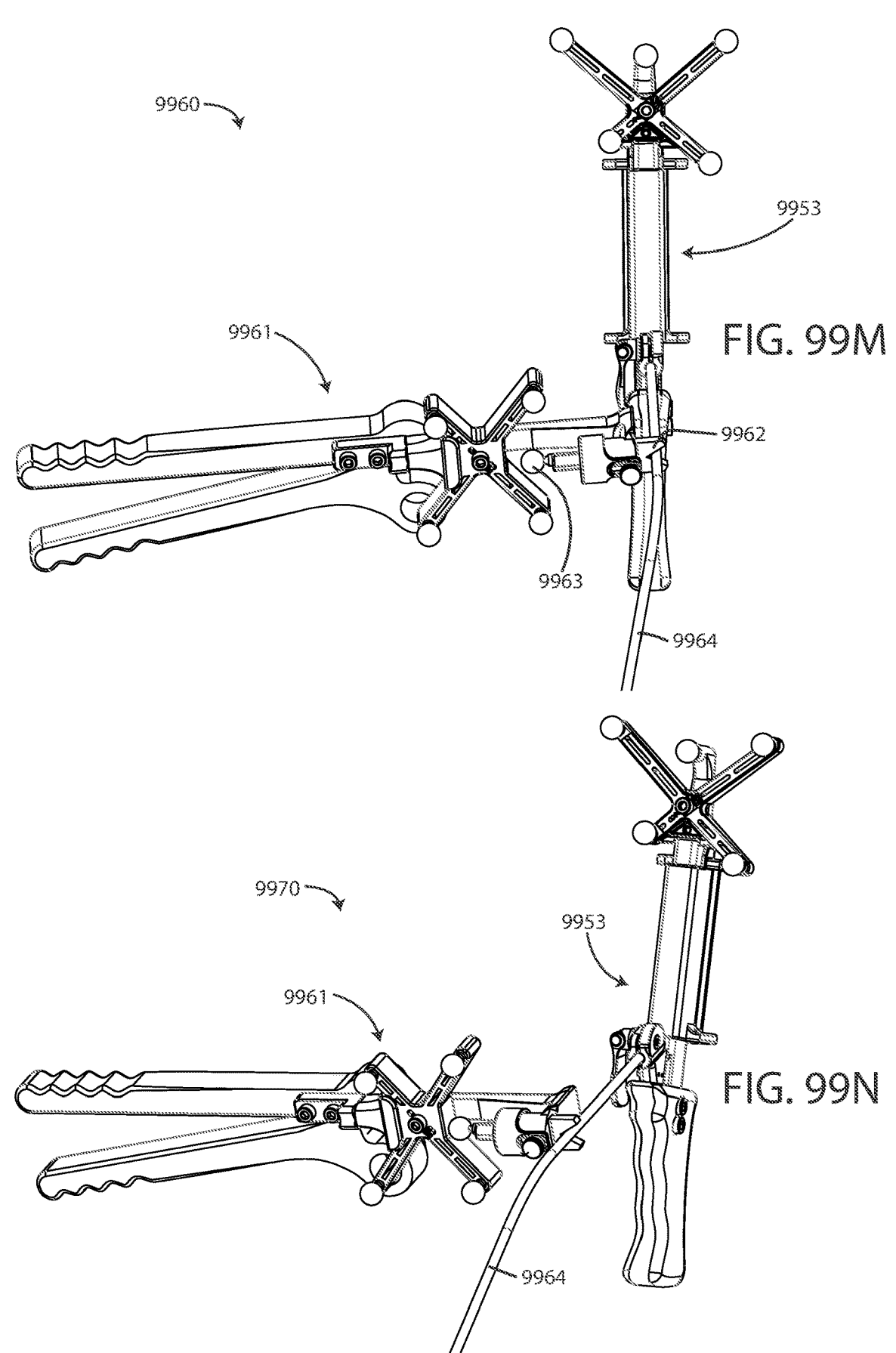

FIGS. 99M-99N illustrate perspective views of a rod bender with a rod contour registration tool attachment mounted onto the rod bender, with the rod bender attachment actively tracing the contour of a rod mounted to a coordinate reference tool, as described previously in relation to FIGS. 99A-99L in accordance with some embodiments of the invention.

Figure 99O:
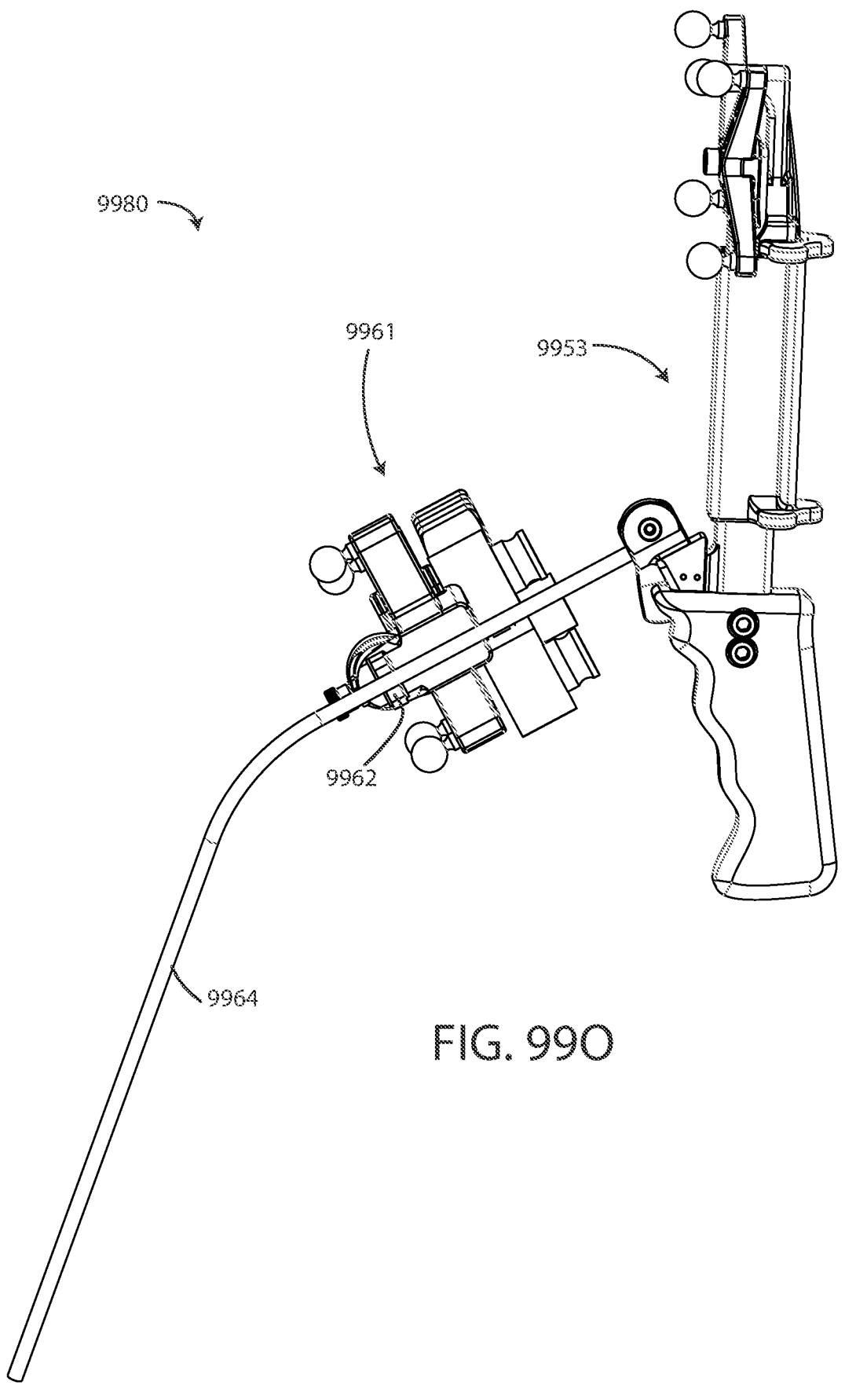

FIG. 99O illustrates a side view of a rod bender with a rod contour registration tool attachment mounted onto the rod bender, with the rod bender attachment actively tracing the contour of a rod mounted to a coordinate reference tool, as described previously in relation to FIGS. 99A-99N in accordance with some embodiments of the invention.

Figures 100A, 100B, 100C:
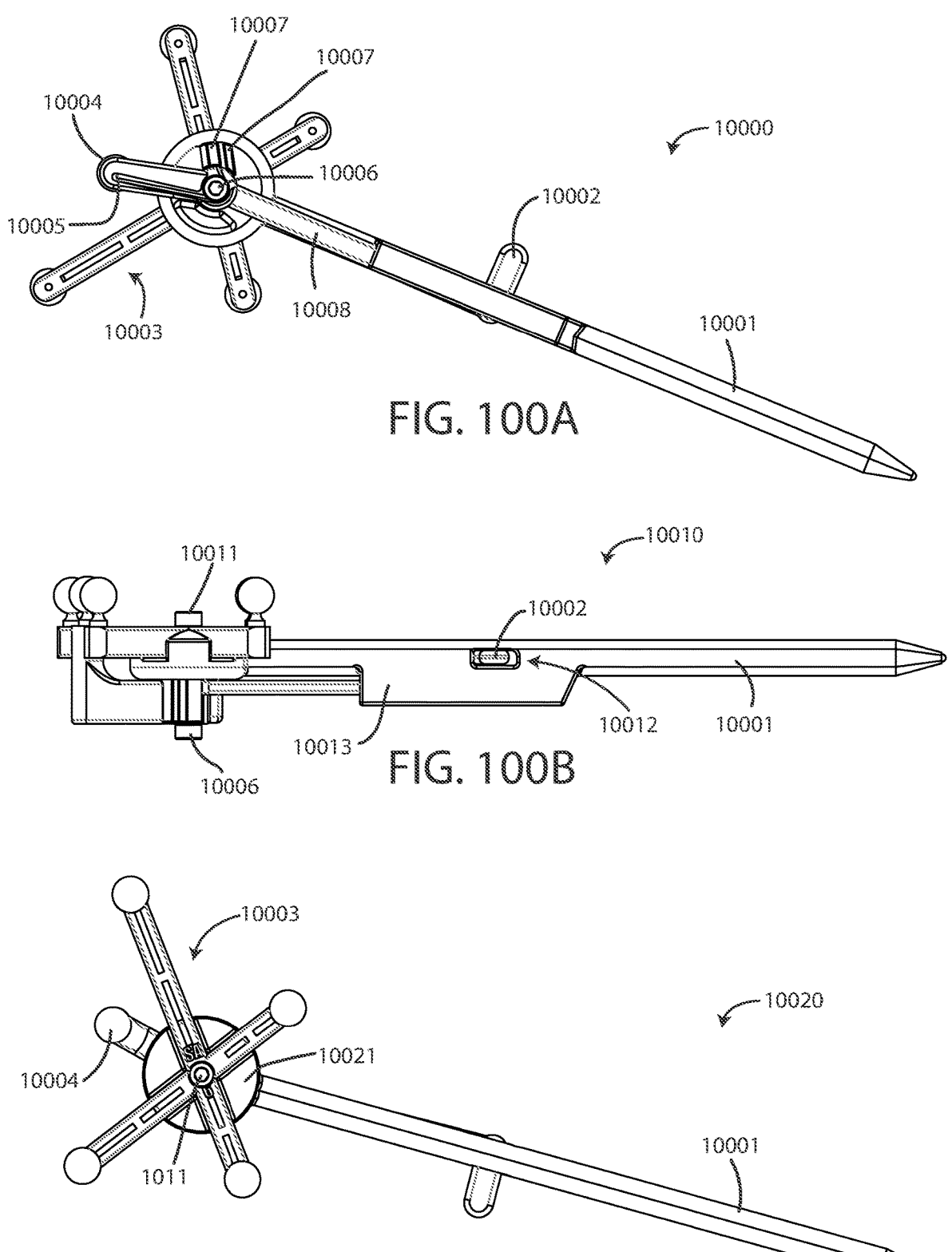

FIG. 100A illustrates a rear view of a 3D-tracked tool with a rotational triggering mechanism and the tool in an inactive state in accordance with some embodiments of the invention.

FIG. 100B illustrates a side view of a 3D-tracked tool with a rotational triggering mechanism and the tool in an inactive state, as described previously in relation to FIG. 100A in accordance with some embodiments of the invention.

FIG. 100C illustrates a front view of a 3D-tracked tool with a rotational triggering mechanism and the tool in an inactive state, as described previously in relation to FIGS. 100A-100B in accordance with some embodiments of the invention.

FIG. 100D illustrates a rear view of a 3D-tracked tool with a rotational triggering mechanism and the tool in an active state, as described previously in relation to FIGS. 100A-100C in accordance with some embodiments of the invention.

FIG. 100E illustrates a side view of a 3D-tracked tool with a rotational triggering mechanism and the tool in an active state, as described previously in relation to FIGS. 100A-100D in accordance with some embodiments of the invention.

FIG. 100F illustrates a front view of a 3D-tracked tool with a rotational triggering mechanism and the tool in an active state, as described previously in relation to FIGS. 100A-100E in accordance with some embodiments of the invention.

Figures 101A, 101B:
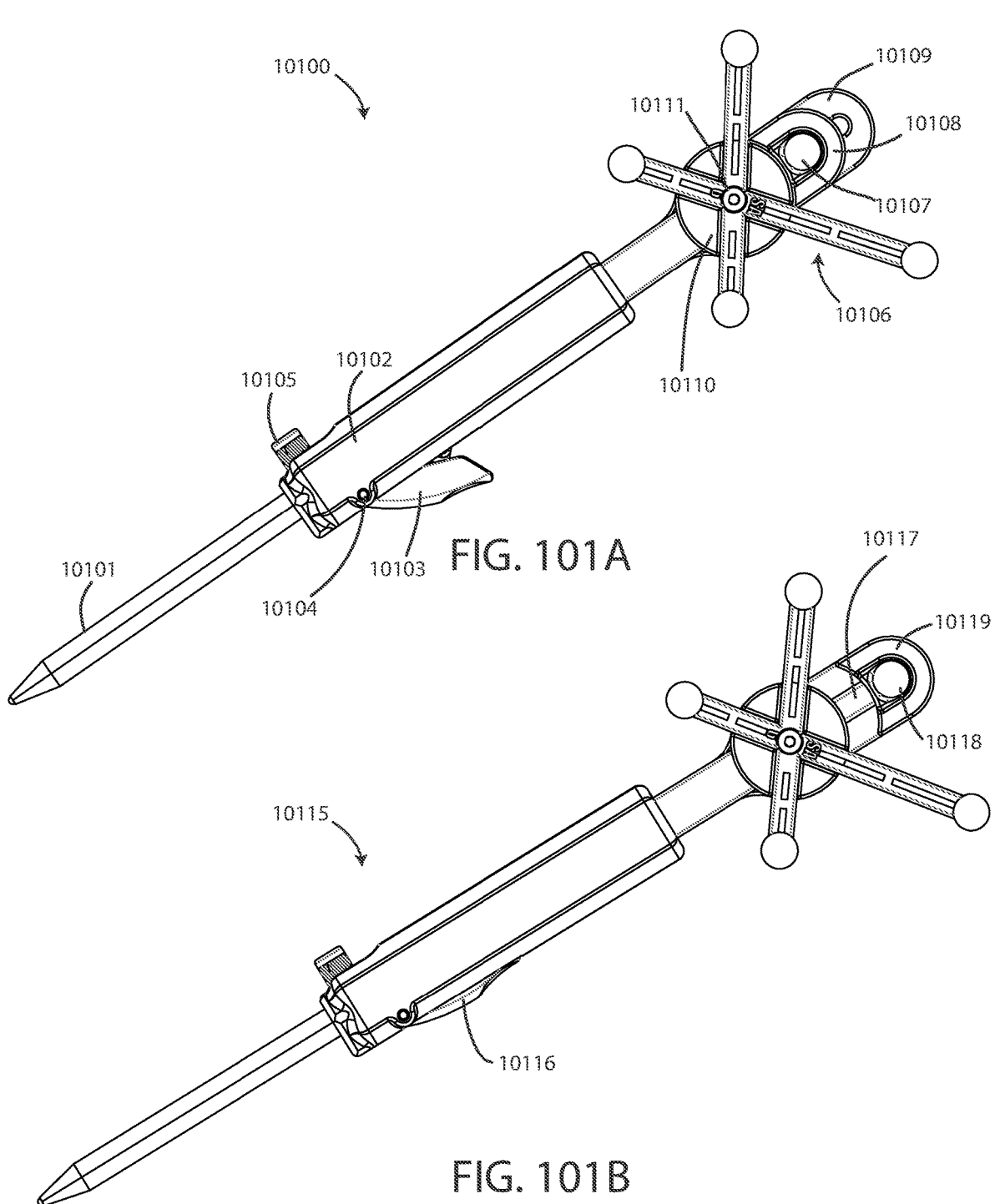

FIG. 101A illustrates a front view of a 3D-tracked tool with a linear triggering mechanism and the tool in an inactive state in accordance with some embodiments of the invention.

FIG. 101B illustrates a front view of a 3D-tracked tool with a linear triggering mechanism and the tool in an active state, as described previously in relation to FIG. 101A in accordance with some embodiments of the invention.

Figures 101C, 101D:
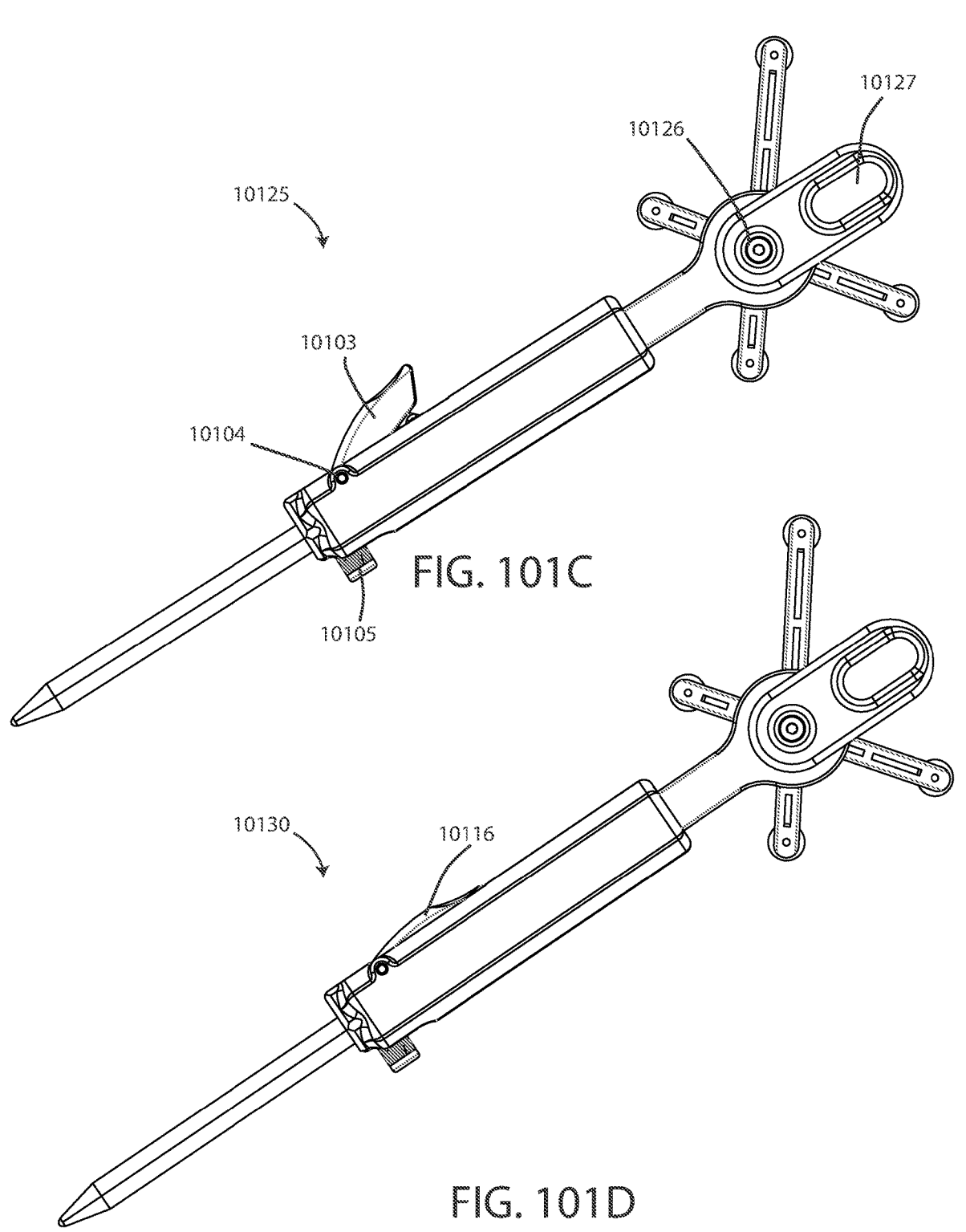

FIG. 101C illustrates a rear view of a 3D-tracked tool with a linear triggering mechanism and the tool in an inactive state, as described previously in relation to FIGS. 101A-101B in accordance with some embodiments of the invention.

FIG. 101D illustrates a rear view of a 3D-tracked tool with a linear triggering mechanism and the tool in an active state, as described previously in relation to FIGS. 101A-101C in accordance with some embodiments of the invention.

Figure 101E:
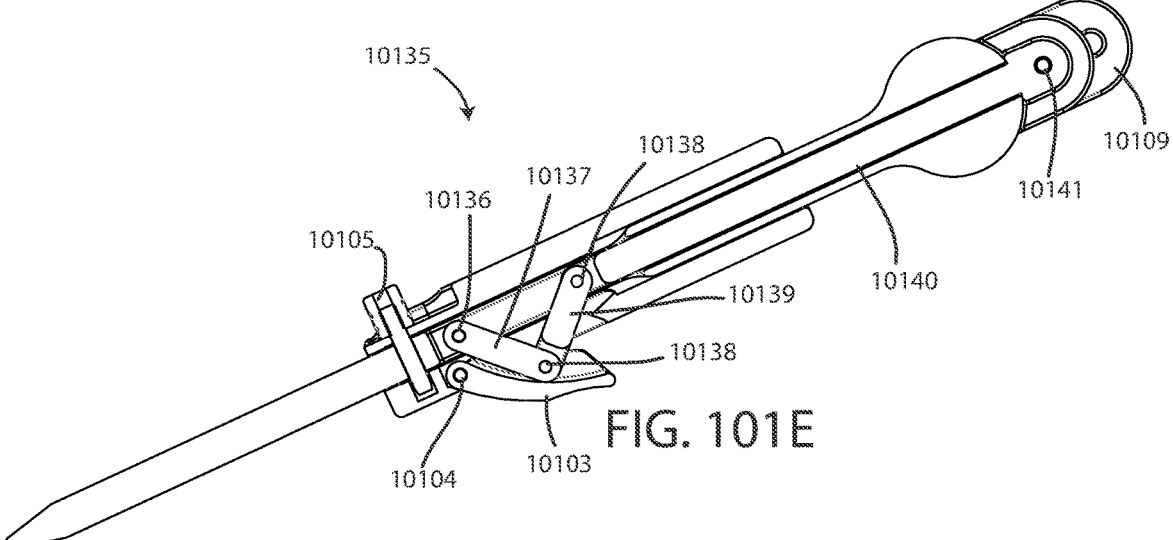

FIG. 101E illustrates a cross-sectional view of a 3D-tracked tool with a linear triggering mechanism and the tool in an inactive state, as described previously in relation to FIGS. 101A-101D in accordance with some embodiments of the invention.

Figure 101F:
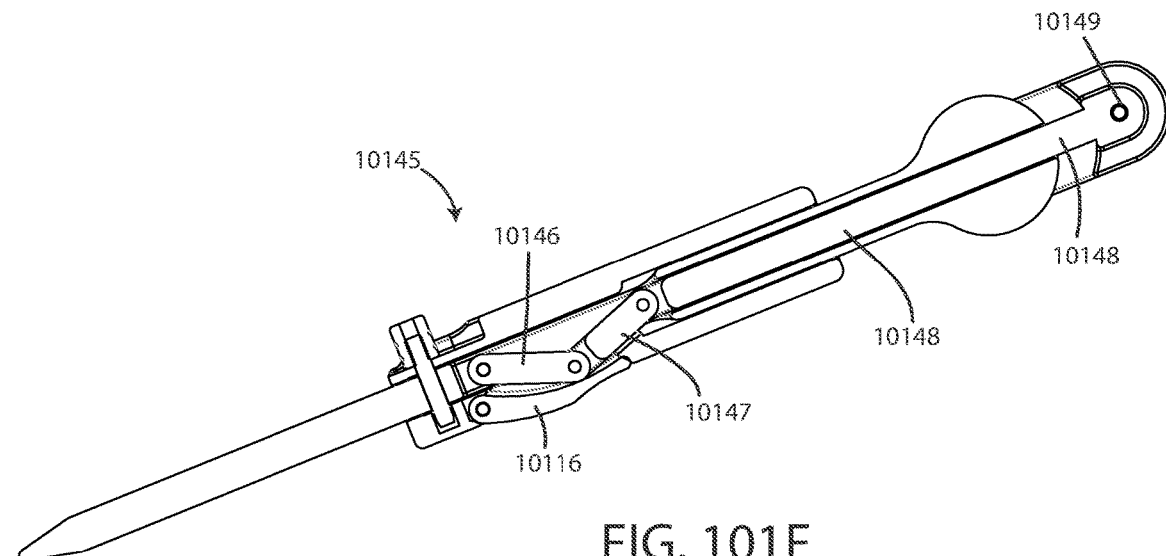

FIG. 101F illustrates a cross-sectional view of a 3D-tracked tool with a linear triggering mechanism and the tool in an active state, as described previously in relation to FIGS. 101A-101E in accordance with some embodiments of the invention.

Figures 101G, 101H:
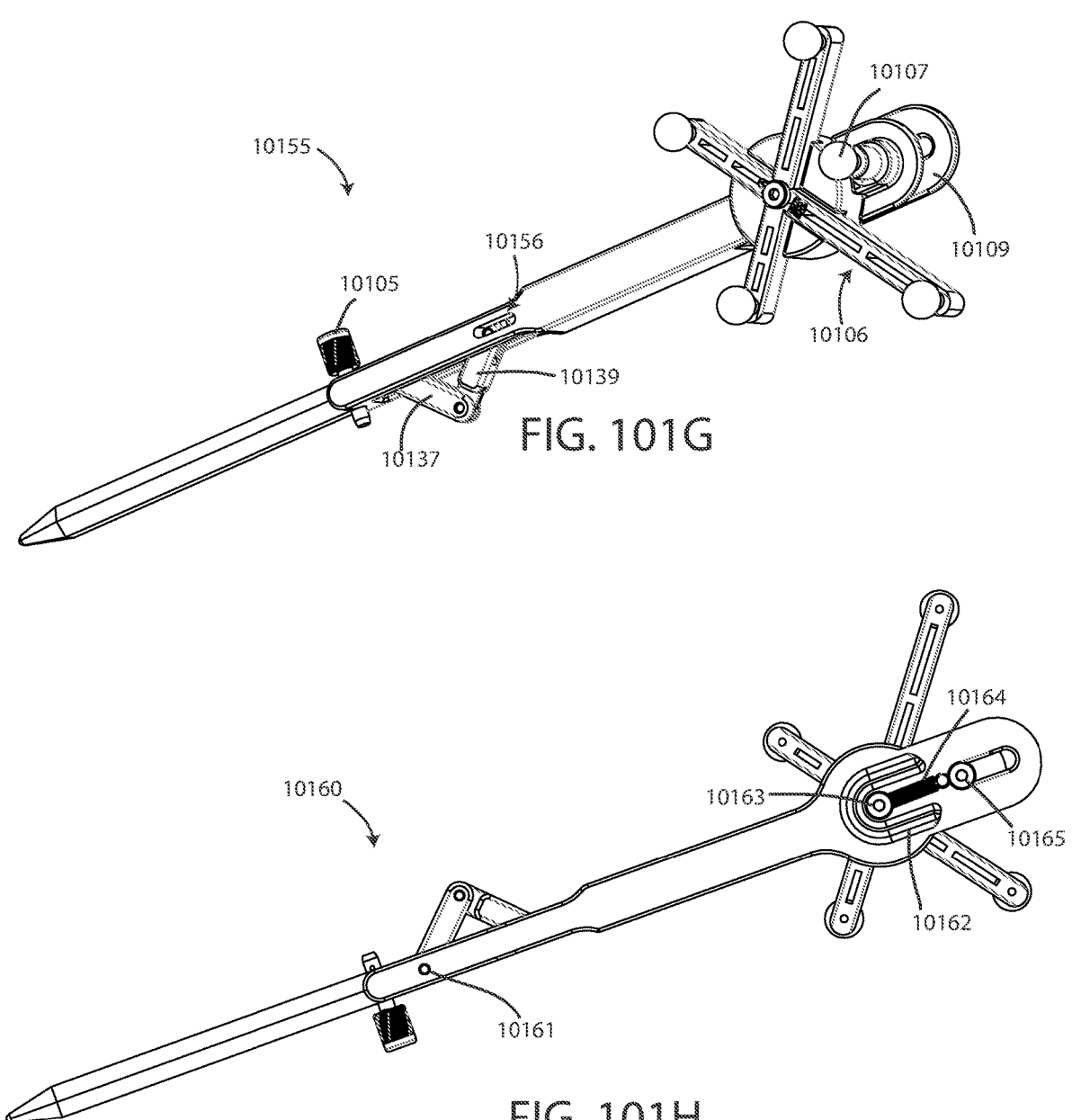

FIG. 101G illustrates a front view of a 3D-tracked tool without a trigger sleeve and with a linear triggering mechanism (oriented for a left-hand-dominant user) and the tool in an inactive state, as described previously in relation to FIGS. 101A-101F in accordance with some embodiments of the invention.

FIG. 101H illustrates a rear view of a 3D-tracked tool without a trigger sleeve and with a linear triggering mechanism (oriented for a left-hand-dominant user) and the tool in an inactive state, as described previously in relation to FIGS. 101A-101G in accordance with some embodiments of the invention.

Figure 101I:
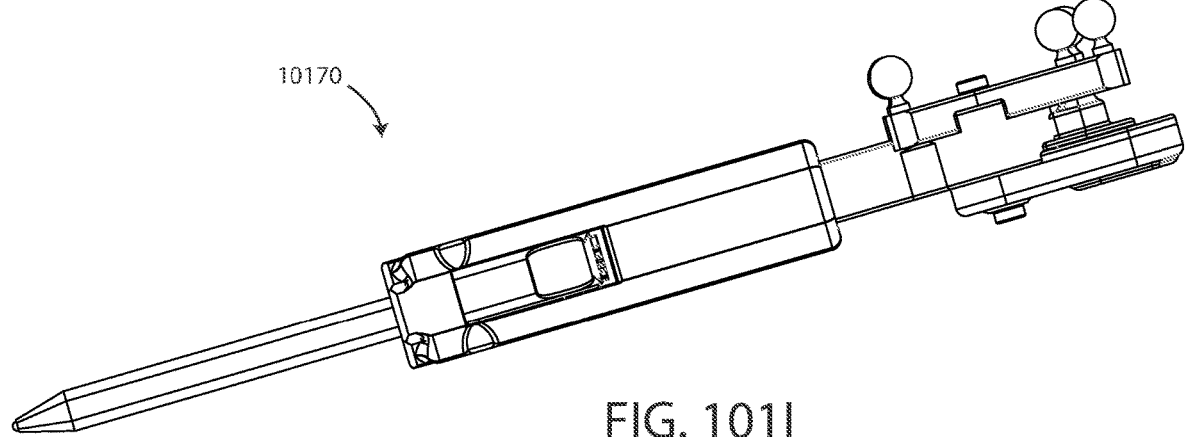

FIG. 101I illustrates a side view of a 3D-tracked tool with a linear triggering mechanism and the tool in an inactive state, as described previously in relation to FIGS. 101A-101H in accordance with some embodiments of the invention.

Figure 101J:
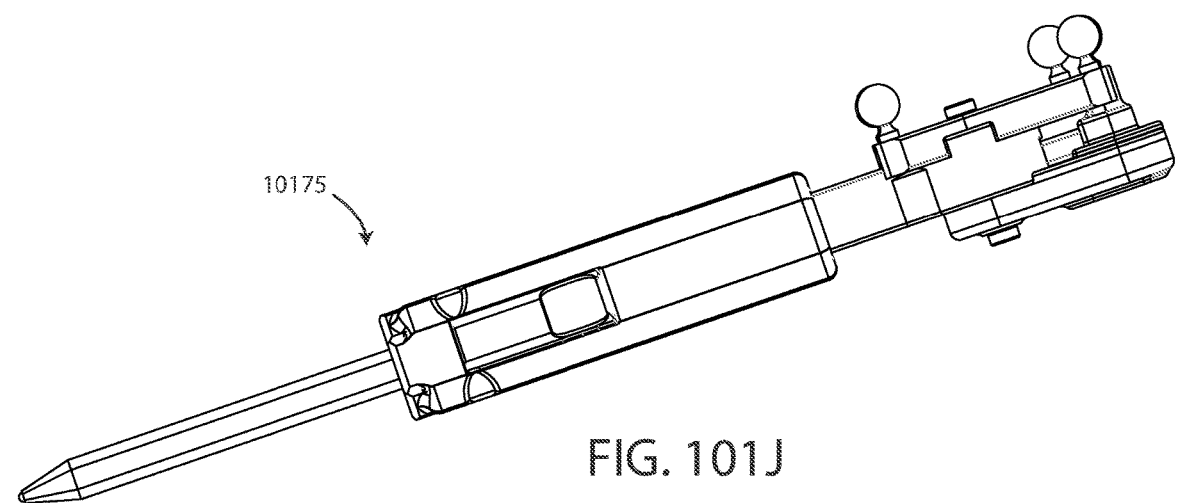

FIG. 101J illustrates a side view of a 3D-tracked tool with a linear triggering mechanism and the tool in an active state, as described previously in relation to FIGS. 101A-101I in accordance with some embodiments of the invention.

Figure 101K:
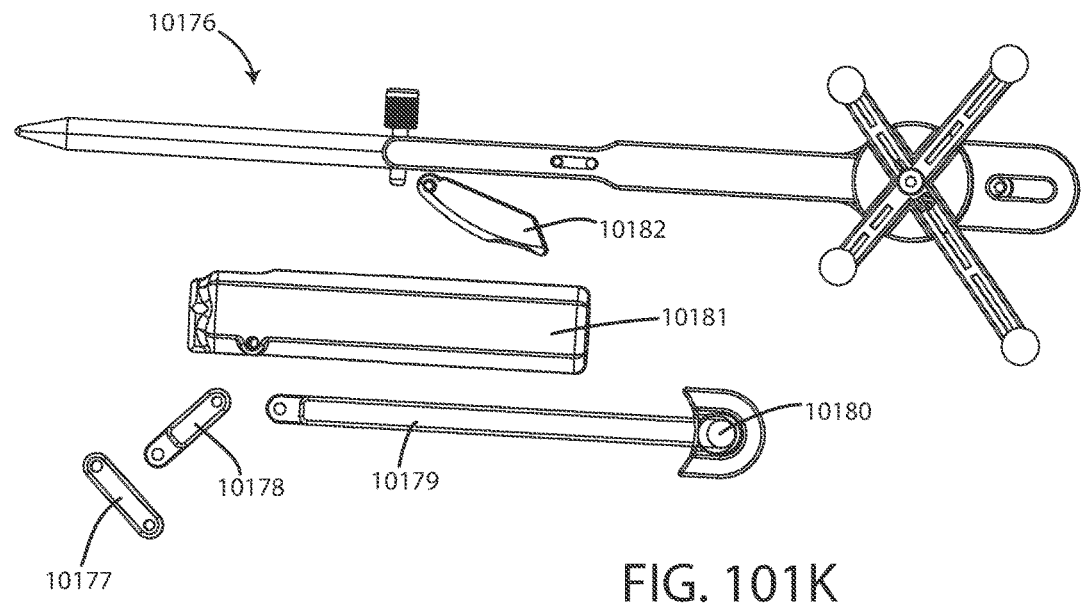

FIG. 101K illustrates an assembly view of a 3D-tracked tool with a linear triggering mechanism as described previously in relation to FIGS. 101A-101J in accordance with some embodiments of the invention.

FIGS. 101L-101O illustrate perspective views of a trigger sleeve of a 3D-tracked tool with a linear triggering mechanism as described previously in relation to FIGS. 101A-101K in accordance with some embodiments of the invention.

Figures 101L, 101M, 101N, 101O:
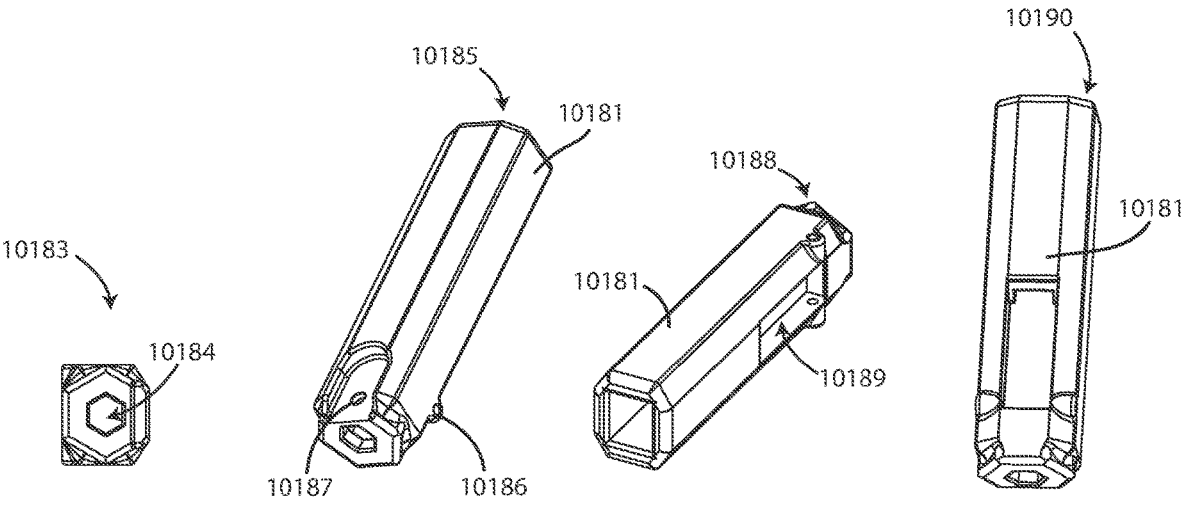
Figure 101P:
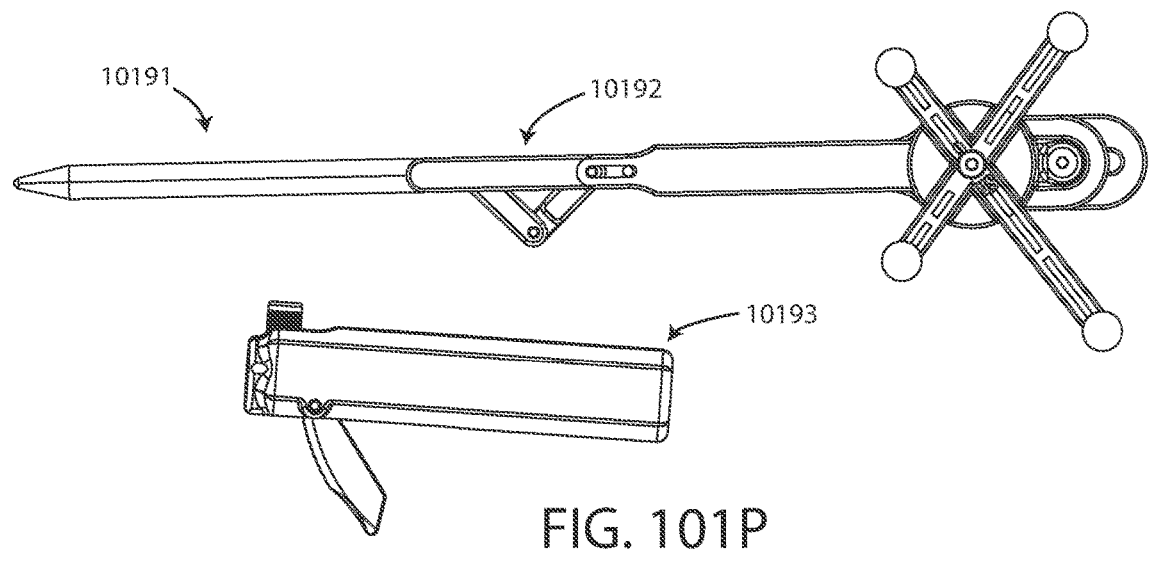

FIG. 101P illustrates an assembly view of a 3D-tracked tool with a linear triggering mechanism, with the trigger sleeve oriented for a left-hand-dominant user, as described previously in relation to FIGS. 101A-101O in accordance with some embodiments of the invention.

Figure 101Q:
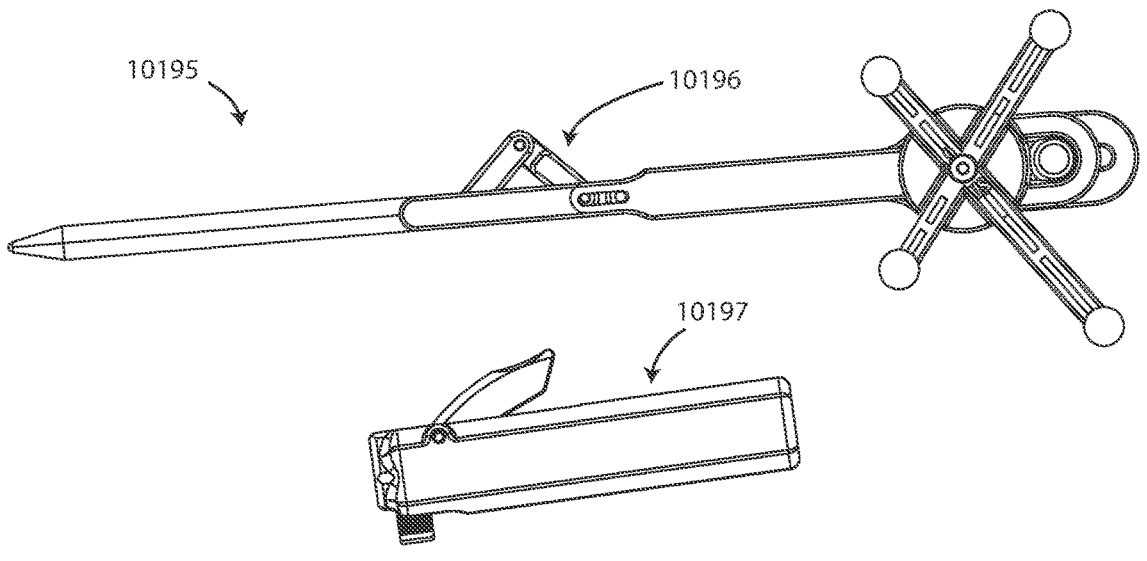

FIG. 101Q illustrates an assembly view of a 3D-tracked tool with a linear triggering mechanism, with the trigger sleeve oriented for a right-hand-dominant user, as described previously in relation to FIGS. 101A-101P in accordance with some embodiments of the invention.

Figures 102A, 102B, 102C:
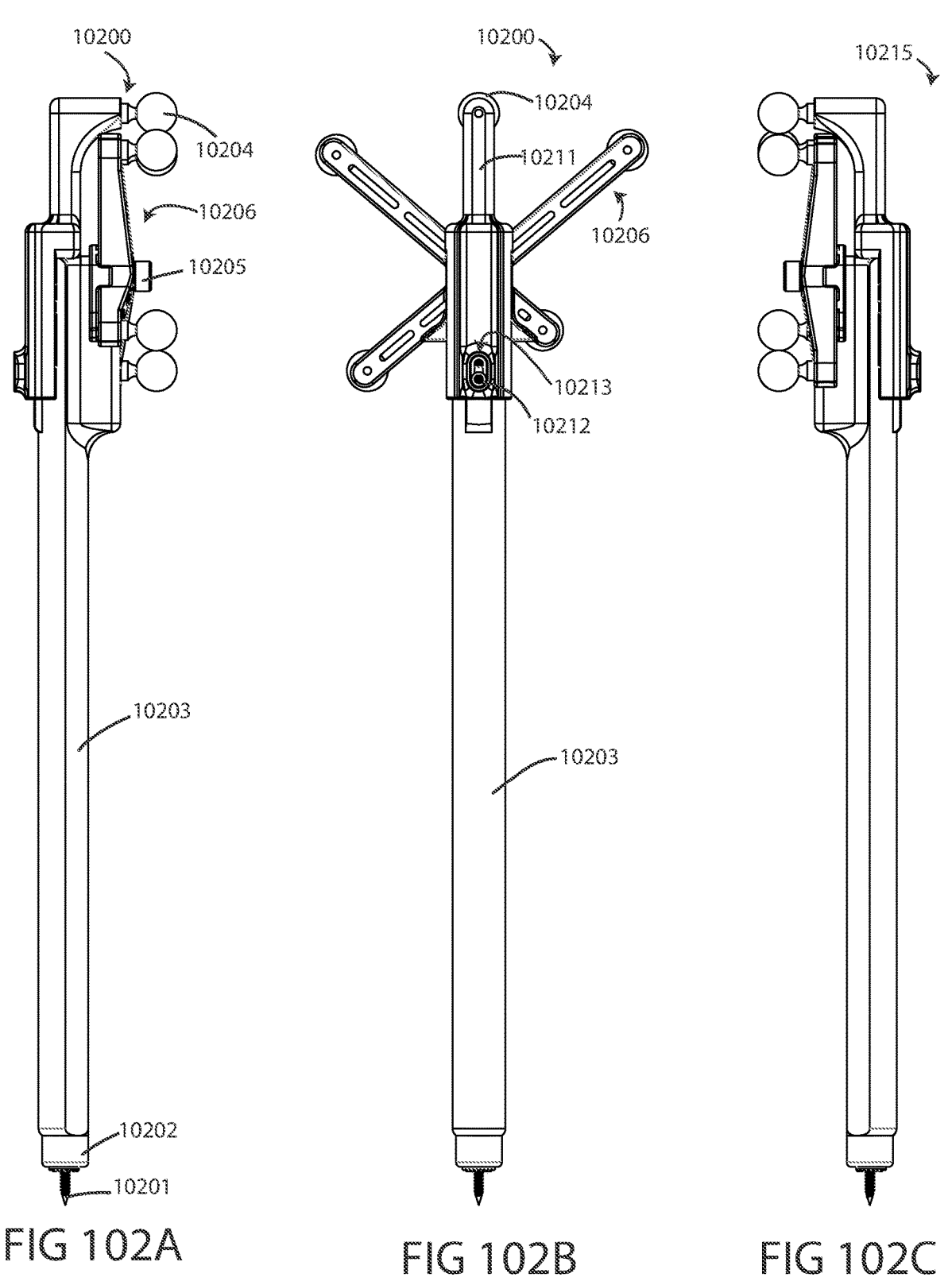

FIG. 102A illustrates a side view of a 3D-tracked tool engaged with an external-mating bone-mounted fiducial in accordance with some embodiments of the invention.

FIG. 102B illustrates a rear view of a 3D-tracked tool engaged with an external-mating bone-mounted fiducial as described previously in relation to FIG. 102A in accordance with some embodiments of the invention.

FIG. 102C illustrates a side view of a 3D-tracked tool engaged with an external-mating bone-mounted fiducial as described previously in relation to FIGS. 102A-102B in accordance with some embodiments of the invention.

Figures 102D, 102E, 102F:
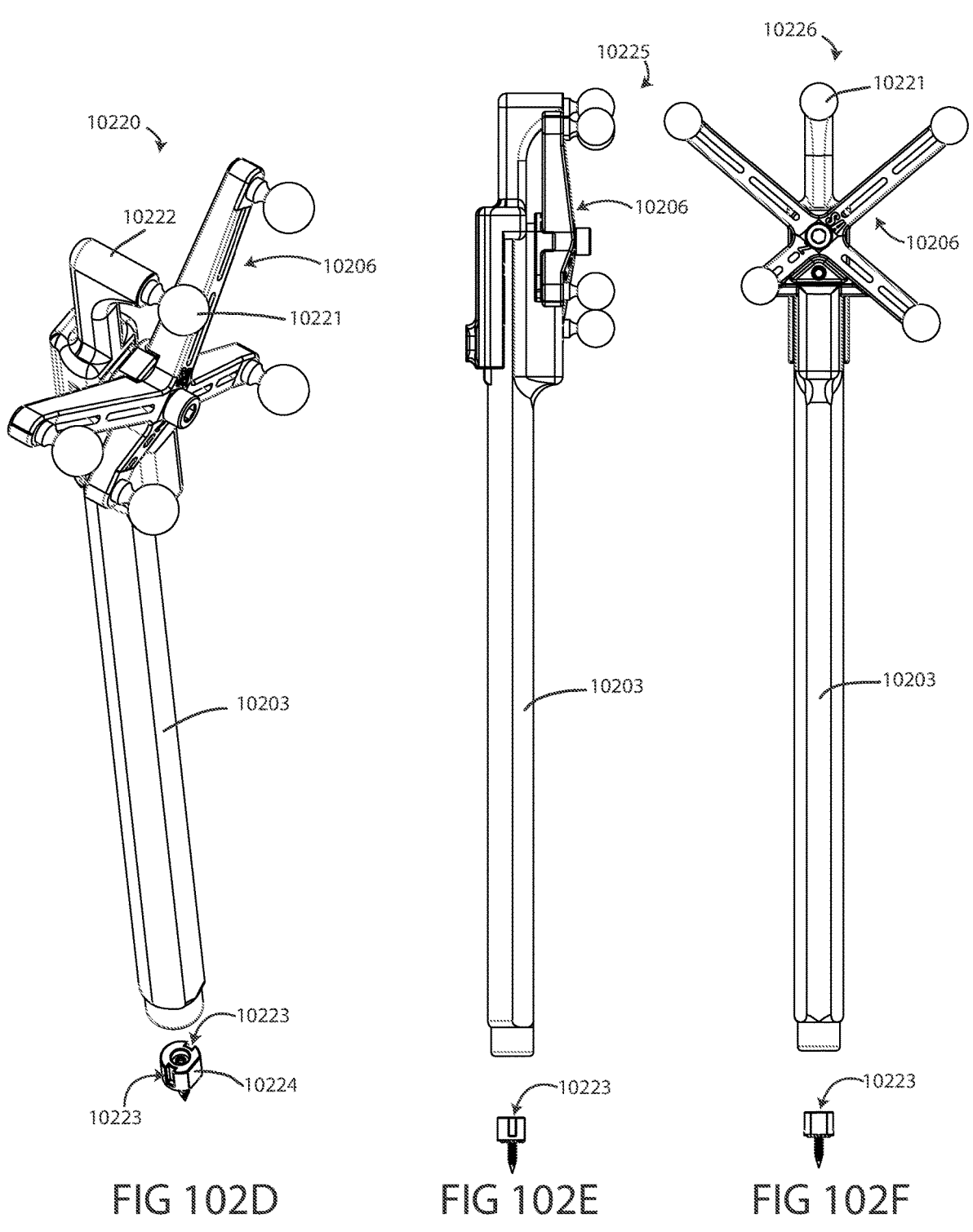

FIG. 102D illustrates a perspective assembly view of a 3D-tracked tool that is not engaged with an external-mating bone-mounted fiducial as described previously in relation to FIGS. 102A-102C in accordance with some embodiments of the invention.

FIG. 102E illustrates a side assembly view of a 3D-tracked tool that is not engaged with an external-mating bone-mounted fiducial as described previously in relation to FIGS. 102A-102D in accordance with some embodiments of the invention.

FIG. 102F illustrates a front assembly view of a 3D-tracked tool that is not engaged with an external-mating bone-mounted fiducial as described previously in relation to FIGS. 102A-102E in accordance with some embodiments of the invention.

FIG. 102G illustrates a perspective view of an external-mating bone-mounted fiducial as described previously in relation to FIGS. 102A-102F in accordance with some embodiments of the invention.

FIG. 102H illustrates a side view of an external-mating bone-mounted fiducial as described previously in relation to FIGS. 102A-102G in accordance with some embodiments of the invention.

FIG. 102I illustrates a perspective view of an external-mating bone-mounted fiducial as described previously in relation to FIGS. 102A-102H in accordance with some embodiments of the invention.

FIG. 102J illustrates a top view of an external-mating bone-mounted fiducial as described previously in relation to FIGS. 102A-102I in accordance with some embodiments of the invention.

FIG. 102K illustrates a side view of an external-mating bone-mounted fiducial as described previously in relation to FIGS. 102A-102J in accordance with some embodiments of the invention.

FIG. 102L illustrates a perspective view of an external-mating bone-mounted fiducial as described previously in relation to FIGS. 102A-102K in accordance with some embodiments of the invention.

FIG. 102M illustrates a perspective view of a 3D-tracked tool that is not engaged with an external-mating bone-mounted fiducial, as described previously in relation to FIGS. 102A-102L in accordance with some embodiments of the invention.

FIG. 102N illustrates a cross-sectional view of a 3D-tracked tool's triggering mechanism for engaging with an external-mating bone-mounted fiducial, as described previously in relation to FIGS. 102A-102M in accordance with some embodiments of the invention.

Figures 102O, 102P:
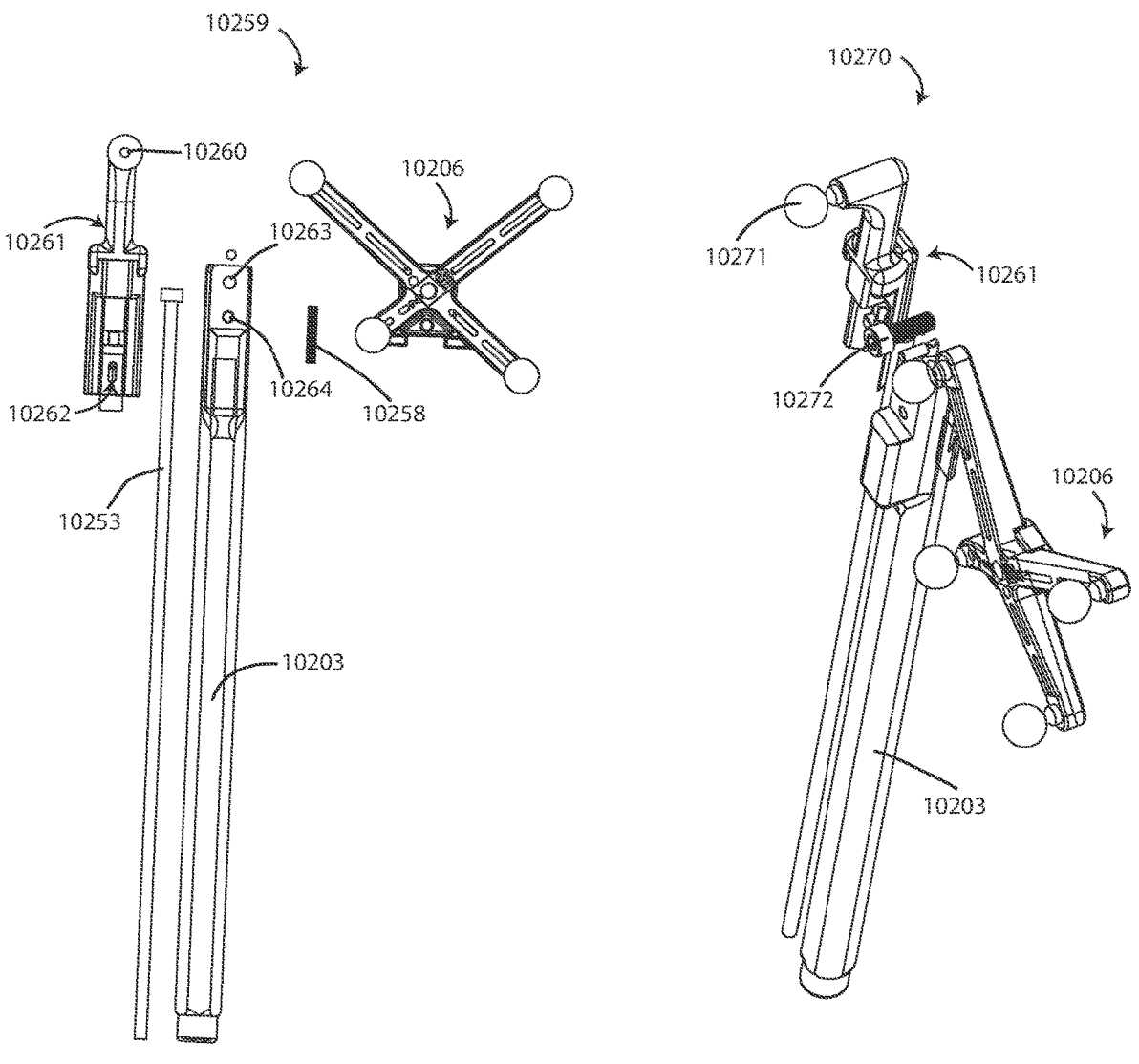

FIGS. 102O-102P illustrate assembly views of a 3D-tracked tool that mates with an external-mating bone-mounted fiducial, as described previously in relation to FIGS. 102A-102N in accordance with some embodiments of the invention.

Figures 103A, 103B, 103C:
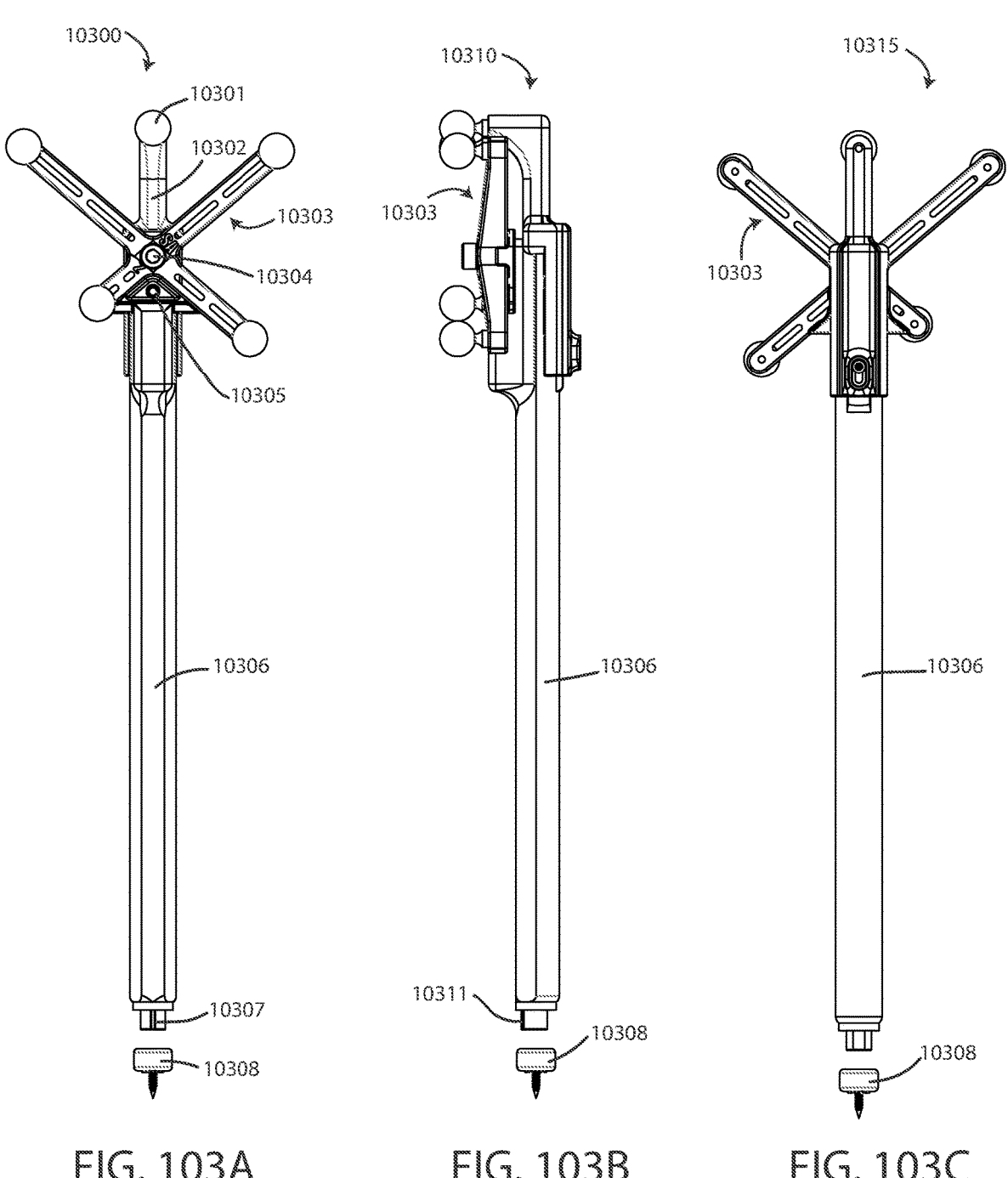

FIG. 103A illustrates a front view of a 3D-tracked tool that mates with an internal-mating bone-mounted fiducial in accordance with some embodiments of the invention.

FIG. 103B illustrates a side view of a 3D-tracked tool that mates with an internal-mating bone-mounted fiducial, as described previously in relation to FIG. 103A in accordance with some embodiments of the invention.

FIG. 103C illustrates a rear view of a 3D-tracked tool that mates with an internal-mating bone-mounted fiducial, as described previously in relation to FIGS. 103A-103B in accordance with some embodiments of the invention.

Figures 103D, 103E, 103F:
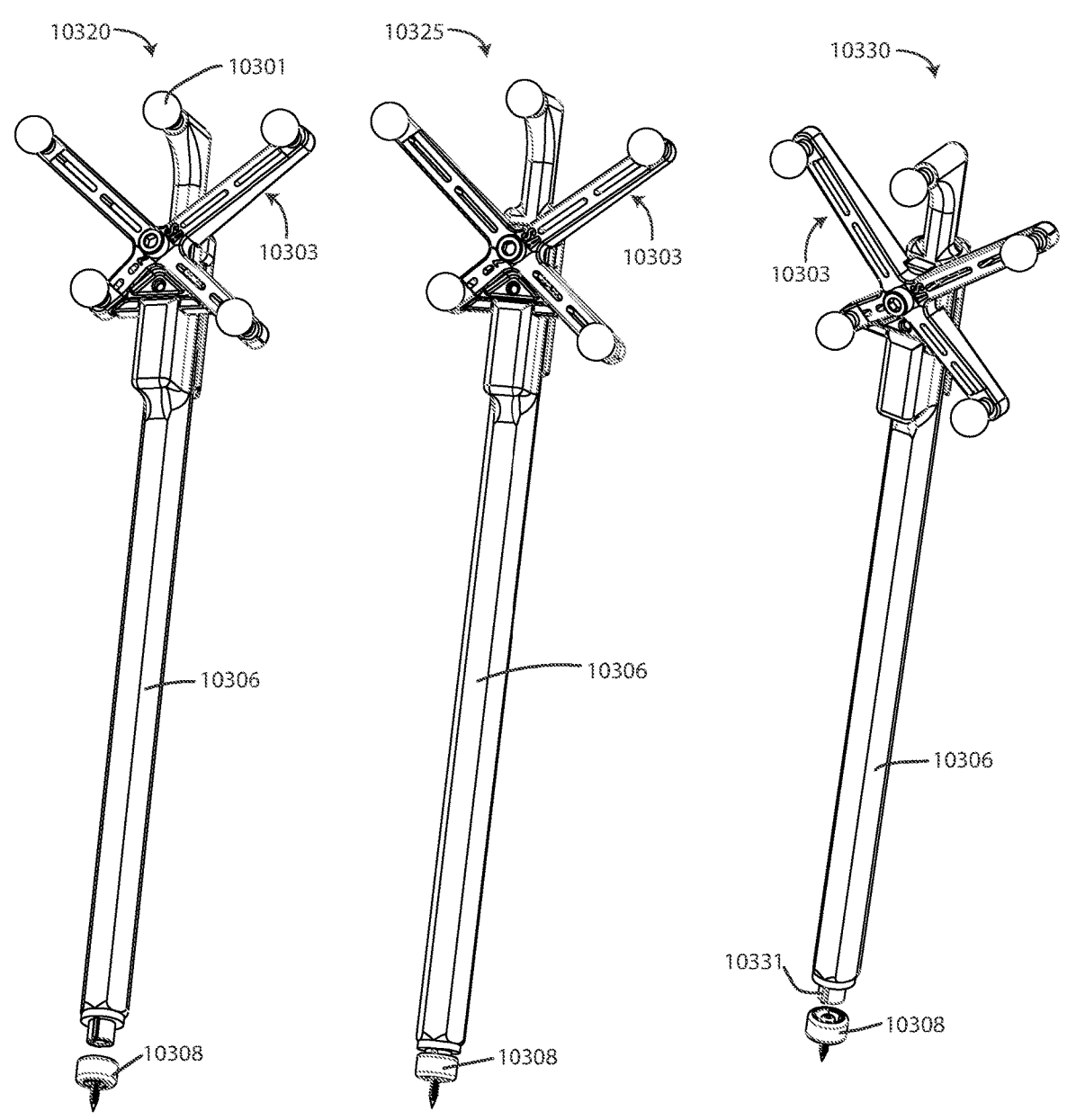

FIGS. 103D-103F illustrate perspective views of a 3D-tracked tool that mates with an internal-mating bone-mounted fiducial, as shown in its various mating trigger states, as described previously in relation to FIGS. 103A-103C in accordance with some embodiments of the invention.

Figures 103G, 103H, 103I:
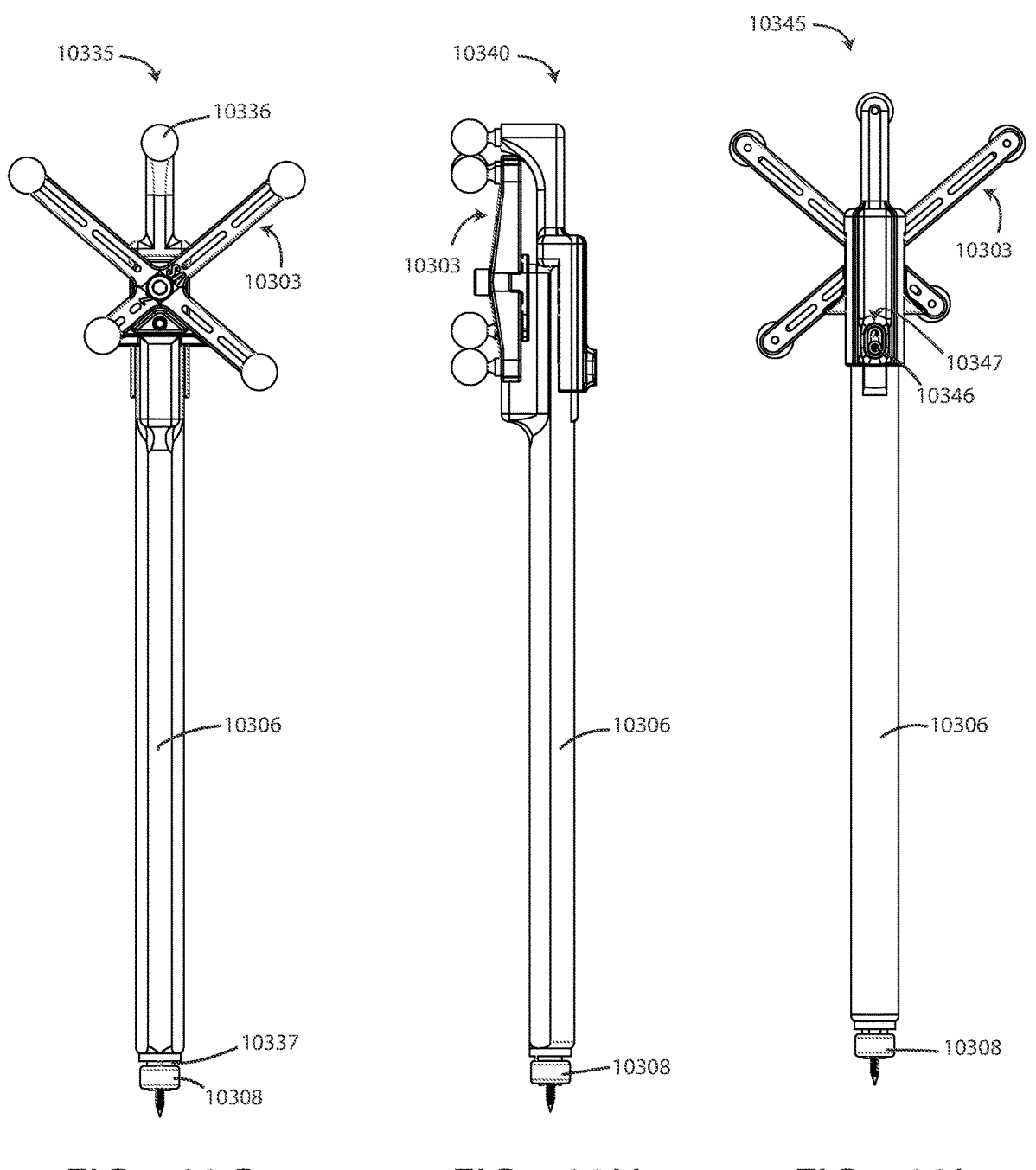

FIG. 103G illustrates a front view of a 3D-tracked tool that mates with an internal-mating bone-mounted fiducial, as shown with both devices fully mated, as described previously in relation to FIGS. 103A-103F in accordance with some embodiments of the invention.

FIG. 103H illustrates a side view of a 3D-tracked tool that mates with an internal-mating bone-mounted fiducial, as shown with both devices fully mated, as described previously in relation to FIGS. 103A-103G in accordance with some embodiments of the invention.

FIG. 103I illustrates a rear view of a 3D-tracked tool that mates with an internal-mating bone-mounted fiducial, as shown with both devices fully mated, as described previously in relation to FIGS. 103A-103H in accordance with some embodiments of the invention.

FIG. 103J illustrates a perspective view of an internal-mating bone-mounted fiducial's assembly components as described previously in relation to FIGS. 103A-103I in accordance with some embodiments of the invention.

FIG. 103K illustrates a side view of an internal-mating bone-mounted fiducial, as described previously in relation to FIGS. 103A-103J in accordance with some embodiments of the invention.

FIGS. 103L-103O illustrate perspective views of an internal-mating bone-mounted fiducial, as described previously in relation to FIGS. 103A-103K in accordance with some embodiments of the invention.

FIG. 103P illustrates a bottom view of a 3D-tracked tool that mates with an internal-mating bone-mounted fiducial, as described previously in relation to FIGS. 103A-103O in accordance with some embodiments of the invention.

FIG. 103Q illustrates a perspective view of a 3D-tracked tool that mates with an internal-mating bone-mounted fiducial, as described previously in relation to FIGS. 103A-103P in accordance with some embodiments of the invention.

Figures 104A, 104B, 104C:
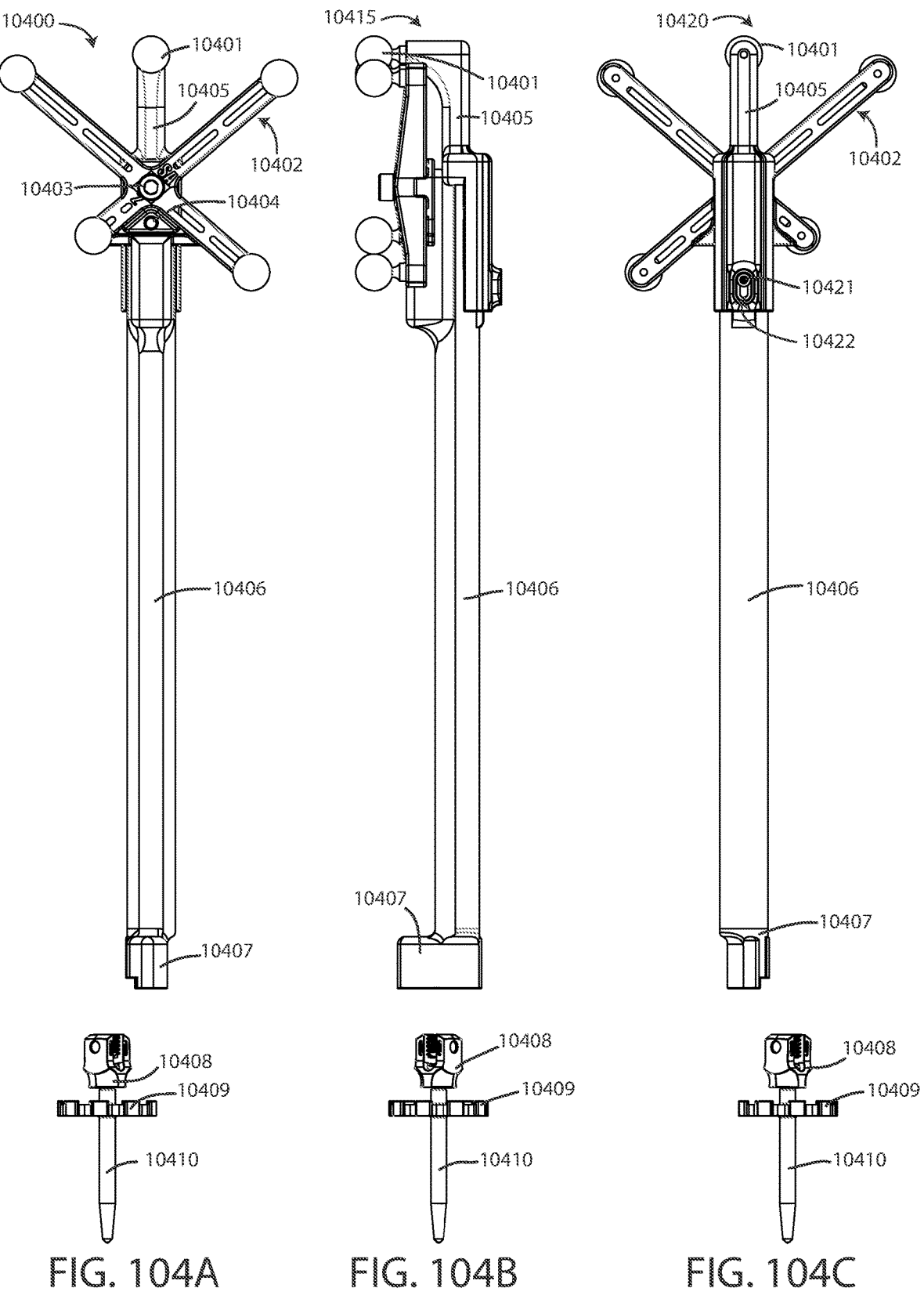

FIG. 104A illustrates a front view of a 3D-tracked tool that mates with a fastener with a depth-stop interface, with the devices not mated as shown, in accordance with some embodiments of the invention.

FIG. 104B illustrates a side view of a 3D-tracked tool that mates with a fastener with a depth-stop interface, with the devices not mated as shown, as described previously in relation to FIG. 104A in accordance with some embodiments of the invention.

FIG. 104C illustrates a rear view of a 3D-tracked tool that mates with a fastener with a depth-stop interface, with the devices not mated as shown, as described previously in relation to FIGS. 104A-104B in accordance with some embodiments of the invention.

Figures 104D, 104E, 104F:
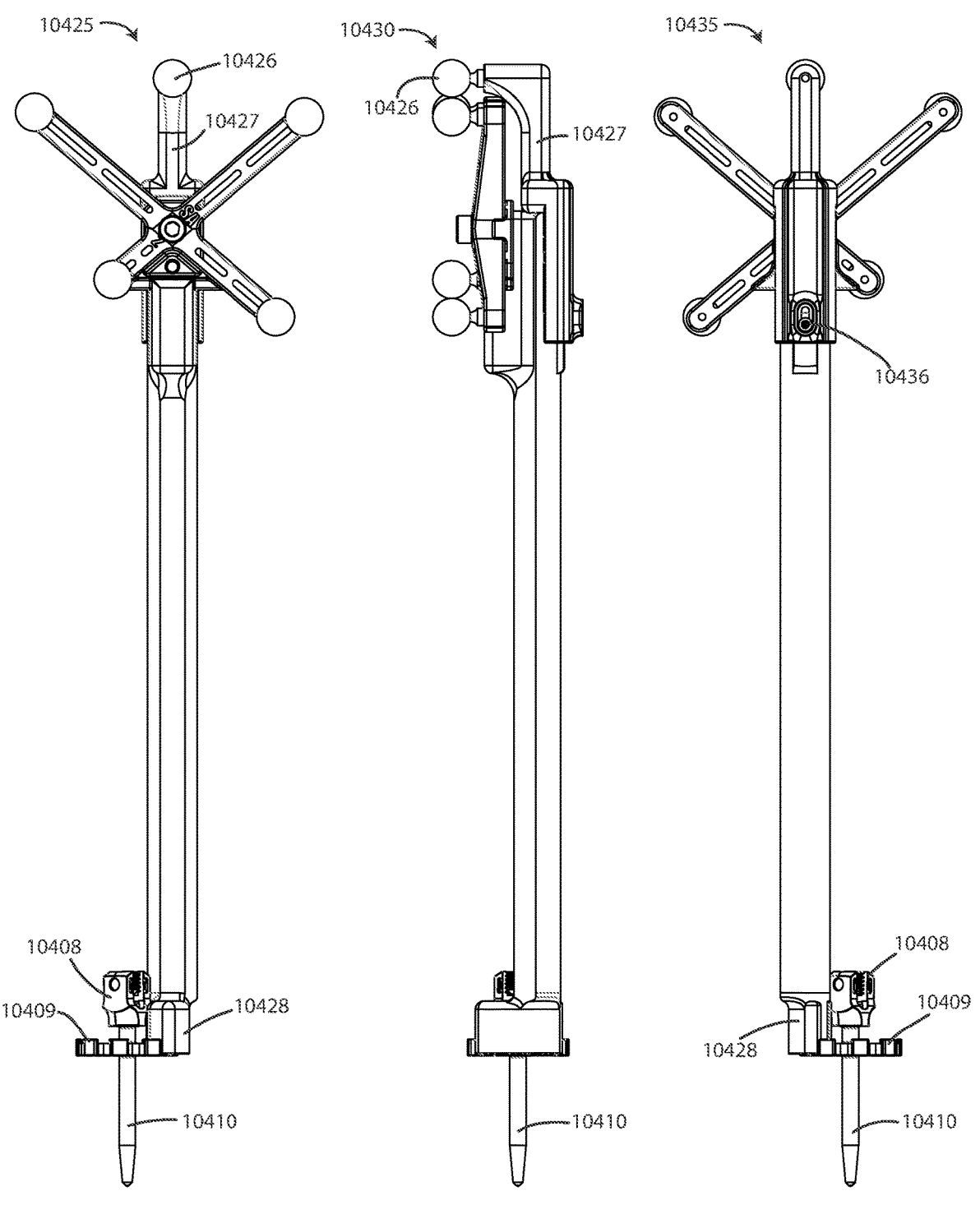

FIG. 104D illustrates a front view of a 3D-tracked tool that mates with a fastener with a depth-stop interface, with the devices mated as shown, as described previously in relation to FIGS. 104A-104C in accordance with some embodiments of the invention.

FIG. 104E illustrates a side view of a 3D-tracked tool that mates with a fastener with a depth-stop interface, with the devices mated as shown, as described previously in relation to FIGS. 104A-104D in accordance with some embodiments of the invention.

FIG. 104F illustrates a rear view of a 3D-tracked tool that mates with a fastener with a depth-stop interface, with the devices mated as shown, as described previously in relation to FIGS. 104A-104E in accordance with some embodiments of the invention.

Figures 104G, 104H, 104I:
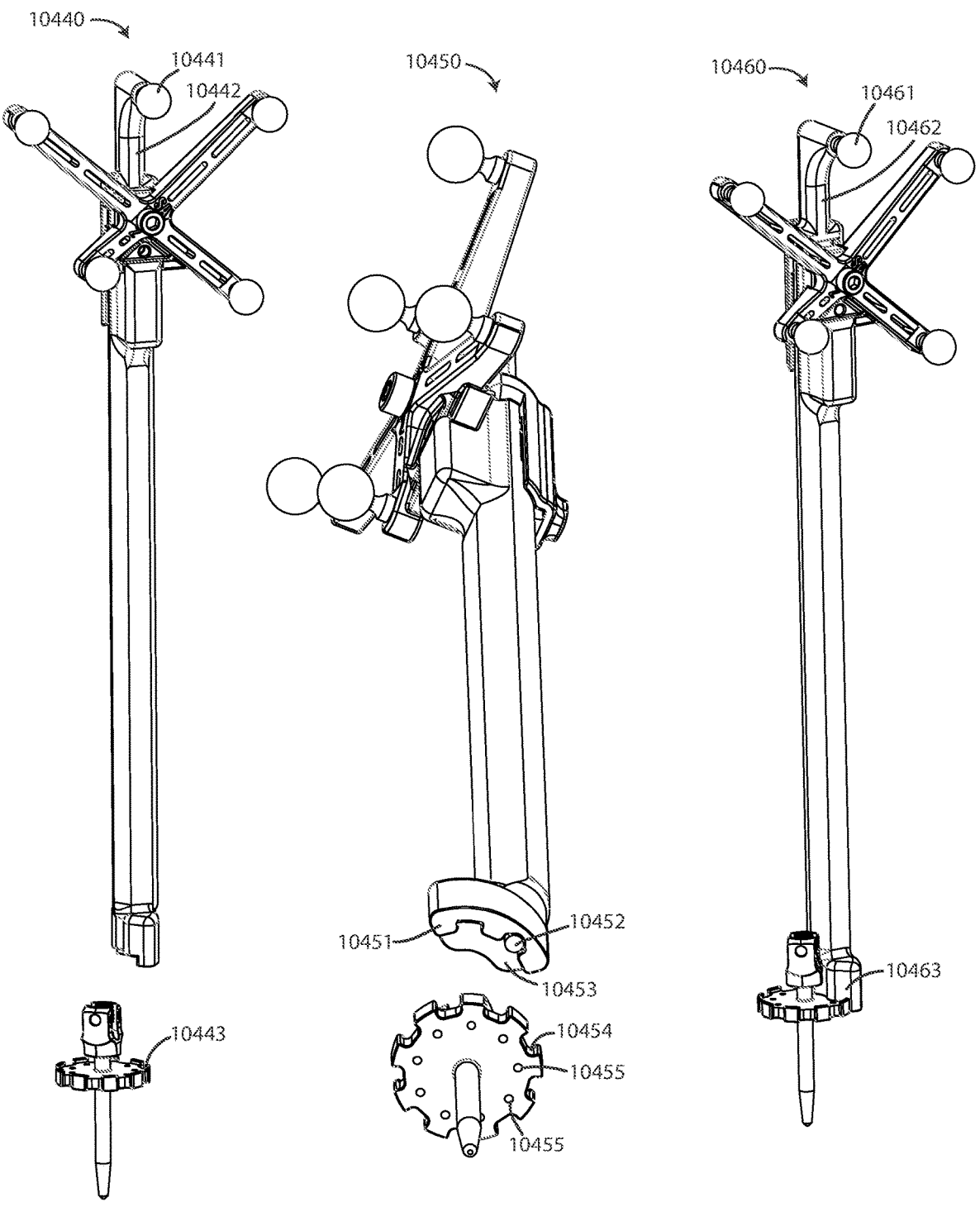

FIG. 104G illustrates a perspective view of a 3D-tracked tool that mates with a fastener with a depth-stop interface, with the devices not mated as shown, as described previously in relation to FIGS. 104A-104F in accordance with some embodiments of the invention.

FIG. 104H illustrates a perspective view of a mating interfaces between a 3D-tracked tool and a fastener with a depth-stop interface, with the devices not mated as shown, as described previously in relation to FIGS. 104A-104G in accordance with some embodiments of the invention.

FIG. 104I illustrates a perspective view of a 3D-tracked tool that mates with a fastener with a depth-stop interface, with the devices mated as shown, as described previously in relation to FIGS. 104A-104H in accordance with some embodiments of the invention.

Figure 104J:
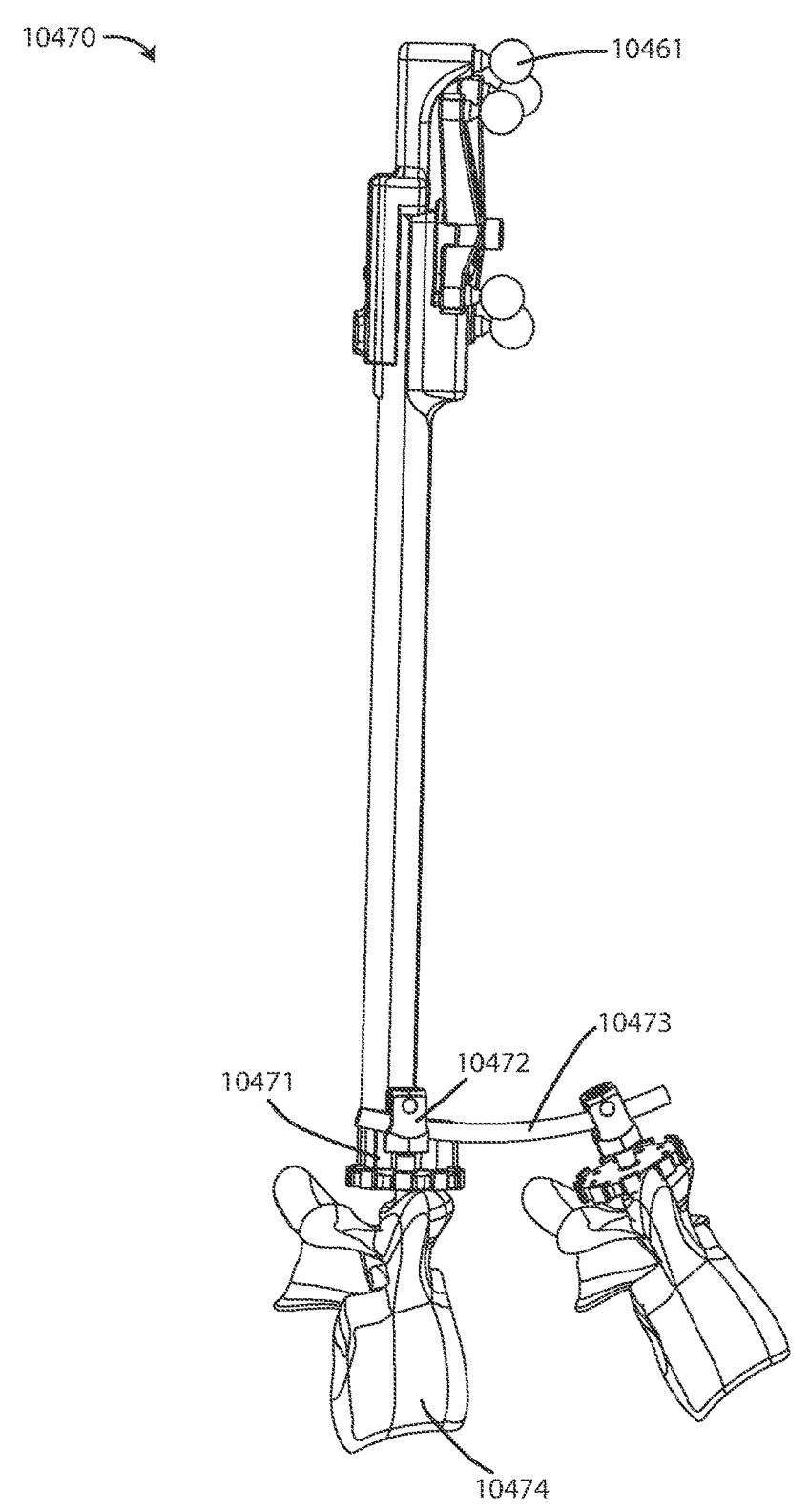

FIG. 104J illustrates a side view of a 3D-tracked tool that mates with a fastener with a depth-stop interface, with the devices mated and engaged to a vertebra with an implanted rod as shown, as described previously in relation to FIGS. 104A-104I in accordance with some embodiments of the invention.

Figure 105A:
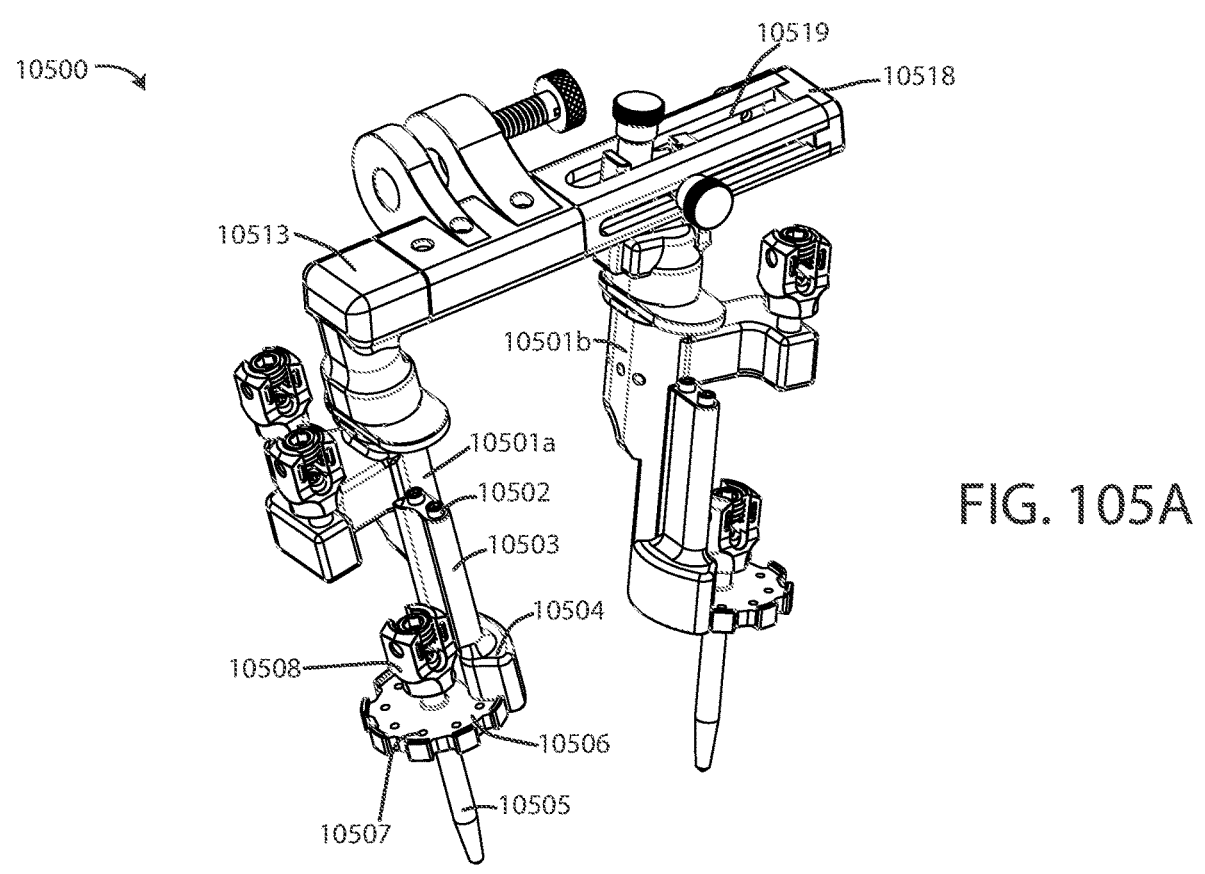

FIG. 105A illustrates a perspective view of an adjustable pedicle screw interface base, with one fixed side arm and one side arm with height and angle adjustments, and with the device mated with a fastener with depth-stop mating interfaces, of a flexibility assessment device in accordance with some embodiments of the invention.

Figure 105B:
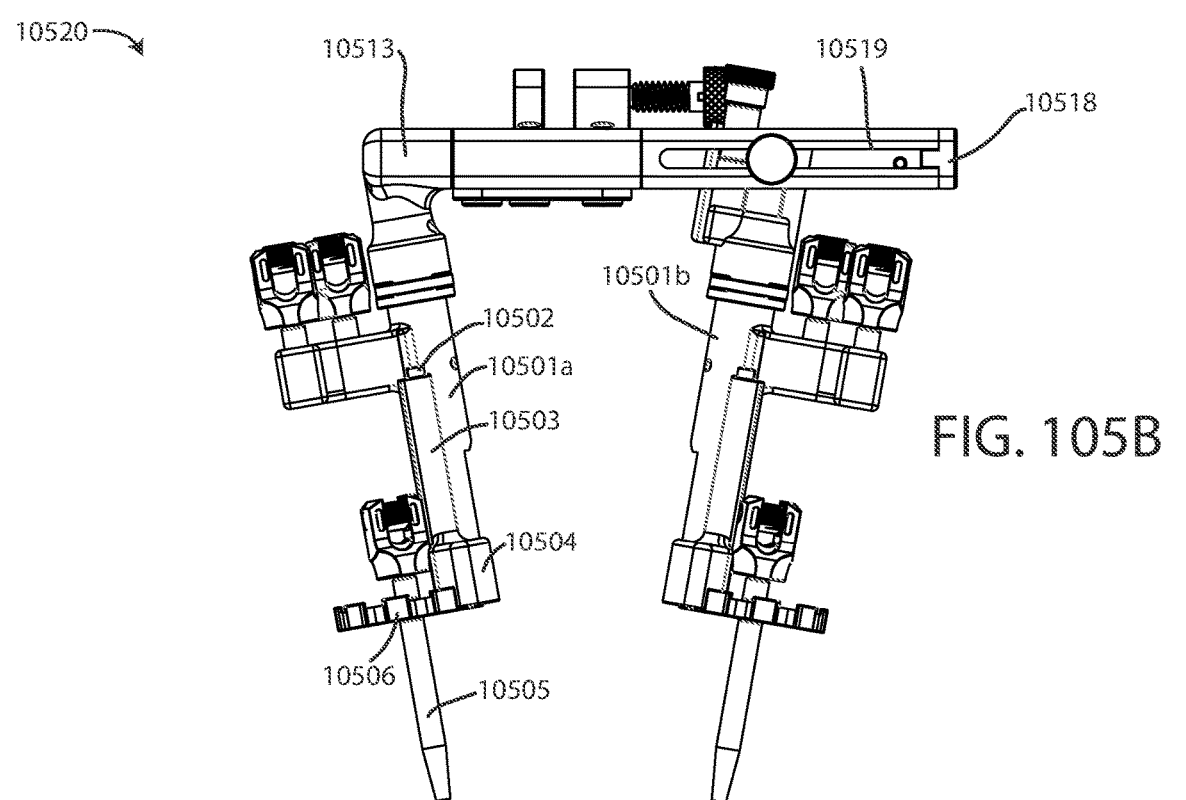

FIG. 105B illustrates a front view of an adjustable pedicle screw interface base, with one fixed side arm and one side arm with height and angle adjustments, and with the device mated with a fastener with depth-stop mating interfaces, of a flexibility assessment device as described previously in relation to FIG. 105A in accordance with some embodiments of the invention.

Figure 105C:
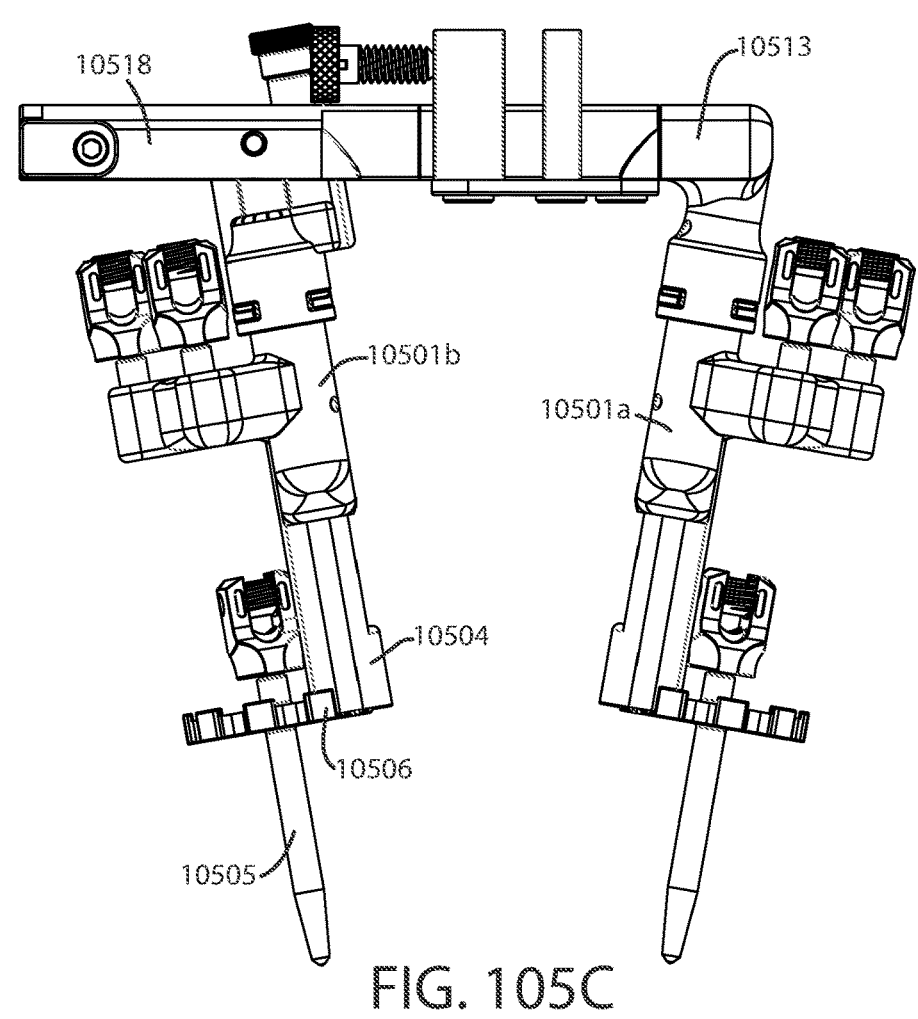

FIG. 105C illustrates a rear view of an adjustable pedicle screw interface base, with one fixed side arm and one side arm with height and angle adjustments, and with the device mated with a fastener with depth-stop mating interfaces, of a flexibility assessment device as described previously in relation to FIGS. 105A-105B in accordance with some embodiments of the invention.

Figure 105D:
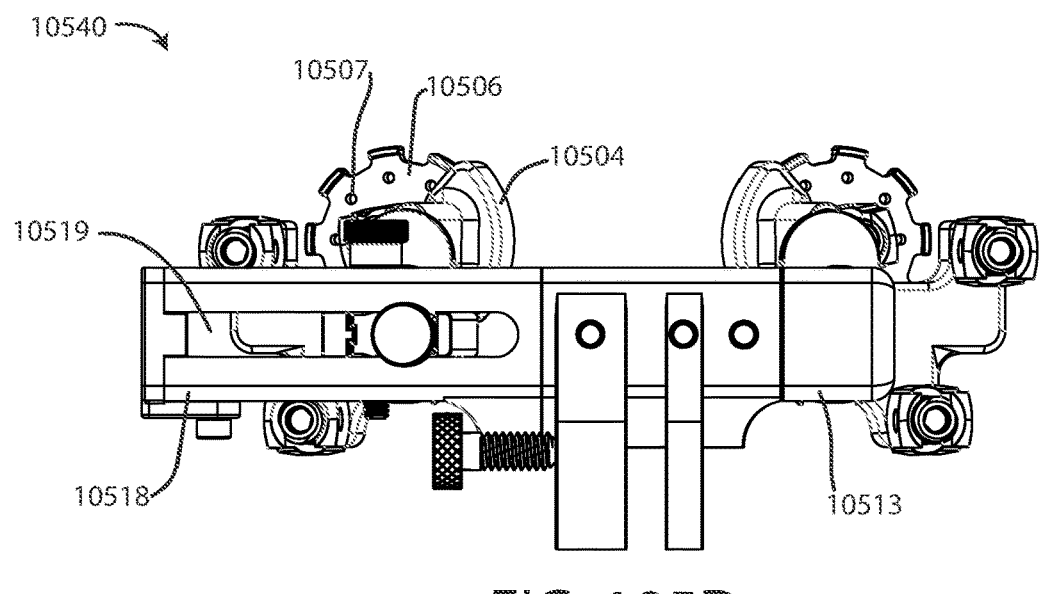

FIG. 105D illustrates a top view of an adjustable pedicle screw interface base, with one fixed side arm and one side arm with height and angle adjustments, and with the device mated with a fastener with depth-stop mating interfaces, of a flexibility assessment device as described previously in relation to FIGS. 105A-105C in accordance with some embodiments of the invention.

Figures 105E, 105F:
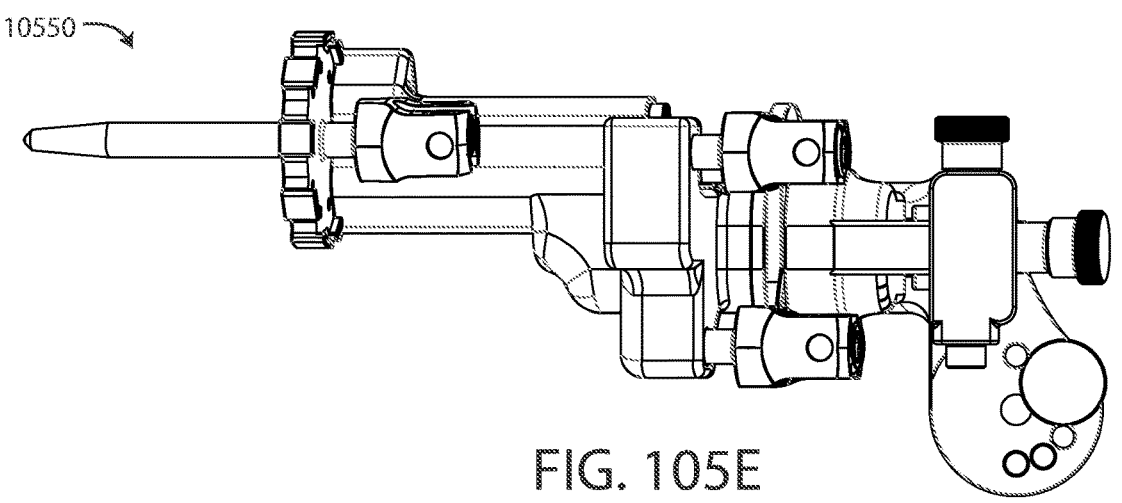

FIG. 105E illustrates a side view of an adjustable pedicle screw interface base, with one fixed side arm and one side arm with height and angle adjustments, and with the device mated with a fastener with depth-stop mating interfaces, of a flexibility assessment device as described previously in relation to FIGS. 105A-105D in accordance with some embodiments of the invention.

FIG. 105F illustrates a perspective view of an adjustable pedicle screw interface base, with one fixed side arm and one side arm with height and angle adjustments, and with the device mated with one of the displayed fasteners with depth-stop mating interfaces, of a flexibility assessment device as described previously in relation to FIGS. 105A-105E in accordance with some embodiments of the invention.

Figure 105G:
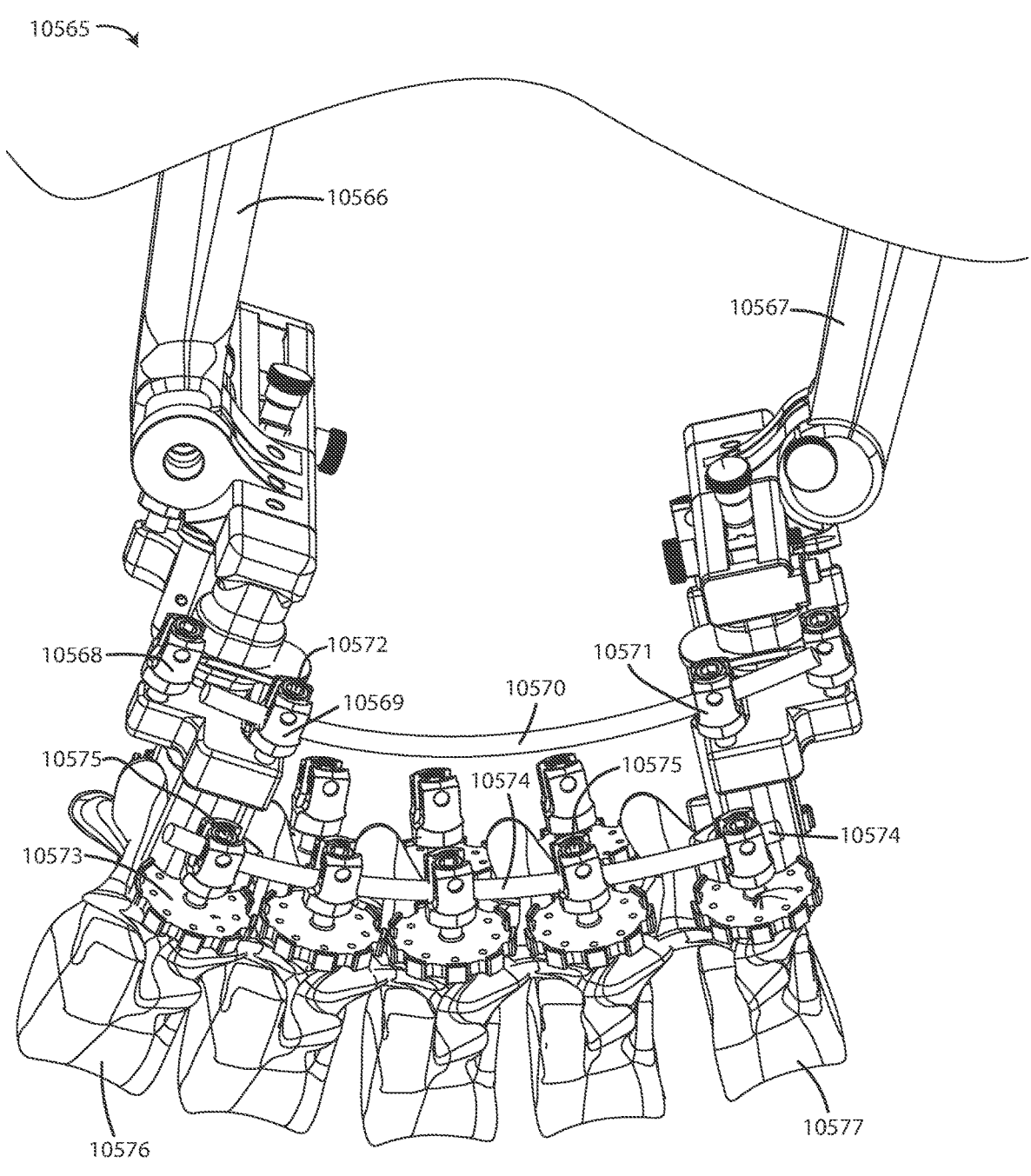

FIG. 105G illustrates a perspective view of flexibility assessment devices with adjustable pedicle screw interface bases, with the devices mated with fasteners with depth-stop mating interfaces, the engaged vertebrae substantially rigidly linked via an implanted rod, and the devices substantially rigidly linked via an accessory rod between the screw interface bases, as described previously in relation to FIGS. 105A-105F in accordance with some embodiments of the invention.

Figures 106A, 106B, 106C:
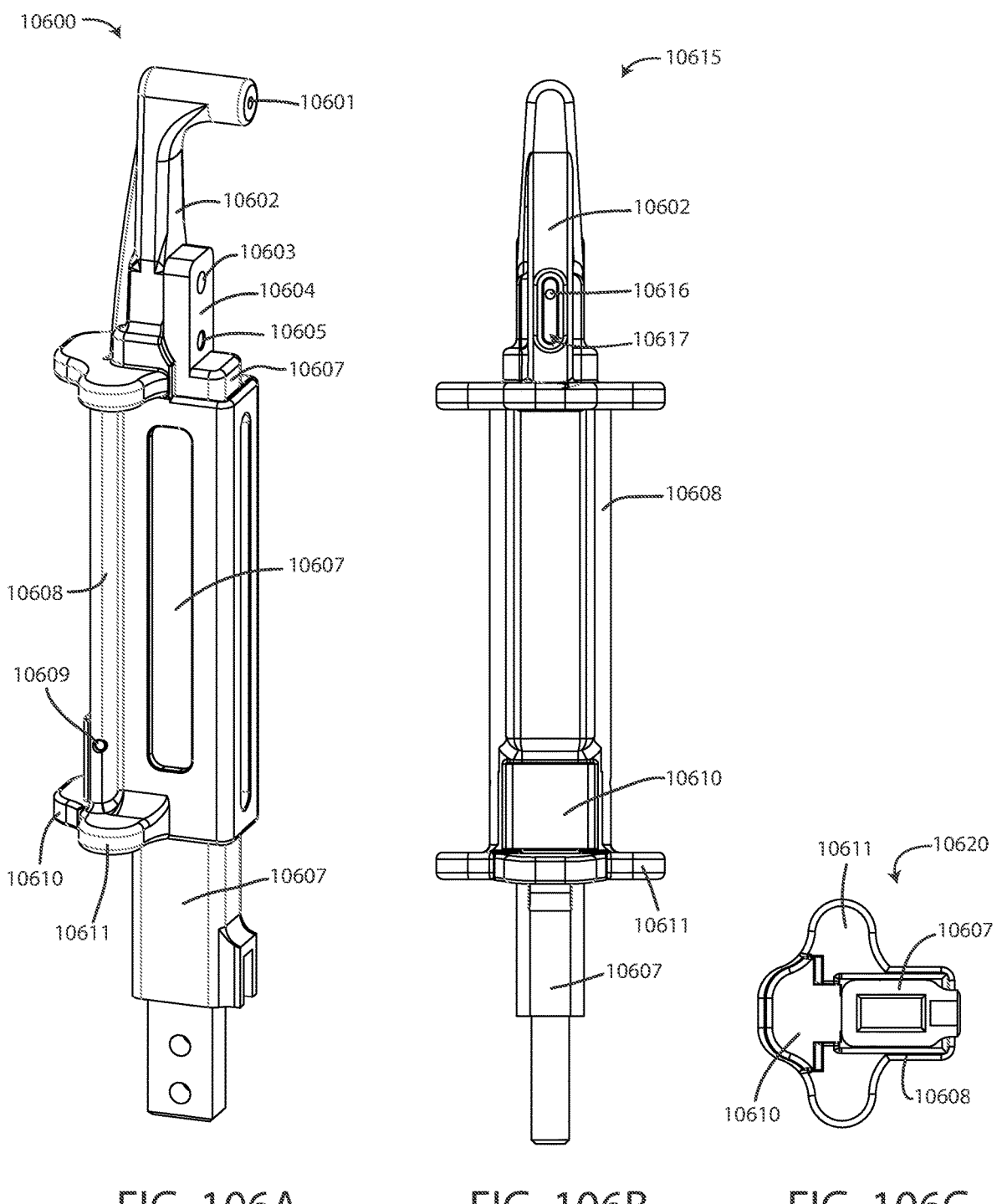

FIG. 106A illustrates a perspective view of a coordinate reference end cap device with a lockable trigger tab in accordance with some embodiments of the invention.

FIG. 106B illustrates a rear view of a coordinate reference end cap device with a lockable trigger tab, as described previously in relation to FIG. 106A in accordance with some embodiments of the invention.

FIG. 106C illustrates a top view of a coordinate reference end cap device with a lockable trigger tab, as described previously in relation to FIGS. 106A-106B in accordance with some embodiments of the invention.

Figures 106D, 106E:
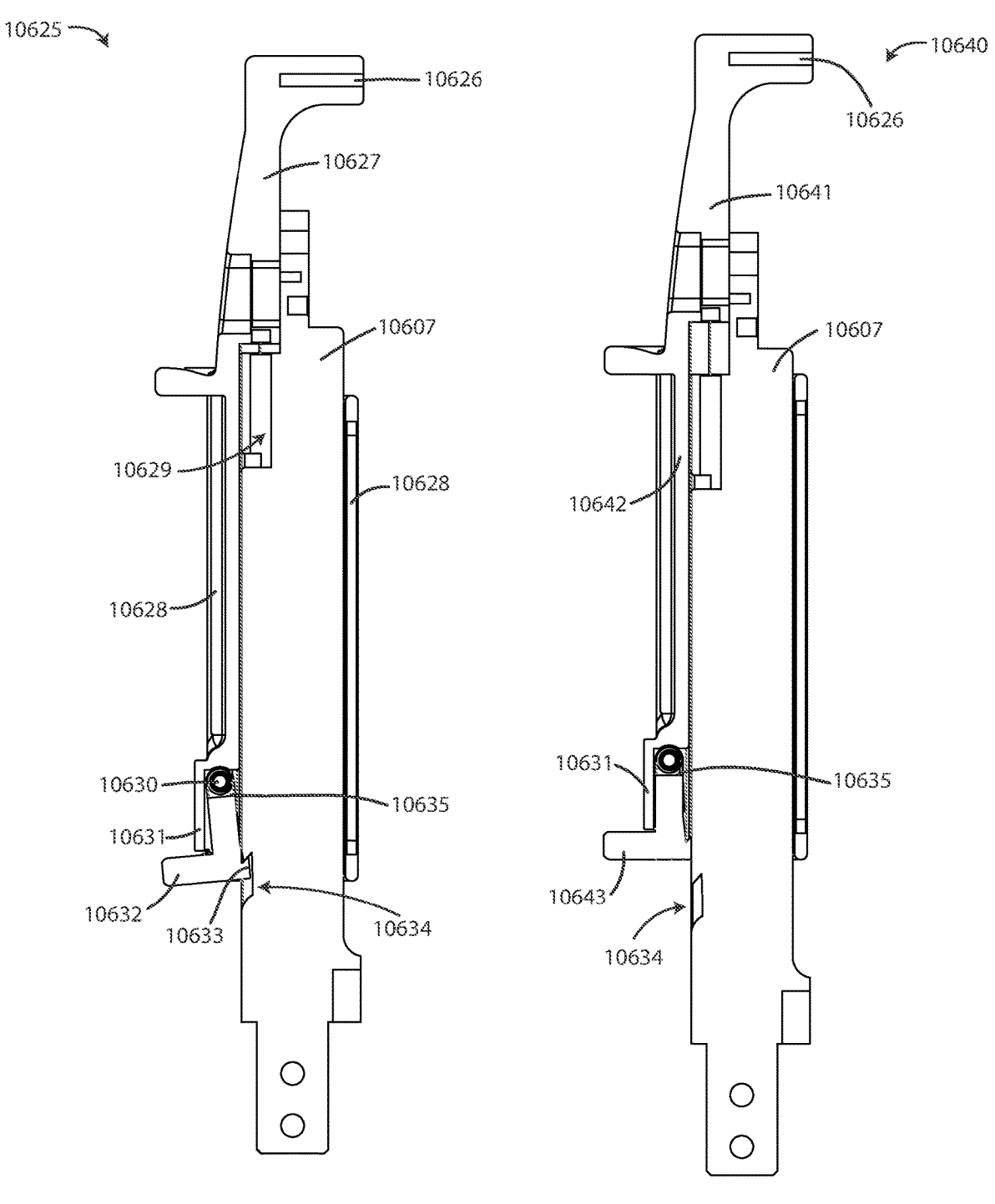

FIG. 106D illustrates a side cross-sectional view of a coordinate reference end cap device with a lockable trigger tab in its active locking state, as described previously in relation to FIGS. 106A-106C in accordance with some embodiments of the invention.

FIG. 106E illustrates a side cross-sectional view of a coordinate reference end cap device with a lockable trigger tab in its inactive locking state, as described previously in relation to FIGS. 106A-106D in accordance with some embodiments of the invention.

Figure 106F:
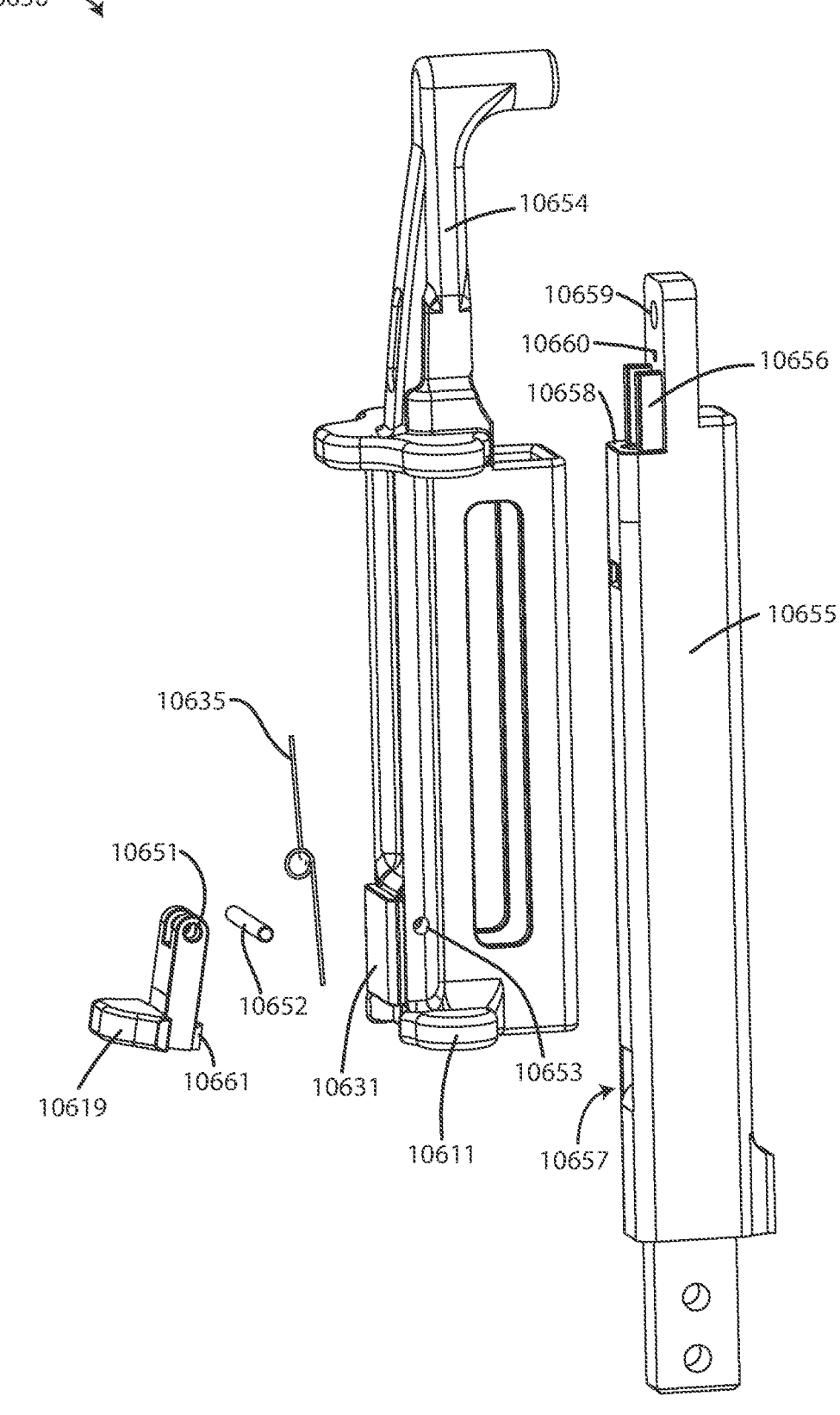

FIG. 106F illustrates an assembly view of a coordinate reference end cap device with a lockable trigger tab, as described previously in relation to FIGS. 106A-106E in accordance with some embodiments of the invention.

Figure 107A:
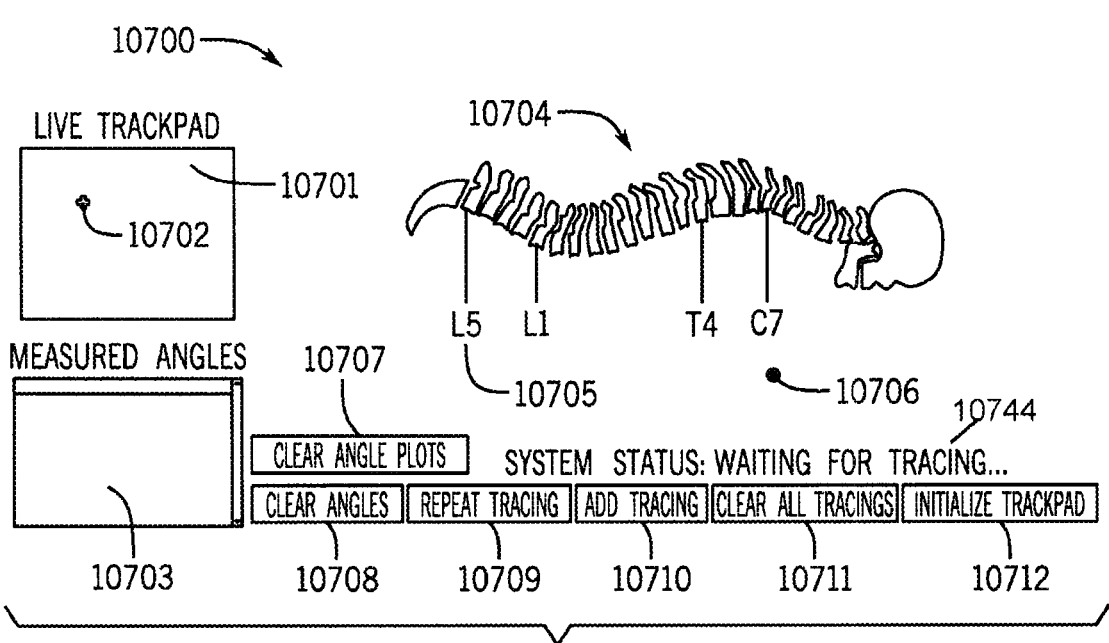

FIG. 107A illustrates a display interface for analyzing the contour of patient and illustrating spinal alignment parameters from landmarks of interest, as well as a trackpad display-controlling interface in its active state, in accordance with some embodiments of the invention.

Figure 107B:
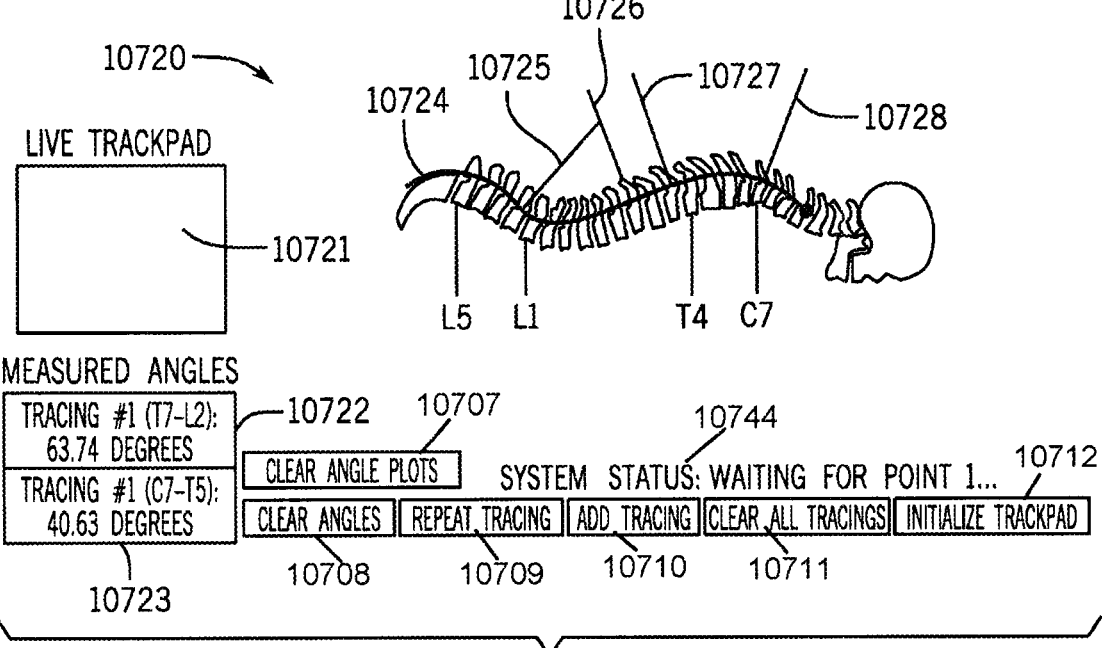

FIG. 107B illustrates a display interface for analyzing the contour of patient and illustrating spinal alignment parameters from landmarks of interest, as well as a trackpad display-controlling interface in its inactive state, as described previously in relation to FIG. 107A in accordance with some embodiments of the invention.

Figure 107C:
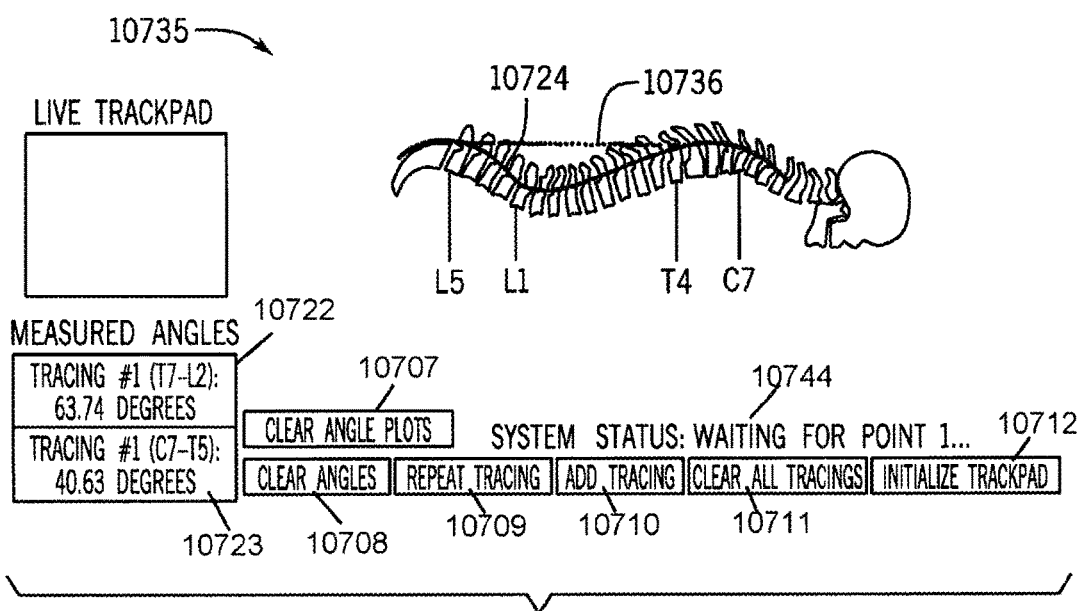

FIG. 107C illustrates a display interface for analyzing the contour of patient and illustrating spinal alignment parameters from landmarks of interest, as well as a trackpad display-controlling interface and overlays of several contour acquisitions, as described previously in relation to FIGS. 107A-107B in accordance with some embodiments of the invention.

Figure 107D:
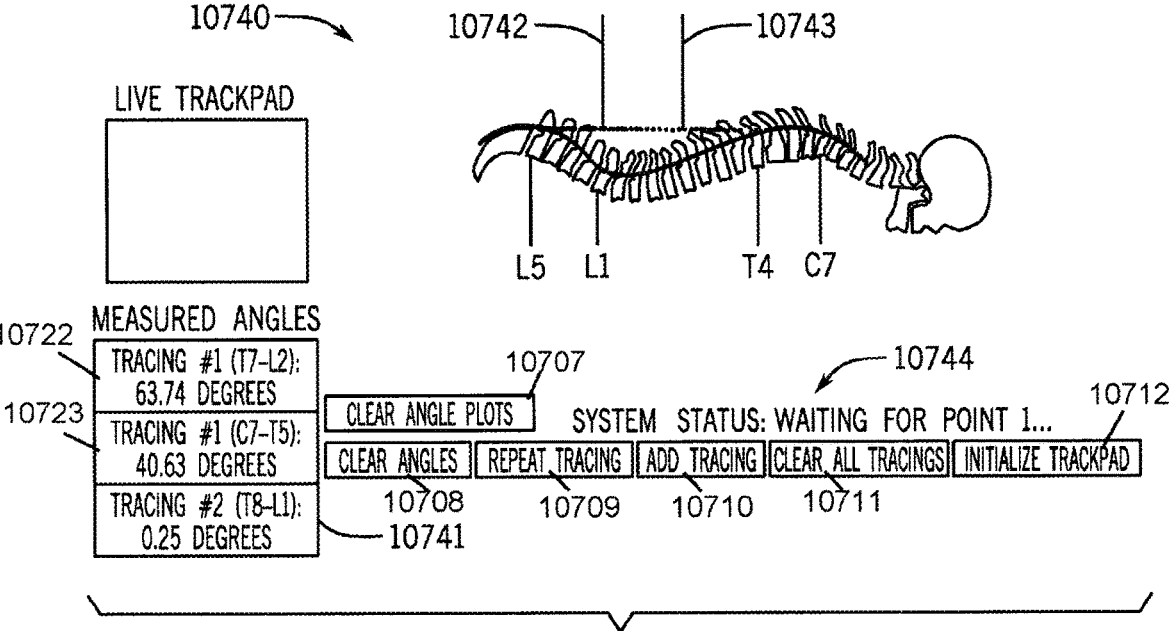

FIG. 107D illustrates a display interface for analyzing the contour of patient and illustrating spinal alignment parameters from landmarks of interest, as well as a trackpad display-controlling interface, overlays of several contour acquisitions, and the latest contour's measurements, as described previously in relation to FIGS. 107A-107C in accordance with some embodiments of the invention.

Figures 108A, 108B:
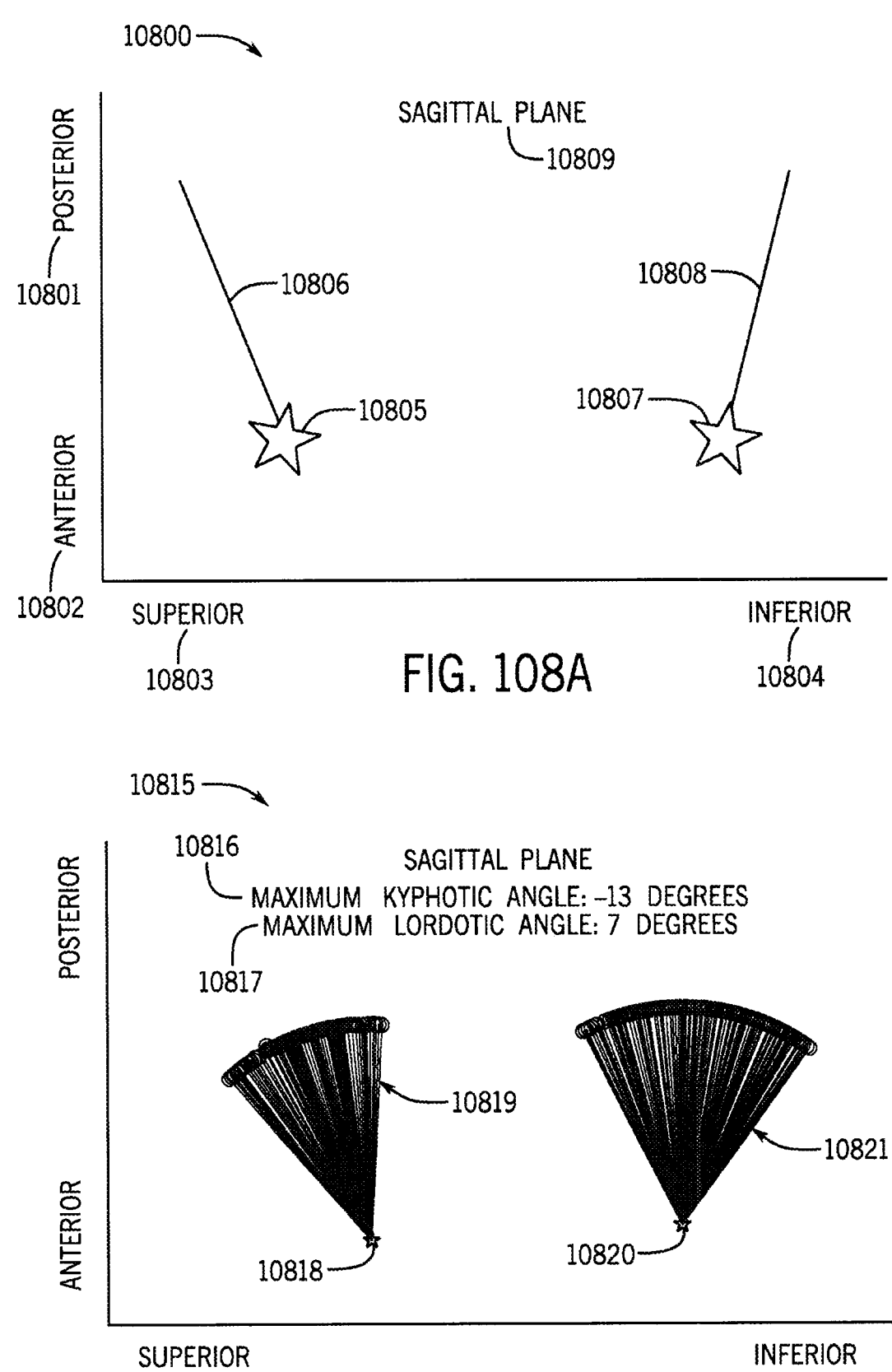

FIG. 108A illustrates a display interface for analyzing the position and orientation of flexibility assessment devices in accordance with some embodiments of the invention.

Figures 108C, 108D:
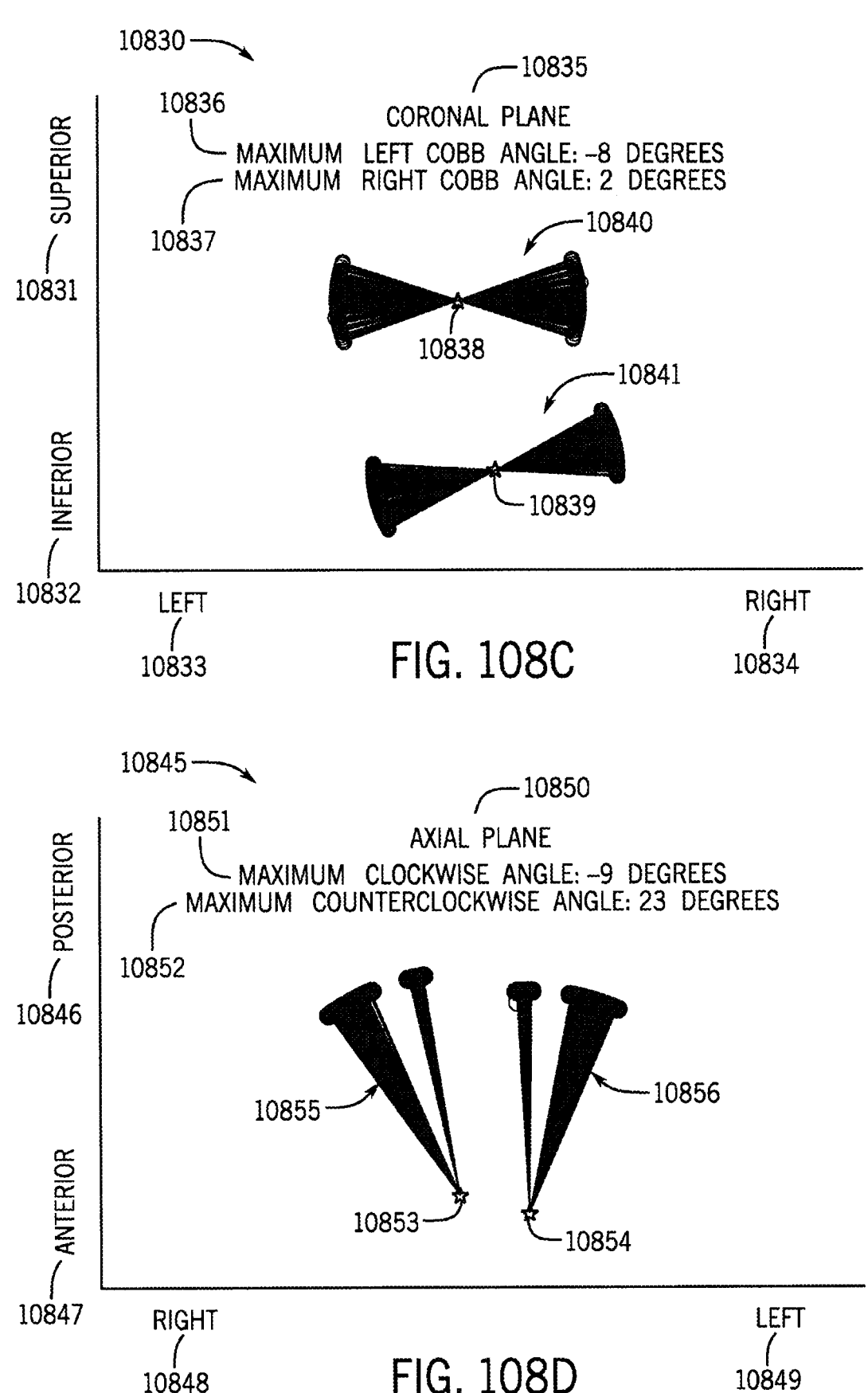

FIGS. 108B-108D illustrate a display interface for analyzing the position and orientation of flexibility assessment devices, with the devices in their active triggering state and displaying the range of the motion of engaged vertebrae across all anatomical planes, as described previously in relation to FIG. 108A in accordance with some embodiments of the invention.

Figure 108E:
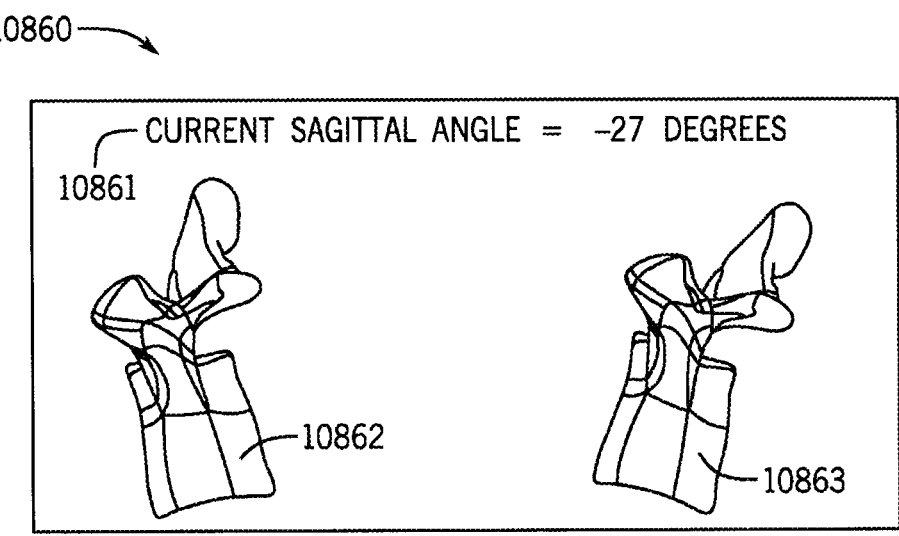

FIG. 108E illustrates a display interface for analyzing the position and orientation of flexibility assessment devices, with the devices in their active triggering state and displaying a rendered view of each engaged vertebra, as described previously in relation to FIGS. 108A-108D in accordance with some embodiments of the invention.

Figure 108F:
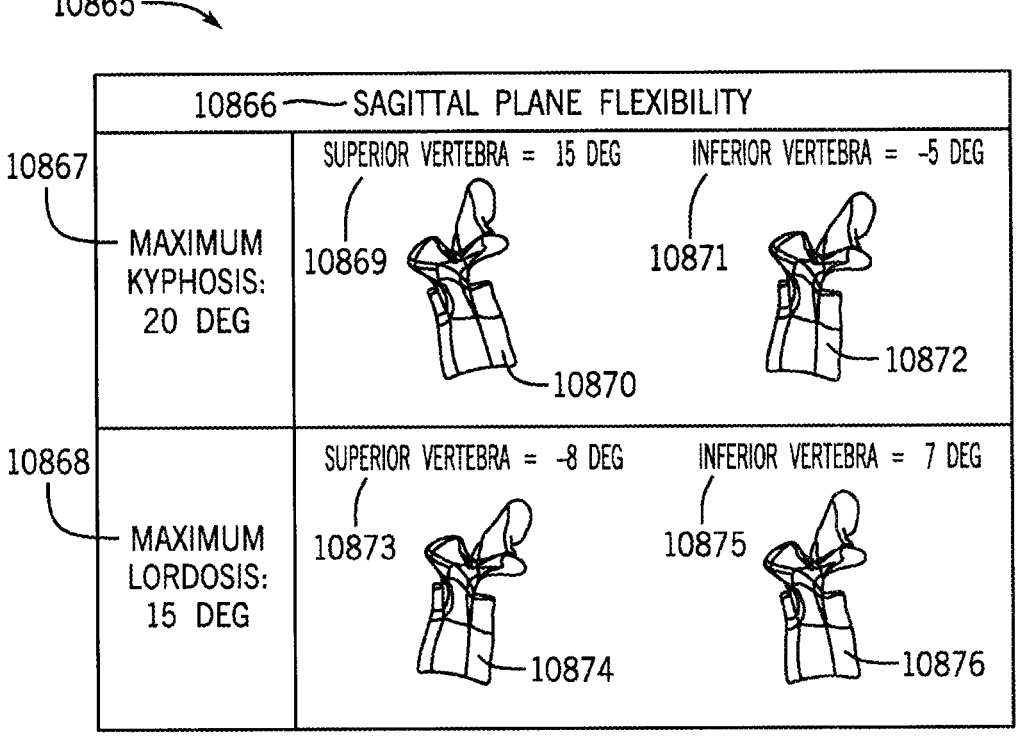
Figure 108G:
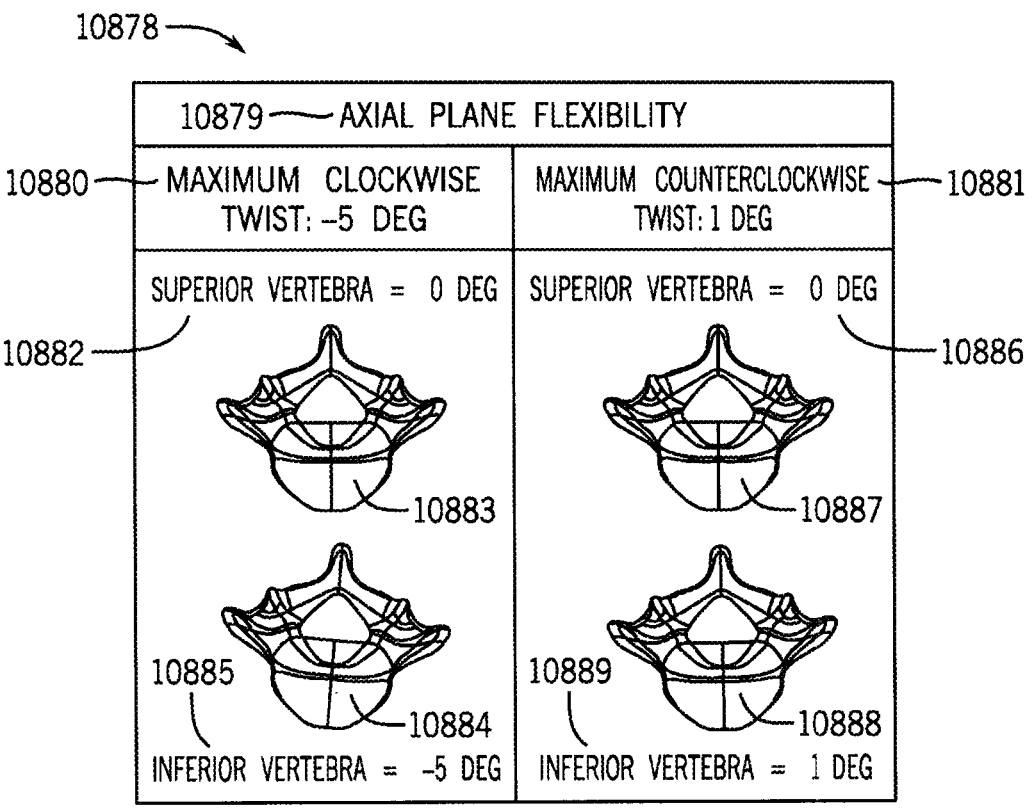
Figure 108H:
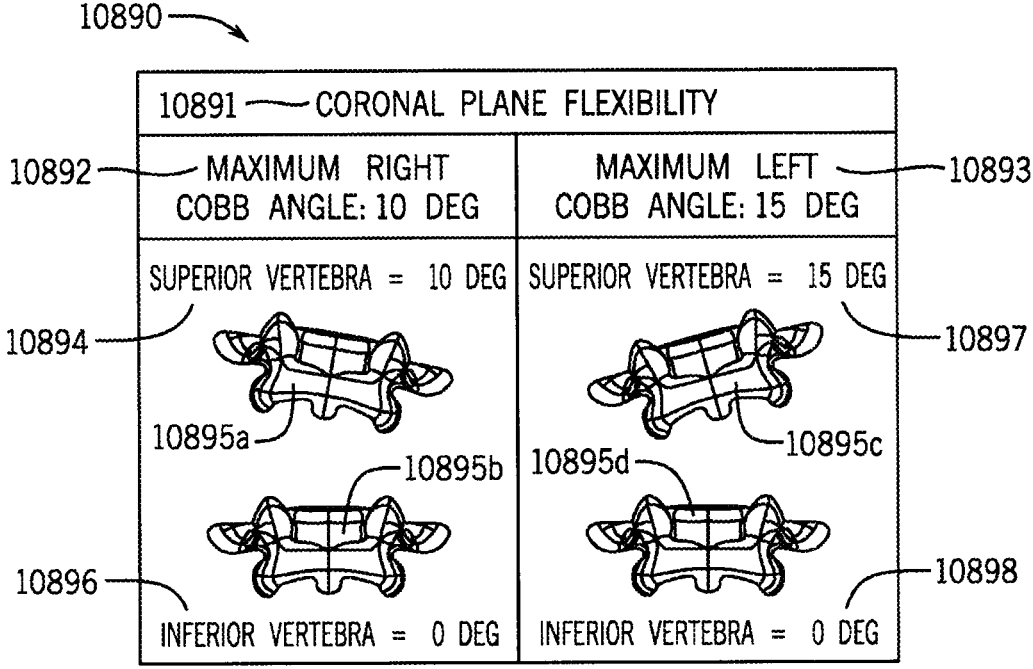

FIGS. 108F-108H illustrate a display interface for analyzing the position and orientation of flexibility assessment devices, displaying a summary view across all anatomical planes of the exhibited range of motion of engaged vertebrae during an assessment, as described previously in relation to FIGS. 108A-108E in accordance with some embodiments of the invention.

Figure 109A:
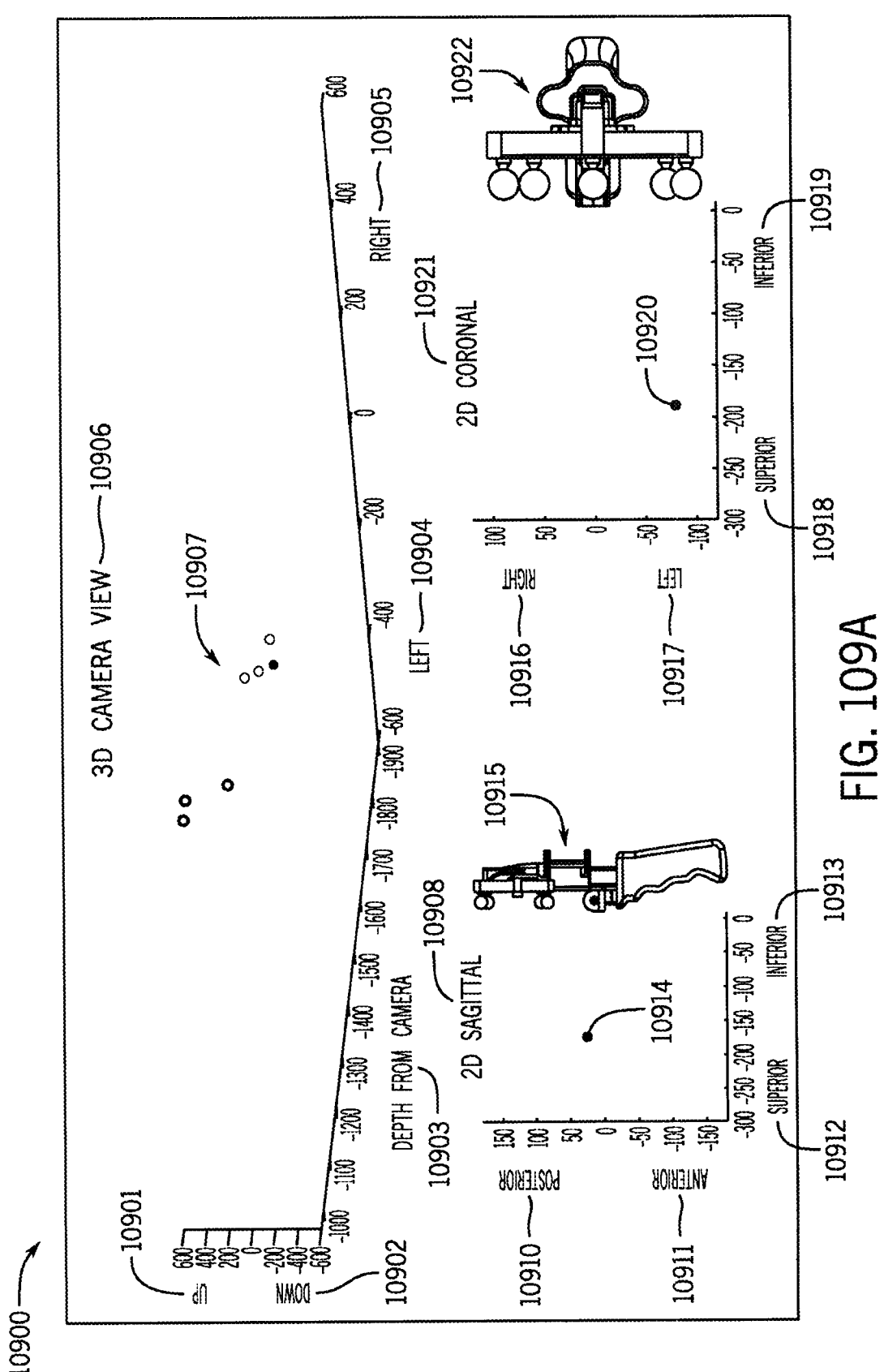

FIG. 109A illustrates a display interface for displaying the live location of devices used for the registration of a rod contour in accordance with some embodiments of the invention.

Figure 109B:
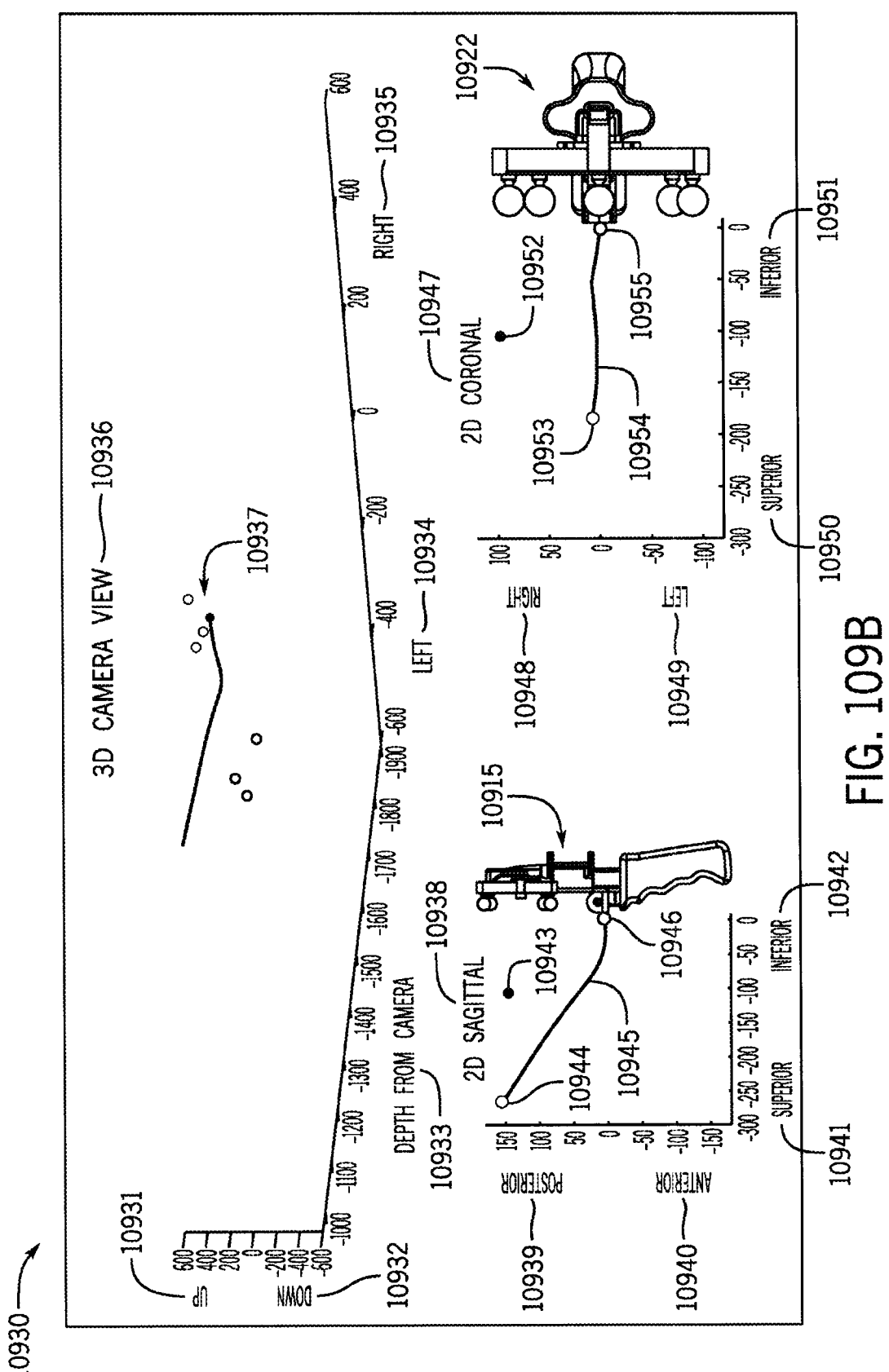

FIG. 109B illustrates a display interface for displaying the live location of devices used for the registration of a rod contour and a completed tracing of the rod's contour as described previously in relation to FIG. 109A in accordance with some embodiments of the invention.

Figure 109C:
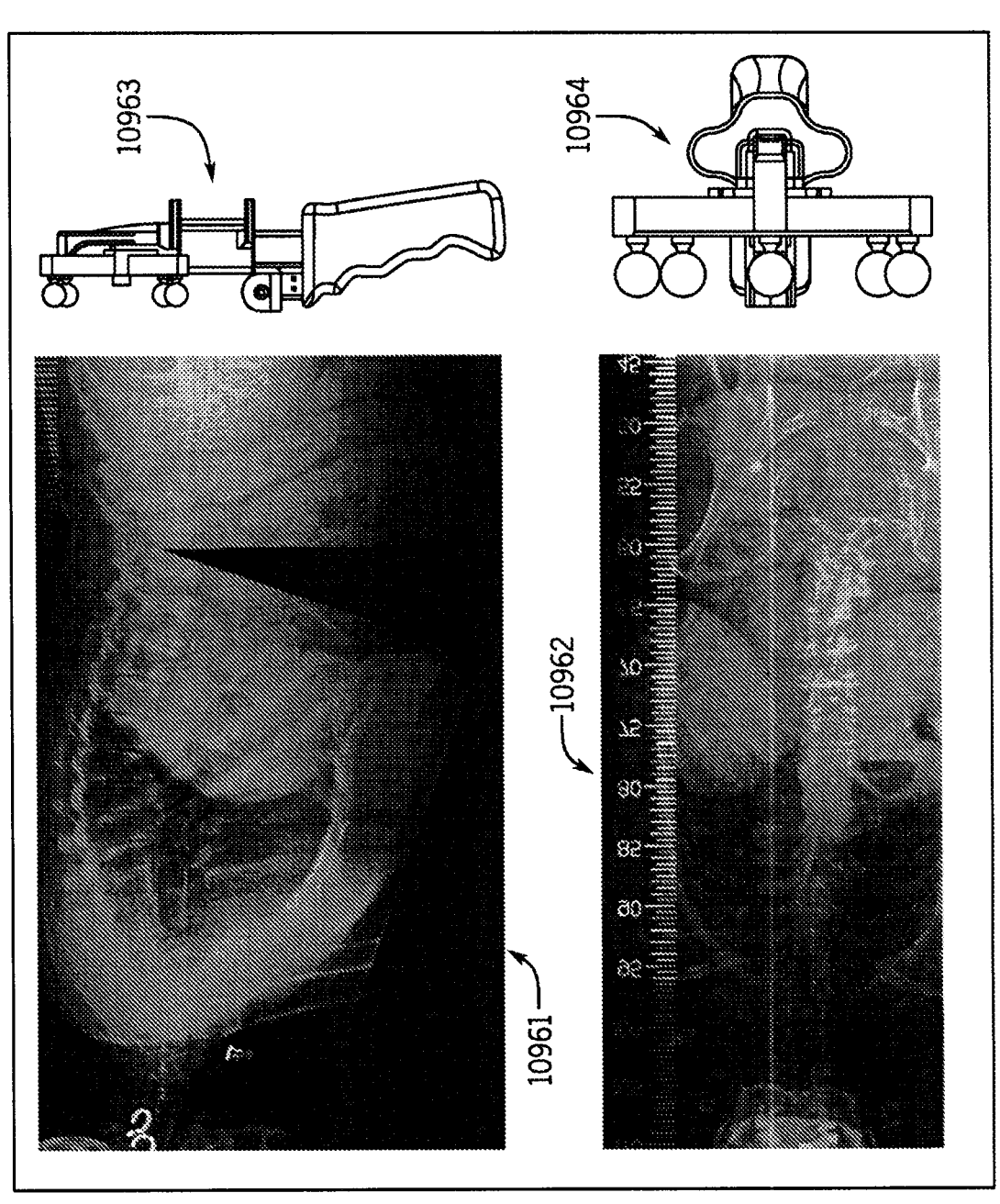
Figure 109D:
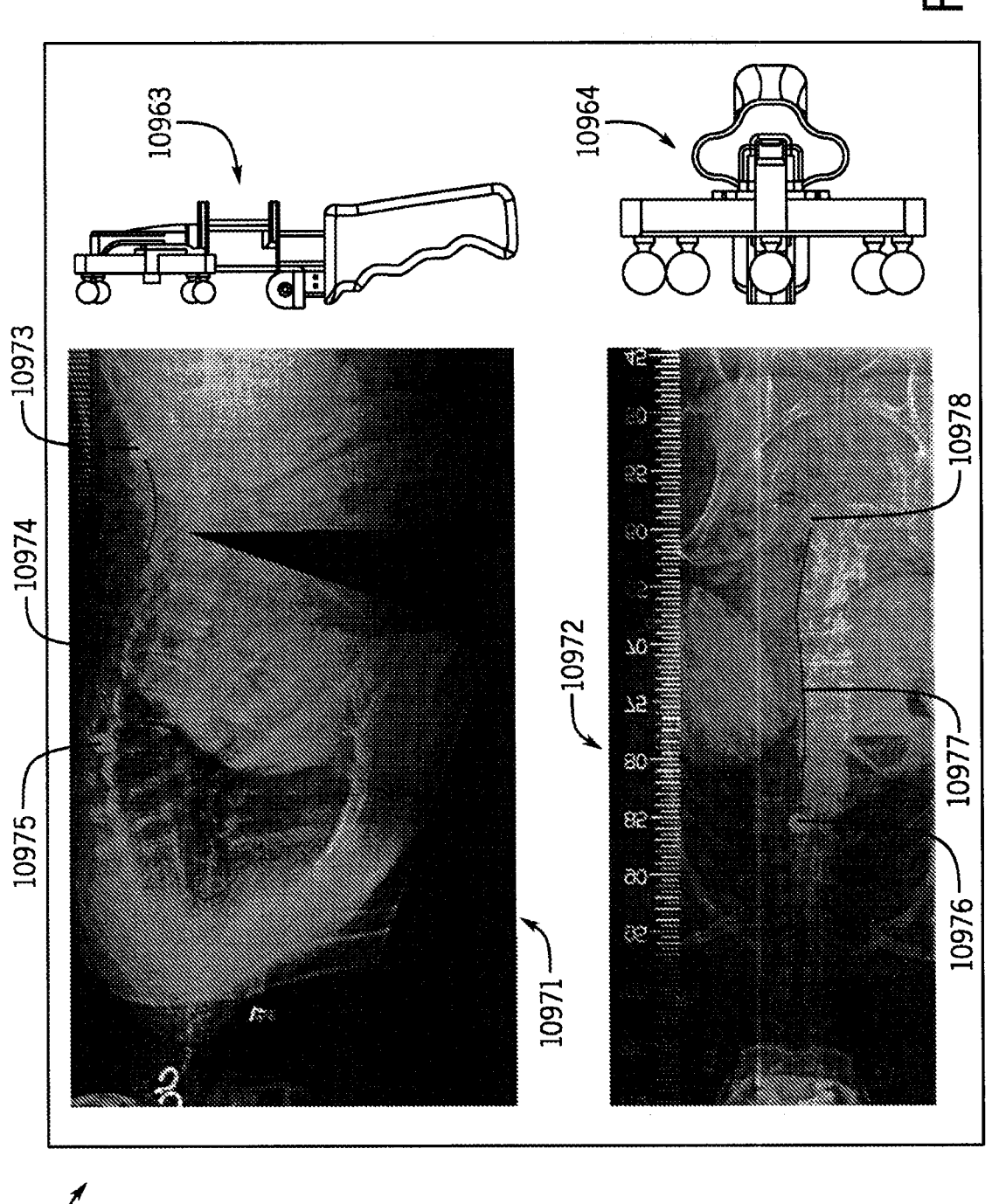

FIGS. 109C-109D illustrate a display interface with patient images and the overlay of a registered rod contour that has been adjusted to match the user's goal for the patient's contour, as described previously in relation to FIGS. 109A-109B in accordance with some embodiments of the invention.

FIGS. 110A-110B illustrate a workflow for adjusting the positions of vertebral holders for an adjustable model holder with inputs from patient imaging in accordance with some embodiments of the invention.

FIGS. 111A-111C illustrate a workflow for analyzing and outputting the range of motion results of engaged vertebrae during and after a flexibility assessment in accordance with some embodiments of the invention.

FIGS. 112A-112C illustrate a workflow for registering and overlaying the contour of a rod and subsequent contours of adjusted rods in accordance with some embodiments of the invention.

Figure 113:
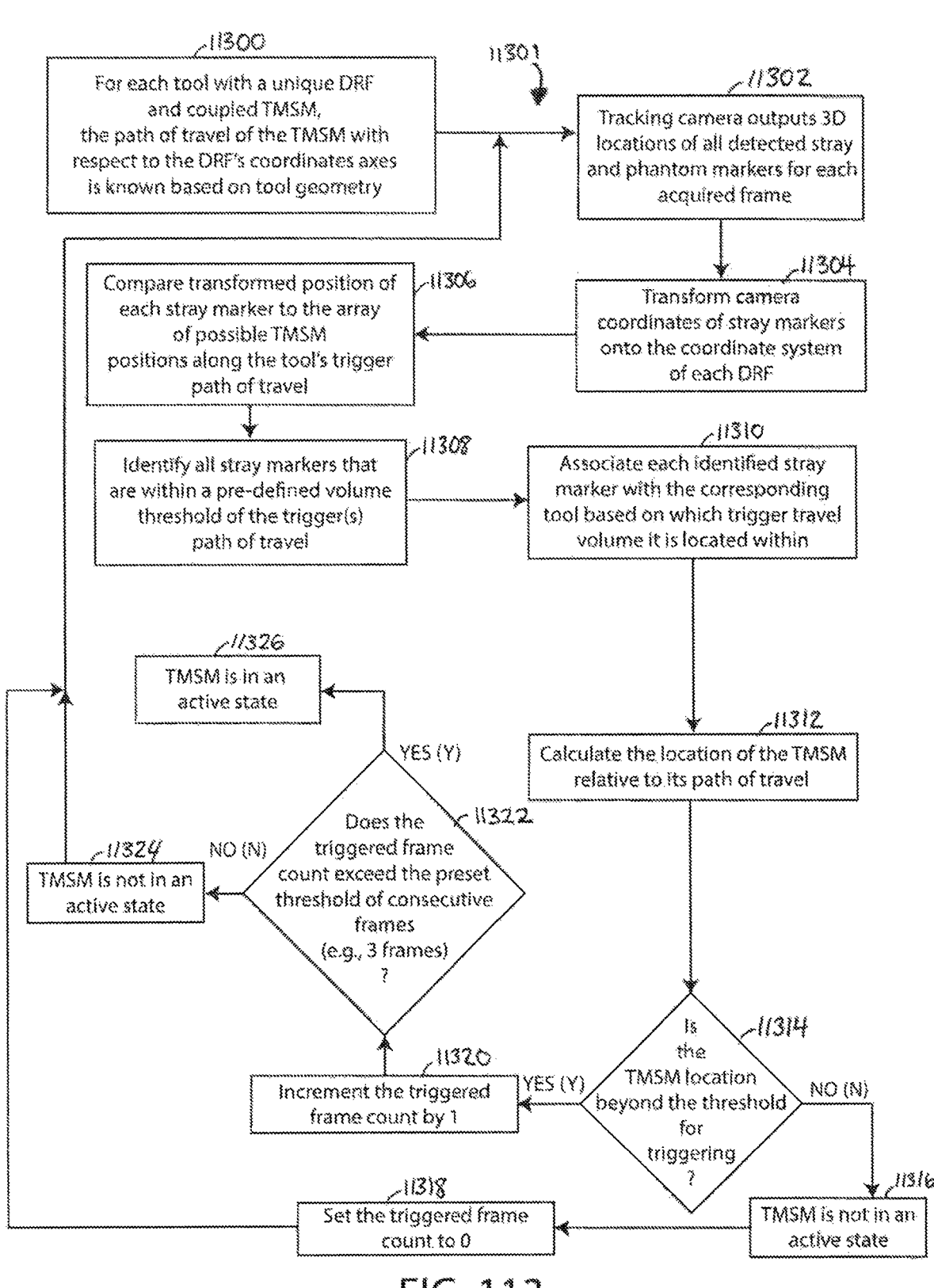

FIG. 113 illustrates a workflow for filtering stray markers outputted by a 3D-tracking camera, identifying the TMSM(s) of DRF-equipped tools with triggering mechanisms, and analyzing if the TMSMs are in an active triggering state, in accordance with some embodiments of the invention.

FIGS. 114A-114F illustrate a workflow for estimating the contour of a rod during and after it is bent in accordance with some embodiments of the invention.

FIG. 115A illustrates a front view of a rod contour and roller surfaces of a rod bender in accordance with some embodiments of the invention.

FIGS. 115B-115C illustrate a front view of a rod contour and roller surfaces of a rod bender during the process of contouring an engaged rod, as described previously in relation to FIG. 115A in accordance with some embodiments of the invention.

FIG. 115D illustrates a front, close-up view of an adjusted, segmented rod contour against the center rod-contouring surface of a rod bender, as described previously in relation to FIGS. 115A-115C in accordance with some embodiments of the invention.

Figure 115E:
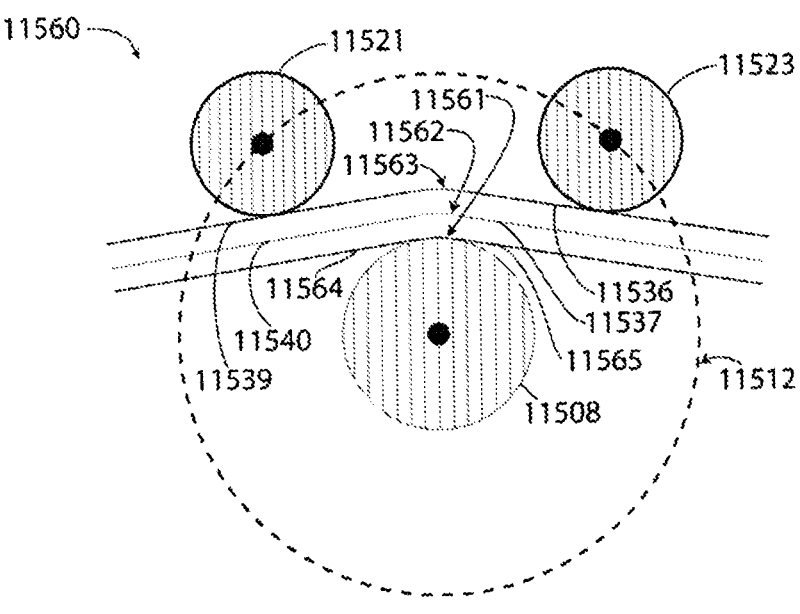

FIG. 115E illustrates a front view of an adjusted rod contour with estimated contour corrections while engaged with the center rod-contouring surface of a rod bender, as described previously in relation to FIGS. 115A-115D in accordance with some embodiments of the invention.

Figure 115F:
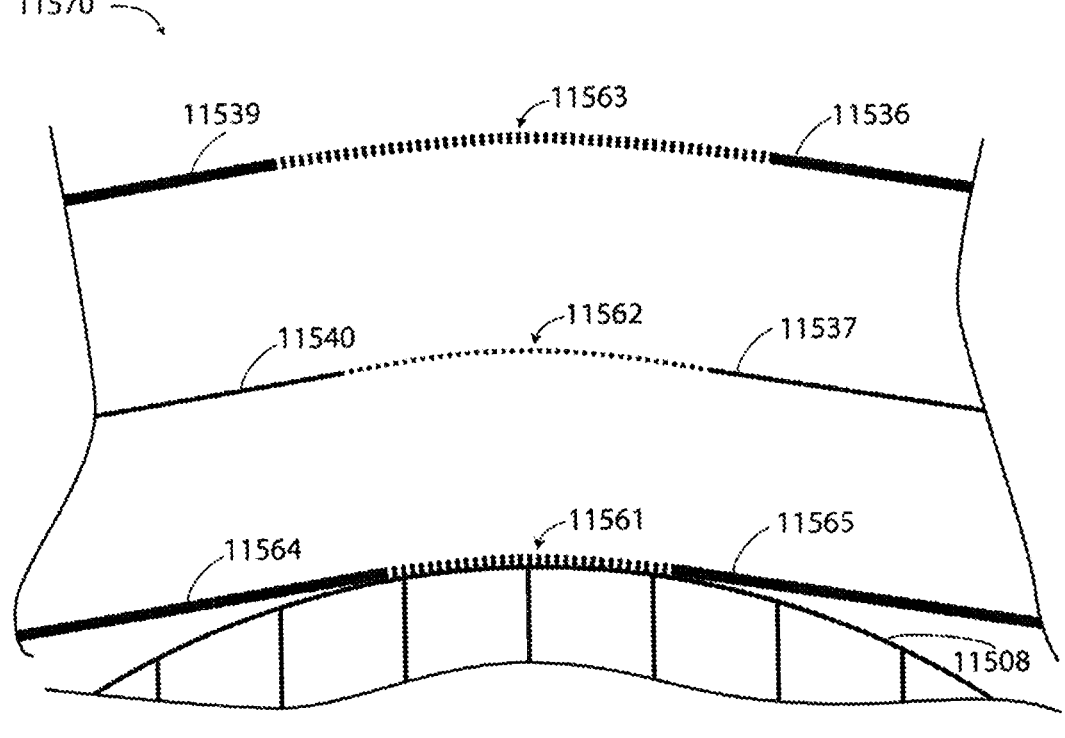

FIG. 115F illustrates a front, close-up view of an adjusted rod contour with estimated contour corrections while engaged with the center rod-contouring surface of a rod bender, as described previously in relation to FIGS. 115A-115E in accordance with some embodiments of the invention.

Figure 116A:
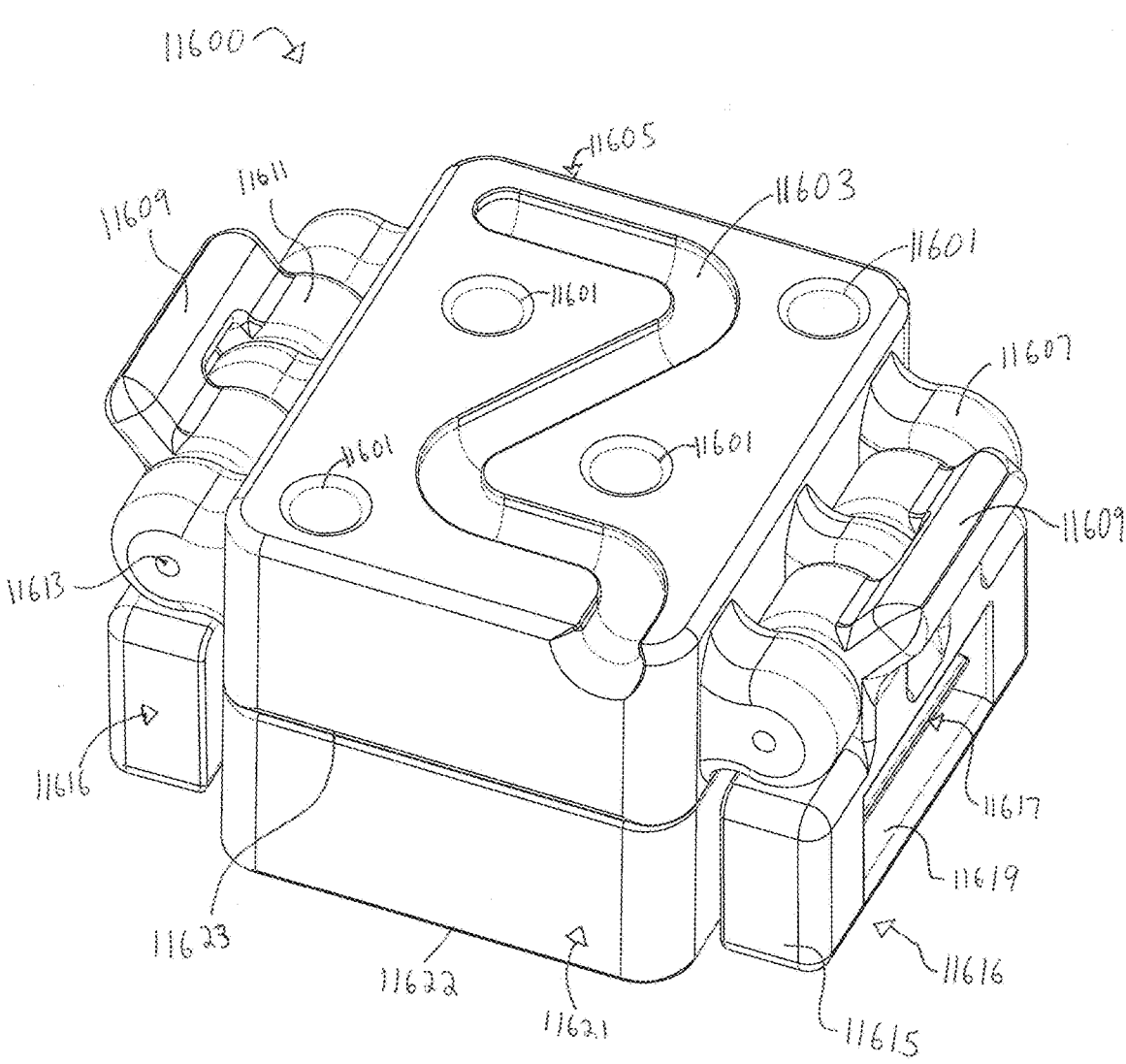

FIG. 116A illustrates a perspective view of a skin-mounted fiducial assembly in accordance with some embodiments of the invention.

Figure 116B:
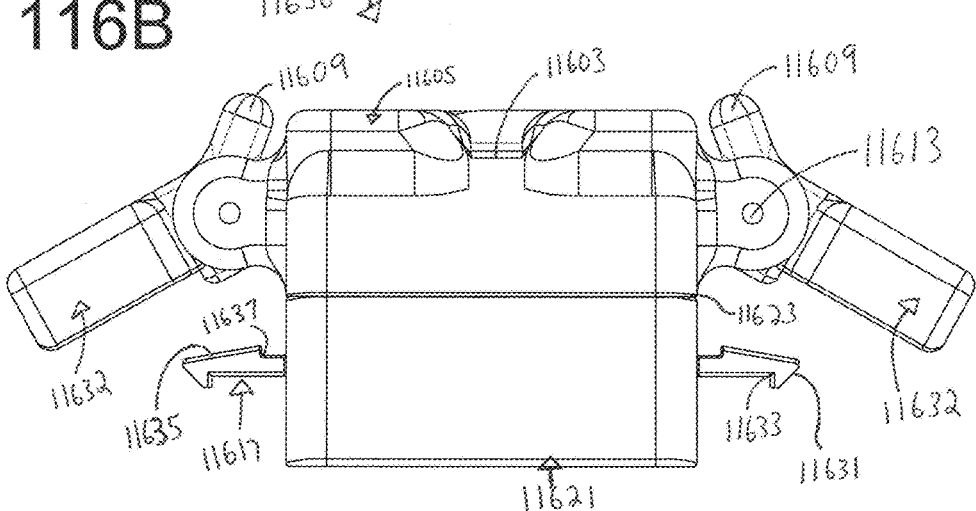

FIG. 116B illustrates a side view of a disengaged skin-mounted fiducial assembly as described previously in relation to FIG. 116A in accordance with some embodiments of the invention.

Figure 116C:
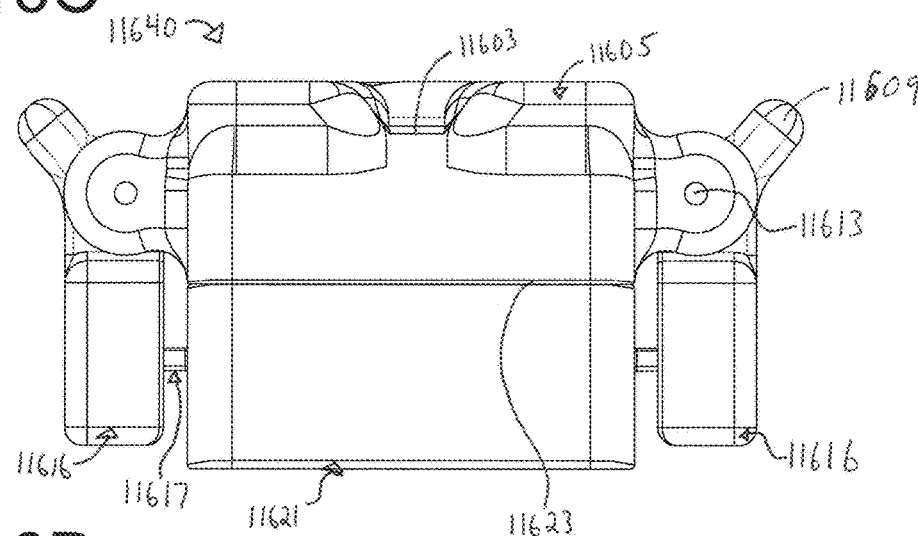

FIG. 116C illustrates a side view of an engaged skin-mounted fiducial assembly as described previously in relation to FIGS. 116A-116B in accordance with some embodiments of the invention.

Figure 116D:
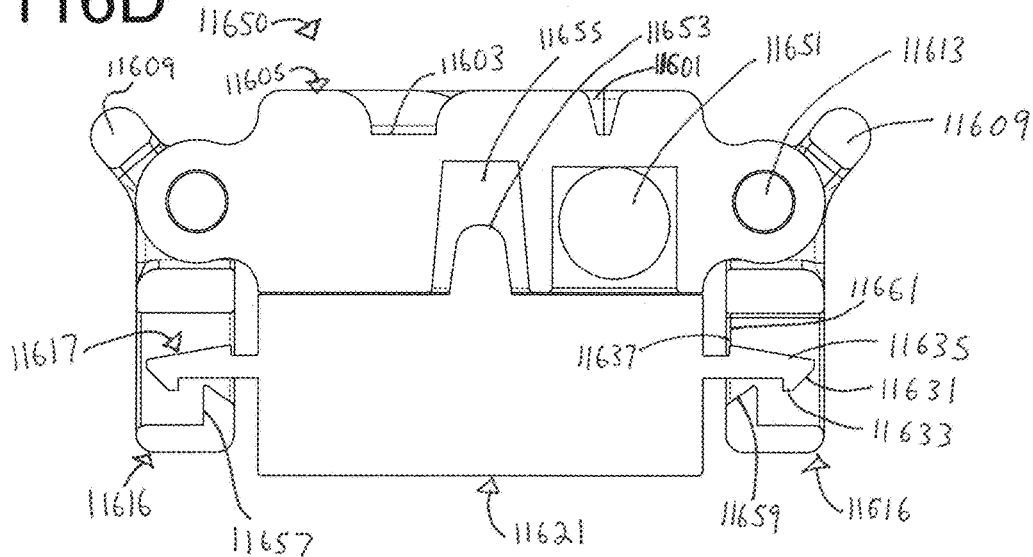

FIG. 116D illustrates a side, cross-sectional view of an engaged skin-mounted fiducial assembly with an embedded radiopaque sphere as described previously in relation to FIGS. 116A-116C in accordance with some embodiments of the invention.

Figure 116E:
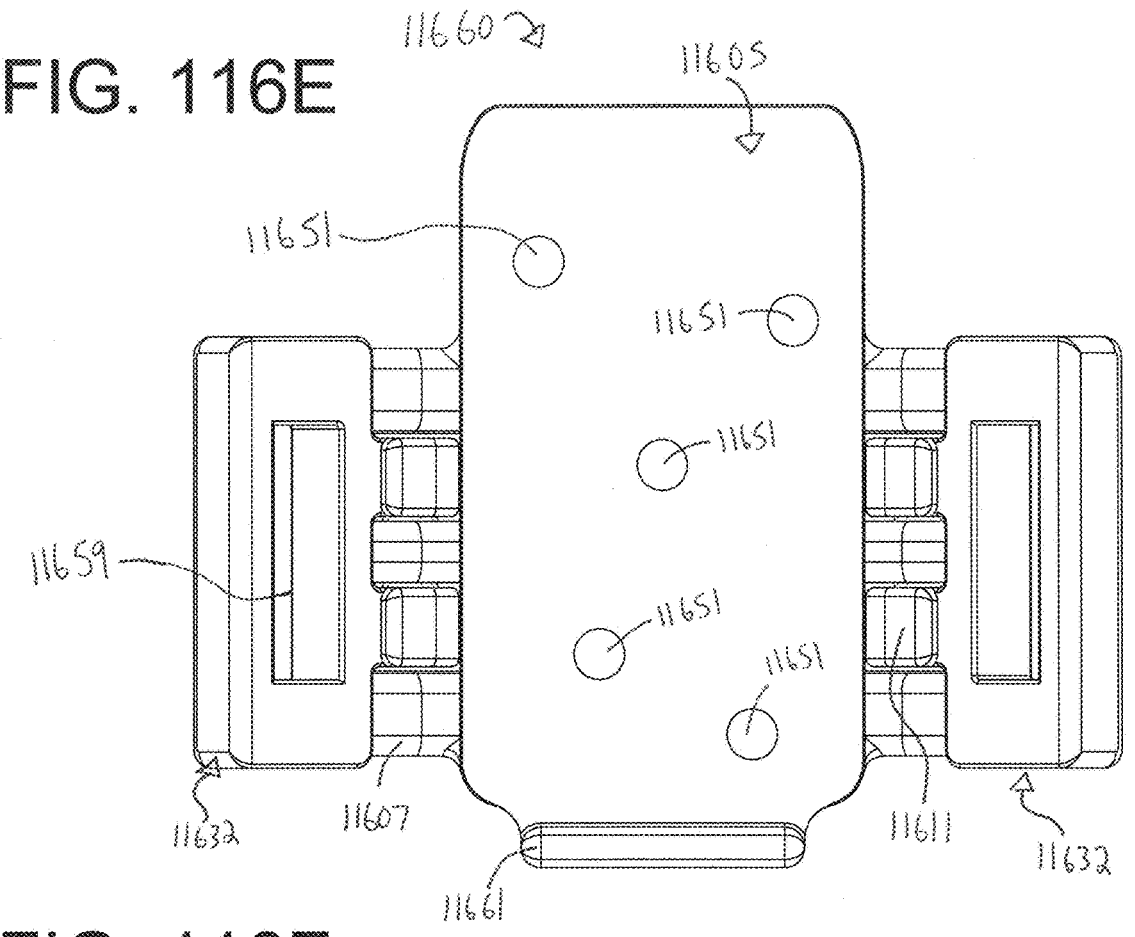

FIG. 116E illustrates a bottom view of the top skin-mounted fiducial with five asymmetrically distributed holes for embedding radiopaque spheres as described previously in relation to FIGS. 116A-116D in accordance with some embodiments of the invention.

Figure 116F:
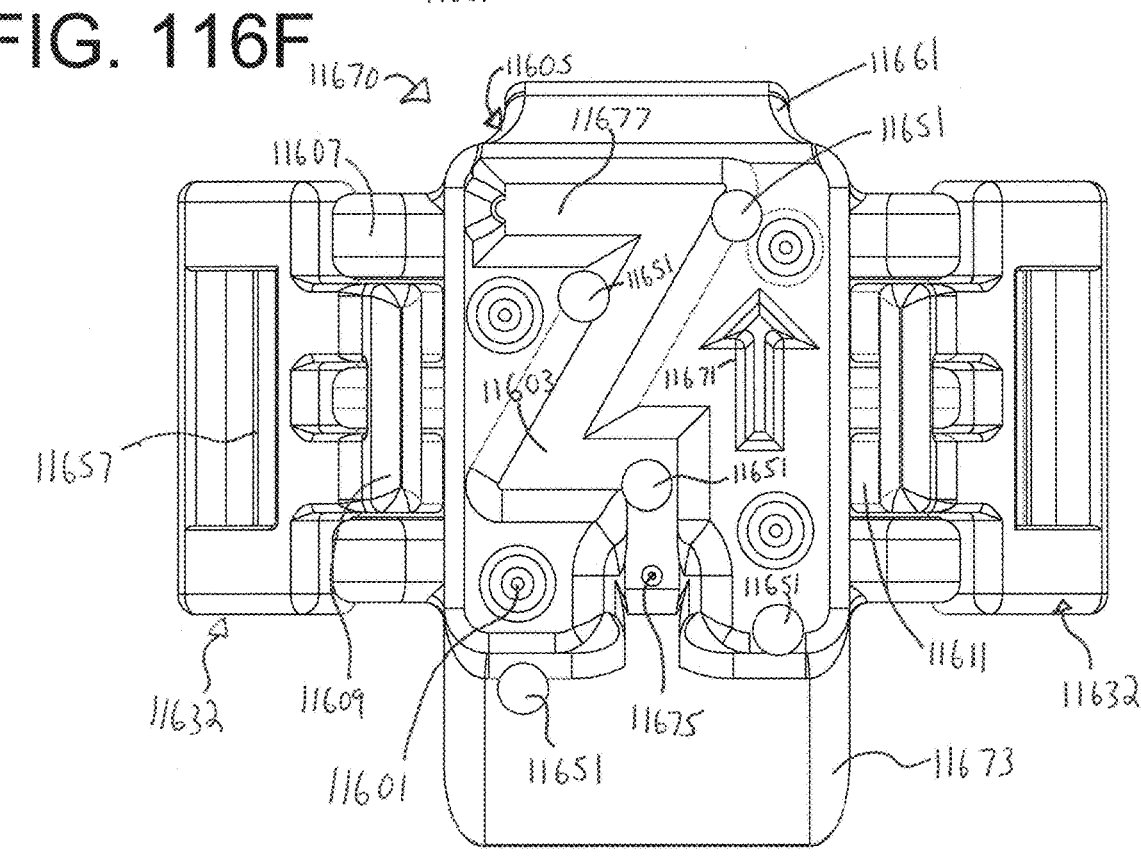

FIG. 116F illustrates a cross-sectional view of the top skin-mounted fiducial as described previously in relation to FIGS. 116A-116E in accordance with some embodiments of the invention.

Figures 116G, 116H:
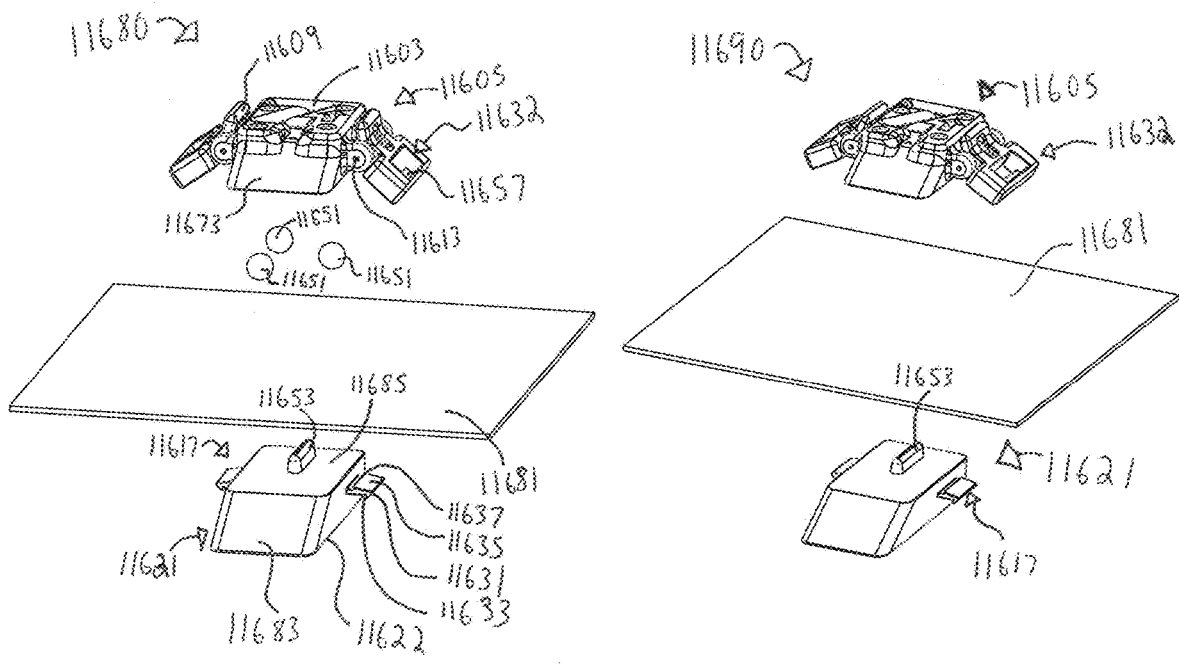

FIG. 116G illustrates an exploded view of the top skin-mounted fiducial, radiopaque spheres, a surgical drape, and bottom skin-mounted fiducial as described previously in relation to FIGS. 116A-116F in accordance with some embodiments of the invention.

FIG. 116H illustrates an exploded view of the top skin-mounted fiducial with embedded radiopaque spheres, a surgical drape, and bottom skin-mounted fiducial as described previously in relation to FIGS. 116A-116G in accordance with some embodiments of the invention.

Figure 116I:
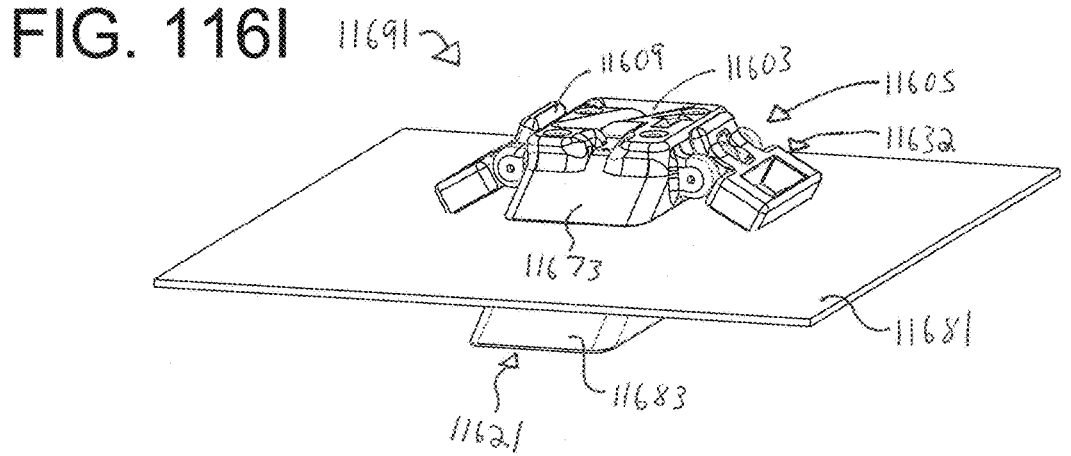

FIG. 116I illustrates a perspective view of the skin-fiducial assembled over the surgical drape and disengaged as described previously in relation to FIGS. 116A-116H in accordance with some embodiments of the invention.

Figure 116J:
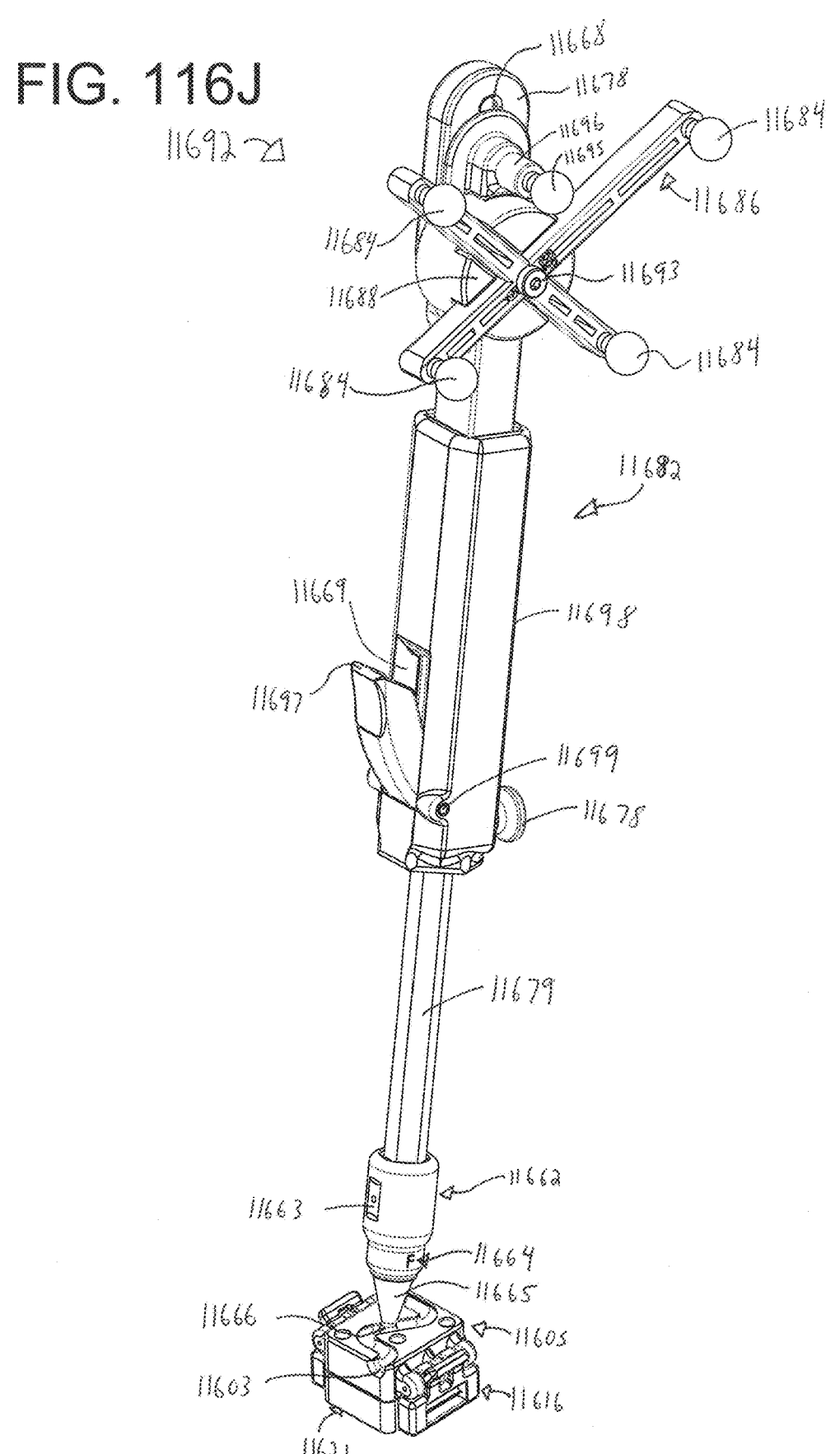

FIG. 116J illustrates a perspective view of a 3D-tracked tool with a tool ball-tip adapter engaged with the "Z-pattern" of the skin-mounted fiducial assembly as described previously in relation to FIGS. 116A-116I in accordance with some embodiments of the invention.

Figures 117A, 117B, 117C:
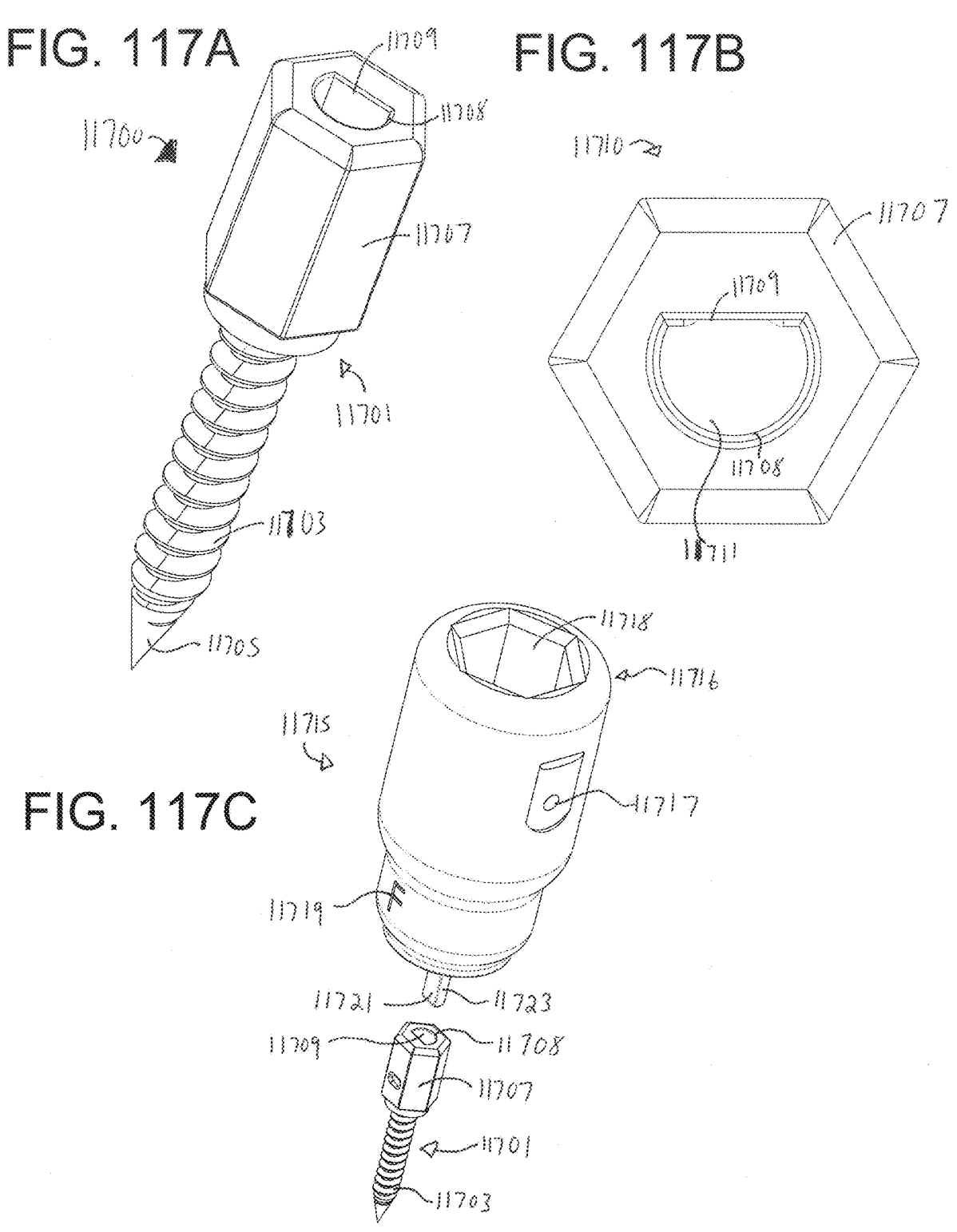

FIG. 117A illustrates a perspective view of an internal-mating bone-mounted fiducial in accordance with some embodiments of the invention.

FIG. 117B illustrates a top view of an internal-mating bone-mounted fiducial as described previously in relation to FIG. 117A in accordance with some embodiments of the invention.

FIG. 117C illustrates perspective views of an internal-mating bone-mounted fiducial and external-mating tool tip adapter of a 3D-tracked tool as described previously in relation to FIGS. 117A-117B in accordance with some embodiments of the invention.

Figures 117D, 117E:
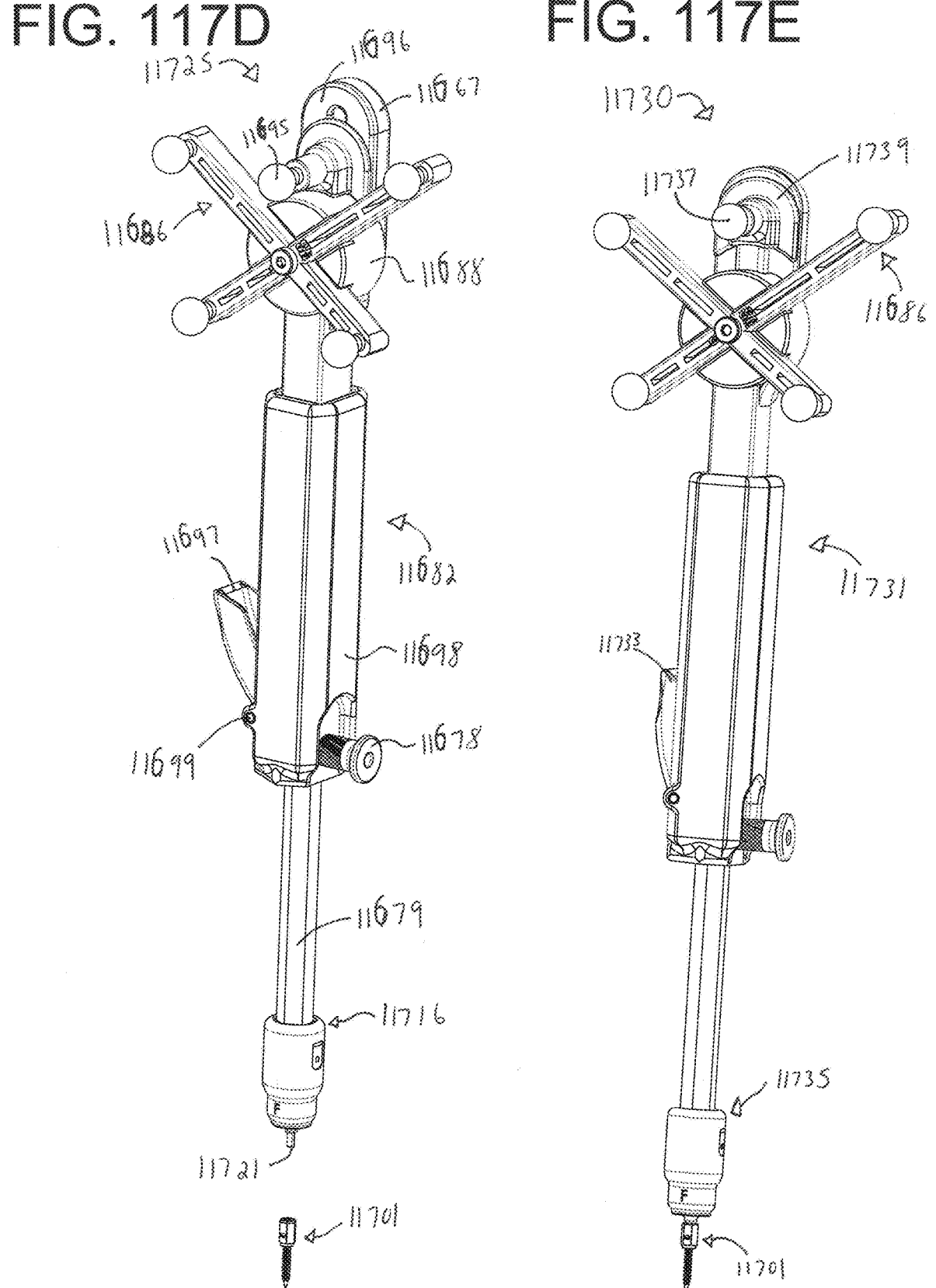

FIG. 117D illustrates perspective views of a 3D-tracked tool with an external-mating tool tip adapter not engaged with an internal-mating bone-mounted fiducial as described previously in relation to FIGS. 117A-117C in accordance with some embodiments of the invention.

FIG. 117E illustrates perspective views of a 3D-tracked tool with an external-mating tool tip adapter engaged with an internal-mating bone-mounted fiducial as described previously in relation to FIGS. 117A-117D in accordance with some embodiments of the invention.

Figure 117F:
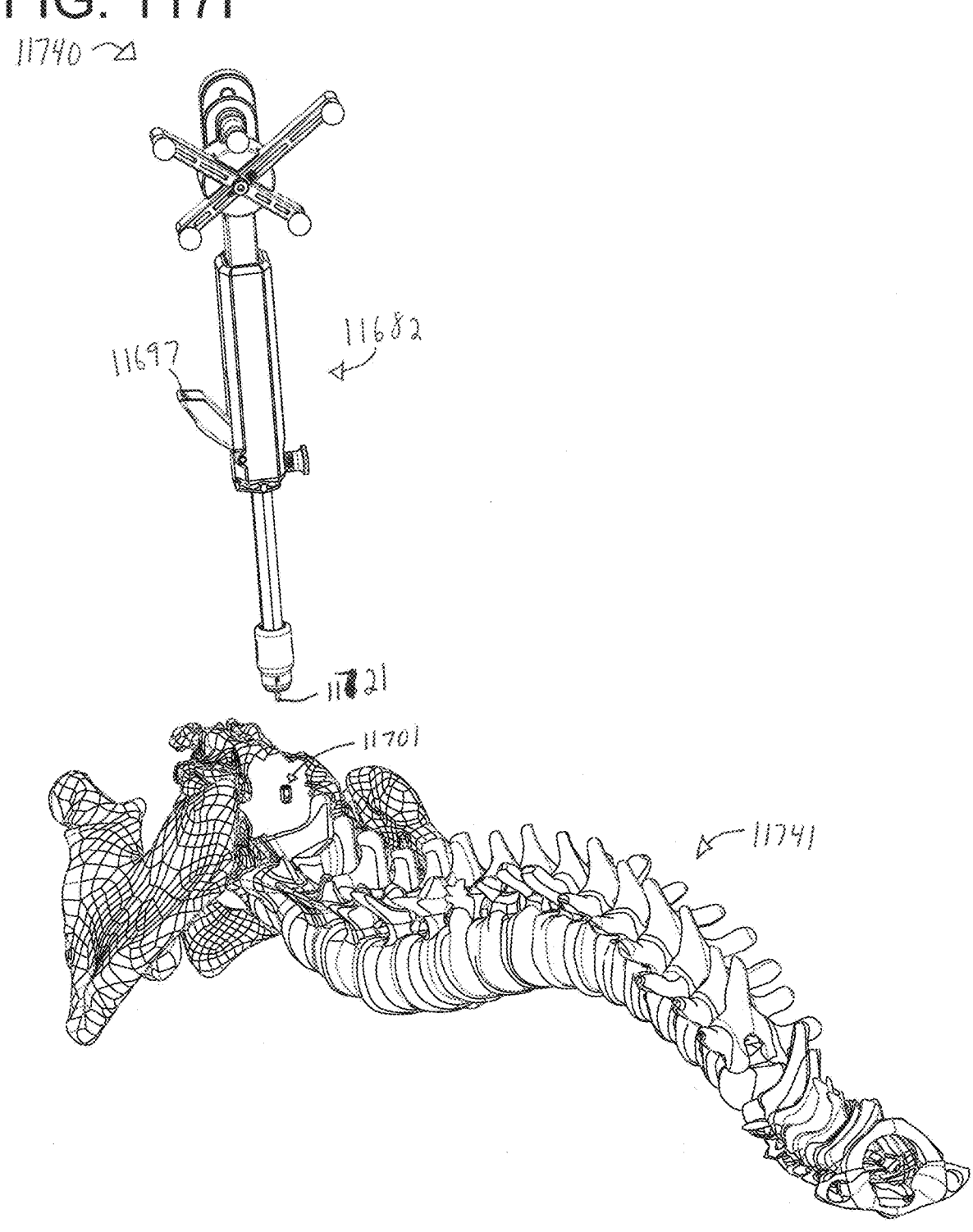

FIG. 117F illustrates perspective views of a 3D-tracked tool with an external-mating tool tip adapter not engaged with an internal-mating bone-mounted fiducial implanted into the sacrum and in an untriggered state as described previously in relation to FIGS. 117A-117E in accordance with some embodiments of the invention.

Figure 117G:
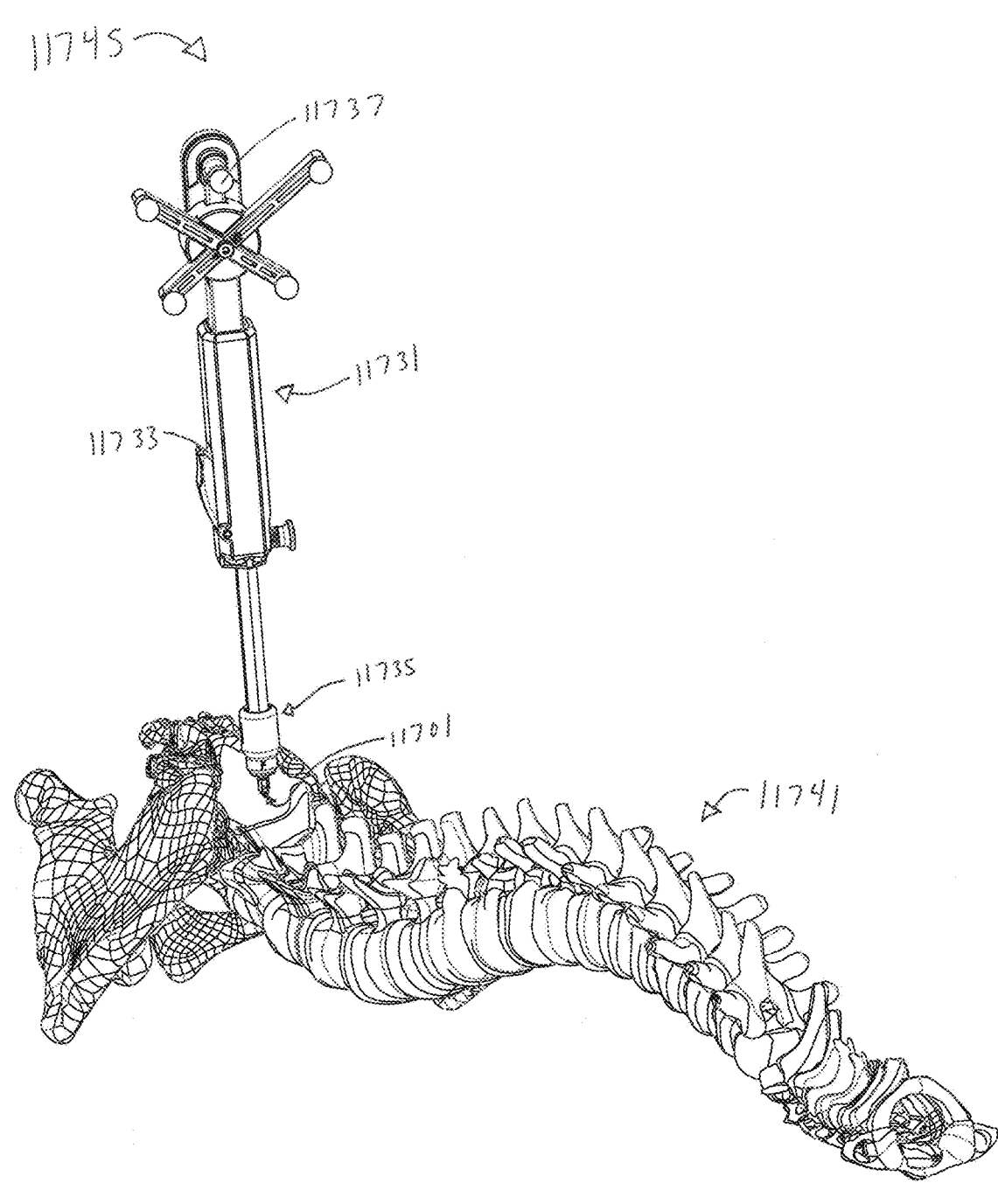

FIG. 117G illustrates perspective views of a 3D-tracked tool with an external-mating tool tip adapter engaged with an internal-mating bone-mounted fiducial implanted into the sacrum and in a triggered state as described previously in relation to FIGS. 117A-117F in accordance with some embodiments of the invention.

Figure 117H:
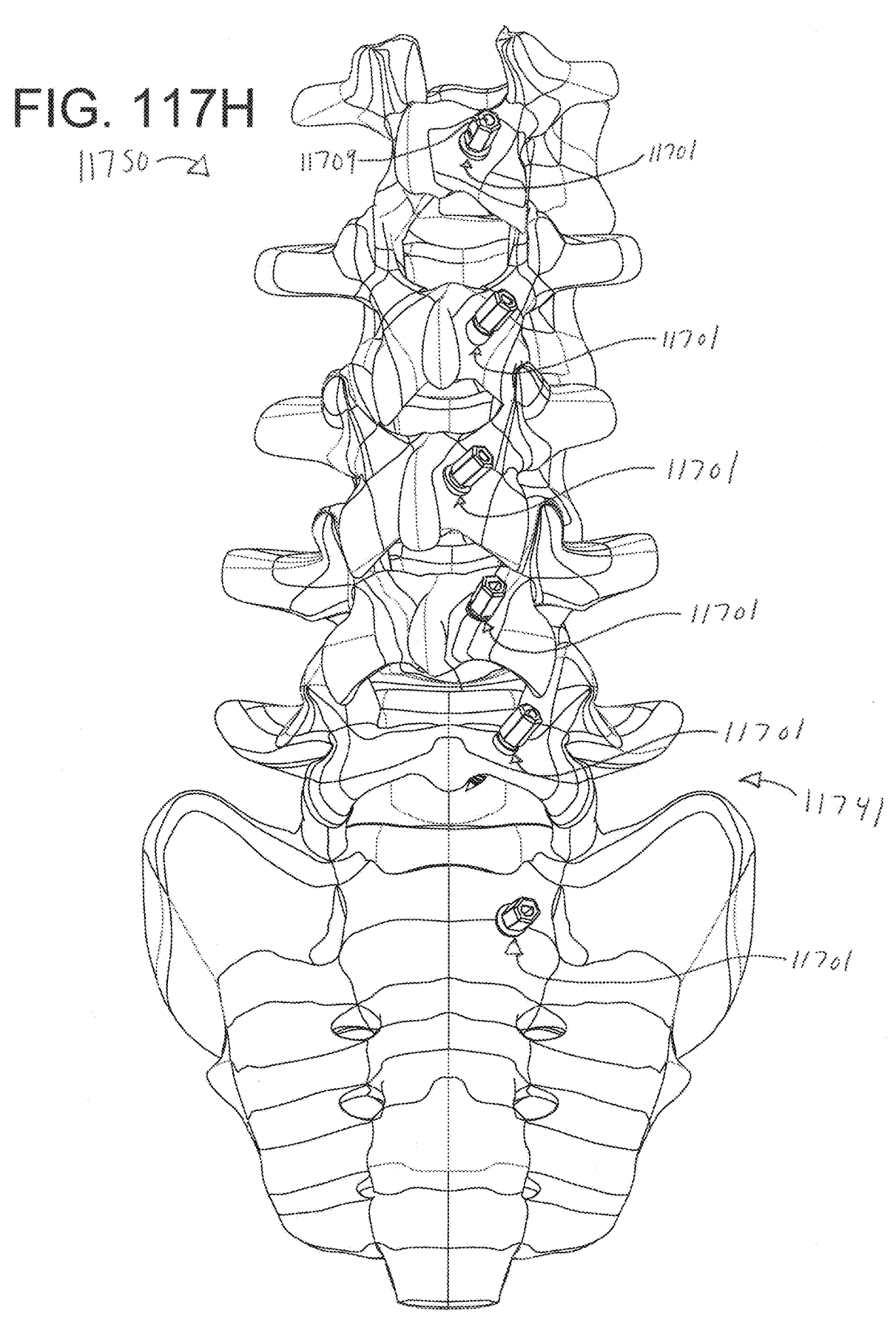

FIG. 117H illustrates a coronal plane view of the spine with bone-mounted fiducials implanted into the sacrum and several laminae as described in relation to FIGS. 117A-117G in accordance with some embodiments of the invention.

Figures 117I, 117J:
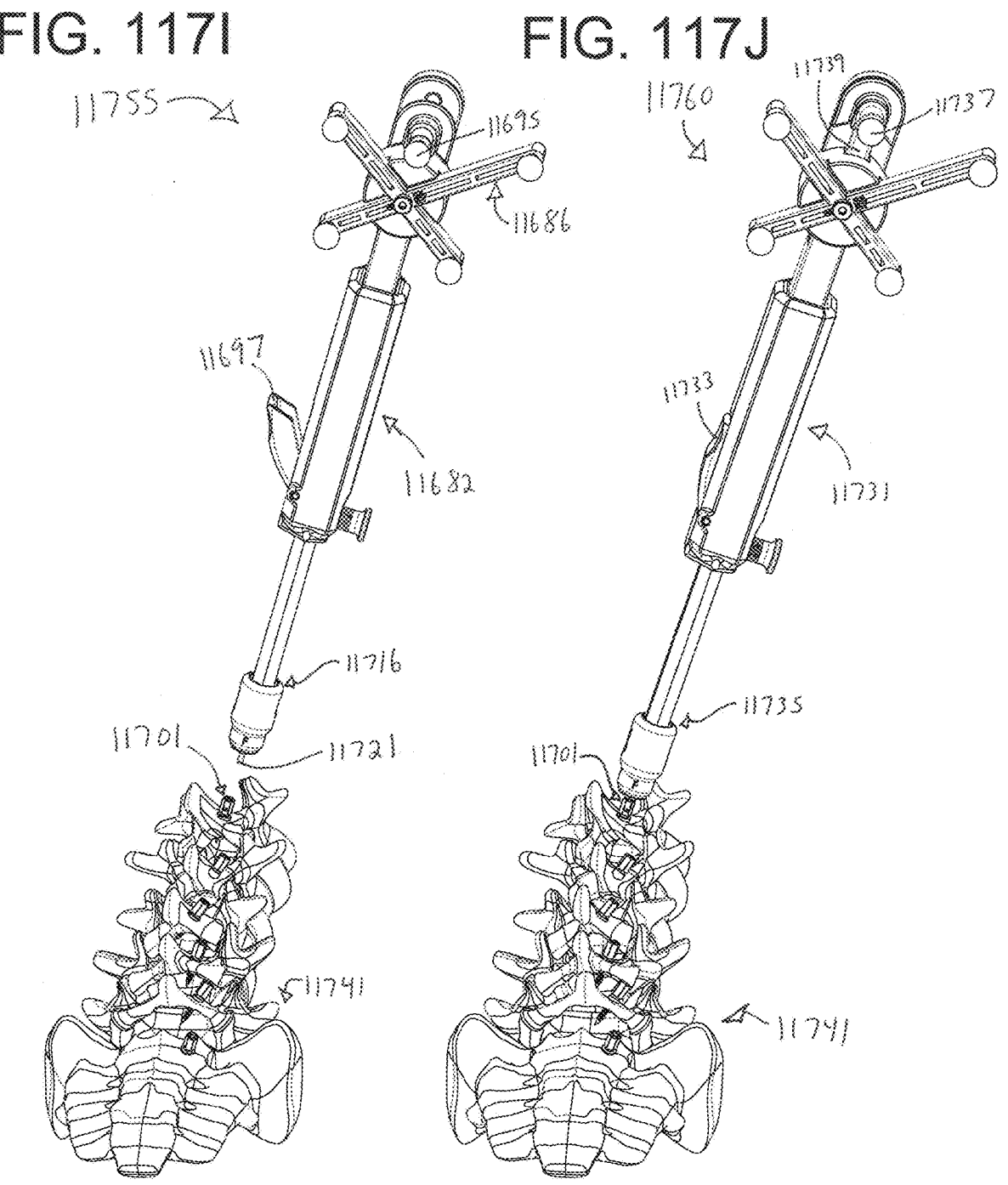

FIG. 117I illustrates perspective views of a 3D-tracked tool with an external-mating tool tip adapter not engaged with internal-mating bone-mounted fiducials implanted into the sacrum and laminae and in an untriggered state as described previously in relation to FIGS. 117A-117H in accordance with some embodiments of the invention.

FIG. 117J illustrates perspective views of a 3D-tracked tool with an external-mating tool tip adapter engaged with internal-mating bone-mounted fiducials implanted into the sacrum and laminae and in a triggered state as described previously in relation to FIGS. 117A-117I in accordance with some embodiments of the invention.

FIG. 118A illustrates a perspective view of an external-mating bone-mounted fiducial in accordance with some embodiments of the invention.

FIG. 118B illustrates a top view of an external-mating bone-mounted fiducial as described previously in relation to FIG. 118A in accordance with some embodiments of the invention.

FIG. 118C illustrates perspective views of an external-mating bone-mounted fiducial and internal-mating tool tip adapter of a 3D-tracked tool as described previously in relation to FIGS. 118A-118B in accordance with some embodiments of the invention.

Figure 118D:
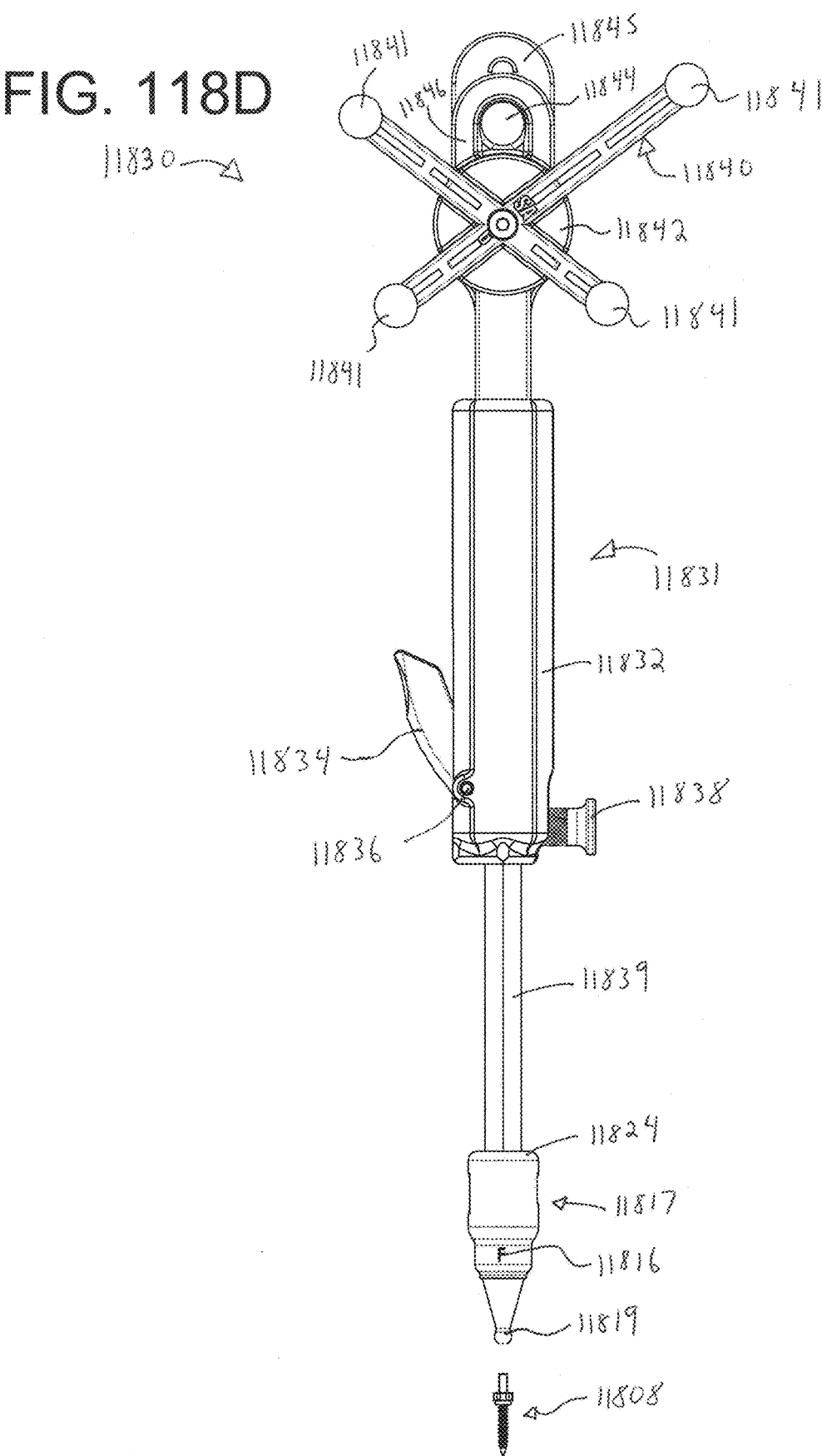

FIG. 118D illustrates a front view of a 3D-tracked tool with an internal-mating tool tip adapter not engaged with an external-mating bone-mounted fiducial and in an untriggered state as described previously in relation to FIGS. 118A-118C in accordance with some embodiments of the invention.

Figures 118E, 118F:
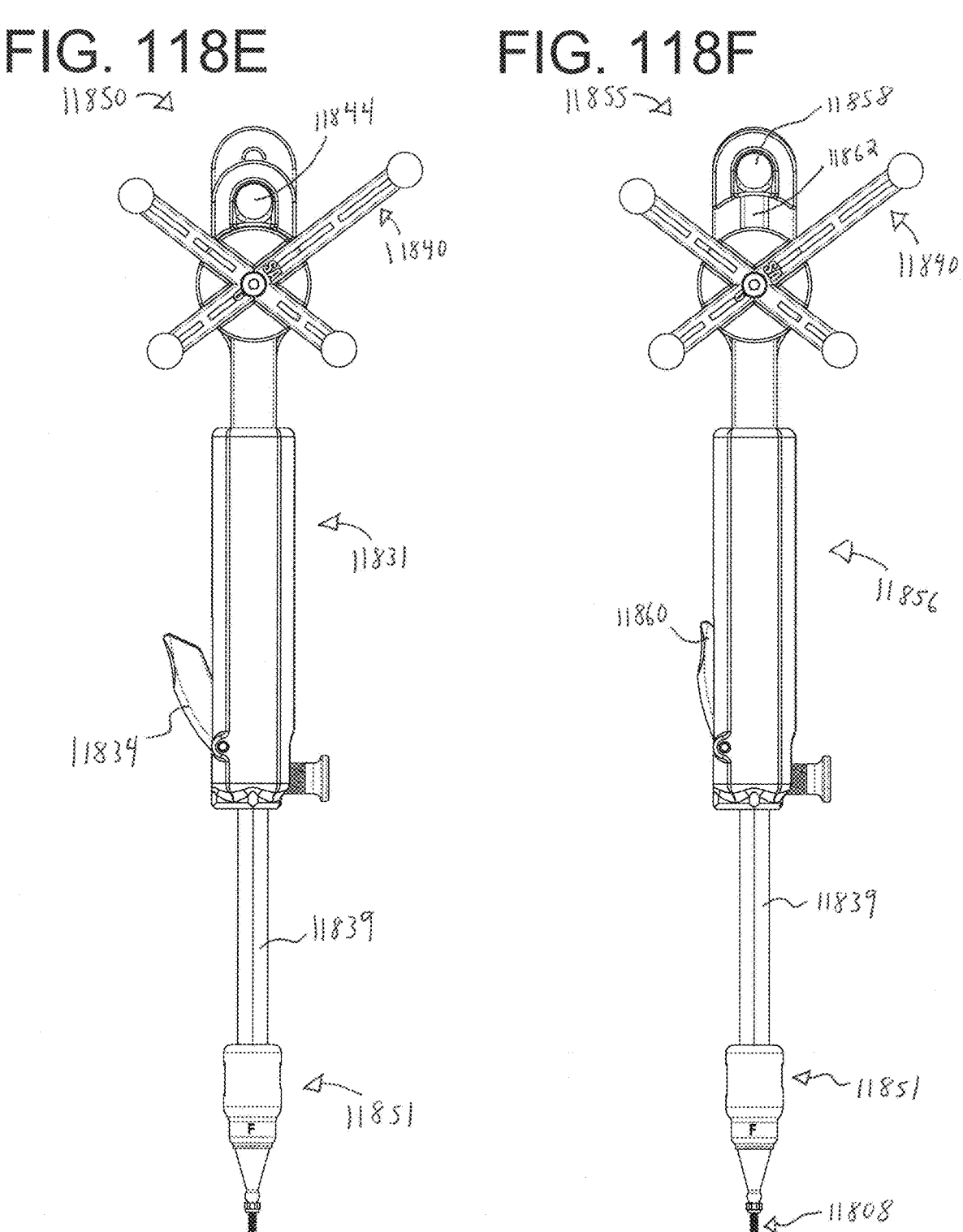

FIG. 118E illustrates frontal views of a 3D-tracked tool with an internal-mating tool tip adapter engaged with an external-mating bone-mounted fiducial and in an untriggered state as described previously in relation to FIGS. 118A-118D in accordance with some embodiments of the invention.

FIG. 118F illustrates frontal views of a 3D-tracked tool with an internal-mating tool tip adapter engaged with an external-mating bone-mounted fiducial and in a triggered state as described previously in relation to FIGS. 118A-118E in accordance with some embodiments of the invention.

Figure 118G:
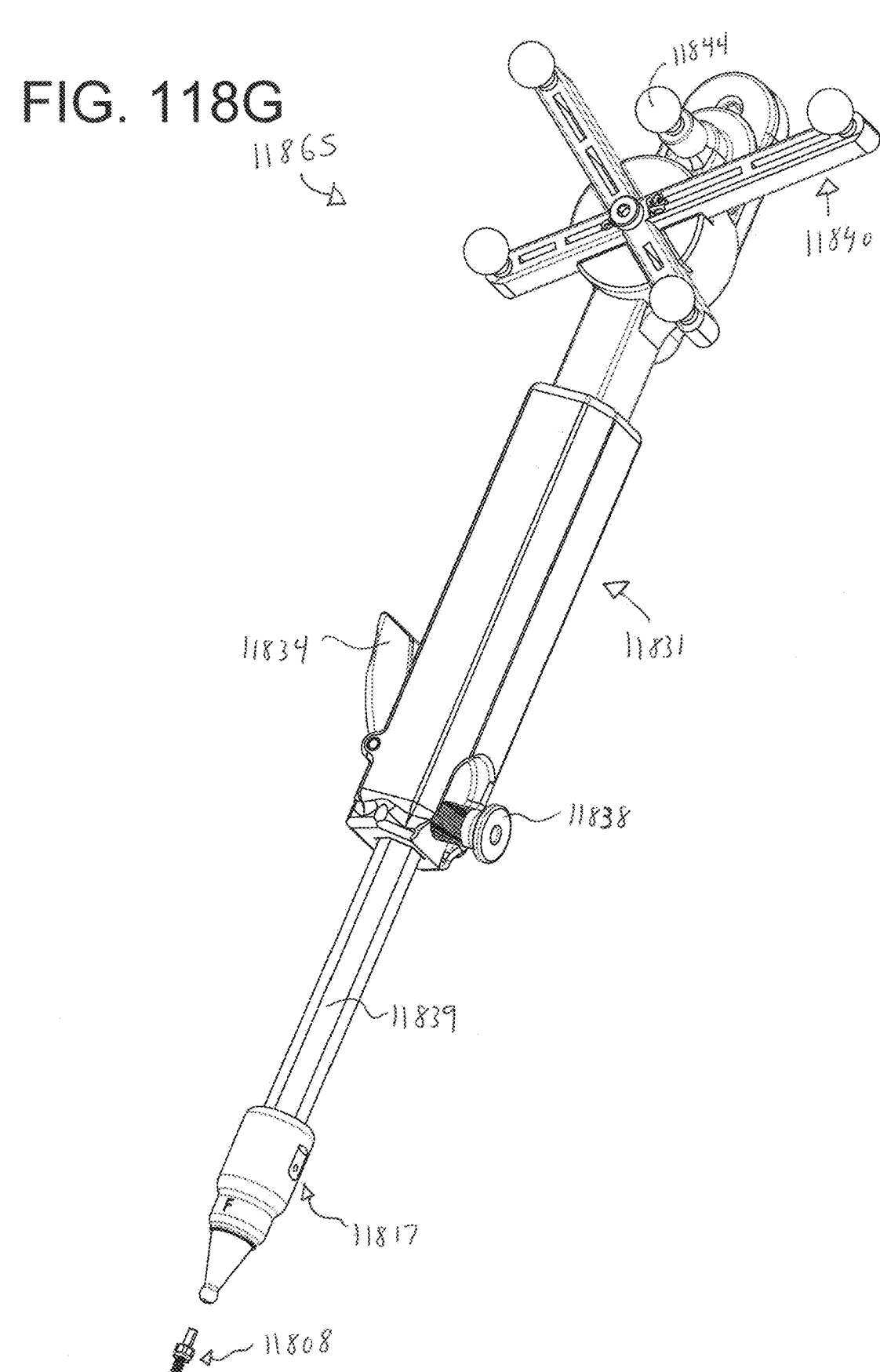

FIG. 118G illustrates perspective views of a 3D-tracked tool with an internal-mating tool tip adapter not engaged with an external-mating bone-mounted fiducial and in an untriggered state as described previously in relation to FIGS. 118A-118F in accordance with some embodiments of the invention.

Figures 118H, 118I:
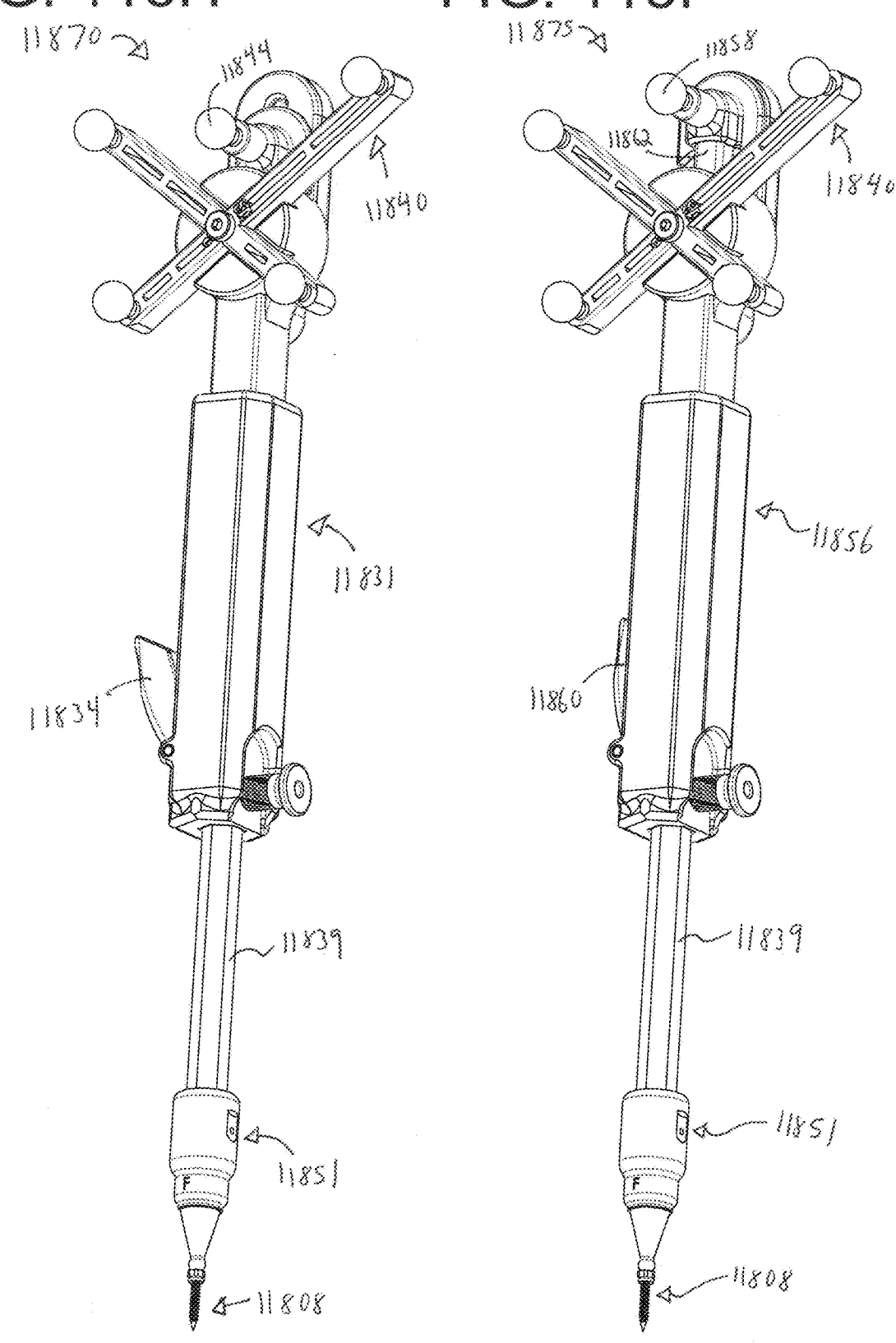

FIG. 118H illustrates perspective views of a 3D-tracked tool with an internal-mating tool tip adapter engaged with an external-mating bone-mounted fiducial and in an untriggered state as described previously in relation to FIGS. 118A-118G in accordance with some embodiments of the invention.

FIG. 118I illustrates perspective views of a 3D-tracked tool with an internal-mating tool tip adapter engaged with an external-mating bone-mounted fiducial and in a triggered state as described previously in relation to FIGS. 118A-118H in accordance with some embodiments of the invention.

Figure 119A:
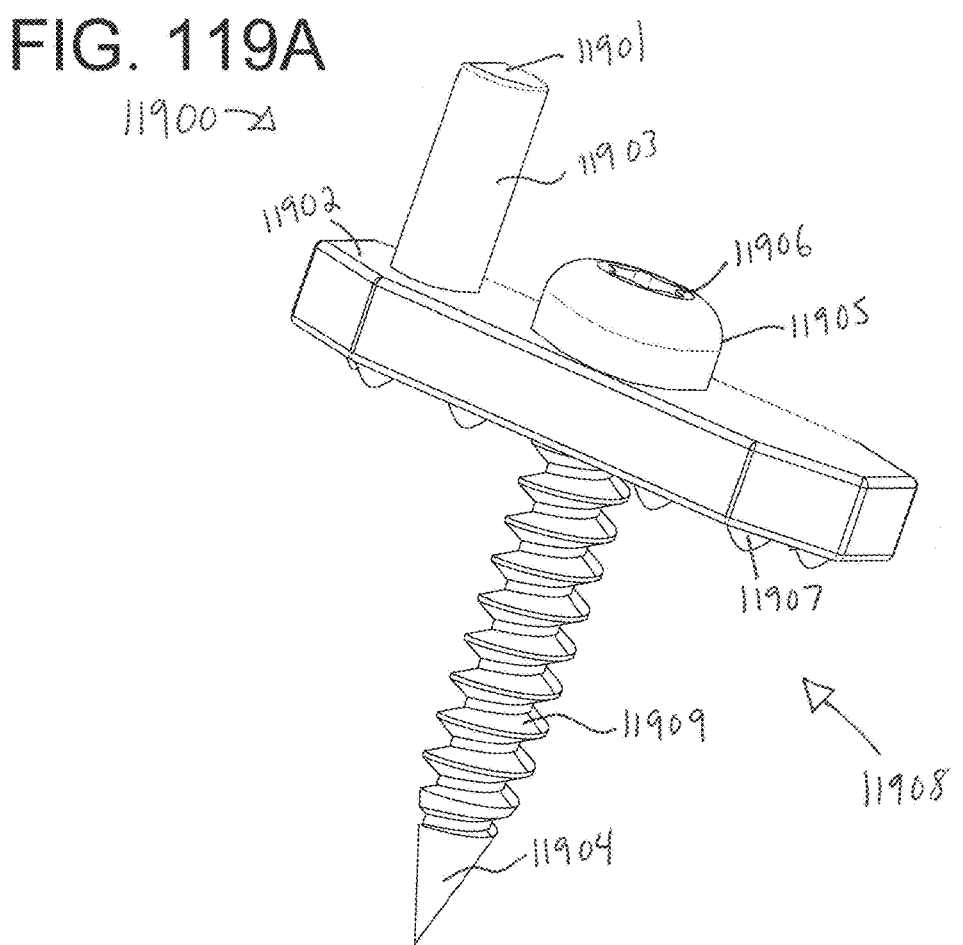

FIG. 119A illustrates a top perspective view of an external-mating bone-mounted fiducial attached to a single-screw plate in accordance with some embodiments of the invention.

Figure 119B:
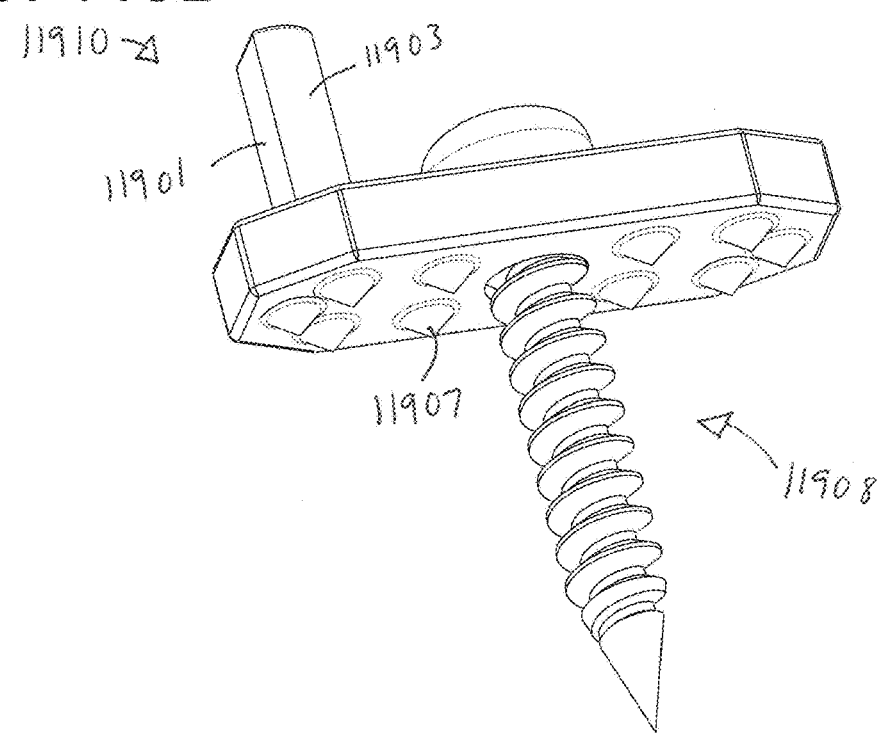

FIG. 119B illustrates a bottom perspective view of an external-mating bone-mounted fiducial attached to a single-screw plate as described previously in relation to FIG. 119A in accordance with some embodiments of the invention.

Figure 119C:
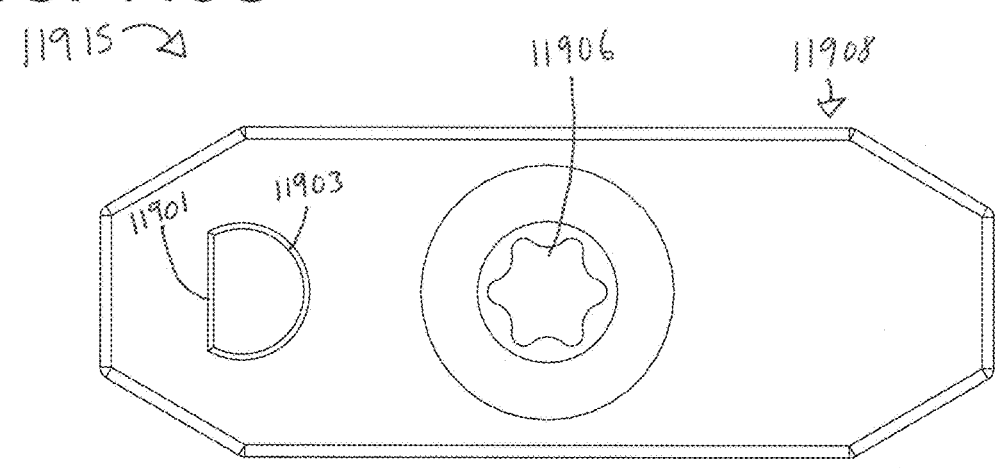

FIG. 119C illustrates a top view of an external-mating bone-mounted fiducial attached to a single-screw plate as described previously in relation to FIGS. 119A-119B in accordance with some embodiments of the invention.

Figure 119D:
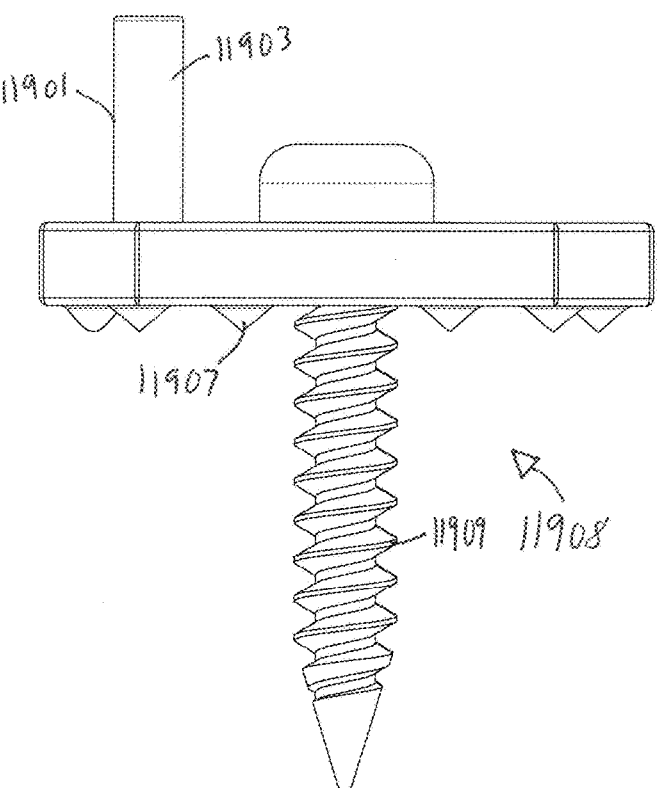

FIG. 119D illustrates a side view of an external-mating bone-mounted fiducial attached to single-screw plate as described previously in relation to FIGS. 119A-119C in accordance with some embodiments of the invention.

Figure 119E:
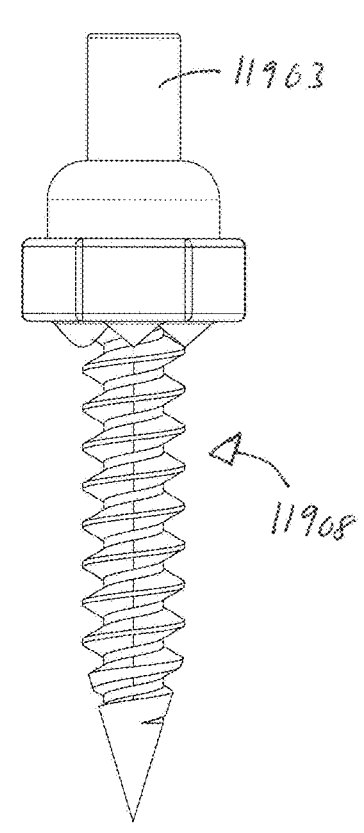

FIG. 119E illustrates a front view of an external-mating bone-mounted fiducial attached to single-screw plate as described previously in relation to FIGS. 119A-119D in accordance with some embodiments of the invention.

Figure 119F:
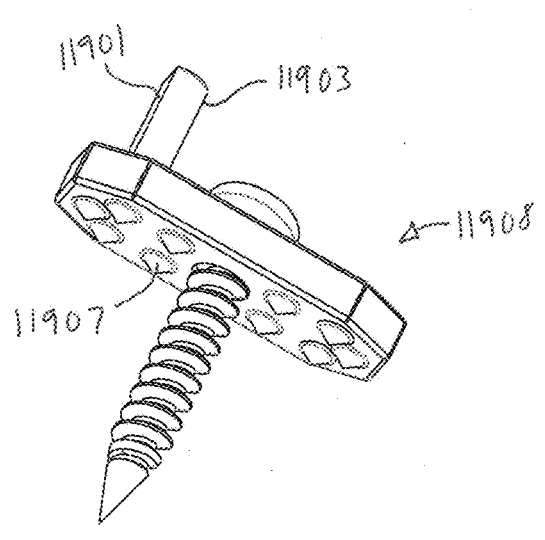

FIG. 119F illustrates perspective views of an external-mating bone-mounted fiducial attached to a single-screw plate and an internal-mating tool tip adapter of a 3D-tracked tool as described previously in relation to FIGS. 119A-119E in accordance with some embodiments of the invention.

Figure 119G:
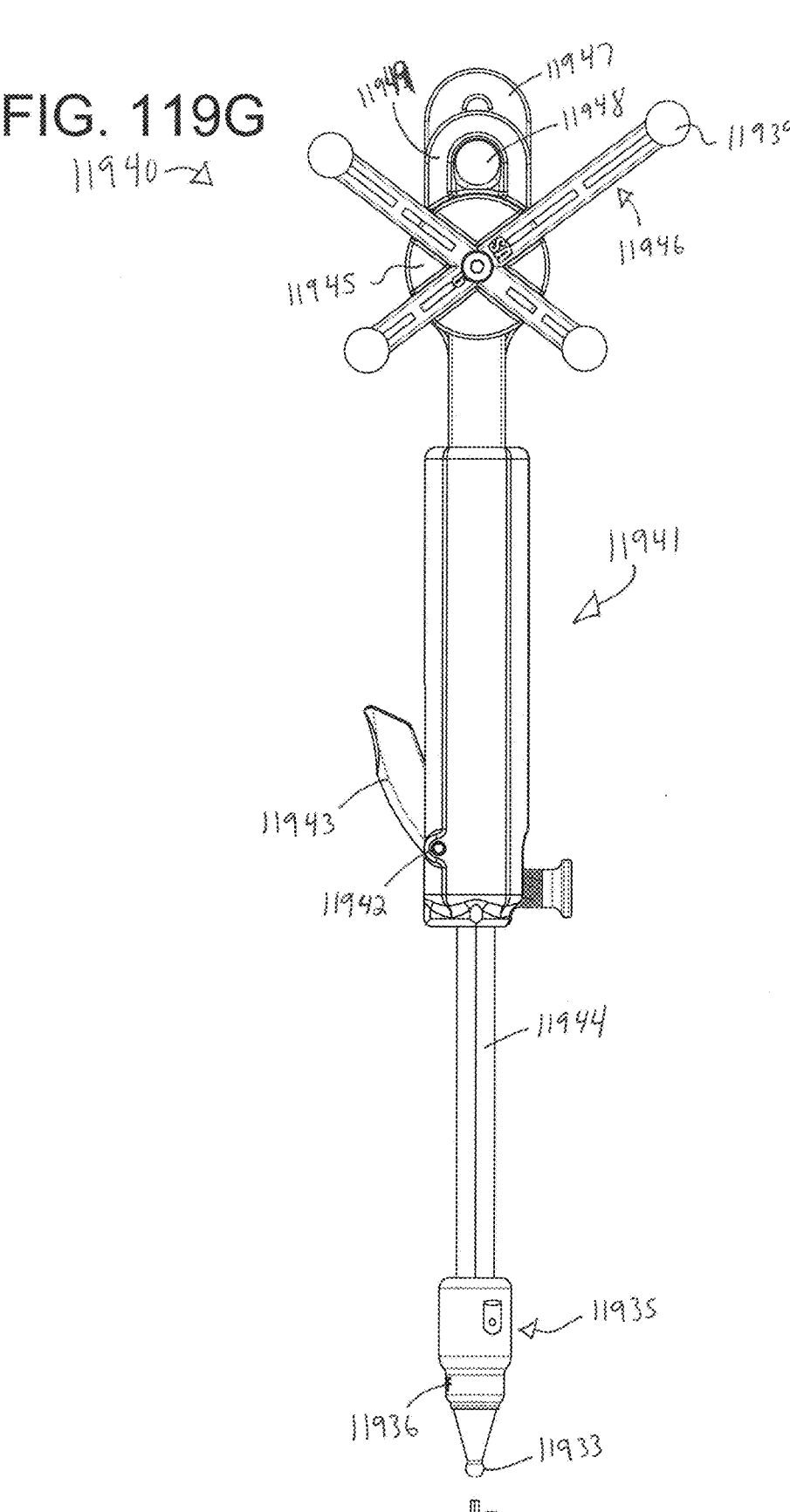

FIG. 119G illustrates a front view of a 3D-tracked tool with internal-mating tool tip adapter not engaged with an external-mating bone-mounted fiducial attached to a single-screw plate and in an untriggered state as described previously in relation to FIGS. 119A-119F in accordance with some embodiments of the invention.

Figure 119H:
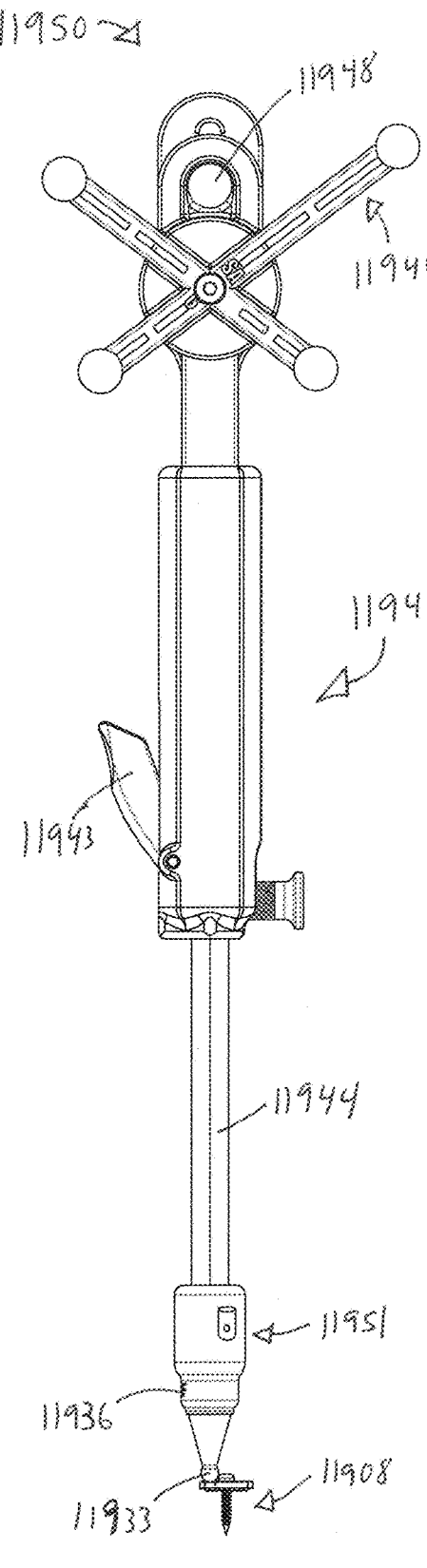

FIG. 119H illustrates a side view of a 3D-tracked tool with internal-mating tool tip adapter engaged with an external-mating bone-mounted fiducial attached to a single-screw plate and in an untriggered state as described previously in relation to FIGS. 119A-119G in accordance with some embodiments of the invention.

Figure 119I:
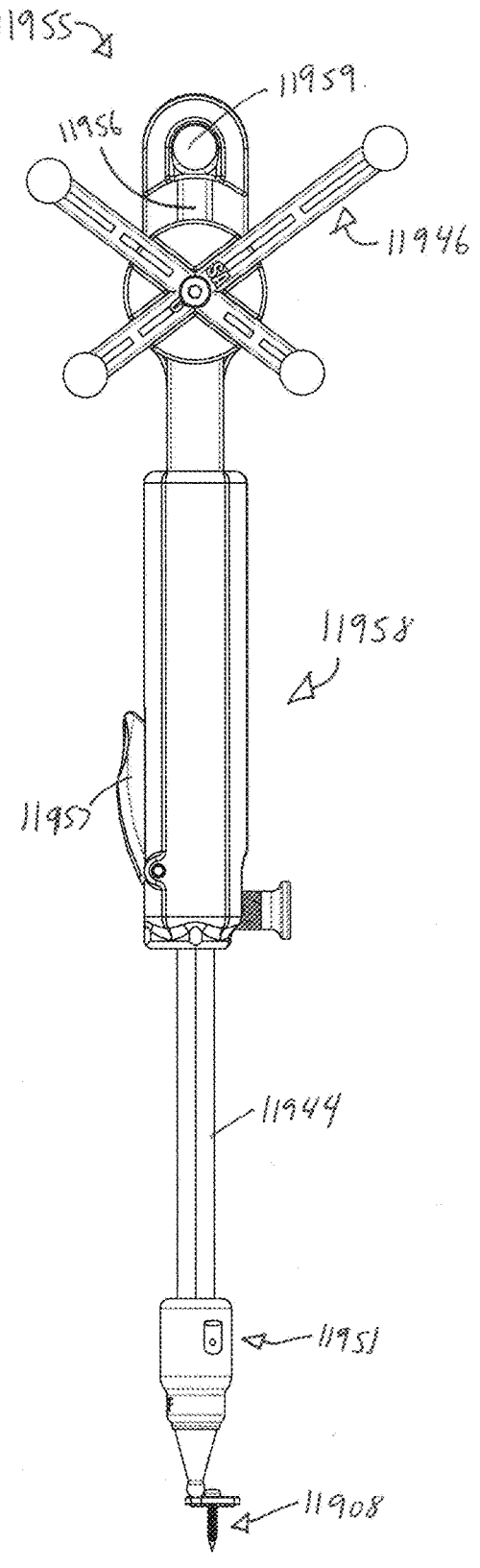

FIG. 119I illustrates a side view of a 3D-tracked tool with internal-mating tool tip adapter engaged with an external-mating bone-mounted fiducial attached to a single-screw plate and in a triggered state as described previously in relation to FIGS. 119A-119H in accordance with some embodiments of the invention.

Figure 119J:
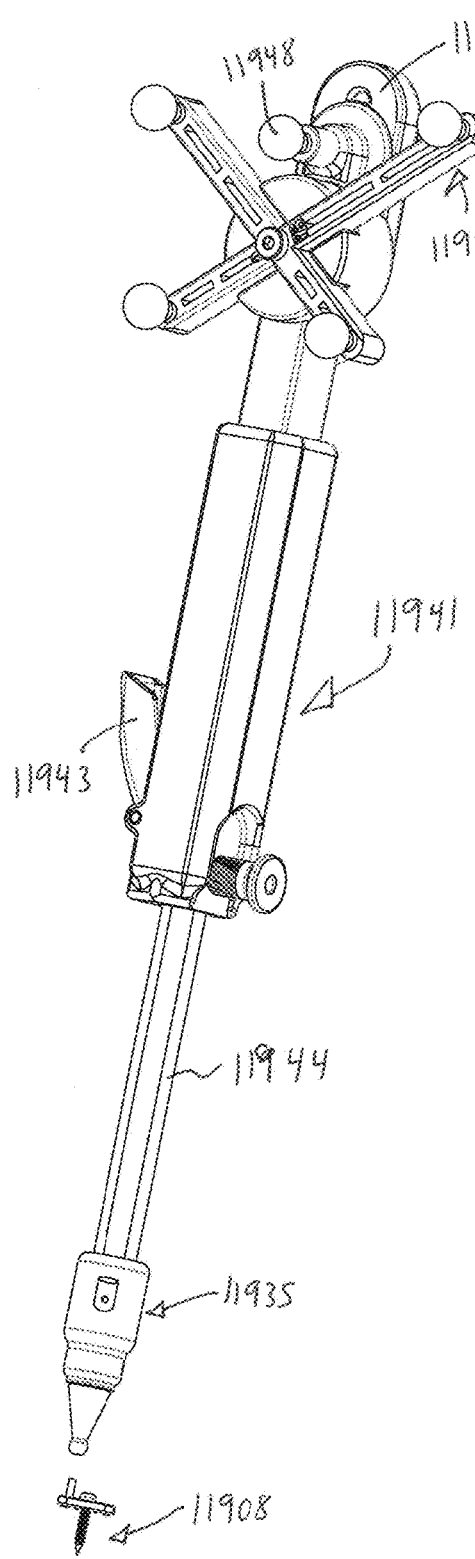

FIG. 119J illustrates a perspective view of a 3D-tracked tool with internal-mating tool tip adapter not engaged with an external-mating bone-mounted fiducial attached to a single-screw plate and in an untriggered state as described previously in relation to FIGS. 119A-119I in accordance with some embodiments of the invention.

Figure 119K:
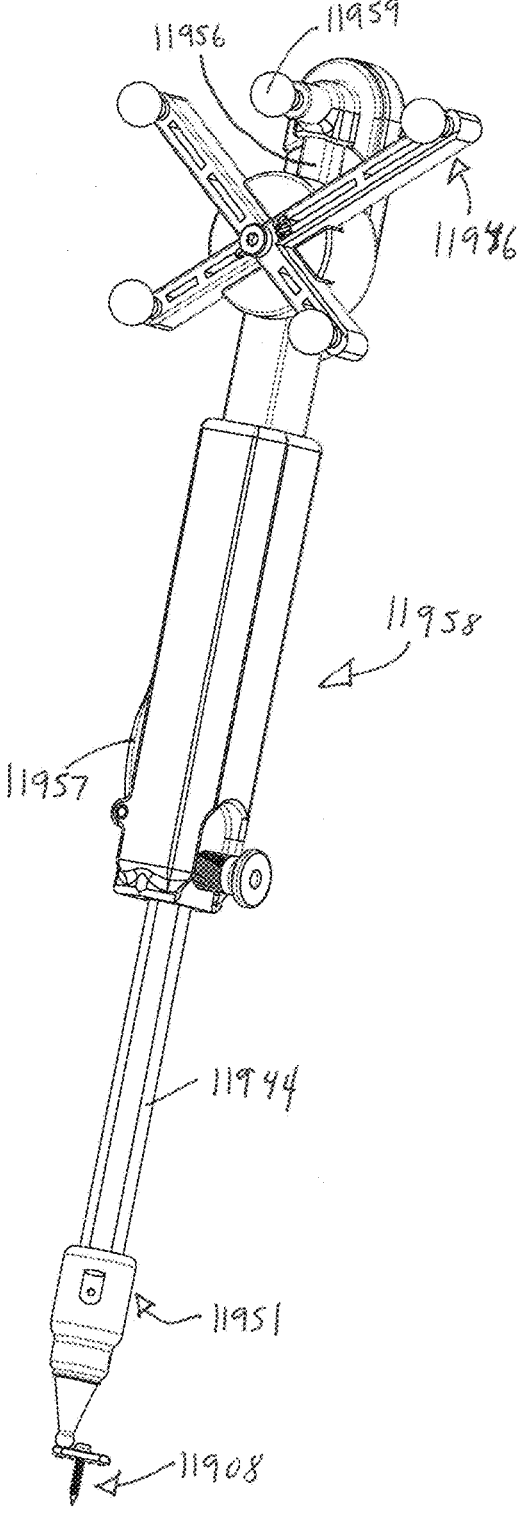

FIG. 119K illustrates a perspective view of a 3D-tracked tool with internal-mating tool tip adapter engaged with an external-mating bone-mounted fiducial attached to a single-screw plate and in a triggered state as described previously in relation to FIGS. 119A-119.1 in accordance with some embodiments of the invention.

Figure 120A:
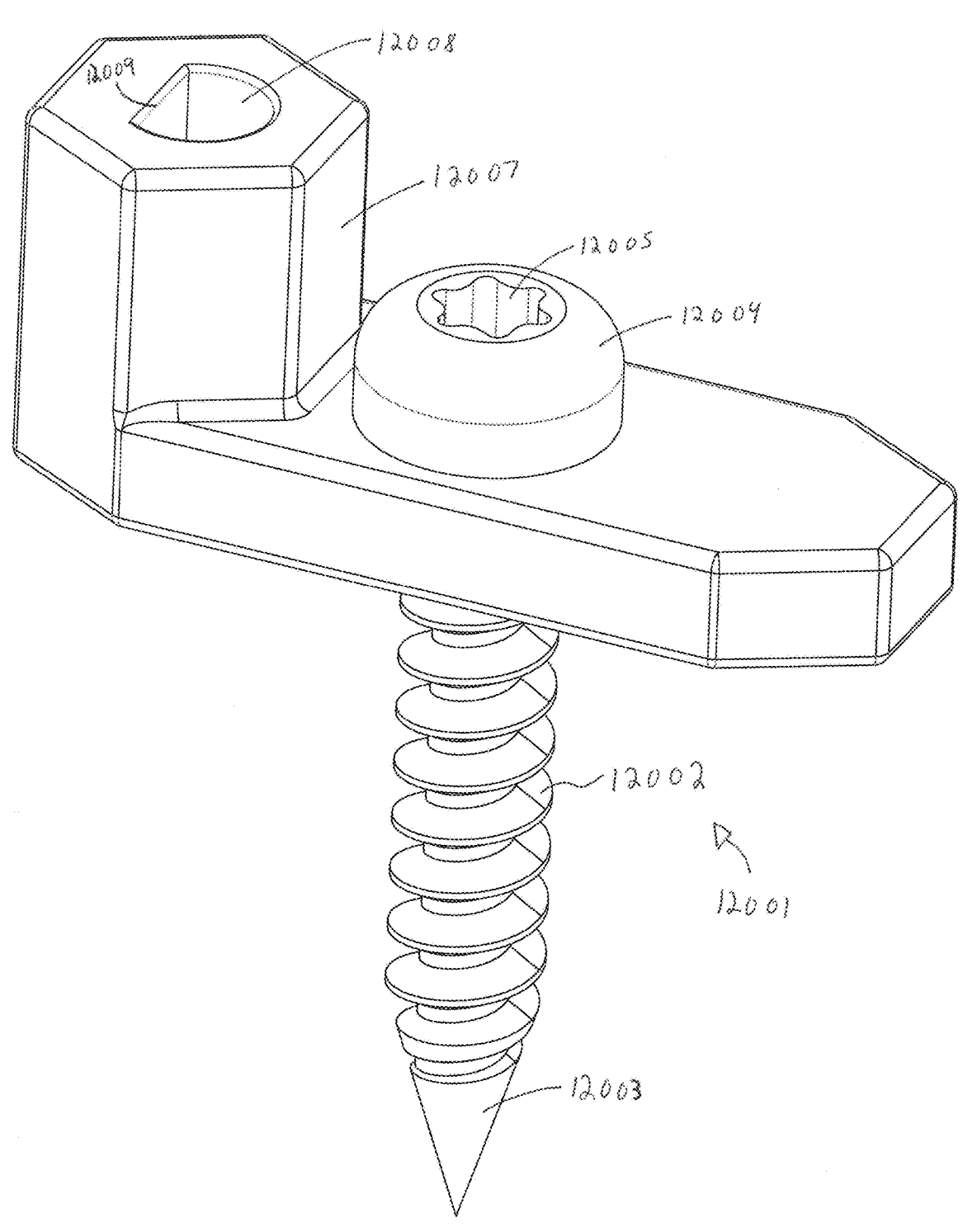

FIG. 120A illustrates a top perspective view of an internal-mating bone-mounted fiducial attached to a single-screw plate in accordance with some embodiments of the invention.

Figures 120B, 120C:
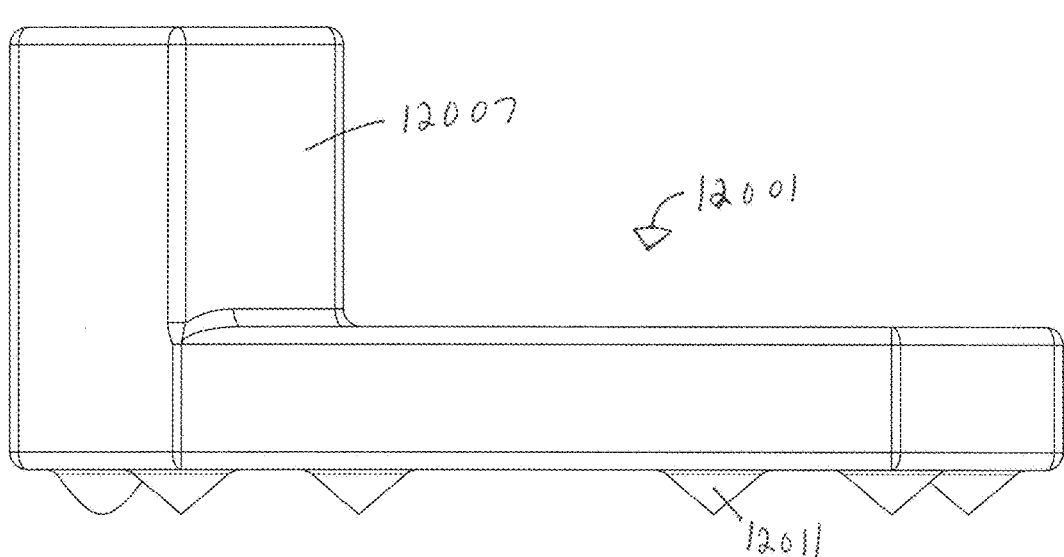

FIG. 120B illustrates a side view of an internal-mating bone-mounted fiducial as described previously in relation to FIG. 120A in accordance with some embodiments of the invention.

FIG. 120C illustrates a top view of an internal-mating bone-mounted fiducial as described previously in relation to FIGS. 120A-120B in accordance with some embodiments of the invention.

Figures 120D, 120E:
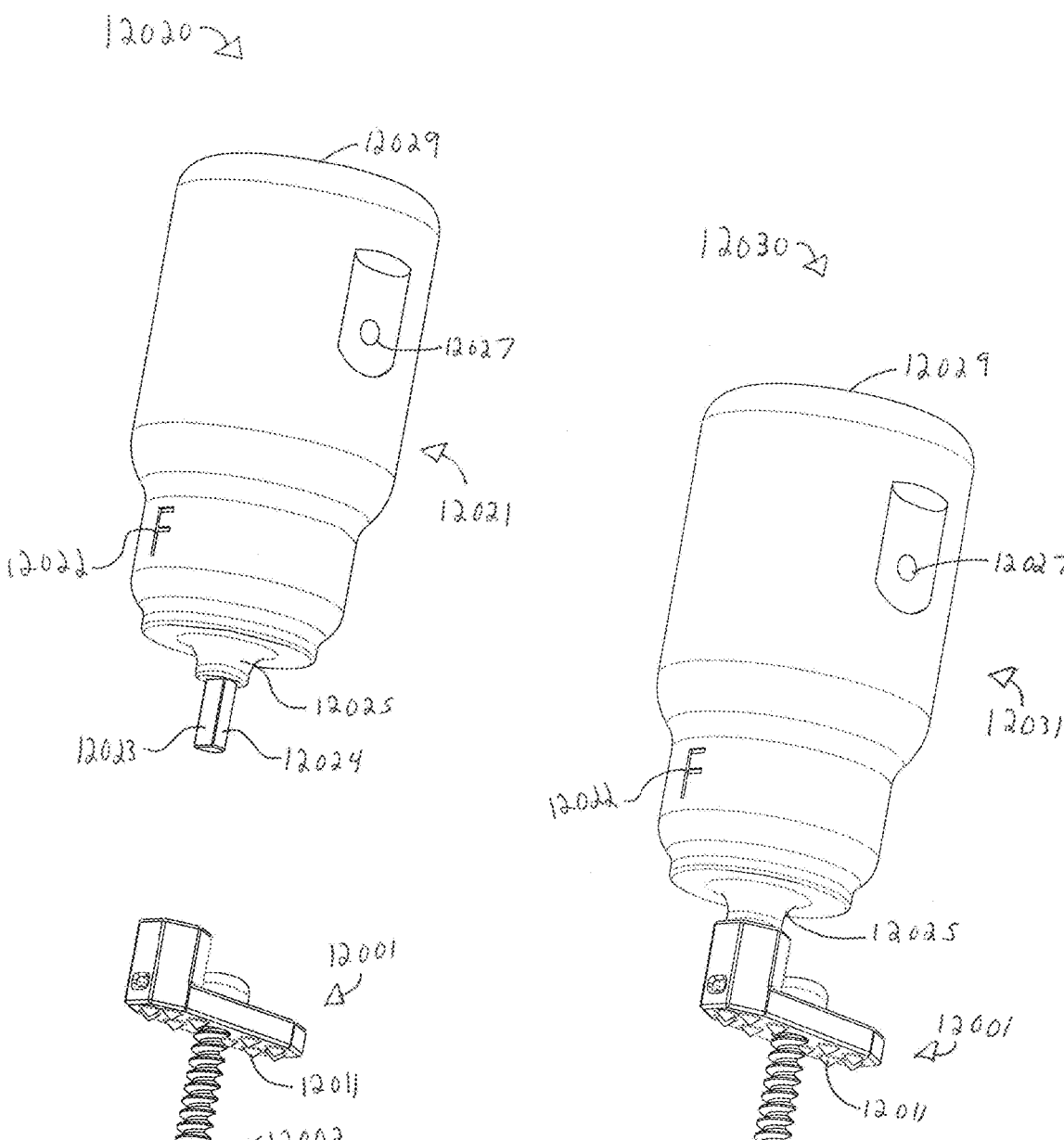

FIG. 120D illustrates perspective views of an internal-mating bone-mounted fiducial attached to single-screw plate and an external-mating tool tip adapter of a 3D-tracked tool as described previously in relation to FIGS. 120A-120C in accordance with some embodiments of the invention.

FIG. 120E illustrates perspective views of an internal-mating bone-mounted fiducial attached to a single-screw plate engaged with an external-mating tool tip adapter of a 3D-tracked tool as described previously in relation to FIGS. 120A-120D in accordance with some embodiments of the invention.

Figure 120F:
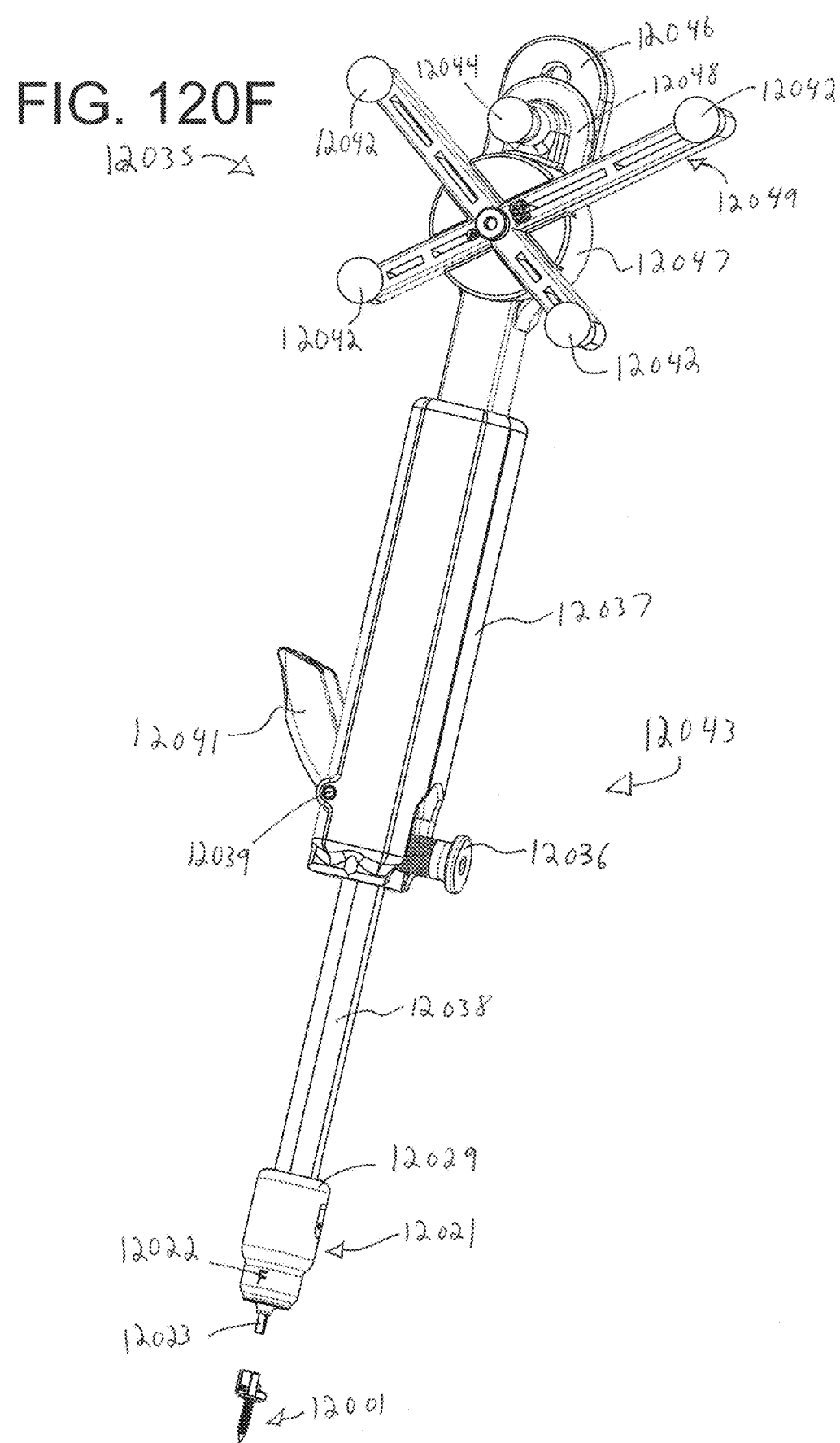

FIG. 120F illustrates a perspective view of a 3D-tracked tool with external-mating tool tip adapter disengaged with an internal-mating bone-mounted fiducial attached to a single-screw plate and in an untriggered state as described previously in relation to FIGS. 120A-120E in accordance with some embodiments of the invention.

Figures 120G, 120H:
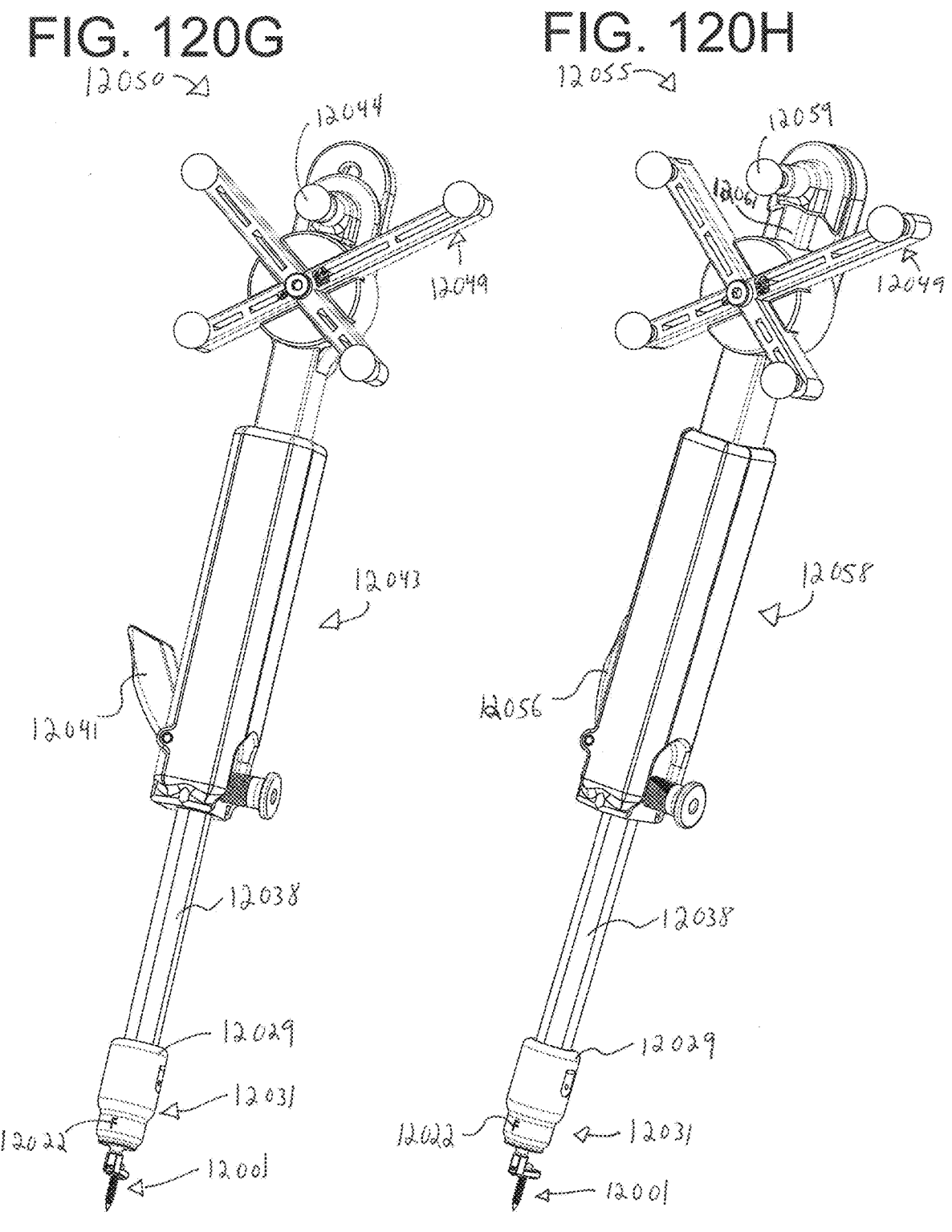

FIG. 120G illustrates a perspective view of a 3D-tracked tool with external-mating tool tip adapter engaged with an internal-mating bone-mounted fiducial attached to a single-screw plate and in an untriggered state as described previously in relation to FIGS. 120A-120F in accordance with some embodiments of the invention.

FIG. 120H illustrates a perspective view of a 3D-tracked tool with external-mating tool tip adapter engaged with an internal-mating bone-mounted fiducial attached to a single-screw plate and in a triggered state as described previously in relation to FIGS. 120A-120G in accordance with some embodiments of the invention.

Figure 121A:
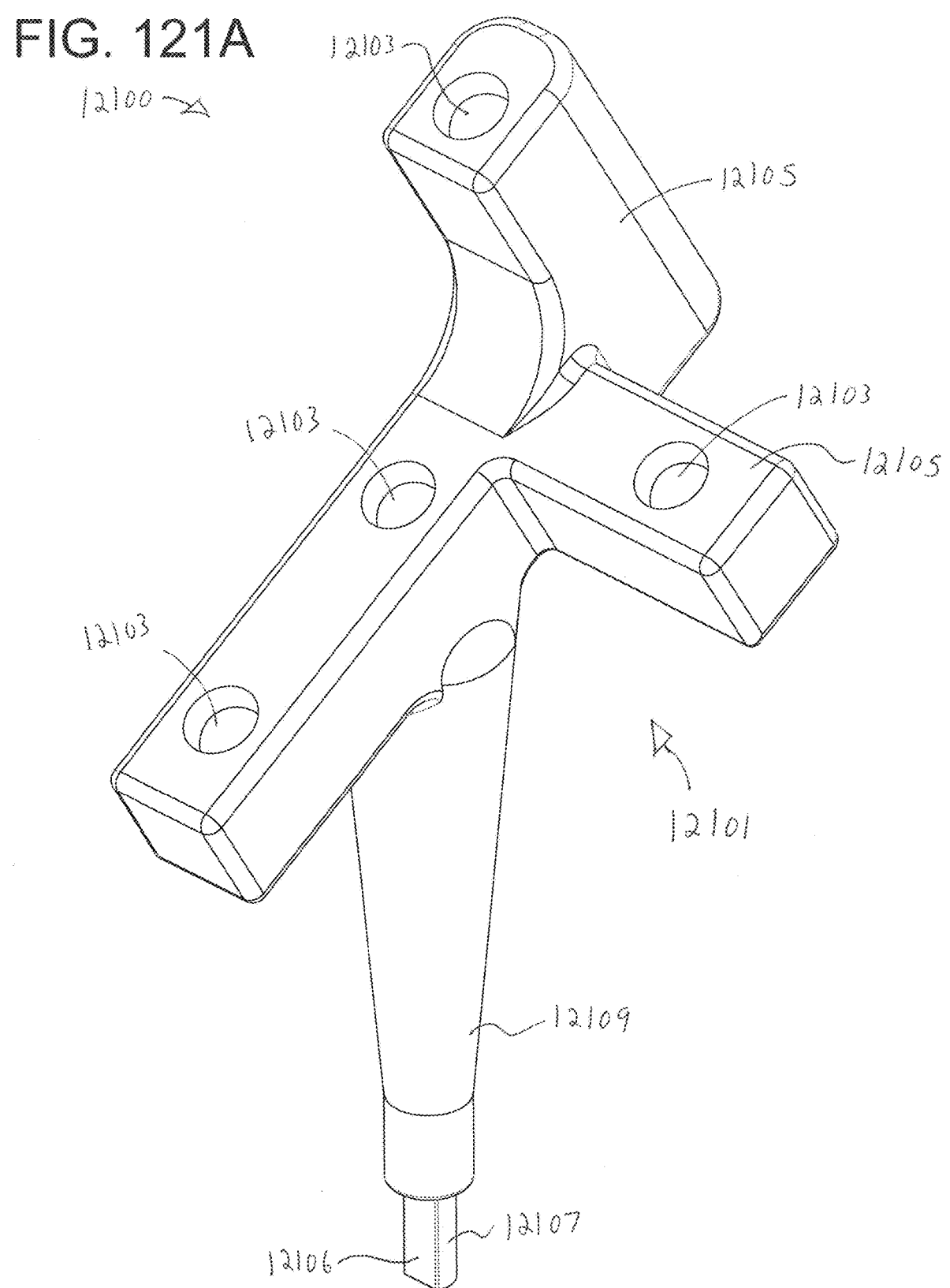

FIG. 121A illustrates a perspective view of an external-mating bone-mounted fiducial X-Ray adapter with asymmetrically distributed holes for embedding radiopaque spheres in accordance with some embodiments of the invention.

Figure 121B:
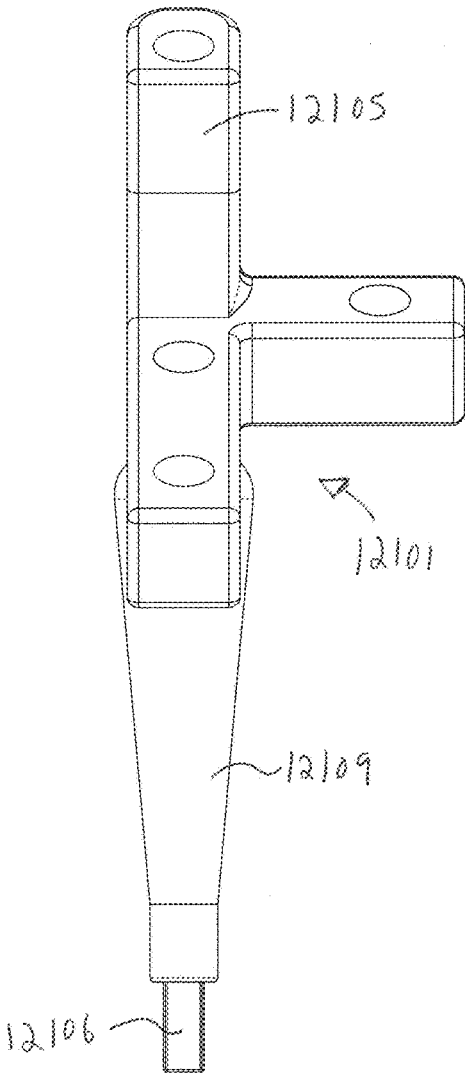

FIG. 121B illustrates a front view of an external-mating bone-mounted fiducial X-Ray adapter with asymmetrically distributed holes for embedding radiopaque spheres as described previously in relation to FIG. 121A in accordance with some embodiments of the invention.

Figure 121C:
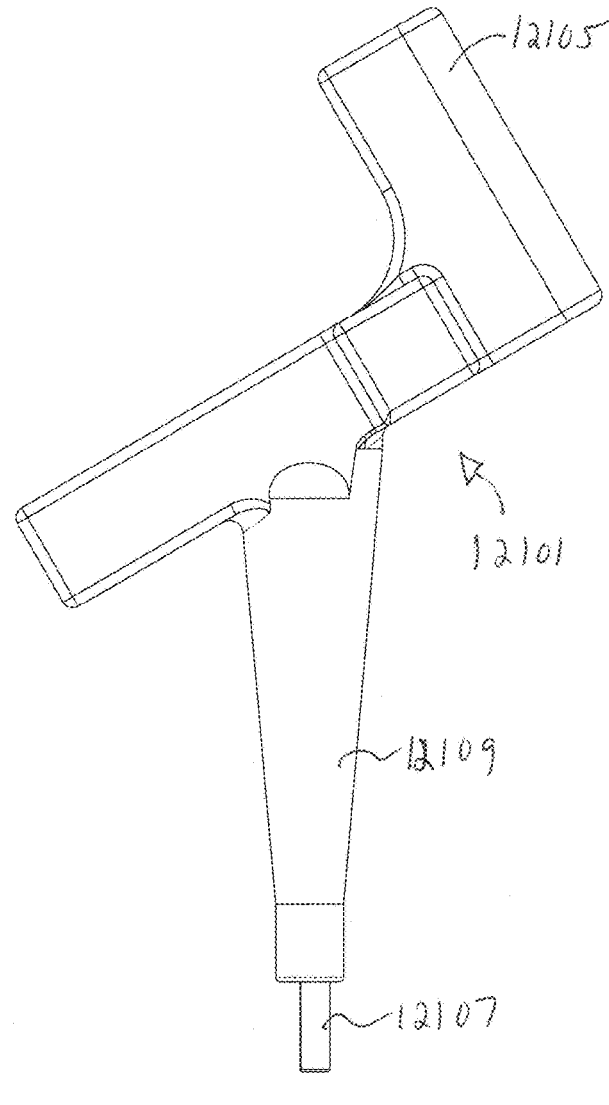

FIG. 121C illustrates a side view of an external-mating bone-mounted fiducial X-Ray adapter with asymmetrically distributed holes for embedding radiopaque spheres as described previously in relation to FIGS. 121A-121B in accordance with some embodiments of the invention.

Figure 121D:
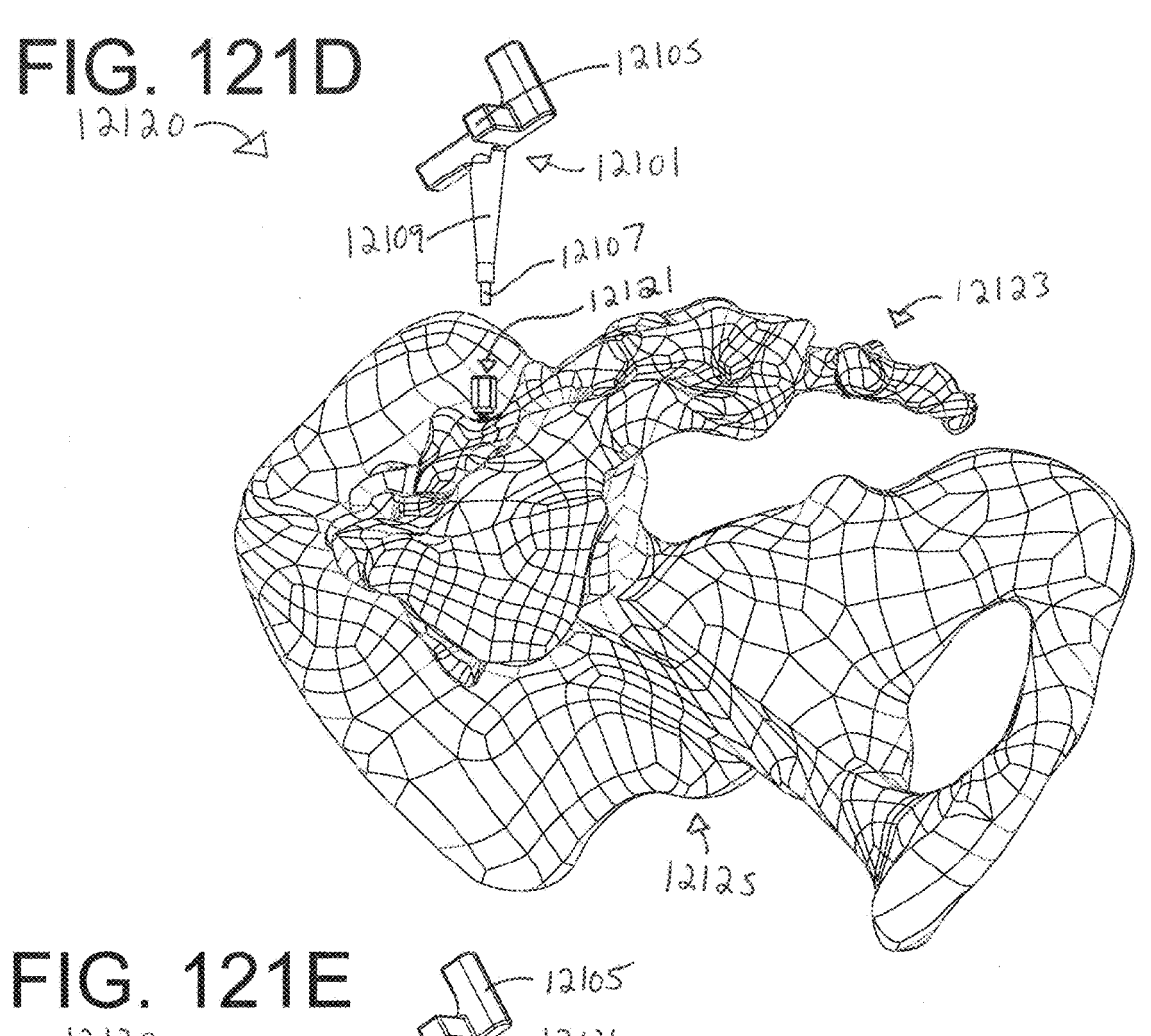
Figure 121E:
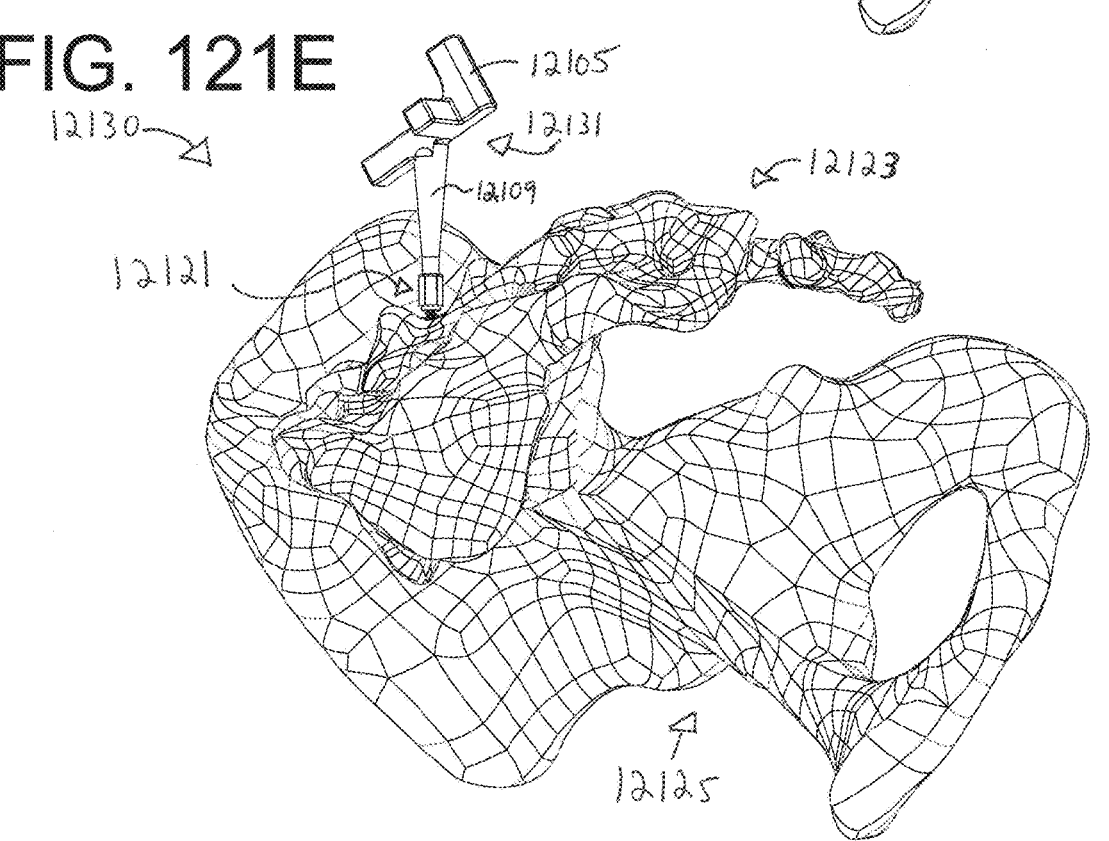
Figure 121F:
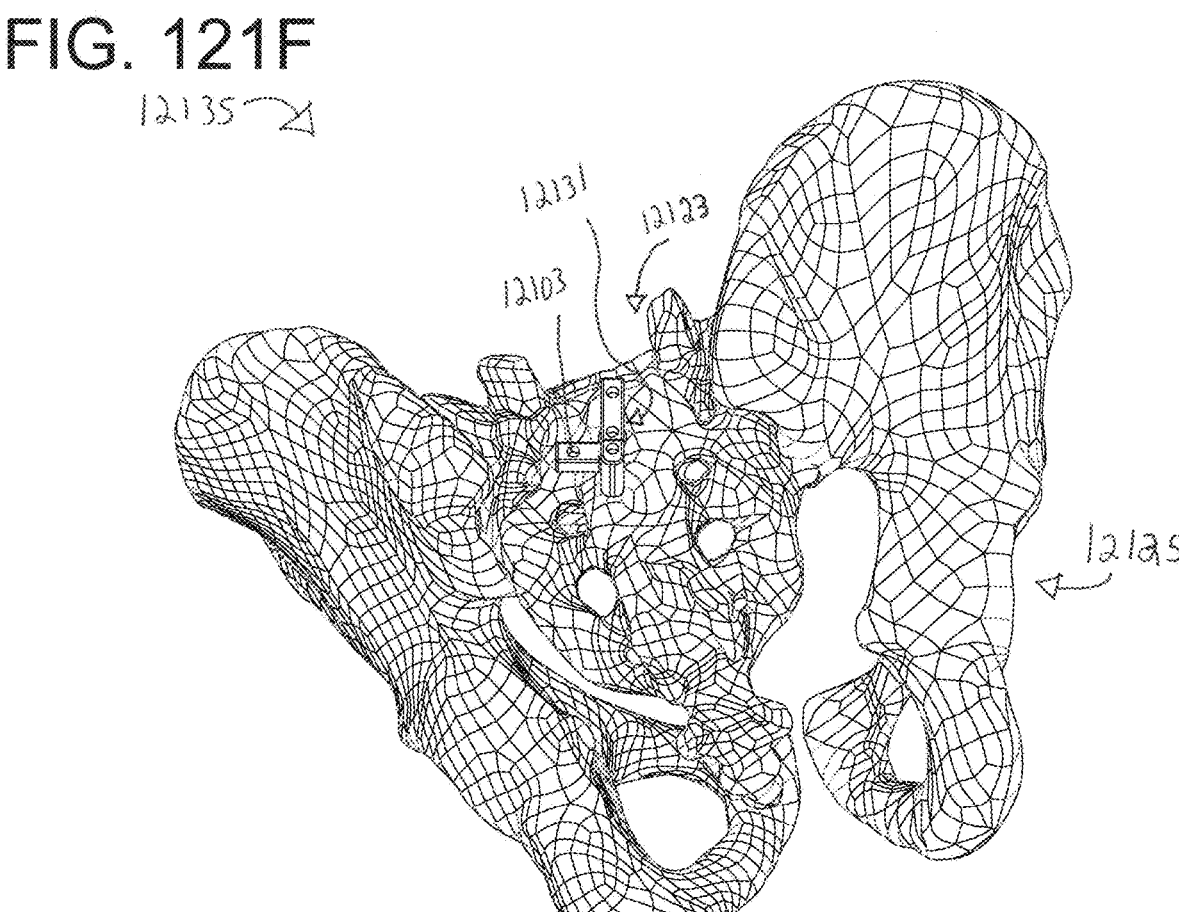

FIGS. 121D-121F illustrate perspective views of an external-mating bone-mounted fiducial X-Ray adapter embedded with asymmetrically distributed radiopaque spheres disengaged and engaged with an internal-mating bone-mounted fiducial implanted into the sacrum as described previously in relation to FIGS. 121A-121C in accordance with some embodiments of the invention.

Figure 121G:
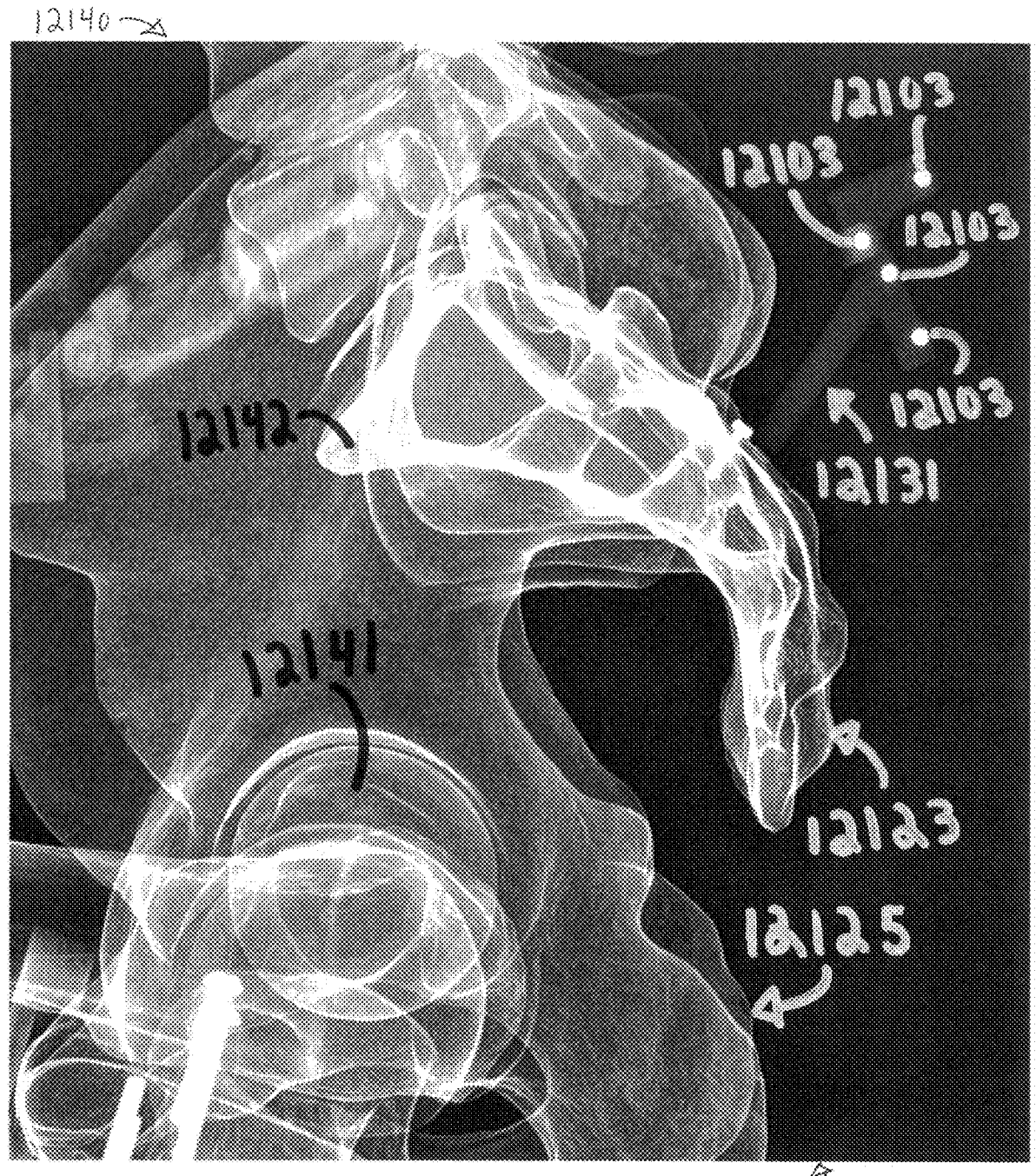

FIG. 121G illustrates an X-Ray image taken from a lateral view visualizing the pelvis and asymmetrically distributed radiopaque spheres of the bone-mounted fiducial X-Ray adapter as described previously in relation to FIGS. 121A-121F in accordance with some embodiments of the invention.

Figure 121H:
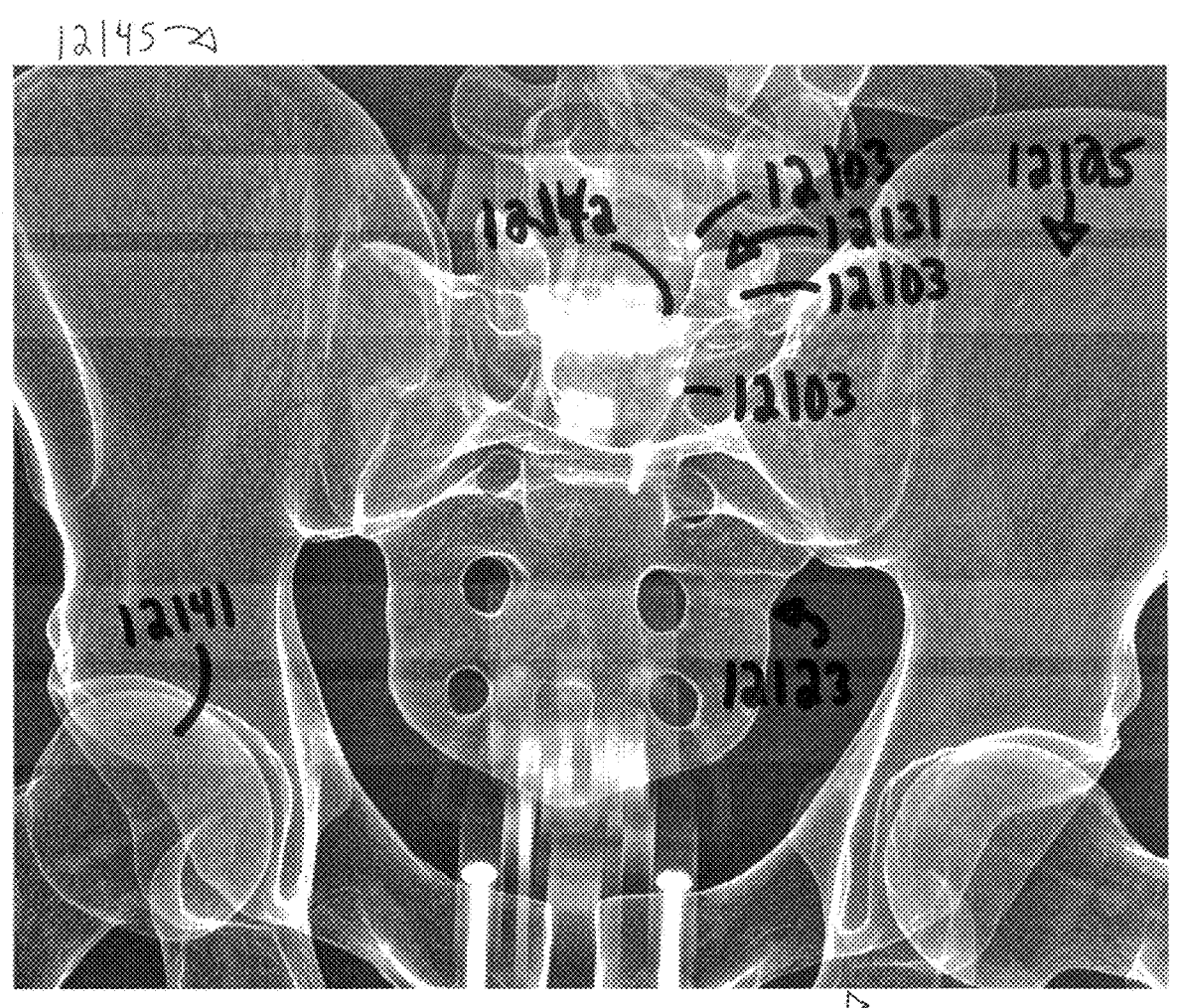

FIG. 121H illustrates an X-Ray image taken from an AP view visualizing the pelvis and asymmetrically distributed radiopaque spheres of the bone-mounted fiducial X-Ray adapter as described previously in relation to FIGS. 121A-121G in accordance with some embodiments of the invention.

FIGS. 122A-122B illustrate top and bottom perspective views of an internal-mating bone-mounted fiducial X-Ray adapter with asymmetrically distributed holes for embedding radiopaque spheres and arrow indicator for determining anatomical axes and an external-mating bone-mounted fiducial in accordance with some embodiments of the invention.

Figure 122C:
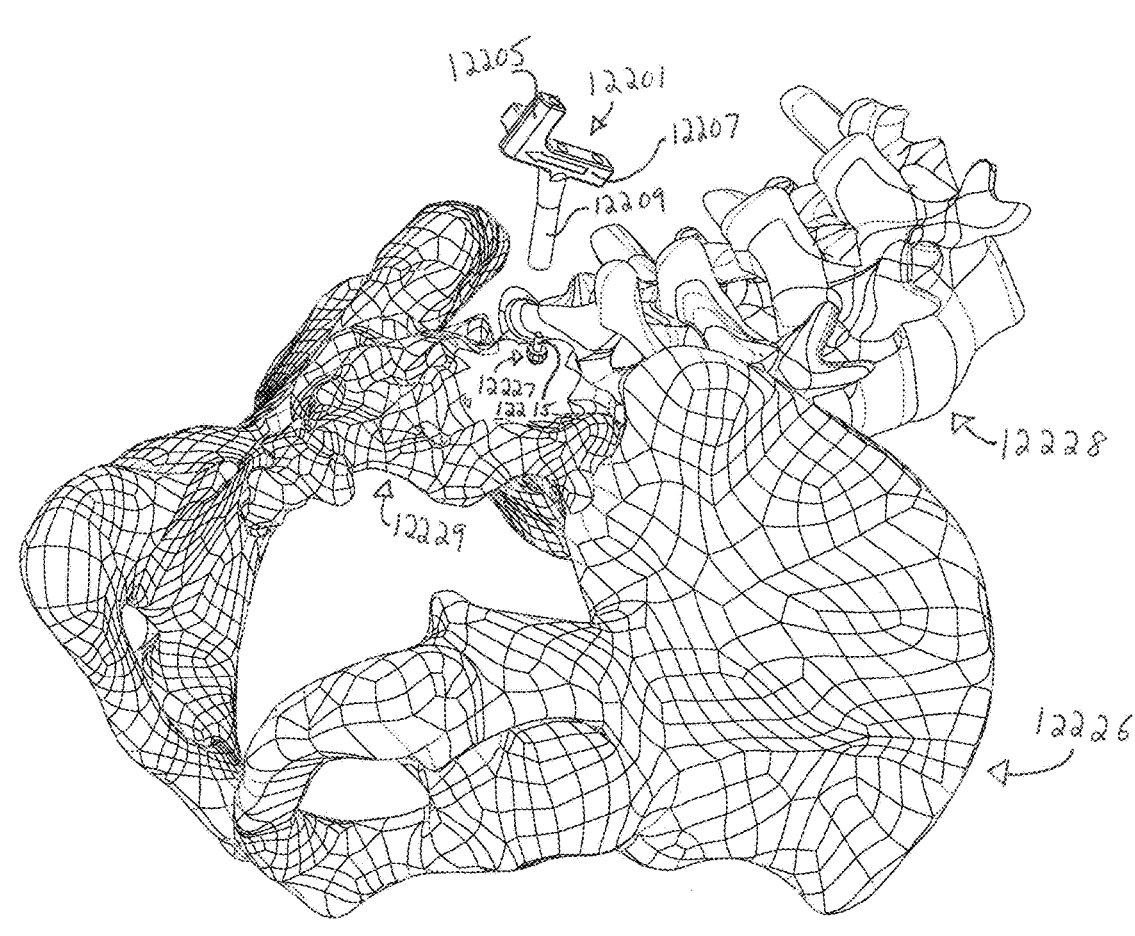

FIG. 122C illustrates a perspective view of an internal-mating bone-mounted fiducial X-Ray adapter embedded with asymmetrically distributed radiopaque spheres disengaged with an external-mating bone-mounted fiducial implanted into the sacrum as described previously in relation to FIGS. 122A-122B in accordance with some embodiments of the invention.

Figure 122D:
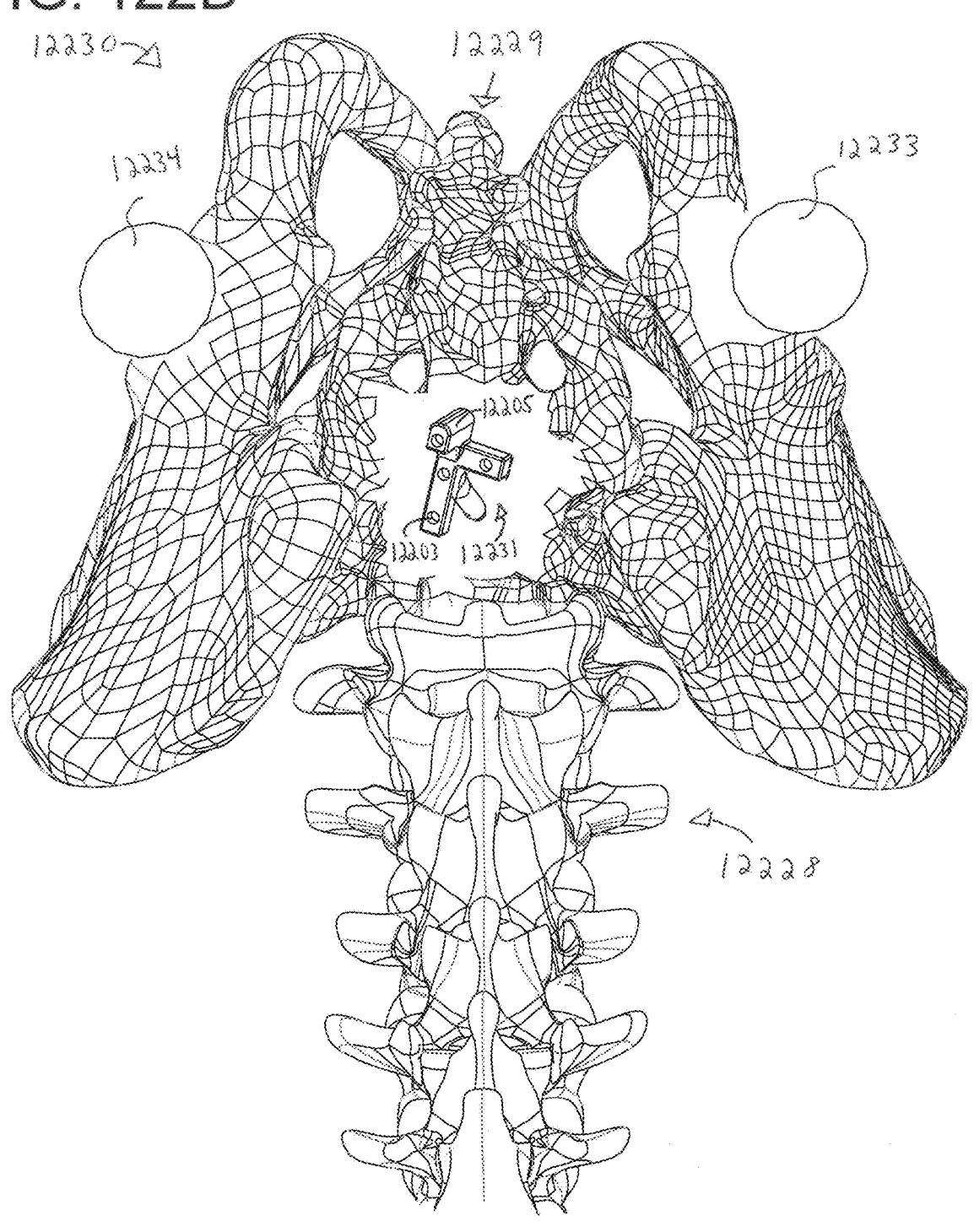

FIG. 122D illustrates a top view of an internal-mating bone-mounted fiducial X-Ray adapter embedded with asymmetrically distributed radiopaque spheres engaged with an external-mating bone-mounted fiducial implanted into the sacrum as described previously in relation to FIGS. 122A-122C in accordance with some embodiments of the invention.

Figure 123A:
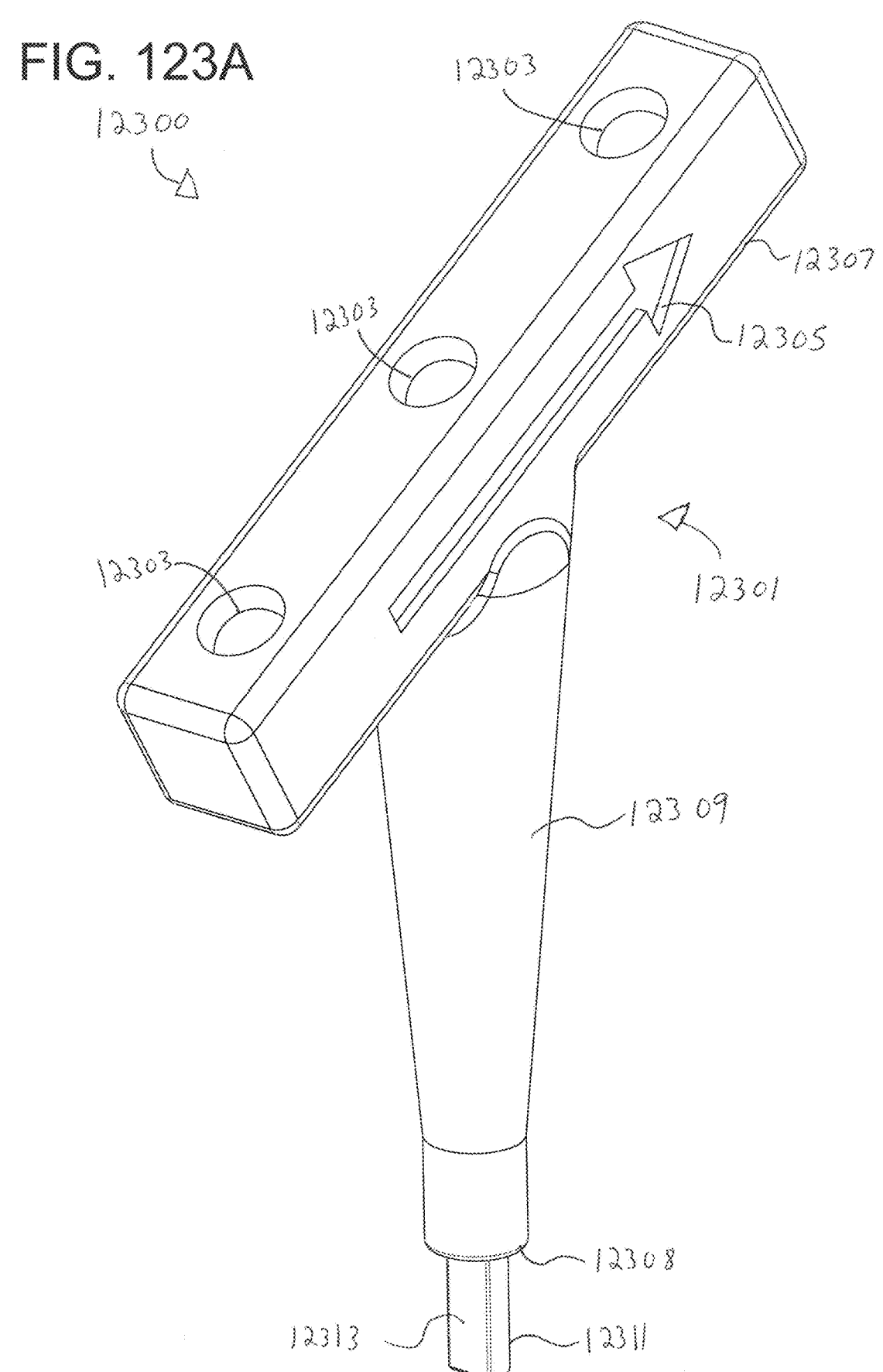

FIG. 123A illustrates a perspective view of an external-mating bone-mounted fiducial X-Ray adapter with three symmetrically distributed holes for embedding radiopaque spheres with an arrow indicator for determining anatomical axes in accordance with some embodiments of the invention.

Figures 123B, 123C, 123D:
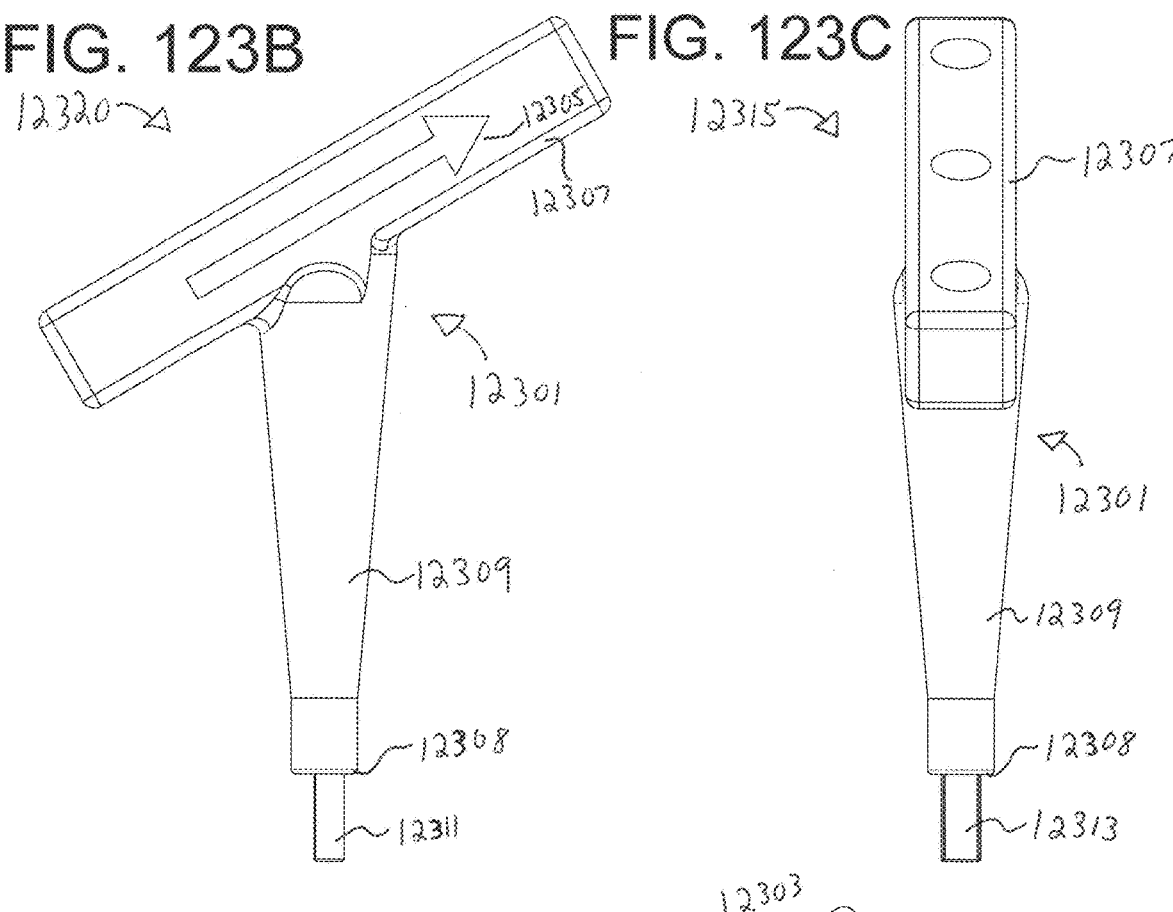

FIG. 123B illustrates a front view of an external-mating bone-mounted fiducial X-Ray adapter with three symmetrically distributed holes for embedding radiopaque spheres with an arrow indicator for determining anatomical axes as described previously in relation to FIG. 123A in accordance with some embodiments of the invention.

FIG. 123C illustrates a side view of an external-mating bone-mounted fiducial X-Ray adapter with three symmetrically distributed holes for embedding radiopaque spheres with an arrow indicator for determining anatomical axes as described previously in relation to FIGS. 123 A-123B in accordance with some embodiments of the invention.

FIG. 123D illustrates a side cross-sectional view of an external-mating bone-mounted fiducial X-Ray adapter with three symmetrically distributed radiopaque spheres embedded as described previously in relation to FIGS. 123A-123C in accordance with some embodiments of the invention.

Figure 123E:
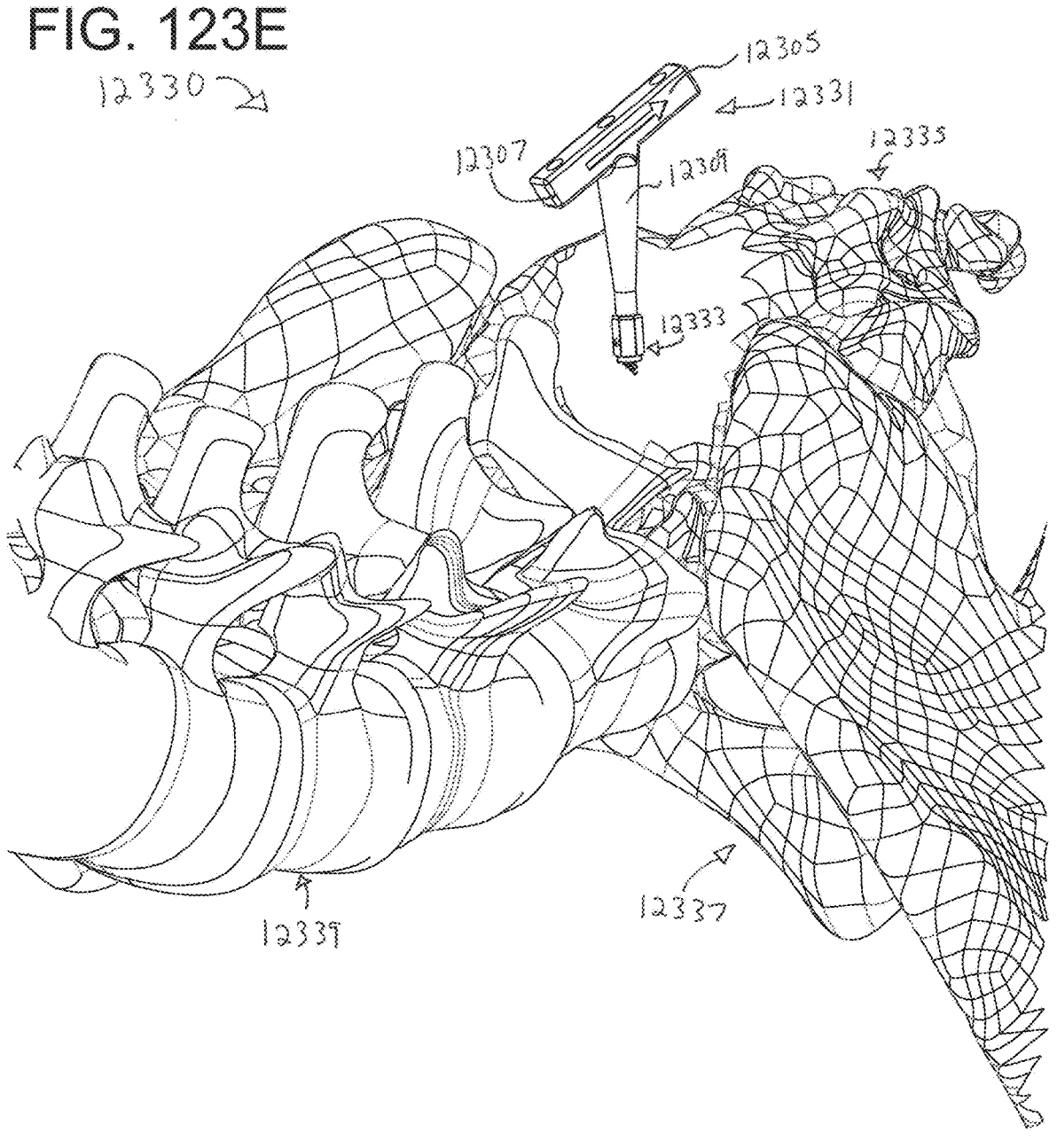

FIG. 123E illustrates a perspective view of an external-mating bone-mounted fiducial X-Ray adapter with three symmetrically distributed radiopaque spheres engaged with an internal-mating bone-mounted fiducial implanted in the sacrum as described previously in relation to FIGS. 123A-123D in accordance with some embodiments of the invention.

Figure 124A:
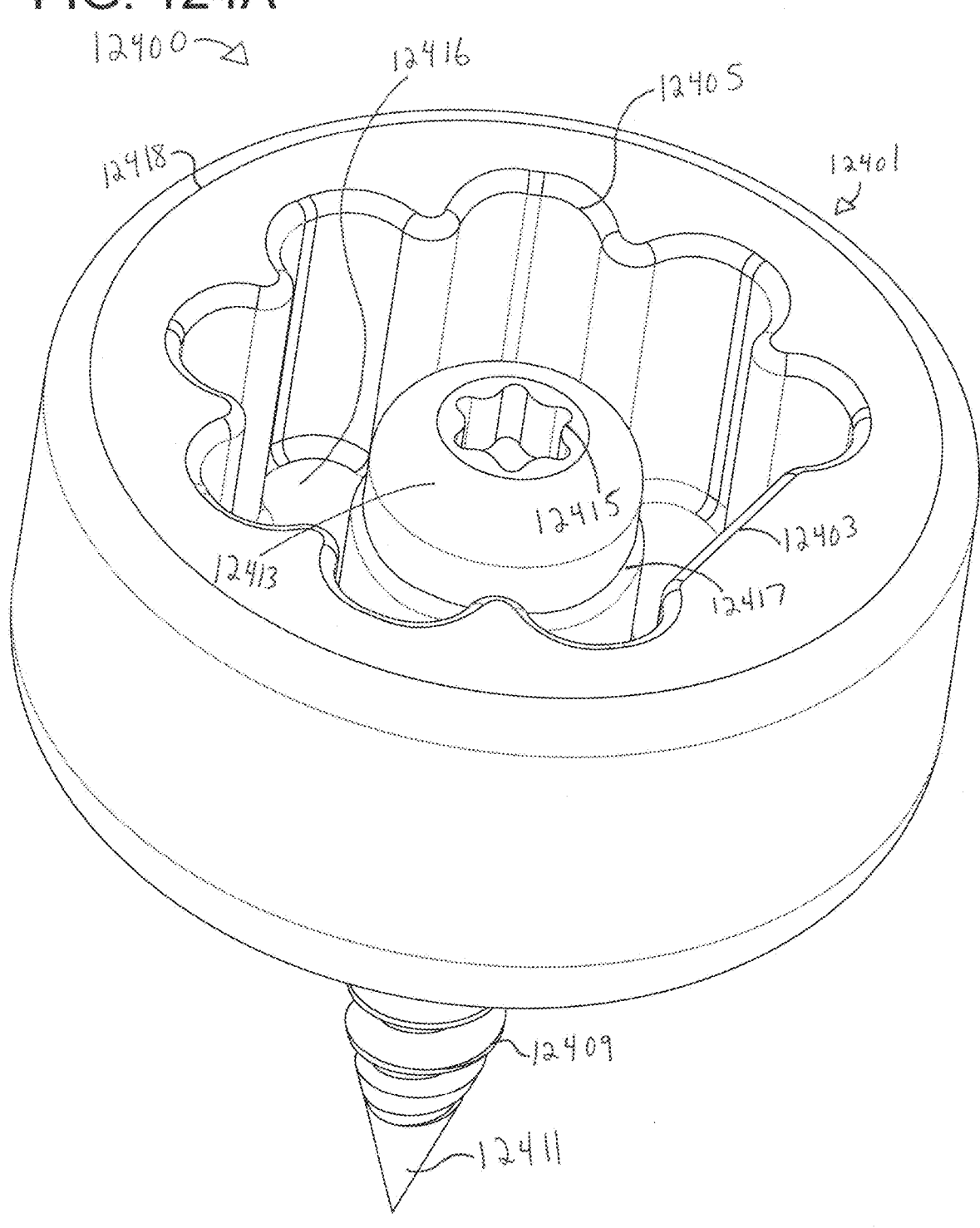

FIG. 124A illustrates a perspective view of a bone-mounted fiducial with a star-shaped internal-mating mechanism in accordance with some embodiments of the invention.

Figure 124B:
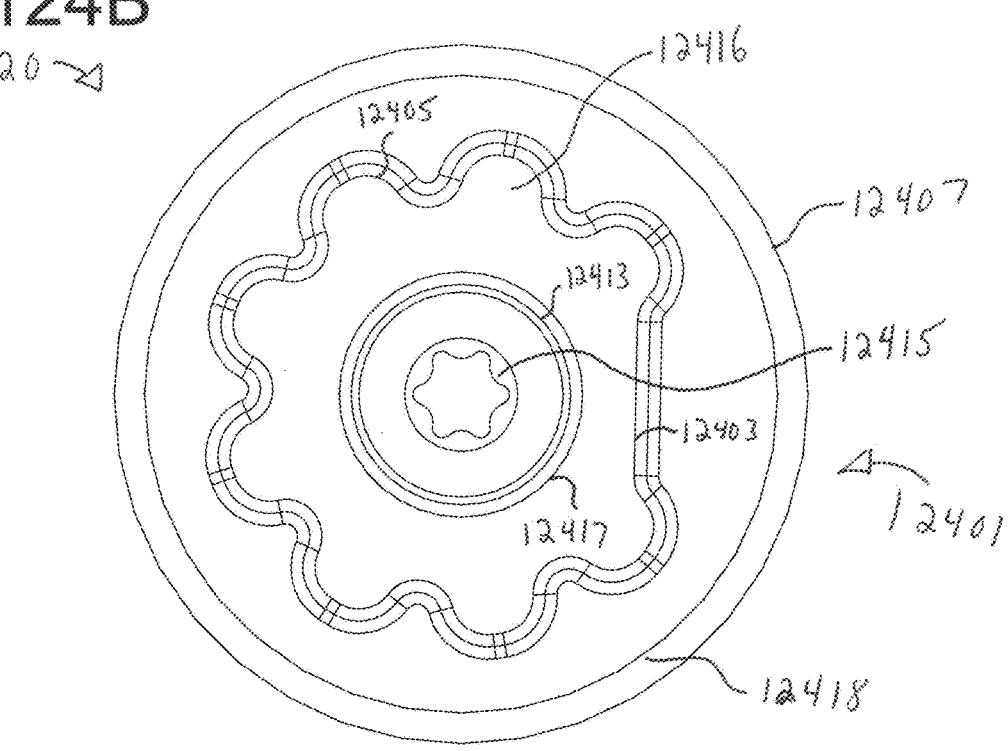

FIG. 124B illustrates a top view of a bone-mounted fiducial with a star-shaped internal-mating mechanism as described previously in relation to FIG. 124A in accordance with some embodiments of the invention.

Figure 124C:
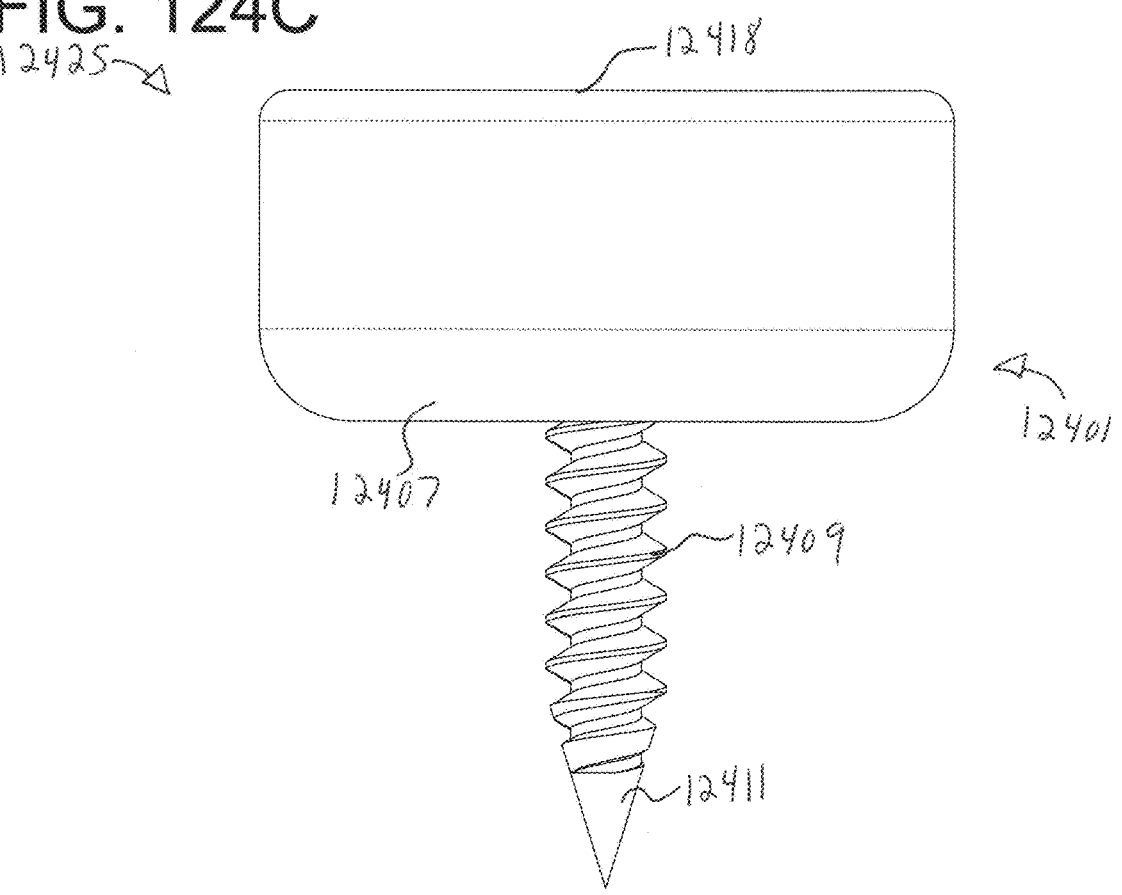

FIG. 124C illustrates a side view of a bone-mounted fiducial with a star-shaped internal-mating mechanism as described previously in relation to FIGS. 124A-124B in accordance with some embodiments of the invention.

Figure 124D:
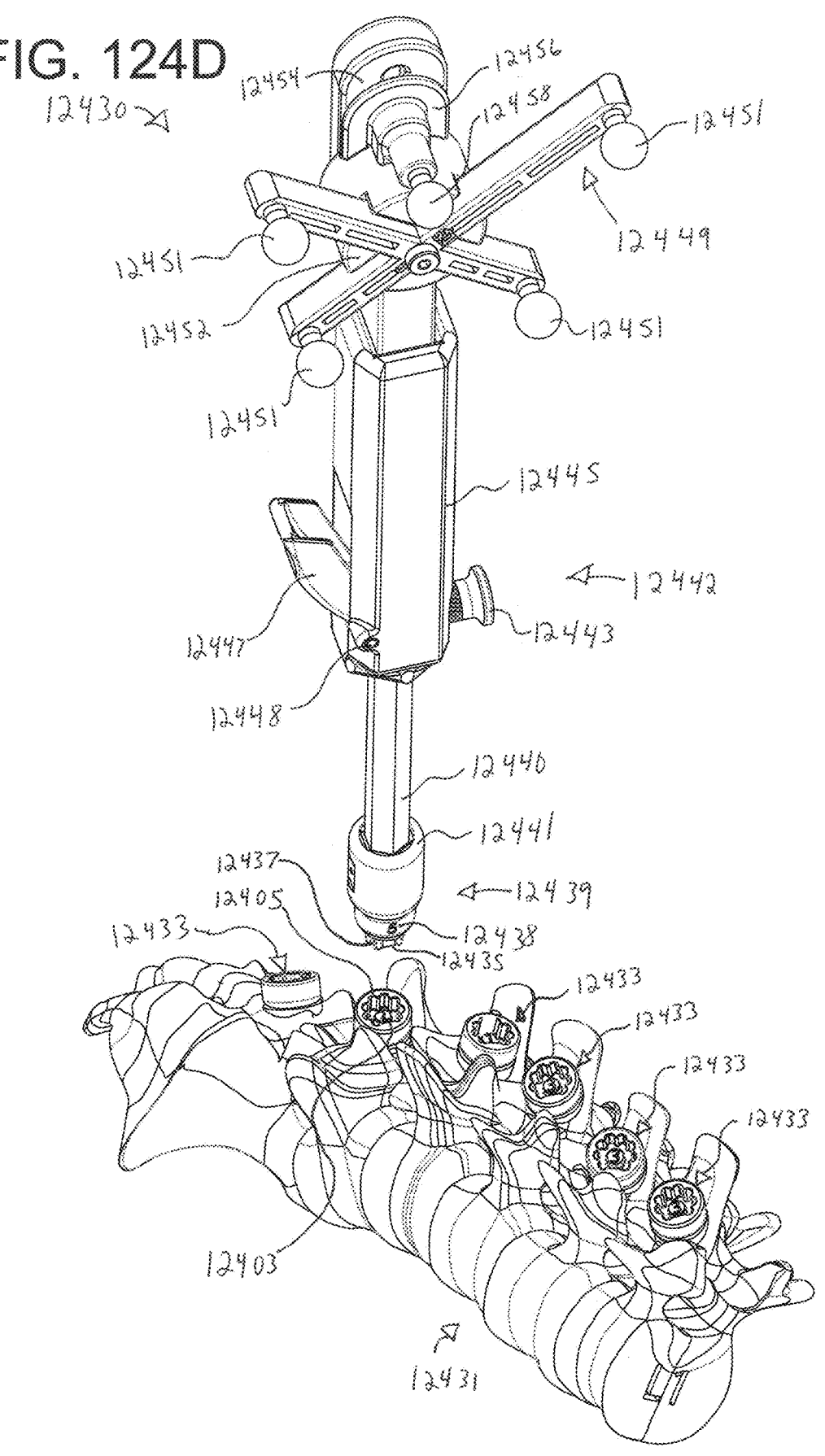

FIG. 124D illustrates a perspective view of a 3D-tracked tool with external-mating tool tip adapter disengaged with an internal-mating bone-mounted fiducial implanted in the vertebra as described previously in relation to FIGS. 124A-124C in accordance with some embodiments of the invention.

Figure 124E:
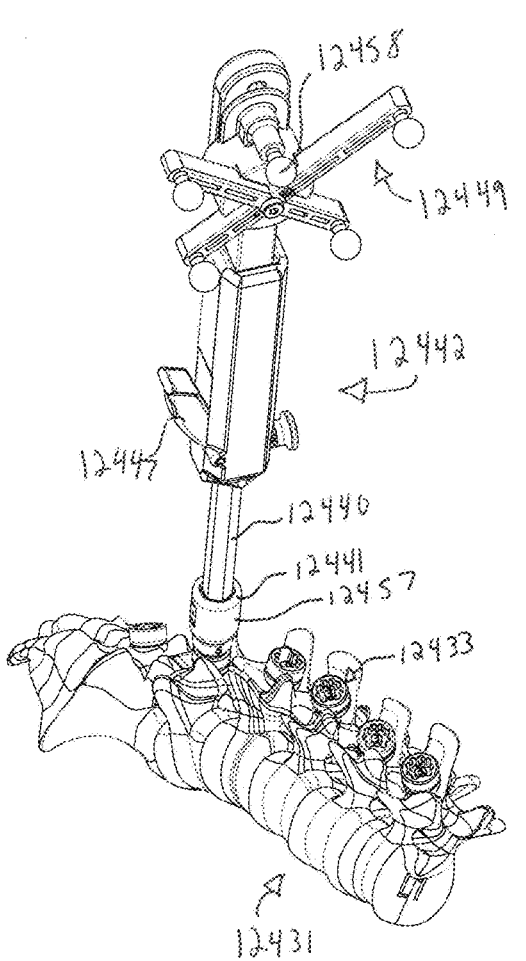
Figure 124F:
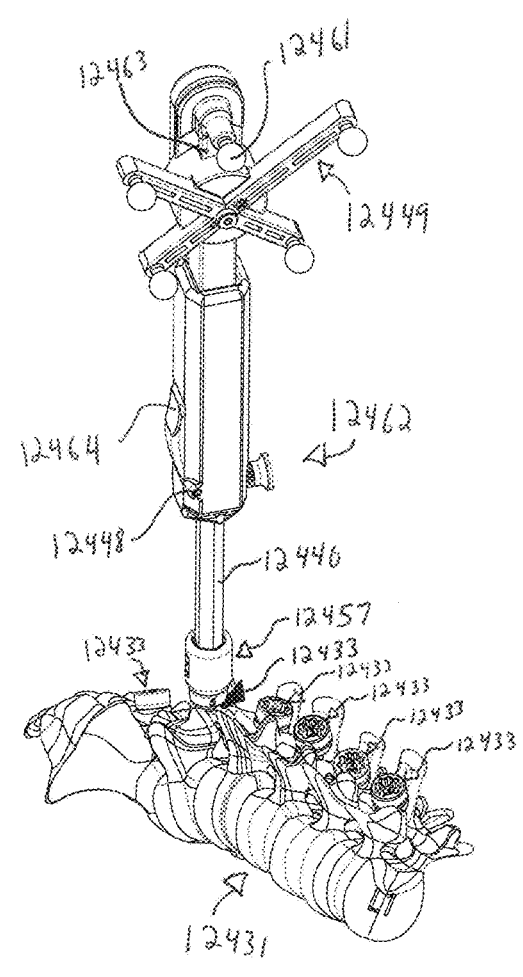

FIGS. 124E-124F illustrate a perspective view of a 3D-tracked tool with external-mating tool tip adapter engaged with an internal-mating bone-mounted fiducial implanted in the vertebra and in an untriggered and triggered state as described previously in relation to FIGS. 124A-124D in accordance with some embodiments of the invention.

Figures 124G, 124H:
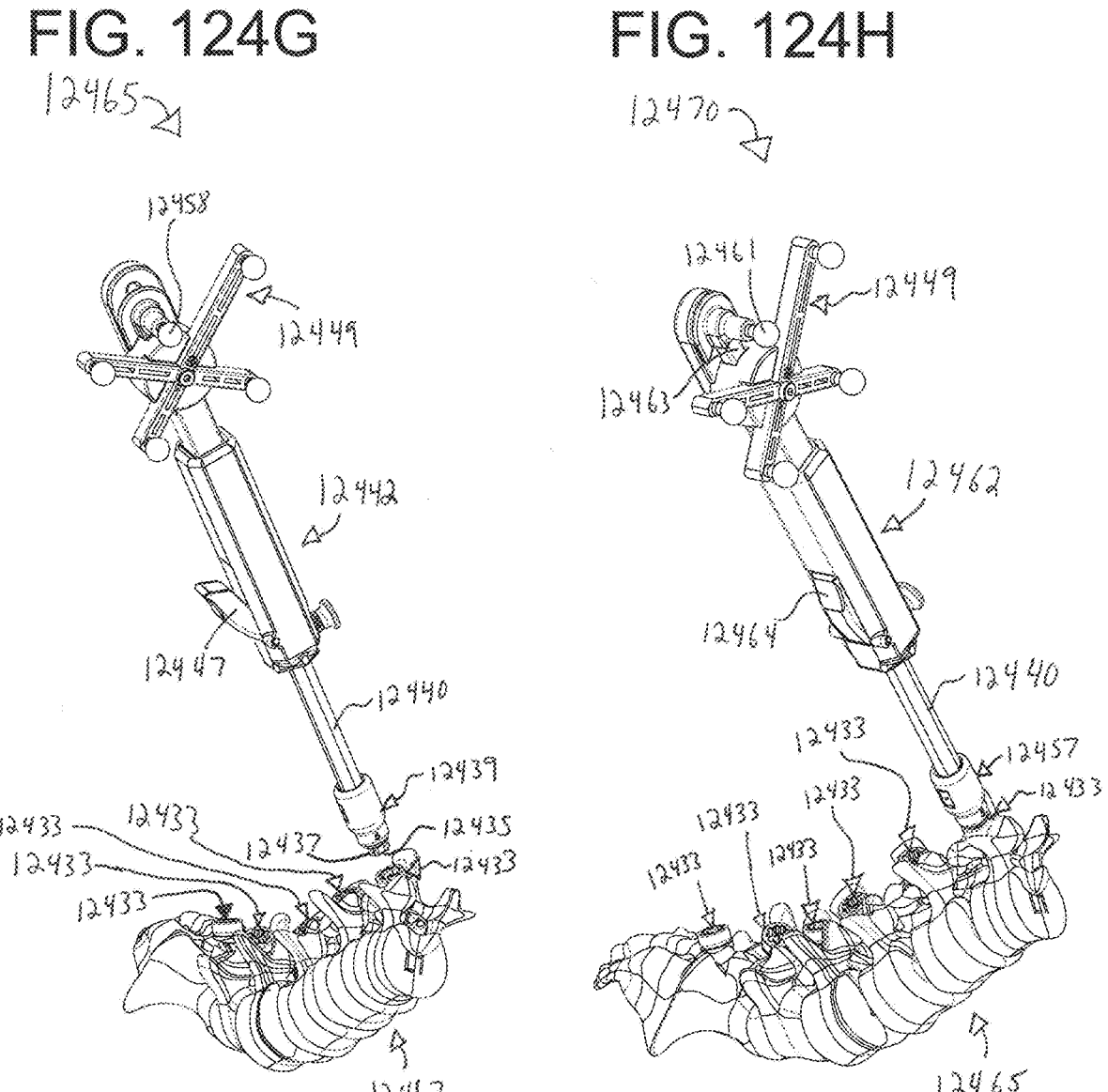

FIG. 124G illustrates a perspective view of a 3D-tracked tool with external-mating tool tip adapter engaged with an internal-mating bone-mounted fiducial implanted in the vertebra and in an untriggered state as described previously in relation to FIGS. 124A-124F in accordance with some embodiments of the invention.

FIG. 124H illustrates a perspective view of a 3D-tracked tool with external-mating tool tip adapter engaged with an internal-mating bone-mounted fiducial implanted in the vertebra and in a triggered state as described previously in relation to FIGS. 124A-124G in accordance with some embodiments of the invention.

Figure 125A:
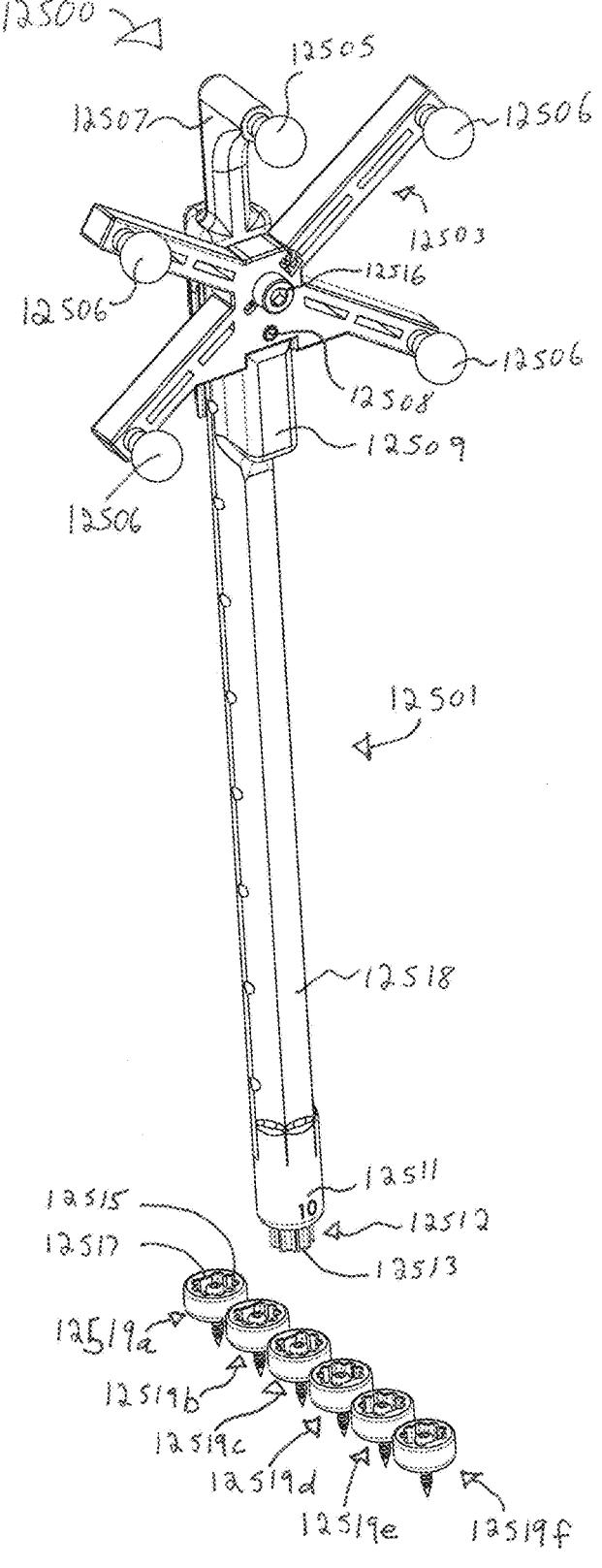

FIG. 125A illustrates a perspective view of a 3D-tracked tool with an external-mating tool tip not engaged with internal-mating bone-mounted fiducials in accordance with some embodiments of the invention.

Figure 125B:
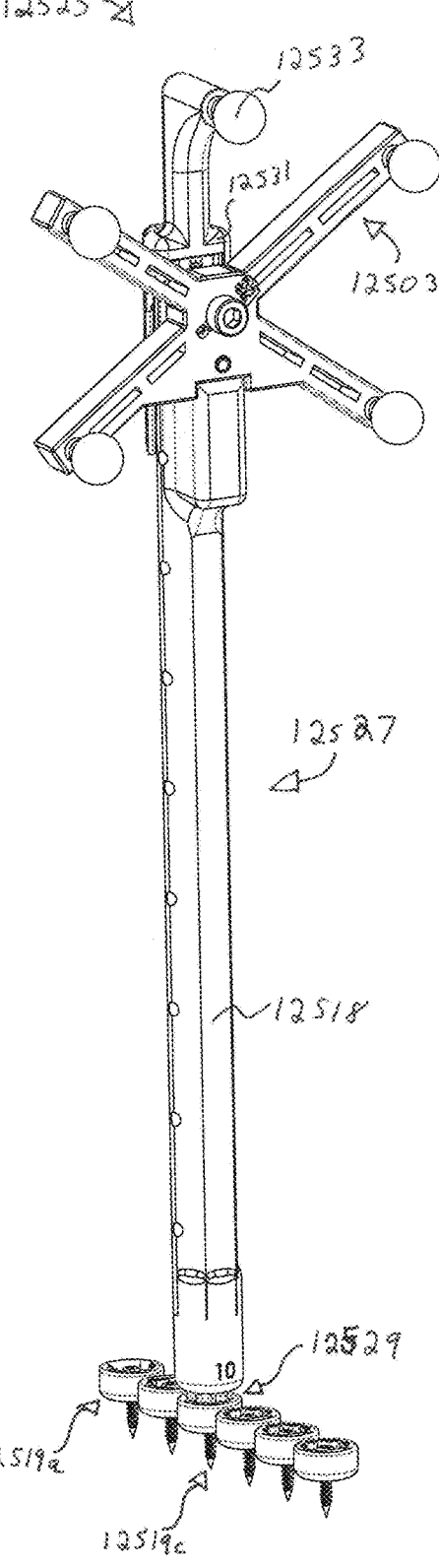

FIG. 125B illustrates a perspective view of a 3D-tracked tool with an external-mating tool tip engaged in a unique orientation with an internal-mating bone-mounted fiducial and in a triggered state as described previously in relation to FIG. 125A in accordance with some embodiments of the invention.

FIG. 125C illustrates a side view of a 3D-tracked tool with an external-mating tool tip not engaged with internal-mating bone-mounted fiducials as described previously in relation to FIGS. 125A-125B in accordance with some embodiments of the invention.

FIG. 125D illustrates a side view of a 3D-tracked tool with an external-mating tool tip engaged in a unique orientation with an internal-mating bone-mounted fiducial and in a triggered state as described previously in relation to FIGS. 125A-125C in accordance with some embodiments of the invention.

Figure 126A:
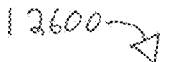

FIG. 126A illustrates a perspective view of a rod contour registration tool with linear triggering mechanism in accordance with some embodiments of the invention.

Figures 126B, 126C:
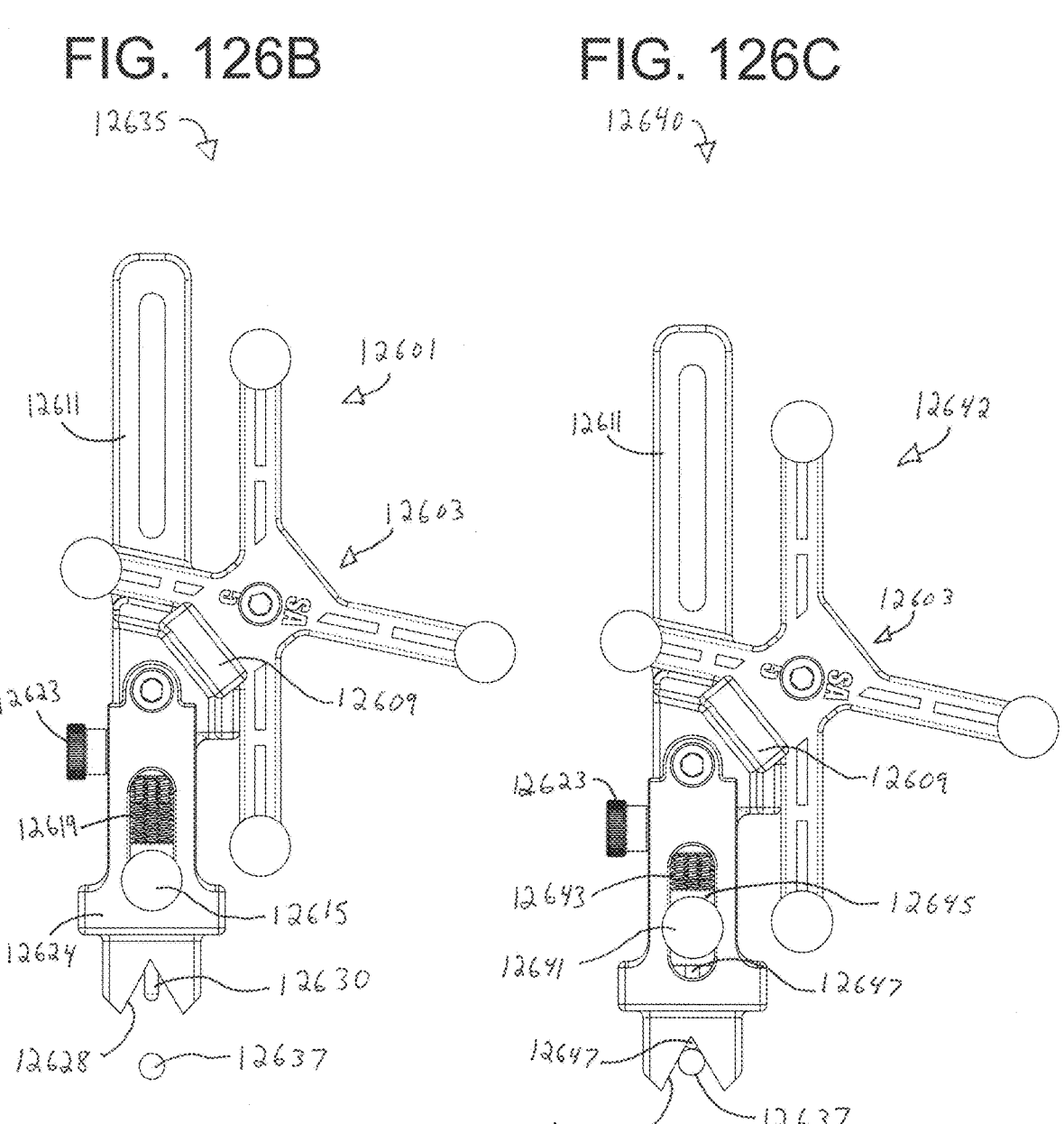

FIG. 126B illustrates a side view of a rod contour registration tool disengaged with a rod and in an untriggered state as described previously in relation to FIG. 126A in accordance with some embodiments of the invention.

FIG. 126C illustrates a side view of a rod contour registration tool engaged with a rod and in a triggered state as described previously in relation to FIGS. 126A-126B in accordance with some embodiments of the invention.

Figure 126D:
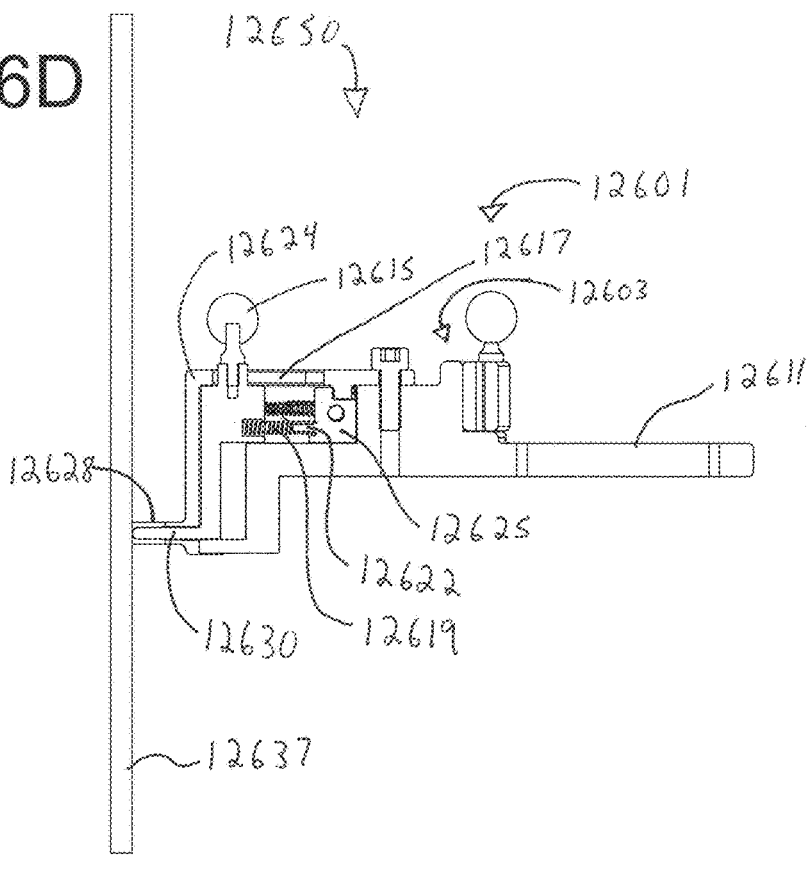

FIG. 126D illustrates a cross-sectional view of a rod contour registration tool disengaged with a rod and in an untriggered state as described previously in relation to FIGS. 126A-126C in accordance with some embodiments of the invention.

Figure 126E:
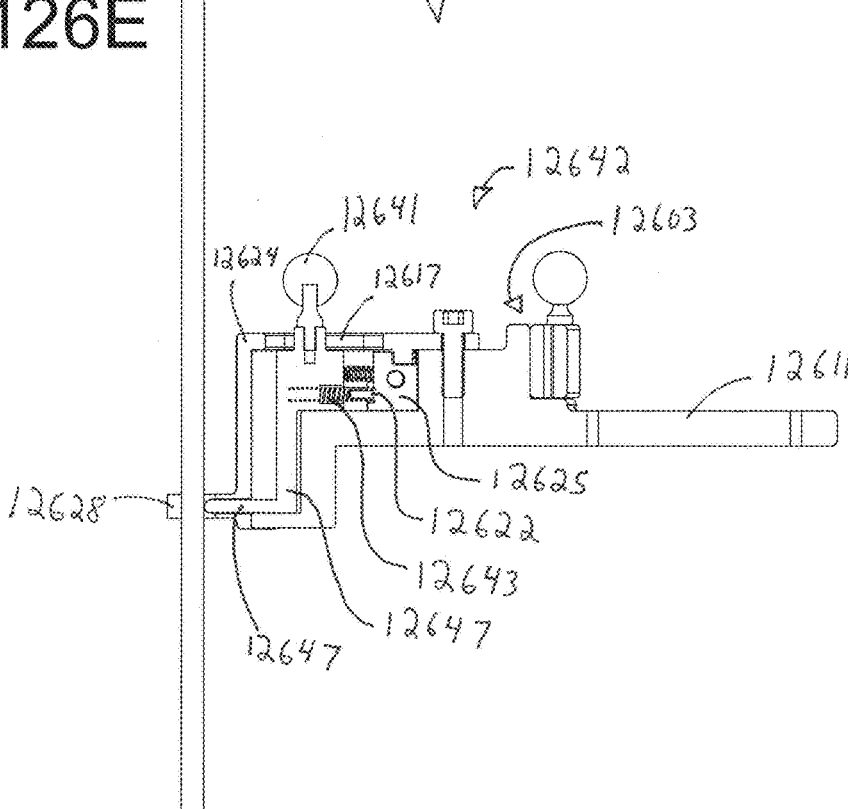

FIG. 126E illustrates a cross-sectional view of a rod contour registration tool engaged with a rod and in a triggered state as described previously in relation to FIGS. 126A-126D in accordance with some embodiments of the invention.

Figure 126F:
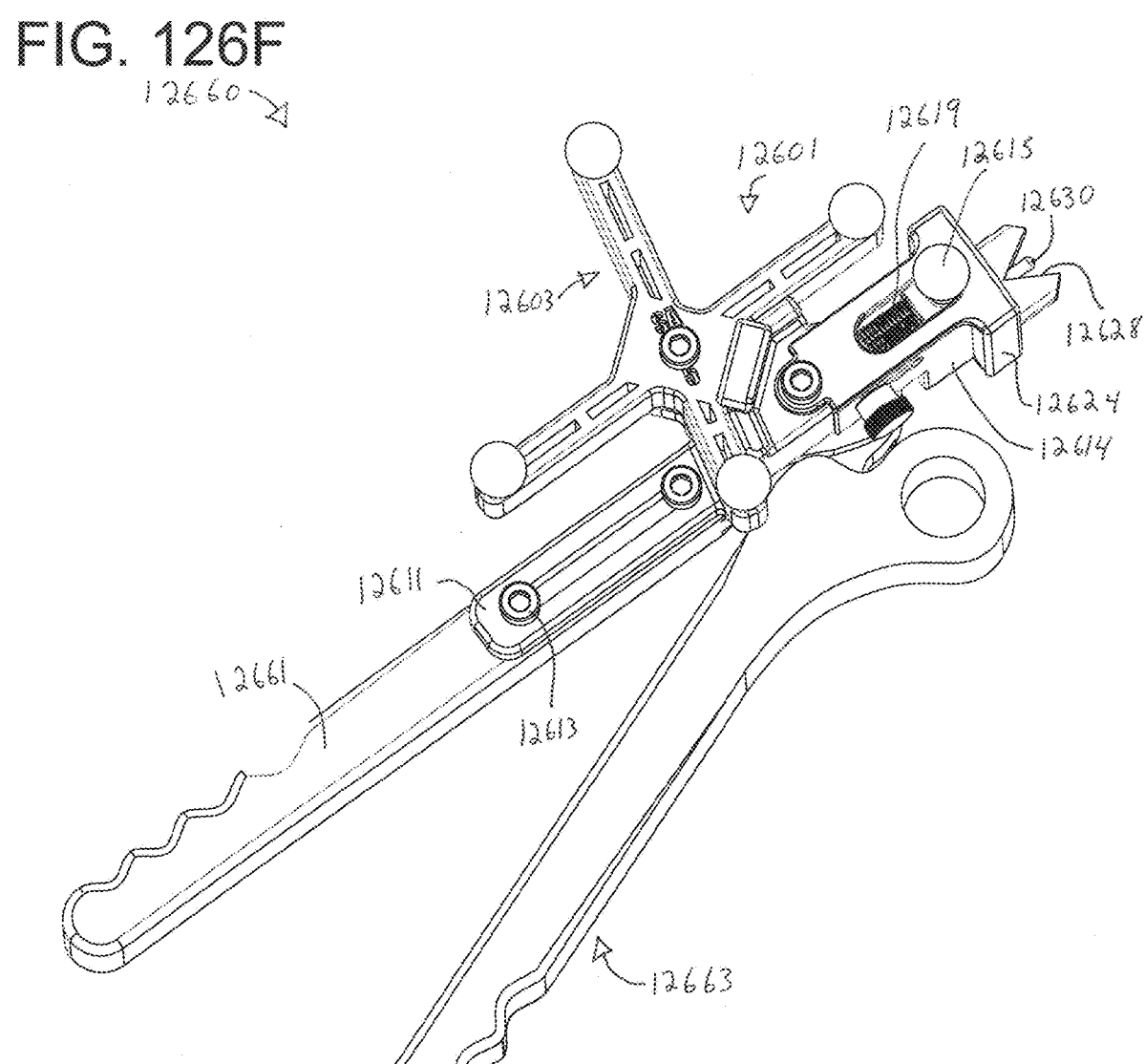

FIG. 126F illustrates a perspective view of a rod contour registration tool attached to a rod bender as described previously in relation to FIGS. 126A-126E in accordance with some embodiments of the invention.

Figures 126G, 126H:
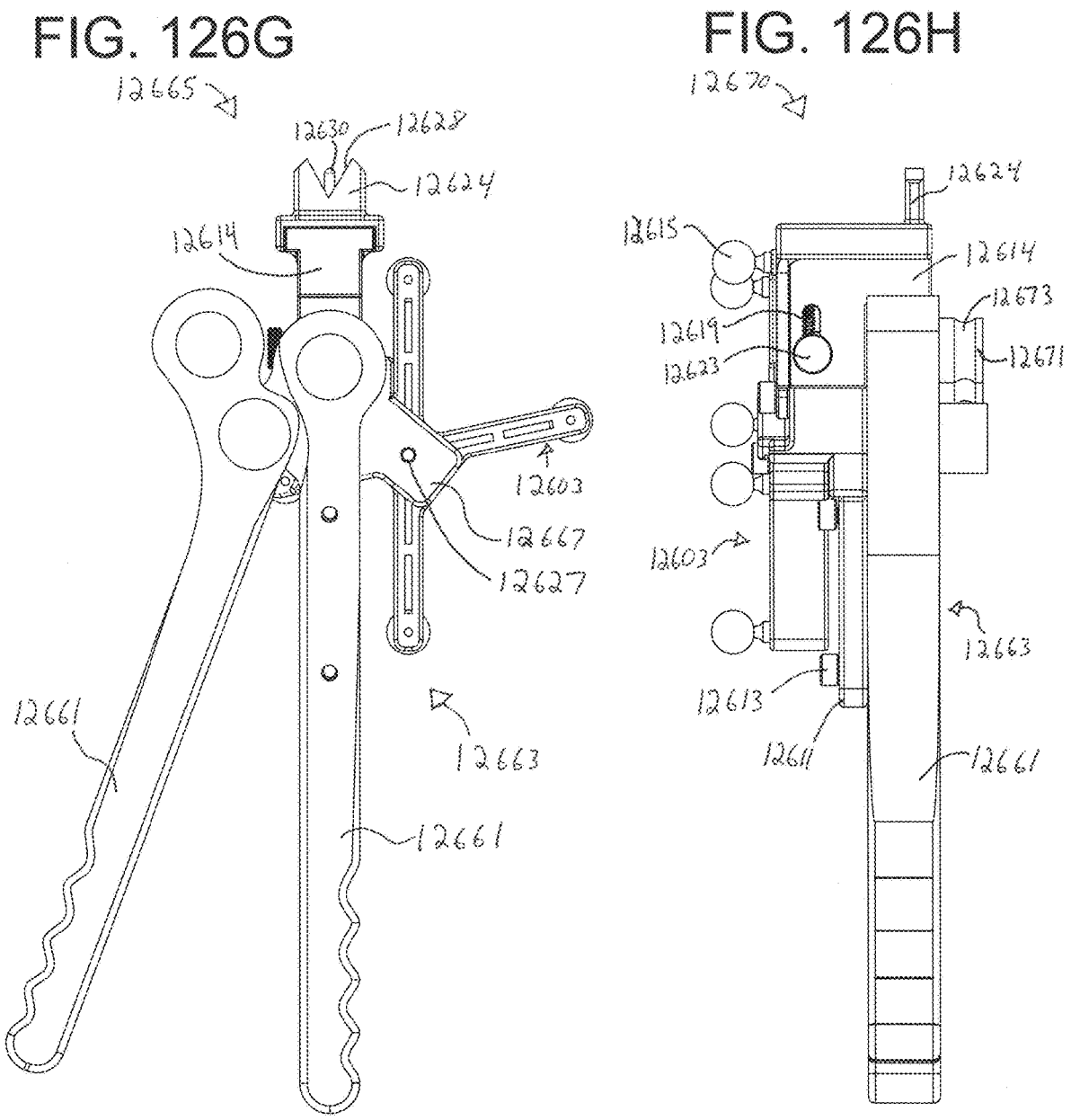

FIG. 126G illustrates a back view of a rod contour registration tool attached to a rod bender as described previously in relation to FIGS. 126A-126F in accordance with some embodiments of the invention.

FIG. 126H illustrates a side view of a rod contour registration tool attached to a rod bender as described previously in relation to FIGS. 126A-126G in accordance with some embodiments of the invention.

Figures 126I, 126J:
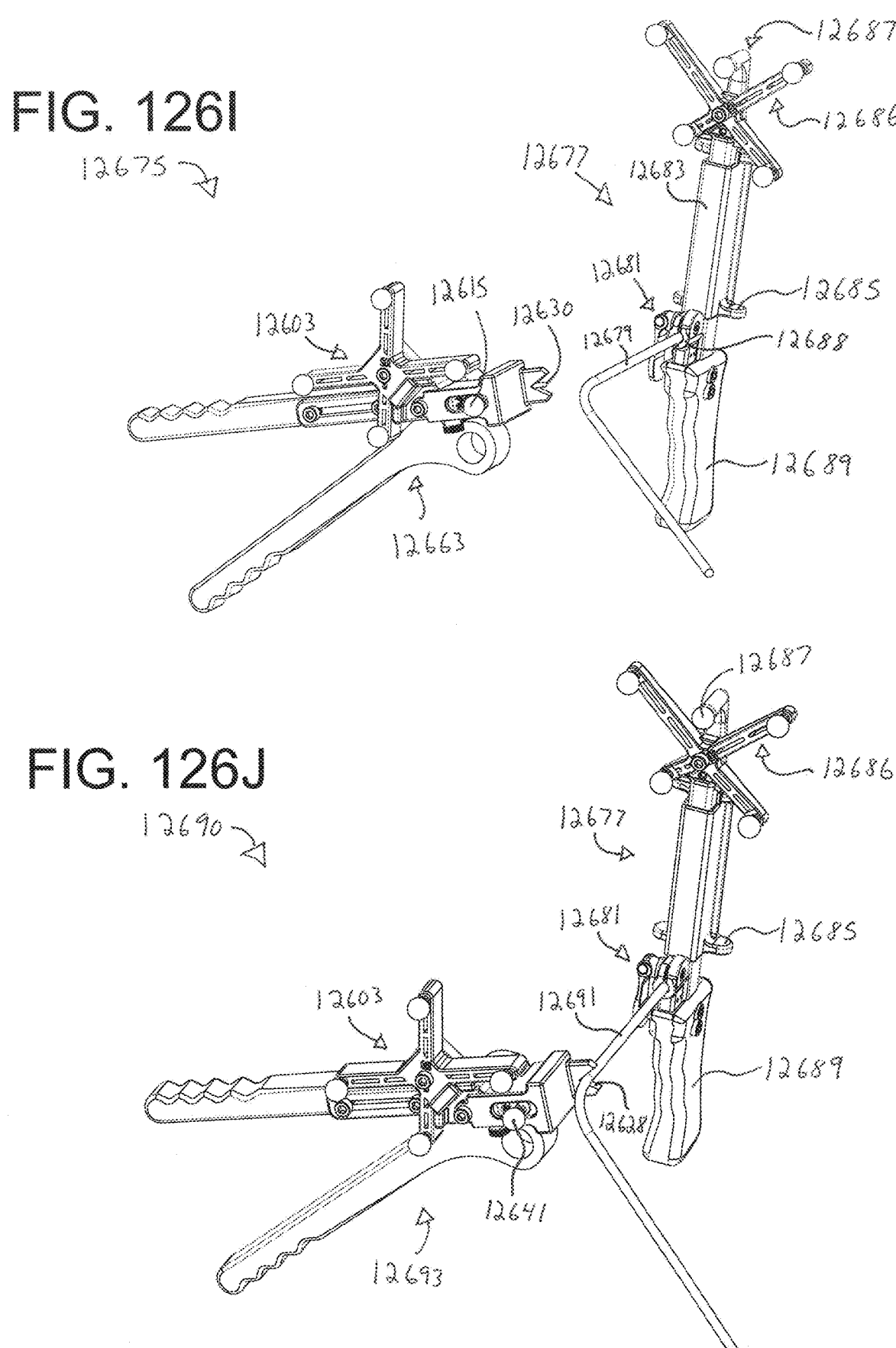

FIGS. 126I-126J illustrate perspective views of a rod contour registration tool attached to a rod bender disengaged and engaged with a bent rod attached to a coordinate reference end cap device as described previously in relation to FIGS. 126A-126H in accordance with some embodiments of the invention.

Figure 127A:
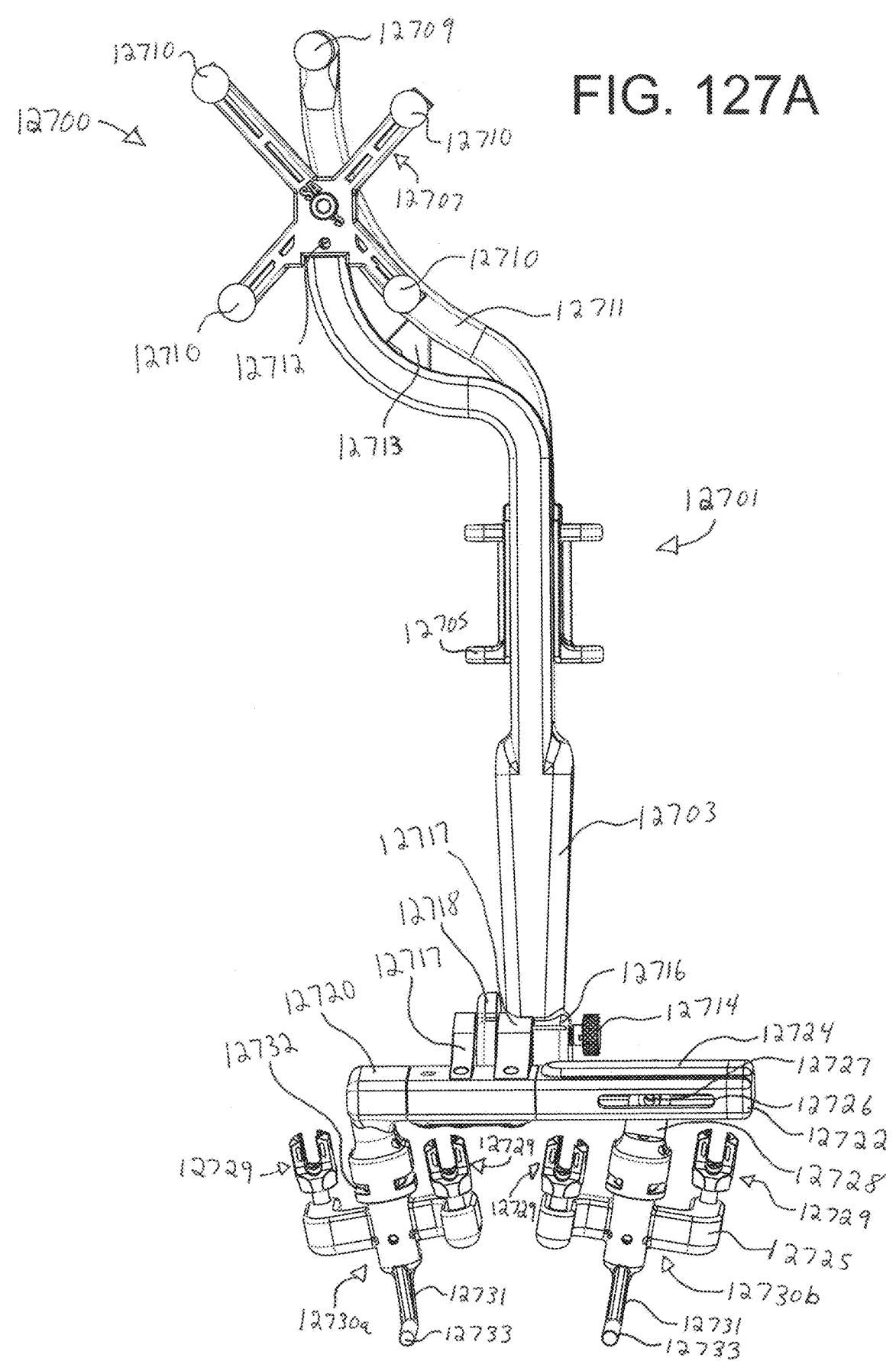

FIG. 127A illustrates a front view of a front-facing flexibility assessment device in accordance with some embodiments of the invention.

Figure 127B:
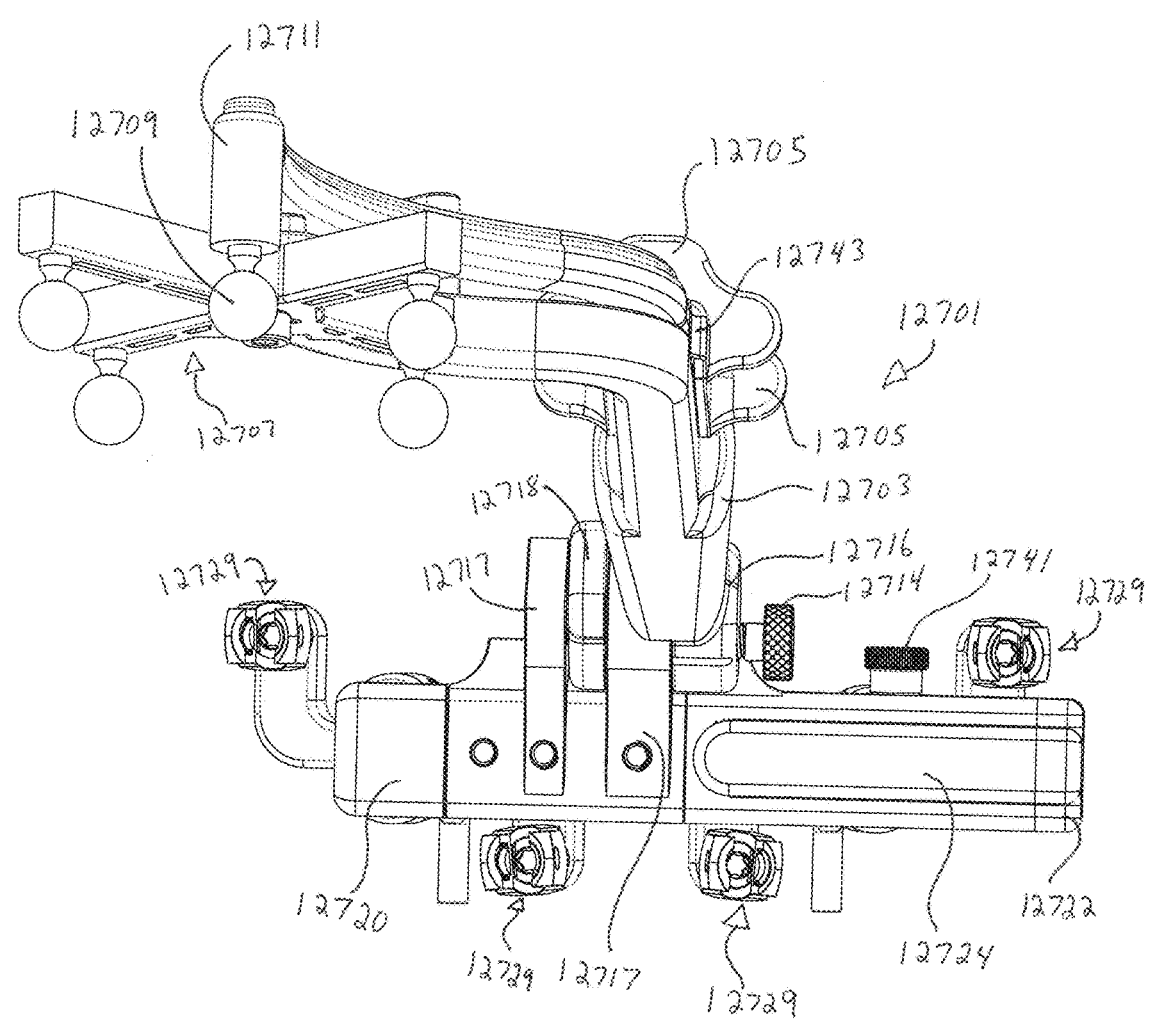

FIG. 127B illustrates a top view of a front-facing flexibility assessment device as described previously in relation to FIG. 127A in accordance with some embodiments of the invention.

Figure 127C:
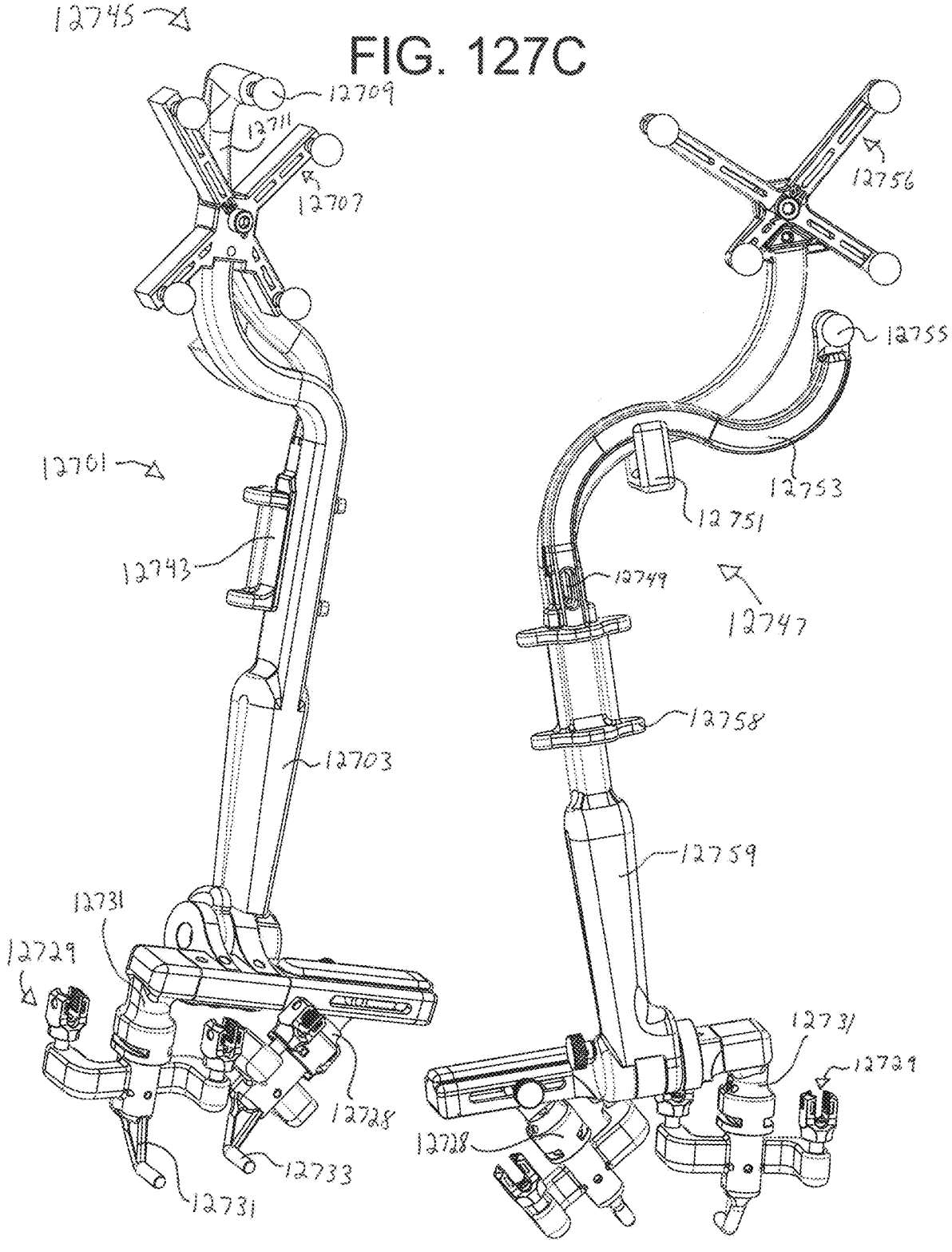
Figure 127D:
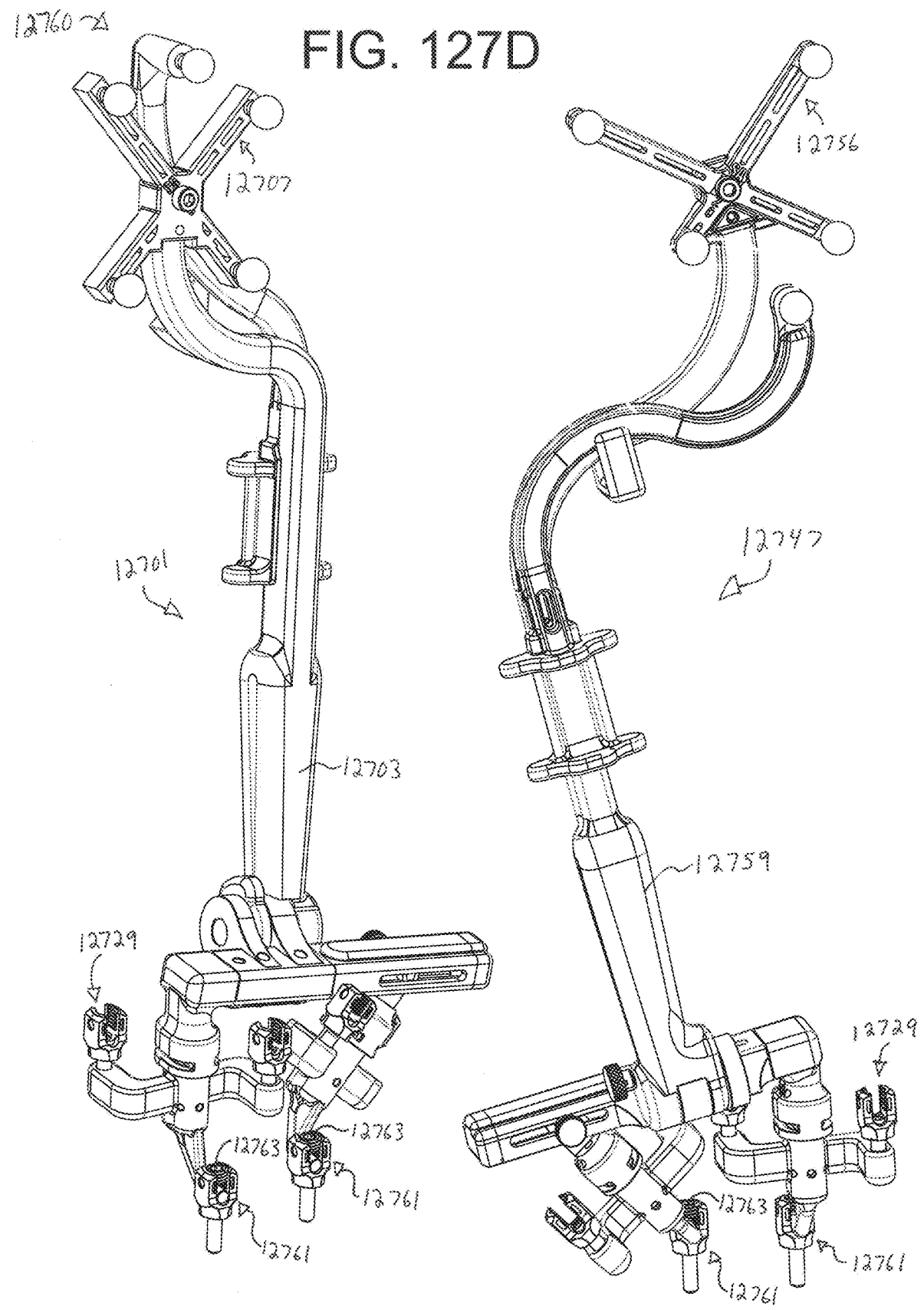

FIGS. 127C-127D illustrate perspective views of a front-facing and back-facing flexibility assessment devices as described previously in relation to FIG. 127A-127B in accordance with some embodiments of the invention.

FIG. 128A illustrates a top view of the adjustable pedicle screw interfaces of a flexibility assessment device rigidly engaged with vertebrae and spinal rods in accordance with some embodiments of the invention.

FIG. 128B illustrates a side view of the adjustable pedicle screw interfaces of a flexibility assessment device rigidly engaged with vertebrae as described previously in relation to FIG. 128A in accordance with some embodiments of the invention.

Figures 128C, 128D:
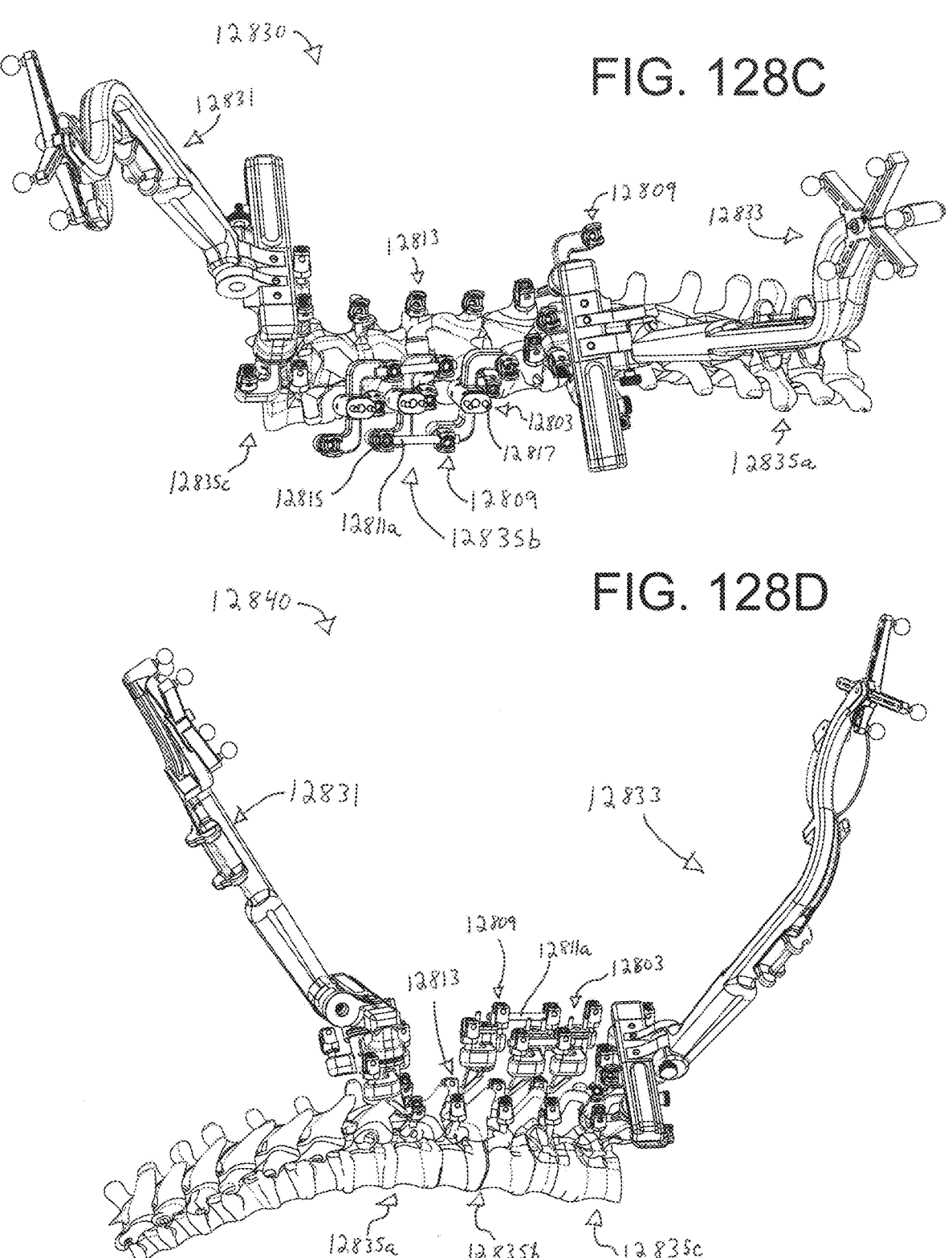

FIG. 128C illustrates a top view of the front-facing and back-facing flexibility assessment devices rigidly engaged with the adjustable pedicle screw interface and corresponding vertebrae as described previously in relation to FIGS. 128A-128B in accordance with some embodiments of the invention.

FIG. 128D illustrates a side view of the front-facing and back-facing flexibility assessment devices rigidly engaged with the adjustable pedicle screw interface and corresponding vertebrae as described previously in relation to FIGS. 128A-128B in accordance with some embodiments of the invention.

Figure 129A:
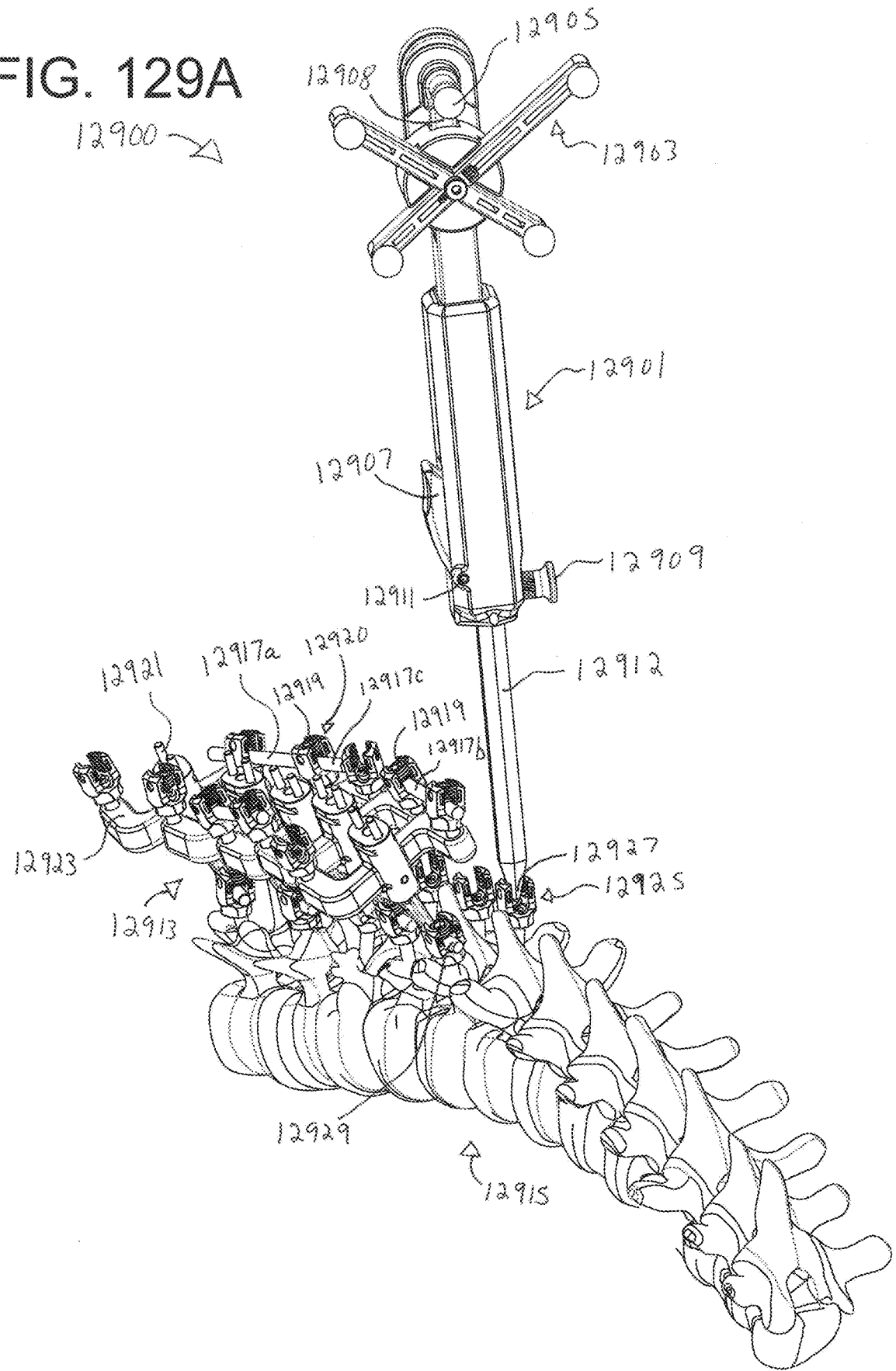

FIG. 129A illustrates a perspective view of a 3D-tracked tool engaged with a pedicle screw inserted in the lamina in accordance with some embodiments of the invention.

Figures 129B, 129C:
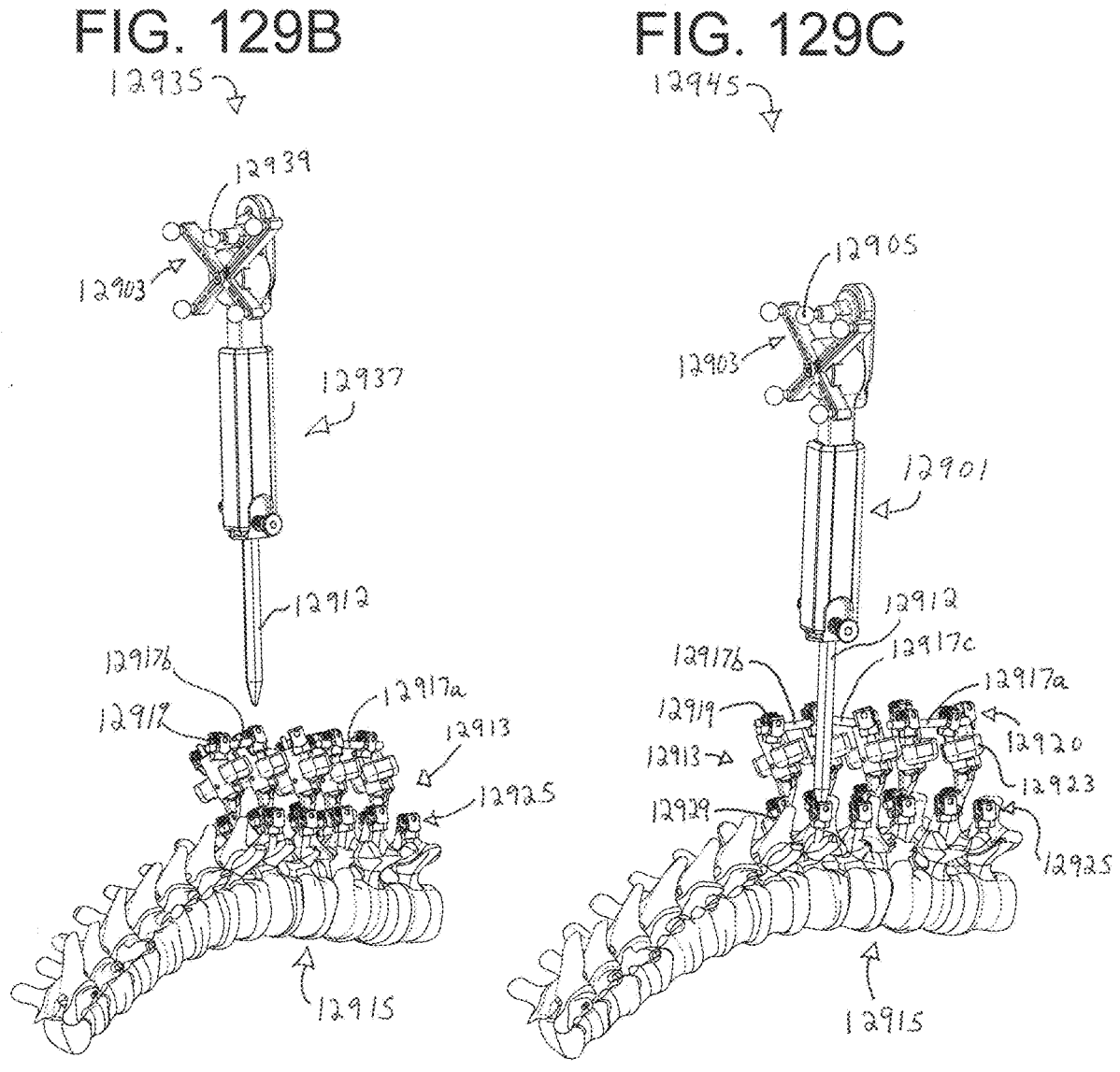

FIG. 129B illustrates perspective views of a 3D-tracked tool and one side of the adjustable pedicle screw interfaces of the flexibility assessment device attached rigidly to vertebrae as described previously in relation to FIG. 129A in accordance with some embodiments of the invention.

FIG. 129C illustrates perspective views of a 3D-tracked tool engaged with a pedicle screw inserted in lamina and one side of the adjustable pedicle screw interfaces of the flexibility assessment device attached rigidly to vertebrae as described previously in relation to FIGS. 129A-129B in accordance with some embodiments of the invention.

Figure 129D:
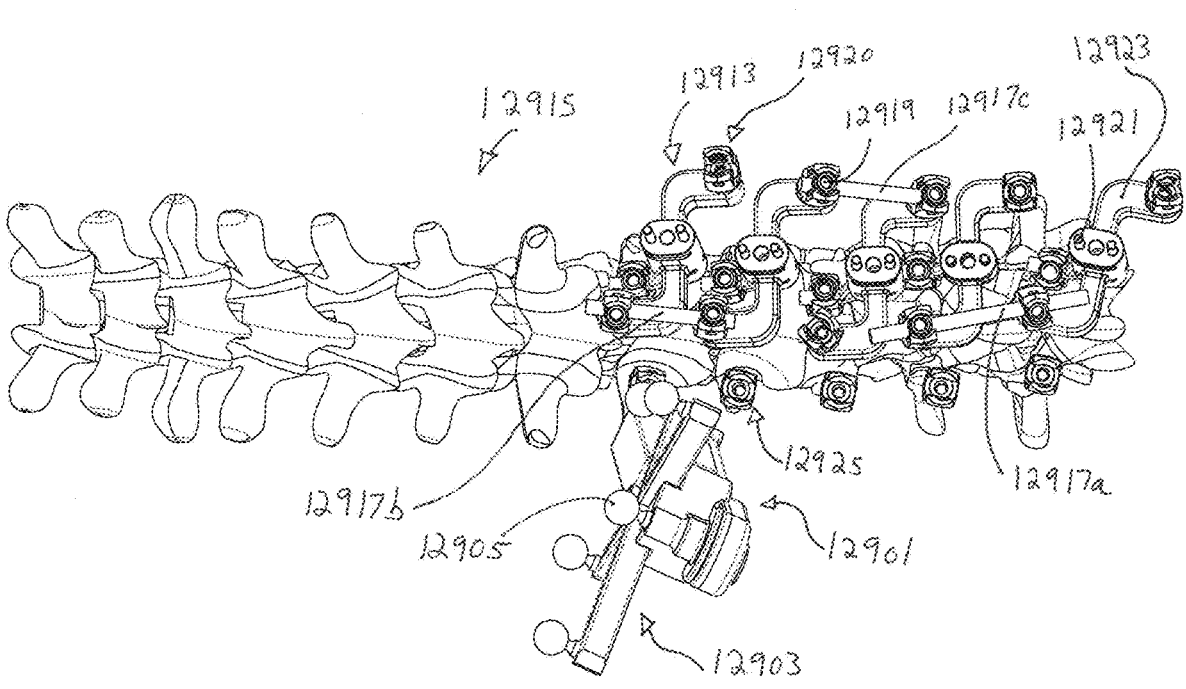

FIG. 129D illustrates a top view of a 3D-tracked tool engaged with a pedicle screw inserted in lamina and one side of the adjustable pedicle screw interfaces of the flexibility assessment device attached rigidly to vertebrae as described previously in relation to FIGS. 129A-129C in accordance with some embodiments of the invention.

Figure 130A:
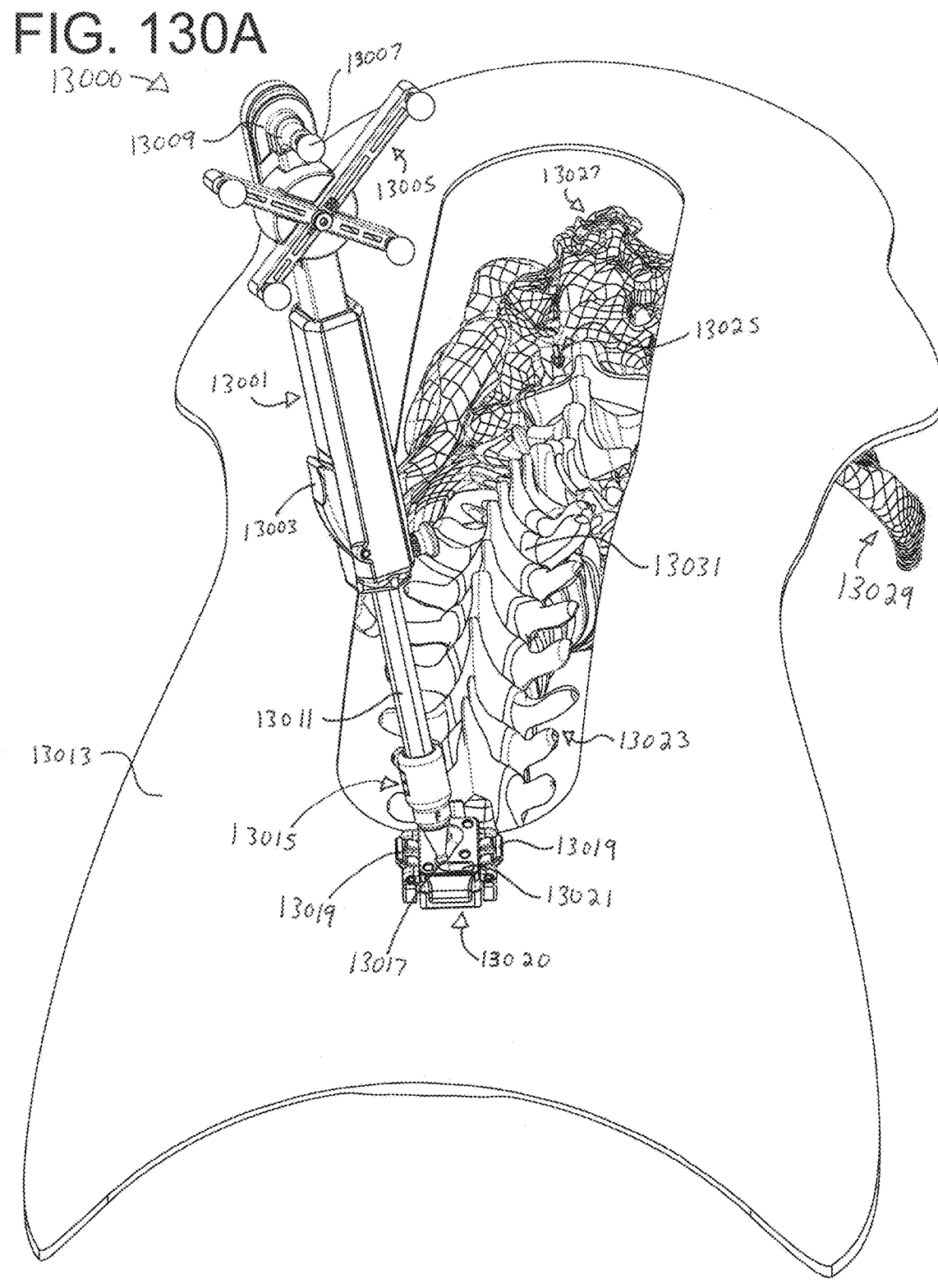

FIG. 130A illustrates a perspective view of a 3D-tracked tool with a tool ball tip adapter engaged with the "Z-pattern" of the top skin-mounted fiducial attached on the skin covering the vertebrae in accordance with some embodiments of the invention.

Figure 130B:
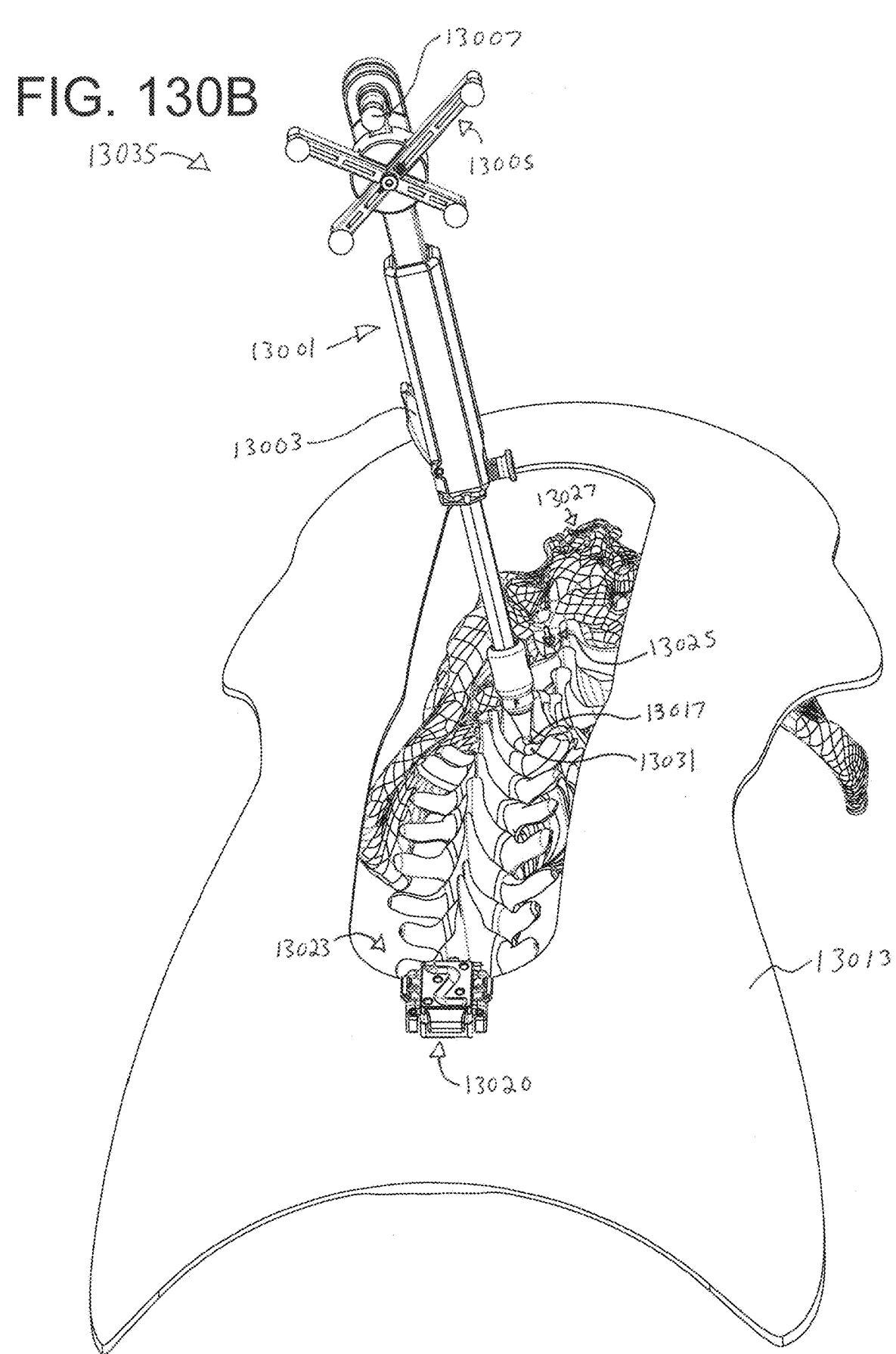

FIG. 130B illustrates a perspective view of a 3D-tracked tool with a tool ball tip adapter tracing the laminae region of the vertebrae as described previously in relation to FIG. 130A in accordance with some embodiments of the invention.

Figure 130C:
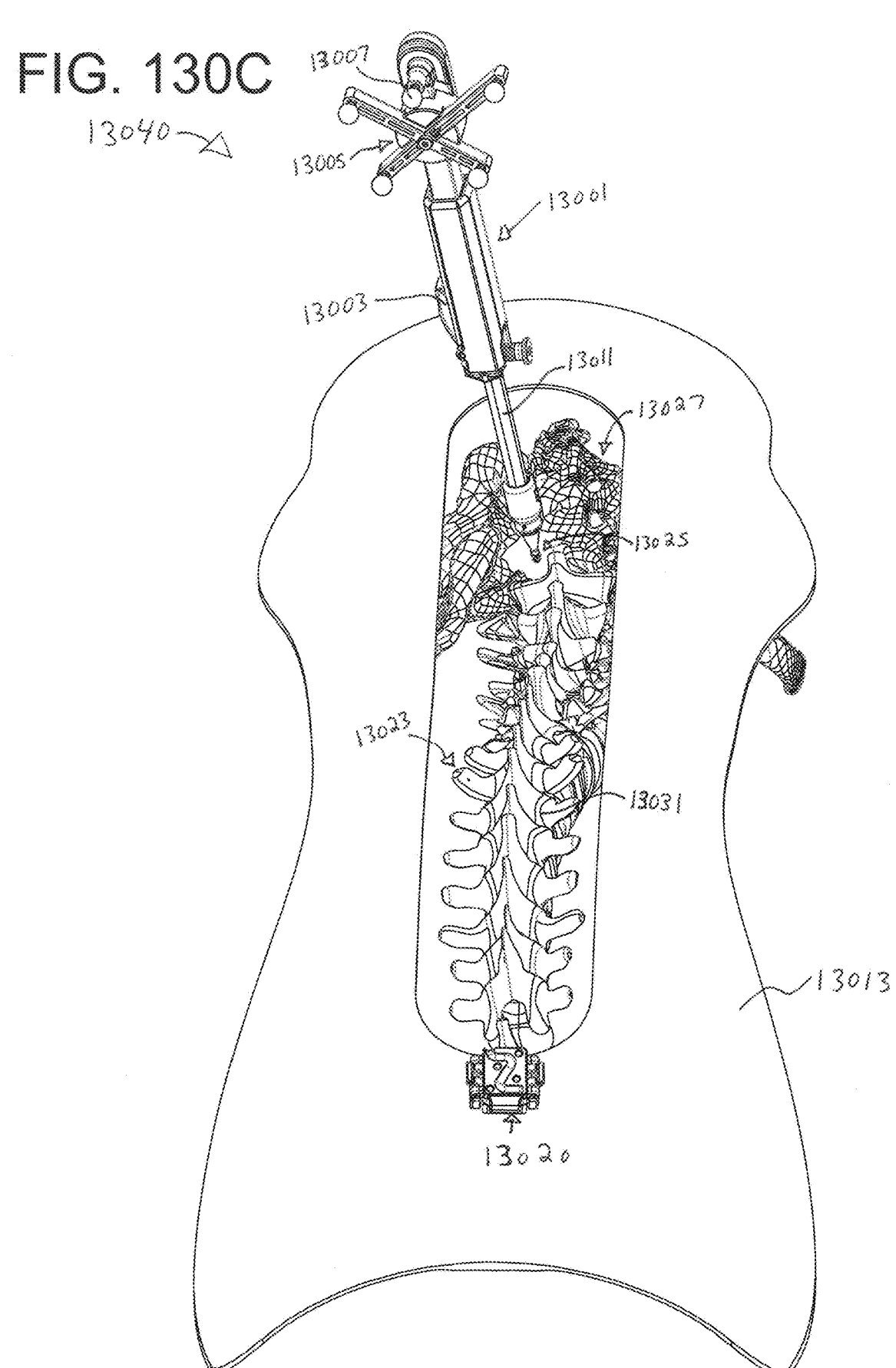

FIG. 130C illustrates a top view of a 3D-tracked tool with a tool ball tip adapter tracing the sacrum region of the vertebrae as described previously in relation to FIGS. 130A-130B in accordance with some embodiments of the invention.

Figures 130D, 130E, 130F:
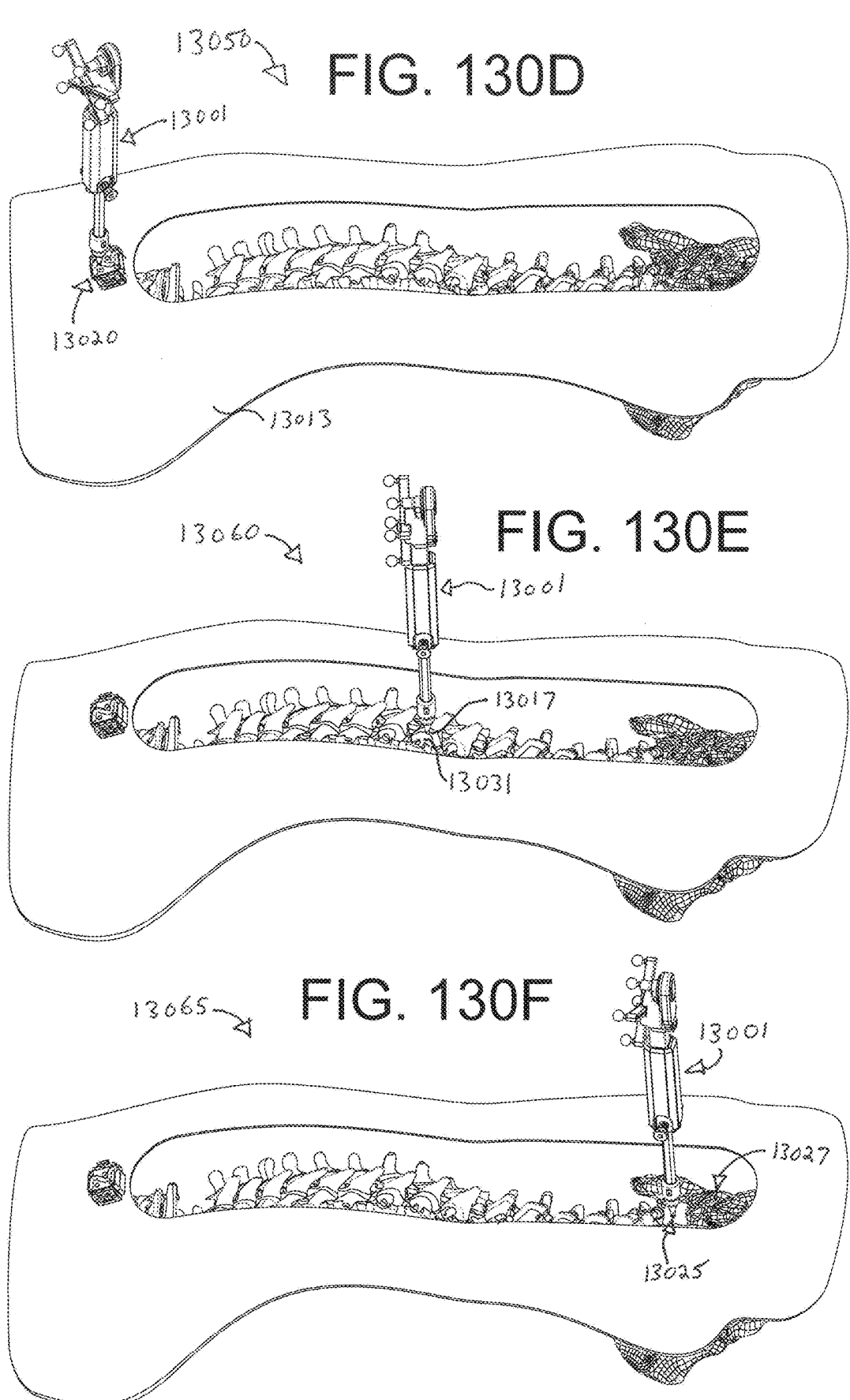

FIG. 130D illustrates a zoomed-out view of a 3D-tracked tool with a tool ball tip adapter engaged with the "Z-pattern" of the top skin-mounted fiducial attached on the skin covering the vertebrae as described previously in relation to FIGS. 130A-130C in accordance with some embodiments of the invention.

FIG. 130E illustrates a zoomed-out view of a 3D-tracked tool with a tool ball tip adapter tracing the laminae region of the vertebrae as described previously in relation to FIGS. 130A-130D in accordance with some embodiments of the invention.

FIG. 130F illustrates a zoomed-out view of a 3D-tracked tool with a tool ball tip adapter tracing the sacrum region of the vertebrae as described previously in relation to FIGS. 130A-130E in accordance with some embodiments of the invention.

Figure 131A:
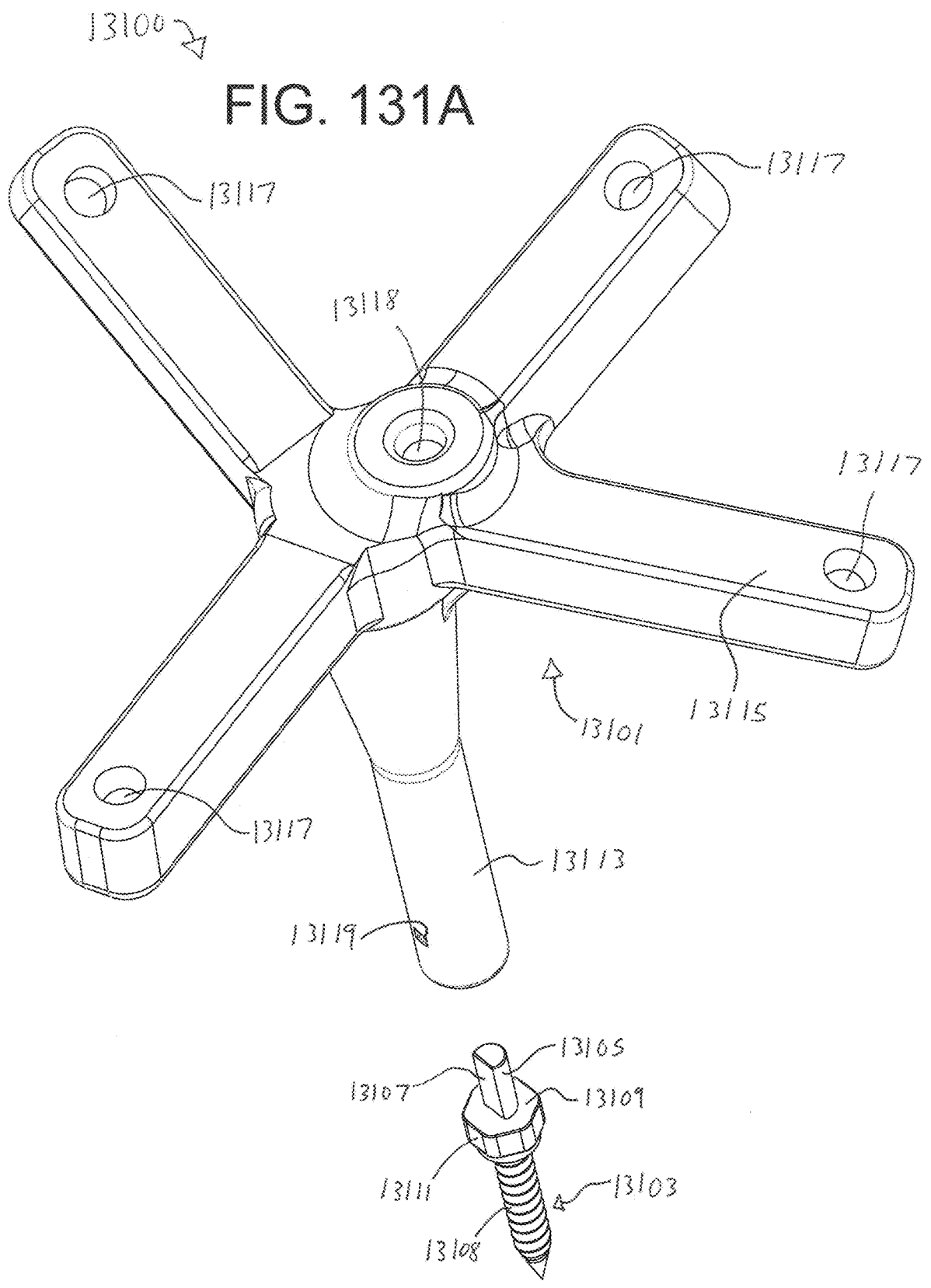

FIG. 131A illustrates a perspective view of an external-mating bone-mounted fiducial and internal-mating bone-mounted fiducial X-Ray adapter with five asymmetrically distributed holes for embedding radiopaque spheres in accordance with some embodiments of the invention.

Figure 131B:
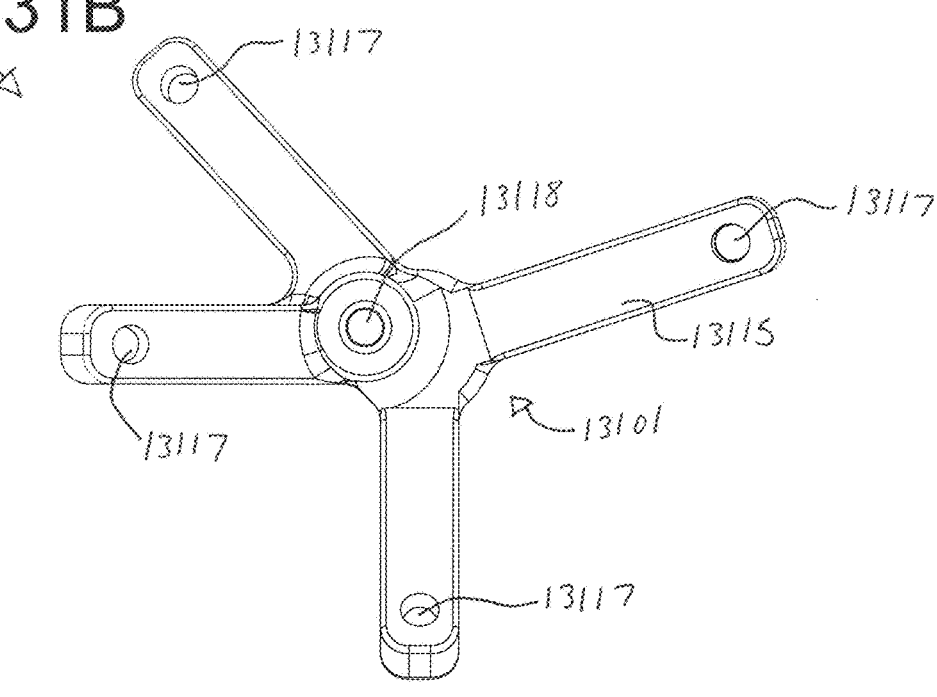

FIG. 131B illustrates a top view of an external-mating bone-mounted fiducial with five asymmetrically distributed holes for embedding radiopaque spheres as described previously in relation to FIG. 131A in accordance with some embodiments of the invention.

Figures 131C, 131D:
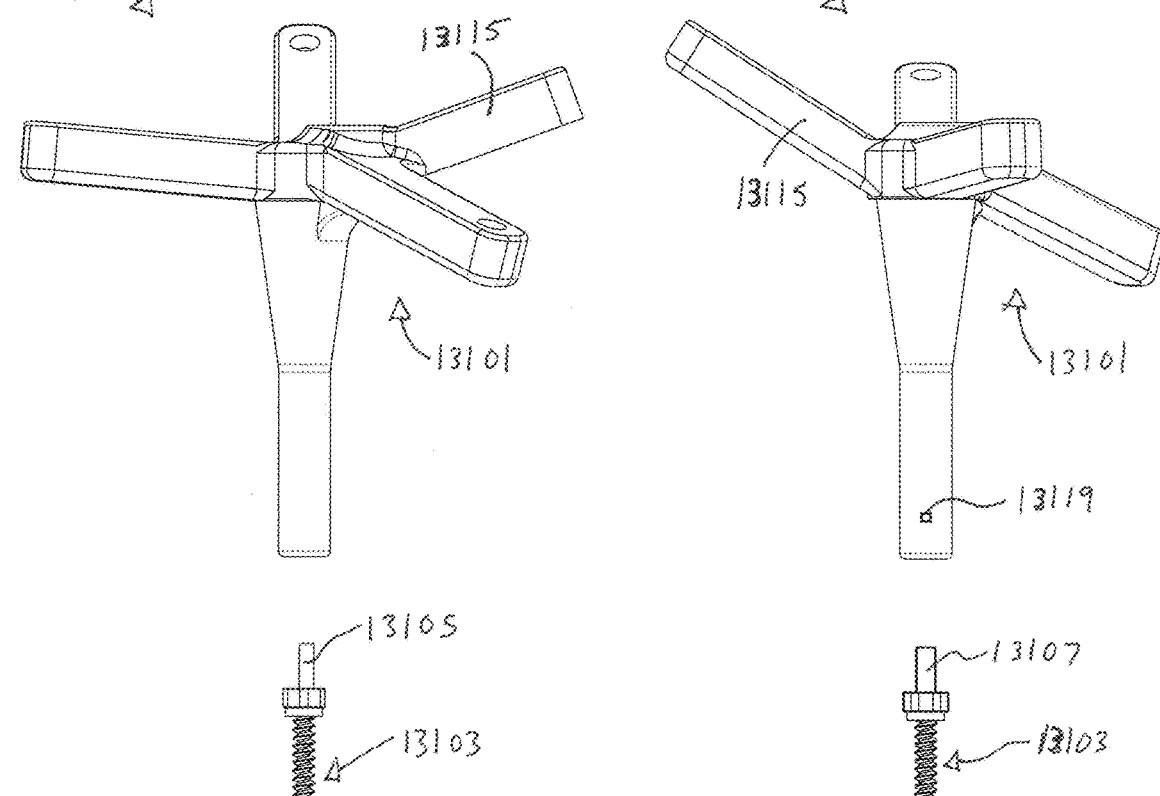

FIGS. 131C-131D illustrate side views of an external-mating bone-mounted fiducial and internal-mating bone-mounted fiducial X-Ray adapter with five asymmetrically distributed holes for embedding radiopaque spheres as described previously in relation to FIGS. 131A-131B in accordance with some embodiments of the invention.

Figure 131E:

FIG. 131E illustrates a bottom view of an external-mating bone-mounted fiducial and internal-mating bone-mounted fiducial X-Ray adapter with five asymmetrically distributed holes for embedding radiopaque spheres as described previously in relation to FIGS. 131A-131D in accordance with some embodiments of the invention.

Figure 131F:
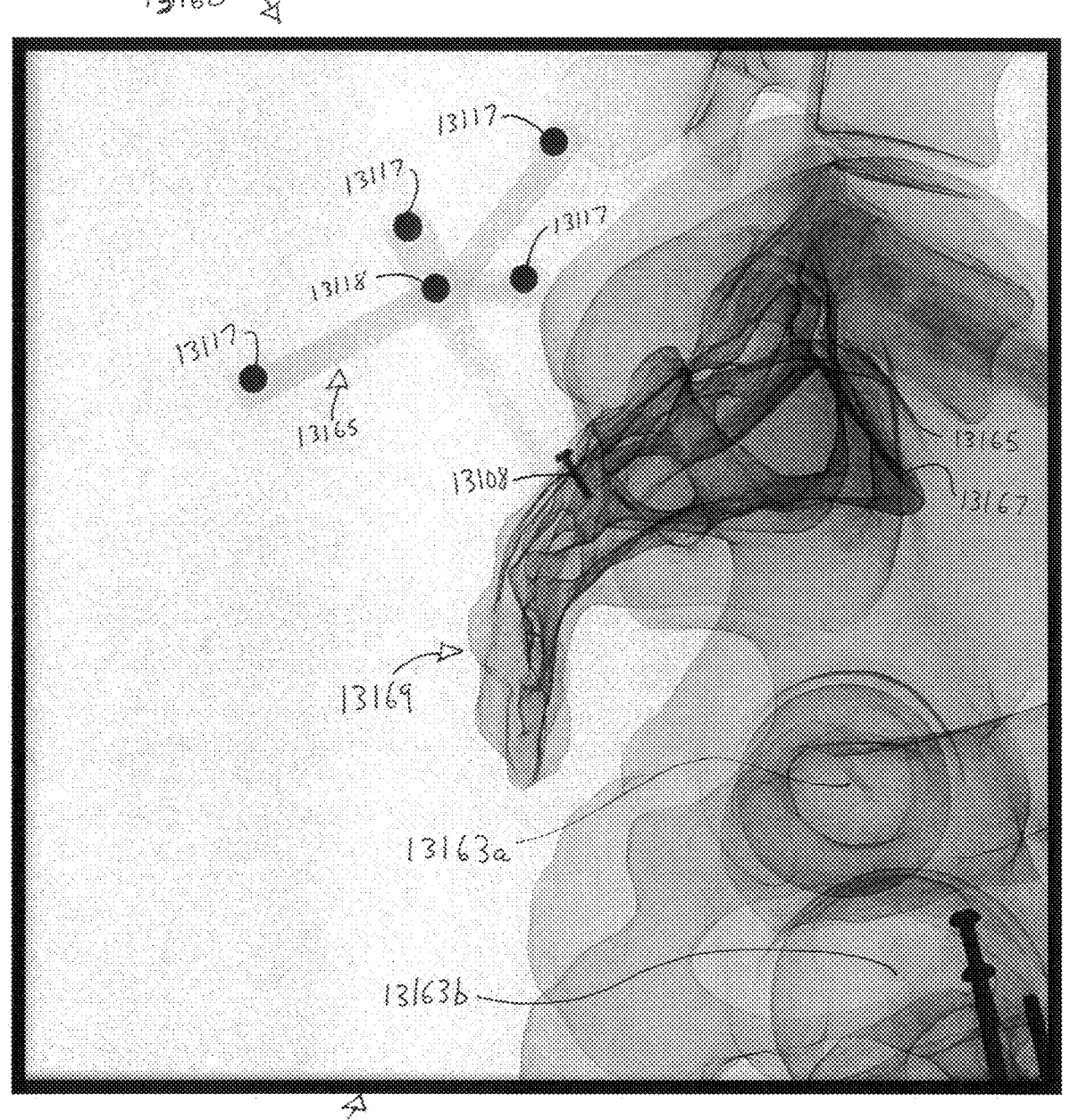

FIG. 131F illustrates an X-Ray image taken from a lateral view visualizing the pelvis and five radiopaque spheres of the bone-mounted fiducial X-Ray adapter as described previously in relation to FIGS. 131A-131E in accordance with some embodiments of the invention.

Figure 131G:
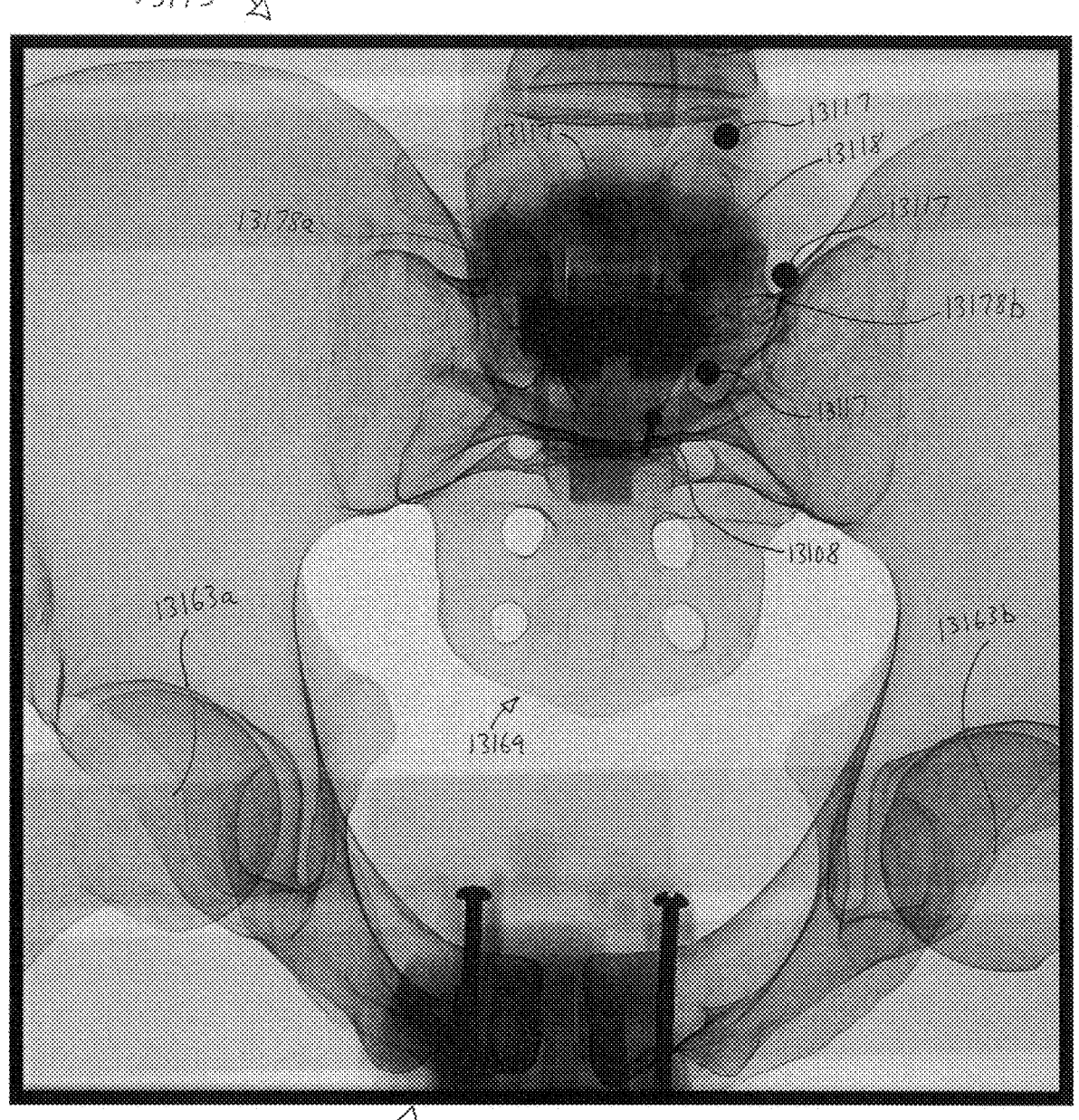

FIG. 131G illustrates an X-Ray image taken from an AP view visualizing the pelvis and five radiopaque spheres of the bone-mounted fiducial X-Ray adapter as described previously in relation to FIGS. 131A-131F in accordance with some embodiments of the invention.

Figure 132A:
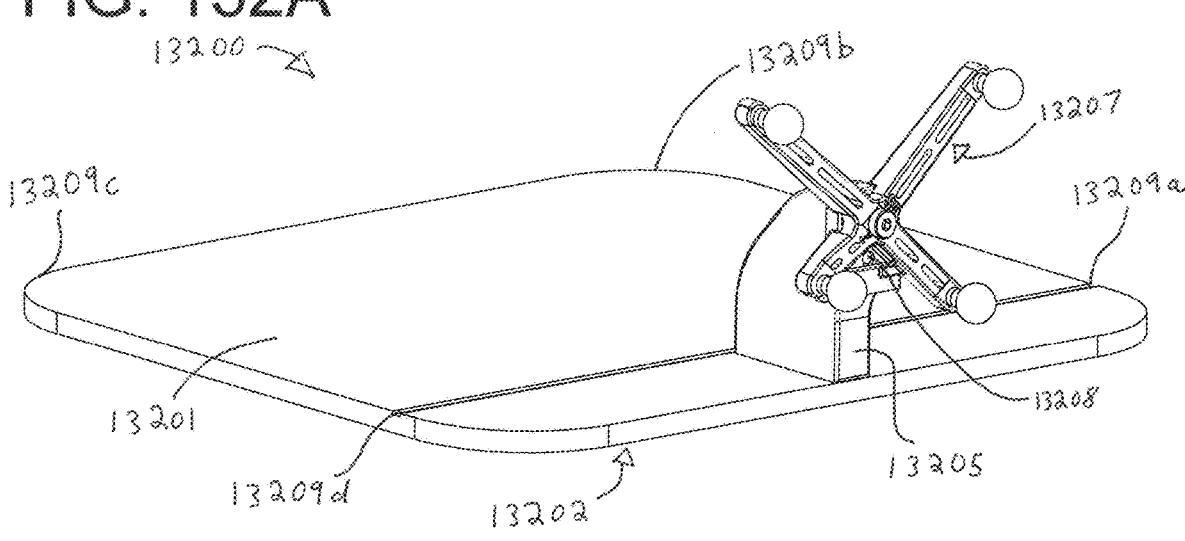

FIG. 132A illustrates a perspective view of a trackpad display-controlling interface with a DRF attached in accordance with some embodiments of the invention.

Figure 132B:
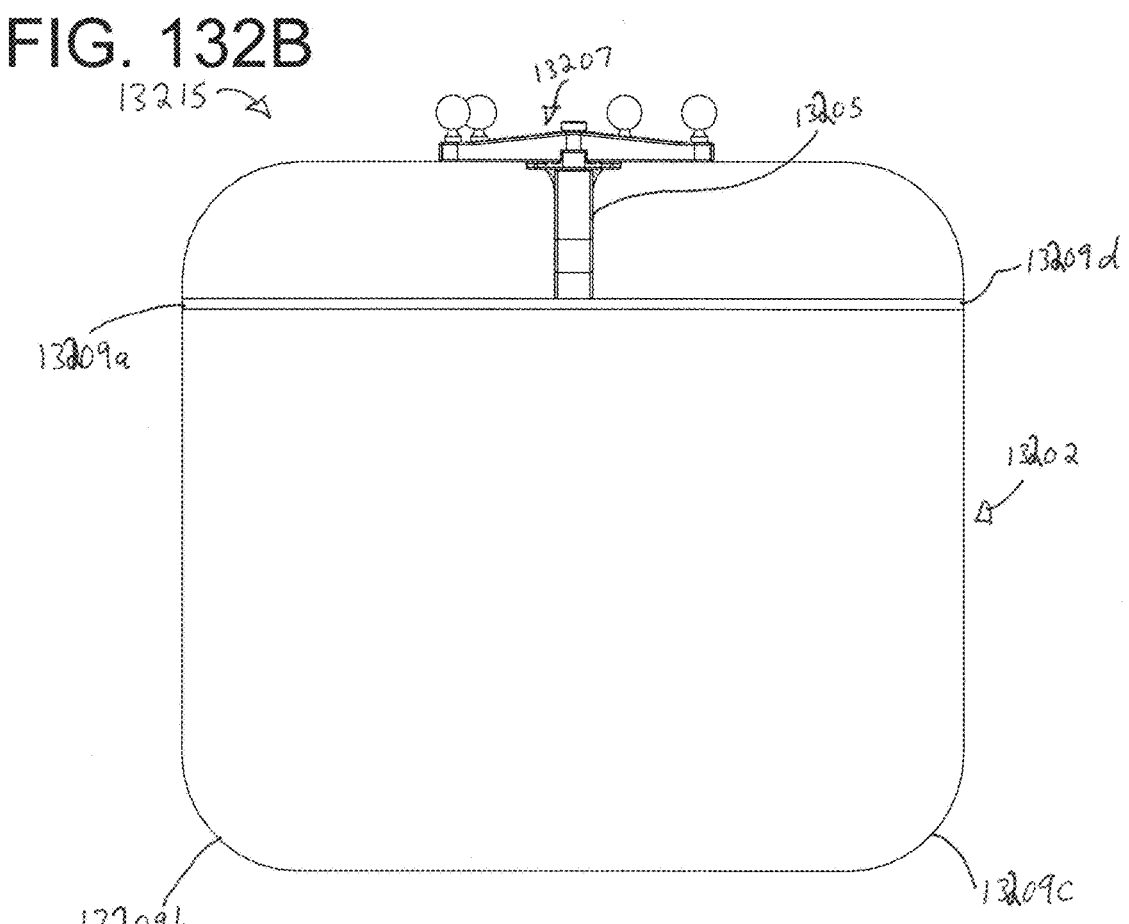

FIG. 132B illustrates a top view of a trackpad display-controlling interface with a DRF attached as described previously in relation to FIG. 132A in accordance with some embodiments of the invention.

Figure 132C:
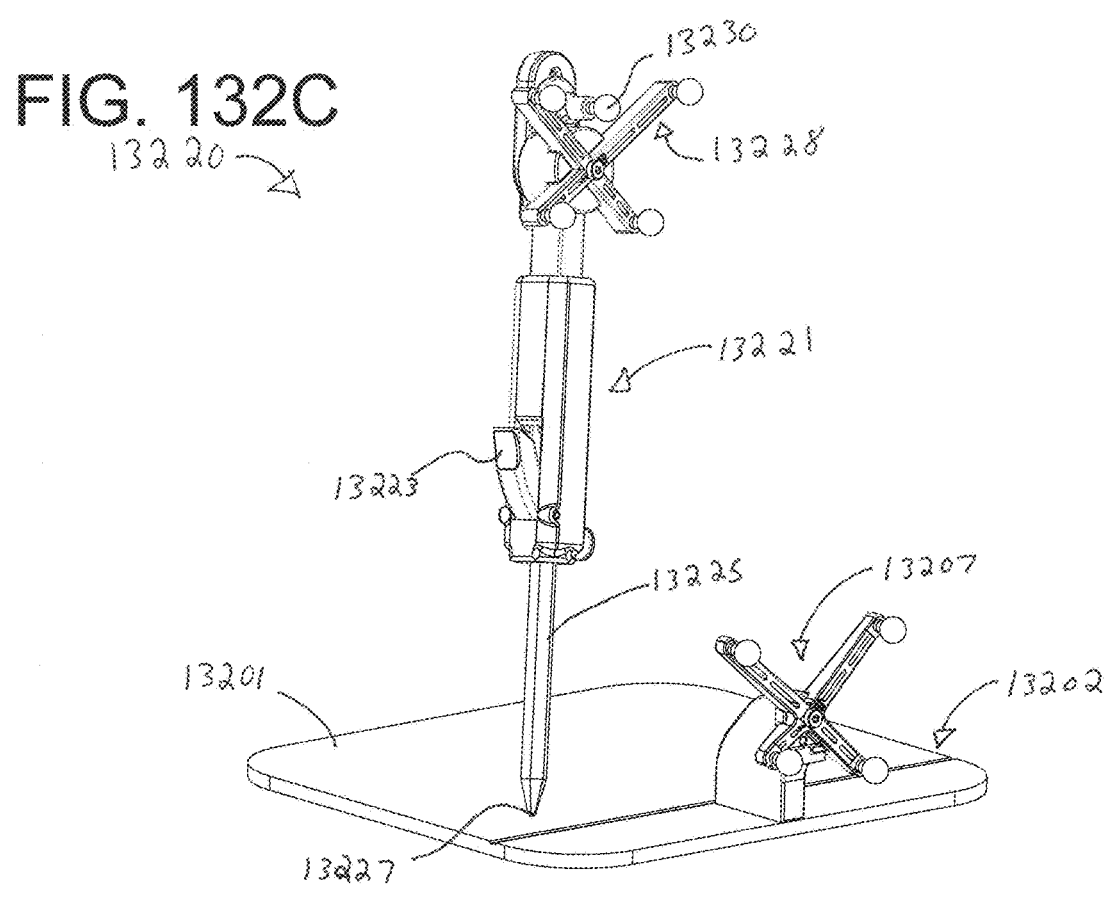

FIG. 132C illustrates a perspective view of a 3D-tracked tool hovering over the DRF-attached trackpad display-controlling interface in an untriggered state as described previously in relation to FIGS. 132A-132B in accordance with some embodiments of the invention.

Figure 132D:
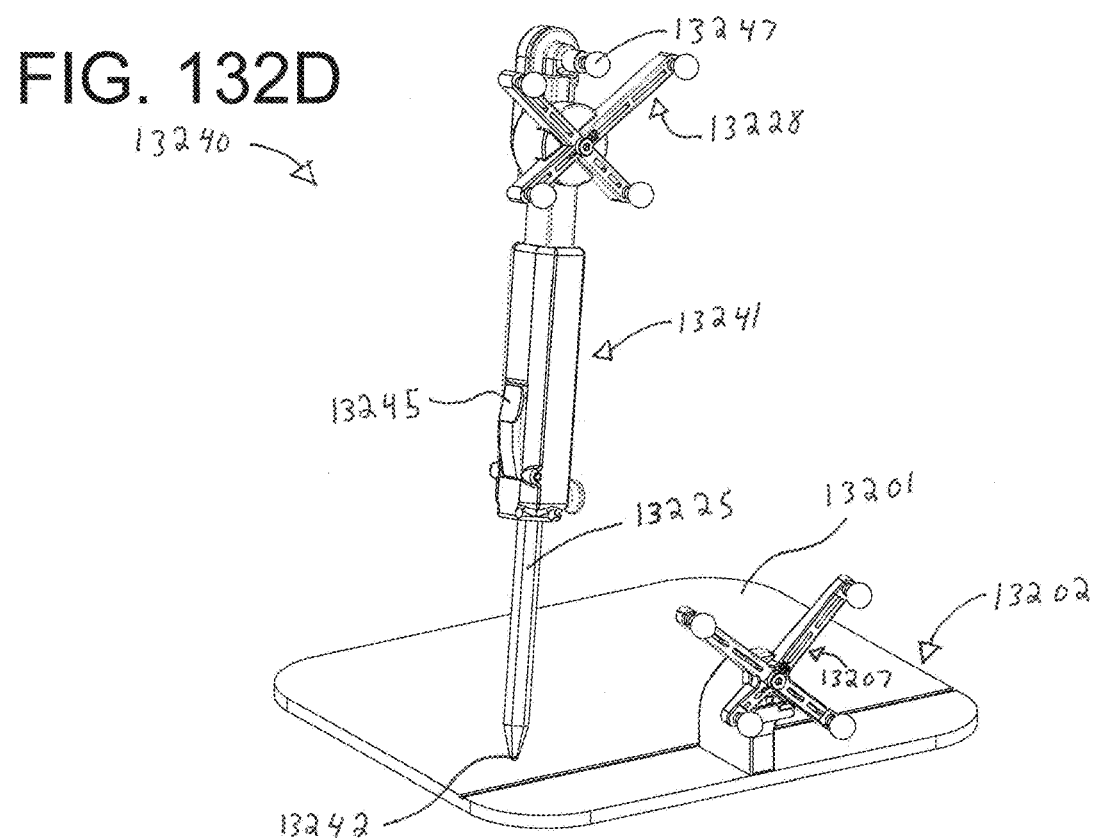

FIG. 132D illustrates a perspective view of a 3D-tracked tool in contact with the DRF-attached trackpad display-controlling interface in a triggered state as described previously in relation to FIGS. 132A-132C in accordance with some embodiments of the invention.

Figure 133A:
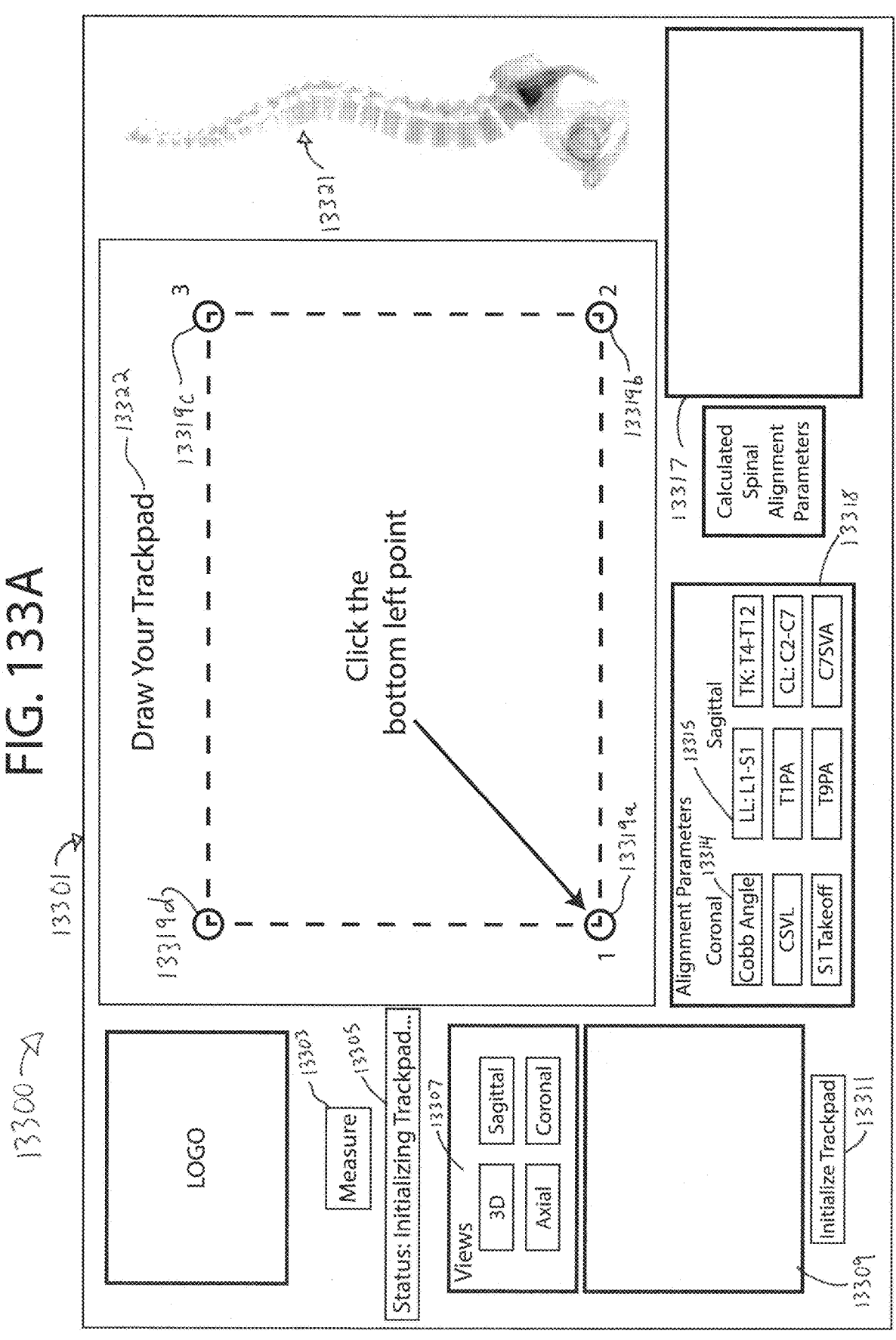
Figure 133B:
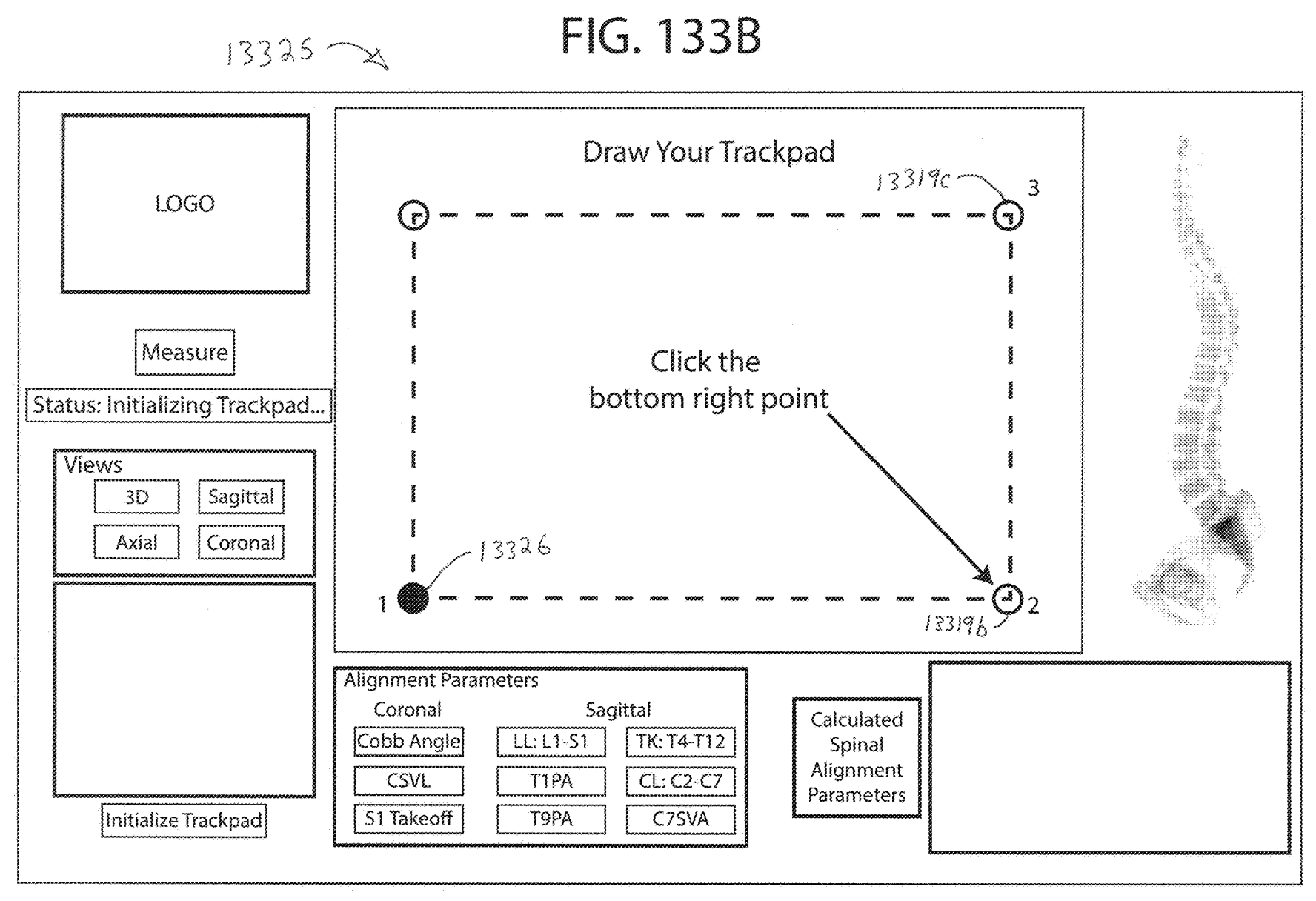
Figure 133C:
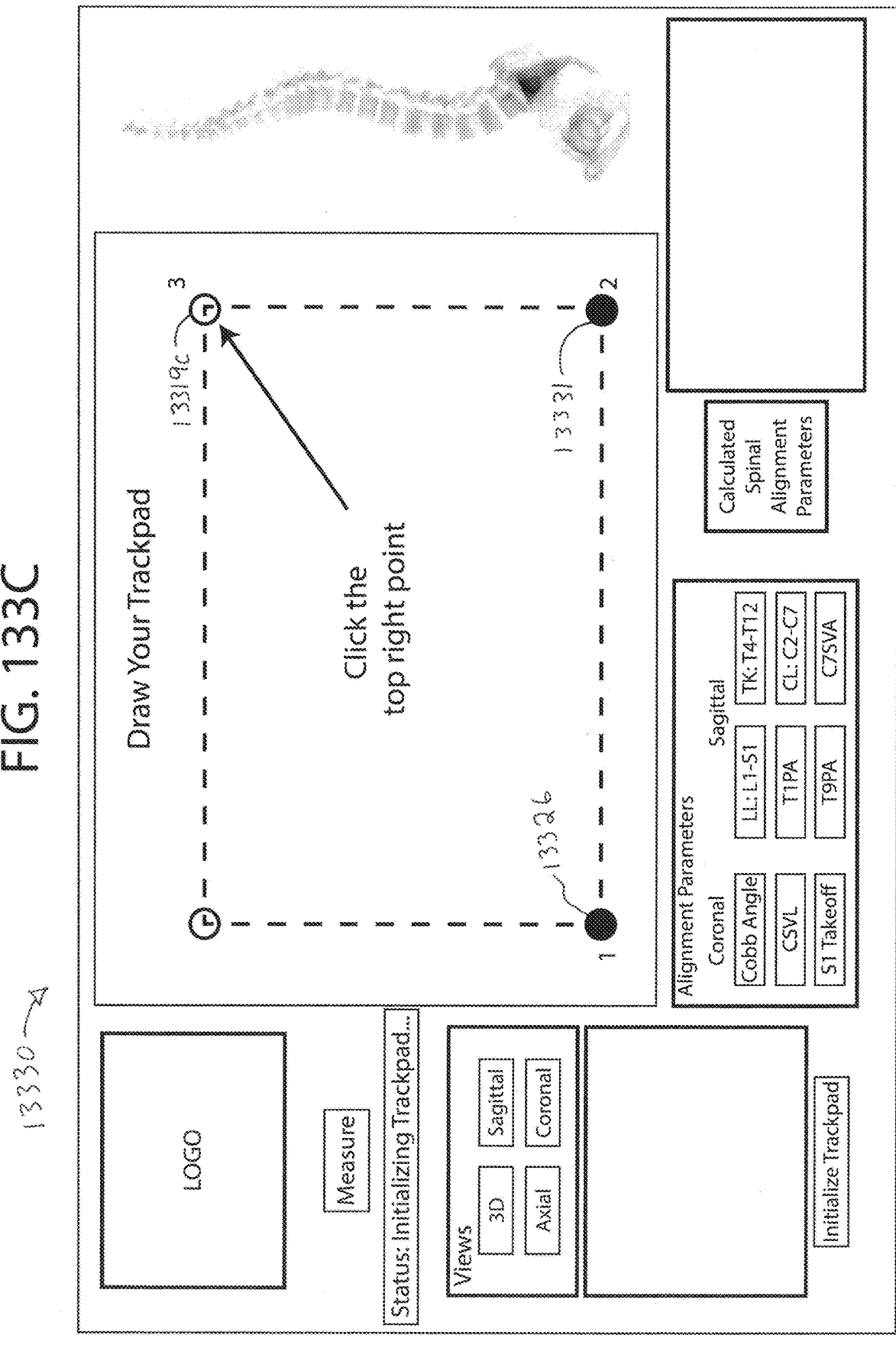

FIGS. 133A-133C illustrate display interfaces for initializing the trackpad display-controlling interface by selecting a bottom left, bottom right, and top right corner of a rectangle that defines the trackpad region in accordance with some embodiments of the invention.

Figure 133D:
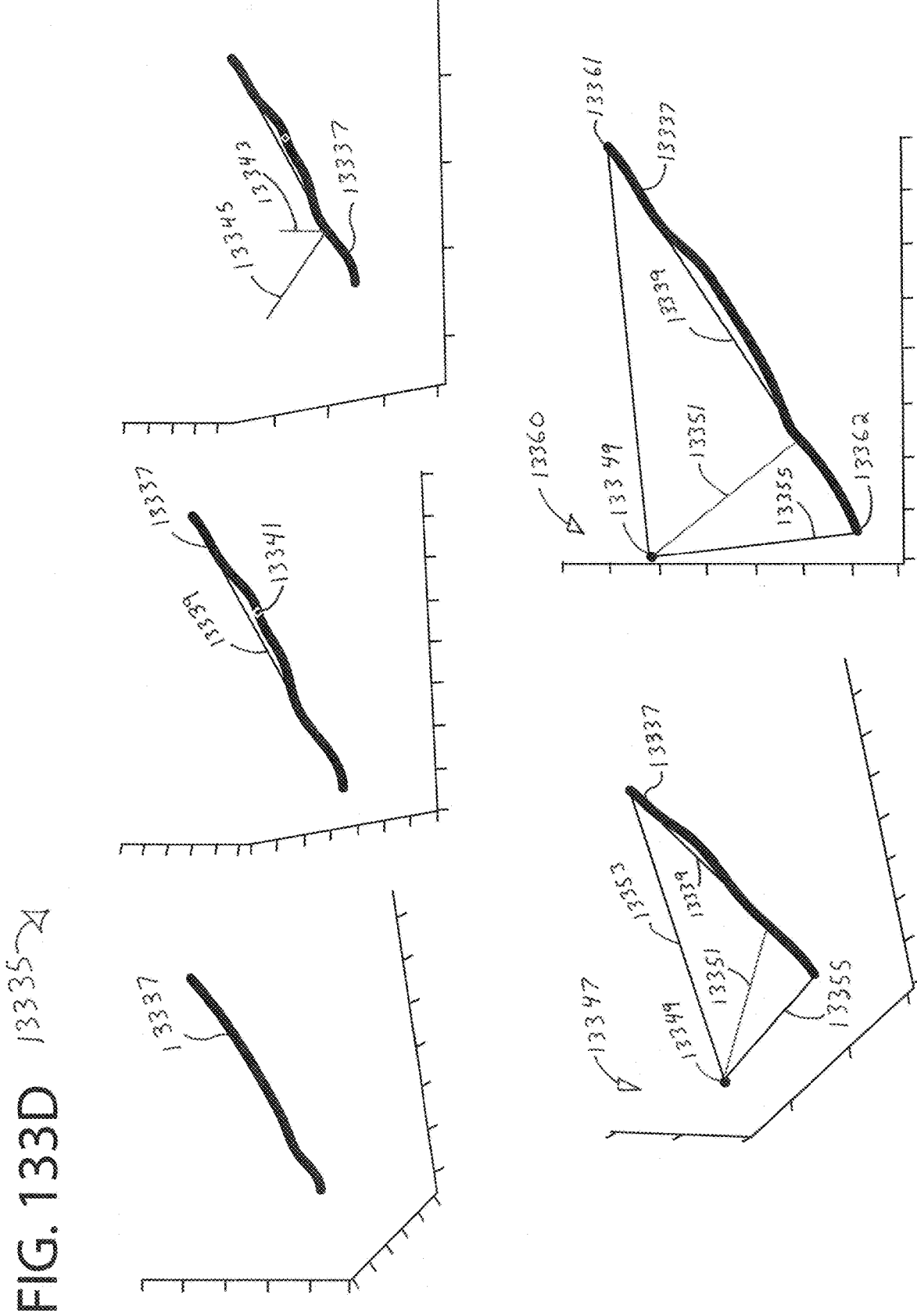

FIG. 133D illustrates outputs of one initialization step of the trackpad display-controlling interface performed by tracing a diagonal line on any surface using a 3D-tracked probe as described previously in relation to FIGS. 133A-133C in accordance with some embodiments of the invention.

Figure 133E:
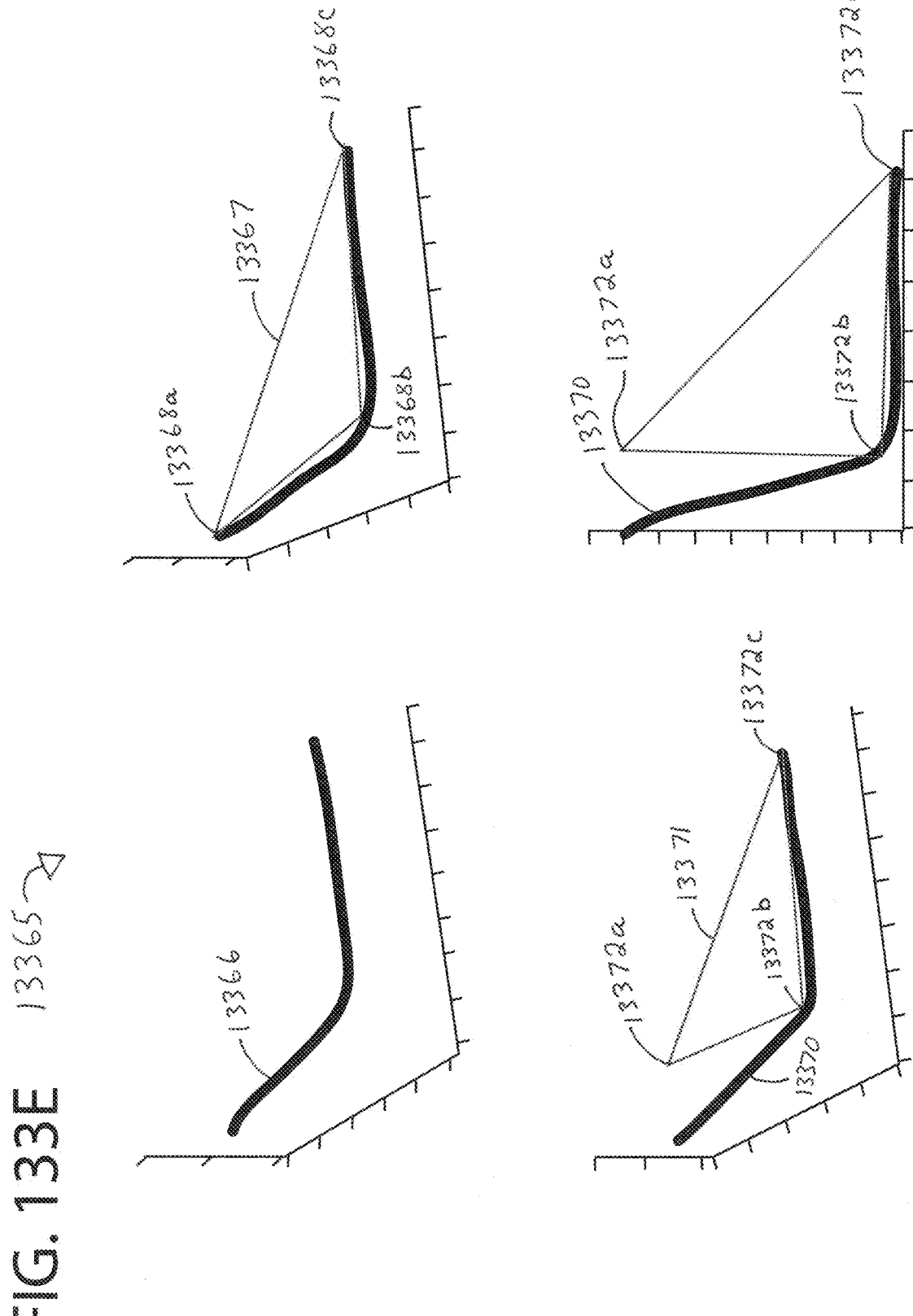

FIG. 133E illustrates outputs of one initialization step of the trackpad display-controlling interface performed by tracing an L-shaped line on any surface using a 3D-tracked probe as described previously in relation to FIGS. 133A-133D in accordance with some embodiments of the invention.

Figure 133F:
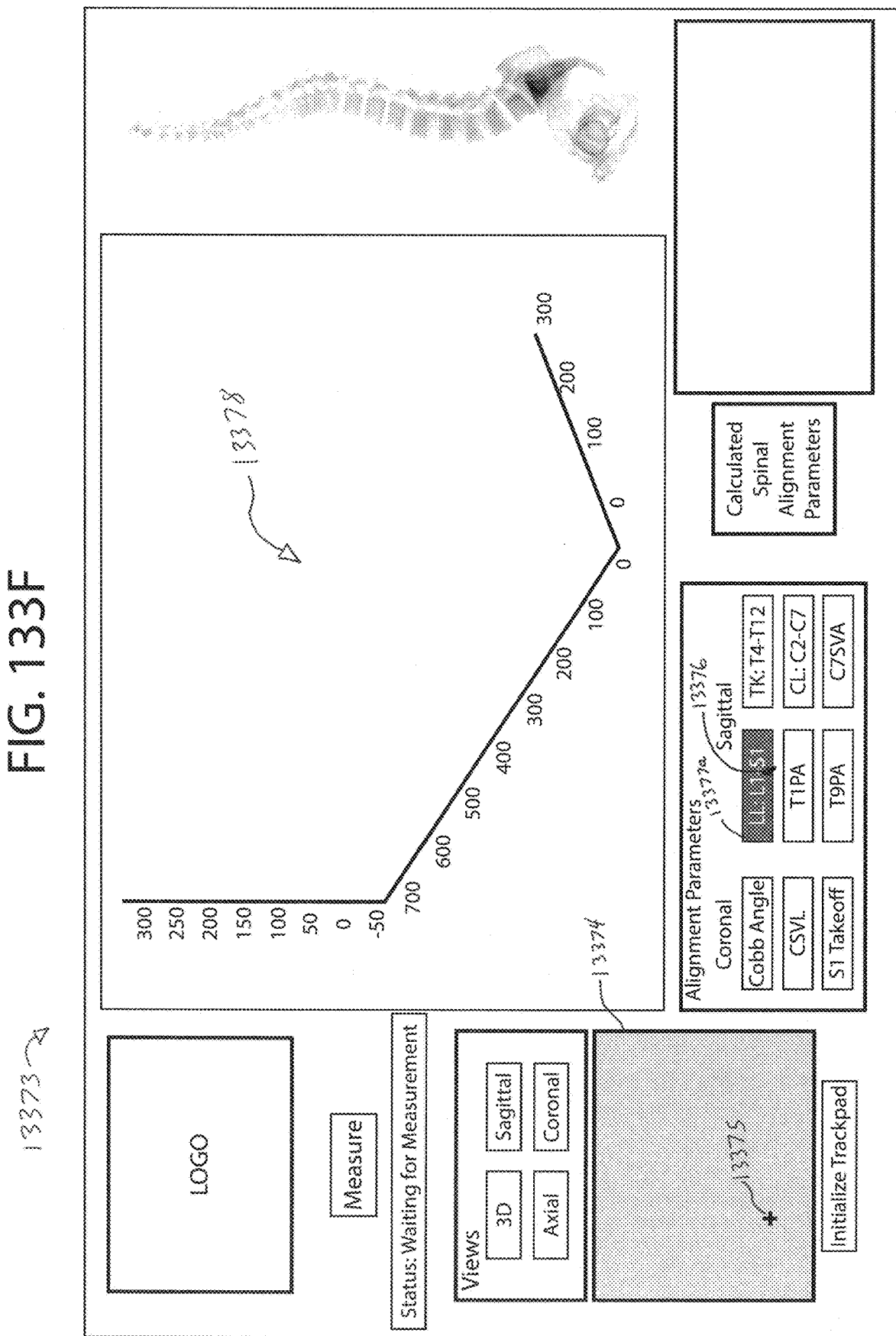

FIG. 133F illustrates a display interface of the trackpad display-controlling interface in its active state as described previously in relation to FIGS. 133A-133E in accordance with some embodiments of the invention.

FIG. 133G illustrates a display interface for the Z-pattern tracing of the skin-mounted fiducial as described previously in relation to FIGS. 133A-133F in accordance with some embodiments of the invention.

Figure 133H:
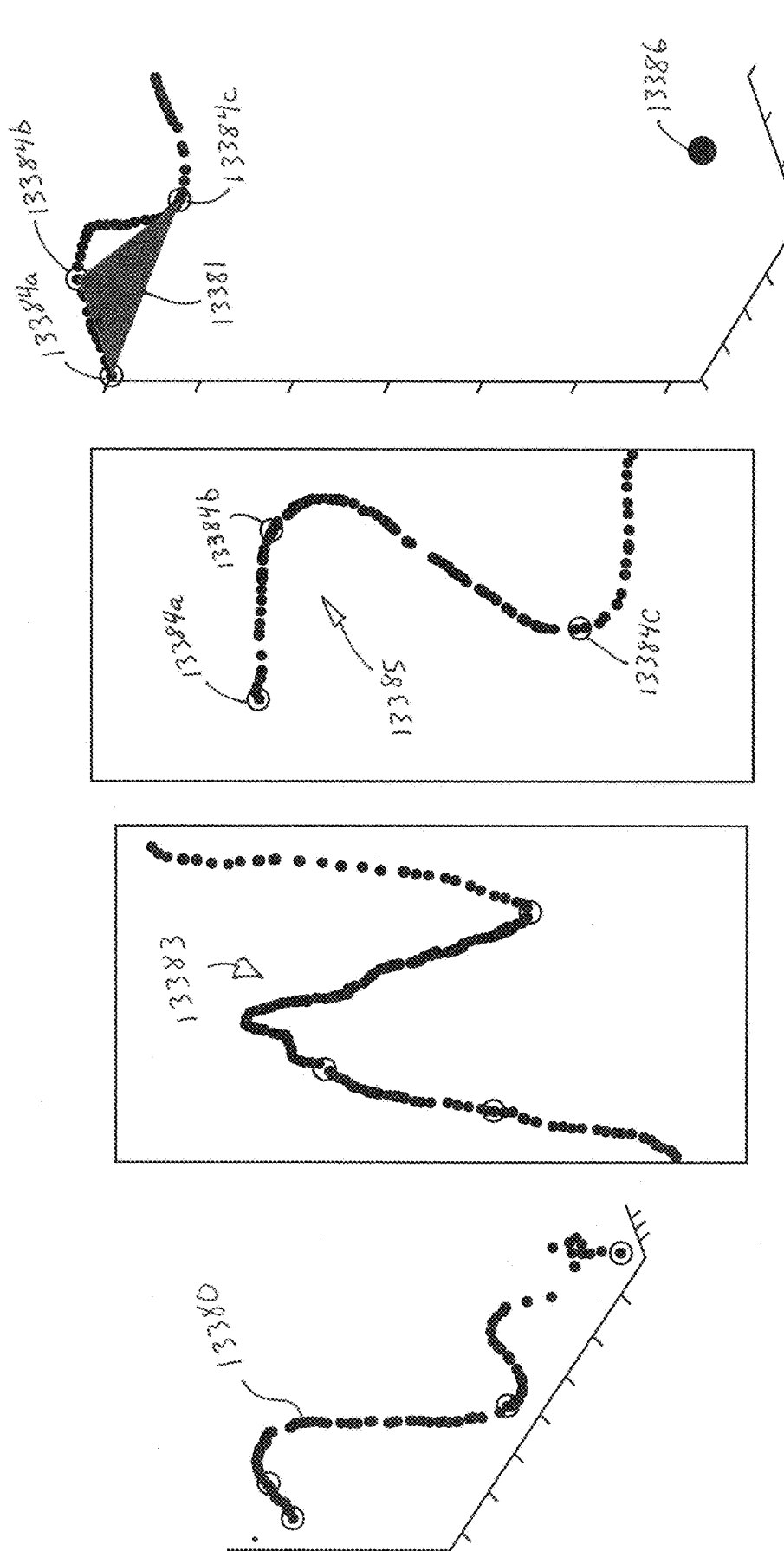

FIG. 133H illustrates outputs of the Z-pattern tracing of the skin-mounted fiducial and the automatic detection of the three corners of the fiducial as well as drop-down to an underlying anatomical landmark as described previously in relation to FIGS. 133A-133G in accordance with some embodiments of the invention.

Figure 133I:
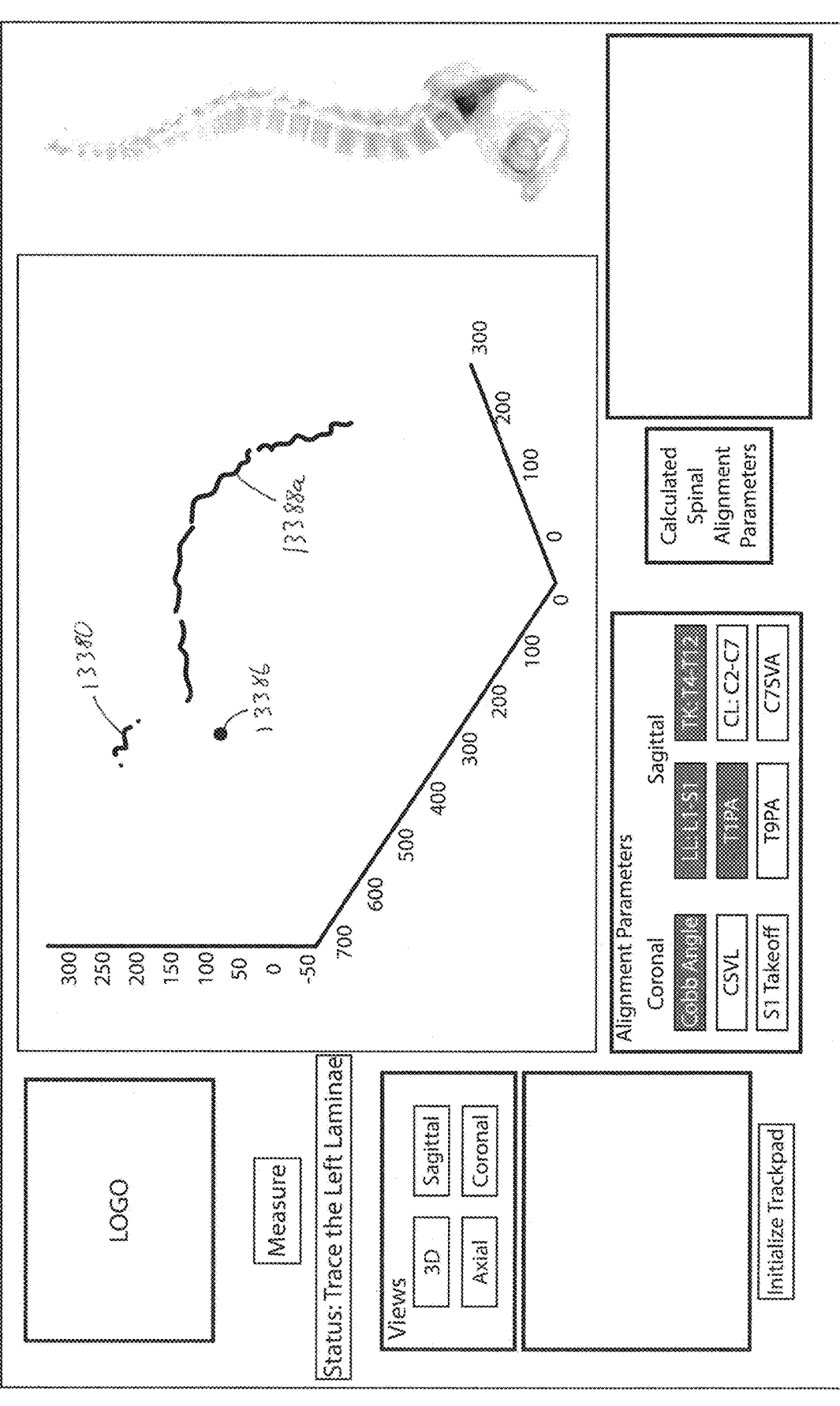

FIG. 133I illustrates a display interface for the tracing of one side of the surgically exposed laminae region of the spine as described previously in relation to FIGS. 133A-133H in accordance with some embodiments of the invention.

Figure 133J:
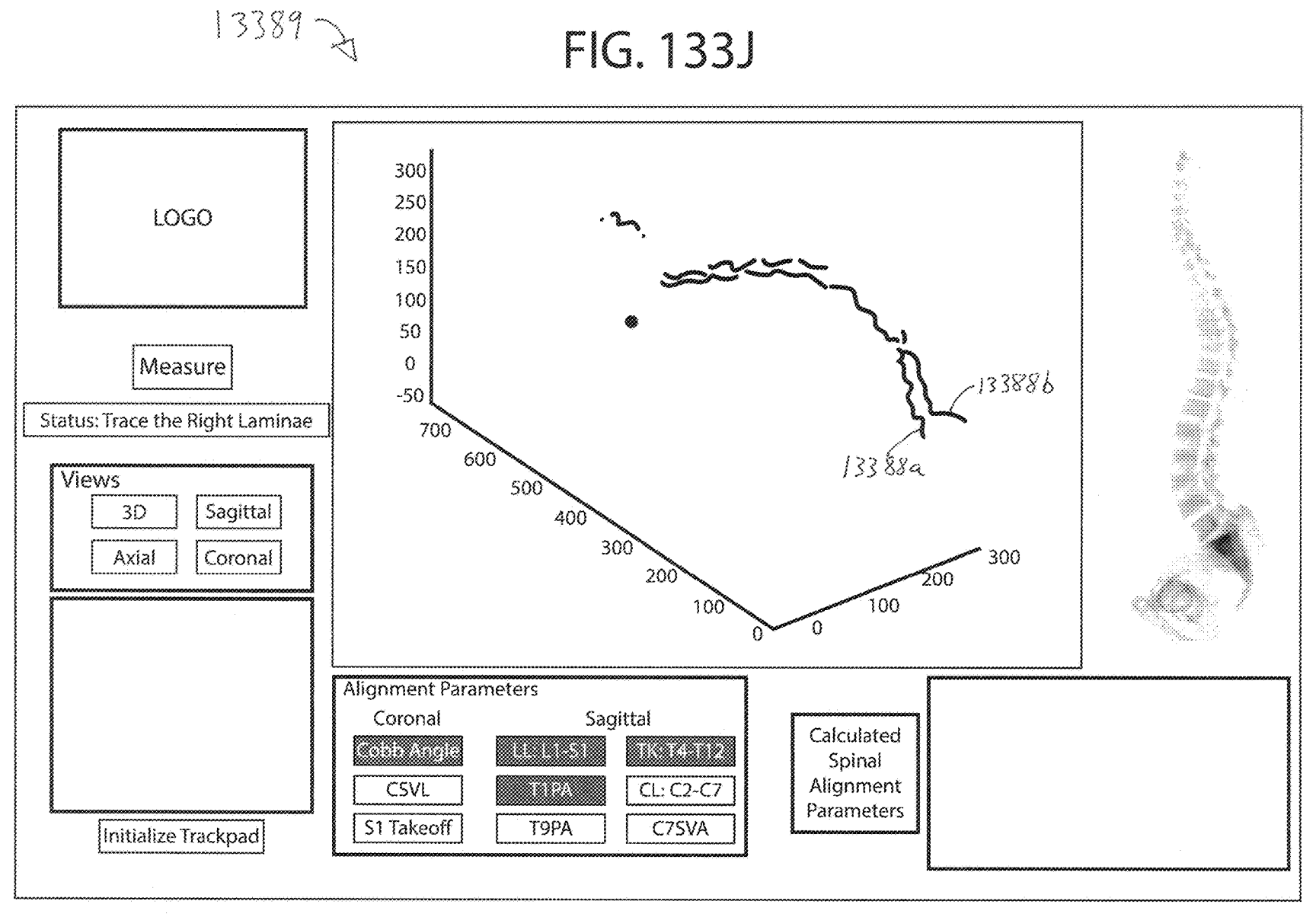

FIG. 133J illustrates a display interface for the tracing of contralateral side of the surgically exposed laminae region of the spine as described previously in relation to FIGS. 133A-133J in accordance with some embodiments of the invention.

Figure 133K:
Figure 133L:
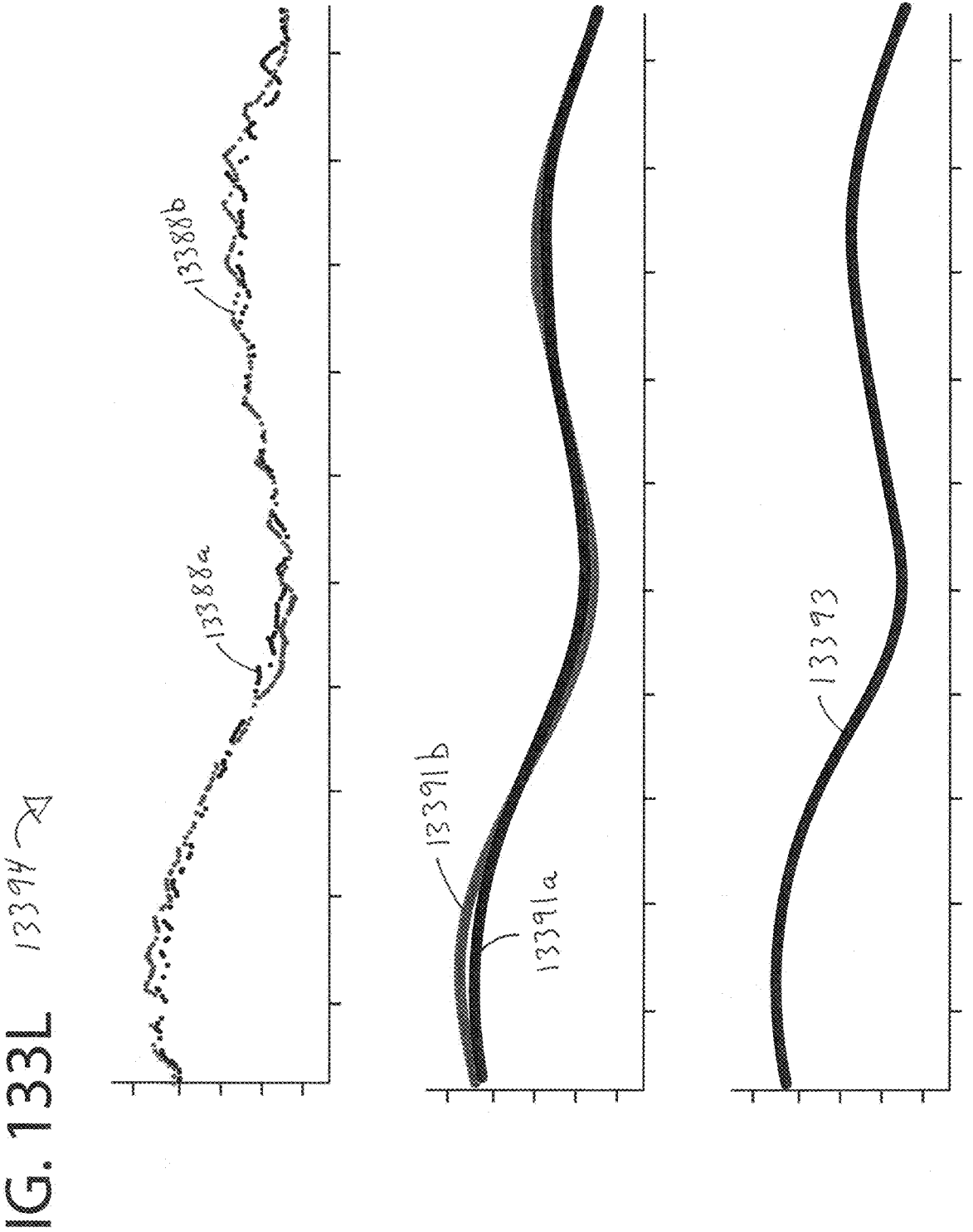

FIGS. 133K-133L illustrates outputs of the computed coronal and sagittal plane midlines of the 2D-projected bilateral laminae tracings as described previously in relation to FIGS. 133A-133J in accordance with some embodiments of the invention.

Figure 133M:

FIG. 133M illustrates an output of the computed 3D midline of the bilateral laminae tracings as described previously in relation to FIGS. 133A-133L in accordance with some embodiments of the invention.

FIG. 133N illustrates a display interface for computing the midline of the bilateral laminae tracings as described previously in relation to FIGS. 133A-133M in accordance with some embodiments of the invention.

FIG. 133O illustrates a display interface for computing the sagittal and coronal S1 endplate lines and femoral head centers as described previously in relation to FIGS. 133A-133N in accordance with some embodiments of the invention.

Figure 133P:
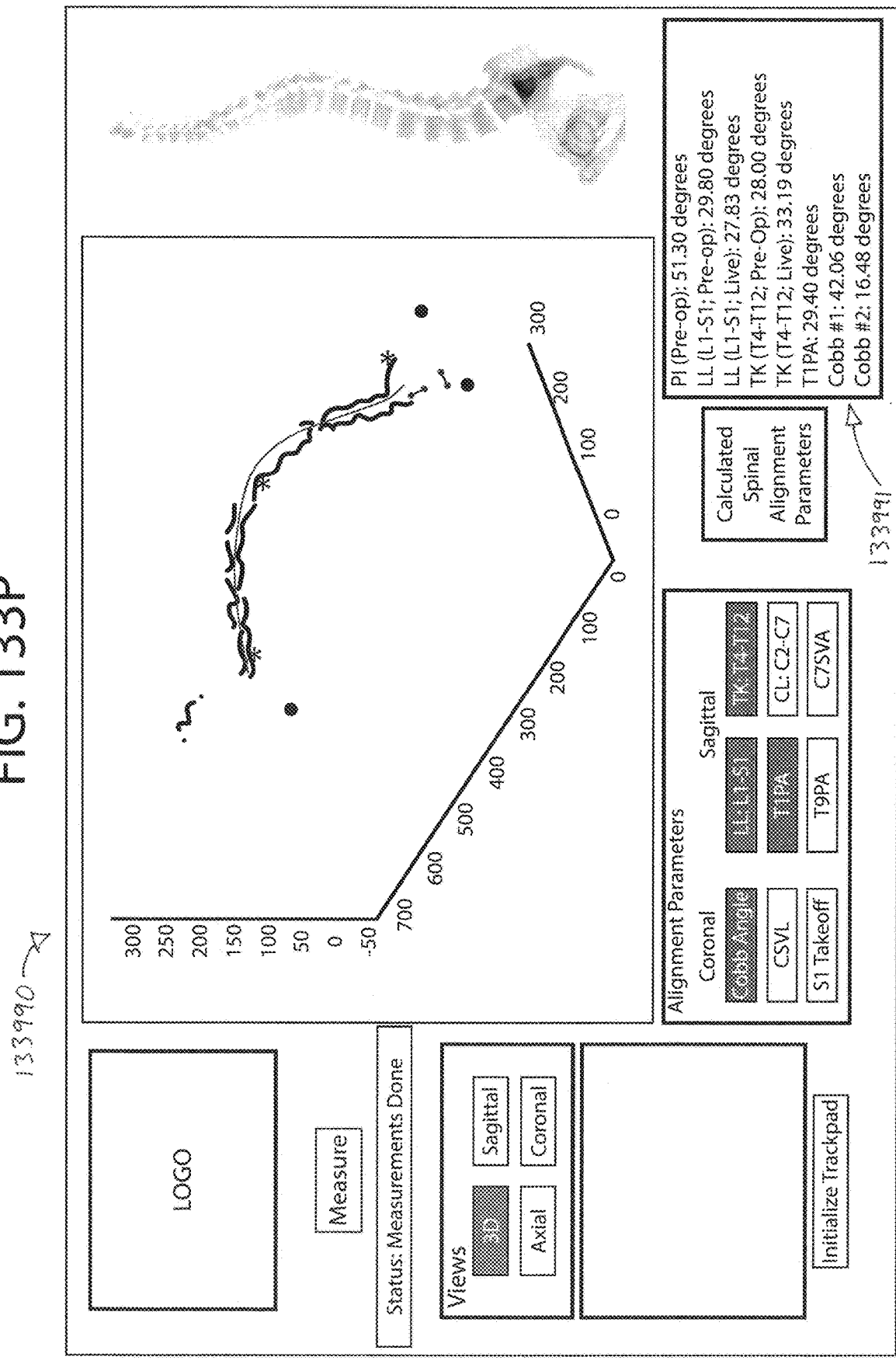

FIG. 133P illustrates a display interface for computing the desired spinal alignment parameters from available anatomical landmarks described previously in relation to FIGS. 133A-133O in accordance with some embodiments of the invention.

Figure 133Q:
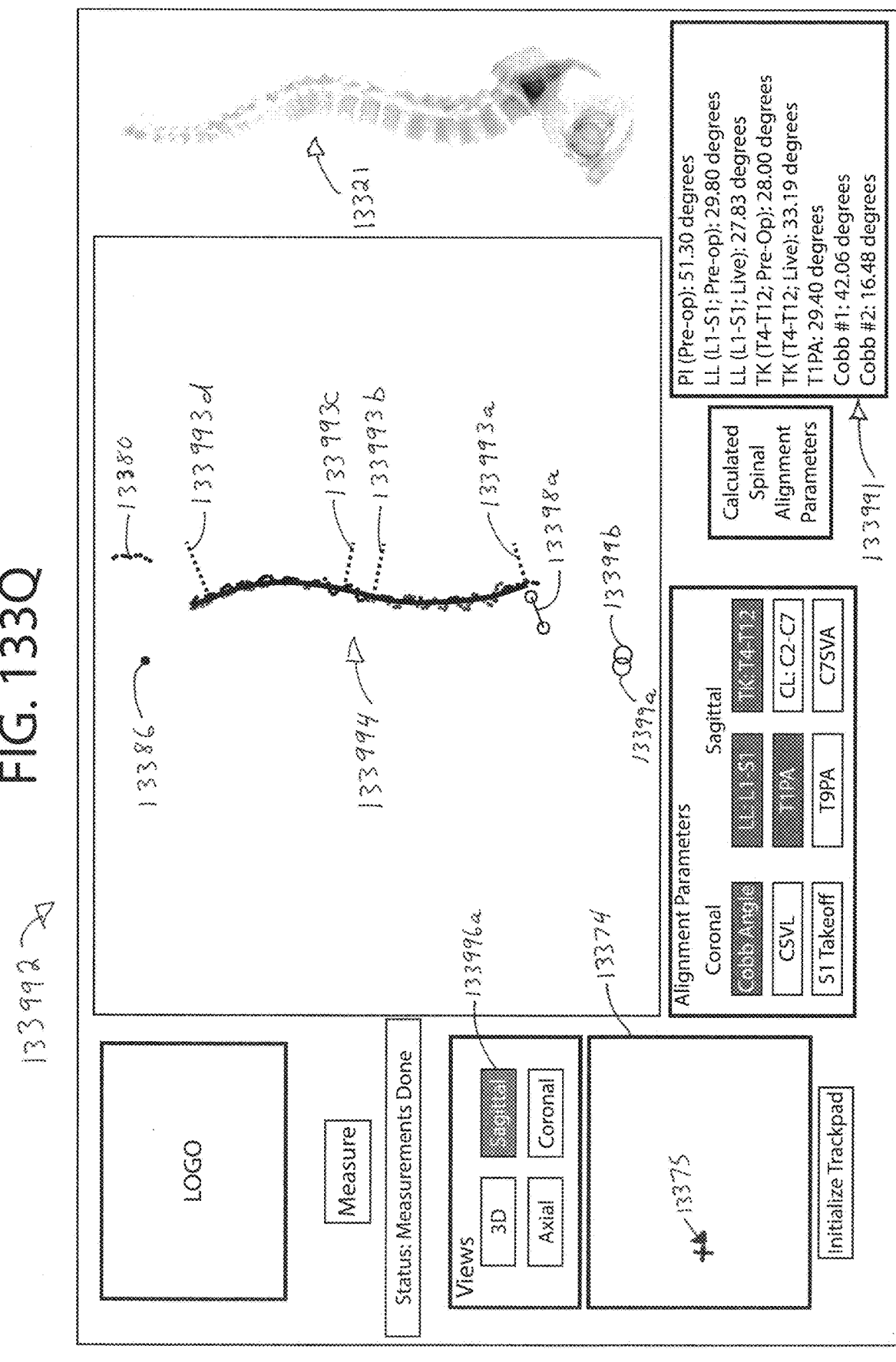

FIG. 133Q illustrates a display interface for displaying the sagittal plane view of the spine tracing as described previously in relation to FIGS. 133A-133P in accordance with some embodiments of the invention.

Figure 133R:
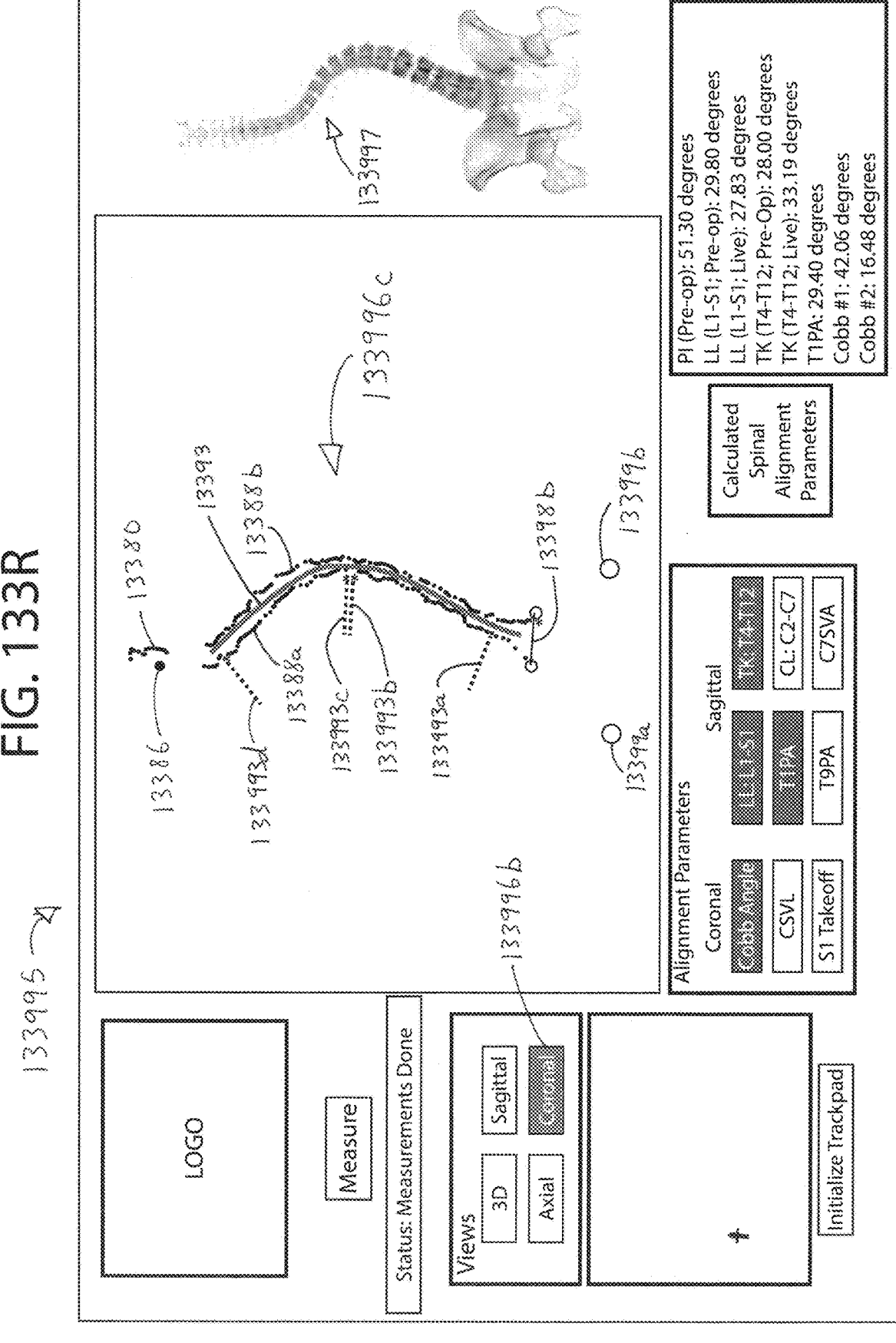

FIG. 133R illustrates a display interface for displaying the coronal plane view of the spine tracing as described previously in relation to FIGS. 133A-133Q in accordance with some embodiments of the invention.

Figure 133S:
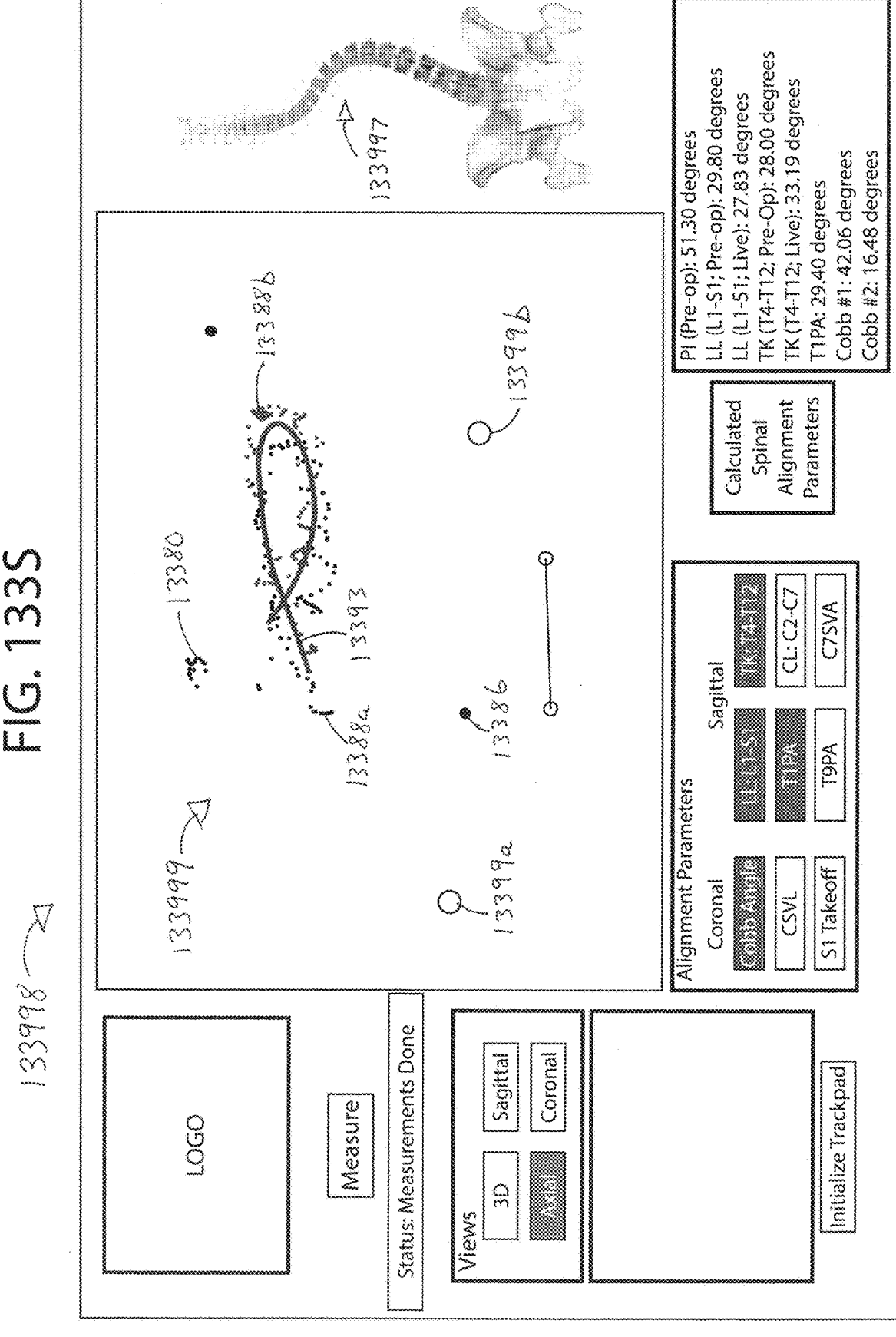

FIG. 133S illustrates a display interface for displaying the axial plane view of the spine tracing as described previously in relation to FIGS. 133A-133R in accordance with some embodiments of the invention.

Figure 134A:
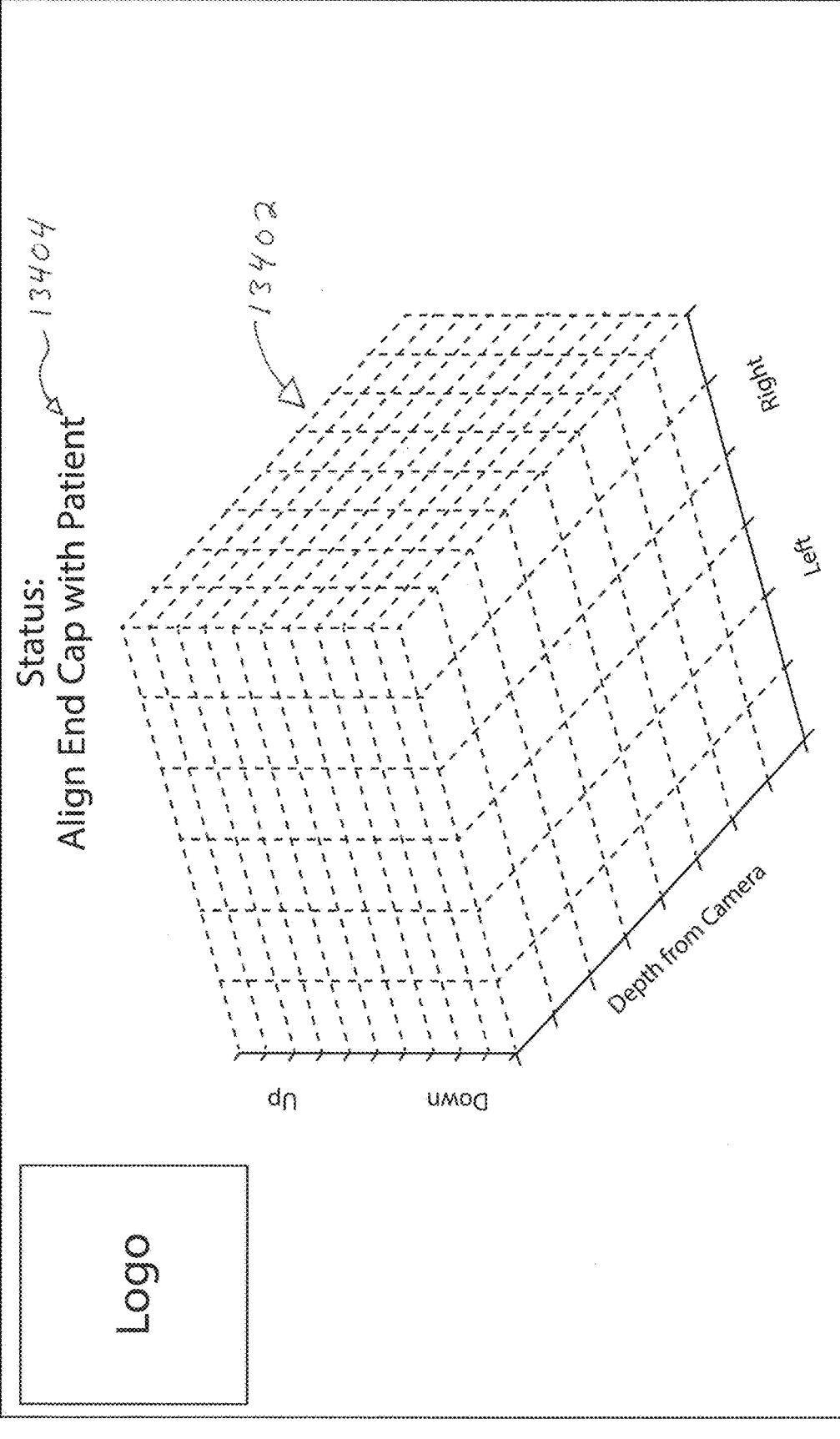

FIG. 134A illustrates a display interface for determining the anatomical axes using the coordinate reference end cap device in accordance with some embodiments of the invention.

Figure 134B:
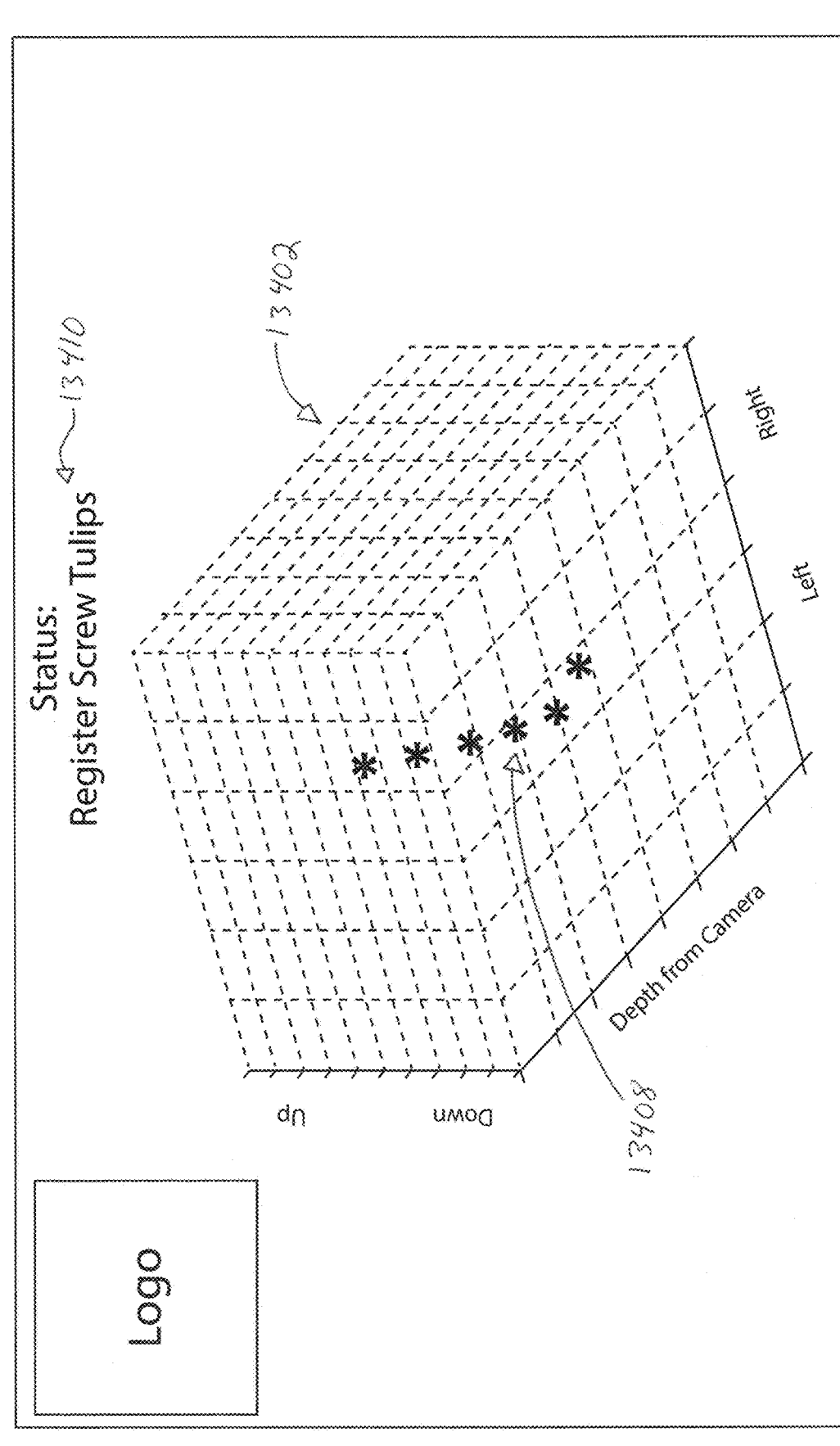

FIG. 134B illustrates a display interface for viewing the 3D locations of pedicle screw tulip-heads acquired using a 3D-tracked probe as described previously in relation to FIG. 134A in accordance with some embodiments of the invention.

Figure 134C:
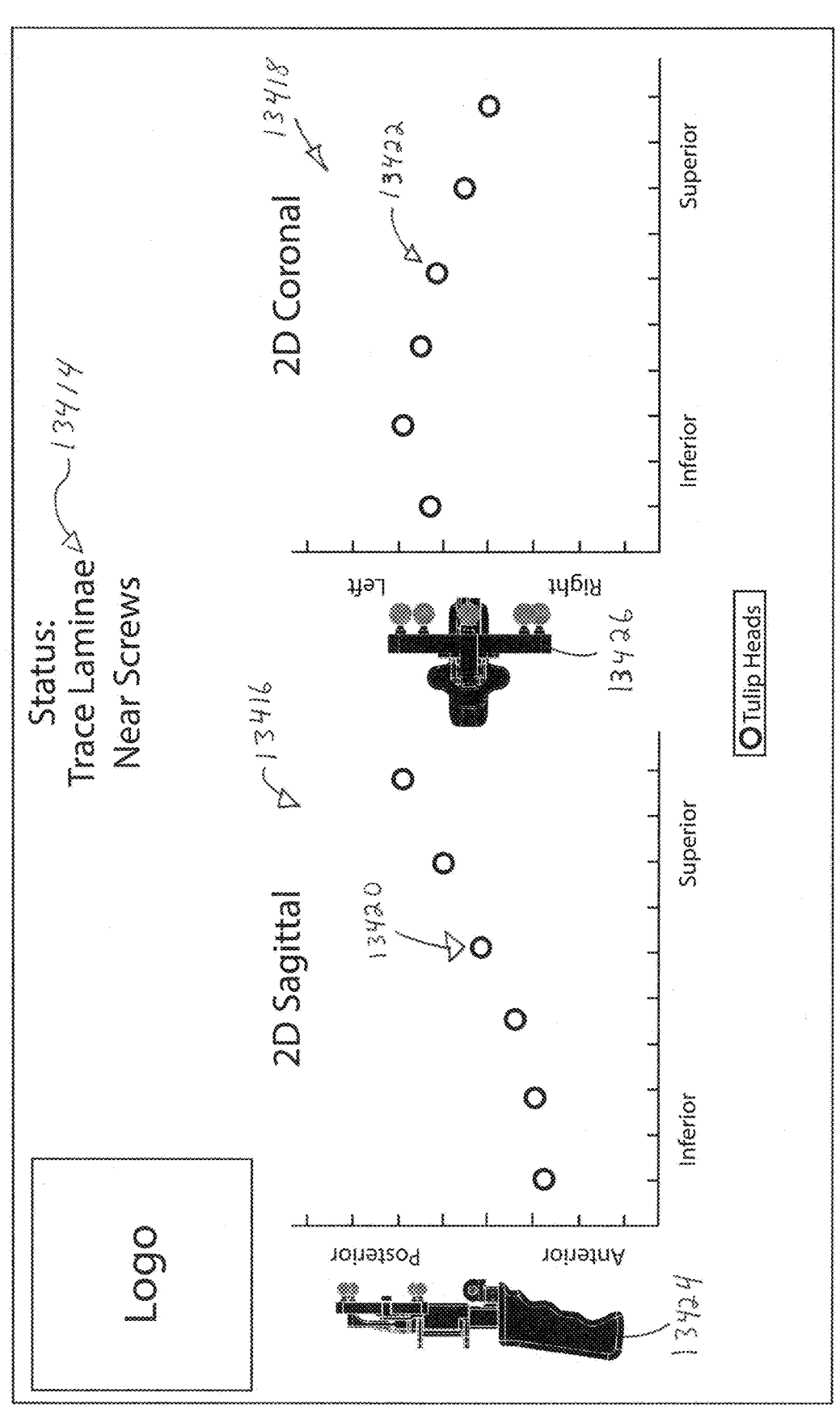
Figure 134D:
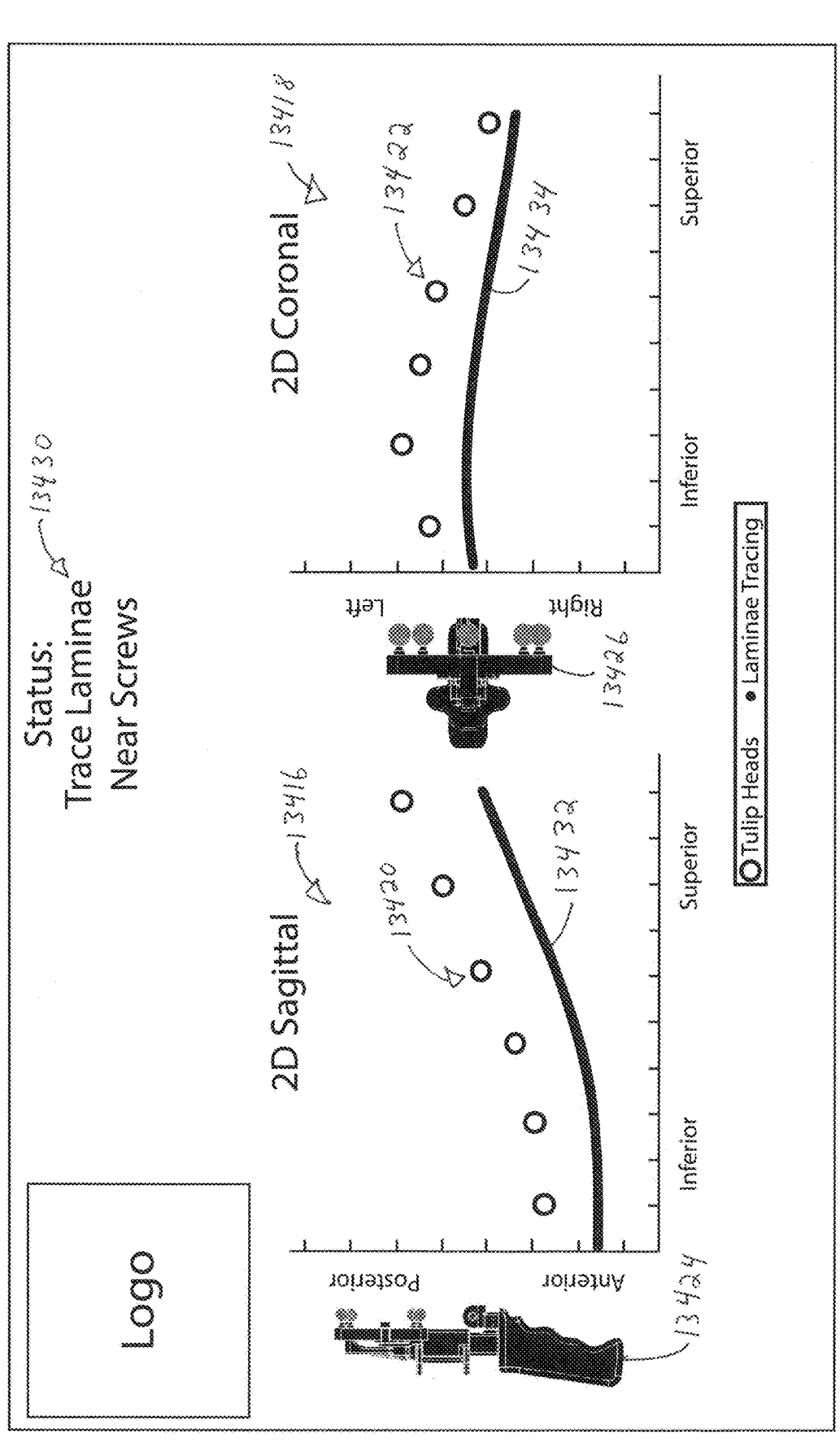
Figure 134E:
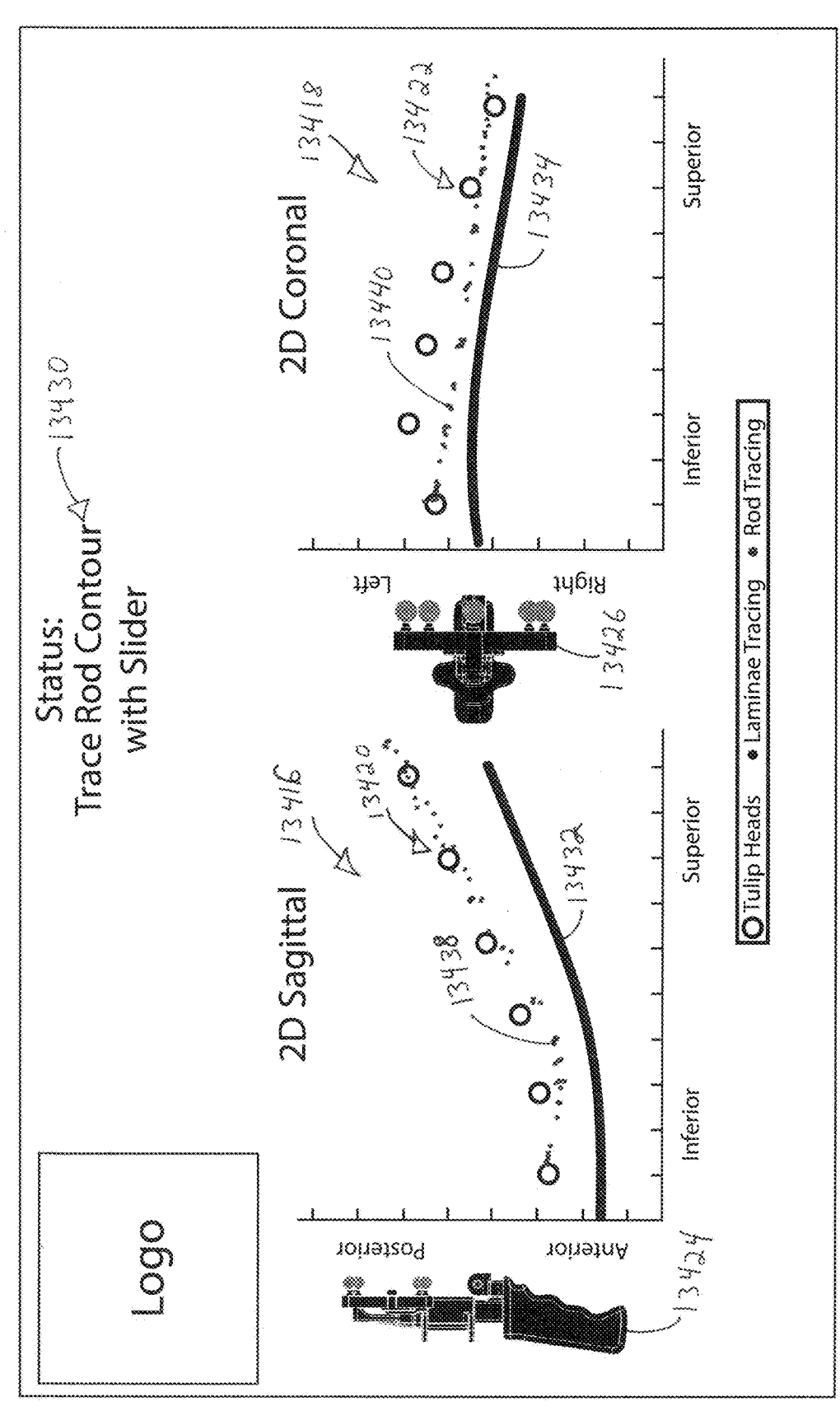

FIGS. 134C-134E illustrate display interfaces for viewing the sagittal and coronal plane projections of the acquired 3D locations of pedicle screw tulip-heads, a completed tracing of the laminae, and a completed tracing of the rod's contour as described previously in relation to FIGS. 134A-134B in accordance with some embodiments of the invention.

Figure 134F:
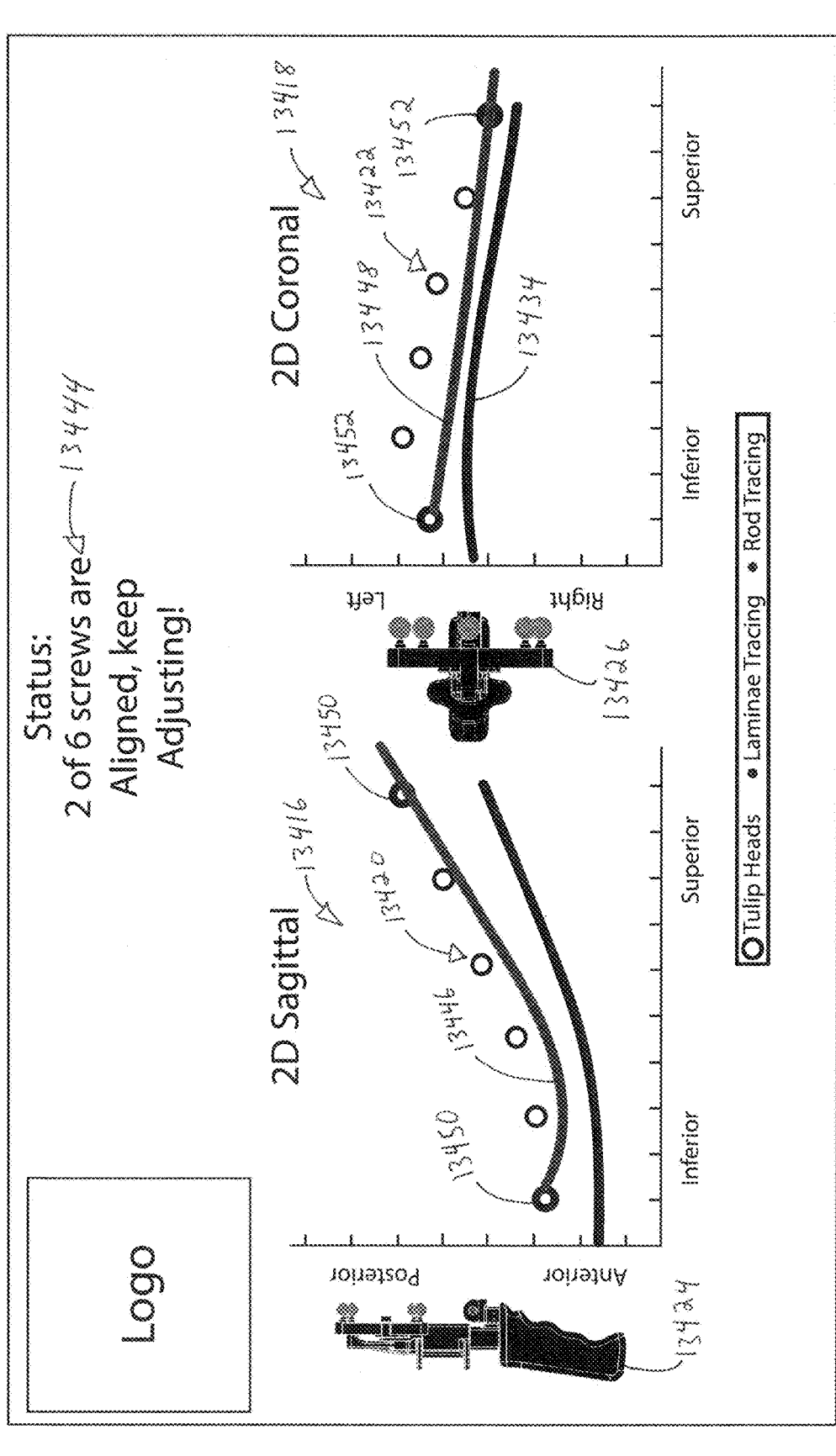

FIG. 134F illustrates a display interface for viewing the sagittal and coronal plane projections of the acquired 3D locations of pedicle screw tulip-heads, a completed tracing of the laminae, a smoothed tracing of the rod's contour, and an indication of screws aligned with the rod as described previously in relation to FIGS. 134A-134E in accordance with some embodiments of the invention.

Figure 134G:
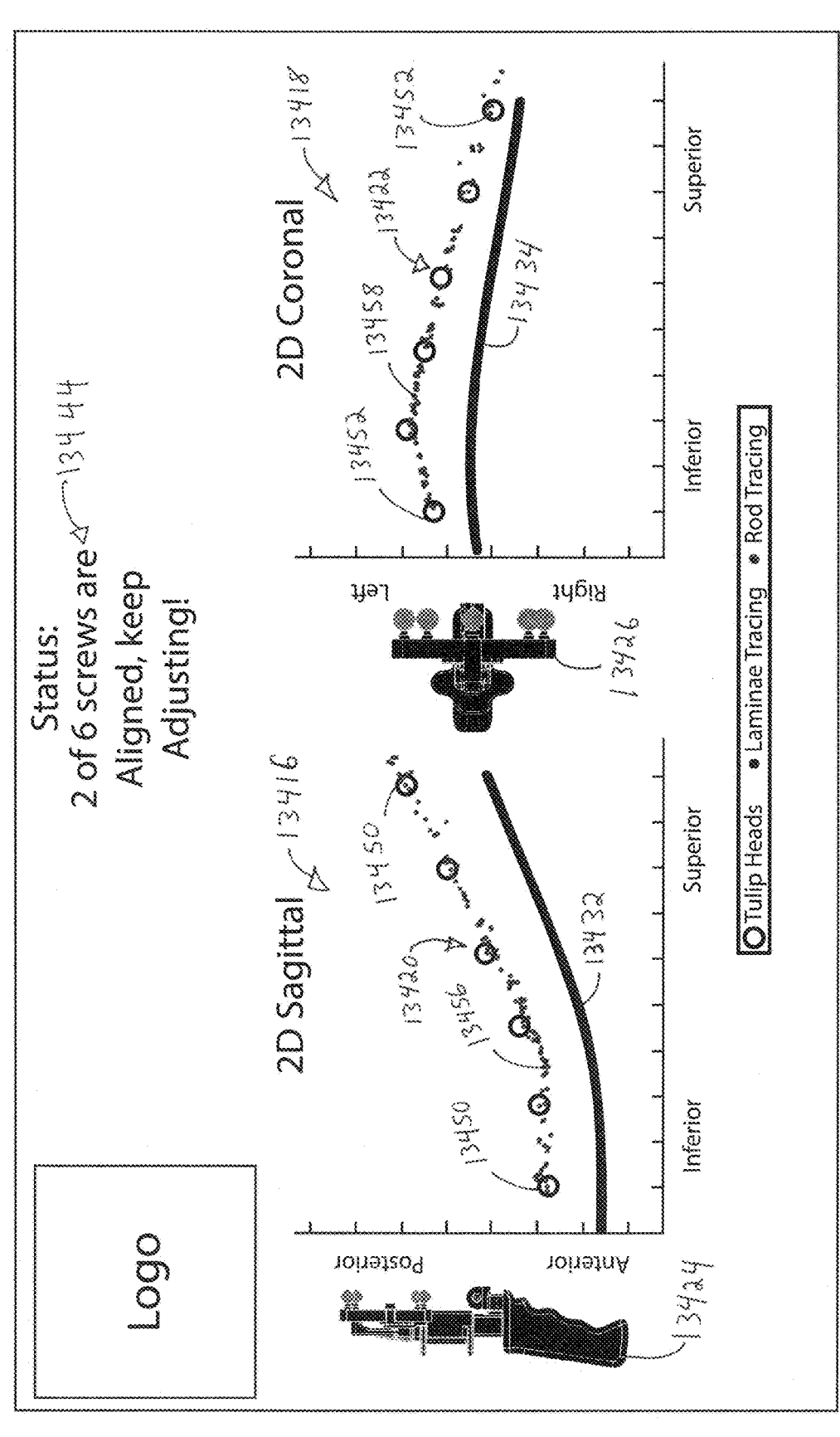
Figure 134H:
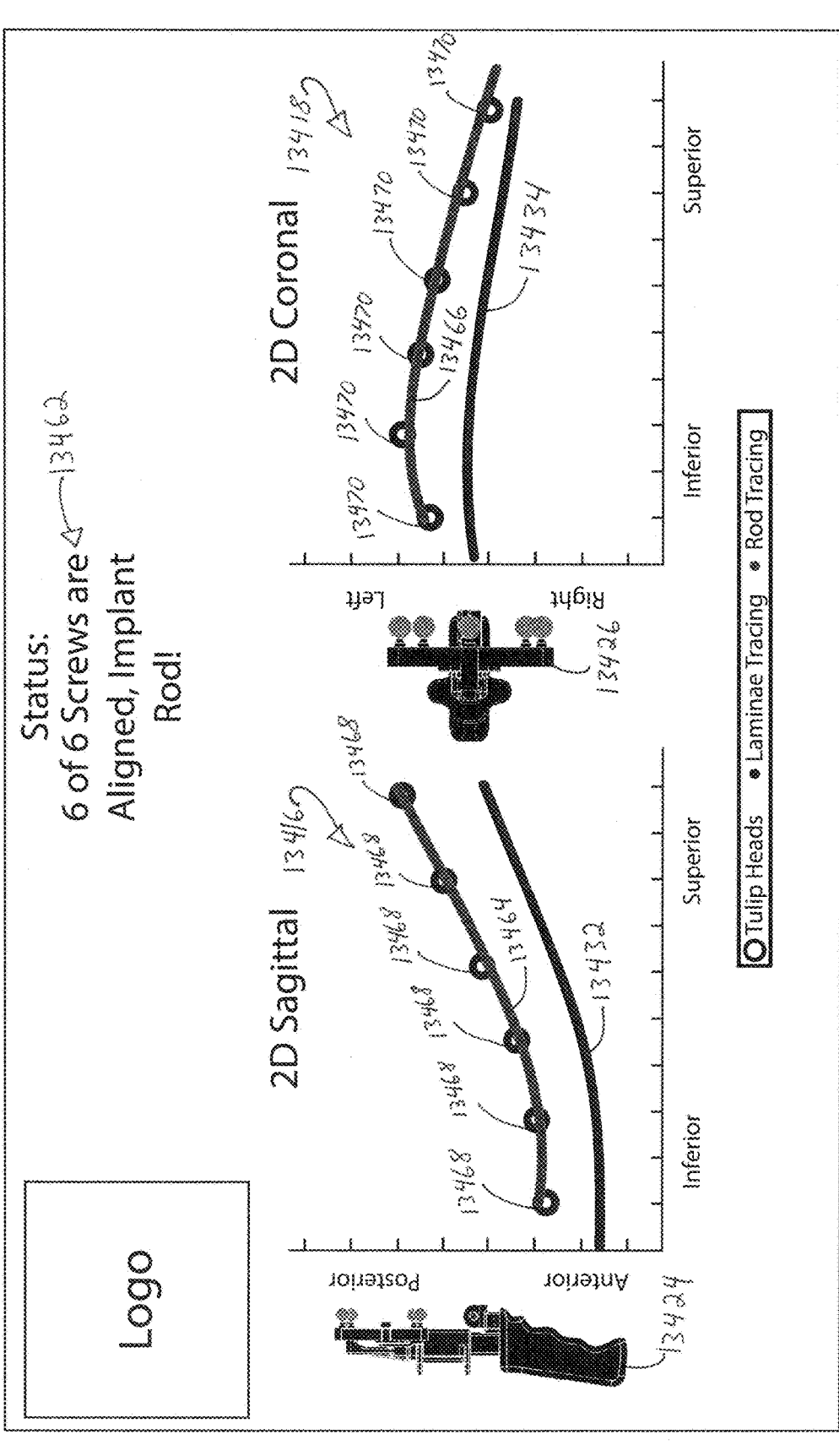

FIGS. 134G-134H illustrate a display interface for viewing the sagittal and coronal plane projections of the acquired 3D locations of pedicle screw tulip-heads, a completed tracing of the laminae, and a completed tracing of a rod's contour modified to align with more screws as described previously in relation to FIGS. 134A-134F in accordance with some embodiments of the invention.

FIGS. 135A-135F illustrate a display interface for viewing the 3D meshworks of the patient's sacrum and vertebrae registered via a 3D-tracked tool that engages with bone-mounted fiducials in accordance with some embodiments of the invention.

Figure 135A:
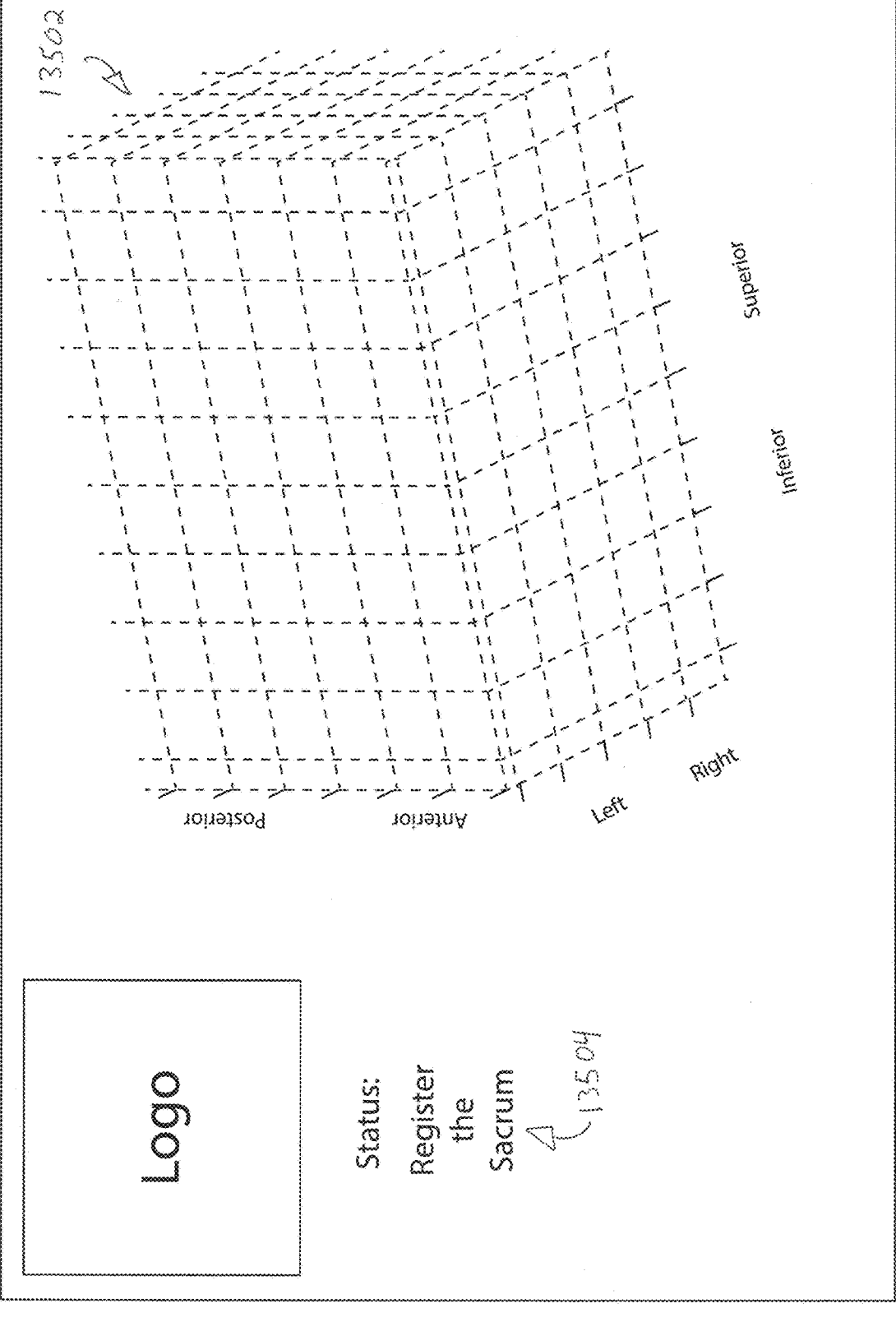
Figure 135B:
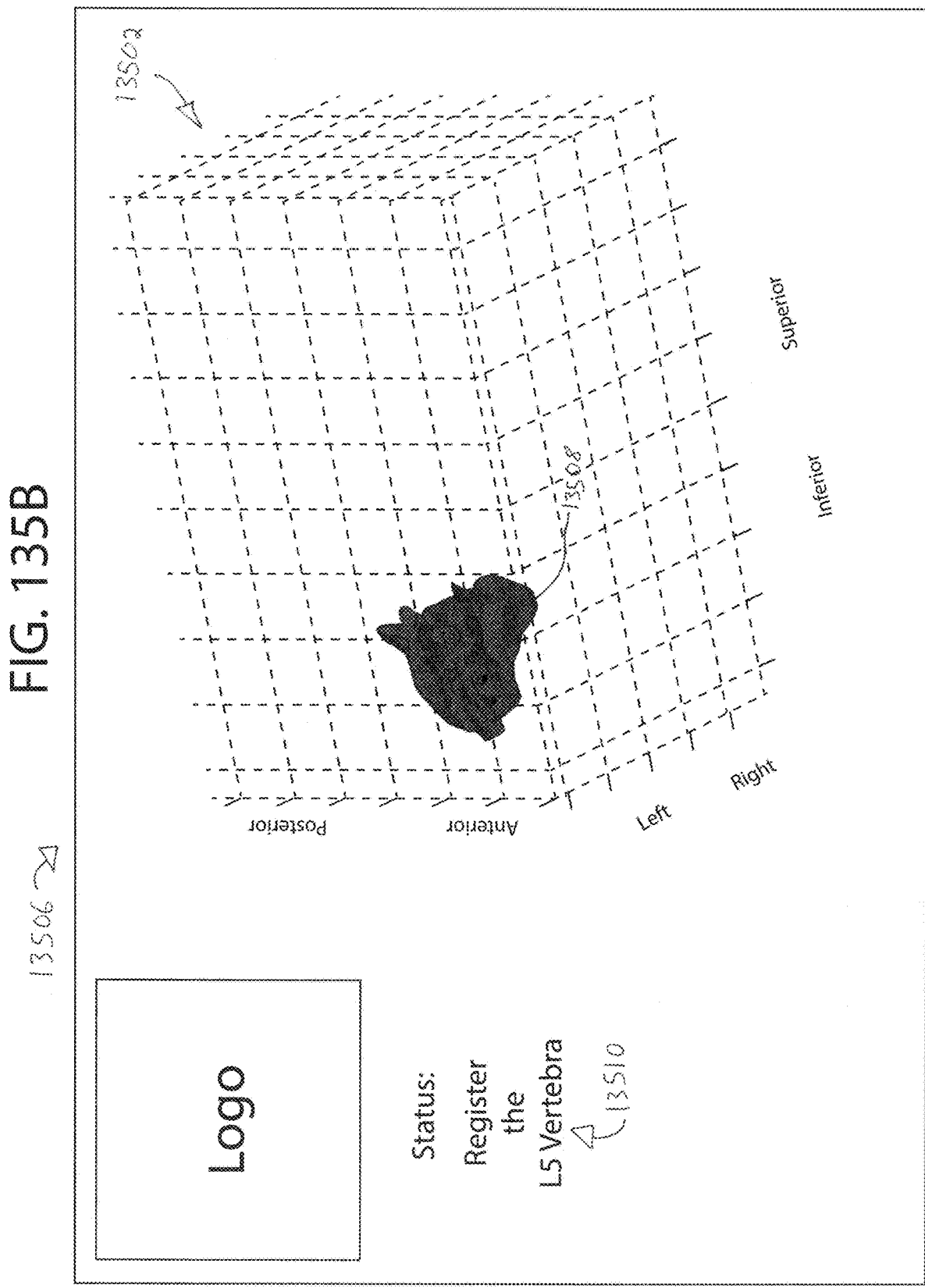
Figure 135C:
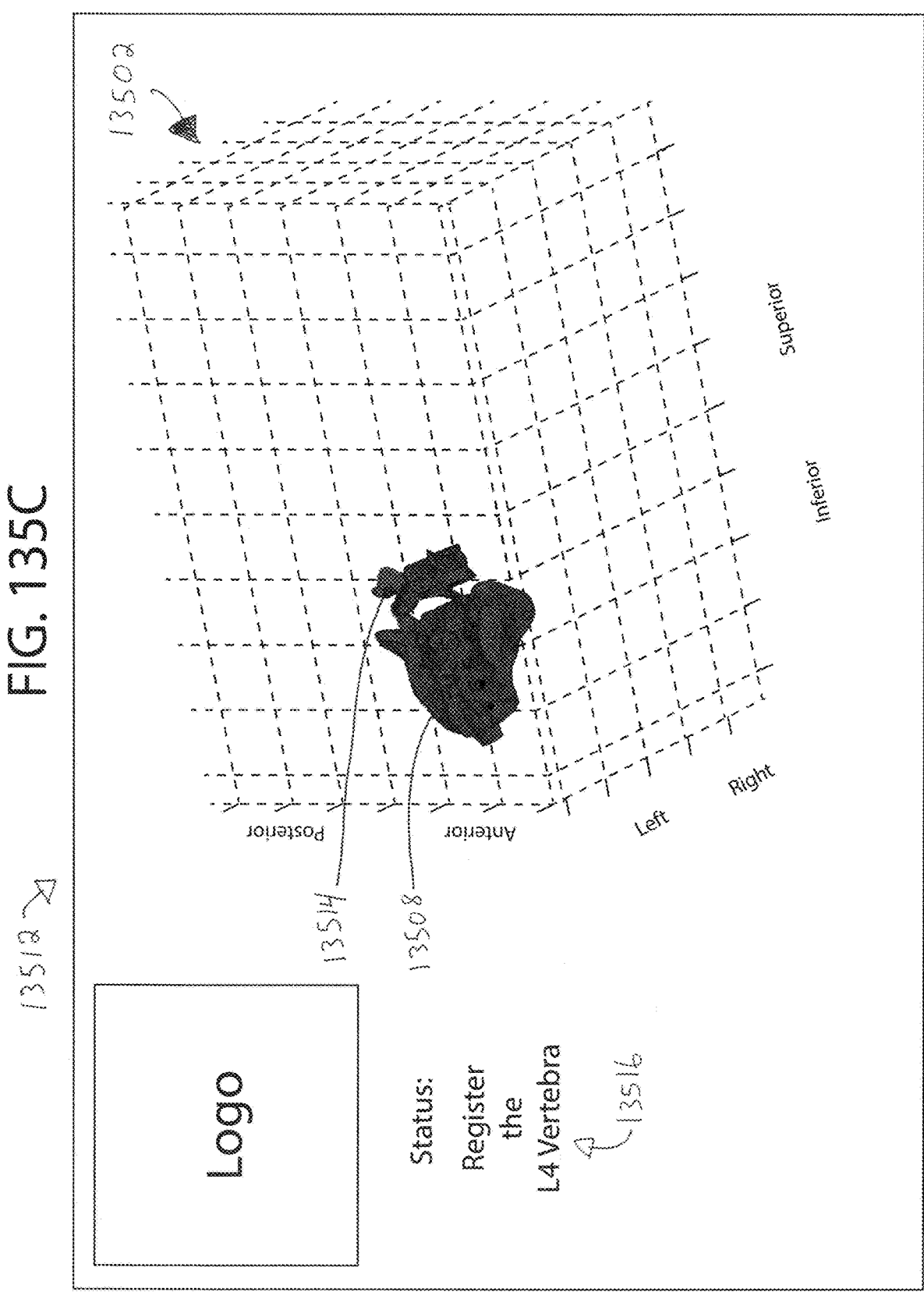
Figure 135D:
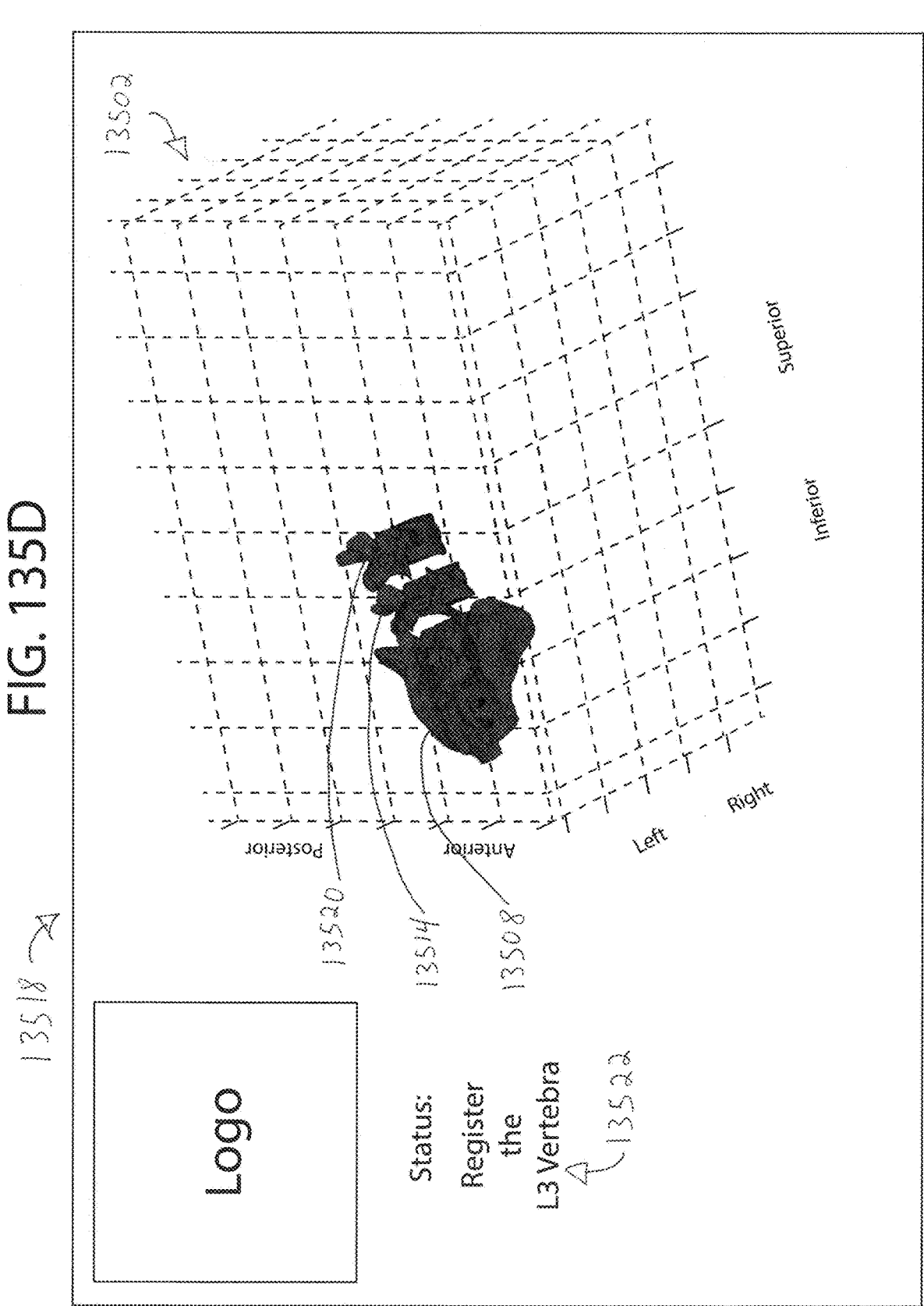
Figure 135E:
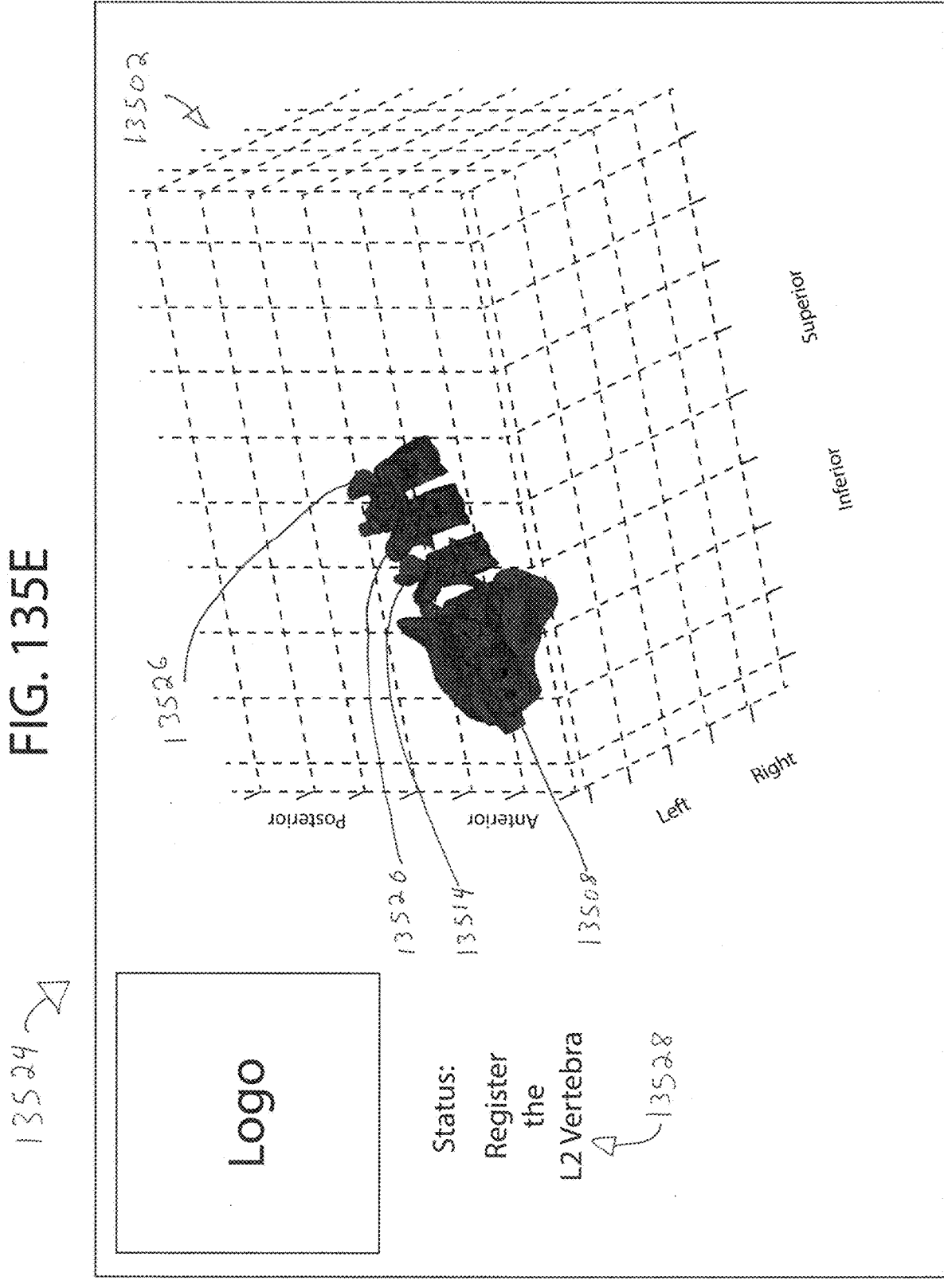
Figure 135F:
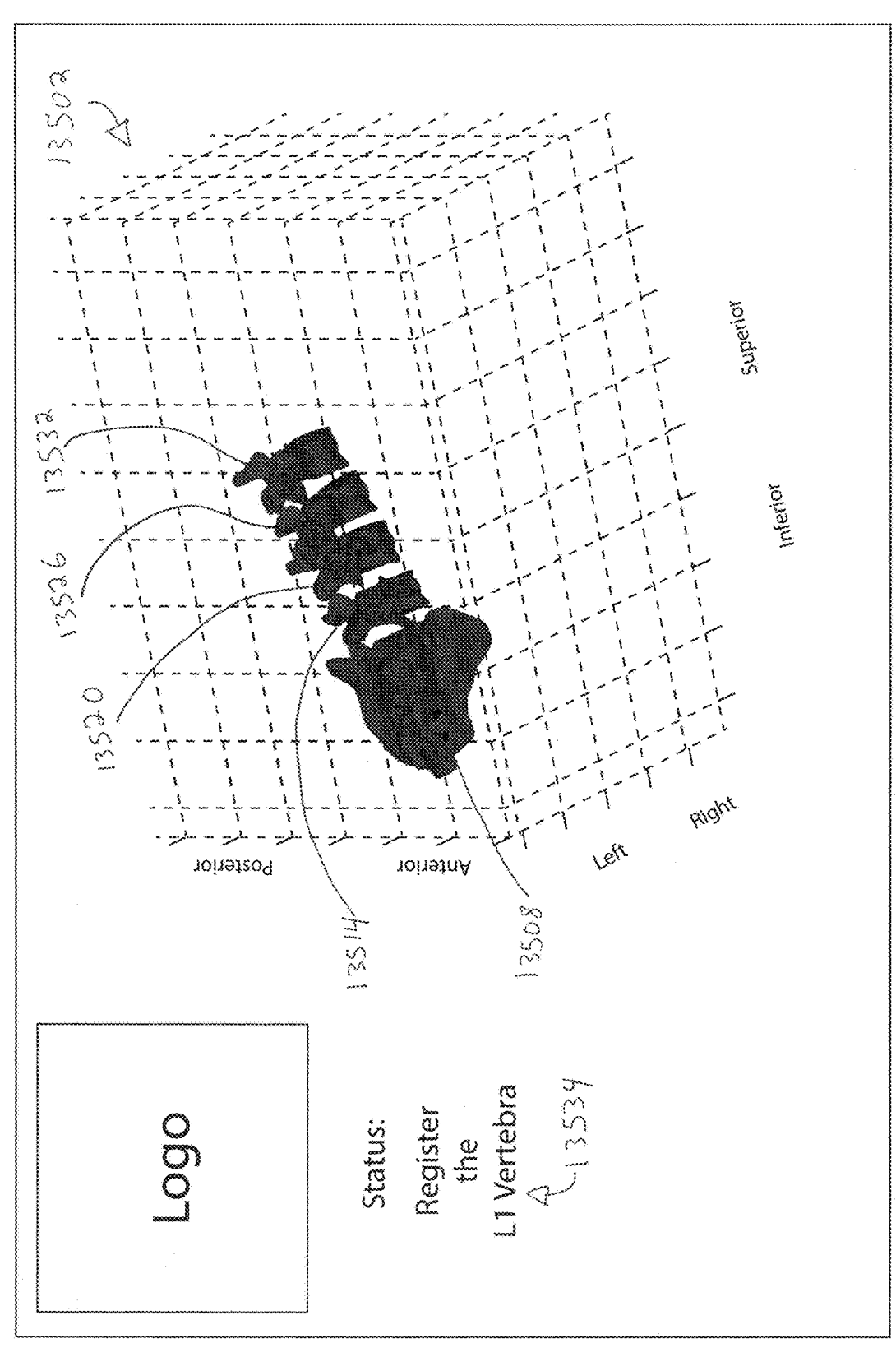
Figure 135G:
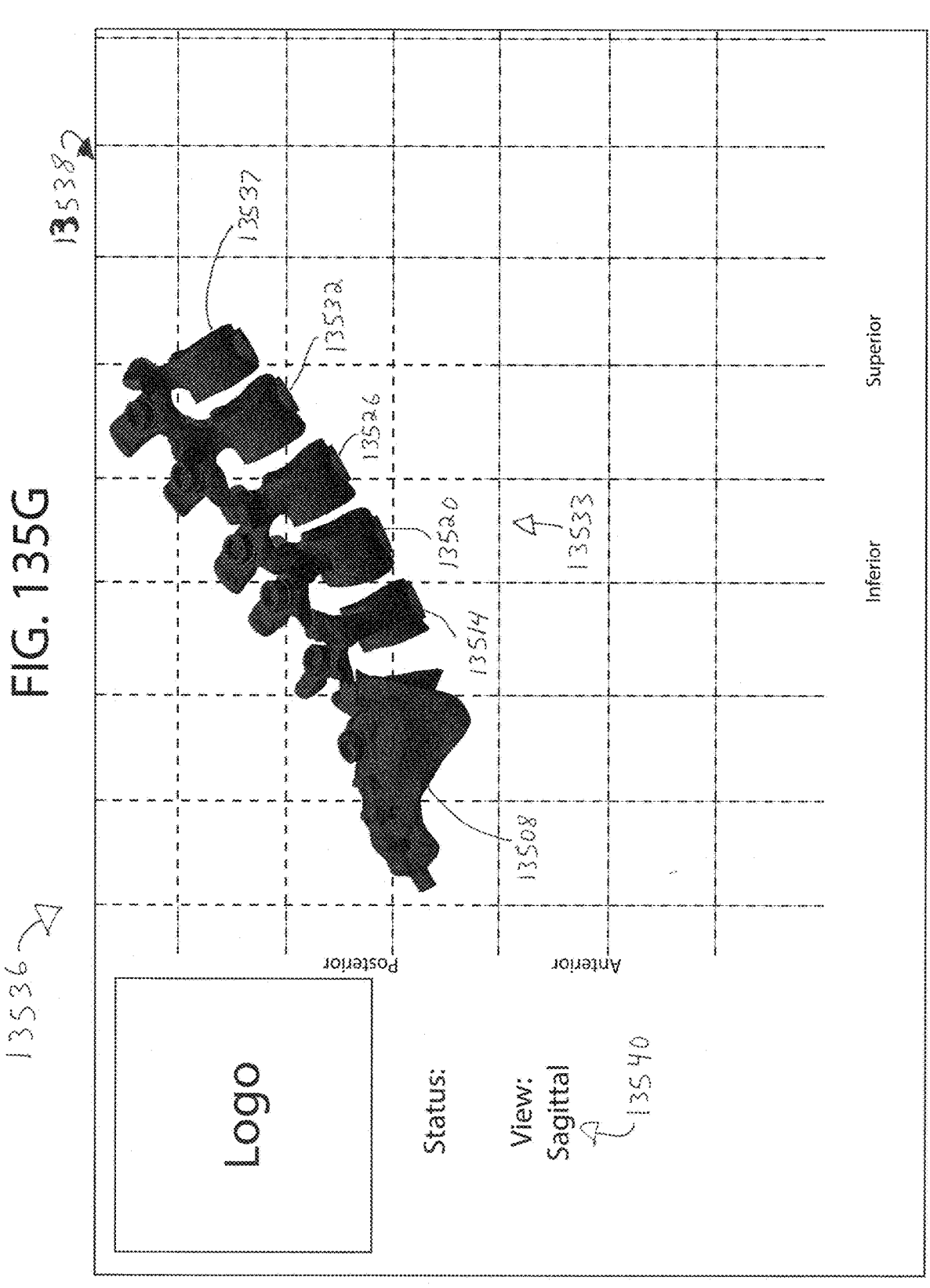
Figure 135H:
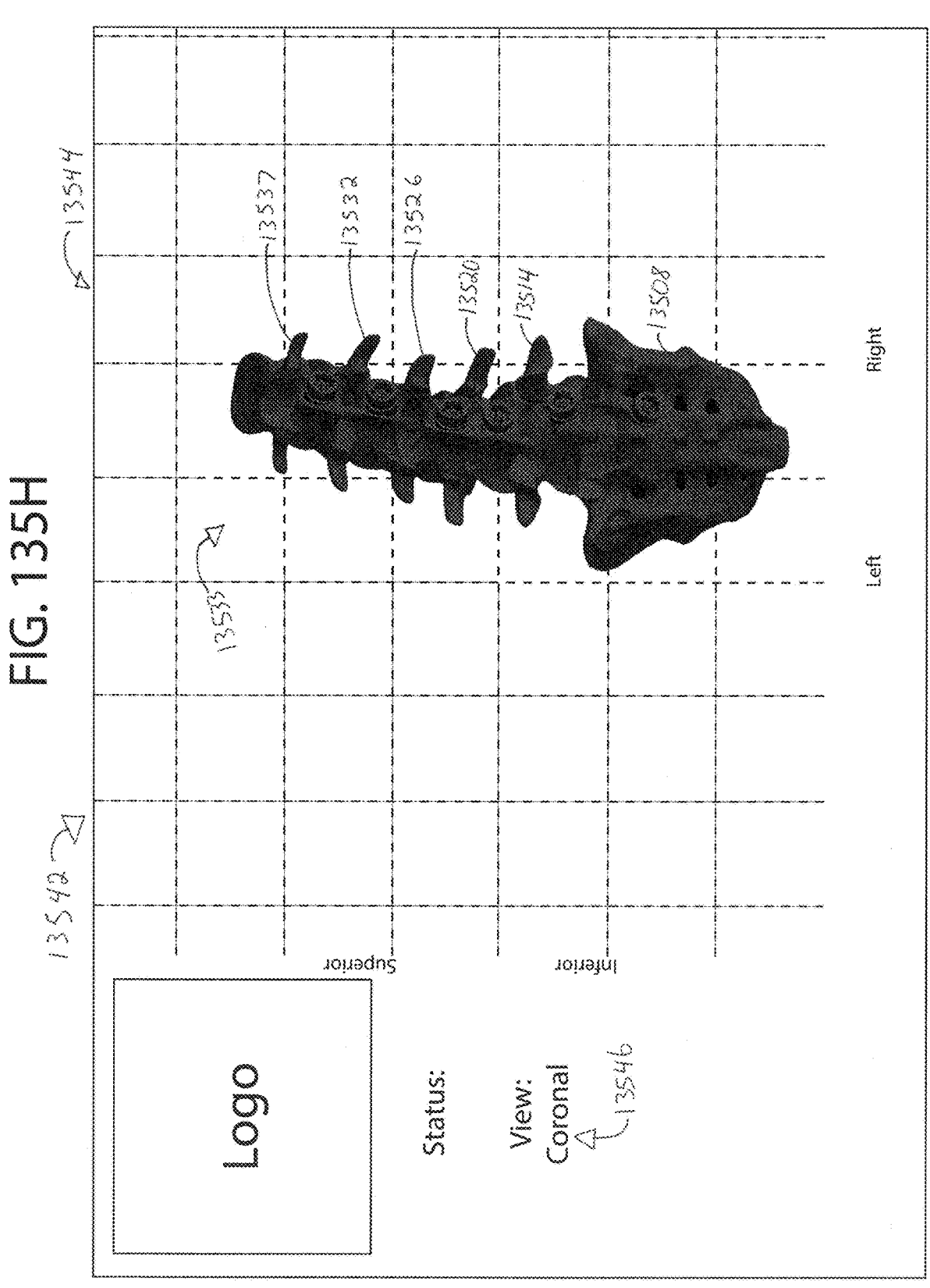
Figure 135I:
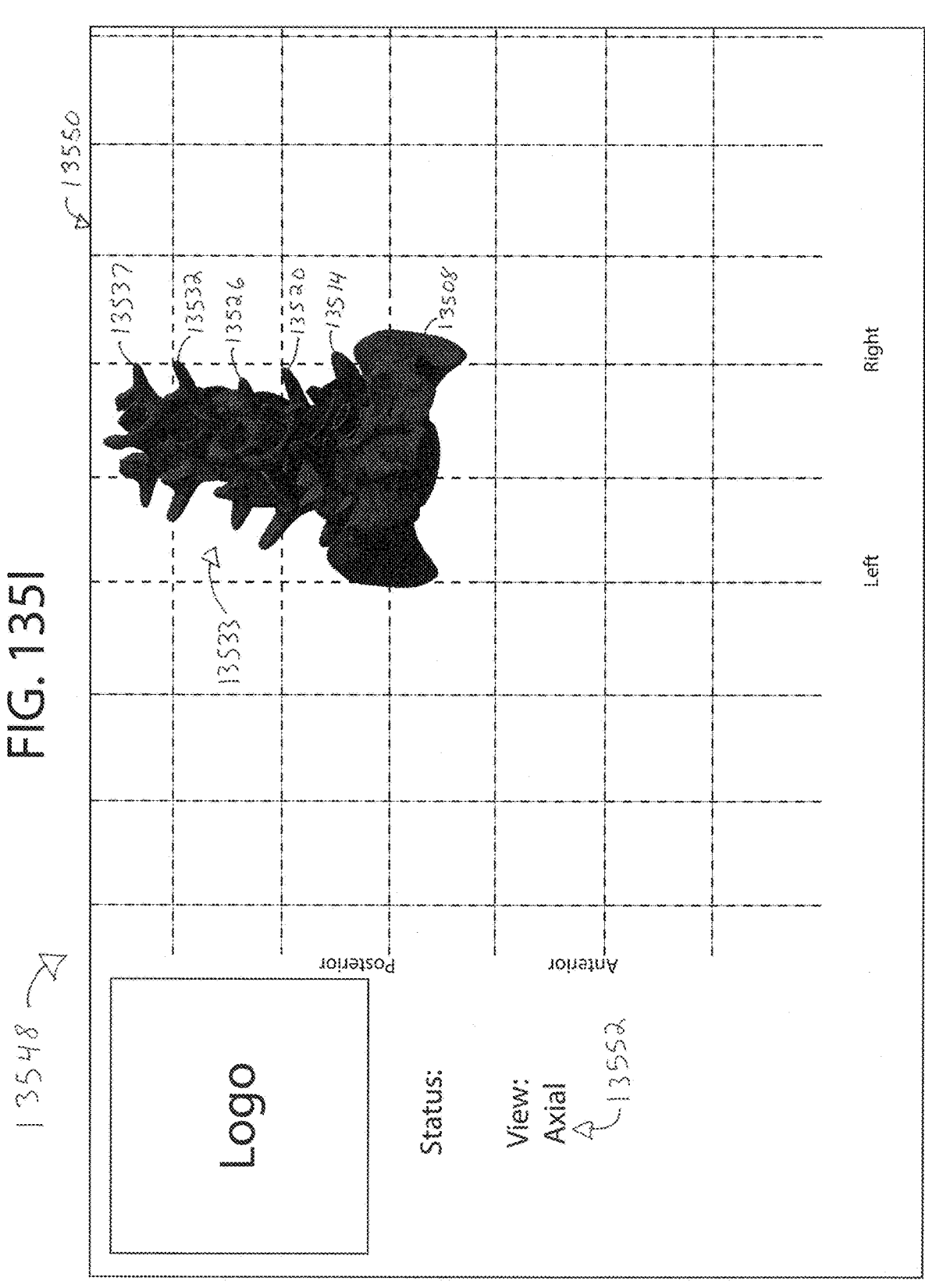

FIGS. 135G-135I illustrate a display interface for displaying the sagittal, coronal, and axial plane views of the patient's sacrum and vertebrae registered via the bone-mounted fiducial as described previously in relation to FIGS. 135A-135F in accordance with some embodiments of the invention.

Figure 135J:
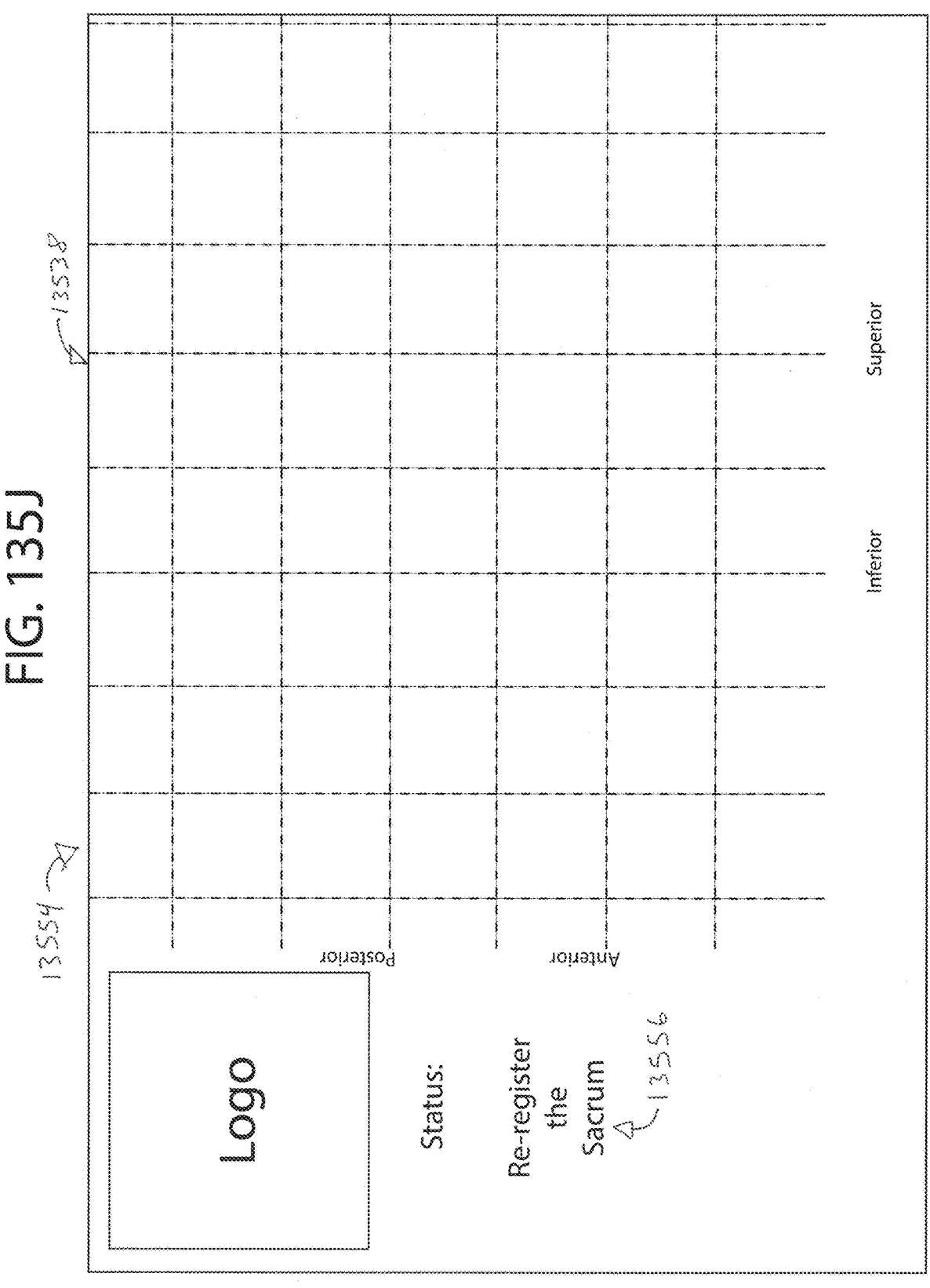
Figure 135K:
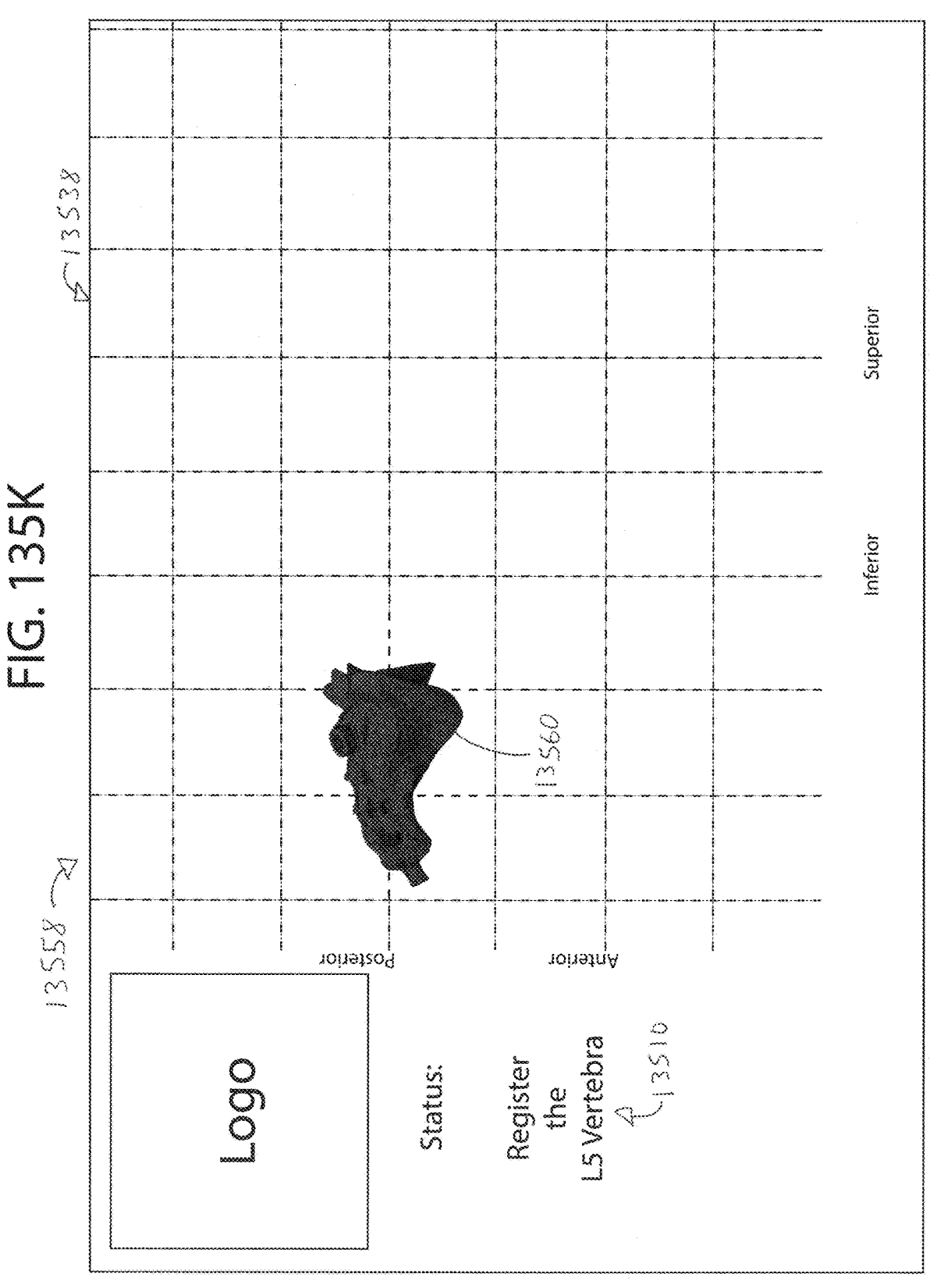
Figure 135L:
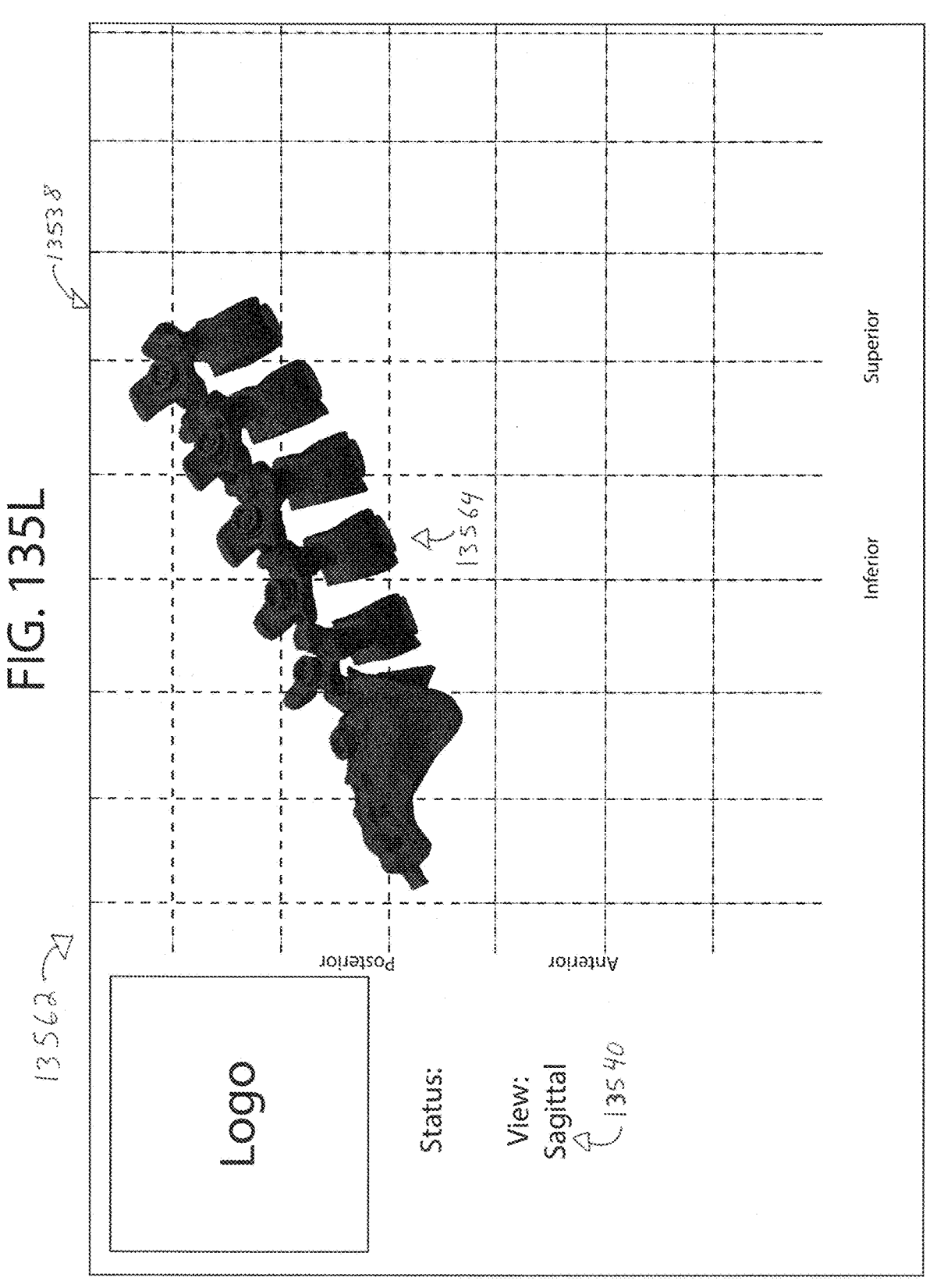

FIGS. 135J-135L illustrate a display interface for re-registering the patient's sacrum and vertebrae after manipulating their positions in 3D space as described previously in relation to FIGS. 135A-135I in accordance with some embodiments of the invention.

Figure 136A:
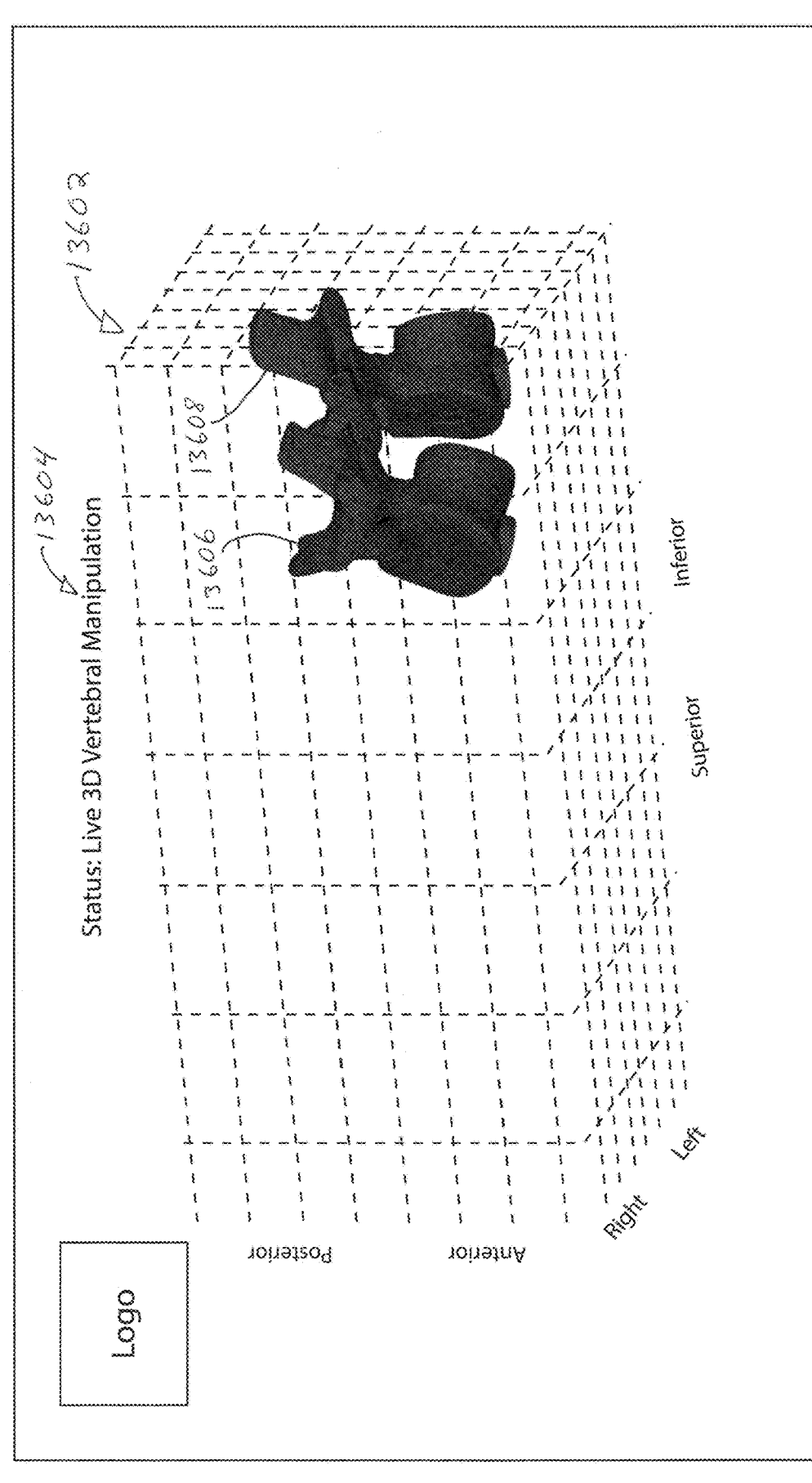
Figure 136B:
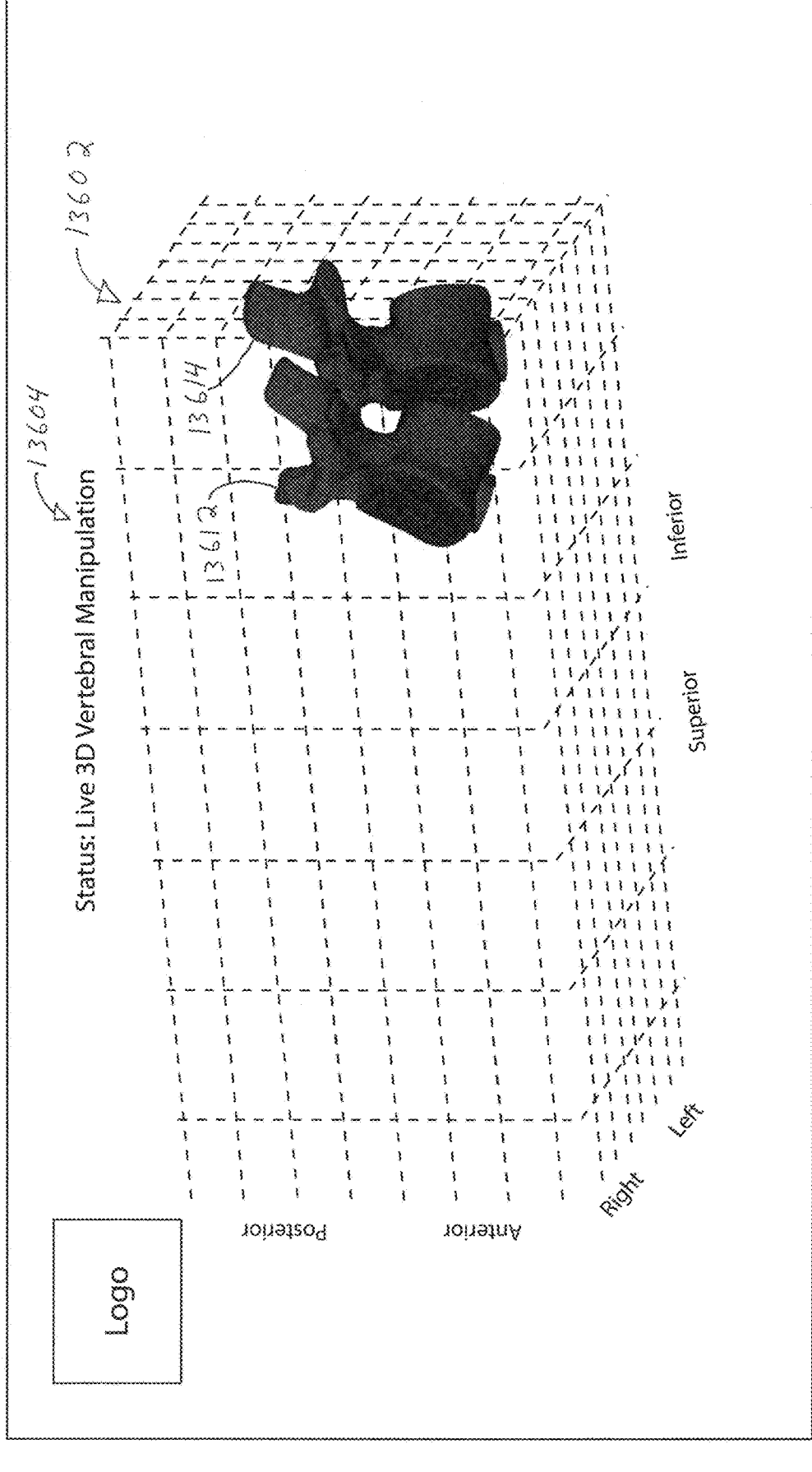

FIGS. 136A-136B illustrate a display interface for viewing the 3D meshworks of vertebrae registered via the flexibility assessment device in a non-measuring and live-measuring state in accordance with some embodiments of the invention.

Figure 136C:
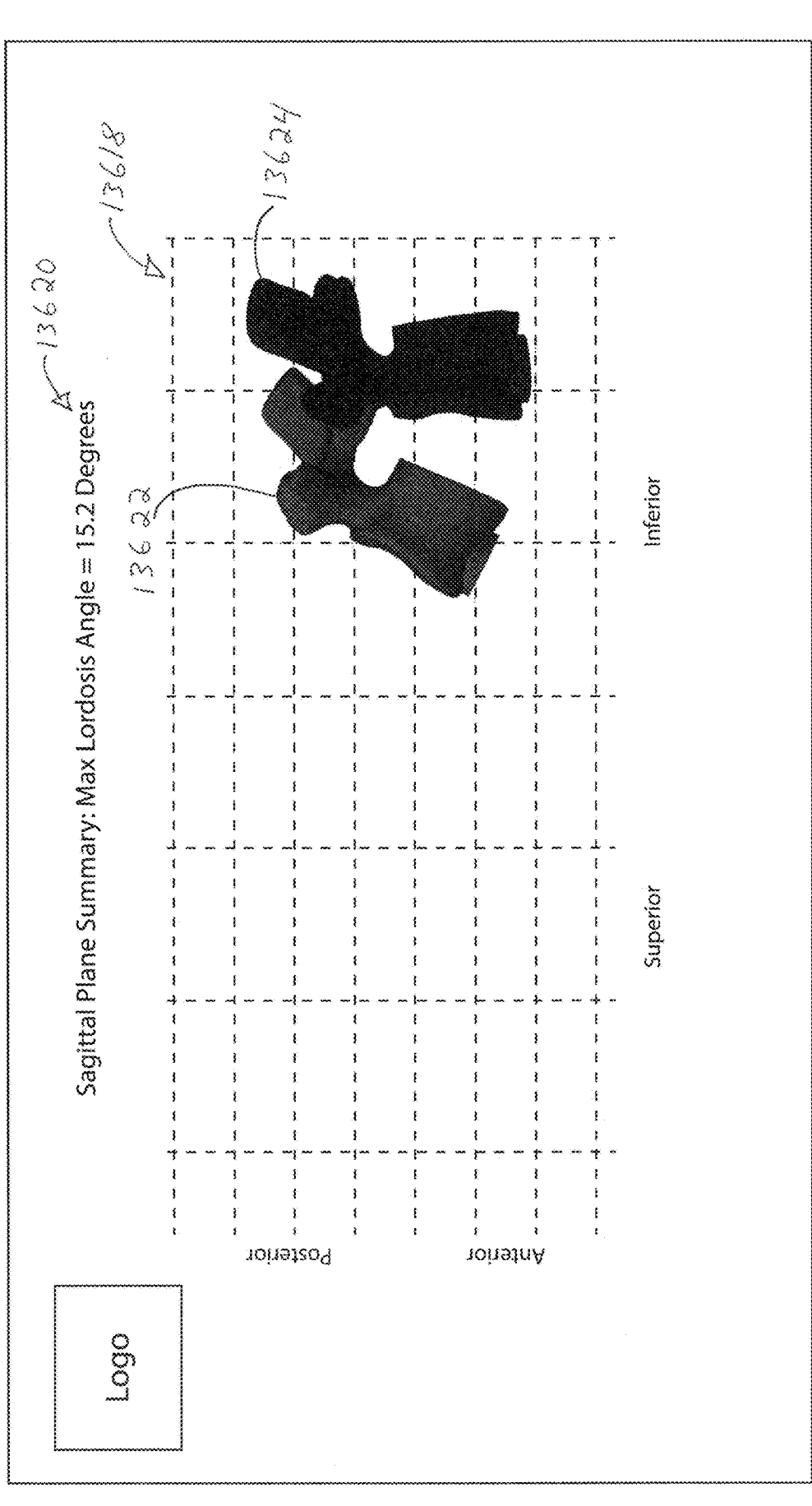
Figure 136D:
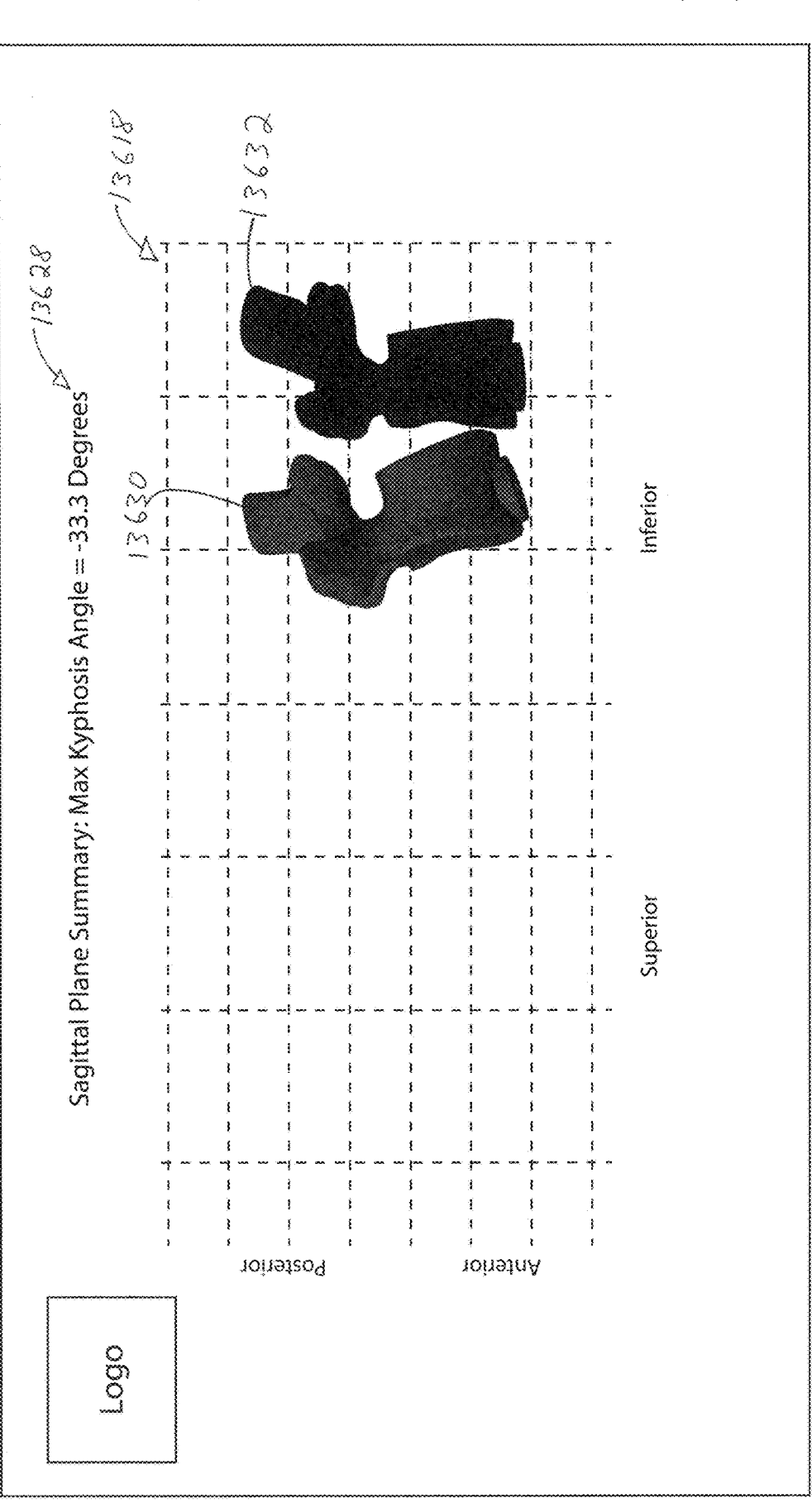

FIGS. 136C-136D illustrate a display interface for displaying the sagittal plane maximum lordosis and maximum kyphosis angles measured during the live manipulation of the vertebra via the flexibility assessment device as described previously in relation to FIGS. 136A-136B in accordance with some embodiments of the invention.

Figure 136E:
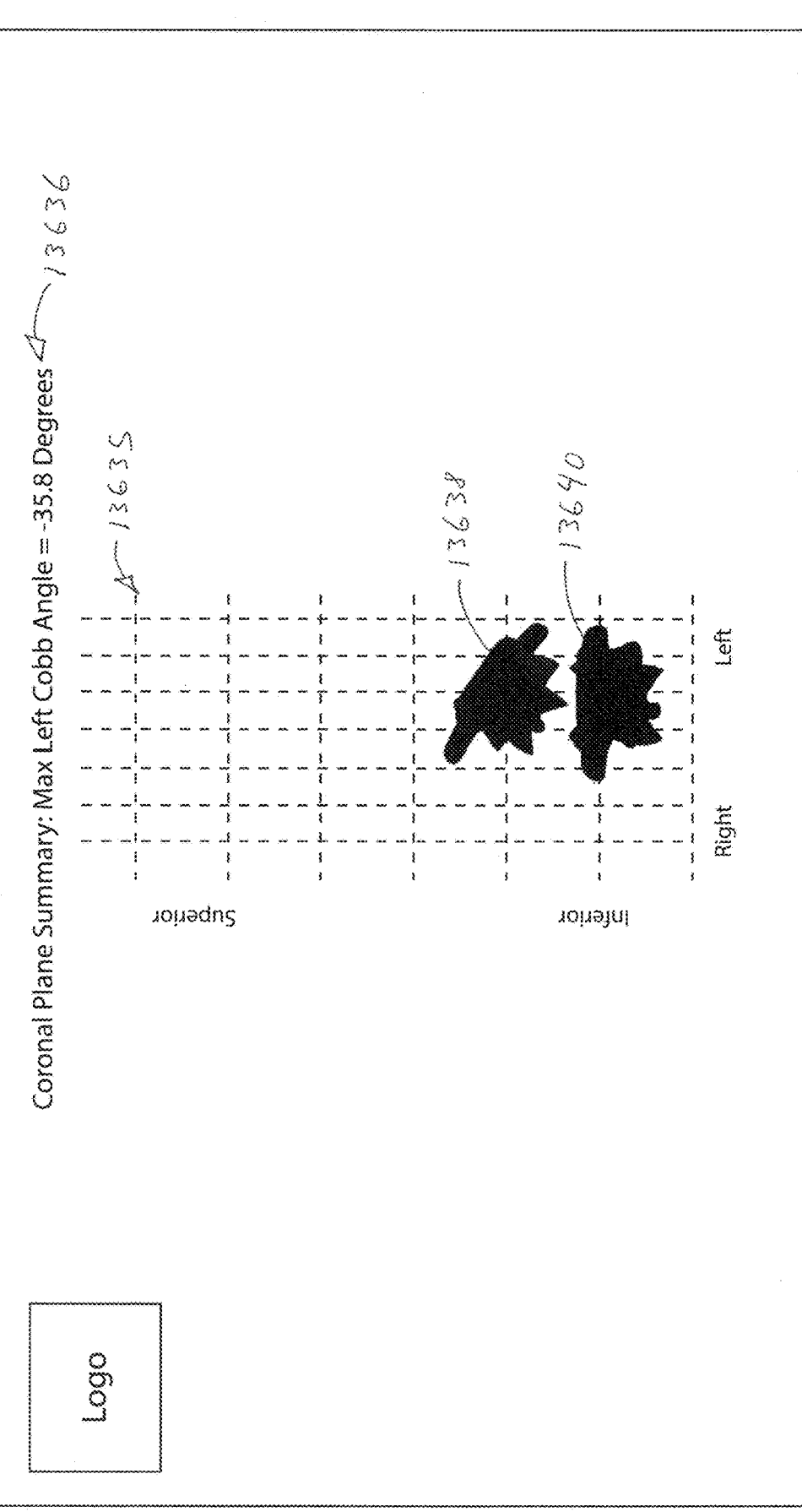
Figure 136F:
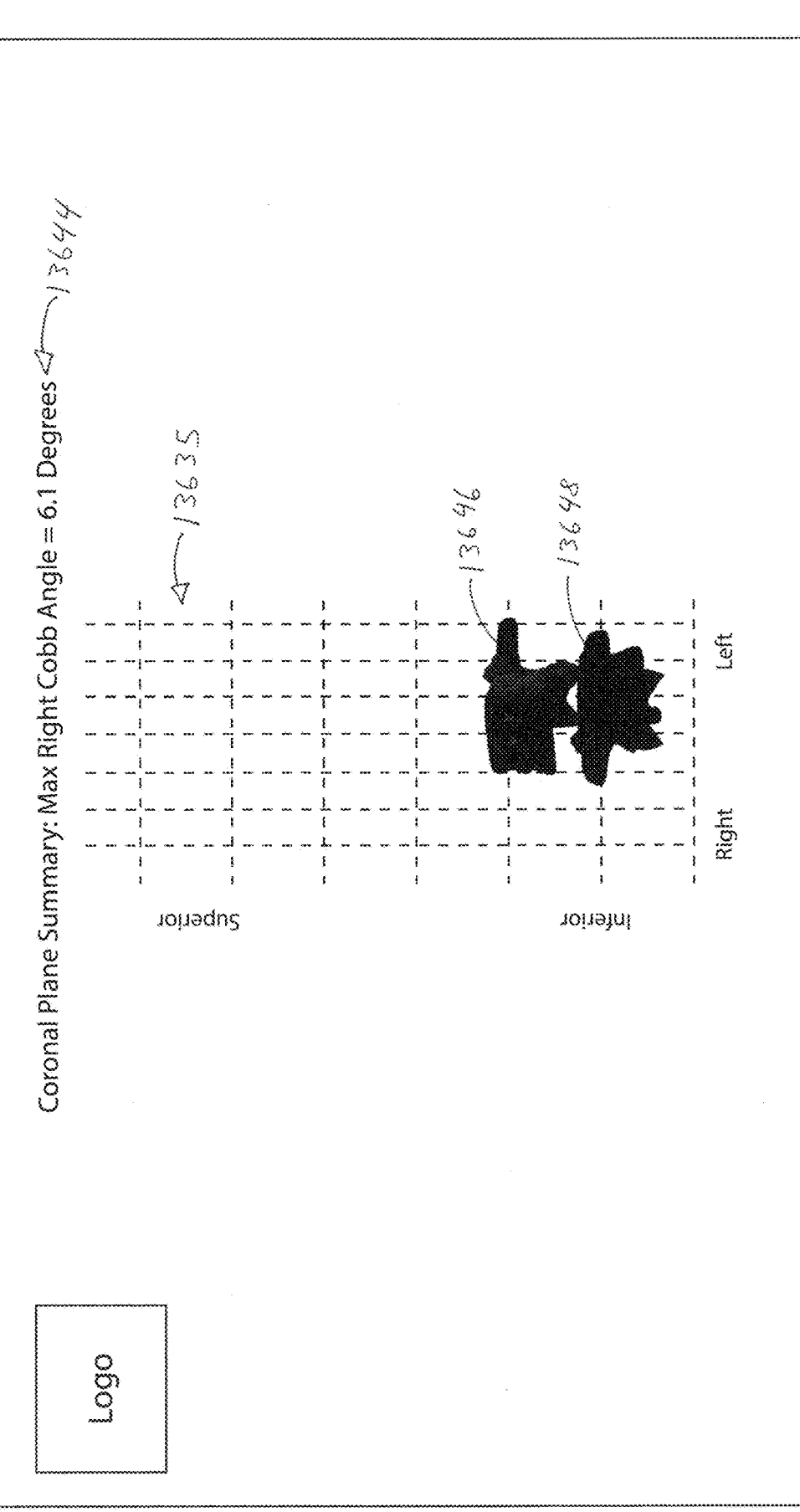

FIG. 136E-136F illustrate a display interface for displaying the coronal plane maximum left Cobb and maximum right Cobb angles measured during the live manipulation of the vertebra via the flexibility assessment device as described previously in relation to FIGS. 136A-136D in accordance with some embodiments of the invention.

Figure 136G:
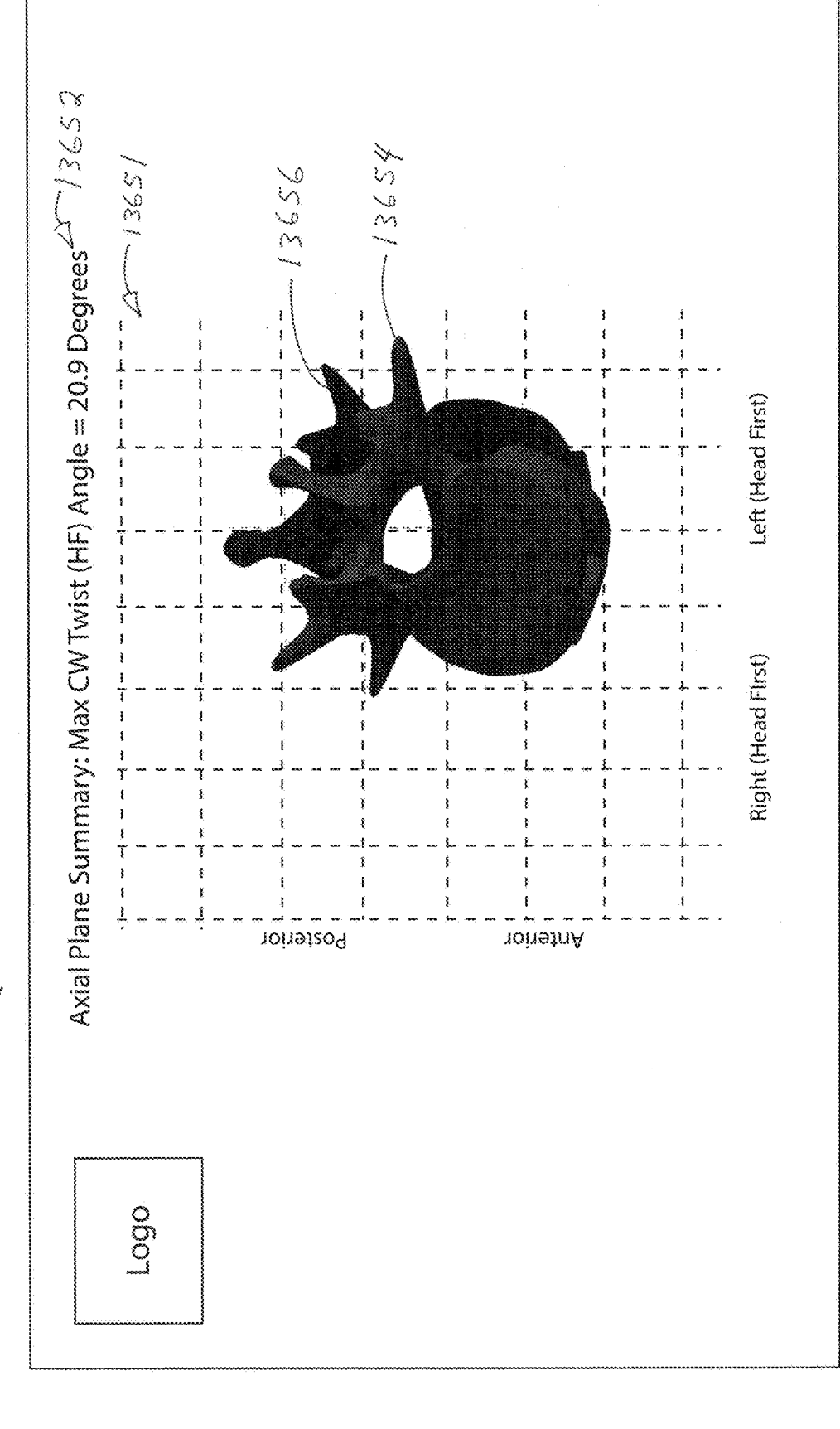
Figure 136H:
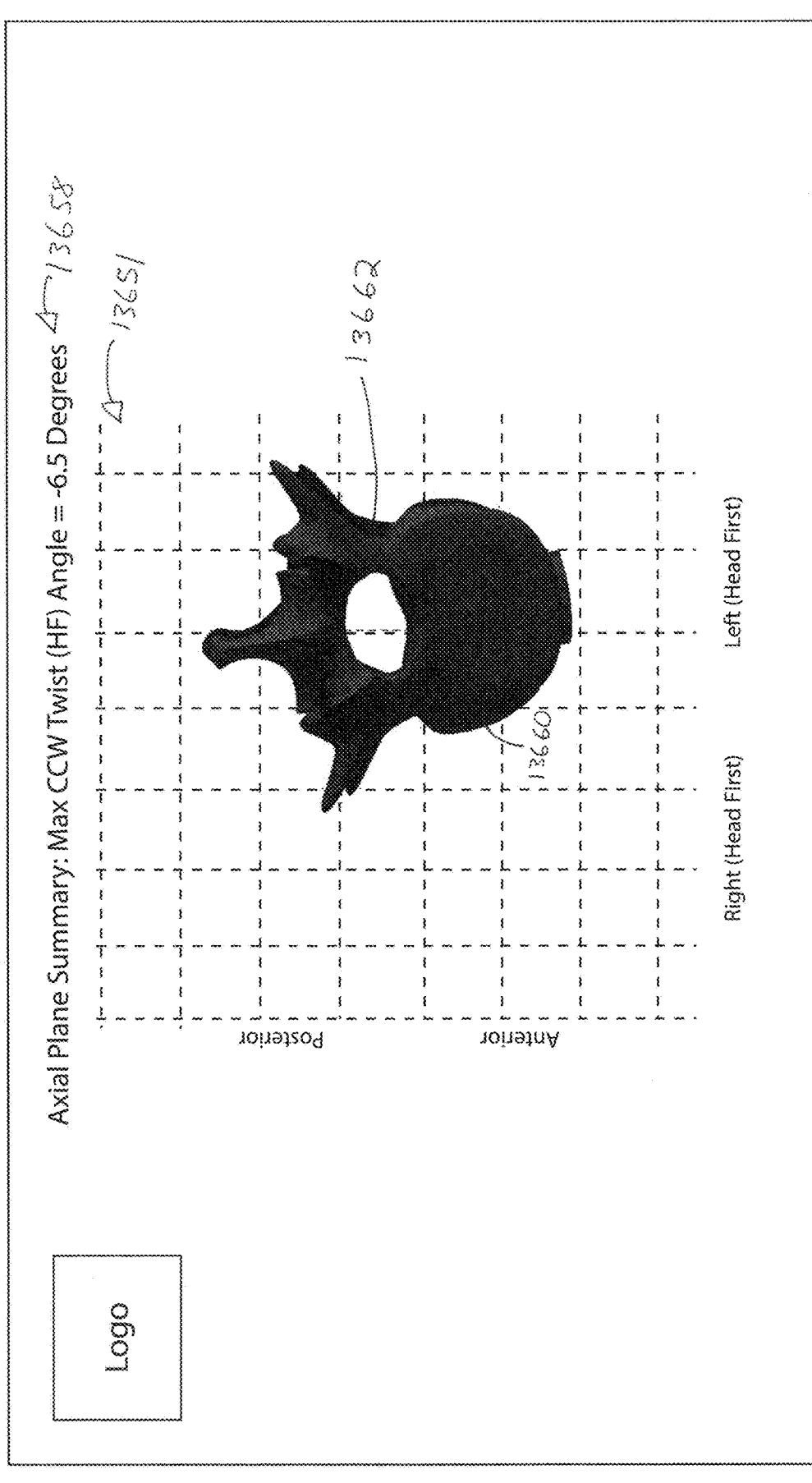

FIG. 136G-136H illustrate a display interface for displaying the axial plane maximum clockwise twist and maximum counter-clockwise twist angles measured during the live manipulation of the vertebra via the flexibility assessment device as described previously in relation to FIGS. 136A-136F in accordance with some embodiments of the invention.

Figure 136I:
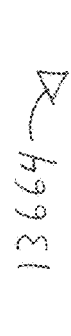

FIG. 136I illustrates a display interface for displaying the full replay of the live vertebrae manipulation via the flexibility assessment device as described previously in relation to FIGS. 136A-136H in accordance with some embodiments of the invention.

Figure 136J:
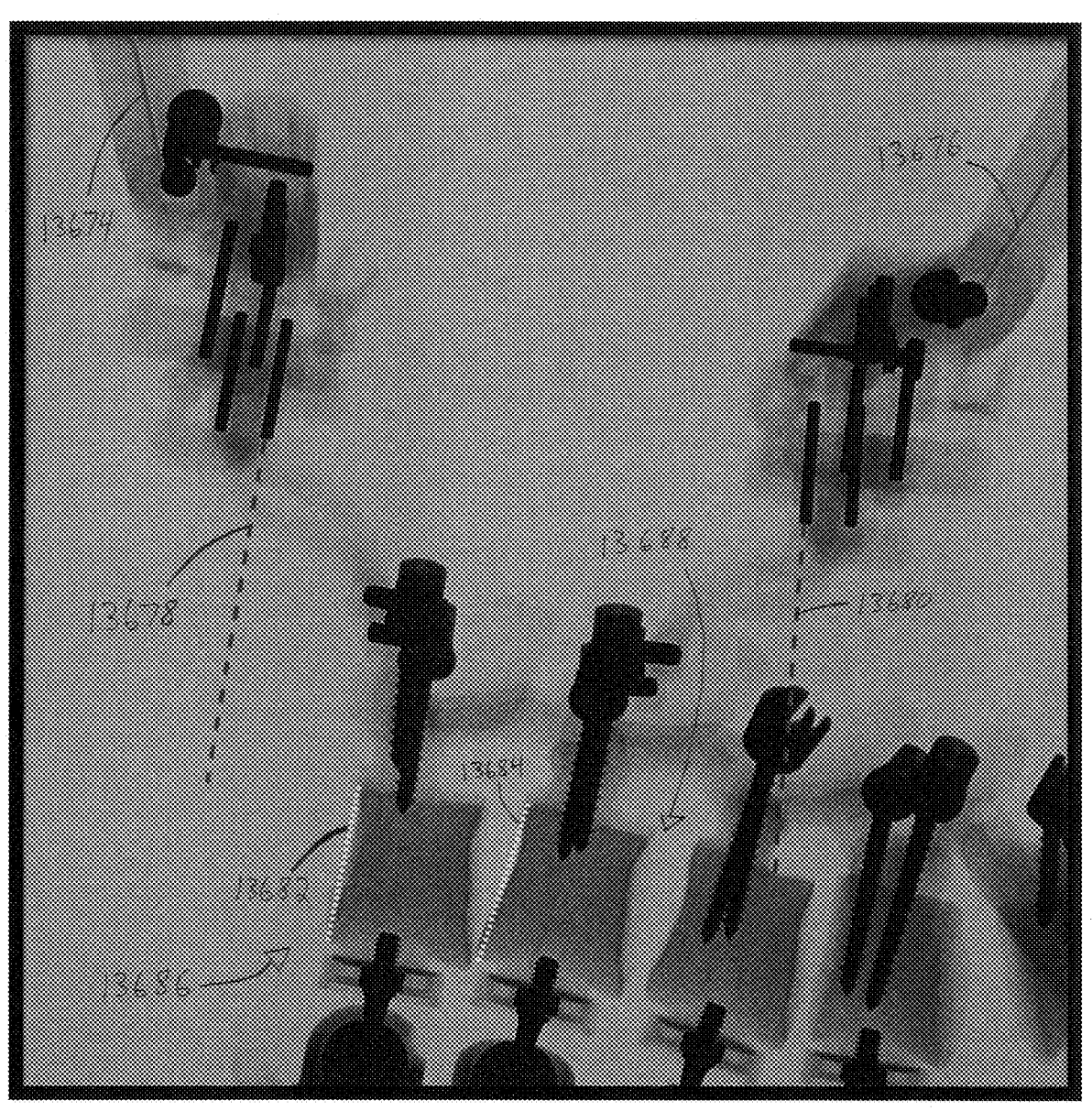
Figure 138C:
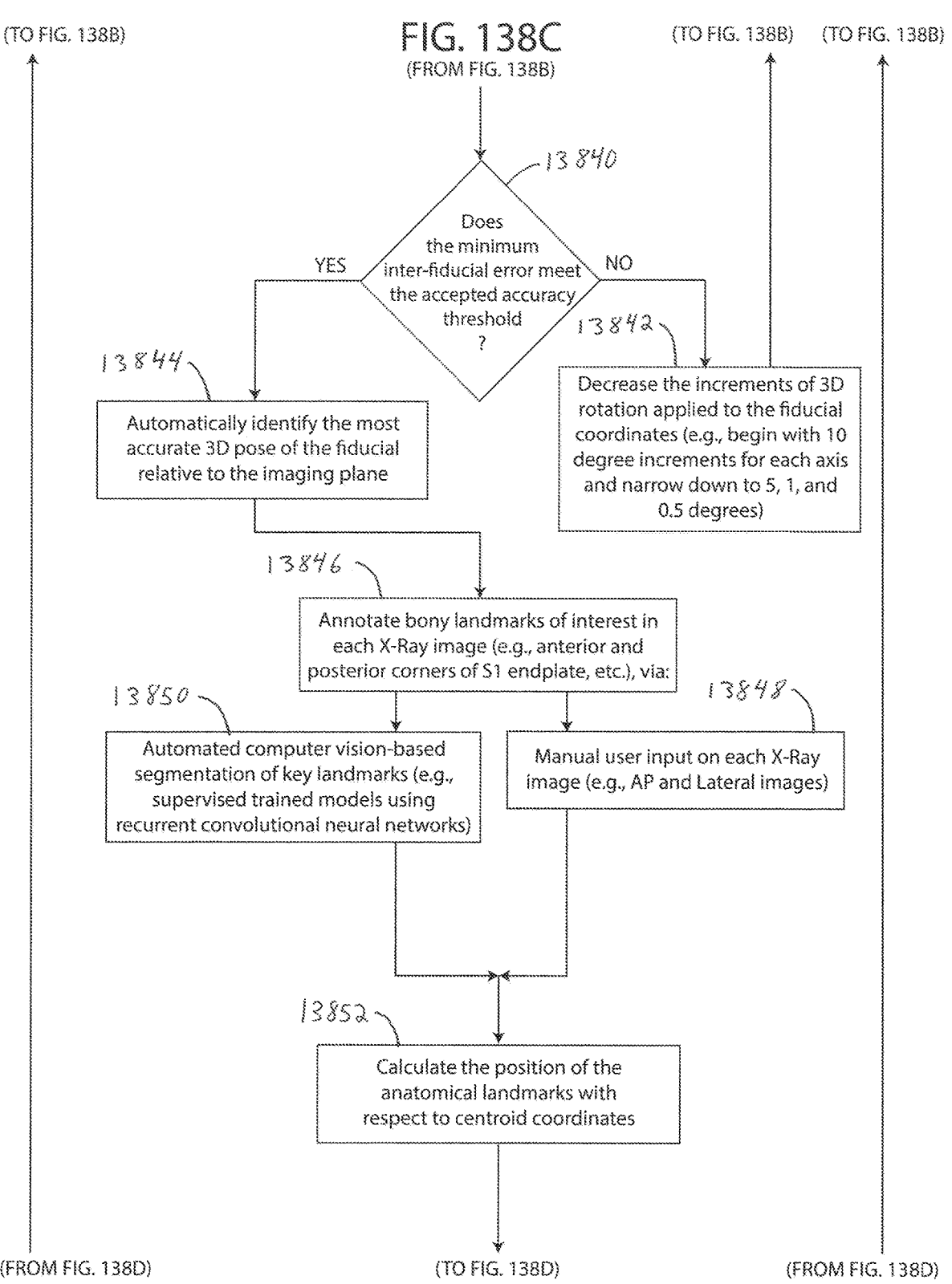

FIG. 136J illustrates an X-Ray-based initialization of the offset angle between the 3D-tracked handles of the flexibility assessment devices and their engaged vertebrae.

FIG. 137 illustrates a workflow for calculating the 3D midline of acquired 3D bilateral tracings of the laminae of the spine in accordance with some embodiments of the invention.

FIGS. 138A-138E illustrate a workflow for automatically detecting the 3D location and pose of vertebrae from two or more multi-planar X-Ray images of the bone-mounted fiducials implanted in the vertebrae in accordance with some embodiments of the invention.

FIGS. 139A-139B illustrate a workflow for registering the 3D location and pose of vertebrae via bone-mounted fiducials in accordance with some embodiments of the invention.

FIGS. 140A-140C illustrate a workflow for defining a trackpad display-controlling interface on any surface using a 3D-tracked probe in accordance with some embodiments of the invention.

FIGS. 141A-141D illustrate a workflow for making quantitative, 3D, intraoperative global spinal alignment assessments using skin-mounted fiducials, bone-mounted fiducials, and/or bilateral tracings of the spine in accordance with some embodiments of the invention.

Figure 142A:
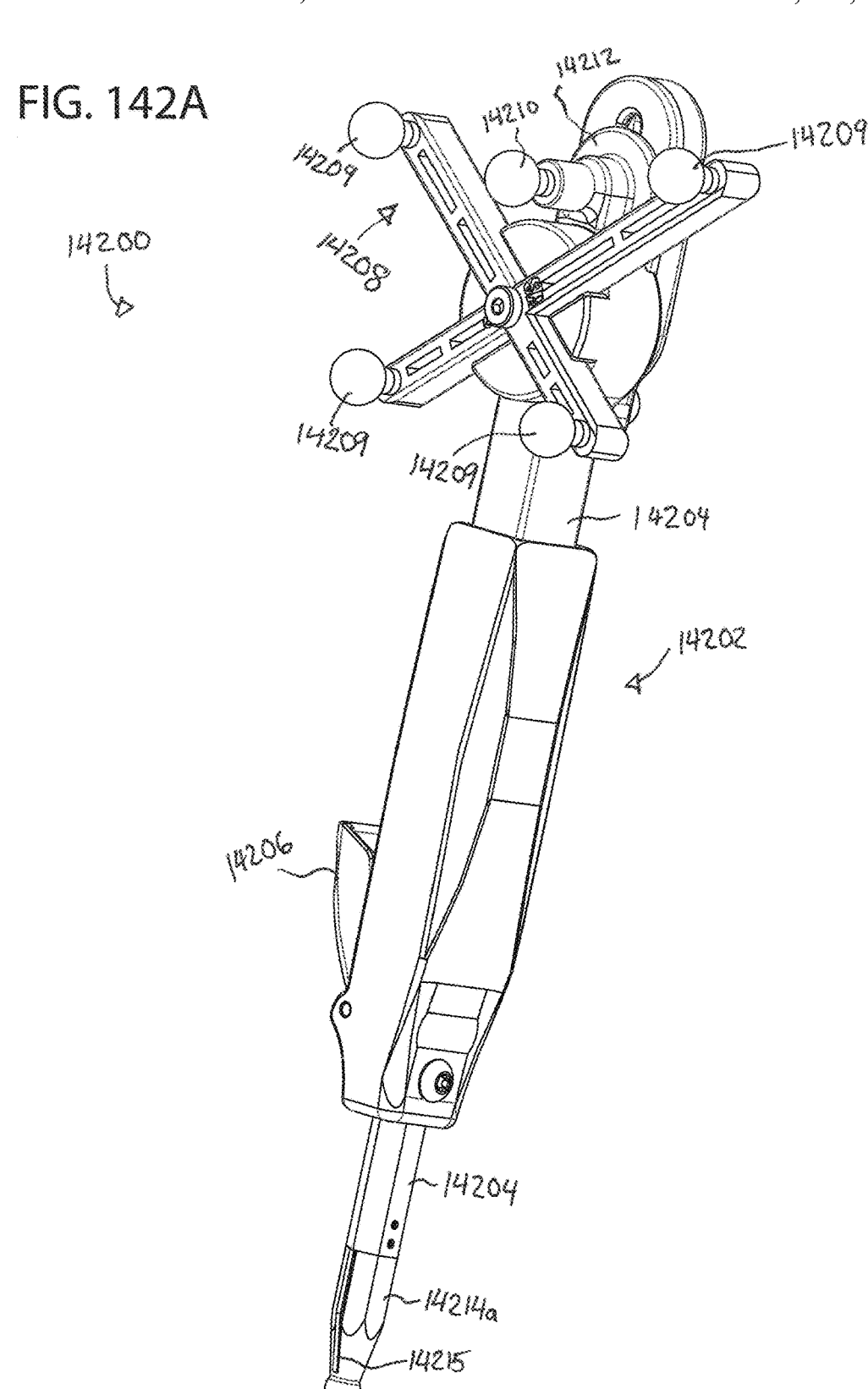

FIG. 142A illustrates a perspective view of a 3D-tracked tool with a tool ball-tip adapter not engaged with a tapered, semi-cylindrical external-mating bone-mounted fiducial and in an untriggered state in accordance with some embodiments of the invention.

Figures 142B, 142C:
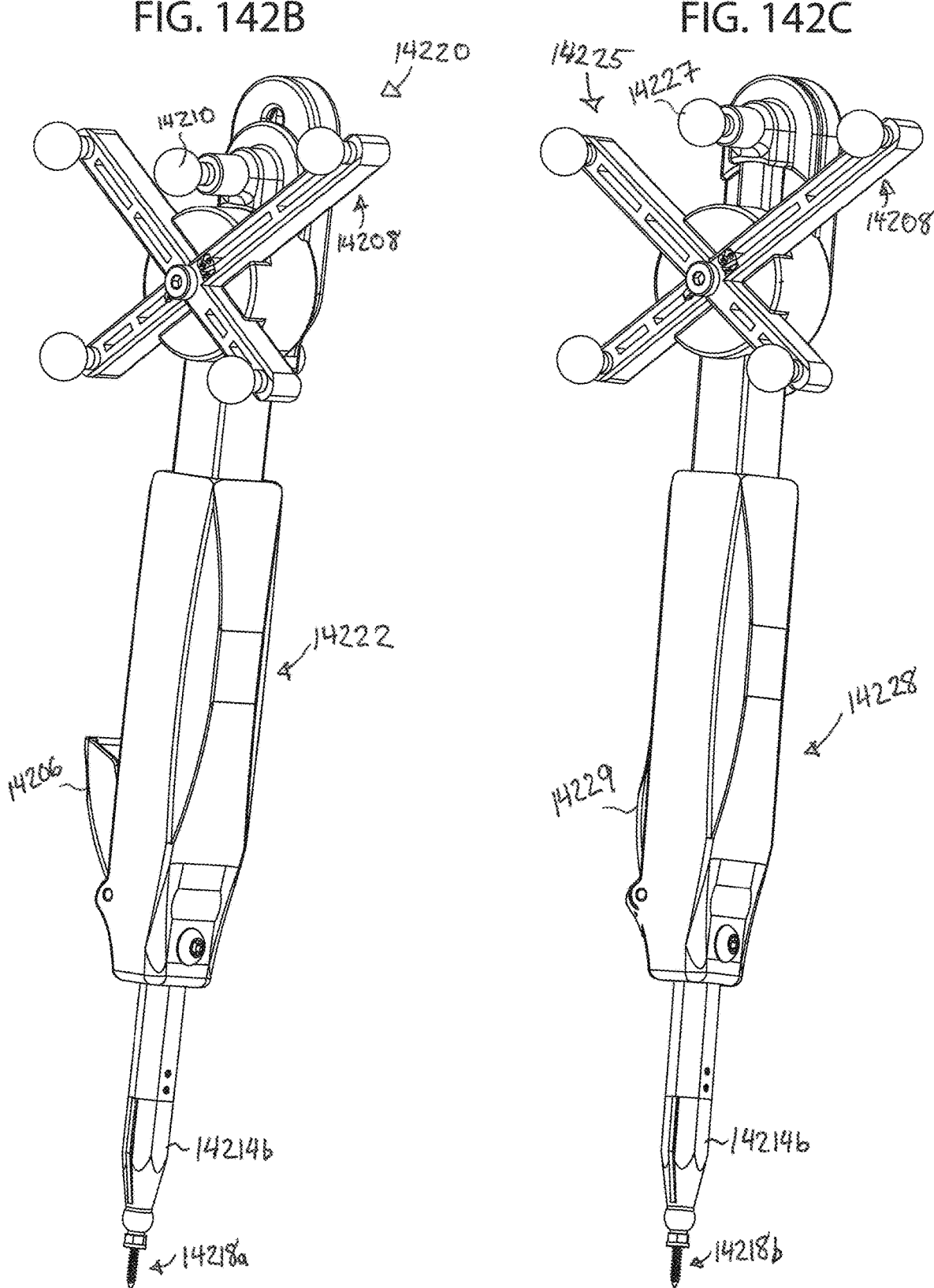

FIG. 142B illustrates a perspective view of a 3D-tracked probe engaged with a tapered, semi-cylindrical external-mating bone-mounted fiducial and in an untriggered state as described previously in relation to FIG. 142A in accordance with some embodiments of the invention.

FIG. 142C illustrates a perspective view of a 3D-tracked probe engaged with a tapered, semi-cylindrical external-mating bone-mounted fiducial and in a triggered state as described previously in relation to FIGS. 142A-B in accordance with some embodiments of the invention.

Figures 142D, 142E, 142F:
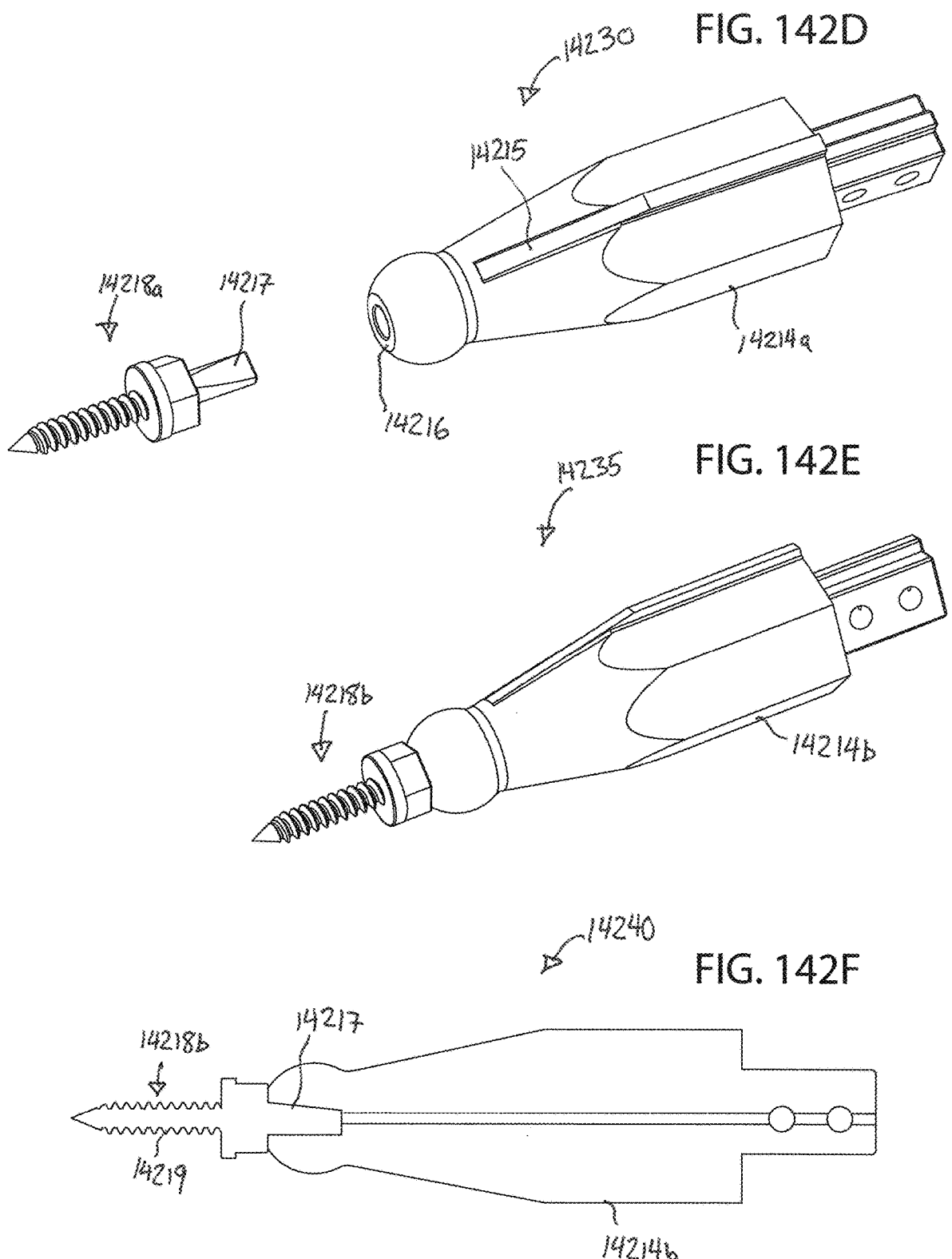

FIG. 142D illustrates a perspective view of a tapered, semi-cylindrical external-mating bone-bounted fiducial not engaged with an internal-mating tool tip adapter of a 3D-tracked probe as described previously in relation to FIGS. 142A-C in accordance with some embodiments of the invention.

FIG. 142E illustrates a perspective view of a tapered, semi-cylindrical external-mating bone-bounted fiducial engaged with an internal-mating tool tip adapter of a 3D-tracked probe as described previously in relation to FIGS. 142A-D in accordance with some embodiments of the invention.

FIG. 142F illustrates a side cross-sectional view of a tapered, semi-cylindrical external-mating bone-bounted fiducial engaged with an internal-mating tool tip adapter of a 3D-tracked probe as described previously in relation to FIGS. 142A-E in accordance with some embodiments of the invention.

Figures 142G, 142H:
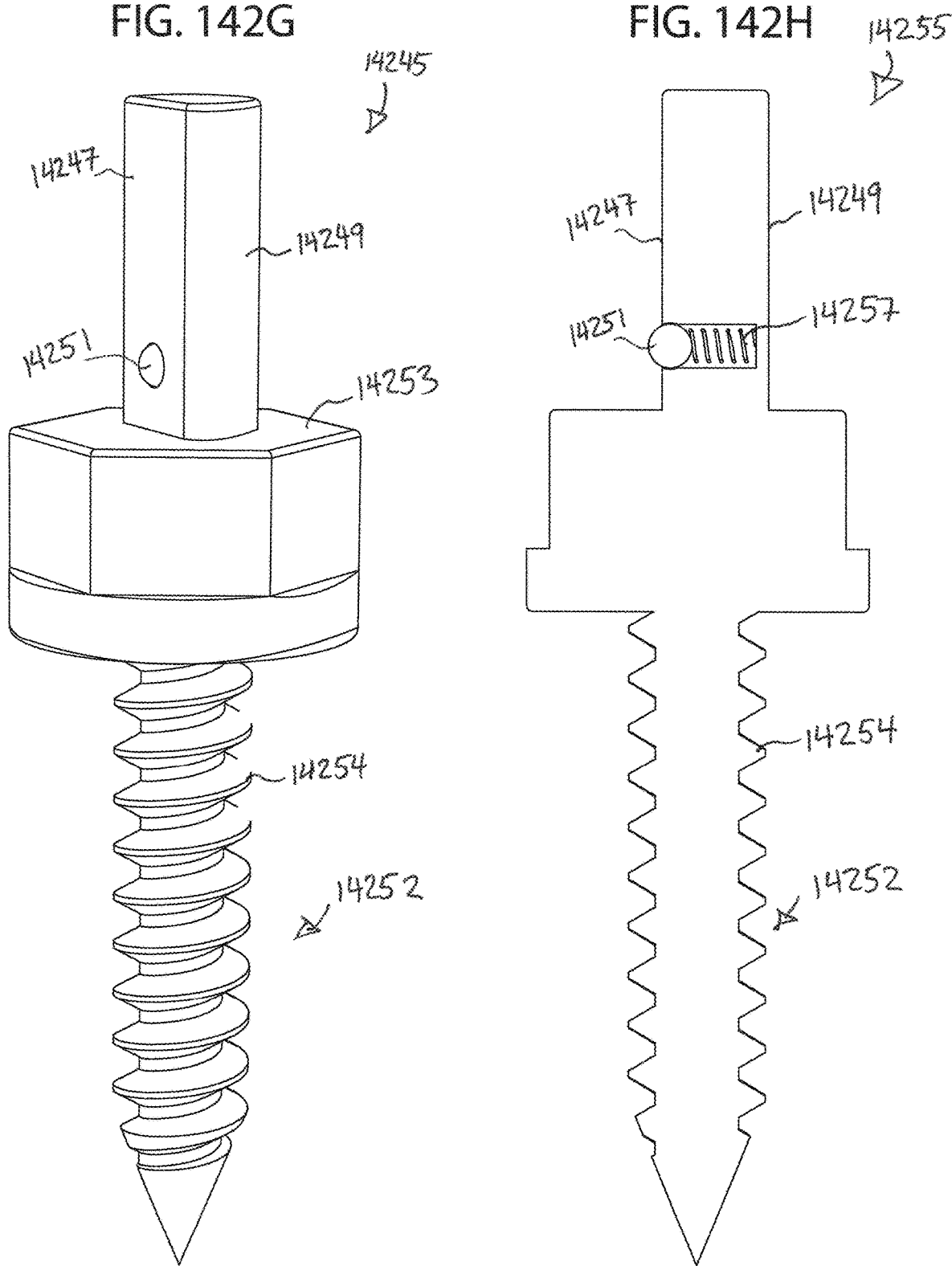

FIG. 142G illustrates a side view of an external-mating bone-mounted fiducial with a spring-loaded detent as described previously in relation to FIGS. 142A-F in accordance with some embodiments of the invention.

FIG. 142H illustrates a side cross-sectional view of an external-mating bone-mounted fiducial with a spring-loaded detent as described previously in relation to FIGS. 142A-G in accordance with some embodiments of the invention.

Figures 142I, 142J, 142K, 142L:
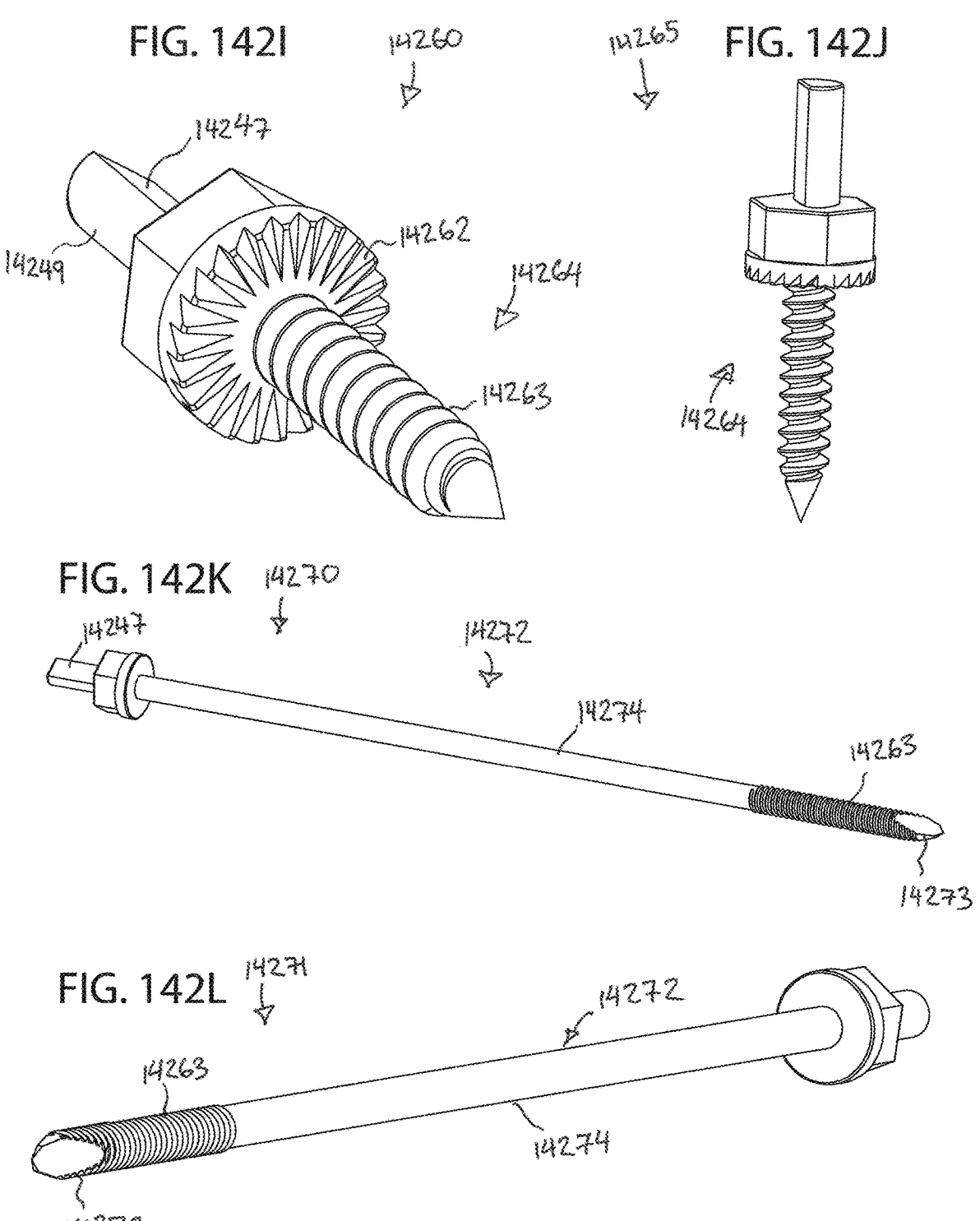

FIG. 142I illustrates a perspective view of an external-mating bone-mounted fiducial with a friction-inducing bone interface as described previously in relation to FIGS. 142A-H in accordance with some embodiments of the invention.

FIG. 142J illustrates a side view of an external-mating bone-mounted fiducial with a friction-inducing bone interface as described previously in relation to FIGS. 142A-I in accordance with some embodiments of the invention.

FIG. 142K illustrates a perspective view of an external-mating bone-mounted fiducial with extended shaft for percutaneous registration of anatomical landmarks of interest as described previously in relation to FIGS. 142A-J in accordance with some embodiments of the invention.

FIG. 142L illustrates a different perspective view of an external-mating bone-mounted fiducial with extended shaft for percutaneous registration of anatomical landmarks of interest as described previously in relation to FIGS. 142A-K in accordance with some embodiments of the invention.

Figure 143A:
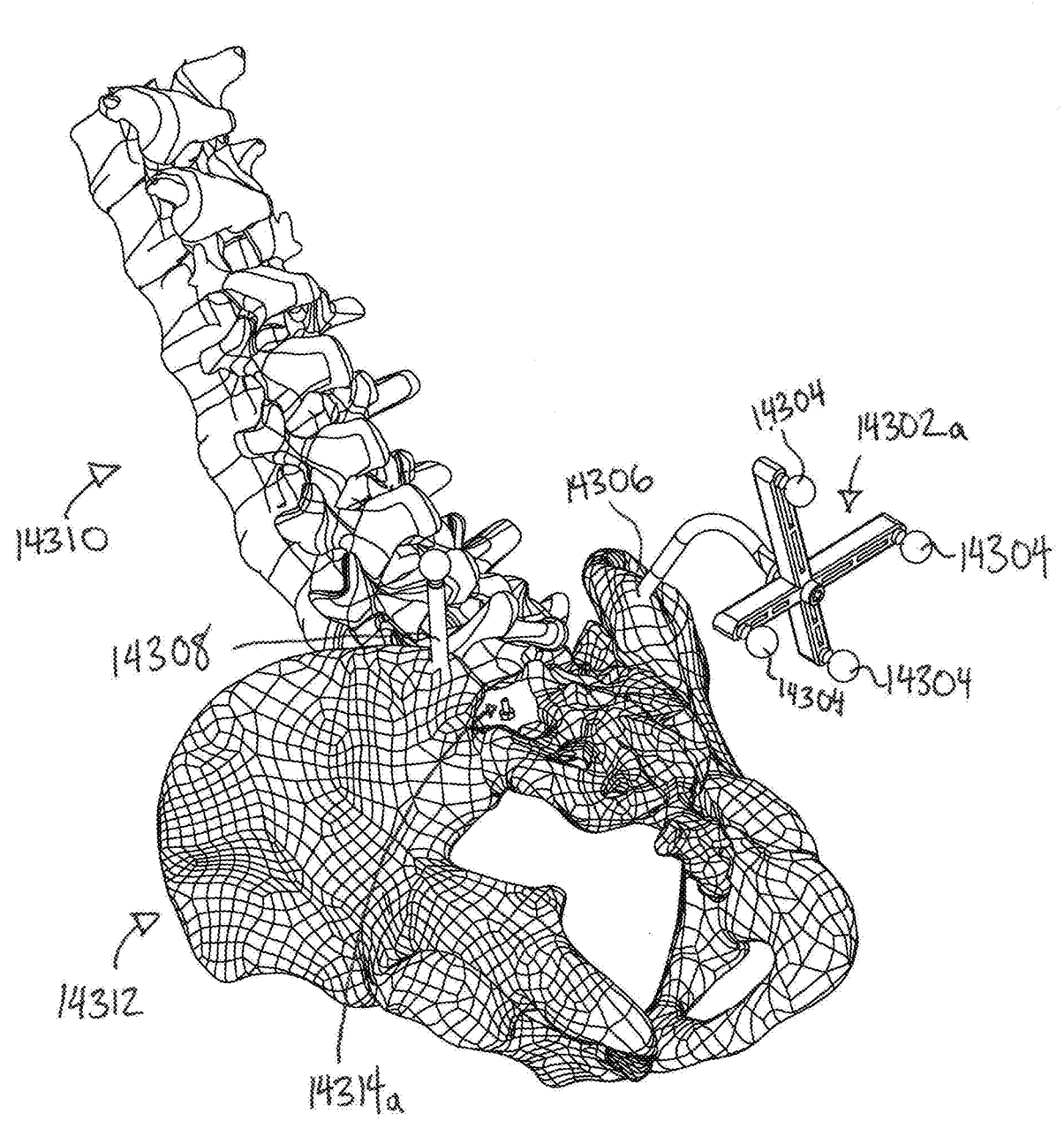

FIG. 143A illustrates a perspective view of the spine with an external-mating bone-mounted fiducial implanted into the sacrum and a frame-bump-monitoring, 3D-tracked marker post and 3D-tracked DRF implanted into the pelvis in accordance with some embodiments of the invention.

Figure 143B:
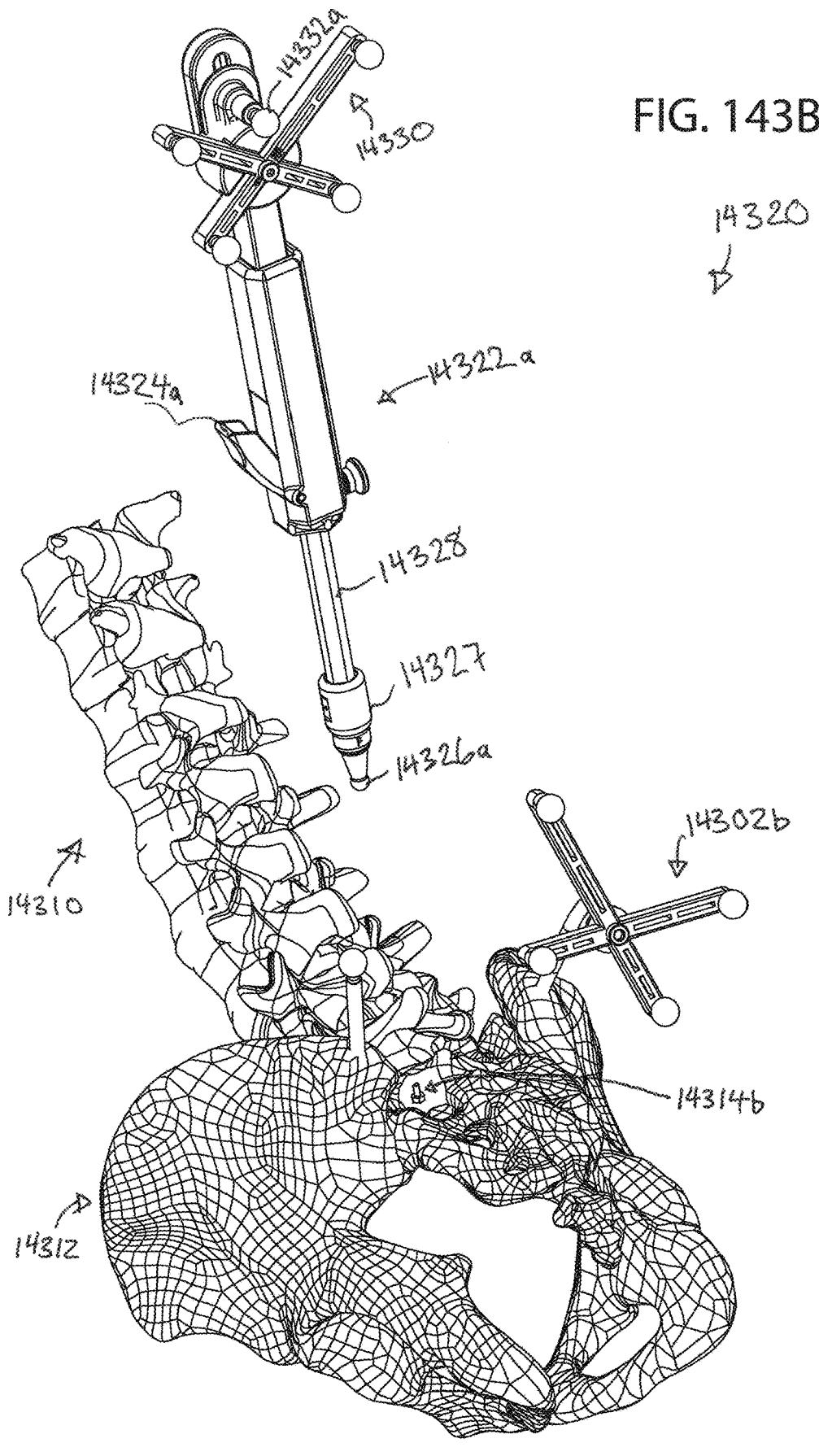

FIG. 143B illustrates a perspective view of a 3D-tracked tool not engaged with an external-mating bone-mounted fiducial implanted into the sacrum and in an untriggered state, along with a frame-bump-monitoring, 3D-tracked marker post and 3D-tracked DRF implanted into the pelvis, as described previously in relation to FIG. 143A in accordance with some embodiments of the invention.

Figure 143C:
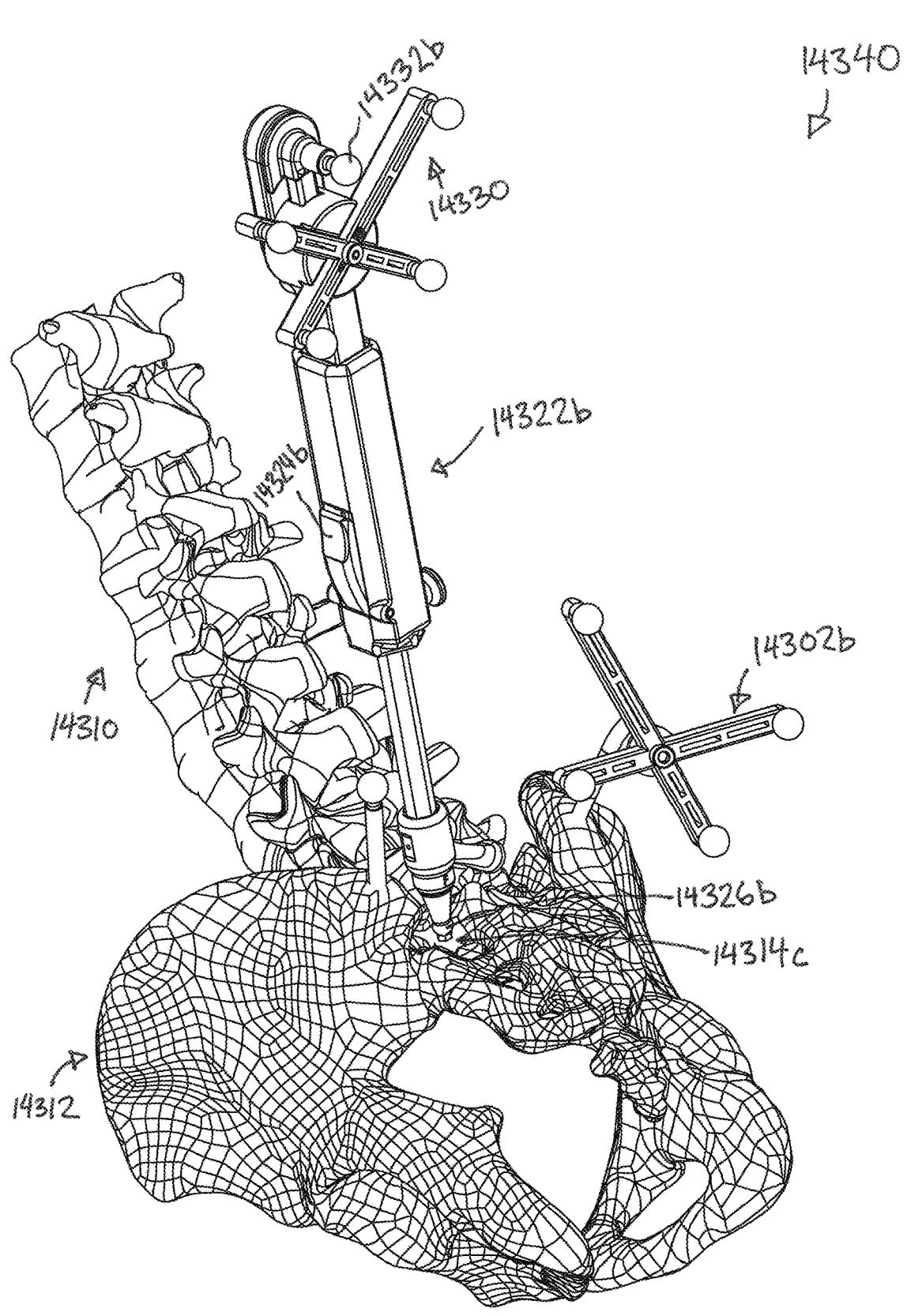

FIG. 143C illustrates a perspective view of a 3D-tracked tool engaged with an external-mating bone-mounted fiducial implanted into the sacrum and in a triggered state, along with a 3D-tracked iliac screw and 3D-tracked DRF implanted into the pelvis, as described previously in relation to FIGS. 143A-B in accordance with some embodiments of the invention.

FIG. 144A illustrates a perspective view of an internal-mating bone-mounted fiducial X-Ray adapter that has a cam-lock mechanism with an undepressed cam-lever. The adapter is not engaged with an external-mating bone-mounted fiducial in accordance with some embodiments of the invention.

Figures 144B, 144C, 144D:
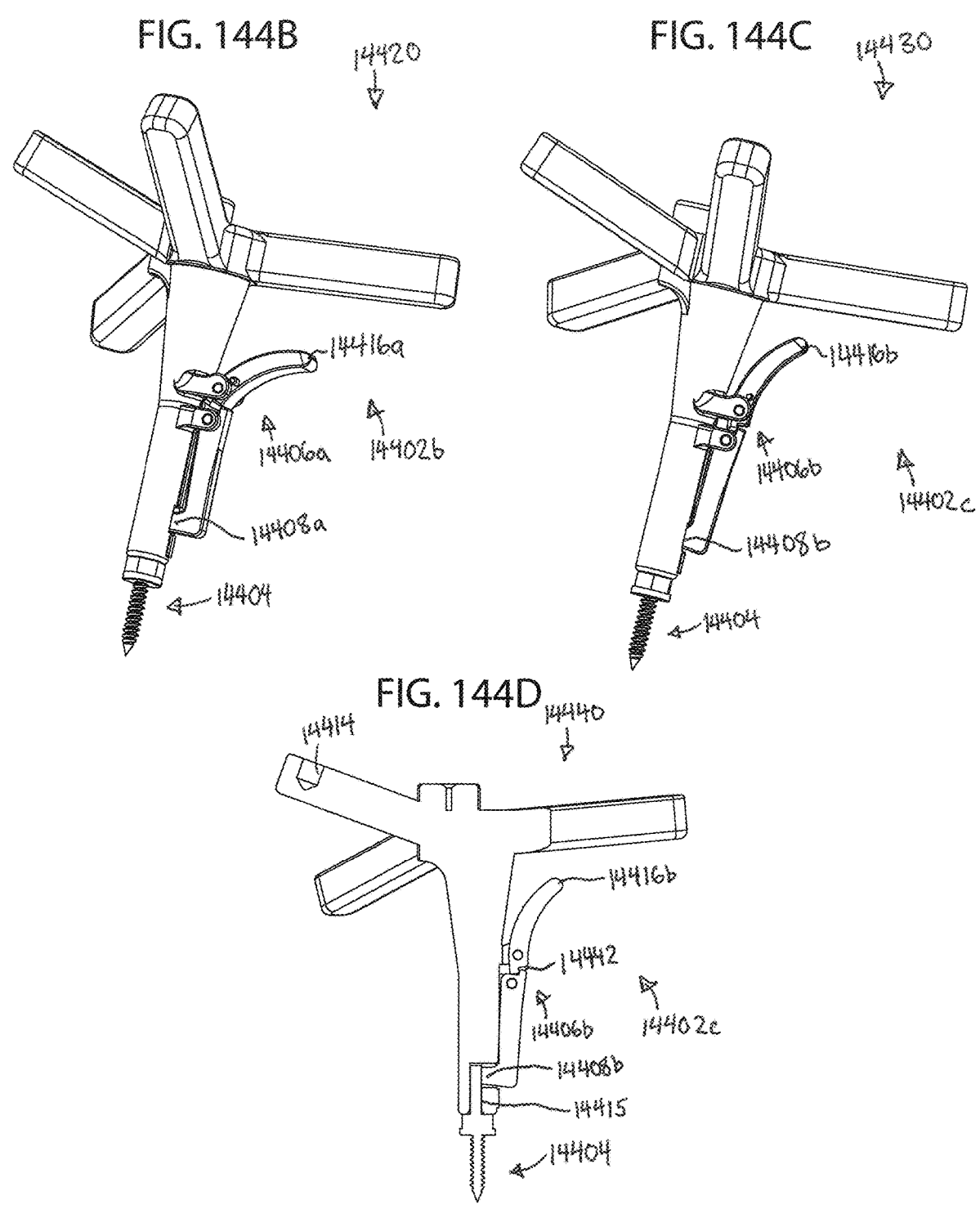

FIG. 144B illustrates a perspective view of an internal-mating bone-mounted fiducial X-Ray adapter that has a cam-lock mechanism with an undepressed cam-lever. The adapter is engaged with an external-mating bone-mounted fiducial as described previously in relation to FIG. 144A in accordance with some embodiments of the invention.

FIG. 144C illustrates a different perspective view of an internal-mating bone-mounted fiducial X-Ray adapter that has a cam-lock mechanism and depressed cam-lever. The adapter is engaged with an external-mating bone-mounted fiducial as described previously in relation to FIGS. 144A-B in accordance with some embodiments of the invention.

FIG. 144D illustrates a side cross-sectional view of an internal-mating bone-mounted fiducial X-Ray adapter that has a cam-lock mechanism. The depressed cam-lever applies compression force to the flat interface of an external-mating bone-mounted fiducial to secure it in place, as described previously in relation to FIGS. 144A-C in accordance with some embodiments of the invention.

Figure 144E:
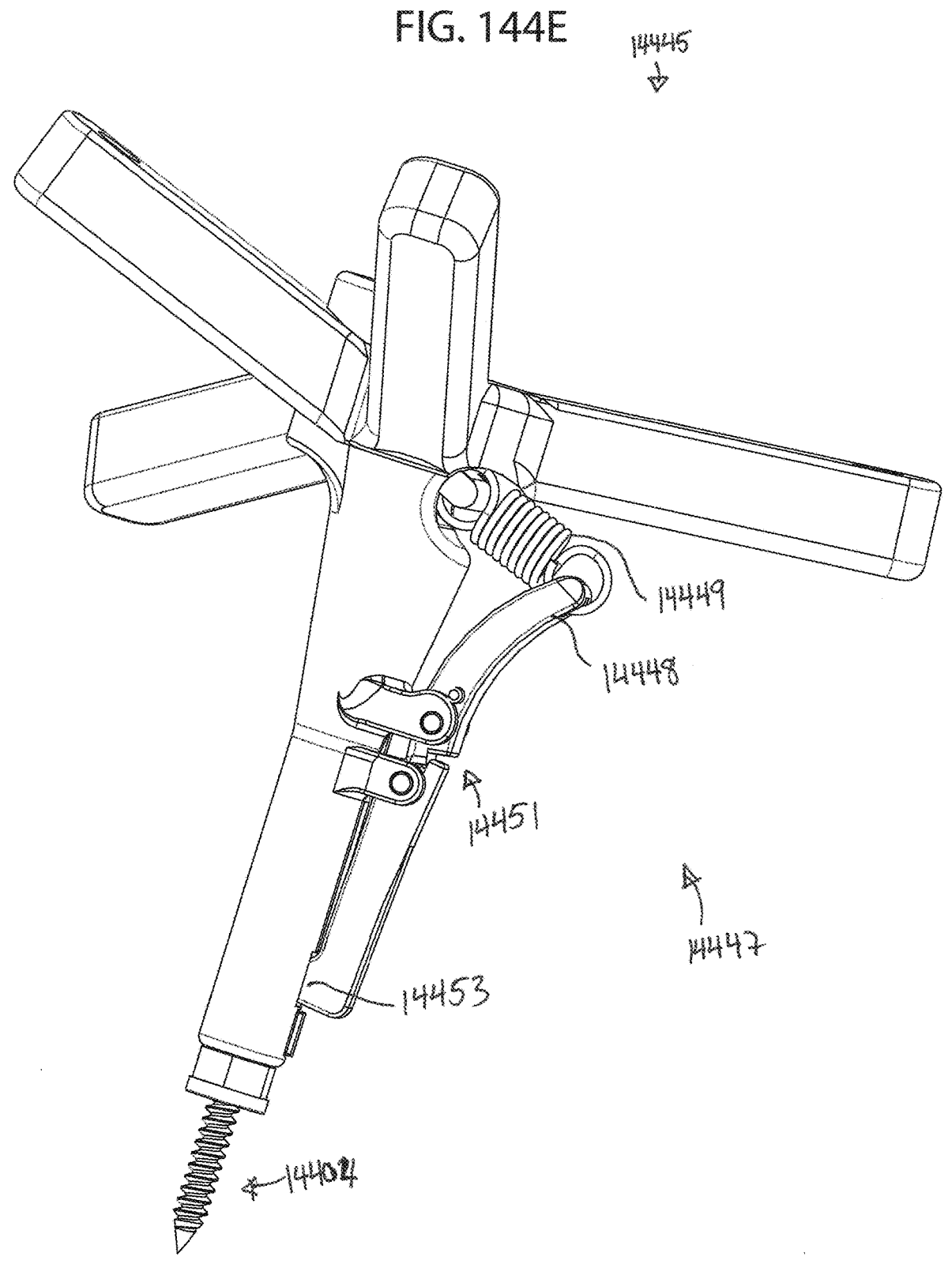

FIG. 144E illustrates a perspective view of an internal-mating bone-mounted fiducial X-Ray adapter that has a cam-lock mechanism. The cam-lever is depressed via a compression spring, which applies compression force to the flat interface of an external-mating bone-mounted fiducial to secure it in place, as described previously in relation to FIGS. 144A-D in accordance with some embodiments of the invention.

FIG. 144F illustrates a side cross-sectional view of an internal-mating bone-mounted fiducial X-Ray adapter with a spring-loaded mating mechanism, not engaged with an external-mating bone-mounted fiducial as described previously in relation to FIGS. 144A-E in accordance with some embodiments of the invention.

Figure 144G:
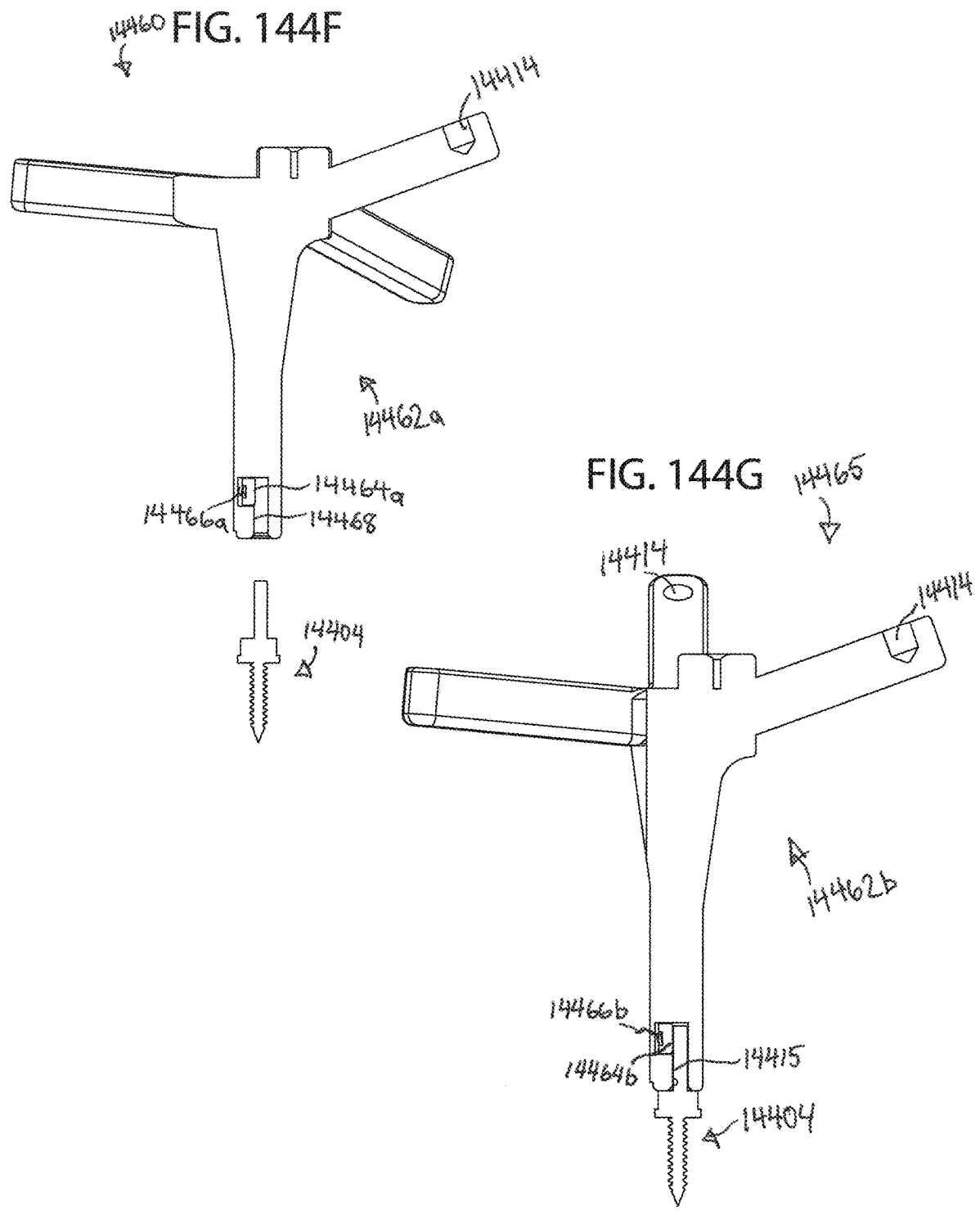

FIG. 144G illustrates a side cross-sectional view of an internal-mating bone-mounted fiducial X-Ray adapter with a spring-loaded mating mechanism, engaged with an external-mating bone-mounted fiducial as described previously in relation to FIGS. 144A-F in accordance with some embodiments of the invention.

Figures 144H, 144I, 144J:
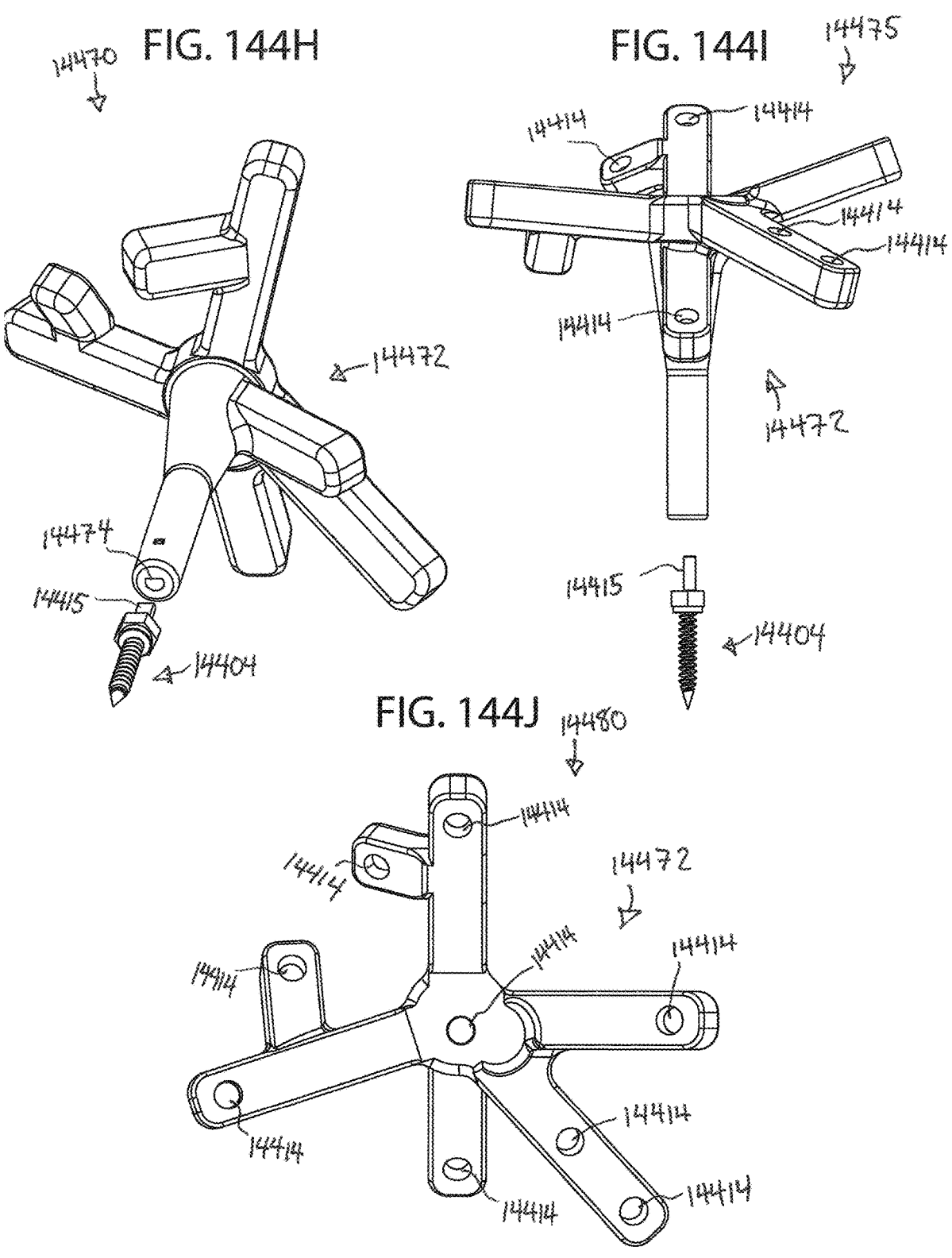

FIG. 144H illustrates a bottom perspective view of an internal-mating bone-mounted fiducial X-Ray adapter embedded with a larger array of asymmetrically distributed radiopaque spheres, not engaged with an external-mating bone-mounted fiducial as described previously in relation to FIGS. 144A-G in accordance with some embodiments of the invention.

FIG. 144I illustrates a top perspective view of an internal-mating bone-mounted fiducial X-Ray adapter embedded with a larger array of asymmetrically distributed radiopaque spheres, not engaged with an external-mating bone-mounted fiducial as described previously in relation to FIGS. 144A-H in accordance with some embodiments of the invention.

FIG. 144J illustrates a top view of an internal-mating bone-mounted fiducial X-Ray adapter embedded with a larger array of asymmetrically distributed radiopaque spheres, as described previously in relation to FIGS. 144A-H in accordance with some embodiments of the invention.

Figures 145A, 145B, 145C:
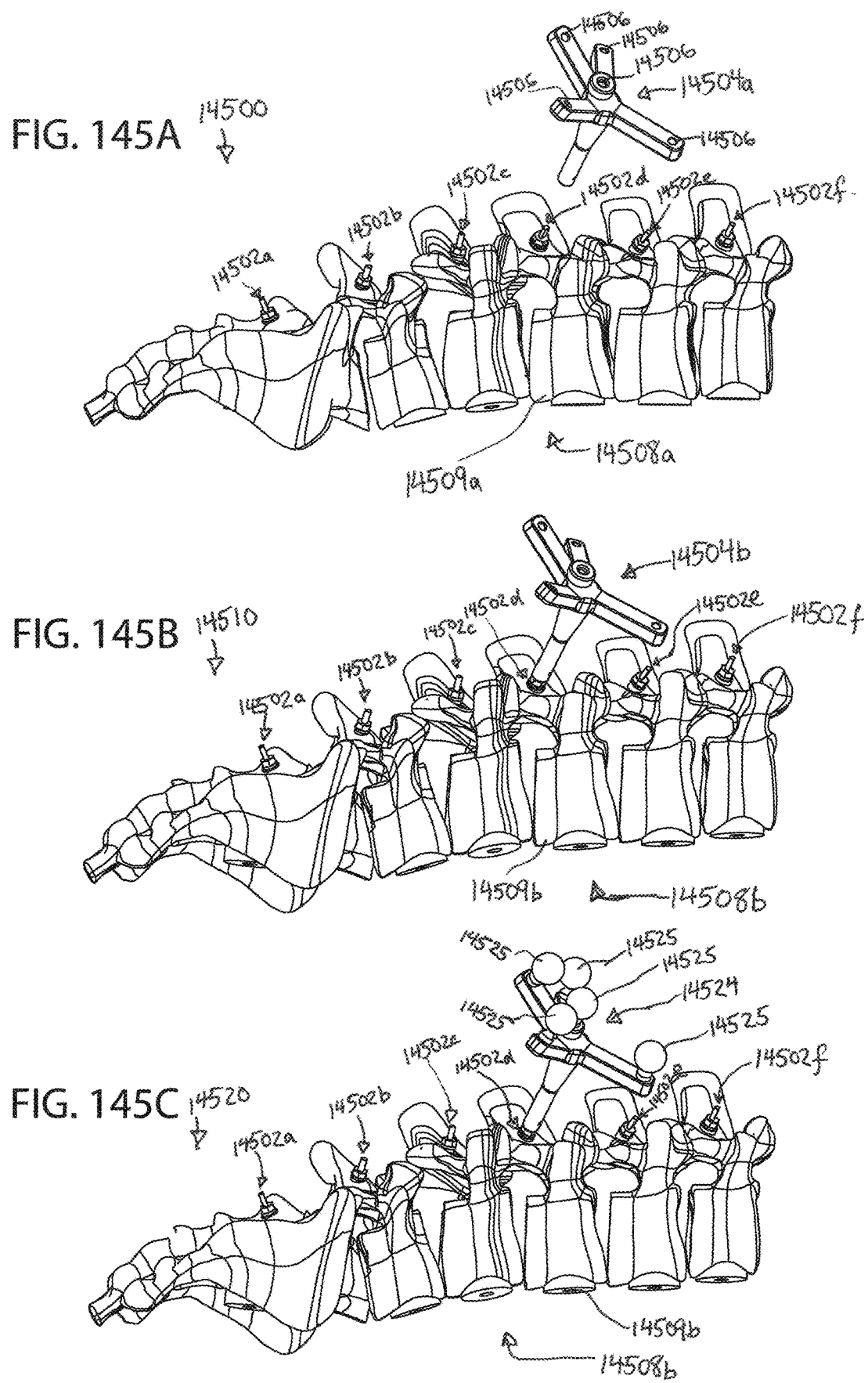

FIG. 145A illustrates perspective views of an internal-mating bone-mounted fiducial X-Ray adapter embedded with asymmetrically distributed radiopaque spheres not engaged with any of the external-mating bone-mounted fiducials implanted into the sacrum and multiple laminae of the spine in accordance with some embodiments of the invention.

FIG. 145B illustrates perspective views of an internal-mating bone-mounted fiducial X-Ray adapter embedded with asymmetrically distributed radiopaque spheres engaged with one of the external-mating bone-mounted fiducials implanted into the sacrum and multiple laminae of the spine as described previously in relation to FIG. 145A in accordance with some embodiments of the invention.

FIG. 145C illustrates perspective views of an internal-mating bone-mounted fiducial X-Ray adapter embedded with asymmetrically distributed radiopaque spheres and equipped with 3D-tracked markers, engaged with one of the external-mating bone-mounted fiducials implanted into the sacrum and multiple laminae of the spine as described previously in relation to FIGS. 145A-B in accordance with some embodiments of the invention.

Figures 145D, 145E:
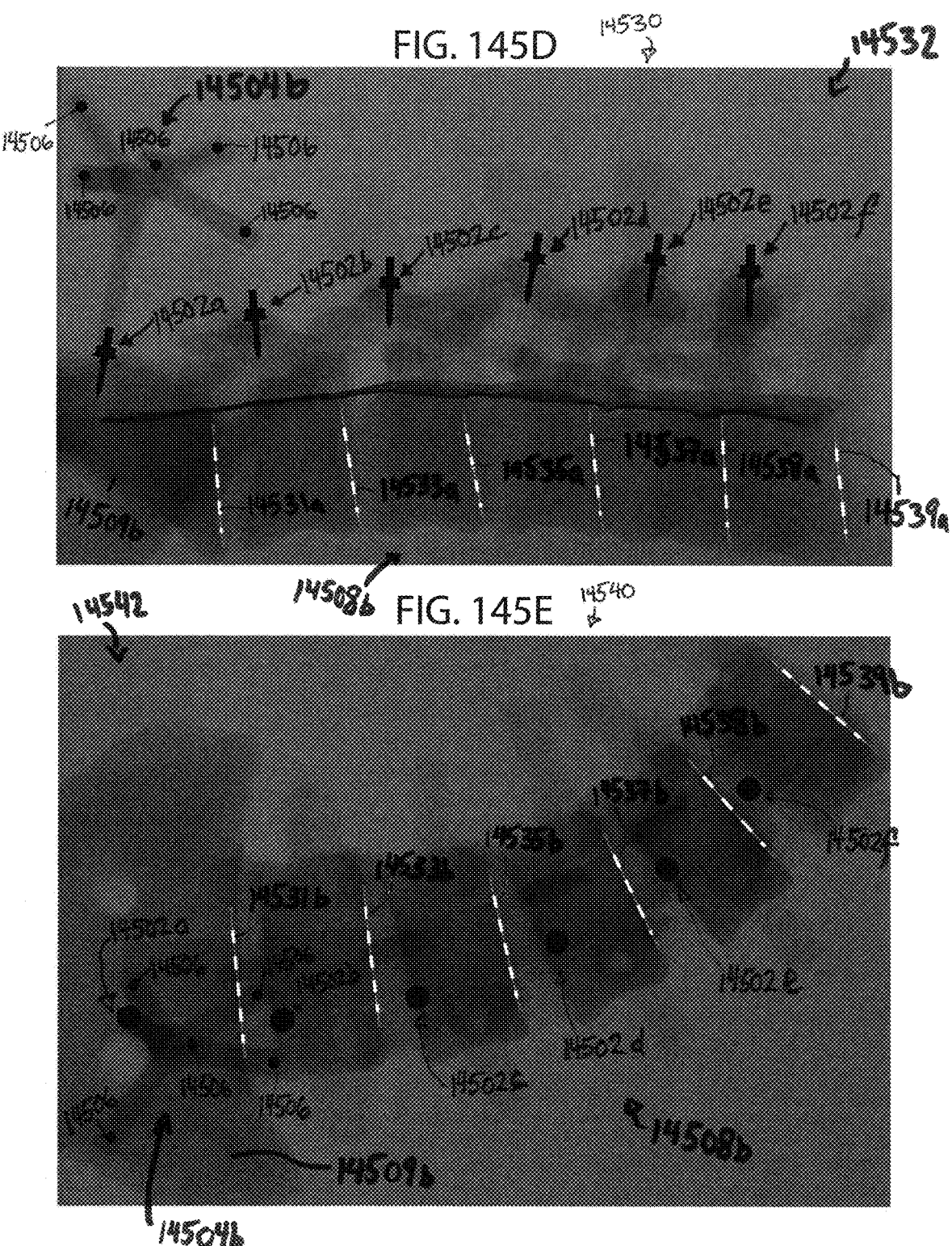

FIG. 145D illustrates an X-Ray image taken from the sagittal view of the spine with an internal-mating bone-mounted fiducial X-Ray adapter engaged with one of the external-mating bone-mounted fiducials implanted into the sacrum and multiple laminae, as well as line annotations of several vertebral endplates, as described previously in relation to FIGS. 145A-C in accordance with some embodiments of the invention.

FIG. 145E illustrates an X-Ray image taken from the coronal view of the spine with an internal-mating bone-mounted fiducial X-Ray adapter engaged with one of the external-mating bone-mounted fiducials implanted into the sacrum and multiple laminae, as well as line annotations of several vertebral endplates, as described previously in relation to FIGS. 145A-D in accordance with some embodiments of the invention.

Figure 146A:
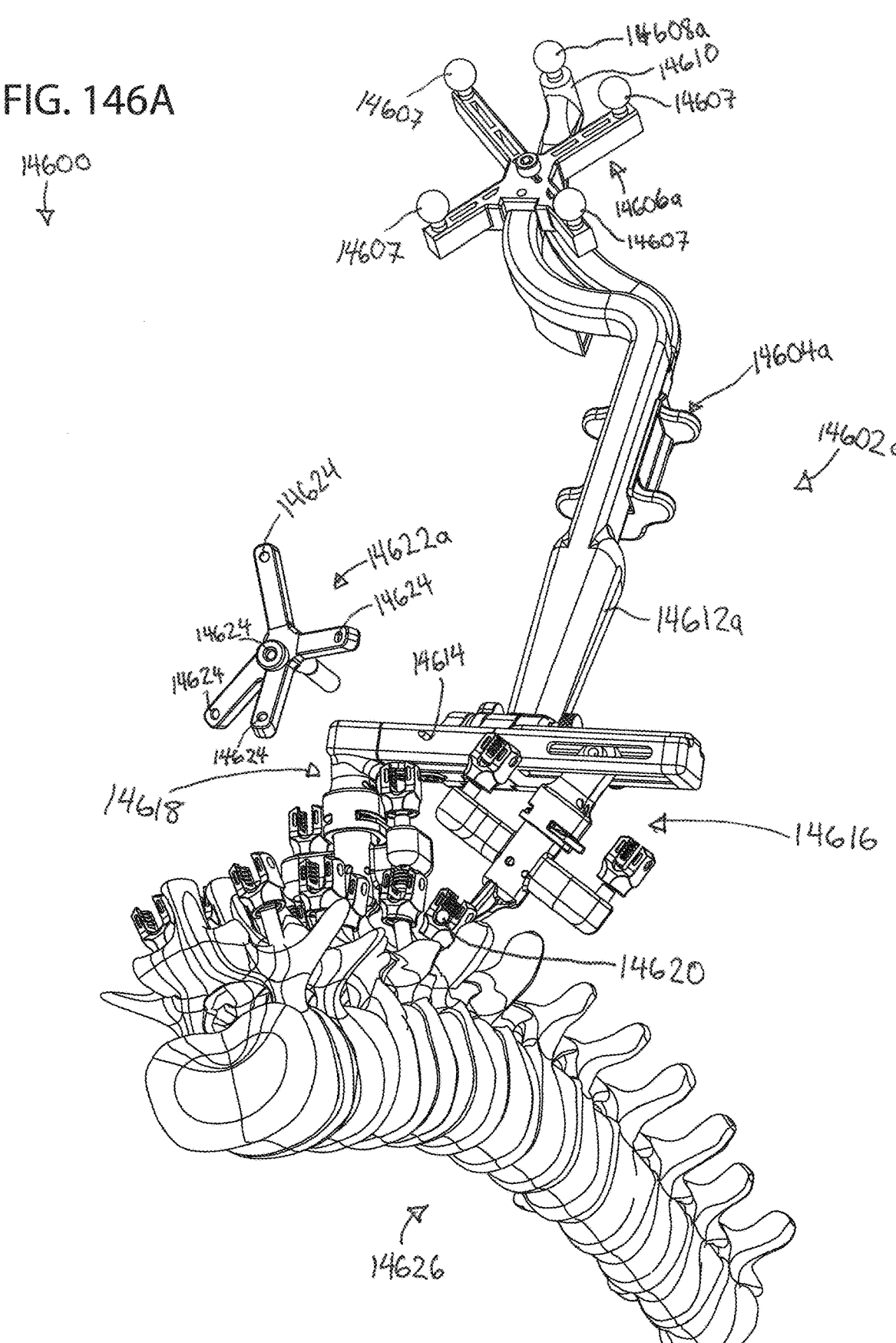

FIG. 146A illustrates perspective views of a front-facing flexibility assessment device rigidly engaged with a vertebra of the spine, as well as an X-Ray adapter not engaged with the male protrusion on the flexibility assessment device, in accordance with some embodiments of the invention.

Figure 146B:
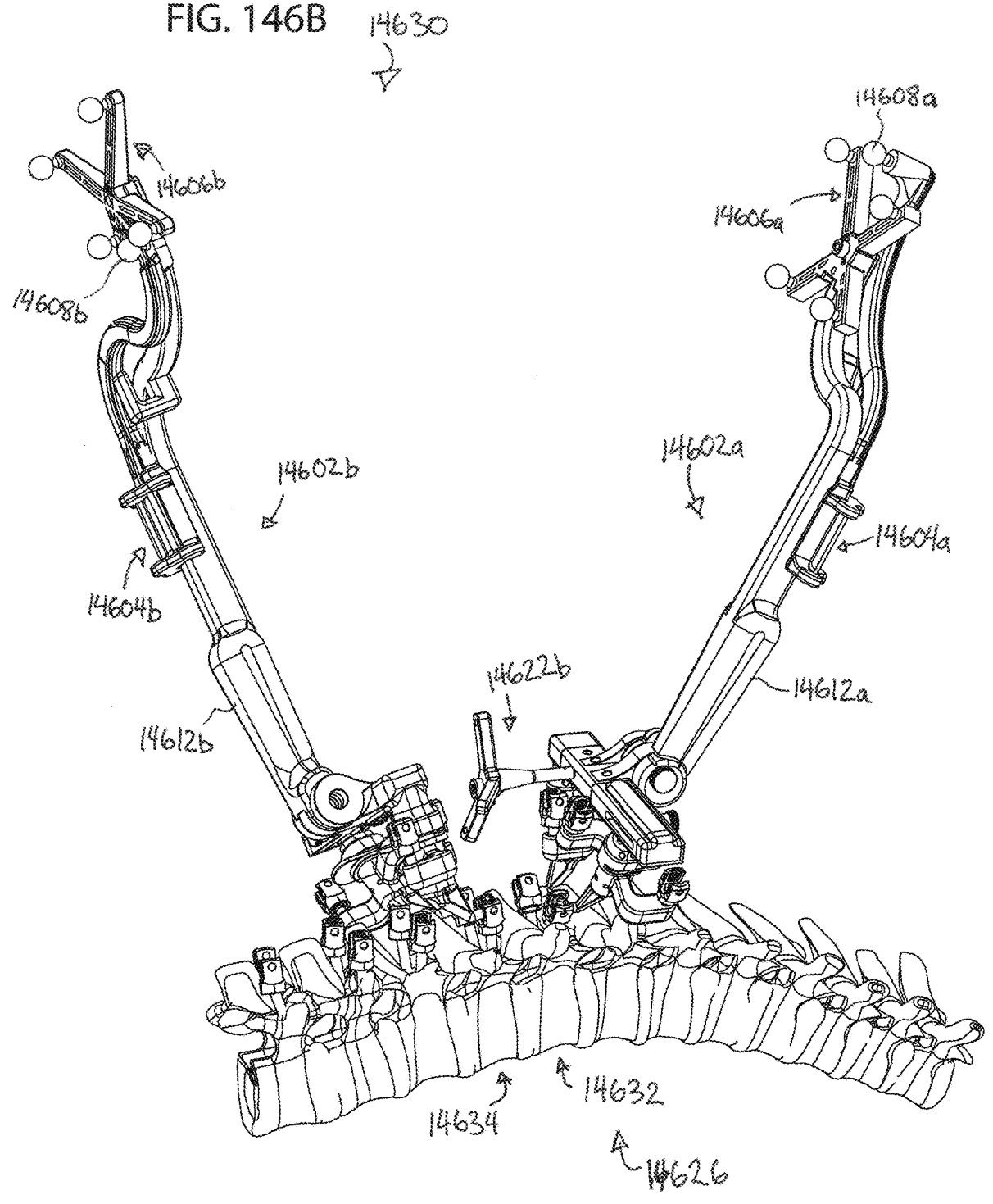

FIG. 146B illustrates perspective views of front-facing and back-facing flexibility assessment devices rigidly engaged with vertebrae of the spine, as well as an X-Ray adapter engaged with the male protrusion on the front-facing flexibility assessment device, as described previously in relation to FIG. 146A in accordance with some embodiments of the invention.

Figure 146C:
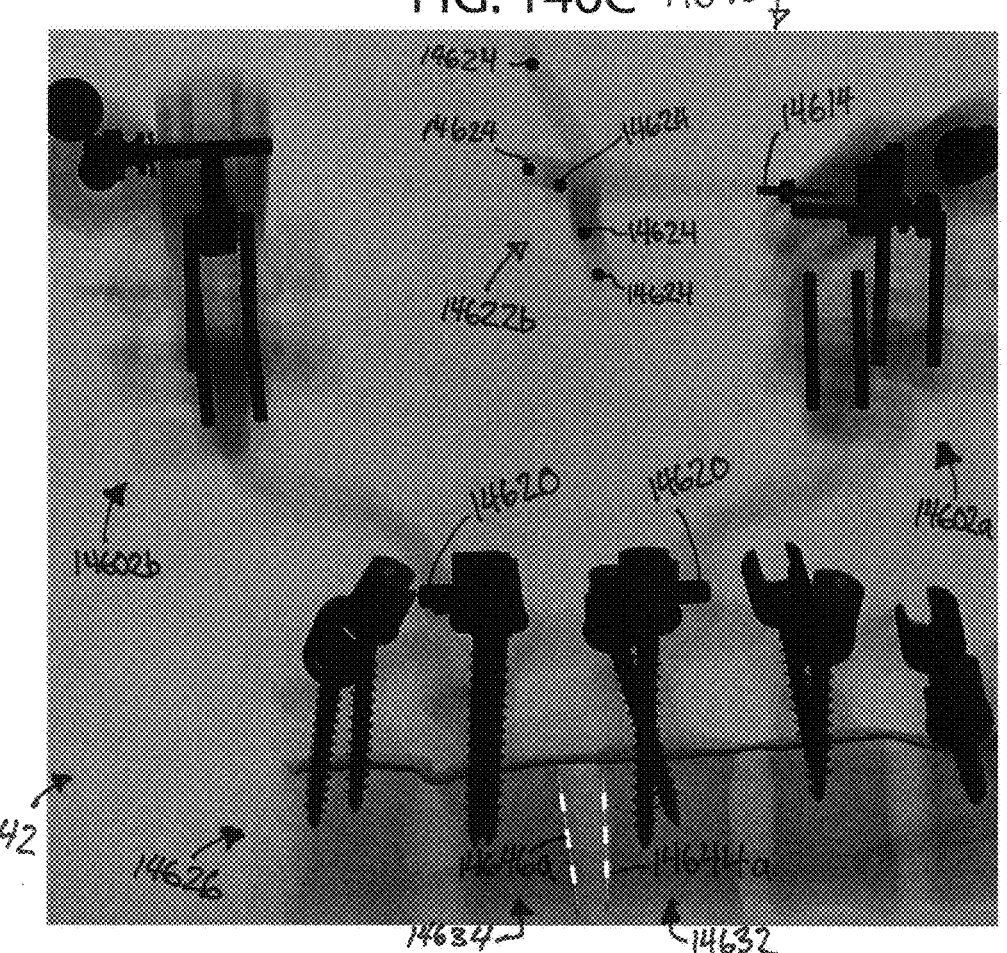

FIG. 146C illustrates an X-Ray image taken from the sagittal view of the spine with front-facing and back-facing flexibility assessment devices rigidly engaged with vertebrae of the spine, an X-Ray adapter engaged with the male protrusion on the front-facing flexibility assessment device, and line annotations of endplates of the vertebrae with flexibility assessment devices attached, as described previously in relation to FIGS. 146A-B in accordance with some embodiments of the invention.

Figure 146D:
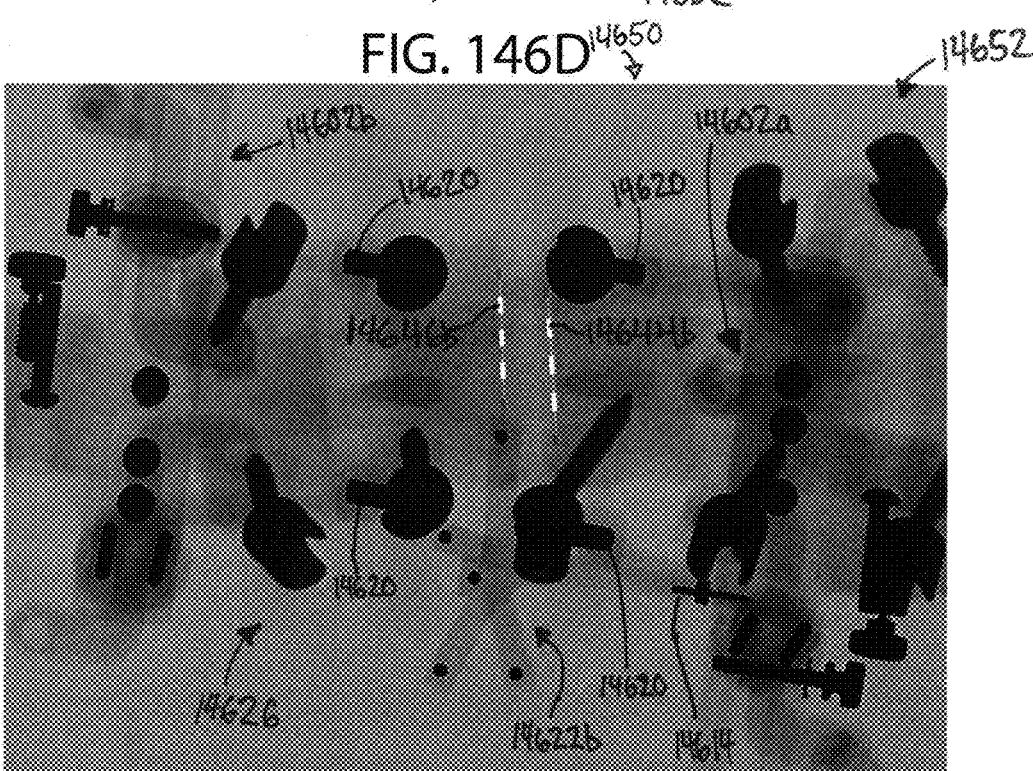

FIG. 146D illustrates an X-Ray image taken from the coronal view of the spine with front-facing and back-facing flexibility assessment devices rigidly engaged with vertebrae of the spine, an X-Ray adapter engaged with the male protrusion on the front-facing flexibility assessment device, and line annotations of endplates of the vertebrae with flexibility assessment devices attached, as described previously in relation to FIGS. 146A-B in accordance with some embodiments of the invention.

Figure 147A:
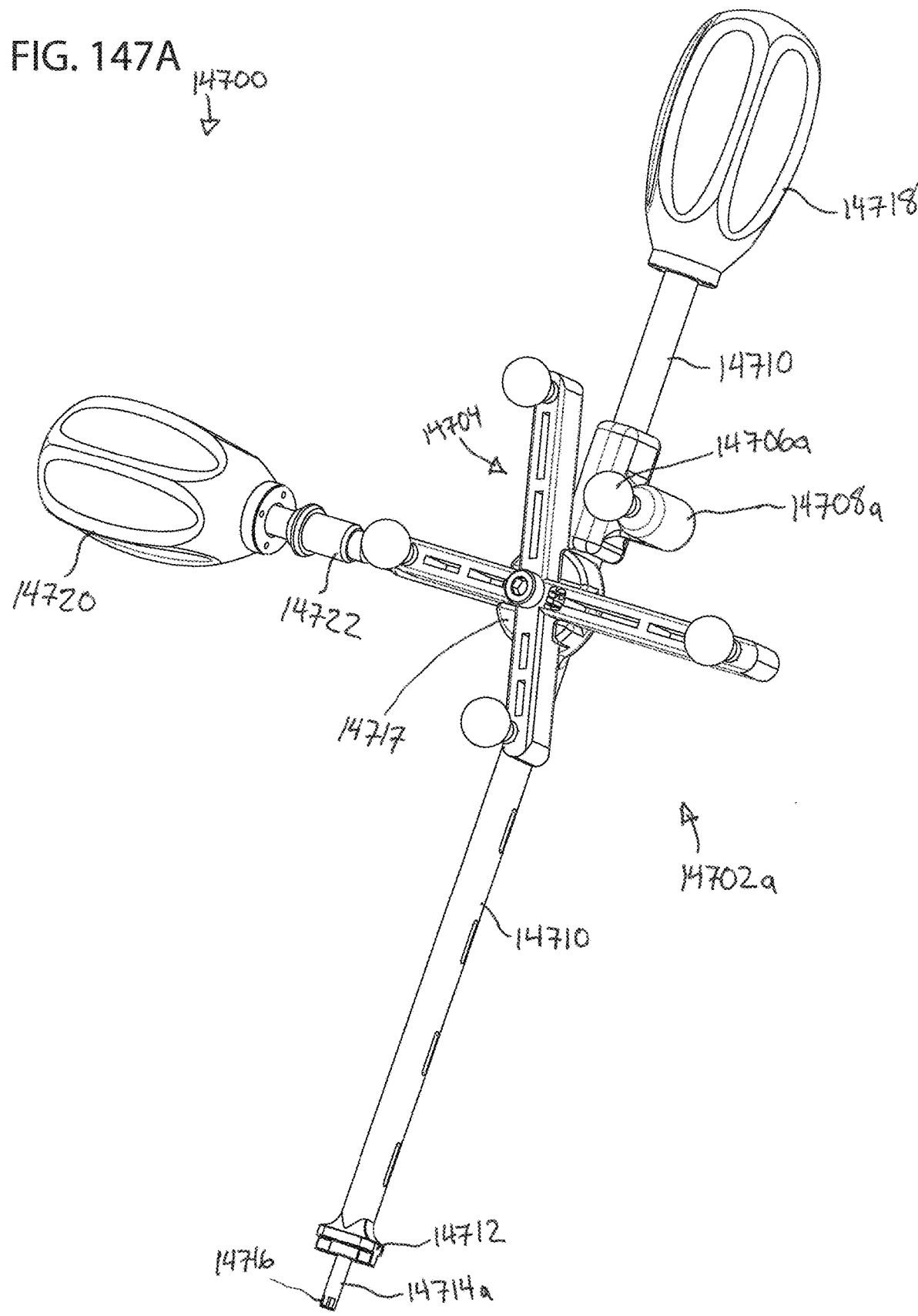

FIG. 147A illustrates a perspective view of a 3D-tracked implant driver with an implant-attachment tip mechanically linked with a TMSM in an inactive state in accordance with some embodiments of the invention.

Figure 147B:
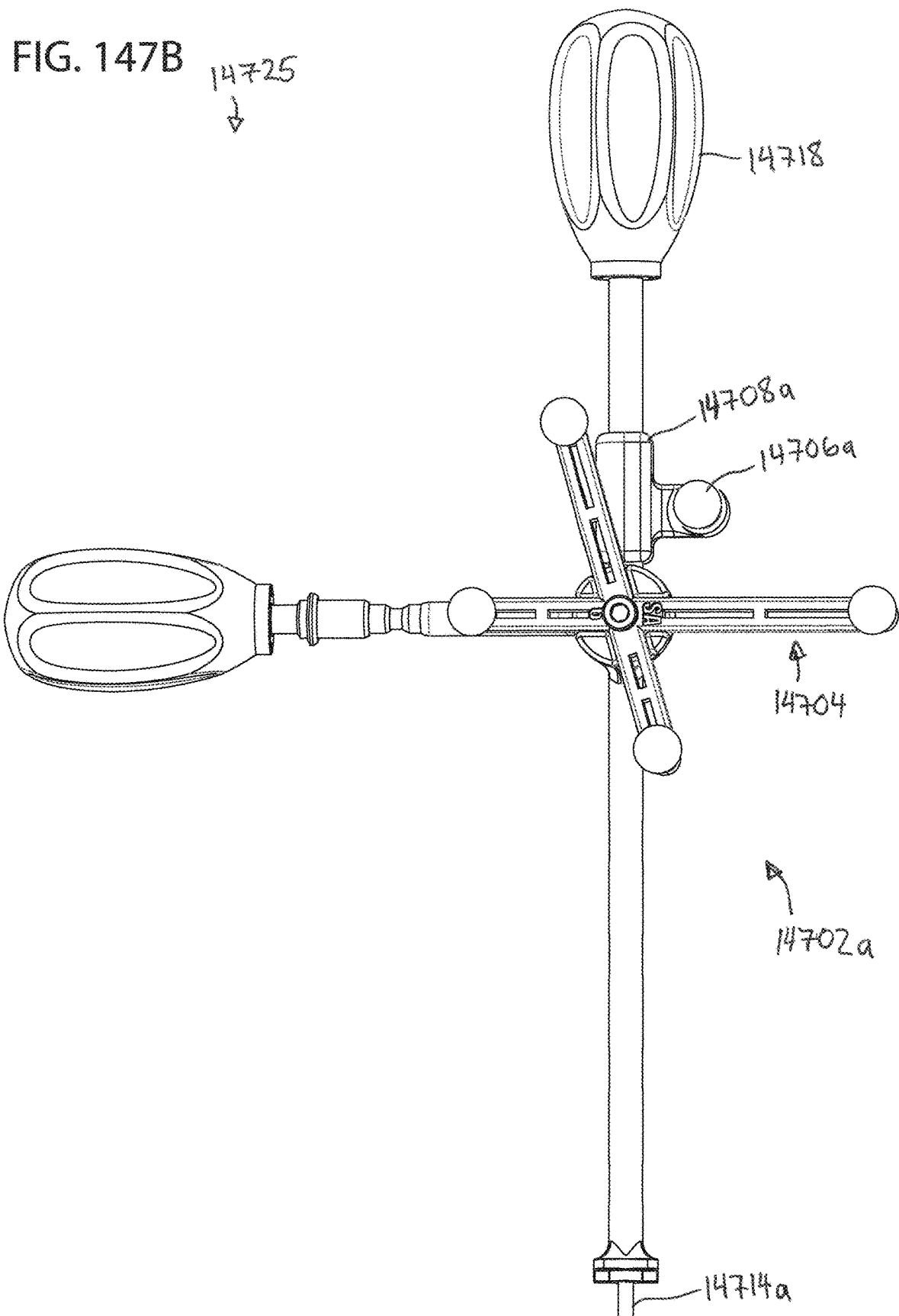

FIG. 147B illustrates a side view of a 3D-tracked implant driver with an implant-attachment tip mechanically linked with a TMSM in an inactive state as described previously in relation to FIG. 147A in accordance with some embodiments of the invention.

Figure 147C:
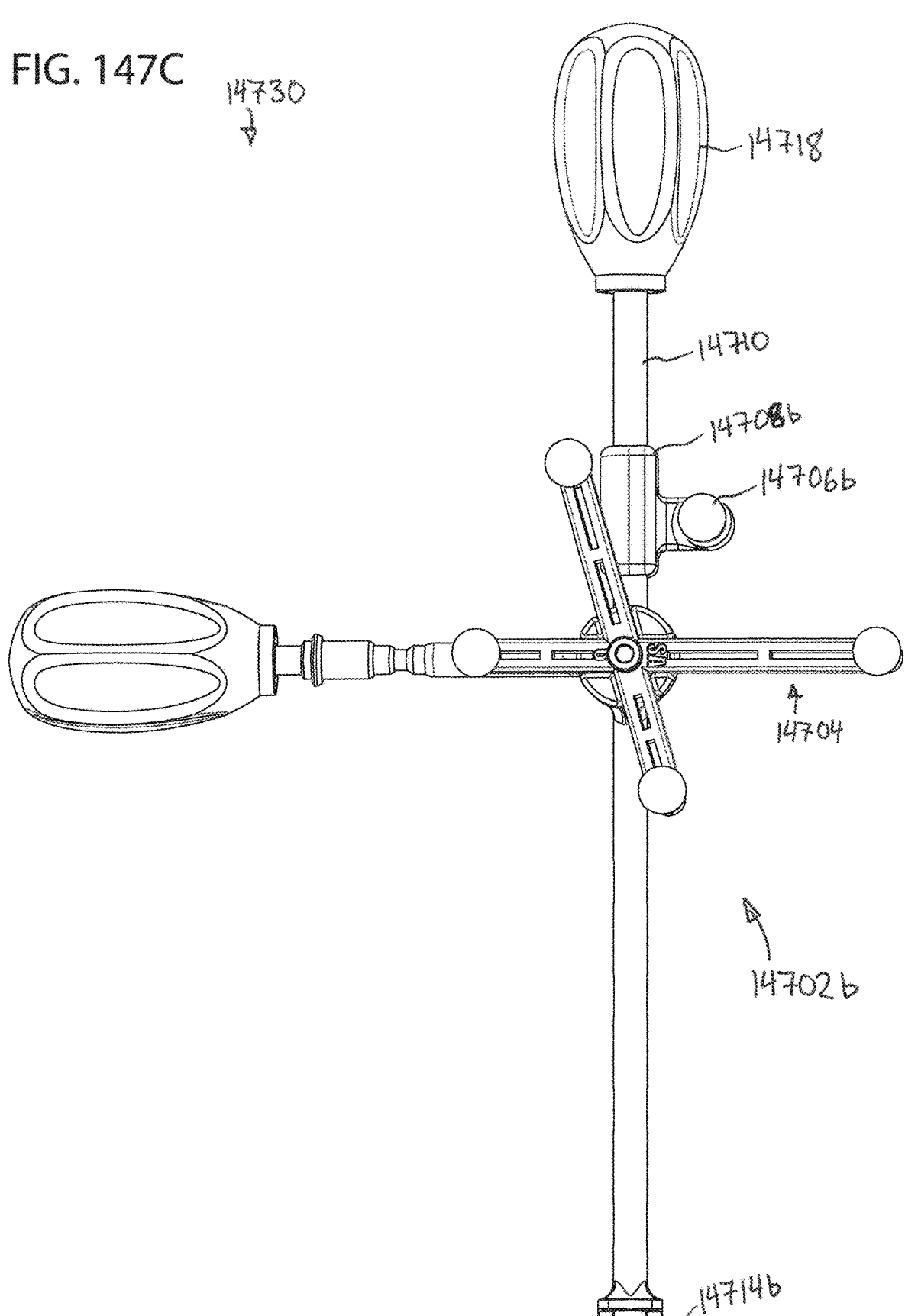

FIG. 147C illustrates a side view of a 3D-tracked implant driver with an implant-attachment tip mechanically linked with a TMSM in an active state as described previously in relation to FIGS. 147A-B in accordance with some embodiments of the invention.

Figures 147D, 147E:
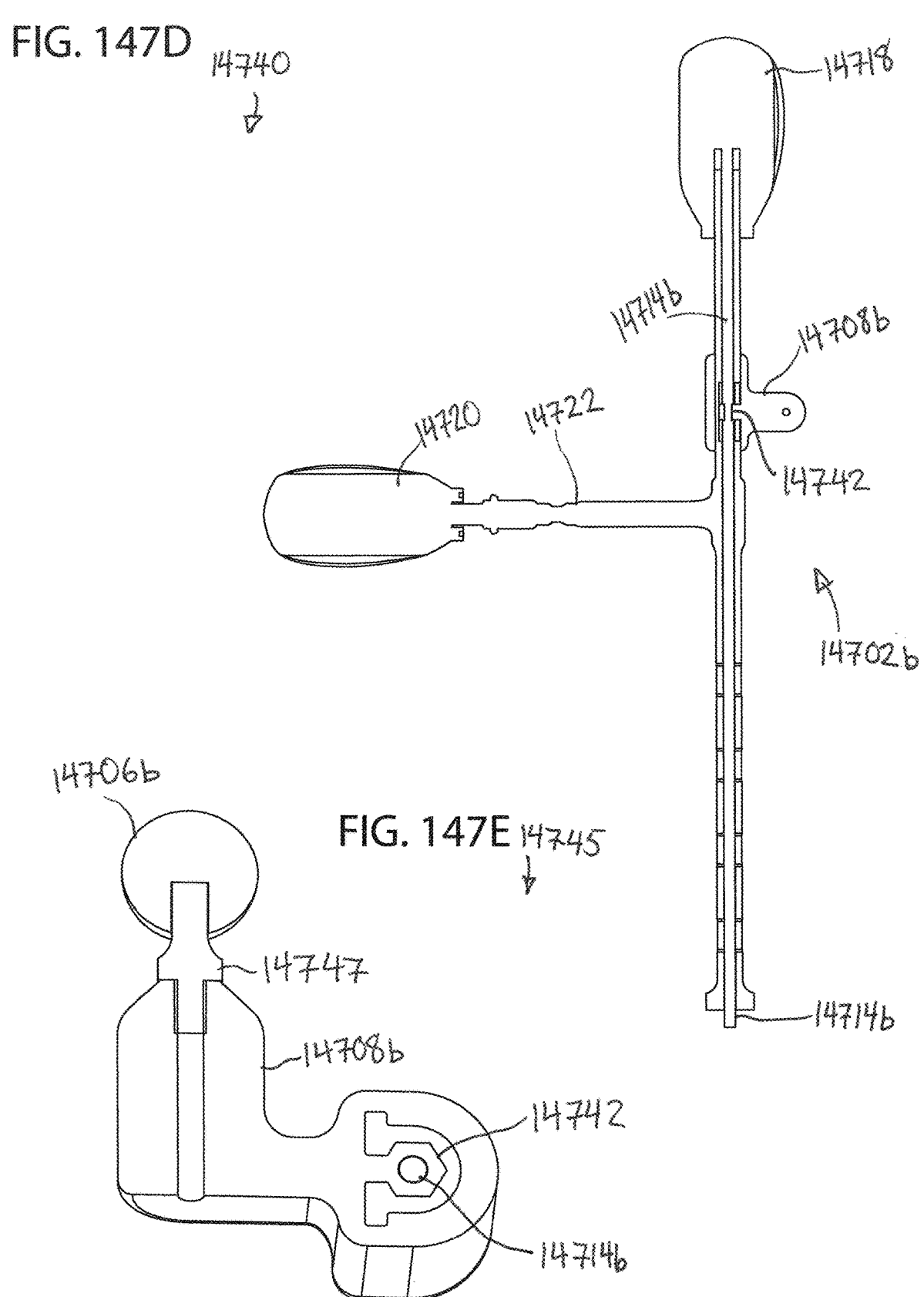

FIG. 147D illustrates a side cross-sectional view of a 3D-tracked implant driver with an implant-attachment tip mechanically linked with a TMSM mount as described previously in relation to FIGS. 147A-C in accordance with some embodiments of the invention.

FIG. 147E illustrates a cross-sectional view of a TMSM mount and attached TMSM as described previously in relation to FIGS. 147A-D in accordance with some embodiments of the invention.

FIG. 147F illustrates a perspective view of a 3D-tracked implant driver with an implant-attachment tip not engaged with an expandable interbody cage and in an inactive state, as described previously in relation to FIGS. 147A-E in accordance with some embodiments of the invention.

FIG. 147G illustrates a side cross-sectional view of a 3D-tracked implant driver with an implant-attachment tip engaged with an expandable interbody cage, as described previously in relation to FIGS. 147A-F in accordance with some embodiments of the invention.

FIG. 147H illustrates a side view of a 3D-tracked implant driver with an implant-attachment tip engaged with an expandable interbody cage and in an inactive state, as described previously in relation to FIGS. 147A-G in accordance with some embodiments of the invention.

FIG. 147I illustrates a side view of a 3D-tracked implant driver with an implant-attachment tip engaged with an expanded interbody cage and in an active state, as described previously in relation to FIGS. 147A-H in accordance with some embodiments of the invention.

FIG. 148A illustrates perspective views of 3D-tracked DRF attachments not engaged with external-mating bone-mounted fiducials, in accordance with some embodiments of the invention.

FIG. 148B illustrates perspective views of 3D-tracked DRF attachments engaged with external-mating bone-mounted fiducials, as described previously in relation to FIG. 148A in accordance with some embodiments of the invention.

Figures 148C, 148D:
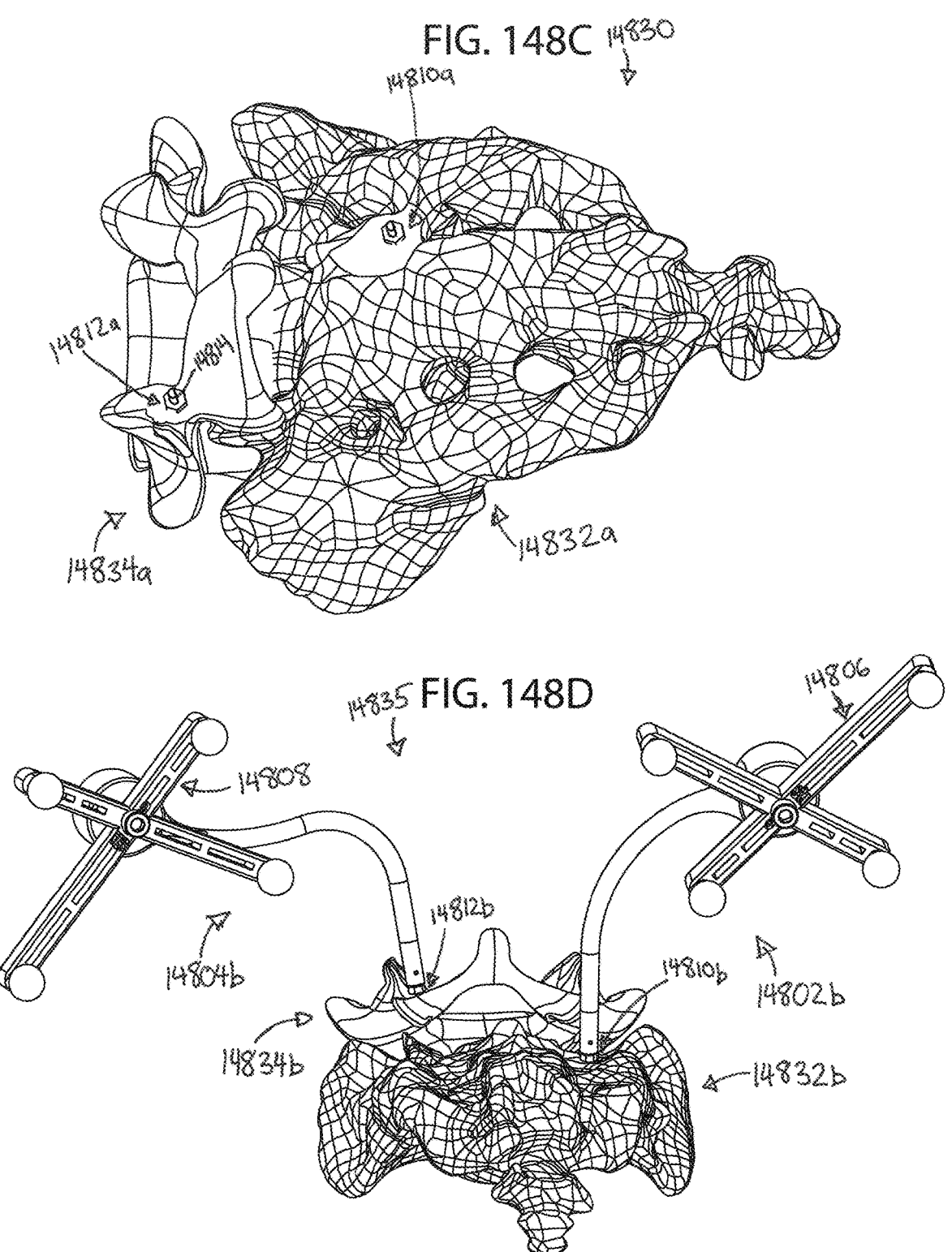

FIG. 148C illustrates a top view of the sacrum and L5 vertebra with external-mating bone-mounted fiducials implanted in them, as described previously in relation to FIGS. 148A-B in accordance with some embodiments of the invention.

FIG. 148D illustrates perspective views of 3D-tracked DRF attachments engaged with external-mating bone-mounted fiducials implanted in the sacrum and L5 vertebra, as described previously in relation to FIGS. 148A-C in accordance with some embodiments of the invention.

FIG. 148E illustrates side views of a 3D-tracked implant driver with an expandable interbody cage. The cage is not inserted between the sacrum and L5 vertebra, which are implanted with external-mating bone-mounted fiducials engaged with 3D-tracked DRF attachments, as described previously in relation to FIGS. 148A-D in accordance with some embodiments of the invention.

Figure 148F:
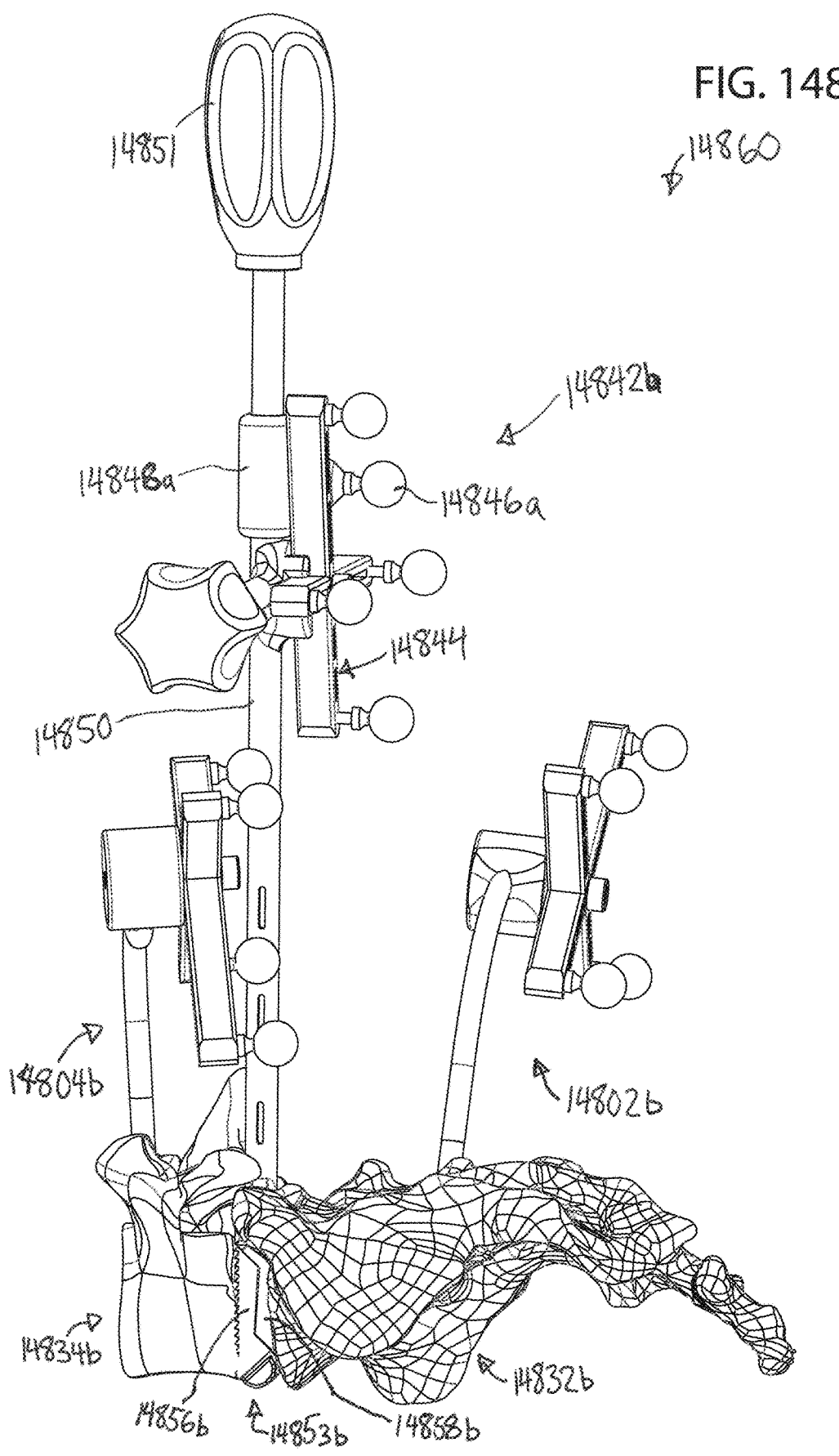

FIG. 148F illustrates a sagittal view of a 3D-tracked implant driver with an expandable interbody cage. The cage is inserted between the sacrum and L5 vertebra, which are implanted with external-mating bone-mounted fiducials engaged with 3D-tracked DRF attachments. The above components are described previously in relation to FIGS. 148A-E in accordance with some embodiments of the invention.

Figure 148G:
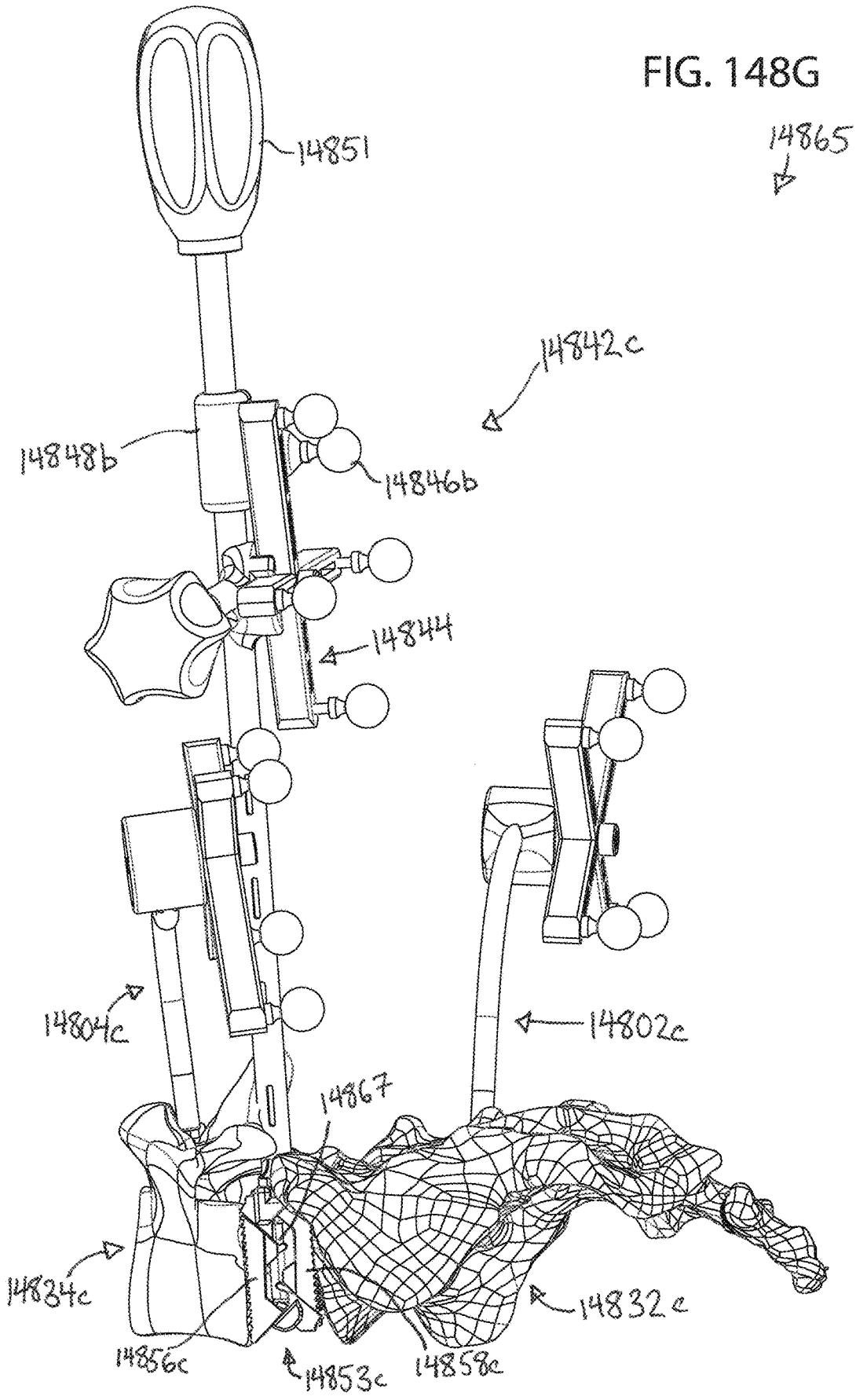

FIG. 148G illustrates a sagittal view of a 3D-tracked implant driver with an expandable interbody cage. The cage is inserted and expanded between the sacrum and L5 vertebra and the implant driver's TMSM is in an active state. The sacrum and L5 vertebra has external-mating bone-mounted fiducials engaged with 3D-tracked DRF attachments. The above components are described previously in relation to FIGS. 148A-F in accordance with some embodiments of the invention.

Figure 148H:
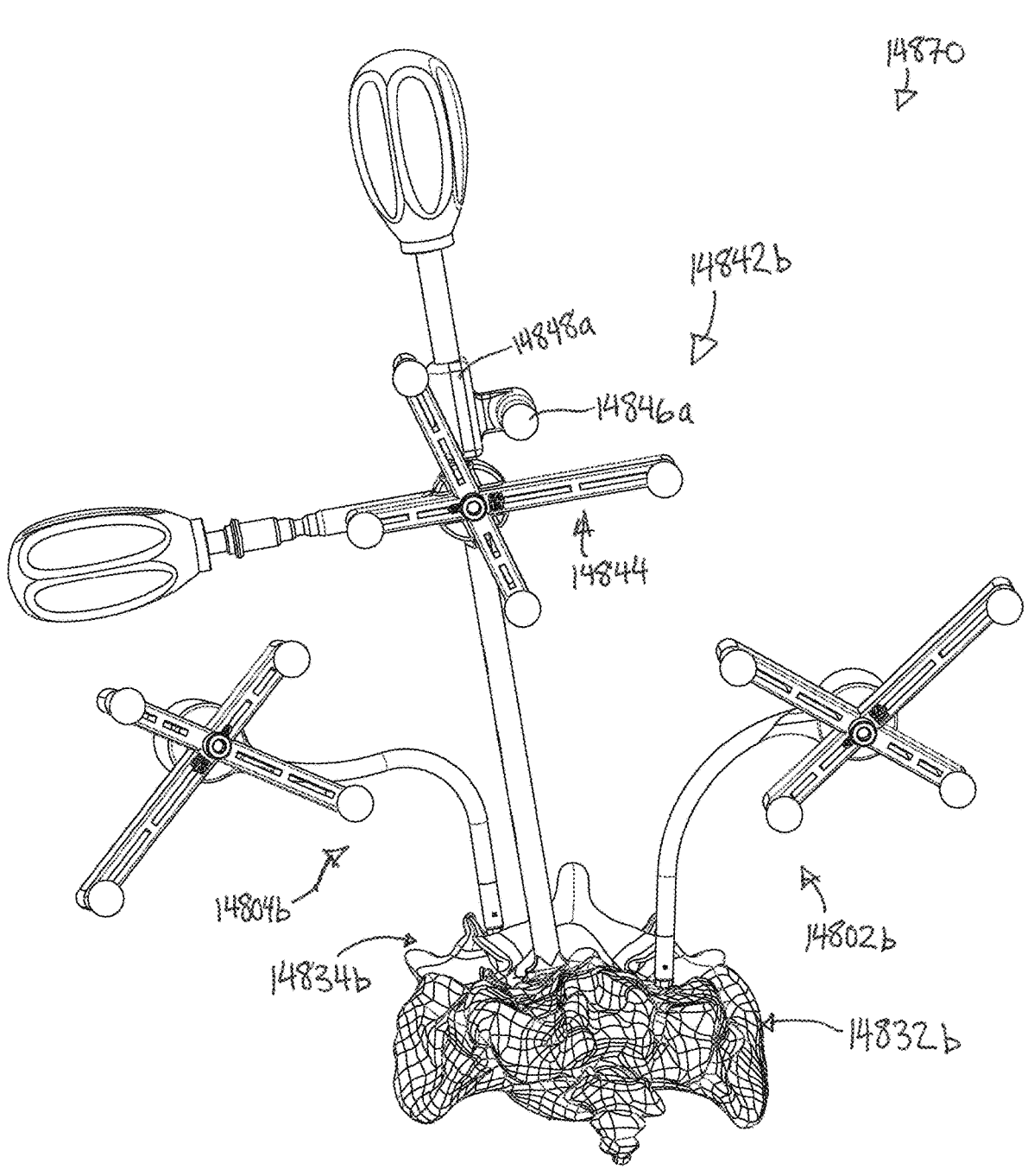

FIG. 148H illustrates an axial view of a 3D-tracked implant driver with an expandable interbody cage. The cage is inserted between the sacrum and L5 vertebra and the implant driver's TMSM is in an inactive state. The sacrum and L5 vertebra has external-mating bone-mounted fiducials engaged with 3D-tracked DRF attachments. The above components are described previously in relation to FIGS. 148A-G in accordance with some embodiments of the invention.

Figure 148I:
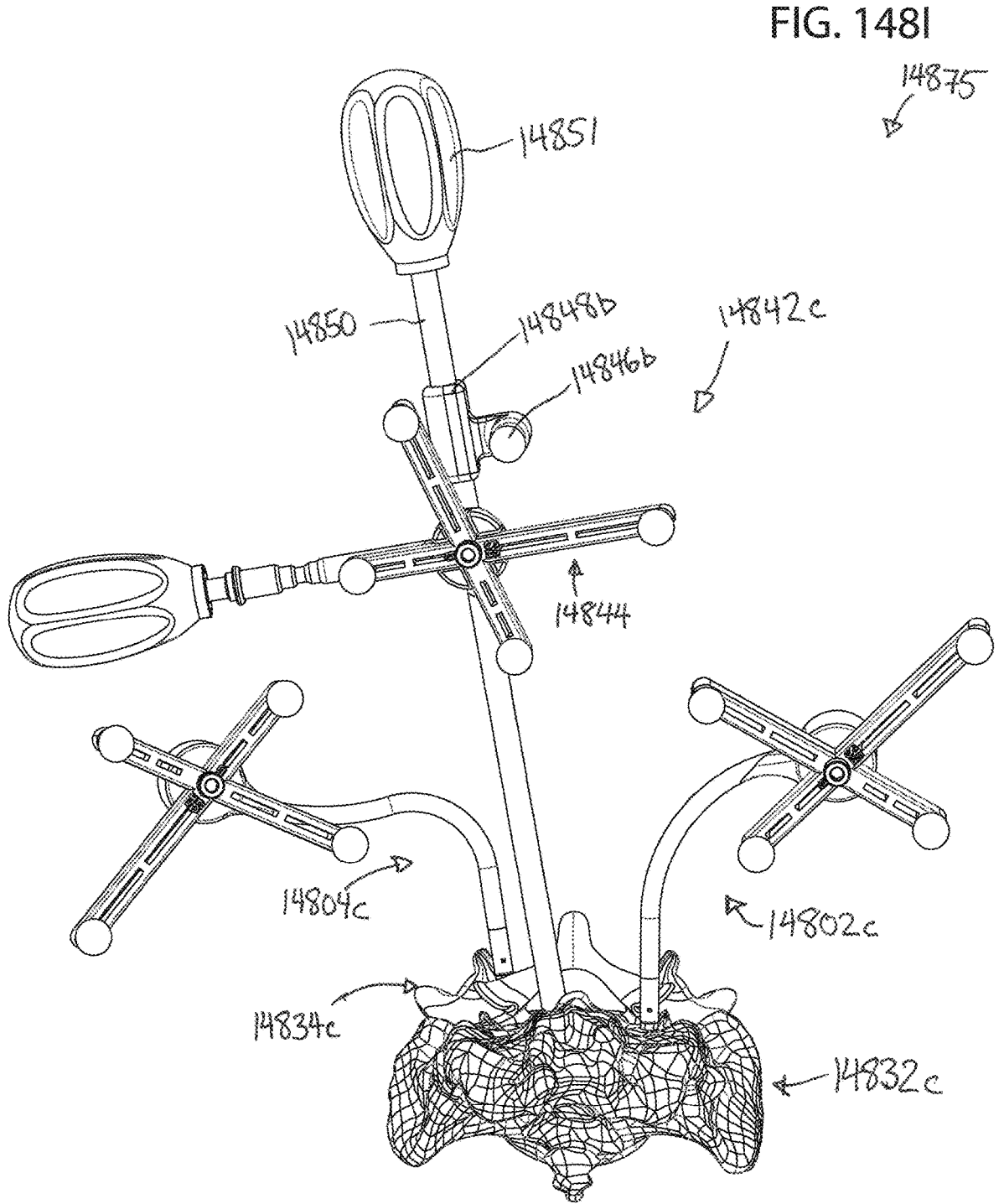

FIG. 148I illustrates an axial view of a 3D-tracked implant driver with an expandable interbody cage. The cage is inserted and expanded between the sacrum and L5 vertebra and the implant driver's TMSM is in an active state. The sacrum and L5 vertebra has external-mating bone-mounted fiducials engaged with 3D-tracked DRF attachments. The above components are described previously in relation to FIGS. 148A-H in accordance with some embodiments of the invention.

Figure 148J:
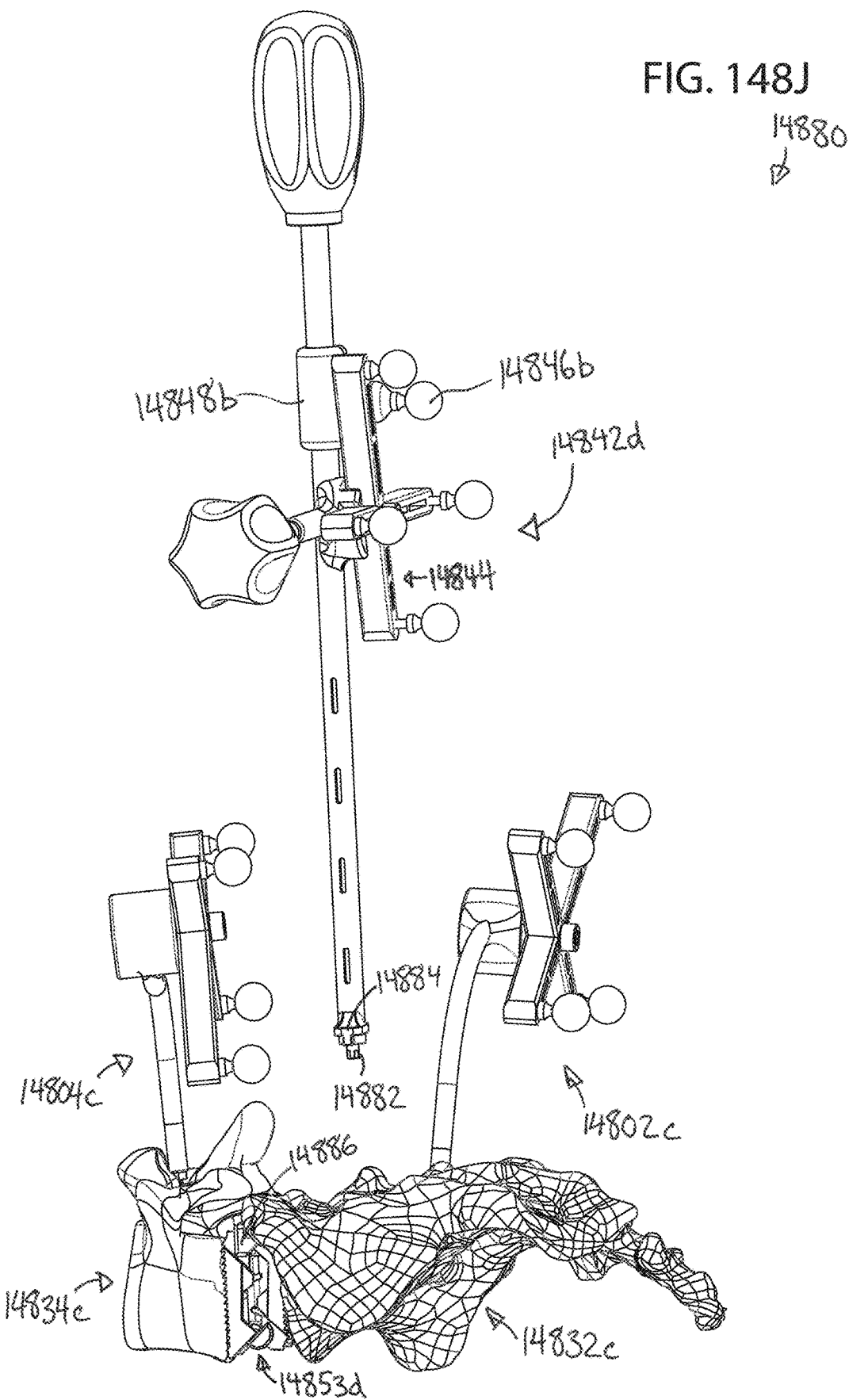

FIG. 148J illustrates a sagittal view of the sacrum and L5 vertebra with an expandable interbody cage inserted and expanded between them, and has external-mating bone-mounted fiducials engaged with 3D-tracked DRF attachments. The 3D-tracked implant driver is disengaged from the interbody cage. The above components are described previously in relation to FIGS. 148A-I in accordance with some embodiments of the invention.

Figure 148K:
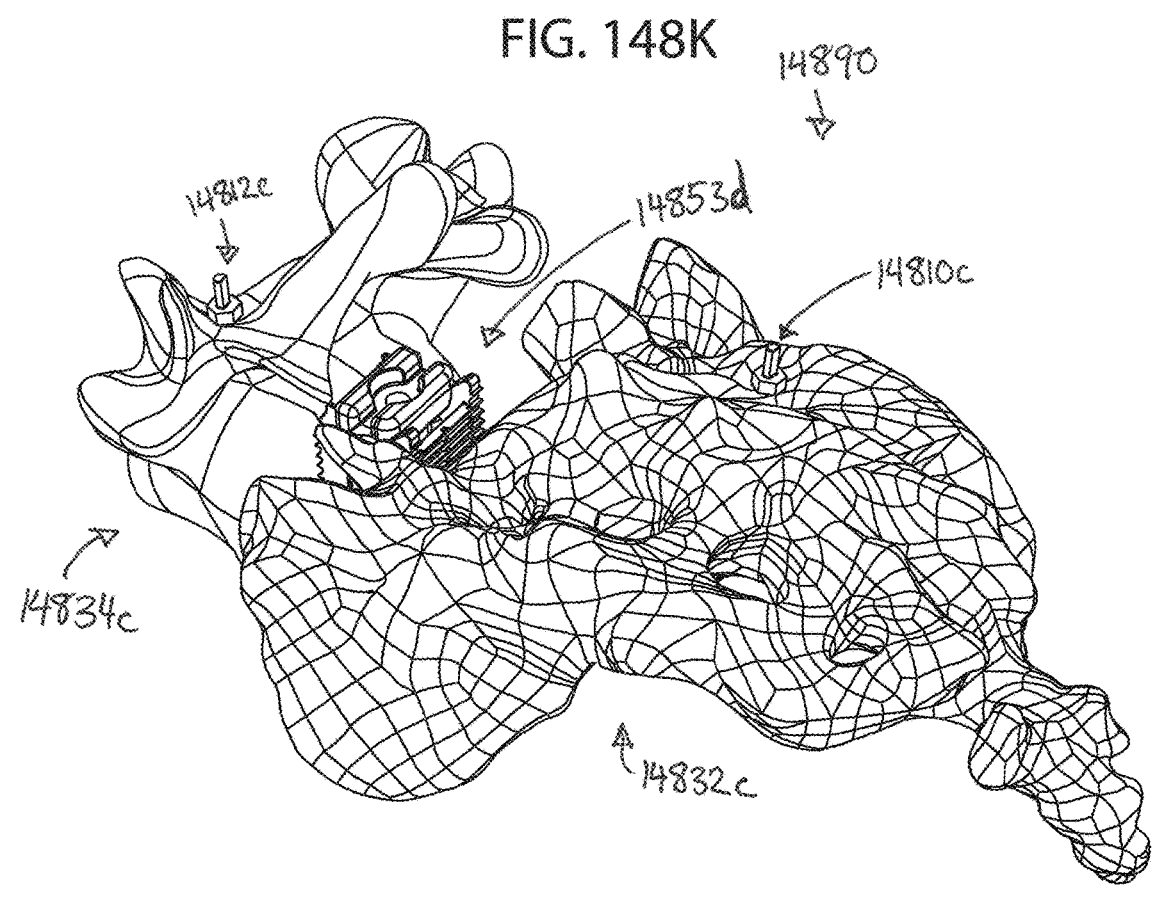

FIG. 148K illustrates a top perspective view of the sacrum and L5 vertebra with an interbody cage inserted and expanded between them, as described previously in relation to FIGS. 148A-J in accordance with some embodiments of the invention.

Figure 148L:
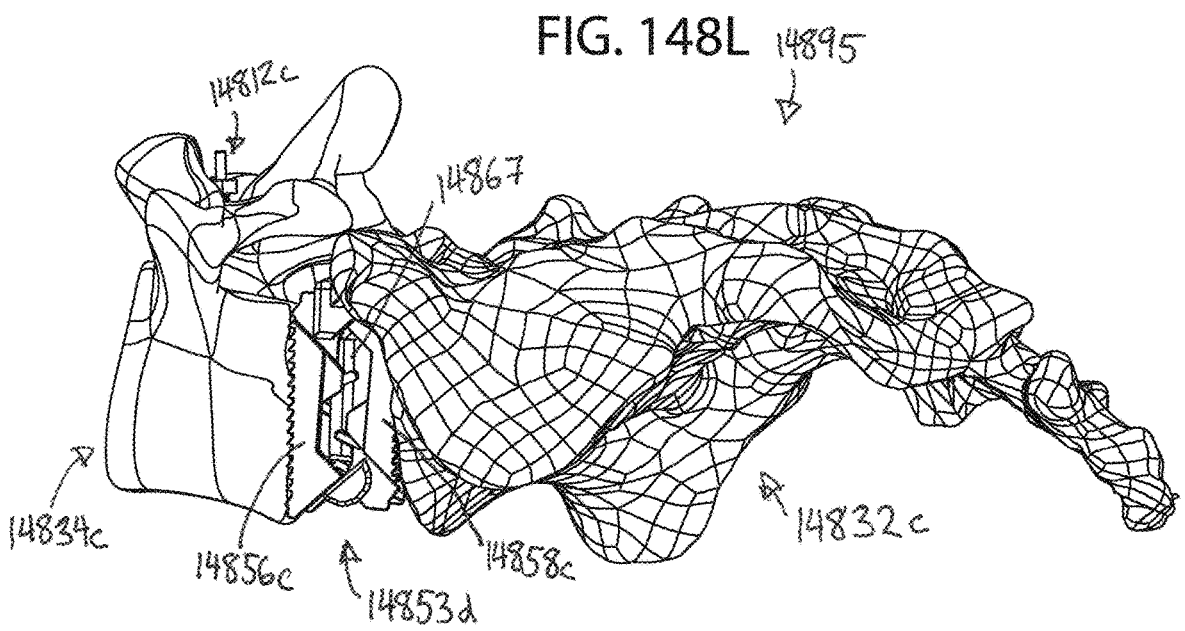

FIG. 148L illustrates a side view of the sacrum and L5 vertebra with an interbody cage inserted between them, as described previously in relation to FIGS. 148A-K in accordance with some embodiments of the invention.

Figure 149A:
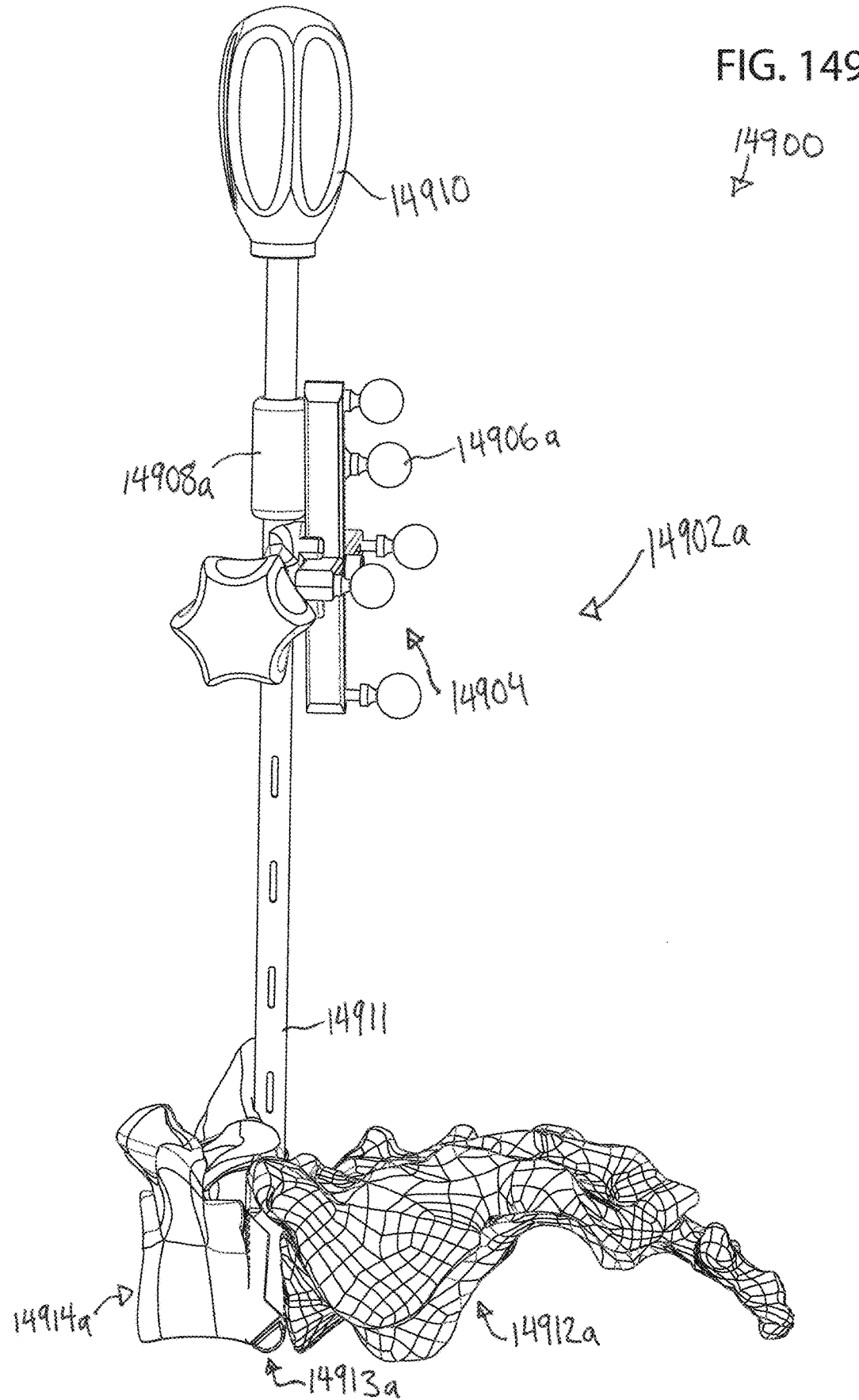

FIG. 149A illustrates a side view of the sacrum and L5 vertebra with an interbody cage inserted between them, still attached to the 3D-tracked implant driver that is in an inactive state, in accordance with some embodiments of the invention.

Figure 149B:
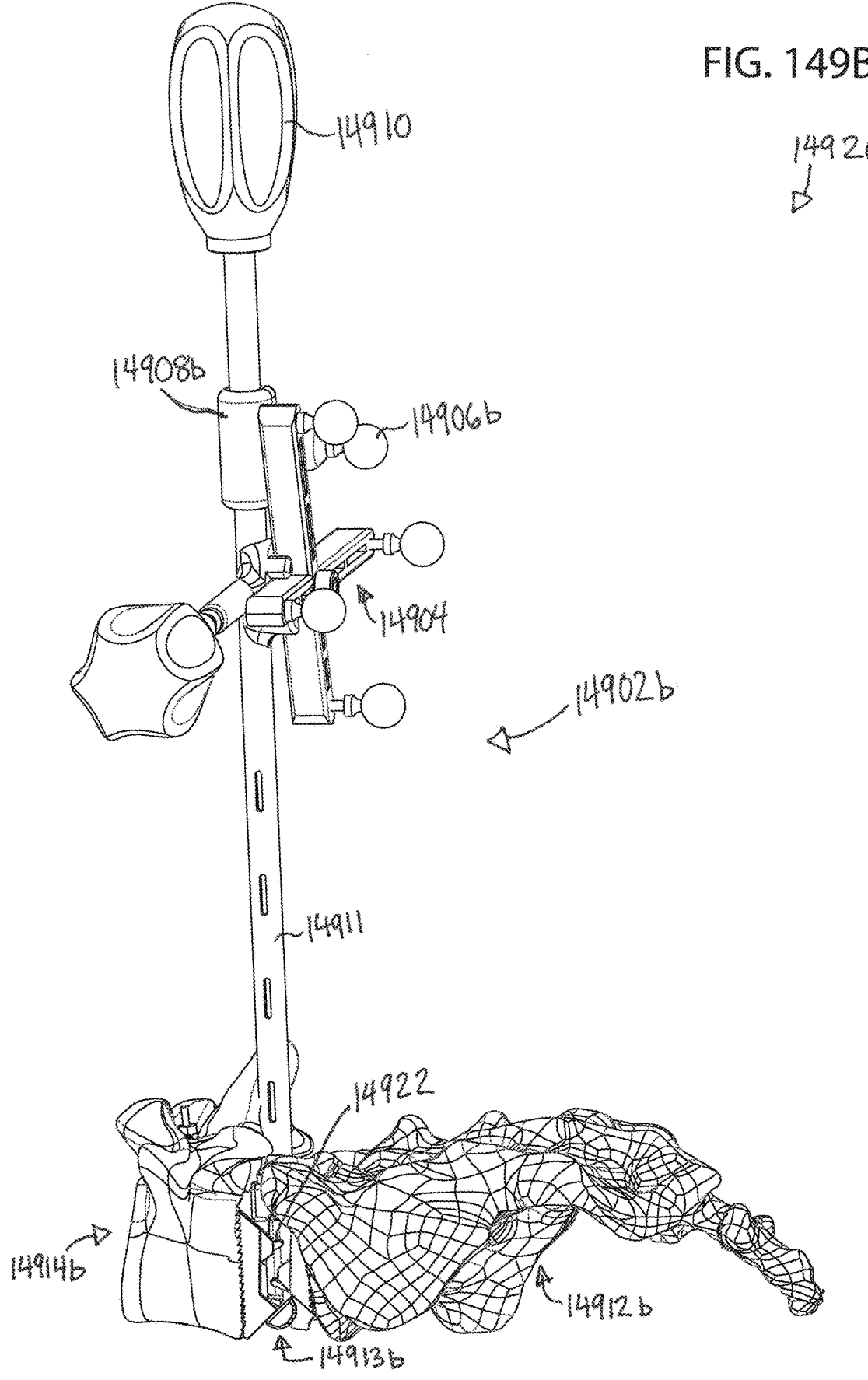

FIG. 149B illustrates a side view of the sacrum and L5 vertebra with an interbody cage inserted and expanded between them, still attached to the 3D-tracked implant driver that is in an active state, as described previously in relation to FIG. 149A in accordance with some embodiments of the invention.

Figure 149C:
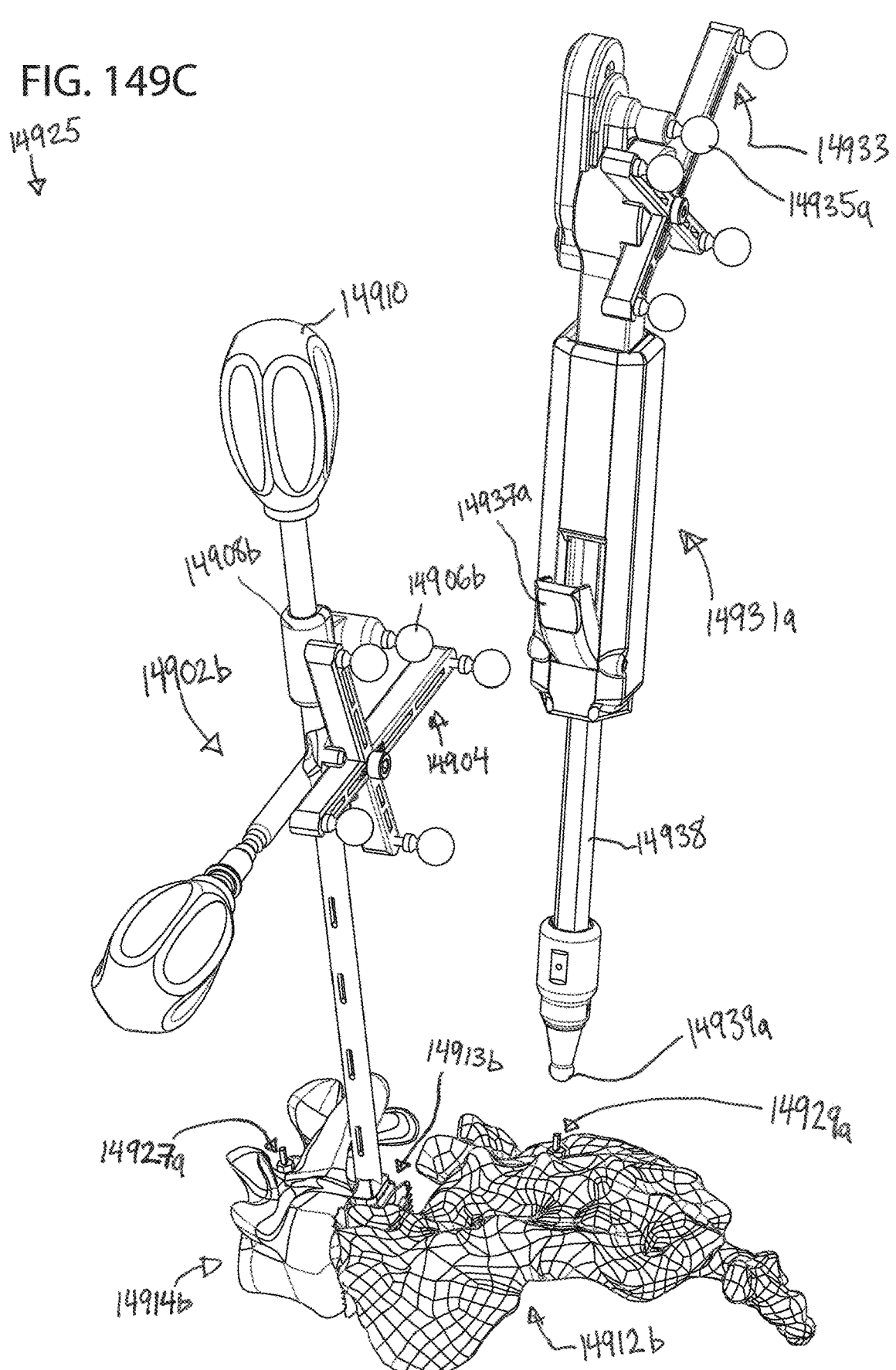

FIG. 149C illustrates a perspective view of the sacrum and L5 vertebra with an interbody cage inserted and expanded between them, still attached to the 3D-tracked implant driver that is in an active state. A 3D-tracked tool is not engaged with an external-mating bone-mounted fiducial implanted in the sacrum and is in an inactive state. The above components are described previously in relation to FIGS. 149A-B in accordance with some embodiments of the invention.

Figure 149D:
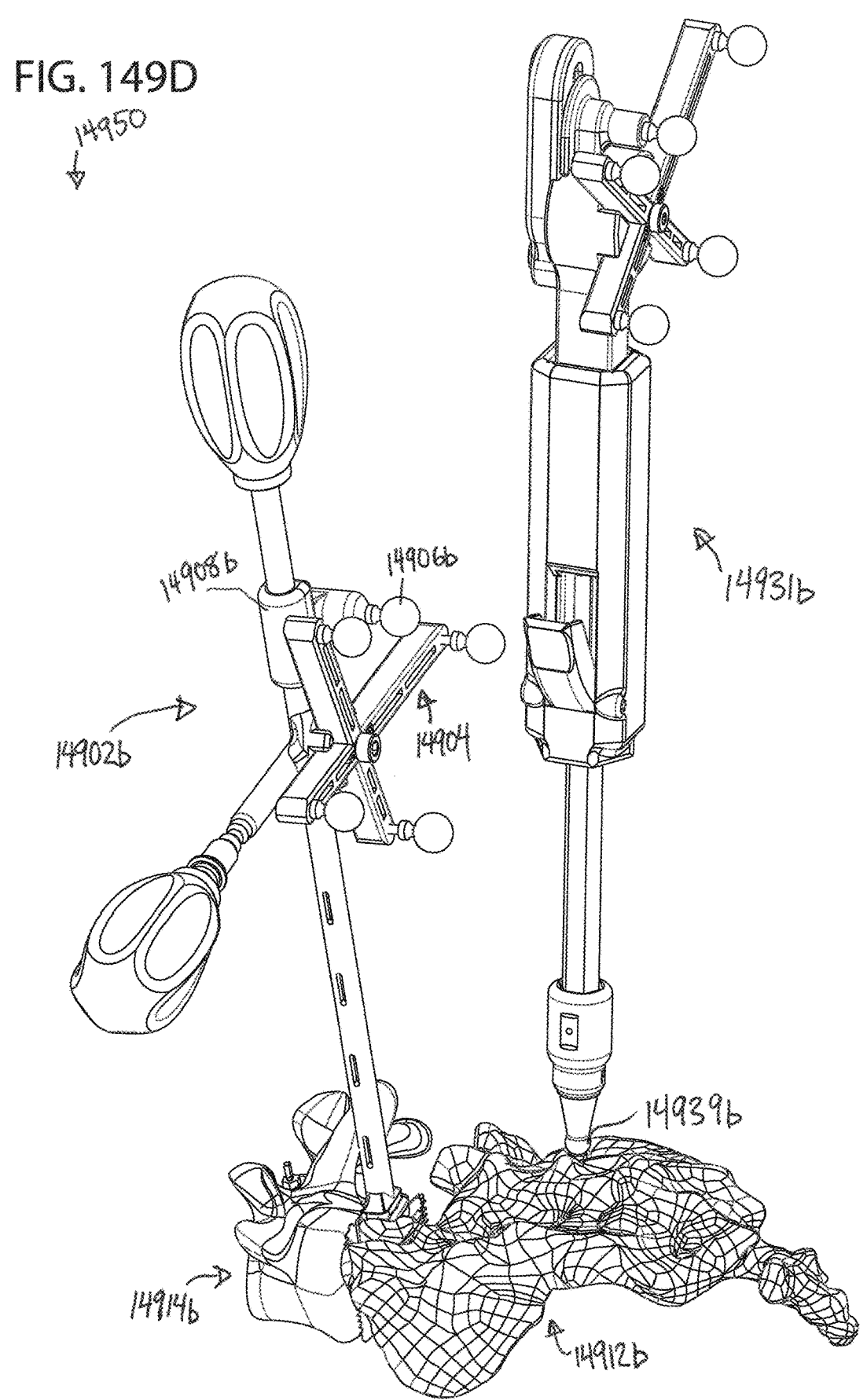

FIG. 149D illustrates a perspective view of the sacrum and L5 vertebra with an interbody cage inserted and expanded between them, still attached to the 3D-tracked implant driver that is in an active state. A 3D-tracked tool is engaged with an external-mating bone-mounted fiducial implanted in the sacrum and is in an inactive state. The above components are described previously in relation to FIGS. 149A-C in accordance with some embodiments of the invention.

Figure 149E:
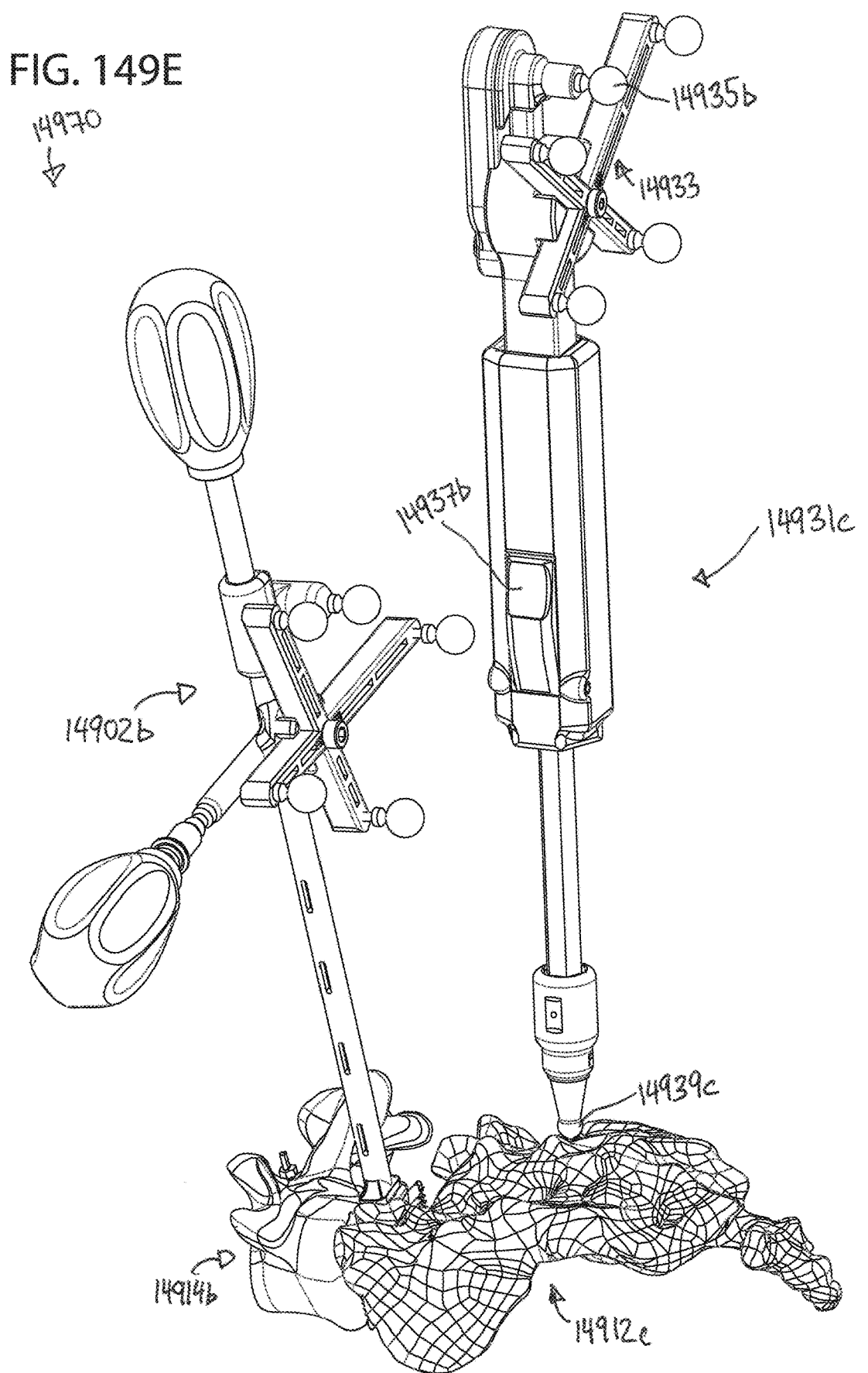

FIG. 149E illustrates a perspective view of the sacrum and L5 vertebra with an interbody cage inserted and expanded between them, still attached to the 3D-tracked implant driver that is in an active state. A 3D-tracked tool is engaged with an external-mating bone-mounted fiducial implanted in the sacrum and is in an active state. The above components are described previously in relation to FIGS. 149A-D in accordance with some embodiments of the invention.

Figure 150A:
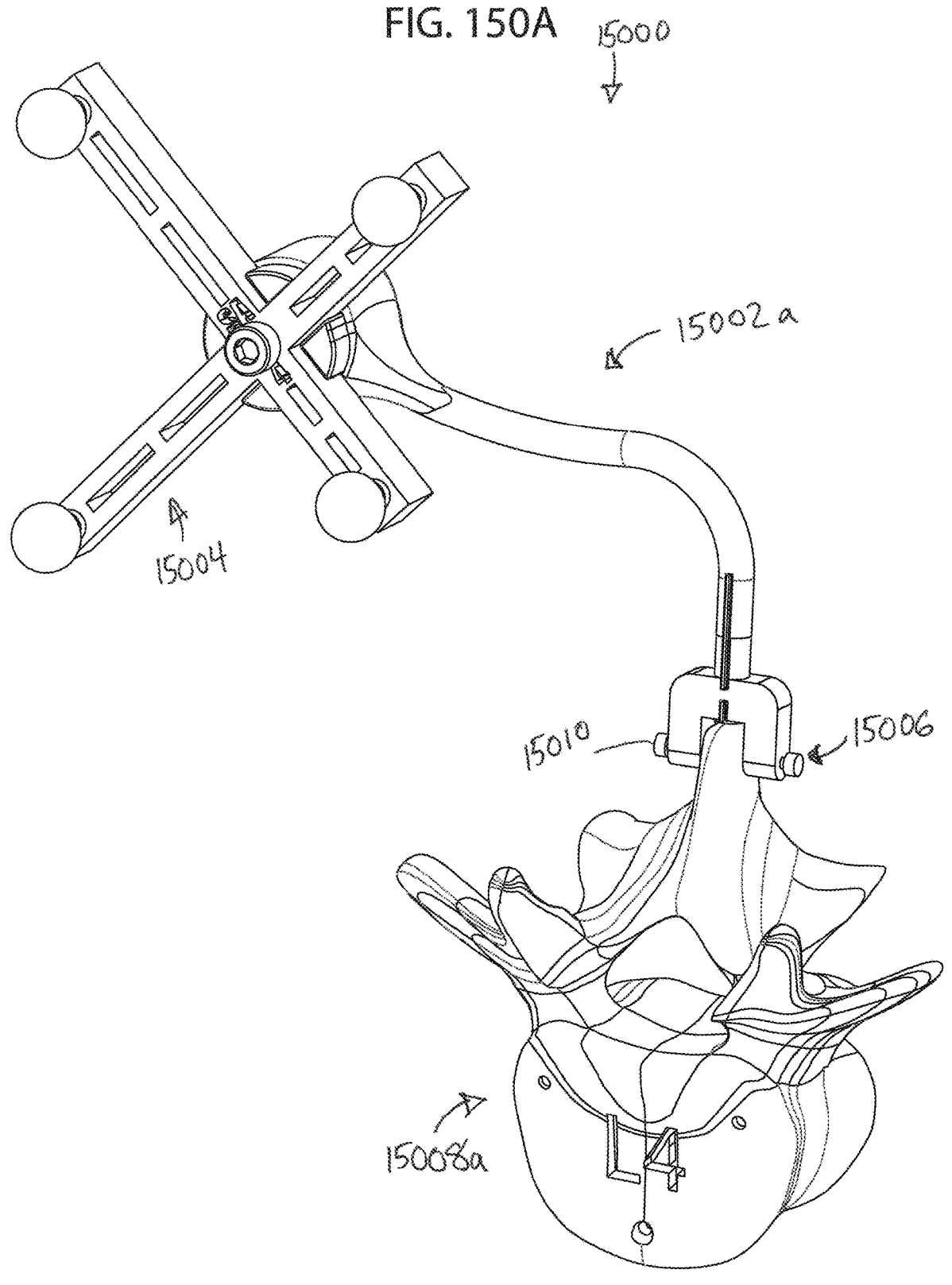

FIG. 150A illustrates a perspective view of a 3D-tracked bone-clamping fiducial attached to the L4 vertebra in accordance with some embodiments of the invention.

Figure 150B:
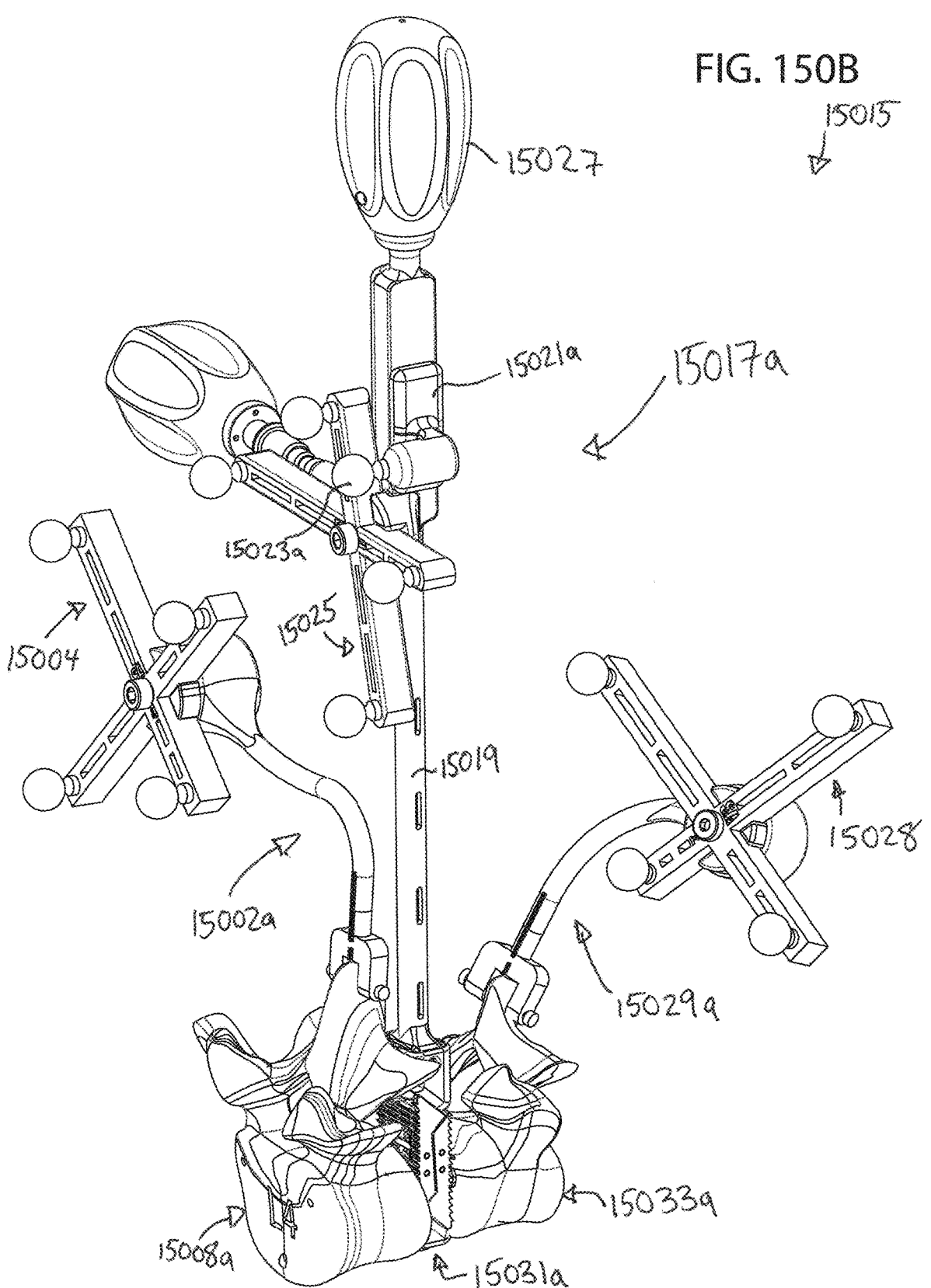

FIG. 150B illustrates perspective views of the L4 and L5 vertebrae with 3D-tracked bone-clamping fiducial attached. An interbody cage is inserted between them via a 3D-tracked implant driver that is in an inactive state. The above components are described previously in relation to FIG. 150A in accordance with some embodiments of the invention.

Figure 150C:
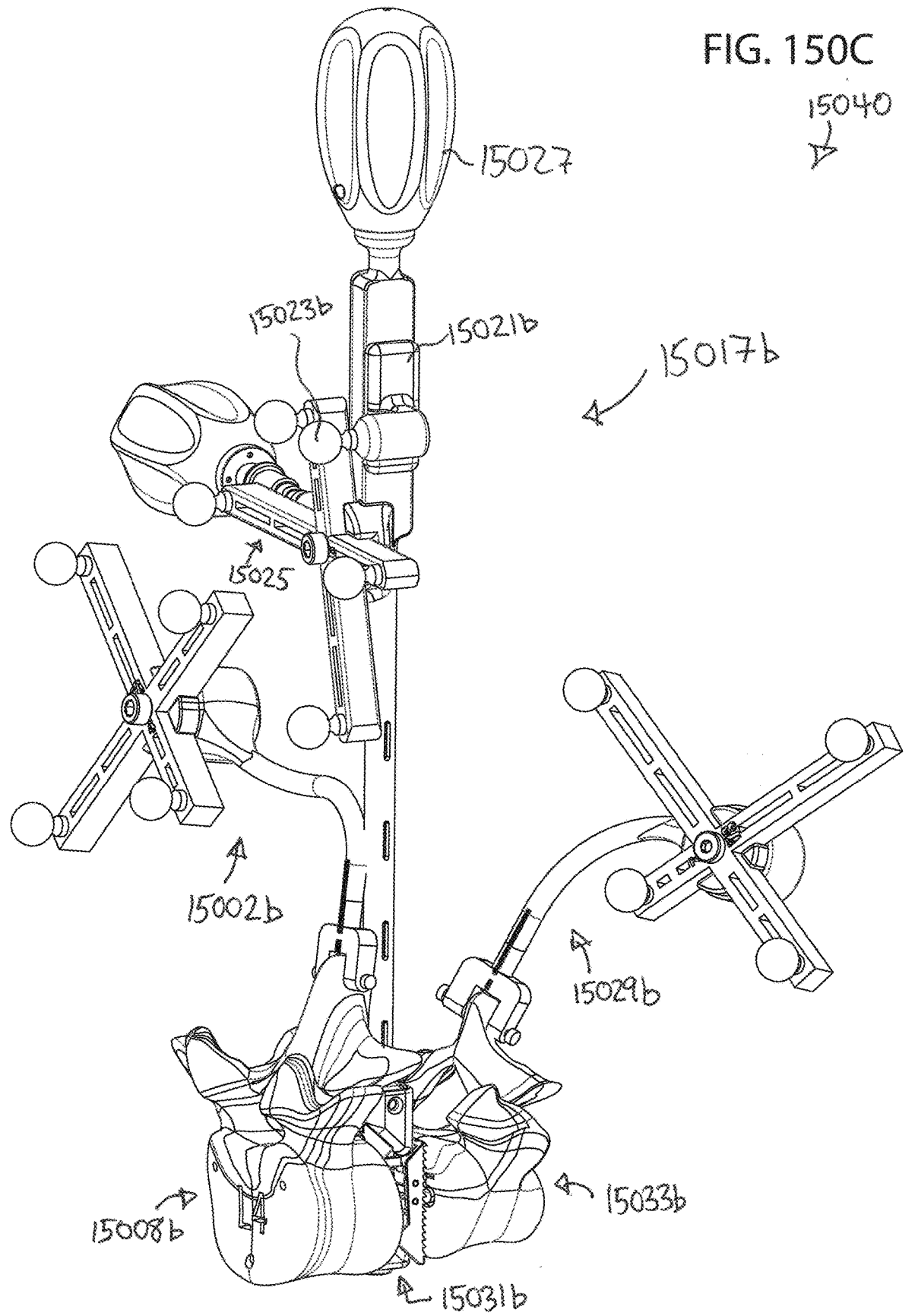

FIG. 150C illustrates perspective views of the L4 and L5 vertebrae with 3D-tracked bone-clamping fiducial attached. An interbody cage is inserted and expanded between them via a 3D-tracked implant driver that is in an active state. The above components are described previously in relation to FIGS. 150A-B in accordance with some embodiments of the invention.

Figures 151A, 151B:
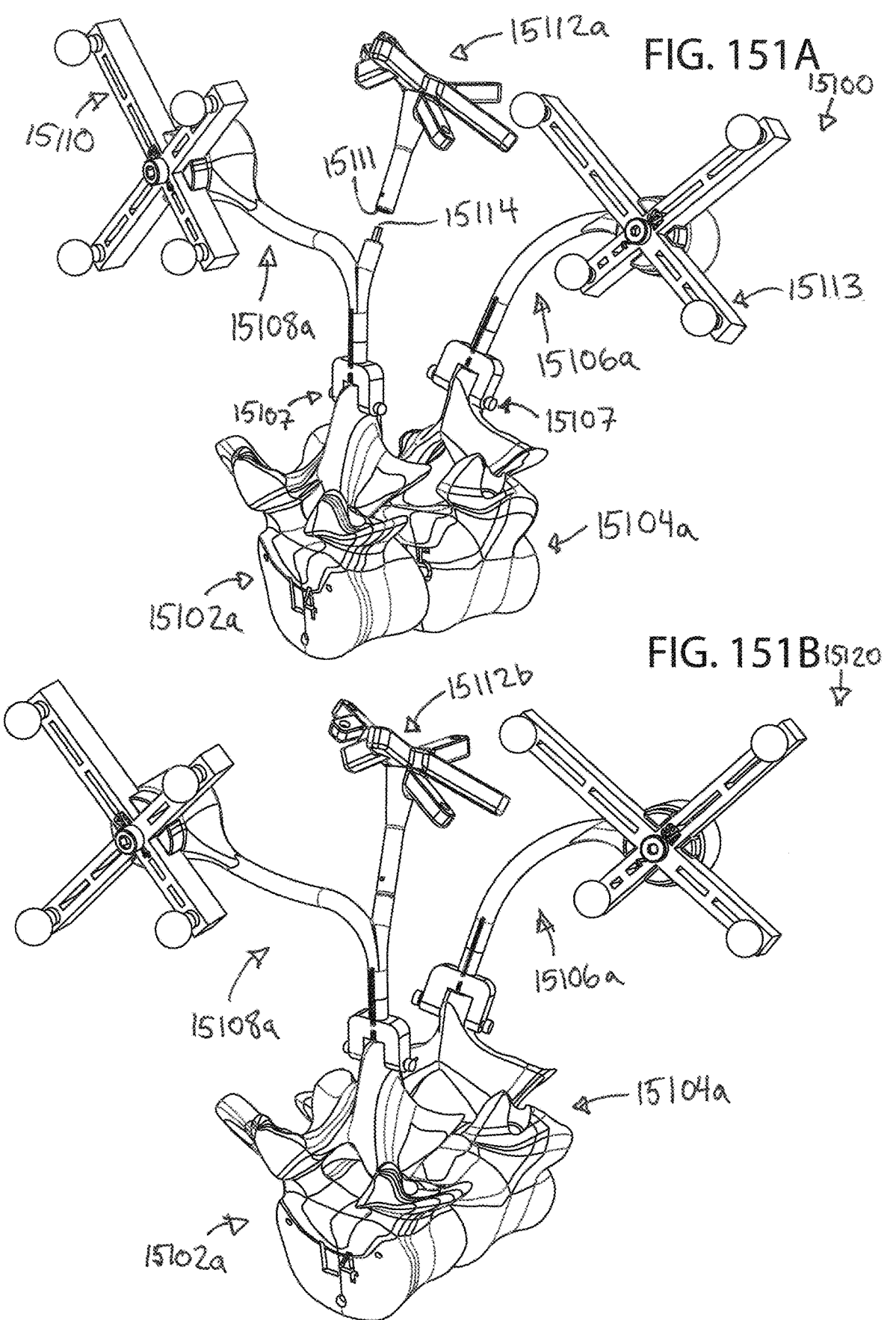

FIG. 151A illustrates perspective views of the L4 and L5 vertebrae with 3D-tracked bone-clamping fiducials attached, and an internal-mating X-Ray adapter not engaged with a male protrusion on one of the bone-clamping fiducials, in accordance with some embodiments of the invention.

FIG. 151B illustrates perspective views of the L4 and L5 vertebrae with 3D-tracked bone-clamping fiducials attached, and an internal-mating X-Ray adapter engaged with a male protrusion on one of the bone-clamping fiducials, as described previously in relation to FIG. 151A in accordance with some embodiments of the invention.

FIG. 151C illustrates sagittal views of the L4 and L5 vertebrae with 3D-tracked bone-clamping fiducials attached, and an internal-mating X-Ray adapter engaged with a male protrusion on one of the bone-clamping fiducials, as described previously in relation to FIGS. 151A-B in accordance with some embodiments of the invention.

Figure 151D:
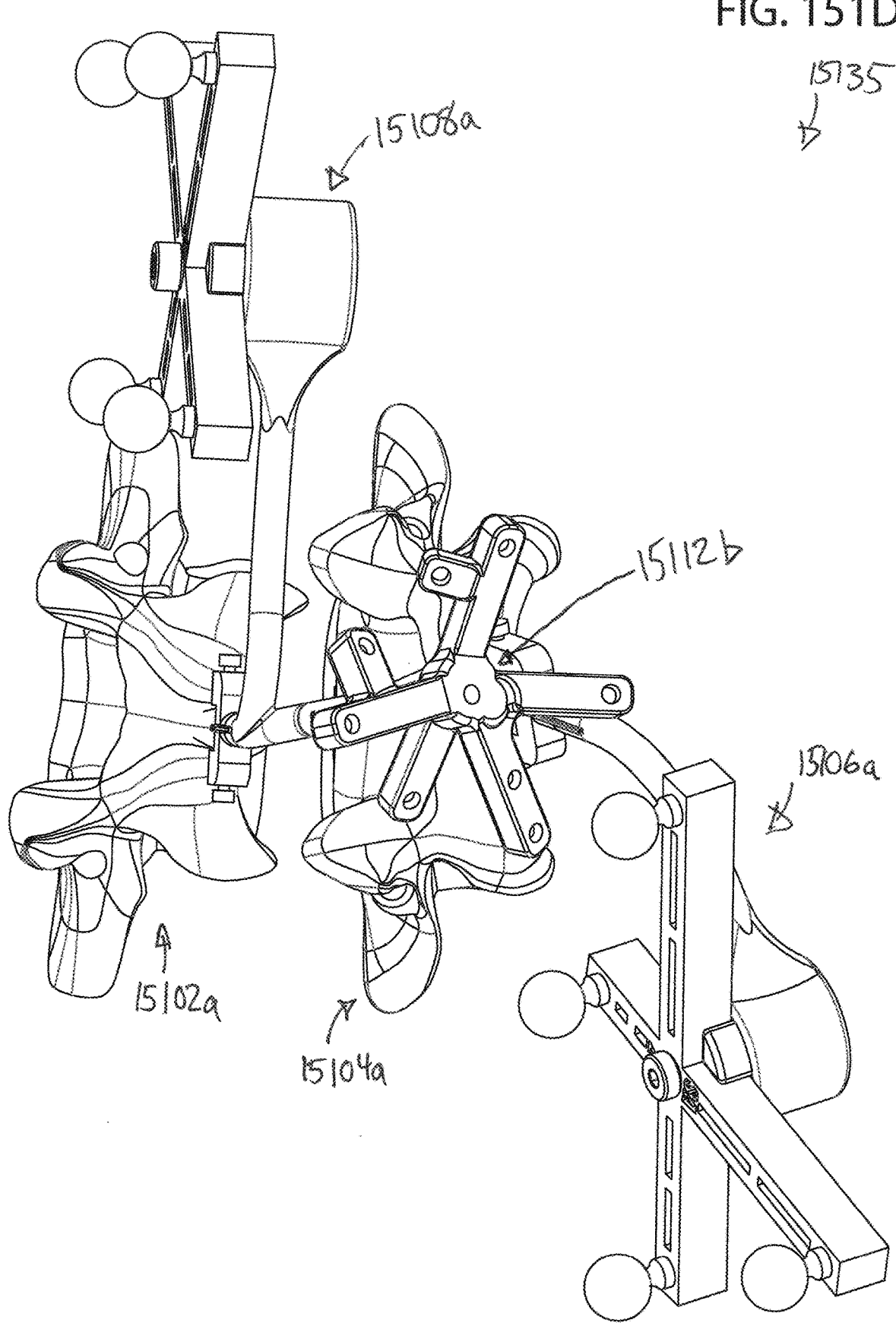

FIG. 151D illustrates coronal views of the L4 and L5 vertebrae with 3D-tracked bone-clamping fiducials, and an internal-mating X-Ray adapter engaged with a male protrusion on one of the bone-clamping fiducials, as described previously in relation to FIGS. 151A-C in accordance with some embodiments of the invention.

Figure 151E:
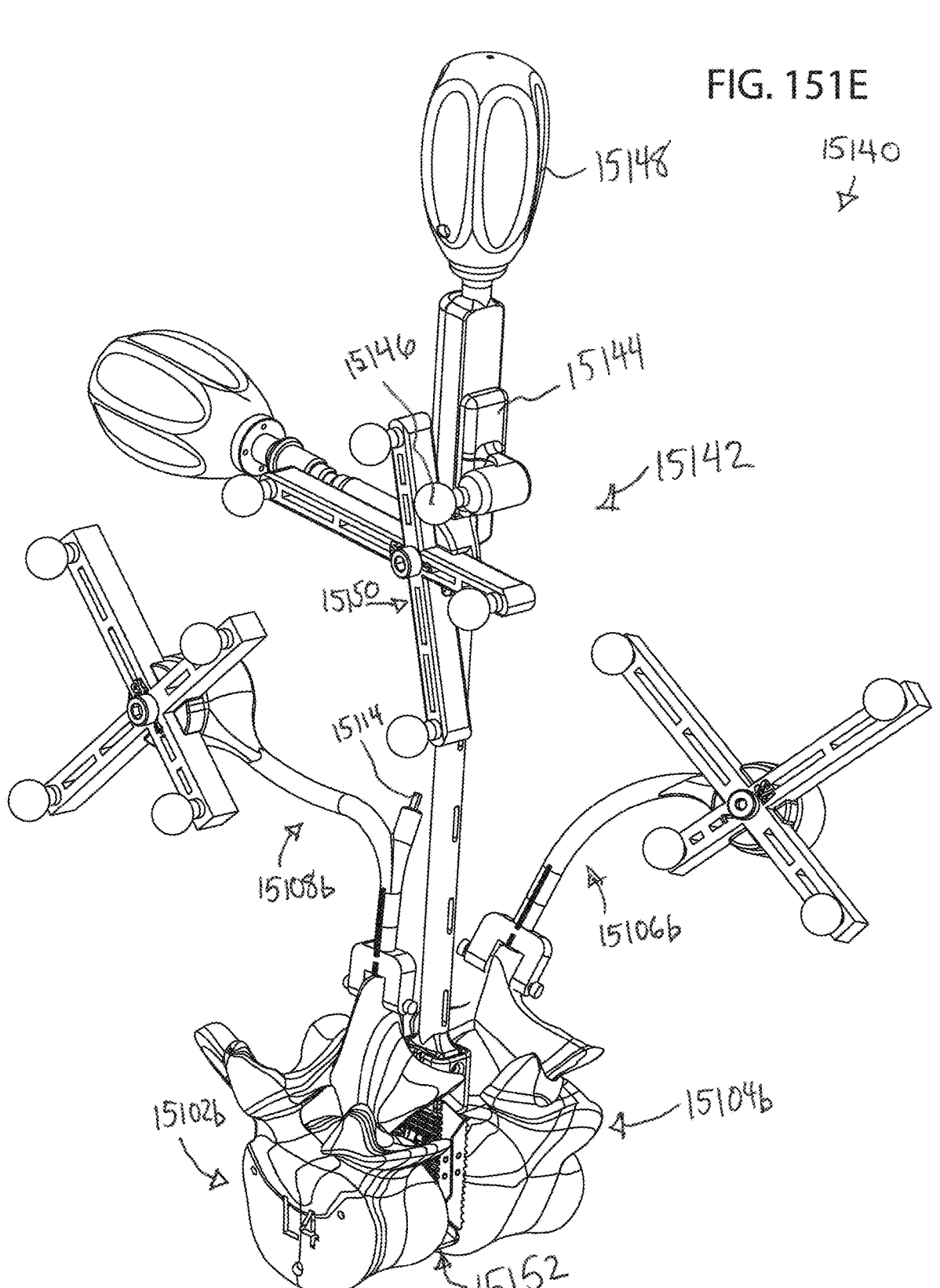

FIG. 151E illustrates perspective views of the L4 and L5 vertebrae with 3D-tracked bone-clamping fiducials attached. An interbody cage is inserted between them via a 3D-tracked implant driver that is in an inactive state. The above components are described previously in relation to FIGS. 151A-D in accordance with some embodiments of the invention.

Figures 152A, 152B, 152C:
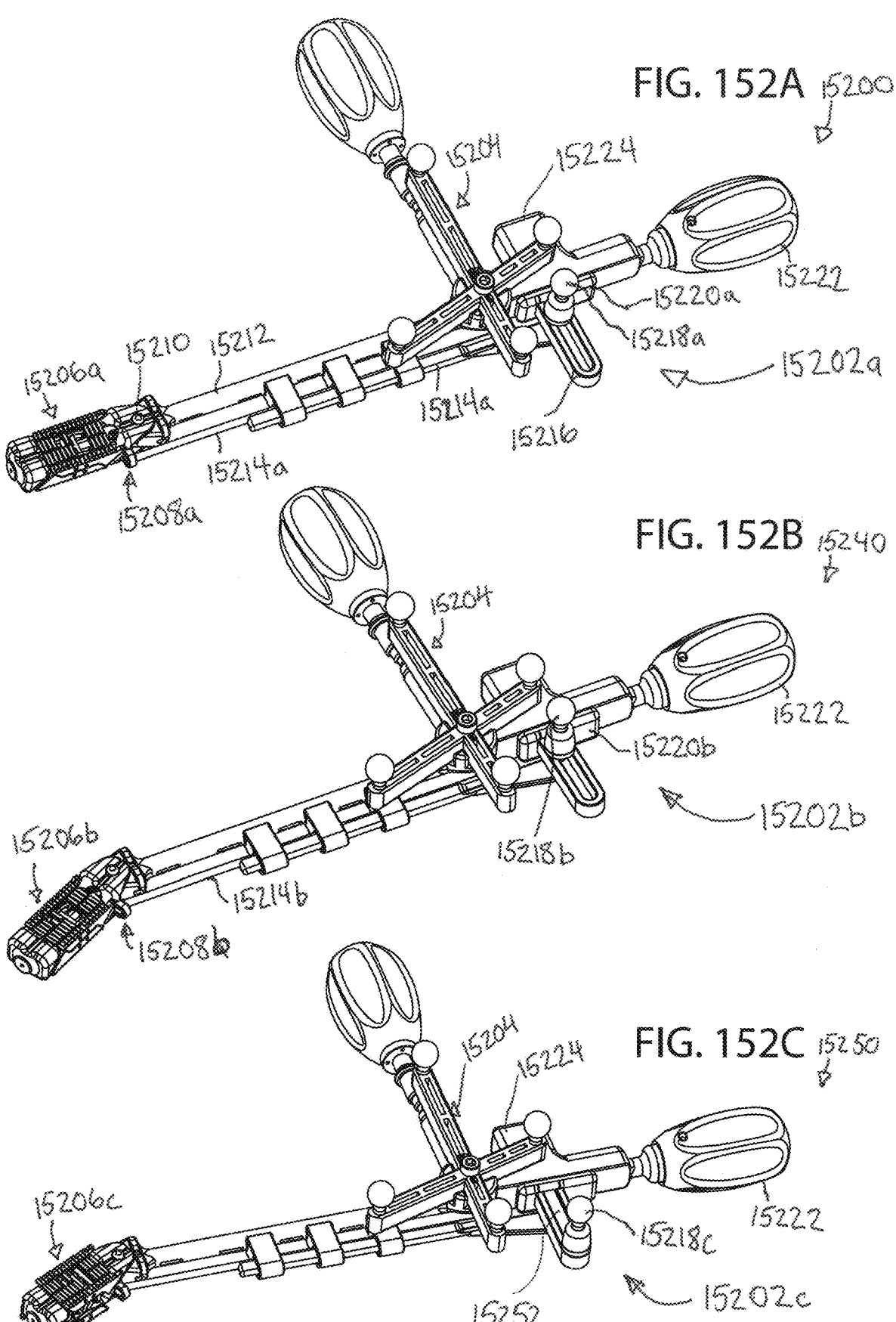

FIG. 152A illustrates a perspective view of a single-actuation 3D-tracked implant driver attached to an interbody cage and in an inactive state, in accordance with some embodiments of the invention.

FIG. 152B illustrates a perspective view of a single-actuation 3D-tracked implant driver attached to a pivoted interbody cage and in an inactive state, as described previously in relation to FIG. 152A in accordance with some embodiments of the invention.

FIG. 152C illustrates a perspective view of a single-actuation 3D-tracked implant driver attached to a pivoted and expanded interbody cage, and in an active state as indicated by the sideways movement of the mechanically-linked TMSM, as described previously in relation to FIGS. 152A-B in accordance with some embodiments of the invention.

FIG. 152D illustrates a perspective view of a single-actuation 3D-tracked implant driver attached to an expanded interbody cage, and in an active state as indicated by the sideways movement of the mechanically-linked TMSM, as described previously in relation to FIGS. 152A-C in accordance with some embodiments of the invention.

FIG. 152E illustrates a perspective view of the orthogonal, geared mechanism for converting cage-expansion motion into orthogonal actuation of the TMSM of the 3D-tracked implant driver as described previously in relation to FIGS. 152A-D in accordance with some embodiments of the invention.

Figure 153A:
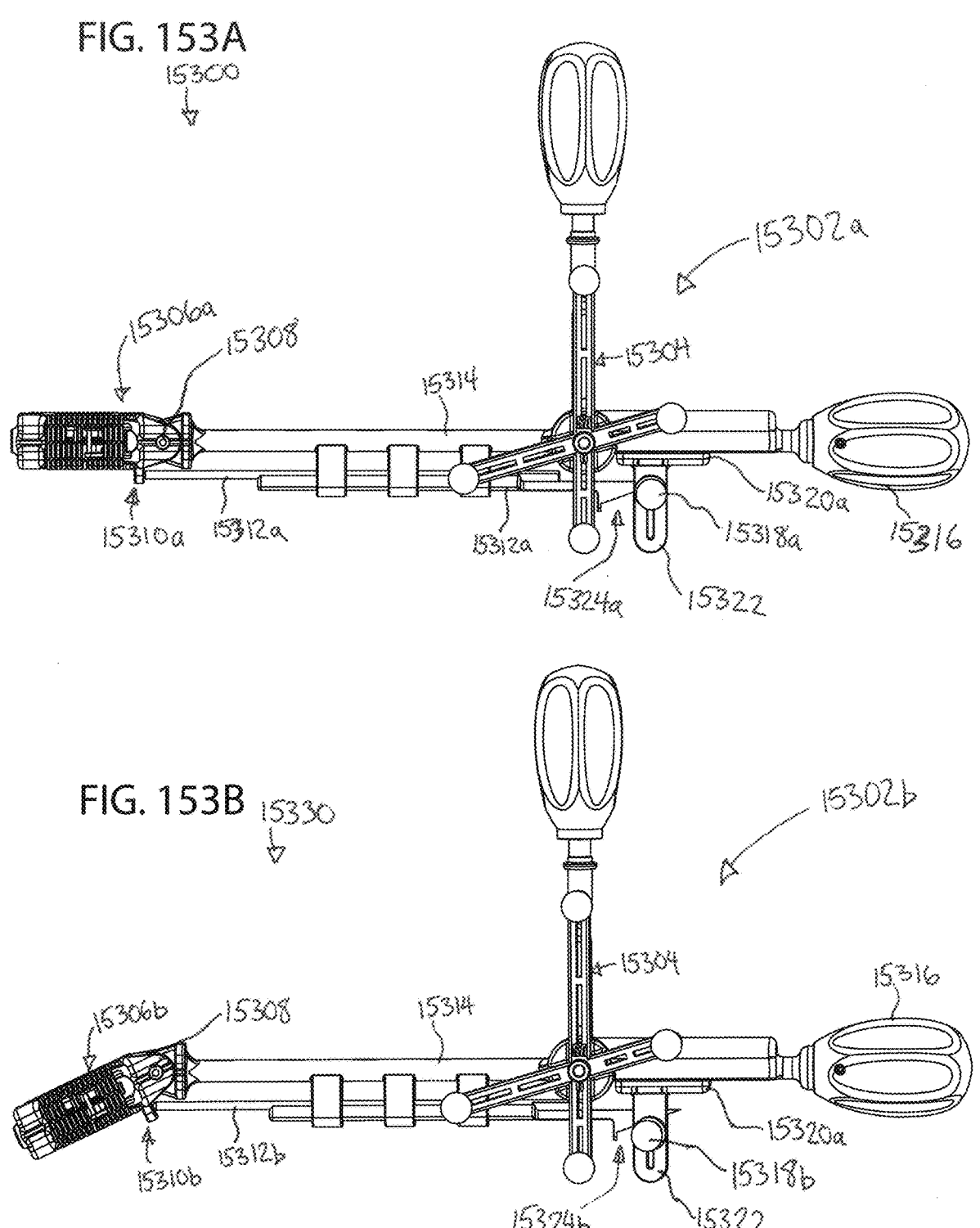

FIG. 153A illustrates a side view of a single-actuation 3D-tracked implant driver attached to an interbody cage and in an inactive state, in accordance with some embodiments of the invention.

FIG. 153B illustrates a side view of a single-actuation 3D-tracked implant driver attached to a pivoted interbody cage and in an inactive state, as described previously in relation to FIG. 153A in accordance with some embodiments of the invention.

Figures 153C, 153D, 153E:
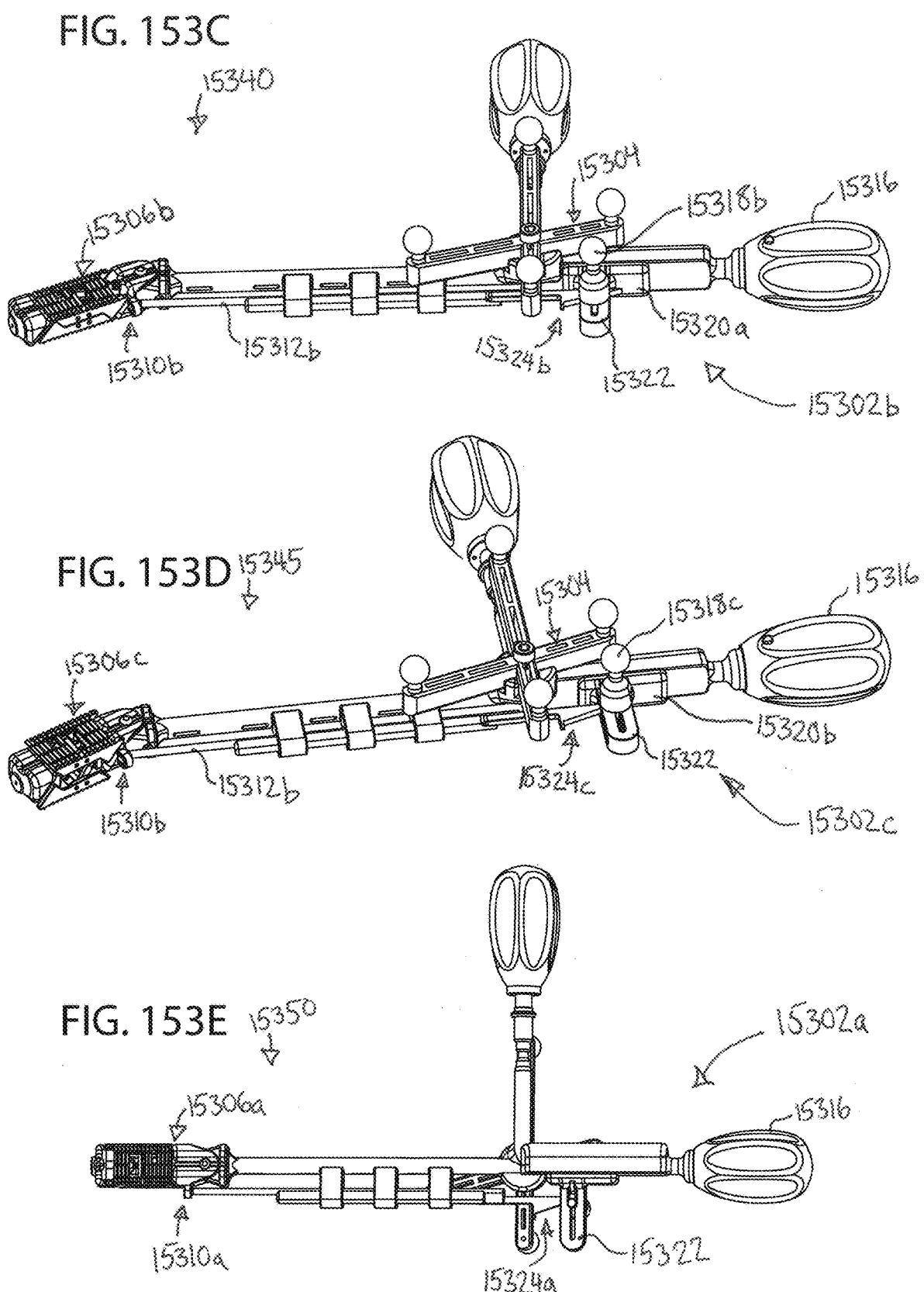

FIG. 153C illustrates a side perspective view of a single-actuation 3D-tracked implant driver attached to a pivoted interbody cage and in an inactive state, as described previously in relation to FIGS. 153A-B in accordance with some embodiments of the invention.

FIG. 153D illustrates another side perspective view of a single-actuation 3D-tracked implant driver attached to a pivoted and expanded interbody cage and in an inactive state, as described previously in relation to FIGS. 153A-C in accordance with some embodiments of the invention.

FIG. 153E illustrates a back view of a single-actuation 3D-tracked implant driver attached to an interbody cage and in an inactive state, as described previously in relation to FIGS. 153A-D in accordance with some embodiments of the invention.

FIG. 153F illustrates a perspective view of a dual-actuation 3D-tracked implant driver attached to a pivoted interbody cage and in an inactive state, as described previously in relation to FIGS. 153A-E in accordance with some embodiments of the invention.

FIG. 153G illustrates a perspective view of a dual-actuation 3D-tracked implant driver attached to a pivoted and expanded interbody cage, and in an active state as indicated by the vertical movement of the mechanically-linked TMSM, as described previously in relation to FIGS. 153A-F in accordance with some embodiments of the invention.

Figures 154A, 154B, 154C:
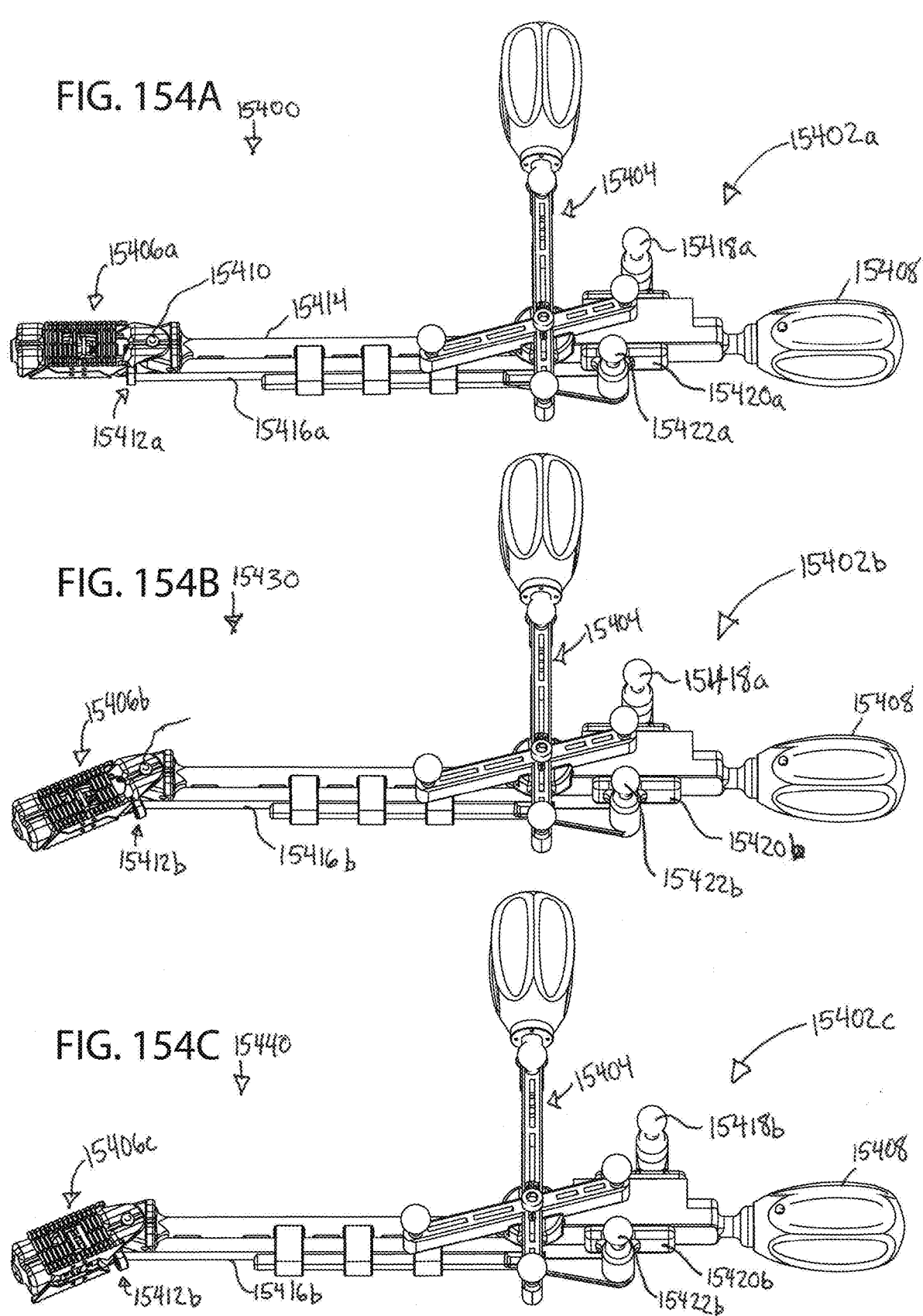

FIG. 154A illustrates a perspective view of a dual-actuation 3D-tracked implant driver attached to an interbody cage and in an inactive state, in accordance with some embodiments of the invention.

FIG. 154B illustrates a perspective view of a dual-actuation 3D-tracked implant driver attached to a pivoted interbody cage and in an inactive state, as described previously in relation to FIG. 154A in accordance with some embodiments of the invention.

FIG. 154C illustrates a perspective view of a dual-actuation 3D-tracked implant driver attached to a pivoted and expanded interbody cage, and in an active state as indicated by the vertical movement of the mechanically-linked TMSM, as described previously in relation to FIGS. 154A-B in accordance with some embodiments of the invention.

Figure 155A:

FIG. 155A illustrates perspective views of a single-actuation 3D-tracked implant driver not engaged with a corpectomy cage, in accordance with some embodiments of the invention.

Figures 155B, 155C:
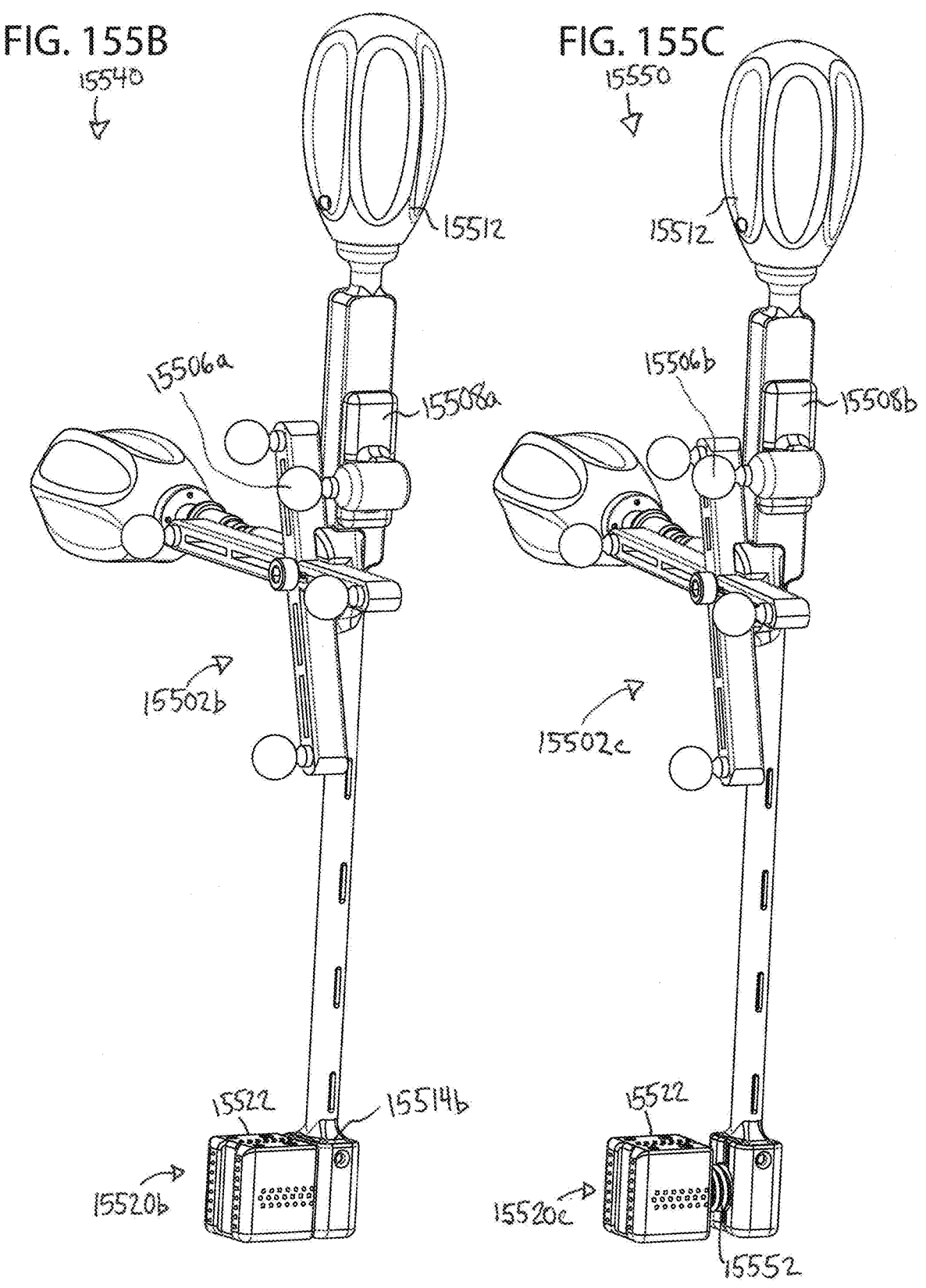

FIG. 155B illustrates perspective views of a single-actuation 3D-tracked implant driver engaged with a corpectomy cage and in an inactive state, as described previously in relation to FIG. 155A in accordance with some embodiments of the invention.

FIG. 155C illustrates perspective views of a single-actuation 3D-tracked implant driver engaged with a corpectomy cage and in an active state as the spring expands, as described previously in relation to FIGS. 155A-B in accordance with some embodiments of the invention.

Figure 156A:
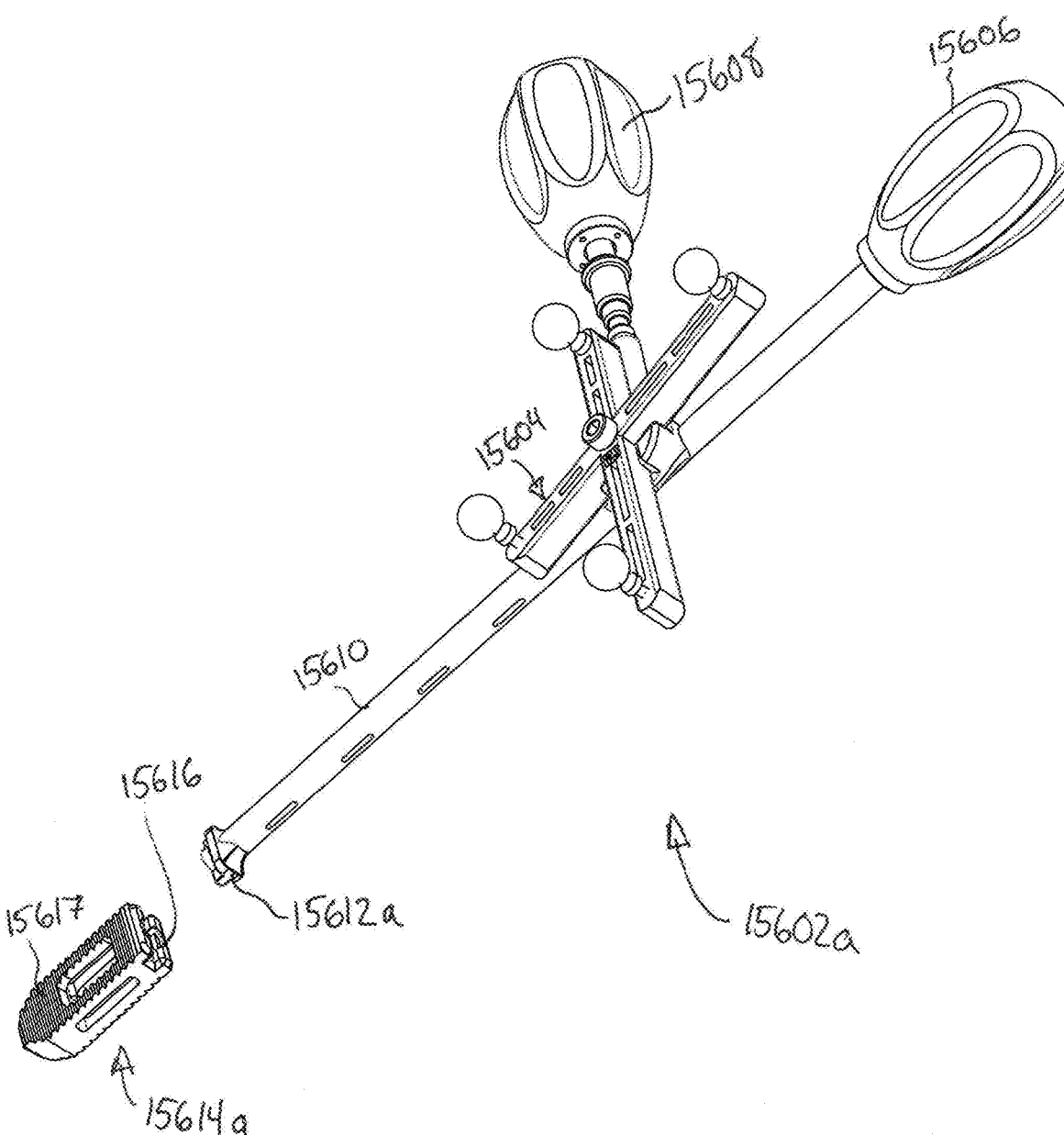

FIG. 156A illustrates perspective views of a 3D-tracked implant driver with no actuation mechanism not engaged with a rigid non-actuating interbody cage in accordance with some embodiments of the invention.

Figure 156B:
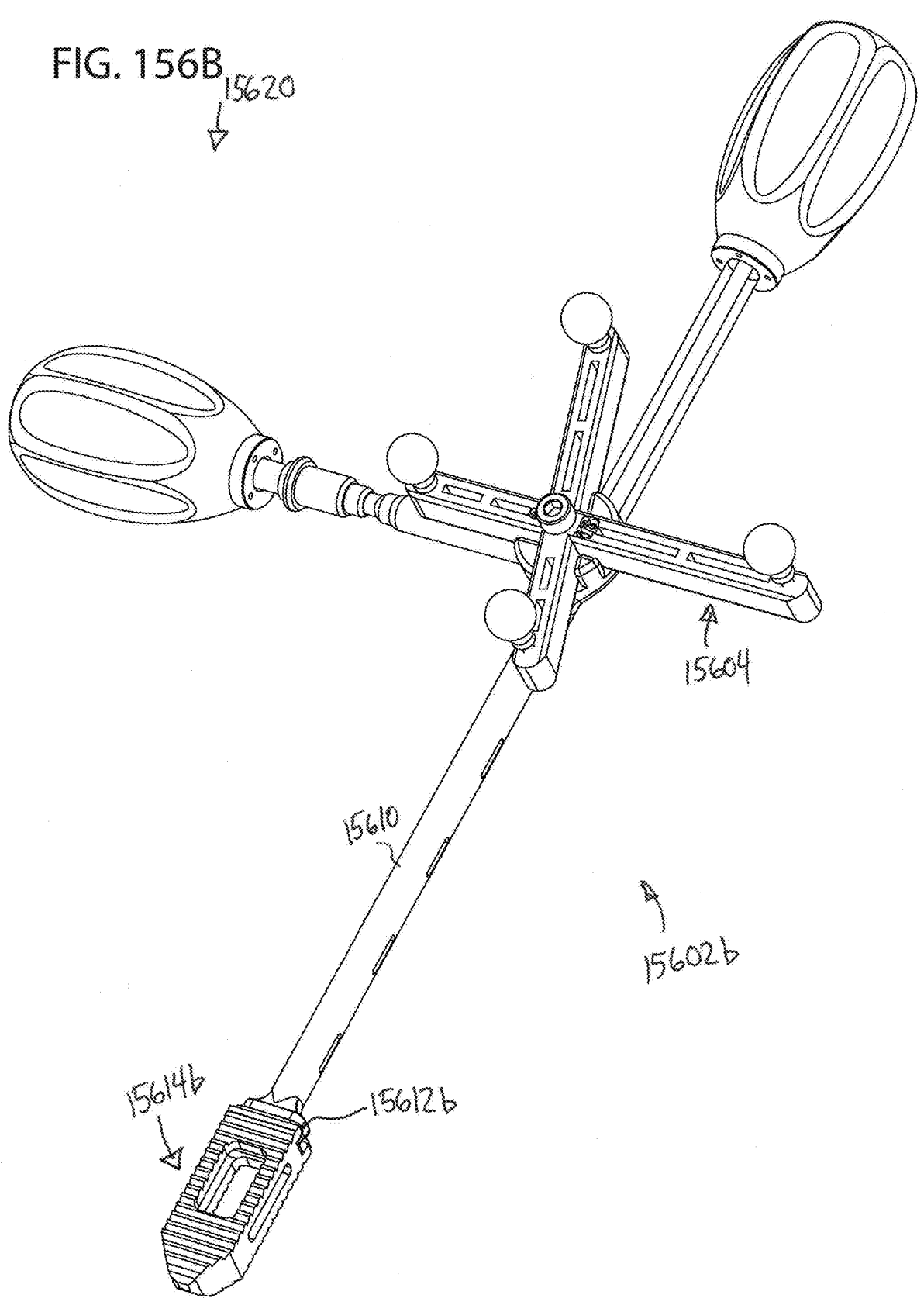

FIG. 156B illustrates perspective views of a 3D-tracked implant driver with no actuation mechanism engaged with a rigid non-actuating interbody cage, as described previously in relation to FIG. 156A in accordance with some embodiments of the invention.

Figure 156C:
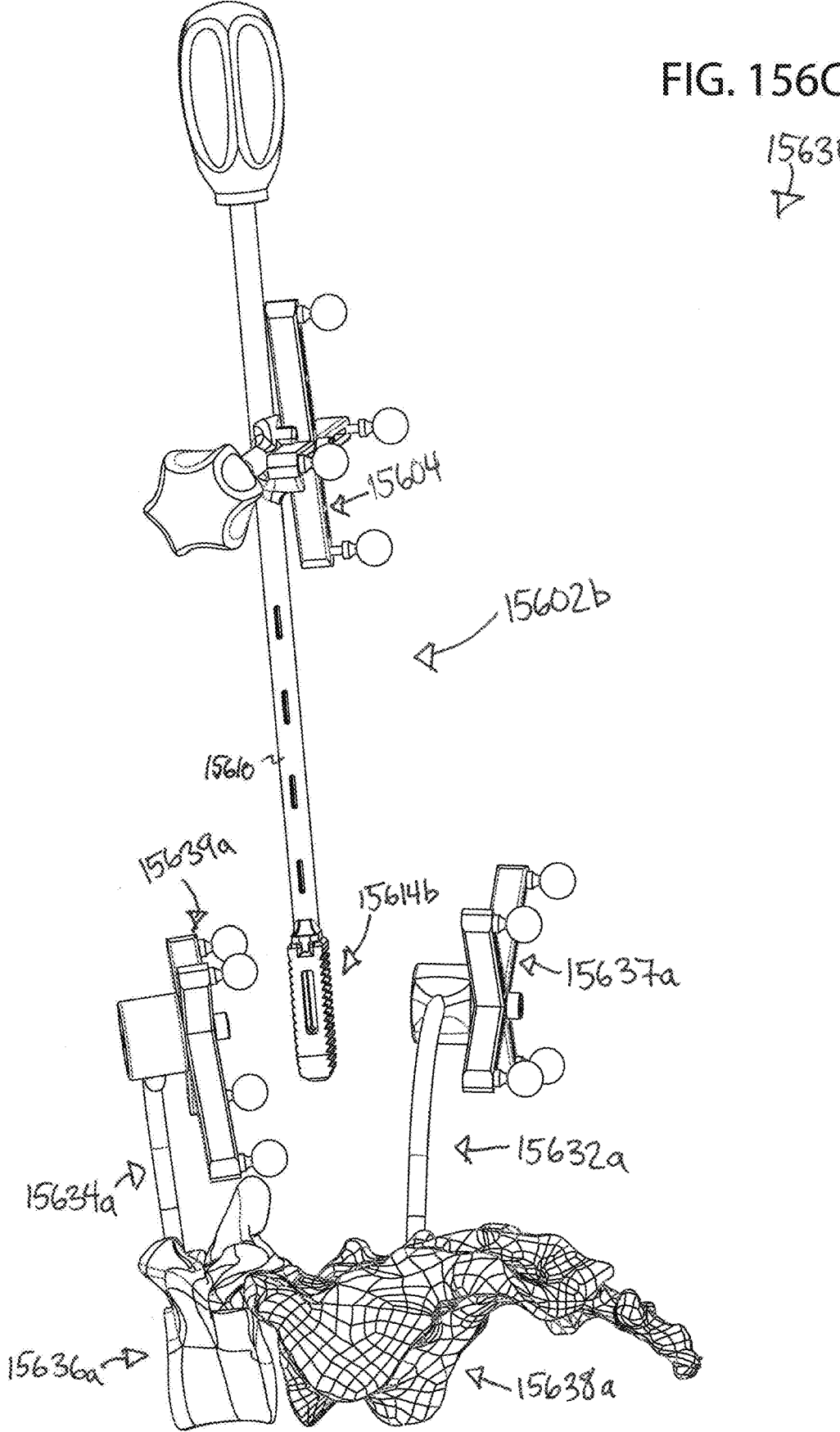

FIG. 156C illustrates side views of a 3D-tracked implant driver with no actuation mechanism engaged with a rigid non-actuating interbody cage and not inserted between the sacrum and L5 vertebra, which are both implanted with bone-mounted fiducials mated with 3D-tracked DRFs, as described previously in relation to FIGS. 156A-B in accordance with some embodiments of the invention.

Figure 156D:
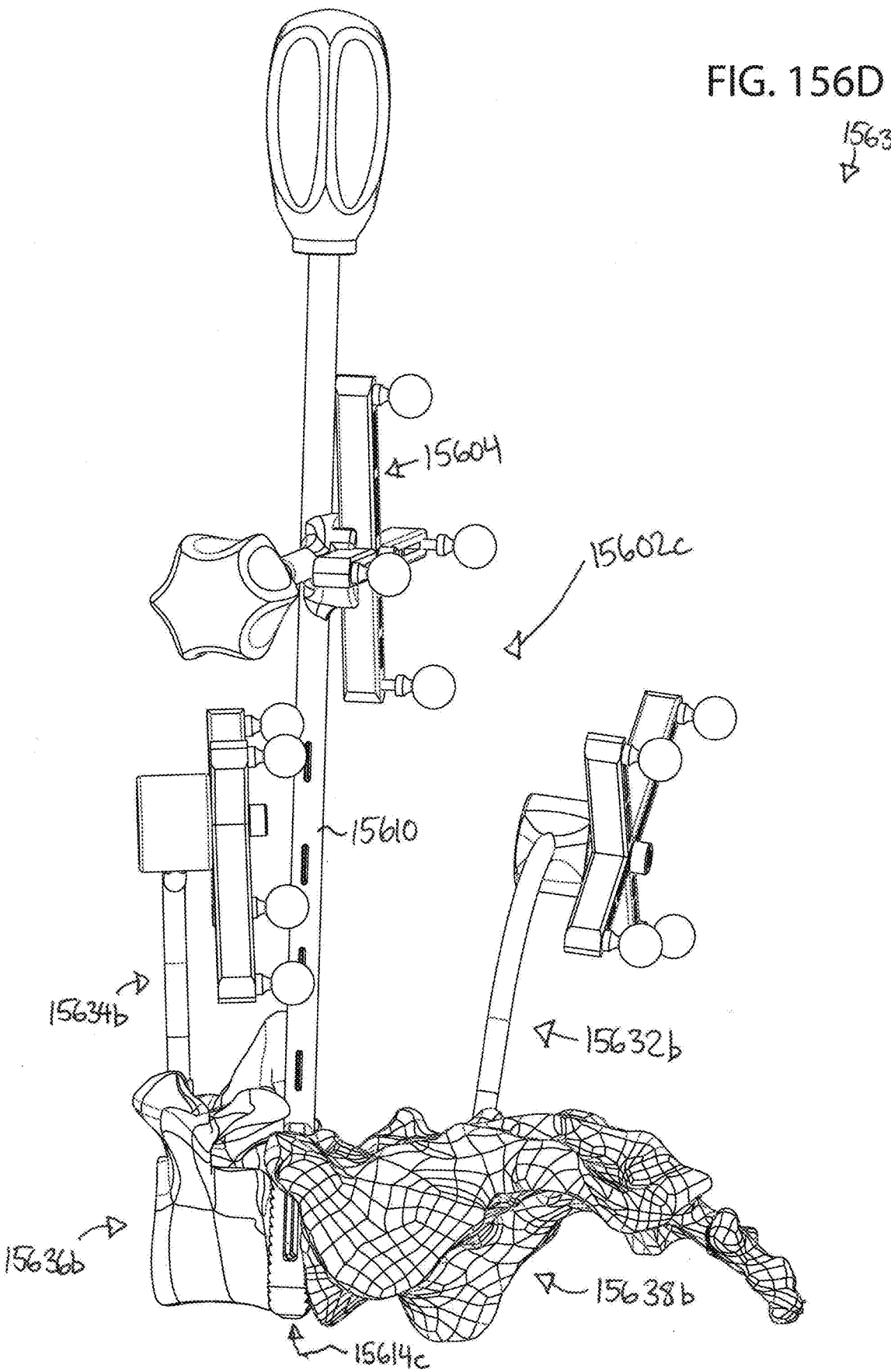

FIG. 156D illustrates side views of a 3D-tracked implant driver with no actuation mechanism engaged with a rigid non-actuating interbody cage inserted between the sacrum and L5 vertebra, which are both implanted with bone-mounted fiducials mated with 3D-tracked DRFs, as described previously in relation to FIGS. 156A-C in accordance with some embodiments of the invention.

Figure 156E:
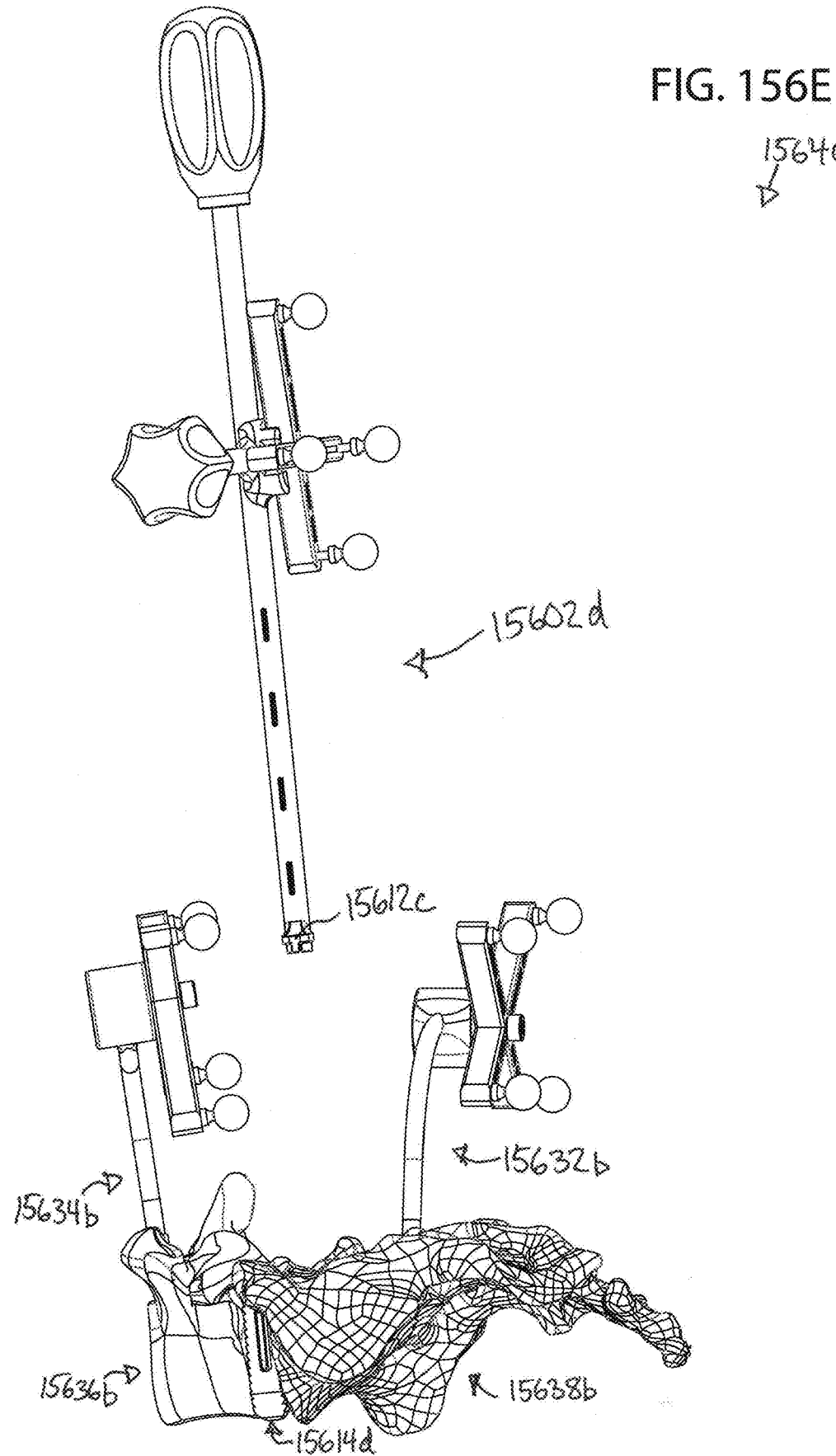

FIG. 156E illustrates side views of a 3D-tracked implant driver with no actuation mechanism removed from a rigid non-actuating interbody cage inserted between the sacrum and L5 vertebra, which are both implanted with bone-mounted fiducials mated with 3D-tracked DRFs, as described previously in relation to FIGS. 156A-D in accordance with some embodiments of the invention.

Figure 156F:
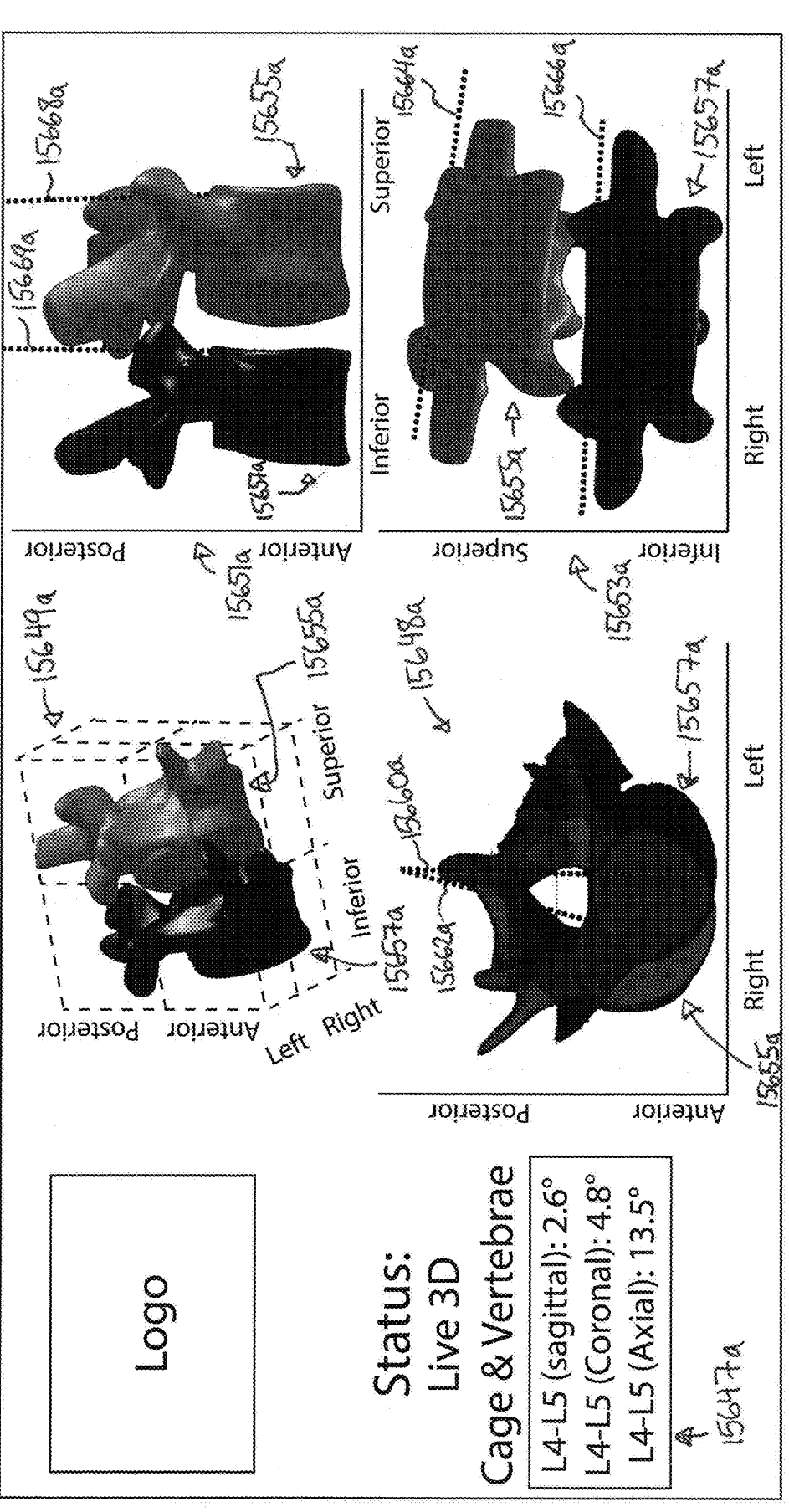

FIG. 156F illustrates a display interface for illustrating in real-time, the 3D motions of vertebrae, visual representations of their endplates, and their associated spinal alignment parameters in sagittal, coronal, axial, and perspective views, as described previously in relation to FIGS. 156A-E in accordance with some embodiments of the invention.

Figure 156G:
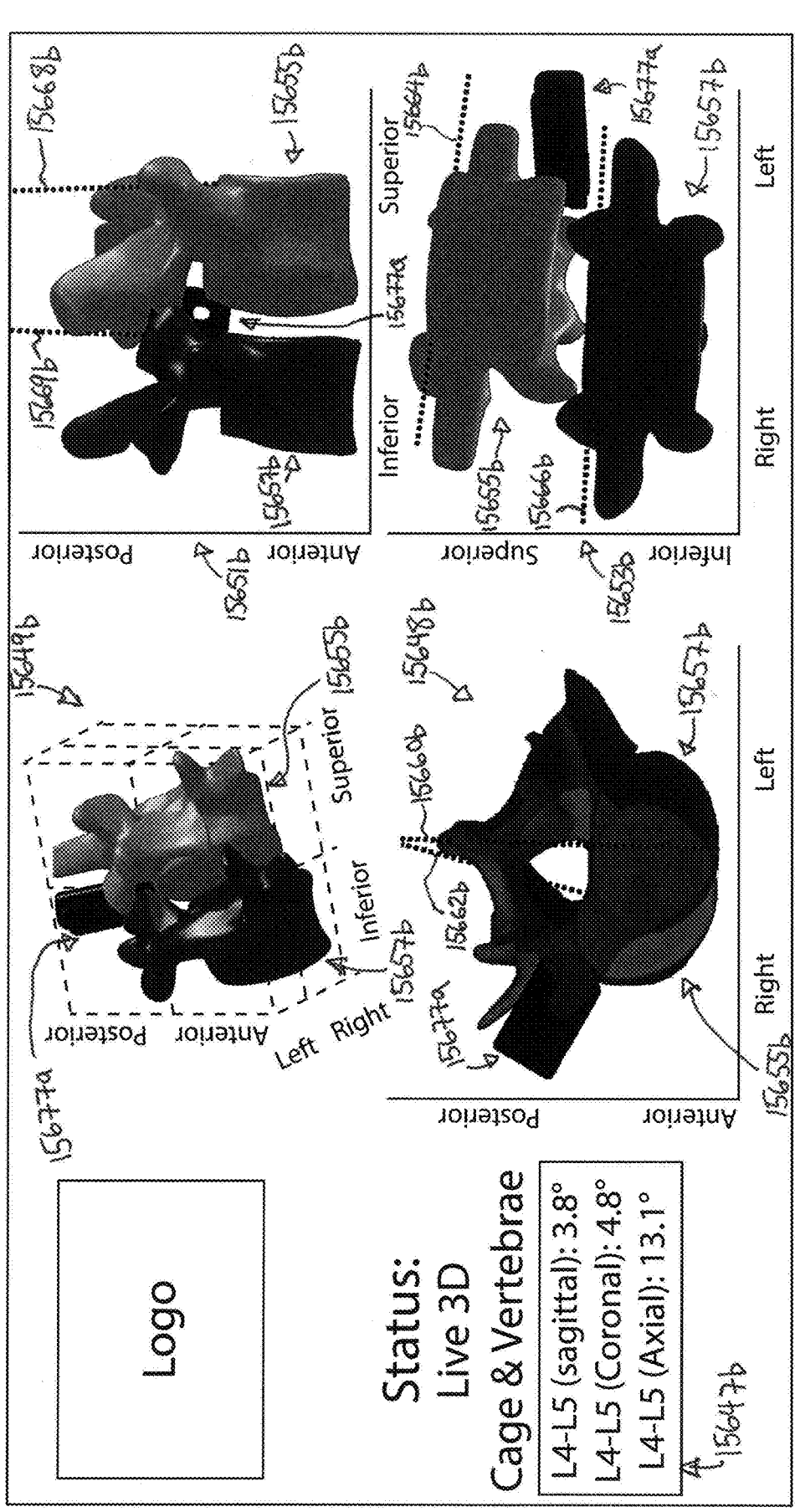

FIG. 156G illustrates a display interface for illustrating in real-time, the 3D motions of vertebrae, visual representations of their endplates, and their associated spinal alignment parameters, as well as the 3D motion of an interbody cage being inserted between the vertebrae, in sagittal, coronal, axial, and perspective views, as described previously in relation to FIGS. 156A-F in accordance with some embodiments of the invention.

Figure 156H:
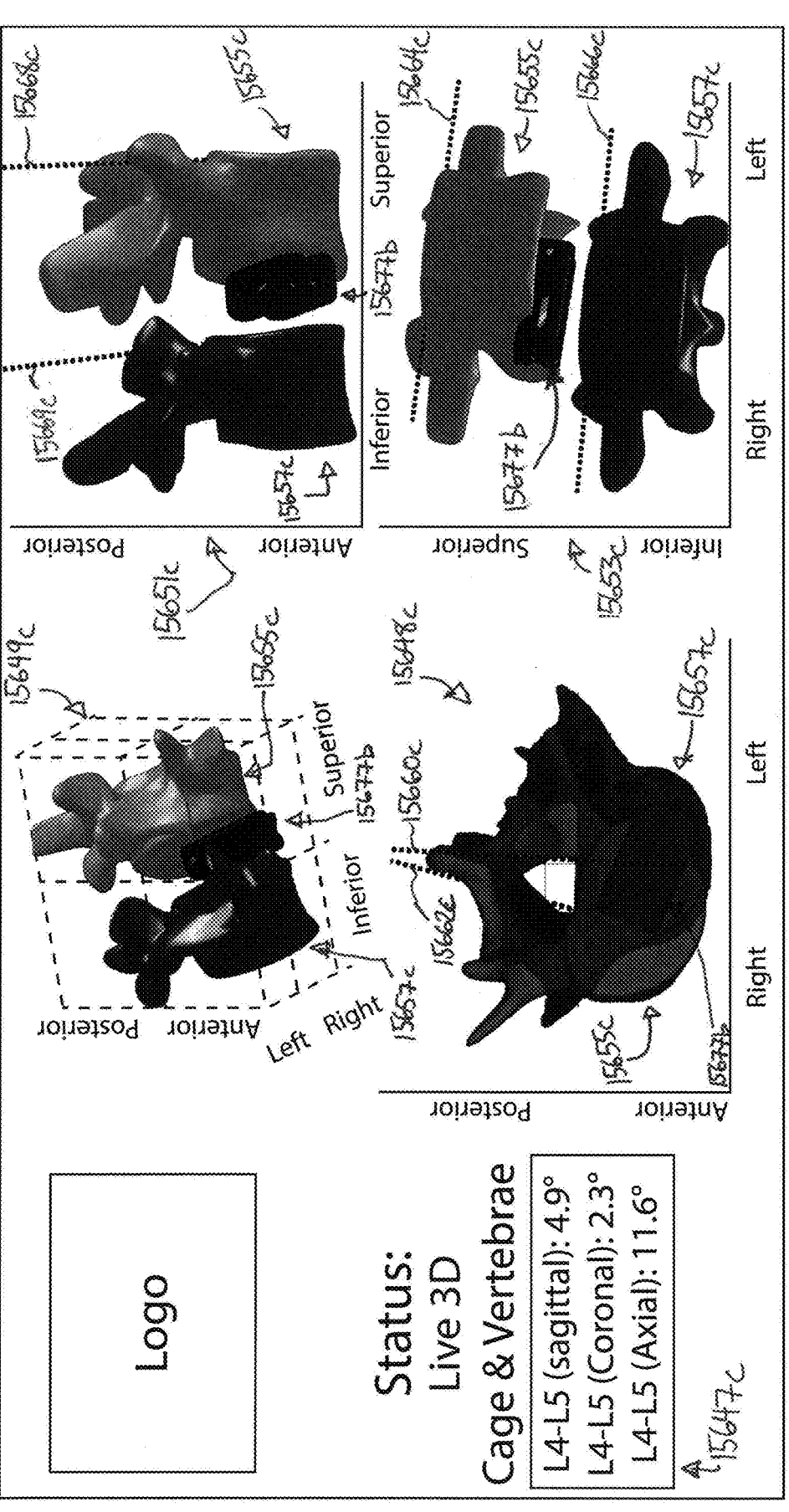
Figure 157A:
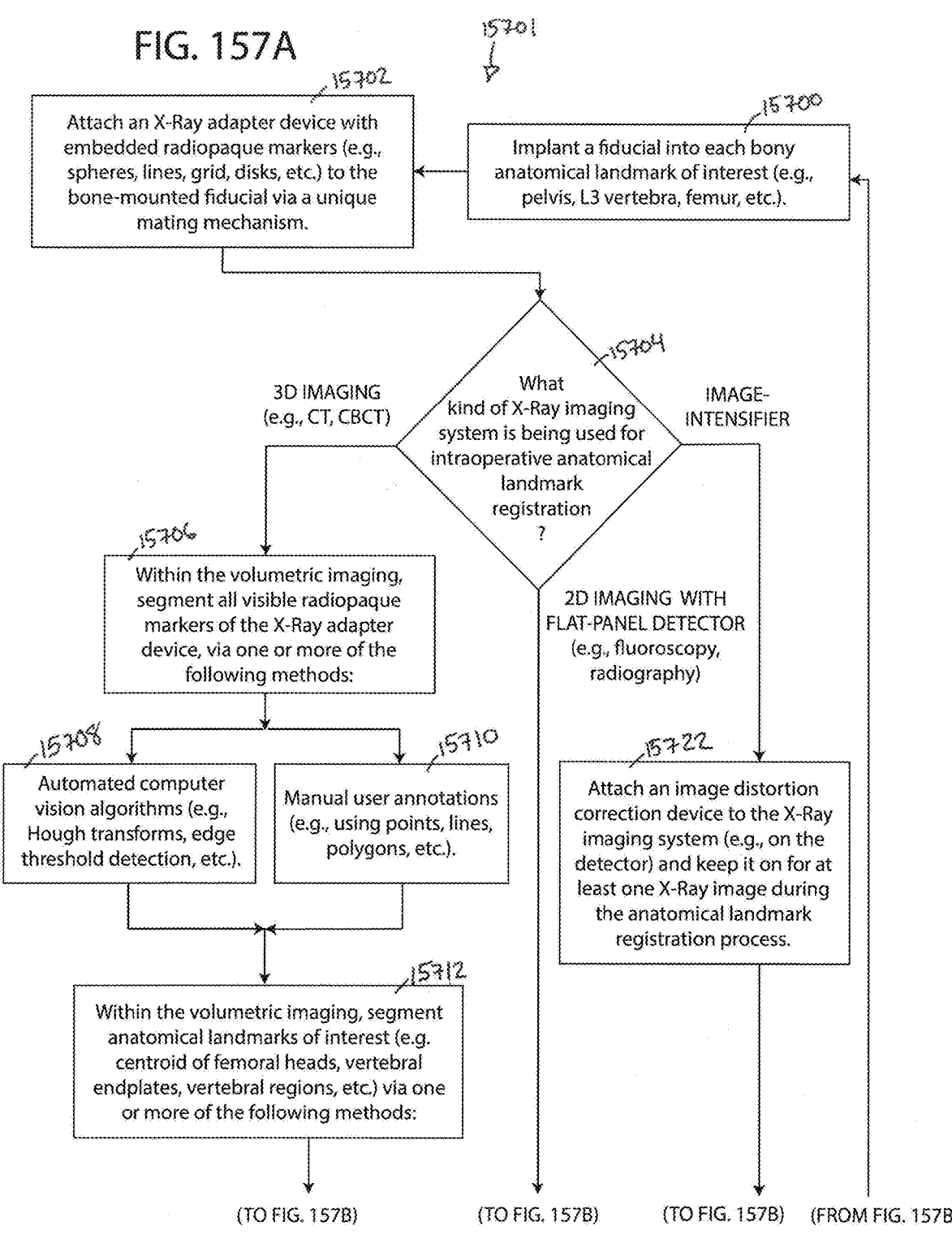
Figure 157G:
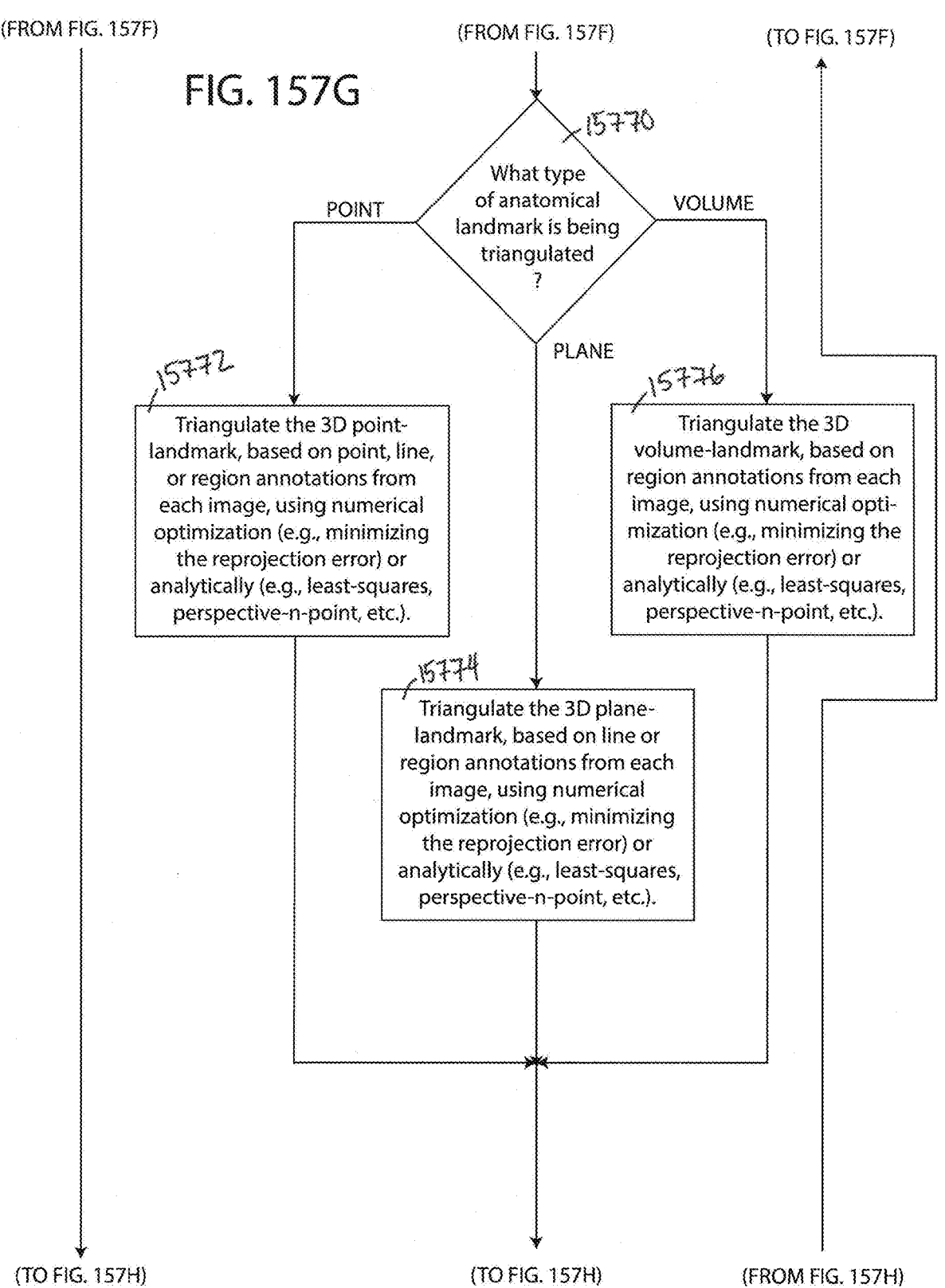
Figure 159G:
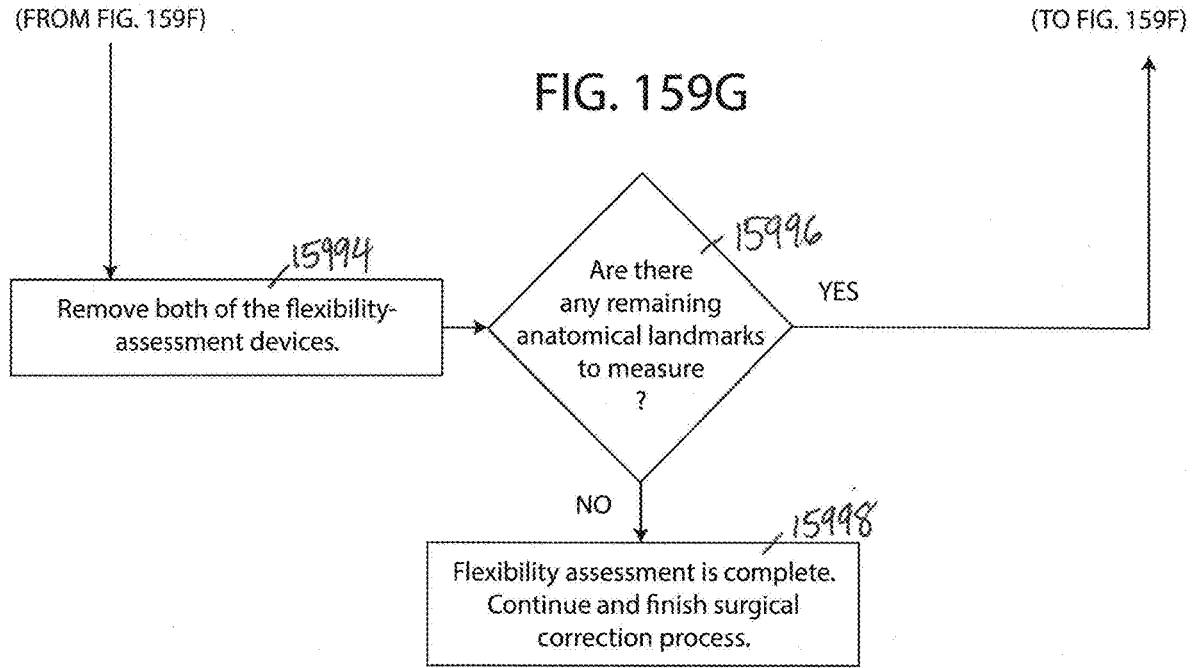

FIG. 156H illustrates a display interface for illustrating in real-time, the 3D motions of vertebrae, visual representations of their endplates, and their associated spinal alignment parameters, as well as the 3D motion of an interbody cage after insertion between the vertebrae, in sagittal, coronal, axial, and perspective views, as described previously in relation to FIGS. 156A-G in accordance with some embodiments of the invention.

FIGS. 157A-J illustrate a workflow for registering the 3D location of anatomical landmarks relative to a bone-mounted fiducial, and using those registered landmarks, in some cases in combination with non-fiducial-based inputs of the patient's anatomy (e.g., bilateral laminae tracings, preoperative planning alignment parameters, patient normative data, etc.), to compute the patient's spinal alignment parameters, in accordance with some embodiments of the invention.

FIGS. 158A-B illustrate a workflow for registering the 3D location of multiple vertebrae relative to its unique bone-mounted fiducials and using those registered landmarks to compute the patient's spinal alignment parameters, in accordance with some embodiments of the invention.

FIGS. 159A-G illustrate a workflow for providing real-time, visual and quantitative feedback of implant (e.g. interbody cage) insertion into the spine in accordance with some embodiments of the invention.

FIGS. 160A-D illustrate a workflow for assessing the 3D range of motion of vertebrae of the spine, and if alignment goals are met, locking the vertebrae in place via a set-and-hold mechanism and securing surgical rods in place, in accordance with some embodiments of the invention.

Figure 161:
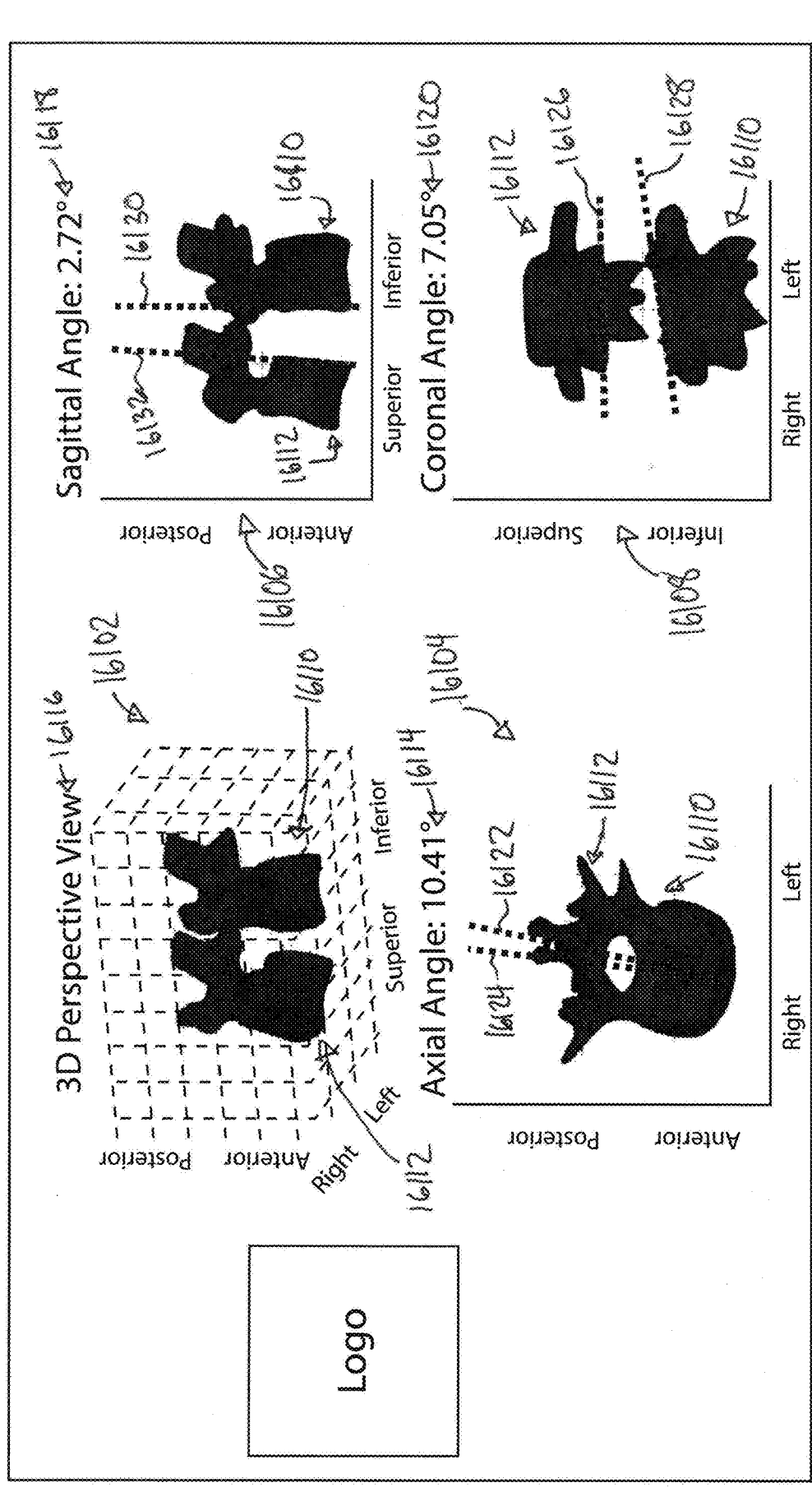

FIG. 161 illustrates a display interface for illustrating in real-time, the 3D motions of vertebrae attached to flexibility-assessment devices, visual representations of their endplates, and their associated spinal alignment parameters, in sagittal, coronal, axial, and perspective views in accordance with some embodiments of the invention.

Figure 162A:
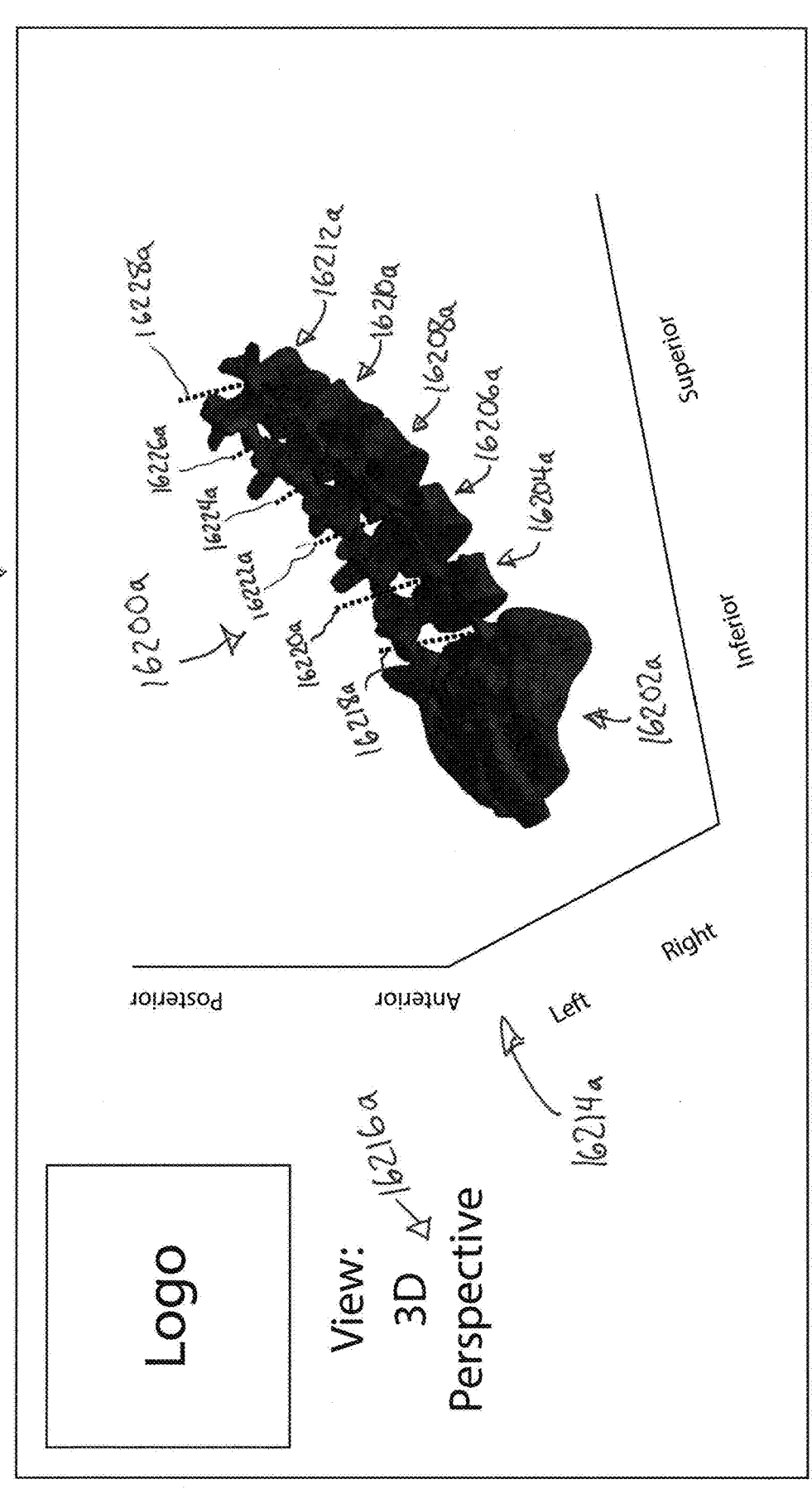

FIG. 162A illustrates a display interface for illustrating the 3D locations and poses of vertebrae (e.g., sacrum and lumbar vertebrae) registered via bone-mounted fiducials, along with visual representations of their endplates in a perspective view in accordance with some embodiments of the invention.

Figure 162B:
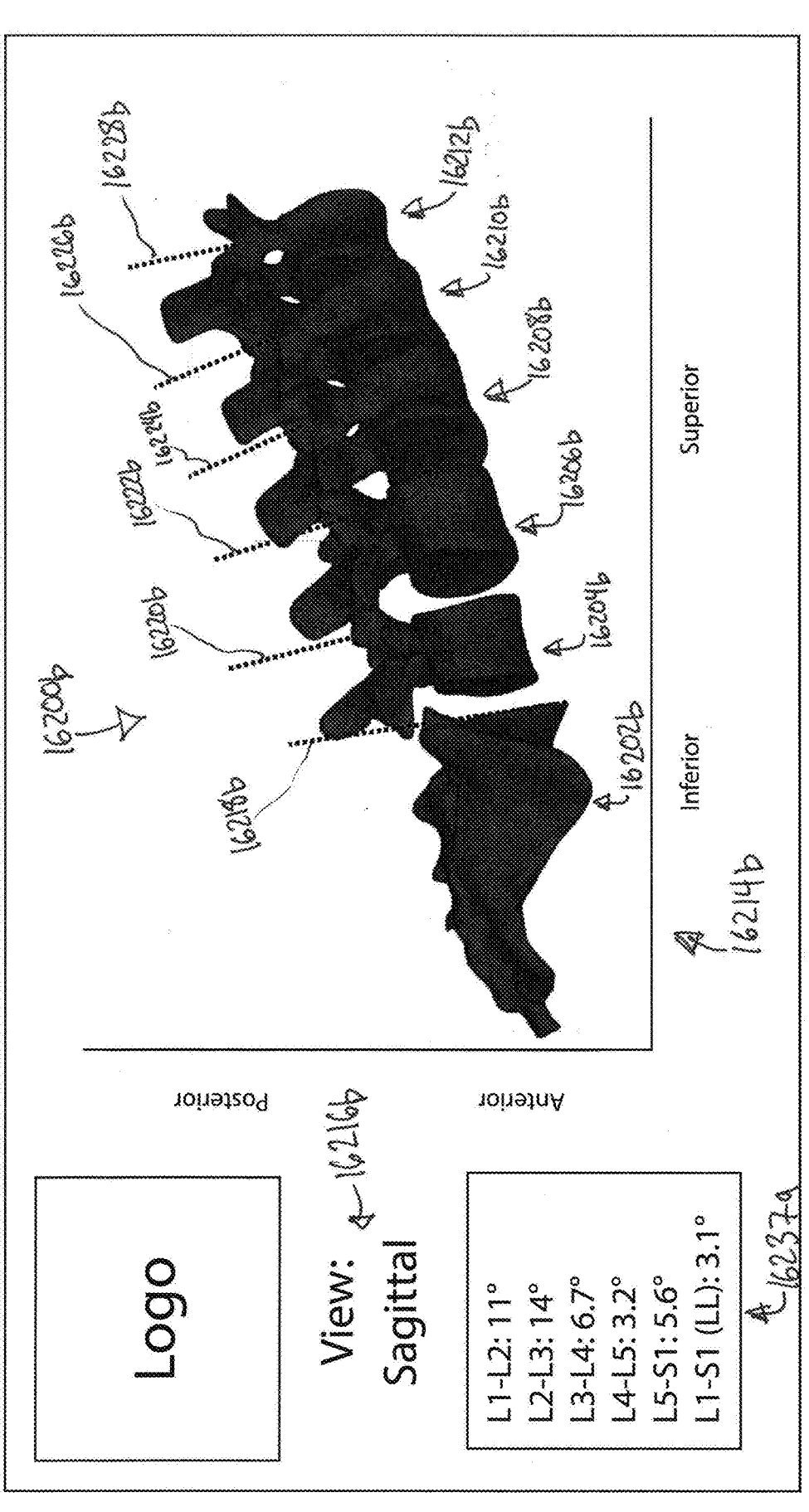

FIG. 162B illustrates a display interface for illustrating the 3D locations and poses of vertebrae (e.g., sacrum and lumbar vertebrae) registered via bone-mounted fiducials, along with visual representations of their endplates and their associated spinal alignment parameters (e.g., inter-vertebral angles), in a sagittal plane view, as described previously in relation to FIG. 162A in accordance with some embodiments of the invention.

Figure 162C:
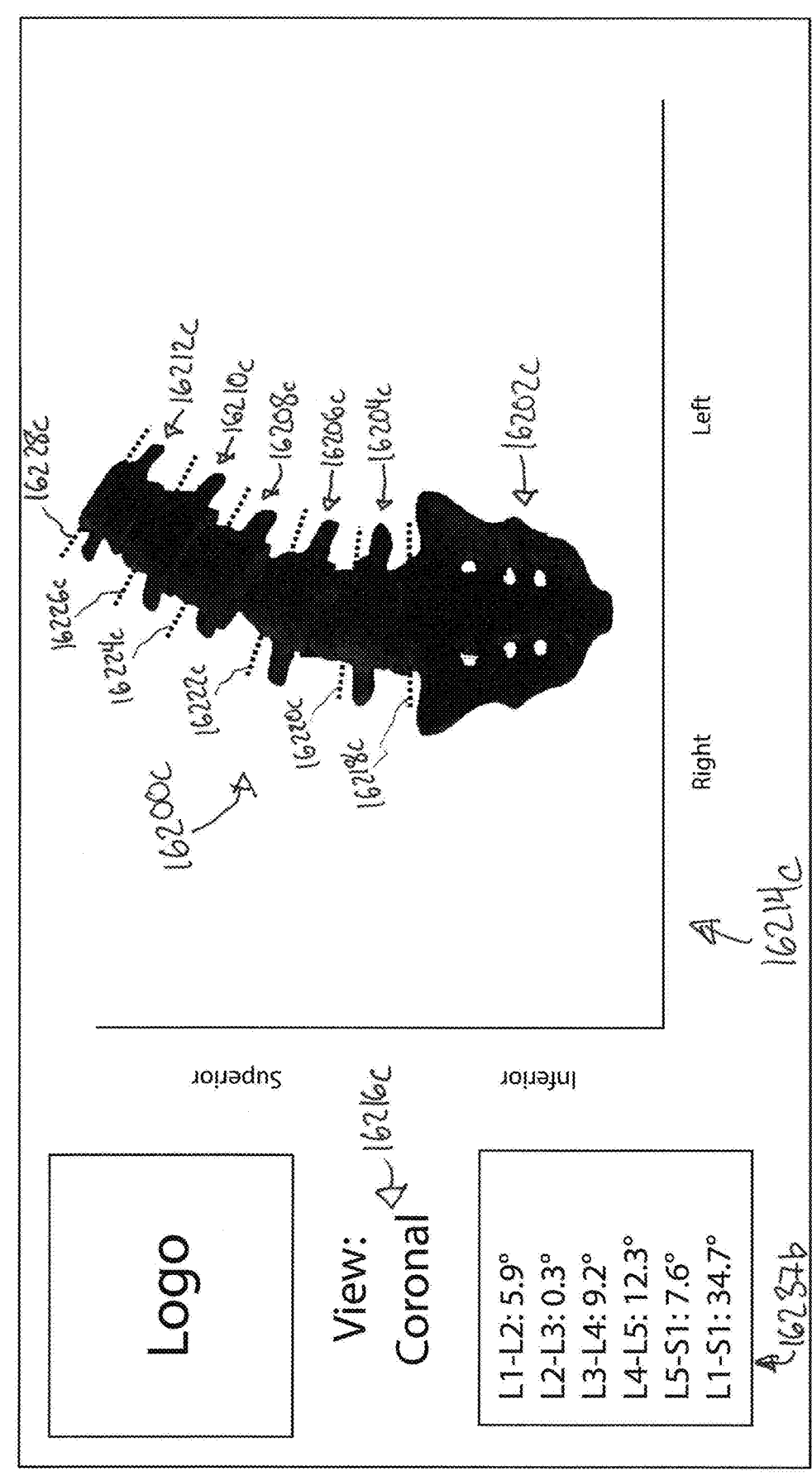

FIG. 162C illustrates a display interface for illustrating the 3D locations and poses of vertebrae (e.g., sacrum and lumbar vertebrae) registered via bone-mounted fiducials, along with visual representations of their endplates and their associated spinal alignment parameters (e.g., inter-vertebral angles), in a coronal plane view, as described previously in relation to FIGS. 162A-B in accordance with some embodiments of the invention.

Figure 162D:
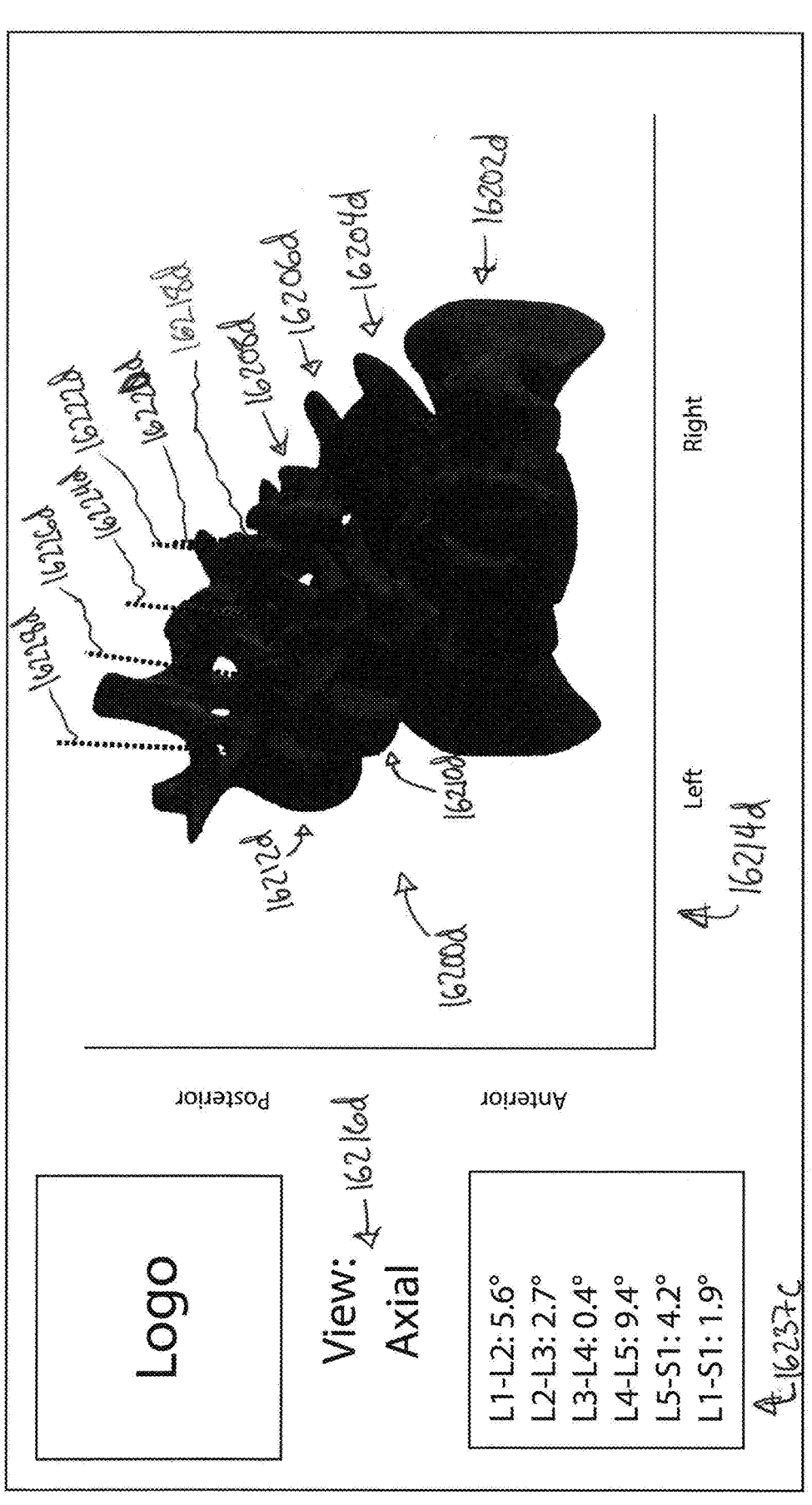

FIG. 162D illustrates a display interface for illustrating the 3D locations and poses of vertebrae (e.g., sacrum and lumbar vertebrae) registered via bone-mounted fiducials, along with visual representations of their endplates and their associated spinal alignment parameters (e.g., inter-vertebral angles), in an axial plane view, as described previously in relation to FIGS. 162A-C in accordance with some embodiments of the invention.

DETAILED DESCRIPTION

Before any embodiments of the invention are explained in detail, it is to be understood that the invention is not limited in its application to the details of construction and the arrangement of components set forth in the following description or illustrated in the following drawings. Some embodiments of the invention are configured to be combined with some other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, in some embodiments, the terms "mounted," "connected," "supported," and "coupled" and variations thereof are used broadly and encompass both direct and indirect mountings, connections, supports, and couplings. Further, in some embodiments, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to some embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

In some embodiments, "tracked" refers to the ability of a particular object to interface with a tracking device (e.g., such as one or more 3D-tracking optical cameras and/or one or more 3D-tracking electromechanical devices) in at least FIG. 4H, FIG. 5B, FIGS. 7-8, FIGS. 10A-10G, FIGS. 11A-11B, FIGS. 14A-14C, FIGS. 15A-15C, FIG. 16, FIGS. 17A-17B, FIGS. 18A-18B, FIGS. 19A-19E, FIGS. 20, and 20A-20E, FIGS. 21A-21B, FIG. 22, FIGS. 23A-23C, FIGS. 24-26, FIGS. 27A-27D, FIGS. 28A-28B, FIGS. 29A-29D, FIG. 30B, FIG. 31, FIG. 38, FIGS. 38A-38G, FIGS. 39A-39F, FIGS. 40A-40C, FIGS. 41A-41D, FIGS. 42A-42K, FIGS. 43A-43F, FIGS. 44A-44D, FIGS. 44A-44B, FIGS. 46A-46G, FIGS. 47A-47B, FIGS. 48A-48C, FIGS. 49A-49D, FIGS. 50A-50E, FIGS. 51A-51I, FIGS. 52A-52D, FIGS. 53A-53F, FIGS. 54A-54D, FIGS. 55A-55I, FIGS. 56A-56F, FIGS. 57A-57D, FIGS. 64A-64B, FIGS. 73A-73B, FIGS. 77A-77C, FIGS. 79A-79G, FIGS. 82A-82B, FIGS. 87A-87K, FIGS. 88A-88F, FIG. 116J, FIGS. 117D-117G, 117I-117J, FIGS. 118D-3H, FIGS. 119G-119K, FIGS. 120F-120H, FIGS. 124D-124H, FIGS. 125A-125D, FIG. 126, FIG. 127, FIGS. 128C-128D, FIGS. 129A-129D, FIG. 130, FIG. 132, etc., that tracks the 3D coordinates of the tracked object relative to the tracking system's coordinate system. One example of an object that is "tracked" is when it possesses a substantially rigidly-attached dynamic reference frame that is tracked in 3D space.

In some embodiments, a dynamic reference frame (hereinafter "DRF") refers to three or more points (markers) that are positioned in a uniquely identifiable configuration such that their discrete locations are associated with an object identity. Some embodiments include uniquely-arranged markers that can allow for the calculation of both the 3D location and pose of a DRF.

Some embodiments can also define a coordinate system relative to the DRF. In some embodiments, a stray marker refers to a 3D-tracked object, typically either light-reflective or light-emitting, which can be visualized by a 3D-tracking camera and is not one of the markers that define a DRF. In some embodiments, a stray marker can be associated with a DRF as well as have its location, pose, and behavior computed relative to one or more DRFs.

In some embodiments, a tracked mobile stray marker (TMSM) refers to a stray marker that is designed to move relative to either other stray markers or to nearby DRFs. In some embodiments, the computation of a TMSM's position and/or motion relative to those other entities can be interpreted to communicate information and/or commands to a computer acquisition system.

In some embodiments, a probe refers and/or defines a device that is tracked in such a way that its location, orientation, and identity are known in 3D space. In some embodiments, the system can extrapolate the location and orientation of other points and/or markers on and/or near the tracked object (e.g., the tip, shaft, unique features, etc.) even if they aren't directly tracked independently.

Some embodiments include a fiducial. In some embodiments, a fiducial can be an object that is used primarily as a reference to another point in space. In some embodiments, a fiducial can be placed near an object/region of interest. In some embodiments, the relative position of the fiducial to the object of interest can be initialized. In some embodiments, the location and orientation of the fiducial can be referenced in the future after initialization. In some embodiments, the precise location of the initialized object/region of interest can be calculated. In some embodiments, fiducials can have unique surface patterns in the form of indentations to be tapped, grooves to be traced, and/or mating features to be coupled. In some embodiments, the fiducial unique surface patterns can interact with a 3D-tracked probe or end-effector. In some embodiments, the fiducial's 3D location and orientation, as well as identity, can be calculated by the acquisition system. In some embodiments, a fiducial can be an object with embedded radiopaque markers, that enable for the fiducial's visualization and registration by radiographic imaging. Some embodiments include, a fiducial marker. In some embodiments, the fiducial maker can be used as an equivalent term to "fiducial", unless referring specifically to the embedded "radiopaque markers" within the fiducial structure that can be visualized on X-rays.

In some embodiments, the term "3D rigid transform" describes the mathematical operation that involves the computational application of a matrix containing both rotation and translation transformations. In some embodiments, the 3D rigid transform can be utilized when the system needs to transform the relations of an object from one coordinate axes to another, without deformation of the object. In some embodiments, an example can be: instead of having a 3D-tracked tool's location coordinates and orientation values to be in reference to a 3D-tracking acquisition system, the 3D-tracked tool can be substantially rigidly transformed to be in reference to the coordinates and orientation of another 3D-tracked tool or DRF within the scene. Further, some embodiments include "rigid body transform", a synonym.

Some embodiments include a pedicle screw. Some embodiments include a pedicle screw that can be inserted into the anatomical structure of a spinal vertebra called a pedicle. In some embodiments, the pedicle screw can be referenced. In some embodiments, the pedicle screw can be assumed that the system can be compatible with any other screws, fasteners, and/or other surgical implants (e.g., cages, rods, etc.).

In some embodiments, a tulip-head can be an object that attaches to a screw-head and can be polyaxial or uniaxial in its range of motion. In some embodiments, the tulip-head typically has internal threads that enable a fastener to engage substantially rigidly with the structure. In some embodiments, the tulip-head can have mating features on the external wall/surface that can enable a device to substantially rigidly attach to the tulip-head. In some embodiments, the tulip-heads can be designed to accept the insertion of a rod implant.

In some embodiments, a rod can be any object with a cross-section similar to a circle. Some embodiments include, additional shapes can include a keyhole, semi-circle, and the like. In some embodiments, a rod can be of any length and curvature. In some embodiments, a rod can be coupled to tracked and non-tracked tools. In some embodiments, a rod can be inserted into the cavity of a tulip-head and can be substantially rigidly fixed in-place via a cap screw that is fastened via threads on the interior wall of a tulip-head.

In some embodiments, register or a registration refers to any time a 3D-tracked tool or object signals information to the computer system regarding an object's state, 3D location, 3D orientation, unique identity, relative position to other objects, or other relevant information for the system's algorithms. Some embodiments include, for example: a 3D-tracked probe can register the position and identity of a fiducial, meaning that the 3D-tracked probe can communicate to the computer system that a particular fiducial can have a specific position and orientation in 3D space relative to the 3D-tracking, acquisition system.

In some embodiments, "sagittal" is an anatomical plane that refers the side view of a patient in which the superior portion of the patient (e.g., the head) is on the right or left side and the inferior portion of the patient (e.g., feet) is on the opposite end, depending on which side of the patient the perspective is from, left or right half. In some embodiments, the posterior aspect of the patient will be visible on either the top or bottom of the view, depending on whether the patient is supine or prone.

In some embodiments, "coronal" is an anatomical plane that refers to the top view of a patient in which the superior portion of the patient (e.g., the head) is on the top or bottom and the inferior portion of the patient (e.g., feet) is on the opposite end, depending on which side of the patient the perspective is from, below or above, as well as which side the left or side of the patient appears in view, right or left.

In some embodiments, "axial" is an anatomical plane that refer to the cross-sectional view of a patient in which the posterior portion of the patient is on the top or bottom and the anterior portion of the patient is on the opposite end, depending on which side of the patient the perspective is from, prone or supine. In some embodiments, the patient view can also change depending on whether the view is pointed towards the inferior or superior aspect of the patient. In some embodiments, "transverse" can be used. In some embodiments, transverse can be an equivalent term to "axial".

In some embodiments, "depressible sliding shaft" or "plunger" refers to a depressible, sometimes spring-loaded, sliding shaft that actuates via pressing against a surface, a spring-loaded button, or other mechanical means of actuation. In some embodiments, a plunger can have a mechanically-linked TMSM that can communicate its position along the plunger relative to the position of a nearby DRF or other tracked stray markers. In some embodiments, the shaft can be coaxial with a 3D-tracked tool. In some embodiments, the shaft does not need to be protruding out of an object. In some embodiments, the shaft can be engaged within an object.

In some embodiments, spinal alignment parameters of an assessment of the segmental and/or full-length spinal alignment can be produced with values for each relevant radiographic alignment parameter (e.g., Cobb angle, lumbar lordosis (LL), thoracic kyphosis (TK), C2-C7 sagittal vertical axis (SVA), C7-S I SVA, C2-S I SVA, central sacral vertical line (CSVL), Tl pelvic angle (TIPA), pelvic tilt (PT), pelvic incidence (PI), chin-brow to vertical angle (CBVA), Tl slope, sacral slope (SS), C1-2 lordosis, C2-C7 lordosis, C0-C2 lordosis, C1-C2 lordosis, PI-LL mismatch, C2-pelvic tilt (CPT), C2-T3 angle, spino-pelvic inclination from Tl (Tl SPi) and T9 (T9SPi), CO slope, mismatch between T-1 slope and cervical lordosis (Tl S-CL), and/or global sagittal angle (GSA)). Additionally, any time alignment assessments or calculation of alignment parameters are mentioned in this document, it can be assumed that any of the above parameters, and others not mentioned but commonly known, can be calculated in that portion of the description.

In some embodiments, a 3D-tracking acquisition system can refer to the use of a 3D-tracking system to acquire points in 3D space and register particular commands via 3D-tracked tools. Some embodiments include, for example: an optical-tracking system that can be used in surgical navigation (e.g., NDI Polaris Spectra stereoscopic camera system, which tracks tools or objects, as depicted in FIG. 126, FIG. 127, etc.).

In some embodiments, a 3D-tracked probe is a tool that can be handheld or robot-held, and can be tracked in 3D physical space by any 3D-tracking acquisition system, such as an optical surgical navigation system (e.g., NDI Polaris stereoscopic camera). In some embodiments, relying on an optical surgical navigation system can include a probe with a substantially rigidly-attached, 3D-tracked DRF. Some embodiments can include the inclusion of a mechanically-linked, 3D-tracked mobile stray marker (TMSM) that can be mounted on, or coupled with, a depressible, spring-loaded, and/or user-actuated shaft that can actuate the motion of the TMSM either linearly or rotationally (e.g., about a hinge pivot on the probe).

In some embodiments, an optical, 3D-tracking system can refer to any optical system that can provide a 3D mapping or image of a scene or calculate the location, orientation, and identity of a tracking-compatible object. Some embodiments include, for example: a 3D-tracking system can be a surgical navigation system (e.g., an NDI Polaris Spectra® stereoscopic camera system, from NDI International, 103 Randall Drive, Waterloo, Ontario, Canada N2V 1C5). In some embodiments, similar information can be gathered from any 3D-tracking, optical-based system.

In some embodiments, a skin-mounted fiducial can be mounted directly on the skin surface of a patient, or within the skin in a percutaneous manner. In some embodiments, an over-the-drape-mating fiducial can be used to mate with another fiducial that is beneath a surgical drape, or any other obstructing material.

In some embodiments, a tracked stray marker ("TSM") refers to an optically-3D-tracked stray marker, which is defined as an independent light-reflective or light-emitting marker that is not registered as part of a DRF. In some embodiments, this particular stray marker does not exhibit direct movement relative to the dynamic reference marker, however, it can be used as a toggle to signal various, unique commands to the acquisition unit.

In some embodiments, a display monitor refers to any display embodiment that can visually depict the output of the system, its feedback systems and instructions, its calculations, and other relevant information or settings that are available.

In some embodiments, a "tracked end cap" refers to a 3D-tracked object that can contain a substantially rigidly-attached, 3D-tracked DRF and can be substantially rigidly attached to a rod or rod-like object. In some embodiments, the end cap can provide a reference frame of the rod in a manner of establishing a dynamic coordinate system for the implant while its contour is traced, structurally manipulated/ contoured, or any other assessment. In some embodiments, this term can be used in the form "tracked DRF-equipped end cap", a synonym.

In some embodiments, a tracked slider refers to a 3D-tracked object that can contain a substantially rigidly-attached, 3D-tracked DRF and can register the contour of a rod via mechanically engaging with its surface and tracing along the length of the rod. In some embodiments, the slider tool can be transformed to output 3D coordinates and orientation values relative to a 3D-tracked end cap tool. In some embodiments, this term can be used in the form "slider tool equipped with a DRF"; typically used for assessing a rod contour.

In some embodiments, an acquisition system is synonymous with the 3D-tracking acquisition system term described above. In some embodiments, this system is a 3D-tracking camera (e.g., NDI Polaris Spectra® stereoscopic camera) and the computer system with which it is communicating.

In some embodiments, an end-effector refers to any component of an object that interfaces with another surface or object in a manner that enables the registration or communication of information including, but not limited to: 3D location, 3D orientation, unique identity, physical or identity-based relations to other objects in a scene, forces applied to an object or forces experienced by an end-effector, and the like. Some embodiments include, for example: a 3D-tracked distal tip of a robotic arm.

In some embodiments, a tracing refers to the method of acquiring discrete or continuous points along a surface via a 3D-traced probe or object.

In some embodiments, an endplate refers to the surface of a spinal vertebra that interfaces with the intervertebral disc and the nearby vertebra coupled on the other side of the intervertebral disc. In some embodiments, the endplate can be a common anatomical landmark used for measuring the spinal alignment parameters of a patient (e.g., Cobb angles), mainly due to the way that an endplate surface X-ray can be utilized to represent an anatomical line segment or vector, from which two or more endplates can be used to calculate relative angles between two or more vertebrae (e.g., LI and SI endplate measurements can be used to calculate the lumbar lordosis angle of the patient's lumbar spine).

In some embodiments, pose refers to the orientation of an object with respect to another object or 3D-tracking acquisition system. In some embodiments, the pose of an object can be redundant from multiple perspectives or it can be unique and identifiable in a way that it distinguishes itself from other objects. In some embodiments, the pose of an object can be outputted via 3D orientation values (e.g., quaternions, Euler angles, rotation matrices, series of vectors, etc.).

In some embodiments, the term "unique" can refer to the distinct identity of an object, or its distinguishable configuration, position, or orientation. In some embodiments, the phrase "unique pattern" can refer to either the I) embedded pattern surface on the ball component in the 3D-tracking system (depicted in FIG. 117, FIG. 118, FIG. 119, FIG. 120, FIG. 121, FIG. 122, FIG. 123, FIG. 124, FIG. 125); or 2) an asymmetric or identifiable arrangement of objects that can be registered in a manner that the group of objects can be identified uniquely compared to another group of tracked/registered objects.

In some embodiments, "level" refers to a specific spinal vertebra within the span of the vertebrae of the spinal column. In some embodiments, a level can refer to any of the vertebrae (e.g., LS, TIO, Cl, S3, etc.). In some embodiments, the abbreviations of the sections of the spinal vertebrae can be: lumbar (L), thoracic (T), cervical (C), and sacral (S) vertebrae.

In some embodiments, "fully engaged" can be used to describe two or more objects that are completely linked, mated, coupled, adhered, joined, fastened, or aligned. In some embodiments, two or more objects can be fully engaged. In some embodiments, the computer system can record an event, collect information, acquire 3D locations or orientations, determine the identity of one or more objects, receive a command, or output information regarding the engagement. In some embodiments, fully-engaged objects can trigger a communication to the computer system of a particular command or acquisition to store.

In some embodiments, a "trigger" can be used to describe either a button or a moment of communication that signals to the computer or acquisition system to store data, output calculations or other relevant information, interpret a command, or register an object's identity.

Figure 1:
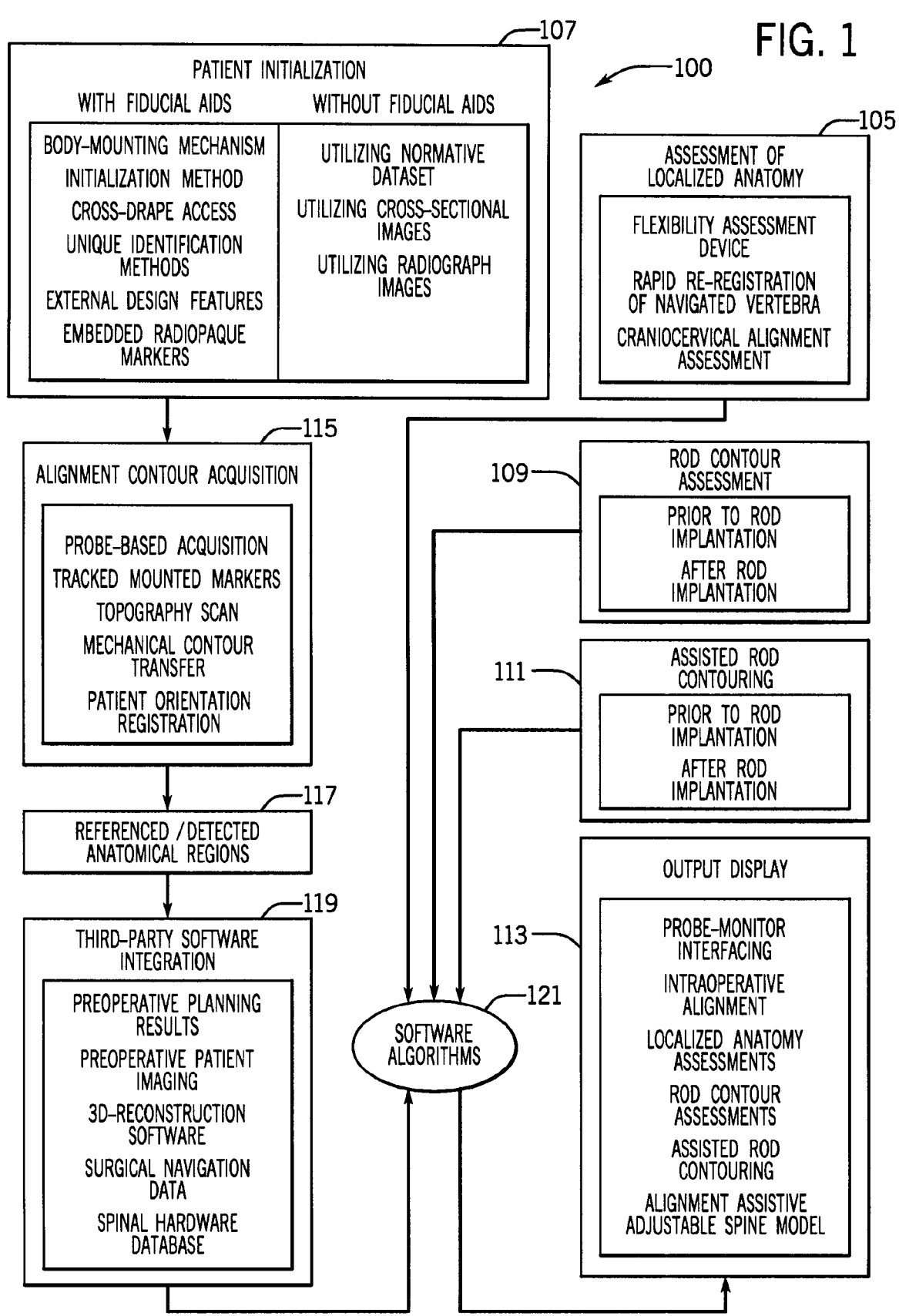
FIG. 1 illustrates a system for assessing spinal alignment, local anatomy biomechanics, rod contours, and active contouring of a rod, as well as initialization of fiducials and interactive displays of various outputs in accordance with some embodiments of the invention.

Some embodiments can be independent inventions and do not have to be precluded by other inventions or categorical system workflows (e.g., patient initialization, alignment contour acquisition, etc.), as illustrated in FIG. 1. For example, some embodiments of the invention described herein include devices, assemblies, systems, and methods to assess the intraoperative alignment of the spine, extract information as to the contour or alignment of instrumented hardware, and evaluate some of the biomechanical qualities of the patient's spine. Some embodiments of the overall system are illustrated in FIG. 1, where a central software system can receive inputs from discrete and/or continuous location data (e.g., inside and/or outside of the surgical site), where the data is gathered by non-radiographic or radiographic systems, algorithmic calculations, or manual user-based interactions, to generate visual and quantitative outputs relating to the intersegmental or full-length alignment, curvature, position, range-of-motion, and biomechanical flexibility of the patient's spine. Some of the embodiments described herein do not have to be within the categorical series of systematic steps (e.g., 3D trace, local anatomy, landmarks, etc.) shown in FIG. 1, illustrating a system for assessing spinal alignment, local anatomy biomechanics, rod contours, and active contouring of a rod, as well as initialization of fiducials and interactive displays of various outputs in accordance with some embodiments of the invention. The overall system 100 of FIG. 1 can include devices, assemblies, systems, and/or methods described in the following description in reference to one or more of the figures, including processes that utilize one or more software modules 121 of one or more computer-implemented methods according to some embodiments. In some embodiments, the system 100 can comprise devices, assemblies, systems, and methods for patient initialization 107, alignment contour acquisition 115, referenced/detected anatomical regions 117, third-party software integration 119, assessment of localized anatomy 105, rod contour assessment 109, assisted rod contouring 111, and output display 113.

Figures 2A, 2B:
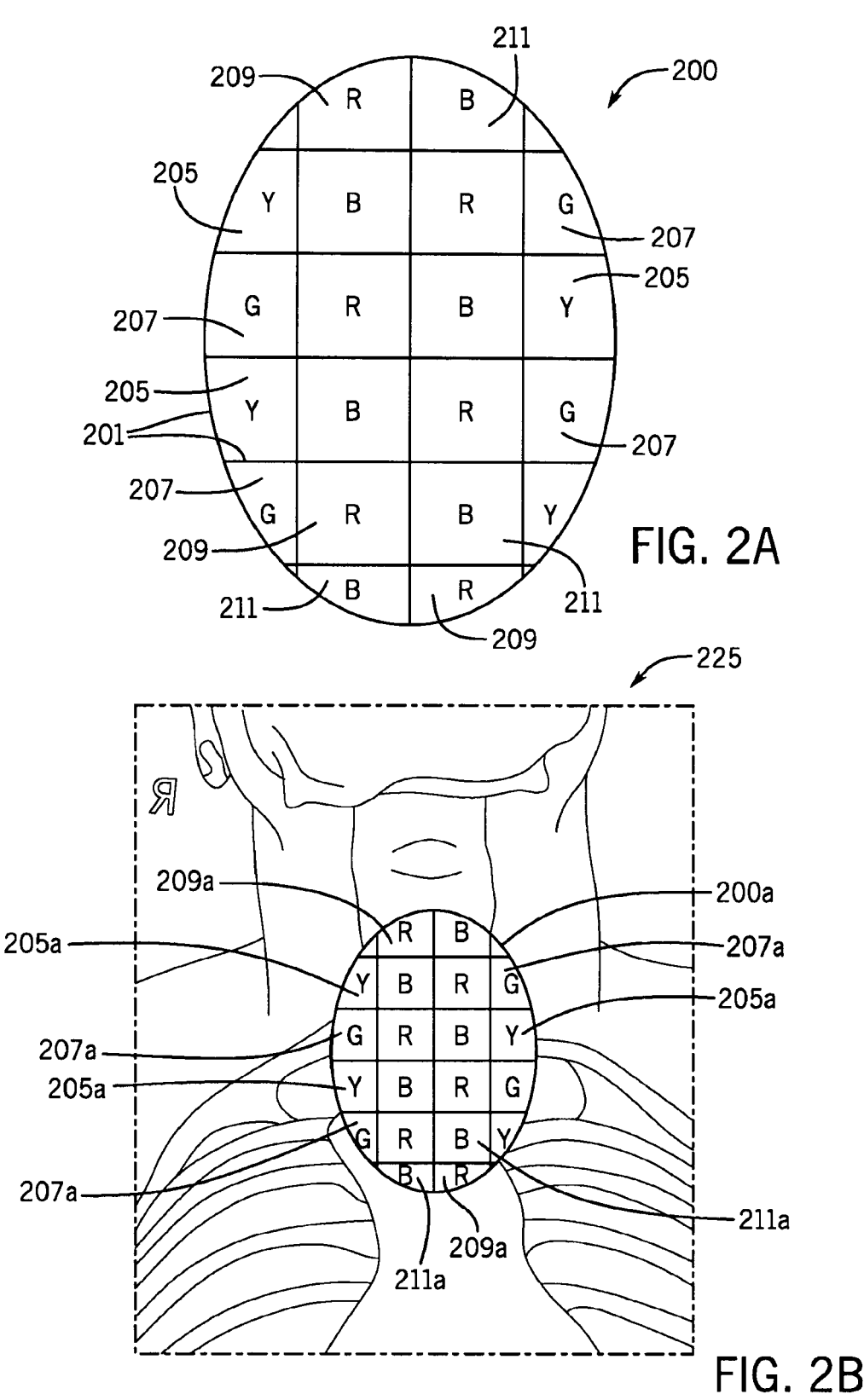
FIG. 2A shows a representation of a body-surface-mountable fiducial patch in accordance with some embodiments of the invention.
FIG. 2B displays the radiopaque elements of the fiducial patch of FIG. 2A as would be visible on an X-ray image of a patient with the patch applied in accordance with some embodiments of the invention.

Some embodiments of the invention relate to systems and methods for precise placement of skin surface markers or percutaneous access devices that provide the relative position of underlying bony anatomy to a visible surface grid. In some embodiments, the systems and methods described herein can reduce the number of X-rays needed to be taken to verify location of overlying or percutaneous devices relative to bony anatomy. Some embodiments can include a skin-mounted patch that has visible markings with colors in the visible spectrum for a user to see. Further, in some embodiments, the patch can include corresponding radiopaque patterns (e.g., grid lines, letters, numbers, symbols, icons, etc.) embedded in the patch such that when an X-ray is taken, the patch provides a large area of landmarks that can aid a user with percutaneous device placement, the placement of one or more additional surface marker fiducials, and/or with localizing surgical incision sites relative to underlying anatomy. For example, FIG. 2A shows a representation of a body-surface-mountable fiducial patch 200 in accordance with some embodiments of the invention, where radiopaque grid lines can be visualized on the X-ray image. Other relevant figures and discussions herein can include those related to skin-fiducial marker examples to apply onto a patch such as FIGS. 6B, 9A-9B, and FIGS. 11A-11B. As shown in FIG. 2A, some embodiments include a body-surface-mountable fiducial patch 200 that can comprise an array of radiopaque markers with visible and/or radiopaque grid lines 201. In some embodiments, the shapes or markers defined by the grid lines 201 can be colored and/or marked with an identifier, including, but not limited to, a red-colored grid surface with a radiopaque "R" (label 209), a blue-colored grid surface with a radiopaque "B" (label 211), a yellow-colored grid surface with a radiopaque "Y" (label 205), and/or a green-colored grid surface with radiopaque "G" (label 207). In some embodiments, the grid lines can be further apart or closer than shown. In some embodiments, the markers can be larger or smaller, as well as fewer or greater in number, than shown in this non-limiting embodiment. In some embodiments, the body-surface-mounted fiducial patch 200 can enable precise placement of surface-mounted objects or percutaneous devices that require recognition or understanding of the relative location of underlying bony or soft-tissue structures.

It should be noted that in some embodiments, the visible surface of the patch 200 need not be a distribution of colors, but can also consist of any recognizable pattern that is also displayed in a meaningful way on X-ray imaging. In some embodiments, the patch can be adhered to surface anatomy via an adhesive (not shown) or other methods. In some embodiments, one side of the patch 200 can include adhesive (e.g., such as the skin-mounted side). In some embodiments, the size and density of unique identifiable grid sections on the patch can be varied based on a particular application. In some embodiments of the invention, a radiopaque lining can be included that at least partially matches one or more overlying visible markings. In some embodiments, the patch 200 can facilitate a user understanding where each visible marking is and how it corresponds with an underlying anatomical region or element. This can facilitate a user making incisions in known or identified regions of a patient according to some embodiments.

FIG. 2B displays the radiopaque elements of the fiducial patch of FIG. 2A as would be visible on an X-ray image of a patient with the patch applied in accordance with some embodiments of the invention. For example, X-ray patient image 225 is shown with radiopaque fiducial grid patch 200a displayed on the image 225 according to some embodiments. In some embodiments, the image displays the radiopaque elements of the fiducial patch 200 as would be visible on an X-ray image 225 of a patient with the patch 200 applied. In some embodiments, after taking an X-ray of the patch 200 applied to the patient, users can place surface fiducials or direct percutaneous access devices towards the bony anatomy of interest based on the corresponding grid location on the patch that represents the underlying anatomy of interest. In this non-limiting example embodiments, the red-colored grid surface with radiopaque "R" (label 209) is shown as 209a, the blue-colored grid surface with radiopaque "B" (label 211) is shown as 211a. Further, in some embodiments, the yellow-colored grid surface with radiopaque "Y" (label 205) is shown as 205a, and the green-colored grid surface with radiopaque "G" (label 207) is shown as 207a in the X-ray image 225. In some embodiments, when used in this way, the patch 200 of FIG. 2A and imaging of FIG. 2B can aid with the precise selection of correct surgical site access points, ensuring that incisions overlay the desired bony anatomy on which will be operated. Additionally, in some embodiments, this patch 200 can be used to precisely place secondary skin-mounted fiducials such that they superimpose underlying bony anatomy of interest. Some example embodiments of fiducials that can be applied onto the imaged patch include FIG. 6B, FIGS. 9A-9B, FIGS. 11A-11B. In some embodiments, the patch 200 can be applied to a patient's skin using adhesive or other conventional methods. In some embodiments, the type of identifiable surface marker can be different than some embodiments shown.

Figure 3A:
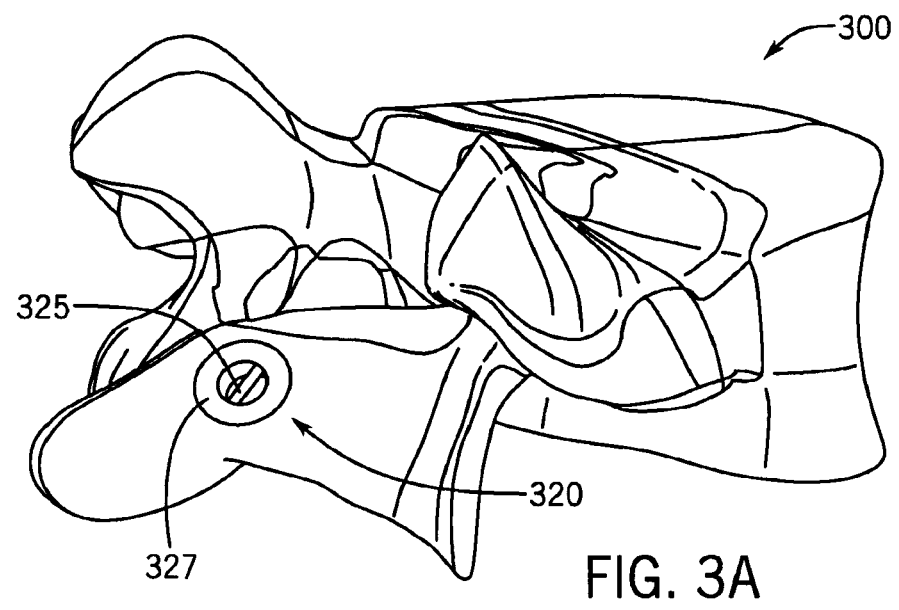
FIG. 3A displays a vertebra with a bone-mounted fiducial fastened to the bone in accordance with some embodiments of the invention.
Figure 3B:
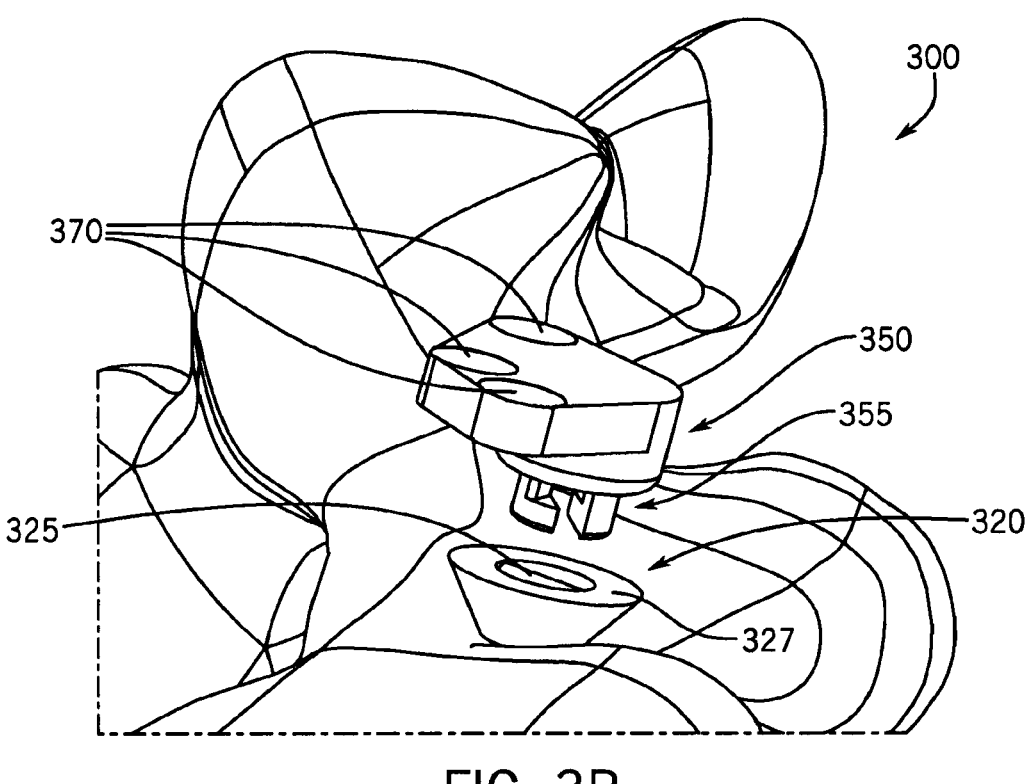
FIG. 3B shows an assembly view of a vertebra with a bone-mounted fiducial and top fiducial for coupling to the bone-mounted fiducial in accordance with some embodiments of the invention.
Figure 3C:
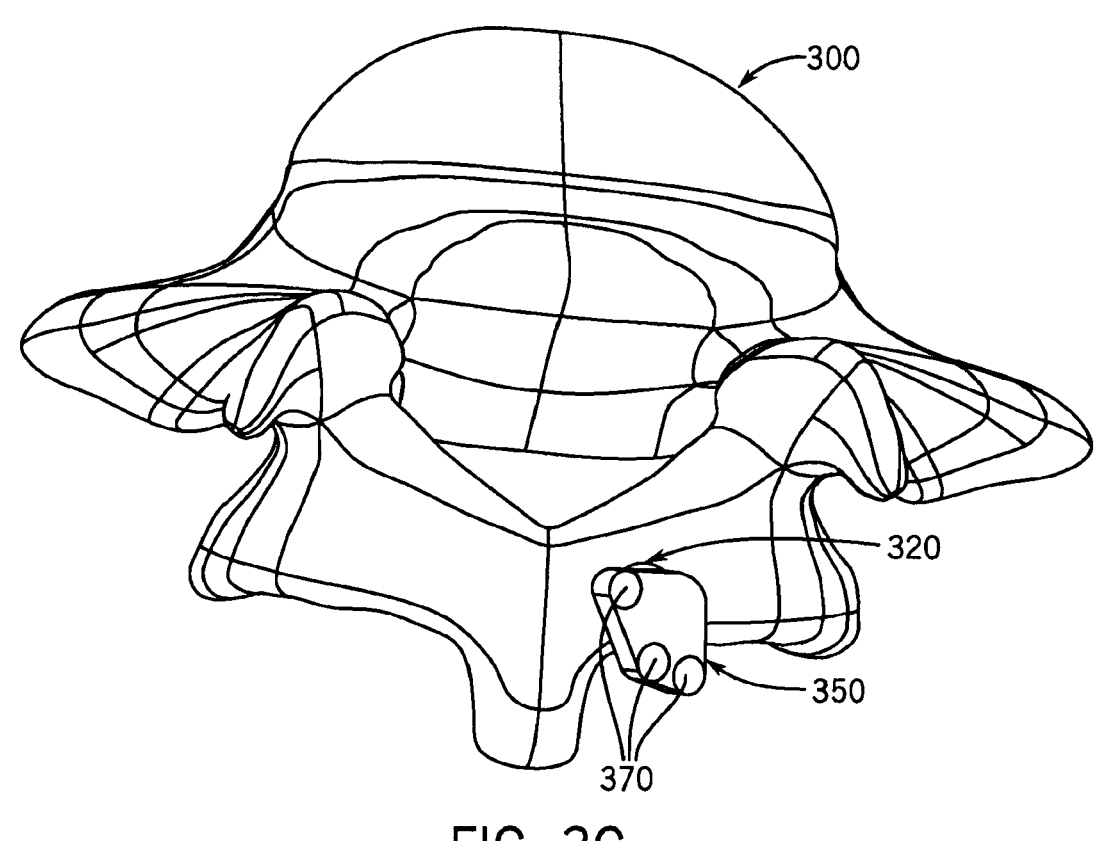
FIG. 3C shows a vertebra with a bone-mounted fiducial coupled with a top fiducial in accordance with some embodiments of the invention.

FIGS. 3A-3C illustrate a bone-mounted fiducial device that is designed with a crossbar to interface with one or more mating devices that can either help to register the fiducial's location and pose in 3D space (e.g., via tracing, tapping discrete locations, being tracked directly), help initialize the fiducial relative to anatomical structures of interest registered with X-ray images or 3D-tracking acquisition systems, or directly manipulate the fiducial and attached bony anatomy after they are coupled according to some embodiments. In some embodiments, after imaging a fiducial mounted to bony anatomy, the fiducial's relative location in space to an anatomical landmark of interest can be registered, such that when the fiducial is located and registered by 3D-tracked tools in the future, the corresponding bony anatomy elements are also localizable and/or identifiable. The vertebra 300 is shown with a bone-mounted fiducial 320 fastened to the bone. In some embodiments, the fiducial 320 can be fastened to the medial border of the right spinal lamina, but because of its small size and profile, it can be mounted anywhere on the bony anatomy. In some embodiments, the bone-mounted fiducial 320 can contain a threaded or smooth bone-piercing component (not shown) so that it can be substantially rigidly fastened to the anatomy of interest (e.g., the vertebra 300). In some embodiments, the bone-piercing component can be significantly miniaturized such that it does not pierce through the opposite side of the bony anatomy, or otherwise harm any sensitive anatomical structures.

In some embodiments, the fiducial 320 can contain one or more rigid crossbars 325 that travel across the fiducial 320. In some embodiments, the crossbars 325 can be positioned such that there is an open space underlying it to allow for a mating interface of a coupled fiducial accessory 350 to directly engage with it. In this instance, in some embodiments, the fiducial 320 can be substantially rigidly fixed to the accessory fiducial 350 (see FIG. 3B below) so as to interpret the pose and location of the fiducial 320 in space when accessed by a 3D-tracked device.

In addition, some embodiments involve a patterned perimeter surface (FIG. 3B), including but not limited to groove 327 (not shown) and other identifiable patterns, that can be traced or discrete registered by a 3D-tracked probe. In some embodiments, FIG. 3B shows an assembly view of a vertebra 300 with a bone-mounted fiducial 320 and accessory fiducial 350 for coupling to the bone-mounted fiducial 320, illustrating the mating capability of the bone-mounted fiducial 320 such that it can mechanically couple with an accessory fiducial 350 via a variety of mechanisms. For example, in some embodiments, one non-limiting mechanism includes a quarter-turn interlocking mechanism 355 such that the accessory fiducial 350 is tightly pulled into the crossbars 325 of the base bone-fiducial 320 when the accessory fiducial 350 is rotated 90 degrees into the interlocking design of the mechanism 355. In some embodiments, the structure of the accessory fiducial 350 is such that it can contain surface features, including, but not limited to, asymmetric pattern of three or more identifiable indentations 370. In some embodiments, the identifiable indentations 370 can enable the registration of the unique position and pose of the fiducial 320 in 3D space by interfacing with 3D-trackable devices, as further described in more detail below in reference to FIG. 3C, and FIGS. 44A-44D. In some embodiments, other conventional mating mechanisms with the fiducial include, but are not limited to, a quarter-turn, half-turn, internal threads, a clamping device, and/or a spring-loaded snap-in device.

Some embodiments of the uniquely identifiable surface structure of the accessory fiducial 350 that can be used for registration of the orientation of the fiducial 320 in 3D space when interacting with a 3D-tracked probe, can include, but not be limited to, 1.) three or more uniquely spaced indentations, 2.) a uniquely identifiable groove in which a 3D-tracked probe can trace in order to identify the location and pose of the fiducial 320, 3.) an insert that contains a set of three or more tracked markers whose location in 3D space are able to be tracked by a 3D-tracking camera, 4.) a tracked DRF, 5.) a larger version with radiopaque features to enable its unique pose and location to be identifiable with X-ray imaging, and 6.) interfacing with a tracked probe that can substantially rigidly couple to the fiducial 320 in such a way that it can interpret the location and pose of the fiducial 320 in 3D space, as described below in reference to FIGS. 44A-44D. For example, FIG. 3C shows a vertebra 300 with a bone-mounted fiducial 320 coupled with a top fiducial (fiducial 350) in accordance with some embodiments of the invention. In some embodiments, the bone-mounted fiducial 320 includes an accessory fiducial 350 substantially rigidly attached and demonstrates some embodiments of a uniquely identifiable surface pattern 370 (surface indentations) that can be registered with a 3D-tracked probe. In some embodiments, the three or more discrete indentations that make up the surface pattern 370 can couple with at least a portion of a 3D-tracked probe that can couple with the surface pattern 370. Consequently, one or more computer systems can then be used to compute the location and unique pose of the fiducial 320 in 3D space according to some embodiments.

FIG. 4A illustrates an assembly or operation process 450 for a skin-surface-mounted fiducial 400 being applied to a patient 425 in accordance with some embodiments of the invention. The skin-surface-mounted fiducial 400 is applied to the patient's posterior skin as they are positioned prone on an operative table 435 according to some embodiments. In some embodiments, this fiducial 400 can be adhered to the patient's skin via attached adhesive compound, staples, suture, or overlying adhesive draping.

FIG. 4B illustrates a sample lateral radiograph of the radiopaque markers 444 embedded within a skin-based fiducial 442 applied to an anatomical model 443, adhered to its skin surface 446, in accordance with some embodiments of the invention. In some embodiments, the radiopaque elements of the fiducial markers 444 allow the fiducial 442 to be clearly visualized and identified on radiograph images. Additionally, in some embodiments, the known sizing of the radiopaque markers 444 allow for reference scaling within the X-ray image 441. Furthermore, the nearby anatomical structures that are also within the field of view of the X-ray image 441 can then be initialized such that a displacement vector can be drawn within the plane of the X-ray image 441 as described below in FIG. 4C and FIG. 4F. In some embodiments, the arrangement of the radiopaque fiducial markers 444 can be designed in an asymmetric pattern to enable an X-ray image of the fiducial from any perspective to visualize a unique pose of the pattern and to subsequently enable the system to automatically estimate the 3D orientation of the fiducial 442. For example, FIG. 4C illustrates the sample lateral radiograph 440 of FIG. 4B with annotated vectors in accordance with some embodiments of the invention. In some embodiments, FIG. 4C displays one aspect of the initialization process for fiducials located nearby anatomical elements whose position is desired to be known relative to that of the fiducial 442. In some embodiments, manual or automated software annotation can enable the identification of the radiopaque markers within the fiducial (shown as vectors 465 and 460 extending between radiopaque markers 444).

In some embodiments, given the relative sizing of the fiducial markers 444 to one another as well as their relative orientations to one another, the pose of the fiducial 442 relative to the plane of the X-ray image 440 can be calculated. In some embodiments, the user interfaces with the system to select one or more additional anatomical points to which the displacement vector 470 from the fiducial 442 will be calculated. In some embodiments, in this example, the central region of a particular vertebral body was selected, indicated by a large circle (e.g., shown as 427), and the software calculated the pixel distance between each radiopaque marker 444 and the annotated region 427 on the display monitor. In some embodiments, based on the known size of the radiopaque markers 444 that are in or on the fiducial 442, the image can be scaled such that length measured in pixels can be converted to length measured in distance units (e.g., mm, cm, etc.). In some embodiments, the software can also calculate displacement vectors from the fiducial to any anatomical landmarks of interest, even across several vertebrae.

FIG. 4D illustrates a C-arm X-ray imaging system 480 that can be utilized for image acquisition and subsequent initialization of fiducial markers 442 in accordance with some embodiments of the invention. In some embodiments, following the first X-ray image that was taken, the relative angle between the patient-fiducial complex and the X-ray emitter is rotated by either a known or unknown amount to take a subsequent image. In some embodiments, the second image allows for added information outside of the plane of the first X-ray image to construct the 3D displacement vector between the fiducial and the bony anatomy of interest. In some embodiments, this X-ray system needs not be a C-arm-based device 480, but can also consist of other image acquisition systems including but not limited to the O-arm, flat-plate X-rays, CT scan, MRI, and wall or bed-mounted acquisition systems.

FIG. 4E illustrates a sample X-ray image 485 of a spine-fiducial pair from a different imaging angle from that of FIGS. 4A and 4B in accordance with some embodiments of the invention, and illustrates the fiducial radiopaque markers (shown as 487a, 487b) as some embodiments of an arrangement of radiopaque markers in or on the fiducial distributed to enable image scaling and localization to nearby anatomical areas of interest.

FIG. 4F illustrates the sample X-ray image 485 of FIG. 4E, including annotated vectors in accordance with some embodiments of the invention. In some embodiments, FIG. 4F displays the X-ray image initialization process for the fiducial-body pair that was imaged and described above in FIG. 4E. In some embodiments, the annotated vectors 488 are used to reference the relative position of each of the radiopaque markers (487a, 487b) within the fiducial 442 (FIGS. 4B-4C) as well as calculate the displacement vector 486 to the user-indicated nearby anatomical region of interest (shown as 489), for which the fiducial 442 can serve as a reference point upon future localization of that fiducial. In some embodiments, the arrangement of the radiopaque fiducial markers can be designed in an asymmetric pattern, as seen by the example unique triangular pattern of vectors between the radiopaque markers 487a, 487b, to enable an X-ray image of the fiducial from any perspective to visualize a unique pose of the pattern that can enable the system to automatically estimate the 3D orientation of the fiducial. In some embodiments, in this respect, the estimation of the fiducial's orientation enables the system to calculate the 3D vector with respect to the fiducial axes.

FIG. 4G displays the 3D axes of a fiducial device 442 in coordinates of the X-ray imaging system, in which the unique location and pose of the fiducial 442 was registered in accordance with some embodiments of the invention. In some embodiments, the X-ray imaging system coordinate axes 492 are shown with a 3D-displacement vector 494a that indicates the relative 3D offset initialized between the fiducial origin 490a and the triangulated position of the anatomical landmark of interest 491a, which was annotated previously (annotations 427 and 489). In some embodiments, displacement vectors drawn over each of the 2D X-rays are able to be combined based on an input or calculated angle between each X-ray image plane in accordance with some embodiments of the invention. In some embodiments, this input enables the calculation of a rigid body transform between the coordinate axes of the two or more X-ray images of the fiducial 442, and thus enable for the calculation of a 3D-displacement vector that combines displacement vector inputs from two or more X-ray images. In some embodiments, it must be noted that the series of X-ray images of a fiducial device 442 relative to the anatomical regions of interest, such as 427 or 489, may not always differ by a purely rotational transformation, and may include a translational transformation, especially if the fiducial 442 is not isocentrically aligned with the volume of the C-arm field-of-view, as it is rotated by its boom (as seen in FIG. 4D). In some embodiments, this non-circularity of the C-arm's field of view may be caused by the center of the imaging cone not aligning with the center of the C-arm's axis of rotation.

FIG. 4H illustrates a system and method of localizing the fiducial in 3D-tracking camera coordinates in accordance with some embodiments of the invention. In some embodiments, shown in the non-limiting embodiment are an identifiable tracing pattern 495, a tracked probe with triggering capability 496 (shown with the probe in an active tracing state 493), and fiducial coordinate axes 497, relative to the 3D-tracking acquisition system. FIG. 4H displays one method of localizing the fiducial in 3D-tracking camera coordinates as a non-limiting embodiment. As shown, the fiducial is equipped with a unique groove pattern 495 into which a tracked probe 496 can trace the fiducial's signature pattern. In some embodiments, as described above in relation to FIG. 4A, the recognizable features of the fiducial are not limited to a uniquely traceable pattern, but also discrete points to tap, mount locations for tracked markers, and substantially rigidly coupling with a tracked probe in a way such that the probe's pose can be used to interpret the fiducial's position and pose. In some embodiments, by tracing the unique surface pattern 495 on the fiducial with a tracked probe 496, the fiducial's axes 497 and origin are able to then be interpreted with respect to the 3D-tracking acquisition system's coordinate system. In some embodiments, the acquisition system will subsequently be able to interpret the location of the initialized nearby anatomical region (such as 427 and 489) as described below in FIG. 4I.

In some embodiments, FIG. 4I illustrates the 3D coordinate axes of the fiducial device 498 relative to the 3D-tracking acquisition system. Some embodiments includes the fiducial coordinate axes 498 relative to that of the 3D-tracking acquisition system and the 3D-displacement vector 494b between the fiducial 442 and the anatomical regions of interest (427 and 489). The 3D-displacement vector 494b, between the fiducial origin 490b and the anatomical region of interest 491b relative to the coordinates of the 3D-tracking acquisition system, represents the vector 494a (shown in FIG. 4G) after it has undergone a 3D rigid transform, utilizing the calculated transform between the fiducial location and orientation in both the X-ray imaging and 3D-tracking acquisition systems, as depicted in FIGS. 4C, 4F, and 4H. In some embodiments, this resultant 3D-displacement vector enables for the calculation of the location of the anatomical region of interest 491b (depicted in FIGS. 4C-4G as labels 427 and 489 relative to the X-ray imaging system coordinates) with respect to the fiducial's origin and coordinate axes relative to the coordinate system of the 3D-tracking acquisition system. In some embodiments, this enables localization of the bony anatomy regions of interest by interpreting the location and pose of the fiducial within other 3D-tracking acquisition system axes, as depicted in FIG. 4H.

Figures 5A, 5B, 5C:
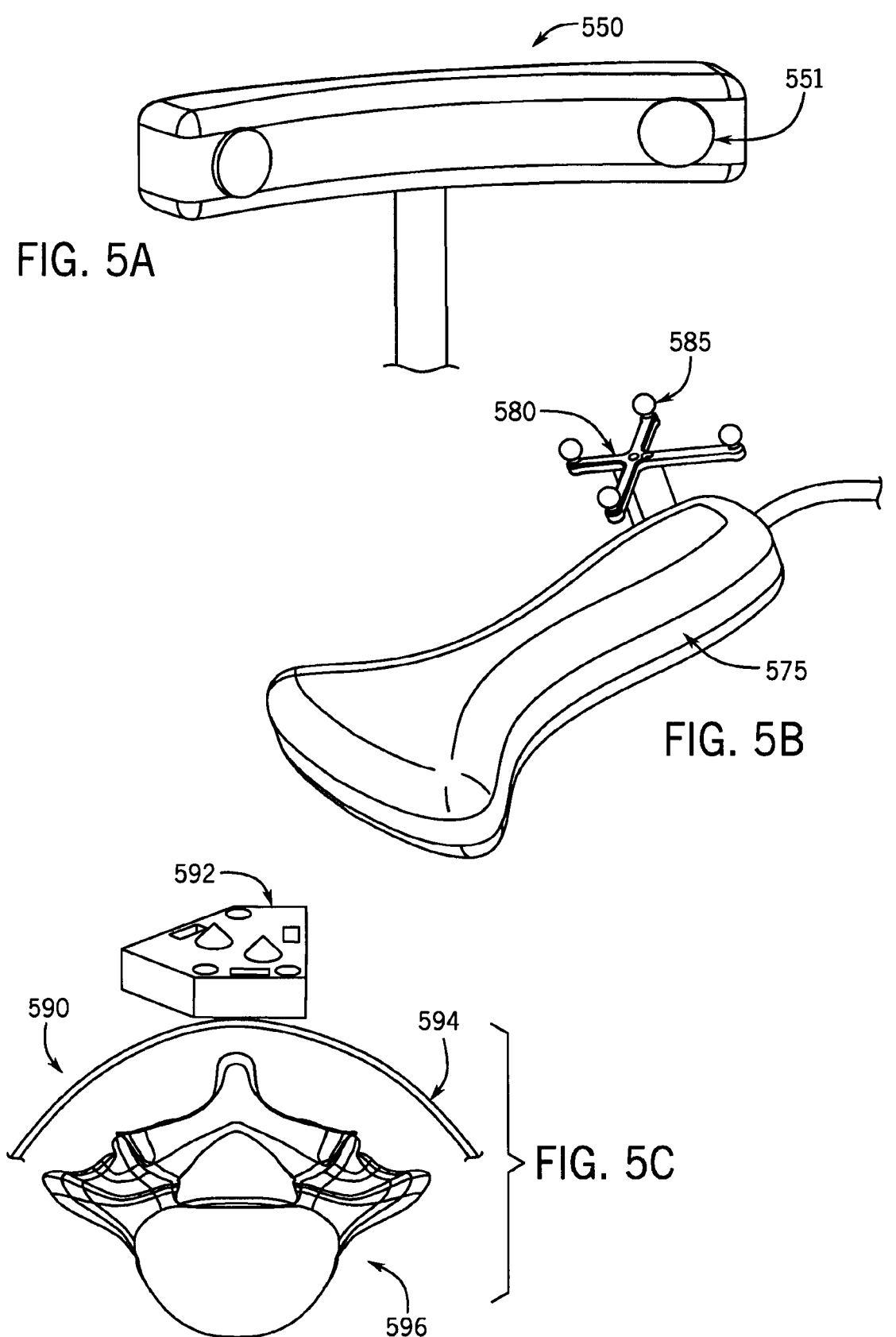
FIG. 5A illustrates an optical tracking system in accordance with some embodiments of the invention.
FIG. 5B illustrates an ultrasound probe equipped with a tracked dynamic reference frame in accordance with some embodiments of the invention.
FIG. 5C illustrates an assembly or process view of a patient's skin surface overlying a cross-sectional view of a vertebra as a representation of a particular region of bony anatomy that could be registered to a skin-mounted fiducial in accordance with some embodiments of the invention.

In some embodiments, FIGS. 5A-5C display components, systems and methods of initializing a fiducial to serve as a reference point for underlying anatomical regions of interest, as described above in reference to FIGS. 4A-4I. However, in some embodiments, instead of utilizing X-ray images, the methods can utilize an ultrasound-based probe 575 equipped with a tracked DRF 580 so that its location and pose are able to be computed when visualized by a 3D-tracking camera. For example, FIG. 5A illustrates an optical 3D-tracking system 550 in accordance with some embodiments of the invention, and FIG. 5B illustrates an ultrasound probe 575 equipped with a tracked DRF 580 in accordance with some embodiments of the invention. Further, FIG. 5C illustrates an assembly or process view 590 of a patient's skin surface 594 overlying a cross-sectional view of a vertebra 596 as a representation of a particular region of bony anatomy that could be registered to a skin-mounted fiducial 592 in accordance with some embodiments of the invention. In some embodiments of the invention, the optical 3D-tracking camera 550 of FIG. 5A can be utilized for the 3D-tracking acquisition system referenced throughout this document. In some embodiments, this system utilizes stereoscopic cameras 551 to detect the location of tracked markers that reflect or emit infrared light. In some embodiments, this is one example of a tracking system that can be used for acquisition of 3D coordinates throughout this document, but this can also be achieved by other methods including but not limited to light-emitting markers, electronic communication, etc. Further, in some embodiments, the ultrasound probe 575 of FIG. 5B is equipped with a tracked DRF 580 that enables the probe's location and pose to be tracked in 3D space using passive, light-reflective markers 585. In some embodiments, tracking the precise location of the probe allows for recording the relative angles between each cross-sectional imaging plane of an acquisition that can be used for creating the 3D-displacement vector to the anatomical point of interest via the computation of 3D rigid transformations of the relative location and pose of the ultrasound probe 575 between acquisitions of the ultrasound cross-sectional images.

In some embodiments, FIGS. 6A-D includes depictions of devices, systems and processes of applying a skin-mounted fiducial along with its top-mating component that enables mating across surgical drapes so that the fiducial can be both visualized and referenced during procedures during which a drape is obstructing the surface overlying bony anatomy for which the location is desired to be known.

Figure 6A:
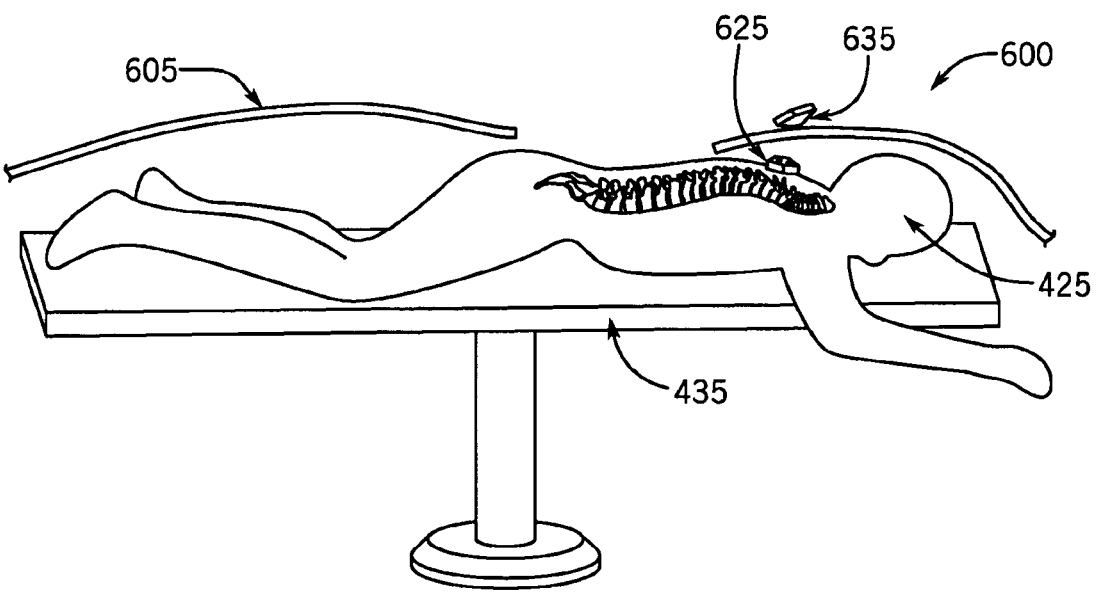
FIG. 6A illustrates an assembly or process view for applying a skin-mounted fiducial and its associated over-the-drape fiducial in accordance with some embodiments of the invention.
Figure 6B:
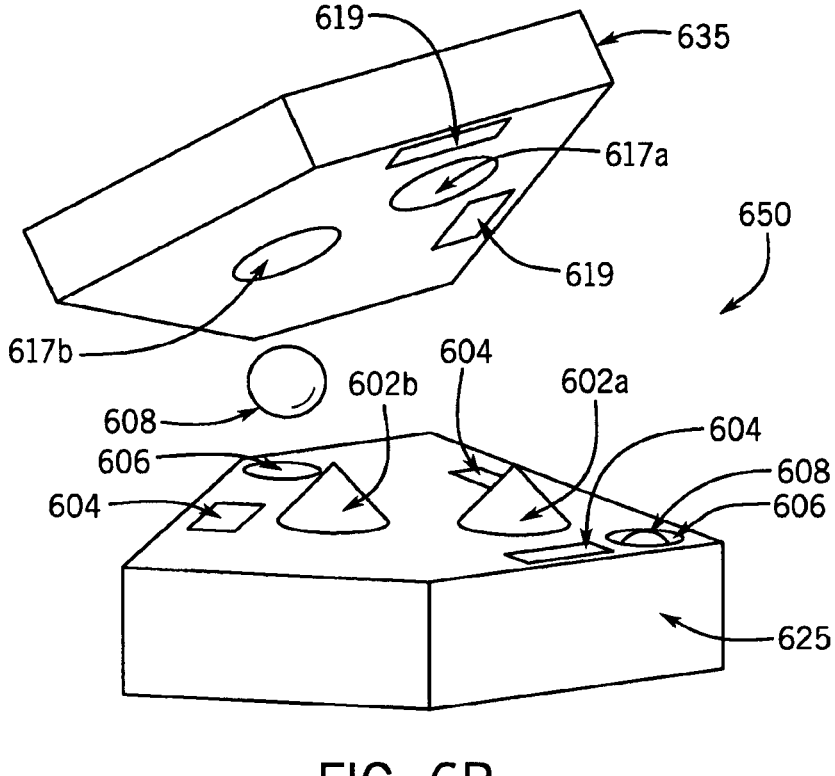
FIG. 6B illustrates an assembly view of a skin-mounted fiducial and its associated over-the-drape mating fiducial in accordance with some embodiments of the invention.

In some embodiments, FIG. 6A portrays a sample scenario for which applying a skin-mounted fiducial 625 and its associated over-the-drape-mating fiducial 635 could be used. In some embodiments, with the patient positioned prone on the operative table, skin-mounted fiducials can be applied over regions that will not be surgically exposed but under which contain bony anatomy for which a location is desired to be known relative to other anatomical regions. In some embodiments, after the surgical drape 605 is applied over the skin-mounted fiducial, the over-the-drape-mating fiducial can then be used to interpret the position of the underlying skin-mounted fiducial, described in more detail below in FIGS. 6B-D. For example, FIG. 6A illustrates an assembly or process view 600 for applying a skin-mounted fiducial 625 and its associated over-the drape fiducial 635 in accordance with some embodiments of the invention, and FIG. 6B illustrates an assembly view 650 of a skin-mounted fiducial 625 and its associated over-the-drape mating fiducial 635 in accordance with some embodiments of the invention. In some embodiments, the fiducial 625 can comprise the fiducial 400 and the fiducial 635 can comprise the fiducial 635.

In reference to FIG. 6B, detailed components depict a skin-mounted fiducial 625 and its associated over-the-drape-mating fiducial 635. In some embodiments, the skin-mounted fiducial 625 can include a method of adhering to the skin surface (not shown), including but not limited to adhesive material, looped regions to be sutured or stapled to the skin, percutaneous or bone-piercing screws, pins, wires, or other common fasteners, and/or attached bands to be tightly wrapped around body surfaces. In some embodiments, contained within or on either of the fiducials can be one or more radiopaque markers 608 that are readily visualized on X-ray images of the fiducials. Furthermore, in some embodiments, these radiopaque markers 608 can be positioned relative to one another via shape-specific cutouts 606 and the fiducial body itself in such a way that the markers can be used to identify the pose of the fiducial on 2D X-ray images, as described above in FIG. 4. In some embodiments, the fiducials can contain magnets (e.g., shown as magnet 604 in the fiducial 625, and 619 in the fiducial 635 embedded in or on the fiducial surfaces in such a way that it helps to securely fasten the two fiducials when separated by a surgical drape (shown as 605 in FIG. 6A). In some embodiments, the magnets can have varying geometry. For example, some embodiments include spherical magnets that can be used to serve both functions of a radiopaque marker as well as feature to help join mating fiducials across drapes. In some embodiments, the skin-mounted fiducial can also be equipped with protrusions to serve as mechanical alignment mates (shown as 602a and 602b). In some embodiments, the mates can protrude from one fiducial (e.g., 625 as shown and/or alternatively from both fiducial 625 and fiducial 635) and have complementary mating cutouts, such as 617a,

617b, within the opposite fiducial to help ensure both fiducials are properly aligned relative to one another. The protrusions are conical in shape in FIG. 6B, but can also be created with other tapered or non-tapered geometry in some embodiments.

Figure 6C:
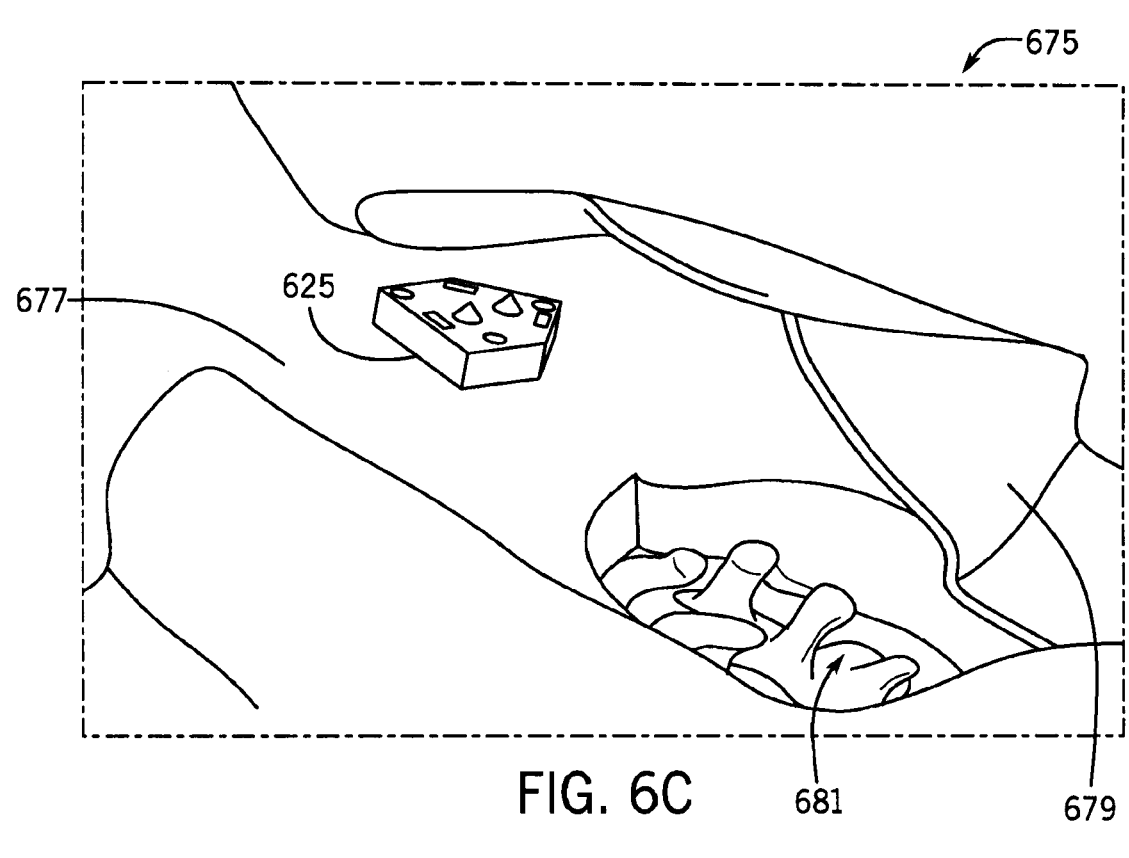
FIG. 6C illustrates a skin-mounted fiducial applied to an anatomical phantom in a region that is outside the surgical site but located over regions of underlying anatomy for which their location within 3D-tracking coordinates is desired to be known in accordance with some embodiments of the invention.
Figure 6D:
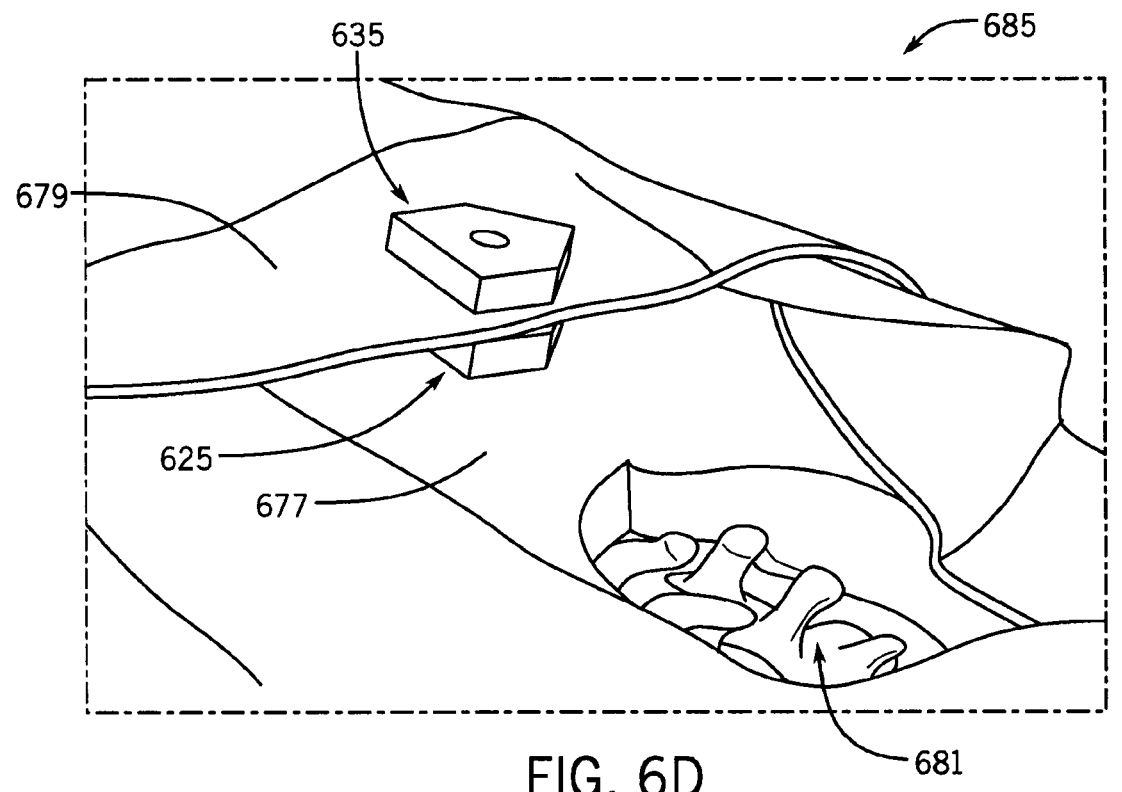
FIG. 6D illustrates a skin-mounted fiducial mating with its over-the-drape fiducial across a surgical drape/towel in accordance with some embodiments of the invention.

In some embodiments, FIG. 6C illustrates a skin-mounted fiducial applied to an anatomical phantom in a region that is outside the surgical site but located over regions of underlying anatomy for which their location within coordinates of the 3D-tracking acquisition system is desired to be known in accordance with some embodiments of the invention. Further, FIG. 6D illustrates some embodiments of a skin-mounted fiducial mating with its over-the-drape fiducial across a surgical drape/towel in accordance with some embodiments of the invention. In reference to FIG. 6C, in some embodiments, the skin-mounted fiducial 625 can be applied to an anatomical phantom 677 in a region that is outside the surgical site 681. For example, FIG. 6D illustrates some embodiments of a skin-mounted fiducial mating 625 with its over-the-drape fiducial 635 across a surgical drape/towel 679 in accordance with some embodiments of the invention. In some embodiments, because the over-the-drape-mating fiducial 635 is mechanically mated in a predictable fashion with the skin-surface fiducial 625, the location and pose of the over-the-drape-mating fiducial 635 can be used to compute the location and pose of the underlying skin-mounted fiducial 625. Furthermore, in some embodiments, if the skin-mounted fiducial 625 had been previously initialized to nearby anatomical structures, as described above in relation to FIGS. 4A-4I, the location and pose of the over-the-drape-mating fiducial 635 can then be used as a surrogate reference point for the underlying anatomy of interest 681.

Figures 7, 8:
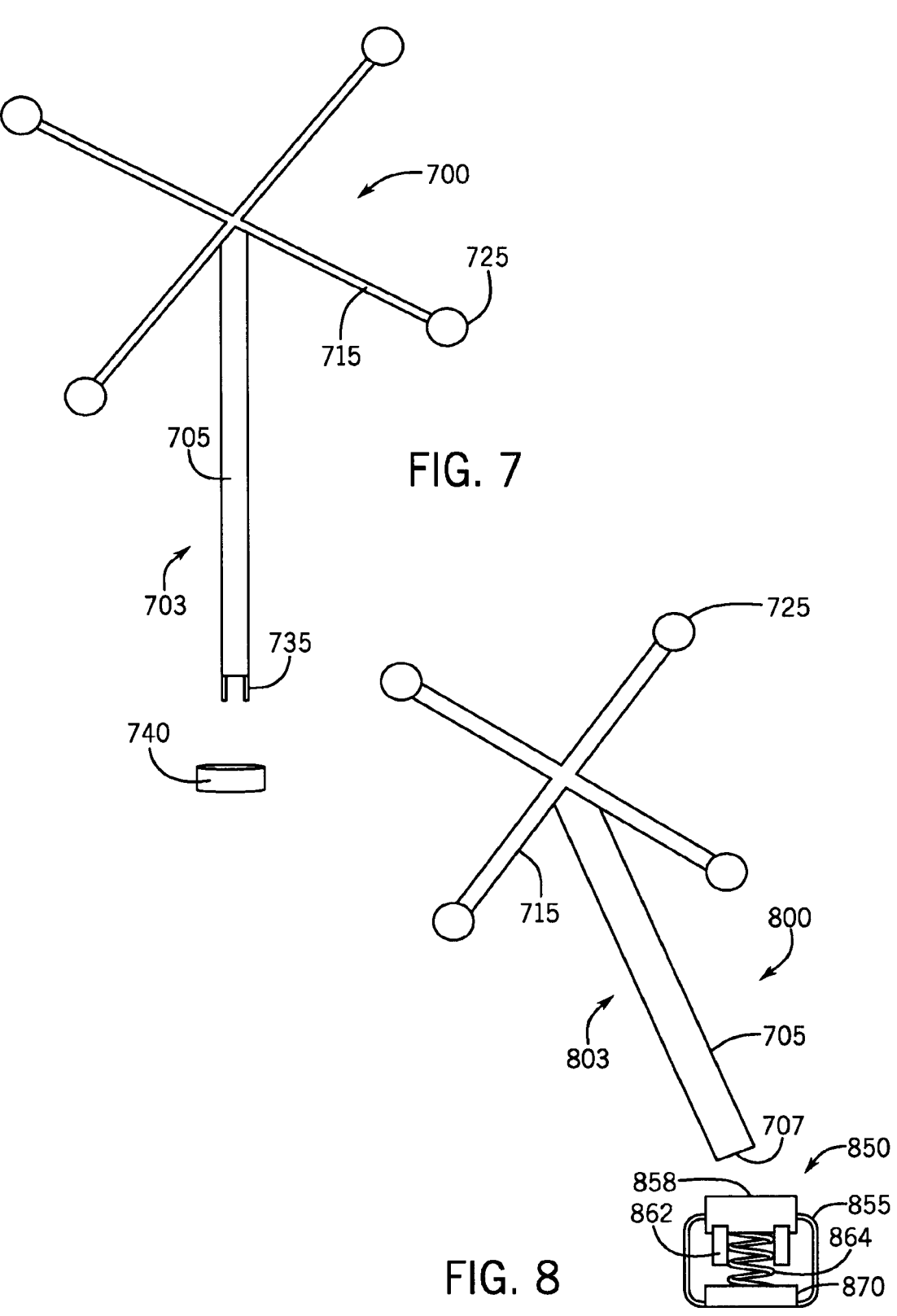
FIG. 7 illustrates an assembly view of a fiducial in accordance with some embodiments of the invention.
FIG. 8 illustrates an assembly view of a fiducial in accordance with some embodiments of the invention.

FIG. 7 illustrates an assembly view 700 of a fiducial 740 in accordance with some embodiments of the invention that enables unique identification of one fiducial to another. In some embodiments, this can be applied to scenarios when more than one fiducial is used, and the identity of the fiducial is required. In some embodiments, an interfacing probe 703 is shown designed with electrodes 735 to mate with the fiducial 740. In some embodiments, the electrodes can be coupled to or inserted into the fiducial 740, and based on the circuit characteristics built into the fiducial material (e.g., electrical resistance, capacitance, etc.), the fiducial's unique identity can be made known by the mating probe. As shown, in some embodiments, the probe 703 can include a probe shaft 705 coupled to a tracked DRF 715 with 3D-trackable markers 725. Further, in some embodiments, the fiducial 740 can include two electrodes built-in, and can possess identifying circuit components (e.g., resistors, capacitors, etc.) embedded between electrodes. In some embodiments, in this way, a probe 703 equipped with a tracked DRF 715 can be designed such that it has mating electrodes 735 that can interface with the fiducial 740, measuring the unique electrical characteristics of the fiducial 740, while simultaneously identifying the location and pose of the fiducial 740 in 3D space. Thus, in some embodiments described above can enable identification of unique fiducials, which can be useful when multiple fiducials are being deployed.

FIG. 8 illustrates an assembly view 800 of a fiducial in accordance with some embodiments of the invention, and enables unique identification of one fiducial compared to another. In some embodiments, this can be applied to scenarios when there is more than one fiducial used, and the unique identity of the fiducial is desired to be known. In this design, in some embodiments, a probe equipped with an RFID-reading circuit interfaces with a spring-embedded RFID-tag circuit within the fiducial. In some embodiments, in this way, the probe 803 is able to simultaneously communicate that the fiducial has been accessed by a depressed spring-loaded momentary push button, and can also acquire information as to which fiducial has been referenced. As shown, the probe 803 can comprise a tracked DRF 715 with trackable markers 725 configured to be coupled to an embedded RFID reader 850 including a spring-loaded button 855. In some embodiments, the tip 707 of the shaft 705 can couple with the surface 858 of the button 855, compressing the spring 864, and eventually enabling contact of the terminals 862 with the RFID tag 870. In some embodiments, if accessed by a probe 803 equipped with an RFID reader 850 in addition to a tracked DRF 715, a probe 803 that depresses the spring 864 can simultaneously perform three tasks 1.) trigger that it has approximated the fiducial, 2.) interpret the location of the fiducial surface, and 3.) interpret the unique identity of the fiducial based on its embedded RFID tag.

Figure 9A:
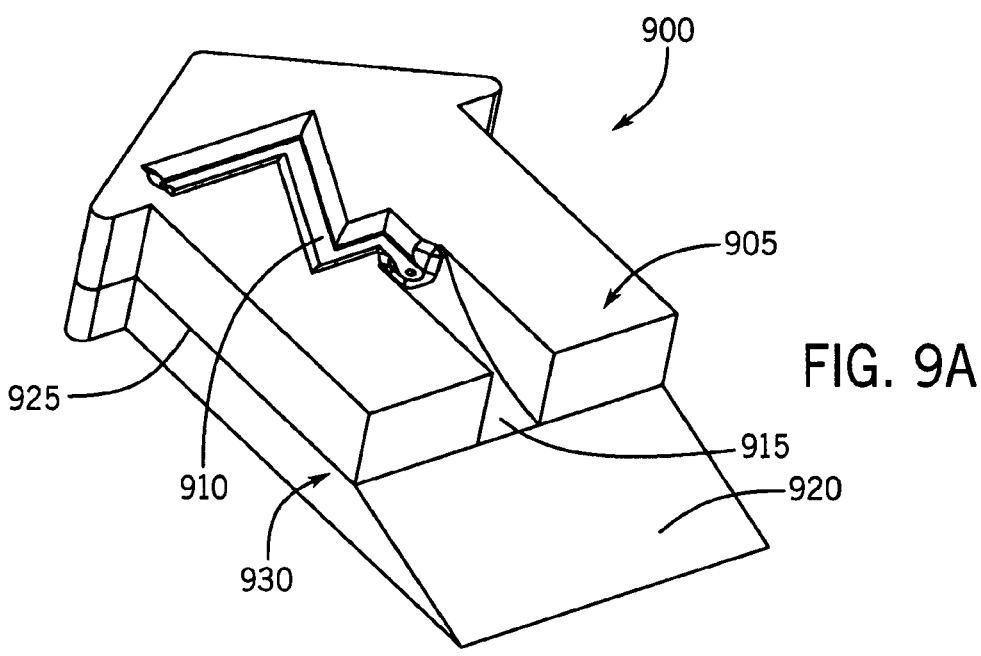
FIG. 9A illustrates an assembled skin-surface fiducial with mating top surface fiducial in accordance with some embodiments of the invention.

In some embodiments, FIG. 9A displays some embodiments of a skin-surface fiducial described previously in relation to FIGS. 6A-6B. In some embodiments, the assembled skin-surface fiducial 900 includes a mating top-surface fiducial 905 coupled to a skin-mountable fiducial. For example, FIG. 9A displays an assembled skin-surface fiducial 930 with its over-the-drape-mating fiducial 905 according to some embodiments. In some embodiments, the bottom surface fiducial 930 is equipped with a mechanism (not shown) of adhering to the skin surface. In some embodiments, the fiducial pair 905, 930 joins together at an interface 925 designed to accommodate surgical drapes or towels, while maintaining a predictable mating configuration. In some embodiments, the top fiducial contains a groove (tracing pattern 910) in a unique geometry (e.g., "z" geometry shown here) such that a 3D-tracked probe (e.g., any of the 3D-tracked probes described herein) can trace the pattern, as depicted previously in relation to FIG. 4H, and from that information interpret the unique identity of the fiducial, as well as interpret its location and pose in space, enabling the identification of a fiducial-based axes as described previously in relation to FIGS. 4A-4I.

The external design of the fiducial 900 is configured to communicate information to the user as embedded instructions according to some embodiments. Some embodiments of the fiducial possesses an external arrow appearance (FIG. 9A depicts an example of fiducial 900 assembled as an arrow) that can be used to indicate how the user should place the fiducial (e.g., position the fiducial on the skin such that the arrow points away from the surgical site). In some embodiments, a sloped decline 920 of known geometry on the bottom fiducial, as well as a curved decline 915 on the top fiducial, can be implemented to facilitate a user tracing a probe from the groove surface 910 of the top-half fiducial 905 down to the bottom surface of the bottom-half fiducial 930, which transitions to skin or drape-covered skin, onto which the top-half fiducial 905 is placed. In some embodiments, the framed structure of the fiducial 900 can allow for more predictable tracing over the transition from the fiducial groove 910 to the underlying surface. Additionally, in some embodiments, it allows for the ability to calculate the location of the underlying body surface given the known geometry of the fiducial slope design.

Figure 9B:
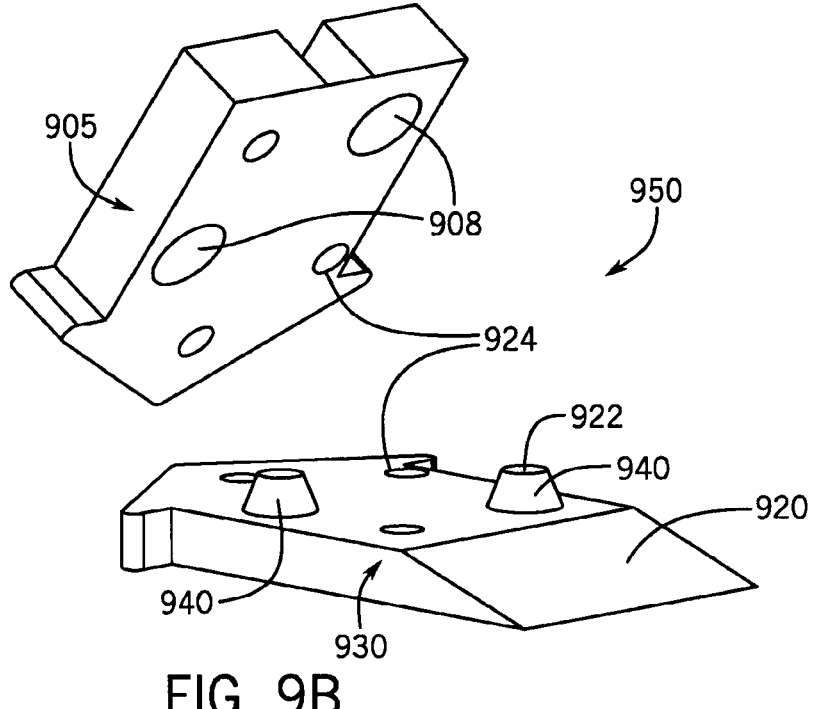
FIG. 9B illustrates an assembly view of the fiducial of FIG. 9A in accordance with some embodiments of the invention.

FIG. 9B illustrates an assembly view of the fiducial 900 of FIG. 9A in accordance with some embodiments of the invention. In some embodiments, the skin-mounted fiducial 930 contains male alignment-aiding protrusions 940, similar to those described previously in relation to FIG. 6B. Further, in some embodiments, the protrusions have a flattened top 922 to accommodate added volume of an overlying material, as in the case of a surgical drape. In some embodiments, in this way, the structure allows for close approximation of the two fiducial mates in the presence of a sandwiched drape by avoiding tenting of the drape in between the two fiducial halves. In some embodiments, the fiducials 905, 930 are equipped with cutouts 924 to accommodate both radiopaque markers and/or magnets, which can also act as radiopaque markers, as described previously in relation to FIG. 6B. In some embodiments, the cutouts 924 involves an asymmetric geometric pattern that substantially rigidly embeds the radiopaque markers in a relative configuration that enable unique pose estimations at any radiographic viewing angle. Instead of magnets used to help approximate the two fiducials, some embodiments can include protrusions with a quarter-turn or twisting mechanism that allows for tight mechanical linking across surgical drapes. In some embodiments, the over-the-drape-mating fiducial 905 is equipped with female alignment-aiding cutouts 908 configured to mate with the location of the protrusions 940, 922 on the skin-mounted fiducial 930. In some embodiments, it should be noted that the location, size, and geometry of these protrusions and mating cutouts can vary and that this is just some embodiments. Furthermore, in some embodiments, it is not necessary for the protrusions to only be located on the skin-mounted fiducial, and the cutouts on the over-the-drape-mating fiducial can include varying combinations of shapes and size.

In place of magnets, some embodiments can include a "clamp-over-drape" feature (e.g., tabs on the top fiducial to clamp down over the lower fiducial sides, while grabbing the drape in between). In some embodiments, this invention includes two or more clamping arms equipped on the over-the-drape fiducial designed to snap onto corresponding regions of the lower fiducial for ensuring proper alignment when separated by a surgical drape.

In some embodiments, the fiducial 905 can be equipped with other components mentioned throughout the document, such as the depth-stop-based fiducial and probe combination described later in reference to FIGS. 10A-10G. In some embodiments, of the fiducial that enable it to be uniquely identifiable include detents of discrete depths designed to mate with a probe equipped with depth-sensing technology, as described below in reference to FIGS. 10A-10G, such that the fiducial and unique location of the detent relative to the fiducial can be determined based on the distribution of measured detent depths.

In some embodiments, the bottom fiducial 930 can have a flexible component to enable it to successfully adhere and/or conform to the uneven surface contour of patient's skin.

Figures 10A, 10B, 10C:
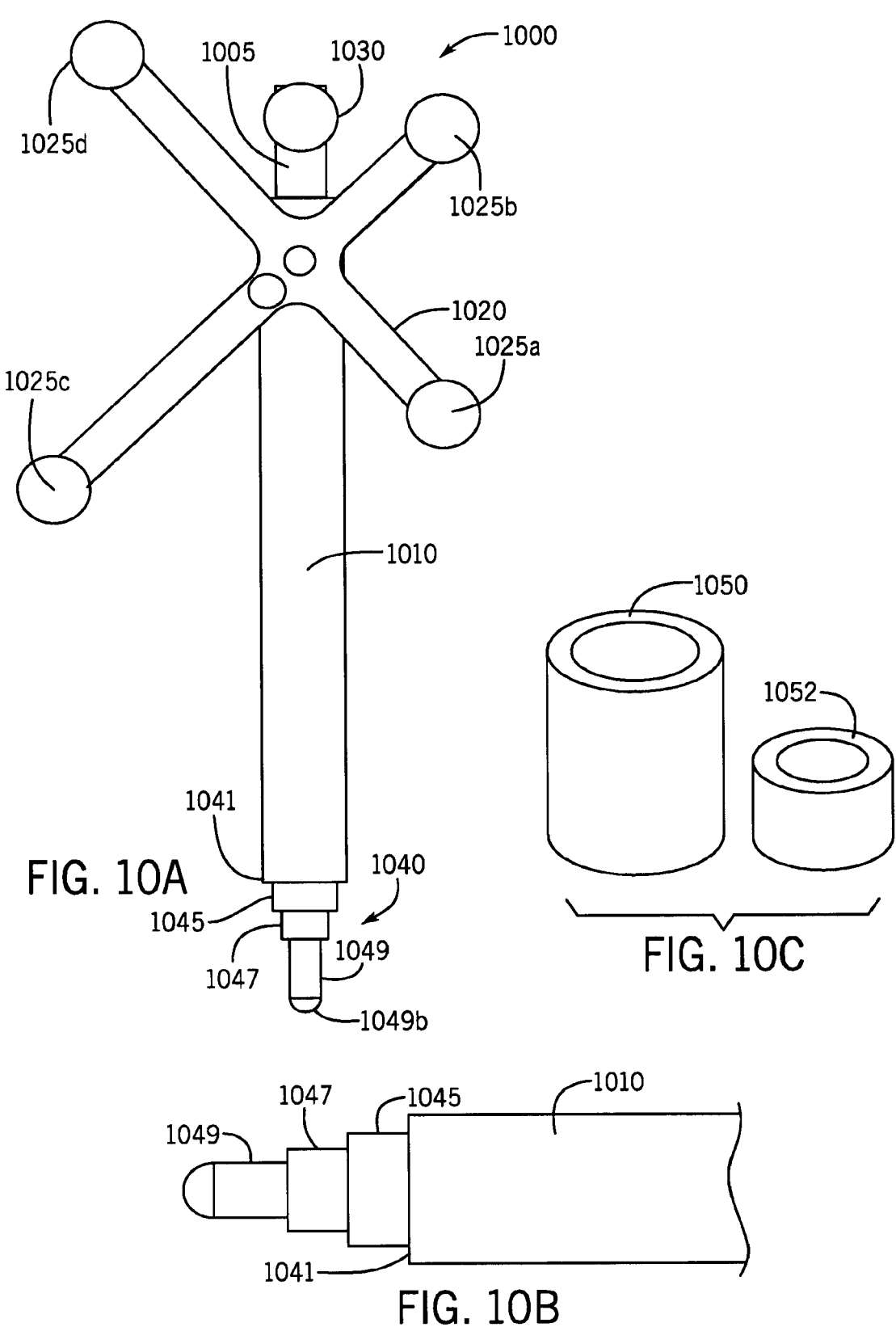
FIG. 10A illustrates a 3D-trackable probe equipped with a substantially rigidly attached trackable dynamic reference frame in accordance with some embodiments of the invention.
FIG. 10B illustrates a close-up perspective of an actuating tip and variable height selection depth-stops of the probe of FIG. 10A in accordance with some embodiments of the invention.
FIG. 10C illustrates receptacles designed to mate with the probe of FIGS. 10A-10B in accordance with some embodiments of the invention.

Some embodiments of the invention described in FIGS. 10A-10G include a 3D-tracked probe coupled with an actuating TMSM that indicates the depth of depression of a spring-loaded sliding shaft, as well as complementary mating fiducials that are designed to interface with and deflect the shaft by discrete amounts. In some embodiments, the purpose of this design is multifactorial. For example, FIG. 10A illustrates a 3D-trackable probe 1000 equipped with a substantially rigidly-attached, 3D tracked DRF 1020 in accordance with some embodiments of the invention. In some embodiments, the actuated TMSM 1030 on the tracked probe 1000 allows for analog communication between the probe 1000 and an acquisition system, as will be described below in reference to at least FIGS. 15A-15C and 63. In some embodiments, the actuated TMSM 1030 conveys information about the depth of deflection of the shaft 1049 at the tip 1049*b* of the probe 1000. Further, in some embodiments, when coupled with mating fiducials that are designed to deflect the shaft tip 1049*b* by set heights when fully-engaged, the probe 1000 can convey the following three things: 1.) when it is fully engaged with a mating fiducial, 2.) the location and pose of the mating fiducial, and 3.) the unique identity of the mating fiducial based on the designed depression depth that the fiducial will deflect the sliding shaft 1049. As shown, in some embodiments, the tracked DRF 1020 includes fixed 3D-tracked markers 1025*a*, 1025*b*, 1025*c*, 1025*d*. Some or all of the markers 1025*a*, 1025*b*, 1025*c*, 1025*d* shown in the DRF frame 1020 can be used in any of the DRFs described herein. In some embodiments, any of the DRFs described herein can use these markers, or may use fewer markers. In some embodiments, any of the DRFs described herein may use more markers similar or identical to any of the markers 1025*a*, 1025*b*, 1025*c*, and/or 1025*d*. In some embodiments, any of the probes or DRFs described herein can include any of the markers 1025*a*, 1025*b*, 1025*c*, and/or 1025*d* but with different geometries and/or shapes (e.g., the markers can be smaller or larger than shown, or can be placed at different distances from the probe shaft).

Some embodiments includes a 3D-tracked probe equipped with a substantially rigidly-attached 3D-tracked DRF 1020. In addition, a TMSM 1030 is substantially rigidly attached to a spring-loaded shaft 1049 that is coaxial with the probe 1000 and actuates within a through-hole down the length of the probe shaft 1010 of the probe 1000. In some embodiments, the sliding shaft 1049 can be actuated via a depressible tip 1049*b* that translates the shaft along with a mount 1005 for the TMSM 1030. In some embodiments, the probe also contains a series of concentrically-oriented, varying-diameter, protrusions 1040 near the probe tip 1049*b*. In some embodiments, these varying diameter protrusions 1040 can serve as variable-depth-stop selections (1041, 1045, 1047) when mating with depth-stop fiducials, as described below in reference to FIG. 10C, designed with varying inner diameters for mating with specific depth-stops 1040 on the probe 1000. For example, in some embodiments, FIG. 10B displays a more detailed perspective of the probe 1000 with actuating tip and variable depth-stops as described previously in FIG. 10A. In some embodiments, the tracked probe shaft 1010 includes coaxial cylindrical extrusions 1040 of various heights that act as a depth-stops to the actuation of the depressible sliding shaft tip 1049*b*, and its associated TMSM 1030, to different heights (1041, 1045, 1047) for unique trigger signals that are communicated to the computer system.

In some embodiments, FIG. 10C displays depth-stop fiducials designed to mate with the probe previously described above in relation to FIGS. 10A-10B. These depth-stop fiducials (1050, 1052) have variable inner diameters and/or heights such that they can couple with varying depth-stops on the probe. In some embodiments, in addition to having variable inner diameters to mate with defined depth-stops on the probe (e.g., such as probe 1000), which can lead to identifiable deflections of the TMSM 1030 relative to the DRF 1020. Further, some embodiments of these depth-stop fiducials also contain variable floor depths, such that the sliding probe tip 1049*b* can be actuating by varying amounts despite mating with depth-stop fiducials with matching inner diameters. In some embodiments, in this way, these depth-stop fiducials (1050, 1052) can be distinguished from one another and their mating inner diameters and/or depth-stops provide for additional, unique identifiers. In some embodiments, these depth-stop fiducials can therefore be coupled as probe-interface components coupled to fiducials previously described in relation to FIGS. 3A-3B, 6A-6D, and 9A-9B.

Figures 10D, 10E:
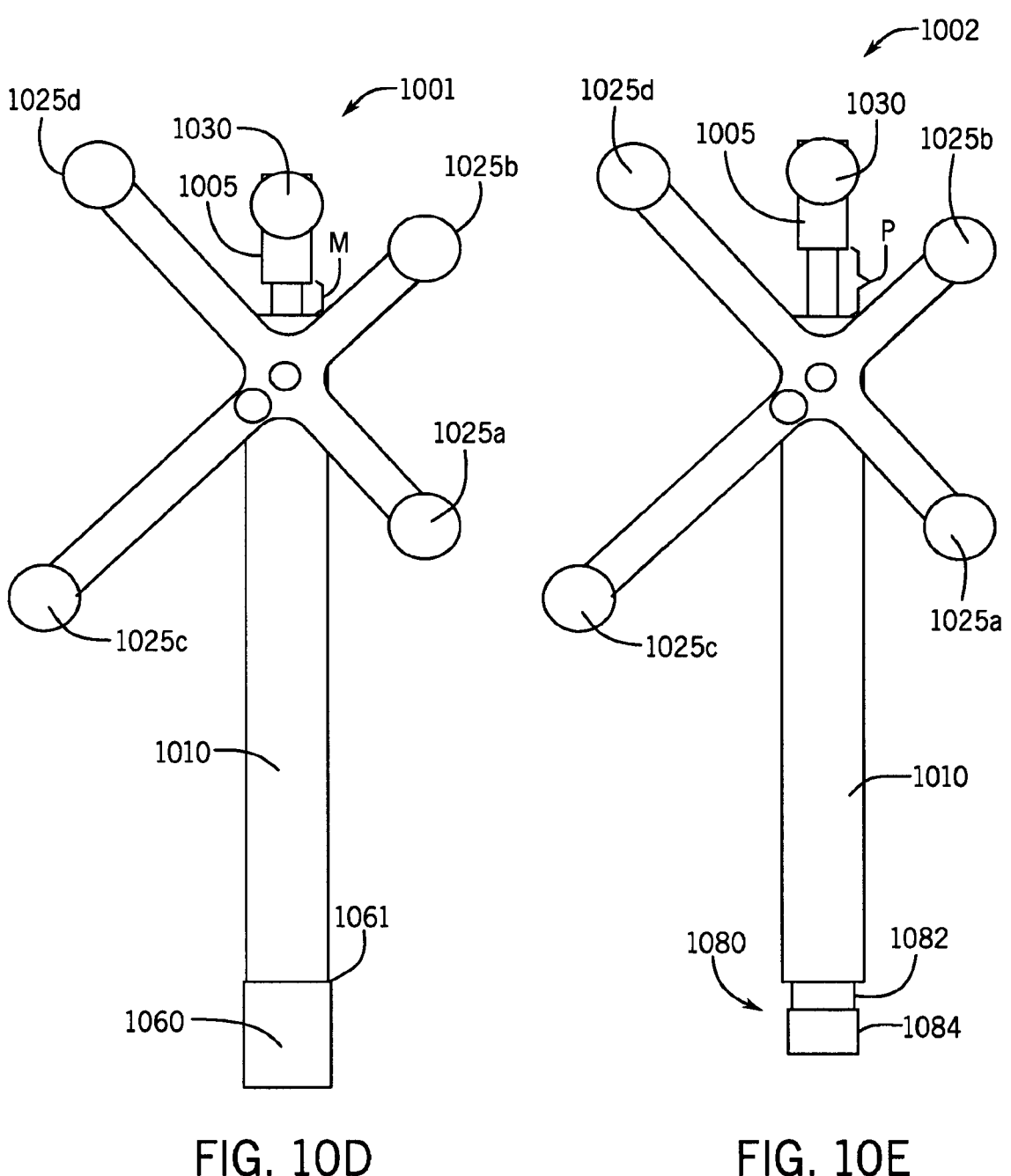
FIG. 10D illustrates the probe of FIG. 10A mated with a particular receptacle of FIG. 10C in accordance with some embodiments of the invention.
FIG. 10E illustrates the probe of FIG. 10A mated with a receptacle designed to mate with a different height selector of the probe than shown in FIG. 10D in accordance with some embodiments of the invention.

In some embodiments, FIG. 10D displays the probe 1000, previously described in relation to FIGS. 10A-10B, mated with a particular depth-stop fiducial 1050, previously described in relation to FIG. 10C. In some embodiments, with these two components coupled in this way, the TMSM 1030 can be actuated coaxially with the probe shaft 1010 and based on the known geometry of both the probe and its mating depth-stop fiducial, the deflection can be measured relative to the tracked DRF and compared to what deflection amounts are anticipated based on particular mates to the probe's depth-stop heights 1061 (previously shown as 1041 in FIG. 10A). In some embodiments, the measured deflection ("M") of the sliding tip and attached TMSM 1030 to the sliding shaft is able to serve as a unique identifier of when the probe (e.g., 1000 and/or 1001) is fully engaged with a specific depth-stop fiducial 1060 (previously shown as 1050 in FIG. 10C).

In some embodiments, FIG. 10E displays a probe 1002, as previously described in relation to FIG. 10A, mated with a depth-stop fiducial 1084 (previously shown as 1052 in FIG. 10C) designed to mate with a unique depth-stop 1082 (previously shown as 1045 in FIG. 10A) of the probe 1000 than was shown previously in relation to FIG. 10D. In some embodiments, as compared to FIG. 10D, this figure displays the different region of mating 1080 on the probe's unique depth-stop 1082 along with the associated difference in deflection height ("P") of the TMSM 1030, indicating the different depression depth of the sliding probe tip (compare "P" in FIG. 10E with "M" in FIG. 10D).

Figure 10F:
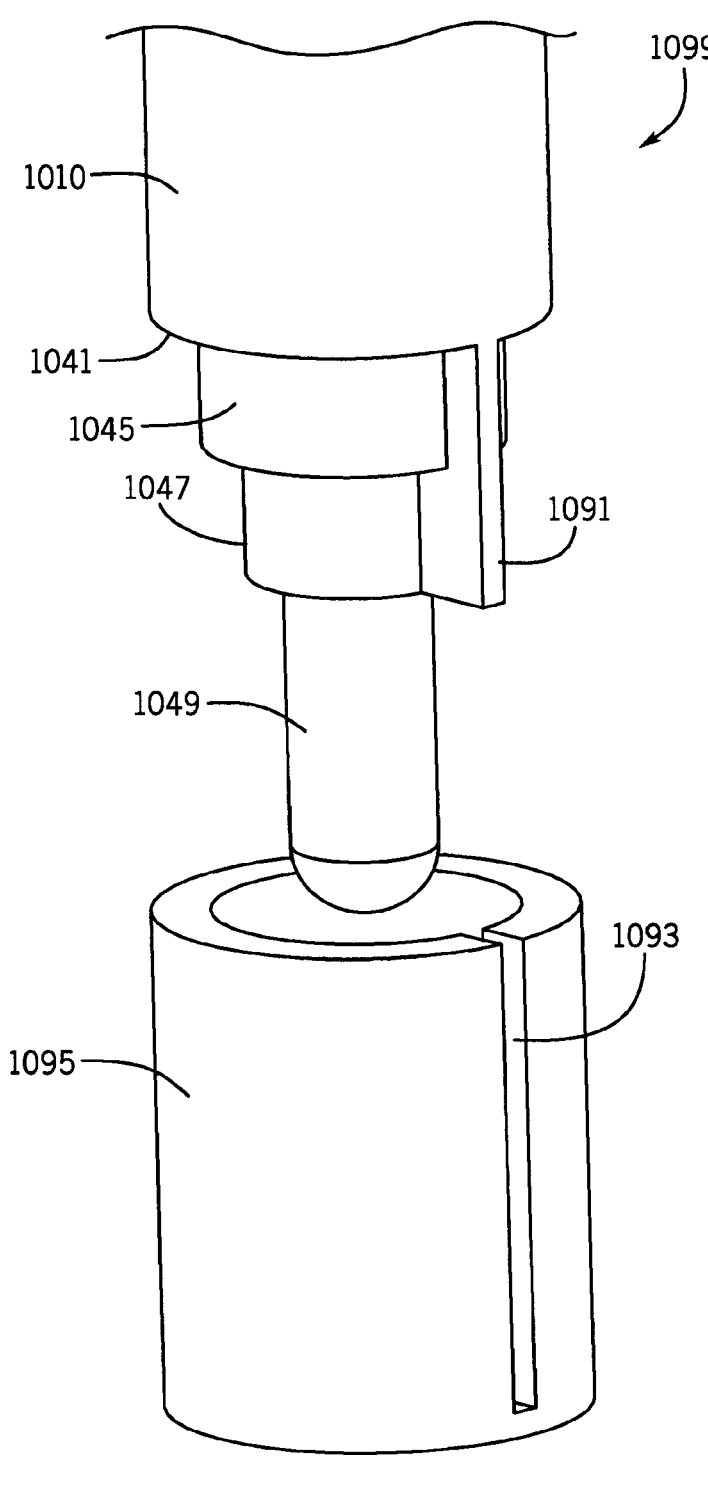
FIG. 10F illustrates an assembly view of a portion of a probe in accordance with some embodiments of the invention.
Figure 10G:
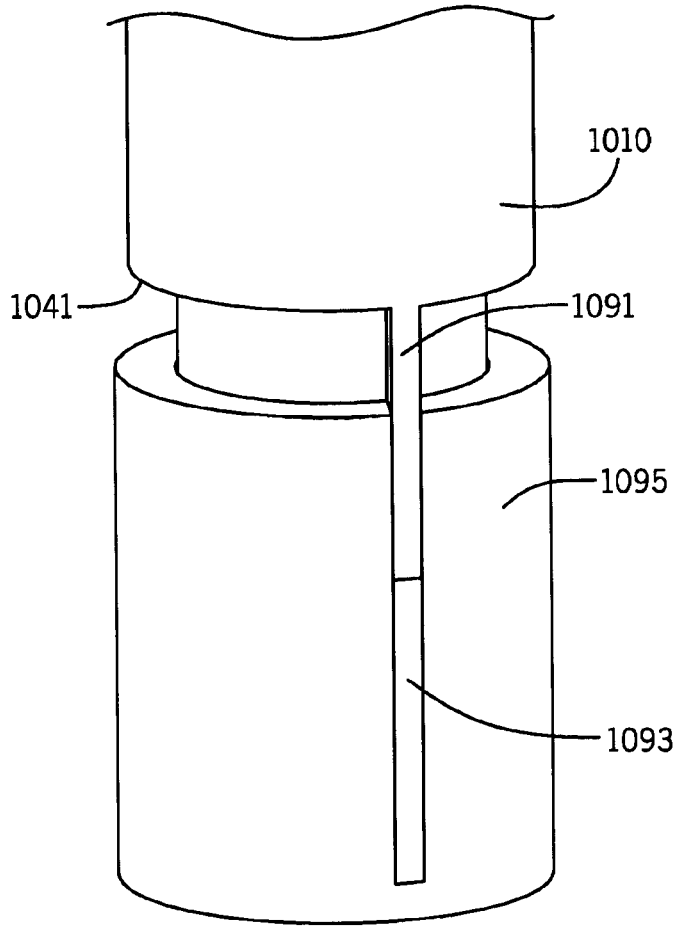
FIG. 10G illustrates a partially assembled view of the probe of FIG. 10F in accordance with some embodiments of the invention.

FIG. 10F illustrates an assembly view 1099 of a portion of the probe 1000 in accordance with some embodiments of the invention. In some embodiments, the 3D-tracked probe 1000, as described previously in relation to FIG. 10A, contains an asymmetric, protruding extrusion 1091 that can engage with any of the depth-stop fiducials, as described previously in relation to FIG. 10C, where a corresponding slot 1093 of a depth-stop fiducial mates with the probe's extrusion 1091. In some embodiments, the probe can only mate in one orientation with the depth-stop fiducial due to the asymmetrical design of the slot cutout 1093. In some embodiments, this asymmetric alignment enables the probe 1099 to register the unique orientation of the coordinate axes of the fiducial 1095, and thus detect how the fiducial 1095 rotates and translates in 3D space between registrations. In some embodiments, FIG. 10G illustrates a perspective view of the depth-stop fiducial 1095 partially engaged with the depth-stop-equipped, 3D-tracking probe 1000, both previously depicted in relation to FIG. 10F.

Figure 11A:
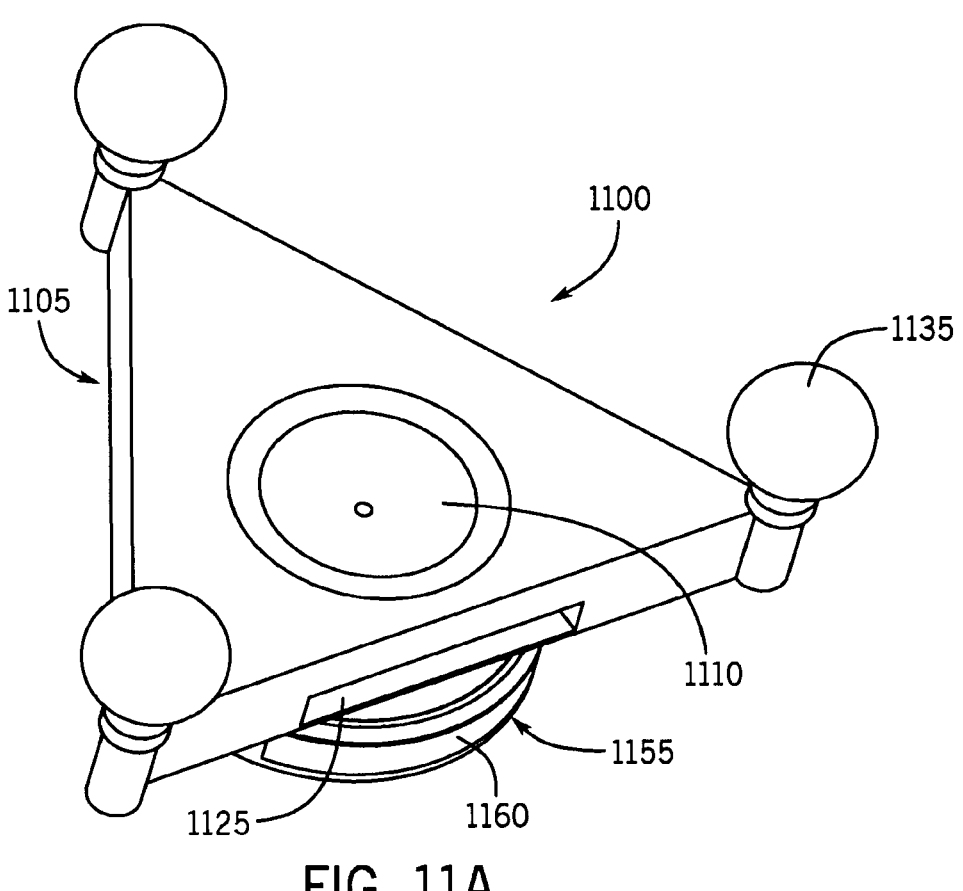
FIG. 11A illustrates a top perspective assembly view of a skin surface fiducial mated with an over-the-drape fiducial that contains three or more tracked markers in accordance with some embodiments of the invention.
Figure 11B:
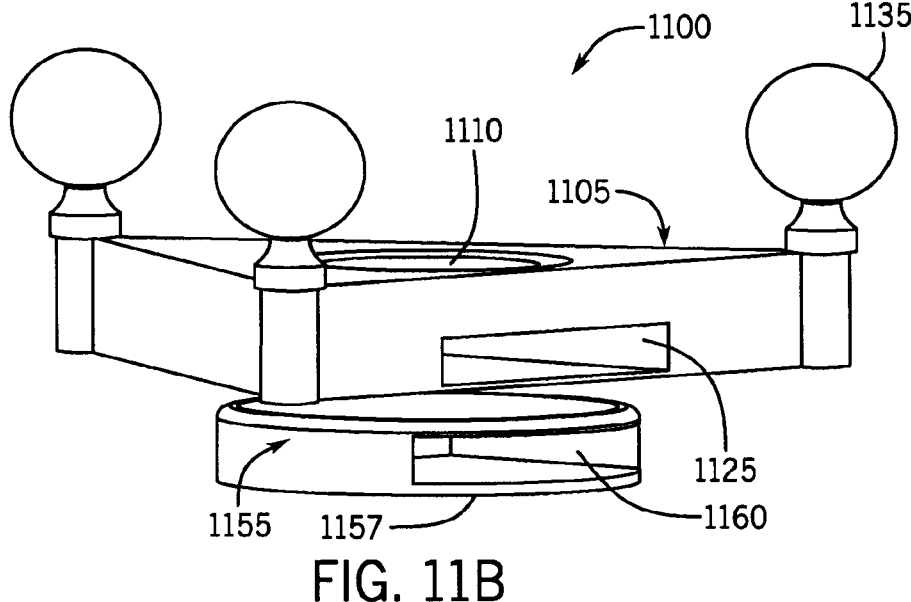
FIG. 11B illustrates a side perspective assembly view of the fiducial of FIG. 11A accordance with some embodiments of the invention.

In some embodiments, FIGS. 11A-11B displays skin-surface and mating fiducial design as previously described in FIGS. 6A-6B and FIGS. 9A-9B. In some embodiments, the primary difference in this design is that there are tracked markers mounted to the top fiducial such that its location, pose, and identity are all able to be registered by a 3D-tracking acquisition system without the need for the fiducial to interface with a tracked probe. In some embodiments, the fiducial's information is constantly being registered provided it is in line of sight of the 3D-tracking camera system. In some embodiments, the assembled fiducial can serve the same purpose as previously described in that once initialized, it serves as a surface reference point for the 3D location in space of underlying anatomical structures. For example, in some embodiments, FIG. 11A displays a top view assembly view 1100 of a skin-surface fiducial 1155 mated with an over-the-drape-mating fiducial 1105 that contains three or more tracked markers 1135. In some embodiments, these markers 1135 are arranged in a predetermined configuration to form a DRF object, such that a camera acquisition system can recognize them as a unique entity related to the fiducial. In some embodiments, these tracked markers 1135 allow for the constant registration of the fiducial's location and pose in 3D space provided that they are within line of sight of the camera. In some embodiments, in the event that these tracked markers 1135 are not within line of sight of the camera, the top fiducial component 1105 also contains a surface contour 1110 that can be accessed and traced and/or tapped by a 3D-tracked probe. In some embodiments, the fiducial assembly (1105, 1155) is designed with redundancy to ensure it can be registered in 3D space, regardless of whether the line of sight of the tracked markers is obstructed or not.

In some embodiments, the markers mounted on the fiducial can be placed in a way to enable unique identification of the fiducial. In some embodiments, include three or more 3D-tracked markers that are arranged in a unique, identifiable pattern (e.g., asymmetric triangle).

Figures 27A, 27B, 27C, 27D:
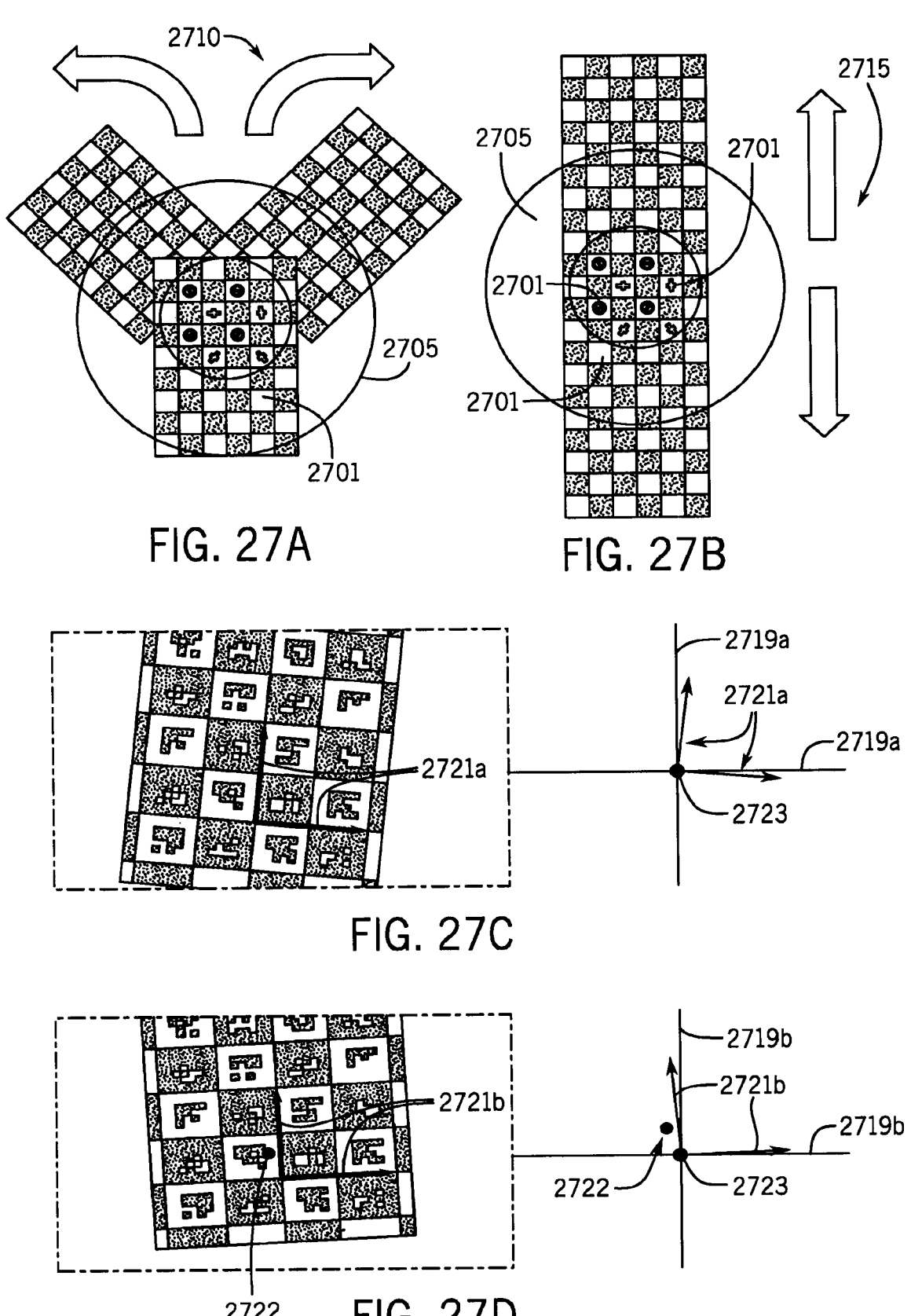
FIGS. 27A-27D includes representations of 3D tracking methods in accordance with some embodiments of the invention.

Some embodiments include embedding the unique pattern, depicted in FIGS. 27A-27B, on a fiducial depicted in FIGS. 6A-6D, 9A-9B, 11A-11B, in order to enable enhanced X-ray imaging fusion with optical systems to provide localization features across two coordinate systems. In some embodiments, a unique pattern (e.g., CALTag/ARtag) can be applied to a fiducial patch or a skin-based fiducial. This design involves a radiopaque, unique-pattern surface (e.g., CALTag) that can be easily visualized in both 3D-tracking camera space and 2D or 3D X-ray imaging space according to some embodiments. Some embodiments involve using the absolute location of the C-arm relative to the unique-pattern surface to calculate the relative location and pose between separate X-ray images and enable a robust stitching algorithm to understand their spatial relationships and overlaps. In some embodiments, this invention could be used with a corresponding optical sensor that is mounted to the X-ray imaging device, and the system knows the relative geometric relationship between the camera and X-ray imaging device's emitter or detector. In some embodiments, this system can enable stitching, unique 3D pose detection, absolute location relations, and should be robust with X-ray images that are acquired with a rotated/oblique X-ray imaging system. In some embodiments, the unique-pattern surface visualized in the X-ray image could enable automated scaling of the image into physical units (e.g., millimeters), as well as automatically detect the pose of the fiducial relative to anatomical landmark of interest, and relative to the X-ray imaging device.

FIG. 11B displays another view of a fiducial equipped with tracked markers on the over-the-drape-mating fiducial 1105 coupled with a skin-mounted fiducial 1155 that is mounted to the patient skin via an adhesive backing 1157 according to some embodiments. Some embodiments can also contain insert slots for inserted radiopaque magnets and/or electronics 1125, 1160. It should be noted that although not shown in FIGS. 11A-11B, this fiducial 1100 can also be equipped with protrusions and mating cutouts for alignment as previously described in relation to FIGS. 6A-6D and FIGS. 9A-9B according to some embodiments.

Figure 12:
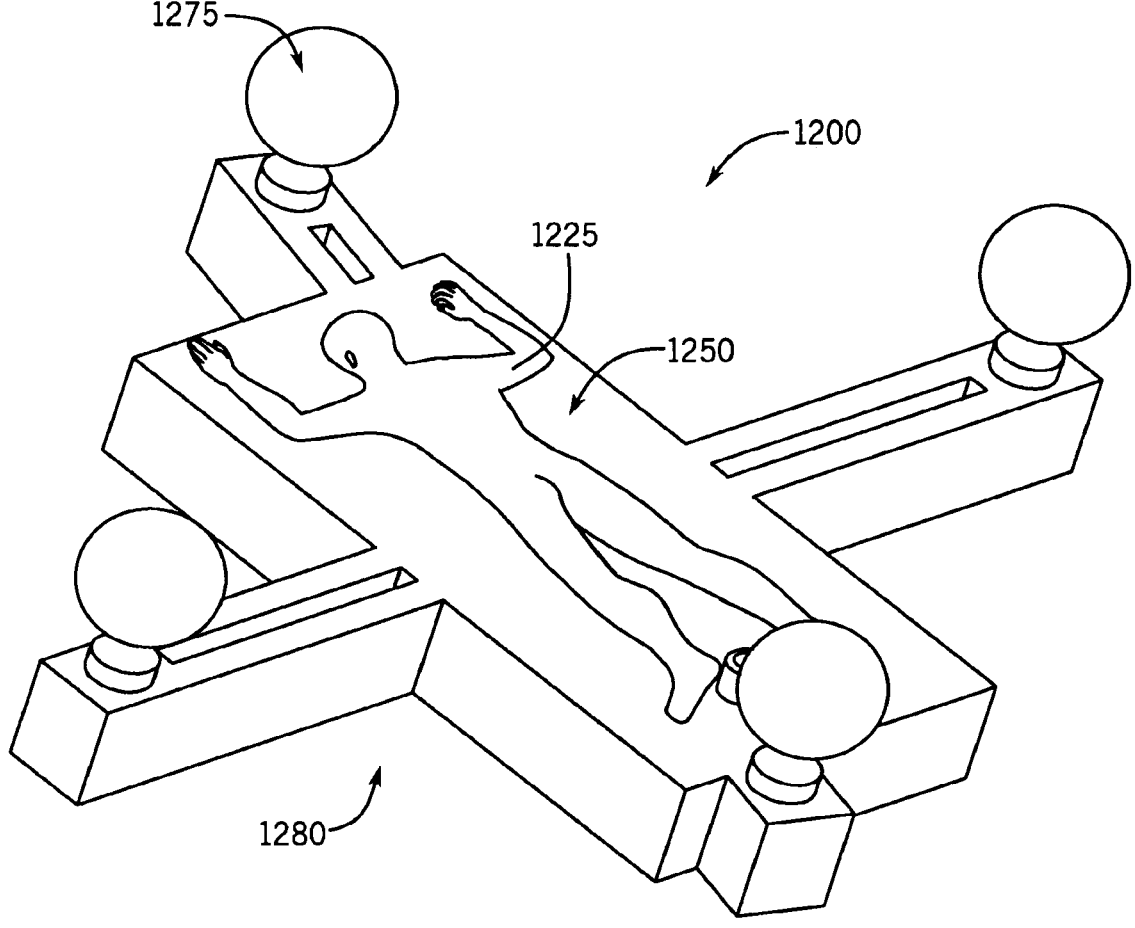
FIG. 12 illustrates a representation of a tracked dynamic reference frame in accordance with some embodiments of the invention.

Some embodiments of the invention depicted in FIG. 12 include a tracked DRF that is equipped with indications of the relative anatomical reference planes. In this instance, the functional aspects reside in the external indication methods to inform the user how to best orient a tracked DRF for it to indicate to the acquisition system how to interpret camera coordinates relative to anatomical axes coordinates according to some embodiments. In some embodiments, FIG. 12 displays a representation 1200 of a tracked DRF 1250 with built-in indication for communicating relative referenced anatomical axes. In some embodiments, this design includes four 3D-tracked markers 1275 that define a DRF, but also an overlying body outline reference 1225 to help instruct the user how to appropriately position the DRF nearby the patient. In some embodiments, attached to this device is an adjustable mounting surface (marked as 1280 as being under the frame 1250) that allows the user to rotate the device until it is aligned with the patient's orientation and then lock it into place via any common fastening mechanism. In some embodiments, this device allows the acquisition system to register not only a DRF, but also define anatomical reference planes relative to the known geometry of the dynamic reference plane. In some embodiments, by utilizing this device, it allows for the acquisition system to display data to the user onto anatomical reference planes (e.g., sagittal, coronal, axial) rather than camera coordinates which often appear skewed and challenging to interpret by a user depending on the camera's orientation relative to the subject. In some embodiments, it should be noted that the methods of indicating anatomical reference axes on this device are not limited to the human body overlay as shown in this figure. In some embodiments, other methods include but are not limited to written text displaying the associated anatomical axes, images of discrete body parts to represent anatomical orientations, and alphanumeric or unique pattern labels for regions that should be aligned with particular anatomical axes so that software interfaces can walk the user through orienting the DRF relative to the patient appropriately. In some embodiments, of note is that the reference frame can be mounted almost anywhere and does not need to have an adjustable mount, and could be rigid/orthogonal relative to the patient or surgical table. For example, in some embodiments, involve the reference frame being mounted substantially rigidly in one orientation to the surgical table, or any rigid surface, or substantially rigidly mounted directly to the patient anatomy (e.g., spinous process of the spine).

Figure 13:
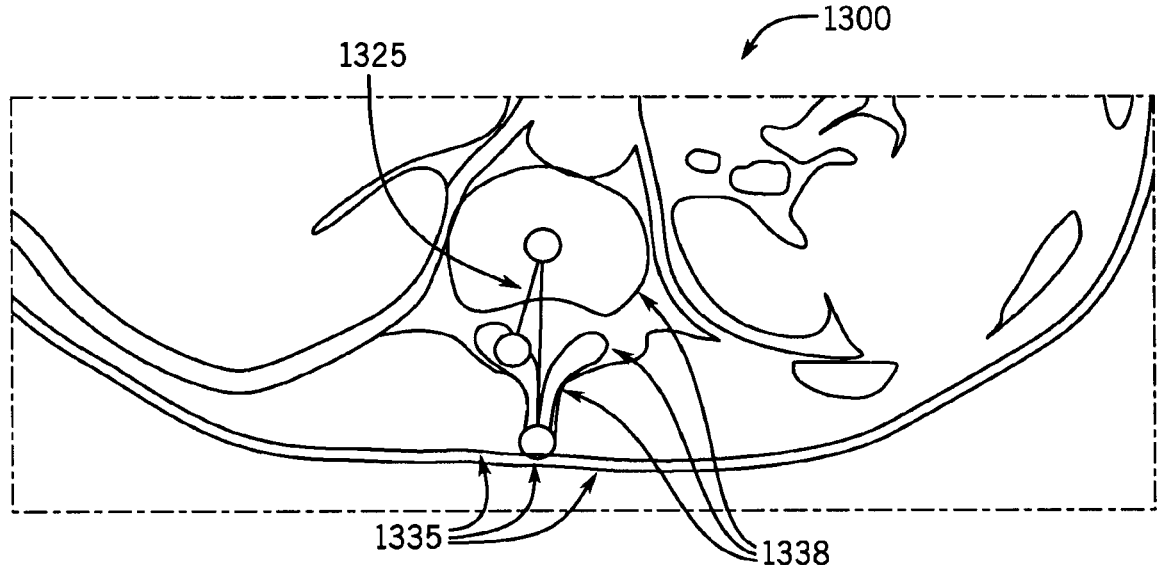
FIG. 13 illustrates a sample cross-sectional CT scan view of a spine in accordance with some embodiments of the invention.

Some embodiments of the invention include a cross-sectional CT scan view of a spine and highlights a few anatomical regions of interest that may be used to initialize patient data prior to performing assessments of the contour of the spine via tracing methods that will be described in more detail below in reference to FIGS. 65A-65E and FIGS. 66A-65B. In some embodiments, this can be used to interpret the cross-sectional displacement vectors between certain regions (e.g., the skin surface, lamina, transverse process) and other regions of interest (e.g., centroid of the vertebral body, anterior segment of the vertebral body, etc.). In some embodiments, using a CT scan to initialize a patient prior to intraoperative assessments of spinal alignment enables software to better interpret localization of exposed regions (e.g., lamina) as a surrogate for the location of other regions (e.g., vertebral body centroid). In some embodiments, in doing this, intraoperative interpretation of acquired data can be performed with or without the use of fiducial landmarks as described previously in relation to FIGS. 3A-3B, 4A-4I, 6A-6B, 9A-9B, and 11A-11B. In some embodiments, for example, FIG. 13 displays a sample cross-sectional CT image 1300 of a patient in which particular anatomical regions are visible including posterior skin surface 1335, and cross-sectional view of the vertebral landmarks 1338 and many of its bony elements. In some embodiments, from CT image sets, it is possible to initialize a patient's anatomy by calculating displacement vectors 1325 from particular regions of interest to another (e.g., skin midpoint to vertebral body centroid, and lamina to vertebral body centroid). In some embodiments, after initialization, it is possible for software to interpret the location of one region in terms of its relative location to other initialized regions of interest. In some embodiments, although the location of the centroid of the vertebral body may be most advantageous for interpreting spinal alignment parameters, if the skin or lamina is all that is exposed during surgery, the coordinates of the exposed elements can be gathered and then interpreted, based on pre-operative and/or intraoperative initialization data, to represent the location of unexposed regions (e.g., vertebral body centroid).

Some embodiments of the invention include an assembly with an arrangement of 3D-tracked markers that can be utilized for discrete signaling to an acquisition system. In some embodiments, four tracked markers that make up a dynamic reference frame (DRF), and two tracked stray markers (TSMs) are included in the assembly. In some embodiments, the center of the assembly can include a rotating shield that can be positioned to cover select TSMs, or none at all. In some embodiments, with the tools geometry known, the acquisition system software can interpret which TSMs are exposed, and based on pre-programmed combinations, the tool is able to communicate discrete messages with the acquisition system. In some embodiments, for example, if a first TSM is covered, this can indicate the system is in a particular state as opposed to if a second TSM is covered, which would indicate another state. In some embodiments, because the tool contains a DRF, its location and pose can be interpreted by a 3D-tracking camera, and the arrangement of covered and uncovered stray markers can then be used for communication particular commands or device states.

Figures 14A, 14B, 14C:
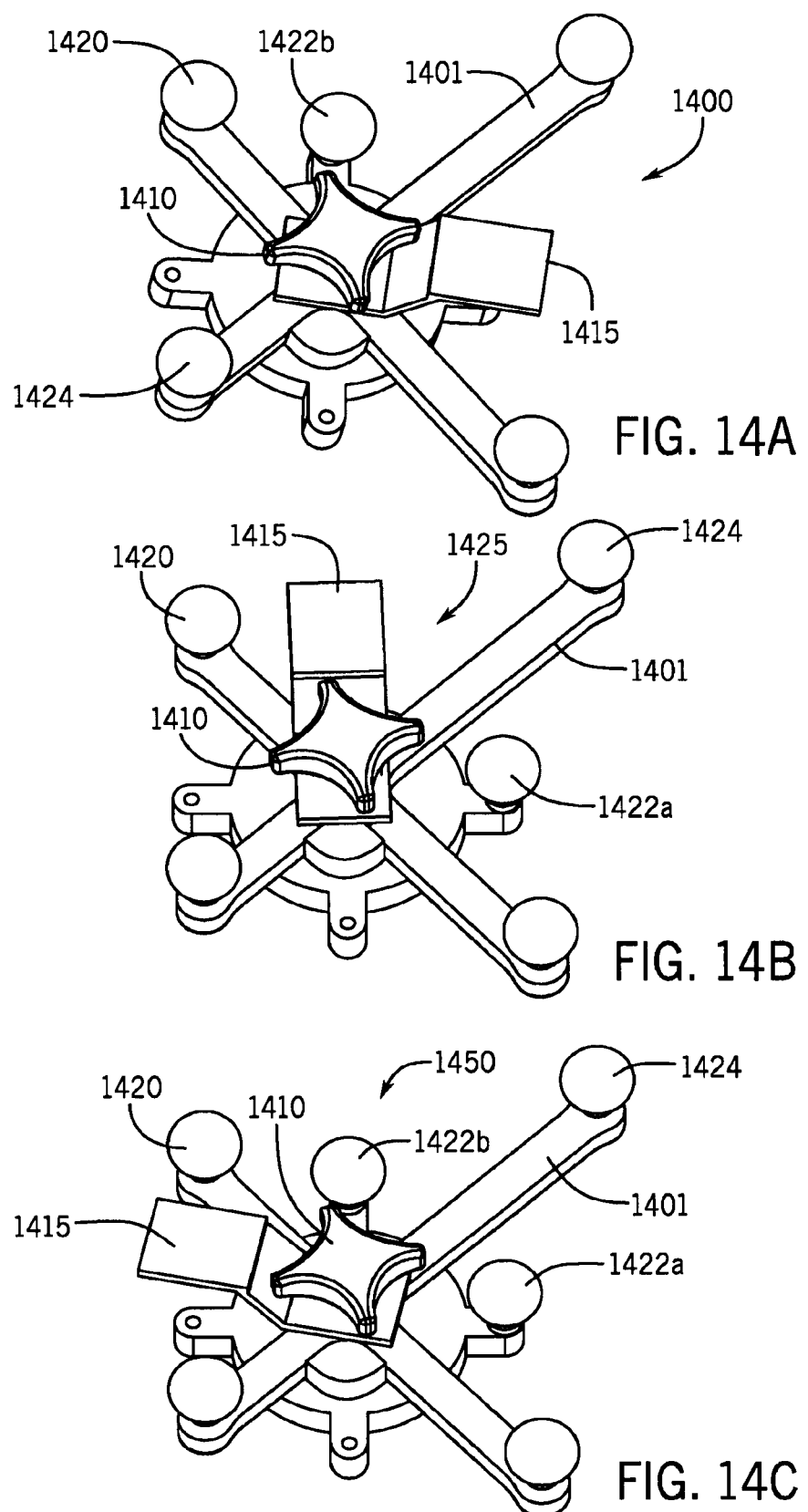
FIG. 14A illustrates a tool equipped with a tracked dynamic reference frame in accordance with some embodiments of the invention.
FIGS. 14B-14C illustrate the tool of FIG. 14A in different arrangements in accordance with some embodiments of the invention.

In some embodiments, FIG. 14A displays a tool equipped with a tracked DRF 1401 with markers (1420, 1424), two TSMs identified as 1422a (not visible) and 1422b. In some embodiments, the tool is also equipped with a rotating shield 1415 that is currently positioned to cover visibility of a TSM 1422a. In some embodiments, because it is equipped with a DRF, a 3D-tracking camera is able to locate the location and pose of tool 1400 in 3D space, as well as distinguish between the four markers serving as a DRF and those serving as TSMs. In some embodiments, the tool can be programmed to communicate with the acquisition system via having varying combinations of the TSMs visible or invisible. In some embodiments, when the 1422a is covered, the system indicates that it is in a certain state, that is different than if 1422b is covered, as is shown in FIG. 14B, which is also different from the state communicated by neither of the TSMs being covered, as is shown in FIG. 14C. In some embodiments, it should be noted that there can be any combination of one or more TSMs associated with this tool, and there can also be any permutation of covering or uncovering individual or combinations of TSMs to communicate various states to the acquisition system. In some embodiments, the static, known location of the TSMs relative to the registered DRF enable the computer system to robustly filter out any phantom markers or additional stray markers not associated with this tool as the computer algorithms can determine which stray markers visible to the camera possess locations relative to the tool (1400, 1425, 1450) that match the pre-set locations of the TSMs via the design of the tool base mount. In some embodiments, the rotating shield shown in this figure is only how to block the 3D-tracking camera's visualization of the TSMs. Some embodiments of blocking visualization include but are not limited to spring-loaded rotational wipers, linear-motion sliders, actuating the TSMs such that they move from covered to uncovered positions, and rotating shields with multiple panels such that varying combinations of TSMs can be covered or uncovered. In some embodiments, it should be noted that this technology of signaling through covering and uncovering TSMs can also be combined with actuating TSMs as was previously described in reference to FIGS. 10A-10G and as will be described in more detail below in relation to FIGS. 15A-15C, 63, and 64A-64B.

FIGS. 14B-14C illustrate the tool of FIG. 14A in different arrangements in accordance with some embodiments of the invention. For example, in some embodiments, FIG. 14B displays a tool previously discussed in relation to FIG. 14A, but in this arrangement, the rotating shield 1415 is covering visualization of the TSM 1422b, and the TSM 1422a is uncovered. In some embodiments, this combination can be used to communicate its unique state to the acquisition system software. Further, in some embodiments, FIG. 14C displays a tool previously discussed in relation to FIG. 14A, but in this arrangement, the rotating shield 1415 is positioned such that both TSMs 1422a and 1422b are visible, which is used to communicate a unique state to the acquisition system software.

Figures 15A, 15B, 15C:
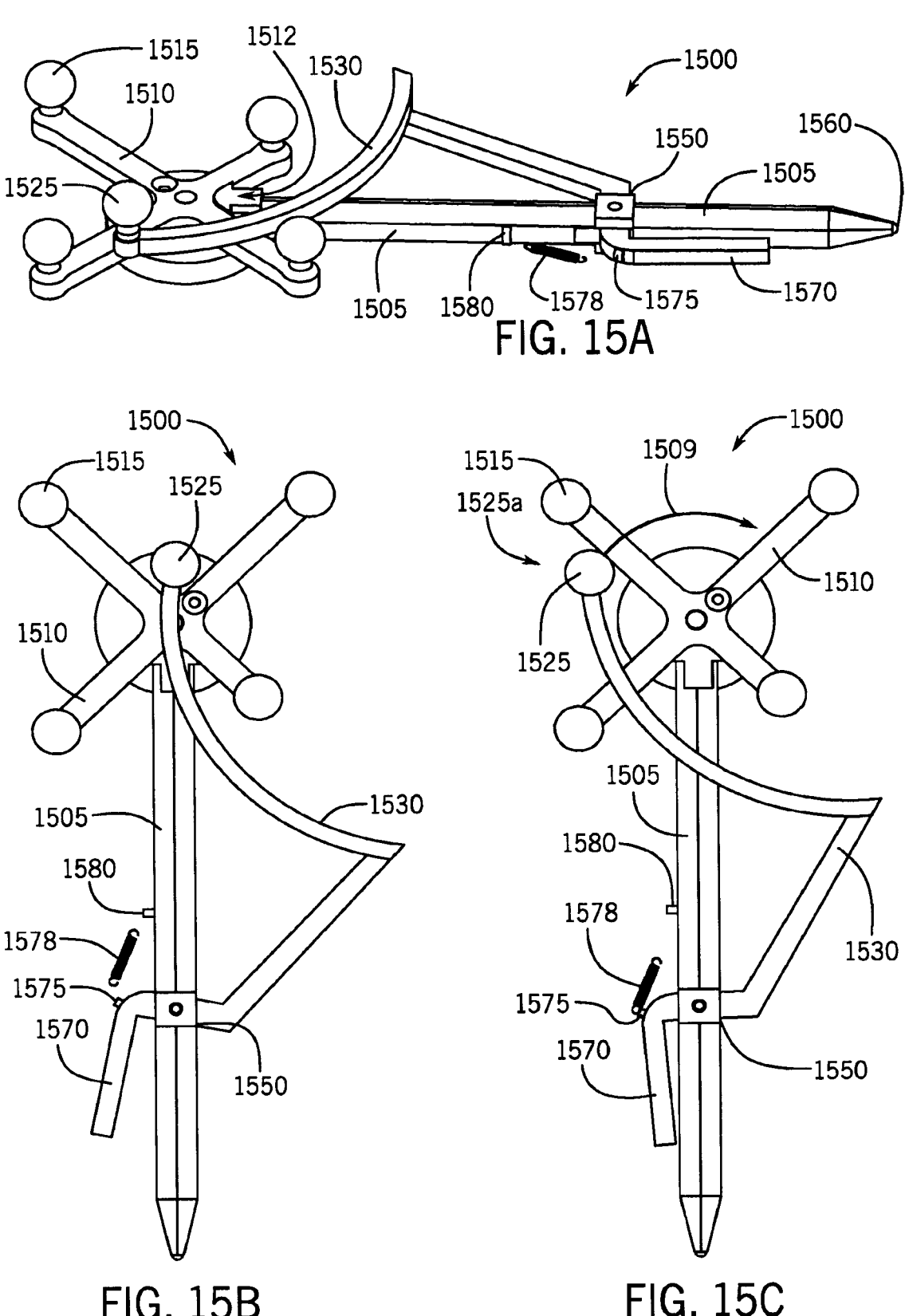
FIGS. 15A-15C shows a probe equipped with a tracked dynamic reference frame (DRF) in various configurations in accordance with some embodiments of the invention.

Some embodiments of the invention include a 3D-tracked probe, equipped with a tracked DRF and a tracked mobile stray marker (TMSM) that can be actuated by a user and utilized to indicate analog and/or binary information to the acquisition system software. For example, FIGS. 15A-15C shows a probe equipped with a tracked dynamic reference frame (DRF) in various configurations in accordance with some embodiments of the invention. In some embodiments, by the user actuating a tracked mobile stray marker that rotates about a pivot point in the probe shaft, the location of the tracked mobile stray marker can be computed relative to the DRF, and when visualized in certain positions, can be used to communicate varying messages to the acquisition system's software. In some embodiments, in reference to FIG. 15A, a probe 1500 can be equipped with a tracked DRF 1510, which is coupled to a mount 1512 that provides structural integrity to the DRF's attachment to the probe 1505, a TMSM 1525 coupled to an arm 1530 that rotates about a pivot hinge 1550 on a hexagonal extruded probe shaft 1505. The arm 1530 is spring-loaded (via spring 1578) via spanning external spring mounts 1580, 1575 that allow for a depressible tab 1570 to be actuated by a user depressing it inward towards the coaxial probe shaft. In some embodiments, the probe 1500 shown has a blunt semi-spherical tip 1560 to avoid damaging sensitive anatomical structures, and also has a hexagonal extruded probe shaft 1505 for added grip by the user. In some embodiments, this probe 1500 is designed to have the TMSM 1525 rotate about the pivot hinge 1550 when a user depresses or releases the depressible tab 1570. In some embodiments, the location and relative angle of the TMSM 1525 to the DRF 1510 is computed by the acquisition software of any of the disclosed systems, and can be used for both binary or analog communication with the system, as will be described in more detail in relation to FIGS. 63 and 64A-64B.

In some embodiments, it should be noted that with regards to the type of motion of components of the TMSM 1525, the TMSM 1525 can move linearly, as described previously in relation to FIGS. 10A-10E, rotationally, as will be described in more detail in relation to FIGS. 63 and 64A-64B, or a combination of the two types of motion. In some embodiments, with regards to the actuation method, includes a user-depressible tab 1570 as shown here but it can also consist of user sliding buttons, rotating buttons, and depressible sliding shafts as described previously in relation to FIG. 10A-10B. In some embodiments, with regards to the spring location, an external compression spring 1578 can also include but is not limited to torsion springs, internal compression springs, deformable materials with shape memory. With regards to the probe shaft 1505, the hexagonal extrusion shape as shown is only one embodiment and some embodiments include, but are not limited to, circular, triangular, rectangular, pentagonal extrusions and non-uniform revolved profiles for both user grip and probe placement within limited-access environments. The probe shaft 1505 need not be linear or symmetric according to some embodiments. With regards to the depressible tab 1570, the location of the tab 1570 can also be positioned anywhere on the body of the tool 1500 according to some embodiments. With regards to the probe tip 1560, the blunted semi-spherical design is only some embodiments as it can also comprise varying shapes and degrees of sharpness of point at the tip 1560. In some embodiments, can include motion type, linear/rotational, and include other actuation methods. Some embodiments include a user button, slider, or depressible sliding shaft (shown before in FIGS. 10A-10B). Some embodiments include a different spring location, internal or external placement, a torsion spring, a compressible spring or a non-compressible spring. Some embodiments include alternative tip shape and size, blunt or sharp. Some further embodiments include a mating tip as shown in other fastening devices such as FIGS. 33D-33F and 44B-44D.

In some embodiments, referring to FIG. 15B, the tracked probe 1500 with a rotating TMSM 1525 can be used for analog and/or binary communication previously described in relation to FIG. 15A. In some embodiments displays the location of the TMSM 1525 when the depressible tab 1570 is in its undepressed location and the spring 1578 in its most compressed state. In some embodiments, the location and angle of the TMSM 1525 relative to the DRF 1510 can be calculated as will be described in more detail in relation to FIG. 63 and FIGS. 64A-64B.

FIG. 15C displays some embodiments of a tracked probe 1500 with a rotating TMSM 1525 used for analog communication previously described in relation to FIG. 15A. Some embodiments display the location of the TMSM 1525 when the depressible tab 1570 is in its depressed location 1525*a*, and the spring 1578 in its most extended state. In some embodiments, the arc that is traveled by the tracked mobile stray marker (marked as 1509) can be visualized and computed by the computer system by comparing the location of the TMSM 1525 relative to the tracked DRF 1510 as it is actuated via the depressible tab 1570, with examples depicted in FIGS. 15A-15C. In some embodiments, the location and angle of the tracked mobile stray marker 1525 relative to the DRF 1510 can be calculated as will be described in more detail in relation to FIGS. 63 and 64A-64B.

Figure 23A:
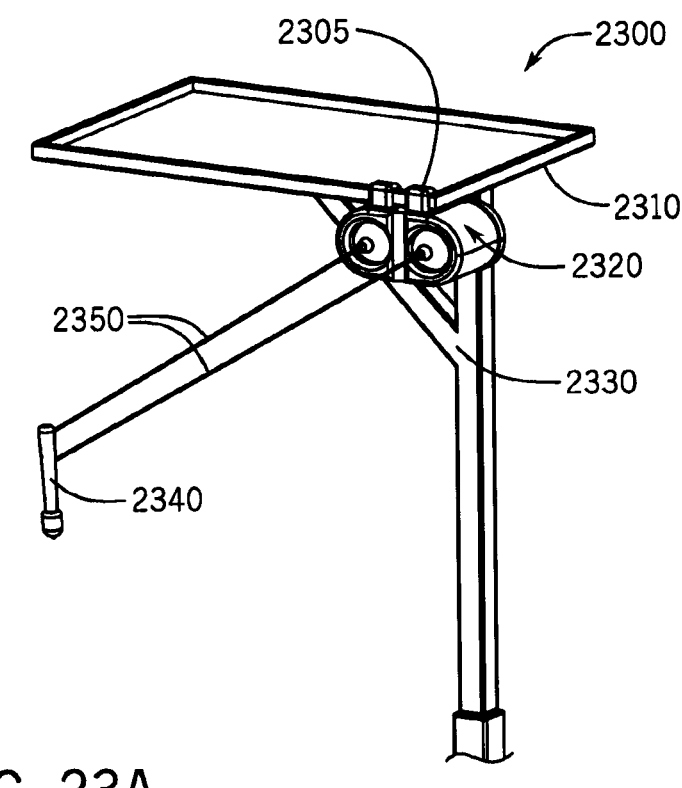
FIG. 23A illustrates an example 3D tracking system in accordance with some embodiments of the invention.
Figure 23B:
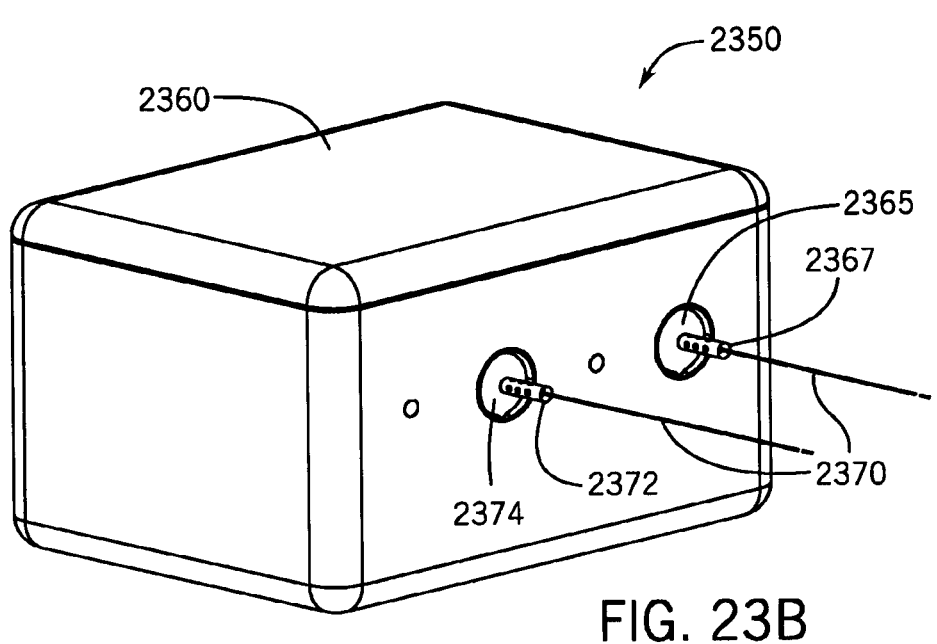
FIG. 23B illustrates 3D tracking system in enclosure in accordance with some embodiments of the invention.
Figure 23C:
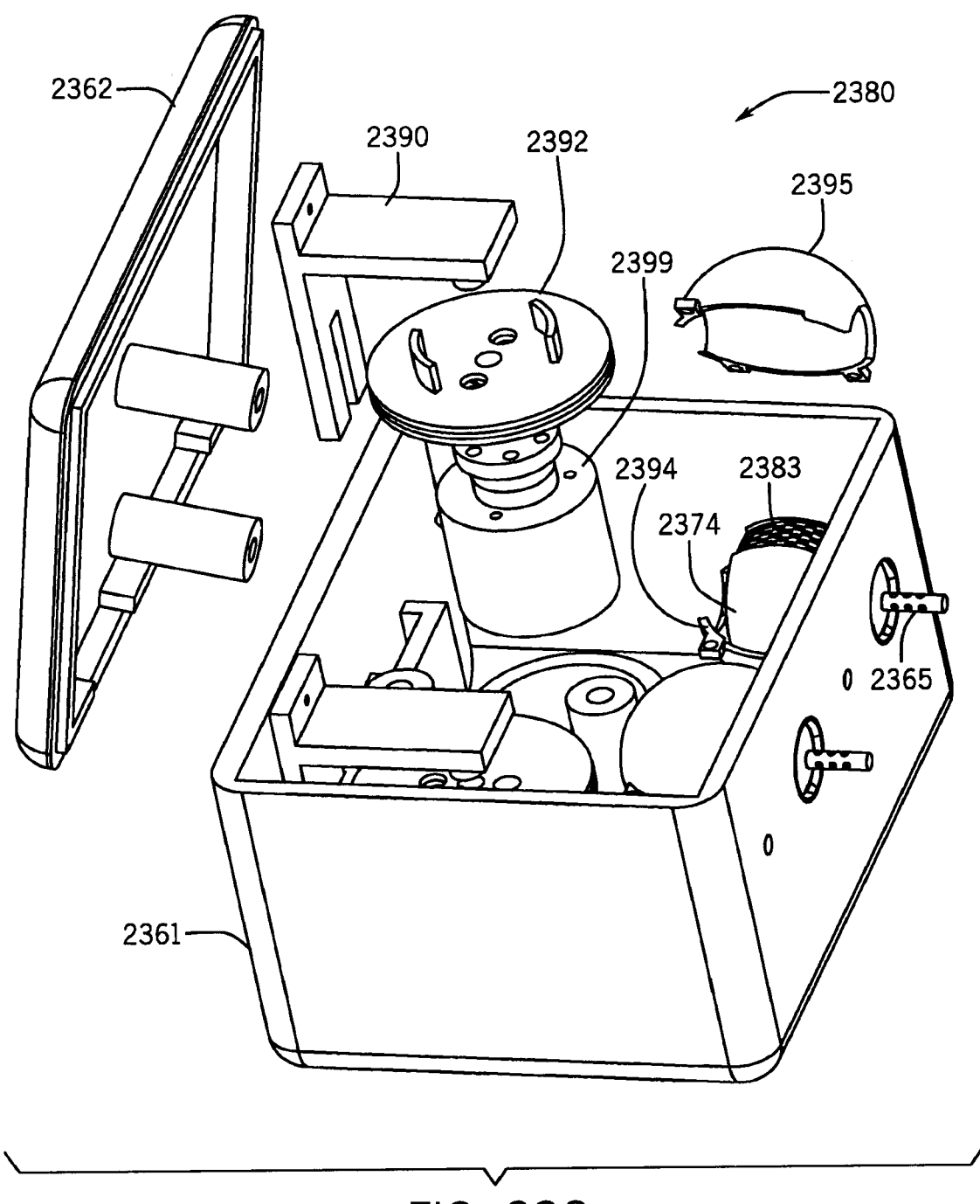
FIG. 23C shows an exploded assembly view of the 3D tracking system of FIG. 23B in accordance with some embodiments of the invention.

Some embodiments of the invention utilize rotary encoders that are used to measure the precise length of an extensible cord that is retracted outside of the electromechanical, 3D-tracking system (e.g., such as the system depicted in FIGS. 23A-23C). In some embodiments, this length calculation is accomplished by the encoder measuring the amount of rotation a mechanically-linked cord causes due to retraction. In some embodiments, the rotary encoder is mechanically linked either directly with the traversing cord or linked with a spool that stores several revolutions of the cord. In some embodiments, this component of the electromechanical tracking system provides accurate length measurements of the extensible cord between the acquisition unit and the probe. In some embodiments, the rotation measurement system of the electromechanical tracking system consists of a system that is capable of measuring the degree of rotation, and any supporting mechanical systems to enable or enhance the rotation measurement process. In some embodiments, the rotation measurement system interfaces mechanically with an extensible cord and/or a retracting spool/tension system to measure the linear distance of extensible cord that has interfaced with the encoder. For example, some embodiments of the rotation measurement system is a rotary encoder 1600 shown in FIG. 16. A rotary encoder is an electromechanical device, which converts the position or motion of a shaft 1630 about the body 1610 to an electrical signal. In some embodiments, the electrical interface 1650 of the rotary encoder is dependent on the type of rotary encoder and the manufacturer. In some embodiments, internal circuitry inside the rotary encoder 1600 can automatically calculate the amount of shaft rotation, the direction of shaft rotation, or communicate the measurement data over a digital or analog interface. In some embodiments, the method and interface over which the rotation measurement data is communicated is of no significance to the encoder system. In some embodiments, only the degree and direction of shaft 1630 rotation is of importance to the calculation of linear distance. In some embodiments, potentiometers can also be used to measure rotation, specifically absolute rotation, which can eliminate the need for length calibrations in order to measure the length of the extensible cord that is actively being retracted outside the electromechanical, 3D-tracking system.

Figures 16, 17A, 17B:
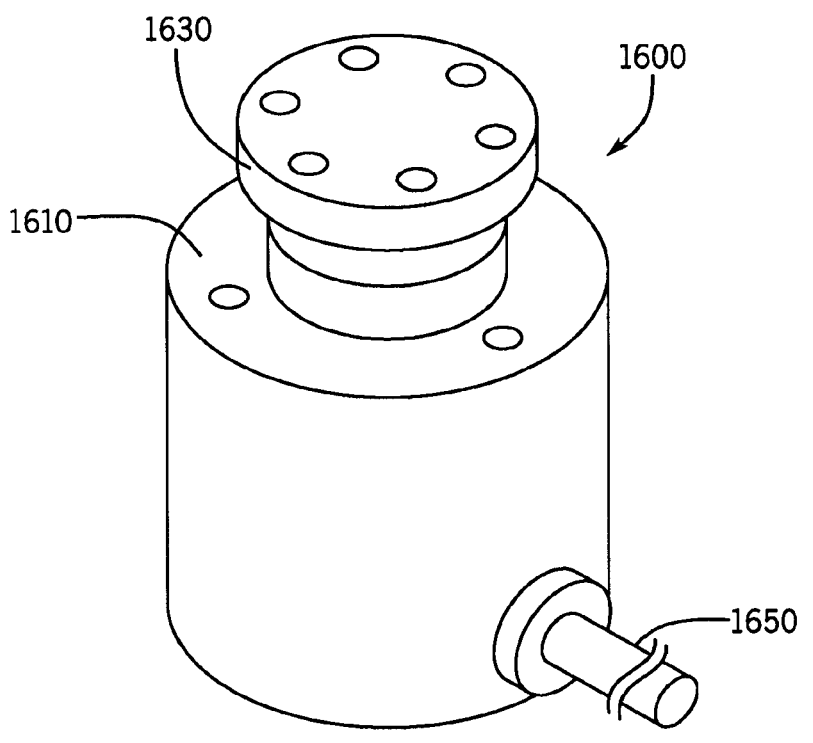
FIG. 16 illustrates a rotary encoder in accordance with some embodiments of the invention.
FIG. 17A illustrates a pulley-gear system for use with the encoder of FIG. 16 in accordance with some embodiments of the invention.
FIG. 17B illustrates a gear of the pulley-gear system of FIG. 17A in accordance with some embodiments of the invention.

In some embodiments, FIG. 17A illustrates a pulley-gear system 1701 for use with the encoder 1600 of FIG. 16 in accordance with some embodiments of the invention, and FIG. 17B illustrates a gear 1710 of the pulley-gear system 1701 of FIG. 17A in accordance with some embodiments of the invention. In some embodiments, this component of the electromechanical, 3D-tracking system depicted in FIGS. 23A-23B enables for the increased accuracy of length measurements of the extensible cord that transverses through the enclosure and extends beyond the system to the probe 2000 illustrated in FIG. 20. In some embodiments, the pulley-gear embodiment 1701 enables for a gear-based actuation of the encoder shaft 1630, depicted in FIG. 16, in a manner that multiplies the sensitivity of rotational measurements made by the encoder by a factor nearly equal to the gear-ratio between the set of gears that are mechanically arranged between the cord-interfacing pulley 1710 and the encoder-shaft gear 1715.

Some embodiments involve a pulley-gear system that is installed between the encoder shaft, the retracting spool/tension system, and/or the extensible cord to increase the accuracy of the rotation measurement system depicted in FIG. 16. In some embodiments, the pulley-gear system is shown in FIG. 17A. Linear movement of the extensible cord 1705 is coupled to the pulley-gear 1710 using surface friction between the extensible cord 1705, passive pulleys 1707 that help wrap the cord 1705 around the pulley-gear 1710 to maximize friction and avoid cord slippage, and the high-friction O-ring 1748 that surrounds the internal diameter of the pulley. In some embodiments, the pulley-gear 1710 (shown in detail in FIG. 17B) mechanically interfaces with a rotary encoder shaft gear 1715, and during linear movement of the extensible cord 1705, any rotation of the pulley-gear 1710 corresponds to a greater degree of rotation of the rotary encoder shaft gear 1715, with the relationship of the corresponding rotations being determined by the gear ratio between 1710 and 1715. In some embodiments, the resolution of the rotary encoder 1720 can been increased by a fixed quantity using the described pulley-gear system 1701, and leads to an increase in the measurement accuracy of the extensible cord length. In some embodiments, the described pulley-gear 1710 can be designed with a notch 1745 to allow for the simple removal of the O-ring, and a cutout 1740 placed at the center of the pulley-gear 1710 is designed to allow for the insertion of a bearing that enables for the minimally-frictional rotation of the pulley-gear 1710 about its center axis, which can have a significant effect on the ease-of-use of the system for the user to retract the probe in a responsive manner.

Some embodiments of the surface of the pulley-gear 1710 that interface mechanically with the extensible cord 1705 can involve specific geometric cross-sectional contours that enhance the friction between the extensible cord 1705 and the pulley-gear 1710 surface. Some embodiments includes a v-shaped groove that the pinches on the surface of the cord 1705, and this design forms a tight-tolerance fit between the cord and the pulley-gear 1710 when the overall system is placed under tension. Some embodiments can include the linkage of the pulley-gear system directly with a tensioned spool system, (described in more detail below in reference to FIG. 18A-18B), that stores multiple revolutions of the extensible cord.

Figure 18A:
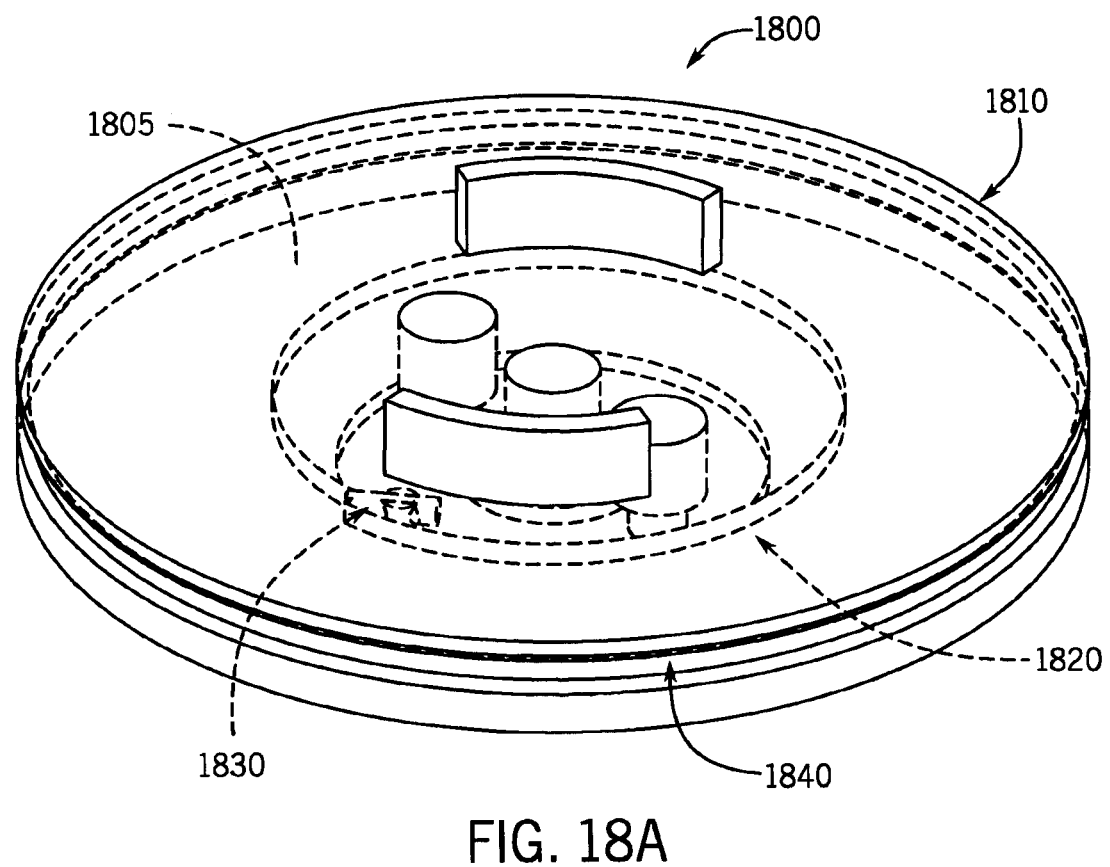
FIG. 18A illustrates a perspective view of a cord spool for use in the pulley-gear system of FIG. 17 in accordance with some embodiments of the invention.
Figure 18B:
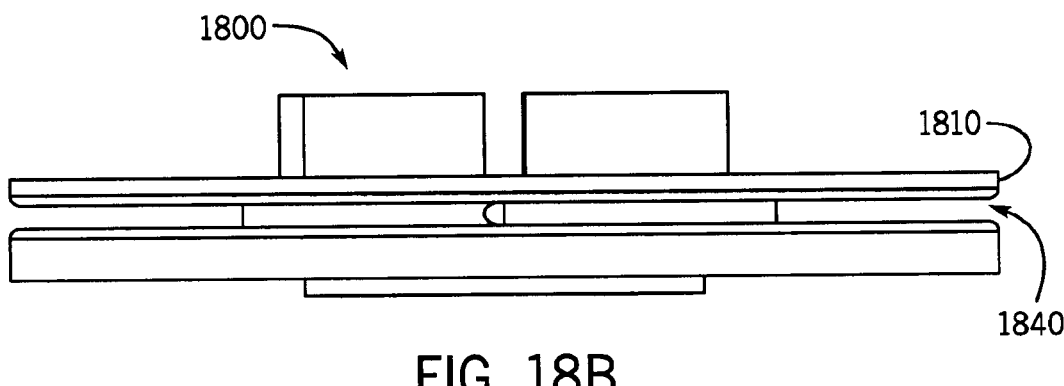
FIG. 18B illustrates a side view of the cord spool for use in the pulley-gear system of FIG. 17 in accordance with some embodiments of the invention.

FIG. 18A shows a perspective view of a cord spool for use in the pulley-gear system of FIG. 17 in accordance with some embodiments of the invention, and FIG. 18B shows a side view. This component of the electromechanical, 3D-tracking system, depicted in FIG. 23C, involves the spiral storage of extensible cord to be exchanged in and out of the spool at pre-defined cord lengths/circumferences per revolution. Some embodiments involve the spool directly interfacing mechanically with a rotary encoder, depicted in FIG. 16, in a coaxial manner between the spool and encoder shaft, to measure the number of revolutions of cord that are extended away from the enclosure at any time.

Some embodiments of the spool system involves a linkage with a tension system that provides an opposing force to the extensible cord 1705 to maximize coupling in the pulley-gear system depicted in FIG. 17A and/or the rotary encoder 1600 depicted in FIG. 16. In some embodiments, the tension system can be pre-loaded with cord and tuned in tension to ensure that there is no slack along the extensible cord. In some embodiments, if slack develops on the cord, accurate measurement of the degree of rotation about the encoder system is less optimal. In some embodiments, the retracting spool/tensioning system is a spring-based system that provides tension to the extensible cord. In some embodiments, the retracting spool/tensioning system can include a sub-system to allow variable degrees of tension of the extensible cord to a user's specification. In some embodiments, the retracting spool/tensioning system can include a mechanism that slows and/or stops the motion of the spool to prevent the extensible cord from traveling at dangerously high speeds, in the event that the pre-tensioned extensible cord is suddenly released.

In some embodiments, the retracting spool provides a system by which the extensible cord can be contained within. In some embodiments, a cord spool 1800, illustrated in FIGS. 18A-18B, is composed of a cylindrical disc 1805 with a cord entry slot 1840 removed from the side such that the cord 1705 can be rotated about center of the spool in set revolution increments. Some embodiments may have the cord entry slot 1840 with a thickness much larger than the diameter of the cord. Some embodiments can have the cord entry slot 1840 be the approximate diameter of the cord, such that the cord is forced to spiral outward from the spool's center in a single-revolution-thick spiral stack. Some embodiments can have the inner cord spool radius 1820 be a fixed value. Some embodiments may have the inner cord spool radius 1820 may be represented by an equation. In some embodiments, the radial distance of the Archimedean spiral is equal to the diameter of the cord such that the extensible cord spools continuously around itself as described by an Archimedes spiral, which simplifies the calculation of the distance between the center of the spool and the center of the cord, in addition to the calculation of the linear cord distance.

Some embodiments involves the cord beginning its fixation to the spool at a known radius set by the designed mount point 1830 of the spool 1805. Some embodiments involves the cord wrapping around inner cord spool surface (defined by inner radius 1820) until the cord length is completely contained within the spool 1800 or when the cord reaches the outer spool edge (defined by outer radius 1810). In some embodiments, the larger the outer spool edge, the more torque that can be applied by the movement of the cord and the less resistance the user will feel when engaging the retraction of the cord tensioning system. In some embodiments, the large inner radius surface leads to a less accurate measurement by increasing the length of cord contained with a single resolution step of the encoder's rotational sensitivity.

In some embodiments, in the rotational measurement system described herein, the extensible cord 1705 provides a mechanical connection between the retracting spool and the rotation measurement sensor. In some embodiments, the extensible cord 1705 provides a mechanical connection between the probe (FIGS. 20A-20E) and the encoder system 1600 (FIG. 16), allowing for the three-dimensional measurement of the probe tip location as the probe moves through space. In some embodiments, the generic embodiment of the extensible cord 1705 is a thin-diameter, low-stretch cord. In some embodiments, the extensible cord is a metal cable, with some embodiments containing special coatings, such as a nylon coating. Some embodiments of the extensible cord is a Kevlar cable.

Figures 19A, 19B, 19C, 19D, 19E:
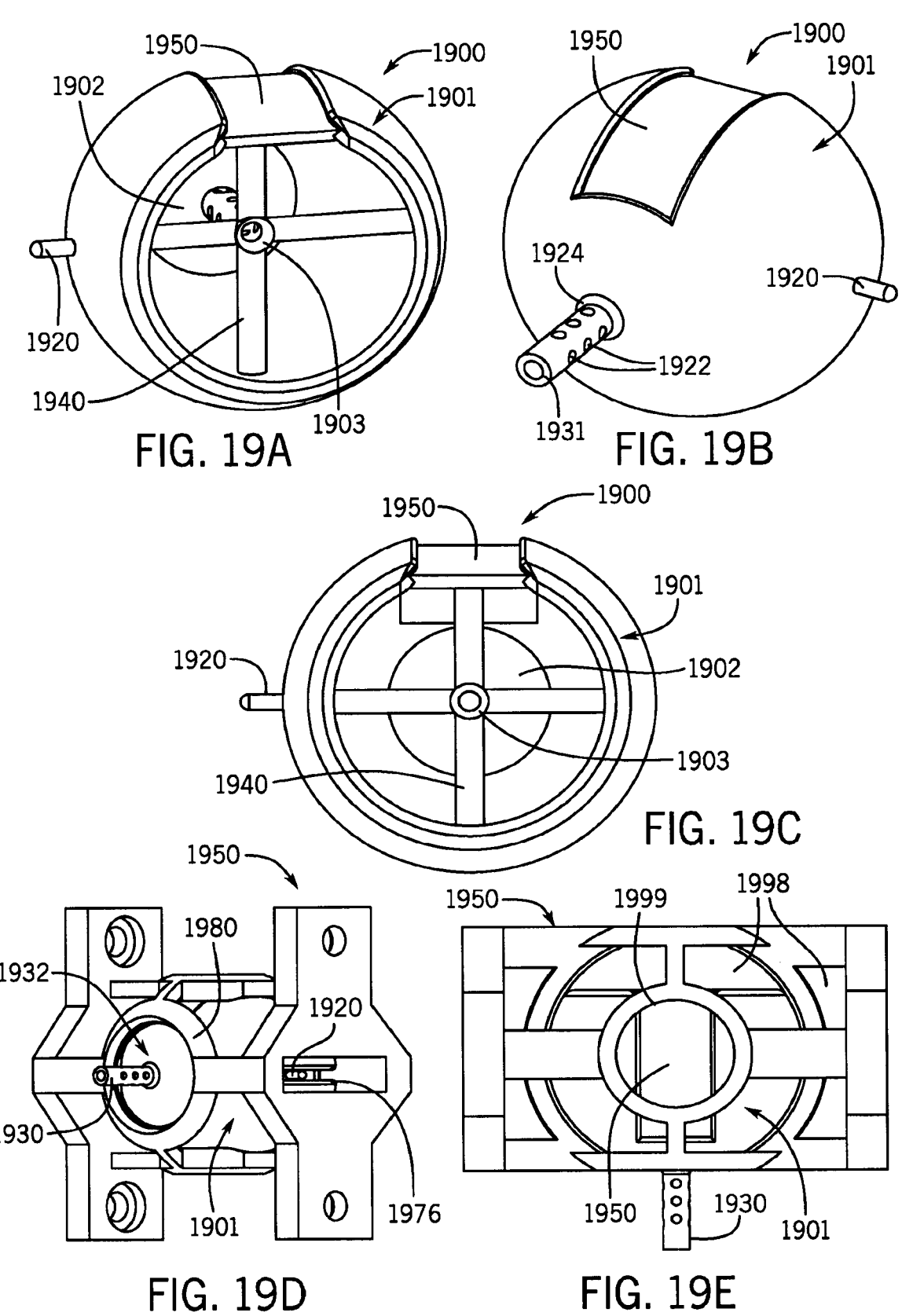
FIGS. 19A-19C illustrates a ball assembly of a 3D-tracking system of FIG. 23A in accordance with some embodiments of the invention.
FIGS. 19D-19E illustrate a ball and socket assembly of the 3D-tracking system of FIG. 23A accordance with some embodiments of the invention.

FIGS. 19A-19C illustrates a ball assembly 1900 of a 3D-tracking system of FIG. 23A in accordance with some embodiments of the invention. In some embodiments, this component of the electromechanical, 3D-tracking system depicted in FIGS. 23B-23C, involves a ball-and-socket interface that is manipulated via the traversing motion of an extensible cord 1705 that passes through the center of the ball. In some embodiments, an extensible cord (e.g., such as cord 1705 shown in FIG. 17A, cord 2120 shown in FIG. 21A, or cord 2150 shown in FIG. 21B) can traverse through the ball-and-socket system via entry to the cord insertion point (cord entry passage 1903) through the central barrel. In some embodiments, the entry point for the cord is designed to intersect with the center of the spherical structure, and subsequently aligned with the sphere's center of rotation. In some embodiments, this alignment of the cord entry point 1903 enables the movement of the cord to be mathematically separated into two sections, the straight line between the cord storage system (e.g., spool depicted in FIGS. 18A-18B) and the center of the ball 1903, as well as the straight line between the center of the ball 1903 and the mounting posts on a probe (e.g., probe depicted in FIG. 20). In some embodiments, the barrel is supported by mechanical structures added to minimize undesired forces and torques imposed by the cord, which can deflect the barrel during movement of the cord. In some embodiments, the ball assembly can include barrel support structures 1940 of ball (or sphere) 1901. In some embodiments, as the barrel exits the front of the ball, the barrel is supported internally by a reinforced wall 1902. In some embodiments, to minimize barrel deflection at the cord entry location, support bars 1940 provide mechanical rigidity to the barrel to minimize deflection created during cord movement.

In some embodiments, the sphere includes a cylindrical groove 1950 extruded out of the top of the spherical surface, which allows for the installation of an image, or any unique pattern, without any spherical distortion of the pattern surface. In some embodiments, an imaging sensor can thus be used to visualize and measure the ball's rotation in the spherical coordinates, theta and phi, by examining how the pattern on the cylindrical groove 1950 rotates and translates relative to an imaging sensor. In some embodiments, in order to maintain the cylindrical groove's alignment with the center of the ball 1901 and imaging sensor, the ball 1901 includes an orthogonal extrusion (roll-prevention rod 1920) relative to the cylindrical window, that prevents the rotation of the ball about the barrel structure when inserted into a complementary mating slot that limits the movement of the roll-prevention rod to a linear arc that is orthogonal to the cylindrical groove 1950.

In some embodiments, as shown in FIGS. 19B and 19D, the ball 1901 contains a cylindrical barrel 1930, which begins inside the ball 1901 and extends radially to a fixed distance in front of the ball 1901. In some embodiments, the cord (e.g., such as cord 1705) can pass through the extrusion in the back of the ball, enters the barrel at the cord insertion point (shown as 1903), passing through and exiting the barrel in front of the ball (through barrel 1930). In some embodiments, the barrel 1930 contains a plethora of holes (barrel fenestrations 1922) to reduce the surface contact area between the inside of the barrel 1931 and the outside of the cord, which helps to ensure smooth cord movement through the barrel 1930. In some embodiments, the barrel design provides the encoder (e.g., such as encoder 1600) with a fixed exit point that is required to calculate of linear cord distance. In some embodiments, as the barrel 1930 extends from the front of the ball 1901, the barrel 1930 is supported externally by a reinforced wall by the barrel shaft base fillet (barrel tip fillet 1924). Further, in some embodiments, the cylindrical groove 1950 provides a cross-sectionally-flat surface from which an imaging sensor can calculate the degree of spherical ball rotation without requiring additional transformations caused by distortion (e.g., barrel distortion) of the pattern. In some embodiments, in reference to FIG. 19C, a cylindrical groove (groove 1950) is extruded out of the top of the spherical surface, and allows for the installation of an image, or any unique pattern, without any spherical distortion of the pattern surface. In some embodiments, the support structures illustrated to reinforce the rigidity of the barrel are not required in the final manufactured product, and can include components for prototypes created via 3D printing with fragile materials.

In some embodiments, FIGS. 19D-19E illustrate a ball and socket assembly of the 3D-tracking system of FIG. 23A accordance with some embodiments of the invention. In some embodiments, the socket enclosure 1950 for the ball 1901 provides a joint surface to rotate within due to traversing motions and trajectory changes in the extensible cord. In some embodiments, the socket contains a window cutout

1980 that restricts the movement of the barrel 1930 to within a defined range-of-motion (in window 1932). In some embodiments, the window's boundaries can help maintain the optimal tracking volume for the electromechanical, 3D-tracking system without having multiple ball-and-socket systems allowing for cord to intersect or obstruct each other. In some embodiments, the system also contains a complementary roll-prevention channel 1976 that allows for the restricted movement of a rod extrusion 1920 from the ball to travel along a path that prevents the rotation of the ball 1901 about its barrel 1930. In some embodiments, the roll-restriction feature (1920, 1976) of the system provides assurance that the cylindrical window is in constant view within the sensor's preview window 1999, such that any movement of the pattern will always be visible to an imaging sensor. In some embodiments, multiple socket regions 1998 are removed from the top and bottom of the socket structure to minimize surface friction between the outside of the ball and the inside of the socket. In some embodiments, as noted multiple times, the need to minimize friction between the socket, ball, and cord is paramount to the functionality of three-dimensional tracking system. Some embodiments include a layer of ball bearings installed between the ball and the socket surfaces. Some embodiments include some form of lubricant placed in between the ball and the socket surfaces. Some embodiments may include some form of lubricant placed in between the barrel and the cord surfaces. In some embodiments, a high-strength and high-durability material is required to maintain the structural integrity of the ball and socket. In some embodiments, the ball-and-socket system may be comprised of metals, polymers, and/or plastics.

Figures 20, 20A, 20B, 20C, 20D, 20E:
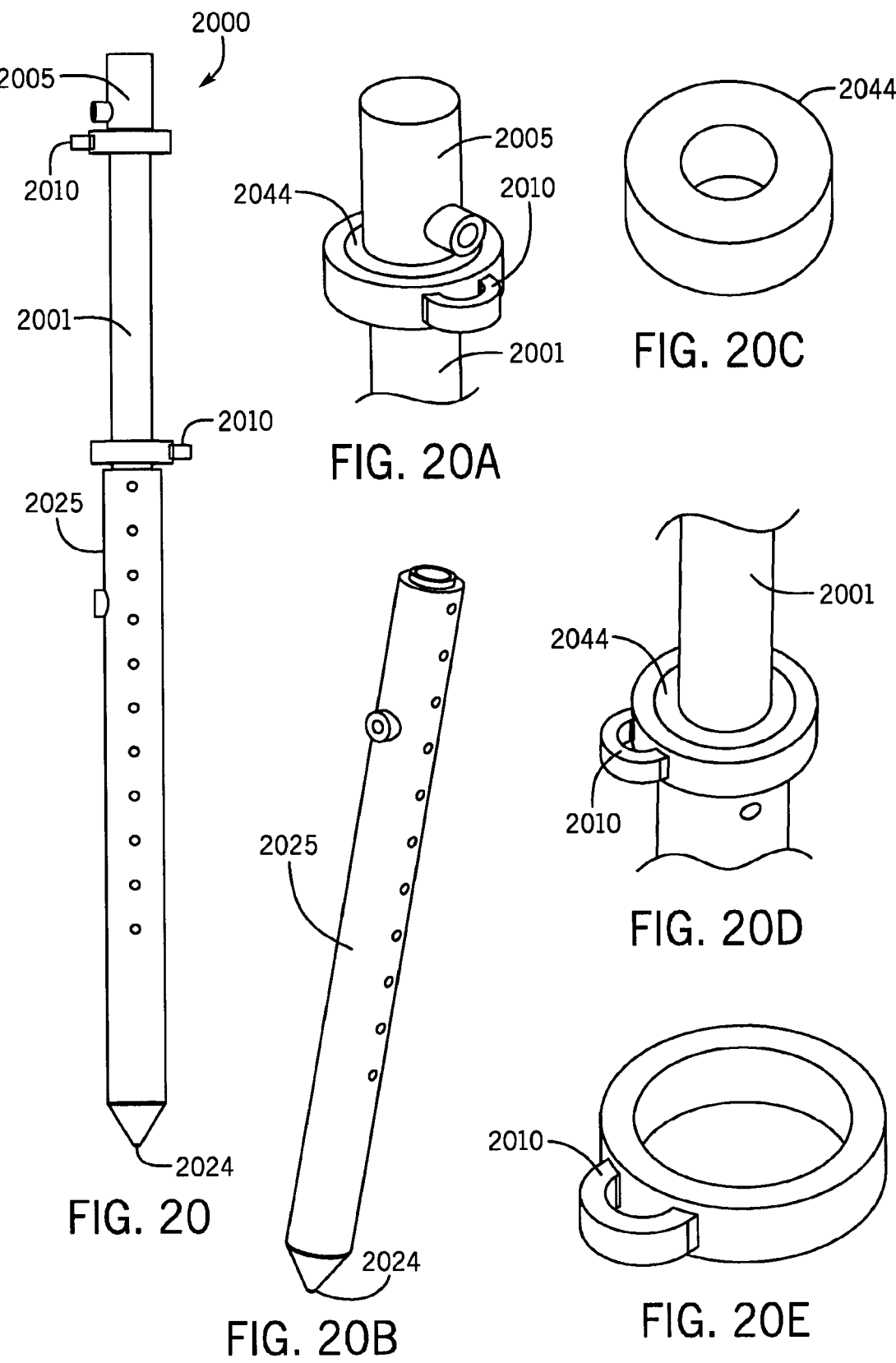
FIG. 20 illustrates a probe of a 3D tracking system in accordance with some embodiments of the invention.
FIGS. 20A-20E show views of components of the probe of FIG. 20 in accordance with some embodiments of the invention.

FIG. 20 illustrates a probe 2000 of a 3D-tracking, electromechanical system in accordance with some embodiments of the invention. FIGS. 20A-20E show views of components of the probe 2000 of FIG. 20 in accordance with some embodiments of the invention. In some embodiments, this component of the electromechanical, 3D-tracking system, depicted in FIGS. 23B-23C, involves a probe that is used to register 3D points in space while the tracking system dynamically registers the probe's 3D location and orientation with respect to the tracking system's coordinate system. In some embodiments, the probe 2000 contains two freely-rotating fixation points 2010 where extensible cord (e.g., 1705) distal ends that are tracked in 3D space mount at a fixed distance apart. In some embodiments, the probe 2000 can comprise a probe shaft 2025. In some embodiments, the probe 2000 provides various functions to the electromechanical, 3D-tracking system. First, in some embodiments, the probe 2000 enables the user to trace along a 3D-surface. Second, in some embodiments, the probe provides a fixed mechanical interface to each encoder's extensible cord. In some embodiments, the 3D pose of the probe 2000 can be derived from the calculated linear cord distances from each encoder, the rotational values (spherical coordinates) of the previously described ball 1901 within its ball-and-socket joint, the fixed distance between each cord connection point, and trigonometric identities. In some embodiments, with the pose of the probe 2000 and the linear cord distances, the exact location of the probe tip 2024 can be extrapolated in 3D-space. Third, in some embodiments, the probe 2000 has the ability to identify interactions with multiple materials through electrical, mechanical, optical, and/or electro-mechanical interfaces. Fourth, in some embodiments, the probe 2000 has a grip area 2025 that allows the user to hold the probe 2000 and trace a three-dimensional surface without interfering with the cords or any additional measurement system.

Some embodiments of a probe 2000 is shown in FIG. 20, has mount points 2010 for two cords. In some embodiments, the cords from an encoder (such as described earlier in FIG. 16) can couple to the cord fixation mounts 2010, each of which is mechanically coupled to individual bearings 2044 that are separated by a cord-mount spacer 2001 coupled to the probe shaft 2025, with each bearing's internal surface linked substantially rigidly to an internal rod structure (not shown) coaxial within the probe enclosure. In some embodiments, the spacer 2001 and bearings 2044 are coaxial with an internal rod that is fixed to the probe half 2025 that the user can grip (e.g., see bearing 2044). In some embodiments, the internal rod structure is maintained within the probe enclosure via a rigid cap 2005. However, in some embodiments, it should be noted that several components, including, but not limited to, the probe cap 2005, are not required for the device's function. In some embodiments, the cord mount and bearing system allows the probe 2000 to move freely in any direction without affecting the accuracy of the measurement system of the encoder embodiment. In some embodiments, the probe grip area (on shaft 2025) provides spacing for the user to trace in three-dimensions.

Figure 21A:
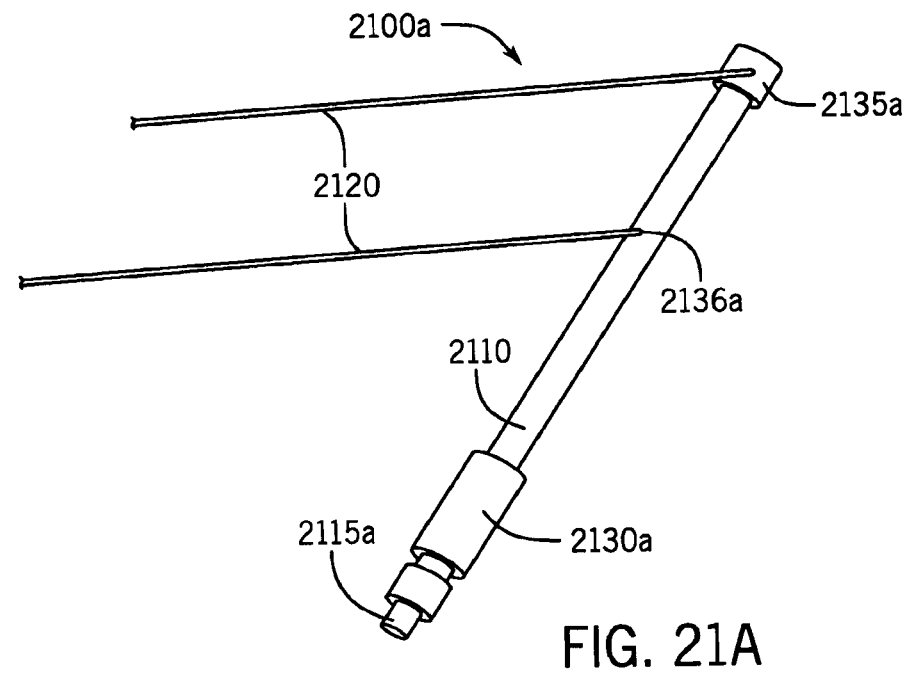
FIGS. 21A-21B illustrate assemblies of a 3D tracking system including a probe coupled to cord fixation points in accordance with some embodiments of the invention.
Figure 21B:
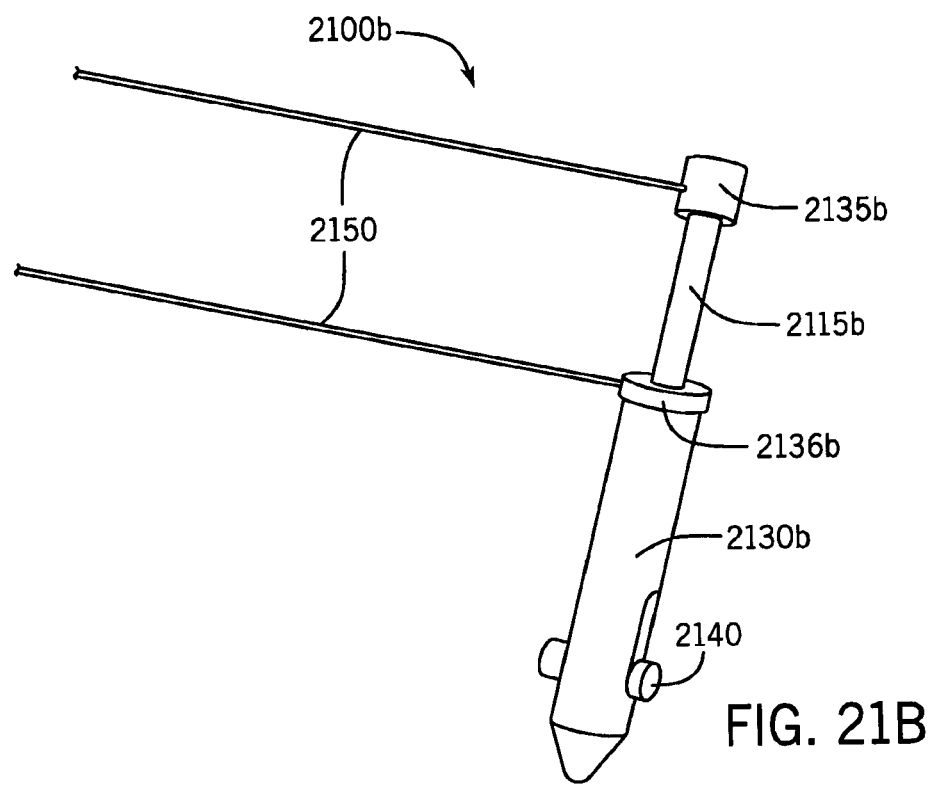

Some embodiments include a component of the electromechanical, 3D-tracking system, depicted in FIGS. 23A-23C, that involves a probe that is mechanically linked to two 3D-tracked cord fixation points that are spaced by adjustable distance via mechanical actuation between the two fixation points. For example, in some embodiments, FIGS. 21A-21B illustrate assemblies of a 3D tracking system including probes 2100a and 2100b coupled to cord fixation points (see extensible cord 2120, 2150 extending from the probes 2100a, 2100b). In some embodiments, the probes comprise probe handle 2130a, 2130b with depressible sliding shaft 2115a, 2115b, and spring-loaded trigger 2140 (of probe 2100b). In some embodiments, each 3D-tracked probe 2100a, 2100b includes an embedded mechanical system such that the distance between the extensible cord fixation mounts is selectively changed when the depressible shaft (spring-loaded; spring not shown) 2115a linked to the probe 2100a is pressed against a surface, or manually actuated by the user via a spring-loaded button 2140 on the shaft 2130b of the probe 2100b, which increases distance between the dynamic cord-fixation mount (2135a for probe 2100a; 2135b for probe 2100b) and the static cord-fixation mount (2136a for probe 2100a; 2136b for probe 2100b). In some embodiments, the extensible cords 2120, 2150 are mechanically linked to the electromechanical, 3D-tracking system (sample embodiments shown in FIG. 23A-23C).

In some embodiments, a processing algorithm detects changes in the relative distance between cord mounts and signals to the electromechanical, 3D-tracking system that it should actively register points at the probe tip, or interpret a specific command that designates what type of measurement the probe is performing, or the object identity the probe is interacting with. In some embodiments, the distance between the two dynamic cord fixation mounts can be calculated with respect to the axes of the probe by substantially rigidly transforming the 3D cord fixation mount coordinates with respect to the probe tip coordinates and pose. In some embodiments, the 3D distance between the cord fixation mounts can be calculated without variability in calculations caused by the changing relationship between a cord fixation mount and its relative distance to the electromechanical, 3D-tracking system, in comparison with that of the other cord fixation mount.

Figure 22:
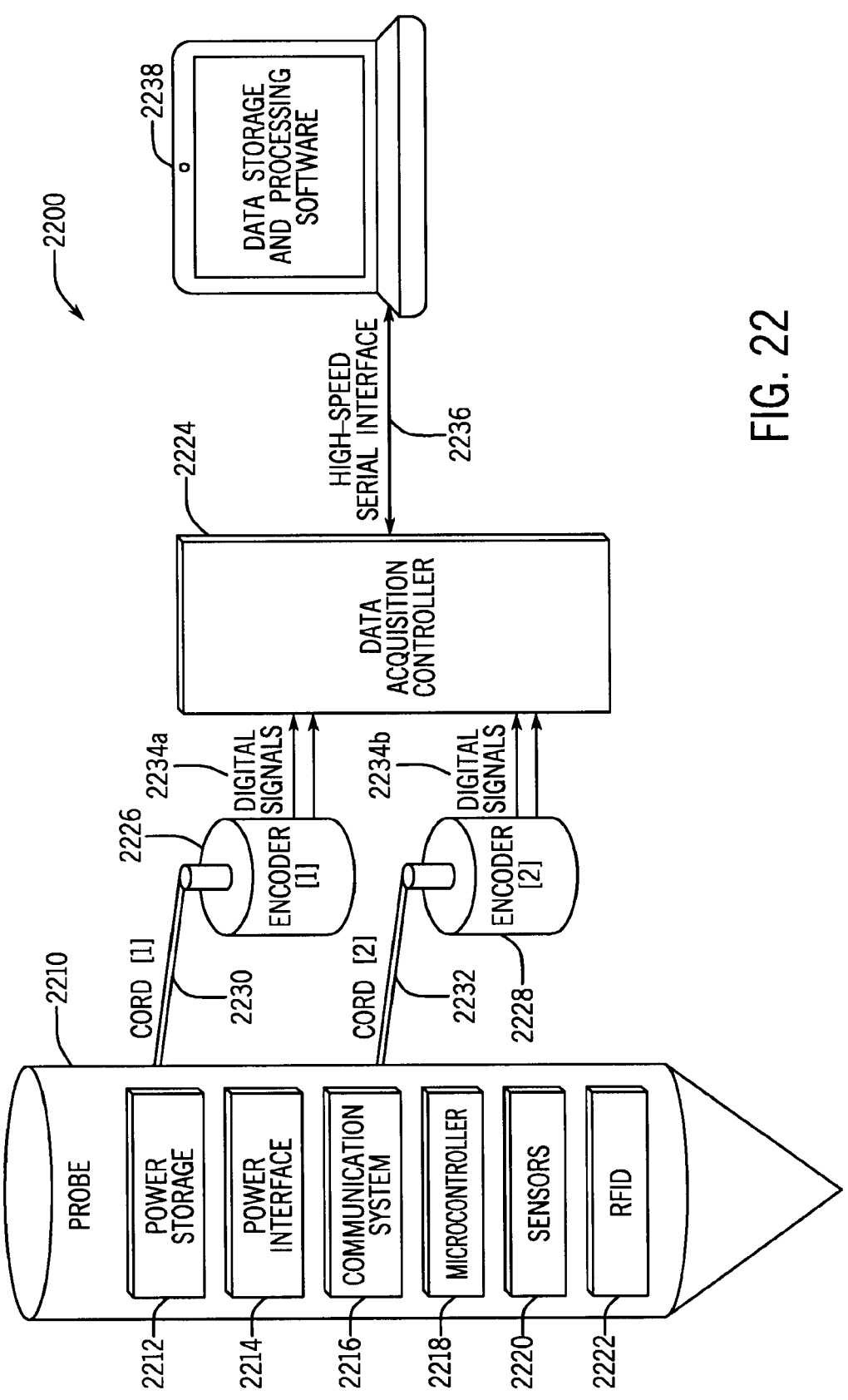
FIG. 22 illustrates an example system enabling 3D tracking of a probe in accordance with some embodiments of the invention.

FIG. 22 illustrates an example system enabling 3D tracking of a probe in accordance with some embodiments of the invention. In some embodiments, this component of the electromechanical, 3D-tracking system depicted in FIGS. 23A-23C, involves a system of active and passive components that communicate to enable the 3D tracking of the probe's location and orientation. In some embodiments, a number of embodiments exist for the probe linked to the electromechanical, 3D-tracking system, with FIG. 22 depicting the interface between a system of components that communicate with each other to enable the 3D tracking of a probe. Some embodiments include a probe with no electrical or mechanical feedback systems for which the encoder embodiment and processing software to detect during tracing, as described in the above embodiment. In some embodiments, a probe with embedded electrical subsystems (FIG. 22) can contain a plethora of user-controlled toggle switches that allow the user to control the registration of points and active tracking of the probe (FIGS. 21A-21B). Some embodiments include a method of communication to a microcontroller or a computer processing system that can be transmitted through a wireless electromagnetic radiation (RF), light-emitting devices. In some embodiments, cords can be mechanically linked to the docked tracking system. Some embodiments include a method of delivering power to the probe through a voltage applied across two cords that are mechanically linked to the probe for positional tracking. In some embodiments, a battery system or equivalent energy source, such as a capacitor, that is capable of being recharged can be included. In some embodiments, an electrical connection that exists between the probe and the enclosure to provide energy during non-use when the probe is located on the enclosure. In some embodiments, a plurality of sensors of a sensing system can be a plurality of inertial measurement unit, accelerometers, and/or gyroscopes to measure the motion and/or pose of the probe. In some embodiments, this may negate the necessity for mechanical linkages with an encoder or extensible cord. Some embodiments can be a tilt sensor. Some embodiments can be a sensor to measure the rotation of the cord mounts on the probe. Some embodiments can be a system to measure mechanical force applied to the probe and/or the probe tip. In some embodiments, a radiofrequency identification (RFID) tag and/or reader placed at a fixed location on the probe can include an RFID is an RFID reader placed in the probe that reads an RFID tag to begin or halt the registration of points and active tracking of the probe tip in 3D. Some embodiments of RFID is an RFID reader placed in the probe that reads an RFID tag placed at specific locations to identify the locations with specific identities during use of the probe. For example, in some embodiments, see power storage 2212, power interface 2214, communication system 2216, microcontroller 2218, sensors 2220, and RFID 2222 of the probe 2210, cord 2230 coupled to encoder 2226, cord 2232 coupled to encoder 2228, digital signals 2234a (from encoder 2226) and digital signals 2234b (from encoder 2228). Further, in some embodiments, see data acquisition controller 2224 coupled to a data storage and processing software in computer system 2238 coupled through interface 2236.

Some embodiments of the invention include an enclosure of the electromechanical, 3D-tracking system that houses all of the components of the tracking system in a compact form that can be mounted onto a multitude of various surfaces.

For example, FIG. 23A illustrates an example 3D-tracking system 2300 in accordance with some embodiments of the invention, including extensible cords 2350 extending from ball-in-socket structures 2320 (e.g., such as those described earlier in related to FIGS. 19A-19E), a coupled probe 2340, and a rigid surface mount 2305 coupled to structures 2310, 2330. As shown, some embodiments contain an interface for fastening mounting mechanisms enabling it to be utilized in a variety of settings. Fastening mounting mechanisms 2305 may include, but are not limited to, a suction cup mount or fastener holes for mating to rigid structures (e.g., such as 2310, 2330). Some embodiments of the mounting mechanism 2305 include hooks and clamps to interface with surgical tables, beds, anesthesia poles, a removable instrument tray on a movable stand that is configured to be positioned over or adjacent to a surgical site of a patient (e.g., a Mayo stand), the patient's anatomy, and/or any other rigid structure. Some embodiments involve extensible cords (shown as 2350) retracted out by the user via the use of a probe 2340 to collected discrete and continuous tracing registrations.

In some embodiments, the components of the electromechanical, 3D-tracking system can be compiled into a compact design and surrounded by an enclosure device 2350. For example, FIG. 23B illustrates a 3D-tracking system in an enclosure 2360 in accordance with some embodiments of the invention. In some embodiments, the enclosure 2360 is shown with extensible cords 2370 extending from barrel 2367, 2372 of spheres 2374, 2365 (with the cord coupling to a probe, such as probe 2000 of FIG. 20). In some embodiments, the enclosure 2360 can shield internal components from debris, trauma, bodily fluids, and light exposure. Further, the enclosure 2360 can contains an external probe mounting system to substantially rigidly fix the probe (e.g., such as the probe 2000 shown in FIG. 20) to the enclosure 2360 for when the extensible probe system is not in use. In some embodiments, the enclosure also houses the spool system (as shown previously in FIGS. 17A-17B, 18A-18B) which outputs two extensible cords to attach to the probe, and each cord 2370 passes through the barrel structure 2367, 2372 of each sphere 2365, 2374 to enable the electromechanical triangulation of the probe (e.g., the probe 2000 shown in FIG. 20).

Some embodiments include internal light sources to prevent variability in lighting for the camera system. Some embodiments include an electrical interface over which power and/or data can be transmitted to and/or received from the probe when it is docked. Some embodiments of the electrical interface can be metal contacts extending from the probe mounting system to couple to electrical contacts on the probe.

FIG. 23C shows an exploded assembly view of the 3D-tracking, electromechanical system of FIG. 23B in accordance with some embodiments of the invention. For example, some embodiments include enclosure 2361 housing a rotary encoder 2399, a fixed spring-tensioner arm 2390 for spool spring (not shown), a spool 2392, a bottom half of a socket 2394, a top half of a socket 2395 (reference FIGS. 19D-19E), an embedded, unique pattern 2383, a ball 2374 (reference FIGS. 19A-19C), a barrel of ball 2365, and enclosure lid 2362 with embedded optical sensors (not shown). In some embodiments, FIG. 23C illustrates the compilation of components from the electromechanical, 3D-tracking system. In some embodiments, each of the two rotary encoders 2399 measure the length of an extensible cord coupled to the probe (not shown). In some embodiments, each extensible cord (not shown) is stored and retracted from the spool 2392 that is being tensioned via a spring (not shown) that is fixed at one end by a spring tensioning arm 2390, which is mounted to the rigid enclosure 2361. In some embodiments, each extensible cord passes through a ball 2374, that can rotate within a socket (2394, 2395) with viewing windows (not shown; as seen in FIGS. 19D-19E), via a barrel 2365 that originates at the center of the ball 2374 to enable controlled movement of the cord during rotation of the ball. In some embodiments, the rotation of the ball is measured via an embedded pattern 2383 on the ball surface 2374 that is aligned above the center of the ball and able to mirror the phi and theta rotation of the ball in spherical coordinates for visualization via an above imaging sensor. In some embodiments, the enclosure includes a lid 2362 that couples with the bottom-component of the enclosure 2361 can help to create a protected environment while also housing the optical sensors (not shown), lights (not shown), and microcontrollers (not shown), for recording and analyzing the visual and electrical outputs from the embedded optical sensors and rotary encoders. In some embodiments, wireless communication components (not shown) are also included within the enclosure.

Figure 24:
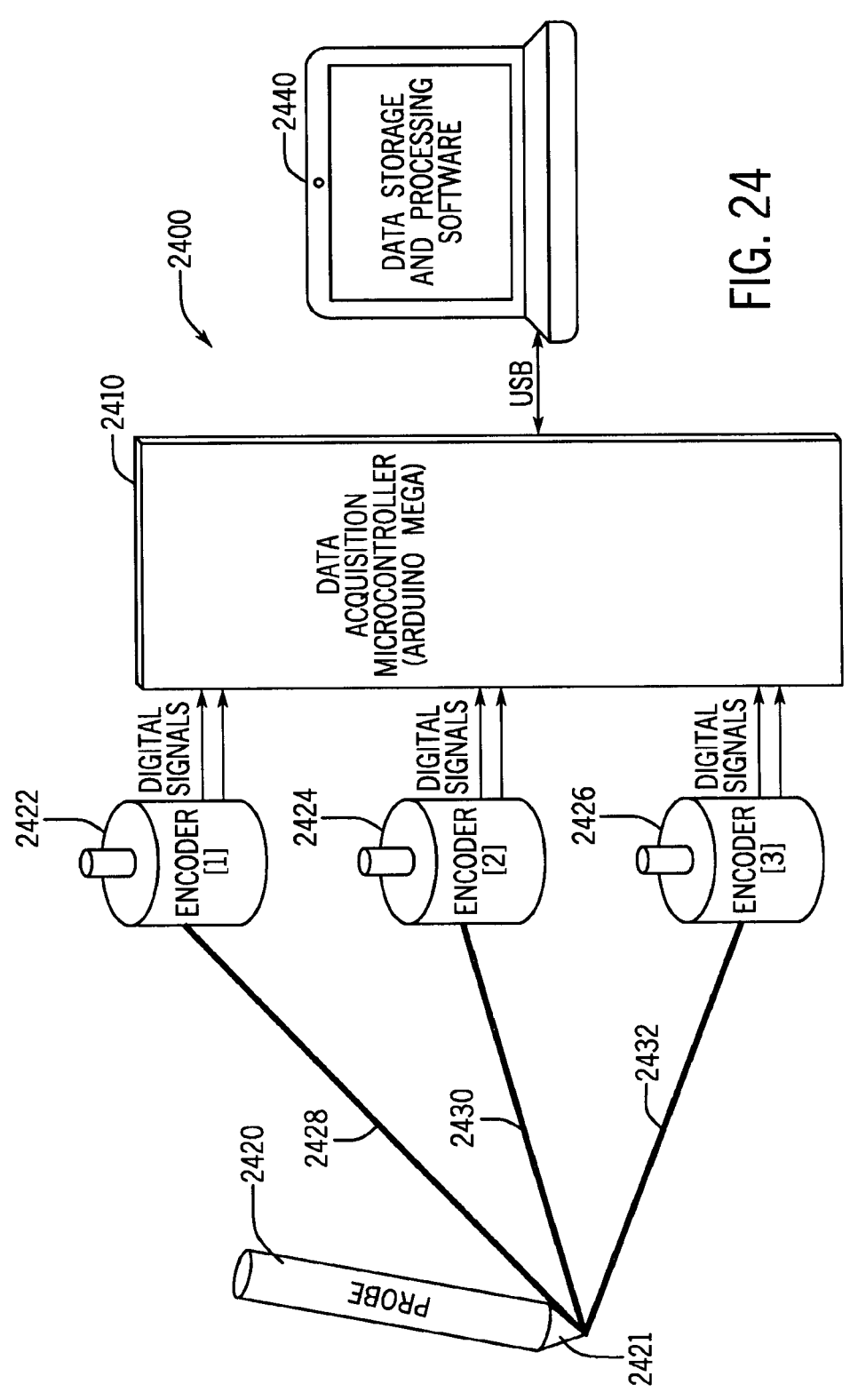
FIGS. 24-26 illustrate systems enabling 3D tracking of a probe in accordance with some embodiments of the invention.

FIG. 24 illustrates a system enabling 3D tracking of a probe in accordance with some embodiments of the invention. Some embodiments depicts a system of components that enable for the electromechanical localization of a 3D point at the tip of a probe (e.g., such as any of the probes described herein). In some embodiments, three extensible cords (2428, 2430, 2432) mechanically link to the probe tip 2421 of probe 2420 via connections extending from three separate rotary encoders 2422, 2424, 2426 that measure the length of each cord, from which the software system calculates the 3D point of the probe tip via triangulation geometric equations. In some embodiments, the encoder (such as those of the encoders 2422, 2424, 2426) is represented by a spool wound with an extensible cord (e.g., 2428, 2430, 2432), a spring-loaded retractor system (not shown), which can be represented by any system that provides a tensioning force, and a rotary encoder, which can be represented by other sensors used to detect the degree of rotation. In some embodiments, the three encoder embodiments are placed at fixed distances relative to each other. In some embodiments, the probe 2420 contains a single cord mount connection at the probe tip 2421, through which all cords 2428, 2430, 2432 interface to the probe 2420. As the probe 2420 is moved in 3D space, the individual, distinct cord lengths are measured via rotary encoders 2422, 2424, 2426 (e.g., as illustrated in FIG. 16), however other sensors can be used to detect the length of the extended cord. In some embodiments, with the known distance between each encoder 2422, 2424, 2426, the measured cord lengths to the probe tip 2421, the system's triangulation algorithm can process the data through a geometric relationship to calculate the 3D location of the probe tip 2421. In some embodiments, the three-cord encoder system requires at least three encoders to calculate the 3D position of the probe 2420.

Figure 25:
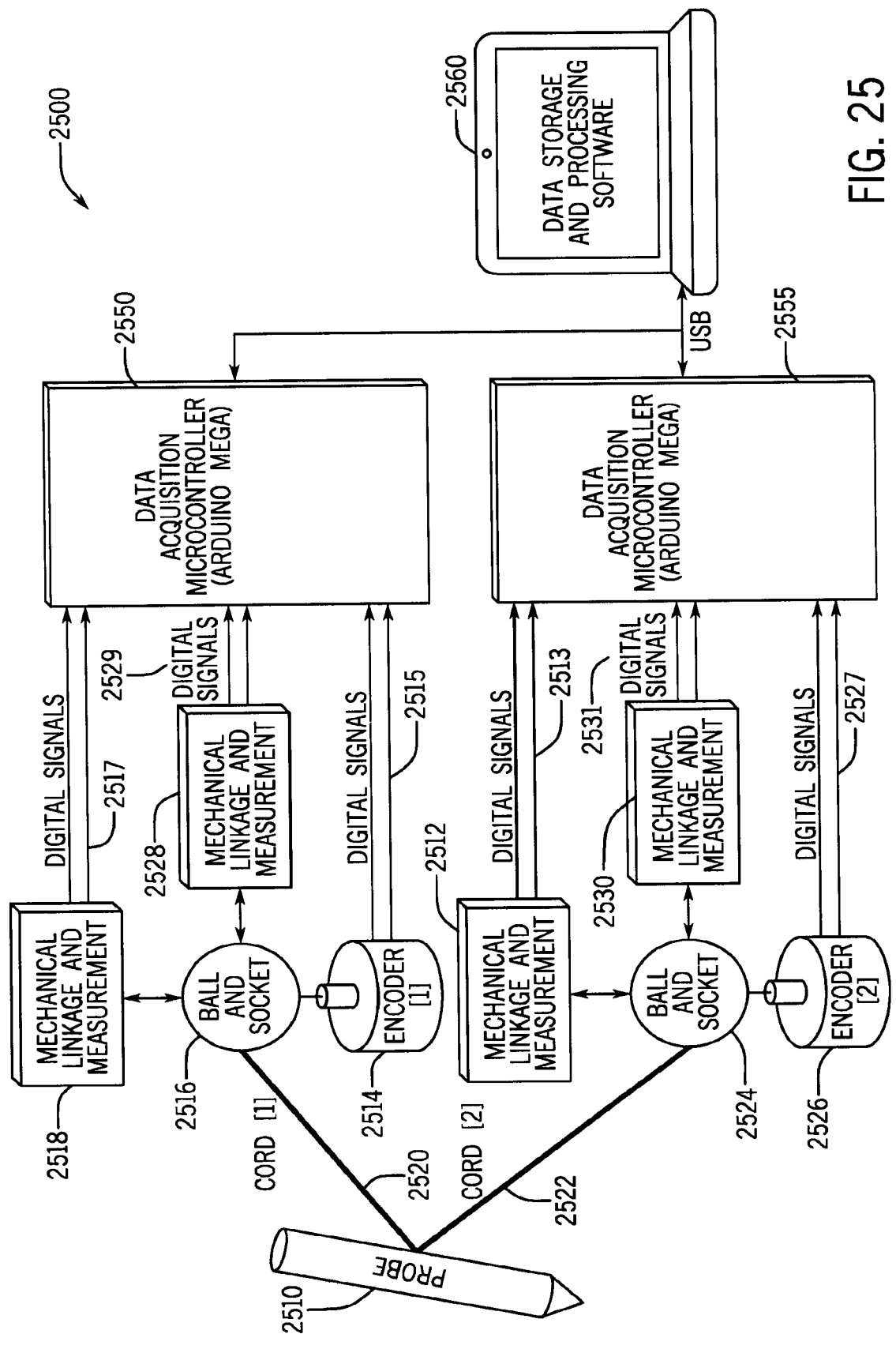

In some embodiments, the electromechanical, 3D-tracking system, illustrated in FIG. 23B-23C, can contain in the system of components shown in FIG. 25, where the ball-and-socket movement is sensed by mechanically-linked rotary encoders that measure the phi and theta movement of the ball in spherical coordinates (e.g., using two encoders per ball and socket system or assembly). In some embodiments, the encoder-based 3D-tracking system shown in FIG. 25 includes probe 2510, cords 2520, 2522, encoders 2514, 2526, mechanical linkage and measurement 2518, 2512, 2528, 2530, ball and socket 2516, 2524, digital signals from encoders 2515, 2527, digital signals from mechanical linkage and measurement 2517, 2529, 2513, 2531, data acquisition controllers 2550, 2555, and computer 2560. Each ball-and-socket 2516, 2524 is mechanically linked to two encoders 2514, 2526. In some embodiments, an extensible cord 2520, 2522 passes radially through the barrel located at the center of the ball and connects to a probe 2510, allowing the barrel to follow the location of the extensible cord. Since the barrel is fixed at the center of the ball and the ball's axis of rotation is fixed by a rod seated in a slot on the socket, the ball is unable to rotate radially about the barrel's axis and the barrel can track the location of the probe. In some embodiments, measurement of the ball's rotation in the socket allows for the calculation of the angular takeoff of the barrel in spherical coordinates as the probe is moved through 3D space. In some embodiments, the cord length is measured via rotary encoders 2514, 2526 as described in relation to FIG. 16, however other sensors can be used to detect the length of the extended cord. In some embodiments, the measurement of cord length and angular takeoff provide sufficient data to calculate the 3D location of the probe in the spherical coordinate system.

Some embodiments of the measurement system used to calculate the angular takeoff is a mechanical linkage between the surface of the ball and a rotary encoder, however other sensors can be used to detect the degree of rotation. In some embodiments, as the ball rotates in the theta and phi directions due to probe translation, a mechanical linkage (2512, 2518, 2528, 2530) rotates the shaft of a rotary encoder (2514, 2526), and the degree of a ball's rotation in each spherical coordinate plane can be calculated.

In some embodiments, one possible mechanical linkage is a spherically or cylindrically-shaped coupling object fixed radially to a rotation measurement system as described in FIG. 16. Some embodiments of a rotation measurement device could be a rotary encoder. In some embodiments, the position of the rotary encoder is fixed such that the cylindrically shaped object makes physical contact with the ball and is mechanically secured to the rotary encoder shaft. Any movement of the probe results in rotation of the ball, rotation of the cylindrically-shaped object, and thus rotation of the rotary encoder shaft. In some embodiments, the described mechanical linkage (2512, 2518, 2528, 2530), oriented orthogonal to each other, are required to calculate the rotation of the ball's barrel in theta and phi directions.

In some embodiments, algorithms calculate the degree of ball rotation in theta and phi from the radius of the cylindrically shaped object, the rotation measured by the rotary encoder, and the radius of the ball. In some embodiments, after calculating phi and theta of the barrel, the system then uses spherical coordinate formulas to calculate a vector from the center of the ball to the location of the first cord as it mates with the probe. In some embodiments, the same process is repeated for the second ball-and-socket pair, also using a mechanical linkage to sense the spherical rotation of the ball. In some embodiments, the second ball-and-socket system calculates a 3D vector from the center of the ball to the end location of the second cord as it mates with the probe.

In some embodiments, the pose of the probe is then calculated from the vector subtraction of two calculated cord vectors. In some embodiments, the three-dimensional position and orientation of the probe tip can be extrapolated given the known dimensions of the probe and the distance between the cord fixation points on the probe.

Figure 26:
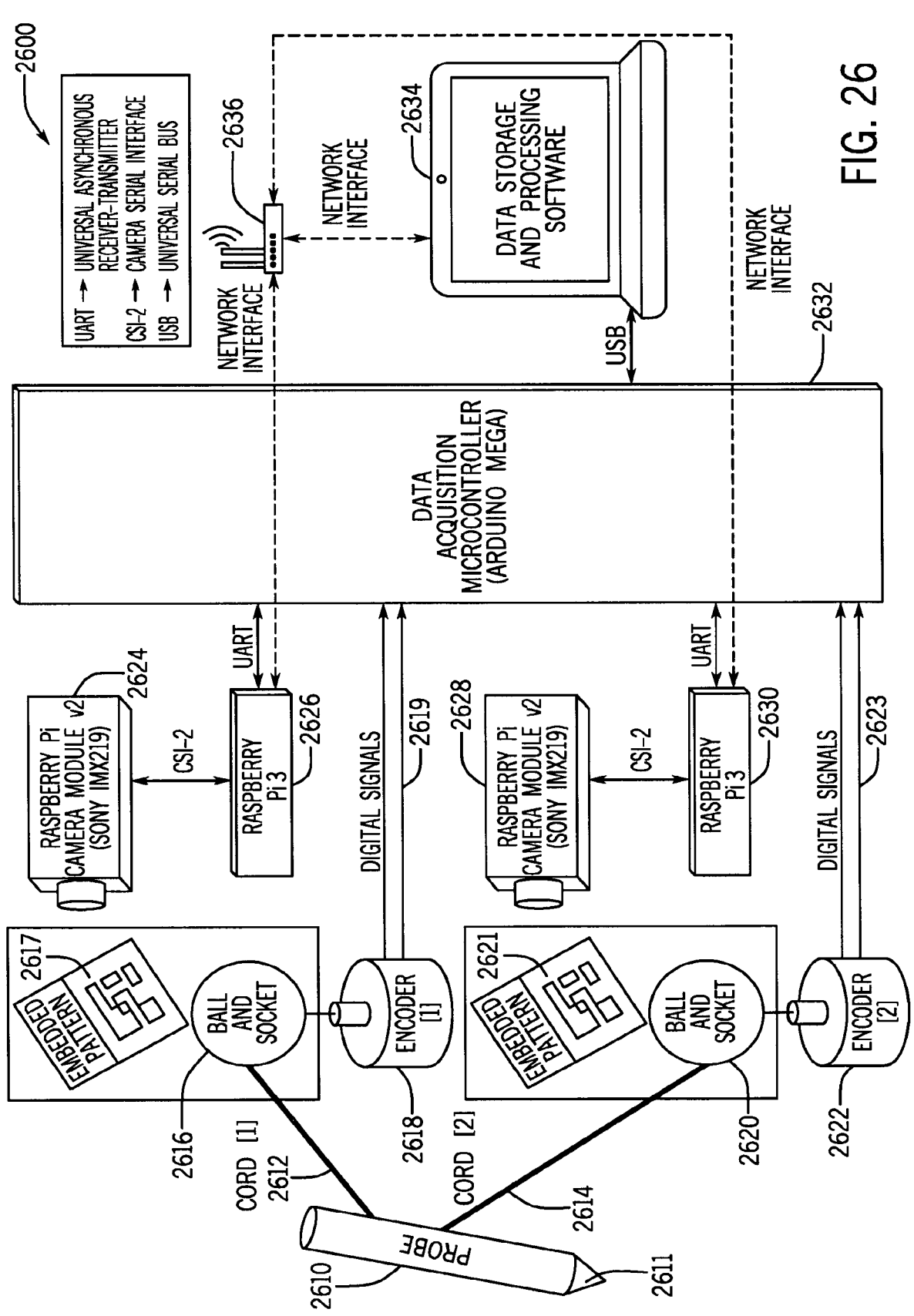

In some embodiments, the electromechanical, 3D-tracking system, illustrated in FIGS. 23A-23C, can contain the system of components shown in FIG. 26, where the ball-and-socket movement is sensed by optical sensors that interpret the rotation and relative location of the ball-mounted pattern with respect to the image sensor. In some embodiments, the system measures the phi and theta movement of the ball in spherical coordinates. In some embodiments, the combined mechanical, electrical, electro-mechanical, and optical components of the system 2600 shown in FIG. 26 that enable for the 3D-tracking of a probe's location and pose include a probe 2610, coupled cords 2612, 2614, coupled ball and socket 2616, 2620, embedded, unique patterns 2617, 2621 on the ball surfaces, encoders 2618, 2622, cameras 2624, 2628 processor or controller 2626, 2630, data acquisition 2632, computer 2634, and modem 2636. Two encoders are able to measure length of the cord, and the two ball-and-socket assemblies enable measurements of cord trajectory for cord that is past the center of the ball (see FIGS. 19A-19E). In some embodiments, one optical-sensing and unique pattern per ball-and-socket embodiment for measuring the spherical rotation of the ball (depicted in FIGS. 27A-27D). In some embodiments, one probe to link the 3D-tracked, extensible cords in 3D space and provide the user a medium for acquiring 3D points (as depicted in FIG. 20).

In some embodiments, an extensible cord passes through the center of rotation of a sphere and exits via a radial barrel that follows the location of the extensible cord end that is mounted to the probe. In some embodiments, the location of the center of the sphere is fixed by the sphere being constrained by a socket with a slot to allow for the free movement of the barrel to track the exiting cord. In some embodiments, the socket ensures that the sphere cannot rotate about its barrel shaft via a radial slot in the socket that receives a complementary rod tip that is mounted to the sphere and is concentric with the center of the sphere.

In some embodiments, the cord length is measured via rotary encoders, however other sensors can be used to detect the change in length of the cord during use (e.g., potentiometers). In some embodiments, since the portion of the extensible cord that has exceeded the center of the sphere is no longer always coaxial with the starting portion of the extensible cord near the encoder, a measurement must be made of the angular takeoff of the sphere's barrel, through which the cord passes, to produce the spherical coordinates needed calculate the 3D location of the cord end that is mounted to the probe.

Some embodiments to calculate the angular takeoff of the sphere's barrel is to embed a pattern on the sphere's cylindrical window such that while the sphere moves due to the translation of the cord in space, the pattern rotates about the center of the sphere in a manner that mimics the phi and theta angles produced by the barrel relative to the coordinate system of the center of the sphere.

In some embodiments, one possible pattern is a checkerboard that has a unique black-and-white tag pattern (as shown by labels 2617, 2621 in FIG. 26), similar to that used in augmented reality registration markers, in each square of the board. In some embodiments, the unique checkerboard has an established x-y coordinate system, such that one corner of the checkerboard is the origin and each square represents one unit of known size.

In some embodiments, an optical sensor embedded in the socket, with the sensor located concentrically to both the center of the sphere and the preview window of the socket, records the viewable portion of the overall pattern that can be seen through the preview window of the socket. In some embodiments, the optical sensor transmits image frames to the processing software to utilize computer vision algorithms to detect all visible corners of checkerboard pattern, identify the signature of each visible square, and reference each square's known location within the overall pattern. In some embodiments, the pixels in the image frame are converted into millimeters, or any other physical unit, by calculating the ratio between pixels and millimeters for a known side length of one of the visible squares of the pattern surface. In some embodiments, the center of the image frame represents the center of the sphere.

In some embodiments, the algorithms then calculate the absolute location of the center of the image along the unique pattern, identifying the exact location in the units of the physical pattern. In some embodiments, the vertical location of the image center is used to calculate the theta of the barrel by identifying the arc length between the current image center in the active image frame and the location on the pattern surface that aligns with the image center when the barrel is concentric with the side window of the socket, producing a theta of zero. In some embodiments, the arc length input is combined with the known radius of the pattern surface relative to the center of the sphere, and then theta is calculated using the arc length formula that extrapolates the angle of the arc section. In some embodiments, the theta angle of the barrel represents the up and down motion of the barrel.

In addition, in some embodiments, a vector is calculated between the checkerboard corner closest to the image center and a corner nearest that first corner that is vertically in-line with respect to each other in the coordinate system of the pattern. In some embodiments, a second vector is calculated along the vertical axis of the image, passing through the image center. In some embodiments, the algorithms calculate the relative angle between these two vectors by calculating the inverse cosine of the cross product of the two vectors; this calculation can also be done several different ways using known geometry formulas. In some embodiments, the angle between these vectors represents the phi angle of the barrel, which indicates the left and right motion of the barrel. In some embodiments, after calculating phi and theta of the barrel via the location of the image center on the unique pattern and the pose of the pattern relative to the optical sensor, the system then uses spherical coordinate formulas to calculate the end location of the cord end that mates with the probe tip, given the input length of the cord that exists past the center of the sphere. In some embodiments, given two cord fixation points with known, calculated 3D locations on the probe shaft, the system can calculate the 3D vector between the two fixation mounts, and then extrapolates the 3D location of the probe tip, given the known dimensions of the probe, and calculating the offset between the probe tip and the 3D line.

In some embodiments, the same process is repeated for the second ball-and-socket pair, which also have an embedded pattern and optical sensor combination, to calculate the 3D location of the second extensible cord end that mounts to the probe. Some embodiments of the electromechanical, 3D-tracking system involves using an optical sensor to measure the spherical rotation of a ball in correspondence with the movement of an extensible cord that transverses through the center of the ball's rotation. In some embodiments, as the barrel translates left and right in the phi plane of the spherical coordinate system of the ball, the embedded pattern also rotates by the same angle, since the pattern viewable to the camera is aligned to be above the center of the ball. In some embodiments, the system thus measures the angle of the pattern with respect to the optical sensor to calculate the phi angle 2710 of the barrel in spherical coordinates. Some embodiments of the electromechanical, 3D-tracking system, illustrated in FIGS. 23A-23C, can involve the use of unique patterns embedded on the ball surface, as shown in FIGS. 27A-27D (and discussed earlier with respect to 2383 of FIG. 23C), where the ball-and-socket movement is sensed by optical sensors that interpret the rotation and relative location of the ball-mounted pattern 2701 with respect to the image sensor. In some embodiments, the unique pattern enables for the computer vision algorithms of the system to calculate the absolute position of the center of the image sensor with respect to coordinate system of the grid-based pattern. In some embodiments, the system measures the phi 2710 and theta 2715 movement of the ball 2705 in spherical coordinates. In some embodiments, unlike a typical optical sensor used in a computer mouse, this system does not lose its sense of position with respect to the pattern if image frames are lost or not able to be calculated for any reason, since the pattern provides the system an ability to calculate absolute position on its surface. In some embodiments, as shown, barrel phi rotation 2710, ball 2705, and pattern 2701.

In some embodiments, in reference to FIG. 27B, and barrel theta rotation 2715, the electromechanical, 3D-tracking system involves using an optical sensor to measure the spherical rotation of a ball in correspondence with the movement of an extensible cord that transverses through the center of the ball's rotation. In some embodiments, as the barrel translates up and down vertically in the theta plane of the spherical coordinate system of the ball, the embedded pattern translates away from the center of the image sensor as the ball rotates about the y-axis. In some embodiments, subsequently, the system measures the location of the image center with respect to the grid coordinate system to calculate the translation along the vertical portion of the grid, and then using the known radius between the ball center and pattern surface, the system calculates the theta angle 2715 of the barrel in spherical coordinates.

In some embodiments, in reference to FIGS. 27C-27D, a vector is calculated between the checkerboard corner closest to the image center and a corner nearest that first corner that is vertically in-line with respect to each other in the coordinate system of the pattern. In some embodiments, a second vector is calculated along the vertical axis of the image, passing through the image center. In some embodiments, the algorithms calculate the relative angle between these two vectors, by calculating the inverse cosine of the cross product of the two vectors; this calculation can also be done several different ways using known geometry formulas. In some embodiments, the angle is calculated using one vector from each of the grid axes 2721a and camera axes 2719a, selecting the two vectors with the closest angles to the zero-phi angle. In some embodiments, the angle between these vectors represents the phi angle of the barrel, which indicates the left and right motion of the barrel. In some embodiments, after calculating phi and theta of the barrel via the location of the image center on the unique pattern and the pose of the pattern relative to the optical sensor, the system then uses spherical coordinate formulas to calculate the end location of the cord end that mates with the probe tip, given the input length of the cord that exists past the center of the sphere. In some embodiments, the theta angle of the barrel represents the up and down motion of the barrel. In some embodiments, the system algorithms calculate the absolute location of the center of the image along the unique pattern, identifying the exact location in the units of the physical pattern. First, 2 in some embodiments, the grid axes 2721b rotation is identified and then the image center 2722 relative to the camera axes 2719*b*. Next, in some embodiments, the projected length of the vector between the grid axes origin 2723 and the image sensor center 2722 is calculated. In some embodiments, this arc length input is combined with the known radius of the pattern surface relative to the center of the sphere, and then theta is calculated using the arc length formula that extrapolates the angle of the arc section.

Figure 28A:
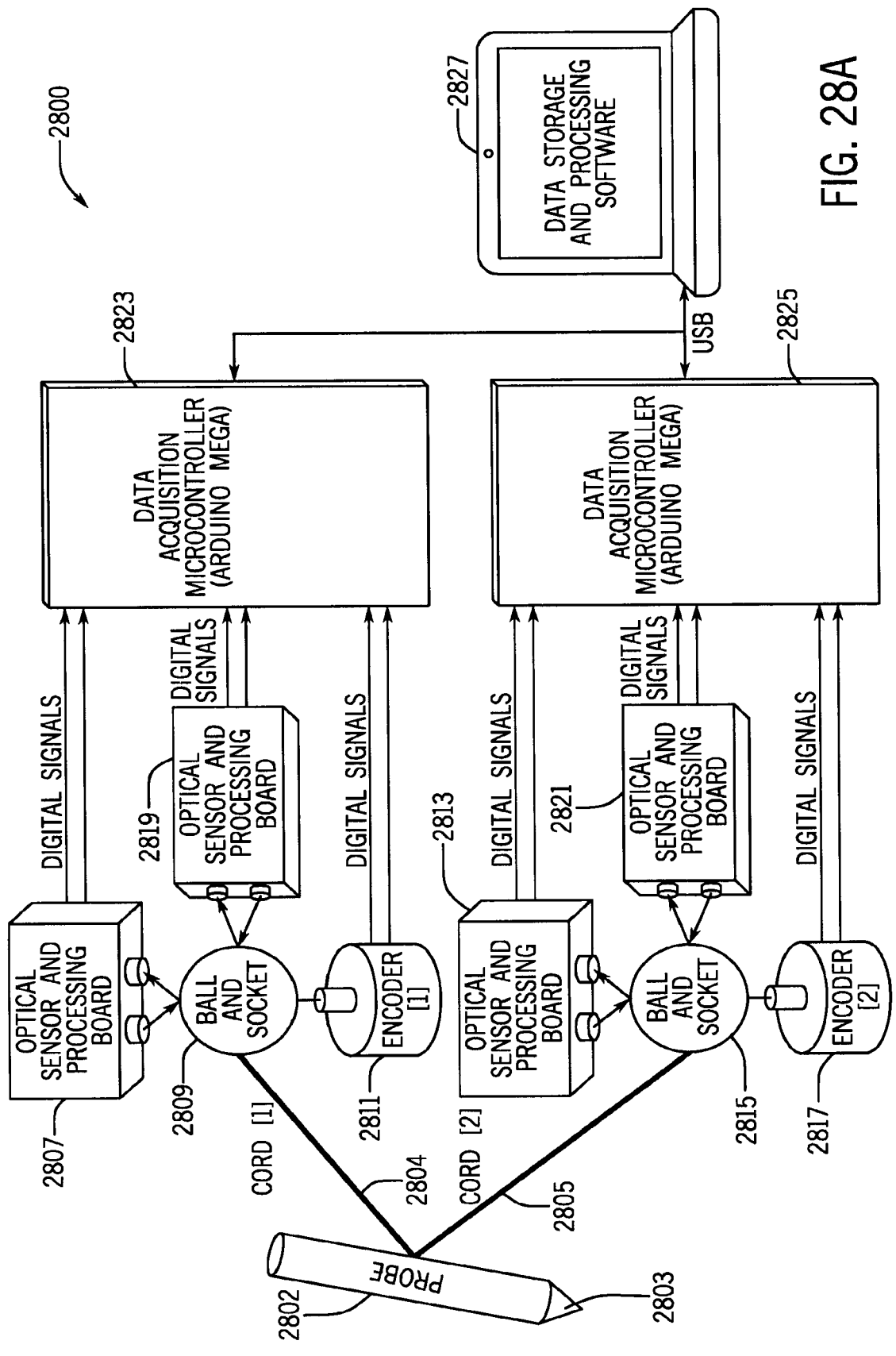
FIG. 28A illustrates an example 3D tracking system in accordance with some embodiments of the invention.

Some embodiment of the electromechanical, 3D-tracking system, illustrated in FIGS. 23A-23C, can contain the system of components shown in FIG. 28A, where the ball-and-socket movement is sensed by optical sensors that interpret the relative translation of the ball surface with respect to the image sensor as the ball rotates due movement of the barrel. In some embodiments, this system measures the phi and theta movement of the ball in spherical coordinates. In some embodiments, the system 2800 can include encoders to measure length of the cord, two ball-and-socket assemblies to enable measurements of cord trajectory for cord that is past the center of the ball, two optical sensors per ball-and-socket assembly for measuring the translation of the ball surface with respect to the image sensor to calculate the spherical rotation of the ball, and one probe assembly to link the 3D-tracked, extensible cords in space and provide the user a medium for acquiring 3D points. For example, in some embodiments, the system 2800 can include couple components comprising probe 2802 with probe tip 2803, cords 2804, 2805, ball and sockets 2809, 2815, optically-coupled sensor and processing boards 2807, 2813, 2819, and 2821, coupled encoders 2811, 2817, data acquisition microcontrollers 2823, 2825, and computer system 2827 with data storage and processing software.

In some embodiments, for each ball-and-socket there is one encoder and two optical sensor. In some embodiments, an extensible cord passes radially through the barrel located at the center of the ball and connects to a probe, allowing the barrel to follow the location of the extensible cord. In some embodiments, since the barrel is fixed at the center of the ball and the ball's axis of rotation is fixed by a rod seated in a slot on the socket, the ball is unable to rotate radially about the barrel's axis and the barrel can track the location of the probe. In some embodiments, measurement of the ball's rotation in the socket allows for the calculation of the angular takeoff of the barrel as the probe is moved through three-dimensional space. In some embodiments, the cord length is measured via rotary encoders as described in FIG. 16, however other sensors can be used to detect the length of the extended cord. In some embodiments, the measurement of cord length and angular takeoff provide sufficient data to calculate the 3D location of the probe in the spherical coordinate system.

Some embodiments of the measurement system used to calculate the angular takeoff is a pair of optical sensors oriented normal to the ball and socket and orthogonal to each other, each one aligned with the theta and phi spherical coordinate planes of the ball system.

In some embodiments, a light-emitting device emits light in a finite spectrum that is reflected off the surface of the ball and is converted to electrical signals via a photodetector array. In some embodiments, the converted data is then processed using an algorithm to transform the photodetector array data into translational changes of the ball surface with respect to the camera. In some embodiments, a data acquisition and computing system converts the translational data from cartesian to spherical coordinates, and subsequently calculates the theta and phi rotation of the sphere, based on the known radius of the ball that is being sensed. Some embodiments of the system may include a laser diode and photodiode array, light-emitting diode and photodiode array, and/or an imaging sensor. In some embodiments, a pattern or image installed on the cylindrical window of the ball to increase the contrast, reflectivity, or sensitivity of the optical signal, as well as to produce higher signal-to-noise ratios, and increase the accuracy of theta and phi spherical coordinate calculations. In some embodiments, the pattern or image may contain repeating variations of patterned and/or colors, and may be manufactured with a reflective surface, which maximizes the optical coupling between the light-emitting device and the photodetector array.

Some embodiments involves a surface pattern that is etched on the ball surface during the manufacturing process, and the surface pattern enhances the sensitivity of optical signals to change at the slightest of translational changes of the ball surface with respect to the image sensor.

Some embodiments can involve additional lighting sources that provide lighting on the ball surface at any possible finite spectrum of light, from which certain light source frequencies provide an optimal sensitivity for the system to have a high-resolution sensing of rotational changes, but not erroneously estimating movement that is not actually occurring, but rather just artifacts of optical noise.

Figure 28B:
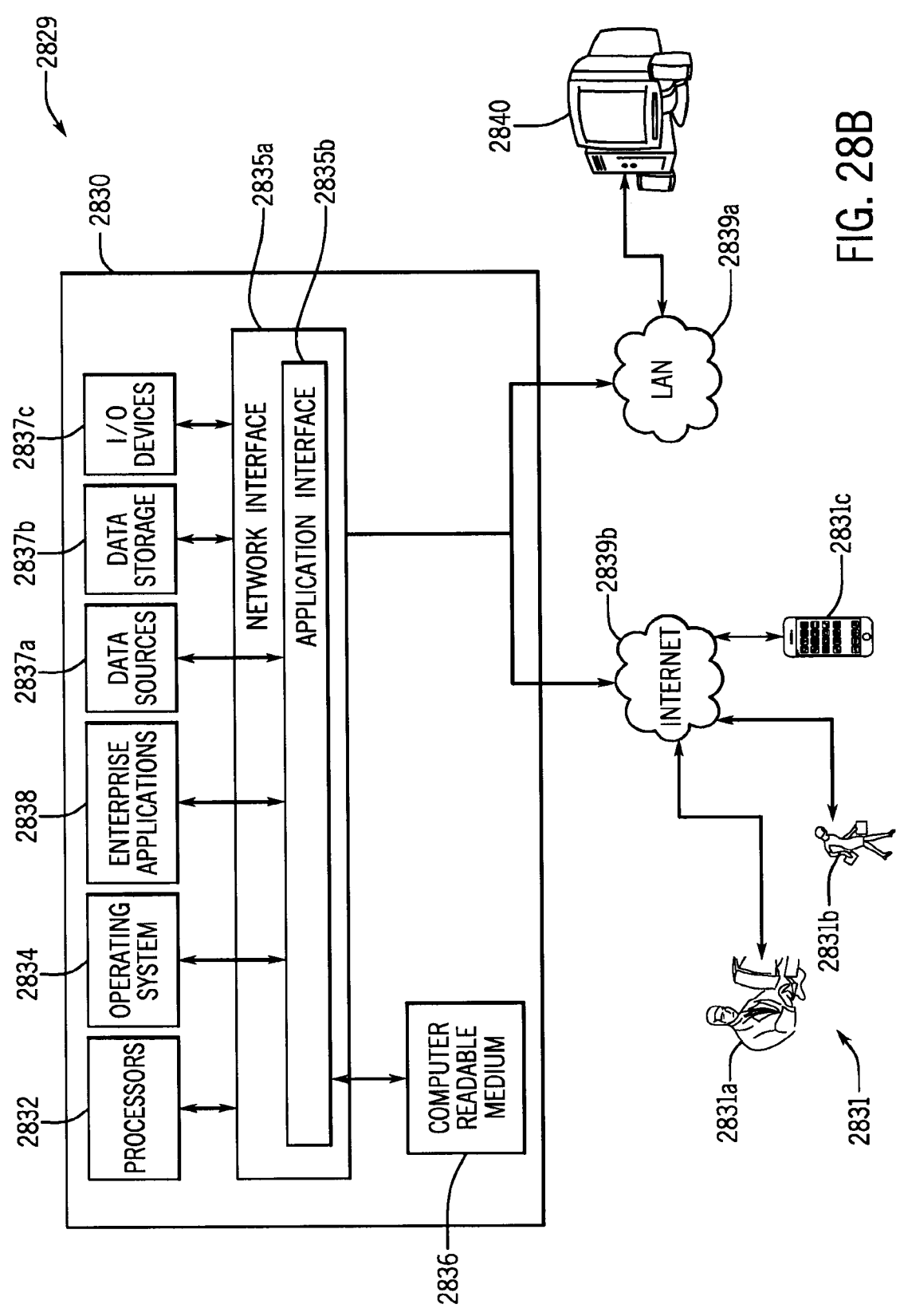
FIG. 28B illustrates a computer system configured for operating and processing components of the system in accordance with some embodiments of the invention.

FIG. 28B illustrates a computer system 2829 configured for operating and processing components of the any of the systems disclosed herein according to some embodiments. For example, in some embodiments, the computer system 2829 can operate and/or process computer-executable code of one or more software modules of any of the systems shown in one or more of the figures herein, including, but not limited to FIGS. 24-26, and 28A. In some embodiments, the system 2829 can comprise at least one computing device including at least one processor 2832. In some embodiments, at least one processor 2832 can include a processor residing in, or coupled to, one or more server platforms. In some embodiments, the system 2829 can include a network interface 2835*a* and an application interface 2835*b* coupled to the least one processor 2832 capable of processing at least one operating system 2834. Further, in some embodiments, the interfaces 2835*a*, 2835*b* coupled to at least one processor 2832 can be configured to process one or more of the software modules 2838 (e.g., such as enterprise applications). In some embodiments, the software modules 2838 can include server-based software and/or can operate to host at least one user account and/or at least one client account, and operating to transfer data between one or more of these accounts using the at least one processor 2832.

In some embodiments, the invention can employ various computer-implemented operations involving data stored in computer systems. Moreover, in some embodiments, the above-described databases and models throughout the system 2829 can store analytical models and other data on computer-readable storage media within the system 2829 and on computer-readable storage media coupled to the system 2829. In addition, in some embodiments, the above-described applications of the 2829 system can be stored on computer-readable storage media within the system 2829 and on computer-readable storage media coupled to the system 2829. In some embodiments, these operations are those requiring physical manipulation of physical quantities. Usually, though not necessarily, in some embodiments, these quantities take the form of electrical, electromagnetic, or magnetic signals, optical or magneto-optical form capable of being stored, transferred, combined, compared and otherwise manipulated. In some embodiments of the invention, the system 2829 can comprise at least one computer readable medium 2836 coupled to at least one data source 2837*a*, and/or at least one data storage device 2837*b*, and/or at least one input/output device 2837*c*. In some embodiments, the invention can be embodied as computer readable code on a computer readable medium 2836. In some embodiments, the computer readable medium 2836 can be any data storage device that can store data, which can thereafter be read by a computer system (such as the system 2829). In some embodiments, the computer readable medium 2836 can be any physical or material medium that can be used to tangibly store the desired information or data or instructions and which can be accessed by a computer or processor 2832. In some embodiments, the computer readable medium 2836 can include hard drives, network attached storage (NAS), read-only memory, random-access memory, FLASH based memory, CD-ROMs, CD-Rs, CD-RWs, DVDs, magnetic tapes, other optical and non-optical data storage devices. In some embodiments, various other forms of computer-readable media 2836 can transmit or carry instructions to a computer 2840 and/or at least one user 2831, including a router, private or public network, or other transmission device or channel, both wired and wireless. In some embodiments, the software modules 2838 can be configured to send and receive data from a database (e.g., from a computer readable medium 2836 including data sources 2837*a* and data storage 2837*b* that can comprise a database), and data can be received by the software modules 2838 from at least one other source. In some embodiments, at least one of the software modules 2838 can be configured within the system to output data to at least one user 2831 via at least one graphical user interface rendered on at least one digital display.

In some embodiments of the invention, the computer readable medium 2836 can be distributed over a conventional computer network via the network interface 2835*a* where the 2829 system embodied by the computer readable code can be stored and executed in a distributed fashion. For example, in some embodiments, one or more components of the system 2829 can be coupled to send and/or receive data through a local area network ("LAN") 2839*a* and/or an internet coupled network 2839*b* (e.g., such as a wireless internet). In some further embodiments, the networks 2839*a*, 2839*b* can include wide area networks ("WAN"), direct connections (e.g., through a universal serial bus port), or other forms of computer-readable media 2836, or any combination thereof.

In some embodiments, components of the networks 2839*a*, 2839*b* can include any number of user devices such as personal computers including for example desktop computers, and/or laptop computers, or any fixed, generally non-mobile internet appliances coupled through the LAN 2839*a*. For example, some embodiments include personal computers 2840 coupled through the LAN 2839*a* that can be configured for any type of user including an administrator. Some embodiments can include personal computers coupled through network 2839*b*. In some embodiments, one or more components of the system 2829 can be coupled to send or receive data through an internet network (e.g., such as network 2839*b*). For example, some embodiments include at least one user 2831 coupled wirelessly and accessing one or more software modules of the system including at least one enterprise application 2838 via an input and output ("I/O") device 2837*c*. In some embodiments, the system 2829 can enable at least one user 2831 to be coupled to access enterprise applications 2838 via an I/O device 2837*c* through LAN 2839*a*. In some embodiments, the user 2831 can comprise a user 2831*a* coupled to the system 2829 using a desktop computer, and/or laptop computers, or any fixed, generally non-mobile internet appliances coupled through the internet 2839*b*. In some further embodiments, the user 2831 can comprise a mobile user 2831*b* coupled to the system 2829. In some embodiments, the user 2831*b* can use any mobile computing device 2831*c* to wireless coupled to the system 2829, including, but not limited to, personal digital assistants, and/or cellular phones 2831*c*, mobile phones, or smart phones, and/or pagers, and/or digital tablets, and/or fixed or mobile internet appliances.

In some embodiments of the invention, the system 2829 can enable one or more users 2831 coupled to receive, analyze, input, modify, create and send data to and from the system 2829, including to and from one or more enterprise applications 2838 running on the system 2829. In some embodiments, at least one software application 2838 running on one or more processors 2832 can be configured to be coupled for communication over networks 2839*a*, 2839*b* through the internet 2839*b*. In some embodiments, one or more wired or wirelessly coupled components of the network 2839*a*, 2839*b* can include one or more resources for data storage. For example, in some embodiments, this can include any other form of computer readable media in addition to the computer readable media 2836 for storing information, and can include any form of computer readable media for communicating information from one electronic device to another electronic device.

Figures 29A, 29B:
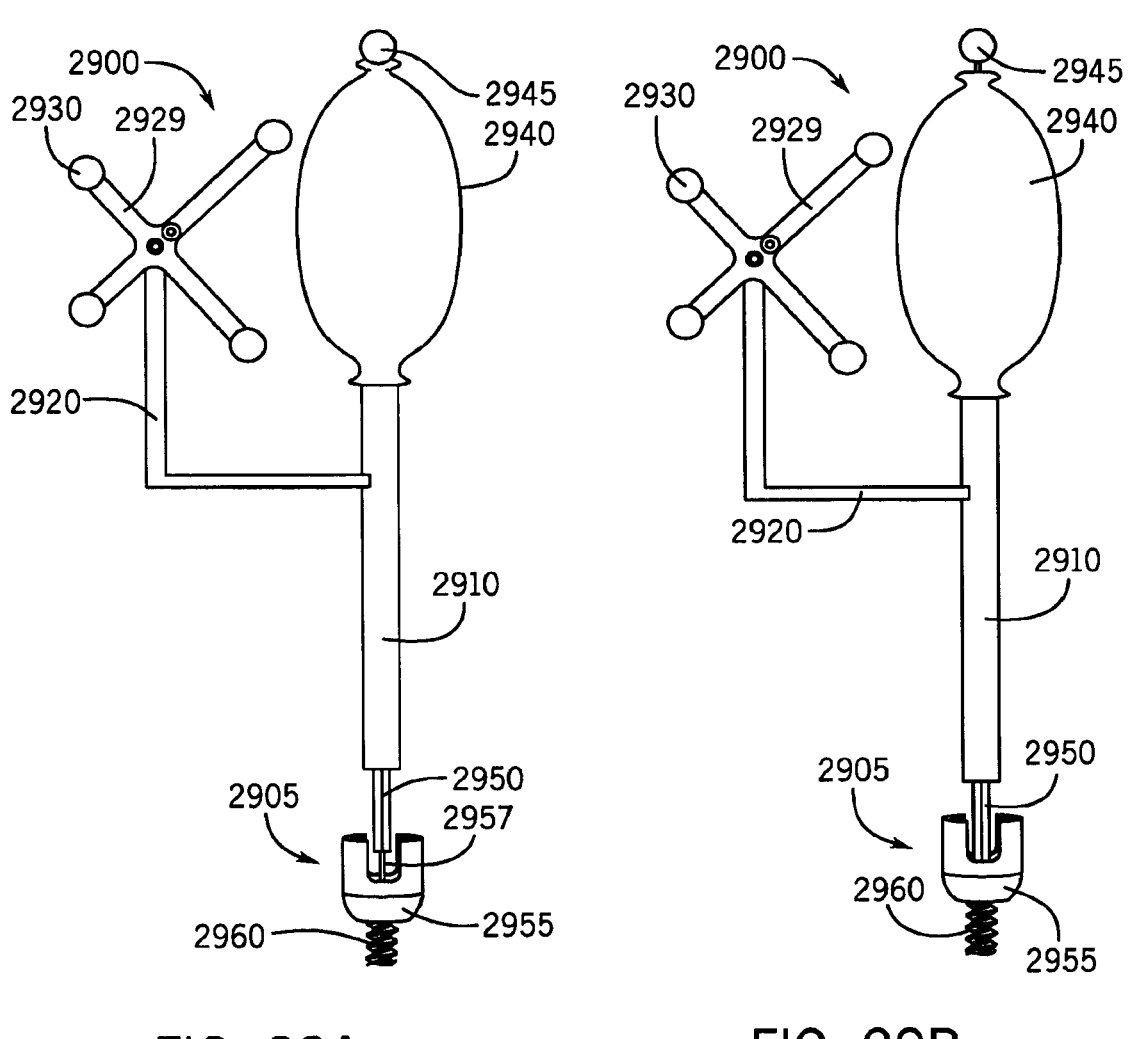
FIGS. 29A-29B illustrates a screw-head-registering screwdriver equipped with a tracked dynamic reference frame in accordance with some embodiments of the invention.
Figure 29C:
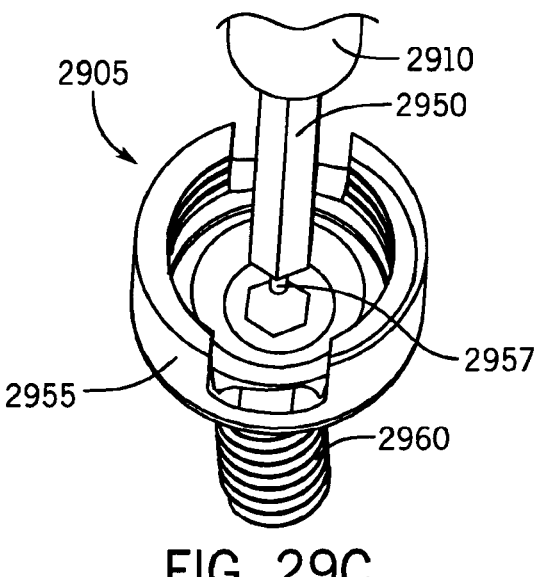
FIG. 29C illustrates a close-up perspective view of a screwdriver head and depressible tip of the screwdriver of FIGS. 29A-29B in accordance with some embodiments of the invention.
Figure 29D:
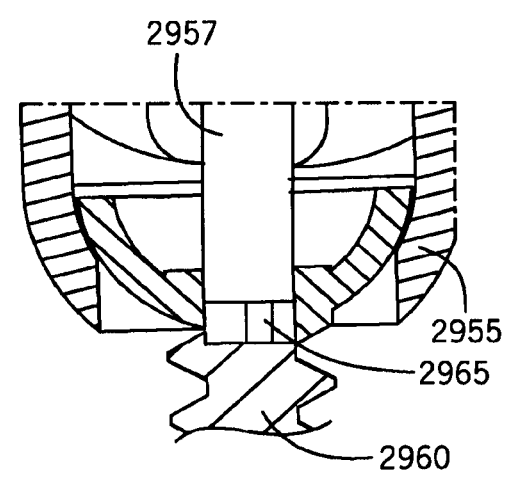
FIG. 29D illustrates a cross-sectional view of the screwdriver-screw interface in accordance with some embodiments of the invention.

FIGS. 29A-29B illustrates a screw-head-registering screwdriver 2900 equipped with a tracked dynamic reference frame in accordance with some embodiments of the invention. FIG. 29C illustrates a close-up perspective view of a screwdriver head and depressible tip 2957 of the screwdriver of FIGS. 29A-29B in accordance with some embodiments of the invention. Further, FIG. 29D illustrates a cross-sectional view of the screwdriver-screw interface in accordance with some embodiments of the invention. FIG. 29A-29B displays a tool that serves three functions: 1.) it registers the 3D position and pose of the screw shaft, 2.) fully engages in the screw head interface, and 3.) signals when it is fully engaged via a depressible sliding shaft 2957 that extends from the probe shaft 2910 of the tool 2900 and is coupled to a tracked mobile stray marker that is actuated when the tool is fully engaged with the mating screw according to some embodiments. In some embodiments, the overall purpose of this invention is to identify the location and pose of a screw via a coupling mechanism with the screw head, and to have a triggering system via the TMSM 2945 to indicate to the acquisition system when the tool is fully engaged with the screw. In some embodiments, this tool 2900 can be applied when there is not a rod seated in the screw obstructing the tool's interface with the screw head. In some embodiments, as shown in FIG. 29A, the tool can comprise tracked DRF 2929 (with markers 2930), a probe shaft 2910, a TMSM (undepressed) 2945, handle 2940, screwdriver head 2950, depressible sliding shaft (undepressed) 2957, pedicle screw shaft 2960, pedicle screw tulip head 2955, and coupling mechanism 2905.

In some embodiments, this tool (screwdriver) 2900 is designed to interface with a pedicle screw shaft 2960 in such a way that it can engage with the head of the screw to both tighten and loosen the screw, but furthermore, that when the tool 2900 is fully engaged in the screw head 2955, its 2910 is fixed in one orientation relative to the screw shaft 2960. In some embodiments, this tool 2900 can be used to quickly register both the location and pose of the screw shaft 2960 by only accessing the screw head 2955 of the screw shaft 2960. In some embodiments, as shown in FIG. 29A, the TMSM 2945 is in the position corresponding with an undepressed, and therefore unengaged, screwdriver depressible shaft 2957. In some embodiments, this possesses a similar design of actuating a TMSM 2945 via a depressible tip 2957 as described previously in relation to FIG. 10A-10G. In some embodiments, it should be noted that the depressible tip 2957 and the screw head interface component 2950 of the tool 2900 can have many different configurations.

In some embodiments, the sliding shaft (tip 2957) can be structured such that it always remains within the shaft of the tool or screwdriver, and the screw head 2960 is designed with a center protrusion to deflect the inner sliding shaft of the screwdriver. In this way, in some embodiments, the tip 2957 of the sliding shaft is unable to be actuated by any object that cannot fit inside the shaft 2950. In some embodiments, when the tracked mobile stray marker 2945 is actuated, the acquisition system's software detects its motion (shown as linear) and is able to distinguish when it is fully or partially engaged with a screw head by the known geometry of the tool and interfacing screw as described in more detail below in reference to FIG. 63. It should be noted that the motion of the TMSM 2945 can be linear, rotational, or any combination thereof according to some embodiments. Further, in some embodiments, the mechanism of detecting the motion of the TMSMs can also consist of covering and uncovering a particular stray marker with actuation of the sliding shaft as described previously in relation to FIG. 14. In some embodiments, additionally, the design of the screwdriver head 2950 can be such that it also has components that allow for ensuring it will mechanically couple with the screw shaft 2960 such that it can only achieve one unique orientation when fully engaged. In some embodiments, structures to help with engaging in a unique configuration include, but are not limited to, expanding screwdriver heads, a depth-stop flange to help the screwdriver head align with the screw head, and screws designed with screw heads of increased depth to ensure the screwdriver shaft firmly engages in one orientation when fully seated into the head. In addition, in some embodiments, since the depicted location of the tracked DRF 2929 is not the only manner to substantially rigidly attached the DRF, it must be noted that the DRF 2929 can be placed anywhere on the surgical tool screwdriver 2900 as long as it can be substantially rigidly attached, even on adjustable joints.

FIG. 29B displays some embodiments of the tool shown previously in reference to FIG. 29A, except in this image, the tool 2900 is fully engaged with the screw head 2960, highlighting the new position of the TMSM 2945 to indicate to the acquisition software system that the screwdriver head 2950 and depressible shaft 2957 is fully seated and the location and pose of the screw shaft 2960 can subsequently be calculated from that position according to some embodiments.

FIG. 29C illustrates a close-up perspective view of a screwdriver head 2950 and depressible tip 2957 of the screwdriver 2900 of FIGS. 29A-29B in accordance with some embodiments of the invention, and shows the aforementioned depressible sliding shaft 2957 in an undepressed position according to some embodiments. FIG. 29C shows a more detailed perspective of the screwdriver head 2950 and the depressible tip 2957 of the screwdriver tool 2900 previously described in relation to FIGS. 29A-29B, and its interface 2905 with a pedicle screw head 2960 according to some embodiments. In some embodiments, in this view it is possible to see the interface of the screwdriver head 2950 and the top of the screw head 2960, as well as the depressible tip 2957, shown undepressed. Some embodiments involve a depressible sliding shaft that is contained within the screwdriver head. In some embodiments, this spring-loaded, depressible shaft can only be engaged when a male protrusion in the screw head engages the screwhead coaxially, and then the depressible shaft 2957 is pushed up, actuating the TMSM 2945 attached to the depressible shaft 2957, to signal that the 3D-tracked tool 2900 and the screw shaft 2960 are fully engaged and coaxial, and thus ready to be registered in 3D space.

FIG. 29D illustrates a cross-sectional view of the screwdriver-screw interface 2905 in accordance with some embodiments of the invention, and shows the depressible sliding shaft tip (partially depressed) 2965. As shown in figure FIG. 29D, the screwdriver tool 2900 would not signal to the acquisition system that it is fully engaged with the screw head 2960, as the partially-depressed depressible shaft 2965 and its mechanically-linked TMSM 2945 would not be fully-actuated relative to the tracked DRF 2929 according to some embodiments.

In some embodiments, the tracked DRF does not have to be substantially rigidly attached to the tool's shaft, but can be allowed to rotate about the tool shaft (e.g., linked with a bearing) and adjust its relative position to the tool (still able to be substantially rigidly locked when desired). As it shown in the simplified drawings FIG. 29A-29B, it makes it very challenging for users to use the tool as a screwdriver if the DRF 2929 gets in the way according to some embodiments. It should be noted that in some embodiments, the tracked DRF 2929 is both located and attached to the screwdriver in different ways that better facilitates the user interface of the handle while maintaining visualization of the DRF 2929 according to some embodiments.

For instance, in some embodiments, the tracked DRF 2929 is coupled to the screwdriver shaft 2910 via a bearing (which can be coupled with or without a lockable ratcheting mechanism), such that it is allowed to rotate about the long-axis of the screw driver shaft. In some embodiments it is positioned above the handle with or without bearings to enable it to rotate about the screwdriver shaft axis.

Figure 30A:
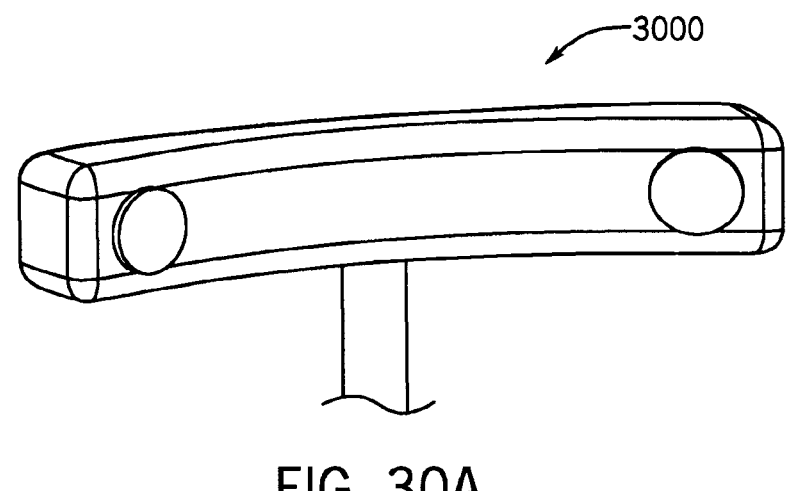
FIG. 30A illustrates a 3D-tracking camera system in accordance with some embodiments of the invention.
Figure 30B:
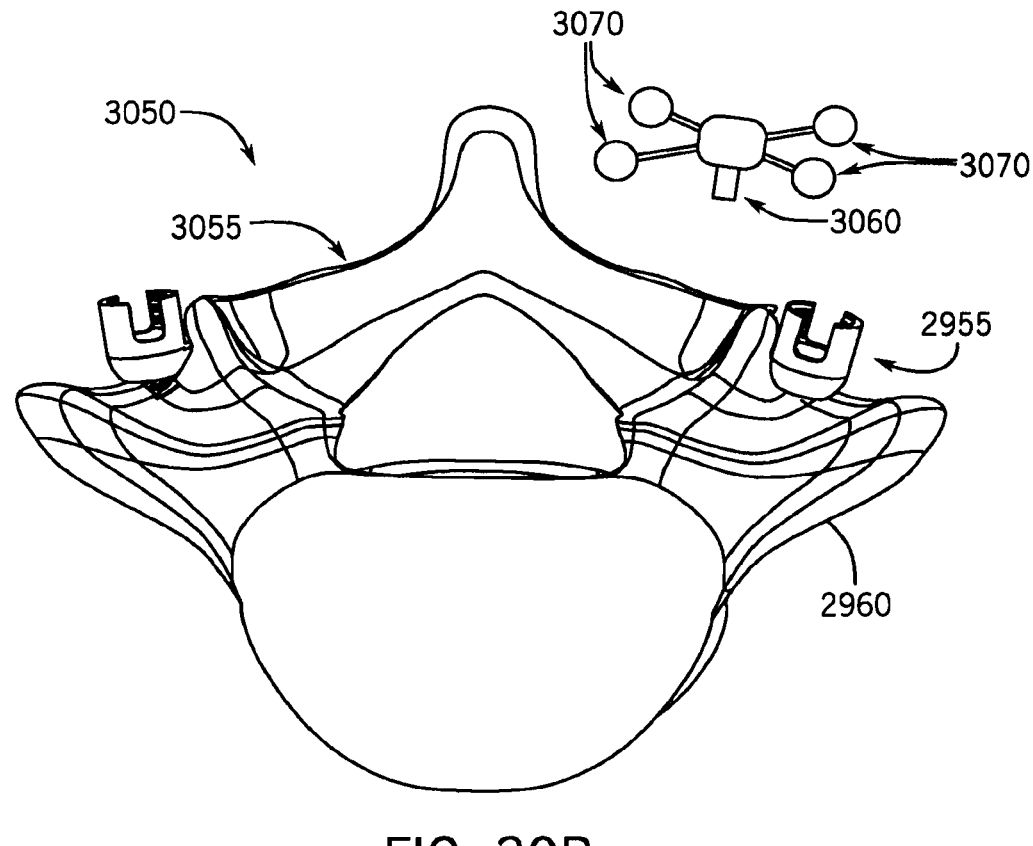
FIG. 30B comprises an image of a tracked reference frame accordance with some embodiments of the invention.

In some embodiments of the invention, as seen in FIG. 30A-30C, a pedicle screw insert cap 3060 with an attached series of 3D-tracked markers 3070, which form a DRF, couples to the tulip head 2955 of a pedicle screw. In this way, in some embodiments, the tulip head can be tracked in 3D space whenever the markers 3070 are within line of sight of the camera 3000, and do not require a probe to interface with them to register their position in space. FIG. 30A displays an optical, 3D-tracking system 3000 that can be used as the acquisition device for these and any other tracked markers throughout this document according to some embodiments. FIG. 30B displays a tracked DRF with 3D-tracked markers 3070 on a cap device equipped with a mating mechanism 3060 to substantially rigidly mount to the tulip head 2955 of a pedicle screw 2960 (not visible; instrumented into spinal vertebrae 3055 in FIG. 30B) according to some embodiments. In some embodiments, with this tracked reference frame of markers 3070 coupled to the screw 2960, the location of the pedicle screw 2960 can be tracked in 3D space, provided it is in line of sight of the 3D-tracking camera 3000. In some embodiments, the interface 3060 between the DRF markers 3070 and the tulip head 2955 can consist of an array of mechanisms, described in more detail below in reference to FIGS. 34A-34F, 35A-35E, 36A-36I, and 37A-37G.

Figure 31:
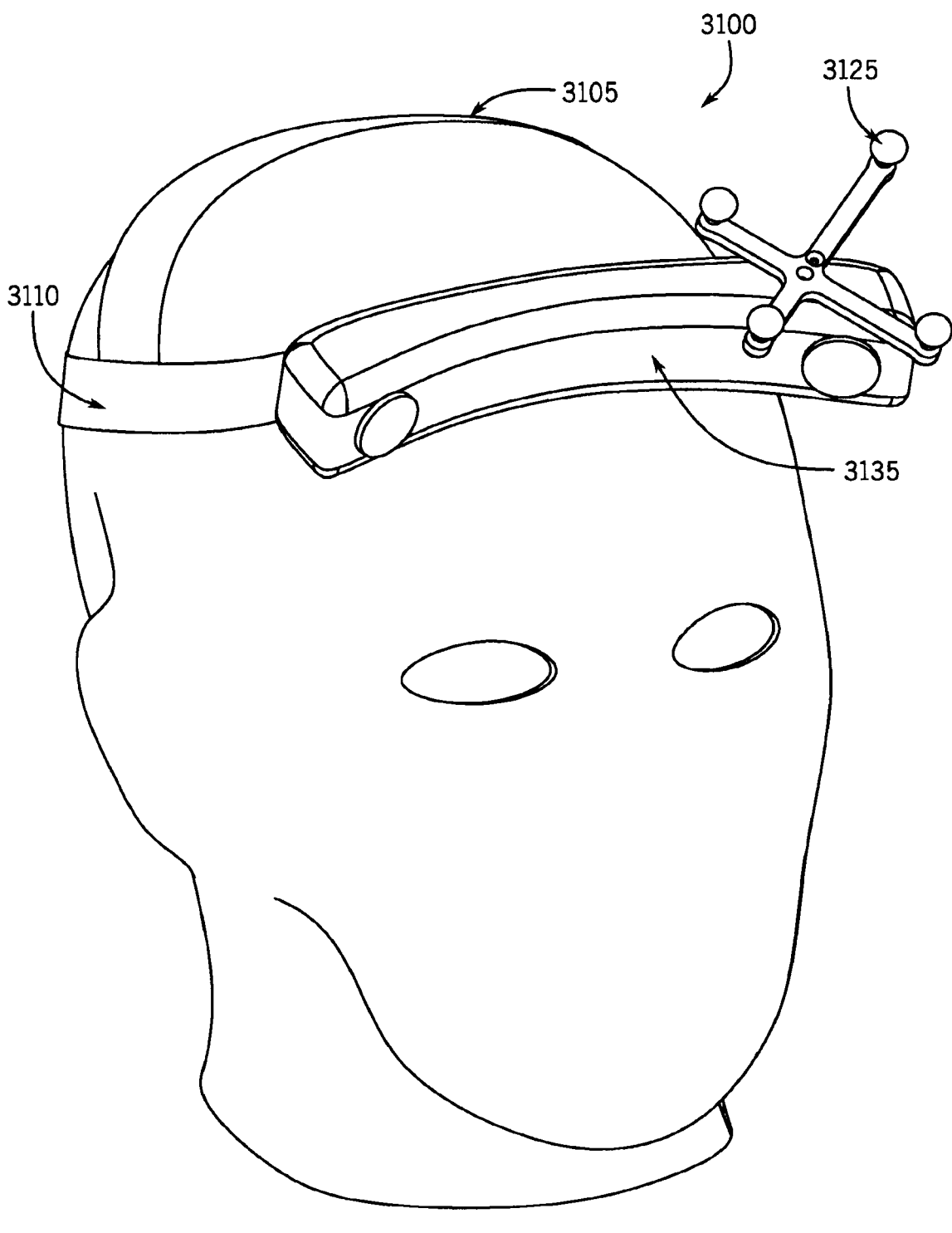
FIG. 31 illustrates a body-mounted 3D-tracking camera in accordance with some embodiments of the invention.

FIG. 31 illustrates a body-mounted 3D-tracking camera in accordance with some embodiments of the invention, and operates in a way to avoid line of sight obstruction between a 3D-tracking camera and a surgical site, or any other area of visualization interest according to some embodiments. In some embodiments, this design involves a user equipped with a body-mounted tracked DRF 3125 substantially rigidly fixed to a body-mounted 3D-tracking camera 3135 such that information can be fused between the user's field of view and the external 3D-tracking camera (not shown) because the location and pose of the body-mounted camera 3135 will typically be visible and known to the larger field-of-view 3D-tracking camera (not shown). FIG. 31 displays the body-mounted 3D-tracking sensor 3135 equipped with a tracked DRF 3125 according to some embodiments. Some embodiments for the mounting mechanism of the 3D-tracking sensor 3135 to the body is via a head-mounted fastener with adjustable components 3110, 3105. In some embodiments, surgical areas that are typically obstructed from the line of sight of a large field-of-view camera can be visualized via the body-mounted, 3D-tracking optical sensor 3135. In some embodiments, since the body-mounted, optical sensor 3135 is equipped with a substantially rigidly-mounted tracked DRF 3125, the larger-field-of-view camera (not shown) can register the body-mounted, optical sensor's location and pose in 3D space, and with that information, interpret the scene visualized by the headset-mounted, 3D-tracking optical sensor 3135 to create a dynamic, 3D stitched mapping of the global coordinate system relative to the large field-of-view camera coordinate system. In some embodiments, the fusion of the coordinate systems of the body-mounted camera 3135 and the larger field-of-view camera (not shown) will be computed via a 3D rigid transform, which will be applied to 3D data collected by the body-mounted camera 3135 for all frames of its acquisition. Thus, in some embodiments, the computation of 3D positions and poses of objects of interest (e.g., 3D-trackable tools, DRFs, anatomical landmarks, fiducials, surgical accessories, other optical or electromagnetic sensors, etc.) within the field of view of the body-mounted camera 3135, which is being tracked by the larger field-of-view camera (not shown).

Figure 32:
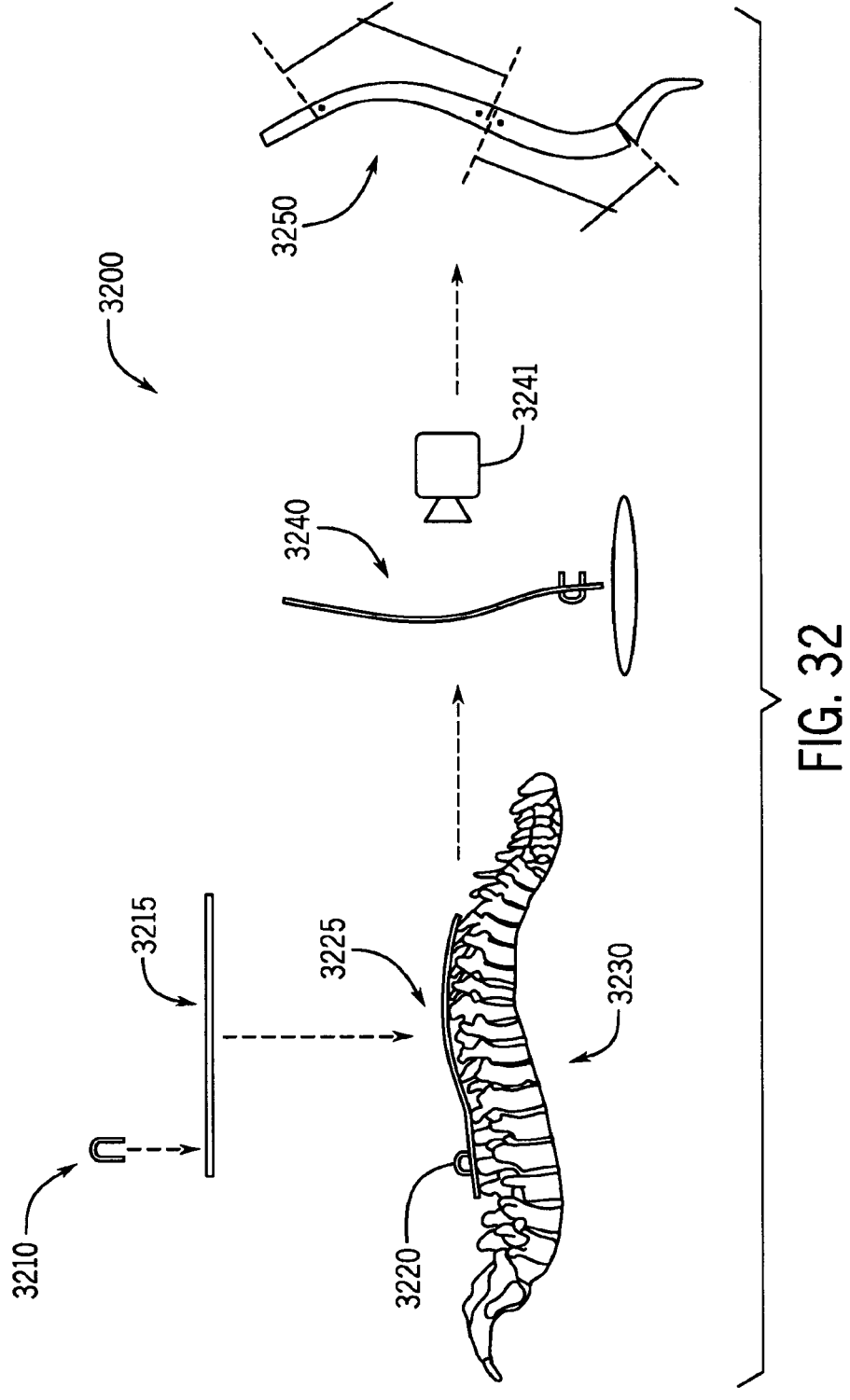
FIG. 32 displays a method of interpreting the contour of the posterior elements of the spine in accordance with some embodiments of the invention.

FIG. 32 displays a method of interpreting the contour of the posterior elements of the spine by placing a malleable object over the surgically-exposed bony elements such that it matches the contour of the exposed spine, and then the malleable object is removed and its contour registered with optical systems, including stereoscopic cameras, and from that information about the surface contour of the malleable object which now serves as a surrogate for the contour of the posterior elements of the spine, the spinal alignment parameters of the contour-matched spine can be calculated according to some embodiments. In some embodiments, other relevant other figures (relating to the calculation of spinal alignment parameters and the location of other anatomical landmarks of interest processed by software algorithms) include FIGS. 65A-65E, 66A-66B, and 68. FIG. 32 displays the system 3200 where a malleable rod 3215 that is placed over the surgically exposed elements of the spine 3230 with an adjustable clip 3210 to register a particular spinal level for software interpretation according to some embodiments. In some embodiments, after the rod 3215 is inserted into the surgical site, the malleable rod 3215 is conformed to match the contour 3225 of the exposed spinal elements, and one or more mounted clips 3220 are aligned along the rod 3215 with nearby anatomical landmarks of interest. In some embodiments, this malleable rod 3215 then undergoes topological registration 3240 by one or more imaging sensors 3241 to interpret the 3D contour of the rod 3215 that matches the contour 3225 of the spinal column 3230. In some embodiments, the 3D contour of the malleable rod 3215 is then processed by software algorithms described in detail below in reference to FIGS. 65A-E, 66A-B, and 68. In some embodiments, the optical registration system 3241 can be any optical system to register 3D surface contours including, but not limited to, one or more depth sensors, stereoscopic vision cameras, and structured light systems, with the rod fixed onto a stationary or movable platform base. In some embodiments, based on some embodiments for registering the 3D contour of the malleable rod 3215 using optical methods, and the associated clip 3210 that indicates spinal levels, the system can calculate the spinal alignment parameters 3250 of each anatomical plane of the rod 3215 an interpret the relative alignment and contour of the spine 3230.

Figures 33A, 33B, 33C, 33D, 33E, 33F, 33G, 33H, 33I:
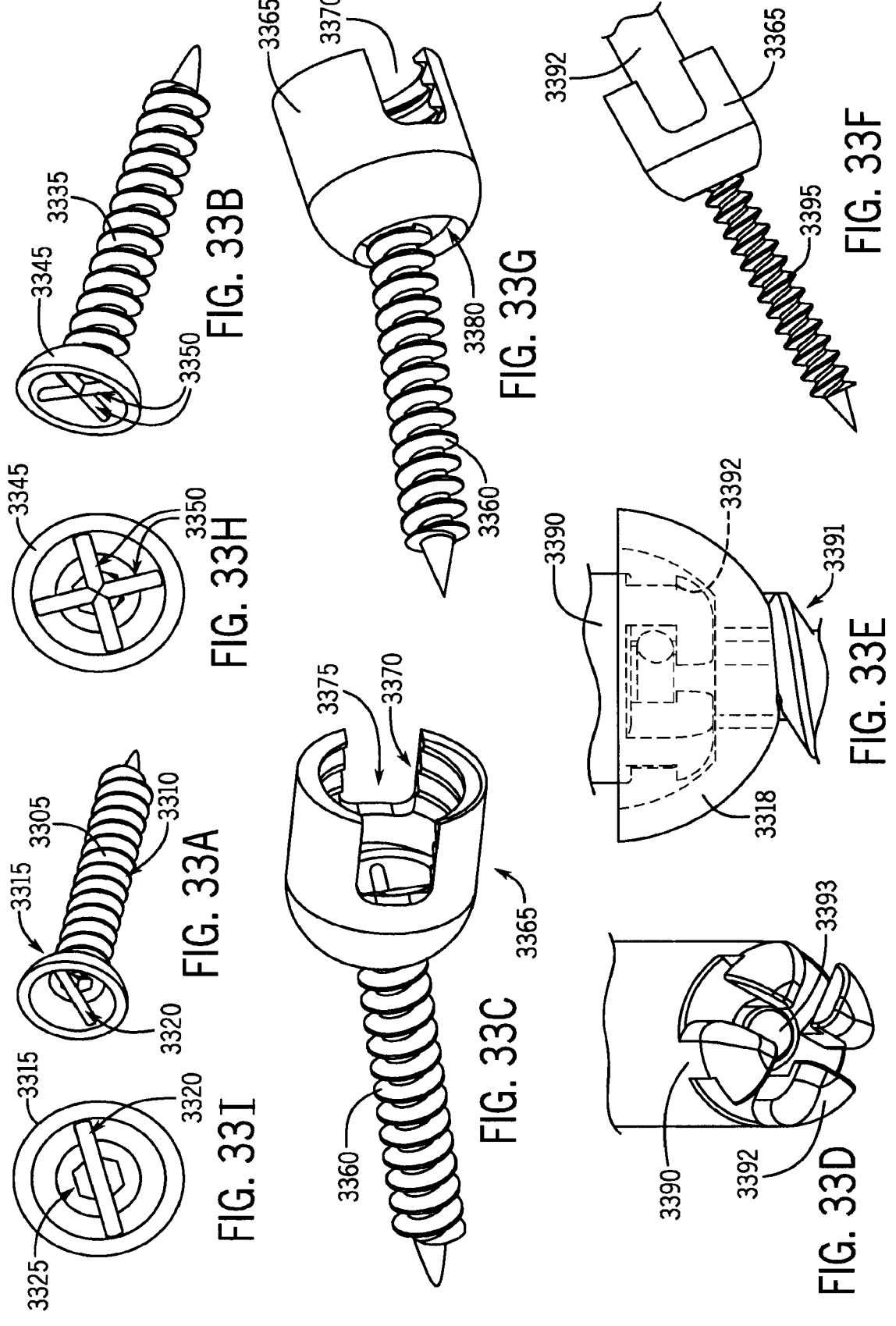
FIG. 33A illustrates pedicle screw in accordance with some embodiments of the invention.
FIG. 33B illustrates a pedicle screw in accordance with some embodiments of the invention.
FIG. 33C illustrates pedicle screw mated with a polyaxial tulip head in accordance with some embodiments of the invention.
FIG. 33D illustrates a tool designed to interface with the pedicle screw of FIG. 33B in accordance with some embodiments of the invention.
FIG. 33E illustrates a visualization of a couple between the tool of FIG. 33D and the screw of FIG. 33C in accordance with some embodiments of the invention.
FIG. 33F illustrates a screwdriver coupled to a pedicle screw in accordance with some embodiments of the invention.
FIG. 33G illustrates a top view of the screw of FIG. 33A in accordance with some embodiments of the invention.
FIG. 33H illustrates a top view of the screw of FIG. 33B in accordance with some embodiments of the invention.
FIG. 33I illustrates a top view of the screw of FIG. 33A in accordance with some embodiments of the invention.

Some embodiments of the invention seen in FIGS. 33A-33I, include a screw and screwdriver combination that allows for the ability to mechanically couple both devices such that the screwdriver becomes coaxial with the screw shaft, and also has the ability to then substantially rigidly manipulate the screw shaft, which if fixed in bone has the ability to then manipulate the associated bony structures. For example, FIG. 33A illustrates a pedicle screw design in accordance with some embodiments of the invention, and FIG. 33B illustrates a pedicle screw in accordance with some embodiments of the invention. Further, FIG. 33C illustrates a pedicle screw mated with a polyaxial tulip head in accordance with some embodiments of the invention, and FIG. 33D illustrates a tool designed to interface with the pedicle screw of FIG. 33B in accordance with some embodiments of the invention. FIG. 33E illustrates a visualization of a couple between the tool of FIG. 33D, and the screw of FIG. 33C in accordance with some embodiments of the invention. Further, FIG. 33F illustrates the coupling tool, depicted in FIG. 33D, coupled to a pedicle screw, as seen in FIG. 33C, in accordance with some embodiments of the invention, FIG. 33G illustrates a top view of the screw of FIG. 33A in accordance with some embodiments of the invention, and FIG. 33H illustrates a top view of the screw of FIG. 33B in accordance with some embodiments of the invention. As shown, some embodiments include an Allen key inset 3325, rigid single crossbar 3320, coupled threaded shaft 3305, and a curved screw head 3315. FIG. 33A and FIG. 33I displays some embodiments of a screw that consists of an Allen key inset 3325, a rigid crossbar 3320 that spans across the sidewalls of the screw head 3315 but allows for a gap above the inset, a threaded shaft 3305 and a curved screw head 3315 to accommodate mating with a tulip head (seen in FIG. 33C as label 3365) according to some embodiments. FIG. 33B displays some embodiments of the screw described in detail above in relation to FIG. 33A. Some embodiments displays the screw head 3345 with two intersecting crossbars 3350, to enable interfacing with a different tool depicted in FIG. 33D. It should be noted that the examples of screws portrayed in these figures only represent some embodiments of the invention. In some embodiments, the crossbars 3350 can be of varying contour, number, and relative arrangement for each screw head. FIG. 33C displays an some embodiments of the screw described previously in relation to FIG. 33B mated with a polyaxial tulip head 3365 with a cutout 3375 to interface with a rod, and a thread 3370 to receive a tightening cap according to some embodiments.

FIG. 33D displays some embodiments of a tool designed to interface with the screw previously described in detail in relation to FIG. 33B. In some embodiments, this tool consists of four mechanically-coupling extensions 3390 designed to engage with the screw head cross-bars via a quarter-turn mechanism. In some embodiments, after performing a quarter-turn, the tool becomes substantially rigidly fixed to a screw head and shaft, as depicted in FIG. 33B. In some embodiments, the end of the center shaft of the screw has a depressible sliding shaft 3393 that can be coupled to a TMSM (not shown) to indicate full engagement of the tool 3390 and screw, as depicted in FIG. 33B, in a communication method previously described in detail in relation to FIGS. 10A-10E and FIGS. 29A-29C. In some embodiments, it should be noted that the center of the tip 3393 of this tool can also consist of a threaded shaft that is tightened down at the top segment (not shown) of the tool 3390 to push a sliding rod against the rigid cross bars of the screw head. In some embodiments, in this way, the tool has increased fixation strength at the screw head interface. In some embodiments, this threaded middle shaft can also be attached to a TMSM (not shown) to indicate its position relative to a tracked DRF (not shown) mounted to the screwdriver. Further, in some embodiments, FIG. 33E displays a transparency view of the interface between the screw head, its crossbars, and the screwdriver coupling end effector, previously discussed in relation to FIGS. 33A-33I. From this view, in some embodiments, the threaded screw shaft 3391, curved screw head walls 3318, and the mechanically-coupling extensions 3390 of the tool are visible as the two tools engage with one another. Further, in some embodiments, unlike FIG. 33E, FIG. 33F displays a different perspective of the screwdriver (3392) and crossbar-equipped screw 3395 interfacing with one another. From this perspective, in some embodiments, the coaxial alignment of the screwdriver shaft with the screw shaft is appreciable. FIG. 33G displays an underside view of the cross-bar-equipped screw previously described in relation to FIG. 33B and this view highlights the circular cutout 3380 of the tulip head interfacing with the curved walls of the screw head (3318, 3345; not shown) according to some embodiments.

Some embodiments include a tool or assembly to interface directly with the tulip heads of pedicle screws, in such a way that it substantially rigidly fixes the rotating tulip head relative to the pedicle screw shaft, to then enable measurement and manipulation devices to act on the coupled spinal elements to aid with alignment measurements and fixation as will be described in more detail below in reference to FIGS. 39A-39F, and 42A-42K.

Figures 34, 34A, 34B, 34C, 34D, 34E, 34F:
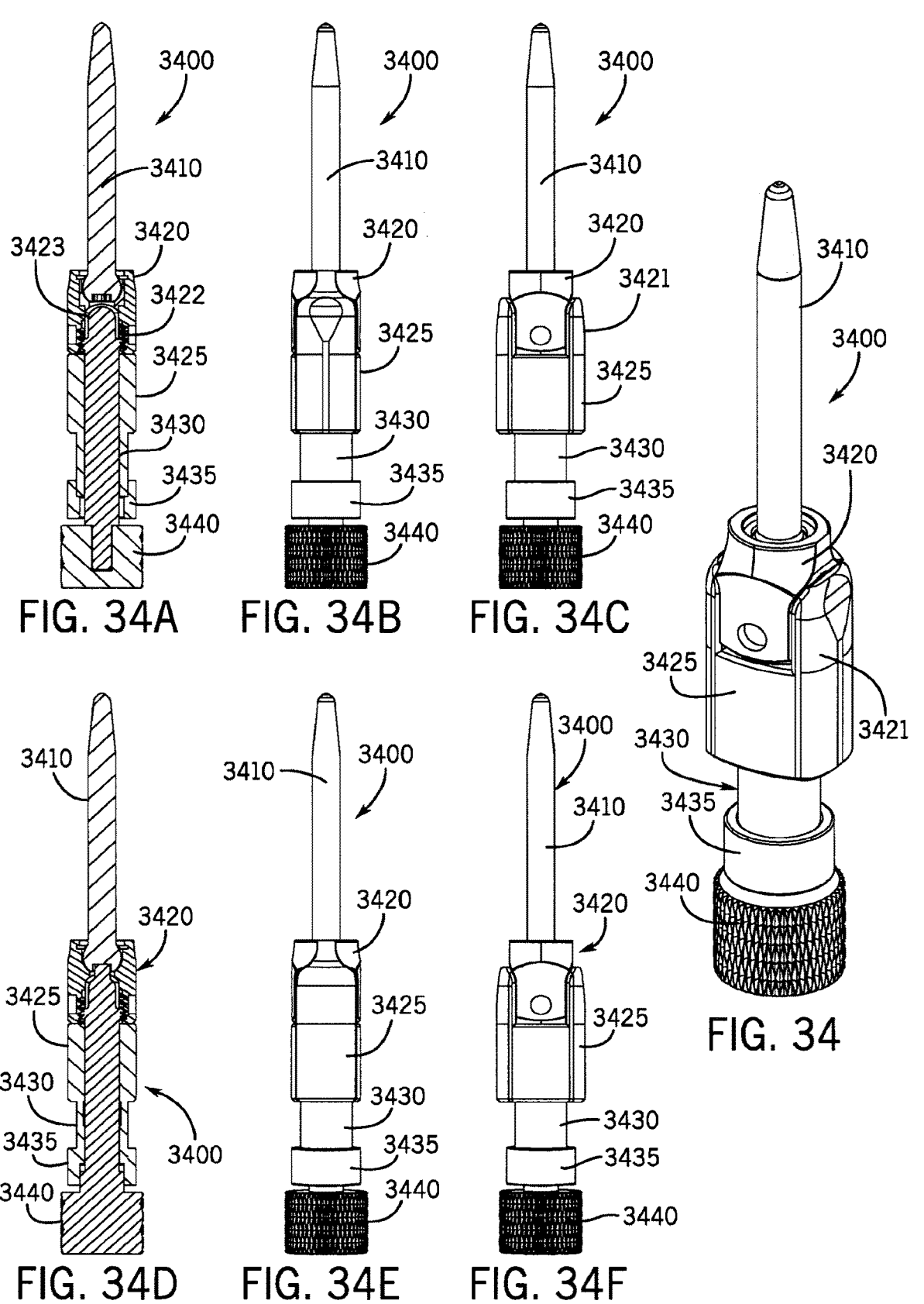
FIG. 34 illustrates a tool for interfacing with a pedicle screw accordance with some embodiments of the invention.
FIGS. 34A-34F illustrate various views of the tool of FIG. 34 in accordance with some embodiments of the invention.

FIG. 34 illustrates a tool for interfacing with a pedicle screw accordance with some embodiments of the invention. FIG. 34A displays a cross-sectional view interfacing directly with the threaded inserts of the tulip heads of pedicle screws according to some embodiments. In some embodiments, this figure displays a pedicle screw shaft 3410 (threading not shown), its associated tulip head 3420, the interfacing device's thread-tightening knob 3440, its sleeve body 3425, device body connection 3430, protruding tip 3423 to substantially rigidly push towards the screw head, and inner shaft threading 3422 of the device. In some embodiments, tightening of the device through the thread-tightening knob 3440 leads the inner shaft threading 3422 to interface directly with the tulip head threads to cause the protruding tip 3423 to push against the screw head. In some embodiments, tightening in this way provides a rigid connection between the device, tulip head, and pedicle screw, such that the motion of the polyaxial tulip head has been restricted and all three parts coupled to one another. In some embodiments, the device body connection 3430 displayed in this figure is designed to interface with a larger tool that will be described in more detail below in reference to FIGS. 39A-39D, 40A-40C, 41C, 42A42-F. Some embodiments include but are not limited to cylindrical extrusion, spherical tip, and a non-rigid cylindrical extrusion coaxial or perpendicular to the inner shaft and coupled via rivet or other mechanism that enables its rotation about the axis of the inner shaft according to some embodiments.

FIGS. 34B-34C display a non-cross-sectional, side view of the device described in relation to FIG. 34 interfacing with a pedicle screw according to some embodiments. In some embodiments, visible are side-tab extensions 3421 that extend over the tulip head cutouts. In some embodiments, these side tabs extensions provide additional rigid interfacing between the device and the tulip head of the screw, further helping to substantially rigidly fix the device, tulip head, and screw to one another.

FIG. 34D displays a cross-sectional view of the device described in relation to FIG. 34A interfacing with a pedicle screw according to some embodiments. FIG. 34E displays a non-cross-sectional, rendered side view of the device described in relation to FIG. 34A interfacing with a pedicle screw according to some embodiments. FIG. 34F displays a non-cross-sectional, rendered front view of the device described in relation to FIG. 34A interfacing with a pedicle screw according to some embodiments.

FIGS. 35A-35F display an assembly or tool 3500 designed to interface directly with the tulip heads of pedicle screws, in such a way that it substantially rigidly fixes the rotating tulip head relative to the pedicle screw shaft, to then enable measurement and manipulation devices to act on the spinal elements to aid with alignment measurements and fixation as will be described in more detail below in reference to FIGS. 39A-39F, and 42A-42K according to some embodiments. As shown, in some embodiments, the tool 3500 comprises pedicle screw shaft 3510, tulip head 3503, drafted shaft advancement knob 3540, sleeve body 3525, device body connection 3530, protruding tip 3504, outer shaft threading 3535, protruding-tip advancement knob 3545, drafted pin 3546, retaining ring 3502, and expanding teeth 3527. In some embodiments, in operations, after interfacing directly with the tulip head 3503, the drafted pin advancement knob 3540 leads the outer shaft threading 3535 to drive the expansion of the expanding teeth 3527 to interface directly with the tulip head threads. In some embodiments, the retaining ring 3502 limits expansion of the device to prevent over stress, and the protruding tip advancement knob 3545 can then be tightened to increase the tension on the expanded teeth with the tulip head threads and thereby substantially rigidly fix the device, tulip head, and screw shaft together. In some embodiments, the device body connection 3530 displayed in this figure is designed to interface with a larger tool that will be described in more detail below in reference to FIGS. 39A-39F, and 42A-42K.

Figures 35A, 35B, 35C, 35D, 35E, 35F:
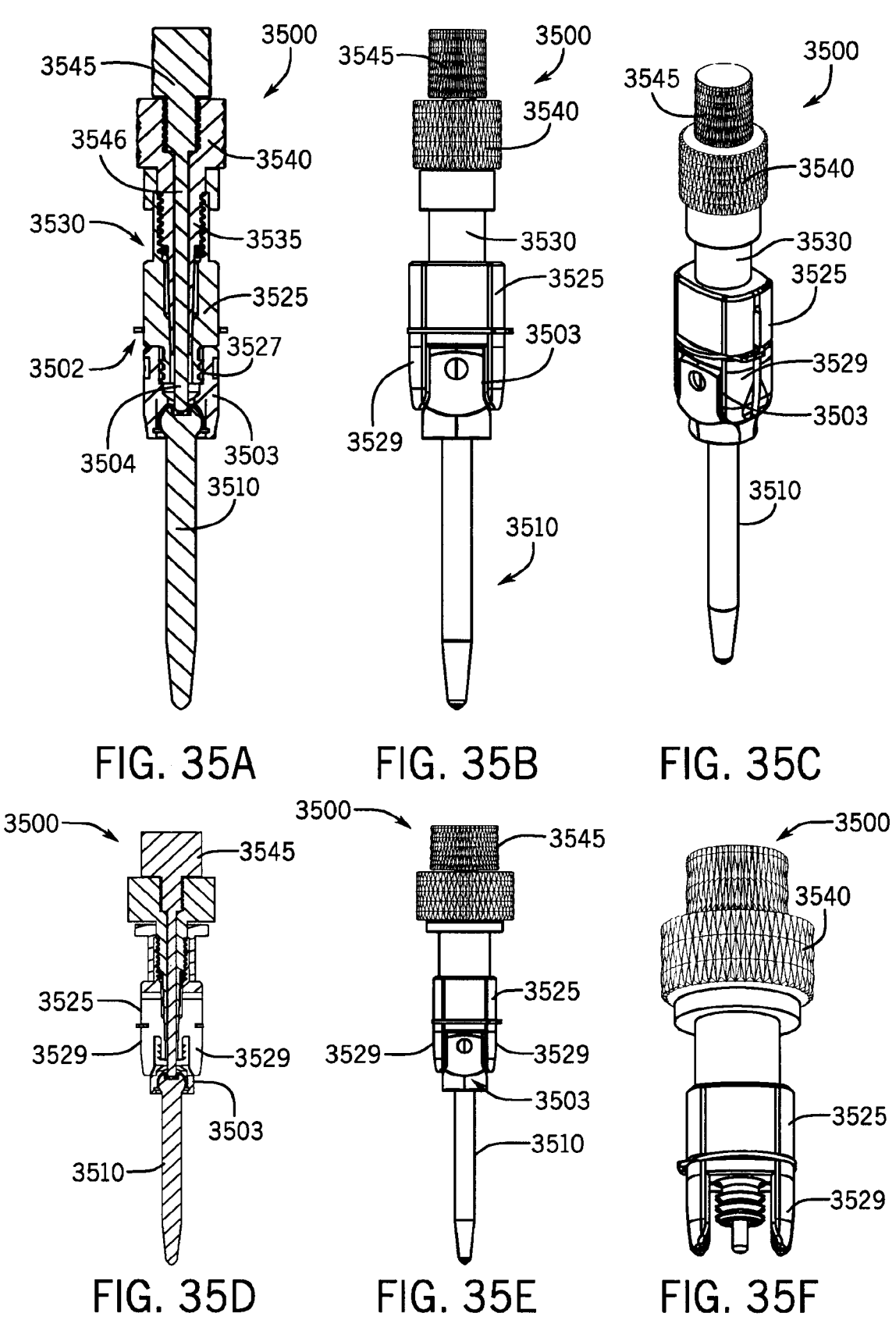
FIGS. 35A-35E illustrate various views of a tool for interfacing with a pedicle screw in accordance with some embodiments of the invention.
FIG. 35F illustrates a close-up perspective view of the tool of FIGS. 35A-35E without a coupled pedicle screw or tulip head in accordance with some embodiments of the invention.

FIG. 35B displays a non-cross-sectional, front view of the device described in relation to FIG. 35A interfacing with a pedicle screw according to some embodiments. Visible in this figure are side-tab extensions 3529 that extend over the tulip head cutouts according to some embodiments. In some embodiments, these side tabs provide additional rigid interfacing between the device and the tulip head of the screw, further helping to substantially rigidly fix the device, tulip head, and screw to one another. FIG. 35C displays a non-cross-sectional, perspective view of the device described in relation to FIG. 35A interfacing with a pedicle screw according to some embodiments. FIG. 35D displays a cross-sectional, rendered view of the device described in relation to FIG. 35A interfacing with a pedicle screw according to some embodiments. FIG. 35E displays a non-cross-sectional, rendered front view of the device described in relation to FIG. 35A interfacing with a pedicle screw according to some embodiments. FIG. 35F illustrates a close-up perspective view of the tool of FIGS. 35A-35E without a coupled pedicle screw or tulip head in accordance with some embodiments of the invention. FIG. 35F displays a non-cross-sectional, rendered front view of the device described in relation to FIG. 35A without the interfacing pedicle screw and tulip head according to some embodiments. In this view, the expanding teeth and side tab extensions are more clearly visual according to some embodiments.

Some further embodiments of the invention include a tool or assembly able to interface directly with the tulip heads of pedicle screws via a quarter-turn mechanism, in such a way that it substantially rigidly fixes the rotating tulip head relative to the pedicle screw shaft, to then enable measurement and manipulation devices to act on the spinal elements to aid with alignment measurements and fixation as will be described in more detail below in reference to FIGS. 39A-39F, and 42A-42K. For example, in some embodiments, FIG. 36A displays a cross-sectional view of an invention for interfacing directly with the threaded inserts of the tulip heads of pedicle screws via a quarter-turn mechanism. In some embodiments, this figure displays a pedicle screw shaft 3610 (threading not shown), its associated tulip head 3620, the quarter-turn knob 3635, its sleeve body 3640, device body connection 3645, protruding tip 3650 to substantially rigidly push towards the screw head, protruding tip advancement knob 3637, side-tab extensions 3695, and quarter-turn retainer 3699. In some embodiments, after inserting the device into the tulip head such that the threads are not engaged, the quarter-turn knob is rotated 90 degrees to engage the quarter-turn threads with the threads of the tulip head. In some embodiments, after rotating 90 degrees, the quarter-turn retainer prevents excess rotation, to ensure the threading is engaged prior to increasing tension on the threads via tightening the protruding tip advancement knob. In some embodiments, by tightening the protruding tip advancement knob, the protruding tip is driven directly against the head of the screw and increasing tension on the quarter-turn threads, thereby removing tolerance from thy polyaxial tulip head. In this way, in some embodiments, this device substantially rigidly fixes the tulip head and screw shaft together. In some embodiments, the device body connection 3645 displayed in this figure is designed to interface with a larger tool that will be described in more detail below in reference to FIGS. 39A-39F, and 42A-42K.

Figures 36A, 36B, 36C, 36D, 36E, 36F, 36G, 36H, 36I:
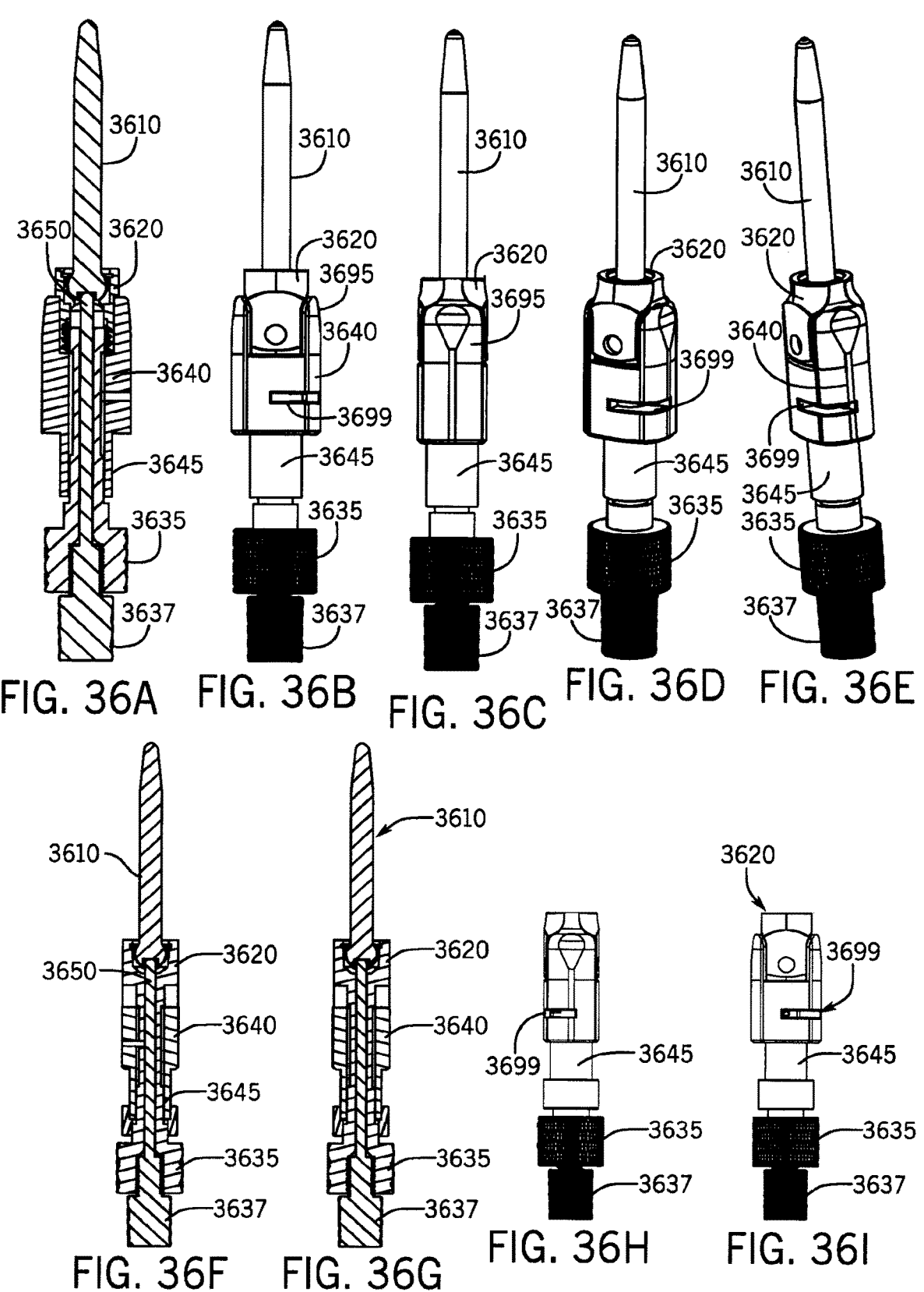
FIGS. 36A-36G illustrate a tool designed to interface directly with tulip heads of pedicle screws in accordance with some embodiments of the invention.
FIGS. 36H-36I illustrate perspective views of the tool of FIGS. 36A-36G without pedicle screw shaft in accordance with some embodiments of the invention.

FIG. 36B displays a non-cross-sectional, front view of the device described in relation to FIG. 36A interfacing with a pedicle screw according to some embodiments. More clearly visible in this figure are side-tab extensions 3695, previously described in detail in relation to FIG. 35B according to some embodiments. Also, more clearly visualized in this figure is the quarter-turn retainer 3699, previously described in detail in relation to FIG. 36A according to some embodiments. Further, FIG. 36C displays a side view of the device described in relation to FIG. 36A interfacing with a pedicle screw, and FIG. 36D displays a non-cross-sectional, perspective view of the device described in relation to FIG. 36A interfacing with a pedicle screw according to some embodiments. FIG. 36E displays a non-cross-sectional, perspective view of the device described in relation to FIG. 36A interfacing with a pedicle screw, and FIG. 36F displays a cross-sectional, rendered view of the device described in relation to FIG. 36A interfacing with a pedicle screw according to some embodiments. In some embodiments, this figure displays the quarter-turn threads engaged with the tulip head threads. FIG. 36G displays a cross-sectional, rendered view of the device described in relation to FIG. 36A interfacing with a pedicle screw according to some embodiments. In some embodiments, this figure displays the quarter-turn threads disengaged from the tulip head threads. FIG. 36H displays a non-cross-sectional, rendered side view of the device described in relation to FIG. 36A interfacing with a tulip head (pedicle screw shaft not shown) according to some embodiments. FIG. 36I displays a non-cross-sectional, rendered front view of the device described in relation to FIG. 36A interfacing with a tulip head (pedicle screw shaft not shown) according to some embodiments.

Some embodiments of the invention include a device for interfacing directly with two implanted pedicle screws in such a way that it substantially rigidly connects to the tulip head and removes tolerance between a polyaxial tulip head and pedicle screw such that the device is mechanically linked to a vertebra or other bony anatomy in which the screw(s) is/are inserted. For clarity, in some embodiments, FIGS. 37A-37G do not include a tracked DRF and triggering mechanism, although they can be attached to this device to allow it to provide quantitative data to the user while manipulating or holding the spinal elements, as will be described in more detail in reference to FIGS. 39A-39F, and 42A-42K. In some embodiments, the invention comprising the assemblies of FIGS. 37A-37G may include various coupled components including a tightening knob 3740, handle 3705, width-adjustment mechanism 3707, guide rail (×2) 3723, tulip head side rests 3727, spring mechanism 3728 for fastening protrusions, tensioning lever 3732 that presses up against internal spring (not shown) when device is actively clamped, footplate 3710, and/or clamp release lever 3750. For example, FIG. 37A displays a front view of the invention designed to substantially rigidly interface two screws already implanted into the spine or other bony elements according to some embodiments. In some embodiments, this embodiment is equipped with a tightening knob 3740, handle 3705, width-adjustment mechanism 3707, two guide rails 3723, tulip head rests 3727 to approximate the sidewall of the tulip heads, footplates 3710 to slide under the tulip head, and a clamp release lever 3750. In some embodiments, not shown (for clarity purposes) are tracked DRF, and tracked stray markers that can be applied to the device to make assessments of the tool's position and motion during use, as described in detail below in reference to FIGS. 39A-39F, and 42A-42K. Further, FIG. 37B displays a rear view of some embodiments of the invention previously described in FIG. 37A. Visible from this perspective is the width-adjustment knob 3709, used to adjust the distance between the handle and the tulip head side rests according to some embodiments. In some embodiments, this viewpoint also provides the front perspective of the width-adjustment mechanism that enables the tulip head side rests to be drawn closer to or farther away from one another. Further, some embodiments include a screw-head interface protrusion 3760, and clamp 3749. For example, FIG. 37C displays a perspective view of the invention previously described in FIG. 37A in the closed position according to some embodiments. Visible from this perspective is the screw-head interface protrusions 3760, the clamp 3749 used to securely fasten the device to the pedicle screws, and footplate 3710 to slide underneath the tulip head according to some embodiments. In some embodiments, this viewpoint displays a better view point of the guide rails 3723, which connects the handle and screw-interfacing arms. Further, FIG. 37E displays a rendered oblique side view of the invention previously described in FIG. 37A in the open position, and FIG. 37D displays a side perspective view of the invention previously described in FIG. 37A in the closed position according to some embodiments. Visible from this perspective is the spring 3728 and over center spring structure 3732 in its collapsed position according to some embodiments.

Figures 37A, 37B, 37C, 37D, 37E, 37F, 37G:
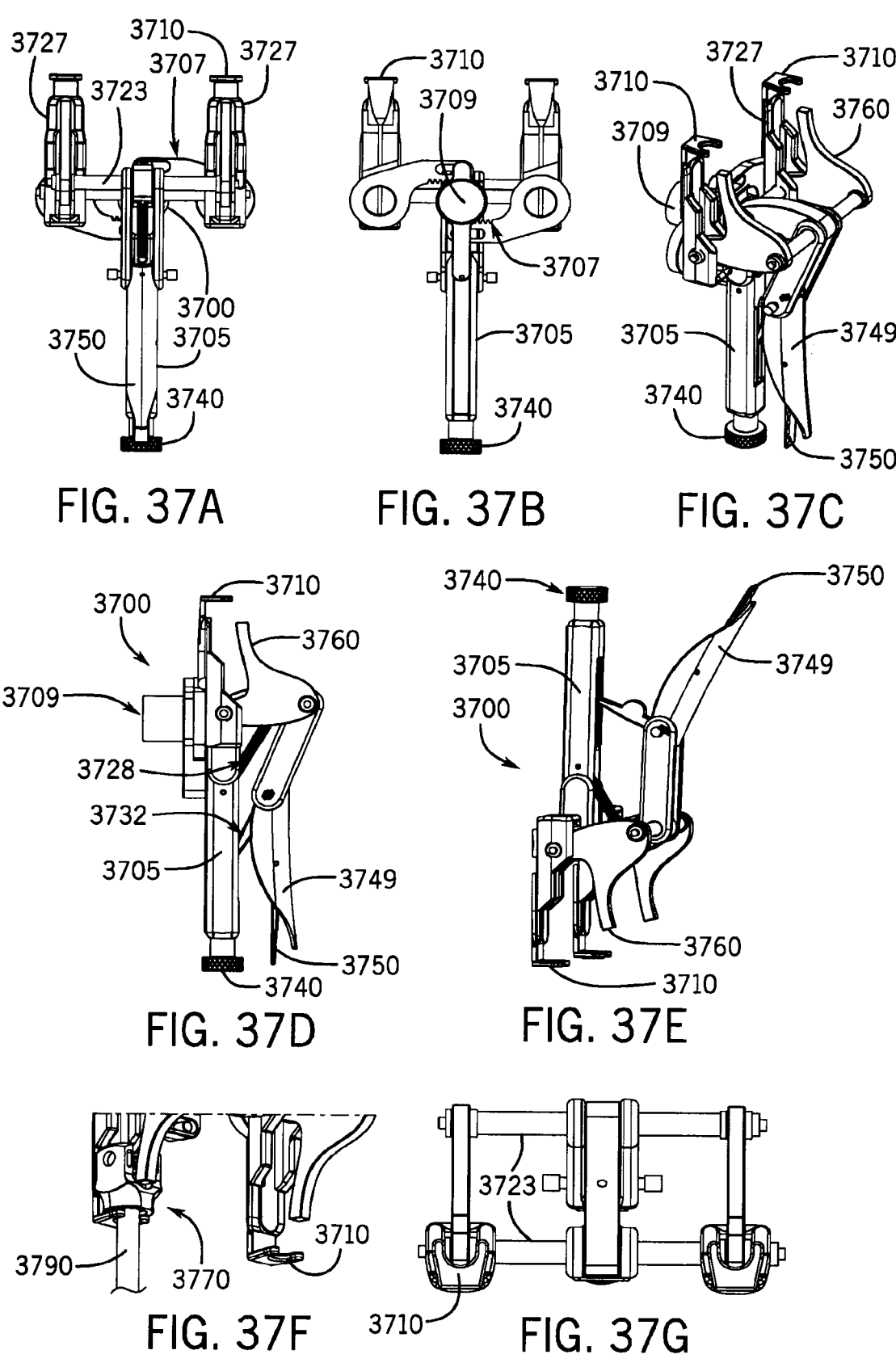
FIGS. 37A-37G illustrate various views of a tool for interfacing directly with two implanted pedicle screws in accordance with some embodiments of the invention.

FIG. 37F displays a rendered oblique side view of the invention previously described in FIG. 37A in the closed position with detailed view of the device interfacing on one side with a tulip head 3770 attached to a pedicle screw shaft 3790 (threads not shown) according to some embodiments. From this perspective, the screw-head interface protrusion is seen engaging with the screw, and by tightly driving the screw head down while the footplate is pulling the tulip head upwards, the tolerance between a polyaxial tulip head and pedicle screw shaft is reduced, resulting in rigid fixation between the three structures according to some embodiments. It should be noted that the design and geometry of the screw-head interface protrusion can have a cylindrical extrusion, spherical head, and a pivoting lever arm according to some embodiments.

FIG. 37G displays a rendered bottom view of the invention previously described in FIG. 37A according to some embodiments. This perspective does not include the width-adjustment mechanism, to aid in visibility of the guide rails, and their cutout groove to enable applying a torque between the tulip head side rests and the screw-head interface protrusion according to some embodiments. It should be noted that because the width-adjustment mechanism is not shown in this figure, the handle is not centered between the two screw head interfacing components of the device according to some embodiments. In some embodiments of this device previously described, the width-selector mechanism ensures that the handle remains centered between the screw head interfacing components.

Figures 38, 38A, 38B, 38C, 38D, 38E, 38F, 38G:
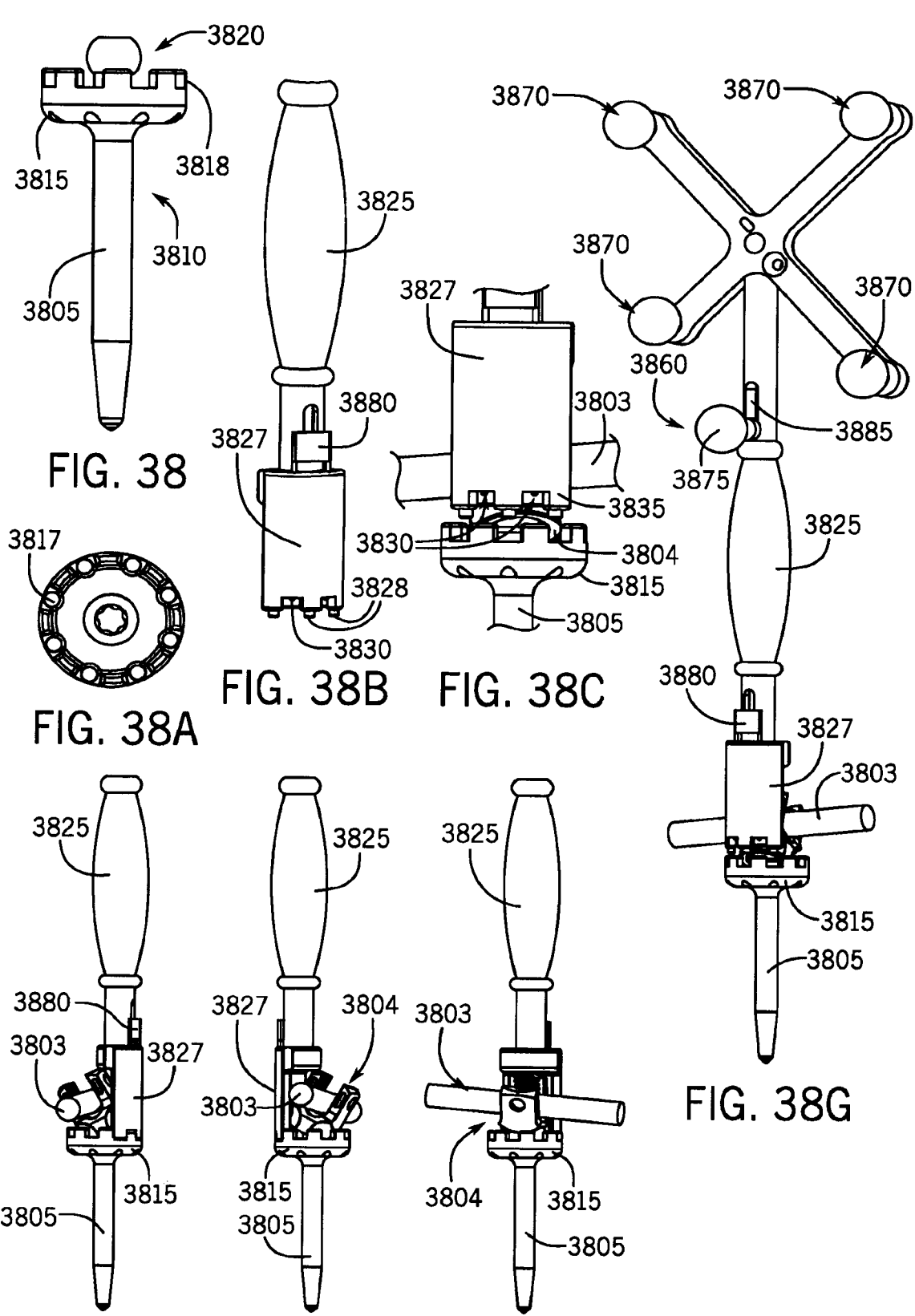
FIG. 38 illustrates a pedicle screw shaft with depth-stop in accordance with some embodiments of the invention.
FIG. 38A illustrates a top view of the pedicle screw shaft with depth-stop of FIG. 38 in accordance with some embodiments of the invention.
FIG. 38B illustrates a screw interface region with coupled handle in accordance with some embodiments of the invention.
FIG. 38C illustrates an example assembly view coupling between the screw interface region of FIG. 38B and the pedicle screw shaft with depth-stop of FIGS. 38-38A in accordance with some embodiments of the invention.
FIGS. 38D-38G illustrates view of the screw interface region of FIG. 38B coupled with the pedicle screw shaft with depth-stop of FIGS. 38-38A in accordance with some embodiments of the invention.

In reference to FIG. 38, and FIGS. 38A-38G, some embodiments include FIG. 38 include a pedicle screw shaft (represented without threads) with depth-stop in accordance with some embodiments of the invention. Some embodiments enable assessment of the screw shaft location and pose when equipped with a polyaxial tulip head and with or without the presence of an already-implanted rod seated into the tulip head. In some embodiments, the first aspect of the embodiment is a screw designed with a depth-stop ring substantially rigidly attached to the screw shaft at a location beneath the tulip head that still enables full mobility of the attached polyaxial tulip head. In some embodiments, the depth-stop possesses a particular pattern that will interface with the second aspect of the embodiment, a tracked depth-stop assessment tool, in such a way that it allows for the interpretation of the screw shaft location and pose in 3D space, as well as indicate when the assessment tool is fully seated in the depth-stop, to ensure assessment of the screw shaft location is only made when the tool is properly engaged. In some embodiments, the indication method shown is via actuation of a TMSM, as previously described in detail in relation to FIGS. 10A-10G, 14A-14C, and 29A-29C, but can also be achieved by other methods including, but not limited to, hand actuation of a TMSM, covering or uncovering of a tracked stray marker, and electronic communication.

FIG. 38A illustrates a top view of the pedicle screw shaft with depth-stop of FIG. 38 in accordance with some embodiments of the invention. For example, some embodiments include a pedicle screw with a shaft 3810 (threads not shown), a depth-stop 3815 substantially rigidly attached to the screw shaft 3805 and designed with a depth-stop mating pattern 3818, depth-stop mating holes 3817, as well as an interface for a polyaxial tulip head (not shown). In some embodiments, the depth-stop distance from the tulip head interface 3820 is designed to stop the screw against bony anatomy such that the polyaxial head maintains full mobility about its ball joint on the screw. In some embodiments, the depth-stop as shown can be circular but can be designed to be of many shapes including interrupted and partial shapes to allow for better fitting within tight anatomical areas. In some embodiments, the mating pattern 3818 and mating holes on the depth-stop 3815 are designed such that an assessment tool, described in detail below in relation to FIGS. 38B-38G, is able to interface with the depth-stop-screw device 3810 and interpret the screw shaft location and pose, irrespective of the position of the tulip head relative to the screw.

FIG. 38B illustrates a screw interface region with coupled handle, with a partial view of an assessment tool designed to mate with the screw previously described in detail in relation to FIG. 38A according to some embodiments. In some embodiments, the tool consists of a handle 3825, partial-cylinder screw interface region 3827, mating protrusions 3828, and spring-loaded (not shown) mating pins 3829. Further, in some embodiments, FIG. 38C illustrates an example assembly view coupling between the screw interface region of FIG. 38B and the pedicle screw shaft with depth-stop of FIGS. 38-38A in accordance with some embodiments of the invention, and FIG. 38C displays the closer perspective of the screw, described previously in relation to FIG. 38A with the assessment tool, described previously in relation to FIG. 38B, aligned and ready to engage with the mating depth-stop. In this image, the tulip head 3804 is visible attached to the top of the screw and an implanted rod 3803 is displayed engaged within the tulip head. In the position displayed, the assessment tool is not engaged with the rigid depth-stop and therefore the mating pins are not depressed according to some embodiments. It is not until the assessment device fully is seated into the depth-stop that the spring-loaded mating pins are depressed and an associated tracked mobile stray marker (not shown) can be actuated to communication to the acquisition system according to some embodiments.

Some further embodiments involve a combination of staggered heights and shapes of the depth-stop protrusions providing several unique permutations of height changes of TMSM linked to the probe. In some embodiments, this could involve two or more TMSMs on the probe. In some embodiments, the depth-stop design can be comprised of a radially-repeating pattern of two or more unique depth heights. In some embodiments, this unique combination of heights, which is also sensitive to direction/order of height changes will interact with two or more mating pins 3830 of the probe and those will interact with one or more TMSMs 3875 that are subsequently actuated to specific heights along the probe shaft, each height signaling a unique screw identity or anatomical identity. In some embodiments, instead of two TMSMs, the two mating pins that get engaged at different depth-stops can add up their depth differences mechanically against one lever that subsequently actuates a single TMSM to unique, identifiable height along the probe shaft.

FIG. 38D displays a front view of the screw, described previously in relation to FIG. 38A with the assessment tool, described previously in relation to FIG. 38B, aligned and fully engaged with the mating pattern on the depth-stop according to some embodiments. From this view it is apparent that the partial-cylinder screw-interface region 3827 allows for engagement of the assessment device with the screw, regardless of the position of the polyaxial tulip head 3804 and/or attached rod 3803 according to some embodiments. FIG. 38E displays a rear view of the screw, described previously in relation to FIG. 38A with the assessment tool, described previously in relation to FIG. 38B, aligned and fully engaged with the mating pattern on the depth-stop according to some embodiments. FIG. 38F displays a side view of the screw, described previously in relation to FIG. 38A with the assessment tool, described previously in relation to FIG. 38B, aligned and fully engaged with the mating pattern on the depth-stop according to some embodiments.

FIG. 38G displays a perspective view of the screw, described previously in relation to FIG. 38A with the full assessment tool, described previously in relation to FIG. 38B, aligned but unengaged with the depth-stop of the screw according to some embodiments. Visible in this figure is the tracked DRF 3870 attached to the tool handle 3825 for a 3D-tracking camera (not shown) to acquire the 3D location and pose of the assessment tool, a TMSM 3875 and a groove 3885 for the sliding shaft 3880 coupled to the mating pins to slide up and down to actuate the TMSM 3875 according to some embodiments. Some embodiments for the linear actuation mechanism for the mating pin depressible shaft 3880 coupled to the TMSM 3875 is a slot 3885 for the TMSM 3875 above, below, and/or near the handle 3825. It should be noted that the location of the TMSM can be positioned anywhere on body of the tool and actuation related to the mating pins 3880 can be achieved via linear motion (as shown), rotational motion, or a combination thereof according to some embodiments. It should also be noted that some embodiments of the device can contain more than one TMSMs, paired to individual spring-loaded mating pins to indicate tool engagement with the screw or to communicate other states to the acquisition system according to some embodiments. In some embodiments, the assessment tool is firmly engaged with the screw depth-stop mating pattern 3815, signaling to the acquisition system to calculate the 3D location and pose of the screw based on the screw's known geometry and the known mating geometry of the tool-screw combination.

Some embodiments of the invention include a device that can be used to assess the intraoperative flexibility of the spine with one or more mountings to substantially rigidly interface with implanted pedicle screws, (as previously described in relation to FIGS. 33A-33H, FIG. 34, FIGS. 35A-35F, and FIGS. 36A-36I). In some embodiments, after substantially rigidly fixing two tools, each to individual spinal levels, the spine can be manipulated via directly pushing on body surfaces or indirectly by interacting with the tool's handles to establish a range of motion between the spinal levels onto which the tools are engaged. In some embodiments, the range of motion can be displayed to the user on a display monitor via a 3D view or 2D projections onto relevant anatomical planes, as described in more detail below in reference to FIG. 70. Furthermore, in some embodiments, after adjusting two or more spinal levels to a desired relative orientation using this tool, some embodiments will be described in which the tools can lock together to temporarily hold the anatomy in that configuration prior to the insertion of a rod, as will be described in more detail in reference to FIGS. 42A-42K.

Figures 39A, 39B, 39C, 39D, 39E, 39F:
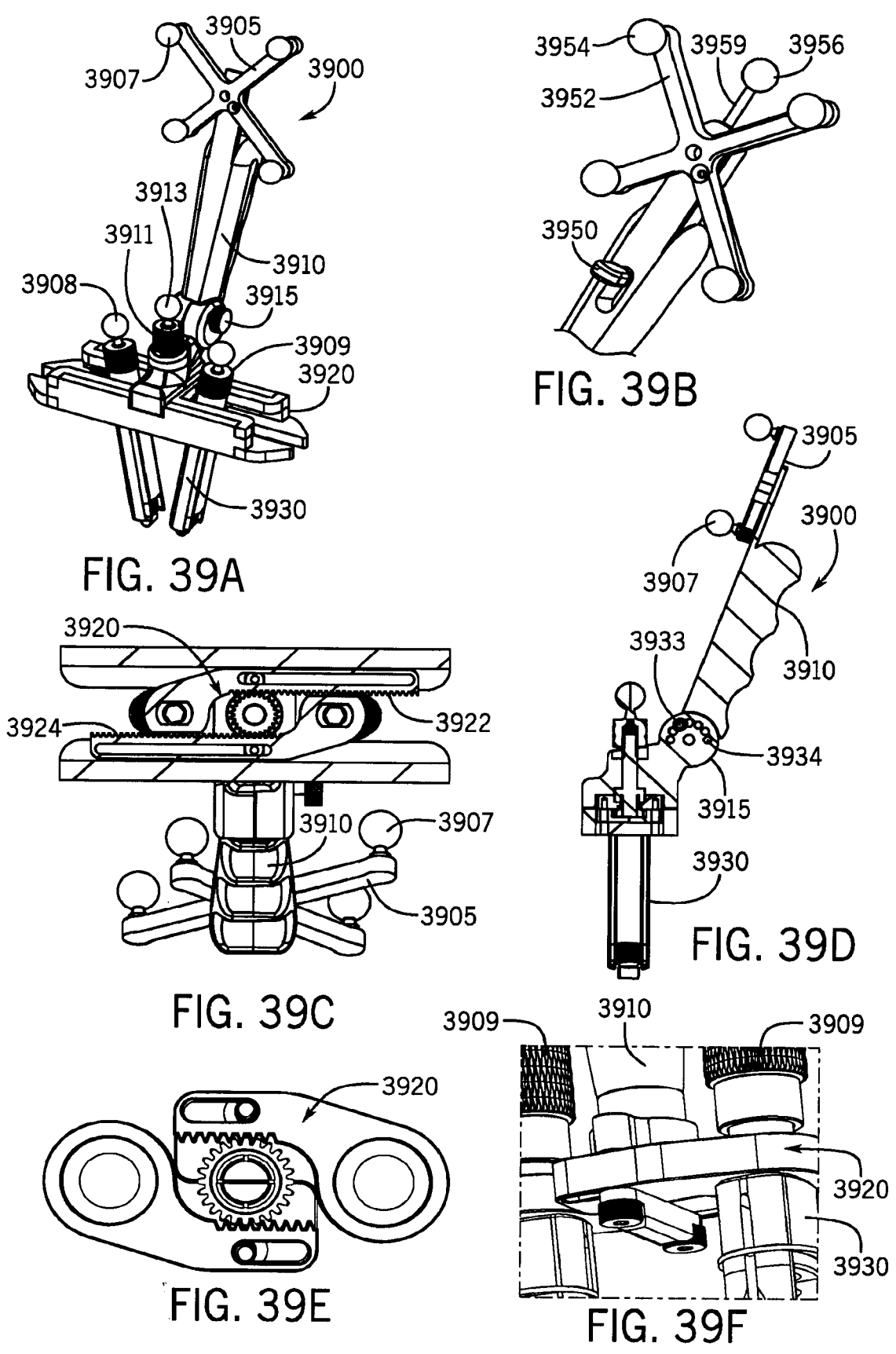
FIG. 39A illustrates a full perspective view of a device used for manipulating bony anatomy and assessing range of motion intraoperatively in accordance with some embodiments of the invention.
FIG. 39B illustrates some embodiments of the handle of the tool described previously in relation to FIG. 39A in accordance with some embodiments of the invention.
FIG. 39C illustrates a bottom view of the embodiment described above in relation to FIGS. 39A-B in accordance with some embodiments of the invention.
FIG. 39D displays a cross-sectional side view of the tool as described previously in relation to FIGS. 39A-39C in accordance with some embodiments of the invention.
FIG. 39E illustrates a bottom view of a width-adjustment mechanism that allows for variation in the distance between screw-interface locations of the tool in accordance with some embodiments of the invention.
FIG. 39F illustrates a close-up perspective of the width-adjustment mechanism, thread-tightening knobs, and sleeve body of the device as described above in relation to FIGS. 39A-E in accordance with some embodiments of the invention.

FIG. 39A displays a full perspective view of a device 3900 used for manipulating bony anatomy and assessing range of motion intraoperatively according to some embodiments. In some embodiments, two devices 3900 can be used at once, such that each securely fasten onto a level of the spine and move each level relative to one another while being tracked in 3D space to assess the achievable ranges of alignment between the two or more spinal segments with coupled devices. Some embodiments of the device consists of a tracked DRF 3905 (with markers 3907) for a 3D-tracking camera (not shown) to interpret its location and pose in 3D space, an adjustable handle 3910, width-adjustment knob 3911 equipped with a TSM 3913 to enable the acquisition system software to interpret the angle of the handle relative to the tool end-effectors based on distance between the tracked DRF and this TSM, width-adjustment mechanism 3920, a retractable spring plunger 3915 to allow for the handle to lock into discrete preset angles, sleeve bodies 3930 for housing the screw-interface component of the tool, thread-tightening knobs 3909 for tightly interfacing with tulip heads as described in detail previously in relation to FIGS. 34, 34A-34F, 35A-35E, and 36A-36G, and TSM 3908 for indicating the location and/or pose of the screw interface component 3930 of the device. It should be noted that this is the device and that in some embodiments the angle of the sleeve bodies relative to the width-adjustment mechanism can either be adjustable or fixed at varying angles to accommodate the pedicle screws with which the tool will interface according to some embodiments. It should also be noted that the handle of the tool can be outfitted with a spring-loaded trigger to actuate the motion of the TMSM, used to indicate its active state and/or signal a command to the acquisition system, as will be described in more detail in reference to FIG. 39B according to some embodiments. It should also be noted that some embodiments of the tool can possess varying numbers of TSMs on and/or near the width-adjustment knob 3911 or screw-interface component 3930 of the tool according to some embodiments.

FIG. 39B displays some embodiments of the handle of the tool described previously in relation to FIG. 39A in which it is equipped with a TMSM 3956 coupled to a spring-loaded trigger 3950 via a sliding shaft 3959 according to some embodiments. In some embodiments, the user is able to communicate to the acquisition system that the probe is in an active state, during which its coordinates can be recorded, by actuating the TMSM relative to the tracked DRF on the tool, as described previously in detail in relation to FIGS. 10A-10G and 29A-29D. Additionally, some embodiments of this tool are designed for it to be used with one or more additional flexibility assessment devices, each equipped with uniquely identifiable tracked DRFs, so that their relative motion can be independently recorded while adjusting patient positioning, as described below in reference to FIGS. 40A-40C, and 42A-42K.

FIG. 39C displays a bottom view of the embodiment described above in relation to FIGS. 39A-39B according to some embodiments. In some embodiments, from this view, the width-adjustment mechanism 3920 is visualized with linear gears 3922, 3924, which allow for adjustment of the distance between the screw-interface components 3930 of the device to accommodate varying anatomical locations of screws with which it will interface. In some embodiments, FIG. 39D displays a cross-sectional side view of the tool describe previously in relation to FIGS. 39A-39C. In some embodiments, from this perspective, the retractable spring plunger 3933 is visualized, engaged within one of the detents 3934 at discrete angles, within the central device connection body 3915, for adjusting the angle of the tool's handle 3910. In some embodiments, in this way, the tool handle 3910 can be adjusted such that it does not interfere with additional tools placed within the surgical site, as described below in relation to FIGS. 40A-40C and 42A-42K. It should be noted that this is only the handle 3910, in which it is joined at the middle of the width adjustment mechanism. In some embodiments, the tool's handle is joined at an off-center location on the width-selection mechanism, and in some embodiments, the tool's handle projects at non-orthogonal angles to the width-adjustment mechanism to allow for enhanced tracking-camera visibility of the tracked DRF markers (3907, 3954) and TMSM 3956 on each tool.

FIG. 39E displays a bottom view of the width-adjustment mechanism 3920 that allows for variation in the distance between screw-interface locations of the tool according to some embodiments. Further, FIG. 39F illustrates a close-up perspective of the width-adjustment mechanism 3920, thread-tightening knobs 3909, and sleeve body 3930 of the device as described above in relation to FIGS. 39A-39E in accordance with some embodiments of the invention.

Some embodiments can be equipped with the quarter-turn tip as described in relation to FIGS. 36A-36I to mate with the screws described. Some embodiments of the device include variations in the screw interface components such that they are able to mate with crossbar-equipped screws, as previously described. For some embodiments interfacing with screws of this design, the screw-interface components are designed with the quarter-turn mechanism previously described in relation to FIGS. 3B, 33D-33F, and 44D.

Figures 40A, 40B:
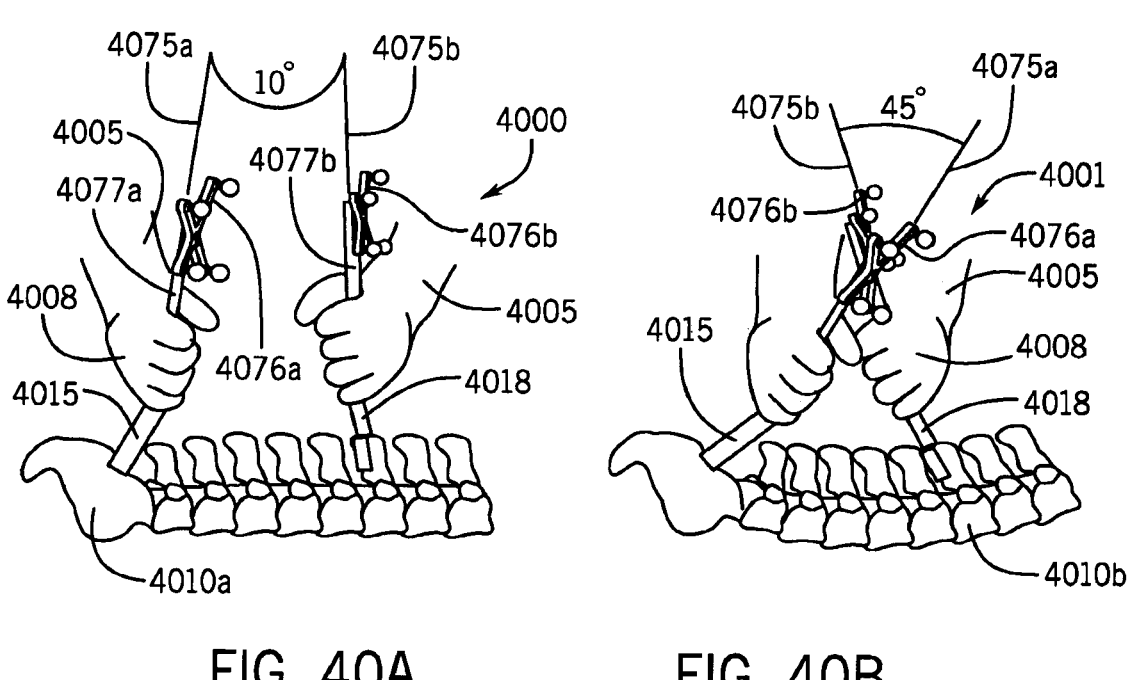
FIG. 40A illustrates a lateral view of a spine model with a straight curve, and two flexibility assessment tools engaged with the model in accordance with some embodiments of the invention.
FIG. 40B illustrates two flexibility assessment devices interfacing with a spine model with a lordotic curve in accordance with some embodiments of the invention.
Figure 40C:
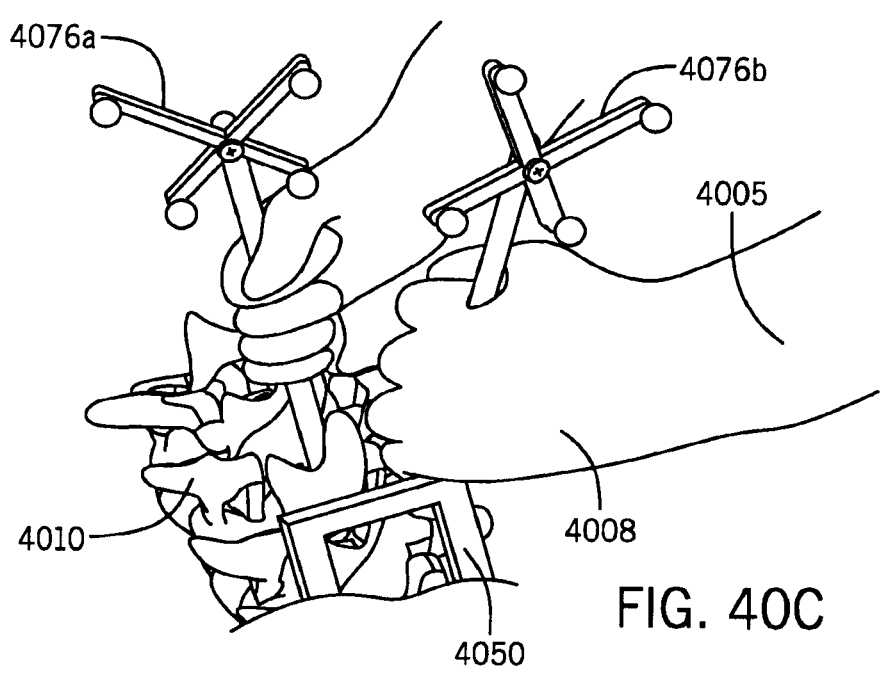
FIG. 40C illustrates the invention from a 3D-tracking camera perspective in accordance with some embodiments of the invention.

FIGS. 40A-40C display the application of the flexibility assessment device previously described in detail in relation to FIGS. 39A-39E, as applied to an anatomical model of the spine according to some embodiments. In some embodiments, the figures show the application of the device as applied across spinal levels L1-S1, an example assessment region. In some embodiments, because the assessment device tools both contain tracked DRFs, their location and pose are tracked during manipulation of the spine such that the maximum and minimum angles as well as positions of the assessment devices can be recorded and the calculations displayed to the user. Furthermore, some embodiments of this device allow for the relative position of two or more of these devices to lock to one another and allow for the insertion of hardware to fix the spine into that conformation, as described below in reference to FIGS. 41A-41C, and 42A-42K.

FIG. 40A illustrates a lateral view of a spine model with a straight curve, and two flexibility assessment tools engaged with the model in accordance with some embodiments of the invention. FIG. 40A displays a straight curve 4010a, and two flexibility assessment tools (4077a, 4077b) engaged with the model and screw-interface components 4015, 4018 according to some embodiments. In some embodiments, the user's hand 4008 interfaces with the handle of each assessment tool 4077a, 4077b and each tool is equipped with a unique tracked DRF (4076a, 4076b) to enable tracking of the device's location and pose in 3D space by a 3D-tracking camera (not shown). In some embodiments, the width and height between the screw-interface components are fixed. In some embodiments, when the assessment devices are activated, their relative 3D angles (4075a, 4075b) can be calculated, and projected onto anatomical reference planes. In FIG. 40A, the angle between handles shown is 10 degrees, which can be displayed to a user as the maximum limit of spine flexion.

FIG. 40B displays two flexibility assessment devices (4077a, 4077b) interfacing with a spine model with a lordotic curve 4010b according to some embodiments. In some embodiments, 3D-tracking acquisition systems can display relative angles (4075a, 4075b) and positions to a user, as described above in relation to FIG. 40A, and as applied to this embodiment, can display the maximum limit of spine extension to be 45 degrees. Further, FIG. 40C displays the invention from a 3D-tracking camera (not shown) perspective according to some embodiments. In some embodiments, both tool's unique tracked DRFs 4076a, 4076b are shown, as well as the mirrored angles of the handles relative to the screw-interface components of the device. Some embodiments of the device position the handles at varying angles to the width adjustment mechanism, and also possess spring-loaded triggers (not shown), to communicate the probe's active state to the acquisition system, as described above in relation to FIG. 39B.

FIGS. 41A-41D displays the flexibility assessment device, described previously in detail in relation to FIGS. 39A-39F and 40A-40C, equipped with detachable components to allow for the removal of the tool handle and body without detaching the screw-interface components according to some embodiments. In some embodiments, the removal of the handle allows for retaining rigid fixation on the screws while regaining workable space within the surgical site. In some embodiments, it also enables utilization with locking the alignment into a certain configuration on one side, removing the handle and body of the device, and then placing a rod to secure the spine in that configuration, as will be described in detail below in FIGS. 42A-42K.

Figures 41A, 41B, 41C, 41D:
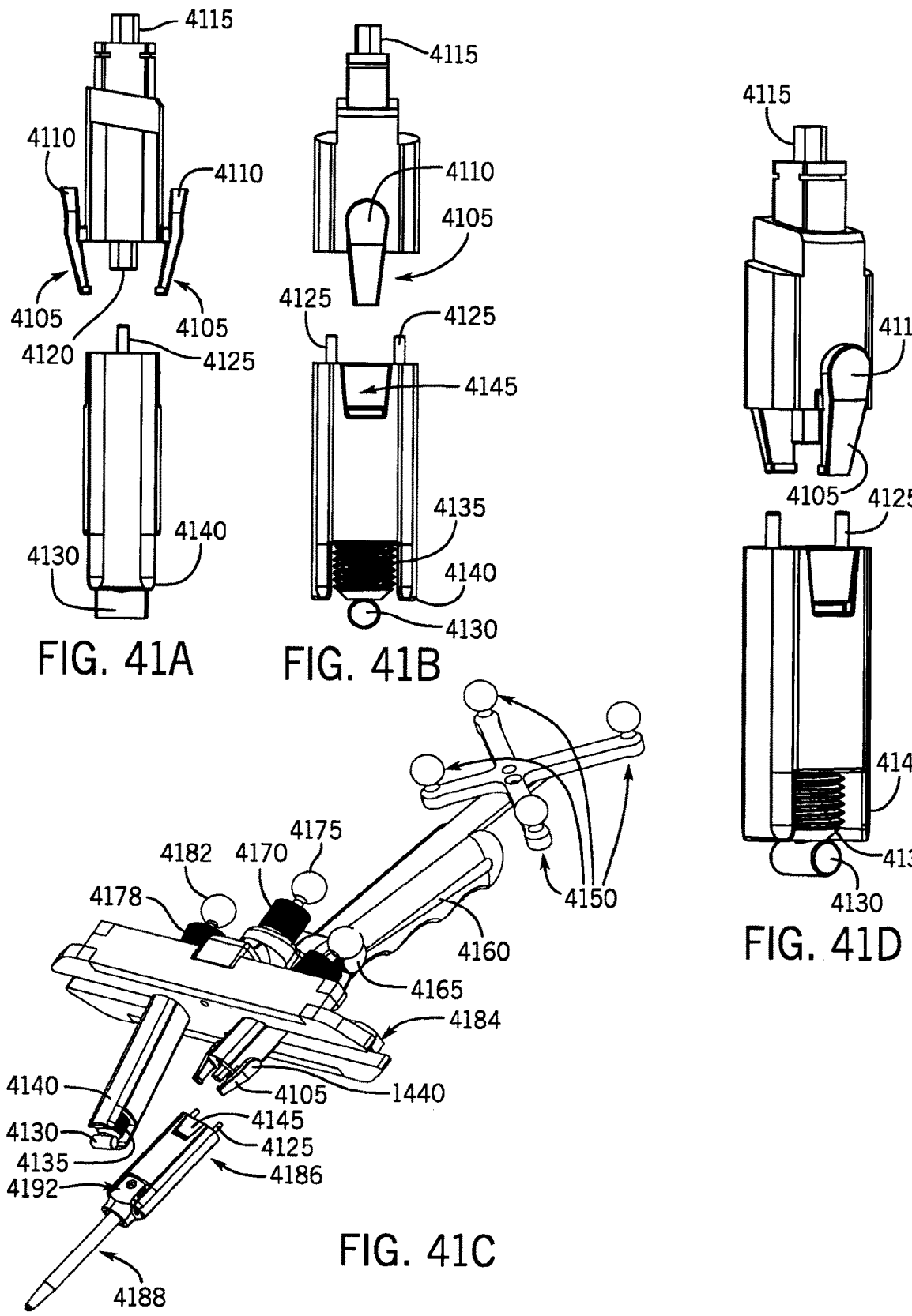
FIG. 41A illustrates a side view of the screw-interface components of the flexibility assessment device described previously in relation to FIGS. 34A-34F, 35A-35E, and 36A-36G, 39A-39F, and 40A-40C in accordance with some embodiments of the invention.
FIG. 41B illustrates a front view of the embodiment described above in relation to FIG. 41A in accordance with some embodiments of the invention.
FIG. 41C illustrates the device of FIGS. 41A-41B assembled with a flexibility assessment device previously described in relation to FIGS. 39A-39F, and 40A-40C in accordance with some embodiments of the invention.
FIG. 41D illustrates a perspective assembly view of a detachable screw-interface component displaying release tabs, center-alignment post, peripheral alignment pins, screw-interface rod, side-tab extensions, and spring-loaded snap arm in accordance with some embodiments of the invention.

Referring to FIG. 41A, illustrating a side view of the screw-interface components of the flexibility assessment device described previously, where a detachable component of the screw-interface devices mates with the bottom component via spring-loaded snap arms 4105 that can be released by pressing the release tabs 4110 according to some embodiments. In some embodiments, the top component contains a post 4115 for the thread-tightening knob (not shown) previously described in relation to FIGS. 34, 34A-34F, 35A-35F, and 36A-36I. In some embodiments, the mating interface of the two components contains a center-alignment post 4120 and peripheral alignment pins 4125 to facilitate alignment and enable rigid mating of the components.

FIG. 41B displays a front view of the embodiment described above in relation to FIG. 41A according to some embodiments. This view of the embodiment displays the screw-interface rod 4130 intended to interface with the top surface of the pedicle screw head while the device threads 4135 interface with the tulip head threads (not shown), side-tab extensions 4140, snap-arm mating detent 4145, and spring-loaded snap arm 4105. Further, FIG. 41C illustrates the device of FIGS. 41A-41B assembled with a flexibility assessment device previously described in relation to FIGS. 39A-39F, and 40A-40C in accordance with some embodiments of the invention. For example, FIG. 41C displays the device in which the detachable screw-interface components previously described in relation to FIGS. 41A-B are assembled with a flexibility assessment device previously described according to some embodiments. In some embodiments, one side of the flexibility assessment device is equipped with a detachable screw-interface component, and the other is equipped with a non-detachable component, as described in FIGS. 34, 34A-34F, 35A-35E, and 36A-36I. For example, in some embodiments, the screw-interface rod 4130 is visible on the non-detachable screw interface component, as is the thread 4135 to interface tulip heads. In some embodiments, the side-tab extension 4140, snap-arm mating detent 4145, and spring-loaded snap arm 4105 are visualized on the detachable screw-interface component. Further, in some embodiments, on the flexibility assessment device, previously described in relation to FIGS. 39A-39B and 40A-40C, the tracked DRF 4150, handle 4160, retractable spring plunger 4165, width-adjustment knob 4170, TSM 4175 for width-adjustment knob 4170, thread-tightening knob 4178, TSM 4182 for thread tightening knob 4178, width-adjustment mechanism 4184, and sleeve body 4186 are all displayed. Additionally, in some embodiments, the detachable screw interface component is shown interfacing with a tulip head 4192 attached to a pedicle screw (threads not shown) shaft 4188.

FIG. 41D displays a perspective assembly view of the detachable screw-interface component displaying the release tabs 4110, center-alignment post 4120, peripheral alignment pins 4125, screw-interface rod 4130, side-tab extensions 4140, and spring-loaded snap arm 4105 according to some embodiments.

Some embodiments include an assessment device equipped with detachable screw interface components and adjustable cross-linking devices. For example, in reference to FIGS. 42A-42C, some embodiments include a spinal flexibility assessment device as described above in relation to FIGS. 39A-39F, 40A-40C, and 41A-41D, equipped with a fixation mechanism, described below in reference to FIGS. 43A-43F, that allows for the flexibility assessment devices to be locked in a particular position, and removed from one side to accommodate the placement of a fixation rod on the contralateral side. In this way, the user can position the spine into a desired conformation with feedback from the 3D tracking acquisition system tracking the location of each flexibility assessment device according to some embodiments. It should be noted that the feedback displayed to the user can either be relative positioning of the tools, or relative positioning of initialized vertebra, as described in detail below in reference to FIG. 70 according to some embodiments.

FIG. 42A, shows the flexibility assessment device 4200, as described previously equipped with detachable screw interface components with adjustable cross-linking devices according to some embodiments. In some embodiments, the device includes a width-adjustment mechanism 4205 (e.g., 4170 of FIG. 41C) to match the distance between screw-interface components with the distance between implanted pedicle screws and their associated tulip heads 4225. In some embodiments, this is intended to be used after the pedicle screws have been placed into the spine 4210 during surgery. In some embodiments, this device can be equipped with a bone-clamping mechanism that enables it to substantially rigidly fix to the spine in the absence of pedicle screw and tulip heads with which to interface.

Further, FIG. 42B illustrates the flexibility assessment device described previously in relation to FIG. 42A substantially rigidly coupled to the pedicle screws by interfacing with the tulip heads in accordance with some embodiments of the invention, and shows thread-tightening knob 4209 according to some embodiments. In some embodiments, illustrated is the flexibility assessment device, where the screw interface components can substantially rigidly couple to the tulip heads via the thread-tightening-knobs 4209. In some embodiments, when they are tightly coupled to the tulip heads, the tolerance between the pedicle screw shaft and polyaxial tulip head is removed, thus resulting in a substantially rigidly fixed system between the screw shaft, tulip head, and flexibility assessment device.

Figures 42D, 42E, 42F:
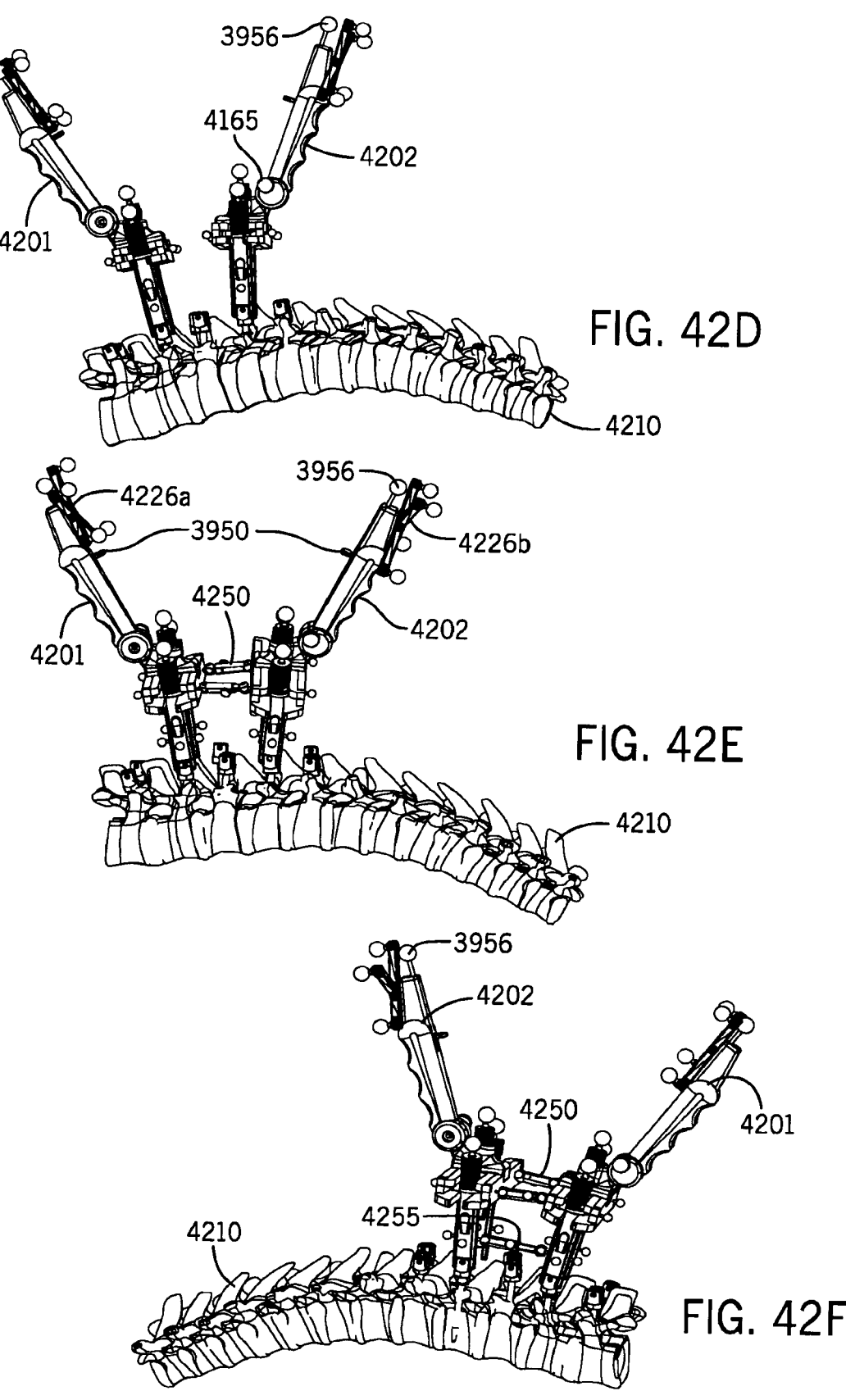
FIG. 42D illustrates two mated flexibility assessment devices, as previously described in relation to FIGS. 39A-39F, 41A-41D, and 42A-42C in accordance with some embodiments of the invention.
FIG. 42E illustrates two flexibility assessment devices substantially rigidly attached to the spine as described previously in relation to FIGS. 39A-39F, 41A-41D, and 42A-42D in accordance with some embodiments of the invention.
FIG. 42F illustrates two flexibility assessment devices substantially rigidly attached to the spine as described previously in relation to FIGS. 39A-39F, 41A-41D, and 42A-42F in accordance with some embodiments of the invention.

Further, FIG. 42C displays a second flexibility assessment device 4202 interfacing with a spinal level at a user-defined distance from the already mated device 4201 described previously according to some embodiments. In some embodiments, because both assessment devices possess unique tracked DRFs 4226a, 4226b, the 3D-tracking acquisition system is able to distinguish them from one another. Further FIG. 42D displays the two mated flexibility assessment devices 4201, 4202 according to some embodiments. In some embodiments, after the devices are substantially rigidly attached to the spine, their handles can be adjusted relative to their screw-interface components by releasing and subsequently re-engaging the retractable spring plunger 4165 to enable greater degrees of freedom without the devices obstructing one another. In some embodiments, the 3D acquisition system interprets the position of the handle by comparing the individual tool's tracked DRF to the location and/or of the TSMs located over the corresponding tools' width-adjustment mechanism or screw-interface components. Furthermore, in some embodiments, after the assessment devices are substantially rigidly fixed to the spine 4210 through mating with screws 4225, they can be placed in an active state by user-triggering (trigger 3950 as seen previously in relation to FIG. 39B) of a TMSM 3956 coupled to a depressible shaft 3959 within each device handle 4201, 4202, and then manipulate the contour of the spine until the user is satisfied with the software-displayed measurements. In some embodiments, the relative contour of the spine between devices can then be held in place by utilization of adjustable cross-linking devices, described below in reference to FIGS. 42E-421, and 43A-43D.

Figures 42G, 42H, 42I:
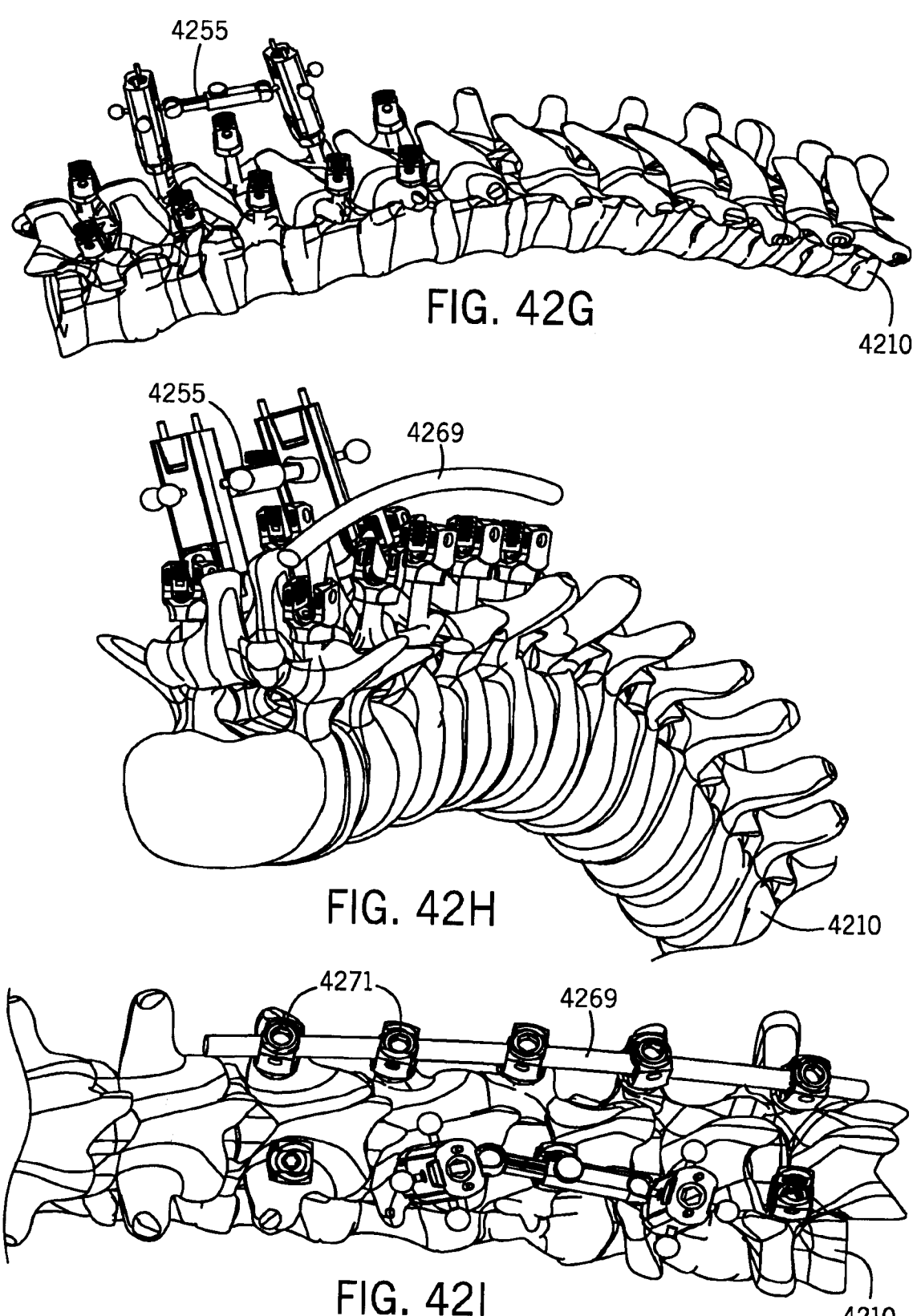
FIG. 42G illustrates an instrumented spine previously described in relation to FIGS. 42A-42F in accordance with some embodiments of the invention.
FIG. 42H displays an instrumented spine previously described in relation to FIGS. 42A-42G in accordance with some embodiments of the invention.
FIG. 42I illustrates an instrumented spine previously described in relation to FIGS. 42A-42H in accordance with some embodiments of the invention.
Figure 42J:
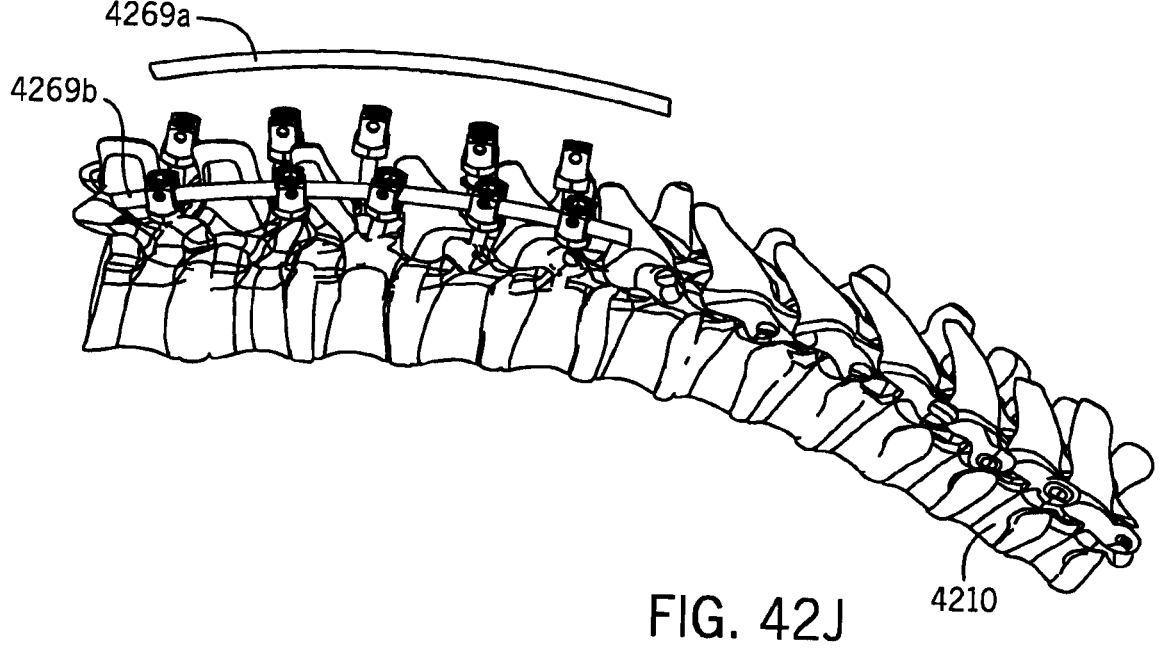
FIG. 42J illustrates an instrumented spine previously described in relation to FIGS. 42A-42I in accordance with some embodiments of the invention.
Figure 42K:
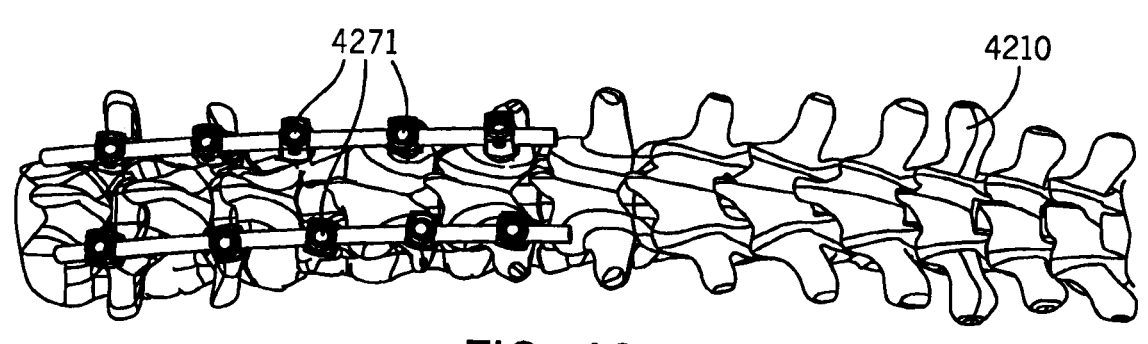
FIG. 42K illustrates an instrumented spine previously described in relation to FIGS. 42A-42J in accordance with some embodiments of the invention.

FIG. 42E displays two flexibility assessment devices substantially rigidly attached to the spine as described previously in relation to FIGS. 39A-39F, 41A-41D, and 42A-42D. When the devices are positioned in a way such that the spine 4210 is held in a desirable contour, they can be locked together utilizing adjustable cross-linking devices 4250 attached to the width-adjustment devices 4201, 4202 according to some embodiments. Further, FIG. 42F illustrates two flexibility assessment devices 4201, 4202 substantially rigidly attached to the spine 4210, further including an adjustable cross-linking device 4250 for screw-interface device 4255 according to some embodiments. For example, in some embodiments, in addition to substantially rigidly connecting the devices between the width-adjustment mechanisms, the screw-interface components can also be substantially rigidly fixed to one another via the adjustable cross-linking devices 4255. FIG. 42G illustrates an instrumented spine 4210 previously described in relation to FIGS. 42A-F in accordance with some embodiments of the invention, and shows adjustable cross-linking device for screw-interface device 4255 coupled to the spine 4210 according to some embodiments. In this instance, the detachable screw-interface components, as described enable the body and one screw-interface component of the assessment device to be removed to leave behind two screw-interface components, held in place by the coupled, adjustable cross-linking device 4255 according to some embodiments.

FIG. 42H displays an instrumented spine 4210 previously described in relation to FIGS. 42A-42G according to some embodiments. In some embodiments, rith the spine 4210 held in a fixed contour, the removed components of the flexibility assessment devices allow for the placement of a rod 4269 within the exposed set of contralateral screws. Further, FIG. 42I illustrates an instrumented spine previously described in relation to FIGS. 42A-42H in accordance with some embodiments of the invention. In some embodiments, the rod 4269 placed within the exposed set of pedicle screws is secured in place with cap screws 4271. In some embodiments, with the rod 4269 holding the spine 4210 in the desired contour, the remaining screw-interface components are now able to be removed. Further, FIG. 42J displays an instrumented spine 4210 previously described in relation to FIGS. 42A-421 according to some embodiments. In some embodiments, with the contour of the spine held in place with the already-secured rod 4269*b*, the remaining components of the flexibility assessment device shown in FIG. 42I are removed, enabling placement of a second rod 4269*a* within the screws. Further, in some embodiments, FIG. 42K displays an instrumented spine previously described in relation to FIGS. 42A-42J. In some embodiments, this figure displays the final step of securing the adjusted alignment of the spine achieved with the lockable pair of flexibility assessment devices. In some embodiments, during this step, the second rod is secured with cap screws 4271.

Figures 43A, 43B, 43C, 43D, 43E, 43F:
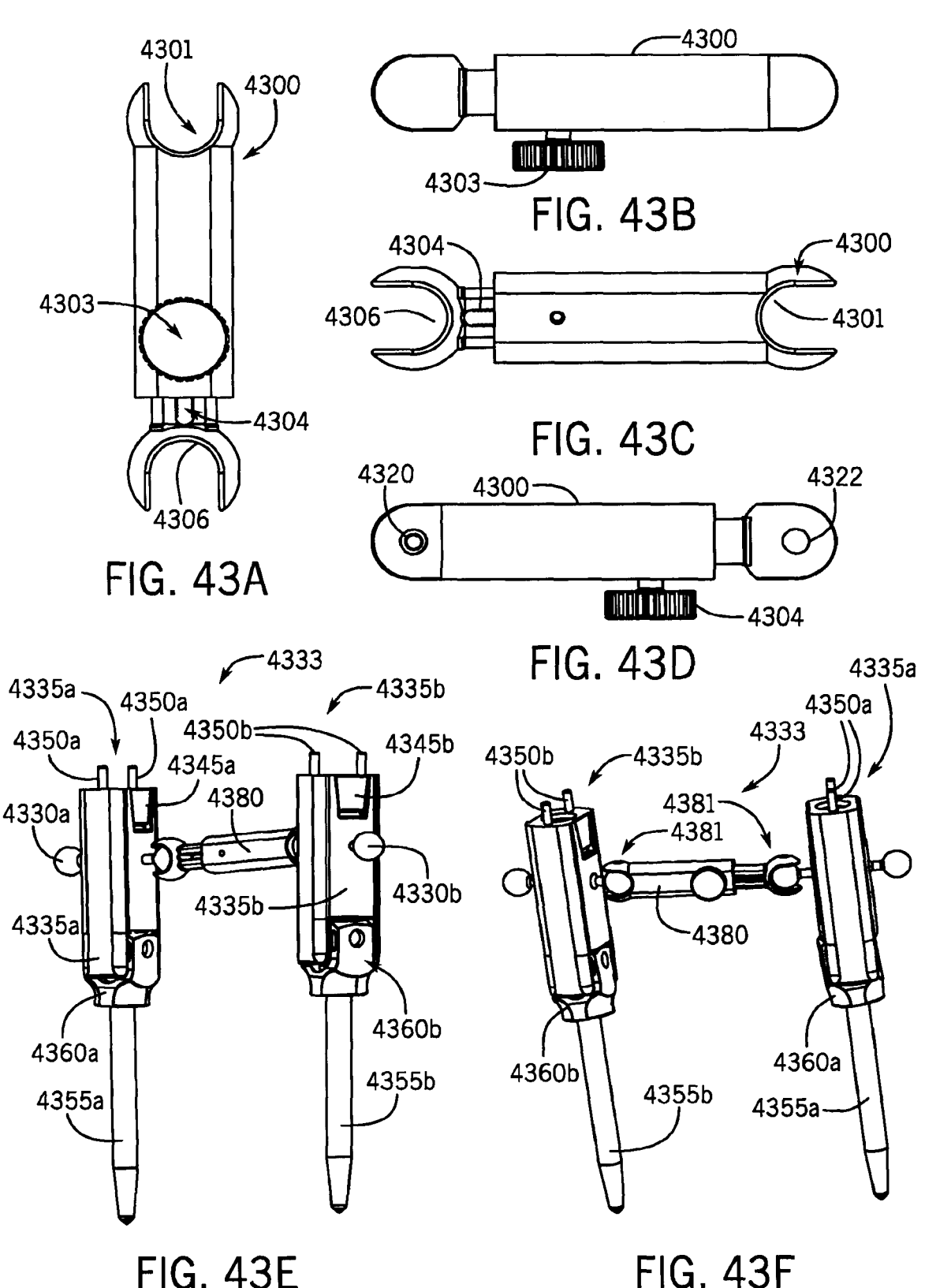
FIGS. 43A-43D includes views of an adjustable cross-linking device in accordance with some embodiments of the invention.
FIGS. 43E-43F illustrate views of an adjustable cross-linking device in accordance with some embodiments of the invention.

FIG. 43A displays a top view of the device 4300 which is an adjustable cross-linking device, as described above in relation to FIGS. 42A-42K, mates with components of the flexibility assessment device, as described previously in relation to FIGS. 39A-39F, 40A-40C, 41A-41D, and 42A-42K according to some embodiments. Some embodiments consists of an outer-slider ball socket 4301 designed to mate with protruding balls on components of the flexibility assessment device including the width-adjustment mechanism, as described previously in relation to FIGS. 39A-39F, 40A-40C, 41A-41D, and 42A-42K, and the screw-interface components of the device, as described previously in relation to FIGS. 34-36, 41A-41D. Some embodiments also contain a retractable spring plunger 4303 with teeth that engages with an internal rack with teeth 4304. Additionally, in some embodiments, there is an inner-slider ball socket 4306 designed to mate with a secondary flexibility assessment device component, as described previously in FIGS. 42A-42K.

FIG. 43B displays a bottom view of the device 4300, shown previously in FIG. 43A, which is an adjustable cross-linking device, a described above in relation to FIGS. 42A-42K according to some embodiments. In some embodiments, from this perspective, the outer-slider ball socket 4301, internal rack with teeth 4304 and inner-slider ball socket 4306 are all visible. In some embodiments, in order to adjust the length of the adjustable cross-linking device, a user depresses the retractable spring plunger with teeth such that it disengages from the internal rack with teeth. In some embodiments, when the length is as desired, the user releases the retractable spring plunger with teeth such that it re-engages with the internal rack with teeth 4304. FIG. 43D illustrates a retractable spring plunger 4303 with teeth 4304, outer-slider set screw 4320, and inner-slider set screw 4322 according to some embodiments.

FIGS. 43E and 43F shows an adjustable cross-linking device 4333, described previously in relation to FIGS. 42A-43K, 43A-43D, engaged with detachable screw-interface components (shown here as 4335*a*, 4335*b*, and adjustably coupled through coupler 4380, with rotation balls or joints 4381) of the flexibility device previously described in relation to FIGS. 41A-41C according to some embodiments. As shown, in some embodiments, coupled components can include fixation ball 4330*a*, 4330*b*, snap-arm mating location 4345*a*, 4345*b* (e.g., shown previously in relation to FIG. 41B as snap-arm mating detent 4145), peripheral alignment pin(s) 4350*a*, 4350*b*, pedicle screw shaft 4355*a*, 4355*b*, and tulip heads 4360*a*, 4360*b*. In some embodiments, the detachable screw-interface devices 4335*a*, 4335*b* possess a fixation ball 4330*a*, 4330*b* to interface with the inner and outer-slider ball sockets, a snap-arm mating locations 4345*a*, 4345*b*, and peripheral alignment pins 4350*a*, 4350*b*. Further, in some embodiments, screw-interface components are engaged with the tulip heads 4360*a*, 4360*b* of pedicle screw (threads not shown) shafts 4355*a*, 4355*b*.

Figures 44A, 44B, 44C, 44D:
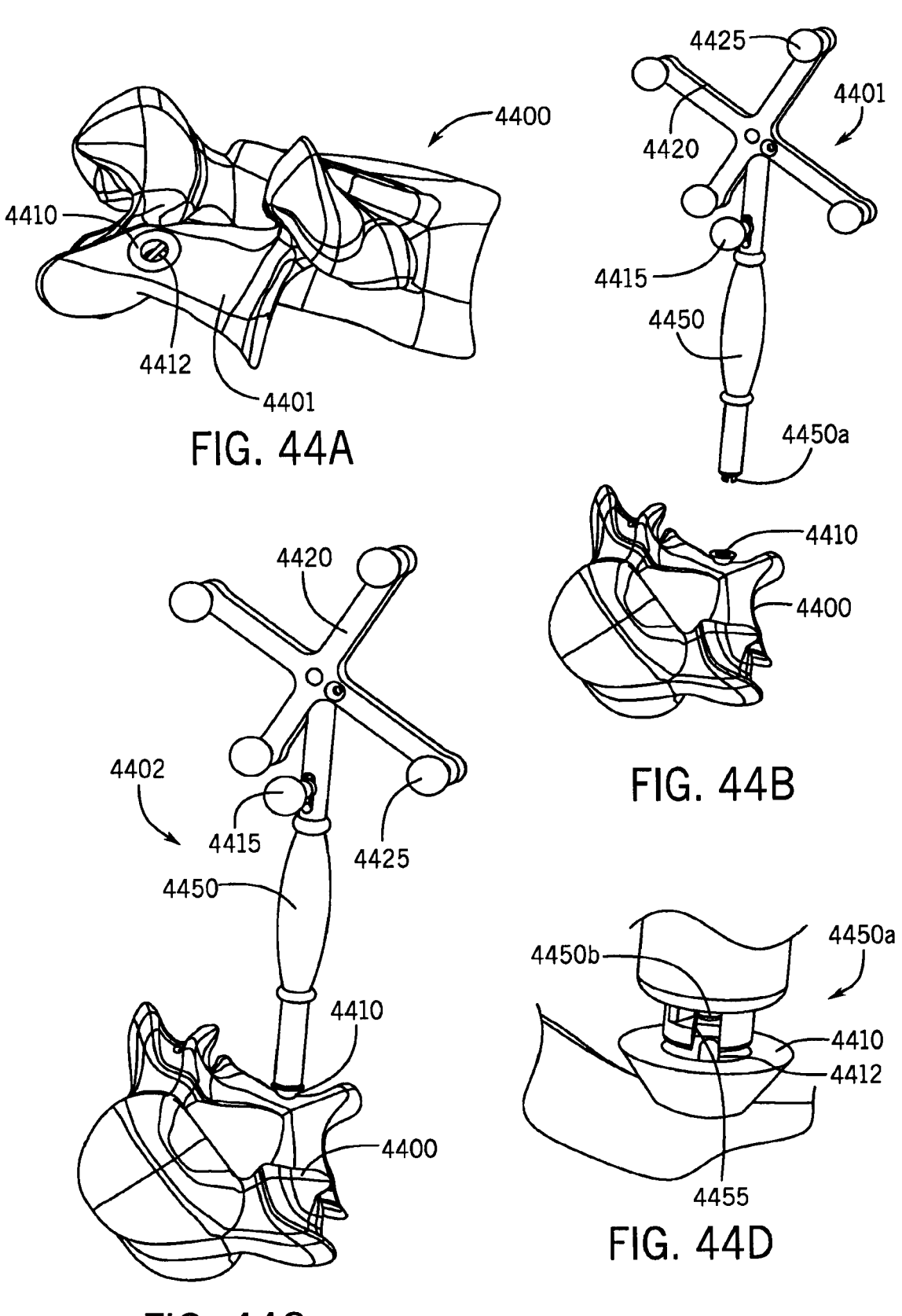
FIG. 44A illustrates a bone-implanted fiducial equipped with a crossbar and substantially rigidly fixed to the lamina of a vertebra as previously described in relation to FIGS. 3A-3C in accordance with some embodiments of the invention.
FIG. 44B illustrates a process view of a pre-engagement of a bone-implanted fiducial and bone-fiducial mating screwdriver equipped with a tracked DRF and a TMSM coupled to a depressible sliding shaft at the end of the screwdriver in accordance with some embodiments of the invention.
FIG. 44C illustrates an engagement of a bone-implanted fiducial and bone-fiducial mating screwdriver equipped with a tracked DRF and a TMSM coupled to a depressible sliding shaft at the end of the screwdriver in accordance with some embodiments of the invention.
FIG. 44D illustrates a bone-implanted fiducia with cross-bar and overlying bone-fiducial-mating screwdriver in accordance with some embodiments of the invention.

Some embodiments of the invention include a bone-implanted fiducial equipped with a rigid crossbar that substantially rigidly mates with a tracked probe equipped with a TMSM to indicate to the acquisition system when it is fully engaged. In some embodiments, because the probe is only able to mate with the fiducial in one conformation, when the tracked probe fully engages with the fiducial, the location and pose of the fiducial can be interpreted. In some embodiments, if the fiducial has been previously initialized to the vertebra, reassessing the location and pose of the fiducial enables re-registration of the location and pose of the vertebra. Furthermore, in some embodiments, if the fiducial is placed under surgical navigation, interfacing the probe with the fiducial enables rapid re-registration of bony anatomy for surgical navigation cases, providing value when anatomy moves relative to a reference DRF or when the anatomy changes conformation from when its imaging was last registered for surgical navigation. In some embodiments, in this way, the bone fiducial serves as another method of rapid re-registration of anatomy, as similarly described in FIGS. 38, and 38A-38G. For example, FIG. 44A illustrates a bone-implanted fiducial equipped with a crossbar and substantially rigidly fixed to the lamina of a vertebra as previously described in relation to FIGS. 3A-3C in accordance with some embodiments of the invention. In some embodiments, the bone-implanted fiducial 4410 is equipped with a rigid crossbar 4412 and substantially rigidly fixed to the lamina 4401 of a vertebra 4400 as previously described. Further, FIG. 44B illustrates a process view of a pre-engagement of a bone-implanted fiducial 4410 and bone-fiducial mating screwdriver 4450 equipped with a tracked DRF 4420 (composed of 3D-tracked markers 4425) and a TMSM 4415 coupled to a depressible sliding shaft (shown later as 4450*b*) at the end of the screwdriver in accordance with some embodiments of the invention. Some embodiments are an alternative to some embodiments used to interpret the location and pose of a vertebra in space, as previously described in FIGS. 3A-3C, 29A-29C, 33A-33H, and 38, 38A-38G. In some embodiments, the probe tip 4450*a* is equipped with a quarter-turn mechanism to tightly engage with the bone-implanted fiducial. In some embodiments, by fully engaging with the crossbar 4412 on the fiducial, the depressible sliding shaft is mechanically actuated to move the linked TMSM 4415 and thereby signal to the 3D-tracking acquisition system to record the coordinates of the screwdriver, and calculate the location and pose of the implanted-bone fiducial, and associated vertebra if it has been initialized. For example, in some embodiments, FIG. 44C illustrates an engagement of a bone-implanted fiducial and bone-fiducial mating screwdriver equipped with a tracked DRF 4420 and a TMSM 4415 coupled to a depressible sliding shaft 4450*b* at the end of the screwdriver 4450, and FIG. 44C displays the bone-fiducial mating screwdriver 4450 engaged with the bone-implanted fiducial 4410. When fully engaged, as shown the bone-fiducial mating screwdriver 4450 is aligned coaxially with the bone-implanted fiducial 4410, and the TMSM 4415 is actuated, indicating to the acquisition system that the screwdriver tip 4450*b* is fully engaged with the bone-implanted fiducial according to some embodiments. Further, FIG. 44D illustrates a bone-implanted fiducial with crossbar and overlying bone-fiducial-mating screwdriver in accordance with some embodiments of the invention. In some embodiments, a quarter-turn mating tip 4455 and depressible sliding shaft 4450*b*. In some embodiments, the quarter-turn mating tip 4455 is shown as is the depressible sliding shaft 4450*b* which is depressed upon complete engagement between the screwdriver 4450 and fiducial 4410 (engaging around cross-bar 4412). It should be noted that in some embodiments, the acquisition system can be triggered to calculate the location of the fiducial, based on user-input to the software, hand-triggering a TMSM or electronic communication system, and can be used for rapid re-registration of a vertebra's location within camera coordinates prior to rod implantation, as described below in FIGS. 45A-45B and 72.

Some embodiments of the invention include rapid re-registration with depth-stop-screws and depth-stop-engaging screw-assessment tool. For example, some embodiments include a system and method to enable rapid re-registration and 3D-rendering of a vertebra's relative location in space by utilizing a depth-stop equipped pedicle screw and depth-stop engaging assessment tool, as previously described in relation to FIGS. 38, and 38A-38G. In some embodiments, the depth-stop attached to the screw can be accessed by the depth-stop engaging assessment tool, with or without an implanted rod present, to accurately calculate the location and pose of the screw in 3D-tracking camera coordinates. In some embodiments, if screws were initially placed under image guidance, the acquisition system has already stored and recorded the relative position of each screw to the vertebra in which they are implanted. In some embodiments, with this information, after re-registering the new location of both screws in space, the acquisition software is able to reconstruct the location of the vertebra in which they are inserted. In some embodiments, if a surgical navigation system becomes decoupled from the patient's anatomy, either through movement of the tracked DRF serving as a patient reference or through change in contour of the spine from the time the image was acquired, the system can be rapidly re-registered to the patient's current position in space.

Figures 45A, 45B:
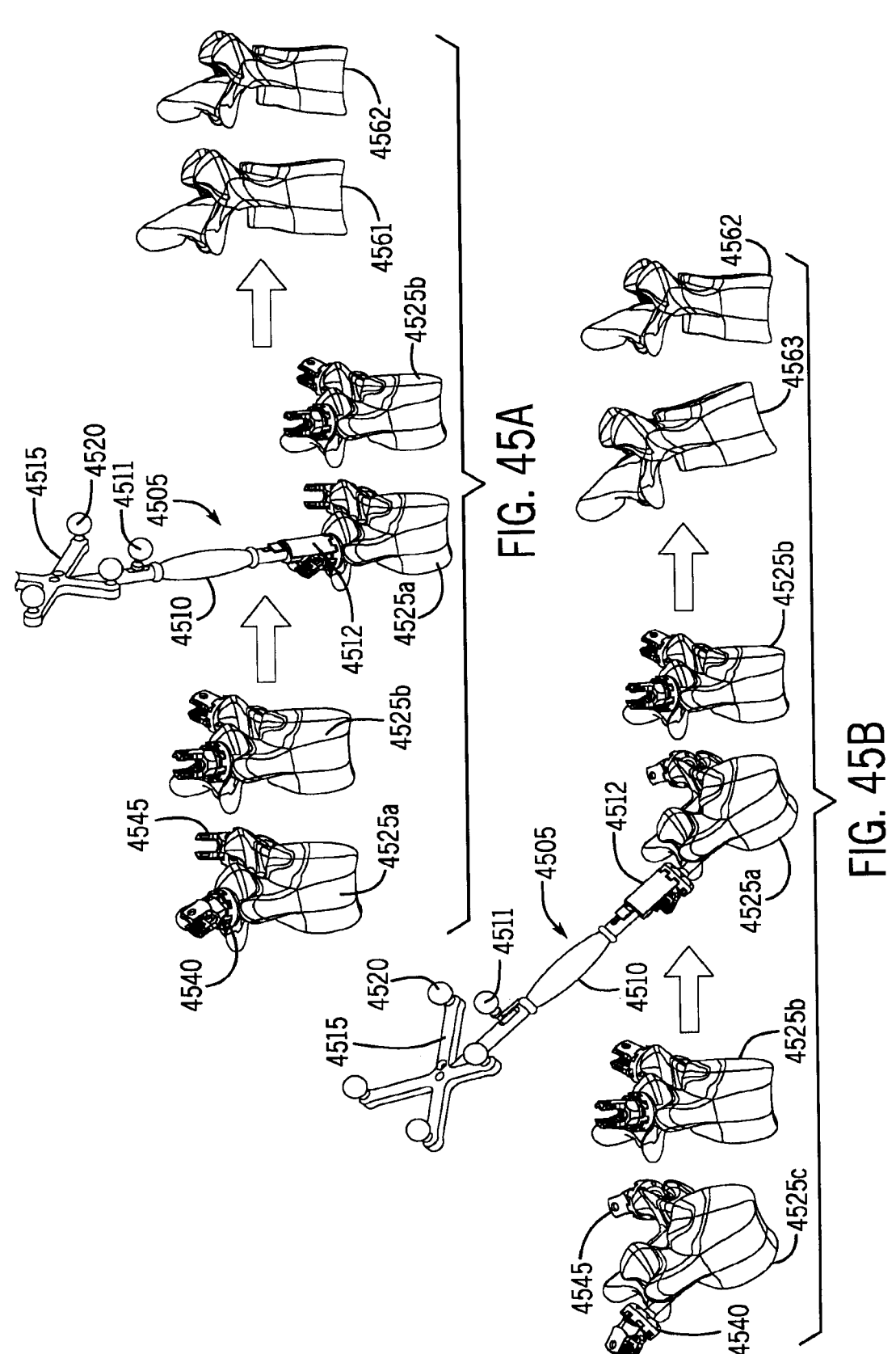
FIGS. 45A-45B illustrate a vertebra engagement and rendering process in accordance with some embodiments of the invention.

FIG. 45A displays the invention in which two vertebra 4525*a*, 4525*b* are instrumented with depth-stop-equipped pedicle screws 4540, described previously in relation to FIGS. 38, 38A-38G, which can be registered in 3D space by having the depth-stop-engaging 3D-tracked tool 4505 interfaces with each screw on each vertebra. In some embodiments, the 3D-tracked tool 4505 for registering the position and orientation of the screws comprises of a handle 4510, a depressible sliding shaft that mates with the screw depth-stop interface that actuates a TMSM 4511 to change the triggering state of the tool to active, and a 3D-trackable DRF 4515 of 3D-tracked markers in a unique configuration. In some embodiments, if the screws were initially placed under surgical navigation, and the position of the screw shafts relative to the vertebrae are known, then assessment of screw shafts' location and pose for each vertebra, is able to yield a 3D rendering of each vertebra (shown as representations 4561, 4562) in space relative to one another. It should be noted that utilizing depth-stop-equipped pedicle screws and their associated assessment tool, is not the only way of obtaining the information needed for the software to make this assessment according to some embodiments. Some embodiments include mating directly with screw heads coaxially to interpret their location and pose, as previously described in FIGS. 29A-29C, and FIGS. 33A-33H. In some embodiments, in cases when an assessment of the screw, and thereby vertebrae locations, are desired after implantation of a rod, the depth-stop-equipped pedicle screws preserve access to the screw shaft with the depicted assessment tool. Further, in some embodiments, FIG. 45B shows the invention previously described in FIG. 45A, in which case the position of vertebra #1 4525*c* has changed relative to that of vertebra #2 4525*b*. In some embodiments, by engaging the depth-stop-equipped tracked assessment tool, into both depth-stop-equipped pedicle screws 4540 in vertebra 4525*c* and vertebra 4525*b*, the acquisition system's software can then reconstruct an updated rendering 4563 on the display monitor of each vertebra in their relative 3D position and orientation to one another.

In some embodiments, the probe depicted in FIG. 38, used to update 3D renderings of a vertebra via re-registration of screws can also be updated via mating with a bone fiducial, depicted in FIGS. 3A-3C and 44A-44D. Some embodiments include mating directly with bone-mounted, percutaneous, or skin-mounted fiducials that are initialized to anatomical landmark(s) of interest for 3D renderings.

Some embodiments of the invention can enable significantly reduced X-ray and radiation exposure during minimally invasive, as well as open, surgeries and procedures. In some embodiments, tracked surgical tools are able to be placed in the field of view of previously-acquired X-ray images, such that their projected outline can be displayed over anatomy visualized in a previously-acquired X-ray image. In some embodiments, the acquisition software interprets the location of the tool surface relative to the X-ray emitter/detector and using that information is able to accurately display a real-time overlay of the tools' position on the previously acquired X-ray image, accounting for the appropriate size scaling of the tool's outline, as described below in reference to FIG. 71.

Figures 46A, 46B, 46C, 46D, 46E, 46F, 46G:
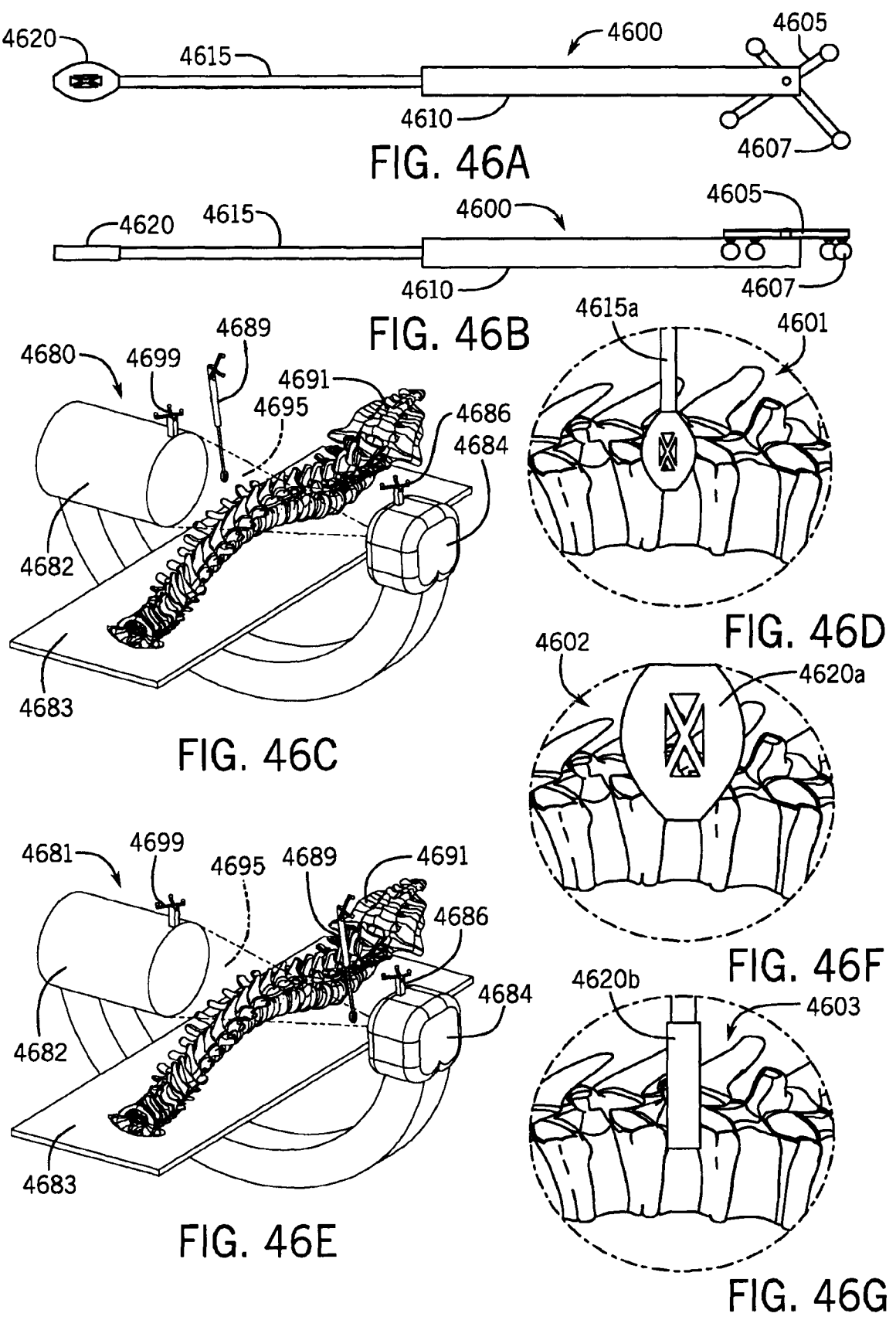
FIGS. 46A-46B illustrate a 3D tracking tool in accordance with some embodiments of the invention.
FIG. 46C illustrates an X-ray imaging and tracking system in accordance with some embodiments of the invention.

FIGS. 46A-46B illustrate a 3D tracking tool in accordance with some embodiments of the invention. In some embodiments, a 3D-tracked tool 4600 includes a handle 4610, tracked DRF 4605 (with markers 4607) and tool tip 4620 (which is often a coupled implant). It should be noted that in some embodiments of this invention, each mobile component of the surgical tool that is used, requires 3D-tracking relative to each of the other components within said tool. FIG. 46C displays the invention in which an X-ray emitter 4684 is equipped with a tracked DRF 4686 positioned in a known location relative to the emitter, and the X-ray detector 4682 can also be equipped with a tracked DRF 4699 positioned in a known location relative to the detector. In some embodiments, with the X-ray system imaging a spine 4691 resting on an operative table 4683, the X-ray emitter produces a conical volume of its X-ray beam 4695. In some embodiments, all objects within this conical volume are then projected onto the X-ray detector 4682. In some embodiments, with known geometry of the X-ray system 4680, the location and pose of this conical volume 4695 is known relative to either of the tracked DRFs (4686, 4699) mounted to the X-ray system. In some embodiments, with a 3D-tracking camera having recorded the location of the emitter, and thereby the conical imaging volume, when an X-ray is taken, the acquisition system can determine when any component of the tracked surgical tool enters within the volume. In some embodiments, when the surgical tool 4689 is positioned within the volume, its virtual projection can be overlaid on the previously-acquired x-ray image, as shown in FIG. 46D. In some embodiments, the proximity of the tracked tool's surface to the emitter, enables the acquisition software to determine its relative size scaling in the overlay image, as described below in reference to FIG. 71.

FIG. 46D illustrates a virtual overlay of a tracked surgical tool positioned close to the X-ray detector on top of an X-ray image of the spine in accordance with some embodiments of the invention. As shown, in some embodiments, the X-ray image of spine 4601 includes an overlay image of surgical tool close to detector 4615a. In some embodiments, this virtual overlay is updated in real-time as the tool moves relative to the previously acquired X-ray's conical volume as described below in reference to FIG. 71. FIG. 46E displays some embodiments of the invention previously described in FIG. 46C, with the tracked surgical tool 4689 positioned closer to the X-ray emitter according to some embodiments. Further, FIG. 46F displays a virtual overlay of a tracked surgical tool in the X-ray image 4602, with the tool 4620a positioned close to the emitter, as shown in FIG. 46E according to some embodiments. In some embodiments, because the tool's surface is located closer to the X-ray emitter, its virtual projection is scaled to be larger to match the case of if a real X-ray image was acquired of the tool in that position. In some embodiments, the software interpretation of the tool's relative scaling size is described below in reference to FIG. 71. Further, FIG. 46G displays an X-ray image 4603 with a virtual overlay of a tracked surgical tool 4620b close to the emitter, turned 90 degrees, from the tool position previously described in FIGS. 46E-46F according to some embodiments. In some embodiments, the tool's real-time location in space relative to the previously acquired X-ray volume, can be displayed via an overlay onto the previously acquired X-ray image. In some embodiments, the virtually-overlaid tool 4689 can also be simultaneously overlaid or interfaced with other 3D-tracked surgical tools that are within, or outside of, the field of view of the X-ray volume 4695. In some embodiments, if 3D-tracked DRFs are mounted onto anatomical landmarks of interest that are also in the X-ray image, the 3D-tracked location and pose of the surgical tool 4689 can be overlaid while the anatomical structures in image also become virtually adjusted to reflect their movements relative to the C-arm DRFs (4699, 4684) and the main surgical tool 4689 (e.g., when the surgical tool 4689 with a coupled implant, such as a cage) is inserted between two vertebrae, with mechanically-linked DRFs, and the corresponding X-ray image virtual overlay adapts the position and orientation of the imaged vertebrae to reflect their approximate real-world positions and orientations relative to one another.

Some embodiments of the invention include components that make up the two-part system for a handheld mechanism of assessing the contour of the rod prior to implantation. For example, FIG. 47A displays components of a tracked end cap, used to substantially rigidly hold a rod, define anatomical reference planes relative to the 3D-tracking camera, and establish the coordinate system within which all coordinates of the rod's location will be recorded according to some embodiments. Further, FIG. 47B displays components of a tracked slider tool, used in combination with the tracked end cap, to slide along the surface of a rod and interpret its coordinates within the coordinate system established by the tracked end cap, as described in detail below in reference to FIG. 74 according to some embodiments. As shown, some embodiments include an end cap handle 4720, mount 4722 for interfacing with the mount-mate 4714 containing anatomical axes reference arrow labels consisting of, but not limited to inferior 4718 and posterior 4719. Some embodiments also consists of a rod mount hole 4712 to insert a rod and a threaded hole 4716 for a set screw to secure the rod in place relative to the end cap, a mounting platform 4710 for a tracked DRF, a tracked DRF 4730, and fasteners 4740. Some embodiments utilize a separate, tracked DRF. In some embodiments, the DRF-based markers mount directly into the tool surface itself, as described below in reference to FIGS. 52A-52B, and 53A-53F. Furthermore, some embodiments of this invention are shown below in reference to FIGS. 48A-48B, 49D, 50E, 51A-51C, 51H-51I, and 56A-56F according to some embodiments.

Figures 47A, 47B:
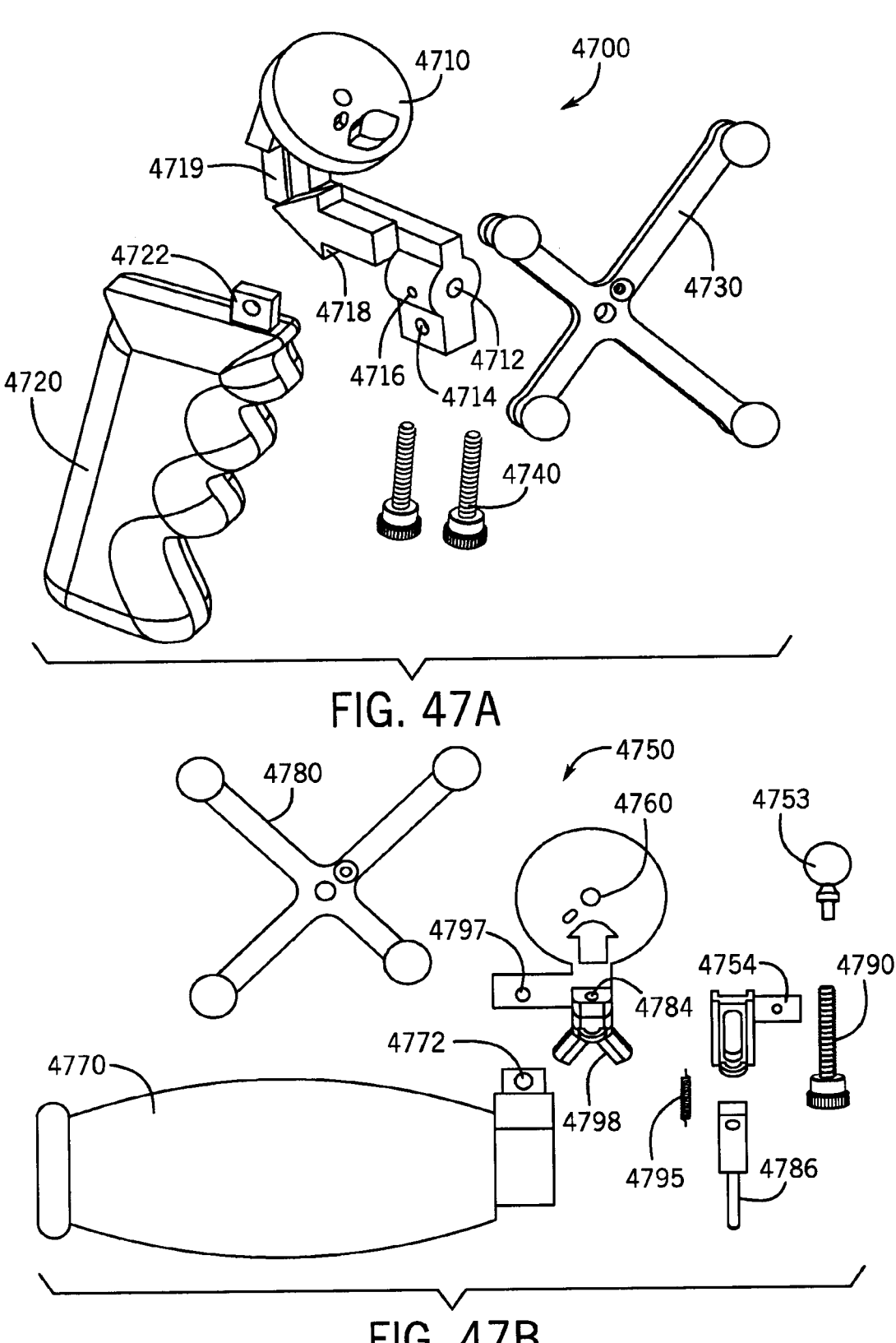

FIG. 47B displays the components of a tracked slider, designed to interface with a rod fixed to a tracked end cap, described previously in relation to FIG. 47A according to some embodiments. Some embodiments of the slider consists of a handle 4770, mount 4772 for joining with the mount-mate 4797, a rod-centering fork 4798 designed to straddle and center the rod during acquisition of the rod's contour, a through hole 4784 for receiving a depressible sliding shaft 4786 that mates with a TMSM mount 4754 via a fastener 4790 and is spring-loaded 4795. Some embodiments also consists of a DRF mount 4760 to receive a tracked DRF 4780 and a TMSM 4753 attached to its corresponding mount. Some embodiments of this device are described below in reference to FIGS. 51D-51I. It should be noted that some embodiments of the rod-centering fork component, meant to interface with the rod, are ring-shaped designs meant to accommodate specific rod diameters, adjustable diameter rings, U-shaped designs, and polygonal-shaped designs including but not limited to triangular, rectangular, pentagonal, etc. according to some embodiments.

Figures 48A, 48B, 48C:
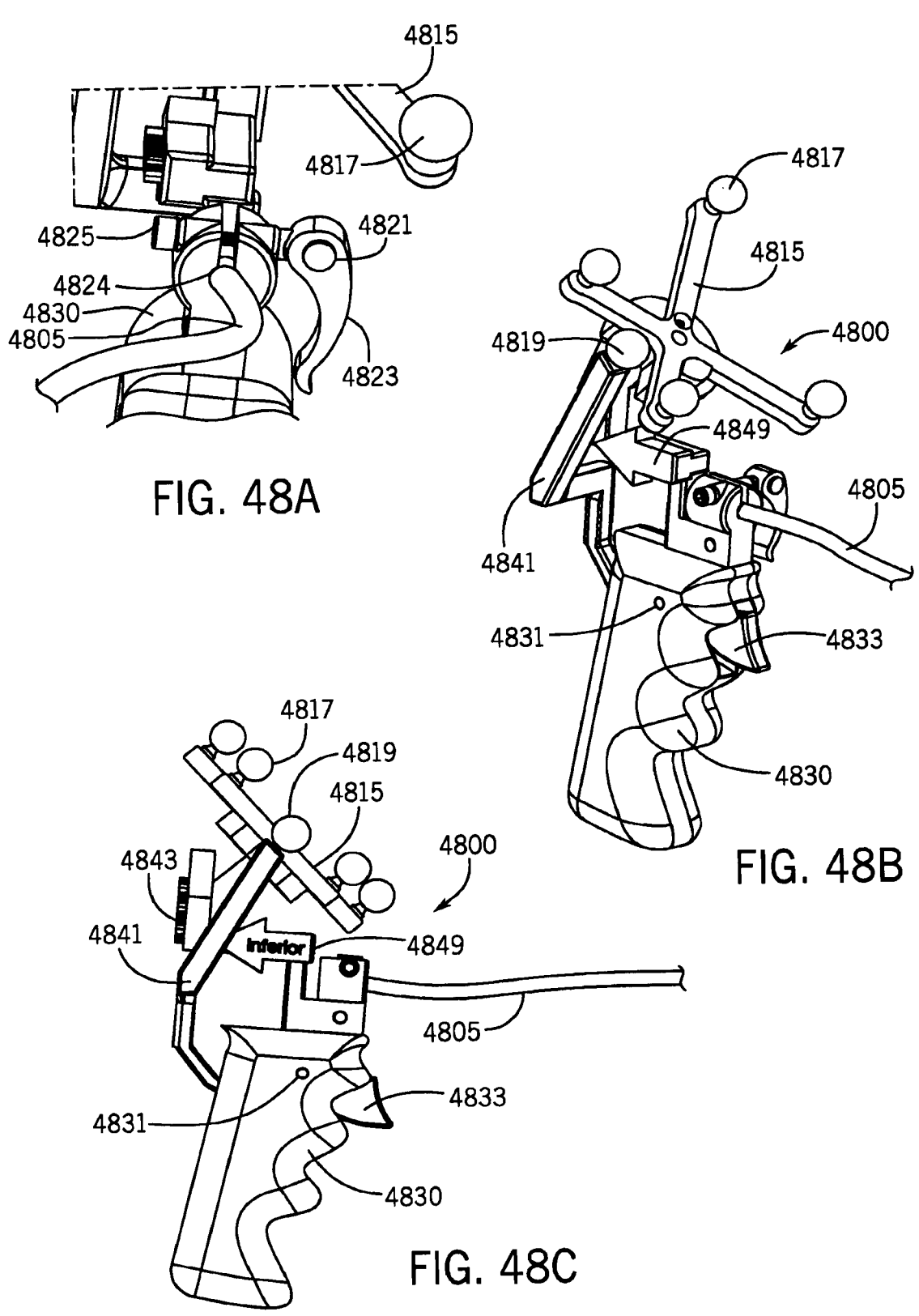

FIGS. 48A-48C relate to the tracked end cap previously described in relation to FIG. 47A according to some embodiments. Some embodiments are equipped with a spring-loaded TMSM actuated by a trigger on the handle used to communicate with the 3D-tracking acquisition system. Additionally, in some embodiments, it contains an alternative method of fixing the rod than a set screw which was previously described in FIG. 47A. In some embodiments, the rod mount hole is split and tightened by the combination of a cam lever and threaded fastener for more rapid exchange and fixation of rods with the end cap, as well as maintaining the center alignment of the rod after fixation. For example, in some embodiments, FIG. 48A illustrates a close-up view of a portion of an end cap in accordance with some embodiments of the invention, showing an assembly comprising a rod mount hole 4824, rod 4805, end cap handle 4830, cam lever 4823, hinge pin 4821, and threaded fastener 4825. In some embodiments, the rod 4805 is inserted into the rod mount hole 4824 and secured in place by a cam lever 4823 rotating about a hinge pin 4821 to tighten against a threaded fastener 4825.

FIG. 48B illustrates a perspective view of an end cap 4800 assembled from components of FIG. 47A in accordance with some embodiments of the invention, and shows a rod 4805, trigger 4833, spring-loaded hinge 4831, trigger arm (4832, 4841), TMSM 4819, and end cap tracked DRF 4815 (with 3D-tracked markers 4817). In some embodiments, the perspective shows the end cap previously shown in FIG. 47A, in which a rod 4805 is fixed. Some embodiments also contain a hand-actuated trigger 4833 that rotates about a spring-loaded hinge 4831 inside the handle 4830, to actuate a trigger arm 4841 with a coupled TMSM 4819. Some embodiments also contain a tracked DRF 4815 used to interpret the location of the end cap and its attached rod via a 3D-tracking camera (not shown). In some embodiments, the location of the TMSM actuated by the trigger on this embodiment is compared to the location of the tracked DRF by the acquisition software, to determine if the user is triggering the device, as described in more detail below in reference to FIGS. 64A-64B and 65A-65E. It should be noted that in some embodiments of this device, the trigger can be actuated via other mechanisms such as covering or uncovering a tracked marker, as described previously in relation to FIG. 14, using linear motion rather than rotational, as described previously in relation to FIGS. 10A-10G, 29A-29D, 38, 38A-38G, 39A-39F, 42A-42K, 44A-44D, and 45A-45B, using electronic communication, or via direct user-input to a display monitor interface according to some embodiments. Further, FIG. 48C illustrates a side view of the end cap 4800 of FIG. 48B in accordance with some embodiments of the invention. In some embodiments, this perspective shows a rod 4805 fixed inside the end cap handle 4830, equipped with a trigger 4833 rotating on a spring-loaded hinge 4831 and mounting a TMSM 4819 on the trigger arm 4841. In some embodiments, this figure also displays the tracked DRF 4815 used for interpreting the end caps location and pose in 3D space, and two relative anatomical axes indicators with inferior 4849 and posterior 4843 shown. Some embodiment can be applied to any application mentioned below with regards to a tracked DRF-equipped end cap, in reference to FIGS. 49D, 50E, 51H-51I, 56, and 87A.

Some embodiments of the invention can be used to assess the contour of a rod prior to implantation via coupling a tracked end cap, previously described in FIGS. 47A and 48A-48C, with a fixed-base, single-ring assessment device. In some embodiments, rather than utilizing two handheld tools to assess the rod contour, as previously described, this device enables rod contour assessments via mounting the rod to one handheld end cap and passing the rod through a substantially rigidly-fixed ring device. In some embodiments, because the diameter of the ring is designed or adjusted to be closely matching the diameter of the rod, this embodiment forces the portion of the rod engaged with the ring to be nearly concentric with the ring. In some embodiments, to compute the contour of the rod from this embodiment, the acquisition system interprets the path traveled by the end cap, rather than the path traveled by the slider relative to the end cap, as previously described. In some embodiments, the software interpretation of this invention is described in detail below in reference to FIG. 75.

Figures 49A, 49B, 49C, 49D:
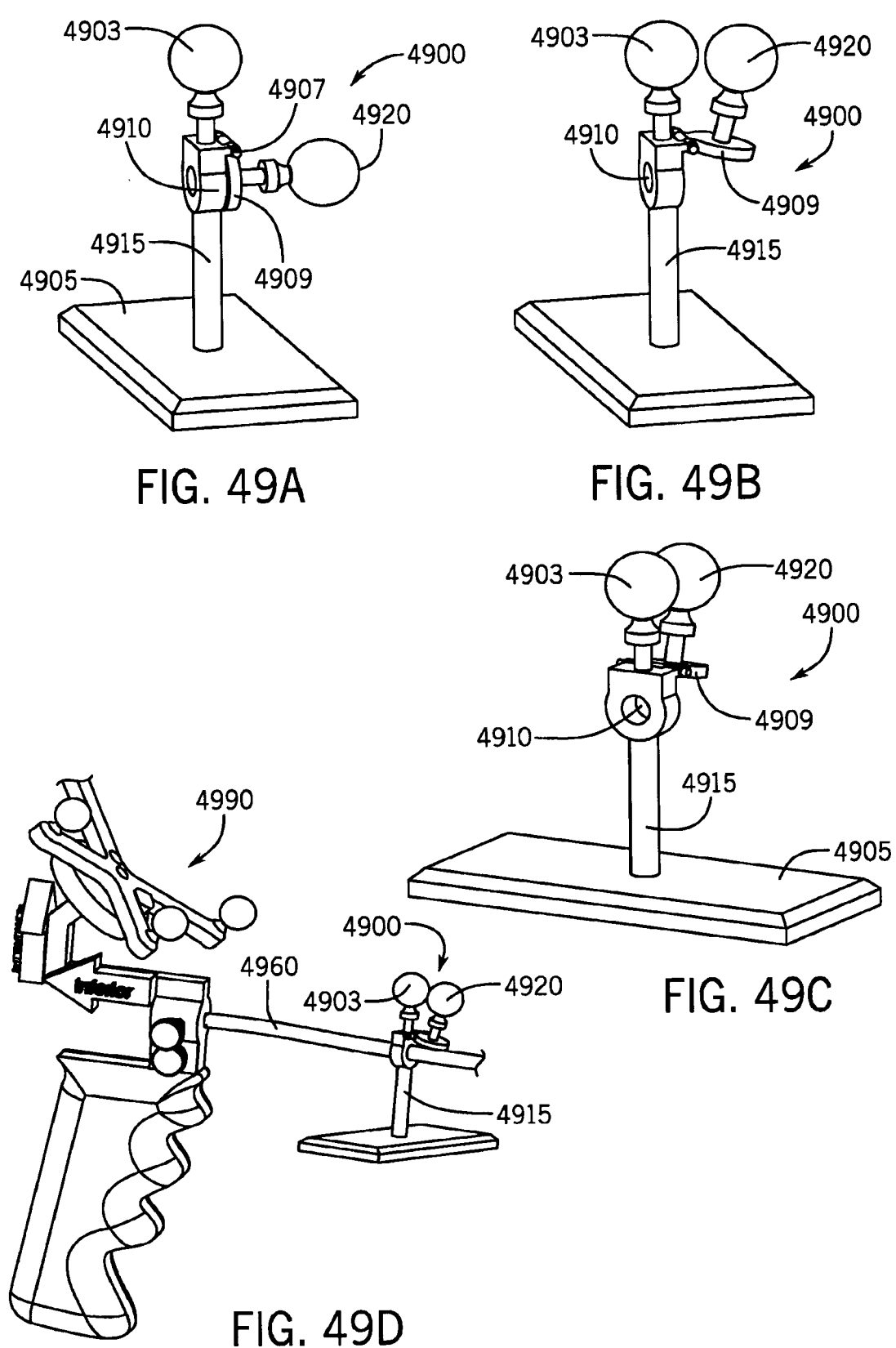

FIG. 49A displays assembly 4900 used to assess the contour of the rod prior to implantation, applied to when a rod is attached to a tracked end cap according to some embodiments. Some embodiments consists of a fixed base 4905 with a coupled post 4915 holding a rod-receiving ring 4910 designed for a rod of set diameter to pass through. In some embodiments, attached to the ring is a TSM 4903 as well as a hinge 4907 about which a hinged flap 4909, shown in the closed position, rotates. In some embodiments, a TMSM 4920 is attached to the hinged flap and used to signal to the acquisition system when a rod is engaged with the ring 4910 via the TMSM 4920 attached to the hinged flap 4909 moving relative to the TSM 4903 attached to the ring. In some embodiments, the software interpretation of this motion is completed by simply comparing the distances between the TSM 4903 and the TMSM 4920 when the hinge 4907 is closed versus opened. In some embodiments, the hinged flap 4909 stays closed in the absence of a rod through the force of gravity acting on the TMSM 4920 attached to the hinged flap 4909. In some embodiments, the hinged flap can also be spring loaded. It should be noted that in some embodiments of this design, the fixed base 4905 can be resting on a surface, or mounted to a rigid surface including a component of a robot according to some embodiments.

FIG. 49B displays the invention described previously in FIG. 49A, except with the hinged flap 4909 and its attached TMSM 4920 in the open position, analogous to its position when a rod 4960 is inserted into the ring 4910 and pushing up on the hinged flap 4909. FIG. 49C displays a different view of some embodiments of the invention described previously in FIGS. 49A-B, with the hinged flap 4909 and its attached TMSM 4920 in the open position, and direct visualization of the rod-receiving ring 4910, held up from the base 4905 by a rigid post 4915. FIG. 49D illustrates the assembly of FIGS. 49A-49C coupled with a rod and tracked end cap previously described in relation to FIGS. 47A, and 48A-48B in accordance with some embodiments of the invention.

FIG. 49D displays the fixed-base, single-ring rod assessment device as previously described in FIGS. 49A-C, coupled with a rod 4960 and tracked end cap 4990, previously described in FIGS. 47A and 48 according to some embodiments. Some embodiments show the rod 4960 pushing the hinged flap 4909 out of the way and by doing so, actuating the TMSM 4920 attached to the hinged flap 4909. In some embodiments, when the software acquisition system detects the distance between the TSM 4903 and the TMSM 4920 closer than that when the hinged flap is closed, it is triggered to record the coordinates of the end cap. In some embodiments, the recorded coordinates of the end cap's path can then be used to calculate the contour of the rod, as described in detail in FIG. 75. In some embodiments, the user can trigger the acquisition via other triggering methods described previously in relation to FIG. 48B. Following registration of the contour of a rod attached to a tracked end cap, the tracked end cap can be used for the user to directly interface with the display monitor portraying the rod contour, as described in detail below in reference to FIG. 78.

FIGS. 50A-50D illustrates embodiments of a fixed-base, variable-ring, mobile rod assessment device in accordance with some embodiments of the invention. In some embodiments, the device assembly is described in FIGS. 49A-49D, in which it is able to accommodate the contour assessment of a series of rod diameters via a variable-ring-size selector component. In some embodiments, after the user rotates the appropriate diameter ring in front of the hinged flap by using the retractable spring plunger, a rod of corresponding diameter attached to a tracked end cap can then be passed through the ring and have its contour interpreted in the same method previously described in relation to FIGS. 49A-49D.

Referring initially, FIG. 50A, illustrating a front view of an embodiment 5000, fixed base 5001 coupled to post 5005 is shown to which a revolving rod-width selector 5007 containing multiple rod-receiving rings 5009 of varying diameter is coupled via a fastener 5011 and can be rotated into preset angles via a retractable spring plunger 5013, and a TSM 5017 fixed to the post 5005 according to some embodiments. In some embodiments, the rod-width selector 5007 containing rings of varying diameter is designed to enable this embodiment of the device to accommodate varying diameter rods rather than necessitating multiple devices.

FIG. 50B displays an oblique view 5001 of the device shown in FIG. 50A with the rotating rod-width selector 5007, retractable spring plunger 5013, and fastener removed according to some embodiments. In some embodiments, discrete-angle detents 5015 receive the retractable spring plunger 5013 at set angles. In some embodiments, a hinge 5019 interfaces with a hinged flap 5021, shown in the closed position, and with an attached TMSM 5023, as previously described in relation to FIGS. 49A-49D. FIG. 50C displays a rear view 5002 of the invention shown in FIG. 50B. FIG. 50D displays an embodiment 5003 of the invention as described previously in relation to FIGS. 50A-C, interfacing with a rod 4960 passing through one of the fixed rings and pushing the hinged flap 5021 and its attached TMSM 5023 to the open position according to some embodiments.

FIG. 50E illustrates the fixed-base, variable-ring, mobile rod assessment device of FIGS. 50A-50D engaged with a rod 4960 coupled to an end cap 5095 in accordance with some embodiments of the invention. In some embodiments, as described previously in FIG. 49D, the end cap 5095 is used to track the path of the end of the rod 4960 as its length is passed through the fixed ring. In some embodiments, the software to calculate the rod's contour from this interaction is described below in reference to FIG. 75. Some embodiments include a linearly-actuated TMSM 5023 that is moved when the rod 4960 is passed through the fixed ring. In some embodiments, following registration of the contour of a rod attached to a tracked end cap, the tracked end cap can be used for the user to directly interface with the display monitor portraying the rod contour, as described in detail below in reference to FIG. 78.

Some embodiments of the invention include a handheld, mobile rod contour assessment device. In reference to FIGS. 51A-51I, some embodiments include a method of using two handheld tracked devices to assess the contour of a rod prior to implantation. In some embodiments, to utilize some embodiments to register the contour of a rod, the rod is substantially rigidly fixed within the tracked end cap, as previously described in FIGS. 48A-C, 49D and 50E, and then the tracked slider, previously described in FIG. 47B, is slid over the surface of the rod one or more times. For example, FIG. 51A displays a side view of 5100 of the invention which is a tracked end cap, previously described in FIGS. 47A, 48, 49D, and 50E according to some embodiments. In some embodiments, it consists of a handle 5101, rod mount hole 5103, anatomical axes reference labels (5105, 5107), a tracked DRF 5189 (made of 3D-trackable markers 5188 in a unique configuration), a set screw 5108 to fasten the DRF mount to the handle 5101, and a set screw 5109 for substantially rigidly fixing the rod in place. In some embodiments, when inserted and fixed within this device, the rod is interpreted by the acquisition software relative to the anatomical labels contained on the device. FIG. 51B displays a front view of the invention, a tracked end cap, shown previously in FIG. 51A. FIG. 51C displays a rear view of the invention, a tracked end cap, shown previously in FIGS. 51A-51B according to some embodiments.

FIG. 51D displays an assembled view of the invention, a tracked slider, described previously in relation to FIG. 47B, consisting of a handle 5129, rod-centering fork 5130, tracked DRF 5136 (made of 3D-trackable markers 3135), spring-loaded depressible shaft 5140, and shaft-mounted TMSM 5145 according to some embodiments. In some embodiments, when used with a rod fixed to the tracked end cap previously described in relation to FIGS. 51A-51C, this embodiment is able to register the coordinates of the rod by sliding along its surface. In some embodiments, when it is fully engaged with the surface of the rod, the sliding shaft and attached TMSM are actuated, and the acquisition system is triggered to record the coordinates corresponding to the center of the rod. In some embodiments, the software to calculate the coordinates of the rod is described below in reference to FIGS. 73A-73B, and 74. Some embodiments include a coupled ring as previously described in reference to FIGS. 49A-49D, and 50A-50E. Additionally, in some embodiments, linearly actuating a TMSM is only one method of triggering to the acquisition system that the slider is fully engaged with the rod. Some embodiments include, but are not limited to, rotational motion of a TMSM, handheld triggering on the tracked slider or tracked end cap, electronic communication from embedded electronics on the tracked end cap or tracked slider, or direct user input via software interface.

FIG. 51E displays a rear view of the embodiment shown previously in FIG. 51D displaying the depressible shaft 5140, rod-centering fork 5130, and tracked DRF 5136. FIG. 51F displays a closeup view of some embodiment shown previously in FIGS. 51D-51E in which the tracked DRF 5136, spring 5150 and spring-loaded depressible shaft tip 5140, and its attached TMSM 5145 are visible. In some embodiments, the sliding shaft 5140 and its mounted TMSM are in the extended position, indicating that the tracked slider is not engaged with a rod.

FIG. 51G displays a closeup view of the embodiment shown previously in FIGS. 51D-F in which the engaged depressible shaft 5155 and its mounted TMSM 5160 are in the depressed location, which if at a preset height corresponding to the rod diameter being used, would indicate to the acquisition software that the tracked slider is firmly engaged with a rod and its coordinates should be recorded according to some embodiments. Further, FIG. 51H displays the invention which is a mechanism of registering the contour of a rod prior to implantation by substantially rigidly fixing a rod 5170 in a tracked end cap and sliding the tracked slider over the rod one or more times according to some embodiments. Following registration of the contour of a rod attached to a tracked end cap, the tracked end cap can be used for the user to directly interface with the display monitor portraying the rod contour, as described in detail below in reference to FIG. 78. FIG. 51I displays another view of some embodiments of the invention previously shown in FIG. 51H.

Some embodiments of the invention include a TMSM-based, implanted rod contour assessment device. Some embodiments are used to assess the contour of a rod after it has been implanted into a patient. Some embodiments utilize the rod-centering fork design with a sliding shaft and spring-loaded TMSM, previously described in FIGS. 47A and 51D-51I on the end of a tracked probe, such that it can fit into the surgical site and trace over the implanted rod. In some embodiments, the probe is able to skip over any obstructing hardware without its coordinates being recorded because the acquisition system is only triggered to record when the TMSM is in the position corresponding to the sliding shaft being depressed by a rod of a preset diameter. In some embodiments, the software for calculating and interpreting the rod contour is described below in relation to FIGS. 76, and 77A-77C.

FIG. 52A illustrates a component of a TMSM-based, implanted rod contour assessment device 5200 in accordance with some embodiments of the invention. In some embodiments, the device 5200 comprises a probe shaft 5210, rod-centering fork 5230, 5235 for interfacing with a rod, mounts 5215 for tracked DRF markers (not shown) to be inserted, mounts 5225 for spring(s), a depth-stop for a sliding shaft 5220 and sliding shaft guides 5205 to prevent the inserted shaft (not shown) from rotating. Some embodiments are intended to be coupled with the embodiment described below in reference to FIG. 52B.

FIG. 52B illustrates a depressible sliding shaft for coupling to the component of FIG. 52A comprising a depressible sliding shaft 5250 with rounded tip 5264, mounts 5260 for springs, threaded hole 5268 for adjustable depth-stop, mount 5209 for a TMSM, and a guide-fitting profile 5252 to prevent rotation when inserted within its complementary probe described above in relation to FIG. 52A according to some embodiments.

FIG. 52C illustrates a top view of the component of FIG. 52A in accordance with some embodiments of the invention, and shows spring mount 5225, and sliding shaft through-hole 5229, able to accommodate the sliding shaft 5250 in relation to FIG. 52B. FIG. 52D displays another view of the embodiment shown previously in FIG. 52B, enabling closer visualization of the depressible sliding shaft 5250, spring mounts 5260, threaded hole 5268 for an adjustable depth-stop, mount 5209 for a TMSM, and a guide-fitting profile 5252.

FIG. 53A displays some embodiments of a device 5300 configured to assess the contour of a rod after it has been implanted within the surgical site. In some embodiments, the this figure comprises an assembly of the components described previously in relation to FIGS. 52A-52D. In some embodiments, the device 5300 comprises a tracked probe 5310 with a rod-centering fork 5315, through-hole (not shown) to accommodate a depressible sliding shaft 5335, with a coupled TMSM 5325, and tracked DRF 5320 (made of several 3D-trackable markers 5330). In some embodiments, this is used to engage with an implanted rod (not shown) such that the rod depresses the depressible sliding shaft 5335, thereby moving the attached TMSM 5325 relative to the attached tracked DRF 5320. In some embodiments, when the TMSM 5325 moves relative to the tracked DRF 5320 by a preset amount based on the rod diameter, the acquisition system is triggered to record the coordinates corresponding to the center of the rod, as described below in reference to FIGS. 76-77. Further, FIG. 53B illustrates a close-up rear view of a portion 5301 of the assembly of FIG. 53A in accordance with some embodiments of the invention. Further, FIG. 53B displays a rear view of the embodiment of the invention shown previously in 53A, visualizing the depressible sliding shaft 5335, its attached TMSM 5325, the tracked DRF 5320, springs 5354, depth-stop 5356 for sliding shaft, and depth-stop set screw 5352 used to adjust the maximum protrusion length of the sliding shaft tip beyond the bifurcation of the fork according to some embodiments. Some embodiments do not possess a mechanism of adjusting the maximum protrusion length of the sliding shaft. Additionally, in some embodiments, the external springs referenced in this embodiment can consist of internal compressible springs, torsion springs, and memory-embedded materials within some embodiments. In some embodiments, this figure displays how the sliding shaft guides prevent rotation of the sliding shaft, restricting the TMSM 5325 to linear motion relative to the tracked DRF 5320.

FIG. 53C displays a closer view of the rod-interface region of the embodiment shown previously in FIGS. 53A-53B according to some embodiments. In some embodiments, the spring-loaded depressible sliding shaft 5335a is in its extended position. In this position the acquisition system is not triggered to record the coordinates of the probe, as it is not indicating that it is interfacing with a rod to be measured. Further, FIG. 53D displays a view of the embodiment described previously in FIGS. 53A-53C interfacing with a rod 5367 within the rod-centering fork 5315 and depressing the sliding shaft 5335b into the depressed position causing the attached TMSM (not shown) to move relative to the probe's attached DRF (not shown), indicating for the acquisition system to record 3D coordinates corresponding to the center of the rod's cross-section according to some embodiments.

FIG. 53E displays a closer view of the tracked DRF portion of the device embodiment described previously in relation to FIGS. 53A-53D according to some embodiments. In some embodiments, the location of the TMSM 5325a relative to the tracked DRF 5320 as shown, corresponds to the depressible shaft being in the extended position, as shown in FIG. 53C. In some embodiments, in this configuration, the acquisition software is not triggered to record the probe's coordinates. FIG. 53F displays a closer view of the tracked DRF 5320 portion of the device embodiment described previously in relation to FIGS. 53A-E showing sliding shaft guide 5329 according to some embodiments. In some embodiments, the location of the TMSM 5325b relative to the tracked DRF 5320 as shown, corresponds to the depressible shaft 5335 being in the depressed position, as shown in FIG. 53D. In some embodiments, the acquisition software is triggered to record the location of the probe, from which the rod's coordinates can be calculated as described below in reference to FIGS. 76-77.

Some embodiments of the invention include a conductivity-based, implanted rod contour assessment device. Some embodiments are intended to assess the contour of a rod after it has been implanted within the surgical site. Some embodiments differ from those previously described in relation to FIGS. 52A-52D, and 53A-53F, in that it possesses electrical contact terminals on the inside walls of the rod-centering fork. In some embodiments, these electrically-isolated terminals are used then to sense conductivity between them. In some embodiments, in the absence of a rod touching both terminals, no current flows between them. In some embodiments, when a rod is fully engaged within the fork however, current flows from one contact to another, indicating that the device is fully engaged with the rod, and the contour assessment device electrically communicates, either wirelessly or through a wire, with the 3D-tracking acquisition system that it should record the coordinates of the device. Therefore, in some embodiments, embedded in the probe is a small power supply via battery or capacitor, and circuit components to communicate with the acquisition system. For example, FIG. 54A displays the invention (assembly 5400) which includes a probe shaft 5410 equipped with a rod-centering fork 5425 on one end and a tracked DRF 5415 on the other according to some embodiments. Some embodiments can be applied to an already-implanted spinal rod and used to assess its 3D contour by sliding the internal sides of the fork 5425 along the exposed surfaces of the rod 5440. In some embodiments, this device fork possesses electrical contact terminals, described below in reference to FIG. 54B, on the inside surfaces of the rod-centering fork 5425, and internal electronics within the rod (not shown) that detect when current flows between them. In some embodiments, when current flows between the terminals, the contour assessment tool signals for the acquisition system to record its location in space. Some embodiments of the probe's communication method with the acquisition system include but are not limited to wireless radiofrequency transmission, optical signaling via infrared or visible light illumination of elements on the probe that are detected by the system, and wired signal transmission. In some embodiments, the process of interpreting the rod's location and contour relative to the probe is described below in reference to FIGS. 76, and 77A-77C.

FIG. 54B illustrates a rod-centering fork and electrical contact pads of the device of FIG. 54A in accordance with some embodiments of the invention. FIG. 54B provides better visualization of the rod-centering fork 5425 and electrical contact pads 5427a, 5427b located on the inner surface of each arm of the fork according to some embodiments. In some embodiments, the probe is unable to signal that it is active, unless an electrical conductor connects both contact terminals. It should be noted that the shape of the contact terminals can be different in some embodiments, including but not limited to cylindrical, semi-cylindrical, flat, and curved surfaces with variation in their distance of protrusion from the inside surface of the fork.

FIG. 54C displays the embodiment previously described in relation to FIGS. 54A-54B interacting with a rod 5440 that is not fully seated within the fork according to some embodiments. In this configuration, in some embodiments, the rod 5440 is not approximating both electrical contact plates, and therefore the assessment device is in the inactive, non-tracking state. Further, FIG. 54D displays the embodiment previously described in relation to FIGS. 54A-54C interacting with a rod 5440 that is fully engaged within the fork according to some embodiments. In this configuration, in some embodiments, the metal rod is approximating both electrical contact pads (5427a, 5427b of FIG. 54B) of the fork and therefore conducting a current across it. In some embodiments, when current is being conducted, the probe then signals to the 3D-tracking acquisition system that it is in the active state and its coordinates are recorded to be used for computing the rod contour as described below in reference to FIGS. 76, and 77A-77C.

Some embodiments include a 3D-tracked, manual mobile rod bender. Some embodiments can be utilized with an already-registered rod attached to a tracked end cap, to both bend and re-register the updated contour of the rod during bending. Some embodiments also allows for visualization of the precise position of the tracked handheld rod bender relative to a previously registered rod on a display monitor. Additionally, in some embodiments, this system also allows for software-assisted and software-directed bending, instructing the user where to place and how to maneuver a tracked, handheld rod bender, to contour the rod to a pre-determined shape. In some embodiments, the capabilities of this embodiment and its variations are described in more detail below in reference to FIGS. 56A-56F, 79A-79G, and 81.

Figures 55A, 55B, 55C, 55D, 55E, 55F, 55G, 55H, 55I:
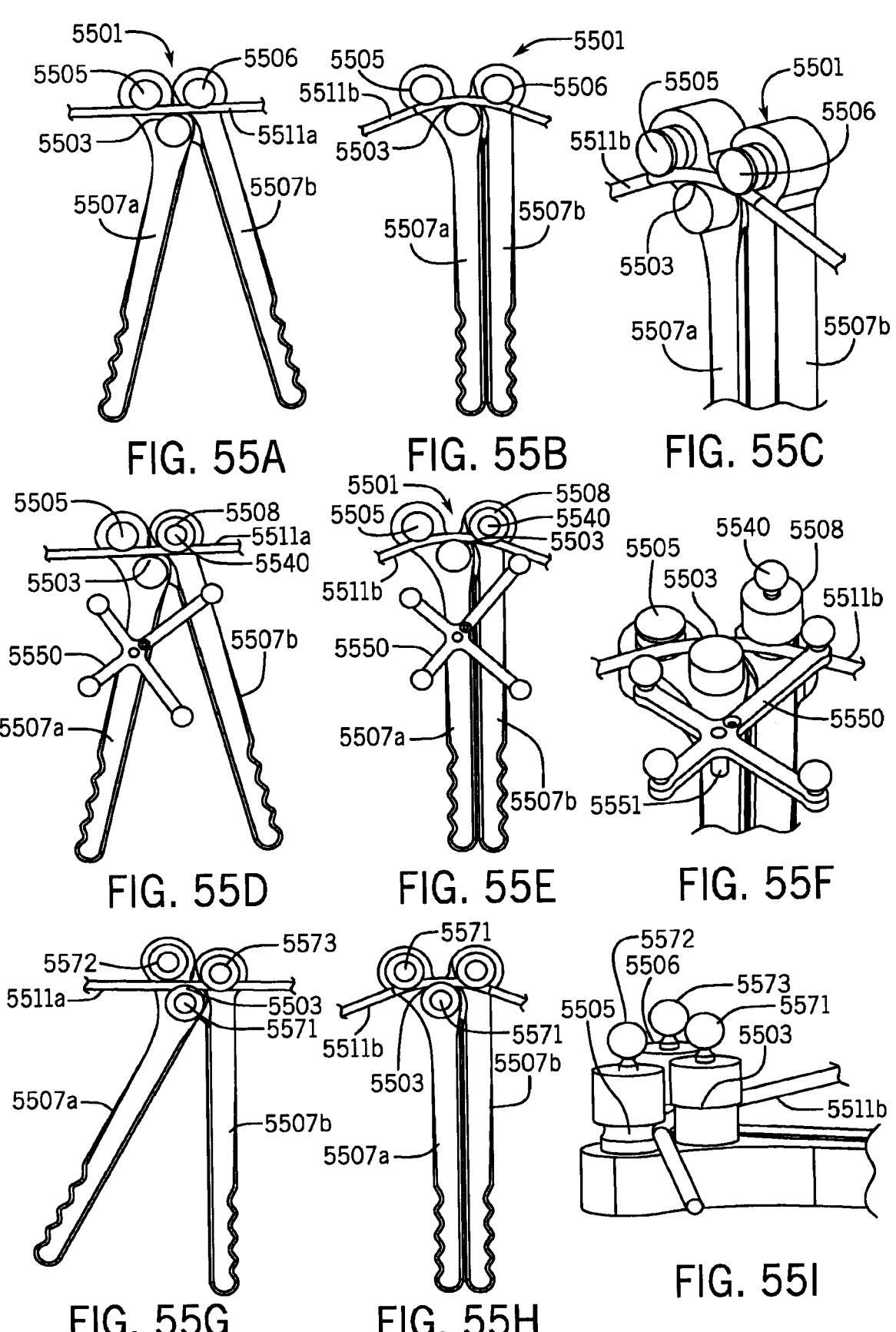

FIG. 55A displays the invention, which is a handheld rod bender 5501 consisting of two handles with handle #1 5507a, containing the center rod contouring surface 5503, and left outer roller 5505 and handle #2 5507b containing the right outer roller 5506 according to some embodiments. Some embodiments shown is interfacing with a straight rod 5511a approximating both rollers and center bend surface, as the bender handles (5507a, 5507b) are positioned at an open angle to one another. Further, FIG. 55B displays the embodiment of the invention described in relation to FIG. 55A, with the rod bender's handles approximated, resulting in a bent rod 5511b contour according to some embodiments. FIG. 55C displays a closer view of the rod-interface points of the bender 5501, shown previously in FIG. 55B interfacing with a bent rod 5511b according to some embodiments.

FIG. 55D displays the invention which consists of a handheld rod bender coupled to rod 5511a, previously described in relation to FIGS. 55A-55C, equipped with a tracked DRF 5550 fixed to handle #1 5507a, a roller mount 5508 on outer roller 5506 and a TMSM 5540 fixed to the roller mount 5508 according to some embodiments. In some embodiments, as displayed, the rod bender 5501 is interfacing with a straight rod 5511a, necessitating that the bender's handles 5507a, 5507b are positioned at a wide angle from one another to accommodate the straight rod. In some embodiments, with the tracked DRF 5550 mounted to handle #1 5507a, the 3D-tracking acquisition system can register the location and pose of both the center rod contouring surface and the left outer roller. In some embodiments, with the TMSM 5540 attached to the right outer-roller 5506, it enables the acquisition system to then register the location of the right outer roller relative to the two-other rod-interface points of the bender. In some embodiments, with the ability to locate all three rod-interface points on the bender in 3D space, the acquisition system can interpret the relative angle between the bend handles, and with known rod diameter, the degree of bending induced into a rod. In some embodiments, when this embodiment of the invention is coupled to a previously registered rod, fixed to a tracked end cap, as described previously in relation to FIGS. 49D, 50E, 51H-51I, the acquisition system is able to interpret when the three rod-interface points on the tracked bender are engaged with the previously registered rod. In some embodiments, when that is the case, the software system is able to provide live tracking of the bender relative to the rod, real-time updates of the rod contour during bending, and software-assisted bending instructions, as described below in reference to FIGS. 56A-56F, 79A-79G, 80-81, 87A-87K, and 88A-88F. Further, FIG. 55E displays the device 5501 as previously described in FIG. 55D, except with the rod bender handles 5507a, 5507b coupled, resulting in a bent rod 5511b according to some embodiments. Further, FIG. 55F displays another view of the embodiment shown in FIG. 55E and described previously in relation to FIG. 55D according to some embodiments. In some embodiments, this perspective enables visualization of the mounting post 5551 for the tracked DRF 5550 attached to handle #1 5507a. It should be noted that in some embodiments, the tracked DRF 5550 is coupled to varying locations on handle #1 5507a and at varying angles and offset heights from the handle. In some embodiments, this figure displays only the relative positioning of the tracked DRF 5550 to the rod bender handle. In some embodiments, the same variation applies for the relative positioning of the TMSM 5508 (as marked in FIG. 55D) to handle #2 5507b. In some embodiments, it is located directly over the right outer roller 5506, it can be positioned anywhere on handle #2 5507b to provide the input information the software needs to calculate the aforementioned embodiments of the invention.

Some embodiments include a spring-loaded TMSM attached to the center rod contouring surface of the rod bender such that it moves the stray marker only when the rod is fully pressed up against the surface of the center rod contouring surface, and thereby serving as an indicator of when the rod is fully engaged with the bender (i.e., only when the rod is "being bent" or "engaged"). For example, some embodiments include a spring-loaded (not shown) TMSM (not shown), coupled to the center rod-contouring surface 5503 in such a way that it is fully deflected only when the rod is fully approximated against the center rod-contouring surface 5503 of the rod bender. In this way, in some embodiments, the acquisition system has an additional method of indicating when the contour of the rod is actively being bent.

In reference to FIGS. 55A-55I, and 56A-56F, in some embodiments, the tracked bender can be a universal adapter design such that it can be applied to other user-operating rod benders, especially table-top benders that are used in the operating room. Further, in some embodiments, it is also essential to note that rod cutters can also be equipped with tracking accessories in a similar manner in order to see where the digital overlay of the rod will be cut. It should be noted that some embodiments can also be applied to other user-operating rod benders that involve two or more contact points with a rod to induce curvature. In some embodiments, these principles are applied to instruments used for rod cutting, such that the location of the cutter relative to a previously registered rod can be visualized.

FIG. 55G displays an alternative bender embodiment of the invention from that described previously in relation to FIGS. 55D-55F, in which the rod bender is equipped with two TMSMs on handle #1 5507a (shown as 5571, 5572), and one TMSM 5573 on handle #2 5507b according to some embodiments. In some embodiments, the three TMSMs 5571, 5572, 5573 are utilized to localize the position of each rod-interface point on the bender. In some embodiments, because the three TMSM mounting points shown are directly over the three rod-interface points of the rod bender, the acquisition software can localize the plane of the rod bender defined by the three markers 5571, 5572, 5573, and then offset it by a known amount based on the known offset between the TMSMs and the rod-interface points on the bender. In some embodiments, the acquisition system is able to reliably interpret the direction of offset from the plane defined by the three TMSMs, based on the viewing angle restrictions of a single optical 3D-tracking system, which defines the normal vector the TMSM plane as that which is less than 90 degrees from the vector drawn from the center of the three markers to the 3D-tracking camera. In some embodiments, in this configuration, the tracked bender is able to achieve the same functionality as described previously in relation to FIG. 55D. Some embodiments include attaching more than three TMSMs to the bender, as well as placing the TMSMs in alternative locations than directly over the rod-interface components of the rod bender. In some embodiments, as shown in this figure, the tracked bender is interfacing with a straight rod 5511a, necessitating that the angle between the bender handles be positioned at a wide angle relative to one another. In some embodiments, in this configuration, because the distance from the center bend surface to each of the outer rollers is the same, the angle between bender handles, and thereby the degree of bending, can be calculated based on the angle between the two equally-spaced TMSMs 5572, 5573 from the center TMSM 5571.

FIG. 55H displays the invention as previously described in FIG. 55G, except with the rod bender handles approximated, resulting in a bent rod 5511b according to some embodiments. FIG. 55I displays another view of the embodiment shown in FIG. 55H and described previously in relation to FIG. 55G according to some embodiments.

FIGS. 56A-56F further describe the invention previously described in relation to FIGS. 55A-55I according to some embodiments. In some embodiments, depicted are the necessary components of the invention to track bending in real-time, as well as utilize software-assisted instructed bending are all displayed. Furthermore, in some embodiments, an additional embodiment of the device is introduced within this figure, that enables the ability to account for shape memory that rod material may experience during and after bending when computing the real-time tracking of bending and computing the re-registered rod. For example, FIG. 56A displays the device 5600 previously described in relation to FIGS. 55G-55I, in which a pre-registered rod 5610 is fixed within a tracked DRF-equipped end cap 5605, and a tracked rod bender 5501b is equipped with three TMSMs interfaces with the rod according to some embodiments. In this configuration, in some embodiments, the acquisition software can interpret the location of the tracked rod bender relative to the previously-registered rod 5610 within the tracked end cap's relative coordinate system. With this configuration, in some embodiments, the acquisition system can provide live tracking of the bender relative to the rod, real-time updates of the rod contour during bending, and software-assisted bending instructions, as described below in reference to FIGS. 79A-79G, 81, 87A-87G, and 88A-88F.

Figures 56A, 56B, 56C, 56D, 56E, 56F:
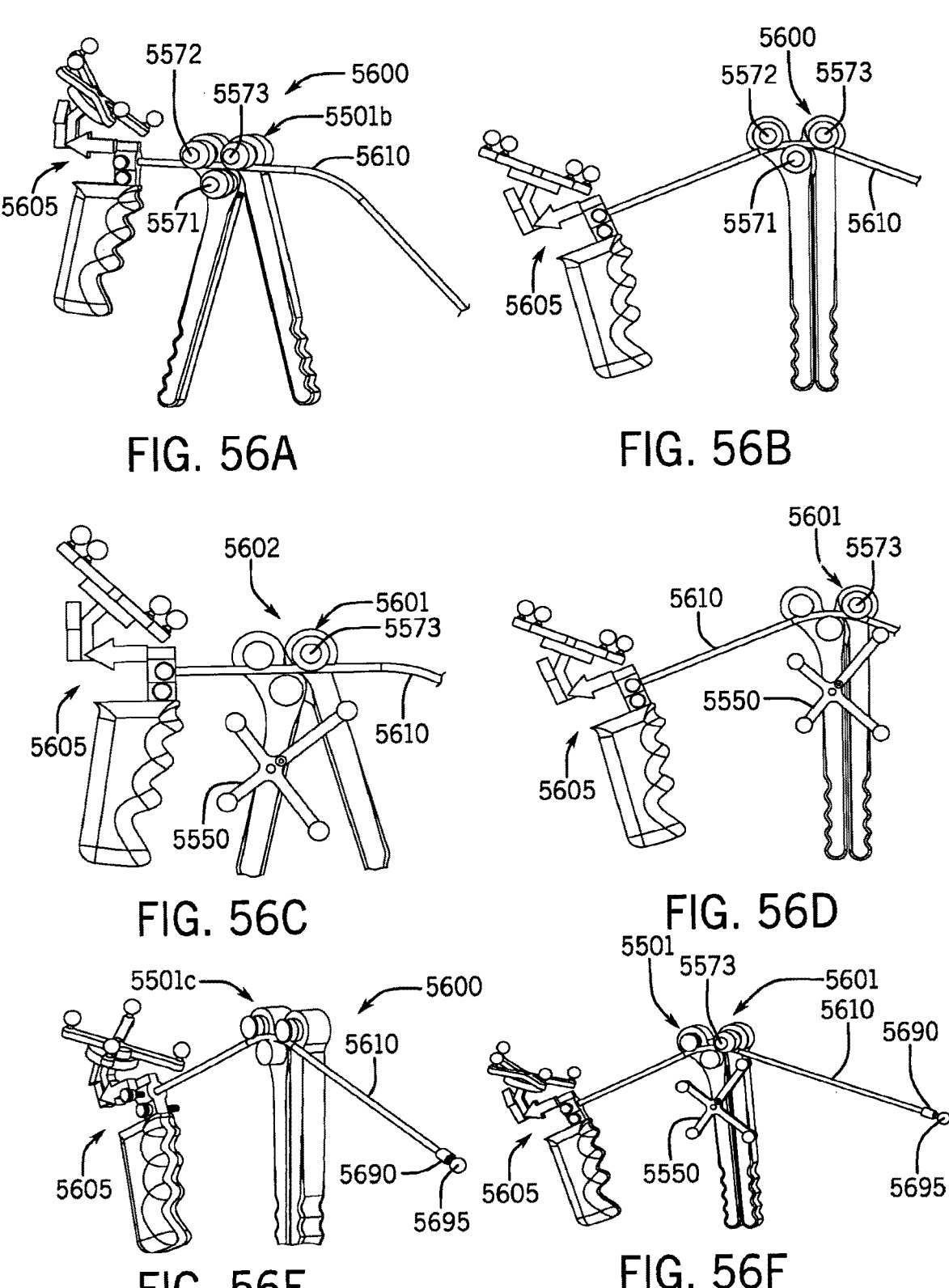

FIG. 56B shows another configuration of the embodiment previously described in relation to FIG. 56A, in which the tracked rod bender 5600 is engaged with an alternative location of the rod that is bent, displaying how the angle between the handles and associated TMSMs changes from when the bender is interfacing with a straight portion of the rod, as shown in FIG. 56A according to some embodiments.

FIG. 56C displays the device (assembly 5602) previously described in relation to FIGS. 55D-55F, in which a pre-registered rod 5610 is fixed within a tracked-DRF-equipped end cap 5605 and a tracked rod bender (assembly 5602 with end cap 5605 and rod bender 5601) is equipped with a tracked DRF 5550 on one handle and a TMSM 5573 on the other according to some embodiments. In some embodiments, with this configuration, the acquisition system is able to provide live tracking of the bender relative to the rod, real-time updates of the rod 5610 contour during bending, and software-assisted bending instructions, as described below in reference to FIGS. 79A-79G, 81, 87A-87K, and 88A-88F.

FIG. 56D shows another configuration of some embodiments 5602 previously described in relation to FIG. 56C, in which the tracked rod bender 5601 is engaged with an alternative location of the rod that is bent 5610, displaying how the angle between the handles and associated TMSM 5573 relative to the tracked DRF 5550 changes from when the bender is interfacing with a straight portion of the rod 5610, as shown in FIG. 56C.

FIG. 56E displays some embodiments of 5600, which consists of a tracked DRF-equipped end cap 5605, fixed to a pre-registered rod 5610, non-tracked manual bender 5501c, and a rod cap 5690 with a TMSM 5695 mounted to it. Some embodiments represent an alternative mechanism and method of updating the previously-registered contour of a rod while it is being bent with a handheld bender. In some embodiments, because the bender is not tracked, the location of the TMSM is detected relative to the tracked end cap to which the rod is fixed. In some embodiments, whenever the system detects relative motion between the TMSM 5695 and the tracked DRF on the end cap 5605, the acquisition system records the path traveled by the TMSM 5695 relative to the end cap 5605. In some embodiments, with known geometry of the rod bender's center bend surface, the path of the TMSM is used to calculate the location and curvature of each bend, as described below in reference to FIG. 80.

FIG. 56F displays 5601 comprising a tracked DRF-equipped end cap 5605, fixed to a pre-registered rod 5610, tracked manual bender 5501 equipped with a tracked DRF 5550 and one TMSM, and rod cap 5690 with a TMSM 5695 mounted to it according to some embodiments. In some embodiments, the contour of the previously-registered rod is updated during bending by the combination of tracking both the rod bender's conformation at interfacing regions of the rod, as described previously in relation to FIGS. 55D-55F, as well as the motion of the TMSM-equipped rod cap relative to the tracked end cap to which the rod is fixed. In this configuration, in some embodiments, the acquisition system is able to account for shape memory within the rod material, that previously described embodiments without the TMSM-mounted rod cap were not. In some embodiments, because the end of the rod opposite to the DRF-equipped end cap is tracked in this embodiment, after the rod bender achieves its minimum angle between handles when interfacing with a particular region of the rod, if the rod material retains some of its shape memory and recoils, the TMSM-equipped rod cap will move relative to the DRF-equipped end cap, and the acquisition system software can now account for this memory when recomputing the rod's contour as described in more detail in relation to FIG. 80. As with some embodiments described in FIGS. 56A-56E, this configuration also enables software-assisted bending and interfacing with display monitor, as described below in reference to FIGS. 79A-79G, 80-81, 87A-87G, and 88A-88F.

Some embodiments of the invention include a 3D-tracked, manual implanted rod bending system which enables the ability to track the bending of a rod that has already been implanted within the surgical site. In some embodiments, the user interfaces with an implanted rod using DRF-tracked and trigger-equipped in-situ benders after already registering the contour of the implanted rod via mechanisms described previously in relation to FIGS. 52A-52D, 53A-53F, and 54A-54B. For example, some embodiments include DRF-tracked and trigger-equipped in-situ benders coupled to a rod in accordance with some embodiments of the invention. In some embodiments, two tracked in-situ benders, each equipped with unique tracked DRFs (5705a, 5705b), can interface with a pre-registered rod to alter its contour after implantation. In some embodiments, because the tracked in-situ benders interface with an already-registered rod 5711, their position relative to the registered rod can be displayed via display monitor. Additionally, in some embodiments, because they are equipped with depressible sliding shafts 5735 to serve as triggers indicating when they are fully engaged with the rod, their movement will not result in alteration in the software-recorded-contour of the registered rod unless two or more in-situ benders are triggered simultaneously and moved relative to one another while triggered. For example, FIG. 57A displays 5700 of the invention consisting of a tracked in-situ bender with handle 5710a, 5710b, rod interface head 5725a, 5725b equipped with depressible sliding shaft tip (not shown) coupled to pre-registered rod 5711, TMSM 5707a, 5707b mounted to depressible sliding shaft, and tracked DRF 5705a, 5705b according to some embodiments. Further, in reference to FIG. 57B, showing some embodiments 5701 with a spine 5713 with instrumented pedicle screw shafts 5718, tulip heads 5739, an implanted pre-registered rod 5750, and cap screws 5738, in some embodiments, both triggers on the benders can be depressed, actuating the TMSMs (5707a, 5707b) relative to the associated DRFs (5705a, 5705b), indicating to the acquisition system that they are fully engaged with the rods.

FIG. 57C illustrates a close-up view of the rod (marked as 5711) of FIG. 57A in accordance with some embodiments of the invention, and FIG. 57C displays another view of some embodiments shown in FIG. 57A engaging with a pre-registered rod 5711. FIG. 57D illustrates a close-up view of a rod-interface head 5725 of the bender show in in FIG. 57A including a view of a depressible sliding shaft 5735 with depressible sliding shaft tip 5735a in an extended position towards the surface 5730 that can accept the rod 5711 in this assembly view according to some embodiments. In some embodiments, at least a portion of the surface 5730 can comprise a curved or concave surface 5730a that can complement and/or maximize engagement and/or surface contact with a curved surface of a rod (e.g., such as rod 5711).

Some embodiments of the invention enable the use of skin-mounted fiducial markers to serve as surrogate markers from which the location of the underlying anatomical landmarks can be calculated. For example, FIG. 58 illustrates a workflow 5800 to initialize skin-mounted, or percutaneous, fiducials with two or more X-ray images intraoperatively in accordance with some embodiments of the invention. In some embodiments, this figure describes the process of the user and acquisition system interfacing to initialize and calculate the 3D-displacement vector between a fiducial marker and the anatomical region of interest. In some embodiments, some figures relevant to the process include X-ray initialization of 3D-displacement vector with multi-planar X-rays (FIGS. 4A-4G, FIG. 13), feedback on fiducial placement on or in a patient's skin surface (FIGS. 2A-2B), a trans-drape, two-halves fiducial design (FIGS. 6A-6D, and FIGS. 9A-9B), registration of a fiducial in camera coordinates+determining its unique identity (FIGS. 4H-4I, FIG. 5, and FIGS. 7-8, FIGS. 10A-10D, and FIGS. 11A-11B).

In some embodiments, one or more steps of the workflow 5800 can be utilized for the registration of a 3D-displacement vector between a skin-mounted or percutaneous fiducial marker and the anatomical landmark of interest. In some embodiments, following a step 5802 of positioning a patient on an operative table, step 5804 can include the placement of a fiducial on or inside the soft tissue within the anatomical region of interest. For example, some embodiments involve the user placing the fiducial on or inside the general region of interest. Some embodiments of the invention can involve the user receiving feedback on the placement of a fiducial marker via a radiopaque patch that identifies the optimal location on the surface to place or insert the fiducial device; this was previously depicted and discussed in related to FIGS. 2A and 2B.

Some embodiments involve the mating of a second-half fiducial to the original fiducial marker placed on or inside soft tissue to maintain access to the fiducial after the introduction of surgical drapes and other obstructing materials outside of the surgical site. Some embodiments to accomplish one or more embodiments of this invention are depicted in FIGS. 6A-6D, and FIGS. 9A-9B. In some embodiments, step 5806 can include obtaining a first X-ray image containing fiducial and desired bone anatomy to be identified with the fiducial. Further, step 5808 can include rotation of the X-ray emitter, and step 5810 can include obtaining a second X-ray image containing fiducial and desired bone anatomy to be identified with the fiducial according to some embodiments.

Some embodiments further include the process of annotating 2D vectors between the fiducial marker and the anatomical landmark of interest for each image acquired from a unique perspective relative to the fiducial. In some embodiments, this displacement vector initialization process is depicted and discussed in reference to FIGS. 4A-4F. In some embodiments, the overall goal of the initialization process can be visualized in the cross-sectional view depicted previously in FIG. 13. Some embodiments include the process of using the relative rotational and translational offset information between two or more X-ray images of the fiducial to calculate the 3D-displacement vector between the fiducial marker and the anatomical landmark of interest using the 2D-displacement vectors for each image as inputs into the calculation. In some embodiments, this process of calculating the 3D-displacement vector based on a rigid transformation between multiple 2D-displacement vectors is previously depicted in FIG. 4G. For example, step 5812 can include annotation of X-ray images with desired bony anatomy locations, and step 5814 can include calibration of X-ray image distances by known size of the radiopaque markers on the fiducials according to some embodiments. Further, step 5816 can include draw a scaled displacement vector on X-ray images from fiducial origin to indicated bony anatomy of interest, and step 5818 can include input or compute displacement angle between X-ray images according to some embodiments. Further, step 5820 can include adding displacement vectors to produce 3D displacement vector from fiducial origin to annotated regions according to some embodiments.

In some embodiments, steps 5822-5830 describe the process of using 3D-tracked devices to register the location and orientation of the fiducial marker relative to the coordinate system of the 3D-tracking acquisition unit, and then applying the acquired positional information as a rigid transformation to the X-ray-based 3D-displacement vector to convert the vector from imaging units into units of the 3D-tracked acquisition system. In some embodiments, this process can be depicted in FIGS. 4H, 4I, 5, 7-8, 10A-10D, and 11A-11B. In addition, these previous figures depict some of the embodiments for determining the unique identity of a fiducial marker in order for the system to be able to utilize several fiducial markers at once and understanding which fiducial is associated with specific mathematical relationships to a unique anatomical landmark of interest. For example, step 5822 can include interpretation of fiducial origin into camera coordinate, and step 5824 can include tracing or tapping the fiducial with tracked probe in discrete points to indicate fiducial pose according to some embodiments. Further, step 5826 can include mechanical mating or coupling of tracked probe with fiducial to obtain fiducial pose, and step 5828 can include directly tracking markers mounted on fiducial, and with step 5830 including access to fiducial which then serves as a reference point to initialized nearby bony points of interest according to some embodiments.

In some embodiments, any of the above processes, methods, or procedures related to the workflow 5800 can include or be accomplished with one or more of steps or processes 5802, 5804, 5806, 5808, 5810, 5812, 5814, 5816, 5818, 5820, 5822, 5824, 5826, 5828, and 5830. In some embodiments, the steps of workflow 5800 can proceed in the order as shown. In some embodiments, any of the steps of the workflow 5800 can proceed out of the order as shown. In some embodiments, one or more of the steps of the workflow 5800 can be skipped.

Some embodiments of the invention enable the registration of bone-mounted fiducial markers to represent anatomical landmarks that are located within or nearby the bony anatomy that the marker is substantially rigidly attached to. For example, FIG. 59 illustrates a workflow 5900 to initialize one or more bone-mounted fiducial placed intraoperatively with two or more X-ray images taken before placement of one or more bone-mounted fiducials in accordance with some embodiments of the invention. In some embodiments, this figure describes the process of the back-end system to use prior X-ray initialization of a skin-based fiducial and its 3D-displacement vector to the anatomical landmark of interest and transform the bone-mounted fiducial location and pose relative to the camera-based registration coordinates of the prior 3D-displacement vector to describe the relationship between the bone-mounted fiducial marker and the anatomical region of interest. In some embodiments, other relevant figures can include some embodiments for bone-mounted fiducial design and coupling to an additional fiducial (see FIGS. 3A-3C), and registration of a fiducial in camera coordinates and determining its unique identity (FIGS. 10A-10D, and FIGS. 44A-44D).

In some embodiments, the steps 5910, 5912 of this process can involve the steps described in the workflow of FIG. 58, which outline the process for registering the 3D-displacement vector for a skin-based or percutaneous fiducial in imaging coordinates as well as units of the 3D-tracking acquisition unit. In some embodiments, if the registered fiducial marker has to be removed due to the location of the surgical site requiring access to the that location of the anatomy, then the user can utilize the process to reinstate access to the 3D-displacement vector that provides information about other anatomical landmarks of interest. In some embodiments, step 5914 can include removal of the skin fiducial, and step 5916 can include skin incision and exposure of the surgical site.

In some embodiments, step 5918 and 5920 can involve the user implanting the miniature fiducial marker into the bony anatomy and then registering its location and orientation relative to a 3D-tracking acquisition unit via a 3D-tracked probe. Some embodiments of this process are depicted in FIGS. 3A-3B, and FIGS. 4A-4D.

Some embodiments, described in steps 5922, and/or 5924, and/or 5926, and/or 5928 can involve the 3D-tracked probe tracing the fiducial surface or tapping discrete points on the fiducial to register the fiducial's 3D location and orientation with respect to the coordinates of the 3D-tracking acquisition unit. Some embodiments are depicted in FIGS. 10A-10D.

In some embodiments, step 5930 can include comparing the location and orientation of the registered bone-mounted fiducial to that of the registered landmarks initialized via the prior 3D-displacement vector converted into coordinates of the 3D-tracking acquisition system via initialization of the skin-based fiducial before the incision of the surgical site. Further, in some embodiments, steps 5932 and 5934 can include utilizing the relationship calculated in step 5930 as in input for the rigid transformation applied to the registered anatomical landmarks with coordinates from the 3D-tracking acquisition system.

In some embodiments, any of the above processes, methods, or procedures related to the workflow 5900 can include or be accomplished with one or more of steps or processes 5910, 5912, 5914, 5916, 5918, 5920, 5922, 5924, 5926, 5928, 5930, 5932, and 5934. In some embodiments, the steps of workflow 5900 can proceed in the order as shown. In some embodiments, any of the steps of the workflow 5900 can proceed out of the order as shown. In some embodiments, one or more of the steps of the workflow 5900 can be skipped.

Similar to embodiments depicted in FIGS. 58 and 59, FIG. 60 shows a workflow to initialize bone-mounted fiducials placed intraoperatively with two or more X-ray images taken after placement of bone-mounted fiducials in accordance with some embodiments of the invention. In some embodiments, once the user has created a surgical site and exposed the bony anatomy, the user can implant the miniature fiducial marker into the bony anatomy surface until it is substantially rigidly fixed to the anatomy. Examples of this bone fiducial embodiment are depicted in FIGS. 3A and 3B according to some embodiments. Some embodiments involve the use of a larger fiducial marker that mates to the surface of the bone-mounted fiducial marker to enhance its visualization in X-ray images for the purpose of annotating the 3D-displacement vector to the anatomical landmark of interest. An example of this embodiment is depicted in FIG. 3C.

In some embodiments, in step 6002, incise skin and expose the surgical site, and step 6004, fasten bone-mounted fiducial to spinal level of interest at accessible location, and further, in step 6006, attach mating device (optional) to bone-mounted fiducial to aid with X-ray initialization. In some embodiments, steps 6012, 6010, 6008, 6014, 6016, 6018, 6020, 6022, and 6024 can include the X-ray-based registration of the fiducial marker as described in FIG. 58 to produce a 3D-displacement vector in imaging coordinates between the bone-mounted fiducial marker and the anatomical landmark of interest. Some embodiments then register the bone-mounted fiducial's 3D-displacement vector to the anatomical landmark of interest in the coordinates of the 3D-tracking acquisition system via acquiring the location and orientation of the fiducial marker with respect to the coordinates of 3D-tracking acquisition system. Examples of this process are depicted in FIGS. 4H-4I, FIGS. 10A-10D, and further in FIGS. 44A-44D.

In some embodiments, once the bone-mounted fiducial is registered in both the X-ray imaging system and the 3D-tracking acquisition system, every time the user returns to register the updated location and orientation, the relative relationship between its current position and that of the prior registration are calculated and applied via a rigid transformation to calculate the most accurate location of the anatomical landmark of interest as they currently exist in relation to the fiducial marker in 3D space. For example, in step 6026, the process can include assess location and pose of initialized fiducial, including, but not limited to step 6028 including trace a unique pattern imprinted over fiducial with tracked probe, step 6030 substantially rigidly couple tracked mating probe to fiducial, step 6032, substantially rigidly coupling tracked markers to fiducial, and step 6034, tap discrete points on fiducial or on fiducial mating attachment with tracked probe according to some embodiments.

In some embodiments, any of the above processes, methods, or procedures related to the workflow 6000 can include or be accomplished with one or more of steps or processes 6002, 6004, 6006, 6012, 6010, 6008, 6014, 6016, 6018, 6020, 6022, 6024, 6026, 6028, 6030, 6032, 6034, and 6036. In some embodiments, any of the steps of the workflow 6000 can proceed out of the order as shown. In some embodiments, one or more of the steps of the workflow 6000 can be skipped.

Some embodiments of this invention pertain to the initialization of the patient's anatomical planes in relation to the coordinates of the 3D-tracking acquisition system to enable the measurements made during a procedure to be accurately referenced to the dimensions of the anatomy being assessed. For example, FIG. 61 illustrates methods of registering anatomical reference planes intraoperatively in accordance with some embodiments of the invention. In some embodiments, if a user has already established the coordinates of the measurement system via the initialization process of surgical navigation technologies, then coordinates of the data outputted by the 3D-tracking acquisition system are already referenced in relation to the anatomical planes of the patient. In some embodiments, if the user has not already established the coordinates of the measurement system via the initialization process of surgical navigation technologies, then the user will utilize a few of the embodiments described in FIG. 61 to initialize the 3D-tracking data outputs with respect to the patient's anatomical planes.

Some embodiments include utilizing a tracked DRF (e.g., FIG. 12) and its associated 3D orientation and location in relation to the 3D-tracking acquisition system as inputs to a 3D rigid transformation of the measurements that are outputted by the 3D-tracked devices to reference the anatomical planes of the patient. In some embodiments, one example of this process of transforming measurements outputted by 3D-tracked devices to be relative to the patient anatomical planes, via a tracked dynamic reference aligned with the patient anatomical planes, is depicted in FIGS. 62A-62C.

Some embodiments for initializing the patient anatomical planes can involve acquiring two or more data points in space with a 3D-tracked probe to define the direction, location, and orientation of the anatomical planes of the patient relative to the 3D-tracking acquisition system. Some further embodiments can involve holding the probe in particular orientation and location in space and registering that position relative to the 3D-tracking acquisition system as the new coordinates system of all acquired measurements outputted by 3D-tracked devices.

In some embodiments, a decision step 6102 can include a determination of whether patient anatomy/imaging has been registered relative to a 3D tracking camera axis. In some embodiments, for a positive answer, the process can include step 6104 including a tracked DRF that serves as a reference for patient cross-sectional imaging fusion with a navigation camera, step 6106, including where the orientation of anatomical planes is interpreted, and step 6126 that can include camera coordinates interpreted within anatomical axis.

In some embodiments, a negative for step 6102 can lead to step 6108 where the position of anatomical planes is indicated relative to camera axis, including, but not limited to step 6110, including adjusting position of a DRF such that it's reference plane labels align with the patient's anatomical planes. Further, step 6112 including tapping two points in space with a tracked probe to represent each anatomical axis aligned with the patient. Further, step 6114, includes temporarily holding a tracked probe in instructed orientation according to some embodiments. In some embodiments, step 6116 (reached from step 6110 or decision step 6118 from a positive) can include substantially rigidly transforming camera axis to the DRF-referenced anatomical axes, and to step 6126, where camera coordinates are interpreted with anatomical axes.

In some embodiments, from decision step 6118, including checking if a dedicated DRF is used to indicate patient anatomy, a negative can proceed to step 6120 of substantially rigidly transforming camera axes to referenced anatomical axes and to decision step 6122. From step 6122, a positive can lead to step 6124 including a return to step 6108, and a negative can include moving to step 6126 (described above).

In some embodiments, any of the above processes, methods, or procedures related to the workflow 6200 can include or be accomplished with one or more of steps or processes 6102, 6104, 6106, 6108, 6110, 6112, 6114, 6116, 6118, 6120, 6122, 6124, and 6126. In some embodiments, at least one of the steps can include a decision step (e.g., such as step 6102 or 6122), where one or more following steps depend on a status, decision, state, or other condition. In some embodiments, the steps of workflow 6100 can proceed in the order as shown. In some embodiments, any of the steps of the workflow 6100 can proceed out of the order as shown. In some embodiments, one or more of the steps of the workflow 6100 can be skipped.

Some embodiments of the invention in the acquisition and interpretation of spinal contour via tracing body surfaces with a 3D-tracked probe and interfacing with previously initialized skin fiducial markers as described previously. In some embodiments, the tracing can be performed with a trigger-equipped probe, as described previously in relation to FIGS. 10A-10G, and FIGS. 15A-15C, to indicate the body surface type that is being traced (e.g., skin, lamina, etc.) and to ensure the probe is only in an active state when in contact with body surfaces as described below in reference to FIG. 69. In some embodiments, the acquired tracing data obtained from this embodiment can then be used to automatically compute spinal alignment parameters as described below in reference to FIGS. 66A-66B, and 67.

FIG. 62A displays some embodiments of the invention which consists of acquiring information regarding the contour of the spine via tracing over body surfaces using a tracked probe. Some embodiments consist of spine bony anatomy 6211, overlying skin 6215 interrupted to represent a surgical site 6220, skin-mounted fiducials 6226, 6228 applied to two regions outside of the surgical site with overlying surgical drapes 6208 and over-the-drape-mating fiducials 6225, 6227. In some embodiments, using a 3D-tracked probe, tracing coordinates are acquired over the skin of the cervicothoracic spine 6202, surgical site anatomy 6204, and skin of the lumbosacral spine 6205. In some embodiments, after acquiring this traced data, the acquisition system software can interpret it with the aid of fiducial initialization data, previously described in relation to FIGS. 4A-4I and 58 to represent one complete bony surface contour from which spinal alignment parameters can be calculated, as described below in reference to FIGS. 67, and 69.

FIG. 62B displays on embodiment of the invention which is a display of the acquired body surface contours via tracing with a 3D-tracked probe within the optical 3D-tracking camera's axes, containing the 3D coordinates of the over-the-drape-mating fiducials 6251, cervicothoracic skin tracing 6253, surgical site tracing 6255, and lumbosacral skin tracing 6257 according to some embodiments. In some embodiments, in order to properly interpret this data, the acquisition software has to substantially rigidly transform the data such that it is represented within anatomical reference axes rather than camera axes. In some embodiments, the mechanism of establishing anatomical reference axes was previously described in relation to FIGS. 12 and 61 and the transformed data is shown below in reference to FIG. 62C.

FIG. 62C displays the invention which is applying a 3D rigid transform to the acquired tracing data as described previously in relation to FIGS. 62A-62B, to be interpreted and displayed within anatomical reference axes including the coordinates of the over-the-drape-mating fiducials 6261, cervicothoracic skin tracing 6263, surgical site tracing 6265, and lumbosacral skin tracing 6267 according to some embodiments. Interpreting and displaying the acquired 3D-tracing data in this way enables subsequent manipulation and calculations as described below in relation to FIGS. 62D and 67 according to some embodiments.

FIG. 62D displays the invention which is the translation of the acquired tracing data previously described in relation to FIGS. 62A-62C according to some embodiments. In some embodiments, based on the displacement vector between the initialized skin fiducial and anatomical regions of interest, and based on the displacement vectors between the skin tracing locations most closely approximating the surgical site tracing and the end points of the surgical site tracing, any skin-surface tracing is translated to represent one continuous tracing of bony anatomy. As shown in the figure, some embodiments consist of the translated coordinates for the cervical fiducial 6281, cervicothoracic skin tracing 6283, lumbosacral skin tracing 6285, and lumbosacral fiducial 6287. In some embodiments, from the data coupling the translated tracings to the surgical site tracing (if applicable), spinal alignment parameters can then be calculated as described below in reference to FIG. 67. Additionally, in some embodiments, if a quantitative assessment of aligning is desired for the surgical site only, that is also achievable with the acquired data in this embodiment, as described in more detail below in reference to FIG. 68.

Some embodiments of this invention include the use of a tracked mobile stray marker (TMSM) to communicate particular commands to the computer system via its tracked dynamic motion relative to the 3D-tracked tool's end effector and/or DRF. For example, FIG. 63 shows a workflow 6300 for analog triggering detection of one or more TMSMs relative to a tracked tool with a DRF in accordance with some embodiments of the invention. In some embodiments, other relevant figures related to linear actuation of the TMSM relative to the probe shaft can include, but not be limited to, FIGS. 10A-10E, FIGS. 29A-29C, FIGS. 38C, 38G, FIGS. 39A-39B, FIGS. 44B-44D, FIGS. 45A-45B, FIGS. 51E-51H, FIGS. 53A, 53C-53D, and FIGS. 57A-57B. In some embodiments, other relevant figures related to rotational actuation of the TMSM on a rigid arm relative to the probe shaft can include, but not be limited to, FIG. 4H, FIGS. 15A-15C, FIGS. 48B-48C, FIGS. 49A-49D, FIGS. 50A-50E, and FIGS. 82A-82B. In some embodiments, some relevant figures related to calculation of angle of TMSM with respect to the probe shaft can include, but not be limited to, FIGS. 64A-64B.

Some embodiments of the invention involve the use of a TMSM that is mechanically linked to a 3D-tracked tool and tracking its dynamic position relative to the coordinates of the 3D-tracked tool, which is defined by a coupled DRF and its associated tool definition file. Some embodiments involve the use of a depressible tip that actuates a rod that is coaxial to the shaft of a 3D-tracked tool. In some embodiments, the TMSM is attached to the depressible rod and subsequently its distance from the tip of the 3D-tracked tool, or any other defined component relative to the DRF of the tool, can dynamically change upon actuation of the depressible tip, following a linear path of motion. Some embodiments of the system use the 3D location of the TMSM and apply to it a 3D rigid transformation of the 3D location and orientation of the 3D-tracked tool relative to the 3D-tracking acquisition unit. In some embodiments, the TMSM location data is now transformed to be relative to the coordinate system of the 3D-tracked tool, and thus does not perturb with respect to moving the 3D-tracked tool in space without triggering the depressible tip to change the location of the TMSM relative to the 3D-tracked tool. In some embodiments, the resulting magnitude of the vector between the transformed TMSM and the 3D-tracked tool end effector is the mathematical output that is tracked for the system to detect when an event has occurred to note information or store data produced by the position and/or behavior of the 3D-tracked tool.

In some embodiments, the dynamic change of the magnitude of the vector between transformed TMSM coordinates and the coordinates of the 3D-tracked tool's end effector can be analyzed for detecting specific thresholds of magnitude for a binary system behavior, or also analyzed at various levels of magnitude across the possible range of motion of the TMSM relative to the 3D-tracked tool's end effector, representing a more analog system behavior. Some example embodiments are depicted in FIGS. 10A-10B, 10D, 10E, FIGS. 29A-29C, FIGS. 38C, 38G, FIGS. 39A-39B, FIGS. 44B-44D, FIGS. 45A-45B, FIGS. 51E-51H, FIGS. 53A, 53C-53D, and FIGS. 57A-57B. In addition, some embodiments of the system can calculate the angle between two vectors to communicate when the behavior of the TMSM is used to communicate a specific command (e.g., such as the vector between the 3D-tracked tool's end effector and the rotation axis of the arm), which is mechanically linked to the 3D-tracked tool, that the TMSM is substantially rigidly attached to, and the vector between the TMSM and the rotation axis of the arm, which is mechanically linked to the 3D-tracked tool, that the TMSM is substantially rigidly attached to. In some embodiments, the system calculates the angle between these two vectors during the use of the 3D-tracked tool and constantly analyzes the angle of the vectors that are defined with respect to the coordinates of the 3D-tracked tool. In some embodiments, this dynamic angle calculation, such as the example described in FIG. 64A and FIG. 65B, can also be sensed in a binary or analog manner such as described above to enable various commands to be communicated to the 3D-tracking acquisition unit for a variety of applications. Some embodiments involve the use of a 3D-tracked tool with a rotationally-actuating TMSM to trace the spine at select regions and communicate to the system to only store location and orientation data of the 3D-tracked tool while the TMSM-based angle has reached a certain threshold via the actuation of a button on the 3D-tracked tool. Some example embodiments are depicted in FIG. 4H, FIG. 15A, FIG. 15B, FIG. 15C, FIG. 48B, FIG. 48C, FIG. 49A, FIG. 49B, FIG. 49C, FIG. 49D, FIG. 50A, FIG. 50B, FIG. 50C, FIG. 50D, FIG. 50E, FIG. 82A, and FIG. 82B.

In some embodiments, any of the above processes, methods, or procedures related to the workflow 6300 can include or be accomplished with one or more of steps or processes 6310, 6312, 6314, 6320, 6318, 6316, 6322, 6324, 6326, 6328, 6330, 6332, 6334, 6336, 6338, 6340, 6342, 6344, 6346, 6350, 6354, and 6356. In some embodiments, at least one of the steps can include a decision step (e.g., such as step 6328), where one or more following steps depend on a status, decision, state, or other condition. In some embodiments, the steps of workflow 6300 can proceed in the order as shown. In some embodiments, any of the steps of the workflow 6300 can proceed out of the order as shown. In some embodiments, one or more of the steps of the workflow 6300 can be skipped.

FIG. 64A displays the invention consisting of a probe with a tip 6415, tracked DRF 6405, pivot arm 6430 containing a TMSM 6425 and pivoting about a pivot hinge 6410. In this embodiment, the 3D coordinates of the probe tip, pivot hinge, and TMSM are known relative to the tracked DRF axes and the position of the TMSM relative to the DRF can be calculated in terms of relative angles as described below in reference to FIG. 64B according to some embodiments. Further, FIG. 64B displays the invention consisting of the interpretation and calculation of the position of a rotating TMSM 6456 relative to the DRF on a probe as described previously in relation to FIG. 64A according to some embodiments. In this software interpretation, a vector V1 6450 is defined from the probe tip 6415 through the pivot hinge 6410 and a vector V2 6444 is defined from the pivot hinge 6410 to the TMSM 6456 according to some embodiments. In some embodiments, the angle theta between V1 and V2 is calculated as described previously in relation to FIG. 63 and used as a method of communicating analog or binary signals to the 3D-tracking acquisition system. Some embodiments can be applied to some embodiments of the invention that involves a TMSM rotating about a hinge relative to a tracked DRF, as in those previously described in reference to FIGS. 15A-15C, 48A-48C, 55A-55I, 56C-56D, and 56F.

In some embodiments of the invention, based on data acquired from cross-sectional imaging (CT shown), a relative body and bony surfaces can be manually or automatically annotated to then calculate relative displacement vectors from points on each surface to one another (e.g., the displacement vector from the midpoint of the lamina to the vertebral body centroid). In some embodiments, the acquisition software can utilize this information as input into the manipulation of data created by tracing body-surfaces with a 3D-tracked probe. For example, FIG. 65A illustrates displays of a discrete body surface or bony surface annotations on cross-sectional images used for initialization of patient-specific interpretation of body and bony surface tracings with a 3D-tracked probe in accordance with some embodiments of the invention. FIG. 65A displays a body surface or bony surface annotations on cross-sectional images (6510, 6512) to be used for initialization of patient-specific interpretation of body and bony surface tracings with a 3D-tracked probe according to some embodiments. These annotated regions include but are not limited to skin surface, spinous process, lamina, transverse process, pedicle, vertebral body, and vertebral body centroid according to some embodiments.

FIG. 65B illustrates 3D perspective of cross-sectional annotations from the CT scan in accordance with some embodiments of the invention, where based on these annotations, software comparison algorithms have a patient-specific reference to compare 3D-tracked tracing contours over bony surfaces to annotated surfaces from the cross-sectional imaging, and use the comparison to attempt to display a 3D perspective of the spine following a contour assessment tracing. Additionally, in some embodiments, this data may be utilized for automatically detecting spinal levels represented by the traced contour within the surgical site.

FIG. 65C illustrates a plot of coronal projected coordinates in accordance with some embodiments of the invention. FIG. 65C displays coronal projected coordinates of annotated transverse processes (6514, 6520), laminae (6516, 6518), vertebral body centroids, skin surface, and spinous processes according to some embodiments. Some embodiments display the similarity in coronal contours of annotations over varying bony elements. Additionally, it displays the basis of computing displacement vectors within the coronal plane. Further, FIG. 65D illustrates a plot of sagittal projected coordinates in accordance with some embodiments of the invention, and includes sagittal projected coordinates of annotated transverse processes 6528, laminae 6520, vertebral body centroids 6526, skin surface 6522, and spinous processes 6524. Some embodiments display the similarity in sagittal contours of annotations over laminae, transverse processes, and vertebral body centroids across the length of the spine, which serves as valuable input into the interpretation of 3D-traced data previously described in FIGS. 62A-62D as well as in the automated calculation of spinal alignment parameters from the tracings, as described below in reference to FIG. 67.

FIG. 65E illustrates computed cross-sectional distances between corresponding anatomical landmarks and vertebral body centroids in accordance with some embodiments of the invention. Shown are computed cross-sectional distances between corresponding anatomical landmarks and the vertebral body centroids (e.g., left lamina midpoints 6530, right lamina midpoints 6532, left transverse process midpoints 6534, and right transverse process midpoints 6536 etc.) according to some embodiments.

In some embodiments of the invention, acquired 3D-tracing data can be interpreted to represent the contour of the vertebral body centroids based on initialization data with or without the aid of fiducials. FIG. 66A illustrates a display of cross-sectional slices of vertebra 6601 in their relative anatomical axes in accordance with some embodiments of the invention, with tracing coordinates 6603 from tracing over surgically exposed left lamina with a 3D-tracked probe, and coordinates from tracing the right lamina (not shown), and the corresponding computed coordinates 6605 representing the vertebral body centroids on cross-sectional imaging.

Some embodiments include a display of a vertebral body calculated via bilaterally traced coordinates and patient initialization data in accordance with some embodiments of the invention. For example, FIG. 66B displays the invention in which the location of a cross-section image's 6601 vertebral body centroid 6615 is calculated via bilaterally traced coordinates and patient initialization data according to some embodiments. Some embodiments also consists of left 6607 and right 6609 lamina coordinates as input from a 3D-tracked probe tracing, a line segment 6611 connecting the two laminae coordinates, and an orthogonal line segment 6613 from the midpoint of the laminae-connecting segment and of a distance based on patient initialization information. It should be noted that there are some embodiments of initialization of patient anatomy in this invention including but not limited to CT imaging annotation, as described in reference to FIGS. 13 and 65A-65E, intraoperative X-ray image annotation, normative patient data sets, fiducial-based initialization as previously described in reference to FIGS. 4A-4I, 6A-6C, 9, 44A-44D, 45A-45B, 58-60, and 62A-62D according to some embodiments.

Some embodiments of this invention involve the process of filtering and segmenting a contour tracing produced by a 3D-tracked tool. In some embodiments, calculations can be derived from tracing data that is generated inside and outside of the surgical site, with or without annotations of particular anatomical landmarks of interest. For example, FIG. 67 illustrates a workflow 6700 to calculate spinal alignment parameters based on intraoperative tracing in accordance with some embodiments of the invention. Some relevant other figures can include, but not be limited to, FIGS. 9A-9B, FIGS. 21A-21B, and FIGS. 64A-64B (for initialization of tracing sequence), FIG. 12 (for initialization of patient's anatomical planes), FIG. 86 (for alignment parameter output), FIGS. 62, and 65A-65E, and 66A-66B (for transforming of tracing data via 3D-displacement offset to curves generated by connecting other anatomical landmark locations) according to some embodiments.

Some embodiments of the invention involve the use of an electromechanical, 3D-tracking system, as depicted in FIG. 23A and FIG. 23B. Some embodiments involve the use of an optical, 3D-tracking system, which is depicted in FIG. 5A. Further, some embodiments involve the initialization of the patient's anatomical planes via coordinate transformation references defined by tracked DRFs (e.g., FIG. 12), or tracings of a unique pattern or a plane that defines the orientation, direction, and location of the anatomical plane references that measurements generated by 3D-tracked tools will be transformed relative to after initialization. Further, some embodiments of the invention involve the classification of tracing data based on its relation to specific anatomical regions of interest (e.g., spinous processes, laminae, skin surface, transverse processes, etc.). Some embodiments of this anatomical classification of the tracing data are a result of software-based user inputs, proximity-based detections near registered fiducial markers or anatomical landmarks that have known associated locations relative to a 3D-tracking acquisition system, registration of a unique pattern with known dimensions, or via user-based, selective toggles actuated with 3D-tracked tools or DRFs, such as triggering of a TMSM attached to the 3D-tracked tool. Some examples include FIG. 9A, FIG. 9B, FIG. 21A, FIG. 21B, FIG. 64A, and FIG. 64B according to some embodiments.

In some embodiments, once a continuous or discrete series of points is acquired via the 3D-tracked tool used in 3D coordinates relative to the 3D-tracking acquisition system, algorithms of the system can utilize data (e.g., including, but not limited to, fiducial-based 3D-displacement vector to one or more anatomical landmarks of interest, normative data of a patient population, or preoperative imaging annotations that define a 3D-displacement vector between anatomical regions that are traced and anatomical landmarks of interest), to transform the tracing data to approximate the contours produced by connecting points at key anatomical landmarks (e.g., curve generated by fitting line to several vertebral body centroids) across the region of the tracing. In some embodiments, examples of this described transformation process are depicted in FIG. 62A, FIG. 62D, FIG. 65A, FIG. 65B, FIG. 65C, FIG. 65D, FIG. 65E, FIG. 66A, and FIG. 66B.

Some embodiments involve the use of first and second derivative calculations of filtered tracing contours to identify maxima, minima, and inflection points of the curves. Some embodiments involve using these calculated inflection points as reference lines used in the calculation of endplate-based coronal measurements (e.g., Cobb angles).

Figures 86A, 86B, 86C, 86D:
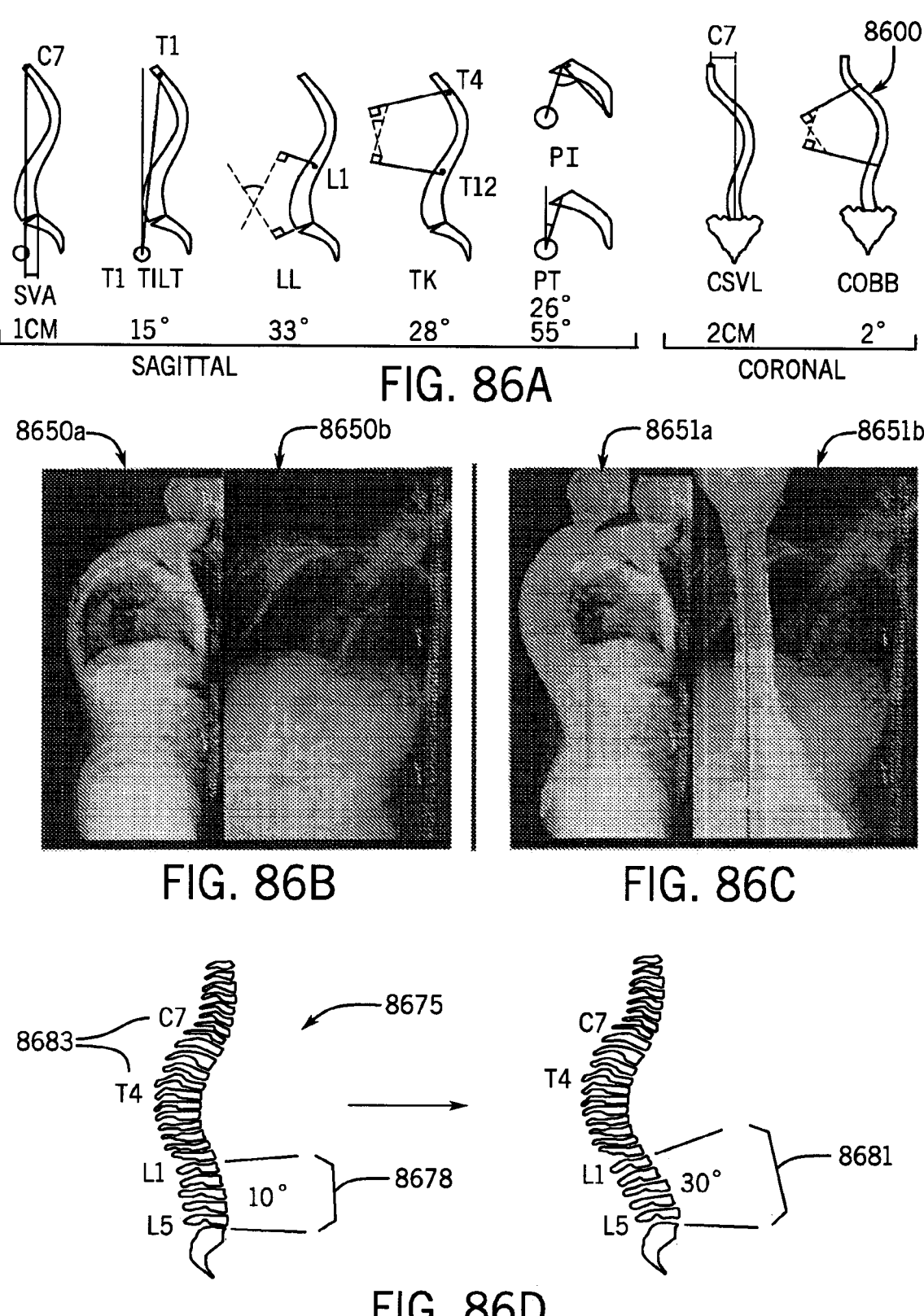

Some embodiments involve the use of annotation of one or more anatomical landmarks of interest as inputs into which segments of the tracing should the algorithm compute perpendicular lines used to make endplate-based measurements of the alignment of vertebral segments in the specific region, defined by one or more annotated anatomical landmarks. Some embodiments of the annotation process involve the registration of anatomical landmarks using 3D-tracked tools, software-based estimations based on registered references to cross-sectional imaging before or during the procedure, or via the location of registered fiducial markers relative to the tracing data. From these segmented annotations of the tracing data, some embodiments involve the algorithmic calculation of spinal alignment parameters (e.g., Cobb angle, lumbar lordosis (LL), thoracic kyphosis (TK), C2-C7 sagittal vertical axis (SVA), C7-S1 SVA, C2-S1 SVA, central sacral vertical line (CSVL), T1 pelvic angle (T1PA), pelvic tilt (PT), pelvic incidence (PI), chin-brow to vertical angle (CBVA), T1 slope, sacral slope (SS), C1-2 lordosis, C2-C7 lordosis, C0-C2 lordosis, C1-C2 lordosis, PI-LL mismatch, C2-pelvic tilt (CPT), C2-T3 angle, spino-pelvic inclination from T1 (T1SPi) and T9 (T9SPi), C0 slope, mismatch between T-1 slope and cervical lordosis (T1S-CL), and/or global sagittal angle (GSA)). Some embodiments of the display of these calculated alignment parameters, along with thresholds pre-defined in the literature for patient-specific surgical goals, is depicted in FIGS. 86A-86C.

In some embodiments, any of the above processes, methods, or procedures related to the workflow 6700 can include or be accomplished with one or more of steps or processes 6702, 6704, 6706, 6712, 6710, 6708, 6714, 6716, 6718, 6720, 6722, 6724, 6726, 6728, 6730, 6732, 6738, 6740, 6734, 6736, 6742, 6744, 6746, and 6748 as shown. In some embodiments, the steps of workflow 6700 can proceed in the order as shown. In some embodiments, any of the steps of the workflow 6700 can proceed out of the order as shown. In some embodiments, one or more of the steps of the workflow 6700 can be skipped.

Some embodiments of this invention involve the process of filtering and segmenting a contour tracing produced by a 3D-tracked tool only registering points within the surgical site. In some embodiments, calculations are derived from tracing data that is generated inside the surgical site, with or without annotations of a particular anatomical landmark of interest, as well as with or without registration of bone-mounted fiducial markers in the surgical site. For example, FIG. 68 illustrates a workflow to acquire a spinal alignment curve using probe-based tracing within only the surgical site in accordance with some embodiments of the invention. Other relevant figures can include those related to registration of bone-mounted fiducial markers with one or more anatomical landmarks of interest (FIGS. 59 and 60), triggering of tracked mobile stray markers attached to 3D-tracked tool (FIG. 63), calculating spinal alignment parameters based on intraoperative tracing (FIG. 67) according to some embodiments.

Some embodiments involve the use of bone-mounted fiducial markers that are registered to one or more nearby anatomical landmarks of interest via a 3D-displacement vector, such as the processes depicted in FIGS. 59-60. Some embodiments involve the communication of commands to the 3D-tracking acquisition system that a tracing or registration is occurring, such as the processes depicted in FIG. 63. Some embodiments involve the user annotating particular anatomical landmarks, via processes such as tracing or discrete-point tapping of registered fiducial markers, or also mechanically coupling between the 3D-tracked tool and the fiducial marker. Some embodiments involve the computer system only storing data that is generated by the 3D-tracked tool while it traces or discretely registers the contour of the anatomical region of interest that begins and ends with the registration of or proximity-detection event of a bone-mounted fiducial marker. Some embodiments involve the user identifying the tracing region of interest in relation to the anatomical sections of the patient via manual display monitor inputs that define the landmarks that the tracing will span. Some embodiments involve the calculation of spinal alignment parameters based on registered contour of the tracing data and/or annotation of one or more anatomical landmarks of interest. Some examples of this process were described in FIG. 67.

In some embodiments, any of the above processes, methods, or procedures related to the workflow 6800 can include or be accomplished with one or more of steps or processes such as 6802, 6804, 6806, 6808, 6810, 6812, 6816, 6814, 6816, 6817, 6822, 6818, 6820, 6822, 6824, 6826, 6828, 6830, 6832, 6834, 6836, 6838, 6840, 6842, and 6844. In some embodiments, at least one of the steps can include a decision step (e.g., such as step 6814), where one or more following steps depend on a status, decision, state, or other condition. In some embodiments, the steps of workflow 6800 can proceed in the order as shown. In some embodiments, any of the steps of the workflow 6800 can proceed out of the order as shown. In some embodiments, one or more of the steps of the workflow 6800 can be skipped.

FIG. 69 illustrates a workflow 6900 to acquire a spinal alignment curve using probe-based tracing data spanning beyond the surgical site in accordance with some embodiments of the invention. Some embodiments of the invention involve the process of filtering and segmenting a contour tracing produced by a 3D-tracked tool registering points within and beyond the surgical site. In some embodiments, calculations are derived from tracing data that is generated inside the surgical site, with or without annotations of one or more particular anatomical landmarks of interest, with or without registration of bone-mounted fiducial markers in the surgical site, as well as with or without registration of skin-mounted fiducial markers beyond the surgical site. Some other relevant other figures include FIGS. 59-60 (for registration of bone-mounted fiducial markers with one or more anatomical landmarks of interest), and FIG. 63 (the triggering of tracked mobile stray markers attached to 3D-tracked tool) according to some embodiments. Others include FIG. 67 (for calculating spinal alignment parameters based on intraoperative tracing), FIG. 68 (outlining a process of calculating alignment using tracings and bone-mounted fiducials, FIGS. 6B, 9A-B, 11A-B (related to skin-based fiducial markers), and FIGS. 62A, 62D, 65A-E, 66A-B (related to calculating the displacement offset between tracing data and anatomical landmarks of interest) according to some embodiments.

Some embodiments of this invention involve initializing the key anatomical landmarks of interest, such as those that are required for spinal alignment parameter calculations. Some embodiments involve depictions that are shown in FIGS. 6B, 9A-B, 11A-11B, 59, 60, and 68. Some embodiments involve tracing anatomical structures within the surgical site as well as registering landmarks, such as skin-based fiducial markers, beyond the surgical site. Some embodiments involve applying offsets based on initialized 3D-displacement vectors, such as the examples depicted in FIGS. 62A, 62D, 65A-65E, and 66A-66B. Further, some embodiments of communicating when to store tracing data and classifying particular tracings as related to an anatomical region involve example embodiments depicted in FIGS. 9A-9B, 62A-62D, 59, and 63.

In some embodiments, any of the above processes, methods, or procedures related to the workflow 6900 can include or be accomplished with one or more of steps or processes such as 6902, 6904, 6906, 6908, 6910, 6912, 6914, 6916, 6918, 6920, 6922, 6924, 6926, 6928, 6930, 6932, and 6934. In some embodiments, at least one of the steps can include a decision step (e.g., such as step 6924), where one or more following steps depend on a status, decision, state, or other condition. In some embodiments, the steps of workflow 6900 can proceed in the order as shown. In some embodiments, any of the steps of the workflow 6900 can proceed out of the order as shown. In some embodiments, one or more of the steps of the workflow 6900 can be skipped.

Some embodiments of this invention involve the process of calculating the flexibility or range of motion of a particular anatomical region of interest. Some embodiments enable the user to mechanically manipulate the conformation of the spine while calculating the quantitative flexibility of a region of the spine. For example, FIG. 70 illustrates a workflow 7000 to assess flexibility of the spine intraoperatively using flexibility assessment device in accordance with some embodiments of the invention. Other relevant figures (e.g., such as in relation to a flexibility assessment device can include FIGS. 34A-34G, FIGS. 35A-35F, FIGS. 36A-36I, FIGS. 37A-37G, FIGS. 39A-39F, and FIGS. 40A-40C) according to some embodiments. Further, flexibility assessment devices on spine, including during set-and-hold manipulation of adjusting the correction of the spine include FIGS. 42A-42F and FIG. 70 according to some embodiments.

Some embodiments of this invention involve the rigid fixation of a 3D-tracked tool, which can be arranged in adjustable configurations, with vertebrae in the exposed surgical site via attachment rigid landmarks, such as the pedicle screws. Further, some embodiments of the system involve the ability of the 3D-tracked tool to substantially rigidly attach to more than one pedicle screw on a vertebra at once. Examples of some embodiments in various applications and forms, but not exhaustive to all possible and developed design permutations, include those depicted in at least FIGS. 34A-34G, 35A-35F, 36A-36I, 37A-37G, 39A-39F, and 40A-40C.

Some embodiments involve the X-ray-based registration of the vertebral endplate angle with respect to the 3D-tracked tool side surface. Some embodiments of the system involve the use of one or more of the specified 3D-tracked tools to manipulate multiple regions of the anatomy and store location and orientation information detected by the 3D-tracking acquisition system. Some embodiments of the system involve the calculation of relative angles between two or more 3D-tracked tools substantially rigidly attached to vertebra at the end of the assessment region of interest. In some embodiments, this angle can provide an assessment of the flexibility of the spine, as the system is able to measure the relative angle between two or more 3D-tracked tools during manipulations that explore the full range of motion of the attached vertebrae. Some examples of this manipulation and measurement process are depicted in FIGS. 42A-42F according to some embodiments.

In some embodiments, any of the above processes, methods, or procedures related to the workflow 7000 can include or be accomplished with one or more of steps or processes such as 7002, 7004, 7006, 7008, 7010, 7012, 7014, 7016, 7018, 7020, 7022, 7024, 7026, and 7028. In some embodiments, at least one of the steps can include a decision step (e.g., such as step 7014), where one or more following steps depend on a status, decision, state, or other condition. In some embodiments, the steps of workflow 7000 can proceed in the order as shown. In some embodiments, any of the steps of the workflow 7000 can proceed out of the order as shown. In some embodiments, one or more of the steps of the workflow 7000 can be skipped.

Some embodiments of this invention involve the process of overlaying a surgical instrument using 3D-tracking dynamic reference markers to approximate the 2D, projected shape of the instrument on the 2D radiograph of an anatomical region of interest. For example, FIG. 71 illustrates a workflow of producing real-time overlays of surgical instruments over intraoperative X-rays in accordance with some embodiments of the invention. Some other figures, for example as related to a process of overlay illustration using 3D-tracked tool and C-arm X-ray images are described in relation to FIGS. 46A-46G according to some embodiments.

Some embodiments of the invention involve utilizing a 3D-tracked tool with a coupled tracked DRF. Some embodiments also involve the use of a DRF substantially rigidly attached to the emitter of an X-ray imaging system, such as a C-arm. Further, some embodiments involve using the relative distance and orientation of the 3D-tracked tool with respect to the X-ray imaging system to calculate the appropriate size and 2D-projected shape of the surgical tool with the attached DRF on the X-ray image.

In some embodiments, the system utilizes the known distance of the 3D-tracked surgical tool away from the X-ray imaging system, the size and dimensions of the surgical tool, the location and orientation of the surgical tool, and the location and orientation of the imaging system, all with respect to the coordinates of the 3D-tracking acquisition system, to produce an accurate 2D projection of the tracked surgical tool with appropriate scaling and pose with respect to the X-ray imaging system. Some embodiments include computing the rigid transformation between the tracked surgical tool and the imaging system to transform the tool's location and orientation to be outputted with respect to the imaging system coordinates. Further, some embodiments of the system enable for the visual overlay of the computed 2D-projection of 3D-tracked surgical tool based on its distance and pose in relation to the volume of the cone beam of the X-ray imaging system.

In some embodiments, any of the above processes, methods, or procedures related to the workflow 7100 can include or be accomplished with one or more of steps or processes such as 7102, 7104, 7106, 7108, 7110, 7112, 7114, 7116, 7118, 7120, 7122, 7124, 7126, 7128, 7130, 7132, 7134, 7136, 7138, 7140, and 7142. In some embodiments, the steps of workflow 7000 can proceed in the order as shown. In some embodiments, any of the steps of the workflow 7000 can proceed out of the order as shown. In some embodiments, one or more of the steps of the workflow 7000 can be skipped.

Some embodiments of this invention involve the process of registering the location and orientation with accessible fiducial markers, surgical implants, or anatomical landmarks, that are registered to the vertebrae and surrounding anatomical landmarks of interest. For example, FIG. 72 shows a workflow 7200 to rapidly re-register a surgical navigation system after a navigated/registered screw insertion in accordance with some embodiments of the invention. In some embodiments, the workflow 7200 describes methods for producing 3D renderings of the vertebrae of interest by registering the location and pose of the vertebrae of interest with respect to known landmarks that are registered in 3D-based images acquired of the vertebra (e.g., CT scan). Some other relevant figures include FIGS. 44A-44D (for a method of registering a substantially rigidly-attached landmark of a vertebra), and FIGS. 45A-45B (for a process of re-registering a manipulated vertebra via a known landmark (e.g., pedicle screw shaft)) according to some embodiments.

Some embodiments of the system involve the use of navigated pedicle screws to register the relationship between the pedicle screw shaft and the vertebral body. Some embodiments of the system involve the use of registered bone-mounted fiducials that are associated with a 3D-displacement vector to anatomical landmarks of interest of the attached vertebra. Some embodiments are depicted in FIGS. 44A-44D.

Some embodiments involve the registration of landmarks of interest of the vertebra with a volumetric 3D reconstruction of the anatomy via modalities such as a CT scan or O-arm scan. Further, some embodiments involve the system registering one or more accessible fiducial markers, surgical implants, or anatomical landmarks as associated components of a 3D reconstruction of the vertebrae. In this way, in some embodiments, each time one or more of the described items are registered by a 3D-tracking acquisition system with location and orientation outputs, the system can calculate the updated position and orientation of anatomical objects of interest that have associated 3D reconstructions. Some embodiments are depicted in FIGS. 45A and 45B.

In some embodiments, any of the above processes, methods, or procedures related to the workflow 7200 can include or be accomplished with one or more of steps or processes such as 7202, 7204, 7205, 7206, 7208, 7210, 7212, 7214, 7216, 7218, 7220, 7222, 7224, 7226, 7228, 7230, 7232, 7234, 7236, 7238, 7240, 7242, 7244, 7246, and 7248. In some embodiments, at least one of the steps can include a decision step (e.g., such as step 7212), where one or more following steps depend on a status, decision, state, or other condition. In some embodiments, the steps of workflow 7200 can proceed in the order as shown. In some embodiments, any of the steps of the workflow 7200 can proceed out of the order as shown. In some embodiments, one or more of the steps of the workflow 7200 can be skipped.

FIGS. 73A-73B display the invention which consists of interpretation of the rod contour via interfacing with a rod-centering fork as described previously in relation to FIGS. 47B, 51D-51I, and 53A-53F, and 54A-54D according to some embodiments. In some embodiments, this acquisition system's calculation is based on the calculated distance from the fork's bifurcation to the rod's cross-sectional center point when a rod of known diameter is fully engaged with the fork of known geometry. For example, FIG. 73A displays 7300 of the invention which consists of a rod-centering fork 7315 on the end of a tool shaft 7305 with attached tracked DRF (not shown), bifurcation at point C 7310, and interfacing with a rod 7311 according to some embodiments. In this configuration, because the fork is not fully engaged with the rod (i.e., the rod is not approximating both side walls of the fork), the tool does not trigger the acquisition system to record the tool's coordinates according to some embodiments. This triggering mechanism to indicate the fork is firmly engaged with the rod can be accomplished via a number of some embodiments including but not limited to a linearly actuated TMSM, rotationally actuated TMSM, electrical conduction through the rod across fork-mounted electrical contact terminals, wireless or wired electronic communication, and optically signaled via visible or infrared lights.

FIG. 73B illustrates the fork of FIG. 73A fully engaged with a rod represented as embodiment 7301 in accordance with some embodiments of the invention. For example, FIG. 73B displays rod-centering fork 7315 on a tool shaft 7305 fully engaged with a rod 7317 such that both inner walls of the fork 7315 are approximating the rod surface according to some embodiments. In some embodiments, point C 7310 indicating the bifurcation of the fork is known relative to the tracked DRF (not shown) attached to the tool. In some embodiments, based on the known diameter of the rod and geometry of the fork, a vector V1 7319 is produced to point from C 7310 to the calculated center point of the rod, C' 7318, located along the line that bisects the fork. In some embodiments, after interpreting the location of point C' 7318 relative to the tracked DRF attached to the fork-equipped tool, the coordinates of C' 7318 undergo a rigid body transformation to be represented within the coordinates of a DRF-equipped end cap, if applicable. For some embodiments that do not involve a coupled end-cap as described previously in relation to FIGS. 52A-52D, 53A-53F, and 54A-54D, the rod coordinates are interpreted relative to the camera coordinates or anatomical reference marker if present.

Some embodiments of this invention involve the process of registering the contour of a rod implant via a combination of 3D-tracked tools. For example, FIG. 74 illustrates a workflow to assess the contour of a rod prior to implantation using two handheld tracked tools in accordance with some embodiments of the invention. Some other relevant other figures (e.g., such as tools used for assessing rod contour include FIGS. 48A-48C, 49D, 50D-50E, 51H-51I, 53C-53D, and 54C-54D) according to some embodiments. Further, other figures and descriptions for tools using a tracked mobile stray marker as a trigger include FIG. 63 according to some embodiments.

Some embodiments of this invention involve the use of one or more 3D-tracked tools that have a substantially rigidly attached tracked DRF. Some embodiments of the system involve using a 3D-tracked tool that substantially rigidly attaches to one end of a surgical rod. Some example embodiments are depicted in FIGS. 48A-C, and 49D. Some embodiments involve selecting a rod diameter via various communication signals (e.g., FIGS. 49D, and 50D-50E) using 3D-tracked tools and substantially rigidly attached TMSMs that the computer system can detect as a trigger, as depicted in FIG. 63.

Some embodiments involve using a second 3D-tracked tool with an end-effector that conforms to a rod surface and contains a depressible shaft that is coaxial with the shaft of the 3D-tracked tool. In some embodiments, when the 3D-tracked tool is pressed against the rod surface, the depressible tip actuates up the 3D-tracked tool and translates a TMSM that is substantially rigidly attached to the depressible shaft, which signals to the 3D-tracking acquisition system that the rod is being engaged. Some embodiments of this system involve using this 3D-tracked tool in an active/triggered state to trace the contour of the rod, and simultaneously to apply a rigid transformation to each discrete point of tracing data to reference the 3D-tracked end cap tool that has dynamic location coordinates and orientation with respect to the 3D-tracking acquisition system.

Some embodiments of this system involve the rod, which is attached to the 3D-tracked end cap tool, where inserting the opposite end through a toroid-shaped object can allow for cross-sections of the rod (that are parallel to the toroidal object's entry way) to pass through. In this instance, the dynamic path traveled by the 3D-tracked end cap can be used to calculate the contour of the rod by association of the constraints of the bends causing a travel path for the 3D-tracked end cap according to some embodiments. Some example embodiments of this system in various applications and forms are depicted in at least FIGS. 48A-48C, 49D, 50D-50E, 51H-51I, 53C-53D, and 54C-54D.

In some embodiments, any of the above processes, methods, or procedures related to the workflow 7400 can include or be accomplished with one or more of steps or processes such as 7402, 7404, 7406, 7408, 7410, 7412, 7414, 7416, 7418, 7420, 7422, 7424, 7426, 7428, 7430, 7432, 7442, 7443, 7440, 7438, 7434, and 7436. In some embodiments, at least one of the steps can include a decision step (e.g., such as step 7404 and 7422), where one or more following steps depend on a status, decision, state, or other condition. In some embodiments, the steps of workflow 7400 can proceed in the order as shown. In some embodiments, any of the steps of the workflow 7400 can proceed out of the order as shown. In some embodiments, one or more of the steps of the workflow 7400 can be skipped.

Some embodiments of this invention involve the process of registering the contour of a rod implant via a combination of 3D-tracked tools and stationary objects. FIG. 75 illustrates a workflow 7500 to assess the contour of a rod prior to implantation using one handheld tracked tool and one substantially rigidly fixed ring in accordance with some embodiments of the invention. In some embodiments, other relevant figures include tools used for assessing rod contour (FIGS. 48A-48C, 50B-50C), a ring-based tracing tool (FIGS. 49A-49D), and similar tracked end cap-based process of rod contour assessments (e.g., such as FIGS. 74-75).

Some embodiments of this system involve a similar process to that described in FIG. 74, in which a 3D-tracked end cap tool with a substantially rigidly tracked DRF is used to serve as a tracked coordinate system reference for the rod contour. Some embodiments of this system involve inserting the rod's opposite end through a toroid-shaped object that is fixed in space, (and that allows for cross-sections of the rod that are parallel to its entry way) to pass through. In some embodiments, in this instance, the dynamic path traveled by the 3D-tracked end cap tool is used to calculate the contour of the rod by association of the constraints of the bends causing a travel path for the 3D-tracked end cap.

Some embodiments involve the use of one or more tracked mobile stray markers (TMSMs) attached to a fixed toroid-shaped object, where one hinge-based TMSM is actuated relative to a fixed TMSM to indicate to the 3D-tracking acquisition system when a rod is being inserted through its passage way. Some example embodiments include FIGS. 49A-49D.

Some embodiments involve applying a rigid transformation to the fixed toroid-shaped object's location and orientation, which is relative to the 3D-tracked acquisition unit, and transforming its position to be relative to the location and orientation of the 3D-tracked end cap tool. Some embodiments in various applications and forms are depicted in FIGS. 48A-48C and 50B-50C.

In some embodiments, any of the above processes, methods, or procedures related to the workflow 7500 can include or be accomplished with one or more of steps or processes such as 7502, 7504, 7506, 7508, 7510, 7512, 7514, 7516, 7518, 7520, 7522, 7524, 7526, 7528, 7530, 7532, 7534, 7536, 7538, 7540, 7542, 7544, 7546, 7548, 7550. In some embodiments, at least one of the steps can include a decision step (e.g., such as step 7504 or 7532), where one or more following steps depend on a status, decision, state, or other condition. In some embodiments, the steps of workflow 7500 can proceed in the order as shown. In some embodiments, any of the steps of the workflow 7500 can proceed out of the order as shown. In some embodiments, one or more of the steps of the workflow 7500 can be skipped.

Some embodiments of this invention involve the process of registering the contour of a rod implant via a combination of 3D-tracked tools after the rod has been implanted into the spinal anatomy. FIG. 76 illustrates a workflow 7600 to assess the contour of a rod after implantation in accordance with some embodiments of the invention. In some embodiments, other relevant figures include those that relate to rod contour triggering of a 3D-tracked tool (FIGS. 53A, and 53C-53D, 54A-54D, and 73A-73B), and rod contour assessment process while rod is implanted (FIGS. 77A-77C).

Some embodiments involve designs with a depressible shaft that is coaxial to the shaft of a 3D-tracked tool, where the depressible shaft is mechanically linked to a TMSM that can signal to the 3D-tracking acquisition system that a rod is being traced when the TMSM is actuated relative to the 3D-tracking tool's end effector. Some examples of embodiments of this process are depicted in FIGS. 53A, and 53C-53D. Some embodiments for sensing when the 3D-tracked tool is pressed against the rod surface are depicted in FIGS. 54A-54D and 73A-73B.

Some embodiments involve using the described rod-sensing, 3D-tracked tool to trace the contour of a rod while it is implanted and collecting the 3D location and pose of the tool during the process. Some embodiments involve the computer system fitting a line between the interruptions in the tracing caused by other surgical implants (e.g., pedicle screw heads) to estimate the full contour of the rod that is implanted. Some embodiments of this system are depicted in FIGS. 77A-77C.

In some embodiments, any of the above processes, methods, or procedures related to the workflow 7600 can include or be accomplished with one or more of steps or processes such as 7602, 7604, 7606, 7608, 7610, 7612, 7614, 7620, 7618, 7616, 7622, and 7624. In some embodiments, any of the steps of the workflow 7600 can proceed out of the order as shown. In some embodiments, one or more of the steps of the workflow 7600 can be skipped.

Some embodiments include interpretation of data generated by the assessment of a rod contour after a rod has been implanted to the tulip heads within the surgical site, including any data from some embodiments previously described in relation to FIGS. 52A-52D, 53A-53F, 54A-54D, 73A-73B, and 76.

FIG. 77A displays the invention which involves spinal vertebra 7711 that have been instrumented with pedicle screw shafts 7745 and a rod 7720 implanted into their tulip heads 7722 according to some embodiments. The contour of this rod can be assessed while implanted within the surgical site in this way via utilization of the some embodiments described previously in FIGS. 52-54. FIG. 77B displays some embodiments of the invention which consists of an implanted rod and surrounding elements described previously in relation to FIG. 77A and use of a post-implantation rod contour assessment device 7780, described previously in relation to FIGS. 52A-52D, 53A-53F, and 54A-54D, to interface with and trace the coordinates of the implanted rod such that the coordinates of the activated device 7728 are recorded while the inactive coordinates 7782 (e.g., tracing probe over pedicle screws 7745 that obstruct the path of the implanted rod) are discarded. The contour assessment device is designed in such a way to trigger only when the device is fully engaged with the rod, so when the device is removed from the rod to navigate around path-obstructing hardware, it is not triggering to the acquisition system to record its coordinates. Some embodiments describing the acquisition process and interpretation of an implanted rod's coordinates based on the coordinates of the assessment device were previously described in relation to FIGS. 73 and 76. Further, FIG. 77C displays some embodiments of the invention for interpreting the data obtained from an implanted rod's contour assessment with a device as previously described in FIGS. 77A-B consisting of the plotted coordinates representing the rod's contour from actively-triggered assessment device 7790 and the reconstructed rod contour 7792 based on the interpretation of the recorded rod data points. In some embodiments, this reconstructed contour is produced via a spline defined by the inputs of the recorded rod coordinates. Some embodiments of producing this reconstructed rod include but are not limited to variable order polynomial fitting and smoothing filters applied to the recorded rod coordinates.

Some embodiments of this invention involve the process of projecting an overlay of a registered 3D contour of a spinal rod onto patient imaging on a display monitor and allowing the user to interactively place and adjust the position of the rod overlay. For example, FIG. 78 illustrates a workflow 7800 for interactive user placement of a registered rod as an overlay on patient images on a display monitor in accordance with some embodiments of the invention. Some other relevant figures and descriptions include FIGS. 74-76 (for processes for assessing the contour of a rod, pre- and post-implantation), and FIGS. 87F-87G (for interactive overlay of registered rod contour on patient imaging) according to some embodiments.

Some embodiments of the invention involve maintaining usage of the 3D-tracked end cap tool that is substantially rigidly attached to a previously-registered rod contour. Some embodiments of the invention involve the user confirming the coordinates of the overlay interaction by pointing the 3D-tracked end cap tool with the registered rod at the display monitor and triggering via a TMSM when the orientation of the 3D-tracked end cap tool matches the up/down and left/right motions that map the overlay in an intuitive manner for the user to manipulate on the display monitor.

Some embodiments involve the user manipulating the 2D projections of the registered contour of the rod via the movement of the 3D-tracked end cap tool along the pre-selected orientation of the tool relative to the orientation of the display monitor. Some embodiments involve the patient preoperative or intraoperative imaging being scaled in physical units (e.g., millimeters) and enabling for the accurate scaling of the overlay of the registered rod contour. Some further embodiments involve the user being able to select two or more points on the image that the rod contour overlay should intersect with and manipulate its contour position and orientation to meet those point intersection constraints. Some examples of embodiments of this invention in various applications and form are depicted in FIGS. 74-76, with the interactive overlay of the rod contour on a display monitor with patient imaging depicted in FIGS. 87F-87G.

In some embodiments, any of the above processes, methods, or procedures related to the workflow 7800 can include or be accomplished with one or more of steps or processes such as 7802, 7804, 7806, 7808, 7810, 7812, 7814, 7816, 7822, 7828, 7830, 7832, 7834, 7836, 7838, 7818, 7820, 7826, 7824, 7844, 7840, 7846, 7848, 7842, and 7850. In some embodiments, any of the steps of the workflow 7800 can proceed out of the order as shown. In some embodiments, one or more of the steps of the workflow 7800 can be skipped.

FIGS. 79A-79G relate to some embodiments of the invention which consists of the process of interpreting and calculating a tracked rod bending device, as previously described in relation to FIGS. 55D-55I, 56A-56D, and 56F, interfacing with a rod which has had its contour previously registered via some embodiments previously described in relation to FIGS. 49D, 50E, and 51H-51I, and enables the interpretation and calculation of the rod's new contour based on acquisition system input from the tracked rod bender as related to the previously registered rod coordinates relative to the tracked-DRF-equipped end cap to which the rod is secured according to some embodiments.

Figures 79A, 79B, 79C, 79D, 79E, 79F, 79G:
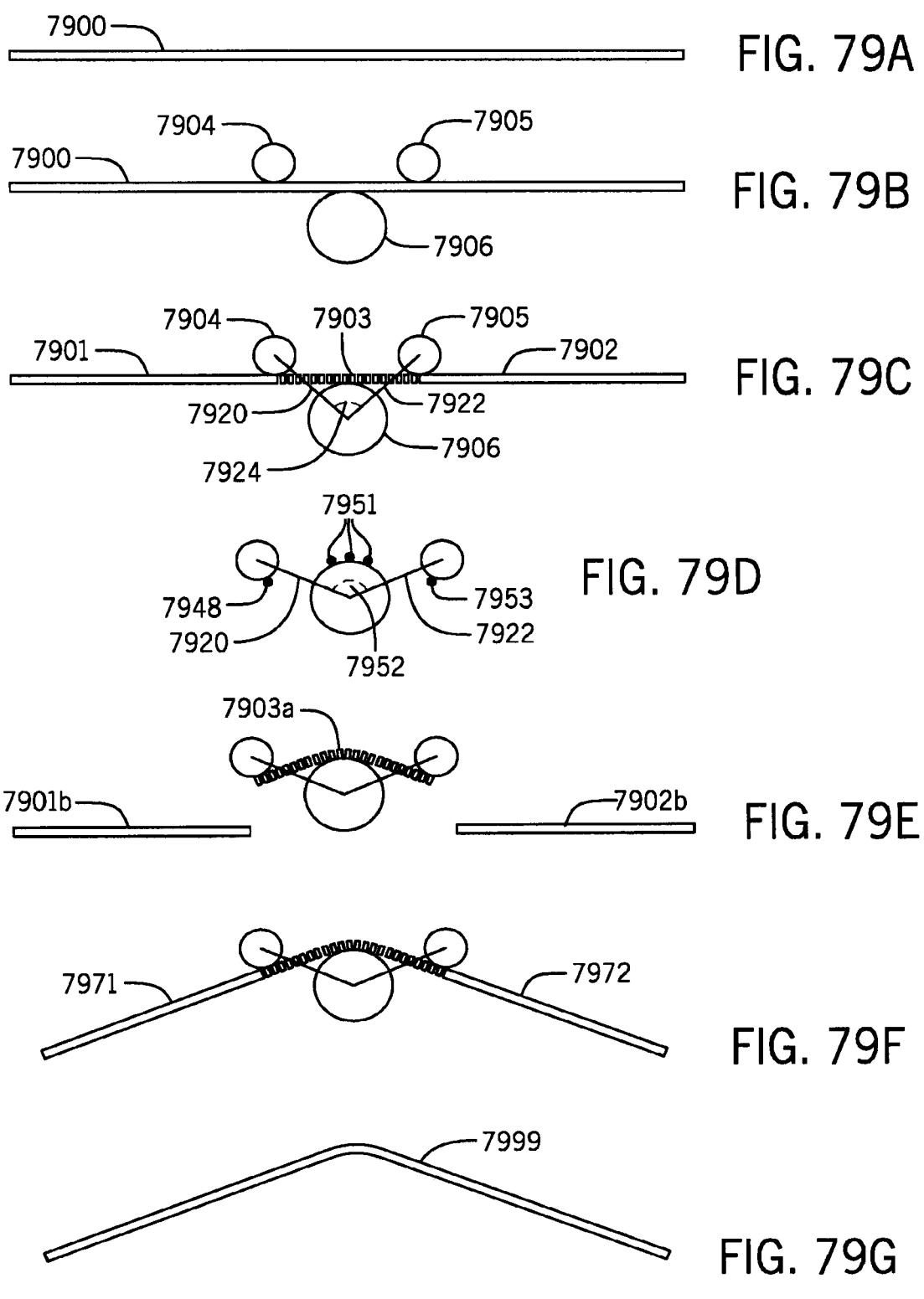

FIG. 79A displays some embodiments of the invention consisting of the coordinates of a previously registered contour of rod 7900 with known diameter, projected onto the 2D plane of the rod bending tool, defined by the middle of the three rod-interface points on the rod bender according to some embodiments. FIG. 79B displays according to some embodiments of the invention consisting of the previously-registered rod contour 7900, described previously in relation to FIG. 79A, and the relative locations of the rod bender's left outer roller 7904, center rod contouring surface 7906, and right outer roller 7905. As shown in some embodiments, the three rod-interface components of the bender are engaged with the rod, indicated by being displayed tangential to the previously registered rod contour.

FIG. 79C displays some embodiments of the invention consisting of the previously registered rod coordinates divided into three segments: the left unengaged rod segment 7901, bender-engaged segment 7903, and right unengaged segment 7902. In addition, some embodiments include lines connecting the center rod contouring surface to the left outer roller 7920 and right outer roller 7922 from which the angle between them 7924 can be calculated. In some embodiments, when the bender is engaged with a straight rod, this angle will be at a minimum, as opposed to when the bender is applying maximum curvature to the rod, this reference angle will be at a maximum.

FIG. 79D displays some embodiments of the invention in which the rod bender's handles are approximated to induce a bend in previously registered rod such that the angle 7952 between inter-roller vectors (7920, 7922) previously described in relation to FIG. 79C is increased. In some embodiments, from the known current bend configuration of the tracked bender, the bender's known geometry, and the known rod diameter, the acquisition system software then computes rod contact points (displayed as solid circles) on the left outer roller 7948, center contour surface 7951, and right outer roller 7953 by solving for tangent lines between each rod-interface surface.

FIG. 79E displays some embodiments of the invention which the rod contact points calculated and described previously in relation to FIG. 79D are used as constraints for defining a spline connecting each of them, and producing the newly computed bender-engaged segment of the rod contour 7903 a and based on the path length of the spline, (which is longer when the bender is in the bent configuration than straight configuration), updated left 7901*b* and right 7902*b* unengaged segments of the rod are interpreted. Further. FIG. 79F displays some embodiments of the invention which involves tangentially re-approximating the left 7971 and right 7972 unengaged segments of the rod contour as previously described in relation to FIG. 79E, by undergoing a rigid body transformation to both translate and rotate to tangentially approximate the spline-produced bender-engaged contour of the rod.

FIG. 79G displays some embodiments of the invention in which described previously in relation to FIG. 79A-79F are utilized to produce updated projected coordinates of the rod's contour 7999 after bending with a tracked bender and combined with 3D contour coordinates prior to the bend to compute and update the registered 3D-curvature of the rod. Some embodiments described previously in relation to FIGS. 79A-79G can be applied to calculate and update pre-registered rod contours when interfacing with tracked rod benders previously described in FIGS. 55D-55I, 56A-56D, and 56F.

Some embodiments of this invention involve the process of tracking the dynamic contour of a registered rod that is being contoured into a new shape prior to implantation of the rod. For example, FIG. 80 illustrates a workflow for manually bending a rod prior to its implantation with real-time feedback of its dynamic contour in accordance with some embodiments of the invention. In some embodiments, other relevant figures and descriptions can include FIGS. 55A-55I, 56A-56F (devices used to bend registered rod and track changes in its contour), FIGS. 79A-79G (for calculation of rod bending of a registered rod contour), and FIGS. 87A-87G, 88A-88F (for display of rod bending feedback of a registered rod contour), and FIGS. 74-76 (for processes for assessing the contour of a rod, pre- and post-implantation). In some embodiments, the workflow 80 can comprise steps 8002, 8004, 8006, 8008, 8010, 8014, 8016, 8018, 8020, 8022, 8024, 8026, 8028, 8030, 8032, 8034, 8036, 8040, 8044, 8038, 8042, and 8046.

Some embodiments of this invention involve tracking the dynamic changes of a registered rod contour that has maintained rigid fixation to a 3D-tracked end cap tool that has a coupled tracked DRF. Some embodiments of this invention involve processes for previously registering the rod, for which some examples are depicted in FIGS. 74-76.

Some embodiments of this system involve using a mobile, 3D-tracked rod bender and a TMSM substantially rigidly attached to the opposite end of the registered rod to that of the 3D-tracked end cap tool attached to the rod. Some embodiments interpret the angle between the handles of the 3D-tracked rod bender's bending points, the position of the rod bender along the contour of the rod, and the orientation of the rod bender relative to that of the 3D-tracked end cap tool relative to the 3D-tracking acquisition system, to calculate the approximate new contour of the registered rod based on the deflected segments of the rod. One example of this algorithmic calculation process is depicted in FIGS. 79A-79G according to some embodiments. Some embodiments and permutations of the system that can assess, manipulate, and update the contour of the registered rod are depicted in FIGS. 55A-55I, 56A-56F. Some embodiments of the system involve an interactive, quantitative-feedback display of the registered rod, an overlay of the 3D-tracked rod bender in its active, relative position and orientation with respect to the 3D-tracked end cap tool. Some embodiments are depicted in FIGS. 87A-87G, and 88A-88F.

In some embodiments, any of the above processes, methods, or procedures related to the workflow 8000 can include or be accomplished with one or more of steps or processes such as 8002, 8004, 8006, 8008, 8010, 8014, 8016, 8018, 8020, 8022, 8024, 8026, 8028, 8030, 8032, 8034, 8036, 8040, 8044, 8038, 8042, and 8046. In some embodiments, any of the steps of the workflow 8000 can proceed out of the order as shown. In some embodiments, one or more of the steps of the workflow 8000 can be skipped.

Some embodiments of this invention involve the process of tracking the dynamic contour of a registered rod that is being contoured into a new shape prior to implantation of the rod and providing directed software interactive feedback based on surgical planning inputs. For example, FIG. 81 shows a workflow 8100 for manually bending a rod prior to its implantation with directed software input to overlay a projection of the dynamic rod contour onto an intraoperative X-ray image in accordance with some embodiments of the invention. Some other relevant figures include FIG. 80 (e.g., a process for manually bending registered rod contour and outputting adjusted form), and FIGS. 88A-88F (for a display of rod bending feedback of a registered rod contour) according to some embodiments.

Some embodiments of this system involve directed software feedback that aids the user in determining where along the rod contour a rod bender must be placed, in which orientation with respect to the 3D-tracked end cap tool, and by how much of a bend angle the 3D-tracked rod bender must apply contouring forces and shapes to the registered rod contour. Some embodiments of the system involve a real-time feedback of the rod contouring process of the registered rod and projections of the rod bender in space relative to the position and orientation of the registered rod contour. Some embodiments of the system involve an interactive feedback display that depicts the amount of bending that is occurring, relative to the angle between the handles of the 3D-tracked rod bender, and how much the user should bend the rod contour at that location and orientation to produce the optimal, final new contour of the rod that best matches the surgical planning goals for the procedure.

Some examples of some embodiments in various applications and forms, including the interactive software-based display of the dynamic rod contouring process are depicted in FIGS. 88A-88F.

In some embodiments, any of the above processes, methods, or procedures related to the workflow 8100 can include or be accomplished with one or more of steps or processes such as 8102, 8104, 8106, 8108, 8110, 8112, 8114, 8116, 8118, 8120, 8122, 8124, 8126, 8128, 8130, 8132, 8134, 8136, 8138, 8140, 8142. In some embodiments, any of the steps of the workflow 8100 can proceed out of the order as shown. In some embodiments, one or more of the steps of the workflow 8100 can be skipped.

Some embodiments include a tracked probe with triggering capability, as described previously in relation to FIGS. 10A-10G, and 15A-15C, can be utilized as a user interface device with a non-tracked display monitor via the calibration process described in this figure coupled with the calculations described in detail below in reference to FIG. 83.

FIG. 82A displays some embodiments of the invention in which a non-tracked display monitor 8210 communicates calibration instructions 8205 and displays calibration markers 8230 on the display monitor to guide a user holding a 3D-tracked probe with triggering capability 8240 to calibrate the probe to the screen dimensions and location in space relative to the 3D-tracking camera by sequentially orienting the probe tip and its computed line of trajectory 8245 to each indicated marker on the display monitor (directed to center marker as shown). In some embodiments, the workflow of interpreting this calibration process is described in detail below in reference to FIG. 83. Some embodiments include using a tracked probe with triggering capability to interface as a laser-pointer analog with a tracked monitor as described in detail below in reference to FIGS. 84A-84B, and others involve using a tracked probe with triggering capability to create a user defined trackpad analog to interface with an untracked display monitor as described in detail below in reference to FIG. 85. Further, FIG. 82B displays 5 of the invention previously described in relation to FIG. 82A, in which the computed line of trajectory 8247 of the tracked probe is directed toward the top left calibration marker on the display monitor according to some embodiments.

Some embodiments of this invention involve the process of using a 3D-tracked tool with attached 3D-tracked triggers to interact with a display monitor and use the tool as a selection cursor. For example, FIG. 83 illustrates a workflow to utilize a trigger-equipped probe to serve as a laser pointer analog for a user-interface system with a non-tracked display in accordance with some embodiments of the invention. Some other relevant figures can include FIGS. 82A-82B (for interactive display of trigger-equipped tool with a display monitor), FIGS. 15A-15C (for a trigger-equipped 3D-tracked tool that can be used for interactive display cursor control), and FIG. 63 (for a process of using tracked mobile stray marker TMSM as a toggling attachment to a 3D-tracked tool) according to some embodiments.

Some embodiments of this system involve the use of a 3D-tracked tool with a coupled tracked DRF, as well as a mechanically-linked TMSM, that can be used as software-based inputs of location, orientation, and state of tool relative to a 3D-tracking acquisition system. Some embodiments are depicted in FIG. 63.

Some embodiments involve the 3D-tracked tool pointing at one or more markers at different locations of a display monitor and signaling a selection at each point once the user is confident that the 3D-tracked tool's shaft is most appropriately aligned for pointing a virtual ray at one or more markers displayed on the screen. Some example embodiments of the 3D-tracked tool in various forms and states of use are depicted in FIGS. 15A-15C. Further, some embodiments involve determining the mapping of the movement, locations, and orientations of the 3D-tracked tool between registered marker points on the display monitor by calculating the lines formed by coupled locations and orientations of the 3D-tracked tool at these registered marker points. Some embodiments also involve using the dimensions and pixel resolution of the display monitor to provide more appropriate mapping of the 3D-tracked tool's motion relative to the display monitor. Further, some embodiments of the system enable the user to be able to use the 3D-tracked tool as a virtual cursor and input-selection tool for the software system visualized by the display monitor. Some embodiments in various applications and forms are depicted in FIGS. 82A-82B.

In some embodiments, any of the above processes, methods, or procedures related to the workflow 8300 can include or be accomplished with one or more of steps or processes 8302, 8304, 8306, 8308, 8310, 8312, 8314, 8316, 8318, 8320, 8322, 8324, 8326, 8328, 8330, 8334, 8336, 8338. In some embodiments, at least one of the steps can include a decision step (e.g., 8318 or 8328), where one or more following steps depend on a status, decision, state, or other condition. In some embodiments, the steps of workflow 8300 can proceed in the order as shown. In some embodiments, any of the steps of the workflow 8300 can proceed out of the order as shown. In some embodiments, one or more of the steps of the workflow 8300 can be skipped.

Some embodiments of this invention involve the process of using a 3D-tracked tool with attached 3D-tracked triggers to interact with a display monitor and use the tool as a selection cursor, while the display monitor has a coupled 3D-tracked DRF. For example, FIGS. 84A-84B illustrates a workflow to utilize a trigger-equipped probe to serve as a laser pointer analog for a user-interface with a 3D-tracked display monitor in accordance with some embodiments of the invention. Some other relevant figures include FIGS. 82A-82B (interactive display of trigger-equipped tool with a display monitor), FIGS. 15A-15C (for a trigger-equipped 3D-tracked tool that can be used for interactive display cursor control), and FIG. 63 (a process of using TMSM as a toggling attachment to a 3D-tracked tool), and FIG. 83 (a process of using a 3D-tracking tool as an interface display monitor cursor) according to some embodiments. Some embodiments of this system involve the processes and references made by FIG. 83.

Some embodiments of the system involve substantially rigidly attaching a 3D-tracked DRF to a display monitor that will be used for interactive software purposes. Further, some embodiments of the system involve using the DRF-equipped display monitor as a reference tool in the tracking volume of the 3D-tracking acquisition system. Some embodiments involve processes outlined in FIG. 83, which describe examples of a process for calibrating a display monitor's dimensions according to the movement, location, and orientation of a trigger-equipped 3D-tracked tool. Some embodiments of this system are depicted in FIGS. 82A-82B.

In reference specifically to FIG. 84B, some embodiments of this system are dependent on process described in FIG. 84A. Some embodiments of this system utilize processes described in FIGS. 83 and 63. Some embodiments of this system involve substantially rigidly attaching a 3D-tracked DRF to a display monitor that will be used for interactive software purposes. Further, some embodiments of this system involve algorithmic calculations of the relative locations and orientations of the 3D-tracked, trigger-equipped tool (e.g., FIGS. 15A-15C) with respect to the 3D-tracking acquisition system to calculate the appropriate ray intersection of the 3D-tracked tool's probe shaft direction and the orientation of the display monitor. Some embodiments involve using the dimensions and pixel resolution of the display monitor to provide more appropriate mapping of the 3D-tracked tool's motion relative to the display monitor. Some embodiment including the attachment of a DRF to the display monitor, are depicted in FIGS. 82A-82B.

In some embodiments, any of the above processes, methods, or procedures related to the workflow 8400 can include or be accomplished with one or more of steps or processes 8402, 8404, 8406, 8408, 8410, 8412, 8414, 8416, 8418, 8420, 8422, 8424, 8426, 8428, 8430, 8452, 8454, 8456, 8458, 8464, 8466, 8468, 8470, 8462, and 8460. In some embodiments, at least one of the steps can include a decision step (e.g., such as step 8402), where one or more following steps depend on a status, decision, state, or other condition. In some embodiments, the steps of workflow 8400 can proceed in the order as shown. In some embodiments, any of the steps of the workflow 8400 can proceed out of the order as shown. In some embodiments, one or more of the steps of the workflow 8400 can be skipped.

Some embodiments of this invention involve the process of using a 3D-tracked tool with attached 3D-tracked triggers to interact with a display monitor and use the tool as a selection cursor, via the calibration of a non-tracked surface. For example, FIG. 85 illustrates a workflow 8500 to utilize a trigger-equipped probe to serve as an interface device for a non-tracked display via a user-defined trackpad analog in accordance with some embodiments of the invention. Some other relevant figures include FIG. 63 (a process of using tracked mobile stray marker (TMSM) as a toggling attachment to a 3D-tracked tool), FIG. 83 (a process of using a 3D-tracking tool as an interface display monitor cursor), FIGS. 15A-15C (a trigger-equipped, 3D-tracked tool that can be used for interactive display cursor control), and FIGS. 82A-82B (an interactive display of trigger-equipped tool with a display monitor). For example, some embodiments of this system utilize processes described in FIGS. 63 and 83. Some embodiments involve the 3D-tracked tool pointing at one or more markers at different locations of a display monitor and signaling a selection at each point once the user is confident that the 3D-tracked tool's shaft is most appropriately aligned to be pointing a virtual ray at the marker(s) displayed on the screen. Some example embodiments of the 3D-tracked tool in various forms and states of use are depicted in FIGS. 15A-15C.

Some embodiments involve the use of the 3D-tracked tool to either trace the border of a rigid, non-tracked object or register multiple discrete points on the border surface of a rigid, non-tracked object in order to register its border dimensions and the orientation of the frame relative to the 3D-tracking acquisition system. Further, some embodiments involve using the dimensions and pixel resolution of the display monitor to provide more appropriate mapping of the 3D-tracked tool's motion relative to the display monitor. Some embodiments involve calculating the mapping between the registered rigid, non-tracked object dimensions and orientation and the dimensions of the display monitor. Some embodiments algorithmically calculate the interactive placement of a cursor on the display monitor based on the location of the 3D-tracked tool end effector on the rigid, non-tracked, registered object surface within its border boundaries. Some embodiments in various applications and forms are depicted in FIGS. 82A-82B and 83.

In some embodiments, any of the above processes, methods, or procedures related to the workflow 8500 can include or be accomplished with one or more of steps or processes 8502, 8504, 8506, 8508, 8510, 8512, 8514, 8516, 8518, 8520, 8522, 8524, 8526, 8528, and 8530. In some embodiments, any of the steps of the workflow 8500 can proceed out of the order as shown. In some embodiments, one or more of the steps of the workflow 8500 can be skipped.

Some embodiments of the system described herein can generate output displays for the alignment assessments performed with some embodiments of the invention previously described in relation to at least FIGS. 62A-62D, and 65A-65E, 66A-66B, and 67-69.

FIG. 86A displays some embodiments of the invention consisting of drawings 8600 of computed spinal alignment parameters and their current value displayed beneath each one as calculated from the alignment assessment. Some embodiments include these displays and/or their quantified values changing colors based on proximity to predetermined surgical goals, enabling the user to visualize and focus on parameters that are farthest away from the predetermined ranges. Some embodiments include the ability of the user to view previously-acquired assessments, and dynamically-responsive spine drawings that change their contour to accurately represent their most recently measured values. In some embodiments, the display as shown and described can be applied to any measurement value between two regions of the spine or between one anatomical region and the spine or pelvis. In some embodiments, the data acquisition and interpretation processes to generate these parameters are described previously as described earlier.

FIG. 86B displays some embodiments of the invention which is an output display of a patient image in the sagittal 8650a and coronal 8650b planes with the option to remove any software overlays. Further, FIG. 86C displays some embodiments of the invention which consists of sagittal and coronal patient images with sagittal and coronal overlays (8651a, 8651b respectively) of the patient's spinal anatomy representing their current spinal alignment based on intra-operative assessments. In some embodiments, to generate these overlays, manual or automated segmentation of previously-acquired patient images is used to isolate the elements of the spine which is then anchored at a reference point to the prior image, and then both rotated and distorted to provide a qualitative representation of the measured alignment. In some embodiments, rather than an overlay of a dynamically modified segmented image, an overlay of a line representing the contour of the spine is displayed on the patient image. In some embodiments, this curve can be with or without discrete spinal level indications and the user is able to toggle previously acquired tracing contour assessments on and off.

FIG. 86D displays some embodiments of the invention which is an output display 8675 of the measured spinal alignment parameters represented by discrete vertebra that both individually translate and rotate to align tangentially with the measured spinal alignment. In this way, the output can dynamically adjust to localized measurements, such as lumbar lordosis, shown going from 10 degrees 8678 to 30 degrees 8681 which include altering the alignment between the related endplates within the output display. Some embodiments also consists of this dynamic display shown in the coronal plane (not shown) and 3D perspective view. Another component of some embodiments is the display of discrete spinal level labels 8683 relative to the output image.

Some embodiments include a rod with previously registered contour fixed to a tracked DRF-equipped end cap and interacting with a tracked rod bender in accordance with some embodiments of the invention. For example, FIG. 87A displays some embodiments of the invention previously described in relation to FIGS. 55D-55I, 56A-D, and 56F, consisting of a rod 8715 with previously registered contour fixed to a tracked DRF-equipped end cap 8710 and interacting with a tracked rod bender 8720.

FIG. 87B displays some embodiments of the invention consisting of a sagittal projection of the registered rod contour 8735, a display indicating the current sagittal location of the tracked rod bender 8755 relative to the registered rod contour as referenced to the end cap DRF axes, and labels 8717 for the anatomical axes for ease of user-interpretation. In some embodiments, the user is able to visualize where the rod bender is located relative to the 2D anatomical projection of the rod, allowing for improved interpretation of complex rod contours as well as interpretation relative to the patient imaging as described below in reference to FIGS. 87F-87G. It should be noted that the rod contour registration process, which takes place prior to utilizing some embodiments of the invention is described above in relation to FIGS. 47A-47B, 51A-51G, and 73A-73B, and 74-75.

FIG. 87C displays some embodiments of the invention consisting of a coronal projection of the registered rod contour 8765, a display indicating the current coronal location of the tracked rod bender 8760 relative to the registered rod contour as referenced to the end cap DRF axes, and labels 8723 for the anatomical axes for ease of user interpretation. In some embodiments, the location of the rod bender is displayed as a projection of the bender onto the displayed plane. In some embodiments, as shown, in this figure, the rod bender is located orthogonal to both the segment of the rod with which it is engaged and the coronal plane, as indicated by the narrow rectangle in this projection. When the bender is bending within the displayed plane, it is displayed as it is shown in relation to FIG. 87B according to some embodiments.

FIG. 87D displays some embodiments of the invention which displays the location of the bender's center rod contouring surface 8730 relative to a cross-sectional view of the rod 8725 with labels for the anatomical axes 8727. Some embodiments allow for interpretation of the location of tracked rod bender's interface components, as rotated about the long axis of each segment of the rod.

FIG. 87E displays some embodiments of the invention which displays a sagittal projection of the registered rod contour 8735, and generates orthogonal lines from the superior rod endpoint 8740, and the inferior rod endpoint 8745, along with the calculated angle between them 8750, in addition to labels 8733 for the anatomical axes. In some embodiments, the user can modify and select discrete locations on the rod between which orthogonal lines will be drawn and angles calculated. In some embodiments, the rod and corresponding measurements between orthogonal lines can be projected onto the coronal plane. Additionally, in some embodiments, these projections and measured angles can be performed after assessing the rod contour both prior to and after implantations, and need not necessitate interfacing with a tracked bender to do so.

FIG. 87F displays a sagittal patient image 8775 with an overlay of a registered rod contour 8777 as well as an overlay display of the location of a tracked rod bender 8779 relative to the previously registered rod according to some embodiments. The placement location of the registered rod's contour can be achieved via some embodiments described previously in relation to FIG. 78.

FIG. 87G displays a sagittal patient image adjusted for operative planning 8781 with an overlay of a registered rod contour 8783 as well as an overlay display of the location of a tracked rod bender 8785 relative to the previously registered rod according to some embodiments. The placement location of the registered rod's contour over this adjusted patient image can be achieved via some embodiments described previously in relation to FIG. 78. In some embodiments, by overlaying the registered rod contour over the image adjusted to mimic operative goals, the contour of the rod can be adjusted with real-time display feedback to a point where it superimposes over the adjusted patient image in such a way that it is located where it would be on a postoperative image, secured to the tulip heads of implanted pedicle screws.

FIG. 87H displays some embodiments of the invention in which the rod bender's location on the display monitor is represented as an arrow 8786 and the rod is represented as a single colored, solid line 8787.

FIG. 87I displays some embodiments of the invention in which the rod bender's location on the display monitor is represented as an arrow 8786 and the segment of the rod engaged with the rod bender is a different color 8789 than the segments of the rod not engaged with the bender 8788, as described previously in relation to FIG. 79. In some embodiments, rather than a change in color, the engaged segment of rod can be differentiated from the unengaged segment of rod via a change in stroke weight of the line, or changing from dashed to solid lines.

FIG. 87J displays some embodiments of the invention in which the rod bender's location on the display monitor is represented as an outline of the manual rod bender with profile outlines 8795 of the handles and rod interface regions adapting the display based on the current orientation of the handles to one another. In some embodiments, in this figure, it is displayed with the handles fully open (i.e., at the largest angle between them) to accommodate interfacing with a straight rod 8793.

FIG. 87K displays some embodiments of the invention in which the rod bender's location on the display monitor is represented as an outline of the manual rod bender with profile outlines 8796 of the handles and rod interface regions adapting the display based on the current orientation of the handles to one another. In some embodiments, in this figure, it is displayed with the handles fully closed (i.e., at the smallest angle between them) and therefore interfacing with a bent region of the rod 8794.

FIG. 87L displays some embodiments of the invention in which the rod bender's location on the display monitor is represented as three filled circles to represent the left outer roller 8789, center rod contouring surface 8790 and right outer roller 8791 engaged with a straight rod 8787. Further, FIG. 87M displays some embodiments of the invention in which the rod bender's location on the display monitor is represented as three filled circles with an outline 8792 to represent the left outer roller 8789, center rod contouring surface 8790 and right outer roller 8791 engaged with a straight rod 8787.

Some embodiments include display monitor interfaces to allow for software-directed bending of a previously registered rod substantially rigidly fixed to a tracked DRF-equipped end cap and interfacing with a tracked rod bender as previously described in relation to FIGS. 87A-87M. Some embodiments enable mechanisms of instructing the user where and how to bend the rod with a tracked rod bender in order for the rod's final contour to match preset inputs. In some embodiments, these preset inputs are embodied in varying forms and can be based on preoperative imaging, preoperative planning, preset measurement inputs, and intraoperative alignment measures among others. The workflow associated with some embodiments is described previously in reference to FIGS. 80-81.

Some embodiments include a sagittal projection of a registered rod contour, a display of the current location of the rod bender relative to the registered rod contour, a display of the software-instructed location where the user should place the rod-bender, and anatomical axes labels in accordance with some embodiments of the invention.

FIG. 88A displays some embodiments of the invention consisting of a sagittal projection of a registered rod contour 8801, a display of the current location of the rod bender 8803 relative to the registered rod contour, a display of the software-instructed location where the user should place the rod bender 8805, and anatomical axes labels 8825. Some embodiments allow for visual display and feedback showing where the rod bender is relative to where the software is instructing the user to place the rod bender on the rod. $11n$ some embodiments, the appearance of the software-instructed location of the bender changes via color, line weight, or shape, to indicate when the user has successfully overlaid the current location of the bender onto the software-instructed location for the bender relative to the registered rod.

FIG. 88B illustrates a display of FIG. 88A as applied to the coronal plane in accordance with some embodiments of the invention, with coronal projection of registered rod contour 8807, coronal display overlay of current bender location relative to rod 8809, software-instructed bending indicator of bender placement location 8811, and anatomical axes labels 8827.

FIG. 88C illustrates a cross-sectional display of the rod, the current location of the rod bender's center contouring surface, the software-instructed location of where the rod bender's center contouring surface should be placed, and anatomical axes labels in accordance with some embodiments of the invention. Shown are the cross-sectional display of rod 8813, current orientation of bender 8815, software-instructed indicator of bender placement location 8817, anatomical axes labels 8829 according to some embodiments.

FIG. 88D displays some embodiments of the invention consisting of a display representation of the current relative position of the bender's handles 8852, directly related to the degree of bending induced on a rod of known diameter. In some embodiments, the angle between the handles is adaptive and changes based on the detected conformation of the tracked rod bender. Further, FIG. 88E illustrates a display representation of the software-instructed relative position of the bender's handles 8854, directly related to the degree of bending induced on a rod of known diameter in accordance with some embodiments of the invention. In some embodiments, the display representation of the software-instructed relative position of the bender's handles 8854, directly related to the degree of bending induced on a rod of known diameter. In some embodiments, the rod bender is displayed in its state of maximum bending (i.e., minimum angle between handles) and any angle within the achievable range of motion of the rod bender's handles can be displayed as the software-instructed degree of bending for the user to match once the bender is placed in the indicated location along the length of the rod, as described in FIGS. 88A-88B, and once the bender is located at the right angle relative to the rod's cross section, as described in FIG. 88C.

FIG. 88F represents some embodiments of the invention consisting of a display representation of an angle gauge 8866 within which the current angle between the tracked rod bender's handles 8862 is shown in addition to the software-instructed indicator 8864 of what angle is necessary at that point of engagement between the previously registered rod and tracked rod bender. In some embodiments, the user is able to watch the current bend angle of the tracked bender changes as the handles are moved closer to or farther from one another. In some embodiments, the user adjusts the angle between handles until the current angle indicator is superimposed over the software-instructed angle indicator, at which point the user-interface displays the next location of bending required to achieve the desired rod contour that was input to the system.

In some embodiments, any of the systems and software can be applied with rod cutters to instruct the user where to cut the rod as mentioned above. Some embodiments of the invention also include indications of where a tracked rod-cutting device is relative to a previously registered rod that is still coupled with the tracked DRF-equipped end cap. Both live tracking of the cutter relative to the previously registered rod, as well as software-instructed placement of a cutting device relative to the rod, is included in some embodiments of the invention.

Some embodiments of this invention involve the process of interactively providing instructions of how to manipulate and position an adjustable spine phantom model to approximate orientations and relations available in imaging of the model. For example, FIG. 89 shows a workflow to match the adjustable benchtop spinal model to mimic alignment parameters from patient-specific imaging in accordance with some embodiments of the invention. Other relevant figures include FIGS. 90A-90D (a display and interactive adjustable components of benchtop spine model) according to some embodiments.

Some embodiments of the system involve the annotation of spinal vertebrae levels of the benchtop spine model based on visualization of the anatomy by imaging technologies (e.g., CT, MM, 2D X-ray radiograph, ultrasound, etc.) Further, some embodiments of the system involve substantially rigidly attaching an arrangement of adjustable, incrementally-measured levers that both substantially rigidly fix the conformation of the spine model in space, and provide quantitative feedback for the user to interpret the position of each multi-lever, adjustable fixation device. Some embodiments of the multi-lever, adjustable fixation device is depicted in FIG. 90C.

Some embodiments involve the rigid attachment of the multi-lever, adjustable fixation device to each spinal vertebra level. Some embodiments involve attaching select levels of the spine model to substantially rigidly attach to a multi-lever, adjustable fixation device. Some embodiments of the system involve instructing the user to adjust specific segments of the spine via the manipulation of one or more multi-lever, adjustable fixation devices to configure the conformation of the spine model in a manner that matches the configuration of anatomies as visualized in the imaging registration of the spine model. Some further embodiments involve produced transformed 3D CT-based reconstructions or cross-sectional visualization estimates of the spine model anatomy as it is currently positioned on the benchtop, assuming that the user followed software directions correctly to adjust the spine model in a specific conformation.

In some embodiments, any of the above processes, methods, or procedures related to the workflow 8900 can include or be accomplished with one or more of steps or processes 8902, 8904, 8906, 8908, 8910, 8912, 8914, 8916, 8918, 8920, 8922, 8924, 8926, 8928, 8930, 8932, 8934, 8936. In some embodiments, at least one of the steps can include a decision step (e.g., such as step 8918), where one or more following steps depend on a status, decision, state, or other condition. In some embodiments, the steps of workflow 8900 can proceed in the order as shown. In some embodiments, any of the steps of the workflow 8900 can proceed out of the order as shown. In some embodiments, one or more of the steps of the workflow 8900 can be skipped.

Some embodiments relate to patient images that are analyzed to indicate their spinal alignment contour and parameters as well as output instructions of how to position adjustable mounts coupled to an anatomical model of the spine in order to mimic the spinal alignment parameters displayed in the patient images. Some embodiments of this device include inputting desired discrete alignment parameter values (e.g., lumbar lordosis of 30 degrees) to the software which then outputs instructions for how to orient the adjustable mounts to configure the anatomical model to possess the input parameters. Some embodiments of the device consists of a user positioning the anatomical model and then inputting all coordinates of the adjustable mounts into the software for it to then output patient images closely matching the alignment parameters of the anatomical model.

FIG. 90A illustrates sagittal and coronal patient images with overlaid sagittal and coronal contour tracings of the spine, discrete software-instructed placement of adjustable mounts onto the anatomical model, and instructions for the coordinates of each of those adjustable mounts to be positioned on the adjustable benchtop model in accordance with some embodiments of the invention. In some embodiments, the sagittal 9001 and coronal 9007 patient images are shown with overlaid sagittal 9003 and coronal 9009 contour tracings of the spine, discrete software-instructed placement of adjustable mounts (9005, 9011) onto the anatomical model, and instructions for the coordinates of each of those adjustable mounts to be positioned on the adjustable benchtop model. The software description for according to some embodiments is described previously in relation to FIG. 89. Further, FIG. 90B illustrates an anatomical model mounting exploded assembly in accordance with some embodiments of the invention.

FIG. 90B displays some embodiments of the invention consisting of a table top base 9020, side-rail 9022 equipped with distance indicators 9024 and meant to interface with a cross rail 9026 equipped with distance indicators 9028 and designed to interface with a cross-rail sliding piece 9034 within its cross-rail mating slot 9038, which is equipped with a slot 9039 for mating with a height-adjustment slider 9032, which mates with an angular adjustment piece 9030 via a fastener 9036 which interfaces with an individual vertebra on an anatomical spine model (not shown). Some embodiments allow for positioning of the coupled anatomical model (not shown) in specific locations anywhere over the table top base.

FIG. 90C displays some embodiments of the invention previously described in relation to FIG. 90B, in its assembled form with the anatomical model interface surface 9040 more easily visualized. In the embodiment shown, this interface is achieved via a through hole for a fastener (not shown) to substantially rigidly couple to the anterior aspect of the anatomical model's vertebral body. In some embodiments, this interface includes a ball joint to allow for the anatomical model to pivot about the interface point. In some embodiments, the fastener to the anatomical model is achieved via a clipping mechanism to pre-installed receptacles on each vertebra of the anatomical model to enable rapid-exchange of interface points.

FIG. 90D displays some embodiments of the invention in which a spine anatomical model 9050 is positioned in a discrete alignment configuration with the adjustable mounts described previously in relation to FIGS. 90B-90C. In some embodiments, each mount is positioned based on software-instructed parameters including: location along the side rail, location along the cross-rail, height from the base piece, angle from the height-adjustment slider, and vertebral level with which it should interface. In some embodiments, the cross rails are cylindrical, allowing for rotation of the base piece about the cross bar. In some embodiments, rather than mating only with select vertebral levels, each vertebra is equipped with an adjustable mount, to allow for matching contours with higher precision.

Some embodiments enable different probe-like extensions to be added or interchanged to a tracked or trackable DRF, while indicating to the acquisition software which extension is currently coupled, and therefore which tool definition file to reference when tracking the associated DRF. For example, some embodiments can enable different probe-like extensions to be added or interchanged to a tracked or trackable DRF (i.e., such as a DRF that can be tracked or is capable of being tracked). Further, in some embodiments, acquisition software of an acquisition system can receive data regarding which extension is currently coupled, and therefore which tool definition file to reference when tracking the associated DRF. For example, FIG. 91A illustrates a non-limiting assembly 9100 with a tracked DRF 9101 with tracked or trackable markers 9101a, and including an engaged, straight probe extension as a selected modular tool tip (shown collectively as probe extension pieces 9105), which includes an associated, unique TMSM 9103 positioned relative to the DRF 9101 when engaged according to some embodiments. Some embodiments of this invention are related to devices and systems described earlier in relation to FIGS. 15A-15C, 46A-46G, and 100104, as well as processes described in relation to FIGS. 63, 64A-64B, and 113.

FIG. 91A illustrates some embodiments of the invention that involves a tracked DRF 9101 with a mating extension containing a mating slot in which a spring-loaded TMSM 9103 slides due to protrusions 9111 (see also FIG. 91B) of discrete distances attached to unique probe extension pieces 9105. In some embodiments, when the TMSM 9103 is detected in a preset location relative to the tracked DRF 9101, the acquisition system registers which probe extension tip is coupled and updates a tool definition file for the DRF 9101 accordingly. Some embodiments of a process to detect the motion of a TMSM 9103 relative to a DRF 9101 was described previously in relation to FIG. 63 (see workflow 6300 for analog triggering detection of one or more TMSMs relative to a tracked tool with a DRF in accordance with some embodiments of the invention).

FIG. 91B illustrates 9110 of some embodiments previously described in FIG. 91A with the probe extension 9105 unengaged or disengaged from the tracked DRF 9101. In this image, the spring-loaded TMSM 9107 is fastened to a sliding insert 9109 that is not depressed by the unique mating protrusion 9111 of the probe extension, and the mating pin 9113 and associated mating slot 9115 are visible. Further, in some embodiments, the mating pin 9113 can securely fasten to the DRF 9101 within the mating slot 9115 via a spring-loaded plunger (not shown).

FIG. 91C illustrates 9120 of some embodiments previously described in relation to FIGS. 91A-91B, and demonstrates coupling an alternate probe extension 9117 with its own unique mating protrusion 9119. In some embodiments, this structure and arrangement can result in the TMSM 9121 being slid to a different position relative to the 9101 in comparison than when other probe extensions are engaged. As shown, in some embodiments, the probe extension 9117 comprises a curved probe tip 9117a. In some embodiments, when the acquisition system detects the 9107 in this specific position relative to the 9101, it can load the appropriate tool definition file according to the alternate probe extension 9117 with curved probe tip 9117a as shown. Some embodiments of the modular probe extension types can include, but are not limited to: a straight probe, a curved probe, and/or a probe with unique mating features for coupling with a fiducial or another accessory device, a screwdriver head, a rod-centering fork, a ring structure or other closed-loop designs.

Some embodiments of the invention can include multiple, permanently or semi-permanently coupled probe extensions to one DRF. Further, in some embodiments, one or more TMSM can be moved to discrete positions relative to the DRF to communicate data to the acquisition system, including, but not limited to, data related or associated with which probe extension is being utilized and therefore which tool definition file it should load. Some embodiments include systems compatible with TMSM-equipped systems: It should be noted that some embodiments of this invention are compatible with previously described, TMSM-equipped probes for triggering, in reference to FIGS. 10A-10G, and FIGS. 15A-15C. In some embodiments, the acquisition system can distinguish between the individual stray markers.

Some embodiments can include one or more TSMs on the extensions: Some embodiments of this invention can comprise probe extensions possessing one or more of their own TSMs, such that when the extension engages with the DRF, one or more of the TSMs are in preset locations.

In some further embodiments of the invention, the mating mechanism between the modular probe extensions and the DRF can include, but are not limited to: quarter-turn, threaded, spring-loaded snap arms, and retractable spring plunger.

Some embodiments relate to the generation and analysis of patient images, where the patient images are analyzed to indicate their spinal alignment contour and parameters. Further, in some embodiments, the images can be analyzed to output instructions of how to position adjustable mounts coupled to an anatomical model of the spine to mimic the spinal alignment parameters displayed in the patient images. Some embodiments of this device include inputting desired discrete alignment parameter values (e.g., lumbar lordosis of 30 degrees) to the software which then outputs instructions for how to orient the adjustable mounts to configure the anatomical model to possess the input parameters. Some embodiments of the invention includes a user positioning the anatomical model, and then inputting one or more positioning coordinates (e.g., side rail position, cross-rail position, height, coronal angle, sagittal angle, etc.) of the adjustable mounts into the software, where in the system can output patient images closely matching the alignment parameters of the anatomical model. FIGS. 110A-110B provide further detail of some embodiments of a process of using one or more patient images to position the model to match one or more of the patient images. Further, some embodiments of this invention are related to devices and systems described in relation to FIGS. 12 and 90A-90D, as well as processes described in relation to FIGS. 89 and 110A-110B.

FIG. 92A illustrates a lateral view 9200 of some embodiments of the invention, similar to that previously described and shown in relation to FIGS. 90A-90D. In this instance, the lateral view 9200 includes a spine model 9201 and pelvis 9202 positioned into an alignment configuration by a series of adjustable assemblies. In some embodiments, at the level of the spine (9201), there are mounts for each level of spine (9204, 9214, 9215, 9216, 9217), with only a few illustrated in some embodiments. In some embodiments, these mounts can be mechanically coupled to the vertebrae via screws 9203. In some embodiments, this coupling mechanism can be achieved in various different ways, including, but not limited to, fasteners, and/or adhesive surfaces, and/or direct protrusions built-into each of the vertebrae. In some embodiments, the lateral view 9200 of FIG. 92A shows the spine model 9201 resting on underside side rails 9213, a base sheet 9212, top side rails with distance indications 9211, and individual cross-rails 9210 for each of the vertebral and pelvic mounts. In some embodiments, attached to each of the cross-rails 9210 can be a base piece 9209, into which fits a sliding height adjustment piece 9208, and which can be enabled to slide vertically up and down. In some embodiments, multiple sizes of adjustable height adjustment assemblies can be used to achieve varying severities of sagittal curvatures. In some embodiments, a coronal angle indicator 9219 on which the coronal rotation piece 9207 sits can rotate in the coronal plane, and can be attached to the top of the sliding height adjustment piece 9208.

In some embodiments, attached to the top of the coronal rotation piece 9207 can be a sagittal rotation basket 9205 that designed to mate with the individual vertebra interface mounts (e.g., T1 vertebra interface mount 9204, 9214, 9215, 9216, 9217), and further, is able to rotate in the sagittal plane with angles indicated by the sagittal angle indicator 9206. In some embodiments, the model's pelvis can be mounted similarly, except it is supported by a more rigid pelvic coronal angle adjustment piece 9225 and its own unique pelvic interface mount 9218. In some embodiments, also contains a tracked DRF 9220 including an orientation indicator 9222 and/or DRF mount 9221, enabling the model to have a coordinate system established from the 3D tracking camera. In addition, in some embodiments, this DRF 9220 can enable the model to be imaged (e.g., CT, X-ray, etc.) and have its anatomical landmarks fused in camera coordinates. In some embodiments, to enable the model to stand up vertically, one or more base feet 9224 can interface with a corresponding base rotation piece 9223 and interface with the model (shown via the base piece 9209 in this image). In some embodiments, this angular adjustment mechanism can allow for a range of continuous angles for the anatomical phantom to stand vertically to represent and visualize alignment of a standing human.

FIG. 92B displays a lateral view 9230 from the opposite side of the lateral view 9200 of that shown in FIG. 92A and provides an alternate viewing angle of the pelvic interface mount 9218, pelvic coronal angle adjustment piece 9225, and pelvic interface mount 9218 according to some embodiments. This viewing perspective also enables visualization of the side height indicator 9231 that can allow for discrete height settings of the sliding height adjustment piece 9208, in accordance with some embodiments of the invention.

FIG. 92C displays an alternative perspective view 9235 of FIGS. 92A-92B including the spinal column model 9201, pelvis model 9202, coronal rotation pieces 9207, sliding height adjustment pieces 9208, base pieces 9209, cross-rail 9210, top side rail 9211, model base sheet 9212, coronal angle indicator 9219, and base foot 9224 with interfacing base rotation piece 9223, shown here interfacing with the model base sheet 9212, in accordance with some embodiments of the invention.

FIG. 92D displays an alternative view 9236 of FIGS. 92A-92C, standing upright on the base feet 9224 and/or base rotation pieces 9223 according to some embodiments. This perspective provides a different viewing angle of the spinal column model 9201, pelvis model 9202, coronal rotation pieces 9207, sliding height adjustment pieces 9208, base pieces 9209, cross-rails 9210, top side rails 9211, model base sheet 9212, underside side rails 9213, a vertebra interface mount (as shown with the L3 spinal level) 9217, pelvic interface mount 9218, DRF 9220, DRF mount 9221, and DRF orientation indicator 9222, in accordance with some embodiments of the invention.

FIG. 92E displays a closer perspective assembly view 9237 of some embodiments's DRF 9220, DRF mount 9221, DRF orientation indicator 9222, and mounting hole 9238 on the DRF mount to allow rigid coupling to the model's base sheet and side rails (not shown). Further, FIG. 92F displays a perspective assembly view illustrating the DRF 9220, DRF mount 9221, and DRF orientation indicator 9222, in accordance with some embodiments of the invention.

FIG. 92G displays a closer assembly view 9240 of the sliding height adjustment piece 9208 and mating base piece 9209 according to some embodiments. In some embodiments, the sliding height adjustment piece 9208 contains a mounting hole 9241 for mating with coronal rotation pieces (not shown), a stop-screw hole 9242, side extensions 9243 to mate around the outside walls of the base piece 9209, a center slot 9244 for sliding around a screw to enable height adjustment, and side screw hole 9245 for height stop selection. In some embodiments, the base piece 9209 contains a side slot 9246 to accommodate height adjustment around a side mounted screw (not shown), and/or a cross-rail-accommodating channel 9247, and/or cross-rail stop-screw holes 9248, and/or front side height indicator markings 9249 to allow visualization of the height set for the mated sliding height adjustment piece 9208, in accordance with some embodiments of the invention.

FIG. 92H displays a different perspective assembly view 9250 from that shown in FIG. 92G, allowing for an alternative view of the sliding height adjustment piece 9208 containing a center slot 9244 for a fastener (not shown), and side height stop hole 9245 for a fastener (not shown). The base piece is also visualized, illustrating its side slot 9246 to accommodate a fastener (not shown) to interface with the side height stop hole 9245 of the sliding height adjustment piece 9208, in accordance with some embodiments of the invention.

FIG. 92I displays a different perspective view 9251 from that shown in FIG. 92H, illustrating the sliding height adjustment piece's mounting hole 9241 for the rotation axis of the coronal rotation piece, and stop-screw hole 9242 for the coronal rotation piece in accordance with some embodiments of the invention.

FIG. 92J displays a closer view 9252 of the side height indicator 9231 that includes height indicator markings 9253 according to some embodiments. In some embodiments, this piece is meant for mating onto the side wall of the base piece (e.g., base piece 9209 not shown) for reading the discrete height setting of a mated sliding height adjustment piece (e.g., using side slot 9246, not shown). Further, FIG. 92K displays a different perspective view 9254 of the side height indicator 9231 from that shown in FIG. 92J, illustrating the height indicator markings 9253 in accordance with some embodiments.

FIG. 92L displays a closer view 9255 of the coronal angle indicator 9219 (FIG. 92A) containing a mounting hole 9256 and coronal angle indicator markings 9257 to be read relative to a mated coronal rotation piece (not shown) according to some embodiments. FIG. 92M displays a different perspective view 9258 of the coronal angle indicator 9219 from that shown in FIG. 92L, illustrating the mounting hole 9256 and coronal angle indicator markings 9257 in accordance with some embodiments.

FIG. 92N illustrates a closer view 9259 of the sagittal angle indicator 9206 containing a mounting hole 9260, alignment tab 9261, and sagittal angle indicator markings 9262 in accordance with some embodiments. Further, FIG. 92O displays a different perspective view 9263 of the sagittal angle indicator 9206 from that shown in FIG. 92N, containing the mounting hole 9260 in accordance with some embodiments.

FIG. 92P displays a closer view 9264 of the coronal rotation piece 9207 displaying its arc-shaped slot 9265 that can be used to slide a coronal angle stopping fastener (not shown) according to some embodiments. Further, a viewing window 9266 is shown that can be used to visualize the angular markings on the underlying coronal angle indicator (not shown) in some embodiments. Further, a mounting hole 9267 is shown that can be used for attaching to the sliding height adjustment piece (not shown) in some embodiments. Further, a support gusset 9268 is shown, and a sagittal angle indicator bar 9269 can be used for reading an angular setting of a mated sagittal rotation basket (not shown) and sagittal angle indicator (not shown) in some embodiments. Further, a sagittal rotation stop-screw hole 9207 and mounting hole 9271 are shown and can be used for attaching a sagittal rotation basket (not shown), in accordance with some embodiments.

FIG. 92Q displays a different perspective view 9272 of the coronal rotation piece from that shown in FIG. 92P, illustrating the coronal angle slot 9265, viewing window 9266 for visualization of the underlying coronal angular markings, sagittal angle indicator bar 9269, sagittal rotation stop-screw hole 9270, a mounting hole 9271, and coronal angle indicator bar 9273 according to some embodiments. In some embodiments, the coronal angle indicator bar 9273 can be used to provide a reference point relative to the underlying coronal angle indicator as previously described in FIGS. 92M-92N, in accordance with some embodiments.

FIG. 92R displays a closer view 9274 of the pelvic coronal angle adjustment piece, illustrating a mounting hole 9275 for interfacing with the pelvic interface mount (not shown), a sagittal rotation stop-screw hole 9276, and side support bars 9277 in accordance with some embodiments.

FIG. 92S displays a different perspective view 9278 of the pelvic coronal angle adjustment piece from that shown in FIG. 92R, and illustrates the side support bars 9277 and sagittal angle indicator bar 9279 that can be used as a reference point relative to a mated pelvic interface mount (not shown) and sagittal angle indicator (not shown) according to some embodiments.

FIG. 92T displays a closer view 9279 of the pelvic interface mount 9218 containing extension bars 9280 to flank the model's pubic symphysis (not shown), a slot 9281 for coronal angle indicator, mounting hole 9282 for interfacing with the pelvic coronal angle adjustment piece as previously described in FIGS. 92R and 92S, and slot 9283 for accommodating a sagittal rotation stop-screw (not shown) while adjusting the sagittal angle of the mount according to some embodiments. Further, FIG. 92U displays a different perspective view 9284 of the pelvic interface mount 9218 from that shown in FIG. 92T, illustrating the slot 9283 for accommodating a sagittal rotation stop-screw (not shown) while adjusting the sagittal angle of the mount and mounting holes 9285 for coupling to the pelvic model according to some embodiments.

FIG. 92V displays a closer view 9286 of the sagittal rotation basket 9205 along with its mounting hole 9287 for mating with the coronal rotation piece previously described in FIGS. 92P-92Q, and slot 9288 for accommodating a sagittal rotation stop-screw (not shown) while adjusting the sagittal angle of the basket, in accordance with some embodiments.

FIG. 92W displays a different perspective view 9289 of the sagittal rotation basket 9205 from that shown in FIG. 92V, illustrating the mounting hole 9290 for interfacing with the coronal rotation piece (not shown) previously described in FIGS. 92P-92Q, in accordance with some embodiments. FIG. 92X displays a different perspective of the sagittal rotation basket 9205 from that shown in FIGS. 92V-92W, illustrating mounting hole 9292 for fastening a vertebra interface mount, in accordance with some embodiments.

FIG. 92Y illustrates a front view 9293 of a vertebral interface component for a vertebral holder of an adjustable phantom spine model holder as described previously in relation to FIGS. 92A-92X in accordance with some embodiments of the invention. As shown, FIG. 92Y displays vertebra interface mount 9214 with mounting extension tab 9294 that is designed to slide into a sagittal rotation basket (not shown) (previously described in FIGS. 92V-92X) according to some embodiments. Also shown is a mounting hole 9295 as a fastener to secure it to the sagittal rotation basket 9205, in accordance with some embodiments.

FIG. 92Z illustrates a perspective view 9296 of a vertebral interface component and sagittal angle adjustment component for a vertebral holder of an adjustable phantom spine model holder as described previously in relation to FIGS. 92A-92Y in accordance with some embodiments of the invention. The perspective view 9296 provides a closer look of both the sagittal rotation basket 9205 and vertebra interface mount 9214 including its mounting holes 9297 for securing fasteners to the spine model (not shown), in accordance with some embodiments.

FIG. 92AA illustrates a perspective view 9298 of an adjustable vertebral holder substantially rigidly engaged with a phantom spine model holder as described previously in relation to FIGS. 92A-92Z in accordance with some embodiments of the invention. For example, FIG. 92AA displays a closer look of some embodiments as previously described in FIGS. 92A-92D illustrating the spinal column model 9201 substantially rigidly coupled to the vertebra interface mount 9214 that is secured to a sagittal rotation basket 9205 with sagittal angle indicator. In some embodiments, the assembly is rotated on a coronal rotation piece 9207 resting on a sliding height adjustment piece 9208 with a discrete height setting able to be read from the side height indicator 9231. Further, in some embodiments, the assembly is mounted on a base piece 9209 fastened to a cross-rail 9210 that slides along top side rails 9211, and is coupled to the model base sheet 9212. This view demonstrates that in some embodiments, the assembly of pieces for adjusting a vertebra can be applied to as many individual vertebrae as needed to accommodate the desired end contour of the spinal model.

FIG. 92AB displays a perspective assembly view 9299 of the base rotation piece 9223 and base foot 9224 according to some embodiments. The base rotation piece 9223 is designed to interface with the model base piece (not shown), in accordance with some embodiments of the invention. Further, FIG. 92AC displays a different perspective (front) assembly view 9299*a* of the base rotation piece 9223 and base foot 9224 from that shown in FIG. 92AB, in accordance with some embodiments of the invention.

FIG. 92AD illustrates a front assembly view 9299*b* of a base platform and cross-rails of an adjustable phantom spine model holder as described previously in relation to FIGS. 92A-92AC in accordance with some embodiments of the invention. For example, FIG. 92AD illustrates the cross-rail 9210 with slot 9210*a* to accommodate fasteners from the base pieces (not shown) and mounting holes 9210*b* to fasten to the top side rails 9211 according to some embodiments. In some embodiments, the top side rails 9211 contain a slot 9211*a* to accommodate sliding movement of the overlying cross-rails, and mounting holes 9211*b* for fastening to the model base sheet 9212. Further, in some embodiments, the model base sheet 9212 contains slots 9212*a* to accommodate sliding of the overlying cross-rail fasteners and corner mounting holes 9212*b* to allow for fastening to the top side rails above and underside side rails 9213 below. Further, in some embodiments, the underside side rails can contain a widened slot 9213*a* to accommodate both the fasteners for the sliding cross-rails, and also nuts (not shown) for tightening the fasteners. Further, in some embodiments, the underside side rails also contain mounting holes 9213*b* for fastening to the model base sheet 9212, top side side rails 9211, cross-rails 9210, and DRF mount (not shown) previously described in FIGS. 92E-92F.

Some embodiments of the invention include a device that can be used to assess the intraoperative flexibility of the spine with one or more mountings that can substantially rigidly interface with implanted pedicle screws, as previously described in relation to FIGS. 33A-33H, FIG. 34, FIGS. 35A-35F, and FIGS. 36A-36I. In some embodiments, after substantially rigidly fixing two tools, each to individual spinal levels, the spine can be manipulated via directly pushing on body surfaces or indirectly by interacting with the tool's handles to establish a range of motion between the spinal levels onto which the tools are engaged. In some embodiments, the range of motion can be displayed to the user on a display monitor via a 3D view or 2D projections onto relevant anatomical planes, as described previously in relation to FIG. 70. Furthermore, in some embodiments, after adjusting two or more spinal levels to a desired relative orientation using this tool, the tools can lock together to temporarily hold the anatomy in a configuration while a rod is inserted to the spine-instrumented pedicle screws to hold the spine in this contour. Some embodiments of this invention are related to devices and systems described in relation to FIGS. 34, 34A-34F, 35A-35F, 36A-36I, 37A-37G, 39A-39F, 40A-40C, 41A-41D, 42A-42K, 43A-43F, 94A-94H, 95A-95I, 96A-96S, 97A-97L, 105A-105G, and 106A-106F, as well as processes described in relation to FIGS. 63, 70, 108A-108H, 111A-111C, and 113.

FIG. 93A illustrates a rear view 9300 of an adjustable pedicle screw interface base, with one fixed side arm (9309*b*) and one side arm with height and angle adjustments (shown as adjustable side arm 9309*a*), of a flexibility assessment device according to some embodiments. In some embodiments, the components of 9309*a* and 9309*b* can be the same and therefore are shown with the same components. In some embodiments, the rear view 9300 shows the lower half of the flexibility assessment device with the handle, its DRF, and associated triggering mechanism removed. As shown, some embodiments comprise handle mount side walls 9303 and a spring-loaded plunger 9301 that can be used to select the relative angle of the handle (not shown). In some embodiments, an assembly (e.g., such as mobile side arm mechanism 9313*a*) including a height adjustment knob 9302 can be used to alter the extension height of one of the side arms (e.g., adjustable side arm 9309*a*), and/or can be used to alter a distance between side arms (e.g., by moving the adjustable side arm 9309*a* towards or away from fixed side arm 9309*b* in cavity or channel 9327, and/or 9325, and/or 9326). Further, in some embodiments, a center mount 9304 body is shown, and a fixed shoulder 9305 that can substantially rigidly hold one of the side arm (fixed side arm 9309*b*) at a fixed angle relative to the center mount body. Further, in some embodiments, one or more device tulip heads 9307 positioned atop tulip head mounting shafts 9308, (four shown), can allow for substantially rigidly fixing of a rod between two or more devices with cap screws 9306. In some embodiments, the device can interface with pedicle screw tulip heads 9311 with pedicle screw shaft 9310 (threads not shown) that is implanted into bony anatomy. In some embodiments, to enable device assembly, there can be a width adjustment housing mounting bracket 9312 secured with a fastener 9314. In some embodiments, the detachable side arms can couple to the upper part of the device via side arm mounting sleeves 9313. In some embodiments, to accommodate varying locations and angles of contralateral pedicle screws, the relative angle and distance between these side arms can be adjusted via the one mobile side arm (left side in this illustration).

FIG. 93B displays a side view 9315 of the device shown previously in FIG. 93A, including its spring-loaded plunger 9301, angle detents 9316 that can receive the spring-loaded plunger 9301 at discrete handle angles, width adjustment tightening knob 9317, handle mounting hole 9320, width adjustment housing mounting bracket 9312, height adjustment knob 9302, and device tulip heads 9307 on tulip head mounting shafts 9308 according to some embodiments. In some embodiments, the side view 9315 further shows the device coupled to pedicle screw tulip heads 9311 with associated pedicle screw shaft 9310 (threads not shown), and has the front arm of the tulip head mount 9319 shown, in addition to the through hole 9318 for applying the end cap when coupling the device to a pedicle screw. Some embodiments of this device are designed to utilize cap screws that are supplied with the implanted pedicle screws as shown here, but some embodiments contain cap screws that are built-in to the screw-interface regions of the side arms (in reference to FIGS. 94A-94H).

FIG. 93C illustrates a perspective view 9321 of an adjustable pedicle screw interface base, with one fixed side arm and one side arm with height and angle adjustments, of a flexibility assessment device as described previously in relation to FIGS. 93A-93B in accordance with some embodiments of the invention. In some embodiments, the perspective view 9321 illustrates the handle mount side walls 9303, the height adjustment knob 9302, and width adjustment tightening knob 9317 that can allow the adjustable side arm to slide in the width adjustment side channel 9325, and width adjustment top channel 9326. Further, a different view of the width adjustment housing mounting bracket 9312 is also shown. In some embodiments, this illustration visualizes the sliding retainer clips 9322 which allow for quick coupling or decoupling of the side arms from the upper part of the device. In some embodiments, mounting holes 9323 can connect the device's tulip head attachment pieces are visualized, in addition to the front arm of the tulip head mount 9319 and its built-in screw interface rod 9324. Further, FIG. 93D displays a side view 9328 of some embodiments opposite of that shown in FIG. 93B including the height adjustment knob 9302, width adjustment tightening knob 9317, tulip head mount front arm 9319, tulip head mount back arm 9329, and attached pedicle screw with tulip head 9311 and screw shaft 9310 (threads not shown), in accordance with some embodiments of the invention.

FIG. 93E displays a front view 9330 of some embodiments previously described in FIGS. 93A-93D illustrating a different view of the width adjustment side channel 9325 which allows for the mobile side arm to adjust both its angle and distance from the fixed side arm. Further, also shown is a front view of the sliding retainer clips 9322 that can secure the side arms to the upper part of the device are shown, in addition to the front end of the screw interface rod 9324, in accordance with some embodiments of the invention.

FIG. 93F displays a top view 9332 of some embodiments previously described in FIGS. 93A-93E showing the through hole 9318 that can allow for placement and tightening of the cap screw when securing the device to pedicle screws. The width adjustment top channel 9326 is also shown, which can accommodate the height adjustment knob while the mobile side arm's distance and angle from the fixed side arm is adjusted, in accordance with some embodiments of the invention.

FIG. 93G displays a partially disassembled illustration 9334 of some embodiments previously described in FIGS. 93A-93F showing the sliding retainer clips 9322 which mate with the retainer clip grooves 9336 on the side arms and pass through the retainer clip slots 9335 on the side arm sleeves. In some embodiments, to aid with alignment of the side arms, there are side alignment pins 9337 built-into the side arm, and center alignment pins built-into the side arm mating sleeve, in accordance with some embodiments of the invention.

FIG. 93H displays a view 9339 of some embodiments previously described in FIGS. 93A-93G with one of side arms (9309*b*) not mated with a pedicle screw. This illustration allows for visualization of the screw interface rod 9324 that is tightened to pedicle screw shafts with an end cap 9340, in accordance with some embodiments of the invention.

FIG. 93I displays a partially disassembled view 9342 of the device from a different view than that shown in FIG. 93G, showing the center alignment pins 9343 attached to the side arm mating sleeves and the side alignment pins 9337 attached to the side arms. The alignment pins in some embodiments are quick release pins that contain a spring-loaded ball bearing.

FIG. 93J displays a cross-sectional view 9345 of one of the side arms mated to a pedicle screw with tulip head 9311 and shaft 9310 (threads not shown). This view allows for visualization of the screw interface rod 9324 securely tightened to the tulip head 9311 with a cap screw 9340. This view also displays the center alignment pin 9343 which aids the rigid coupling between the side arm and the side arm sleeve, in accordance with some embodiments of the invention.

Some embodiments of the invention include a device that can be used to assess the intraoperative flexibility of the spine with one or more mountings to substantially rigidly interface with implanted pedicle screws, as previously described in relation to FIGS. 33A-33H, FIG. 34, FIGS. 35A-35F, and FIGS. 36A-36I. In some embodiments, after substantially rigidly fixing two tools, each to individual spinal levels, the spine can be manipulated via directly pushing on body surfaces or indirectly by interacting with the tool's handles to establish a range of motion between the spinal levels onto which the tools are engaged. In some embodiments, the range of motion can be displayed to the user on a display monitor via a 3D view or 2D projections onto relevant anatomical planes, as described previously in reference to FIG. 70. Furthermore, in some embodiments, after adjusting two or more spinal levels to a desired relative orientation using this tool, the tools can interlock together to temporarily hold the anatomy in that configuration while a rod is inserted to the spine-instrumented pedicle screws to hold the spine in this contour. Some embodiments of this invention are related to devices and systems described in relation to FIGS. 34, 34A-34F, 35A-35F, 36A-36I, 37A-37G, 39A-39F, 43A-43F, 93A-93J, 95A-95I, 97A-97L, 105A-105G, and 106A-106F, as well as processes described in relation to FIGS. 63, 70, 108A-108H, 111A-111C, and 113.

FIG. 94A displays 9400 of the lower half of the device as previously described in FIGS. 93A-93J, except without the mechanism of adjusting the height of the mobile side arm and with a built-in, elongated cap screw 9401 according to some embodiments. However, in this instance, as in the some embodiments of FIGS. 93A-93J, the mobile side arm 9419*b* can be moved in a cavity or channel 9424 of adjustment housing mounting bracket 9426. In some embodiments, this can be used to secure the device to a pedicle screw's tulip head 9407 and shaft 9410 with a tulip head mount front arm 9409 and back arm 9408 flanking the tulip head 9407, and substantially rigidly securing the screw interface rod (not shown). Further, in some embodiments, visualized in this illustration is the width adjustment tightening knob 9402 that firmly locks the angle and location of the mobile side arm in place. Also shown is a spring-loaded plunger 9403 and its associated angle detents 9404 that can be used to adjust the relative angle of the device's handle (not shown), which is mounted with the mounting hole 9405 according to some embodiments. The device's tulip heads 9406 are also shown, which enable coupling between two or more devices with a rod to hold the devices and anatomy in position while a rod or other hardware is implanted into the surgical site, in accordance with some embodiments of the invention. Further, FIG. 94B displays a top view 9412 of some embodiments 9400 previously described in FIG. 94A containing the spring-loaded plunger 9403, device tulip heads 9406, and cap screws 9413 that can be used to secure the rod(s) connecting devices, handle mount side walls 9414, and width adjustment top channel 9415, in accordance with some embodiments of the invention.

FIG. 94C displays a front view 9417 of some embodiments previously described in FIGS. 94A-94B containing width adjustment tightening knob 9402, center mount 9421, and width adjustment tightening knob 9403. In some embodiments, a fixed shoulder 9420 can be substantially rigidly coupled to the fixed side arm 9419*a* and secured via a sliding retainer clip 9418. Further, in some embodiments, one side arm can include height and angle adjustments (shown as adjustable side arm 9419*b*). Similar to the embodiment of FIGS. 93A-93J, in some embodiments, the components of the side arms 9419*a* and 9419*b* can be the same and therefore are shown with the same components. Further, as shown, the pedicle screw to which the device is mated are shown including the tulip heads 9407 and screw shafts 9410 (threads not shown), in accordance with some embodiments of the invention.

FIG. 94D displays a different view 9423 previously described in FIGS. 94A-94C containing width adjustment tightening knob 9402, width adjustment mechanism with a top channel 9415, and sliding retainer clips 9418 to secure the detachable side arms 9419*a*, 9419*b*, equipped with built-in cap screws 9401 that can allow for mating with the threads of tulip heads on the implanted pedicle screws, in accordance with some embodiments of the invention.

FIG. 94E displays a rear view 9425 of the embodiment previously described in FIGS. 94A-D displaying the width adjustment housing mounting bracket 9426 that enables assembly of the mobile slide arm mechanism 9413*a* including a height adjustment knob 9403 (not shown) that can be used to alter the extension height of the side arm 9419*b*, in accordance with some embodiments of the invention. Further, as discussed earlier, the mobile side arm 9419*b* can be moved in a cavity or channel 9424 of adjustment housing mounting bracket 9426 using the mobile slide arm mechanism 9413*a*, allowing the distance between the side arms 9419*a*, 9419*b* to be increased or decreased by moving mobile side arm 9419*b* in cavity or channel 9424 according to some embodiments.

Further, FIG. 94F displays a side view 9427 opposite to that shown previously in in FIG. 94A displaying the width adjustment tightening knob 9402, mounting hole 9405 for handle (not shown), fixed shoulder 9420 to attach to the fixed side arm, and the tulip head 9407 of the attached pedicle screw, in accordance with some embodiments of the invention.

FIG. 94G displays a front view 9429 of the device previously described in FIGS. 94A-94F. In this illustration, one of the mated pedicle screws has been removed from the fixed side arm 9419*a* to provide improved visualization of the built-in cap screw 9401 and front arm of the tulip head mount (front arm 9409). Further, FIG. 94H displays a different perspective view 9431 of that shown in FIG. 94G illustrating the built-in cap screw 9401 and its threads designed to interface with the tulip head threads of the implanted pedicle screws according to some embodiments.

Some embodiments of the invention include a device that can be used to assess the intraoperative flexibility of the spine with one or more mountings to substantially rigidly interface with implanted pedicle screws, as previously described in relation to FIGS. 33A-33H, FIG. 34, FIGS. 35A-35F, and FIGS. 36A-36I. In some embodiments, after substantially rigidly fixing two tools, each to individual spinal levels, the spine can be manipulated via directly pushing on body surfaces or indirectly by interacting with the tool's handles to establish a range of motion between the spinal levels onto which the tools are engaged. In some embodiments, the range of motion can be displayed to the user on a display monitor via a 3D view or 2D projections onto relevant anatomical planes, as described previously in reference to FIG. 70. Some embodiments of this invention are related to devices and systems described in relation to FIGS. 34, 34A-34F, 35A-35F, 36A-36I, 37A-37G, 39A-39F, 40A-40C, 41A-41D, 42A-42K, 43A-43F, 94A-94H, 96A-96S, 97A-97L, 105A-105G, and 106A-106F, as well as processes described in relation to FIGS. 63, 70, 108A-108H, 111A-111C, and 113.

FIG. 95A displays 9500 that enables assessment of spinal flexibility via 3D-tracked motion of the device containing an upper portion 9595 comprising a device handle grip 9509 of a handle containing a tracked DRF 9503 secured to a DRF arm with a mounting screw 9504 and alignment pin 9505 according to some embodiments. In some embodiments, the handle also contains a spring-loaded sliding trigger 9508 with sliding arm 9502 with TMSM 9501 attached such that the TMSM moves linearly up and down, supported by the back wall 9507 for sliding arm, relative to the tracked DRF to communicate with the acquisition system. In this non-limiting embodiment. In some embodiments, the TMSM 9501, sliding arm 9502, and trigger 9508 are shown in the undepressed position. Further, in some embodiments, the device handle grip 9509 is mounted to a lower portion 9599 comprising a pedicle screw interface tools 9585 of the device, and is able to have its angle adjusted via a spring-loaded plunger 9510 fitting into discrete angle detents (not shown). In some embodiments, the lower portion 9599 of the device can contain a tracked fixed stray marker 9511 mounted to the width adjustment knob 9515 used to adjust the width between the two screw interface tools 9585. Some embodiments also contains two screw tightening knobs 9512 used to thread into the tulip heads of the implanted pedicle screws. In some embodiments, tracked fixed stray markers (9511, 9514) can be mounted to these screw tightening knobs in order to compute plane of the device when using the location of all three tracked stray markers 9513, (9514, 9511). In some embodiments, the lower part of this device contains a width adjustment guides 9516, and the screw interface tools 9585 can be disconnected from the device via snap arms 9517. In some embodiments, the screw interface tools 9585 of the device contain pseudo rods 9518 at their most distant end to be tightened into the saddle of the mating pedicle screws and substantially rigidly fix the position of a polyaxial tulip head (if applicable) to its associated pedicle screw shaft allowing the device to substantially rigidly couple to the bony anatomy into which the pedicle screws are secured.

In some embodiments, 9520 of FIG. 95B displays some embodiments described previously in FIG. 95A, except with the TMSM 9521, sliding arm 9522, and trigger 9523 in the fully depressed position. Further, FIG. 95C displays a rear view 9525 shown in FIG. 95A including the DRF 9503, handle grip 9509 and back wall 9507 for supporting the sliding arm 9502 according to some embodiments. The sliding arm 9502 for the TMSM and trigger 9508 are shown in the undepressed position in some embodiments. This view allows for visualization of the trigger motion-restricting slot 9426 in the back of the trigger which allows for sliding motion until the slot walls are stopped by the trigger-retaining screw, in accordance with some embodiments of the invention.

FIG. 95D displays a rear view 9529 of the device previously described in FIG. 95C except with the trigger 9523 and sliding arm 9522 for the TMSM in the fully depressed position, in accordance with some embodiments of the invention. Further, FIG. 95E displays a rear view 9531 of the device previously described in FIGS. 95A-D, except it is equipped with a trigger with a unique DRF 9532 on a DRF arm 9533 and sliding arm 9535 with unique geometry (shown as upper portion 9595*a*) according to some embodiments. In some embodiments, the sliding arm holds a TMSM 9534 and is supported by a back wall 9536, and can signal to the acquisition system by pressing down on the trigger 9537, in accordance with some embodiments of the invention. Further, 9539 of FIG. 95F displays described in FIG. 95E except with the trigger 9542, sliding arm 9541 and mounted TMSM 9540 in the depressed position, in accordance with some embodiments of the invention.

Reference number 9544 of FIG. 95G illustrates both devices described previously in FIGS. 95A-F with unique DRFs (9503, 9532), associated sliding TMSMs (9502, 9540) mounted to sliding arms (9502, 9541) with trigger 9542 according to some embodiments. Shown in this configuration from the 3D-tracking camera's perspective, it can be appreciated that the tracked markers for each tool are facing in the same direction according to some embodiments. Additionally, in some embodiments, the DRF arms and sliding arms (9541, 9502) are offset away from one another to avoid adjacent tools obstructing the tracking camera's visualization of any of the tracked markers.

FIG. 95H displays a side view 9550 of FIG. 95G, showing flexibility assessment tool #1 9551 and flexibility assessment tool #2 9552 with their pseudo rods 9553 extending to mate with the tulip heads of implanted pedicle screws (lower portion 9599 comprising lower portion 9599a with screw interface tools 9585a), in accordance with some embodiments of the invention.

FIG. 95I displays a cross-sectional view 9560 of the handle of FIGS. 95A-95D containing the sliding trigger 9561, compression spring 9562 to provide the restoring force to the trigger, a dowel pin 9563 to compress the spring and help keep the sliding trigger aligned with its path of motion, and a trigger-retaining screw 9564 which restricts motion of the sliding trigger to the region of the trigger motion-restricting slot according to some embodiments. In some embodiments, the handle 9566, mounting hole 9567 for the spring-loaded plunger (not shown), and mounting hole 9567 for the handle to coupled with the lower portion of the device (not shown) are also illustrated. In some embodiments, the uppermost region of the handle is not visualized due to it curving out of the plane of this cross-sectional image.

Some embodiments of the invention include a device that can be used to assess the intraoperative flexibility of the spine with one or more mountings to substantially rigidly interface with implanted pedicle screws, as previously described in relation to FIG. 33A-33H, FIG. 34, FIGS. 35A-35F, and FIGS. 36A-36I. In some embodiments, after substantially rigidly fixing two tools, each to individual spinal levels, the spine can be manipulated via directly pushing on body surfaces or indirectly by interacting with the tool's handles to establish a range of motion between the spinal levels onto which the tools are engaged. In some embodiments, the range of motion can be displayed to the user on a display monitor via a 3D view or 2D projections onto relevant anatomical planes, as described previously in reference to FIG. 70. Furthermore, in some embodiments, after adjusting two or more spinal levels to a desired relative orientation using this tool, the tools can interlock together to temporarily hold the anatomy in that configuration while a rod is inserted to the spine-instrumented pedicle screws to hold the spine in this contour. Some embodiments of this invention are related to devices and systems described in relation to FIGS. 34, 34A-34F, 37A-37G, 39A-39F, 40A-40C, 41A-41C, 42A-42K, 43A-43F, 93A-93J, 95A-95I, 96A-96S, 97A-97L, 105A-105G, and 106A-106F, as well as processes described in relation to FIGS. 63, 70, 108A-108H, 111A-111C, and 113.

FIG. 96A illustrates the flexibility assessment tool top halves consisting of DRFs and sliding triggers previously described in reference to FIG. 95A-95H (e.g., comprising upper portions 9595, 9595a), coupled with the tool bottom halves previously described in reference to FIG. 93A-93J equipped with the built-in cap screw design to mate with pedicle screws (shown as embodiment 9400), previously described in reference to FIG. 94A-94H according to some embodiments. In some embodiments, this illustration includes a front view of both flexibility assessment tool #1 9602 (which can comprise all or part of upper portion 9595a as described previously) and flexibility assessment tool #2 9601 (which can comprise all or part of upper portion 9595 described previously). Further, FIG. 96B illustrates a rear view of both flexibility assessment tool #1 9602 and flexibility assessment tool #2 9601 according to some embodiments. FIG. 96C illustrates a different view from that shown in FIGS. 96A-B of flexibility assessment tool #1 9602 and flexibility assessment tool #2 9601 according to some embodiments. FIG. 96D illustrates a side view of FIG. 96C, containing flexibility assessment tool #1 9602 and flexibility assessment tool #2 9601. FIG. 96E illustrates a top view of FIG. 96D, containing flexibility assessment tool #1 9602 and flexibility assessment tool #2 9601 according to some embodiments.

FIG. 96F illustrates 9612 of a bottom portion of the embodiments previously described in FIGS. 96A-96E with the handle removed and includes the fixed shoulder 9613, handle mount side walls 9614, spring-loaded plunger 9615 for adjusting the angle of the handle, height adjustment knob 9616 usable to adjust the height of the mobile side arm 9697, width adjustment top channel 9617, width adjustment housing mounting bracket 9618, width adjustment tightening knob 9619, side arm extension 9620 containing device tulip heads 9621 and cap screws 9622 according to some embodiments. In some embodiment, the built-in cap screws 9623 can be designed to interface with tulip heads 9624 of implantable pedicle screws 9625 (screw threads not shown), and sliding retaining clips 9626 that when removed, enable quick release of the side arms 9627. Further, in some embodiments, the mobile side arm 9697 can be moved within the cavity or channel 9699 as described previously with regard to similar or same structures utilizing a mobile side arm moveably positioned in an adjustment housing mounting bracket (e.g., such as bracket 9618).

FIG. 96G displays a different view 9630 of 9612 previously described in reference to FIG. 96F showing the width adjustment housing mounting bracket 9618 among the other previously described components according to some embodiments. FIG. 96H displays a different view 9632 of 9612 previously described in relation to FIGS. 96F-96G according to some embodiments. Further, FIG. 96I displays a different view 9634 of the embodiment previously described in reference to FIGS. 96F-96H, except with the mated pedicle screws removed enabling better visualization of the built-in cap screw 9635. In some embodiments, this illustration shows the mobile side arm 9636 positioned at an inward facing angle to the fixed side arm. Further, FIG. 96J displays a view 9637 of some embodiments described previously in relation to FIG. 96J except with the mobile side arm 9638 positioned parallel to the fixed side arm. In some embodiments, this illustrates the ability of the mobile side arm to not only translate but also rotate about the axis of the width adjustment tightening knob.

FIG. 96K displays an exploded assembly perspective view 9640 of some embodiments similar to that described in relation to FIGS. 96I-96J, except that it contains a unique screw interface region with pseudo rods 9644 without the front and back walls shown previously in FIGS. 96I-96J. Some embodiments also contains previously described components including a fixed shoulder 9641, width adjustment track 9642, width adjustment housing mounting bracket 9618, screws 9643 to fasten the top three components, the width adjustment pivot piece 9645 to which the mobile shoulder 9650 mates, the side alignment pins 9648 and their mating blind holes 9646, and center alignment pins 9649 and their mating blind holes 9647. Further, FIG. 96L displays a front view 9655 of the disassembly shown from a different view in FIG. 96K containing spring-loaded plunger 9615, width adjustment housing mounting bracket 9618, sliding retainer clips 9626, fixed shoulder 9641, width adjustment track 9642, width adjustment pivot piece 9645, side alignment pins 9648, center alignment pins 9649, mobile shoulder 9650 and center mount 9656 according to some embodiments.

FIG. 96M displays an assembled view 9660 described previously in relation to FIGS. 96K-96L, including fixed arm portion 9660*a* and mobile arm portion 9660*b* according to some embodiments. In this view, in some embodiments, one of the mating pedicle screws is removed to better visualize the pseudo rod (mating pedicle screw 9660*a* is shown on pseudo rod 9644 but not on the other). Moreover, in some embodiments, this illustration does not include an attached handle with triggering and 3D-tracked tracked components.

FIG. 96N displays a rear view 9670 of the assembled flexibility assessment device #1 9602 as previously described in relation to FIGS. 96A-96E according to some embodiments.

FIG. 96O displays a side view 9672 of both flexibility assessment tool #1 9602 and flexibility assessment tool #2 9601 coupled to pedicle screws implanted into a vertebra 9674 and an inter-tool connecting rod 9673 joining the two assessment tools together (e.g., such as 9400) according to some embodiments. In some embodiments, while using the device, the user can be enabled to adjust each of the tracked assessment devices to position the vertebrae relative to one another as desired, and the inter-tool connecting rod 9673 can be attached to each assessment device to hold the vertebrae in their desired relative positions while a rod connecting pedicle screws is bent and implanted prior to fully removing all components of the assessment devices. Further, FIG. 96P displays a top view described in relation to FIG. 96O, containing flexibility assessment tool #1 9602 and flexibility assessment tool #2 9601, along with the inter-tool connecting rod 9673 according to some embodiments.

In some embodiments, FIG. 96Q displays a side view 9678 of two side arms coupled via an inter-tool connecting rod 9679 and disconnected from the side arm sleeves after being attached to the pedicle screws implanted in vertebrae 9674, and the side alignment pins 9680 shown. In some embodiments, this illustration highlights how the assessment devices can be substantially rigidly coupled to one another after positioning the vertebrae in their desired relative orientations, and assessment devices can be disassembled to leave behind unilaterally positioned side arms to expose the contralateral pedicle screws to secure a rod to the implanted pedicle screws, thereby locking the spine segment into the measured and desired relative alignment. In some embodiments, after implanting the rod into the exposed contralateral implanted pedicle screws, the remaining side arms can be removed, with the vertebrae held into the desired contour by the implanted contralateral rod, so then a second rod can be secured to the previously occupied, implanted pedicle screws.

In some embodiments, FIG. 96R displays an embodiment 9685 similar to that previously described in relation to FIG. 96Q, except with a rod implanted contralateral to the remaining side arms that are coupled via an inter-tool connecting rod 9679. In some embodiments, FIG. 96S displays a top view 9690 of the embodiment described previously in relation to FIG. 96R, including both the inter-tool connecting rod 9679 and the implanted rod 9691 for pedicle screws. In some embodiments, after the cap screws are fully tightened to secure the implanted rod 9691 to the implanted pedicle screws, the remaining side arms are removed from the pedicle screws. In some embodiments, after removing the last side arms, the implanted rod 9691 holds the spine in alignment while the contralateral pedicle screws are now exposed to receive an additional implanted rod.

Some embodiments of the invention include a device that can be used to assess the intraoperative flexibility of the spine with one or more mountings to substantially rigidly interface with implanted pedicle screws, as previously described in relation to FIGS. 33A-33H, 34, 35A-35F, and 36A-36I. In some embodiments, after substantially rigidly fixing two tools, each to individual spinal levels, the spine can be manipulated via direct forces on anatomical structures or indirectly by interacting with the assessment tool's handles to establish a range of motion between the spinal levels onto which the tools are engaged. In some embodiments, the range of motion can be displayed to the user on a display monitor via a 3D view or 2D projections onto relevant anatomical planes, as described previously in reference to FIG. 70. In some embodiments, after adjusting two or more spinal levels to a desired relative orientation using this tool, the tools can interlock together to temporarily hold the anatomy in that configuration while a rod is inserted to the spine-instrumented pedicle screws to hold the spine in this contour. In some embodiments, FIG. 97 illustrates the system's utility within minimally invasive spine surgery, such as percutaneous-access surgeries, including both robotically-assisted and non-robotically-assisted cases. Some embodiments of this invention are related to devices and systems described in relation to FIGS. 34, 34A-34F, 35A-35F, 36A-36I, 37A-37G, 39A-39F, 40A-40C, 41A-41D, 42A-42K, 43A-43F, 93A-93J, 95A-95I, 96A96S, 97A-97L, 105A-105G, and 106A-106F, as well as processes described in relation to FIGS. 63, 70, 108, 111, and 113.

In some embodiments, FIG. 97A illustrates an elongated side arm embodiment 9700 that can be used as the screw-interface portion of the flexibility assessment devices, enabling it to access pedicle screws implanted through a percutaneous, minimally invasive approach. In some embodiments of the invention, this embodiment mates via a built-in extended screw 9717 with the tulip head 9707 of a pedicle screw shaft 9708 (threads not shown). In some embodiments, the device involves a minimally invasive sleeve 9701 that extends from the side arm 9702 that contains a retainer clip groove 9709, side alignment pins 9703, device tulip heads 9704, and cap screws 9705 for coupling two or more of these side arms together across vertebrae. In some embodiments, the device (pedicle screw shaft 9708) disengages with the pedicle screw, and the side arm is disconnected from flexibility assessment device's side arm sleeves (not shown) and handle (not shown). In some embodiments, the view 9710 of FIG. 97B displays an embodiment previously described in relation to FIG. 97A including the side alignment pins 9710, except the device is mated to the pedicle screw (pedicle screw shaft 9708) via tulip head 9707.

In some embodiments, FIG. 97C displays a top view 9712 of the embodiment described previously in relation to FIG. 97B, containing the extended screw head 9714 that enables tightening the device to a pedicle screw, side alignment pins 9703 for mating with the side arm sleeve, blind hole 9713 for mating with the center alignment pin, and device tulip head 9704 and cap screw 9705 for coupling 2 or more of these side arms together across vertebrae, in accordance with some embodiments of the invention.

In some embodiments, FIG. 97D displays a cross-sectional view 9716 of the embodiment described previously in relation to FIGS. 97B-97C containing the side arm mated to the tulip head 9707 of a pedicle screw shaft 9708 (threads not shown), via extended screw threads 9717 coupled to the extended screw shaft 9714*b* that passes through the minimally invasive sleeve 9701 and side alignment pins 9703 for mating with the side arm sleeve (not shown). In some embodiments, FIG. 97E displays a cross-sectional view 9720 of an embodiment previously described in FIGS. 97B-97D containing an extended screw 9714 that passes through a minimally invasive sleeve 9701, and a side alignment pin 9703 and retainer clip groove 9709 that can be used to aid in attaching the side arm to a side arm sleeve on fixed or mobile shoulder pieces (not shown).

In some embodiments, FIG. 97F displays an assembly view 9725 of the device previously described in relation to FIGS. 97B-97E containing two minimally invasive side arm sleeves 9701 with extended screws 9714 and side alignment pins 9703 for mating with the mobile shoulder 9729 on one side and fixed shoulder 9728 on the other. In some embodiments, the shoulders contain center alignment pins 9727 that can further aid with alignment when mating the side arms with the upper portion of the device. In some embodiments, the angle and position of the mobile shoulder 9729 can be adjusted using the width adjustment tightening knob 9730 and height adjustment knob 9731. In some embodiments, the 3D-tracked handle, including its connected upper comments (e.g., sliding trigger, DRF, etc.), is disconnected from the middle portion of the device and not shown in view 9725.

In some embodiments, FIG. 97G displays a side view 9735 of two fully assembled embodiments of the device previously described in relation to FIGS. 97B-97F including the minimally invasive flexibility assessment tool #1 9736, and the minimally invasive flexibility assessment tool #2 9737, each mated to pedicle screws. In some embodiments, FIG. 97H displays a different view 9745 of the two fully assembled embodiments described previously in relation to FIG. 97G including the minimally invasive flexibility assessment tool #1 9736 and the minimally invasive flexibility assessment tool #2 9737, each mated to pedicle screws. In some embodiments, FIG. 97I displays a side view 9745 opposite of that shown in FIG. 97G, containing assembled minimally invasive flexibility assessment tool #1 9736 and the assembled minimally invasive flexibility assessment tool #2 9737, each mated to pedicle screws (pedicle screw shaft 9708). In some embodiments, FIG. 97J displays a front view 9750 of the embodiments described previously in relation to FIGS. 97G-97I including the minimally invasive flexibility assessment tool #1 9736 and the assembled minimally invasive flexibility assessment tool #2 9737, each mated to pedicle screws, in accordance with some embodiments of the invention.

In some embodiments, FIG. 97K displays a top view 9755 of the embodiments described previously in relation to FIGS. 97G-97J including the minimally invasive flexibility assessment tool #1 9736 and the assembled minimally invasive flexibility assessment tool #2 9737. In some embodiments, FIG. 97L displays a rear view 9760 of the embodiments described previously in relation to FIGS. 97G-97K including the minimally invasive flexibility assessment tool #1 9736 and the assembled minimally invasive flexibility assessment tool #2 9737, each mated to pedicle screws, in accordance with some embodiments of the invention.

Some embodiments of the invention include a rod contour registration system that can be used to enable a measurement of a rod's contour prior to implantation. Some embodiments of this invention are related to devices and systems described in relation to FIGS. 47A-47B, 48A-48C, 49A-49D, 50A-

50E, 51A-51I, 52A-52D, 53A-53F, 54A-54D, 55A-55I, 56A-56F, 99A-990, 106A-106F, 115A-115F, as well as processes described in relation to FIGS. 63, 73A-73B, 74-76, 77A-77C, 78, 109A-109D, 112A-112C, 113, and 114A-114F. In some embodiments, FIG. 98A illustrates a front view of a rod contour registration system 9800 in accordance with some embodiment of the invention. In some embodiments, the rod contour registration system 9800 comprises a DRF 9801, mounting screw 9802, DRF aligning wall 9803, mounting screw 9804, handle 9805, TMSM (undepressed plunger) 9806, TMSM sliding post 9807, spring tensioning cap 9808, tensioning screw 9809, rod-engaging fork 9810, and a spring-loaded-plunger (undepressed) 9811. In some embodiments, the spring-loaded plunger 9811 is not depressed, and thus the coupled TMSM 9806 is located at or near its baseline location relative to the DRF 9801. In some embodiments, the system interprets that the tool is in an inactive state, according to processes that include, but are not limited to, those described in relation to FIGS. 63 and 113. In some embodiments, the plunger 9811 is spring-loaded via an internal spring mechanism (not shown) housed under the spring tensioning cap 9808, which applies a tensioning force on the internal spring(s) (not shown), as indicated via the tensioning screw's 9809 relative position along the slot of the spring tensioning cap 9808. In some embodiments, the rod-engaging fork 9810 can enable the device 9800 to be oriented in-line with the cross-section of the rod during tracing the device 9800 along the rod contour. In some embodiments, the device 9800 can position the DRF 9801 and TMSM 9806 a significant distance apart in order to enable the user to comfortably grip the handle 9805 and not obstruct any of the 3D-tracked markers, either on the DRF 9801 or TMSM 9806. In some embodiments, this arrangement also helps to avoid the congregation of markers in a congested volume, which tends to enable a higher yield of phantom and occluded 3D-tracked markers. In some embodiments, the handle 9805 can be attached to the DRF aligning wall 9803 mount via a mounting screw 9804 in a modular fashion, but these components can also be manufactured as one component (e.g., can be coupled and/or integral). In some embodiments, the DRF 9801 is substantially rigidly attached to the DRF aligning wall 9803 via a mounting screw 9802, however, these modular components can also be manufactured as one component in some embodiments of the invention.

In some embodiments, FIG. 98B illustrates a front view of a rod contour registration system 9815, similar to the system 9800 previously described in relation to FIG. 98A, in accordance with some embodiment of the invention, showing an assembly comprising a TMSM (depressed plunger) 9816, TMSM sliding post (depressed) 9817, and a spring-loaded plunger (depressed) 9818. In some embodiments, the rod contour registration system 9815 can comprise at least some components or assemblies of the previously described system 9800 shown in FIG. 98A. In some embodiments, the spring-loaded plunger 9818 is fully depressed within the rod-engaging fork 9810 and thus the coupled TMSM 9816 is located at or near its active location, via elevation of the coupled TMSM sliding post 9817, relative to the DRF 9801. In some embodiments, the system can interpret that the tool is in an active state, according to processes that include, but are not limited to, those described in relation to FIGS. 63 and 113 described earlier.

In some embodiments, FIG. 98C illustrates a side view of a rod contour registration system 9820, similar to the systems 9800, 9815 previously described in relation to FIGS. 98A-98B, in accordance with some embodiment of the invention, showing an assembly comprising a DRF 9801, mounting screw 9802, spring tensioning cap 9808, tensioning screw 9809, handle 9805, and TMSM 9821. In this embodiment, an example location of the TMSM 9821 illustrates how the actuation of the TMSM 9821 is in-line with the plane of the DRF 9801 relative to the 3D-tracking camera system, and thus this relative location simplifies the trigger state interpretation, according to processes that include, but are not limited to, those described in relation to FIGS. 63 and 113 described earlier.

In some embodiments, FIG. 98D illustrates a perspective view of a rod contour registration system 9823, similar to the systems previously described in relation to FIGS. 98A-98C, in accordance with some embodiment of the invention, showing an assembly comprising a compression spring 9824. In some embodiments, the rod contour registration system 9823 can comprise at least some components or assemblies of the previously described system 9800, 9815 shown in FIGS. 98A-98B.

In some embodiments, FIGS. 98E-98F illustrates perspective views of a triggering mechanism of a rod contour registration tool as described previously in relation to FIGS. 98A-98D in accordance with some embodiments of the invention. In some embodiments, FIG. 98E illustrates a partial perspective view of a rod contour registration system 9826, similar to the systems previously described in relation to FIGS. 98A-98D, in accordance with some embodiment of the invention, showing an assembly comprising a tensioning screw 9809, rod-engaging fork 9810, TMSM (depressed plunger) 9816, and a compression spring 9824. In some embodiments, the TMSM sliding post 9817 is coupled with three symmetrically-spaced compression springs 9824 that facilitate the spring-loaded triggering mechanism of the plunger 9818 while mitigating uneven spring force along the sides of the TMSM sliding post 9817. In some embodiments, there can be one spring that tensions the TMSM sliding post 9817 and/or other features on/in/near the spring that facilitate the smooth and un-twisting movement of the TMSM sliding post 9817 during actuation of the plunger 9818.

In some embodiments, FIG. 98F illustrates a perspective view of a rod contour registration system 9828, similar to the systems previously described in relation to FIGS. 98A-98E, showing an assembly comprising a tensioning screw 9809, compression spring 9824, spring-loaded plunger 9829, and a plunger wall 9830. In some embodiments, the plunger wall 9830 is pressed against the receptacle on the top of the rod-engaging fork 9810 until the plunger 9818 is depressed, which compresses the compression springs 9824, against the preset tension initialized via the tensioning screw 9809, and actuates the coupled TMSM (not shown) 9816 on top of the TMSM sliding post 9817 (e.g., reference FIG. 98E).

In some embodiments, FIG. 98G illustrates a side view of a rod contour registration system 9835, similar to the systems previously described in relation to FIGS. 98A-98F, in accordance with some embodiment of the invention, showing an assembly comprising a TMSM (depressed plunger) 9816, compression spring 9824, and a spring-loaded plunger 9829. In some embodiments, as the plunger 9829 is depressed, while the spring tensioning cap 9808 is substantially rigidly fixed to the rod-engaging fork 9810 via the tensioning screw 9809, the coupled TMSM 9816 is elevated relative to the spring tensioning cap 9808 top surface, and thus the TMSM 9816 elevates relative to the position of the DRF, and triggers an active state interpretation by the system via processes that include, but are not limited to, those described in relation to FIGS. 63 and 113.

In some embodiments, FIG. 98H illustrates a side view of a rod contour registration reference system 9837, similar to the systems previously described in relation to FIGS. 98A-98G, in accordance with some embodiments of the invention. In some embodiments, the rod contour registration reference system 9837 comprises a DRF 9838, including markers 9839a, sliding trigger body (undepressed) 9839, end cap shaft 9840, end cap handle 9841, cam lock lever 9842, trigger tab (undepressed) 9843, and mounting holes 9844. In some embodiments, the end cap tool 9837 is not in an active state as it's trigger tab 9843 is not depressed, and thus the TMSM 9852 is located at or near its baseline location relative to the DRF 9838. In some embodiments, the handle 9841 is a modular component that can be replaced and installed with the end cap shaft 9840 via mounting holes 9844 that contain fasteners (not shown) for rigid fixation. In some embodiments, the sliding trigger body 9839 wraps around the end cap shaft 9840 to ensure that the trigger mechanism does not actuate out of its primary intended axis and remains only vertical during use. In some embodiments, a rod can be inserted into the device and substantially rigidly fixed to end cap shaft 9840 region via a fastened cam lock lever 9842.

In some embodiments, FIG. 98I illustrates a side view of a rod contour registration reference system 9846, similar to the systems previously described in relation to FIGS. 98A-98H, in accordance with some embodiments of the invention, showing an assembly comprising a TMSM (depressed) 9847, sliding trigger body (depressed) 9848, and a trigger tab (depressed) 9849. In some embodiments, the device 9846 is in an active state, since the trigger tab 9849 has been depressed, lowering the position of the substantially rigidly attached TMSM 9847 relative to the DRF 9838, in which the system interprets as an active device state, according to processes that include, but are not limited to, those described in relation to FIGS. 63 and 113.

In some embodiments, FIG. 98J illustrates a front view of a rod contour registration reference system 9851, similar to the systems previously described in relation to FIGS. 98A-98I, in accordance with some embodiments of the invention. In some embodiments, the rod contour registration reference system 9851 comprises a DRF 9838, sliding trigger body (undepressed) 9839, end cap handle 9841, cam lock lever 9842, trigger tab (undepressed), TMSM (undepressed) 9852, DRF mounting screw 9853, dowel pin 9854, rod-interface receptacle 9855, and a mounting screw 9856. In some embodiments, the device 9851 is in an inactive state because the trigger tab 9843 is not depressed, and consequently the TMSM 9852 is at or near its baseline location relative to the DRF 9838. In some embodiments, the DRF 9838 is a modular component of the system 9851 and can be removed, replaced, or installed via a DRF-mounting screw 9853 and a dowel pin 9854 through the DRF, and linked to the end cap shaft 9840, that restricts the unwanted rotation of the DRF against its predefined geometry relative to the end cap shaft 9840. In some embodiments, a rod can be inserted into the rod-interface receptacle 9855 and substantially rigidly fixed via a fastened cam lock lever 9842 that compresses the tolerance gap out of the receptacle 9855. In some embodiments, where the handle 9841 is a modular component of the system 9851, the handle 9841 can be substantially rigidly engaged with the end cap shaft 9840 via one or more mounting screws 9856.

In some embodiments, FIG. 98K illustrates a front view of a rod contour registration reference system 9858, similar to the systems previously described in relation to FIGS. 98A-98J, in accordance with some embodiments of the invention. In some embodiments, the rod contour registration reference system 9858 comprises a DRF 9838, TMSM (depressed) 9847, sliding trigger body (depressed) 9848, and a trigger tab (depressed) 9849. In some embodiments, the system 9858 is in an active trigger state because the trigger tab 9849 is depressed, and consequently the substantially rigidly coupled TMSM 9847 is lowered relative to the DRF 9838. In some embodiments, the system interprets this modified relative position as a triggering event, according to processes that include, but are not limited to, those described in relation to FIGS. 63 and 113.

In some embodiments, FIG. 98L illustrates a side view of a rod contour registration reference system 9860, similar to the systems previously described in relation to FIGS. 98A-98K, in accordance with some embodiments of the invention. In some embodiments, the rod contour registration reference system 9860 comprises a TMSM trigger mount (in an undepressed state) 9861, sliding trigger body (in an undepressed state) 9862, and a trigger tab (in an undepressed state). In some embodiments, the illustration depicts the opposite side of the system 9860 than that depicted in FIG. 98H, and is also classified to be in an inactive state.

In some embodiments, FIG. 98M illustrates a side view of a rod contour registration reference system 9865, similar to the systems previously described in relation to FIGS. 98A-98L, in accordance with some embodiments of the invention, showing an assembly comprising a TMSM trigger mount (depressed) 9866, sliding trigger body (depressed) 9867, and a trigger tab (depressed) 9868. In some embodiments, the illustration depicts the opposite side of the system 9860 than that depicted in FIG. 98I, and is also classified to be in an active state.

In some embodiments, FIG. 98N illustrates a side cross-sectional view of a rod contour registration reference system 9870, similar to the systems previously described in relation to FIGS. 98A-98M, in accordance with somes embodiment of the invention. In some embodiments, the rod contour registration reference system 9870 comprises an end cap shaft 9840, TMSM trigger mount (depressed) 9871, dowel pin 9872, compression spring 9873, trigger-retaining screw 9874, trigger motion-restricting slot 9875, mounting hole 9876, rod-interface receptacle 9877, cam-lever mounting hole 9877*a*, and a rod-interface depth-stop 9877*b*. In some embodiments, there is a rod-interface depth-stop 9877*a* within the rod-interfacing receptacle 9855 that provides a rigid wall for the inserted rod to rest against as the cam lock lever is fastened via threads that are tightened through the cam-lever mounting hole 9877*b*. In some embodiments, the mating interface of the modular handle 9841 and the end cap shaft 9840 are substantially rigidly coupled via fasteners inserted into the mounting holes 9876. Some embodiments of the invention comprise an embedded compression spring 9873 within the end cap shaft 9840 that is compressed via a dowel pin that is substantially rigidly engaged with the TMSM trigger mount 9871. In some embodiments, when the trigger body is depressed via the actuation of a trigger tab 9863, the TMSM 9852 is lowered as the spring 9873 is compressed, and provides a restoring force when the triggering is completed.

In some embodiments, FIG. 98O illustrates a perspective view of a rod contour registration system 9878, similar to the systems previously described in relation to FIGS. 98A-98N, in accordance with some embodiment of the invention. In some embodiments, the rod contour registration system 9878 comprises a rod-equipped end cap 9879 including coupled DRF 9879*a* with markers 9879*b*, 30-degree rod-interface receptacle 9880, straight rod 9881, tracked slider

9882 with DRF 9888 including markers 9888*a*, and TMSM (depressed) 9883. In some embodiments, a straight rod 9881 is substantially rigidly engaged within a 30-degree (downward facing) receptacle 9880. In some embodiments, the straight rod 9881 is subsequently substantially rigidly engaged with the rod-equipped end cap 9879, which provides the reference 3D coordinate system to which the rod contour will be registered relative to, as was previously described in relation to FIGS. 73A-73B, 74-76, 77A-77C, and 78.

In some embodiments, the tracked slider 9882 is tracing along the exterior surface of the rod 9881 in an active trigger state, as indicated by the elevated TMSM 9883, and subsequently registered the 3D contour of the rod. In some embodiments, angled rod-interfacing receptacles (e.g., receptacles with 10, 15, 30-degree declines, relative to the end cap shaft 9840) facilitate robust visualization of both tools (9879, 9882) and their respective DRFs during a tracing acquisition of the contour of a rod with any shape. In some embodiments, FIG. 98P illustrates a perspective view of a rod contour registration system 9885, similar to the systems previously described in relation to FIGS. 98A-98O, in accordance with some embodiment of the invention, showing an assembly comprising a rod-equipped end cap (with 30-degree receptacle) 9879, 30-degree rod-interface receptacle 9880, and a tracked slider 9882. Some embodiments of the invention depict a front view of the same system 9878 as that in FIG. 98O. In some embodiments, FIG. 98Q illustrates a side view of a rod contour registration system 9887, similar to the systems previously described in relation to FIGS. 98A-98P, in accordance with some embodiments of the invention. In some embodiments, the rod contour registration system 9887 comprises a rod-equipped end cap (with 30-degree receptacle) 9879, straight rod 9881, and a tracked slider 9882. This embodiment depicts a side view of the same system 9878 of FIG. 98O.

In some embodiments, FIG. 98R illustrates a perspective view of a rod contour registration system 9889, similar to the systems previously described in relation to FIGS. 98A-98Q, in accordance with some embodiments of the invention. In some embodiments, the rod contour registration system 9889 comprises a rod-interface receptacle 9877, straight rod 9881, tracked slider 9882, and a rod-equipped end cap (with 0-degree receptacle) 9890. In some embodiments, a straight rod 9881, substantially rigidly attached to a tracked end cap 9890 can be traced by a tracked slider tool 9882, similar to process as the system 9878 depicted in FIG. 98O. In some embodiments, the rod-interface receptacle 9877 does not have a set slope offset away from the end cap shaft 9840. In some embodiments, it can be appreciated that the horizontally-level rod-interface receptacle 9877 can make it more likely for the tracked slider tool 9882 to occlude the tracked end cap 9890 during a tracing acquisition, and thus presents the receptacle with a slope offset as a potential solution for maintaining visualization of all 3D-tracked markers during tracing acquisition of a rod contour, especially if the rod contour is bent into a lordotic (upward) curve.

In some embodiments, FIG. 98S illustrates a perspective view of a rod contour registration system 9890, similar to the systems previously described in relation to FIGS. 98A-98R, in accordance with some embodiments of the invention. In some embodiments, the rod contour registration system 9890 can comprise a rod-equipped end cap (30-degree receptacle) 9879, 30-degree rod-interface receptacle 9880, tracked slider 9882, and a curved rod 9891. In some embodiments, the 30-degree rod-interface receptacle 9880 can improve upon the system 9889 depicted in FIG. 98R in which the curved rod contour 9891 can be robustly traced while maintaining a similar visualization of both tools (9882, 9879) relative to a nearby 3D-tracking camera system, as demonstrated in an example embodiment in FIG. 98R.

In some embodiments, FIG. 98T illustrates a rear perspective view of a rod contour registration system 9892, similar to the systems previously described in relation to FIGS. 98A-98S. Some embodiments of the invention include a rod contour registration system 9892 comprising a DRF 9893 and a DRF-mounting post 9894 coupled to a handle (e.g., similar to or the same as handle 9805 described earlier). In some embodiments, the modular DRF 9893 can be removed from the DRF-mounting post 9894, and can be re-engaged in the opposing direction, as depicted in an example embodiment in FIG. 98U. In some embodiments, the system 9892 can be used in the user's right hand, while the end cap tool 9879 is held in the left hand. In some embodiments, the system 9892 automatically detects the orientation of the TMSM 9883 relative to the DRF 9893 according to processes that include, but are not limited to, those described in relation to FIGS. 112 and 113.

In some embodiments, FIG. 98U illustrates a rear perspective view of a rod contour registration system 9895, similar to the systems previously described in relation to FIGS. 98A-98T. In some embodiments, the rod contour registration system 9895 comprises a DRF 9893 and a DRF-mounting post 9894. In some embodiments, the modular DRF 9893 has been positioned in the opposing direction, as the direction that was depicted previously in an example embodiment in FIG. 98T. In some embodiments, FIG. 98V illustrates a rear perspective view of a rod contour registration system 9897, similar to the systems previously described in relation to FIGS. 98A-98U, in accordance with some embodiment of the invention. In some embodiments, the rod contour registration system 9897 comprises a DRF 9893. In some embodiments, the DRF 9893 can be repositioned and re-installed on the DRF-mounting post 9894 (FIG. 98U). In some embodiments, the tracked slider system 9897 can be used in the user's left hand, while the end cap tool 9879 is held in the right hand.

Some embodiments of the invention include a rod contour registration system that is coupled to a rod bending system to enable contouring and/or registration of a rod implant. Some embodiments of this invention are similar to devices and systems described in relation to FIGS. 47-57, 98, 106, and 115, as well as processes described in relation to FIGS. 63, 73A-73B, 74-76, 77A-77C, 78, 79A-79G, 80-81, 87A-87K, 88A-88F, 109A-109D, 112A-112C, 113, and 114A-114F. In some embodiments, FIG. 99A illustrates a front view of a rod contour registration system 9900 in accordance with some embodiments of the invention. In some embodiments, the rod contour registration system 9900 comprises one or more mounting screws 9901, and/or DRF aligning wall 9902, and/or DRF 9903, and/or mounting screw 9904, and/or trigger extension arm 9905, and/or TMSM 9906 (shown in an undepressed condition), and/or TMSM sliding post 9907 (shown in an undepressed condition), and/or spring tensioning cap 9908, and/or tensioning screw 9909, and/or rod-engaging fork 9910, and/or a spring-loaded plunger 9911 (shown in an undepressed condition). In some embodiments, the TMSM 9906 is in an inactive state because the spring-loaded plunger 9911 is undepressed, and thus the TMSM 9906 is located at or near its baseline position relative to the DRF 9903. In some embodiments, the DRF 9903 is modular, and can be removed as well as substantially rigidly attached to the rod contour registration device via the DRF aligning wall 9902 mount. In some embodiments, the mounting screws 9901 can substantially rigidly attach the rod contour registration system 9900 to another tool, such as a rod bender. In some embodiments, the TMSM 9906 is spring-loaded using a sub-assembly mechanism similar to those depicted previously in relation to FIGS. 98D-98G.

In some embodiments, FIG. 99B illustrates a front view of a rod contour registration system 9915, similar to rod contour registration system 9900 (and using some similar or same components of the system 9900), in accordance with some embodiments of the invention. In some embodiments, the rod contour registration system 9915 can comprise a spring-loaded plunger 9916 (shown in a depressed state), and/or a TMSM sliding post 9917 (shown in a depressed state), and/or a TMSM 9918 (shown in a depressed state). In some embodiments, the system 9915 is in an active state as the spring-loaded plunger 9916 is in a fully depressed state, and the associated TMSM 9918 is actuated into an active position relative to its baseline position, relative to the DRF 9903.

In some embodiments, FIG. 99C illustrates a perspective view of a rod contour registration system 9920, similar to the systems previously described in relation to FIGS. 99A-99B, and using some similar or same components, in accordance with some embodiments of the invention. In some embodiments, the rod contour registration system 9920 comprises a mounting screw 9901, and/or a DRF 9903, and/or a mounting screw 9904, and/or a trigger extension arm 9905, and/or a TMSM 9906 (shown in an undepressed condition), and/or a tensioning screw 9909, and/or a rod-engaging fork 9910.

In some embodiments, FIG. 99D illustrates a side view of a rod contour registration system 9925, similar to the systems previously described in relation to FIGS. 99A-99C, and using some similar or same components, in accordance with some embodiments of the invention. In some embodiments, in some embodiments, the rod contour registration system 9925 comprises a mounting screw 9901, and/or DRF aligning wall 9902, and/or trigger extension arm 9905, and/or spring tensioning cap 9908, and/or tensioning screw 9909, and/or a rod-engaging fork 9910. In some embodiments, the TMSM 9906 is in-line with the DRF 9903, and thus facilitates simplified processing by the system to interpret the trigger state.

In some embodiments, FIG. 99E illustrates a front view of a rod contour registration system 9927, similar to the systems previously described in relation to FIGS. 99A-99D, and using some similar or same components, in accordance with some embodiments of the invention. In some embodiments, the rod contour registration system 9927 comprises a tracked-slider-equipped rod bender 9928, and/or a spring-loaded plunger 9929 (shown in an undepressed state), and/or a TMSM 9930 (shown in an undepressed state), and a mounting screw 9931. In some embodiments, the rod contour registration system 9925, as depicted previously in relation to FIG. 99D, is substantially rigidly coupled to a rod bender 9928 via mounting screws 9931. In some embodiments, the rod contour registration system 9925 can be a built-in or integrated with the rod bender 9928, and may not require any attachment processes. In some embodiments, the spring-loaded plunger 9929 is undepressed, and thus the system 9927 is in an inactive tracing state.

In some embodiments, FIG. 99F illustrates a front view of a rod contour registration system 9933, similar to the systems previously described in relation to FIGS. 99A-99E, and using some similar or same components, in accordance with some embodiments of the invention. Some embodiments of the invention comprise a rod contour registration system 9933 including a tracked-slider-equipped rod bender 9928, and/or a mounting screw 9931, and/or a spring-loaded plunger (shown in a depressed state) 9934, and/or a TMSM 9935 (shown in a depressed state). In some embodiments, the spring-loaded plunger 9934 is depressed, and thus the rod contour registration system 9933 is in an active tracing state, as illustrated by the actuated position of the TMSM 9935 relative to its baseline location (e.g., as further illustrated in FIG. 99E), relative to the DRF 9903.

In some embodiments, FIG. 99G illustrates a perspective view of a rod contour registration system 9937, similar to the systems previously described in relation to FIGS. 99A-99F, and using some similar or same components. In some embodiments, the rod contour registration system 9937 includes a tracked-slider-equipped rod bender 9928, and/or spring-loaded plunger 9929 (shown in an undepressed state), and/or TMSM 9930 (shown in an undepressed state), and/or mounting screws 9931. Some embodiments of the invention also provide an oblique perspective to the system depicted previously in relation to FIG. 99E, which depicts an inactive system.

In some embodiments, FIG. 99H illustrates a perspective view of a rod contour registration system 9940, similar to the systems previously described in relation to FIGS. 99A-99G and using some similar or same components, in accordance with some embodiments of the invention. In some embodiments, the rod contour registration system 9940 can comprise a tracked-slider-equipped rod bender 9928, and/or a TMSM 9935 (shown in a depressed state). Some embodiments of the invention also provide an oblique perspective to the system depicted previously in relation to FIG. 99F, which depicts an active system.

In some embodiments, FIG. 99I illustrates a side view of a rod contour registration system 9942, similar to the systems previously described in relation to FIGS. 99A-99H, and using some similar or same components, in accordance with some embodiments of the invention. Some embodiments comprise a rod contour registration system 9942 including a spring tensioning cap 9908, and/or tensioning screw 9909, and/or rod-engaging fork 9910, and/or tracked-slider-equipped rod bender 9928, and/or TMSM (undepressed) 9930, and/or mounting screw 9931, and/or center rod-contouring surface 9944, and/or a left outer roller 9952. Some embodiments of the invention provide a side perspective of the system depicted previously in relation to FIG. 99E, which depicts an example inactive system. In some embodiments, the tracked slider-equipped rod bender 9928 handles can be grasped by the user and the bending surfaces (9952, 9944) can be fully accessed while still providing the system with the ability to trace the contour of a rod via the slider attachment (e.g., FIG. 99D).

In some embodiments, FIG. 99J illustrates a side view of a rod contour registration system 9946, similar to the systems previously described in relation to FIGS. 99A-99I, and using some similar or same components, in accordance with some embodiments of the invention. In some embodiments, the rod contour registration system 9946 can comprise a TMSM sliding post 9947 (shown in a depressed state). Some embodiment of the invention illustrate a side perspective to the system depicted previously in relation to FIG. 99F, which depicts an example active system.

In some embodiments, FIG. 99K illustrates a perspective view of a rod contouring system 9949, similar to the systems previously described in relation to FIGS. 99A-99J, and using some similar or same components, in accordance with some embodiments of the invention. Some embodiments include a rod contouring system 9949 comprising a right outer roller 9943, and/or a center rod-contouring surface 9944, and/or a rod 9950, and/or a tracked-slider-equipped rod bender 9951, and/or a left outer roller 9952, and/or a rod-equipped tracked end cap 9953. In some embodiments, the tracked-slider-equipped rod bender 9951 demonstrates how the contouring surfaces (9943, 9952, 9944) can be fully accessible for contouring a rod while the tracked slider attachment is engaged, and not actively utilized with the bender 9951. In some embodiments, a rod 9950 can be attached into a tracked end cap 9953, and then contoured by the tracked-slider-equipped rod bender 9951 until the user is ready to register the contour of the adjusted rod 9950. In some embodiments, the system (e.g., rod contour registration system 9942 of FIG. 99I) can be oriented to enable the rod-engaging fork of the slider attachment to trace the rod contour with respect to the tracked end cap 9953. Some embodiments of the invention of these two primary processes is depicted below in reference to FIG. 99L (rod contouring mode) and FIG. 99M (rod tracing mode).

In some embodiments, FIG. 99L illustrates a perspective view of a rod contouring system 9955, similar to the systems previously described in relation to FIGS. 99A-99K, and using some similar or same components, in accordance with some embodiments of the invention. In some embodiments, the rod contouring system 9955 comprises a rod 9950, tracked-slider-equipped rod bender 9951, and a rod-equipped tracked end cap 9953.

In some embodiments, FIG. 99M illustrates a perspective view of a rod contour registration system 9960, similar to the systems previously described in relation to FIGS. 99A-99L, and using some similar or same components, in accordance with some embodiments of the invention. Some embodiments comprise a rod contour registration system 9960 including a rod-equipped tracked end cap 9953, tracked-slider-equipped rod bender 9961, rod-engaging fork 9962, TMSM 9963 (shown in a depressed state), and a rod 9964. In some embodiments, the sliding attachment is fully engaged with the rod 9964, and the plunger is fully depressed (i.e., within the rod-engaging fork 9962), which actuates the TMSM 9963 to an active position relative to DRF 9903. In some embodiments, a rod-interfacing receptacle with a slope offset, relative to the end cap shaft, is depicted, as was previously shown in relation to FIGS. 98O-98Q and 98S.

In some embodiments, FIG. 99N illustrates a perspective view of a rod contour registration system 9970, similar to the systems previously described in relation to FIGS. 99A-99M, and using some similar or same components, in accordance with some embodiments of the invention. In some embodiments, the rod contour registration system 9970 shows an assembly comprising a rod-equipped tracked end cap 9953 and a tracked-slider-equipped rod bender 9961.

In some embodiments, FIG. 99O illustrates a side view of a rod contour registration system 9980, similar to the systems previously described in relation to FIGS. 99A-99N, and using some similar or same components, in accordance with some embodiments of the invention, showing an assembly comprising a rod-equipped tracked end cap 9953, tracked-slider-equipped rod bender 9961, and a rod-engaging fork 9962. In some embodiments, the system 9960 previously depicted in relation to FIG. 99M is shown from a side view perspective to appreciate the robust visualization of both the tracked end cap and the tracked-slider-equipped rod bender tools, and their respective DRFs, with respect to the 3D-tracked camera system during a rod tracing acquisition.

Some embodiments of the invention include a selective-triggering probe system that is able to selectively signal to a 3D-tracking camera system when it is in an "active" and/or "inactive" binary state, and/or analog states in between those two boundaries via a rotational triggering mechanism. Some embodiments of this invention are related to devices and systems described in relation to FIGS. 10A-10G, 14A-14C, 15A-15C, 91A-91C, and 101A-101Q, as well as processes described in relation to FIGS. 24-26, 27A-27D, 28A, 58-61, 62A-62D, 63, 64A-64B, 65A-65E, 66A-66B, 67-69, 82A-82B, 83, 84A-84B, 85, and 113.

In some embodiments, FIG. 100A illustrates a rear view of a selective-triggering probe system 10000 in accordance with some embodiments of the invention. In some embodiments, the selective-triggering probe system 10000 comprises a probe shaft 10001, and/or a trigger tab 10002 (shown in an undepressed state), and/or a DRF 10003, and/or a spring-loaded TMSM 10004 (showing an undepressed trigger). In some embodiments, the selective-triggering probe system 10000 further comprises a torsion spring 10005, and/or a mounting screw 10006, and/or a torsion spring side wall 10007, and/or a rotating trigger arm 10008 (shown undepressed). In some embodiments, the trigger tab 10002 is undepressed and the probe is thus in an active state due to the spring-loaded TMSM 10004 positioned at or near its baseline location relative to the DRF 10003. In some embodiments, the TMSM 10004 is tensioned via the torsion spring 10005 that is substantially rigidly attached to the TMSM mount and the probe shaft via a mounting screw 10006. In some embodiments, the torsion spring side walls 10007 can restrict the torsion spring probe-engaged arm to remain substantially rigidly fixed as the TMSM moves the opposing spring arm, which creates a restoring spring force as the trigger tab 10002 is depressed. In some embodiments, the dynamic position of the TMSM 10004 is monitored relative to the probe's DRF 10003, and interpreted into a trigger state via processes that include, but are not limited to, those shown and described in FIGS. 63 and 113.

In some embodiments, FIG. 100B illustrates a side view of a selective-triggering probe system 10010, similar to the systems previously described in relation to FIG. 100A, and using some similar or same components, in accordance with some embodiments of the invention. In some embodiments, the selective-triggering probe system 10010 comprises a probe shaft 10001, and/or trigger tab 10002 (shown undepressed), and/or mounting screw 10006, and/or mounting screw 10011, and/or slot for trigger tab 10012, and/or a finger rest 10013. In some embodiments, the user can grip the probe 10010 via the finger rest 10013, and actuate the trigger tab 10002 via one of their fingers. In some embodiments, as the trigger tab 10002 is depressed, the TMSM 10004, (which is mounted on an arm that is a rigid extension of the rotating trigger arm 10008), can be actuated in a concentric arc pathway in which the smaller arm extension of the trigger arm 10008 matches the angular displacement of the larger arm via depression of the trigger tab 10002. In some embodiments, the trigger tab 10002 can travel through a slot 10012 through the finger rest 10013. In some embodiments, the DRF 10003 can be substantially rigidly attached to the probe shaft 10001 via the engagement of a mounting screw 10011, while the torsion spring and rotating trigger arm are held in place (i.e., vertical distance from probe shaft 10001) via another mounting screw 10006.

In some embodiments, FIG. 100C illustrates a front view of a selective-triggering probe system 10020, similar to the systems previously described in relation to FIGS. 100A-

100B, and using some similar or same components, in accordance with some embodiments of the invention. Some embodiments include a selective-triggering probe system 10020 comprising a DRF 10003, and/or spring-loaded TMSM (undepressed trigger) 10004, and/or mounting screw 10011, and/or a DRF-aligning mount 10021. In some embodiments, the DRF 10003 is inserted into the DRF-aligning mount 10021, enabling rigid fixation of the DRF 10003 in a manner that resists its displacement and/or rotation with respect to the probe (probe shaft 10001). In some embodiments, the DRF 10003 can be substantially rigidly attached to the probe shaft 10001 via a mounting screw 10011. In some embodiments, the TMSM 10004 is in an inactive trigger position as the trigger tab 10002 is undepressed.

In some embodiments, FIG. 100D illustrates a rear view of a selective-triggering probe system 10030, similar to the systems previously described in relation to FIGS. 100A-C, and using some similar or same components, in accordance with some embodiments of the invention. In some embodiments, the selective-triggering probe system 10030 comprises a DRF 10003, probe shaft 10031, trigger tab (depressed) 10032, and a rotating trigger arm (depressed) 10033. In some embodiments, the TMSM 10004 is in an active trigger position as the trigger tab 10032 is fully depressed, which rotates the trigger arm 10033 to a position that rotates the substantially rigidly coupled TMSM 10004 towards an active position relative to the DRF 10004. In some embodiments, the rotating trigger arm 10033 can also be fully enclosed within a sheath that is substantially rigidly attached to the probe shaft 10031 to enable the trigger arm 10033 to not be obstructed in its actuation by any external forces (e.g., user hand, gloves, bodily tissue and fluids, etc.)

In some embodiments, FIG. 100E illustrates a side view of a selective-triggering probe system 10040, similar to the systems previously described in relation to FIGS. 100A-D, and using some similar or same components, in accordance with some embodiments of the invention. In some embodiments, the TMSM 10004 is in an active trigger position as the trigger tab 10032, and is fully depressed and inaccessible for further actuation while inside the slot 10012 inside the probe shaft 10001.

In some embodiments, FIG. 100F illustrates a front view of a selective-triggering probe system 10050, similar to the systems previously described in relation to FIGS. 100A-E, and using some similar or same components, in accordance with some embodiments of the invention. Some embodiments include a selective-triggering probe system 10050, and/or a trigger tab 10032 (shown depressed), and/or a TMSM 10051 (shown with depressed trigger). In some embodiments, the TMSM 10051 is in an active trigger position as the trigger tab 10032 is fully depressed, which rotates the trigger arm 10033 to a position that rotates the substantially rigidly coupled TMSM 10051 to the left with respect to the DRF 10004. In some embodiments, this rotation comprises an arc pathway defined by the radius of the trigger arm's upper extension coupled to the TMSM 10051.

Some embodiments of the invention include a selective-triggering probe system that is able to selectively signal to a 3D-tracking camera system when it is in an "active" and/or "inactive" binary state, and/or analog states in between those two boundaries via a linear triggering mechanism. In some embodiments, the probe can be configured for a left-hand-dominant or right-hand-dominant user. Some embodiments of this invention are related to devices and systems described in relation to FIGS. 10, 14, 15, 91, and 100, as well as processes described in relation to FIGS. 24-26, 27A-27D, 28A-28B, 58-61, 62A-62D, 63, 64A-64B, 65A-65E, 66A-66B, 67-69, 82A-82B, 83, 84A-84B, 85, and 113.

In some embodiments, FIG. 101A illustrates a front view of a selective-triggering probe system 10100 in accordance with some embodiments of the invention, showing an assembly comprising a probe shaft 10101, and/or a trigger sleeve 10102, and/or trigger 10103 (shown in an undepressed state), and/or dowel pin 10104, and/or quick-release pin 10105, and/or DRF 10106, and/or TMSM 10107 (showing undepressed trigger), and/or TMSM sliding mount 10108 (showing undepressed trigger), and/or TMSM sliding mount backing 10109, and/or DRF mount 10110, and/or a mounting screw 10111. In some embodiments, the trigger 10103 is undepressed, and the probe is thus in an inactive state due to the TMSM 10107 positioned at or near its baseline location relative to the DRF 10106. In some embodiments, the boundaries of TMSM sliding mount backing 10109 depict the full possible range of motion of the probe's TMSM 10107. In some embodiments, the trigger sleeve 10102 encloses the internal trigger mechanism (not shown) and enables for the trigger mechanism to bias to one side, depending on the user's dominant hand preference. In some embodiments, the trigger sleeve 10102 can be substantially rigidly engaged with the probe shaft 10101 via quick-release pin 10105 that enters the trigger sleeve 10102 and substantially rigidly fixates to the probe shaft 10101. In some embodiments, when the quick-release pin 10105 is removed, the trigger sleeve 10102 can be removed, reversed in its orientation relative to the probe shaft 10101, and then re-engaged by re-inserting the quick-release pin 10105. In some embodiments, the trigger 10103 rotates about a dowel pin 10104 within the trigger sleeve 10102, and enables for controlled triggering actuations by the user and/or system.

In some embodiments, FIG. 101B illustrates a front view of a selective-triggering probe system 10115, similar to the systems previously described in relation to FIG. 101A, and using some similar or same components, in accordance with some embodiments of the invention. Some embodiments include a selective-triggering probe system 10115 comprising a trigger (depressed) 10116, and/or spring-loaded sliding shaft 10117, and/or TMSM 10118 (depressed trigger), and/or a TMSM sliding mount 10119 (depressed trigger). In some embodiments, the trigger 10116 can be fully depressed against the internal trigger mechanism (not shown), which elevates the position of the TMSM 10118 on the TMSM sliding mount backing 10119, and reaches a position relative to the DRF 10106 that signals to the system that the probe is in an active trigger state.

In some embodiments, FIG. 101C illustrates a rear view of a selective-triggering probe system 10125, similar to the systems previously described in relation to FIGS. 101A-101B, and using some similar or same components, in accordance with some embodiments of the invention. In some embodiments, the selective-triggering probe system 10125 can comprise a trigger 10103 (undepressed), and/or a dowel pin 10104, and/or a quick-release pin 10105, and/or a back cover mounting screw 10126, and/or a back cover 1027. In some embodiments, the back cover 10127 can house the spring system (not shown) for the probe's internal sliding shaft (not shown). In some embodiments, the back cover mounting screw 10126 can substantially rigidly attach the back cover 10127 to the probe shaft 10101, and can also provide a point of fixation for one end of the spring (not shown), to which the other end is substantially rigidly attached to the TMSM sliding mount backing 10119. In some embodiments, FIG. 101D illustrates a rear view of a selective-triggering probe system 10130, similar to the systems previously described in relation to FIGS. 101A-C, and using some similar or same components, in accordance with some embodiment of the invention, showing an assembly comprising a trigger (depressed) 10116.

In some embodiments, FIG. 101E illustrates a front cross-sectional view of a selective-triggering probe system 10135, similar to the systems previously described in relation to FIGS. 101A-101D, and using some similar or same components, in accordance with some embodiments of the invention. In some embodiments, the selective-triggering probe system 10135 can comprise a trigger 10103 (shown undepressed), and/or a dowel pin 10104, and/or a quick-release pin 10105, and/or a TMSM sliding mount backing 10109, and/or a dowel pin 10136, and/or a two-link arm (lower link: undepressed trigger) 10137, and/or a dowel pin 10138, and/or a two-link arm (upper link: undepressed trigger) 10139, and/or a spring-loaded sliding shaft (undepressed trigger) 10140, and/or a TMSM mount (undepressed trigger) 10141. In some embodiments, the trigger 10103 is not depressed, and thus the probe is in an inactive trigger state. Some embodiments of the internal triggering mechanism are depicted to demonstrate its baseline position against an undepressed trigger 10103. In some embodiments, the two-link arm (lower link: undepressed trigger) 10137 can be fixed at one end relative to the probe shaft 10101 via the lower dowel pin 10136, with the other end of the two-link arm attached to the second two-link arm (upper link: undepressed trigger) 10139 via an intersecting dowel pin 10138. In some embodiments, the upper end of the second two-link arm (upper link: undepressed trigger) 10139 can be linked to the spring-loaded sliding shaft 10140 via an intersecting dowel pin 10138. In some embodiments, the spring-loaded sliding shaft 10140 can be substantially rigidly attached to the TMSM mount 10141, and thus when the trigger 10103 actuates the two-link arm system and elevates the position of the spring-loaded sliding shaft 10140, the TMSM 10107 on the TMSM mount 10141 can be positioned away from the DRF, which signals to the system that the probe is transitioning to an active trigger state.

In some embodiments, FIG. 101F illustrates a front cross-sectional view of a selective-triggering probe system 10145, similar to the systems previously described in relation to FIGS. 101A-101E, and using some similar or same components, in accordance with some embodiments of the invention. In some embodiments, the selective-triggering probe system 10145 can comprise a trigger (depressed) 10116, and/or two-link arm (lower link: depressed trigger) 10146, and/or two-link arm (upper link: depressed trigger) 10147, and/or spring-loaded sliding shaft (depressed trigger) 10148, and/or a TMSM mount (depressed trigger) 10149. In some embodiments, the trigger 10116 can be fully depressed against the lower two-link arm 10146, which straightens out to extend the position of the upper two-link arm 10147, and consequently can elevate the position of the spring-loaded sliding shaft 10148, which is substantially rigidly fixed to a TMSM 10118 on a TMSM mount 10149. In some embodiments, this position of the TMSM 10118 relative to the fixed DRF (not shown) is interpreted by the system to signal an "active" state for the probe trigger.

In some embodiments, FIG. 101G illustrates a front perspective view of a selective-triggering probe system 10155, similar to the systems previously described in relation to FIGS. 101A-101F, and using some similar or same components, in accordance with some embodiments of the invention. Some embodiments comprise a selective-triggering probe system 10155 comprising a quick-release pin

10105, DRF 10106, TMSM (undepressed trigger) 10107, TMSM sliding mount backing 10109, two-link arm (lower link: undepressed trigger) 10137, two-link arm (upper link: undepressed trigger), and a dowel-loading access slot 10156. In some embodiments, the two-link arms (10137, 1039) are restricted in their vertical range of motion during actuation via a defined dowel-loading access slot 10156, in which the triggering process elevates the position of the dowel 10138 relative to the slot 10156.

In some embodiments, FIG. 101H illustrates a rear perspective view of a selective-triggering probe system 10160, similar to the systems previously described in relation to FIGS. 101A-101G, and using some similar or same components, in accordance with some embodiments of the invention. Some embodiments comprise a selective-triggering probe system 10160 including a dowel pin 10161, and/or back cover aligning extrusion 10162, and/or mounting screw 10163, and/or compression spring 10164, and/or a mounting screw for spring 10165. In some embodiments, the dowel pin 10161 (previously 10136) of the lower two-link arm is fixed to the probe shaft 10101, enabling the actuation of the trigger to elevate the spring-loaded sliding shaft away from the probe tip, and against the compression spring, and thus subsequently elevating the position of the TMSM 10107 relative to the DRF 10106. In some embodiments, the enclosed compression spring 10164 is fixed at one end by the mounting screw (previously 10126) and attached to a mobile mounting screw 10165 that is attached to the spring-loaded sliding shaft 10148 via the TMSM mount 10149, allowing the spring 10164 to extend during actuation.

In some embodiments, FIG. 101I illustrates a side view of a selective-triggering probe system 10170, similar to the systems previously described in relation to FIGS. 101A-101H, and using some similar or same components, in accordance with some embodiments of the invention. In some embodiments, the trigger is not depressed, and thus the TMSM is not offset from its baseline, inactive position relative to the DRF. In some embodiments, FIG. 101J illustrates a side view of a selective-triggering probe system 10175, similar to the systems previously described in relation to FIGS. 101A-101I, and using some similar or same components, in accordance with some embodiment of the invention. In some embodiments, the trigger is depressed, the TMSM is fully offset from its baseline, inactive position relative to the DRF, and the TMSM is thus in an active trigger state.

In some embodiments, FIG. 101K illustrates an assembly view of a selective-triggering probe system 10176, similar to the systems previously described in relation to FIGS. 101A-101J, in accordance with some embodiments of the invention, showing an assembly comprising a two-link arm (lower arm) 10177, and/or two-link arm (upper arm) 10178, and/or spring-loaded sliding shaft 10179, and/or TMSM 10180, and/or trigger sleeve 10181, and/or a trigger 10182.

In some embodiments, FIGS. 101L-1010 illustrate perspective views of a trigger sleeve of a 3D-tracked tool with a linear triggering mechanism as described previously in relation to FIGS. 101A-101K in accordance with some embodiments of the invention. In some embodiments, FIG. 101L illustrates an end view of a probe cover system 10183, similar to the systems previously described in relation to FIGS. 101A-101K, in accordance with some embodiments of the invention, showing an assembly comprising a channel for probe shaft 10184. In some embodiments, the channel for the probe shaft 10184 represents a geometric cutout that matches the exterior surface outline of the probe shaft's cross-section. In some embodiments, this channel can embody any shaft that enables the trigger sleeve to be engaged and removed from the probe shaft.

In some embodiments, further, FIG. 101M illustrates a perspective view of a probe cover system 10185, similar to the systems previously described in relation to FIGS. 101A-101L, in accordance with some embodiments of the invention. In some embodiments, the probe cover system 10185 includes a hole for dowel pin 10186 and a hole for quick release 10187. In some embodiments, the quick-release pin 10105 can be inserted through the hole 10187 on the trigger sleeve 10181. In some embodiments, the dowel pin 10104 for the trigger is inserted through another hole 10186 on the trigger sleeve (e.g., such as trigger sleeve 10181). In some embodiments, FIG. 101N illustrates a perspective view of a probe cover system 10188, similar to the systems previously described in relation to FIGS. 101A-101M, in accordance with some embodiment of the invention, showing an assembly comprising a slot for trigger 10189. In some embodiments, the trigger 10182 is inserted in and is restricted within the slot 10189 within the trigger sleeve 10181. In some embodiments, FIG. 101O illustrates a perspective view of a probe cover system 10190, similar to the systems previously described in relation to FIGS. 101A-101N.

In some embodiments, FIG. 101P illustrates an assembly view of a selective-triggering probe system 10191, similar to the systems previously described in relation to FIGS. 101A-101O, and using some similar or same components, in accordance with some embodiments of the invention. In some embodiments, the selective-triggering probe system 10191 comprises a left-hand dominant probe configuration 10192 and a left-hand dominant trigger configuration 10193. In some embodiments, the trigger sleeve 10193 is oriented for left-hand dominant trigger configuration, in which the accompanying probe configuration 10192 of the internal trigger mechanism is positioned to have a bias in its range of motion towards the probe's left side.

In some embodiments, FIG. 101Q illustrates an assembly view of a selective-triggering probe system 10195, similar to the systems previously described in relation to FIGS. 101A-101P, in accordance with some embodiments of the invention. Some embodiments comprise a selective-triggering probe system 10195 comprising a right-hand dominant probe configuration 10196 and a right-hand dominant trigger configuration 10197. In some embodiments, the trigger sleeve 10197 can be oriented for right-hand dominant trigger configuration, in which the accompanying probe configuration 10196 of the internal trigger mechanism is positioned to have a bias in its range of motion towards the probe's right side.

Some embodiments of the invention include a fiducial-registration probe system that can mate with a fiducial that has an outer, embedded depth-stop mating interface and register the position and orientation of the fiducial with respect to a 3D-tracking camera system. In some embodiments, the user can mate the probe with the patterned interface within the fiducial, and when the probe is fully engaged with the fiducial interface, an internal spring-loaded depressible sliding shaft can actuate a TMSM relative to a fixed DRF mounted on the probe to trigger a registration event to the system. In some embodiments, the trigger mechanism of the probe can be actuated by the user, instead of by the successful mating of the probe with the fiducial, via systems that include, but are not limited to, those depicted previously in relation to FIGS. 95A-95I, 98A-98V, etc. Some embodiments of this invention are related to devices and systems described in relation to FIGS. 3A-3C, 10A-10G, 14A-14C, 15A-15C, 29A-29D, 33A-33G, 38A-38G, 44A-44D, 45A-45B, 91A-91C, 101A-101Q, 103A-103Q, 104A-104J, and 106A-106F, as well as processes described in relation to FIGS. 58-60, 62A-62D, 63, 64A-64B, 65A-65E, 66A-66B, 68-69, 72, and 113

In some embodiments, FIG. 102A illustrates a front view of a fiducial-registration probe system 10200 in accordance with some embodiment of the invention, showing an assembly comprising a bone fiducial screw threading 10201, and/or probe mating region 10202, and/or probe shaft 10203, and/or TMSM 10204, and/or mounting screw 10205, and/or a DRF 10206. In some embodiments, the probe is fully engaged with the bone fiducial, and thus the TMSM 10204 is elevated to an active triggering state. In some embodiments, FIG. 102B illustrates a rear view of a fiducial-registration probe system 10210, similar to the systems previously described in relation to FIG. 102A, and using some similar or same components, in accordance with some embodiments of the invention. In some embodiments, the fiducial-registration probe system 10210*a* comprises a probe shaft 10203, and/or TMSM 10204, and/or DRF 10206, and/or TMSM sliding post 10211, and/or trigger retaining screw 10212, and/or a trigger motion-restricting slot. In some embodiments, the spring-loaded trigger mechanism (not shown) is housed within the TMSM sliding post 10211. In some embodiments, the spring-loaded trigger mechanism is restricted in its range of motion of triggering via a trigger-retaining screw 10212 fastened against the probe shaft 10203 within the trigger motion-restricting slot 10213, which is a component of the TMSM sliding post 10211. In some embodiments, FIG. 102C illustrates a side view of a fiducial-registration probe system 10215, similar to the systems previously described in relation to FIGS. 102A-102B, and using some similar or same components, in accordance with some embodiment of the invention.

In some embodiments, FIG. 102D illustrates an assembly view of a fiducial-registration probe system 10220, similar to the systems previously described in relation to FIGS. 102A-102C, and using some similar or same components, in accordance with some embodiments of the invention. In some embodiments, the fiducial-registration probe system 10220 comprises assembly comprising a probe shaft 10203, and/or DRF 10206, TMSM 10221 (undepressed), and/or TMSM sliding post 10222, and/or mating groove 10223, and/or a flat mating surface 10224. In some embodiments, the probe is not engaged with the bone fiducial mating features (10223, 10224), and thus the TMSM 10221 is not in an active triggering state.

In some embodiments, FIG. 102E illustrates a side assembly view of a fiducial-registration probe system 10225, similar to the systems previously described in relation to FIGS. 102A-102D, and using some similar or same components, in accordance with some embodiments of the invention, showing an assembly comprising a mating groove 10223. In some embodiments, FIG. 102F illustrates a front assembly view of a fiducial-registration probe system 10226, similar to the systems previously described in relation to FIGS. 102A-102E, and using some similar or same components, in accordance with some embodiments of the invention. In some embodiments, the fiducial-registration probe system 10226 comprises a DRF 10206, and/or TMSM 10221 (in an undepressed state), and/or a dowel pin 10227. In some embodiments, the DRF 10206 can be restricted from rotational movement via the insertion of a dowel pin 10227 through the DRF 10206 and substantially rigidly fixed to the probe shaft 10203. In some embodiments, the DRF 10206 can be manufactured as one component with the probe shaft 10203, and does not need a rotation-preventing dowel pin 10227.

In some embodiments, FIG. 102G illustrates a perspective view of a bone fiducial screw system 10230, similar to the systems previously described in relation to FIGS. 102A-102F, and using some similar or same components, in accordance with some embodiments of the invention. Some embodiments comprise a bone fiducial screw system 10230 comprising a bone fiducial screw threading 10231, and/or mating groove 10232, and/or screw head 10233, and/or access hole for drive 10234, and/or a flat mating surface 10235. In some embodiments, the bone fiducial mating features (10232, 10235) can enable the fiducial to be mated and registered by a probe (e.g., as depicted previously in relation to FIG. 102A) in only one unique orientation. In some embodiments, the mating features of the probe and fiducial must be aligned and fully engaged for the mating system to actuate the probe's internal depressible spring-loaded plunger (not shown) and trigger the attached TMSM (not shown) towards an active trigger state. In some embodiments, multiple mating grooves 10232 are implemented on the bone fiducial to facilitate a rigid mating interface that mitigates any unnecessary rotations.

In some embodiments, FIG. 102H illustrates a side view of a bone fiducial screw system 10238, similar to the systems previously described in relation to FIGS. 102A-102G, and using some similar or same components, in accordance with some embodiments of the invention. Some embodiments include a bone fiducial screw system 10238 comprising a mating groove 10232 and traction spikes 10239. In some embodiments, the bone fiducial screw system 10238, or similar surfaces that interface with the anatomy of interest, can include features such as a series of traction spikes 10239 that can aid in the rigid fixation of the bone fiducial screw system 10238 with the surface of the screw-engaged anatomy. In some embodiments, when the bone fiducial screw is fully engaged with the anatomy of interest, then the mating fiducial attachment and screw head 10233 are pressed against each other and become completely rigid as one component, to which the probe then mates and registers the fiducial's location and orientation.

In some embodiments, FIG. 102I illustrates a perspective view of a bone fiducial screw system 10241, similar to the systems previously described in relation to FIGS. 102A-102H, and using some similar or same components, in accordance with some embodiments of the invention, showing an assembly comprising a mating groove 10232. In some embodiments, FIG. 102J illustrates a top view of a bone fiducial screw system 10245, similar to the systems previously described in relation to FIGS. 102A-102I, and using some similar or same components, in accordance with some embodiment of the invention, showing an assembly comprising a mating groove 10232, screw head 10233, and a flat mating surface 10235. In some embodiments, FIG. 102K illustrates a side view of a bone fiducial screw system 10247, similar to the systems previously described in relation to FIGS. 102A-102J, and using some similar or same components, in accordance with some embodiment of the invention showing an assembly comprising a traction spikes 10239. In some embodiments, FIG. 102L illustrates a perspective view of a bone fiducial screw system 10250, similar to the systems previously described in relation to FIGS. 102A-102K, and using some similar or same components, in accordance with some embodiment of the invention.

In some embodiments, FIG. 102M illustrates a perspective assembly view of a fiducial-registration probe system 10252, similar to the systems previously described in relation to FIGS. 102A-102L, and using some similar or same components, in accordance with some embodiments of the invention. Some embodiments comprise a fiducial-registration probe system 10252 including a probe shaft 10203, mating groove 10232, spring-loaded plunger 10253, and mating extrusions 10254. In some embodiments, probe's mating extrusions 10254 can engage with the mating groove 10232 of the bone fiducial, and simultaneously can actuate a spring-loaded plunger 10253 that elevates the position of a TMSM 10204 mounted on a TMSM sliding post 10222 towards a position relative to the DRF. In some embodiments, this action signals to the system that the probe is in an active trigger state, initiating the registration of the bone fiducial's unique orientation and location.

In some embodiments, FIG. 102N illustrates a side cross-sectional view of a fiducial-registration probe system 10256, similar to the systems previously described in relation to FIGS. 102A-102M, and using some similar or same components, in accordance with some embodiments of the invention. Some embodiments comprise a fiducial-registration probe system 10256 including a spring-loaded plunger 10253, and/or TMSM 10257, and/or a compression spring 10258. In some embodiments, the actuation of the spring-loaded plunger 10253, such as via mating with a bone fiducial with complementary mating features, can compress a compression spring 10258 that can elevate the position of a TMSM 10257 located on the TMSM sliding post 10222.

In some embodiments, FIG. 102O illustrates a front assembly view of a fiducial-registration probe system 10259, similar to the systems previously described in relation to FIGS. 102A-102N, and using some similar or same components, in accordance with some embodiments of the invention. In some embodiments, the fiducial-registration probe system 10259 comprises a probe shaft 10203, and/or DRF 10206, and/or spring-loaded plunger 10253, and/or compression spring 10258, and/or TMSM mounting hole 10260, and/or TMSM sliding post 10261, and/or trigger motion-restricting slot 10262, and/or mounting hole 10263, and/or a dowel pin hole 10264. In some embodiments, a mounting hole 10263 behind the DRF 10206 serves as a fixation point for a screw (not shown) that substantially rigidly attaches the DRF 10206 to the mounting surface of the probe shaft 10203. In some embodiments, the spring-loaded plunger 10253 directly compresses a spring 10258 housed within the TMSM sliding post 10261, and actuates the attached TMSM 10260 into an active position.

In some embodiments, FIG. 102P illustrates a perspective assembly view of a fiducial-registration probe system 10270, similar to the systems previously described in relation to FIGS. 102A-102O, and using some similar or same components, in accordance with some embodiments of the invention. Some embodiments comprise a fiducial-registration probe system 10270 comprising a DRF 10206, spring-loaded plunger, TMSM sliding post 10261, TMSM 10271, probe shaft 10203, and a mounting screw 10272. In some embodiments, a mounting screw 10272 can be inserted through the DRF 10206 and into threads in the mounting hole 10263, enabling for the rigid fixation of the DRF 10206 against the probe shaft 10203.

Some embodiments of the invention include a fiducial-registration probe system that can mate with a fiducial that has an inner, embedded depth-stop mating interface and register the position and orientation of the fiducial with respect to a 3D-tracking camera system. In some embodiments, the user can mate the probe with the patterned interface within the fiducial, and when the probe is fully engaged with the fiducial interface, an internal spring-loaded depressible sliding shaft actuates a TMSM relative to a fixed DRF mounted on the probe to trigger a registration event to the system. In some embodiments, the trigger mechanism of the probe can be actuated by the user, instead of by the successful mating of the probe with the fiducial, via systems that include, but are not limited to, those depicted previously in relation to FIGS. 95, 98, etc. Some embodiments of this invention are related to devices and systems described in relation to FIGS. 3A-3C, 10A-10G, 14A-14C, 15A-15C, 29A-29D, 33A-33G, 38A-38G, 44A-44D, 45A-45B, 91A-91C, 101A-101Q, 102A-102P, 104A-104J, and 106A-106F, as well as processes described in relation to FIGS. 58-60, 62A-62D, 63, 64A-64B, 65A-65E, 66A-66B, 68-69, 72, and 113.

In some embodiments, FIG. 103A illustrates a front view of a fiducial-registration probe system 10300 in accordance with some embodiments of the invention, showing an assembly comprising a TMSM 10301 (in an undepressed state), and/or a TMSM sliding post 10302 (in an unde-pressed state), and/or a DRF 10303, and/or a mounting screw 10304, and/or a dowel pin 10305, and/or a shaft 10306, and/or a probe tip extrusion tab 10307, and/or bone fiducial screw 10308. In some embodiments, the probe is not engaged with the bone fiducial screw 10308, and thus the TMSM 10301 is not in an active triggering state. In some embodiments, the fiducial-registration probe system 10300 can contain a probe tip extrusion tab 10307 that engages with the bone fiducial screw 10308 in one unique orientation to enable registration of the bone fiducial screw's unique pose and location in 3D space.

In some embodiments, FIG. 103B illustrates a side view of a fiducial-registration probe system 10310, similar to the systems previously described in relation to FIG. 103A, and using some similar or same components, in accordance with some embodiments of the invention, showing an assembly comprising a probe tip extrusion tab 10311, similar to that depicted previously in relation to FIG. 103A.

In some embodiments, FIG. 103C illustrates a rear view of a fiducial-registration probe system 10315, similar to the systems previously described in relation to FIGS. 103A-103B, and using some similar or same components, in accordance with some embodiments of the invention. In some embodiments, the spring-loaded trigger mechanism (not shown) is housed within the TMSM sliding post 10302, and is restricted in its range of motion of triggering via a trigger-retaining screw fastened against the probe shaft 10306 within the trigger motion-restricting slot, which is a component of the TMSM sliding post 10302.

In some embodiments, FIG. 103D illustrates a perspective view of a fiducial-registration probe system 10320, similar to the systems previously described in relation to FIGS. 103A-103C, and using some similar or same components, in accordance with some embodiments of the invention, show-ing an assembly comprising a TMSM 10301 (in an unde-pressed state). In some embodiments, the fiducial-registration probe system 10320 is not engaged with the bone fiducial screw 10308, and thus the TMSM 10301 is not in an active triggering state. In some embodiments, FIG. 103E illustrates a perspective view of a fiducial-registration probe system 10325, similar to the systems previously described in relation to FIGS. 103A-103D, and using some similar or same components, in accordance with some embodiment of the invention. In some embodiments, the probe is fully engaged with the bone fiducial screw 10308, and thus the TMSM 10301 is elevated to an active triggering state. In some embodiments, FIG. 103F illustrates a perspective view of a fiducial-registration probe system 10330, similar to the systems previously described in relation to FIGS. 103A-103E, and using some similar or same components, in accordance with some embodiments of the invention showing an assembly comprising a probe tip extrusion tab 10331. In some embodiments, the probe is not engaged with the bone fiducial screw 10308, and thus the TMSM 10301 is not in an active triggering state. In some embodiments, FIG. 103G illustrates a perspective view of a fiducial-registration probe system 10335, similar to the systems previously described in relation to FIGS. 103A-103F, and using some similar or same components, in accordance with some embodiment of the invention, showing an assembly comprising a TMSM 10336 (in a depressed state) and probe tip flat mating surface 10337. In some embodiments, the probe is fully engaged with the bone fiducial screw 10308, and thus the TMSM 10336 is elevated to an active triggering state. In some embodiments, the probe tip flat mating surface 10337 aids with the unique alignment of the probe with the bone fiducial screw 10308. In some embodiments, FIG. 103H illustrates a side view of a fiducial-registration probe system 10340, similar to the systems previously described in relation to FIGS. 103A-103G, and using some similar or same components, in accordance with some embodiment of the invention. In some embodiments, the probe is fully engaged with the bone fiducial screw 10308, and thus the TMSM 10336 is elevated to an active triggering state.

In some embodiments, FIG. 103I illustrates a rear view of a fiducial-registration probe system 10345, similar to the systems previously described in relation to FIGS. 103A-103H, and using some similar or same components, in accordance with some embodiments of the invention. Some embodiments include a fiducial-registration probe system 10300 comprising a trigger-retaining screw 10346 and trigger motion-restricting slot 10347. In some embodiments, the fiducial-registration probe system 10345 is fully engaged with the bone fiducial screw 10308, and thus the TMSM 10336 is elevated to an active triggering state. In some embodiments, the spring-loaded trigger mechanism (not shown) can be housed within the TMSM sliding post 10302, and is restricted in its range of motion of triggering via a trigger-retaining screw 10346 fastened against the probe shaft 10306 within the trigger motion-restricting slot 10347, which is a component of the TMSM sliding post 10302.

In some embodiments, FIG. 103J illustrates a perspective view of a bone fiducial screw system 10350, similar to the systems previously described in relation to FIGS. 103A-103I, in accordance with some embodiments of the invention. Some embodiments include a bone fiducial screw system 10350 comprising a screw head 10351, and/or mating fiducial attachment 10352, and/or fiducial flat mating surface 10353, and/or fiducial alignment groove 10354, and/or fiducial screw head offset 10355. In some embodiments, the bone screw with screw head 10351 can be a separate component of the fiducial system, in which the mating fiducial attachment can freely rotate about the screw shaft. In some embodiments, the screw head 10351 interfaces with the fiducial screw head offset 10355, which enhances the triggering mechanism for depressing the sliding shaft (not shown) of the probe. In some embodiments, the mating fiducial attachment 10352 includes, but is not limited to, one or more unique, asymmetric extrusions (e.g., fiducial alignment groove 10354, fiducial flat mating surface 10353, etc.) that enable the probe (e.g., such as probe with probe shaft 10306) to mate with the fiducial attachment 10352 securely and in only one unique orientation, using complementary extrusions such as the probe tip extrusion tab 10311 as depicted in FIG. 103B. In some embodiments, every time the probe mates with the fiducial attachment 10352, the probe can register the unique orientation and location of the bone fiducial screw 10308. In some embodiments, when the bone fiducial screw is fully engaged with the anatomy of interest, then the mating fiducial attachment and screw head are pressed against each other and become completely rigid as one component, to which the probe mates and registers the fiducial's location and orientation.

In some embodiments, FIG. 103K illustrates a front view of a bone fiducial screw system 10360, similar to the systems previously described in relation to FIGS. 103A-103J. In some embodiments, the screw 10351a is fully inserted into the mating fiducial attachment 10352. In some embodiments, the bottom surface of the mating fiducial attachment 10352, or similar surfaces that interface with the anatomy of interest can include features, such as a series of spikes or hooks, that aid in the rigid fixation of the mating fiducial attachment 10352 with the surface of the screw-engaged anatomy.

In some embodiments, FIGS. 103L-103O illustrate several perspective views of a bone fiducial screw system (10365, 10370, 10375, 10380), similar to the systems previously described in relation to FIGS. 103A-103K, in accordance with some embodiments of the invention, showing assemblies comprising a fiducial flat mating surface 10353, and fiducial alignment groove 10354.

In some embodiments, FIG. 103P illustrates a top view of a bone fiducial screw system, similar to the systems previously described in relation to FIGS. 103A-103O, in accordance with some embodiments of the invention, showing an assembly comprising a fiducial flat mating surface 10353, and a fiducial alignment groove 10354. In some embodiments, the unique orientation of the fiducial attachment 10352 is apparent and illustrates how the probe registers the unique pose of the fiducial system, regardless of whether the engaged anatomy it is fastened against happens to move.

In some embodiments, FIG. 103Q illustrates a perspective view of a fiducial-registration probe system 10390, similar to the systems previously described in relation to FIGS. 103A-103P, in accordance with some embodiments of the invention, showing an assembly comprising a probe shaft 10306, and/or probe tip extrusion tab 10307, and/or probe flat-face mating extension 10391, and/or a spring-loaded plunger 10392. In some embodiments, once the mating extensions of the probe tip (e.g., 10391, 10307, etc.) are fully engaged with the mating fiducial attachment 10352, the spring-loaded plunger 10392 within the probe shaft 10306 can be actuated against the surface of the screw head 10351 of a bone screw, and consequently can elevate the position of the attached TMSM 10336 into an active triggering state.

Some embodiments of the invention include a screw-registration probe system that is able to mate with a fastener with an embedded depth-stop mating interface and register the position and orientation of the fastener's shaft with respect to a 3D-tracking camera system. In some embodiments, the user can mate the probe with the patterned interface attached to a screw shaft and when the probe is fully engaged with the screw mating interface, an internal spring-loaded depressible sliding shaft actuates a TMSM relative to a fixed DRF mounted on the probe to trigger a registration event to the system. In some embodiments, the trigger mechanism of the probe can be actuated by the user, instead of by the successful mating of the probe with the fastener, via systems that include, but are not limited to, those depicted previously in relation to FIGS. 95A-95I, and 98A-98V, etc. Some embodiments of this invention are related to devices and systems described in relation to FIGS. 3A-3C, 10A-10G, 14A-14C, 15A-15C, 29A-29D, 33A-33G, 38A-38G, 44A-44D, 45A-45B, 91A-91C, 101A-101Q, 103A-103Q, and 106A-106F, as well as processes described in relation to FIGS. 58-60, 62A-62D, 63, 64A-64B, 65A-65E, 66A-66B, 68-69, 72, and 113.

In some embodiments, FIG. 104A illustrates a front view of a screw-registration probe system 10400 in accordance with some embodiments of the invention. Some embodiments include a screw-registration probe system 10400 comprising a TMSM 10401 (undepressed), and/or DRF 10402, and/or mounting screw 10403, and/or dowel pin 10404, and/or TMSM sliding post 10405 (undepressed), and/or shaft 10406, and/or tool mating tip 10407, and/or tulip head 10408, and/or screw mating attachment 10409, and/or a pedicle screw shaft 10410 (threads not shown). In some embodiments, the tool mating tip 10407 can be a partial-cylinder shape to enable a rod to be implanted into the screw's tulip head, and can maintain the range of motion of the tulip head without losing access to registration sites on the screw. In some embodiments, once the tool mating tip 10407 is completely and substantially rigidly engaged with the screw mating attachment, a depressible sliding shaft (not shown) can be actuated, moving the location of a substantially rigidly-linked TMSM 10401 on a TMSM sliding post 10405 relative to the DRF 10402 of the tool, and signaling to the system that a triggering event of screw registration is occurring. In some embodiments, the screw-registration probe system 10400 is not engaged with the fastener system, and the TMSM 10401 is consequently not in an active triggering position. In some embodiments, the DRF can be modularly attached to the probe device, and can be replaced by other DRF and/or associated tool definition files to change the system's understanding of the probe's function and/or tracking location.

In some embodiments, FIG. 104B illustrates a side view of a screw-registration probe system 10415, similar to the systems previously described in relation to FIG. 104A, and using some similar or same components, in accordance with some embodiments of the invention. Some embodiments include a screw-registration probe system 10415 comprising a TMSM 10401 (shown in an undepressed state), TMSM sliding post 10405 (shown in an undepressed state), and tool mating tip 10407. In some embodiments, the tool's geometrical design has the TMSM 10401 that can be located in-line with the 3D-tracked markers of the DRF 10402 to simplify the processing of filtering stray markers, classifying a TMSM, and measuring its relative location for a triggering event as described in at least FIGS. 63, 113.

In some embodiments, FIG. 104C illustrates a rear view of a screw-registration probe system 10420, similar to the systems previously described in relation to FIGS. 104A-104B, and using some similar or same components, in accordance with some embodiments of the invention, showing an assembly comprising a TMSM 10401 (in an undepressed state), and/or DRF 10402, and/or TMSM sliding post 10405 (undepressed), and/or shaft 10406, and/or tool mating tip 10407, and/or trigger-retaining screw 10421, and/or a trigger motion-restriction slot 10422. In some embodiments, the spring-loaded trigger mechanism (not shown) can be housed within the TMSM sliding post 10405, and can be restricted in its range of motion of triggering via a trigger-retaining screw 10421 fastened against the probe shaft 10406 within the trigger motion-restriction slot 10422, which is a component of the TMSM sliding post 10405.

In some embodiments, FIG. 104D illustrates a front view of a screw-registration probe system 10425, similar to the systems previously described in relation to FIGS. 104A-104C, and using some similar or same components, in accordance with some embodiments of the invention. In some embodiments, the screw-registration probe system 10425 can comprise a TMSM 10426 (in a depressed state), TMSM sliding post 10427 (in a depressed state), and an engaged tool mating tip 10428. In some embodiments, the tool mating tip 10428 can be fully engaged with the screw mating attachment 10409, and the depressible sliding shaft (not shown) can elevate the TMSM 10426 of the TMSM sliding post 10427 away from the DRF 10402 to signal to the system that the registration probe is fully aligned and engaged with the screw mating attachment. In some embodiments, the screw mating attachment can be co-axial with the screw shaft in order to enable the probe to rapidly register the accurate orientation of the screw shaft via the registration of the screw mating attachment location. In some embodiments, the mating attachment of the screw can have features that include, but are not limited to, co-linear mates or ones that are off-angle with the central axis of the screw shaft.

In some embodiments, FIG. 104E illustrates a side view of a screw-registration probe system 10430, similar to the systems previously described in relation to FIGS. 104A-104D, and using some similar or same components, in accordance with some embodiments of the invention. In some embodiments, the screw-registration probe system 10430 can comprise a TMSM 10426 (shown in depressed state) and/or TMSM sliding post 10427 (shown in depressed state). In some embodiments, similar to that depicted in FIG. 104D, the screw-registration probe is in an active state via being fully engaged with the mating attachments of the screw.

In some embodiments, FIG. 104F illustrates a rear view of a screw-registration probe system 10435, similar to the systems previously described in relation to FIGS. 104A-104E, and using some similar or same components, in accordance with some embodiments of the invention, in accordance with some embodiment of the invention. Some embodiments include a screw-registration probe system 10435 comprising an engaged tool mating tip 10428 and/or a trigger-retaining screw with trigger depressed 10436. In some embodiments, similar to that depicted in FIGS. 104D-104E, the screw-registration probe can be in an active state via being fully engaged with the mating attachments of the screw. In some embodiments, the trigger-retaining screw with trigger depressed 10436 is located within the bottom of trigger motion-restricting slot 10422 because the TMSM sliding post 10427 has elevated relative to the DRF 10402 and probe shaft 10406, which is farther away from the trigger-retaining screw, and which is substantially rigidly attached to the probe shaft 10406.

In some embodiments, FIG. 104G illustrates a perspective view of a screw-registration probe system 10440, similar to the systems previously described in relation to FIGS. 104A-104F, in accordance with some embodiment of the invention, showing an assembly comprising an TMSM 10441 (undepressed state), TMSM sliding post 10442 (undepressed state), and a screw mating attachment 10443. In some embodiments, similar to that depicted in FIGS. 104A-104C, the screw-registration probe is in an inactive state.

In some embodiments, FIG. 104H illustrates a perspective view of a screw-registration probe system 10450, similar to the systems previously described in relation to FIGS. 104A-104G, in accordance with some embodiments of the invention. Some embodiments include a screw-registration probe system 10450 comprising a tool mating extrusion pattern 10451, and/or spring-loaded plunger (undepressed) 10452, and/or tool mating depth-stop 10453, and/or screw mating pattern 10454, and/or a threaded hole 10455. In some embodiments, the tool mating extrusion pattern 10451 can include different draft angles that complement the screw mating pattern 10454 to enable a unique, well-aligned, and full-engaged mate between the probe and the screw mating attachment. In some embodiments, when the tool mating extrusion pattern is fully engaged with the screw mating pattern 10454, the spring-loaded plunger 10452 is depressed and subsequently elevates the position of the TMSM 10441 until it reaches an active triggering location relative to the DRF 10402. In some embodiments, the threaded holes 10455 within the screw mating pattern 10454 can be utilized in order to substantially rigidly secure the probe mating tip to the screw attachment via fasteners (not shown) that are inserted through the body of the tool mating extrusion pattern 10451.

In some embodiments, FIG. 104I illustrates a perspective view of a screw-registration probe system 10460, similar to the systems previously described in relation to FIGS. 104A-104H, in accordance with some embodiments of the invention, showing an assembly comprising an TMSM 10461 (depressed), and/or TMSM sliding post 10462 (depressed), and/or an engaged tool mating tip 10463. In some embodiments, similar to that depicted in FIGS. 104D-104F, the screw-registration probe is in an active state.

Some embodiments of the invention include an adjustable screw interface system of a flexibility assessment device that can mate with fasteners with an embedded depth-stop mating interface and substantially rigidly cross-link with other similar adjustable screw interface systems attached to other anatomical landmarks. In some embodiments, the user can mate a 3D-tracked flexibility assessment device with a vertebra of interest via pedicle screws with depth-stop mates that are engaged at various relative orientations and positions, accounted for via a variable width and angle adjustment mechanism of the screw interface system. In some embodiments, the depicted screw interface system is compatible with flexibility assessment device handles and/or accompanying systems that include, but are not limited to, those depicted previously in relation to FIGS. 40-43 and 95-97. In some embodiments, the flexibility assessment device handles can be adjusted into various handle orientations relative to the screw interface system via a mechanism that includes, but is not limited to, a spring-loaded fastener that can be released or engaged to securely adjust the device handle to a desired orientation relative to the 3D-tracking camera, nearby screw interface devices, other flexibility assessment device handles, DRF-equipped tools, etc. Some embodiments of this invention are related to devices and systems described in relation to FIGS. 34, 34A-34F, 35A-35E, 36A-36I, 37A-37G, 38, 38A-38G, 39A-39F, 40A-40C, 41A-41D, 42A-42K, 43A-43K, 94A-94H, 95A-95I, 96A-96S, 97A-97L, 105A-105G, 106A-106F, as well as processes described in relation to FIGS. 44A-44D, 45A-45B, 58-60, 62A-62D, 63, 64A-64B, 65A-65E, 66A-66B, 68-69, 70, 72, 107A-107D, 108A-108H, 111, and 113.

In some embodiments, FIG. 105A illustrates a perspective view of an adjustable screw interface assembly 10500 in accordance with some embodiments of the invention. In some embodiments, the adjustable screw interface assembly 10500 can comprise side arms such as side arm 10501a and/or side arm 10501b, and/or extension screw 10502, and/or extension screw sleeve 10503, and/or tool mating tip 10504, and/or pedicle screw shaft (threads not shown) 10505, and/or screw mating attachment 10506, and/or threaded hole 10507, and/or tulip head 10508. In some embodiments, the side arm 10501a can be a fixed side arm (coupled to shoulder 10513) and/or the side arm 10501b can be an adjustable side arm (adjustably positioned in cavity or channel 10519 of adjustment bracket 10518). In some embodiments, the distance between the arms 10501a and 10501b can be adjusted by sliding arm 10501b towards or away from arm 10501a using the cavity or channel 10519). In some embodiments, the components of the side arm 10501a and side arm 10501b can be the same, can use at least some common components, and described similarly. In some embodiments, the screw interface assembly 10500 can substantially rigidly engage with a flexibility assessment system (e.g., see example FIG. 96N). In some embodiments, the screw interface system's tool mating tip 10504 can engage with depth-stop patterns on the screw mating attachment 10506, regardless of whether there is an implanted rod within the tulip head 10508 of the screw. In some embodiments, one of the side arm 10501 assemblies can be linked in a fixed orientation with the adjustable width mechanism of the overall assembly 10500, while the other side arm assembly can vary in its relative width, height, and orientation with respect to the corresponding side arm 10501 assembly. In some embodiments, the extension screws 10502 in the extension screw sleeves 10503 can enable the side arm 10501 and tool mating tip 10504 to substantially rigidly link with the depth-stop interface of the screw mating attachment 10506. In some embodiments, the overall screw interface assembly 10500 includes, but is not limited to, accessory tulip heads that enable for the rigid fixation of two or more flexibility assessment devices (e.g., as depicted below in reference to FIG. 105G) via a rod linkage between the devices that is substantially rigidly linked by way of cap screws inserted on the tulip heads, with the rod within the cavity of the tulip head.

In some embodiments, FIG. 105B illustrates a front view of an adjustable screw interface system 10520, similar to the systems previously described in relation to FIG. 105A, and using some similar or same components, in accordance with some embodiments of the invention. Some embodiments include an adjustable screw interface system 10520 comprising at least a side arm 10501a, and/or extension screw 10502, and/or extensions screw sleeve 10503, and/or tool mating tip 10504, and/or pedicle screw shaft (threads not shown) 10505, and/or screw mating attachment 10506. In some embodiments, the adjustable orientation of the adjustable side arm (unlabelled) can enable the screw interface system 10520 to mate with pedicle screws that are instrumented into the spine in orientations that are not mirrored about the screw interface system's 10520 central axis.

In some embodiments, FIG. 105C illustrates a rear view of an adjustable screw interface system 10530, similar to the systems previously described in relation to FIGS. 105A-105B, in accordance with some embodiments of the invention, showing an assembly comprising a tool mating tip 10504, and screw mating attachment 10506. In some embodiments, the spinal rod implant can be implanted from behind or above the tulip head while the screw interface system 10530 is fully engaged with the pedicle screws.

In some embodiments, FIG. 105D illustrates a top view of an adjustable screw interface system 10540, similar to the systems previously described in relation to FIGS. 105A-105C, in accordance with some embodiments of the invention, showing an assembly comprising a tool mating tip 10504, and/or screw mating attachment 10506, and/or threaded hole 10507. In some embodiments, the screw interface system 10540, as depicted, the cap screws and accessory tulip heads of the screw interface system 10540 can be accessed from above via complementary instruments (e.g., screwdriver). In some embodiments, FIG. 105E illustrates a side view of an adjustable screw interface system 10550, similar to the systems previously described in relation to FIGS. 105A-105D.

In some embodiments, FIG. 105F illustrates a perspective of an adjustable screw interface system 10560, similar to the systems previously described in relation to FIGS. 105A-105D, in accordance with some embodiments of the invention. Some embodiments of the invention include an adjustable screw interface system 10560 comprising an extension screw 10502, and/or a mating-equipped screw (detached from tool) 10561, and/or extension screw threads 10562. In some embodiments, the extension screw threads of the tool mating tip 10504 are not engaged into a mating-equipped screw 10561. In some embodiments, the adjustable side arm sub-assembly can mate with a mating-equipped screw with the orientation-locking fastener not fully engaged, and thus enable the fixed-orientation side arm subassembly to orient itself about the screw interface system 10560 to properly align with the mating interface of the mating-equipped screw 10561.

In some embodiments, FIG. 105G illustrates a perspective of an adjustable screw interface system 10565, similar to the systems previously described in relation to FIGS. 105A-105E, in accordance with some embodiments of the invention. In some embodiments, the adjustable screw interface system 10565 can comprise a handle #1 10566, and/or handle #2 10567, and/or device outer tulip head 10568, and/or device inner tulip head 10569, and/or inter-tool connecting rod 10570, and/or device inner tulip head 10571, and/or cap screw 10572, and/or screw-mating attachment 10573, and/or implanted rod for pedicle screws 10574, and/or cap screw 10575, and/or tool-engaged vertebra #1 10576, and/or a tool-engaged vertebra #2 10577. In some embodiments, as shown in the non-limiting embodiment of FIG. 105G, the adjustable screw interface system 10565 illustrates two flexibility assessment devices, substantially rigidly linked via an inter-tool connecting rod 10570 that is substantially rigidly fixed via the device inner tulip head 10571 and cap screw 10572 that are substantially rigidly engaged with vertebrae of interest (10576, 10577), that can be subsequently manipulated into a desired conformation. In some embodiments, instrumented vertebrae, those linked to the flexibility assessment devices and those that are not, can be substantially rigidly linked together via an implanted rod 10574 that ensures the contour of the spine between the flexibility assessment devices can be substantially rigidly fixed in a desired conformation. In some embodiments, the handles (10566, 10567) of the flexibility assessment devices, which are substantially rigidly engaged with vertebrae of interest, can be maneuvered by the user and/or system to manipulate the contour and flexibility of the vertebrae that are linked to and positioned between the flexibility assessment devices. In some embodiments, a desired conformation can be achieved by the flexibility assessment devices (e.g., adjustable screw interface system 10565 can comprise a handle #1 10566, and/or handle #2 10567), and detected by systems including, but not limited to, those described below in reference to FIG. 111. In some embodiments, once one side of the spine has an implanted rod within the instrumented pedicle screws and the rod is substantially rigidly linking the associated vertebrae via tightened cap screws, then the respective handles (10566, 10567) can be detached from the overall screw interface systems, and another rod can be implanted into the contralateral of the spine into the instrumented pedicle screw tulip heads, and thus substantially rigidly fix the overall construct of the manipulated region of the spine. In some embodiments, the two accessory device tulip heads (10568, 10569) on each side of a screw interface system, can enable for multiple constructs to be linked between separately assessed and/or fixed regions of the spine that also have attached screw interface systems. In some embodiments, adjustable side arm and/or the fixed side arm assemblies of a screw interface system can also be adjusted to be able to rotate about the axis of the side arm shaft, enabling the screw interface mating surface to be able to properly align and substantially rigidly engage with the mating patterns of the screw mating attachments of the pedicle screws of interest.

Some embodiments of the invention include a device sub-assembly with a triggering mechanism that contains a lockable mechanism for maintaining the active triggering state of the device. In some embodiments, in reference to FIGS. 106A-106F, some embodiments include a trigger mechanism that is compatible with any DRF-equipped system including, but not limited to, devices and systems described in relation to FIGS. 3A-3C, 10A-10G, 14A-14C, 15A-15C, 38, 38A-38G, 44A-57D, 91A-91C, 95A-990, 101A-103Q, 105A-105G, and 115A-115F, as well as processes described in relation to FIGS. 45A-45B, 58-88F, 91A-91C, 93A-105G, 107A-109D, 111A-113, and 114A-114F.

In some embodiments, FIG. 106A illustrates a perspective view of a triggering system 10600 in accordance with some embodiments of the invention. In some embodiments, the triggering system 10600 comprises a TMSM trigger mount 10601, and/or spring-loaded (not shown) TMSM sliding post 10602, and/or screw mount 10603 for substantially rigidly attaching the DRF to the device body, and/or DRF mounting surface 10604, and/or hole for dowel pin 10605 for restricting rotation of the DRF, and/or end cap shaft 10607, and/or sliding trigger body 10608, and/or dowel pin 10609, and/or pivoting trigger lock tab 10610, and/or static trigger tab 10611.

In some embodiments, the trigger system 10600 can contain a mounting surface to enable the selected tool DRF to be modular. In some embodiments, the DRF can be directly embedded within the trigger system 10600 main body. In some embodiments, the sliding trigger body 10608 can contain one or more cutouts to facilitate a reduction in friction with other interfacing components, such as the end cap shaft 10607. In some embodiments, FIGS. 106A-106C are non-limiting example embodiments of a triggering mechanism with locking functionality, and although the device body interfacing with the triggering mechanism is most related to the end cap tool used in assemblies related to a rod contour assessment system, such as those depicted in FIGS. 98A-98V, and 99A-990, this trigger mechanism is compatible with any DRF-equipped system, including, but not limited to, devices and systems described in relation to FIGS. 3A-3C, 10A-10G, 14A-14C, 15A-15C, 38A-38G, 44A-57D, 91A-91C, 95A-990, 101A-103Q, and 105G, as well as processes described in relation to FIGS. 45A-45B, 58-88F, 91A-91C, 93A-105G, 107A-109D, and 111A-113. In some embodiments, the spring-loaded (not shown) pivoting trigger lock tab 10610 can be substantially rigidly engaged with the end cap shaft 10607 upon triggering of the sliding trigger body 10608. In some embodiments, a similar trigger locking mechanism, or other alternatives, can be utilized for other TMSM triggering motions than the linear actuation depicted in FIG. 106A, such as rotational actuation, as seen in an example embodiment, such as FIG. 15. In some embodiments, the sliding trigger body 10608 can be designed to wrap around the entire end cap shaft 10607 in order to minimize unwanted rotation and wobble of the trigger body during or after triggering. In some embodiments, a TMSM can be attached to the TMSM trigger mount 10601 to enable the tracking of a marker with respect to the attached DRF for the tool.

In some embodiments, FIG. 106B illustrates a rear view of a triggering system 10615, similar to the system 10600 previously described in relation to FIG. 106A, in accordance with some embodiments of the invention. Some embodiments include a triggering system 10615 comprising a TMSM sliding post 10602, and/or end cap shaft 10607, and/or sliding trigger body 10608, and/or pivoting trigger lock tab 10610, and/or static trigger tab 10611, and/or trigger-retaining screw 10616, and/or a trigger motion-restricting slot 10617. In some embodiments, when the trigger-retaining screw 10616 is located at the top of the trigger motion-restricting slot 10617, the TMSM is defined to be in an inactive trigger state, as the sliding trigger body 10608 has not been actuated downward against its internal spring mechanism (not shown).

In some embodiments, FIG. 106C illustrates a top view 10625 of a triggering system 10640, similar to the systems previously described in relation to FIGS. 106A-106B, in accordance with some embodiments of the invention, showing an assembly comprising the end cap shaft 10607, and/or sliding trigger body 10608, and/or pivoting trigger lock tab 10610, and/or static trigger tab 10611. In some embodiments, the static trigger tab 10611 includes extensions on both sides of the sliding trigger body 10608 to facilitate compatibility with left or right-hand-dominant users.

In some embodiments, FIG. 106D illustrates a side cross-sectional view of a triggering system 10640 shown in view 10625 in a depressed (active) state, similar to the systems previously described in relation to FIGS. 106A-106C, in accordance with some embodiments of the invention. In some embodiments, the triggering system 10625 comprises the end cap shaft 10607, and/or TMSM mount 10626, and/or TMSM sliding post (depressed) 10627, and/or slider trigger body (depressed) 10628, and/or compression spring housing (spring not shown) 10629, and/or dowel pin 10630, and/or locking tab motion-restricting wall 10631, and/or pivoting trigger lock tab (locked) 10632, and/or locking extension 10633, and/or trigger lock receptacle 10634, and/or torsion spring 10635. In some embodiments, the pivoting trigger lock tab 10632 can be engaged into the trigger lock receptacle 10634 when the sliding trigger body is in a depressed state 10628, allowing the locking extension 10633 to be inserted into the receptacle 10634 by actuating against the internal torsion spring 10635 of the pivoting trigger lock tab 10632. In some embodiments, as the sliding trigger body 10608 is depressed via the triggering tabs (e.g., actuating the static trigger tab 10611, pivoting trigger lock tab 10632, etc.), the TMSM (not shown) can be engaged on the TMSM mount 10626, and can change its 3D-tracked location relative to the DRF (not shown), engaged on the DRF mounting surface 10604, and can be subsequently interpreted as a triggering event according to processes including, but not limited to, those described in relation to FIGS. 63, 113. In some embodiments, the locking feature of the trigger mechanism does not have to include a pivoting extension tab that mates with a receptacle. In some embodiments, the trigger mechanism can include, but not be limited to, a spring-loaded detent that is released when the sliding trigger body 10608 is depressed beyond the boundary of the receptacle, and/or a passive latch (either on the sliding trigger body or the end cap shaft) that mates with a receptacle on the opposing mating body (either the end cap shaft or the sliding trigger body, respectively), and that restricts the compression spring from decompressing and returning to its baseline state, etc.

In some embodiments, FIG. 106E illustrates a side cross-sectional view of a triggering system 10640 in an undepressed (inactive) state, similar to the systems previously described in relation to FIGS. 106A-106D, in accordance with some embodiments of the invention. In some embodiments, the triggering system 10640 can comprise an end cap shaft 10607, and/or TMSM mount 10626, and/or locking tab motion-restricting wall 10631, and/or trigger lock receptacle 10634, and/or torsion spring 10635, and/or TMSM sliding post (undepressed) 10641, and/or sliding trigger body (undepressed) 10642, and/or pivoting trigger lock tab (unlocked) 10643. In some embodiments, since the sliding trigger body 10608 is undepressed, the TMSM (not shown) engaged on the TMSM mount 10626 can remain at its baseline 3D-tracked location relative to the DRF (not shown), engaged on the DRF mounting surface 10604, and will subsequently be interpreted as a non-triggering inactive tool state according to processes including, but not limited to, those described in relation to FIGS. 63, 113.

In some embodiments, FIG. 106F illustrates a perspective exploded view of a triggering system 10650, similar to the systems previously described in relation to FIGS. 106A-106E, in accordance with some embodiments of the invention. Some embodiments include a triggering system 10650 comprising a pivoting trigger lock tab 10610, and/or static trigger tab 10611, and/or locking tab motion-restricting wall 10631, and/or torsion spring 10635, and/or hole for dowel pin 10651 of the pivoting trigger lock tab 10610, and/or dowel pin 10652, and/or hole for dowel pin 10653 of the locking tab motion-restricting wall 10631, and/or TMSM sliding post 10654, and/or end cap shaft 10655, and/or dovetail tracks 10656, and/or trigger lock receptacle 10657, and/or compression spring housing (spring not shown) 10658, and/or DRF mounting hole 10659, and/or hole for dowel pin 10660, and/or locking extension 10661.

In some embodiments of the invention, the torsion spring 10635 can be replaced with any other spring or tensioning system. In some embodiments, the sliding tracks example embodiment shown in the dovetail tracks 10656 of FIG. 106F can be replaced by some embodiments that mechanically or electromagnetically enables smooth and unrotated travel of the sliding trigger body 10608 over the end cap shaft 10607. In some embodiments, this then facilitates the compression of the spring (not shown) within the compression spring housing 10658 via the actuation of a dowel (not shown), or similar compressing object, substantially rigidly coupled to the TMSM sliding post 10654 of the sliding trigger body 10608.

Some embodiments of the invention include a display interface for a spinal alignment system and display monitor controller. In some embodiments, the system can receive input data from a tracing acquisition of the spine's contour using a 3D-tracked probe, with an example embodiment depicted previously in relation to FIG. 101. In some embodiments, the acquired tracing data obtained from this embodiment can then be used to automatically compute spinal alignment parameters and intervertebral angles as described previously in relation to FIGS. 66A-66B and 67. Some embodiments of this invention are related to devices and systems described in relation to FIGS. 101A-101Q, 100A-

100F, 91A-91C, 32, 23A-23C, and 2A-15C, as well as processes described in relation to FIGS. 113, 82A-86D, 58-69, and 24-28B.

In some embodiments, FIG. 107A illustrates a display interface 10700 that includes acquiring information regarding the contour of the spine via tracing over anatomical surfaces (e.g., laminae) using a 3D-tracked probe (e.g., example embodiment depicted previously in relation to FIG. 101). Some embodiments of this display interface 10700 include, but are not limited to, a spine drawing 10704, and/or vertebral level label 10705 annotations, and/or live plotting of the 3D-tracked probe's tip 10706 relative to the patient anatomical coordinate system, and/or a selectable button or icon that can be used to clear angle plots 10707, and/or a selectable button or icon that can be used to clear angles 10708, and/or a selectable button or icon that can be used to repeat tracing 10709, and/or a selectable button or icon that can be used to add tracing 10710, and/or a selectable button or icon that can be used to clear all tracings 10711, and/or a selectable button or icon that can be used to initialize trackpad 10712, and/or a live trackpad software display 10701 (active state), and/or live plotting of the 3D-tracked probe's tip on trackpad 10702, and/or a list of measured angles 10703. In some embodiments, the display interface 10700 can include the listbox 10703, and/or a status update box 10744. In some embodiments, the spine drawing 10704 can be replaced by or supplemented with embodiments that include, but are not limited to, patient images (e.g., X-ray, CT, MRI, O-arm, fluoroscopy, etc.), 3D renderings of the patient anatomy, drawings of the spinal alignment parameters, etc.

In some embodiments of the invention, the live trackpad software display 10701 can be interfaced using a 3D-tracked probe (e.g., example embodiment depicted previously in relation to FIG. 101) and processes described previously in relation to FIGS. 82A-85. In some embodiments, as the 3D-tracked probe is moved within the initialized trackpad volume, the live probe tip plot 10702 can be scaled in its movement amount and relative location according to scaling processes, such as those described previously in relation to FIGS. 82A-85, that map the position of the 3D-tracked probe tip with respect to the trackpad to the display monitor dimensions and pixel resolution, in which this input from the probe movement is converted into the mirrored live movement of the display's mouse cursor. In some embodiments, the location of the initialized trackpad, relative to the system communicating information to the display interface can remain either static or dynamically adjustable, according to where the relative system is located, where the trackpad may be re-initialized (e.g., initiated via the button to initialize the trackpad 10712), etc. In some embodiments, the trackpad software display 10701 can change colors, or provide another indicator when the 3D-tracked probe is located within the volume defined by the trackpad initialization processes, including, but are not limited to, those described in FIGS. 82A-85. In some embodiments, the listbox 10703 can include, but is not limited to, intervertebral angle and/or distance measurements, 3D or 2D-projected measurements, labels that include anatomical landmarks, labels that include tool positions, identities, and orientations, inter-tool distance and/or angle measurements, etc. In some embodiments, one or more of the the buttons or icons 10707, 10708, 10709, 10710, 10711, 10712 on the display interface 10700 can be actuated via user input (e.g., manual mouse clicks, tool-based cursors control as described previously in FIGS. 82A-85, etc.), and control the processes of the display interface outputs, including, but not limited to, the recorded tracing contours, respective measurements per tracing contour, the orthogonal vectors that represent the endplate angle trajectories, etc. In some embodiments, the live plotting of the 3D-tracked probe tip 10706 can actively update its position on the display interface 10700 relative to its relative location with respect to the patient's anatomical coordinate system, which can be initialized via processes that include, but are not limited to, those described previously in relation to FIGS. 61-63.

In some embodiments, FIG. 107B illustrates a display interface 10720 that consists of acquiring information regarding the contour of the spine via tracing over anatomical surfaces using a 3D-tracked probe (e.g., example embodiment depicted previously in relation to FIG. 101), in which this display interface embodiment is described previously in relation to FIG. 107A. Some embodiments of this display interface 10720 can include, but is not limited to, a live trackpad software display 10721 (inactive state), a listbox 10703 that includes the prior angular measurement 10722 and the current angular measurement 10723 between the selected anatomical landmarks (e.g., between T7-L2 and C7-T5, respectively), a spinal tracing contour 10724 (e.g., as acquired via a 3D-tracked probe), previously generated vertebral endplate line #1 10725 and line #2 10726, current generated vertebral endplate line #1 10727 and line #2 10728. In some embodiments, the live trackpad software display (inactive) 10721 is depicting (as shown) to be in an inactive state by way of the 3D-tracked probe not being located within the volume defined by the trackpad initialization processes that include, but are not limited to, those described in FIGS. 82A-85. In some embodiments, the depicted overlay of endplate lines (10725, 10726, 10727, 10728) involves, but is not limited to, calculating the orthogonal vector from the tracing contour at specific locations along the curve indicated by discrete points inputted by the triggering of the 3D-tracked probe at specific anatomical landmarks of interest (e.g., T7 and L2 vertebrae). In some embodiments, the identified vertebral level involved with the measurement is determined by locating the vertebral segment along the tracing contour with the closest location to the discrete point indicated by the triggering of the 3D-tracked probe. In some embodiments, the calculations illustrated in the listbox (10722, 10723) are intervertebral angles measured between vertebrae as inputted by orthogonal lines along the tracing contour, labelled at discrete vertebral levels by the triggering of a 3D-tracked probe, in which the orthogonal vectors represent the estimated relative angle of the vertebral endplate trajectory for the select vertebrae of interest. In some embodiments, prior measurements (e.g., endplate line #1 10725 and line #2 10726) are illustrated by colors, shapes, transparencies, line types, etc., that are different than those illustrated in the current measurements (e.g., endplate line #1 10727 and line #2 10728).

In some embodiments, FIG. 107C illustrates some embodiments of the display interface 10735 that consists of acquiring information regarding the contour of the spine via tracing over anatomical surfaces using a 3D-tracked probe (e.g., example embodiment depicted previously in relation to FIG. 101). Some embodiments of this display interface 10735 includes, but is not limited to, the prior spinal tracing contour 10724 (e.g., as acquired via a 3D-tracked probe) and the new repeat tracing overlaid 10736. In some embodiments, the overlay of multiple tracing contours illustrates the progression of the patient's contour over the course of a procedure and/or during a biomechanical assessment in which the spine is being manipulated. In some embodiments, the measurements depicted in the listbox (10722, 10723) can be color and/or pattern matching to that of the spinal contour overlay so that the user can interpret which measurements correspond with which spinal conformations. In some embodiments, there can be an association between the prior and current spinal contour tracings and/or measurements with the time and/or order in which they were acquired, so that the user, or system can best understand and interpret the progression of the procedure. In some embodiments, the measurements depicted in the listbox can be updated according to the most recent spinal contour tracings that are acquired as well as the respective angular and/or distance measurements that are made along the spine.

In some embodiments, FIG. 107D illustrates a display interface 10740 that consists of acquiring information regarding the contour of the spine via tracing over anatomical surfaces using a 3D-tracked probe (e.g., example embodiment depicted previously in relation to FIG. 101). Some embodiments of this display interface 10740 includes, but is not limited to, the prior spinal tracing contour 10724 (e.g., as acquired via a 3D-tracked probe), and/or the new repeat tracing overlaid 10736, and/or the current generated endplate line #1 10742 and line #2 10743 that are measured with respect to the repeat tracing contour 10736, and/or the measured angle 10741 from tracing #2 10736 listed within the listbox 10703, and/or a status update box 10744 that communicates to the user and/or system the current status of operations of the display interface system and/or its associated algorithms. In some embodiments, the overlay of the new orthogonal vectors represents the vertebral endplate trajectories according to discrete locations along the spinal contour tracing that were labelled by triggering of a 3D-tracked probe at those specific locations. In some embodiments, the orthogonal vectors (10742, 10743) along the contour of tracing #2 emanate from the contour of the associated tracing.

Some embodiments of the display interface 10740 include, but are not limited to, orthogonal vectors and other measurement indicators that are overlaid on multiple tracing contours that have been acquired, not just the most current tracing acquisition 10736. In some embodiments, the system update field 10744 indicates to the user and/or system that it is waiting for discrete point selections to be made on or near the most recent spinal contour tracing to provide inputs to the system with regards to the vertebrae that are desired for the measurement (e.g., intervertebral angle, distance, identities, etc.). In some embodiments, the system does not require any manual inputs from the user or system with regards to a vertebral level to make measurements, as the system can automatically segment vertebral levels, and other information regarding anatomical landmarks, and make a variety of measurements across the spine with all important spinal alignment parameters and/or biomechanical assessments of interest. Some embodiments of the invention include input from discrete and/or continuous tracings acquired of the skin outside of and the bone and tissue within the surgical site. In some embodiments, the system can also accept input from fiducial devices that are initialized to represent anatomical landmarks (e.g., vertebral body of C7) outside of the surgical site but beneath the surface of the skin and/or surgical drapes, for which processes to achieve this input have been previously described in relation to FIGS. 58-60.

Some embodiments of the invention involve a display interface that illustrates the live position of tool-engaged vertebrae while they are being manipulated (e.g., flexibility assessment). Some embodiments of the processes that generate this display interface system include, but is not limited to, the processes depicted below in reference to FIGS. 111A-111C. Some embodiments of the system that interfaces with the display monitor displaying the display interface includes, but is not limited to, one or more flexibility assessment tools (e.g., FIG. 95A) engaged, directly or indirectly, with vertebrae, and/or other anatomical landmarks, of interest. Some embodiments of this system actively manipulating engaged vertebrae are illustrated previously in relation to FIGS. 40A-40C, 960, etc. Some embodiments of this invention are related to devices and systems described in relation to FIGS. 34, 34A-37G, 39A-43F, 93A-93J, 95A-95I, 97A-97L, 105A-105G, and 106A-106F, as well as processes described in relation to FIGS. 63, 70, and 113.

In some embodiments, FIG. 108A displays the invention comprising a display interface 10800 that illustrates a 2D sagittal plane view 10809 of the projected shaft angle of flexibility assessment tool #1 10806 and tool #2 10808 (e.g., depicted in the form of line vectors). Some embodiments of the display interface 10800 include, but are not limited to, posterior 10801, and/or anterior 10802, and/or superior 10803, and/or inferior 10804 axis labels. Some embodiments of the system display 10800 include the screw-end of the flexibility assessment tool #1 10805 and tool #2 10807. Some embodiments of the invention enable the user to toggle between different anatomical planar views of the tracked devices via processes described below in reference to FIG. 111.

In some embodiments, FIG. 108B illustrates a sagittal plane display interface 10815 in which the flexibility assessment tools are in an active trigger state while engaged with vertebrae. Some embodiments of this display interface can include, but not be limited to, a series of lines representing the 2D projected endplate angles of flexibility assessment tool #1 10819 and tool #2 10821 during dual-triggered acquisition. In some embodiments, the line vectors representing the 2D sagittal projection endplate angles (10819, 10821) illustrate the relative displacement of orientation of the assessment tool handles. Some embodiments include depictions for the screw-end component of the flexibility assessment tool #1 10818 and tool #2 10820. In some embodiments, as the system calculates the intervertebral angles, including the maximum kyphotic angle 10816 and lordotic angle 10817.

In some embodiments, FIG. 108C illustrates a coronal plane 10835 display interface 10830 in which the flexibility assessment tools are in an active trigger state while engaged with vertebrae. Some embodiments of this display interface include, but are not limited to, a series of lines representing the 2D projected endplate angles of flexibility assessment tool #1 10840 and tool #2 10841 during dual-triggered acquisition. In some embodiments, the line vectors representing the 2D coronal projection endplate angles (10840, 10841) illustrate the relative displacement of orientation of the assessment tool handles. Some embodiments include depictions for the screw-end component of the flexibility assessment tool #1 10838 and tool #2 10839. In some embodiments, as the system calculates the intervertebral angles, including the maximum left Cobb angle 10836 and maximum right Cobb angle 10837. In some embodiments, the coronal display interface 10830 can include, but is not limited to, inferior 10832, superior 10831, left 10833, and right 10834 axis labels.

In some embodiments, FIG. 108D illustrates an axial plane 10850 display interface 10845 in which the flexibility assessment tools are in an active trigger state while engaged with vertebrae. Some embodiments of this display interface can include, but is not limited to, a series of lines representing the 2D projected endplate angles of flexibility assessment tool #1 10855 and tool #2 10856 during dual-triggered acquisition. In some embodiments, the line vectors representing the 2D axial projection endplate angles (10855, 10856) illustrate the relative displacement of orientation of the assessment tool handles. Some embodiments include depictions for the screw-end component of the flexibility assessment tool #1 10853 and tool #2 10854. In some embodiments, as the system calculates the intervertebral angles, including the maximum clockwise angle 10851 and maximum counterclockwise angle 10852. In some embodiments, the axial display interface 10845 can include, but is not limited to, anterior 10847, posterior 10846, right 10848, and left 10849 axis labels.

In some embodiments, FIG. 108E illustrates a sagittal plane display interface 10845 in which the flexibility assessment tools are engaged with vertebrae. Some embodiments of this display interface can include, but not be limited to, rendered vertebrae (10862, 10863) that represent the engaged vertebrae attached to and manipulated by flexibility assessment tool #1 and tool #2. In some embodiments, as the system displays the live relative position of engaged vertebrae, it also calculates and/or displays the current sagittal angle between the vertebral endplates 10861 of engaged anatomy.

In some embodiments, FIG. 108F illustrates a sagittal plane display interface 10865 in which the flexibility assessment tools are in an active trigger state while engaged with vertebrae during an assessment of sagittal plane flexibility 10866. Some embodiments of this display interface can include, but are not limited to, rendered vertebrae (superior 10870, 10874 and inferior 10872, 10876) that represent the engaged vertebrae attached to and manipulated by flexibility assessment tool #1 and tool #2. In some embodiments, while both flexibility assessment devices are in an active trigger state, the system can display the live relative position of engaged vertebrae and calculate the live and range of intervertebral angles. In some embodiments, the system can compute and display a series of range of motion results including, but not limited to, the superior vertebra's endplate angle relative to vertical at time of maximum kyphosis 10869, and/or the inferior vertebra's endplate angle relative to vertical at time of maximum kyphosis 10871, and/or the superior vertebra's endplate angle relative to vertical at time of maximum lordosis 10873, and/or the inferior vertebra's endplate angle relative to vertical at time of maximum lordosis 10875. In some embodiments, the system can also compute and displays the maximum lordosis intervertebral angle 10868 achieved during acquisition, as well as the maximum kyphosis intervertebral angle 10867 achieved during acquisition. In some embodiments (not shown), the system can calculate and display the estimated position of adjacent vertebrae that may be between or on the outside of the engaged vertebrae. In some embodiments (not shown), the system can compute and display live renderings and calculations for several simultaneously engaged vertebrae.

In some embodiments, FIG. 108G displays the invention consisting of an axial plane display interface 10878 in which the flexibility assessment tools are in an active trigger state while engaged with vertebrae during an assessment of axial plane flexibility 10879. Some embodiments of this display interface can include, but not be limited to, rendered vertebrae (superior 10883, 10887 and inferior 10884, 10888) that represent the engaged vertebrae attached to and manipulated by flexibility assessment tool #1 and tool #2. In some embodiments, while both flexibility assessment devices are in an active trigger state, the system can display the live relative position of engaged vertebrae, and calculate the range of intervertebral angles. In some embodiments, the system can compute and displays a series of range of motion results including, but not limited to, the superior vertebra's endplate angle relative to vertical at time of maximum clockwise twist 10882, the inferior vertebra's endplate angle relative to vertical at time of maximum clockwise twist 10885, the superior vertebra's endplate angle relative to vertical at time of maximum counterclockwise twist 10886, and/or the inferior vertebra's endplate angle relative to vertical at time of maximum counterclockwise twist 10889. In some embodiments, the system can also compute and display the maximum clockwise twist angle 10880 achieved during acquisition, as well as the maximum counterclockwise twist angle 10881 achieved during acquisition. In some embodiments (not shown), the system can calculate and display the estimated position of adjacent vertebrae that may be between or on the outside of the engaged vertebrae. In some embodiments (not shown), the system can compute and display live renderings and calculations for several simultaneously engaged vertebrae.

In some embodiments, FIG. 108H illustrates a coronal plane display interface 10890 in which the flexibility assessment tools are in an active trigger state while engaged with vertebrae during an assessment of coronal plane flexibility 10891. Some embodiments of this display interface include, but are not limited to, rendered vertebrae (superior 10895*a*, 10895*b* and inferior 10895*c*, 10895*d*) that represent the engaged vertebrae attached to and manipulated by flexibility assessment tool #1 and tool #2. In some embodiments, while both flexibility assessment devices are in an active trigger state, the system can display the live relative position of engaged vertebrae and calculates the live and range of intervertebral angles. In some embodiments, the system can compute and display a series of range of motion results including, but not limited to, the superior vertebra's endplate angle relative to horizontal at time of maximum right cobb angle 10894, and/or the inferior vertebra's endplate angle relative to horizontal at time of maximum right cobb angle 10896, and/or the superior vertebra's endplate angle relative to horizontal at time of maximum left cobb angle 10897, and/or the inferior vertebra's endplate angle relative to horizontal at time of maximum left cobb angle 10898. In some embodiments, the system can also compute and display the maximum left cobb angle 10893 achieved during acquisition, as well as the maximum right cobb angle 10892 achieved during acquisition. In some embodiments (not shown), the system can calculate and display the estimated position of adjacent vertebrae that may be between or on the outside of the engaged vertebrae. In some embodiments (not shown), the system can compute and display live renderings and calculations for several simultaneously engaged vertebrae.

Some embodiments of this invention involve a display interface that illustrates the registration of a rod contour and the overlay and manipulation of this contour on patient images. Some embodiments of the processes that generate this display interface embodiment include, but are not limited to, the processes depicted below in reference to FIGS. 112A-112C. Some embodiments of the devices that interface with the display monitor include, but are not limited to, a rod contour registration tool (e.g., FIG. 98A) and a rod-engaged registration reference device (e.g., FIG. 98J), with an example embodiment of their combined utilization depicted previously in relation to FIG. 98S. Some embodiments of the rod registration tool that communicate with the display interface include, but are not limited to, a rod bender tool that can also registration the contour of a rod (e.g., example embodiment depicted previously in relation to FIG. 99M). Some embodiments of this invention are related to devices and systems described in relation to FIGS. 47A-53F, 98A-98V, 99A-99O, and 115A-115F, as well as processes described in relation to FIGS. 63, 73A-78, 113, and 114A-114F.

In some embodiments, FIG. 109A illustrates a display interface 10900 that illustrates the 3D camera view 10906 and 2D projection views (i.e., coronal 10921 and sagittal 10908) of registered rod coordinates and the tools used to register its rod contour. Some embodiments of the 3D camera view 10906 include axes labels for the left 10917 and right 10916 sides of the camera view, the depth axis 10903 away or towards the camera, and the up 10901 or down 10902 directions relative to the camera, as well as the displayed locations of the end cap and slider tool coordinates 10907 relative to the tracking camera coordinate system. Some embodiments of the invention include 2D projection views of the registered rod contour with respect to the registration reference device's coordinate system, with an example embodiment of the tool's sagittal 10915 and coronal 10922 orientation reference depicted for visual reference. Some embodiments include a 2D sagittal projection view 10908 with anterior 10911 and posterior 10910 axis labels, superior 10912 and inferior 10913 axis labels, an example embodiment of the end cap registration reference device from a sagittal perspective 10915, and a live location of the 2D sagittal projection of the rod-engaging region of the slider tool 10914 with respect to the coordinate system of the end cap registration reference device. Some embodiments include a 2D coronal projection view 10921 with left 10917 and right 10916 axis labels, superior 10918 and inferior 10919 axis labels, an example embodiment of the end cap registration reference device from a coronal perspective 10922, and a live location of the 2D coronal projection of the rod-engaging region of the slider tool 10920 with respect to the coordinate system of the end cap registration reference device.

In some embodiments, FIG. 109B illustrates a display interface 10930 that illustrates the 3D camera view 10936 and 2D projection views (i.e., coronal 10938 and sagittal 10947) of registered rod coordinates and the tools used to register its rod contour. Some embodiments of the 3D camera view 10936 include axes labels for the left 10934 and right 10935 sides of the camera view, the depth axis 10933 away or towards the camera, and the up 10931 or down 10932 directions relative to the camera, as well as the displayed locations of the end cap, slider tool, and registered rod 3D coordinates 10937 relative to the tracking camera coordinate system. Some embodiments of the invention include 2D projection views of the registered rod contour with respect to the registration reference device's coordinate system, with an example embodiment of the tool's sagittal 10915 and coronal 10922 orientation reference depicted for visual reference. Some embodiments include a 2D sagittal projection view 10938 with anterior 10940 and posterior 10939 axis labels, superior 10941 and inferior 10942 axis labels, an example embodiment of the end cap registration reference device from a sagittal perspective 10915, a live location of the 2D sagittal projection of the rod-engaging region of the slider tool 10943 with respect to the coordinate system of the end cap registration reference device, the registered rod coordinates projected onto the sagittal plane 10945, the end point of the registered rod sagittal coordinates closest to the end cap 10946, and the end point of the registered rod sagittal coordinates farthest from the end cap

10944. Some embodiments include a 2D coronal projection view 10947 with left 10949 and right 10948 axis labels, superior 10950 and inferior 10951 axis labels, an example embodiment of the end cap registration reference device from a coronal perspective 10922, a live location of the 2D coronal projection of the rod-engaging region of the slider tool 10952 with respect to the coordinate system of the end cap registration reference device, the registered rod coordinates projected onto the coronal plane 10954, the end point of the registered rod coronal coordinates closest to the end cap 10955, and the end point of the registered rod coronal coordinates farthest from the end cap 10953.

In some embodiments, FIG. 109C illustrates a display interface 10960 that depicts the 2D views of selected patient images. Some embodiments of the system include a sagittal patient image 10961 oriented for holding the end cap in the user's right hand, as well as a coronal patient image 10962 oriented for holding the end cap in the user's right hand. In some embodiments, illustrations of the end cap registration reference device are adjacent to the patient image, including from its sagittal 10963 and coronal 10964 perspectives.

In some embodiments, FIG. 109D illustrates a display interface 10970 that depicts the 2D views of selected patient images. Some embodiments of the system include a sagittal patient image 10971 oriented for holding the end cap in the user's right hand, as well as a coronal patient image 10972 oriented for holding the end cap in the user's right hand. In some embodiments, illustrations of the end cap registration reference device are adjacent to the patient image, including from its sagittal 10963 and coronal 10964 perspectives. In some embodiments, the registered rod sagittal projection coordinates 10974 are overlaid on the sagittal image 10971 and the registered rod coronal projection coordinates 10977 are overlaid on the coronal image 10972. Some embodiments include the sagittal projection of the rod contour end point farthest from the end cap 10975, as well as a sagittal projection of the rod contour end point closest to the end cap 10973 (rotation point), overlaid on the sagittal patient image 10971. Some embodiments include the coronal projection of the rod contour end point farthest from the end cap 10976, as well as a coronal projection of the rod contour end point closest to the end cap 10978 (rotation point), overlaid on the coronal patient image 10972.

Some embodiments, involve multiple registered rod contours overlaid onto the patient images, enabling the user to view the progression of adjustments made to the contour of a rod (e.g., via rod contouring with a french bender, robotic bender, etc.). In some embodiments, the user can manipulate the relative translation and rotation of this registered rod contour overlay via processes including, but not limited to, those described below in reference to FIG. 112.

Some embodiments of this invention involve analyzing and annotating a patient's medical images (e.g., X-ray, CT, MRI, etc.) in order to output instructions enabling a user to position an adjustable spinal and pelvic anatomical phantom model to represent a scaled matching contour. In some embodiments, FIGS. 110A-110B illustrate a workflow for adjusting the positions of vertebral holders for an adjustable model holder with inputs from patient imaging in accordance with some embodiments of the invention. In some embodiments, the workflow 11001 includes steps or processes that can be used to analyze patient images and generate instructions for how to adjust the conformation of an adjustable phantom spine model to match that of the patient in the images. Some embodiments of the adjustable spine holder system can be depicted in, but are not limited to, FIGS. 90A-90C and 92A-92AD with processes also contained in FIG. 89.

Some embodiments involve scaling adjustments made to analyze a contour of the anatomy in the patient's images. In some embodiments, the processes can operate in reverse order, in which the user uses the workflow 11001 to register the conformation of anatomy of a phantom spine model, and then the system to output a patient image embodiment. Some embodiments of the selected patient image can include, but are not limited to, a virtual rendering or a best-match image selection from a library of patient images that represent the spectrum of spinal contours. In some embodiments, the system-selected patient image can represent the best match for the conformation and/or spinal alignment parameters of the registered phantom spine model.

In some embodiments, any of the above processes, methods, or procedures related to the workflow 11001 can include or be accomplished with one or more of steps or processes such as 11000, 11002, 11004, 11006, 11008, 11010, 11012, 11014, 11016, 11018, 11020, 11022, 11024, 11026, 11028, 11030, 11032, 11034, 11036, 11038, 11040, 11042, 11044, 11046, 11048, 11050, 11052, 11054, 11056, 11058, 11060, 11062, 11064, and 11066. In some embodiments, at least one of the steps can include a decision step, where one or more following steps depend on a status, decision, state, or other condition. In some embodiments, the steps of workflow 11001 can proceed in the order as shown. In some embodiments, any of the steps of the workflow 11001 can proceed out of the order as shown. In some embodiments, one or more of the steps of the workflow 11001 can be skipped.

In some embodiments, FIGS. 111A-111C illustrate a workflow 11101 for analyzing and outputting the range of motion results of engaged vertebrae during and after a flexibility assessment in accordance with some embodiments of the invention. Some embodiments of this invention involve the process of displaying the relative alignment and calculated angles of the vertebrae. In some embodiments, the workflow 11101 can be used to display 3D and/or 2D views of engaged vertebrae that actively update their displayed positions while the vertebrae are manipulated. In some embodiments, the workflow 11101 describes methods for visualizing the live manipulation of substantially rigidly-engaged vertebrae and calculating their relative 3D and 2D alignments. Some embodiments of the flexibility assessment device can be depicted in, but are not limited to, FIG. 96A. In some embodiments, relevant figures include example embodiments of devices and systems in FIGS. 34, 34A-37G, 39A-42K, 93A-97L, and 105A-105G and embodiments of processes in FIGS. 63, 70, 79A-79G, 108A-108H, and 113.

Some embodiments involve displaying a live view of rendered vertebrae in one or more of the three anatomical planar views, and then, once both vertebra-engaged devices are triggered, the system can calculate the range of motion and live intervertebral angles between the engaged vertebrae experience during a flexibility assessment. Some embodiments of the available display outputs include, but are not limited to, a live view of rendered tool-engaged vertebrae in all three anatomical planar views at once, and/or a live view of rendered tool-engaged vertebrae in one of three anatomical planar views (e.g., FIGS. 108F-108H), and/or a live view of line vectors representing each tool-engaged vertebra's endplate in one or more of the three anatomical planar views (e.g., FIG. 108A), and/or a live view of line vectors representing each tool-engaged vertebra's endplate in one or more of the three anatomical planar views for the duration of a flexibility assessment (e.g., FIGS. 108B-108D), and/or a live view of rendered tool-engaged vertebrae with overlaid line vectors along the individual endplates in one or more of the three anatomical planar views at once, a live view of concentric circles with radial line vectors extending from each circle that represent the relative endplate angle between the engaged vertebrae in one or more of the three anatomical planar views at once, and a live view of rendered vertebrae and/or line vectors that are displayed over a background reference of rendered vertebrae and/or line vectors from the prior range of motion assessment (if available), etc.

Some embodiments for the system involve calibrating the angle of the device handle relative to its screw-interfacing sleeves, and/or the device's relative position to the engaged vertebrae. In some embodiments, the system can automatically calculate the relative orientation of the handle to the screw interface bodies via measuring the displacement orientation of the handle while the screw interface bodies remain substantially rigidly fixed, and the preset orientation of the handle is known prior to beginning the calibration. In some embodiments, the system can calculate the relative orientation between the assessment device's handle and its screw interface bodies via tracked markers that indicate the position and orientation of the screw interface bodies relative to those of the handles. In some embodiments, the system can receive user inputs regarding the angle of the device handle relative to its screw interface bodies (e.g., tick marks on the angular-adjustment base component).

Some embodiments involve the initialization of the relative angle between the endplates of the engaged vertebrae and the device's screw interface bodies. In some embodiments, if the pedicle screws were instrumented via navigation guidance, the system can automatically compute the angle between the endplates of the engaged vertebrae and the device's handle, which has a mounted DRF.

Some embodiment of the methods for assessing the range of motion and relative alignment of the engaged vertebrae include, but are not limited to, manipulating the spine manually while the vertebrae-engaged assessment devices remain in a triggered state, manipulating the spine directly via the movement of the vertebrae-engaged assessment devices while they are in a triggered state, and manipulating the spine via the insertion of implants (e.g., interbody cages, inserts, rods, screws, etc.) while the vertebrae-engaged devices remain in a triggered state, etc.

In some embodiments, once the trigger state of both devices returns to an inactive state, some embodiments involve the completion of the live alignment feedback and a displayed output of a summary view of the range of motion, along with quantitative relative intervertebral angles, experienced by each engaged vertebra in one or more anatomical planes of interest for the duration of the flexibility assessment. In some embodiments, the user can adjust the selected view of the live and/or summary measurement outputs via user input (e.g., FIGS. 82-85) or device trigger activity (e.g., double-click to switch views, single-click to begin live view, click-and-hold of both devices simultaneously to initiate flexibility measurements of intervertebral range of motion, etc.).

In some embodiments, any of the above processes, methods, or procedures related to the workflow 11101 of FIGS. 111A-111C can include or be accomplished with one or more of steps or processes such as 11100, 11102, 11104, 11106, 11108, 11110, 11112, 11114, 11116, 11118, 11120, 11122, 11124, 11126, 11128, 11130, 11132, 11134, 11136, 11138, 11140, 11142, 11144, 11146, 11148, 11150, 11152, 11154, 11156, 11158, 11160, 11162, 11164, and 11166. In some embodiments, at least one of the steps can include a decision step (e.g., such as step 11110), where one or more following steps depend on a status, decision, state, or other condition. In some embodiments, the steps of workflow 11101 can proceed in the order as shown. In some embodiments, any of the steps of the workflow 11101 can proceed out of the order as shown. In some embodiments, one or more of the steps of the workflow 11101 can be skipped.

Some embodiments of this invention involve the process of registering the contour of a rod implant, overlaying the registered contour on patient images, and updating the overlay with newly modified rod contours. In some embodiments, FIGS. 112A-112C illustrate a workflow 11201 for registering and overlaying the contour of a rod and subsequent contours of adjusted rods in accordance with some embodiments of the invention. In some embodiments, the workflow 11201 can include displaying 3D and 2D projection views of a registered rod contour on patient images and then adjusting their displayed position on the images via various available user inputs. In some embodiments, the workflow 11201 describes methods for applying a transformation to 2D projections of a registered rod contour that is overlaid onto patient images. Some embodiments for applying this rigid body transformation include a two-point snap method in which the user inputs two points on the image for the registered rod contour to intersect with, one at the proximal end of the rod and the other along its contour. Some embodiments for this transformation process include using the 3D-tracked end cap tool (e.g., FIGS. 98L-98N) to mirror the relative translation and rotation of the registered rod in the end cap tool onto the patient image (e.g., FIGS. 109C-109D). In some embodiments, relevant figures include example embodiments of devices and systems in FIGS. 47A-56F, 98A-98V, 99A-990, 106A-106F, and 115A-115F, and embodiments of processes in FIGS. 45A-45B, 58-60, 63, 64A-64B, 70, 72-78, 87A-87K, 109A-109D, 113, and 114A-114F.

Some embodiments of the system involve a continuous process of adjusting the contour of the rod implant (e.g., contouring the rod with a french rod bender, robotic system, etc.), registering the new contour of the adjusted rod, and then overlaying the new contour on the patient image over the prior rod contour overlays, and repeating until the desired rod contour has been achieved for the patient. Some embodiments involve a separate device for rod contouring (e.g., FIG. 55A) and contour registration (e.g., FIG. 98A), and some embodiments use one device for both processes (e.g., FIGS. 98E, 98K, and 98N). Some embodiments of the rod registration tool involve a mounting interface that enables the DRF to be mounted onto the tool forward and backward, and thus enable it to be utilized by the left or right hand of the user. In some embodiments, the system can automatically detect which side the TMSM is located on the tool relative to the location of the front face of the mounted DRF for the rod registration tool. Some embodiments involve user inputs to identify which hand is holding the rod registration tool. Some embodiments of the hand-identification process involve automatically orienting the patient images to optimize the processes for rod contour registration and live overlays relative to the display monitor and 3D-tracking camera system. Some embodiments for the input of patient images for overlays of the rod contour to be displayed upon include, but are not limited to, pre-operative standing X-ray films, flexion and extension films, CT or MRI slice images, 3D volume reconstructions of the patient, surgical-plan-adjusted X-ray images, intraoperative O-arm scans, fluoroscopy, ultrasound, cone-beam CT imaging, etc.

In some embodiments, FIGS. 112A-112C and any of the above processes, methods, or procedures related to the workflow 11201 can include or be accomplished with one or more of steps or processes such as 11200, 11202, 11204, 11206, 11208, 11210, 11212, 11214, 11216, 11218, 11220, 11222, 11224, 11226, 11228, 11230, 11232, 11234, 11236, 11238, 11240, 11242, 11244, 11246, 11248, 11250, 11252, 11254, 11256, 11258, 11260, 11262, 11264, 11266, 11268, 11270, 11272, 11274. In some embodiments, further steps can include 11276, 11278, 11280, 11282, 11284, and 11286. In some embodiments, at least one of the steps can include a decision step (e.g., such as step 11202), where one or more following steps depend on a status, decision, state, or other condition. In some embodiments, the steps of workflow 11201 can proceed in the order as shown. In some embodiments, any of the steps of the workflow 11201 can proceed out of the order as shown. In some embodiments, one or more of the steps of the workflow 11201 can be skipped.

Some embodiments of this invention involve the process of filtering the 3D-tracking camera's output of all visible stray markers and classifying select ones as TMSMs, TSMs, that are associated with particular DRF-equipped tools. In some embodiments, FIG. 113 shows a workflow 11301 that can be utilized to filter out undesired stray and phantom markers, classify detected TMSMs with their associated DRF-equipped tools, and then determine if each TMSM-equipped tool is in an active state. In some embodiments, the workflow 11301 describes methods for utilizing the known travel path of a TMSM for a specific tool to filter out visible stray and phantom markers, and then adding a secondary filtering layer by setting a threshold for consecutive frame counts of the TMSM being in a triggered state to mitigate the likelihood of errant marker classification leading to a false, active triggering event for a tool. In some embodiments, relevant figures include example embodiments of devices and systems in FIGS. 3A-3C, 4A-4I, 10A-10G, 14A-14C, 15A-15C, 29A-29D, 33A-33H, 38, 38A-42K, 44A-57D, 91A-91C, 95A-106F, and 115A-115F, and embodiments of processes in FIGS. 58-88F, 107A-112C, and 114A-114F.

Some embodiments of the system involve the use of location thresholds of stray markers transformed onto a DRF-equipped tool's coordinate system in that the stray marker must be located within a specified tolerance of a tool's known TMSM travel path. Some embodiments of the process for identifying the triggering state of a TMSM of a DRF-equipped tool involve calculating how far along the TMSM is located within the full, known range of the TMSM's possible travel path, and then assessing if this relative location is beyond a preset threshold (e.g., 70% of the full travel path) by the system. In some embodiments, the user is enabled to adjust this preset triggering threshold as a means to adjust the sensitivity of a tool's triggering mechanism, in which tuning the triggering threshold to be more sensitive results in the location threshold being a distance closer to the baseline location of the TMSM. Some embodiments of the system depicted in workflow 11301 involve the filtering and classification of TMSMs, and associated trigger-state thresholding, of several DRF-equipped tools simultaneously (e.g., FIGS. 98S, 95G, etc.) for all acquisition frames of a 3D-tracking camera system that has stored the tool definition files for these tools.

Some embodiments involve TMSMs that exhibit a linear actuation (e.g., FIGS. 101A-101Q) and have restricted motion to one axis of the 3D travel path relative to the associated tool's coordinated system. Some embodiments involve TMSMs that exhibit a rotational actuation (e.g., FIGS. 15A-15C, 101A-101Q). In some embodiments, a similar filtering process depicted in workflow 11301 can be utilized for both single and multi-faced tools in some embodiments.

In some embodiments, any of the above systems, assemblies, processes, methods, or procedures related to the workflow 11301 can include or be accomplished with one or more of steps or processes such as 11300, 11302, 11304, 11306, 11308, 11310, 11312, 11314, 11316, 11318, 11320, 11322, 11324, and 11326. In some embodiments, at least one of the steps can include a decision step (e.g., such as step 11314), where one or more following steps depend on a status, decision, state, or other condition. In some embodiments, the steps of workflow 11301 can proceed in the order as shown. In some embodiments, any of the steps of the workflow 11301 can proceed out of the order as shown. In some embodiments, one or more of the steps of the workflow 11301 can be skipped.

Some embodiments of this invention involve the process of continuously adjusting the contour of a rod (e.g., contouring the rod with a french rod bender, robotic system, etc.) and registering the contour of the adjusted rod. In some embodiments, FIGS. 114A-114F shows a workflow 11401 that can be used to detect when a rod has been bent and modify the previously registered rod contour to match the new rod contour. In some embodiments, relevant figures include example embodiments of devices and systems in FIGS. 47A-57D, 98A-990, 106A-106F, and 115A-115F and embodiments of processes in FIGS. 63, 73A-81, 87A-88K, 109A-109D, 112A-112C, and 113.

Some embodiments of this system involve registering a rod contour with a rod registration tool (e.g., FIGS. 47A-57D, 63, 73A-81, 87A-88F, 98A-990, 106A-106F, 109A-109D, 112A-112C, 113, etc.). Some embodiments involve using a 3D-tracked rod bender that can localize the three rod-interface components of the bender, which include the left and right-side rollers and the center rod-contouring surface (e.g., FIGS. 115A-115F). Some embodiments for accurately representing the rod prior to bending include calculating the rod's outer diameter projections onto the current plane of the rod bender's rod-interface components (e.g., FIG. 115A). In some embodiments, this includes an outer surface that comes in contact with the bender's left and right rollers and an inner surface that comes in contact with the bender's rod-contouring surface (e.g., FIG. 115A).

Some embodiments for detecting when a rod is just about to be contoured involve having a spring-loaded (not shown) TMSM that actuates when all three rod-interface components are in contact with a rod. Some embodiments include a mechanism to detect electrical conductivity when all three rod-interface components are in contact with a rod (e.g., FIG. 54). In some embodiments, this step may be bypassed by detecting only when the rod has been contoured or is actively being contoured. Some embodiments for detecting rod bending include assessing whether any of the rod's outer surface coordinates are intersecting the 2D-enclosed areas occupied by the left and right rollers (e.g., FIG. 115B). Some embodiments may include attaching a TMSM to the end of the rod and detecting the relative motion of the TMSM with the end cap device (e.g., FIG. 56). In some embodiments, once rod contouring has been detected, some embodiments for modifying the rod contour include dividing the rod contour into "left unbent", "right unbent", and "bent" segments with each segment having their outer and inner segments (e.g., FIG. 115C). Some embodiments for this include applying a transformation (rotation and translation) to both left and right (or either left or right) unbent rod segments until they are both tangential with their respective rollers (e.g., FIG. 115C). Some embodiments involve reconstructing the outer bent rod segment using the contour of the inner bent rod segment (e.g., FIG. 115D). Some embodiments involve filling in gaps in the newly constructed rod's outer surface coordinates to account for metallurgic stretching of the rod material when the rod is bent (e.g., FIGS. 115E, 115F, etc.). Some embodiments involve removing overlaps in the newly constructed rod's inner surface coordinates to account for metallurgic shrinking of the rod material when the rod is bent (e.g., FIGS. 115E, 115F, etc.). Some embodiments for reconstructing the final rod contour may involve accounting for shape memory of the rod material which causes the rod to spring back slightly towards its previous contour when released from the bender (e.g., FIG. 56).

In some embodiments, FIGS. 114A-114F and any of the above processes, methods, or procedures related to the workflow 11401 can include or be accomplished with one or more of steps or processes such as 11400, 11402, 11404, 11406, 11408, 11410, 11412, 11414, 11416, 11418, 11420, 11422, 11424, 11426, 11428, 11430, 11432, 11434, 11436, 11438, 11440, 11442, 11444, 11446, 11448, 11450, 11452, 11454, 11456, 11458, 11460, 11462, 11464, 11466, 11468, 11470, 11472, 11474, 11476, 11478, 11480, 11482, 11484, 11486, 11488, 11490, 11492, 11494, 11496, 11498, 11403, 11405, 11407, 11409, 11411, 11413, 11415, 11417, 11419, 11421, 11423, 11425, 11427, 11429, 11431, 11433, 11435, 11437, 11439, 11441, 11443, 11445, 11447, 11449, and 11451. In some embodiments, at least one of the steps can include a decision step (e.g., such as step 11448), where one or more following steps depend on a status, decision, state, or other condition. In some embodiments, the steps of workflow 11401 can proceed in the order as shown. In some embodiments, any of the steps of the workflow 11401 can proceed out of the order as shown. In some embodiments, one or more of the steps of the workflow 11401 can be skipped.

Some embodiments of the invention include the ability to equip a rod bender with tracked markers, such that the 3D coordinates of its rod-interface components can be tracked in space. In some embodiments, when coupling this embodiment with the embodiments to assess the contour of the rod prior to implantation, as previously described in relation to FIGS. 47A-56F, 63, 73A-75, 78-80, 98A-98V, 99A-990, 106A-106F, 109A-109D, and 112A-114F, the acquisition system can interpret when the tracked bender is adjusting the contour of the rod and can reconstruct a rendering of the rod's contour to generate real-time feedback during contouring of the rod.

In some embodiments, FIG. 115A illustrates a display 11500 of the software containing the rod bender's three rod-interface components consisting of the center rod-contouring surface 11508, left roller 11503, and right roller 11504. In some embodiments, the outer roller's path of travel 11512 is displayed as a circle surrounding the centroid 11509 of the center rod-contouring surface. In some embodiments, the center of the left roller 11502 and center of the right roller 11505 are located along this path of travel. In some embodiments of the invention, the raw data points of a previously registered rod 11506 can be used to generate a filtered curve 11511 to represent the center curve of the rod, from which the rod's outer surface 11507 and inner surface 11510 are computed based on the known cross-sectional diameter of the rod, and projected onto the plane defined by the rod bender's three rod-interface components, as described previously in relation to FIGS. 114A-114F. In some embodiments, this illustration provides an example embodiment of a rod that is not currently being bent, as it is only in contact with the bender's center rod-contouring surface and not in contact with either of the rollers.

In some embodiments, FIG. 115B illustrates a display 11515 representing the software calculations as previously described in relation to FIGS. 114A-114F. In some embodiments, the coordinates of the left roller 11521 and right roller 11523 are shown intersecting with the rod's outer segment 11507 and center curve 11511. In some embodiments, the left roller 11521, right roller 11523, and center rod-contouring surface 11508 are each segmented by vertical lines as the algorithms utilize these infinitesimally small divisions of each component to assess if the coordinates of the previously-registered rod 11507, 11511, 11510 are intersecting with any of these components, as is the case when the rod is being bent. In some embodiments, a region of the rod 11519 is intersecting with the area of the left roller 11521, as well as another area 11520 that is intersecting with the right roller 11523. In some embodiments, this intersection is detected via the software's analysis of each vertical line, as previously described in relation to FIGS. 114A-114F. In some embodiments, the right roller contains some vertical lines 11517 that are intersecting with the rod's surface and others 11522 that are not. In some embodiments, the left roller 11521 contains vertical lines 11519 that are intersecting with the registered rod's coordinates, and other vertical lines 11516 that are not intersecting with the rod's coordinates. In some embodiments, the area of the center rod contouring surface 11508 is also segmented with multiple vertical lines 11526, one of which is tangential to the rods inner surface 11510.

In some embodiments, FIG. 115C displays the partially reconstructed rod to accommodate the geometry of the rod bender previously described in relation to FIG. 115B. Some embodiments of the invention display the center vertical line 11532 that is coincident with the centroid 11509 of the bender's rod-contouring surface, in addition to the left rotated line 11531 and right rotated line 11533 that can be used to incrementally assess how much the rod is being bent based on the current geometry of the rod bender, as previously described in relation to FIGS. 114A-114F. Some embodiments of this illustration display the left unbent rod segment, consisting of the left outer unbent rod segment 11539, left center unbent rod segment 11540, and left inner unbent rod segment 11541 in addition to the right unbent rod segment consisting of the outer right unbent rod segment 11536, right center unbent rod segment 11537, and inner right unbent rod segment 11538. In some embodiments, these unbent segments have been rotated by the angle that enables them to no longer intersect with any of the bender's rod-interface components, but rather be tangential to each as is visualized by the left roller's perimeter 11521 being tangential with the outer left unbent rod segment and the right roller's perimeter 11523 being tangential with the outer right unbent rod segment 11536. In some embodiments, the reconstructed inner left bent rod segment 11542 and reconstructed inner right bent rod segment 11543 are defined by the curve of the center rod-contouring surface in between the intersection of its perimeter 11508 and the left 11531 and right 11533 rotated lines. In some embodiments, the left and right inner bent rod segments 11542, 11543 are then utilized to compute the left outer bent rod segment 11534 and right outer bent rod segment 11535.

In some embodiments, FIG. 115D displays a zoomed-in view 11550 of an embodiment portrayed in FIG. 115C containing the center vertical line 11532, left rotated line 11531, right rotated line 11533, perimeter of center rod-contouring surface 11508 (shown here as circle but does not need to be circular for algorithm to function properly), reconstructed outer left bent rod segment 11534, reconstructed outer right bent rod segment 11535, reconstructed inner left bent rod segment 11542, reconstructed inner right bent rod segment 11543, the left unbent rod segments consisting of the left outer unbent rod segment 11539, left center unbent rod segment 11540, and left inner unbent rod segment 11541, as well as the right unbent rod segments consisting of the right outer unbent rod segment 11536, right center unbent rod segment 11537, and right inner unbent rod segment. In some embodiments, the outer surface of the bender's center rod-contouring surface 11508 is visualized, along with its segmenting vertical lines 11553. In some embodiments, the closer view allows for a more detailed perspective of the reconstructed inner left bent rod segment 11542 and reconstructed inner right bent rod segment which are defined by the curve of the perimeter of the bender's center rod-contouring surface 11508 in between the intersection of the left rotated line 11531 and right rotated line 11533. Some embodiments of the illustration also display the reconstructed outer left bent rod segment 11534 and reconstructed right outer bent rod segment 11535 at the stage prior to a spline connecting these segments to the right-most point of the left outer unbent rod segment 11539, and the left-most point of the right outer unbent rod segment 11536, as previously described in relation to FIGS. 114A-114F. In some embodiments, at the stage of the software algorithm that the illustration displays, there is an outer rod surface gap region 11551 between the outer bent rod segments 11534, 11535 and the outer unbent rod segments 11539, 11536. In some embodiments, there is an overlap region 11552 of the inner rod surface following the rotation and translation of the right unbent rod segments and prior to the removal of rod coordinates in between the left 11531 and right 11533 rotated lines that enable non-overlapping reconstruction of the inner and outer bent rod segments as previously described in relation to FIGS. 114A-114F.

In some embodiments, FIG. 115E displays the fully reconstructed rod for the same bender position previously described in relation to FIGS. 115B-115D containing the perimeter of the bender's center rod-contouring surface 11508, the perimeter of the left roller 11521, perimeter of the right roller 11523, left outer unbent rod segment 11539, left center unbent rod segment 11540, and left inner unbent rod segment 11564 with its coordinates to the right of the left rotated line (not shown) removed, as well as the right outer unbent rod segment 11536, right center unbent rod segment 11537, and right inner unbent rod segment 11565 with its coordinates to the left of the right rotated line (not shown) removed. In some embodiments, the reconstructed inner bent rod segment 11561 is made from fusing the left and right inner bent rod segments as shown previously in relation to FIGS. 115C-115D. In some embodiments, the reconstructed outer bent rod segment 11563 is calculated from the inner reconstructed bent rod segment 11561 as described previously in relation to FIGS. 114A-114F and any potential gap between the outer unbent rod segments 11539, 11536 and the reconstructed outer bent rod segment 11563 has been filled via a previously fit curve (not shown) between the right-most point of the left outer unbent rod segment 11539, reconstructed outer bent rod segment 11563, and left-most point of the right outer unbent rod segment 11536. Some embodiments of this illustration display the software-rendered updated contour of the rod that would be updated on a display monitor for a user.

In some embodiments, FIG. 115F displays a zoomed-in view of that which was shown previously in FIG. 115E containing the perimeter of the bender's center rod-contouring surface 11508, right outer unbent rod segment 11536, right center unbent rod segment 11537, right inner unbent rod segment 11565, left outer unbent rod segment 11539, left center unbent rod segment 11540, left inner unbent rod segment 11564, reconstructed inner bent rod segment 11561 which is utilized to compute the reconstructed center bent rod segment 11562 and reconstructed outer bent rod segment 11563.

In some embodiments, a system can allow a surgeon to make intraoperative assessments and adjustments of the patient's alignment and biomechanical abilities. In some embodiments, the system can register the patient's local and/or full-length spinal curvature and flexibility. In some embodiments, the system can register the instruments and/or implants used to assess and/or manipulate the conformation of the spine. In some embodiments, the system can use various calculations and algorithms to produce a quantitative assessment of the patient's spinal biomechanical qualities and the customized implants used to enhance these qualities. In some embodiments, these quantitative assessments can include, but are not limited to, calculated values for various radiographic parameters related to both global and segmental alignment of the spine (e.g., lumbar lordosis, central sacral vertical line, Tl pelvic angle, thoracic kyphosis, Cobb angle, etc.).

Some embodiments include key features. In some embodiments, one or more of the embodiments described herein can include anatomical landmark(s) of interest (e.g., C7, SI, etc.) that are initialized relative to the 3D-tracking acquisition system. In some embodiments, a continuous or discrete 3D-tracked acquisition can be made along the surface (e.g., posterior, anterior, or lateral) of the spine, both within and beyond the surgical site (e.g., skin surface). Some embodiments include a series of algorithms filter continuous or discrete 3D-tracked probe data to identify a relationship between the acquired points and anatomical regions of interest (e.g., centroids of the vertebral bodies). In some embodiments, an assessment of the segmental and/or full-length spinal alignment can be produced with values for each relevant radiographic parameter (e.g., Cobb angle, lumbar lordosis, thoracic kyphosis, C2-C7 lordosis, C7-S I sagittal vertical axis, central sacral vertical line, Tl pelvic angle, pelvic incidence, pelvic-incidence-lumbar-lordosis mismatch, etc.). In some embodiments, an assessment of the contour, position, and/or alignment of instrumented hardware, such as screws, rods, or cages, can be produced.

Some embodiments include a visual display and quantitative feedback system for assessing and adjusting implants that can be implanted into/onto the anatomy, including 3D, dynamic renderings of registered anatomical landmark(s) of interest. In some embodiments, an assessment of segmental, regional, or full-length flexibility and range of motion can be produced between a selected range of vertebral segments. In some embodiments, the display outputs the information about the spine's curvature and alignment, quantitative radiographic alignment parameter values, instrumented hardware analysis, flexibility or range of motion of the spine, and also various ways to acquire or analyze radiographic images. In some embodiments, the display enables interactive feedback and interfaces for the user to signal specific commands to the system for computing, beginning operations for, or outputting the quantitative or visual analysis of a system or anatomical region(s) of interest.

Some embodiments include a skin-mounted fiducial device for registering the 3D location and pose of key anatomical landmarks of interest outside the surgical site. In some embodiments, the locations of underlying anatomical landmarks can be used for calculations of spinal alignment parameters and other related biomechanical analyses. In some embodiments, FIG. 116A illustrates an assembly 11600 for a skin-mounted, two-part fiducial device that comprises of a top-half fiducial 11605 and a bottom-half fiducial 11621 with an adhesive backing 11622. In some embodiments, the top-half fiducial 11605 features a surface tracing registration groove 11603 for rapid registration of the fiducial 3D coordinates axes in navigation camera coordinates via a 3D-tracked probe tracing within the groove. In some embodiments, the top-half fiducial 11605 contains an array of asymmetrically-arranged, embedded radiopaque fiducial markers 11651 for X-ray-based registration of the fiducial's 3D location and pose relative to underlying anatomical landmarks of interest.

In some embodiments, two or more multi-planar X-Ray images of the fiducial device are to be acquired with the anatomical landmarks of interest also visible in the same X-Ray images. In some embodiments, in each image, using the known asymmetric geometric distribution between radiopaque fiducial markers 11651, the system automatically calculates the 3D pose of the fiducial relative to the X-Ray imaging detector plane. In some embodiments, the user annotates the key anatomical landmarks of interest in each X-Ray image and then the system automatically computes the 3D locations of all annotated landmarks with respect to the fiducial centroid coordinates axes. In some embodiments, once the user registers the surface location and pose of the top-half fiducial 11605 with a tracing of the registration groove 11603 or tapping three or more detents 11601, the system then computes the location of all initialized anatomical landmarks with respect to the coordinate axes of the navigation camera, thus enabling computation of spinal alignment parameters with respect to 3D probe tracings or other registrations of spinal landmarks.

In some embodiments, since surgical drapes are applied frequently to the area surrounding the surgical site, the fiducial device is comprised of two complementary halves that mate across surgical drapes to enable for continued updates on the 3D location and pose of underlying anatomical landmarks of interest without additional X-Ray images. Some embodiments of the invention involve mechanical mating mechanisms to rigidly link the top-half fiducial 11605 to the bottom-half fiducial 11621. Some embodiments involve a winged clamping mechanism that features one or more side-clamps 11609 that revolve about a hinge joint 11607 via a pivot bearing 11613. In some embodiments, the side-clamp wall 11615 features a sloped mating surface 11619 that mechanically engages with a bottom fiducial protrusion mate 11617, and in doing so the pair of fiducial halves pinch across the surgical drape interface 11623 to enable a rigid, bump-resistant mate.

In some embodiments, FIG. 116B illustrates a side view 11630 of the fiducial device assembly described previously in relation to FIG. 116A in a disengaged position. In some embodiments, in this assembly the side-clamp walls 11632 are in an open position. In some embodiments, the bottom fiducial's clamping features include a series of upward and downward sloping mating surfaces that help mechanically retain the sloped surface of the side-clamp wall 11632 and its mating feature 11619. In some embodiments, FIG. 116C illustrates a side view 11640 of the fiducial device assembly described previously in relation to FIGS. 116A-B in an engaged, closed position with the intermediate surgical drape not shown. In some embodiments, FIG. 116D illustrates a side, cross-sectional view 11650 of the skin-mounted fiducial assembly. The primary mating features of the fiducial halves surrounding both sides of the surgical drape include the male alignment protrusion 11653 which is received by the female alignment groove 11655. In some embodiments, the side-clamp walls 11616 have a series of sloped mating surfaces 11659 that press against the downward sloped mating surface 11631 of the bottom-half fiducial's protrusion mates 11617.

In some embodiments, FIG. 116E illustrates a side view 11660 of the top-half fiducial 11605 device described previously in relation to FIGS. 116A-D in an open, disengaged position. In some embodiments, the underside of the top-half fiducial involves three or more radiopaque marker spheres in an asymmetric, unique arrangement, and in some embodiments one of the spheres is located at the centroid of the pattern. In some embodiments, by locating one sphere at the centroid of the pattern, greater accuracies can be achieved for registering the centroid and subsequent pose of the fiducial pattern in X-Ray images, since the imaged patterns are compared relative to a ground-truth coordinate database with spheres being rotated about the centroid of the fiducial. In some embodiments, FIG. 116F illustrates an assembly side view 11670 that demonstrate that the radiopaque fiducial spheres 11651 can be visualized in relation to the top surface of the fiducial. In some embodiments, when a 3D-tracked probe traces and registers the 3D coordinate axes of the top-half fiducial 11605, the system calculates where the centroid of the radiopaque fiducial spheres 11651 are with respect to the fiducial surface coordinates measured relative to the navigation camera. In some embodiments, using this registration of the fiducial sphere coordinates relative to the navigation camera, a 3D rigid body transform is computed to convert the 3D displacement vectors of the anatomical landmarks of interest measured relative to X-Ray fiducial coordinates to now be calculated in navigation camera coordinates.

In some embodiments, FIGS. 116G-116I illustrate exploded perspective views (11680, 11690, 11691) of the fiducial assembly device described previously in relation to FIGS. 116A-F. In some embodiments, these views illustrate the process of mating the top-half fiducial 11605 to the bottom-half fiducial 11621 across the surface of the surgical drape 11681 that sandwiches between both device halves.

In some embodiments, FIG. 116J illustrates an assembly view 11692 of a 3D-tracked probe 11682 that is engaged with the skin-mounted fiducial assembly described previously in relation to FIGS. 116A-I. In some embodiments, the 3D-tracked probe comprises a probe shaft 11679 encased in a trigger sleeve handle 11698, and a 3D-tracked dynamic reference frame (DRF) 11686 that comprises a unique array of 3D-tracked markers 11684 and is linked to the probe via a screw 11693 attaching the array to a DRF mount 11699 along the probe shaft 11679. In some embodiments, the 3D-tracked probe contains a tracked mobile stray marker (TMSM) 11695 that is substantially rigidly linked to a triggering spring-loaded link mechanism (not shown) that is actuated via a trigger button 11697. In some embodiments, the system automatically detects the TMSM's location within a known 3D volume boundary with respect to the location and pose of the DRF, and based on user-selected triggering sensitivity thresholds, the location of the TMSM beyond a set threshold signals an active probe state to the computer. In some embodiments, the TMSM 11695 is linked to the triggering mechanism via a backing mount 11696 that slides along a sliding mount backing 11667 via a spring-loaded (not shown) or otherwise conventionally biased screw sliding in a groove 11668 along the probe shaft axis. In some embodiments, the 3D-tracked probe 11682 contains a spherical probe tip 11666 that is used to both mate with fiducial devices initialized within and beyond the surgical site. In some embodiments, the spherical probe tip 11666 mates with the tracing registration groove 11603, and when the probe TMSM 11695, the system analyzes a 3D tracing of the groove pattern 11603 to compute the fiducial coordinate axes with respect to the navigation camera (not shown).

Some embodiments of the invention include a fiducial device that is implanted into bony tissue of anatomical landmarks of interest for precise registration of their 3D locations and poses for purposes of calculating spinal alignment parameters, 3D visualization of anatomy, and updating the registration of image-guided navigation systems and their associated reference systems. In some embodiments, the bone-mounted fiducial devices can be placed anywhere within or near the surgical site when registration of key landmarks linked to the fiducial device are desired, and the device is designed to avoid obstructing the routine anatomical structures manipulated or removed during spine surgical surgeries. In some embodiments, FIG. 117A illustrates the bone-mounted fiducial 11701 that contains a female mating mechanism for registration with a 3D-tracked tool that contains a complementary mating interface. In some embodiments, the fiducial device has screw threads 11703 that align with the mating interface and its screwdriver wall interface 11707. In some embodiments, the mating mechanism of the female direct-screw bone-mounted fiducial 11701 involve a female flat mating interface 11709 and a cylindrical mating interface 11708. In some embodiments, the fiducial mating interface can be any cross-sectional, asymmetric pattern that enables a 3D-tracked tool to register the unique 3D orientation and location of the fiducial device. In some embodiments, the flat mating surface 11709 thus represents the true north orientation axis of the device and enable reliable registration of the device's 3D coordinates axes via probe-based acquisitions.

In some embodiments, FIG. 117B illustrates a top view of the bone-mounted fiducial 11701 as described previously in relation to FIG. 117A. In some embodiments, the female floor mating interface 11711 of the fiducial provides a depth-stop interface for the 3D-tracked probe tip to enable repeatable, uniform measurements of the fiducial's location and orientation with probe acquisitions. In some embodiments, FIG. 117C illustrates a disengaged probe tip adapter 11716 that contains a male fiducial flat protrusion mating interface 11721 and a cylindrical mating interface 11723. In some embodiments, given this complementary, asymmetric mating mechanism, a 3D-tracked probe can only mate with the bone-mounted fiducial 11701 in one unique trajectory and orientation.

In some embodiments of the invention, a 3D-tracked probe registers the unique 3D location and orientation of the bone-mounted fiducial device with a probe tip that can features a complementary mating interface. In some embodiments, FIG. 117D illustrates a perspective view of the bone-mounted fiducial as described previously in relation to FIGS. 117A-C. In some embodiments, the 3D-tracked probe 11682 in this view is not engaged with the bone-mounted fiducial and is in an inactive triggering state. In some embodiments, FIG. 117E illustrates that the 3D-tracked probe 11731 is fully mated with the female bone-mounted fiducial 11701 and the trigger button 11733 actuated the TMSM 11737 into an active state, which signals to the computer to record the current 3D location and orientation of the bone-mounted fiducial 11701.

In some embodiments, FIG. 117F illustrates a perspective view of the bone-mounted fiducial 11701, described previously in relation to FIGS. 117A-E, in which the fiducial is implanted into the posterior sacrum of the spine 11741. In some embodiments, the 3D-tracked probe 11682 is not engaged with the bone-mounted fiducial in this view. In some embodiments, FIG. 117G illustrates that the 3D-tracked probe 11731 is fully mated with the implanted bone-mounted fiducial 11701 and the TMSM 11737 is in active state to signal to the computer that the 3D location and pose of the bone-mounted fiducial should now be recorded into the system. In some embodiments, based on prior initialization (e.g., processes shown in FIG. 121 and other enclosed inventions) of the relations of the bone-mounted fiducial device to nearby anatomical landmarks of the interest, the probe-based registration of the bone-mounted fiducial enables for the automated calculation of the up-to-date 3D locations and poses of all bony landmarks of interest relative to the new location and pose of the bone-mounted fiducial.

In some embodiments of the invention, such as FIG. 117H, bone-mounted fiducials 11701 are implanted into multiple vertebrae of the spine to enable the 3D registration of multiple segments of the spine. In some embodiments, after all engaged vertebrae are initialized in relative location and pose to that of each implanted bone-mounted fiducial device 11701, then the probe-based acquisitions of each bone-mounted fiducial provides updated information as to the new location and pose of individual vertebrae. In some embodiments, a useful benefit of this system is simplifying the re-registration of image-guided navigation with the ability to minimize the requirement for additional imaging or complex registration steps that are typically used with current state of the art systems whenever bony landmarks are adjusted relative to their initial registered positions. In some embodiments of the invention, after initialization of each engaged vertebrae, the re-registration of each bone-mounted fiducial can be performed throughout the duration of the surgery with acquisitions via a 3D-tracked tool with a complementary mating interface, without the need for additional imaging or anatomical reference registrations. In some embodiments, FIGS. 117I-117J illustrate the registration process of a bone-mounted fiducial 11701 that is implanted into the spine 11741 which is being rapidly registered via a 3D-tracked probe 11682. In some embodiments, after the 3D-tracked probe 11731 is fully engaged with the bone-mounted fiducial 11701, the trigger button 11733 can actuate the TMSM 11737 and signal to the computer the active registration of a unique bone-mounted fiducial. In some embodiments of the invention, this system of devices and algorithms is used to rapidly update the registration of image-guided surgical navigation systems. In some embodiments, this system rapidly registers the 3D spinal alignment parameters between vertebrae that contain implanted bone-mounted fiducials 11701.

Some embodiments of the invention include a bone-mounted fiducial device with a male mating protrusion that enables precise registration of the fiducial's 3D location and pose for purposes of calculating spinal alignment parameters, 3D visualization of anatomy, and updating the registration of image-guided navigation systems and their associated reference systems. In some embodiments, FIG. 118A illustrates a perspective view of a male bone-mounted fiducial 11808 that is similar in function to previously described devices in relation to FIG. 117. In some embodiments, the fiducial contains screw threads 11808 that are aligned with the long axis of the male protrusion shaft. In some embodiments, the male mating mechanism of the fiducial comprises a male flat mating interface 11801 and a male cylindrical mating interface 11803. In some embodiments, the cross-sectional design of the mating interface can be any pattern that enables unique orientation registration of the fiducial device.

In some embodiments, FIG. 118B illustrates a top view of a bone-mounted fiducial device as described previously in relation to 118A. In some embodiments, the fiducial comprises depth-stop mating interface 11806 that engages directly with a 3D-tracked tool (not shown) to provide a reliable mating interface location and pose to be registered for the fiducial device. In some embodiments, the walls 11811 of the bone-mounted fiducial device are a hexagonal cross-section to enable simple engaging of the fiducial device via a screwdriver for implantation of the fiducial into a vertebra or bony structure of interest. In some embodiments of the invention, the bone-mounted fiducial device is implanted into any rigid bony structure of the human body, including the pelvis, sacrum, femur and other lower extremities, shoulders and other upper extremities, the skull, etc. for precise 3D registration and alignment measurements of engaged bony structures.

In some embodiments, FIG. 118C illustrates a perspective view of a bone-mounted fiducial 11808, as described previously in relation to FIGS. 118A-B, in the process of mating with a 3D-tracked probe tip 11815 (shaft and upper device not shown), in which the probe tip contains a female flat mating surface 11821 and a female cylindrical mating surface 11823. In some embodiments of the invention, a 3D-tracked probe 11831 is used to register the 3D location and orientation of a bone-mounted fiducial device 11808. In some embodiments, FIGS. 118E-118F illustrate the process of engaging a bone-mounted fiducial device 11808 with a 3D-tracked probe 11831 and then depressing the trigger button 11860 to actuate the TMSM 11858 into an active-state location with respect to the fixed position of the 3D-tracked DRF 11840. In some embodiments, FIGS. 118G-118I illustrate perspective views of the process of engaging a 3D-tracked probe 11831 with a probe tip adapter 11817 that contains a spherical tip and internal female mating mechanism that engages with the bone-mounted fiducial and then registers the current 3D location and pose of the bone-mounted fiducial device 11808. In some embodiments, once the 3D-tracked probe 11831 is rigidly, uniquely engaged with the bone-mounted fiducial 11808, the TMSM 11844 is actuated via depression of the probe's trigger button 11834 and then the 3D-tracked probe 11856 is actively registering the location and orientation of the bone-mounted fiducial for at least one camera frame in which the TMSM 11858 remains in an active-state location with respect to the probe's DRF 11840.

Some embodiments of the invention include a bone-mounted fiducial device with a male mating interface that, when registered, enables precise registration of the fiducial's 3D location and pose for purposes of calculating spinal alignment parameters, 3D visualization of anatomy, and updating the registration of image-guided navigation systems and their associated reference systems. In some embodiments, FIG. 119A illustrates a perspective view of the bone-mounting fiducial device, which is similar in function to previously described devices in relation to FIGS. 117-118, shown with a male mating protrusion offset from the device screw shaft axis. In some embodiments, the bone-mounted fiducial 11908 comprises a male mating component that contains a flat mating interface 11901 and a cylindrical mating interface 11903. In some embodiments, the device screw threads 11909 are offset from the axis of the mating interface's shaft to enable simplified implantation of the bone-mounted fiducial in a particular orientation on the attached anatomy that enables the direct visualization of a 3D-tracked tool registering the fiducial device 11908 via a 3D-tracking camera. In some embodiments, the flat mating interface 11901 determines the north orientation of the fiducial device 11908 and thus needs to be oriented towards the direction of the 3D-tracking camera. In some embodiments, FIG. 119B illustrates a perspective view of the underside of the bone-mounted fiducial device 11908, which in some embodiments contains a series of frictional surface spikes 11907 on the bottom surface of the depth-stop mating interface 11902.

In some embodiments, FIG. 119C illustrates a top view of a bone-mounted fiducial device 11908 as described previously in relation to FIGS. 119A-B. In some embodiments, the bone-mounting screw contains a torx head driver interface 11906. In some embodiments, FIGS. 119D-119E illustrate side views of the bone-mounted fiducial device 11908.

In some embodiments, FIG. 119F illustrates a perspective view of a bone-mounted fiducial device 11908, as described previously in relation to FIGS. 119A-C, in the process of mating with a 3D-tracked probe tip 11935 (probe not shown) that contains a complementary, female mating interface that contains a flat surface 11932 and a cylindrical surface 11931.

In some embodiments, FIGS. 119G-I illustrates a front view of a bone-mounted fiducial device 11908, as described previously in relation to FIGS. 119A-D, and the complete process of mating with a 3D-tracked probe 11941, which contains a complementary, female mating interface. In some embodiments, the bone-mounted fiducial device's 3D location and orientation are registered via a 3D-tracked probe with a complementary mating interface and a trigger button 11943 that actuates a TMSM 11948 beyond a defined 3D location threshold relative to the fixed position of a 3D-tracked DRF 11946. In some embodiments, when the trigger button 11957 is fully depressed, the TMSM 11959 surpasses a defined location threshold that the system interprets as the 3D-tracked probe 11958 being in an active, registration state. In some embodiments, FIGS. 119J-119K illustrate perspective views of the bone-mounted fiducial device 11908 and a 3D-tracked probe 11941 in the process of mating as described previously in relation to FIGS. 119A-119I.

Some embodiments of the invention include a bone-mounted fiducial device with a female mating interface that, when registered, enables precise registration of the fiducial's 3D location and pose for purposes of calculating spinal alignment parameters, 3D visualization of anatomy, and updating the registration of image-guided navigation systems and their associated reference systems. In some embodiments, FIG. 120A illustrates a perspective view of a bone-mounted fiducial device 12001, which is similar in function to previously described devices in relation to FIGS. 117-119. In some embodiments, the bone-mounted fiducial device 12001 includes a female mating mechanism with a flat mating surface 12009 and a cylindrical mating surface 12008 that is offset from the screw shaft axis. In some embodiments, the screw threads 12002 come to a tapered tip 12003 in some embodiments. In some embodiments, the screw head 12004 is a torx head driver interface 12005.

In some embodiments, FIG. 120B illustrates a side view of the bone-mounted fiducial device 12001 that is previously described in relation to FIG. 120A. In some embodiments, the device is equipped with friction spikes 12011 on the bottom surface to enable rigid fixation to engaged bony structures. In some embodiments, FIG. 120C illustrates a top view of the fiducial device 12001. In some embodiments, the female flat mating surface 12009 indicates the north orientation of the device when registered via a 3D-tracked tool (not shown) that contains a complementary mating surface.

In some embodiments, FIGS. 120D-120E illustrate a perspective view of a 3D-tracked male mating probe tip 12021 (probe not shown) in the process of engaging in a unique trajectory with the bone-mounted female device 12001. In some embodiments, when the male mating probe tip 12031 is fully engaged with the female bone-mounted fiducial device 12001, the 3D-tracked probe (not shown) can acquire the 3D location and pose of the fiducial device. In some embodiments, FIGS. 120F-120H illustrate a perspective view of a 3D-tracked probe 12043 and the female mating bone-mounted fiducial device 12001 in the process of mating together and the 3D-tracked probe 12043 acquiring the 3D location and orientation of the fiducial device 12001. In some embodiments, FIG. 120H illustrates the 3D-tracked probe 12058 with a male mating probe tip 12023 fully engaged into the female mating bone-mounted fiducial device 12001, and as the trigger button 12056 is fully depressed, the TMSM 12059 actuated via the TMSM backing mount 12061 is in an active-state location with respect to the fixed location of the DRF 12049.

Some embodiments of the invention include an X-Ray adapter device that mates in a unique orientation with a bone-mounted fiducial device. In some embodiments, the X-Ray adapter device contains radiopaque sphere fiducials used for initialization of the location and pose of nearby anatomical landmarks of interest relative to the implanted bone-mounted fiducial device. In some embodiments of the invention, the X-Ray adapter device is used to initialize the 3D location and pose of key anatomical landmarks such as the S1 endplate, femoral heads, L5, L1, T10, T9, T4, T1, C1, C7, occiput, etc. to calculate spinal alignment measurements. In some embodiments, FIG. 121A illustrates a perspective of an example embodiment of the X-Ray adapter device 12101 that contains three or more radiopaque fiducial spheres 12103 within the fiducial body 12105, and a male mating interface comprising a male flat surface 12106 and male cylindrical surface 12107 that engages with a female mating interface of a fiducial device (not shown) in a unique orientation. In some embodiments, the arrangement of radiopaque fiducial spheres 12103 involves an asymmetric distribution of spheres in a 3D-offset pattern that produces a unique 3D pose for all rotational views of the sphere arrangement. In some embodiments, the system can use the projection of inter-sphere relations in an X-Ray image to automatically detect the 3D pose of the fiducial with respect to the X-Ray detector imaging plane. In some embodiments, FIGS. 121B-121C illustrate a side view of the X-Ray adapter device 12101 and highlight the unique orientation of the flat 12106 and cylindrical 12107 mating surfaces.

In some embodiments, FIGS. 121D-121E illustrates a side view of the process of mating the male X-Ray adapter device 12101 into an implanted female bone-mounted fiducial device 12121, as described previously in relation to FIGS. 117A-117J. In some embodiments, the X-Ray adapter device 12131 engages into an implanted bone-mounted fiducial device 12121 that is engaged with the sacrum 12123 and the pelvis 12125 of the spine. In some embodiments, two or more multi-planar X-Ray images are acquired of the X-Ray adapter device 12101 while engaged into a bony landmark of interest for 3D registration of the anatomical landmark's 3D location and unique pose. In some embodiments, FIG. 121F illustrates a top view of the X-Ray adapter device 12131 engaged in the sacrum 12123, with the engaged adapter device containing four radiopaque fiducial spheres arranged in a unique, asymmetric geometric distribution to facilitate auto-pose detection of the fiducial in X-Ray images relative to the detector imaging plane.

In some embodiments, FIG. 121D illustrates a lateral X-Ray image 12124*a* of the X-Ray adapter device 12131 engaged into an implanted bone-mounted fiducial device. In some embodiments, the radiopaque fiducial spheres can be visualized in their unique pose relative to the imaging detector plane. In some embodiments, the user annotates key anatomical landmarks of interest and the system calculates their respective locations relative to the calculated centroid of the four, radiopaque sphere 12103 coordinates. In some embodiments, the S1 endplate 12142, femoral heads 12141, and other landmarks of the sacrum 12123 and pelvis 12125 are annotated and automatically registered by the computer in relation to the fiducial device. In some embodiments, FIG. 121H illustrates an AP X-Ray image 12124*b* of the X-Ray adapter device 12131 engaged into an implanted bone-mounted fiducial device. In some embodiments, the detected 3D-pose of the fiducial adapter device 12131 relative to the imaging detector plane is converted in a rigid body transform and then applied to all annotated anatomical landmarks of interest to compute the 3D vectors of each anatomical landmark relative to the fiducial adapter device's 12131 coordinate axes.

In some embodiments, the mating interface of the adapter device 12101 comprises a quarter-turn twist mating mechanism to ensure reliable, complete mating of the adapter device with the bone-mounted fiducial device. In some embodiments, the inter-sphere angles computed between the 2D-projected coordinates of radiopaque fiducial spheres 12103 are automatically analyzed by the computer to identify the anatomical axes of the patient relative to the X-Ray images (e.g., inferior end, posterior end, and right end of patient relative to image).

In some embodiments of the invention, the X-Ray adapter device includes an orientation indicator to aid in defining patient anatomical axes and orientation relative to the X-Ray images of the adapter device. In some embodiments, FIGS. 122A-122B illustrate a perspective view of a female-mating X-Ray adapter device 12201, which is described previously in relation to FIGS. 121A-121H, that mates in a unique 3D trajectory and orientation with a bone-mounted, male-mating fiducial device 12213, as previously described in relation to FIGS. 118A-118I. In some embodiments, the orientation indicator 12208 is used to aid the user to indicate in the X-Ray image which direction the arrow of the fiducial orientation indicator 12208 is pointed with relation to nearby anatomical axes. In some embodiments, the female mating interface of the X-Ray adapter device comprises a flat edge surface 12221 and a cylindrical surface 12223 that matches the cross-sectional male interface pattern of the bone-mounted fiducial device 12213. In some embodiments, FIGS. 122C-122D illustrate the mating process of the X-Ray adapter device 12201 to the implanted bone-mounted male-mating fiducial device 12225 engaged in the sacrum 12229. In some embodiments, the X-Ray adapter device is fully engaged with the bone-mounted fiducial device when the adapter's shaft mating interface 12211 engages with the top surface of the bone-mounted fiducial's depth-stop mating interface 12216. In some embodiments, FIG. 122D illustrates an example embodiment of the X-Ray adapter device 12231 from a top view as the system is ready for X-Ray images for initialization of anatomical landmarks of the spine 12228, such as the femoral heads 12234, and other engaged landmarks of the sacrum 12228 or pelvis 12226.

In some embodiments of the invention, the X-Ray adapter device, which is similar in function to the previously described embodiments in relation to FIGS. 121A-121H, 122A-122D, contains a linear or co-planar arrangement of embedded, radiopaque fiducial spheres and an associated orientation indicator sign for the user. In some embodiments, FIG. 123A illustrates a perspective view of the example embodiments of an X-Ray adapter device 12301 with a linear arrangement of radiopaque fiducial spheres 12303 that are parallel in orientation to that of the orientation indicator 12305 of the device. In some embodiments, the X-Ray adapter device 12301 contains a male mating mechanism comprising a flat edge surface 12313 and a cylindrical surface 12311 that fully engages with a bone-mounted fiducial device (not shown) when the adapter-to-fiducial, depth-stop mating interface 12308 is engaged with a fiducial device's depth stop.

In some embodiments, FIGS. 123B-123D illustrate side and cross-sectional views of the X-Ray adapter device as previously described in relation to FIG. 123A. In some embodiments, the sloped angle of the fiducial body 12307 can be adjusted to better accommodate the normative anatomical geometric dimensions of the spine. In some embodiments, the fiducial body 12307 is sloped to accommodate the adapter device being able to mate with a fiducial device on the sacrum, or other steeply-sloped anatomical landmarks, without colliding with nearby anatomical structures and to ensure that the primary plane connecting the radiopaque fiducial spheres 12303 are parallel to the imaging detector plane for maximal accuracy of 3D pose detection. In some embodiments, the X-Ray adapter device 12331 engages in a unique trajectory and orientation with a female-mating bone-mounted fiducial device 12333 implanted into a bony landmark of interest in the sacrum 12335. In some embodiments, the user indicates anatomical axes directions, via the orientation indicator 12305, to the computer system that is analyzing the X-Ray images of this device with respect to nearby anatomical landmarks.

In some embodiments of the invention, a bone-mounted fiducial device with an internal protrusion enables a system for rapidly registering the 3D location and pose of bone-mounted fiducial devices for purposes of calculating spinal alignment parameters, 3D visualization of anatomy, and updating the registration of image-guided navigation systems and their associated reference systems.

In some embodiments, FIG. 124A illustrates a perspective view of a bone-mounted fiducial device 12401 with a female mating interface that contains an internal male depth-stop mating interface 12416 for engaging with a 3D-tracked tool with an end-effector that contains a similar mating interface. In some embodiments, the bone-mounted fiducial 12401 has a uniquely-defined depth of engagement set by the difference in heights between the screw-head 12413 and the depth-stop mating interface 12416 which is registered by the 3D-tracked probe with complementary mating surfaces and an internal actuating trigger shaft that is depressed via the screw-head 12413 of the bone-mounted fiducial. In some embodiments, the bone-mounted fiducial 12401 can be registered by a 3D-tracked probe with a probe tip adapter 12439 that features the complementary mating surfaces for engaging the bone-mounted fiducial. In some embodiments, FIG. 124B illustrates a top view of the bone-mounted fiducial device 12401. In some embodiments, the fiducial mating interface comprises a torx curved surface and a flat-edge surface to enable registration of the unique orientation of the fiducial by a 3D-tracked tool (not shown). In some embodiments, FIG. 124C illustrates a side view of the bone-mounted fiducial device 12401 that is described previously in relation to FIGS. 124A-B.

In some embodiments, FIG. 124D illustrates a perspective view of a 3D-tracked probe 12442 about to engage with a bone-mounted fiducial device 12433 in a unique trajectory and orientation. In some embodiments, the observed size of the fiducial device 12433 in FIG. 124D does not reflect the end sizing of the manufactured device which is approximately 10% of the seen sizing footprint. In some embodiments, when the user is registering a vertebra of the spine, the 3D-tracked probe 12442 and its linked probe tip adapter 12439 with embedded flat mating surface 12435 and torx-head mating surface 12437 that mates uniquely with the bone-mounted fiducial female mating surface. In some embodiments, FIGS. 124E-124F illustrates the process of mating the 3D-tracked probe 12442 to a bone-mounted fiducial device 12433 and then activating the TMSM 12461 via depressing the trigger button 12464 and actuating the TMSM backing mount 12463. In some embodiments, FIGS. 124G-124H illustrate some embodiments of the invention for use as a rapid re-registration system for updating the 3D position and orientation of initialized vertebrae relative to their individually engaged bone-mounted fiducials 12433. In some embodiments, after the spine 12465 has been corrected into a healthier shape, a 3D-tracked probe 12462 is used to register the new 3D conformation of the spine 12465.

In some embodiments of the invention, a bone-mounted fiducial device with an internal protrusion, as described previously in relation to FIGS. 124A-124H, is registered via a 3D-tracked probe with a self-triggering mechanism that automatically activates upon fully engaging and mating with the mating features between the fiducial and the probe tip. In some embodiments, FIG. 125A illustrates a perspective view of a 3D-tracked probe 12501 with a probe shaft 12518 that encloses an internal shaft (not shown) that is rigidly linked to the TMSM 12505 via the TMSM sliding mount 12507. In some embodiments, when the male mating features 12512 of the 3D-tracked probe 12501 are fully engaged with a bone-mounted fiducial 12519c in a specific orientation in which the mating features align during engagement, the internal shaft 12551 (not shown) is then depressed via the male protruding screw profile base within the internal features of the bone-mounted fiducial. In some embodiments, the internal shaft of the probe cannot be depressed unless the mating features between the fiducial and probe are perfectly aligned to each other. In some embodiments, FIG. 125B illustrates a 3D-tracked probe 12527 once fully engaged with a bone-mounted fiducial 12519c, after which the TMSM 12533 is actuated into an active state.

In some embodiments, FIGS. 125C-125D illustrate a side cross-sectional view of the mating process of the 3D-tracked probe 12527 engaging with a bone-mounted fiducial 12519c, and in the process actuating the internal sliding trigger shaft 12565 which is spring-loaded via a mechanically-linked compression spring 12567 and is also linked to the TMSM sliding mount 12531 that actuates the TMSM 12533 into an active state. In some embodiments, the system automatically identifies which bone-mounted fiducial devices are being registered by analyzing the depth of triggering engagement registered by the 3D-tracked probe 12527. In some embodiments, the greater depth of engagement shown in the far-right bone-mounted fiducial 12519f will signal a different fiducial identity to the system than engaging the third bone-mounted fiducial 12519c with a shallower depth of engagement of the internal sliding trigger shaft 12565.

In some embodiments of the invention, a system of 3D-tracked tools is used to register the 3D conformation of a spinal rod implant throughout the rod contouring process. In some embodiments of the invention, a rod is rigidly fixed within a 3D-tracked end cap device and then a 3D-tracked slider device engages the rod and slides along its external contour. In some embodiments, as the 3D-tracked slider device traces the 3D contour of the rod, the 3D-tracked end cap is constantly updating the location and pose of the reference coordinate axes for the rod contour registration. In some embodiments, FIG. 126A illustrates one example embodiment of the 3D-tracked slider device 12601 in which the tracked slider assembly can mount onto a standard universal rod bender for ease-of-use and rapid integration in the current workflow of iteratively contouring the shape of the rod implant until its shape is satisfactory to the user. In some embodiments, the 3D-tracked slider comprises a DRF 12603, made of three or more 3D-tracked markers 12607, that is attached to an aligning wall mount 12609 that is connected to a rod bender mounting interface 12611 that is also connected to a trigger offset L-shape arm 12614 that places the triggering mechanism off-axis from the DRF to minimize the device profile protruding from the rod bender top boundary. In some embodiments, within the trigger offset arm 12614, there is a spring-loaded TMSM 12615 that is attached to a sliding mount 12616 that is linked to a series of compression springs 12619 that are retained in place via spring guide protrusions 12622 within a spring mount 12625 that is fixed in-place at a certain distance from the TMSM sliding mount 12616 via a tensioning screw 12623 within a slot 12621 that determines the distance between the sliding mount 12616 and the spring mount 12625. In some embodiments, the TMSM 12615 trigger mechanism is actuated via a spring-loaded plunger 12630 that protrudes slightly out of the fork body and is surrounded by a rod-engaging wall interface 12628.

In some embodiments, FIGS. 125B-125C illustrate a top view of the 3D-tracked slider device 12601 in the process of engaging with the surface contour of a spinal rod implant 12637. In some embodiments, as the 3D-tracked slider 12642 engages with the rod 12637 within the fork surface interface 12628, the spring-loaded plunger 12647 is depressed, which actuates the TMSM 12641 into an active state by compressing the spring 12643 of the trigger mechanism. In some embodiments, as the TMSM 12641 actuates away from the fork surface 12628 and moves closer to the DRF 12603, the system automatically analyzes if the TMSM 12641 has passed a 3D location threshold defined in the system to indicate an active tool state for registering the 3D contour of the rod. In some embodiments, by inputting the known diameter of the rod, the system can automatically adjust the 3D register of the contour of the rod to represent the center of the rod as opposed to the external surface. In some embodiments, FIGS. 125D-E display side, cross-sectional views of the 3D-tracked slider device 12601 in the process of mating with a rod 12637 within the fork interface 12628.

In some embodiments, FIG. 126F illustrates a perspective view of the 3D-tracked slider device, as described previously in relation to FIGS. 126A-126E, attached to the back surface of a standard rod bender 12663. In some embodiments, the 3D-tracked slider device triggering axis is in-line with one of the rod bender handles 12661 and thus enables rod contour registrations to occur about the central axis of the rod bender, and thus also enable the user to register the contour of the rod with either a left or right hand holding the 3D-tracked slider. In some embodiments, FIGS. 126G-126H illustrate a front and side view of an example embodiment of the assembly of the 3D-tracked slider device 12601 attached to a rod bender 12663. In some embodiments, the user can iteratively register the 3D contour of the rod and then adjust the contour on the opposite side of the rod bender with the contour rollers 12671 and rod-engaging interfaces 12673.

In some embodiments, FIGS. 126I-126J illustrate perspective views of the process of registering the 3D contour of a rod during the contouring process via engaging the spring-loaded plunger 12630 against the rod 12679 with the 3D-tracked, slider-equipped rod bender 12693, which is tracing the contour of the rod 12691 while it is being rigidly fixed in place by the clamping mechanism 12681 of the 3D-tracked end cap device 12677. In some embodiments, the end cap 12677 is also equipped with a trigger mechanism 12685 and associated TMSM 12687 to enable the pair of devices to be used to communicate different steps of the rod contouring and registration process. In some embodiments, after a rod tracing registration occurs, the user can click on the end cap trigger 12685 to communicate to the computer that the registration is complete and ready for overlaying and comparison visualizations.

Some embodiments of the invention involve a flexibility and biomechanical analysis system that directly manipulates the conformation of the spine while tracking the position of engaged and nearby anatomical landmarks that are attached to the flexibility assessment devices. In some embodiments, the flexibility assessment devices attach directly to instrumented pedicle screws within the spine via a pseudo-rod component that is compressed with a standard screw cap to convert a polyaxial screw into a monoaxial screw and enable rigid manipulation of the attached vertebrae.

In some embodiments, FIG. 127A illustrates a front view of an example embodiment of a 3D-tracked flexibility assessment device 12701. In some embodiments of the invention, the flexibility assessment device 12701 includes a 3D-tracked DRF 12707, an actuating trigger arm 12711 that is depressed via trigger buttons 12705 that actuate the position of a TMSM 12709. In some embodiments of the invention, the trigger arm 12711 and device handle 12703 are curved in shape to enable multiple flexibility assessment devices in the surgical site to be simultaneously visualized by a 3D-tracking camera without obstructing line-of-sight during a flexibility assessment. In some embodiments of the invention, the device handle 12703 can be adjusted in angle relative to the width-adjustment mechanism 12624 via a spring-loaded plunger 12714 that releases and engages predefined angular detents within the handle mount side walls 12717. In some embodiments of the invention, the device comprises a width-adjustment mechanism 12624 that connects two side arm devices (12730a, 12730b), one attached to the primary device via a fixed shoulder 12720 and the other via an adjustable shoulder 12728 that can adjust the inter-side-arm distance and angle for matching the distance and angles between pedicle screw tulips instrumented into a vertebra of interest. In some embodiments, the adjustable shoulder 12728 slides within the width adjustment channel 12726 and can rotate about the width adjustment pivot 12727 that can be fixed in-place via tightening width-adjustment knob 12741 (not shown). In some embodiments, the device side arms engage with the pedicle screws of the engaging vertebra via a pair of pseudo rod mating interfaces 12733 that insert into the tulip of the pedicle screws and can be compressed in-place via standard screw caps. In some embodiments, to enable more rigid structural support during manipulation of vertebrae, the side arm devices (12730a, 12730b) can be reinforced with gusset structures 12731 between the side arm and the pseudo rod interface 12733. In some embodiments, after the side arms are rigidly attached to the pedicle screws of interest and the manipulating spine conformation has been achieved, the side arm devices (12730a, 12730b) can be detached from the primary device 12701 via removal of a retaining clip (not shown) that slides within the shoulder clip groove 12732. In some embodiments, the side arm devices (12730a, 12730b) are equipped with device pedicle screws 12729 that are used to connect a rigid rod connector (not shown) between two or more flexibility assessment devices once a desired alignment or 3D spinal conformation has been achieved with the assessment devices 12701.

In some embodiments, FIG. 127B illustrates a top view of the flexibility assessment device 12701. In some embodiments, the positioning and shape of the side arm devices (12730a, 12730b) enable for the device pedicle screws 12729 to all be accessible and not occluded from above for access of inter-tool rod placement. In some embodiments, FIGS. 127C-127D illustrate perspective views of two flexibility assessment devices (12701,12747) in an example embodiment of arranging the orientation of devices within the surgical site and maintaining visualization of both DRFs (12707,12756) during flexibility assessments. In some embodiments, FIG. 127D illustrates a perspective view of the flexibility assessment devices (12701,12747) engaged into pedicle screws 12761 and rigidly linked in-place via screw caps 12763 that are tightened onto the pseudo rod mating interface 12733.

In some embodiments of the invention, two or more flexibility assessment device handles can be rigidly fixed in-place, and subsequently the nearby vertebrae maintain a desired conformation, via the placement of inter-tool connecting rods, and then the device handles can be detached from the side arm devices via removal of a retaining clip or connecting mechanism. In some embodiments of the invention, multiple interconnected side arm devices can be daisy-chained along the spine to provide a large construct that has been individually measured and locked in-place via rigidly linked, and then detached, flexibility assessment devices.

In some embodiments, FIGS. 128A-128B illustrate a top and side view of an example embodiment of the invention that include multiple engaged, connected side arms 12803 that are linked to one another via multiple inter-tool connecting rods (12811a, 12811b, 12811c). In some embodiments, the side arm device 12803 includes alignment pins 12817 that help rigidly, reliably link the side arm device with their respective flexibility assessment device (not shown).

In some embodiments, FIGS. 128C-128D illustrate a top and side view of another example embodiment of the invention that demonstrates that flexibility assessment devices (12831, 12833) can be rigidly engaged with empty pedicle screw tulips on surrounding sides of the spine (12835a, 12835c) around engaged, connected side arms that are rigidly holding the conformation of a middle segment of the spine 12835b. In some embodiments, the system can continue evaluating the range of motion and 3D alignment of engaged vertebrae not rigidly linked to the fixed construct to enable adding additional measurement-approved fixed segments to the construct or to assess that the final global alignment of the full construct is as desired relative to the operative goals.

In some embodiments of the invention, the 3D location pedicle screw tulips can be registered to provide input to automated, manual, or assisted rod contouring systems as to the desired 3D contour of the final rod implant. In some embodiments, FIG. 129A illustrates a perspective view of an example embodiment of the system in which a 3D-tracked probe 12901 registers the 3D location of pedicle screw tulips 12925 via inserting the probe tip 12927 within the tulip cavity and depressing the trigger button 12907 of the probe which actuates the TMSM 12905 via depressing the TMSM sliding mount 12908. In some embodiments of the invention, the spine 12915 is instrumented with pedicle screws 12925 and a select segment of the spine is rigidly fixed via a series of engaged, inter-connected side arm devices 12913 that are connected via inter-tool connecting rods (12917a, 12917b, 12917c). In some embodiments, the engaged side arms are linked to pedicle screws on the right side of the patient, and the contralateral array of pedicle screw tulips are empty and able to be localized in 3D via acquisitions of the 3D-tracked probe 12901. In some embodiments, FIGS. 129B-129D illustrate side and top views of an example embodiment of the system that depicts the process of inserting the probe tip of the 3D-tracked probe 12937 and activating its TMSM 12905 to signal to the computer to acquire the pedicle tulip 3D location. In some embodiments, this system of acquiring the 3D locations of contralateral pedicle screw tulips can be inputted into a feedback system that overlays the current registration of a contoured spinal rod relative to the contour of the spine and the conformation of screw tulips in sagittal and coronal anatomical projections, as depicted in example system embodiments shown in FIGS. 134A-134H. In some embodiments, the 3D registered location of the pedicle tulips can be inputs to automated or assisted rod bending devices. In some embodiments, one useful feature of this system is the ability to provide feedback as to how the current rod contour compares with the current arrangement of pedicle screw tulips, which are already in their final corrected position due to manipulations made by the flexibility assessments devices.

In some embodiments of the invention, a system of a 3D-tracked probe and fiducial devices are used to register the 3D location and orientation of key anatomical landmarks of interest of the spine for the calculation of spinal alignment parameters during surgery. In some embodiments, FIG. 130A illustrates a perspective view of an example embodiment of the system that demonstrates the clinical workflow of the invention. In some embodiments, for regions of the spine that are required or desired inputs for alignment parameter calculations but are outside the surgical site, a skin-mounted fiducial assembly 13020 can be applied over the anatomical landmarks of interest covered by skin tissue 13013 and surgical drapes. In some embodiments, after the skin-mounted fiducial 13020 is initialized via multi-planar X-Ray images or image-guided navigation, the 3D-tracked probe 13001 traces the Z-pattern registration groove 13021 to register the 3D coordinate axes of the fiducial device. In some embodiments, updating the 3D location and pose of the skin-mounted fiducial produces a rigid body transform calculation to convert the image-based initialization of anatomical landmarks with respect to the fiducial axes into 3D-tracking camera coordinates. In some embodiments, tracing the Z-pattern registration groove instantly calculates the up-to-date virtual, 3D location of the T1 vertebral body centroid (not shown; illustrated in FIGS. 133H-I), which is located in the region beneath the skin-mounted fiducial 13020.

In some embodiments, FIG. 130B illustrates a perspective view of the spinal alignment assessment workflow as described previously in relation to FIG. 130A. In some embodiments of the invention, after the skin-mounted fiducial has been registered, the user now traces the exposed bony landmarks along the spine 13023, such as the laminae 13031 via applying a probe tip 13017 of a 3D-tracked probe 13001 to the surface of the spine and tracing along the full exposed range of the spinal column 13023.

In some embodiments, FIG. 130C illustrates a perspective view of the spinal alignment assessment workflow as described previously in relation to FIGS. 130A-130B. In some embodiments of the invention, after the skin-mounted fiducial and the exposed laminae surface have been registered, the 3D-tracked probe 13001 is used to acquire the 3D location and orientation of the implanted, male-mating bone-mounted fiducial device 13025 that is attached to the sacral vertebral body 13027. In some embodiments, the design of the probe tip is such that the spherical ball tip exterior surface can be used for fiducial surface registrations, bony anatomy tracings, as well as mating with male protrusion devices of similar cross-sectional pattern. In some embodiments, FIGS. 130D-130F illustrate side views of the workflow described previously in relation to FIGS. 130A-130C. In some embodiments, any of these three components of the workflow can be conducted in isolation and do not depend on each other in all cases, and in some cases a single component or device may be used multiple times in a particular workflow of assessing spinal alignment, such as having multiple bone-mounted fiducial devices implanted and no skin-mounted fiducials, even without the tracing registration of bony landmarks within the surgical site.

Some embodiments of the invention include an X-Ray adapter device that mates in a unique orientation with a bone-mounted fiducial device. In some embodiments, the X-Ray adapter device contains radiopaque sphere fiducials used for initialization of the location and pose of nearby anatomical landmarks of interest relative to the implanted bone-mounted fiducial device. In some embodiments of the invention, the X-Ray adapter device is used to initialize the 3D location and pose of key anatomical landmarks such as S1 endplate, femoral heads, L5, L1, T10, T9, T4, T1, C1, C7, occiput, etc. to calculate spinal alignment measurements. In some embodiments, FIG. 131A illustrates a perspective of an example embodiment of the X-Ray adapter device 13101 that contains five radiopaque fiducial spheres 13117 within the fiducial body 13115, and a female mating interface (not shown) in a unique orientation. In some embodiments, the arrangement of radiopaque fiducial spheres 13117 involves an asymmetric distribution of spheres in a 3D-offset pattern that produces a unique 3D pose for all rotational views of the sphere arrangement. In some embodiments of the invention, one of the radiopaque fiducial spheres 13118 is located at the centroid of the inter-sphere arrangement of fiducial markers. In some embodiments, the location of the centroid radiopaque fiducial sphere enhances the accuracy of the registration of the fiducial's 3D pose relative to the imaging detector plane and the subsequent initialization of anatomical landmarks in the image that are desired for registration with respect to the coordinates of a 3D-tracking camera. In some embodiments, using the known distribution of radiopaque fiducial spheres (13117,13118) with respect to the origin bottom surface of the adapter device's stem 13113, and along axes in-line and orthogonal to that of the orientation indicator 13119, the registration of the bone-mounted fiducial 13103 via a 3D-tracked probe (not shown) automatically produces the coordinates of the radiopaque fiducial spheres in 3D-tracking camera coordinates. In some embodiments, a 3D rigid body transform can be calculated between the fiducial sphere coordinates relative to the fiducial centroid 13118 in X-Ray image coordinates and the location of the fiducial spheres with respect to the coordinate axes of the 3D-tracking camera. In some embodiments of the invention, the X-Ray adapter device 13101 mates with a male-protruding bone-mounted fiducial device that provides a depth-stop mating interface 13109 for reliable acquisitions of the initialized bony landmarks of interest between the X-Ray adapter device and subsequent 3D-tracked probe acquisitions.

In some embodiments, FIGS. 131B-131D illustrate top and side views of the X-Ray adapter device 13101 in the process of aligning orientations with the mating surfaces (13105,13107) of the male bone-mounted fiducial device 13103, which are described previously in relation to FIG. 131A. In some embodiments, FIG. 131E illustrates a perspective, underside view of the X-Ray adapter device as described previously in relation to FIGS. 131A-131D. In some embodiments, the female mating interface of the X-Ray adapter device 13101 feature a flat mating interface 13151 and a female cylindrical mating interface 13153.

In some embodiments, FIG. 131F illustrates a Lateral X-Ray image 13161 of the X-Ray adapter device 13165, as described previously in relation to FIGS. 131A-131E, fully engaged onto the male bone-mounted fiducial device 13108. In some embodiments, the unique arrangement of asymmetric radiopaque fiducial spheres (13117,13118) can be clearly visualized without occlusion. Some embodiments of the invention involve user input annotations of bony anatomical landmarks of interest that are to be initialized relative to the fiducial coordinate 13118 of the X-Ray adapter device 13165. In some embodiments, FIG. 131G illustrates an AP X-Ray image 13177 of the X-Ray adapter device 13165, as described previously in relation to FIGS. 131A-131F, along with the key anatomical landmarks of interest for pelvic spinal alignment parameters, including S1 coronal left and right endplate corners, femoral head centroids, and the midpoint of the S1 endplate.

Some embodiments of the invention include a 3D-tracked trackpad surface that can be utilized for controlling the display interface of the computer system while being able to move the trackpad in 3D space as a mobile mouse controller. In some embodiments, FIG. 132A illustrates one example embodiment of the invention, in which a 3D-tracked trackpad 13202 comprises a trackpad surface 13201 with pre-defined dimensions and trackpad corner locations (13209a, 13209b, 13209c, 13209d), and a 3D-tracked DRF 13207 that is mounted to the trackpad surface 13201 via a mounting bracket 13205 and alignment dowel 13208. In some embodiments, FIG. 132B illustrates a top view of an example embodiment of the invention, as described previously in relation to FIG. 132A. In some embodiments, since the dimensions of the trackpad surface 13201 are pre-defined, the location and pose of the 3D-tracked DRF 13207 enables the system to constantly calculate the 3D location and pose of the entire trackpad volume boundary.

In some embodiments, FIG. 132C illustrates a perspective view of a 3D-tracked probe 13221 with a probe tip 13227 that is in the vicinity of the defined 3D-tracked volume boundary of the initialized trackpad surface 13201. In some embodiments, the 3D-tracked probe tip 13227 does not need to be in contact with the physical surface of the trackpad 13201, and only needs to be within a threshold volume defined by the system (e.g., 5 mm away from the virtual trackpad surface), for which the probe tip projection onto the trackpad surface 13201 is calculated to manipulate the display interface without touching the trackpad surface 13201.

In some embodiments, FIG. 132D illustrates a perspective view of a 3D-tracked probe 13221 with a probe tip 13227 that is in the vicinity of the defined 3D-tracked volume boundary of the initialized trackpad, as described previously in relation to FIGS. 132A-132C. In some embodiments, the 3D-tracked probe 13241 is in an active trigger state as the trigger button 13245 is depressed and has actuated the TMSM 13247 relative to the fixed location of the DRF 13228. In some embodiments, the probe trigger event is automatically interpreted by the computer as a "mouse-click" event. In some embodiments, the 3D-tracked probe does not need to be triggered in order to register a "mouse-click" event. In some embodiments, when the probe tip 13242 is quickly brought onto the surface of the trackpad and then released after a duration less than a pre-defined threshold (e.g., 0.5 seconds), the system automatically interprets this surface tap as a "mouse-click" event.

Some embodiments of the invention involve a display interface for a spinal alignment calculation system and trackpad display monitor controller. In some embodiments, the system can receive input data from a tracing acquisition of the spine's contour using a 3D-tracked probe. In some embodiments, the acquired tracing data obtained from this embodiment can then be used to automatically compute spinal alignment parameters and intervertebral angles via processes described in relation to FIG. 141. Some embodiments of this invention are related to device systems described in relation to FIG. 130, as well as processes described in relation to FIG. 141.

In some embodiments, FIG. 133A illustrates a display interface 13300 for the spinal alignment system and trackpad display monitor controller. In some embodiments, the main user display 13301 includes components such as the trackpad display monitor controller 13309, initialization button 13311 of the trackpad display monitor controller, a selection box 13307 of the different anatomical views, the alignment parameter output box 13313 with coronal (e.g. Cobb Angle 13314) and sagittal (e.g., Lumbar Lordosis 13315) parameters, the patient's X-Ray image 13321, the instructions box to measure spinal alignment parameters 13303, and the status message box 13305. In some embodiments, the center of the main view includes another message box 13322 instructing the user to initialize the trackpad display monitor controller, and the bottom left 13319a, bottom right 13319b, top right 13319c, and top left 13319d corners of the display monitor controller initialization instructions.

In some embodiments, FIG. 133B illustrates a display interface 13325 that illustrates the bottom right 13319b and top right 13319c corners, as well as the acquired bottom left corner 13326 of the trackpad display monitor controller during the initialization process.

In some embodiments, FIG. 133C illustrates a display interface 13330 that illustrates the top right 13319c corner, as well as the acquired bottom left 13326 and bottom right 13331 corners of the trackpad display monitor controller during the initialization process.

In some embodiments, FIG. 133D illustrates a method 13335 of the trackpad display monitor controller initialization process. In some embodiments, the user traces a diagonal line 13337 in 3D camera space using a 3D-tracked probe. In some embodiments, a line segment is defined between the start and end of the diagonal tracing, and the midpoint 13339 of the line segment, as well as the point along the diagonal tracing 13341 that is farthest from the line segment are computed. In some embodiments, two normal vectors 13343 and 13345 to the diagonal tracing are computed, and this, along with predetermined desired trackpad dimensions, are used to compute the top left corner 13349 of the trackpad to generate a 3D trackpad view 13347. In some embodiments, a line segment 13351 perpendicular to the diagonal tracing and connects to the top left corner is defined. In some embodiments, using similar right triangle rules, the width and height 13355 components are computed to generate the 2D-trackpad view 13360 defined by the bottom left 13362, top left 13349, and top right 13361 corners.

In some embodiments, FIG. 133E illustrates a method 13365 of the display monitor controller initialization process. In some embodiments, the user traces an L-shaped line 13366 in 3D camera space using a 3D-tracked probe. In some embodiments, a line segment 13367 is defined between the start 13368a and end 13368c of the L-shaped tracing, and the point 13368b along the L-shaped tracing that is farthest from the line segment is computed. In some embodiments, the system automatically corrects the oblique L-shape 13370 to be a right-angle L-shape and determines the top left 13372a, bottom left 13372b, and bottom right 13372c corners of the right-angle L-shape to define the trackpad surface.

In some embodiments, FIG. 133F illustrates a display interface 13373 that illustrates the first user interface step of the alignment measuring sequence. In some embodiments, this view consists of the sub-display 13374 of the trackpad display controlling monitor, the cursor position representation 13375 within the trackpad sub-display, the active cursor 13376 controlled by the trackpad, the selected lumbar lordosis desired measurement 13377a, and a perspective view of the 3D space 13378 where the tracings will be displayed.

In some embodiments, FIG. 133G illustrates a display interface 13379 that illustrates the active cursor 13376 controlled by the trackpad hovering over the instruction box 13303 to begin measuring spinal alignment parameters, selected desired spinal alignment parameters (e.g., Lumbar Lordosis 13377a, Cobb Angle 13377b, T1 Pelvic Angle 13377c, and Thoracic Kyphosis 13377d), a perspective view of the 3D space 13378, and the Z-pattern 13380 of the skin-mounted fiducial traced using a 3D-tracked probe.

In some embodiments, FIG. 133H illustrates a method 13382 for registering the skin-mounted fiducial via 3D tracing 13380 of the Z-pattern on the top portion of the skin-mounted fiducial. In some embodiments, the 2D projection 13383 of the Z-tracing is determined. In some embodiments, the tracing is oriented in 2D for the fiducial corner detection analysis 13385, and the three turning points/corners of the Z-pattern 13384a, 13384b, and 13384c are detected. In some embodiments, the three corners define a plane 13381 of the skin-mounted fiducial, and from this, the drop-down point 13386 to a key anatomical landmark (e.g., vertebral body centroid) is computed.

In some embodiments, FIG. 133I illustrates comprising a display interface 13387 that illustrates the Z-tracing 13380 of the skin-mounted fiducial, the drop-down point 13386 to a key anatomical landmark (e.g., T1 vertebral body centroid), and the left laminae tracing 13388a.

In some embodiments, FIG. 133I illustrates a display interface 13389 that illustrates the 3D left laminae tracing 13388a and 3D right laminae tracing 13388b.

In some embodiments, FIG. 133K illustrates an example of the bilateral laminae tracing midline calculation method 13390. In some embodiments, the raw acquired 3D left 13388a and 3D right 13388b laminae tracings are projected onto the coronal plane. In some embodiments, smoothing filters are applied to each of the tracings to generate a smoothed 2D left laminae tracing 13391a and smoothed 2D right laminae tracing 13391b. In some embodiments, line segments 13392 between corresponding points from each tracing are computed, as well as the midpoints 13393 of all line segments. In some embodiments, the midpoints are them combined to form the 2D midline tracing 13391c.

In some embodiments, FIG. 133L illustrates an example of the bilateral laminae tracing midline calculation method 13394 performed in the sagittal plane, using the same method as in the coronal plane described previously in FIG. 133K. In some embodiments, smoothing filters are applied to each of the tracings to generate a smoothed 2D left laminae tracing 13391a, smoothed 2D right laminae tracing 13391b, and 2D midline tracing 13393.

In some embodiments, FIG. 133M illustrates the final output of the bilateral laminae tracing midline calculation 13395, comprising the raw 3D left laminae tracing 13388a, raw 3D right laminae tracing 13388b, and 3D midline 13393.

In some embodiments, FIG. 133N illustrates a display interface 13396 that illustrates the computed 3D midline 13393 of the raw bilateral laminae tracings.

In some embodiments, FIG. 133O illustrates a display interface 13397 that illustrates the 3D locations of the left femoral head center 13399a, right femoral head center 13399b, S1 anterior-posterior endplate line 13398a, and the S1 left-right endplate line 13398b computed via the bone-mounted fiducial registration system.

In some embodiments, FIG. 133P illustrates a display interface 133990 that illustrates the computed desired spinal alignment parameters 13399.

In some embodiments, FIG. 18Q illustrates a display interface 133992 that illustrates the sagittal plane view 133994 of the acquired bilateral tracings and computed midline, registered fiducials (i.e., skin-mounted fiducial Z-pattern 13380), and computed anatomical landmarks (i.e. drop down vertebral body centroid point 13386, left femoral head center 13399a, right femoral head center 13399b, S1 anterior-posterior line 13398a). In some embodiments, perpendicular lines 133993a, 133993b, 133993c, and 133993d are drawn at multiple discrete points acquired along the laminae tracing for which intervertebral angles are desired. Some embodiments of this invention include a sub-display of the trackpad 13374, the active cursor representation 13375 within the trackpad sub-display, the sagittal plane view box 133996a, computed spinal alignment parameters 133991, and sagittal plane X-Ray image 13321 of the patient.

In some embodiments, FIG. 133R illustrates a display interface 133995 that illustrates the coronal plane view 133996c of the acquired bilateral tracings (i.e., left laminae 13388a and right laminae tracing 13388b) and computed midline 13393, registered fiducials (i.e., skin-mounted fiducial Z-pattern 13380), and computed anatomical landmarks (i.e. drop down vertebral body centroid point 13386, left femoral head center 13399a, right femoral head center 13399b, S1 left-right line 13398b). In some embodiments, perpendicular lines 133993a, 133993b, 133993c, and 133993d are drawn at discrete points acquired along the laminae tracing for which intervertebral angles are desired. Some embodiments of this invention include the coronal plane view box 133996b, and coronal plane X-Ray image 133997 of the patient.

In some embodiments, FIG. 133S illustrates a display interface 133998 that illustrates the axial plane view 133999 of the acquired bilateral tracings (i.e., left laminae 13388*a* and right laminae tracing 13388*b*) and computed midline 13393, registered fiducials (i.e., skin-mounted fiducial Z-pattern 13380), and computed anatomical landmarks (i.e. drop down vertebral body centroid point 13386, left femoral head center 13399*a*, and right femoral head center 13399*b*). Some embodiments of this invention include the coronal plane X-Ray image 133997 of the patient.

Some embodiments of the invention involve a display interface that illustrates the registration of a rod contour and the overlay and manipulation of this contour on 2D-anatomical plane projections of registered pedicle screw tulip-head locations. Some embodiments of devices that interface with the display monitor include, but are not limited to, a rod contour registration tool attached to a rod bender (e.g., FIG. 126A) and a rod-engaged registration reference device (FIGS. 126I-126J) which when used together allow the user to trace, register, and bend the rod without using any additional tools. Some embodiments of this invention are related to device systems described in relation to FIG. 126.

In some embodiments, FIG. 134A illustrates a display interface 13400 that illustrates the 3D camera view 13402 and a status message box 13404 instructing the user to align the registration reference device with the patient in order to initialize the rod contour registration tool with the patient's anatomical axes.

In some embodiments, FIG. 134B illustrates a display interface 13406 that illustrates the 3D camera view 13402, a status message box 13410 instructing the user to register pedicle screw tulip-heads, and the discrete 3D coordinates of the registered pedicle screw tulip-heads 13408 plotted within the 3D camera space. In some embodiments of the invention, the pedicle screw tulip-heads are registered via tapping the inside of each of the tulip-heads using a 3D-tracked tool depicted, for example, in FIG. 129A.

In some embodiments, FIG. 134C illustrates a display interface 13412 that illustrates the 2D projection planes (i.e. sagittal 13416 and coronal 13418) that also aligns with the end cap registration reference device's coordinate axes and the 2D projection views (i.e., sagittal 13420 and coronal 13422) of registered pedicle screw tulip-head coordinates. Some embodiments include 2D projection views (i.e., sagittal 13424 and coronal 13426) of the end cap registration reference device. Some embodiments of the invention include a status message box 13414 instructing the user to trace the laminae region of the spine near the implanted pedicle screws.

In some embodiments, FIG. 134D illustrates a display interface 13428 that illustrates the 2D projection planes (i.e. sagittal 13416 and coronal 13418) that also aligns with the end cap registration reference device's coordinate axes and the 2D projection views (i.e., sagittal 13420 and coronal 13422) of registered pedicle screw tulip-head coordinates. Some embodiments include 2D projection views (i.e., sagittal 13424 and coronal 13426) of the end cap registration reference device, as well as the 2D projection views (i.e. sagittal 13432 and coronal 13434) of the laminae tracing filtered using a smoothing parameter. Some embodiments of the invention include a status message box 13430 instructing the user to trace the rod contour with the rod-registration tool.

In some embodiments, FIG. 134E illustrates a display interface 13436 that illustrates the 2D projection planes (i.e. sagittal 13416 and coronal 13418) that also aligns with the end cap registration reference device's coordinate axes and the 2D projection views (i.e., sagittal 13420 and coronal 13422) of registered pedicle screw tulip-head coordinates.

Some embodiments include 2D projection views (i.e., sagittal 13424 and coronal 13426) of the end cap registration reference device, as well as the 2D projection views (i.e. sagittal 13432 and coronal 13434) of the laminae tracing filtered using a smoothing parameter. Some embodiments of the invention include a status message box 13430 instructing the user to trace the rod contour with the rod-registration tool. In some embodiments of the invention, 2D projection views (i.e. sagittal 13438 and coronal 13440) of the raw rod tracing coordinates are displayed such that the beginning of the tracing snaps to the most inferior registered pedicle screw and the end of the tracing snaps to the most superior registered pedicle screw.

In some embodiments, FIG. 134F illustrates a display interface 13442 that illustrates the 2D projection planes (i.e. sagittal 13416 and coronal 13418) that also aligns with the end cap registration reference device's coordinate axes and the 2D projection views (i.e., sagittal 13420 and coronal 13422) of registered pedicle screw tulip-head coordinates. Some embodiments include 2D projection views (i.e., sagittal 13424 and coronal 13426) of the end cap registration reference device, as well as the 2D projection views (i.e. sagittal 13432 and coronal 13434) of the laminae tracing filtered using a smoothing parameter. In some embodiments of the invention, 2D projection views (i.e. sagittal 13446 and coronal 13448) of the smoothed rod tracing coordinates are displayed such that the beginning of the tracing snaps to the most inferior registered pedicle screw and the end of the tracing snaps to the most superior registered pedicle screw. Some embodiments of the invention include indicating to the user which pedicle screws are aligned with the current rod contour (e.g., in the form of a different color plot of the aligned pedicle screw) in both the sagittal 13450 and coronal 13452 projection views. Some embodiments of the invention include a status message box 13444 indicating to the user the number of pedicle screws that the rod is aligned to.

In some embodiments, FIG. 134G illustrates a display interface 13454 that illustrates the 2D projection planes (i.e. sagittal 13416 and coronal 13418) that also aligns with the end cap registration reference device's coordinate axes and the 2D projection views (i.e., sagittal 13420 and coronal 13422) of registered pedicle screw tulip-head coordinates. Some embodiments include 2D projection views (i.e., sagittal 13424 and coronal 13426) of the end cap registration reference device, as well as the 2D projection views (i.e. sagittal 13432 and coronal 13434) of the laminae tracing filtered using a smoothing parameter. In some embodiments of the invention, the user, at this point, utilizes the rod bender attached to the rod-registration tool to bend the rod into a conformation that better aligns with the implanted pedicle screws, and acquires a tracing of the rod in its new conformation. In some embodiments of the invention, 2D projection views (i.e. sagittal 13456 and coronal 13458) of the new, raw rod tracing coordinates are displayed such that the beginning of the tracing snaps to the most inferior registered pedicle screw and the end of the tracing snaps to the most superior registered pedicle screw.

In some embodiments, FIG. 134H illustrates a display interface 13460 that illustrates the 2D projection planes (i.e. sagittal 13416 and coronal 13418) that also aligns with the end cap registration reference device's coordinate axes. Some embodiments include 2D projection views (i.e., sagittal 13424 and coronal 13426) of the end cap registration reference device, as well as the 2D projection views (i.e. sagittal 13432 and coronal 13434) of the laminae tracing filtered using a smoothing parameter. In some embodiments of the invention, 2D projection views (i.e. sagittal 13464 and coronal 13466) of the new, smoothed rod tracing coordinates are displayed such that the beginning of the tracing snaps to the most inferior registered pedicle screw and the end of the tracing snaps to the most superior registered pedicle screw. In some embodiments, all of the registered pedicle screw coordinates (i.e., sagittal 13468 and coronal 13470) align with the new rod contour, indicated by all of the pedicle screw location plots being a green color, or some other form of visual indication. Some embodiments of the invention include a status message box 13462 indicating to the user that the rod is now aligned to all of the registered pedicle screw implants.

Some embodiments of the invention involve a display interface that displays the position and orientation of vertebrae with respect to the patient's anatomical axes. In some embodiments, the displayed vertebrae are implanted with bone-mounted fiducials and registered via a unique mating mechanism with the fiducial-registration probe system. In some embodiments, device systems that interface with the display include, but are not limited to, the bone-mounted fiducial (e.g., FIGS. 124A-124C) and the fiducial-registration probe (e.g., FIG. 125). Some embodiments of this invention are related to device systems described in FIGS. 117-125 as well as processes described in FIG. 139.

In some embodiments, FIG. 135A illustrates a display interface 13500 that illustrates a 3D volume 13502 defining the patient's anatomical axes. Some embodiments of the display interface include a status message box 13504 instructing the user to register the sacrum.

In some embodiments, FIG. 135B illustrates a display interface 13506 that illustrates a 3D volume 13502 defining the patient's anatomical axes and the sacrum 13508 registered using the fiducial-registration probe, displayed in the form of a 3D mesh rendering. Some embodiments of the display interface include a status message box 13510 instructing the user to register the L5 vertebra.

In some embodiments, FIG. 135C illustrates a display interface 13512 that illustrates a 3D volume 13502 defining the patient's anatomical axes and the sacrum 13508 and L5 vertebra 13514 registered using the fiducial-registration probe, displayed in the form of 3D mesh renderings. Some embodiments of the display interface include a status message box 13516 instructing the user to register the L4 vertebra.

In some embodiments, FIG. 135D illustrates a display interface 13518 that illustrates a 3D volume 13502 defining the patient's anatomical axes and the sacrum 13508, L5 vertebra 13514, and L4 vertebra 13520 registered using the fiducial-registration probe, displayed in the form of 3D mesh renderings. Some embodiments of the display interface include a status message box 13522 instructing the user to register the L3 vertebra.

In some embodiments, FIG. 135E illustrates a display interface 13524 that illustrates a 3D volume 13502 defining the patient's anatomical axes and the sacrum 13508, L5 vertebra 13514, L4 vertebra 13520, and L3 vertebra 13526 registered using the fiducial-registration probe, displayed in the form of 3D mesh renderings. Some embodiments of the display interface include a status message box 13528 instructing the user to register the L2 vertebra.

In some embodiments, FIG. 135F illustrates a display interface 13530 that illustrates a 3D volume 13502 defining the patient's anatomical axes and the sacrum 13508, L5 vertebra 13514, L4 vertebra 13520, L3 vertebra 13526, and L2 vertebra 13532 registered using the fiducial-registration probe, displayed in the form of 3D mesh renderings. Some embodiments of the display interface include a status message box 13534 instructing the user to register the L1 vertebra.

In some embodiments, FIG. 135G illustrates a display interface 13536 that illustrates a 2D sagittal plane view 13538 and the current conformation of the patient's lumbar spine 13533, comprising the registered sacrum 13508, L5 vertebra 13514, L4 vertebra 13520, L3 vertebra 13526, L2 vertebra 13532, and L1 vertebra 13537. Some embodiments of the display interface include a status message box 13540 indicating that the user is seeing the sagittal plane view.

In some embodiments, FIG. 135H illustrates a display interface 13542 that illustrates a 2D coronal plane view 13544 and the current conformation of the patient's lumbar spine 13533, comprising the registered sacrum 13508, L5 vertebra 13514, L4 vertebra 13520, L3 vertebra 13526, L2 vertebra 13532, and L1 vertebra 13537. Some embodiments of the display interface include a status message box 13546 indicating that the user is seeing the coronal plane view.

In some embodiments, FIG. 135I illustrates a display interface 13548 that illustrates a 2D axial plane view 13550 and the current conformation of the patient's lumbar spine 13533, comprising the registered sacrum 13508, L5 vertebra 13514, L4 vertebra 13520, L3 vertebra 13526, L2 vertebra 13532, and L1 vertebra 13537. Some embodiments of the display interface include a status message box 13552 indicating that the user is seeing the axial plane view.

In some embodiments, FIG. 135J illustrates a display interface 13554 that illustrates a 2D sagittal plane view 13538. In some embodiments, the vertebrae of the lumbar spine have been moved in relation to each other during the spinal alignment correction surgery and re-registration of fiducial-implanted vertebra allows the user to view the new, precise location and orientation of the patient's lumbar spine. Some embodiments of the display interface include a status message box 13556 instructing the user to re-register the sacrum.

In some embodiments, FIG. 135K illustrates a display interface 13558 that illustrates a 2D sagittal plane view 13538 and the sacrum 13508 registered using the fiducial-registration probe, displayed in the form of a 3D mesh rendering. Some embodiments of the display interface include a status message box 13510 instructing the user to register the L5 vertebra.

In some embodiments, FIG. 135L illustrates a display interface 13562 that illustrates a 2D sagittal plane view 13538 and the lumbar spine in its new conformation 13564 registered using the fiducial-registration probe, displayed in the form of a 3D mesh rendering. Some embodiments of the display interface include a status message box 13540 indicating that the user is seeing the sagittal plane view.

Some embodiments of this invention involve a display interface that illustrates the live position of tool-engaged vertebrae while they are manipulated (e.g., flexibility assessment), displayed in the form of 3D mesh renderings of the manipulated vertebrae. Some embodiments of the system that interfaces with the display monitor includes, but is not limited to, one or more flexibility assessment tools (e.g., FIG. 127D) engaged, directly or indirectly, with vertebrae and/or other anatomical landmarks of interest. In some embodiments, this system of actively manipulating engaged vertebrae is illustrated previously in FIGS. 128D-128D. Some embodiments of this invention are related to device systems described in FIGS. 127-129.

In some embodiments, FIG. 136A illustrates a display interface 13600 that illustrates the 3D perspective view 13602 of the vertebrae engaged with flexibility assessment tool #1 13606 and tool #2 13608. Some embodiments of the display interface include a status message box 13604 that tells the user that the displayed vertebrae are updated in real time as the user moves around the flexibility assessment tools.

In some embodiments, FIG. 136B illustrates a display interface 13610 that illustrates the 3D perspective view 13602 of the vertebrae engaged with flexibility assessment tool #1 13612 and tool #2 13614. Some embodiments of the system display the vertebrae in a different color from those described in relation to FIG. 136A to indicate that both of the flexibility assessment tools are triggered, and the real-time manipulation of the vertebrae is now being actively recorded for making angular measurements. Some embodiments of the display interface include a status message box 13604 that tells the user that the displayed vertebrae are updating in real time as the user moves around the flexibility assessment tools.

In some embodiments, FIG. 136C illustrates a display interface 13616 that illustrates a 2D sagittal plane view 13618 in which the displayed vertebrae 13622 and 13624 represent the maximum lordosis angle achieved during the live dual-triggered acquisition with the flexibility assessment tools. Some embodiments of the display interface include a status message box 13620 that displays the value of the maximum lordosis angle achieved.

In some embodiments, FIG. 136D illustrates a display interface 13626 that illustrates a 2D sagittal plane view 13618 in which the displayed vertebrae 13630 and 13632 represent the maximum kyphosis angle achieved during the live dual-triggered acquisition with the flexibility assessment tools. Some embodiments of the display interface include a status message box 13628 that displays the value of the maximum kyphosis angle achieved.

In some embodiments, FIG. 136E illustrates a display interface 13634 that illustrates a 2D coronal plane view 13635 in which the displayed vertebrae 13638 and 13640 represent the maximum left Cobb angle achieved during the live dual-triggered acquisition with the flexibility assessment tools. Some embodiments of the display interface include a status message box 13636 that displays the value of the maximum left Cobb angle achieved.

In some embodiments, FIG. 136F illustrates a display interface 13642 that illustrates a 2D coronal plane view 13635 in which the displayed vertebrae 13646 and 13648 represent the maximum right Cobb angle achieved during the live dual-triggered acquisition with the flexibility assessment tools. Some embodiments of the display interface include a status message box 13644 that displays the value of the maximum right Cobb angle achieved.

In some embodiments, FIG. 136G illustrates a display interface 13650 that illustrates a 2D axial plane view 13651 in which the displayed vertebrae 13654 and 13656 represent the maximum clockwise twist angle achieved during the live dual-triggered acquisition with the flexibility assessment tools. Some embodiments of the display interface include a status message box 13652 that displays the value of the maximum clockwise twist angle achieved.

In some embodiments, FIG. 136H illustrates a display interface 13656 that illustrates a 2D axial plane view 13651 in which the displayed vertebrae 13660 and 13662 represent the maximum counter-clockwise twist angle achieved during the live dual-triggered acquisition with the flexibility assessment tools. Some embodiments of the display interface include a status message box 13658 that displays the value of the maximum counter-clockwise twist angle achieved.

In some embodiments, FIG. 136I illustrates a display interface 13664 that illustrates a 3D perspective view 13602 in which the displayed vertebrae 13668 and 13670 is showing the replay of the live dual-triggered acquisition. Some embodiments of the display interface include a status message box 13666 that tells the user that a replay of the live dual-triggered acquisition is being displayed.

In some embodiments, FIG. 21J illustrates a sagittal plane X-Ray image 13690 taken of the flexibility assessment tool #1 attached to the L2 vertebra 13686 and tool #2 attached to the L3 vertebra 13688. In some embodiments, this X-Ray initialization of the handle-to-vertebra angle is only required for surgeries that are not being conducted with the use of image-guided navigation and processes by which the location of key anatomical landmarks is already provided in 3D space. In some embodiments, key measurement landmarks are annotated, including the handle angles of tool #1 13674 and the handle of tool #2 13676, the alignment pin angles of tool #1 13678 and tool #2 13680, and the superior endplates of L2 vertebra 13682 and L3 vertebra 13684. In some embodiments of the invention, these described initialization landmarks of the handle-to-vertebrae offsets can be acquired via manual user-annotated lines, computer vision edge detection, automated method of initializing DRF angle relative to vertebral endplates via image-guided navigation, etc. In some embodiments, the same handle-to-vertebrae offset initialization occurs for the AP X-Ray image (not shown), in which the handle and alignment pins of each attached flexibility assessment device is compared to the coronal X-Ray projection of the vertebral endplate. In some embodiments, once these X-Ray-based initializations are completed, manipulating the engaged, initialized flexibility assessment devices generate automated, real-time measurements of the inter-vertebral endplate angles for all initialized anatomical axes. In some embodiments, the handle-to-vertebra offset angles can be initialized via registration of fiducial devices such as the bone-mounted fiducial, which can be initialized either via X-Ray images of its associated X-Ray adapter device or image-guided navigation registration.

In some embodiments, after X-Ray-based initialization define the 3D geometric relations between the 3D-tracked handles of the flexibility assessment devices, the system can display the real-time inter-vertebral assessment view to the user via any of the following outputs: polygonal representation of vertebrae based on normative data, polygonal representation of vertebrae based on registered endplate angles and distances relative to the nearby, attached flexibility assessment device, cropped sections of the respective X-Ray image that show only the segmented vertebra of interest for each attached flexibility assessment device.

Some embodiments of this invention involve the process of calculating the 3D midline of bilateral tracings of the spine, which will be used as the contour from which the patient's spinal alignment parameters are calculated. In some embodiments, FIG. 137 shows a workflow 13700 for acquiring bilateral tracings (e.g., left and right laminae) of the spine exposed within the surgical site, applying a smoothing filter to each tracing, and computing the midpoints of corresponding perpendicular vectors between tracings. In some embodiments, a tracing acquisition can be depicted in, but is not limited to, FIGS. 130D-130F, in which the laminae of the spine are traced from the C7 vertebra superiorly to the sacrum inferiorly. In some embodiments, a software display of the acquired bilateral tracings and computed midline can be depicted in, but is not limited to, FIGS. 133N-133S. In some embodiments, relevant system figures include example embodiments of device systems in FIG. 130 and embodiments of processes in FIG. 133.

Some embodiments involve projecting the 3D coordinates of the bilateral tracings on to 2D-anatomical planes such as the coronal (e.g., FIG. 133K) and coronal planes (e.g., FIG. 133L). In some embodiments, for each anatomical plane, some embodiments involve fitting a smoothing spline to the bilateral tracings and increasing their point density to filter out jaggedness of the raw acquired coordinates (e.g., FIGS. 133K-133L). In some embodiments, for each anatomical plane, some embodiments include selecting one side of the bilateral tracings, computing the midpoint between each adjacent point along the selected tracing, and computing perpendicular vectors that originate from each midpoint and shoot in the direction of the contralateral tracing. In some embodiments, for each anatomical plane, some embodiments involve determining the point along the contralateral tracing that is the closest distance to the perpendicular vector. In some embodiments, for each anatomical plane, some embodiments involve defining a line segment between the determined closest-distance point and the starting point of the perpendicular vector. In some embodiments, for each anatomical plane, some embodiments involve computing the midpoint of the defined line segment (e.g., FIGS. 133K-133L).

In some embodiments, for each anatomical plane, some embodiments involve determining the coordinate indices that define the overlapping regions of each 2D-midline along a common axis. In some embodiments, for each anatomical plane, some embodiments involve truncating each 2D-midline according to the defined common-axis indices and evaluating each truncated tracing at the same set of common-axis indices to ensure that each side of the smoothed bilateral tracing has the same number of points. Some embodiments include combining the unique components (e.g., x-coordinate from coronal plane, y-coordinate from sagittal plane, and z-coordinate from sagittal plane) of the 2D-midline tracings from each anatomical plane to generate a smoothed 3D-midline tracing (e.g., FIG. 133M). Some embodiments may include, in the case that each side of the bilateral tracings already has the same number of points, simply taking the average of the corresponding x-, y-, and z-coordinates in order to compute the 3D-midline tracing.

In some embodiments, any of the above processes, methods, or procedures related to the workflow 13700 can include or be accomplished with one or more of steps or processes such as 13700, 13702, 13704, 13706, 13708, 13710, 13712, 13714, 13716, 13718, 13720, 13722, and 13724. In some embodiments, the steps of workflow 13700 can proceed in the order as shown. In some embodiments, any of the steps of the workflow 13700 can proceed out of the order as shown. In some embodiments, one or more of the steps of the workflow 13700 can be skipped.

Some embodiments of this invention involve the process of detecting the pose of radiopaque markers of a fiducial from a series of multi-planar X-Ray images and initializing the 3D location and pose of nearby anatomical landmarks of interest relative to the centroid of each associated fiducial device. In some embodiments, FIG. 138 shows a workflow 13800 to calculate the rotational transform of a fiducial in each X-Ray image based on the fiducial labels and apply these transformations to the annotated landmarks. Some embodiments for labelling the fiducial include a manual user input of each sphere's diameter and an automatic detection of sphere center and diameter.

Some embodiments of the system involve the creation of and iteration through a database of rotation matrices and their subsequent effects on the fiducial coordinates with respect to the centroid. Some embodiments of the system involve the comparison of these coordinates to the fiducial labels of the X-Ray images and determining the rotation matrix that observes the minimal discrepancy. Some embodiments of the system involve applying an inverse rotation to all landmarks annotated in order to create a 3D vector with respect to a predetermined observation plane. Some embodiments of the system involve combining the 3D vectors of the landmarks and fiducial annotations from all X-Ray views to obtain an accurate 3D distance measure from the centroid of the fiducial.

Some embodiments of the system involve automatically converting the location of the fiducial radiopaque spheres from centroid coordinates to camera coordinates through the application of a rigid body transform to transform all 3D vectors. Some embodiments of the system involve computing spinal alignment parameters and conducting biomechanical analyses from the registered landmarks. Some embodiments of the system allow for adjustment of the spine during surgery and acquisition of the new 3D vectors of landmarks without requiring additional images to be taken.

In some embodiments, any of the above processes, methods, or procedures related to the workflow 13800 can include or be accomplished with one or more of steps or processed such as 13802, 13804, 13806, 13808, 13810, 13812, 13814, 13816, 13818, 13820, 13822, 13824, 13826, 13828, 13830, 13832, 13834, 13836, 13838, 13840, 13842, 13844, 13846, 13848, 13850, 13852, 13854, 13856, 13858, 13860, 13862, 13864, 13866, 13868, 13870, 13872, 13874, 13876, 13878, 13880, 13882, 13884. In some embodiments, at least one of the steps can include a decision step (e.g., such as step 13862), where one or more following steps depend on a status, decision, state, or other condition. In some embodiments, the steps of workflow 13800 can proceed in the order as shown. In some embodiments, any of the steps of the workflow 13800 can proceed out of the order as shown. In some embodiments, one or more of the steps of the workflow 13800 can be skipped.

Some embodiments of this invention involve the process 13900 of initializing the 3D location and pose of bone-mounted fiducials implanted into vertebrae of the spine, registering key anatomical landmarks required for making spinal alignment measurements using the initialized bone-mounted fiducials, and computing desired spinal alignment measurements. In some embodiments, relevant figures include example embodiments of device systems in FIGS. 117-125 and embodiments of processes in FIG. 135.

Some embodiments of the system involve the implantation of bone-mounted fiducial devices into each vertebra that is involved is desired spinal alignment parameter calculations and thus must be registered in 3D space. Some embodiments of the bone-mounted fiducial registration process pertain to image-guided surgeries, whereby the vertebrae of the spine are automatically segmented from volumetric imaging (e.g. CT scan, etc.). In some embodiments, the user registers the 3D location and pose of implanted bone-mounted fiducials using a 3D-tracked probe, and the system computes a 3D rigid body transform between the vertebrae segmented from volumetric imaging and the vertebrae implanted and registered using bone-mounted fiducials. Some embodiments of the bone-mounted fiducial registration process pertain to non-image-guided surgeries, whereby the 3D spatial location and orientation of vertebrae are not known through volumetric imaging. In some embodiments, the user acquires two or more X-Rays of the bone-mounted fiducials with X-Ray adapter devices mated with each bone-mounted fiducial, in order to initialize a 3D displacement vector between the bone-mounted fiducial and anatomical landmarks of interest. Some embodiments of the invention involve displaying to the user the 3D meshwork of registered vertebra or other anatomical landmarks (e.g., endplate lines), as depicted previously in relation to FIG. 135.

Some embodiments of this invention involve the step of identifying which vertebra each bone-mounted fiducial is implanted into, via user software input, unique engagement depth of the 3D-tracked probe, a predetermined order of implanted bone-mounted fiducials, or a normative path length segmentation of tracings of the spine's contour.

Some embodiments of the invention include computing the desired 3D spinal alignment parameters from the 3D location and pose of vertebrae and other key anatomical landmarks (e.g., femoral heads, vertebral body centroids, etc.) registered via the bone-mounted fiducial. Some embodiments of the invention allow the user to toggle the display interface view of the registered vertebrae between perspective, sagittal, coronal, and axial plane view by triggering the 3D-tracked probe.

Some embodiments of the invention allow the user to continue manipulating the vertebrae and quickly obtain the most up-to-date 3D spinal alignment parameters by re-registering the implanted bone-mounted fiducials, until the displayed alignment parameters meet the surgeon's operative goals.

In some embodiments, any of the above processes, methods, or procedures related to the workflow 13900 can include or be accomplished with one or more of steps or processed such as 13902, 13904, 13906, 13908, 13910, 13912, 13914, 13916, 13918, 13920, 13922, 13924, 13926, 13928, 13930, 13932, 13934, 13936, 13938, 13940, 13942, 13944, 13946, 13948, 13950, 13952. In some embodiments, at least one of the steps can include a decision step (e.g., such as step 13936), where one or more following steps depend on a status, decision, state, or other condition. In some embodiments, the steps of workflow 13900 can proceed in the order as shown. In some embodiments, any of the steps of the workflow 13900 can proceed out of the order as shown. In some embodiments, one or more of the steps of the workflow 13900 can be skipped.

Some embodiments of this invention involve the definition of a surface as a virtual trackpad to utilize a 3D-tracked probe to control the interface in real-time. In some embodiments, FIG. 140 shows a workflow 14000 comprising ways to initialize the virtual trackpad as well as to control the mouse cursor while the user navigates the interface with the 3D-tracked probe.

Some embodiments of the system involve the use of a trackpad with an attached DRF where the system automatically calculates and updates the coordinates of the four trackpad corners throughout the surgery.

Some embodiments of the system involve the definition of the four trackpad corners through the acquisition of three points as depicted in FIGS. 133A-133C. In some embodiments, the coordinates of the three points on any surface define the bottom left, bottom right and top right corners of the virtual trackpad.

Some embodiments of the system involve the definition of the four trackpad corners by tracing a diagonal line with the 3D-tracked probe on a surface as depicted in FIG. 133D. In some embodiments, the starting point of the tracing defines the bottom left corner while a final tracing point defines the top right corner of the virtual trackpad. In some embodiments, by setting a desired trackpad dimension, the virtual width and height of the trackpad is calculated from the traced diagonal. In some embodiments, using similar right triangle geometry principles and these calculated width and height values, the magnitude of the horizontal and vertical offsets of the top left corner with respect to the diagonal is determined. In some embodiments, under the assumption that the user will not draw a perfectly straight line, three points on the raw diagonal tracing is used to define the virtual plane of the trackpad. In some embodiments, after defining a vector from the diagonal to the top left corner of the trackpad, the coordinates of this corner are determined.

Some embodiments of the system involve the definition of the four trackpad corners by drawing an L-shaped curve on a surface as shown in FIG. 133E. In some embodiments, the starting point of the drawing defines the top left corner while the final point defines the bottom right corner of the virtual trackpad. In some embodiments, the bottom left corner of the trackpad is determined by selecting the coordinate with the greatest distance from the diagonal created by connecting the starting and ending coordinates of the L-shaped curve. In some embodiments, three corners define the trackpad boundaries and may be adjusted to ensure the virtual trackpad contains right angles. In some embodiments, if the original corners define the an acute angle, the bottom left corner is adjusted. In some embodiments, if the original corners define an obtuse angle, the top left corner is adjusted. In some embodiments, after the three corners are defined using these methods, a 3D rigid body transform is used to calculate the coordinates of the four corners in navigation camera coordinates.

In some embodiments, after the virtual trackpad is initialized, whenever the 3D tracked probe tip enters the defined 3D volume, the probe tip is mapped to the monitor and allows the user to control the interface's mouse as well as signal "mouse clicks" as described in workflow 14000.

In some embodiments, any of the above processes, methods, or procedures related to the workflow 14000 can include or be accomplished with one or more of steps or processed such as 14002, 14004, 14006, 14008, 14010, 14012, 14014, 14016, 14018, 14020, 14022, 14024, 14026, 14028, 14030, 14032, 14034, 14036, 14038, 14040, 14042, 14044, 14046, 14048, 14050, 14052. In some embodiments, at least one of the steps can include a decision step (e.g., such as step 14002), where one or more following steps depend on a status, decision, state, or other condition. In some embodiments, the steps of workflow 14000 can proceed in the order as shown. In some embodiments, any of the steps of the workflow 14000 can proceed out of the order as shown. In some embodiments, one or more of the steps of the workflow 14000 can be skipped.

Some embodiments of the invention involve the process of intraoperatively computing the patient's spinal alignment via one or more of modalities including registration of a bone-mounted fiducial device, skin-mounted fiducial device, bilateral tracing of the exposed laminae, and/or discrete laminae vertebral level identity acquisitions. In some embodiments, the latter two modalities can be depicted in, but is not limited to, FIGS. 130D-130F, in which the Z-pattern of the skin-mounted fiducial is traced, followed by tracing of the laminae of the spine from the superior C7 vertebra to the inferior sacrum. In some embodiments, relevant systems include those previously described in relation to FIGS. 116-126 and FIGS. 130-132, as well as display interfaces described in relation to FIG. 133.

Some embodiments of the invention involve the use of bone-mounted fiducials, when the vertebrae involved in spinal alignment calculations are already exposed within the surgical site. In some embodiments, any of the steps of workflow processes described previously in relation to FIG. 139 and display interfaces described previously in relation to FIG. 135 may take place in order to register the precise 3D location and pose of the vertebra implanted with a bone-mounted fiducial device.

Some embodiments of the invention involve the use of a skin-mounted fiducial, when the vertebra involved in spinal alignment calculations is not exposed within the surgical site and the surgeon does not have physical access to the vertebra of interest. In some embodiments, the user applies an adhesive-backed fiducial onto the skin near the vertebra of interest and acquires two or more X-Ray images of the skin-mounted fiducial from oblique or orthogonal views. In some embodiments, after annotating key anatomical landmarks in the X-Ray images, a 3D displacement vector is computed between the skin-mounted fiducial and the anatomical landmarks of interest. In some embodiments, the 3D location and pose of the skin-mounted fiducial is registered with a 3D-tracked probe, via three or more detents on the fiducial surface, tracing of a unique Z-pattern (e.g., FIG. 130), or a unique mechanical mating of the probe with the fiducial. In some embodiments, the 3D rigid body transform is then computed between the skin-mounted fiducial's radiopaque spheres and those in camera coordinates determined from the manufactured geometric design of the fiducial. In some embodiments, the rigid body transform is then used to compute the 3D locations and poses of anatomical landmarks of interest in 3D-tracking camera coordinates.

Some embodiments of the invention include acquiring bilateral (e.g. left and right laminae) tracings of the spine using a 3D-tracked probe, when the vertebrae involved in spinal alignment calculations are neither registered using the bone-mounted fiducial nor the skin-mounted fiducial. In some embodiments, any of the steps of workflow processes described previously in relation to FIG. 137 and display interfaces described previously in relation to FIG. 133 may take place in order to calculate the 3D midline of the bilateral tracings. In some embodiments the user then acquires two or more discrete points within the traced region to indicate the levels for which intervertebral angle calculations are desired.

In some embodiments, after all of the vertebrae involved in desired spinal alignment calculations are registered in 3D space via one or more of the modalities described above, some embodiments of the invention involve computing the spinal alignment calculations and displaying them to the user. In some embodiments, one or more of the above steps are repeated until operative goals of the alignment correction are achieved. In some embodiments, the system does not require any additional initialization steps beyond the first set of processes for localizing anatomical landmarks to fiducial devices or bony-landmark-based tracings of the exposed spine, and can continue producing real-time measurements of spinal alignment throughout surgery without additional X-Ray images or complex registration steps.

In some embodiments, any of the above processes, methods, or procedures related to the workflow 14100 can include or be accomplished with one or more of steps or processed such as 14102, 14104, 14106, 14108, 14110, 14112, 14114, 14116, 14118, 14120, 14122, 14124, 14126, 14128, 14130, 14132, 14134, 14136, 14138, 14140, 14142, 14144, 14146, 14148, 14150, 14152, 14154, 14156, 14158, 14160, 14162. In some embodiments, at least one of the steps can include a decision step (e.g., such as step 14140), where one or more following steps depend on a status, decision, state, or other condition. In some embodiments, the steps of workflow 14100 can proceed in the order as shown. In some embodiments, any of the steps of the workflow 14100 can proceed out of the order as shown. In some embodiments, one or more of the steps of the workflow 14100 can be skipped.

In some embodiments of the invention, current spinal alignment measurements during surgery are compared to measurements from a large database of prior patients with similar indications and surgical procedure types to identify how the current measurements correspond with data-driven success outcomes for surgical corrections. In some embodiments, the system compares the current patient's demographics and current alignment measurements to normative and historical databases. Some embodiments of the invention enable prior measurements acquired preoperatively or from prior surgeries to be compared to current alignment measurements. In some embodiments, the surgeon can stratify the available database comparison by time period (e.g., last 5 years, last 1 year, last 6 months), surgeon's colleagues (e.g., within the same hospital or within other hospital systems), thresholds for success set by trusted specialty groups (e.g., international spine study group), key opinion leaders in the field (e.g., match to similar patients that identified 'experts' have previously operated on), all patients, etcera. In some embodiments, the system stratifies the database according to the type of surgical approach currently being attempted (e.g., posterior open fusion from T12 to pelvis). In some embodiments, machine learning algorithms such as support vector machines, deep-learning, decision forests, convolutional neural networks, etc., can be applied to the above discussed input variables of the database to aid in predicting how the patient may appear after surgery and assessing standing balance alignment parameters (e.g., predicting SVA, PT, SS, LL, TK, etc.). In some embodiments, the system constantly updates the database according to new surgeries and patient data profiles that are submitted into the system, further enabling the algorithms to fine tune hyperparameters for optimal accuracy of predictive analytics, including preoperative planning recommendations, intraoperative report card analyses, and postoperative feedback on achieved results.

Some embodiments of the invention include a 3D-tracked probe and bone-mounted fiducial which when used together can continuously update the registration of anatomical landmarks of interest without the need for excessive X-Ray imaging or workflow delays. In some embodiments, the fiducial marker can rigidly attach to any bony anatomical landmark in the body and serves as a registerable marker that, once initialized, can provide the 3D location and pose of any component of the landmark (e.g., vertebral endplate, femoral head centroid, etc.) without the need for additional imaging. In some embodiments, the fiducial's location and pose can be registered with a 3D-tracked probe, 3D-tracked DRF, robotic end effector, optical scanner, or any other localization tool.

In some embodiments, FIG. 142A illustrates an assembly 14200 of the 3D-tracked probe 14202 and the bone-mounted, unregistered fiducial 14218*a*. In some embodiments, the bone-mounted fiducial utilizes screw threads 14219 to rigidly attach to a bony landmark of interest. In some embodiments, the fiducial also comprises an asymmetric, unique registration interface. In some embodiments, the fiducial's registration interface is a tapered, semi-cylindrical protrusion 14217 that only enables for registration from one precise 3D pose. In some embodiments, the 3D-tracked probe 14202 comprises a shaft 14204, probe tip 14214*a* with an orientation indicator 14215 for the user's visual reference, trigger button (undepressed) 14206, 3D-tracked DRF 14208 that contains a unique configuration of three or more 3D-tracked markers 14209, TMSM (unde-pressed) 14210, TMSM mount (undepressed) 14212, and a fiducial-mating interface 14216. In some embodiments, the probe's female, fiducial-mating interface is also tapered, like the fiducial's tapered male registration interface. In some embodiments, this process enables for rapid, yet still accu-rate, registration of the fiducial with less pressure on the user to accurately align the two devices for the mating process.

In some embodiments, FIG. 142B illustrates an assembly 14220 of the 3D-tracked probe 14222 engaged with the fiducial 14218*a*, and ready for the registration trigger event. In some embodiments, once the user determines that the 3D-tracked probe 14222 is fully engaged with the fiducial 14218*a*, they can depress the trigger button 14206 to actuate the rigidly-linked TMSM 14210 linearly away from the probe's DRF 14208. In some embodiments, once the trigger is depressed, the system calculates the TMSM's 14210 relative positive from the DRF 14208 and determines if its 3D location relative to the origin of the DRF 14208 is beyond a determined threshold to define the probe to be in an active state. In some embodiments, FIG. 142B illustrates the 3D-tracked probe 14222 in the inactive state as the trigger button 14206 has yet to be depressed. In some embodiments, FIG. 142C illustrates an assembly of the 3D-tracked probe 14228 engaged with the registered fiducial 14218*b*. In some embodiments, the user depresses the trig-ger 14229 and actuates the rigidly-linked TMSM 14227 far enough from the DRF 14208 for the system to automatically determine that the probe's state is now "active" and to record the 3D location and pose of the fiducial 14218*b*.

In some embodiments, FIGS. 142D and 142E illustrate a sub-assembly (14230, 14235) of the 3D-tracked probe tip (14214*a*, 14214*b*) and a bone-mounted fiducial (14218*a*, 14218*b*) in the mating registration process. In some embodi-ments, the probe tip 14214*a* contains a tapered, female fiducial-mating interface 14216 that can accept a wider range of 3D orientations for initial mating between the probe and fiducial to commence, and then the tolerance between the probe's mating interface 14216 and the fiducial's mating interface 14217 gets much smaller and ensures an accurate, reliable registration. In some embodiments, the fiducial's tapered mating interface 14217 can involve a variety of possible draft angles and divisions of the taper to ensure reliable mating.

In some embodiments, FIG. 142F illustrates a cutaway view 14240 of the mated assembly between the probe tip 14214*b* and the fiducial 14218*b*. In some embodiments, the fiducial's tapered mating interface 14217 is tightly encap-sulated by the probe's mating interface to ensure very little wobble and robust reliability for mating the two devices together many times.

In some embodiments, FIG. 142G illustrates a 3D view 14245 of a bone-mounted fiducial 14252 with a spring-loaded detent within its probe-mating interface. In some embodiments, the fiducial 14252 comprises screw threads 14254, a male mating interface with a flat face 14247 and a round face 14249 and a spring-loaded detent 14251 (spring not shown), and a depth-stop surface 14253. In some embodiments, the spring-loaded detent 14251 is used to reduce the tolerance gap with another device (e.g., 3D-tracked probe, X-Ray adapter device (not shown), etc.) during the mating process. In some embodiments, FIG. 142H illustrates a 2D cutaway view 14255 of a bone-mounted fiducial 14252 with a spring-loaded detent within its probe-mating interface. In some embodiments, the fidu-cial's mating interface involves a detent 14251 that is protruding from the flat face 14247 and its tension is support by an internal spring 14257 that presses the detent 14251 against a device the fiducial intends to mate with.

In some embodiments, FIGS. 1421 and 1421 illustrate 3D views (14260, 14265) of a bone-mounted fiducial with a friction-inducing surface for interfacing with bony tissue. In some embodiments, the fiducial 14264 comprises screw threads 14263, a male mating interface with a flat face 14247 and a round face 14249, and a friction-inducing surface 14262 for interfacing with bony tissue. In some embodi-ments, the friction-inducing surface 14262 can consist of a lock washer or spikes to bolster fixation and security (e.g., mitigating motion such as twisting) of the fiducial's attach-ment to a bony landmark of interest.

In some embodiments, FIGS. 142K and 142L illustrate 3D views (14270, 14271) of a bone-mounted fiducial with a long shaft for attaching the fiducial to bony landmarks via a percutaneous approach. In some embodiments, the long-shaft fiducial 14272 comprises screw threads 14263, tapered cutting flute 14273, a smooth shaft 14274, and a mating interface 14247. In some embodiments, a long-shaft fiducial 14272 is used to attach a fiducial marker to an underlying bony landmark of interest via a percutaneous, minimally-invasive approach in which the long shaft traverses layers of tissue until the fiducial can securely engage the bony anatomy via its screw threads 14263.

Some embodiments of the invention involve using a bone-mounted fiducial to re-register anatomical landmarks, which are already being tracked using image-guidance navi-gation, after their 3D-tracked DRF is manipulated out of its intended position. In some embodiments, typically in image-guidance navigation (e.g., CT guidance), the navigation system is relying on the careful 3D-tracking of a DRF, attached to one or more anatomical structures (e.g., pelvis, vertebrae, femur, etc.), that is registered to those underlying anatomical structures in a particular relative position. In some embodiments, as the DRF moves, typically due to the patient's movement or the user manipulating the spine, the system adjusts the view of surgical instruments relative to the volumetric or 2D imaging that they are being tracked relative to. In some embodiments, if the DRF is bumped or manipulated, the traditional image-guided navigation is no longer accurate or safe, and the system will need to redo its navigation initialization process. In some embodiments, this invention can eliminate the need for additional imaging or navigation re-initialization processes by rigidly attaching a fiducial marker to the anatomy before the navigation system is initialized and can thus provide a reliable recovery of navigational guidance at any time during surgery after its first initialization.

In some embodiments, FIG. 143A illustrates an assembly view 14300 of a lumbar spine and pelvis that are registered and 3D-tracked by an attached DRF, an image-guided-navigation reference. In some embodiments, a 3D-tracked DRF navigation reference 14302*a*, made of three or more 3D-tracked markers 14304, is in its initialized registration position relative to the anatomy to which is rigidly attached to via a fixation interface 14306. In some embodiments, the 3D-tracked DRF navigation reference 14302*a* is attached to the pelvis 14312 and once initialized provides a coordinate frame reference for image-guided navigation that displays volumetric imaging of the pelvis 14312 and nearby anatomy, such as the lumbar spine 14310. In some embodiments, the 3D-tracked DRF navigation reference 14302*a* is accompa-nied by a frame-bump-monitoring, 3D-tracked marker post

14308, and this post's 14308 3D location relative to that of the 3D-tracked DRF navigation reference 14302*a* is continuously monitored by the system to detect any accidental dislodging or manipulation of the 3D-tracked DRF navigation reference 14302*a*. In some embodiments, a bone-mounted fiducial 14314*a* is rigidly attached to the same anatomical structure as the 3D-tracked DRF navigation reference 14302*a*, and the fiducial 14314*a* thus provides a backup reference marker of the anatomical structure's 14312 3D location and pose with respect to the coordinate frame of the navigation camera system (not shown) and the coordinate frame of the DRF 14302*a*. In some embodiments, whenever the 3D-tracked DRF navigation reference 14302*a* is bumped or manipulated, instead of re-initializing the image-guidance system based on the DRF's 14302*a* new location and pose, the system just has to register the fiducial's 14314*a* updated location and pose. In some embodiments, when the fiducial's 14314*a* new location and pose are registered after the manipulation of the DRF 14302*a*, this will update the 3D location and pose of the registered anatomical landmarks of interest and transform those landmarks to be with respect to the DRF navigation reference's new position.

In some embodiments, FIG. 143B illustrates an assembly view 14320 of a lumbar spine and pelvis that are registered and 3D-tracked by an attached DRF, an image-guided-navigation reference, but the DRF has been manipulated or dislodged from its initialization position. In some embodiments, the DRF navigation reference 14302*b* becomes dislodged and subsequently changes its 3D location and pose relative to its attached anatomical structure 14312. In some embodiments, once the system or the user detects this DRF manipulation event, commonly known as "frame bump", the user can utilize a 3D-tracked probe 14322*a* to register the updated 3D location and pose of a bone-mounted fiducial 14314*b* attached to the same anatomical structure 14312 as the dislodged DRF navigation reference 14302*b*. In some embodiments, the 3D-tracked probe comprises a probe shaft 14328, probe tip 14327, fiducial-registration interface (disengaged) 14326*a*, 3D-tracked DRF 14330, made of three or more 3D-tracked markers, TMSM (untriggered) 14332*a*, and trigger button (undepressed) 14324*a* that controls the actuation of the TMSM 14332*a*.

In some embodiments, FIG. 143C illustrates an assembly view 14340 of a lumbar spine and pelvis that are registered and 3D-tracked by an attached DRF, an image-guided-navigation reference, but the DRF has been manipulated or dislodged from its initialization position and then re-registered via a bone-mounted fiducial. In some embodiments, the 3D-tracked probe (triggered) 14322*b* engages with the bone-mounted fiducial (registered) 14314*c* and the trigger button 14324*b* is depressed to actuate the rigidly-linked TMSM (triggered) 14332*b*, which communicates to the system to record the 3D location and pose of the engaged fiducial 14314*c* via the 3D location and pose of the engaged probe tip 14326*b*. In some embodiments, once the new location and pose of the fiducial 14314*c* are recorded, the system calculates a rigid body transform between the fiducial 14314*c* and the navigation camera system's (not shown) coordinate frame. In some embodiments, the system then applies that rigid body transform to the previously-initialized anatomical landmarks to update their registration and once again enable image-guided navigation (e.g., placing screws via CT image guidance), without the need for any additional imaging or traditional navigation re-registration processes.

Some embodiments of the invention involve using an X-Ray adapter device to initialize a bone-mounted, or skin-mounted, fiducial relative to anatomical landmarks of interest via X-Ray or volumetric imaging. In some embodiments, the X-ray adapter device has a unique mating interface (female) that enables for mating with a fiducial mating interface (male) in only one unique 3D configuration. In some embodiments of the invention, the X-Ray adapter device's fiducial-mating interface can be further enhanced with additional mechanisms (e.g., cam lock, spring-loaded detent, indent to receive spring-loaded detent, etc.) to reduce the tolerance with the fiducial of interest and maximize repeatability of the initialization process.

In some embodiments, FIG. 144A illustrates an assembly view 14400 of an X-Ray adapter device equipped with a cam-lock mechanism and a bone-mounted fiducial before the two devices have mated. In some embodiments, the X-Ray adapter device (disengaged) 14402*a* comprises a device body 14401, fiducial-mating interface 14418, mating-orientation indicator 14417, embedded radiopaque markers 14414, cam-locking lever mechanism (disengaged) 14406*a*, cam lever (undepressed) 14416*a*, and a fiducial-to-cam interface (disengaged) 14408*a*. In some embodiments, the cam-locking mechanism 14406*a* is rigidly attached to the X-Ray adapter's device body 14401. In some embodiments, once the lever 14416*a* is depressed this will actuate the lever mechanism 14406*a* to then press the fiducial-to-cam interface 14408*a* against the fiducial and securely mate the devices together. In some embodiments, the bone-mounted fiducial 14404, mentioned previously in relation to FIG. 142, comprises a unique mating interface (flat face) 14415, a depth-stop interface 14410, and screw threads. In some embodiments, once the adapter's 14402*a* cam-lock mechanism 14406*a* becomes engaged, the adapter will be securely mated to the bone-mounted fiducial's 14404 mating interface (flat face) 14415.

In some embodiments, FIG. 144B illustrates an assembly view 14420 of an X-Ray adapter device engaged with a bone-mounted fiducial via a cam-lock mechanism (disengaged). In some embodiments, the X-Ray adapter device 14402*b* engages with the bone-mounted fiducial 14404 via the internal mating interfaces (14418, 14415, 14410; not shown). In some embodiments, FIG. 144C illustrates an assembly 14430 of an X-Ray adapter device engaged with a bone-mounted fiducial via a cam-lock mechanism (engaged). In some embodiments, the X-Ray adapter device 14402*c* engages the fiducial-mating interface 14408*b* against the bone fiducial's mating interface 14415 (not shown) after engaging the cam-lock mechanism 14406*b* via the depression of a cam lever 14416*b*. In some embodiments, FIG. 144D illustrates an assembly cutaway view 14440 of the X-Ray adapter device engaged with a bone-mounted fiducial via a cam-lock mechanism (engaged). In some embodiments, the X-Ray adapter device's (engaged) 14402*c* cam-lock mechanism (engaged) 14406*b* is actuated by a cam lever (depressed) 14416*b* that actuates a pivoting lever 14442 that rotates and adds compression force to the fiducial-mating interface 14408*b*, which compresses against the fiducial's 14404 unique mating interface (flat face) 14415. In some embodiments, the X-Ray adapter device's cam-lock mechanism can be spring-loaded to facilitate auto-mated, secured mating with the fiducial upon engagement. In some embodiments, FIG. 144E illustrates an assembly view 14445 of an X-Ray adapter device engaged with a bone-mounted fiducial via a spring-loaded, cam-lock mechanism. In some embodiments, the X-Ray adapter device's 14447 cam-lock mechanism 14451 involves a cam lever 14448 that is depressed under compression via a compression spring 14449 attached to the device body. In some embodiments, once the bone-mounted fiducial 14404 engages with the X-Ray adapter device 14447, the fiducial's mating interface (not shown) 14415 engages with the spring-loaded, fiducial-mating interface 14453 of the cam-lock mechanism 14447. In some embodiments, the fiducial mating interface (not shown) 14415 or the X-Ray adapter device's fiducial-mating interface 14453 have a tapered slope so that the initial engagement of the fiducial's mating interface (not shown) 14415 is smooth and unobstructed by the spring-loaded, cam-lock mating interface 14453.

In some embodiments, FIG. 144F illustrates an assembly cutaway view 14460 of an X-Ray adapter device engaged with a bone-mounted fiducial via a spring-loaded mating mechanism (disengaged). In some embodiments of the invention, the X-Ray adapter device (disengaged) 14462a contains a mating interface that comprises a female, fiducial-mating interface 14468 that aligns with the fiducial's flat face mating interface 14415, spring-loaded wall mating interface (disengaged) 14464a that is supported by an internal spring (relaxed) 14466a, and radiopaque markers (not shown) 14414. In some embodiments, FIG. 144G illustrates an assembly cutaway 14465 of an X-Ray adapter device engaged with a bone-mounted fiducial via a spring-loaded mating mechanism (engaged). In some embodiments, the X-Ray adapter device (engaged) 14462b engages with the bone fiducial 14404 and produces a secure mate via the adapter device's spring-loaded wall mating interface (engaged) 14464b, supported by an internal spring (compressed) 14466b, pressing against the flat face mating interface 14415 of the fiducial 14404.

In some embodiments, FIG. 144H illustrates an assembly view 14470 of an X-Ray adapter device with an array of embedded radiopaque markers and a bone-mounted fiducial. In some embodiments, the X-Ray adapter device 14472 has a larger array of embedded radiopaque markers (e.g., 9 spheres) 14414, of which one or more of them are utilized as a redundant backup sphere in case one or more spheres are occluded during the X-Ray imaging registration process. In some embodiments, if one or more radiopaque markers are occluded during the imaging process, the remaining spheres that can be visualized will be sufficient for reliable, accurate image-based registration. In some embodiments, the X-Ray adapter device 14472 mates to a bone-mounted fiducial 14404 via the adapter device's female mating interface 14474 and the fiducial's male flat-face interface 14415. In some embodiments, FIGS. 144I and 144I illustrate assembly views (14475, 14480) of the X-Ray adapter device and the bone-mounted fiducial. In some embodiments, the array of embedded radiopaque markers 14414 are designed to avoid occluding each other during imaging, and also have an asymmetric configuration that prevents several spheres from being co-linear and subsequently introducing indefinite solutions to the image registration process.

Some embodiments of the invention involve using an X-Ray adapter device to initialize a bone-mounted fiducial relative to multiple anatomical landmarks of interest via X-Ray or volumetric imaging. In some embodiments, when a user wishes to register multiple anatomical landmarks relative to individual bone-mounted fiducials, a single X-Ray adapter device can be used to register each anatomical landmark to its attached fiducial marker via two or more X-Ray images. In some embodiments, FIG. 145A illustrates an assembly view 14500 of an X-Ray adapter device with an array of embedded radiopaque markers and a group of spinal vertebrae, each with their own attached, bone-mounted fiducial. In some embodiments, the X-Ray adapter device (disengaged) 14504a contains multiple embedded radiopaque markers 14506. In some embodiments, the X-Ray adapter device (disengaged) 14504a is mated to one of the bone-mounted fiducials 14502d, attached to one of the unregistered landmarks (e.g., L3 vertebra) 14509a, for each group of anatomical landmarks (unregistered) 14508a that can fit in a single X-Ray image.

In some embodiments, FIG. 145B illustrates an assembly view 14510 of an X-Ray adapter device engaged with one bone-mounted fiducial for X-Ray-image-based registration of a group of spinal vertebrae, each with their own individual bone-mounted fiducial markers. In some embodiments, the X-Ray adapter device 14504b engages with the bone-mounted fiducial 14502d that is attached to one of the anatomical landmarks (e.g., L3 vertebra) 14509b within the group of landmarks 14508b. In some embodiments, once the X-Ray adapter device 14504b mates with one of the bone-mounted fiducials 14502d, then the user can acquire two or more X-Ray images and follow processes described below in relation to FIG. 158 to register each anatomical landmark (e.g., L1, L2, L3, L4, L5, S1 vertebrae) relative to their respective, engaged bone-mounted fiducials (14502f, 14502e, 14502d, 14502c, 14502b, 14502a). In some embodiments, once the registration process of the group of anatomical landmarks relative to their respective bone-mounted fiducials is complete, the user removes the X-Ray adapter device 14504b, and then registers the 3D location and pose of each initialized bone-mounted fiducial (14502f, 14502e, 14502d, 14502c, 14502b, 14502a) with a 3D-tracked probe (not shown), or any other localization tool.

In some embodiments, FIG. 145C illustrates an assembly view 14520 of an X-Ray adapter device, with an array of embedded 3D-tracked markers, engaged with one bone-mounted fiducial for X-Ray-image-based registration of a group of spinal vertebrae, each with their own individual bone-mounted fiducial markers. In some embodiments, the X-Ray adapter device 14524 contains an array of embedded 3D-tracked markers 14525. In some embodiments, these 3D-tracked markers 14525 are able to be both visualized by X-Ray imaging and also tracked by a navigation camera system (not shown). In some embodiments, this multi-purpose functionality of the 3D-tracked markers 14525 enables for accurate image-based registration as it does not require separate registration by a 3D-tracked probe (not shown), or any other localization tool.

In some embodiments, FIGS. 145D and 145E illustrate assembly views (14530, 14540) of X-Ray images (e.g., AP and Lateral views) of an X-Ray adapter engaged with one of several bone-mounted fiducials for a group of anatomical landmarks of interest. In some embodiments, the X-Ray adapter device 14504b is engaged to one of the bone-mounted fiducials 14502a within the region of interest. In some embodiments, for each unique X-Ray image view, such as Lateral 14532 and AP 14542 views, the system segments the anatomical landmarks of interest (e.g., sagittal vertebral endplates of interest: 14531a, 14533a, 14535a, 14537a, 14538a, 14539a; coronal vertebral endplates of interest: 14531b, 14533b, 14535b, 14537b, 14538b, 14539b), and then triangulates the 3D location of each landmark relative to their attached bone-mounted fiducials, using one or more processes defined below in FIGS. 157-158. In some embodiments, the imaged X-Ray adapter device 14504b can be replaced with other described X-Ray adapter devices (e.g., 14524, 14402c, 14447, 14462b, 14472, etc.).

Some embodiments of the invention involve using an X-Ray adapter device to initialize one or more flexibility assessment devices relative to their attached anatomical landmarks of interest. In some embodiments, using an X-Ray adapter device attachment and processes for image-based registration to anatomical landmarks of interest, the system can enable flexibility-assessment devices to be initialized without the need for image-guided navigation (e.g., CT-guided navigation).

In some embodiments, FIG. 146A illustrates an assembly view 14600 of a flexibility-assessment device attached to a vertebra via mating with instrumented pedicle screws, as well as an X-Ray adapter device that can mate with the flexibility-assessment device. In some embodiments, the X-Ray adapter device (disengaged) 14622*a*, comprising multiple radiopaque markers 14624, mates uniquely with the fiducial protrusion interface 14614 embedded on the flexibility-assessment device 14602*a*. In some embodiments, the flexibility-assessment device 14602*a* comprises a handle 14612*a*, trigger button (undepressed) 14604*a*, 3D-tracked DRF 14606*a* made of three or more 3D-tracked markers 14607, TMSM (undepressed) 14608*a* which is rigidly linked to the trigger button 14604*a*, fixed, screw-interfacing arm 14618, adjustable, screw-interfacing arm 14616, and a screw-interfacing pseudo rod 14620. In some embodiments, FIG. 146B illustrates an assembly view 14630 of flexibility-assessment devices attached to individual vertebrae of interest, as well as an X-Ray adapter device that is mated with one of the flexibility-assessment devices for image-based registration. In some embodiments, two or more flexibility-assessment devices (14602*a*, 14602*b*) engage with individual vertebrae of interest (14632, 14634), and then the X-Ray adapter device 14622*b* engages with one of the flexibility-assessment devices 14602*a* via a fiducial protrusion interface (not shown) 14614. In some embodiments, both flexibility-assessment devices (14602*a*, 14602*b*) have 3D-tracked DRFs (14606*a*, 14606*b*) and a TMSM (14608*a*, 14608*b*), and are tracked by a navigation camera system (not shown). In some embodiments, the assembly is now ready for image-based registration, which includes processes defined below in relation to FIG. 159.

In some embodiments, FIGS. 146C and 146D illustrate assembly views (14640, 14650) of X-Ray images (e.g., AP and Lateral views) of an X-Ray adapter device engaged with a flexibility-assessment device to initialize attached anatomical landmarks of interest. In some embodiments, the X-Ray adapter device 14622*b* is engaged to one of the flexibility-assessment devices 14602*a* and can be visualized simultaneously along with the anatomical landmarks of interest 14626. In some embodiments, for each unique X-Ray image view, such as Lateral 14642 and AP 14652 views, the system segments the anatomical landmarks of interest (e.g., sagittal vertebral endplates of interest; 14646*a*, 14644*a*, coronal vertebral endplates of interest: 14646*b*, 14644*b*), and then triangulates the 3D location of each landmark relative to the attached bone-mounted fiducial 14614, using one or more processes defined below in FIGS. 157-159. In some embodiments, once this image-registration process is completed, the system stores the 3D location and pose of each attached anatomical landmark of interest (e.g., L2 and L3 vertebrae; 14634, 14632) in the relative coordinate frame of each engaged flexibility-assessment device (14602*a*, 14602*b*). In some embodiments, once image-based initialization is completed, as the flexibility-assessment devices (14602*a*, 14602*b*) are manipulated, and subsequently their rigidly-attached anatomical landmarks of interest (14634, 14632), the system can compute the real-time 3D locations of each attached anatomical landmark of interest and use that data to compute relevant spinal alignment parameters and visual representations of the engaged, manipulated vertebrae.

Some embodiments of the invention involve a 3D-tracked implant driver that tracks the real-time 3D location and actuation (e.g., expansion) of an implant (e.g., interbody cage). In some embodiments, the 3D-tracked driver tracks only one actuation mechanism (e.g., expansion, pivoting, splitting, etc.). In some embodiments, the 3D-tracked implant driver can track multiple actuations, as illustrated below in relation to FIGS. 152-154 and 160. In some embodiments, whether or not the implant is being tracked or not during insertion, 3D-tracked DRFs on each implant-interfacing anatomical landmark of interest can provide real-time feedback about the spine's dynamic changes of spinal alignment during the implantation process. In some embodiments, FIG. 147A illustrates an assembly view 14700 of a 3D-tracked implant driver that tracks the 3D location and actuation of an engaged implant (e.g., cage). In some embodiments, the 3D-tracked implant driver (disengaged, inactive) 14702*a* comprises a driver shaft 14710, 3D-tracked DRF 14704 attached to a DRF mount 14717 on the shaft 14710, TMSM (inactive) 14706*a* attached to a TMSM mount 14708*a*, side arm 14722 and handle grip 14720, implant-actuation grip 14718, implant-mating interface 14712, internal, implant-actuation shaft (inactive) 14714*a* with threads (not shown), and implant-actuation interface driver 14716. In some embodiments, when the implant-actuation grip 14718 is rotated, it subsequently rotates a rigidly-linked internal, implant-actuation shaft (inactive) 14714*a* that actuates the TMSM mount (inactive) 14708*a*, which pushes the attached TMSM (inactive) 14706*a* away from the 3D-tracked DRF 14704. In some embodiments, as the implant-actuation grip 14718 is rotated, the rigidly-linked driver 14716 engages the implant's actuation mechanism (e.g., cage expansion, pivoting, or splitting, etc.) and subsequently converts the implant motion into a simultaneous relative movement of the rigidly-linked TMSM 14706*a*. In some embodiments, the process of real-time tracking the implant and the engaged vertebrae, as well as embodiment systems that enable this invention, are described in relation to FIGS. 148-157 and FIG. 160.

In some embodiments, FIGS. 147B and 147C illustrate assembly views (14725, 14730) of a 3D-tracked implant driver that tracks the 3D location and actuation of an engaged implant (e.g., cage) in the process of actuating an implant driver. In some embodiments, when the implant-actuation grip 14718 is rotated, this action rotates the internal, implant-actuation shaft (active) 14714*b*, which subsequently actuates the TMSM mount 14708*b* and TMSM 14706*b* away from the device's DRF 14704. In some embodiments, this actuation of the TMSM 14706*b* away from the DRF 14704 is analyzed by the system and communicates that the device's engaged implant (not shown) is being actively actuated (e.g., cage expansion, pivoting, splitting, etc.). In some embodiments, this process of analyzing the TMSM's 14706*b* location relative to the DRF 14704 is described below in relation to FIG. 160.

In some embodiments, FIGS. 147D and 147E illustrate assembly cutaway views of the 3D-tracked implant driver implant-to-TMSM-actuation mechanism. In some embodiments, the TMSM mount 14708*b* is rigidly-linked with the internal, implant-actuating shaft 14714*b* via a shaft-mating interface 14742, and the TMSM 14706*b* moves linearly along the axis of the driver shaft 14710 while the implant is actuated via the rotation of the implant-actuation grip 14718.

In some embodiments, FIG. 147F illustrates an assembly view 14750 of the 3D-tracked implant driver and the expandable cage that the driver actuates, tracking its live location and actuation configuration. In some embodiments, the 3D-tracked driver (disengaged) 14702a attaches to the expandable cage (unexpanded) 14752a, and tracks the implant's live location and actuation. In some embodiments, the expandable cage (unexpanded) 14752a comprises two or more expandable walls (14756a, 14758a), each with a anatomy-engaging interface 14762, driving front face 14760, driver-mating interface 14754, and an internal crank mechanism (not shown) that is actuated via the 3D-tracked driver's driver face 14716.

In some embodiments, FIG. 147G illustrates an assembly cutaway view 14770 of the 3D-tracked implant driver and the expandable cage that the driver actuates, tracking its live location and actuation configuration. In some embodiments, the driver's internal shaft 14714a actuates the expansion of the cage implant 14752a via the driver face 14716 engaging the cage's internal crank interface 14772. In some embodiments, as the cage is expanded via rotation of the driver's internal shaft 14714a (threads not shown), this motion actuates the TMSM mount 14708a and its attached TMSM 14706a away from the driver's DRF 14704.

In some embodiments, FIGS. 147H-147I illustrate assembly views (14775, 14780) of the 3D-tracked implant driver and the engaged expandable cage, shown in both the unexpanded (inactive TMSM) and expanded (active TMSM) configurations. In some embodiments, during the process of the unexpanded cage 14752a becoming an expanded cage 14752b, the internal shaft (active) 14714b incrementally actuates the TMSM mount 14708b and its attached TMSM 14706b. In some embodiments, as the TMSM 14706b incrementally moves away from the DRF 14704 via the implant-actuation mechanism, every step of actuation of the cage 14752b is recorded in real-time, and the system analyzes the TMSM's 14706b relative motion to the DRF 14704 to calculate the amount of cage expansion that has been accomplished. In some embodiments, the system utilizes this calculated amount of cage expansion to provide the user with real-time, 3D visualization of the cage expanding while it is implanted into the spine. In some embodiments, this real-time visualization feedback of the cage implantation is illustrated below in relation to FIG. 156 (expandable cage example not shown) and the system process is described below in relation to FIG. 160.

Some embodiments of the invention involve tracking vertebrae in real-time (or real-time), using DRF attachments on bone-mounted fiducials, during the insertion of implants via a 3D-tracked implant driver. In some embodiments, when the user desires real-time tracking of engaged vertebrae, a 3D-tracked DRF attachment can mate with bone-mounted fiducials on each vertebra and provide feedback on the vertebra's 3D location and pose while the system also provides feedback on the real-time location and actuation configuration of an implant engaged to a 3D-tracked driver. In some embodiments, the engaged vertebrae of interest are initialized relative to their attached, bone-mounted fiducial via image-registration processes defined below in relation to FIG. 160. In some embodiments, these anatomy initialization processes include compatibility for both image-guided navigation (e.g., CT-guidance and automated segmentation of 3D vertebrae) and X-Ray imaging surgical workflows. In some embodiments, FIGS. 148A and 148B illustrate assembly views (14800, 14820) of 3D-tracked DRF attachments, each with unique marker configurations, that mate with bone-mounted fiducials. In some embodiments, the 3D-tracked DRF adapter attachments (14802a, 14804a) mate with individual bone-mounted fiducials (14810a, 14812a). In some embodiments, as the vertebrae are manipulated during the process of inserting an implant (e.g., interbody cage), the DRF attachments on the bone-mounted fiducials track the 3D location and pose of the engaged anatomical landmarks. In some embodiments, the process of real-time tracking the implant and the engaged vertebrae, as well as embodiment systems that enable this invention, are described in relation to FIGS. 147-157 and FIG. 160.

In some embodiments, FIGS. 148C and 148D illustrate assembly views (14830, 14835) of bone-mounted fiducials engaged with vertebrae, and the bone-mounted fiducials are 3D-tracked via DRF adapter attachments. In some embodiments, 3D-tracked DRF adapter devices (14802b, 14804b) engage with individual, bone-mounted fiducials (14810b, 14812b) and provide real-time feedback on the 3D location and pose of engaged vertebrae (14832b, 14834b). In some embodiments, each adapter attachment comprises a 3D-tracked DRF (14806, 14808), device body with anti-occlusion features (14819, 14818), fiducial-mating interface 14817 with a female front-face mating wall 14816 that engages the fiducial's flat-face interface 14814.

In some embodiments, FIGS. 148E-148G illustrate assembly views (14840, 14860) of a 3D-tracked implant driver with an attached cage implant being inserted between vertebrae that are equipped with 3D-tracked DRF adapter attachments engaged on bone-mounted fiducials. In some embodiments, the 3D-tracked implant driver 14842a comprises a 3D-tracked DRF 14844, TMSM mount (14848a, 14848b), TMSM (14846a, 14846b), driver external body shaft 14850, implant-mating interface 14852, and an implant-actuation grip 14851. In some embodiments, the engaged, 3D-tracked implant driver 14842b inserts between two or more vertebrae (14832b, 14834b) and interface with the vertebral endplates via the cage's anatomy-interfacing walls (14858b, 14856b). In some embodiments, as the cage 14853c is expanded (starts as unexpanded cage 14853b) via rotation of the implant-actuation grip 14851, the TMSM mount 14848b is actuated via the rotation of the cage's internal crank 14867 and thus moves the rigidly-linked TMSM 14846b away from the driver's DRF 14844. In some embodiments, as the cage 14853c expands against the engaged vertebrae (14834c, 14832c), via contact with the cage's wall interfaces (14856c, 14848c), the 3D-tracked DRF adapter attachments (14804c, 14802c), rigidly-linked to the vertebrae via bone-mounted fiducials (14812c, 14810c), move and the system uses the rigid body transform of each DRF with respect to the coordinate frame of the navigation camera (not shown) to calculate the new, 3D location and pose of the engaged vertebrae (14834c, 14832c). In some embodiments, the process of real-time tracking the implant and the engaged vertebrae, as well as embodiment systems that enable this invention, are described in relation to FIGS. 147-157 and FIG. 160.

In some embodiments, FIGS. 148H-I illustrate assembly views (14870, 14875) of the previously described system of tracking vertebrae and a cage implant during the process of cage insertion and expansion. In some embodiments, FIGS. 148J-K illustrate assembly views (14880, 14890, 14895) of the 3D-tracked implant driver disconnecting from the cage implant and then removing the 3D-tracked DRF adapters. In some embodiments, the 3D-tracked implant driver 14842d disconnects from the implanted cage 14853d via the disengagement of the driver's mating interface 14884 and shaft driver 14882 with the cage's driver-mating interface 14886. In some embodiments, in order to leave the surgical site unobstructed after cage implantation, the 3D-tracked DRF adapter attachments (14804*c*, 14802*c*) disconnect from the bone-mounted fiducials (14812*c*, 14810*c*) in their new, post-cage-implantation positions.

Some embodiments of the invention involve intermittent tracking of vertebrae, during the insertion of implants via a 3D-tracked implant driver. In some embodiments, a 3D-tracked implant driver, such as that described previously in relation to FIGS. 147-148, is inserted between vertebrae of interest. In some embodiments, the vertebral landmarks of interest are not tracked in real-time, but are rather initialized relative to implanted bone-mounted fiducials, which can be intermittently updated as the cage is inserted and actuated (e.g., expanded), which moves the fiducial's attached vertebrae of interest. In some embodiments, the process of real-time tracking the implant and the engaged vertebrae, as well as embodiment systems that enable this invention, are described in relation to FIGS. 147-157 and FIG. 160. In some embodiments, FIGS. 149A-B illustrate assembly views (14900, 14920) of a 3D-tracked implant driver with an attached cage implant, and vertebrae that can be intermittently registered via bone-mounted fiducials. In some embodiments, as the unexpanded cage 14913*a* becomes an expanded cage 14913*b* via the rotation of the implant-actuation grip 14910 on the 3D-tracked implant driver (14902*a*, 14902*b*), the engaged vertebrae of interest (14914*b*, 14912*b*) are manipulated. In some embodiments, FIGS. 149C-E illustrate assembly views (14925, 14950, 14970) of the 3D-tracked implant driver with a fully-expanded cage implant inserted in between vertebrae of interest, and a 3D-tracked probe registering the new 3D locations and poses of bone-mounted fiducials on each vertebrae. In some embodiments, the 3D-tracked probe 14931*c*, similar to those previously described above (e.g., FIG. 142), engages with each bone-mounted fiducial (14929*b*, 14927*b*) via the probe's fiducial-mating interface 14939*c*, and then registers each vertebra's new location and pose as a result of the implantation and expansion of the inserted cage implant. In some embodiments, the user depresses the trigger button 14937*b* of the 3D-tracked probe 14931*c*, which actuates its rigidly-linked TMSM (active) 14935*b*, and subsequently the system registers the 3D location and pose of each probe-engaged, bone-mounted fiducial (14929*b*, 14927*b*). In some embodiments, the system can intermittently re-register the 3D location and pose of the vertebrae of interest (14914*b*, 14912*b*) during the process of implant insertion and expansion, and does not need to occur just at the end of the implantation process.

Some embodiments of the invention involve tracking vertebrae in real-time, using DRF-equipped, bone-clamping fiducials, during the insertion of implants via a 3D-tracked implant driver. In some embodiments, when the user desires real-time tracking of engaged vertebrae, a 3D-tracked DRF attachment device can clamp onto vertebrae of interest, and provide feedback on the vertebra's 3D location and pose, as well as on the real-time location and actuation configuration of an implant attached to a 3D-tracked driver. In some embodiments, the engaged vertebrae of interest are initialized relative to their attached DRF-equipped, bone-clamping fiducials via image-registration processes defined below in relation to FIG. 160. In some embodiments, these anatomy initialization processes include compatibility for both image-guided navigation (e.g., CT-guidance and automated segmentation of 3D vertebrae) and X-Ray imaging surgical workflows. In some embodiments, the process of real-time tracking the implant and the engaged vertebrae, as well as embodiment systems that enable this invention, are described in relation to FIGS. 147-157 and FIG. 160. In some embodiments, FIG. 150A illustrates an assembly view 15000 of a DRF-equipped, bone-clamping fiducial attached to a vertebra of interest. In some embodiments, the bone-clamping fiducial (initial position) 15002*a* comprises a 3D-tracked DRF 15004 and a device body with a bone-clamping mechanism 15006, which includes one or more set screws to rigidly attach the device to the vertebra 15008*a*. In some embodiments, FIGS. 150B-C illustrate assembly views (15015, 15040) of a 3D-tracked implant driver with an attached interbody cage implant, as well as vertebrae of interest each with a unique-DRF-equipped, bone-clamping fiducial that track the vertebra's 3D location and pose during insertion and actuation of an implant (e.g., interbody cage). In some embodiments, the unexpanded cage 15031*a* becomes an expanded cage 15031*b* via the rotation of the implant-actuation grip 15027 of the 3D-tracked implant driver 15017*b*. In some embodiments, as the cage 15031 expands and engages with the nearby vertebrae (15008*b*, 15033*b*), each vertebra's attached, DRF-equipped, bone-clamping fiducial (15002*b*, 15029*b*) tracks the 3D location and pose of the manipulated anatomical landmarks of interest.

Some embodiments of the invention involve tracking vertebrae in real-time, using DRF-equipped, bone-clamping fiducials, during the insertion of implants via a 3D-tracked implant driver, that are initialized with X-Ray imaging via an X-Ray adapter device. In some embodiments, the X-Ray adapter device, described previously in relation to FIG. 144.

In some embodiments, FIGS. 151A-B illustrate assembly views (15100, 15120) of DRF-equipped, bone-clamping fiducials that can be initialized relative to their engaged anatomical landmarks via image registration using an X-Ray adapter mated to one of the bone-clamping fiducial devices. In some embodiments, the X-Ray adapter device 15112*a* mates with one of the bone-clamping fiducials 15108*a* via the fiducial's male mating interface 15114, which engages the X-Ray adapter device's female mate 15111. In some embodiments, processes for image-based registration of the anatomical landmarks of interest relative to the X-Ray adapter are described in relation to FIGS. 145, 157, and 158. In some embodiments, the process of real-time tracking the implant and the engaged vertebrae, as well as embodiment systems that enable this invention, are described in relation to FIGS. 147-157 and FIG. 160. In some embodiments, FIGS. 151C-D illustrate assembly views (15130, 15135) of the X-Ray adapter device attached to a bone-clamping fiducial device from the perspective of two X-Ray image views (e.g., Lateral, AP, etc.). In some embodiments, the engaged X-Ray adapter device 15112*b* contains a configuration of embedded radiopaque markers that avoids self-occlusion of spheres from most views. In some embodiments, FIG. 151E illustrates an assembly view of a 3D-tracked implant driver manipulating anatomical landmarks of interest after the insertion and actuation of an implant (e.g., interbody cage). In some embodiments, as the expanded cage 15152 is actuated against nearby vertebrae (15104*b*, 15102*b*), the driver's 15142 TMSM mount 15144 and TMSM 15146 incrementally move farther from the 3D-tracked DRF 15150.

Some embodiments of the invention involve a 3D-tracked implant driver with a dual-action TMSM that can track at least two implant actuations (e.g., expansion, pivoting, splitting, etc.). In some embodiments, certain interbody implant devices can contain multiple actuations and thus require tracking mechanisms that capture multiple implant actuations. In some embodiments, a dual-action TMSM mechanism attached to a 3D-tracked implant driver is able to track multiple actuations simultaneously. In some embodiments, the process of real-time tracking the implant and the engaged vertebrae, as well as embodiment systems that enable this invention, are described in relation to FIGS. 147-157 and FIG. 160. In some embodiments, FIG. 152A illustrates an assembly view 15200 of a 3D-tracked implant driver with dual-action tracking, and the attached interbody cage in its neutral position. In some embodiments, the 3D-tracked implant driver 15202a comprises a driver shaft 15212, 3D-tracked DRF 15204, implant-actuating grip 15222, TMSM linear mount 15220a, TMSM 15218a, orthogonal groove 15216 for the TMSM 15218a, implant-pivoting joint 15208a, pivoting lever 15214a, and a housing 15224 for the orthogonal TMSM actuation mechanism (not shown).

In some embodiments, FIGS. 152B-C illustrate assembly views (15240, 15250) of a 3D-tracked implant driver with dual-action tracking, and the attached interbody cage exhibits its two primary actuations (e.g., pivoting and expansion). In some embodiments, when the interbody cage pivots from its neutral position 15206a to its pivoted configuration 15206b about its pivoting pin 15210, the attached pivoting joint 15208a actuates the pivoting lever arm 15214b subsequently elevates the TMSM mount 15220b which pushes the TMSM 15218b away from the DRF 15204 along the axis of the driver shaft 15212. In some embodiments, when the implant driver 15202b transitions from tracking a pivoting cage 15206b to an implant driver 15202c that tracks a pivoting, expanding cage 15206c, the implant-actuation grip 15222 is rotating the internal driver shaft (not shown) that expands the crank lever of the cage 15206c. In some embodiments, as the cage is expanded, the driver's orthogonal gear mechanism (not shown) 15276 converts the cage-expansion motion into an orthogonal motion via a geared lever arm 15252 attached to the TMSM 15218c, moving the TMSM away from the DRF 15204, orthogonal to the central axis of the driver shaft 15212. In some embodiments, FIGS. 152D-E illustrate assembly views (15260, 15270) of the 3D-tracked implant driver and its orthogonal, geared mechanism for converting cage-expansion motion into orthogonal actuation of the TMSM. In some embodiments, the 3D-tracked probe 15202d experiences a single implant 15206d actuation (e.g., expansion) and this moves the TMSM in only one direction (e.g., orthogonal to the axis of the driver shaft). In some embodiments, the orthogonal actuation mechanism 15276 involves a threaded internal driver shaft 15272, which is attached to a cylindrical gear 15278, which subsequently actuates a mechanism 15274 that moves an orthogonal lever arm 15252.

Some embodiments of the invention involve a 3D-tracked implant driver with a dual-action TMSM that can track at least two implant actuations (e.g., expansion, pivoting, splitting, etc.). Some embodiments of this invention of the 3D-tracked implant driver are described previously in relation to FIGS. 147-152. In some embodiments, FIGS. 153A-E illustrate assembly views (15300, 15330, 15340, 15345, 15350) of a 3D-tracked probe that uses one TMSM to track multiple actuations of rigidly-linked interbody devices. In some embodiments, the 3D-tracked implant driver contains a sloped lever arm 15324b that converts linear motion from the pivoting arm 15312b via the pivoting joint 15310b, and that lever arm 15324b actuates the device's TMSM 15318c away from the axis of the driver shaft. In some embodiments, the process of real-time tracking the implant and the engaged vertebrae, as well as embodiment systems that enable this invention, are described in relation to FIGS. 147-157 and FIG. 160.

In some embodiments, FIGS. 153F-G illustrate assembly views (15360, 15361) of a 3D-tracked implant driver with its engaged interbody device in both pivoting and expansion configurations. In some embodiments, the pivoting, expansion cage configurations (15306b, 15306c) actuate two or more TMSM markers on the 3D-tracked relative to its DRF 15304. In some embodiments, as the cage pivots, the pivoting lever arm 15324b is actuated upwards and thus trigger the TMSM #1 15318b to move orthogonally away from the DRF. In some embodiments, as the cage expands, the internal crank lever (not shown) actuates TMSM #2 15362b upwards away from the device's DRF 15304.

Some embodiments of the invention involve a 3D-tracked implant driver with a dual-action TMSM that can track at least two implant actuations (e.g., expansion, pivoting, splitting, etc.). Some embodiments of this invention of the 3D-tracked implant driver are described previously in relation to FIGS. 147-153. In some embodiments, the process of analyzing the TMSM's location relative to the DRF is described below in relation to FIG. 160. In some embodiments, both TMSMs on a 3D-tracked implant driver are driven by lever arms that linearly actuate along the axis of the drive shaft. In some embodiments, FIGS. 154A-154C illustrate assembly views (15400, 15430,15440) of a 3D-tracked implant driver with two implant-actuation-tracking, linear-actuating TMSMs (15418b, 15422b). In some embodiments, as the cage pivots about the pivoting joint 15412b actuates a pivoting lever arm 15416b against one of the TMSMs 15422b, and while the cage expands, the internal driver mechanism cranks the attached TMSM mount 15418b away from the DRF 1504. In some embodiments, the dual-action, 3D-tracked implant driver can capture different implant actuations beyond just expansion and pivoting. In some embodiments, the process of real-time tracking the implant and the engaged vertebrae, as well as embodiment systems that enable this invention, are described in relation to FIGS. 147-157 and FIG. 160.

Some embodiments of the invention involve a 3D-tracked implant driver with an attached implant that has orthogonal actuation motion relative to the mating axis of the driver. In some example embodiments, the implant is a corpectomy interbody cage, and the 3D-tracked driver tracks the expansion motion of the cage by using the driver tip's cage-actuation interface 15516 to twist the internal screw mechanism of the cage to expand or contract. Some embodiments of this invention of the 3D-tracked implant driver are described previously in relation to FIGS. 147-154. In some embodiments, the process of analyzing the TMSM's location relative to the DRF is described below in relation to FIG. 160. FIGS. 155A-C illustrate assembly views (15500, 15540, 15550) of a 3D-tracked implant driver for corpectomy interbody devices. In some embodiments of the invention, the implant driver (15502b, 15502c) actuates the internal expansion mechanism 15552 of the corpectomy cage (15520b, 15520c), and while doing so, simultaneously moves the location of the TMSM 15506b relative to the driver's DRF 15504. In some embodiments, the process of real-time tracking the implant and the engaged vertebrae, as well as embodiment systems that enable this invention, are described in relation to FIGS. 147-157 and FIG. 160.

Some embodiments of the invention involve a 3D-tracked implant driver with an attached implant that has no actuations, and a set of vertebrae that engage with the inserted implant (e.g., interbody cage). In some embodiments, the process of analyzing the TMSM's location relative to the DRF is described below in relation to FIG. 160. In some embodiments, the process of real-time tracking the implant and the engaged vertebrae, as well as embodiment systems that enable this invention, are described in relation to FIGS. 147-157 and FIG. 160. In some embodiments, FIGS. 156A-C illustrate assembly views (15600, 15620, 15630) of a 3D-tracked implant driver equipped with a non-actuating implant (e.g., interbody cage). In some embodiments, the 3D-tracked implant driver 15602a comprises a driver shaft 15610, implant-mating interface 15612a, 3D-tracked DRF 15604, side handle 15608, and central handle 15606. In some embodiments, the non-actuating interbody implant 15614a involves a driver-mating interface 15616 and vertebra-engaging walls 15617. In some embodiments, as the 3D-tracked implant driver is inserted into the spine, the interbody cage manipulates the engaged vertebrae. In some embodiments, FIGS. 156D-E illustrate assembly views (15635, 15640) of a 3D-tracked implant driver equipped with a non-actuating implant during the implantation and disengagement process. In some embodiments, once the interbody 15614d insertion process is completed, at which time the engaged vertebrae (15636b, 15638b) have changed positions and subsequently update the 3D location and pose of each DRF (15634b, 15632b), the system calculates the new locations of initialized landmarks of interest.

In some embodiments, FIG. 156F illustrates an assembly software view 15645 of a 3D-tracked implant driver, equipped with an interbody cage implant, along with real-time location tracking of registered vertebrae that the implant is interfacing with. In some embodiments, processes for registering the anatomical landmarks of interest and providing real-time qualitative and quantitative feedback of the implantation process and related spinal alignment measurements are described below in relation to FIG. 160. In some embodiments, once the engaged vertebrae are initialized (e.g., image-guided navigation, X-Ray initialization) to their attached DRF adapter devices, the system displays real-time 3D location and pose of each vertebra (15655a, 15657a) and their associated alignment parameters 15647a in each anatomical plane of interest (e.g., sagittal, coronal, axial, etc.). In some embodiments, the system displays the real-time location of initialized endplates (15660a, 15662a, 15669a, 15668a, 15664a, 15666a) of each vertebra (15655a, 15657a) in each anatomical view of interest (15649a, 15648a, 15651a, 15653a). In some embodiments, FIG. 156G illustrates an assembly software view 15675 of a 3D-tracked implant driver, equipped with an interbody cage implant, along with real-time location tracking of registered vertebrae that the implant is interfacing with. In some embodiments, processes for registering the anatomical landmarks of interest and providing real-time qualitative and quantitative feedback of the implantation process and related spinal alignment measurements are described below in relation to FIG. 160. In some embodiments, once the engaged vertebrae are initialized (e.g., image-guided navigation, X-Ray initialization) to their attached DRF adapter devices, the system displays real-time 3D location and pose of each vertebra (15655b, 15657b) and their associated alignment parameters 15647a in each anatomical plane of interest (e.g., sagittal, coronal, axial, etc.). In some embodiments, the system displays the real-time location of initialized endplates (15660b, 15662b, 15669b, 15668b, 15664b, 15666b) of each vertebra (15655b, 15657b) in each anatomical view of interest (15649b, 15648b, 15651b, 15653b). In some embodiments, as the 3D-tracked interbody implant 15677a is inserted into the spine, the system provides real-time updates on the 3D location and pose of the interbody as well as the surrounding vertebrae (15655b, 15657b) that are tracked with attached DRF adapters (not shown). In some embodiments, this combined feedback display provides both visual confirmation of appropriate placement of every interbody implant and final assurance that the desired alignment correction has been achieved. In some embodiments, the non-actuating interbody implant 15677a can be interchanged with multi-actuating implant designs illustrated previously in relation to FIGS. 147-155, and the system can provide all of the same visual and quantative feedback, including the additional visual feedback associated with the actuation mechanisms (e.g., expansion, compression, pivoting, splitting, etc.) of the interbody implant device. In some embodiments, FIG. 156H illustrates an assembly software view 15680 of a 3D-tracked implant driver, equipped with an interbody cage implant, along with real-time location tracking of registered vertebrae that the implant is interfacing with. In some embodiments, processes for registering the anatomical landmarks of interest and providing real-time qualitative and quantitative feedback of the implantation process and related spinal alignment measurements are described below in relation to FIG. 160. In some embodiments, once the engaged vertebrae are initialized (e.g., image-guided navigation, X-Ray initialization) to their attached DRF adapter devices, the system displays real-time 3D location and pose of each vertebra (15655c, 1565c) and their associated alignment parameters 15647a in each anatomical plane of interest (e.g., sagittal, coronal, axial, etc.). In some embodiments, the system displays the real-time location of initialized endplates (15660c, 15662c, 15669c, 15668c, 15664c, 15666c) of each vertebra (15655c, 15657c) in each anatomical view of interest (15649c, 15648c, 15651c, 15653c). In some embodiments, once the 3D-tracked interbody implant 15677b is fully inserted into the spine and deployed, including any possible actuations used (e.g., expansion, pivoting, splitting, etc.), the system provides real-time updates on the 3D location and pose of the interbody as well as the surrounding vertebrae (15655c, 15657c) that are tracked with attached DRF adapters (not shown). In some embodiments, this combined feedback display provides both visual confirmation of appropriate placement of every interbody implant and final assurance that the desired alignment correction has been achieved. In some embodiments, the non-actuating interbody implant 15677b can be interchanged with multi-actuating implant designs illustrated previously in relation to FIGS. 147-155, and the system can provide all of the same visual and quantative feedback, including the additional visual feedback associated with the actuation mechanisms (e.g., expansion, compression, pivoting, splitting, etc.) of the interbody implant device.

In some embodiments of the invention, FIG. 157A-J illustrate the process 15701 of using X-Ray images to register the 3D locations of anatomical landmarks relative to a bone-mounted fiducial via the aid of an X-Ray adapter device. In some embodiments, the registered anatomical landmarks are then used, in some cases in combination with non-fiducial-based inputs of the patient's anatomy (e.g., bilateral laminae tracings, preoperative planning alignment parameters, patient normative data, etc.), to compute the patient's spinal alignment parameters. In some embodiments, some relevant figures include example embodiments of device systems in FIGS. 116-124, 130-132, and 142-145 and embodiments of processes in FIG. 133. In some embodiments, the process of real-time tracking the implant and the engaged vertebrae, as well as embodiment systems that enable this invention, are described in relation to FIGS. 147-157 and FIG. 160.

Some embodiments of the invention involve implanting a fiducial nearby one or more bony anatomical landmarks of interest (e.g., on the pelvis, on a vertebral lamina, etc.) for geometric calibration and 3D registration. In some embodiments, an X-Ray adapter device with embedded radiopaque markers (e.g., spheres, lines, grid, disks etc.) is then attached to the bone-mounted fiducial via a unique mating mechanism.

Some embodiments of the system involve handling different calibration requirements for different X-Ray imaging systems (e.g., 3D imaging, 2D imaging with flat-panel detector, image intensifier, etc.). In some embodiments, imaging systems, such as an image intensifier, require correcting for image distortions. In some embodiments, this is accomplished by attaching an image distortion correction device to the imaging system (e.g. to the detector). In some embodiments, the radiopaque markers (e.g., spheres, lines, grid, disks, etc.) of the image distortion correction device are then segmented and analyzed in X-Ray images to compute distortion correction parameters. In some embodiments, the distortion correction parameters are used to correct each X-Ray image. In some embodiments, the surgeon may track the X-Ray imaging system to perform the 3D registration of anatomical landmarks. In some embodiments, a 3D-tracked dynamic reference frame (DRF) is attached to the X-Ray imaging system, and the locations of the X-Ray source and the principal point are estimated (e.g. by tapping the centers of the detector and emitter with a 3D-tracked probe). In some embodiments, X-Ray images of the bone-mounted fiducial are then acquired from two or more different views ensuring that both the X-Ray adapter device and the anatomical landmarks of interest are visualized. In some embodiments, for each acquired image, the 3D location and pose of the DRF on the X-Ray imaging system is recorded. In some embodiments, the surgeon does not track the X-Ray imaging system and simply proceeds with the image acquisitions from two or more views of the bone-mounted fiducial and X-Ray adapter device.

In some embodiments, the system calibrates the projective geometry of the acquired X-Ray images, identifying an appropriate projection mapping from 3D-space to the 2D-image plane. Some embodiments of this process include using numerical optimization (e.g., minimizing the reprojection error of the X-Ray adapter's radiopaque markers), while some embodiments utilize algorithms such as the Direct Linear Transform (DLT) and its variants. In some embodiments, the system employs different geometric models (e.g., 6-DOF, 7-DOF, 9-DOF solutions) depending on the X-Ray imaging system and the desired calibration process (e.g., tracking the X-Ray imaging system, using bone-mounted fiducials, using offline calibrations provided by manufacturer or technician, etc.). Some embodiments of the invention calibrate the geometry based on the tracked X-Ray imaging system, using the location and pose of the 3D-tracked DRF in each image.

In some embodiments, bony anatomical landmarks of interest (e.g., S1 endplate, femoral head, etc.) are segmented in each X-Ray image. Some embodiments involve using automated computer vision algorithms to detect the edges and boundaries of the landmarks of interest, while some embodiments rely on the user to manually annotate the landmarks using points, lines, polygons, or region inputs.

In some embodiments, the landmarks are then triangulated in 3D space with respect to the X-Ray adapter device's coordinate frame. In some embodiments, the landmark of interest is a "point" landmark (e.g., femoral head centroid) triangulated via numerical optimization (e.g., minimizing the reprojection error) or analytically (e.g., least-squares, Perspective-n-Point) from point, line, or region segmentations in the image. In some embodiments, the landmark of interest is a "plane" landmark (e.g., S1 endplate), triangulated from line or region segmentations in the image. In some embodiments, the landmark of interest is a "volume" landmark (e.g., L5 vertebra, pelvis, etc.), triangulated from region segmentations in the image.

In some embodiments, if a 3D imaging system is used (e.g., CT, CBCT, etc.), the step of determining the locations of anatomical landmarks relative to the X-Ray adapter device is accomplished by simply segmenting them in the 3D volume.

In some embodiments, any landmarks that were not segmented in X-Ray images may be localized based on known anatomical measurements of the patient (e.g., preoperative planning alignment parameters, such as pelvic incidence and bicoxofemoral axis distance, or 3D imaging inputs, etc.) in relation to landmarks that are already triangulated, or based on normative patient data. In some embodiments, this process will typically be used if an anatomical landmark of interest is challenging to visualize in X-Ray images.

In some embodiments, once the anatomical landmarks have been triangulated relative to the X-Ray adapter device, the fiducial-to-landmark 3D registration process is complete, and the X-Ray adapter device is removed from the bone-mounted fiducial. In some embodiments, the aforementioned processes may be repeated to register additional bony landmarks of interest.

Some embodiments of this invention enable the user to update the location of anatomical landmarks at any time during surgery, without the need for additional X-Ray imaging. In some embodiments, the user mates a 3D-tracked probe to the bone-mounted fiducial and records the probe's location and pose in the navigation camera's coordinate frame. In some embodiments, based on the probe's location and pose and the identical probe-to-fiducial and fiducial-to-adapter mating mechanisms, the system computes the virtual positions of the X-Ray adapter markers. In some embodiments, using the virtual positions of the X-Ray adapter markers, the system computes the rigid body transform between the X-Ray adapter's coordinate frame and the navigation camera's coordinate frame. In some embodiments, this rigid body transform is applied to the registered anatomical landmarks, which computes the new 3D coordinates of the anatomical landmarks in the navigation camera's coordinate frame. In some embodiments, the locations of the anatomical landmarks and non-fiducial-based inputs (e.g., bilateral laminae tracings) can be transformed to align with the patient's anatomical planes using one of the anatomical landmarks to define the origin and axes (e.g., S1 endplate defines patient left, right, posterior, anterior, superior, inferior). In some embodiments, the user holds the probe parallel with the patient's body and triggers the probe to record its location and pose, and the system sets that as the coordinate frame for subsequent measurements.

In some embodiments, the updated 3D locations of the anatomical landmarks, along with any available non-fiducial-based inputs, are used to compute the spinal alignment parameters of the patient. In some embodiments, if non-fiducial-based inputs are not available, the anatomical landmarks themselves may be used to compute desired spinal alignment parameters.

In some embodiments, the process of updating the 3D locations of the anatomical landmarks and computing new spinal alignment parameters may be repeated any number of times during surgery without taking additional X-Ray images.

In some embodiments, any of the above processes, methods, or procedures related to the workflow 15701 can include or be accomplished with one or more of steps or processes such as 15700, 15702, 15704, 15706, 15708, 15710, 15712, 15714, 15716, 15718, 15720, 15722, 15724, 15726, 15728, 15730, 15732, 15734, 15736, 15738, 15740, 15742, 15744, 15746, 15748, 15750, 15752, 15754, 15756, 15758, 15760, 15762, 15764, 15766, 15768, 15770, 15772, 15774, 15776, 15778, 15780, 15782, 15784, 15786, 15788, 15790, 15792, 15794, 15796, 15798, 157100, 157102, 157104, 157106, 157108, 157110, 157112, and 157114. In some embodiments, at least one of the steps can include a decision step (e.g., such as step 15704), where one or more following steps depend on a status, decision, state, or other condition. In some embodiments, the steps of workflow 15701 can proceed in the order as shown. In some embodiments, any of the steps of the workflow 15701 can proceed out of the order as shown. In some embodiments, one or more of the steps of the workflow 15701 can be skipped.

In some embodiments of the invention, FIG. 158A-B illustrate the process 15801 of using X-Ray images and an X-Ray adapter device to register the 3D location and pose of anatomical landmarks relative to bone-mounted fiducials implanted in multiple vertebral levels of the spine. In some embodiments, the registered anatomical landmarks are then used to compute desired spinal alignment parameters of the patient. In some embodiments, relevant figures include example embodiments of device systems in FIGS. 116-124, 130-132, and 142-145 and embodiments of processes in FIG. 135.

Some embodiments of the invention involve implanting fiducials into multiple bony anatomical landmarks of interest (e.g., pelvis and multiple lumbar vertebrae) for geometric calibration and 3D registration. In some embodiments, for a group of bone-mounted fiducials that can all be visualized in an X-Ray image, just one of them is attached to an X-Ray adapter device with embedded radiopaque markers (e.g., spheres, lines, grid, disks etc.) via a unique mating mechanism.

In some embodiments, depending on the type of X-Ray imaging system used (e.g., image-intensifier), image distortion correction processes as described previously in relation to FIG. 157 are performed. In some embodiments, this image-distortion-correction step is not required (e.g. 2D imaging with flat-panel detector), and the surgeon simply proceeds with acquiring at least two X-Ray images of the bone-mounted fiducials and the X-Ray adapter device.

In some embodiments, the system calibrates the projective geometry of the acquired X-Ray images, identifying an appropriate projection mapping from 3D-space to the 2D-image plane. In some embodiments, this process is performed in accordance with processes described previously in relation to FIG. 157.

In some embodiments (e.g., 3D imaging), the anatomical landmark triangulation processes described above are circumvented, by simply segmenting the anatomical landmarks within the provided 3D volume, to compute the 3D locations of the landmarks relative to the X-Ray adapter device.

Some embodiments of this invention enable the user to update the location of anatomical landmarks at any time during surgery, without the need for additional X-Ray imaging. In some embodiments, the user engages a 3D-tracked probe to the bone-mounted fiducials in a software-guided order. In some embodiments, this process defines the unique vertebral-level identities of the bone-mounted fiducials (e.g., fiducial #1 is mounted to the L3 vertebra) and records their 3D locations and poses in the navigation camera's coordinate frame.

In some embodiments, for each vertebral level (e.g., L3 vertebra), the system computes the 3D location of its corresponding anatomical landmark (e.g., endplate of L3 vertebra) in its unique fiducial's coordinate frame (e.g., fiducial mounted to the L3 vertebra). In some embodiments, this process is performed by using the defined vertebra-fiducial pairing and a rigid body transform applied to the registered anatomical landmarks in the navigation camera's coordinate frame. In some embodiments, the system is now ready to compute spinal alignment parameters of the patient. In some embodiments, the user may repeat the 3D registration process for other anatomical landmarks of interest before proceeding.

In some embodiments of this invention, the 3D locations and poses of anatomical landmarks are used to compute the spinal alignment parameters of the patient. In some embodiments, if the anatomy has been manipulated or accidentally moved during the surgical correction process, new spinal alignment parameters can be measured by engaging the 3D-tracked probe with each of the bone-mounted fiducials in the same software-guided order as prior and updating the 3D locations and poses of anatomical landmarks.

In some embodiments, the user may repeat the aforementioned processes until 3D alignment surgical goals are met. In some embodiments, the user may continue or finish the surgical correction process.

In some embodiments, any of the above processes, methods, or procedures related to the workflow 15801 can include or be accomplished with one or more of steps or processes such as 15800, 15802, 15804, 15806, 15808, 15810, 15812, 15814, 15816, 15818, 15820, 15822, 15824, 15826, 15828, 15830, and 15832. In some embodiments, at least one of the steps can include a decision step (e.g., such as step 15818), where one or more following steps depend on a status, decision, state, or other condition. In some embodiments, the steps of workflow 15801 can proceed in the order as shown. In some embodiments, any of the steps of the workflow 15801 can proceed out of the order as shown. In some embodiments, one or more of the steps of the workflow 15801 can be skipped.

In some embodiments of the invention, FIG. 159A-G illustrate process 15901 of using flexibility-assessment devices to measure the 3D range of motion of vertebrae of the spine. In some embodiments, if after this assessment the user deems the desired 3D alignment surgical goals can be achieved by the vertebrae, the user may stabilize the vertebrae in that exact position using the devices' rod placement mechanism. In some embodiments, relevant figures include example embodiments of device systems in FIGS. 127-129 and 146 and embodiments of processes in FIG. 136.

Some embodiments of this invention involve securing the front-facing and back-facing flexibility-assessment devices to the bilateral pedicle screws of the vertebral levels of interest (e.g., L4 and L5 vertebrae).

In some embodiments, if image-guided surgical navigation is used, the system automatically segments each vertebra attached to a flexibility-assessment device from the registered volumetric imaging (e.g., CT, CBCT, MRI, etc.), and generates 3D meshworks of the vertebrae (e.g., L4 and L5 vertebrae). In some embodiments, the user indicates to the software that the device-to-vertebra mating is completed by actuating one of the triggers on the flexibility-assessment device or by providing manual input (e.g., mouse click, touchscreen input, etc.). In some embodiments, the system then identifies the unique pairing between each flexibility-assessment device and each vertebra (e.g. device #1 is engaged with L4 vertebra). In some embodiments, this process is done by manual user input or by computing the distance between the 3D-tracked end-effectors of each flexibility-assessment device and the known 3D locations of the screw tulip head centers and selecting the minimum distance pair.

In some embodiments, in a non-navigated case, an X-Ray adapter device with embedded radiopaque markers (e.g., spheres, lines, grid, disks etc.) is attached to the male protrusion on one of the flexibility-assessment devices. In some embodiments, depending on the type of X-Ray imaging system used (e.g., image-intensifier), image distortion correction processes as described previously in relation to FIG. 157 are performed. In some embodiments, if this image-correction process is not required (e.g. 2D imaging with flat-panel detector, 3D imaging), the surgeon simply proceeds with acquiring at least two X-Ray images of the X-Ray adapter device and anatomical landmarks of interest (e.g., endplates of the L4 and L5 vertebrae) to register the anatomical landmarks in relation to the flexibility-assessment devices. In some embodiments, the system then calibrates the projective geometry of the acquired X-Ray images, identifying an appropriate projection mapping from 3D-space to the 2D-image plane. In some embodiments, this process is performed in accordance with processes described previously in relation to FIG. 157. In some embodiments, this completes the process of 3D registration of the key landmarks of the vertebrae and the X-Ray adapter device is removed. In some embodiments, the user indicates to the software, in a similar manner as in the aforementioned embodiment, that the device-to-vertebra mating is completed. In some embodiments, the system then computes the 3D locations of the registered anatomical landmarks in the coordinate frame of the flexibility-assessment device. In some embodiments, this process is done by computing the X-Ray adapter device's markers in the navigation camera's coordinate frame, based on the known geometric configuration of the markers when mated to the male protrusion on the 3D-tracked flexibility-assessment device.

In some embodiments of this invention, as the vertebrae are being manipulated by the flexibility-assessment devices or by other surgical maneuvers, the system displays the real-time 3D locations and poses of the 3D meshworks (navigated case) or 3D landmarks (non-navigated case) of the vertebrae, along with their associated 3D spinal alignment parameters (e.g., sagittal, coronal, and axial cobb angles between the L4 and L5 vertebrae, etc.).

Some embodiments enable the user to record the 3D motion and corresponding changes in alignment parameters of the vertebrae as they are being manipulated, by clicking on both triggers of the flexibility-assessment devices. In some embodiments, the system subsequently displays the minimum and maximum inter-vertebral angles achieved in all anatomical planes during the range of motion assessment. In some embodiments, the user double-clicks or long-holds the trigger to return to the real-time alignment-measurement mode.

In some embodiments, if after the range of motion assessment, the vertebrae are able to achieve the user's 3D alignment goals, the user may stabilize the vertebrae and secure them in place with surgical rods. In some embodiments, this process is done by holding the vertebrae in the desired position and securing a temporary rod between the satellite device tulip heads on one side (e.g., patient's right side) of the flexibility-assessment devices. In some embodiments, if there are no more anatomical landmarks to measure, a final surgical rod is placed bilaterally. In some embodiments, this process is done by detaching the screw-interface arms, first on the side without the temporary rod (e.g., patient's left side) and placing a surgical rod. In some embodiments, this process is followed by removing the temporary rod on the contralateral side (e.g., patient's right side) and then similarly placing a surgical rod. In some embodiments, the user may instead choose to assess the range of motion of adjacent vertebral levels (e.g., L3 vertebra) that are not currently attached to a flexibility-assessment device. In some embodiments, the user removes the flexibility-assessment device from the vertebra that is not involved (e.g. L5 vertebra) with the new vertebra, secures it to the bilateral pedicle screws of the new vertebra, and repeats some or all of the aforementioned processes from the beginning.

In some embodiments, if the user deems that the engaged vertebrae may not have adequate range of motion to achieve the 3D alignment surgical goals, the user may remove both flexibility-assessment devices and continue with the surgical correction process.

In some embodiments, any of the above processes, methods, or procedures related to the workflow 15901 can include or be accomplished with one or more of steps or processes such as 15900, 15902, 15904, 15906, 15908, 15910, 15912, 15914, 15916, 15918, 15920, 15922, 15924, 15926, 15928, 15920, 15922, 15924, 15926, 15928, 15930, 15932, 15934, 15936, 15938, 15940, 15942, 15944, 15946, 15948, 15950, 15952, 15954, 15956, 15958, 15960, 15962, 15964, 15966, 15968, 15970, 15972, 15974, 15976, 15978, 15980, 15982, 15984, 15986, 15988, 15990, 15992, 15994, 15996, and 15998. In some embodiments, at least one of the steps can include a decision step (e.g., such as step 15902), where one or more following steps depend on a status, decision, state, or other condition. In some embodiments, the steps of workflow 15901 can proceed in the order as shown. In some embodiments, any of the steps of the workflow 15901 can proceed out of the order as shown. In some embodiments, one or more of the steps of the workflow 15901 can be skipped.

In some embodiments of the invention, FIG. 160A-D illustrate the process 16001 of measuring the patient's spinal alignment parameters after inserting implants (e.g. interbody cage) into the spine. In some embodiments, if desired by the user, real-time visual and quantitative alignment feedback of this implant insertion process can be provided. In some embodiments, relevant figures include example embodiments of device systems for real-time tracking of implants and engaged vertebrae of interest in FIGS. 147-156.

Some embodiments of this invention involve implanting fiducials into each vertebra of interest surrounding the implant target location (e.g. implant fiducials in the L5 and S1 vertebrae if the cage will be inserted in the disk space between L5 and S1).

In some embodiments, if image-guided surgical navigation is used, the system automatically segments each vertebra of interest from the registered volumetric imaging (e.g., CT, CBCT, MRI, etc.), and 3D meshworks of the vertebrae are generated. In some embodiments, in a non-navigated case, an X-Ray adapter device with embedded radiopaque markers (e.g., spheres, lines, grid, disks etc.) is attached to at least one of the bone-mounted fiducials via a unique mating mechanism. In some embodiments, depending on the type of X-Ray imaging system used (e.g., image-intensifier), image distortion correction processes as described previously in relation to FIG. 157 are performed. In some embodiments, if this image-distortion-correction step is not required (e.g. 2D imaging with flat-panel detector, 3D imaging), the surgeon simply proceeds with acquiring at least two X-Ray images of the bone-mounted fiducials and the X-Ray adapter device. In some embodiments, the system then calibrates the projective geometry of the acquired X-Ray images, identifying an appropriate projection mapping from 3D-space to the 2D-image plane. In some embodiments, this process is performed in accordance with processes described previously in relation to FIG. 157, completing the process of 3D registration of the key landmarks (e.g., endplates) of the vertebrae of interest.

In some embodiments, to begin the maneuver, an implant (e.g. interbody cage) is attached to the 3D-tracked implant driver. In some embodiments, the user may choose to see real-time feedback of the implant insertion. In some embodiments, a 3D-tracked DRF is attached to each bone-mounted fiducial. In some embodiments, the system then transforms the coordinates of the registered anatomical landmarks (e.g., in a non-navigated case) or the 3D vertebral meshworks (e.g. in a navigated case) to be in the corresponding bone-mounted fiducial's coordinate frame. In some embodiments, as the vertebrae are being manipulated, the system continuously updates the 3D locations and poses of the vertebrae via rigid body transforms. In some embodiments, when the vertebrae are in a desired configuration, the implant is inserted and deployed.

Some embodiments of this invention involve various actuation mechanisms (e.g., cage expansion or pivoting) of the 3D-tracked implant driver and its attached implant. In some embodiments, if the driver has one actuation (e.g., FIGS. 147, 148, 149, 150, 151, and 155), the actuation is tracked via a mechanically-linked TMSM that moves vertically, sideways, or rotationally relative to the driver shaft's axis. In some embodiments, as the implant is actuated, the visual representation of the implant continuously updates based on incremental movements of the TMSM relative to the driver's DRF. In some embodiments, when the implant is dual-actuated (e.g., FIGS. 152, 153, 154), this process is similar, but the implant's movement is tracked based on the movement of one or more mechanically-linked TMSMs. In some embodiments, for both aforementioned embodiments, as the implant is inserted and deployed, the system displays the real-time locations and poses of the 3D-tracked vertebrae, the implant, and corresponding spinal alignment parameters in multiple anatomical planes (e.g., sagittal, coronal, axial plane parameters).

In some embodiments, if the driver has no actuations (e.g., FIG. 156), the user simply manipulates the spine without real-time feedback of the vertebrae and inserts the implant. In some embodiments, the 3D-tracked probe is engaged with the bone-mounted fiducials to update the 3D locations and poses of previously registered vertebrae or anatomical landmarks. In some embodiments, based on those coordinates, the system displays the real-time locations and poses of the 3D-tracked vertebrae, the implant, and corresponding spinal alignment parameters in multiple anatomical planes (e.g., sagittal, coronal, axial plane parameters).

In some embodiments, if the user wants to place additional implants, the aforementioned processes may be repeated. In some embodiments, the user may continue or finish the surgical correction process.

In some embodiments, any of the above processes, methods, or procedures related to the workflow 16001 can include or be accomplished with one or more of steps or processes such as 16000, 16002, 16004, 16006, 16008, 16010, 16012, 16014, 16016, 16018, 16020, 16022, 16024, 16026, 16028, 16030, 16032, 16034, 16036, 16038, 16040, 16042, 16044, 16046, 16048, 16050, and 16052. In some embodiments, at least one of the steps can include a decision step (e.g., such as step 16020), where one or more following steps depend on a status, decision, state, or other condition. In some embodiments, the steps of workflow 16001 can proceed in the order as shown. In some embodiments, any of the steps of the workflow 16001 can proceed out of the order as shown. In some embodiments, one or more of the steps of the workflow 16001 can be skipped.

Some embodiments of this invention involve using flexibility-assessment devices to measure the 3D range of motion of the spine. In some embodiments, the 3D locations and poses of the flexibility-assessment devices are known based on 3D-tracked dynamic reference frames (DRFs) attached to their handles, as shown previously in hardware figures such as FIG. 136. In some embodiments, the user rigidly secures the flexibility-assessment devices on the pedicle screws implanted in the vertebrae of interest (e.g., L4 and L5 vertebrae). In some embodiments, key landmarks of the vertebrae (e.g., 3D meshwork, endplate lines of L4 and L5) are then registered in relation to the flexibility-assessment devices using X-Ray images. In some embodiments, if image-guided surgical navigation is used, the system can automatically segment the vertebrae attached to the flexibility-assessment devices from the registered volumetric imaging (e.g., CT, CBCT, MRI, etc.), and generate 3D meshworks of the vertebrae. In some embodiments, in a non-navigated case, an X-Ray adapter device is used to calibrate the projective geometry and triangulate the key vertebral landmarks from two or more X-Ray images, as described previously in software figures such as FIG. 159. In some embodiments, if after the range-of-motion assessment, the user deems the desired 3D alignment surgical goals can be achieved by the engaged vertebrae, the user may stabilize the vertebrae in that exact position using the devices' surgical rod placement system.

In some embodiments, FIG. 161 illustrates a display interface 16100 of the visual and quantitative feedback of the engaged vertebrae's 3D range of motion. In some embodiments, as the vertebrae are being manipulated by the flexibility-assessment devices, the system displays the real-time 3D locations and poses of the 3D meshworks and endplate lines of the vertebrae, along with their associated 3D spinal alignment parameters (e.g., sagittal, coronal, and axial cobb angles between the L4 and L5 vertebrae, etc.).

In some embodiments, the top-left plot shows the 3D perspective view 16116 of the two engaged vertebrae (16110, 16112) in the 3D axes 16102 which are aligned with the patient's anatomical planes (e.g., right and left, superior and inferior, anterior and posterior). In some embodiments, the bottom-left plot shows the axial plane view 16104 (e.g., right-left and anterior-posterior) of the two engaged vertebrae (16110, 16112), along with their adjacent axial endplate lines (16122, 16124) and angle between those lines in degrees 16114. In some embodiments, the top-right plot shows the sagittal plane view 16106 (e.g., superior-inferior and anterior-posterior) of the two engaged vertebrae (16110, 16112), along with their adjacent sagittal endplate lines (16130, 16132) and angle between those lines in degrees 16118. In some embodiments, the bottom-right plot shows the coronal plane view 16108 (e.g., right-left and inferior-superior) of the two engaged vertebrae (16110, 16112), along with their adjacent coronal endplate lines (16126, 16128) and angle between those lines in degrees 16120.

Some embodiments of this invention provide the user with visual and quantitative alignment feedback of multiple vertebral levels of the spine (e.g., the sacrum and multiple lumbar vertebrae) and enable the user to update the locations and associated alignment parameters of those vertebrae each time the spine is manipulated or accidentally moved. In some embodiments, this process is achieved by implanting fiducials into the vertebral levels of interest, and using X-Ray images and an X-Ray adapter device to register the 3D location and pose of anatomical landmarks relative to the bone-mounted fiducials. In some embodiments, the registered anatomical landmarks are then used to compute desired spinal alignment parameters of the patient. In some embodiments, the device systems and processes mentioned above are described previously in hardware figures such as FIG. 135 and software figures such as FIG. 158.

In some embodiments, FIG. 162A illustrates a display interface 16201 for displaying the 3D locations and poses of multiple vertebral levels of the spine 16200a in a 3D perspective view 16216a, with the axes 16214a aligned with the patient's anatomical planes (e.g., left-right, inferior-superior, anterior-posterior). In some embodiments, the plotted objects in the 3D axes are the sacrum 16202a and the five lumbar vertebrae (16204a, 16206a, 16208a, 16210a, 16212a), along with visual representations of their endplates (16218a, 16220a, 16222a, 16224a, 16226a, 16228a).

In some embodiments, FIG. 162B illustrates a display interface 16235 for displaying the 3D locations and poses of multiple vertebral levels of the spine 16200b in a 2D sagittal view 16216b, with the axes 16214b aligned with the patient's sagittal anatomical planes (e.g., inferior-superior, anterior-posterior). In some embodiments, plotted in the axes are the sacrum 16202b and the five lumbar vertebrae (16204b, 16206b, 16208b, 16210b, 16212b), along with visual representations of their endplates (16218b, 16220b, 16222b, 16224b, 16226b, 16228b) and intervertebral angles 16237a (e.g., angle between each adjacent vertebra as well as the lumbar lordosis, the angle between L1 and S1).

In some embodiments, FIG. 162C illustrates a display interface 16240 for displaying the 3D locations and poses of multiple vertebral levels of the spine 16200c in a 2D coronal view 16216c, with the axes 16214c aligned with the patient's coronal anatomical planes (e.g., left-right, inferior-superior). In some embodiments, plotted in the axes are the sacrum 16202c and the five lumbar vertebrae (16204c, 16206c, 16208c, 16210c, 16212c), along with visual representations of their endplates (16218c, 16220c, 16222c, 16224c, 16226c, 16228c) and intervertebral angles 16237b (e.g., angle between each adjacent vertebra as well as the coronal Cobb angle between L1 and S1).

In some embodiments, FIG. 162D illustrates a display interface 16250 for displaying the 3D locations and poses of multiple vertebral levels of the spine 16200d in a 2D axial view 16216d, with the axes 16214d aligned with the patient's axial anatomical planes (e.g., left-right, anterior-posterior). In some embodiments, plotted in the axes are the sacrum 16202d and the five lumbar vertebrae (16204d, 16206d, 16208d, 16210d, 16212d), along with visual representations of their endplates (16218d, 16220d, 16222d, 16224d, 16226d, 16228d) and intervertebral angles 16237c (e.g., angle between each adjacent vertebra as well as the axial Cobb angle between L1 and S1).

Any of the operations described herein that form part of the invention are useful machine operations. The invention also relates to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general-purpose computer selectively activated or configured by one or more computer programs stored in the computer memory, cache, or obtained over a network. When data is obtained over a network the data can be processed by other computers on the network, e.g. a cloud of computing resources.

The embodiments of the present invention can also be defined as a machine that transforms data from one state to another state. The data can represent an article, that can be represented as an electronic signal and electronically manipulate data. The transformed data can, in some cases, be visually depicted on a display, representing the physical object that results from the transformation of data. The transformed data can be saved to storage generally, or in particular formats that enable the construction or depiction of a physical and tangible object. In some embodiments, the manipulation can be performed by a processor. In such an example, the processor thus transforms the data from one thing to another. Still further, some embodiments include methods can be processed by one or more machines or processors that can be coupled over a network. Each machine can transform data from one state or thing to another, and can also process data, save data to storage, transmit data over a network, display the result, or communicate the result to another machine. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way.

It will be appreciated by those skilled in the art that while the invention has been described above in connection with particular embodiments and examples, the invention is not necessarily so limited, and that numerous some embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

We claim:

1. A system for registering at least a portion of a patient's spinal curvature and/or flexibility, comprising: an acquisition system for acquiring data using a continuous or discrete 3D-tracked acquisition along a skin surface of a spine of the patient, wherein a 3D-tracked probe visible to a tracking camera system is used to acquire the data by tracing over skin of the spine of the patient, wherein the data is used to identify a relationship between acquired points of data and centroids of vertebral bodies of the patient; a mechanical mechanism configured to link a top-half fiducial of a skin-mounted fiducial device to a bottom-half fiducial of the skin-mounted fiducial device that includes a winged clamping mechanism having one or more side clamps that revolve about a hinge joint via a pivot bearing: non-transient computer readable media for storing at least a portion of the acquired data; one or more computer processors implementing analyses on least a portion of the acquired data and generating a quantitative assessment of the patient's spinal biomechanical qualities; and the skin-mounted fiducial device containing a radiopaque marker visible in an x-ray image containing the spine, wherein the 3D-tracked probe is used to trace a portion of the skin-mounted fiducial device to register fiducial 3D coordinates axes in navigation camera coordinates; and wherein the acquisition system uses the acquired trace data to construct a bone surface contour of the spine based on the skin-mounted fiducial device as located in the x-ray image to generate at least one spine alignment parameter.

2. The system of claim 1,
wherein the system provides location-based input regarding one or more implants used to enhance the biomechanical qualities.

3. The system of claim 1,
wherein the system acquires data both within and beyond a proposed surgical site.

4. The system of claim 1,
wherein the system registers at least one instrument or implant used to assess and/or manipulate the conformation of the spine.

5. The system of claim 1,
wherein the quantitative assessments include calculated values for one or more radiographic parameters related to both global and segmental alignment of the spine.

6. The system of claim 1,
wherein the one or more radiographic parameters include at least one of lumbar lordosis, central sacral vertical line, T1 pelvic angle, thoracic kyphosis, and Cobb angle.

7. The system of claim 1, wherein the one or more processors implement filtering to aid in identifying a relationship between acquired points and anatomical regions of interest.

8. The system of claim 1,
wherein the assessment includes values for Cobb angle, lumbar lordosis, thoracic kyphosis, C2-C7 lordosis, C7-S I sagittal vertical axis, central sacral vertical line, T1 pelvic angle, pelvic incidence, and pelvic-incidence-lumbar-lordosis mismatch.

9. The system of claim 1,
further including a visual display and quantitative feedback system for assessing and adjusting implants that can be implanted into or onto the patient.

10. The system of claim 9,
wherein the display outputs at least one of information about the patient's spine's curvature and alignment, quantitative radiographic alignment parameter values, instrumented hardware analysis, flexibility or range of motion of the spine, and one or more ways to acquire or analyze radiographic images.

11. The system of claim 1, wherein the skin-mounted fiducial device is used for registering a 3D location and pose of key anatomical landmarks of interest outside of the surgical site.

12. The system of claim 1, wherein the acquisition system is configured to generate a sagittal vertical axis (SVA) as one of the at least one spine alignment parameter from the constructed bone surface contour of the spine.

13. The system of claim 1, wherein the acquisition system is configured to generate a lumbar lordosis (LL) as one of the at least one spine alignment parameter from the constructed bone surface contour of the spine.

* * * * *